(12) United States Patent
Butler et al.

(10) Patent No.: US 12,428,442 B2
(45) Date of Patent: *Sep. 30, 2025

(54) COMPOUNDS, COMPOSITIONS AND METHODS FOR SYNTHESIS

(71) Applicant: WAVE LIFE SCIENCES LTD., Singapore (SG)

(72) Inventors: David Charles Donnell Butler, Medford, MA (US); Christopher P. Hencken, Boston, MA (US); Naoki Iwamoto, Boston, MA (US); Pachamuthu Kandasamy, Lexington, MA (US); Alvaro Andres Lanao, Middlebury, CT (US); Genliang Lu, Winchester, MA (US); Mamoru Shimizu, Arlington, MA (US); Sethumadhavan Divakaramenon, Lexington, MA (US); Chandra Vargeese, Schwenksville, PA (US); Gopal Reddy Bommineni, Belmont, MA (US); Subramanian Marappan, Acton, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,932

(22) Filed: May 12, 2023

(65) Prior Publication Data
US 2024/0174710 A1 May 30, 2024

Related U.S. Application Data

(63) Continuation of application No. 16/624,896, filed as application No. PCT/US2018/038835 on Jun. 21, 2018, now Pat. No. 11,718,638.

(60) Provisional application No. 62/560,169, filed on Sep. 18, 2017, provisional application No. 62/523,175, filed on Jun. 21, 2017.

(51) Int. Cl.
| | |
|---|---|
| C07H 21/04 | (2006.01) |
| C07C 213/00 | (2006.01) |
| C07C 215/20 | (2006.01) |
| C07C 215/44 | (2006.01) |
| C07D 207/08 | (2006.01) |
| C07D 211/22 | (2006.01) |
| C07F 7/08 | (2006.01) |
| C07F 9/6564 | (2006.01) |
| C07H 19/06 | (2006.01) |

(52) U.S. Cl.
CPC ........... *C07H 21/04* (2013.01); *C07C 213/00* (2013.01); *C07C 215/20* (2013.01); *C07C 215/44* (2013.01); *C07D 207/08* (2013.01); *C07D 211/22* (2013.01); *C07F 7/0812* (2013.01); *C07F 7/083* (2013.01); *C07F 9/6564* (2013.01); *C07H 19/06* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 5,221,736 A | 6/1993 | Coolidge et al. |
| 6,384,209 B1 | 5/2002 | Tang et al. |
| 8,420,821 B2 | 4/2013 | Matsuda et al. |
| 8,470,987 B2 | 6/2013 | Wada et al. |
| 8,729,036 B2 | 5/2014 | Zamore et al. |
| 8,822,671 B2 | 9/2014 | Shimizu et al. |
| 8,859,755 B2 | 10/2014 | Wada et al. |
| 9,394,333 B2 | 7/2016 | Wada et al. |
| 9,476,044 B2 | 10/2016 | Tuschl et al. |
| 9,598,458 B2 | 3/2017 | Shimizu et al. |
| 9,605,019 B2 | 3/2017 | Verdine et al. |
| 9,617,547 B2 | 4/2017 | Gemba |
| 9,695,211 B2 | 7/2017 | Wada et al. |
| 9,744,183 B2 | 8/2017 | Verdine et al. |
| 9,982,257 B2 | 5/2018 | Butler et al. |
| 10,144,933 B2 | 12/2018 | Gemba et al. |
| 10,149,905 B2 | 12/2018 | Gemba et al. |
| 10,160,969 B2 | 12/2018 | Meena et al. |
| 10,167,309 B2 | 1/2019 | Shimizu et al. |
| 10,280,192 B2 | 5/2019 | Verdine et al. |
| 10,307,434 B2 | 6/2019 | Verdine et al. |

(Continued)

FOREIGN PATENT DOCUMENTS

| | | |
|---|---|---|
| CN | 101437801 A | 5/2009 |
| CN | 102596204 A | 7/2012 |

(Continued)

OTHER PUBLICATIONS

U.S. Appl. No. 17/605,998, filed Oct. 22, 2021, Byrne et al.

(Continued)

*Primary Examiner* — Layla D Berry
(74) *Attorney, Agent, or Firm* — Choate, Hall & Stewart LLP; Xiaodong Li; Yuxiang Chen

(57) ABSTRACT

The present disclosure, among other things, provides technologies for synthesis, including reagents and methods for stereoselective synthesis. In some embodiments, the present disclosure provides compounds useful as chiral auxiliaries. In some embodiments, the present disclosure provides reagents and methods for oligonucleotide synthesis. In some embodiments, the present disclosure provides reagents and methods for chirally controlled preparation of oligonucleotides. In some embodiments, technologies of the present disclosure are particularly useful for constructing challenging internucleotidic linkages, providing high yields and stereoselectivity.

21 Claims, 1 Drawing Sheet
Specification includes a Sequence Listing.

(56) References Cited

U.S. PATENT DOCUMENTS

| | | |
|---|---|---|
| 10,322,173 B2 | 6/2019 | Gemba et al. |
| 10,329,318 B2 | 6/2019 | Wada et al. |
| 10,428,019 B2 | 10/2019 | Wada et al. |
| 10,450,568 B2 | 10/2019 | Butler et al. |
| 10,479,995 B2 | 11/2019 | Vargeese et al. |
| 10,590,413 B2 | 3/2020 | Butler et al. |
| 10,696,711 B2 | 6/2020 | Shimizu et al. |
| 10,724,035 B2 | 7/2020 | Vargeese et al. |
| 10,815,482 B2 | 10/2020 | Meena et al. |
| 11,013,757 B2 | 5/2021 | Zhang et al. |
| 11,136,346 B2 | 10/2021 | Shimizu et al. |
| 11,596,646 B2 | 3/2023 | Zhang et al. |
| 11,597,927 B2 | 3/2023 | Vargeese et al. |
| 11,603,532 B2 | 3/2023 | Vargeese et al. |
| 11,634,710 B2 | 4/2023 | Frank-Kamenetsky et al. |
| 11,643,657 B2 | 5/2023 | Butler et al. |
| 11,718,638 B2 | 8/2023 | Butler et al. |
| 11,739,325 B2 | 8/2023 | Vargeese et al. |
| 11,873,316 B2 | 1/2024 | Butler et al. |
| 2013/0345462 A1 | 12/2013 | Matsuda et al. |
| 2015/0211006 A1 | 7/2015 | Butler et al. |
| 2019/0127733 A1 | 5/2019 | Butler et al. |
| 2019/0249173 A1 | 8/2019 | Vargeese et al. |
| 2019/0264267 A1 | 8/2019 | Yang et al. |
| 2019/0375774 A1 | 12/2019 | Butler et al. |
| 2019/0390197 A1 | 12/2019 | Butler et al. |
| 2020/0080083 A1 | 3/2020 | Vargeese et al. |
| 2020/0362337 A1 | 11/2020 | Dodart et al. |
| 2021/0032620 A1 | 2/2021 | Vargeese et al. |
| 2021/0115444 A1 | 4/2021 | Meena et al. |
| 2021/0198305 A1 | 7/2021 | Vargeese et al. |
| 2021/0254062 A1 | 8/2021 | Zhang et al. |
| 2022/0098585 A1 | 3/2022 | Brown et al. |
| 2022/0127301 A1 | 4/2022 | Shimizu et al. |
| 2022/0145300 A1 | 5/2022 | Liu et al. |
| 2022/0162598 A1 | 5/2022 | Vargeese et al. |
| 2022/0401467 A1 | 12/2022 | Zhang et al. |
| 2023/0089442 A1 | 3/2023 | Kandasamy et al. |
| 2023/0136645 A1 | 5/2023 | Butler et al. |
| 2023/0145795 A1 | 5/2023 | Byrne et al. |
| 2023/0203087 A1 | 6/2023 | Kandasamy et al. |
| 2023/0220384 A1 | 7/2023 | Monian et al. |
| 2023/0295617 A1 | 9/2023 | Vargeese et al. |
| 2023/0295619 A1 | 9/2023 | Maguire et al. |
| 2023/0329201 A1 | 10/2023 | Yang et al. |
| 2023/0348524 A1 | 11/2023 | Bowman et al. |
| 2023/0392137 A1 | 12/2023 | Monian et al. |
| 2024/0026358 A1 | 1/2024 | Monian et al. |
| 2024/0109931 A1 | 4/2024 | Vargeese et al. |
| 2024/0117347 A1 | 4/2024 | Butler et al. |
| 2024/0132894 A1 | 4/2024 | Vargeese et al. |
| 2024/0150756 A1 | 5/2024 | Frank-Kamenetsky et al. |
| 2024/0175016 A1 | 5/2024 | Liu et al. |
| 2024/0175018 A1 | 5/2024 | Vargeese et al. |
| 2024/0229026 A1 | 7/2024 | Butler et al. |

FOREIGN PATENT DOCUMENTS

| | | |
|---|---|---|
| CN | 104661664 A | 5/2015 |
| CN | 104684893 A | 6/2015 |
| JP | 62-289589 A | 12/1987 |
| JP | 2003-238586 A | 8/2003 |
| JP | 2015-528002 A | 9/2015 |
| WO | WO-94/19363 A1 | 9/1994 |
| WO | WO-2004/007718 A2 | 1/2004 |
| WO | WO-2005/014609 A2 | 2/2005 |
| WO | WO-2005/023828 A1 | 3/2005 |
| WO | WO-2005/028494 A1 | 3/2005 |
| WO | WO-2005/070859 A1 | 8/2005 |
| WO | WO-2005/085272 A1 | 9/2005 |
| WO | WO-2005/092909 A1 | 10/2005 |
| WO | WO-2010/064146 A2 | 6/2010 |
| WO | WO-2011/005761 A1 | 1/2011 |
| WO | WO-2011/034072 A1 | 3/2011 |
| WO | WO-2011/108682 A1 | 9/2011 |
| WO | WO-2012/039448 A1 | 3/2012 |
| WO | WO-2012/073857 A1 | 6/2012 |
| WO | WO-2013/012758 A1 | 1/2013 |
| WO | WO-2014/010250 A1 | 1/2014 |
| WO | WO-2014/010718 A1 | 1/2014 |
| WO | WO-2014/012081 A2 | 1/2014 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2017/015555 A1 | 1/2017 |
| WO | WO-2017/015575 A1 | 1/2017 |
| WO | WO-2017/062862 A2 | 4/2017 |
| WO | WO-2017/160741 A1 | 9/2017 |
| WO | WO-2017/192664 A1 | 11/2017 |
| WO | WO-2017/192679 A1 | 11/2017 |
| WO | WO-2017/210647 A1 | 12/2017 |
| WO | WO-2018/022473 A1 | 2/2018 |
| WO | WO-2018/067973 A1 | 4/2018 |
| WO | WO-2018/098264 A1 | 5/2018 |
| WO | WO-2018/223056 A1 | 12/2018 |
| WO | WO-2018/223073 A1 | 12/2018 |
| WO | WO-2018/223081 A1 | 12/2018 |
| WO | WO-2018/237194 A1 | 12/2018 |
| WO | WO-2019/002237 A1 | 1/2019 |
| WO | WO-2019/032607 A1 | 2/2019 |
| WO | WO-2019/032612 A1 | 2/2019 |
| WO | WO-2019/055951 A1 | 3/2019 |
| WO | WO-2019/075357 A1 | 4/2019 |
| WO | WO-2019/200185 A1 | 10/2019 |
| WO | WO-2019/217784 A1 | 11/2019 |
| WO | WO-2020/118246 A1 | 6/2020 |
| WO | WO-2020/160336 A1 | 8/2020 |
| WO | WO-2020/191252 A1 | 9/2020 |
| WO | WO-2020/196662 A1 | 10/2020 |
| WO | WO-2020/219981 A2 | 10/2020 |
| WO | WO-2020/219983 A2 | 10/2020 |
| WO | WO-2020/227691 A2 | 11/2020 |
| WO | WO-2021/071788 A2 | 4/2021 |
| WO | WO-2021/071858 A1 | 4/2021 |
| WO | WO-2021/178237 A2 | 9/2021 |
| WO | WO-2021/234459 A2 | 11/2021 |
| WO | WO-2021/237223 A1 | 11/2021 |
| WO | WO-2022/046667 A1 | 3/2022 |
| WO | WO-2022/046723 A1 | 3/2022 |
| WO | WO-2022/099159 A1 | 5/2022 |
| WO | WO-2023/049475 A1 | 3/2023 |
| WO | WO-2023/049477 A2 | 3/2023 |
| WO | WO-2023/075766 A1 | 5/2023 |
| WO | WO-2023/076352 A2 | 5/2023 |
| WO | WO-2023/154528 A1 | 8/2023 |
| WO | WO-2023/168014 A2 | 9/2023 |
| WO | WO-2023/201095 A2 | 10/2023 |
| WO | WO-2023/220440 A1 | 11/2023 |
| WO | WO-2024/035946 A1 | 2/2024 |

OTHER PUBLICATIONS

U.S. Appl. No. 17/766,680, filed Apr. 5, 2022, Liu et al.
U.S. Appl. No. 18/062,422, filed Dec. 6, 2022, Butler et al.
U.S. Appl. No. 18/178,470, filed Mar. 3, 2023, Vargeese et al.
U.S. Appl. No. 18/204,895, filed Jun. 1, 2023, Vargeese et al.
U.S. Appl. No. 18/252,029, filed May 5, 2023, Monian et al.
U.S. Appl. No. 18/305,195, filed Apr. 21, 2023, Frank-Kamenetsky et al.
U.S. Appl. No. 18/522,146, filed Nov. 28, 2023, Butler et al.
Ami, E. and Ohrui, H., Lipase-catalyzed Kinetic Resolution of (+)-trans- and cis-2-Azidocycloalkanols, Biosci. Biotechnol. Biochem., 63(12):2150-2156 (1999).
Bench, B. J. et al., Proline Promoted Synthesis of Ring-Fused Homodimers: Self-Condensation of α,β-Unsaturated Aldehydes±, J. Org. Chem., 71(25):9458-9463 (2006).
Cui, H. et al., Direct aldol condensation reaction of ethyl diazoacetate with trfluoromethyl ketones, Tetra., 67(44):8470-8476 (2011).
Demir, A. S. et al., Novel Enantioselective Synthesis of Both Enantiomers of Furan-2-yl Amines and Amino Acids, Helvet. Chim. Acta, 86(1):91-105 (2003).

(56) References Cited

OTHER PUBLICATIONS

Gil-Av, E., Condensation Products of the Epimeric 2-Aminocyclohexanols with Carbonyl Compounds, J. Am. Chem. Soc., 81(7):1602-1606 (1959).
International Search Report for PCT/US2018/038835, 4 pages (mailed Oct. 29, 2018).
International Search Report for PCT/US2018/051398, 4 pages (mailed Feb. 1, 2019).
Koch, T., LNA Therapeutics—update, Navigate the phosphorothioate diastereoisomer space, Roche pRED RNA Therapeutics Research, EuroTIDES, PostillionConventionCenter, Amsterdam, Netherlands (Nov. 6-9, 2018).
Lysenko, I. L. and Kulinkovich, O. G., Stereoselective Synthesis of (7aS)-1-Methylenehexahyrdro-1H-pyrrolizine and (-)-Heliotridane from N-Diphenylmethyl-(S)-proline Ethyl Ester, Russ. Jrnl. Org. Chem., 41:70-74 (2005).
Masui, M. and Takayuki, S., A practical method for preparation of optically pure oxazaborolidines from α-Pinene, Tetra., 51(30):8363-8370 (1995).
Pubchem, Compound Summary for CID 522583, Create Date: Mar. 27, 2005, 16 pages (Retrieved Aug. 23, 2018). Retrieved from the Internet: <URL: https://pubchem.ncbi.nlm.nih.gov/compound/522583>.
Written Opinion for PCT/US2018/038835, 6 pages (mailed Oct. 29, 2018).
Written Opinion for PCT/US2018/051398, 16 pages (mailed Feb. 1, 2019).
Xie, J. et al., Organocatalytic and direct asymmetric vinylogous Michael addition of α,α-dicyanoolefins to α,β-unsaturated aldehydes, Chem. Commun., 14:1563-1565 (2006).
U.S. Appl. No. 18/613,034, filed Mar. 21, 2024, Vargeese et al.
U.S. Appl. No. 18/695,346, filed Mar. 25, 2024, Monian et al.
U.S. Appl. No. 18/695,348, filed Mar. 25, 2024, Acker et al.
U.S. Appl. No. 18/704,629, filed Apr. 25, 2024, Byrne et al.
U.S. Appl. No. 18/836,993, filed Aug. 8, 2024, Kandasamy et al.
U.S. Appl. No. 18/843,171, filed Aug. 30, 2024, Hu et al.
U.S. Appl. No. 18/856,553, filed Oct. 11, 2024, Lu et al.
Zon, G., Oligonucleoside Phosphorothioates, Methods in Mole. Biol., 20:165-189 (1993).

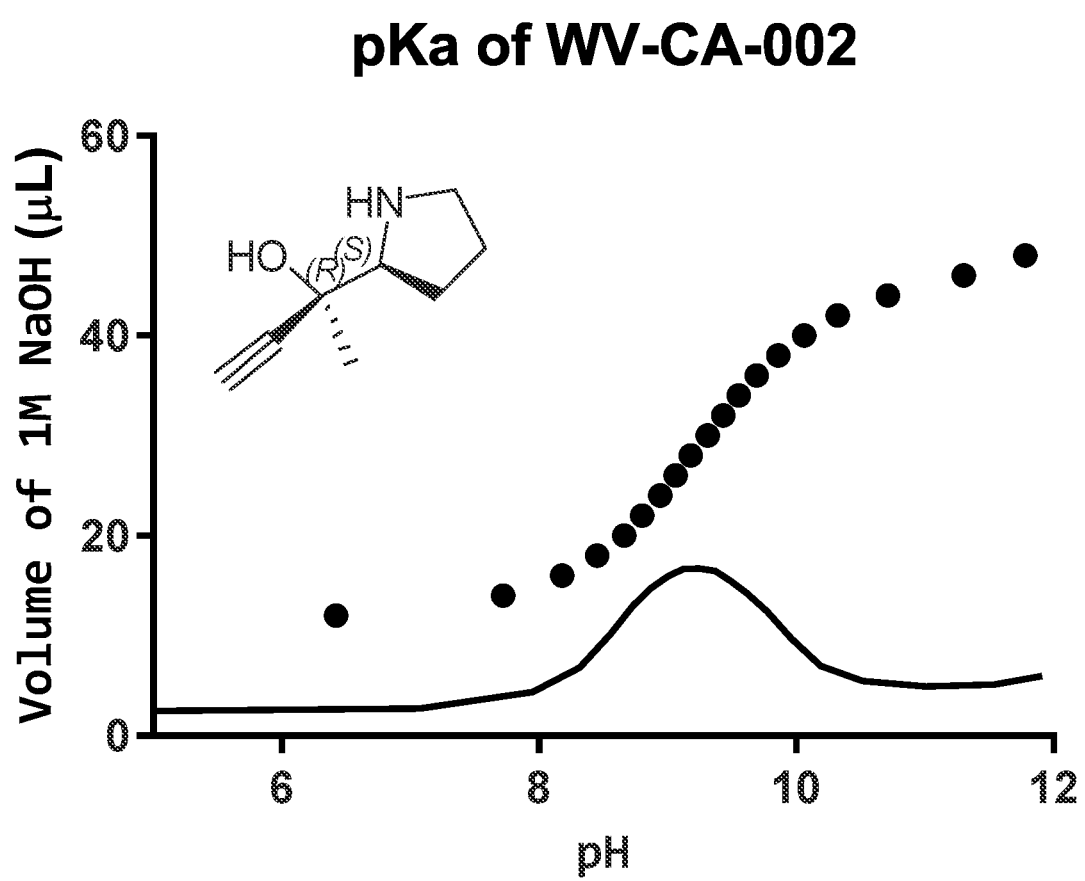

COMPOUNDS, COMPOSITIONS AND METHODS FOR SYNTHESIS

CROSS-REFERENCE TO RELATED APPLICATIONS

This application is a continuation of U.S. application Ser. No. 16/624,896 filed Dec. 19, 2019, issued as U.S. Pat. No. 11,718,638, which is a National Stage Entry of PCT/US2018/038835 filed Jun. 21, 2018, which claims priority to U.S. Provisional Application Nos. 62/523,175, filed Jun. 21, 2017, and 62/560,169, filed Sep. 18, 2017, the entirety of each of which is incorporated herein by reference.

SEQUENCE LISTING

The present application contains a Sequence Listing which has been submitted electronically in XML format and is hereby incorporated by reference in its entirety. Said XML copy, created on Dec. 19, 2023, is named Sequence-Listing.xml and is 3,751 bytes in size.

BACKGROUND

Many compounds contain chiral centers. Stereoisomers can have different properties, activities, etc.

SUMMARY

Various types of compounds, including oligonucleotides comprising chiral, modified internucleotidic linkages, contain chiral centers. Among other things, the present disclosure provides technologies (e.g., compounds, compositions, methods, etc.) for stereoselective preparation of various types of chiral compounds. In some embodiments, the present disclosure provides compounds, compositions, and methods for stereoselective (chirally controlled) preparation of chiral internucleotidic linkages in nucleic acids, for example, oligonucleotides. In some embodiments, an internucleotidic linkage comprising a chiral linkage phosphorus atom, and has the structure of formula VII, described infra. In some embodiments, a chiral internucleotidic linkage is a phosphorothioate triester linkage. In some embodiments, a chiral internucleotidic linkage is a phosphorothioate linkage.

Among other things, technologies (e.g., compounds, compositions, methods, etc.) of the present disclosure are capable of providing higher yields, stereoselectivity, product purity, and/or chemical compatibility. For example, in some embodiments, provided technologies are particularly useful for formation of challenging internucleotidic linkages in oligonucleotides, by providing surprisingly higher yields, stereoselectivity, and/or product purity. In some embodiments, for formation of challenging internucleotidic linkages, provided technologies are capable of delivering unexpectedly high yields while maintaining very high stereoselectivity, generally the same or comparable to that achieved by the best chiral auxiliaries reported (e.g., 99:1).

In some embodiments, the present disclosure provides technologies that are compatible with various chemical conditions, so that provided technologies can be used for many types of reactions and/or conditions. For example, for oligonucleotide synthesis, the present disclosure provides enormous versatility, in part by providing technologies that have various compatibility so that they can be utilized, and can be removed when desired, under a number of chemical conditions, to provide enormous flexibility for the synthesis of oligonucleotides comprising a vast array of modifications, e.g., base modifications, sugar modifications, internucleotidic linkage modifications, etc.

In some embodiments, the present disclosure provides compounds for stereoselective synthesis. In some embodiments, provided compounds are chiral auxiliaries.

In some embodiments, the present disclosure provides a compound having the structure of formula I:

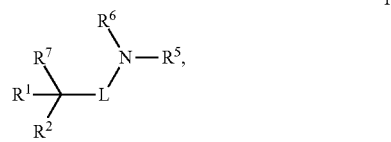

or a salt thereof, wherein:

L is a covalent bond, or optionally substituted $C_{1-6}$ alkylene, wherein one or more methylene units are optionally and independently replaced with -L'-;

each L' is independently a covalent bond, optionally substituted bivalent $C_{1-3}$ alkylene, $—C(R^3)(R^4)—$, $—C(R^3)(R^4)—C(R^3)(R^4)—$, -Cy-, or $—C(R^3)[C(R^4)_3]—$;

each of $R^1$, $R^2$, $R^3$, $R^4$, and $R^5$ is independently —H, $-L^s$-R, halogen, —CN, —NO$_2$, $-L^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, $—C(R')_2—$, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —CO$_2$R, or —SO$_2$R;

R$^6$ is R';

R$^7$ is —OH or SH;

at least one of R$^1$, R$^2$, R$^3$ and R$^4$ is not —H;

each R is independently —H, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, C$_{6-30}$ aryl, C$_{6-30}$ arylaliphatic, C$_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, L is a covalent bond. In some embodiments, a provided compound has the structure of

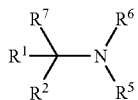

or a salt thereof. In some embodiments, R$^5$, and one or both of R$^1$ and R$^2$, are taken together with their intervening atoms to form an optionally substituted, 3-20 membered monocyclic, bicyclic or polycyclic ring having 1-5 heteroatoms. In some embodiments, one of R$^1$ and R$^2$ are taken together with R$^5$ and their intervening atoms to form an optionally substituted, 3-20 membered monocyclic, bicyclic or polycyclic ring having 1-5 heteroatoms. As extensively described in the present disclosure, a formed ring can be of various sizes, monocyclic, bicyclic or polycyclic, and contain various numbers of heteroatoms. In some embodiments, a ring is a 3-membered ring. In some embodiments, a ring is a 4-membered ring. In some embodiments, a ring is a 5-membered ring. In some embodiments, a ring is a 6-membered ring. In some embodiments, a ring is monocyclic. In some embodiments, a ring contains additional ring heteroatoms other than the intervening heteroatoms. In some embodiments, a ring is a 3-membered ring containing one ring heteroatom. In some embodiments, a ring is a 3-membered ring containing two ring heteroatoms. In some embodiments, a ring is a 3-membered ring containing one carbon, one nitrogen, and one oxygen ring atom.

In some embodiments, L is —C(R$^3$)(R$^4$)—. In some embodiments, a provided compound has the structure of formula I-a:

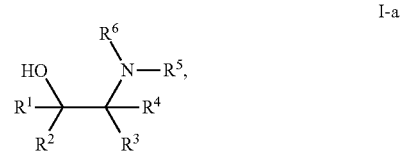

I-a or a salt thereof, wherein each variable is independently as described in the present disclosure. In some embodiments, a compound of formula I has the structure of formula I-a. In some embodiments, a provided compound has the structure of

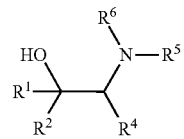

or a salt thereof, wherein each variable is independently as described in the present disclosure, wherein R$^4$ and R$^5$ are not hydrogen.

In some embodiments, a provided compound has the structure of formula (I-a-1):

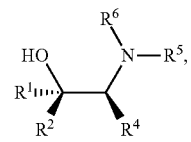

I-a-1 or a salt thereof, wherein each variable is independently as described in the present disclosure, and wherein R$^4$ and R$^5$ are not hydrogen, and R$^2$ has a larger size than R$^1$. In some embodiments, a compound of formula I-a has the structure of formula I-a-1.

In some embodiments, a provided compound has the structure of formula (I-a-2):

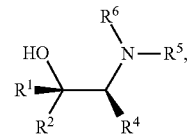

I-a-2 or a salt thereof, wherein each variable is independently as described in the present disclosure, and wherein R$^4$ and R$^5$ are not hydrogen, and R$^2$ has a larger size than R$^1$. In some embodiments, a compound of formula I-a has the structure of formula I-a-2.

In some embodiments, R$^6$ is —H. In some embodiments, R$^6$ is —H, and R$^4$ and R$^5$ are taken together with their intervening atoms to form an optionally substituted 3-20 membered heterocyclyl ring having 1-5 heteroatoms. In some embodiments, R$^4$ and R$^5$ are taken together with their intervening atoms to form an optionally substituted 4-10 membered heterocyclyl ring with the intervening nitrogen atom as the only ring heteroatom. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is substituted. In some embodiments, a formed ring is unsubstituted. In some embodiments, a formed ring is monocyclic. In some embodiments, a formed ring is bicyclic. In some embodiments, a formed ring is polycyclic. In some embodiments, a formed ring is saturated. In some embodiments, a formed ring has no ring heteroatoms in addition to the nitrogen to which $R^5$ is attached.

In some embodiments, at least one of $R^1$ and $R^2$ is not hydrogen. In some embodiments, $R^1$ is hydrogen and $R^2$ is not hydrogen. In some embodiments, $R^1$ is not hydrogen and $R^2$ is hydrogen. In some embodiments, neither of $R^1$ and $R^2$ is hydrogen.

In some embodiments, one of $R^1$ and $R^2$ is —H, and the other is R, wherein R is not hydrogen. In some embodiments, one of $R^1$ and $R^2$ is —H, and the other is optionally substituted $C_{1-6}$ aliphatic. In some embodiments, one of $R^1$ and $R^2$ is —H, and the other is optionally substituted $C_{1-4}$ aliphatic. In some embodiments, one of $R^1$ and $R^2$ is —H, and the other is optionally substituted $C_{1-3}$ aliphatic. In some embodiments, one of $R^1$ and $R^2$ is —H, and the other is optionally substituted $C_{1-2}$ aliphatic. In some embodiments, one of $R^1$ and $R^2$ is —H, and the other is optionally substituted $C_{1-6}$ alkenyl. In some embodiments, one of $R^1$ and $R^2$ is —H, and the other is vinyl. In some embodiments, one of $R^1$ and $R^2$ is —H, and the other is optionally substituted $C_{1-6}$ alkynyl. In some embodiments, one of $R^1$ and $R^2$ is —H, and the other is ethynyl. In some embodiments, one of $R^1$ and $R^2$ is —H, and the other is optionally substituted benzyl. In some embodiments, one of $R^1$ and $R^2$ is —H, and the other is benzyl wherein the phenyl group of the benzyl is optionally substituted. In some embodiments, $R^1$ is —H and $R^2$ is benzyl. In some embodiments, $R^1$ is —H and $R^2$ is —R, wherein R is as described in the present disclosure and is not hydrogen. In some embodiments, $R^2$ is optionally substituted $C_{1-6}$ aliphatic. In some embodiments, $R^2$ is optionally substituted —$CH_2$—$CPh_2Me$. In some embodiments, $R^2$ is —$CH_2$—$CPh_2Me$. In some embodiments, $R^2$ is optionally substituted phenyl. In some embodiments, $R^2$ is optionally substituted benzyl. In some embodiments, a provided compound is

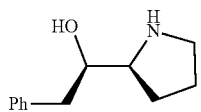 [SMILES: O[C@H](Cc1ccccc1)[C@@H]1CCCN1]

or a salt thereof.

In some embodiments, $R^1$ is not —H and $R^2$ is not —H. In some embodiments, $R^1$ and $R^2$ are independently R, wherein R is not —H. In some embodiments, $R^1$ is optionally substituted $C_{1-6}$ aliphatic, and $R^2$ is optionally substituted phenyl. In some embodiments, $R^1$ is methyl and $R^2$ is phenyl.

In some embodiments, one of $R^1$ and $R^2$ is R, wherein R comprises a ring moiety. In some embodiments, R is an optionally substituted group selected from $C_{3-20}$ cycloaliphatic, $C_{6-20}$ aryl, 5-20 membered heteroaryl having 1-5 heteroatoms, and 3-20 membered heterocyclyl having 1-5 heteroatoms. In some embodiments, R is optionally substituted $C_{3-20}$ cycloaliphatic. In some embodiments, R is optionally substituted $C_{3-10}$ cycloaliphatic. In some embodiments, R is optionally substituted $C_{3-10}$ cycloalkyl. In some embodiments, R is optionally substituted $C_{4-10}$ cycloalkyl. In some embodiments, R is optionally substituted cyclopropyl. In some embodiments, R is optionally substituted cyclobutyl. In some embodiments, R is optionally substituted cyclopentyl. In some embodiments, R is optionally substituted cyclohexyl. In some embodiments, R is optionally substituted cycloheptyl. In some embodiments, R is cyclopropyl. In some embodiments, R is cyclobutyl. In some embodiments, R is cyclopentyl. In some embodiments, R is cyclohexyl. In some embodiments, R is cycloheptyl. In some embodiments, R is optionally substituted $C_{6-20}$ aryl. In some embodiments, R is optionally substituted phenyl. In some embodiments, R is phenyl. In some embodiments, R is optionally substituted 5-20 membered heteroaryl having 1-5 heteroatoms. In some embodiments, R is optionally substituted 5-membered heteroaryl having 1-5 heteroatoms. In some embodiments, R is optionally substituted 6-membered heteroaryl having 1-5 heteroatoms. In some embodiments, R is optionally substituted 3-20 membered heterocyclyl having 1-5 heteroatoms. In some embodiments, the other of $R^1$ and $R^2$ is R wherein R is not hydrogen. In some embodiments, R is optionally substituted $C_{1-6}$ aliphatic. In some embodiments, R is optionally substituted $C_{1-6}$ alkyl. In some embodiments, R is $C_{1-6}$ alkyl. In some embodiments, R is methyl. In some embodiments, R is substituted methyl. In some embodiments, R is ethyl. In some embodiments, R is substituted ethyl. In some embodiments, one of $R^1$ and $R^2$ is R comprising a cyclic moiety as described in the present disclosure, and the other is an alkyl group as described in the present disclosure.

In some embodiments, each of $R^1$ and $R^2$ is independently R, wherein R is optionally substituted $C_{1-20}$ aliphatic. In some embodiments, R is unsubstituted $C_{1-20}$ aliphatic. In some embodiments, R is optionally substituted $C_{1-20}$ alkyl. In some embodiments, R is optionally substituted $C_{1-6}$ alkyl. In some embodiments, R is linear $C_{1-6}$ alkyl. In some embodiments, one of $R^1$ and $R^2$ is optionally substituted $C_{1-6}$ alkyl, and the other is optionally substituted $C_{1-6}$ alkyl. In some embodiments, $R^1$ and $R^2$ are the same. In some embodiments, $R^1$ and $R^2$ are different.

In some embodiments, one of $R^1$ and $R^2$ is optionally substituted $C_{1-6}$ alkyl, and the other is optionally substituted $C_{1-6}$ alkenyl. In some embodiments, one of $R^1$ and $R^2$ is optionally substituted methyl or ethyl, and the other is vinyl. In some embodiments, one of $R^1$ and $R^2$ is methyl, and the other is vinyl.

In some embodiments, one of $R^1$ and $R^2$ is optionally substituted $C_{1-6}$ alkyl, and the other is optionally substituted $C_{1-6}$ alkynyl. In some embodiments, one of $R^1$ and $R^2$ is optionally substituted methyl or ethyl, and the other is ethynyl. In some embodiments, one of $R^1$ and $R^2$ is methyl, and the other is ethynyl.

In some embodiments, one of $R^1$ and $R^2$ is optionally substituted $C_{1-6}$ alkyl, and the other is optionally substituted $C_{1-6}$ alkyl. In some embodiments, $R^1$ and $R^2$ are the same optionally substituted $C_{1-6}$ alkyl. In some embodiments, $R^1$ and $R^2$ are the same optionally substituted $C_{1-2}$ alkyl, and $R^1$ and $R^2$ comprise no more than two carbon atoms. In some embodiments, both $R^1$ and $R^1$ are methyl. In some embodiments, both $R^1$ and $R^1$ are ethyl. In some embodiments, both $R^1$ and $R^1$ are isopropyl. In some embodiments, one of $R^1$ and $R^2$ is optionally substituted $C_{1-3}$ linear alkyl, and the other is optionally substituted $C_{3-10}$ cycloalkyl. In some embodiments, one of $R^1$ and $R^2$ is optionally substituted $C_{1-3}$ linear alkyl, and the other is optionally substituted $C_{5-6}$ cycloalkyl. In some embodiments, $R^1$ is methyl. In some embodiments, $R^2$ is cyclopentyl. In some embodiments, $R^2$ is cyclohexyl. In some embodiments, one of $R^1$ and $R^2$ is optionally substituted $C_{1-3}$ linear alkyl, and the other is optionally substituted benzyl. In some embodiments, $R^1$ is methyl and $R^2$ is optionally substituted benzyl. In some embodiments, $R^2$ is benzyl. In some embodiments, $R^2$ is p-$CH_3O$—$C_6H_4$—$CH_2$—. In some embodiments, $R^1$ is selected from methyl, ethyl, cyclohexyl, and benzyl which is optionally substituted at the phenyl. In some embodiments, $R^2$ is selected from methyl, ethyl, cyclohexyl, and benzyl which is optionally substituted at the phenyl. In some embodiments, each of $R^1$ and $R^2$ is independently selected from methyl, ethyl, cyclohexyl, and benzyl which is optionally substituted at the phenyl. In some embodiments, a provided compound is

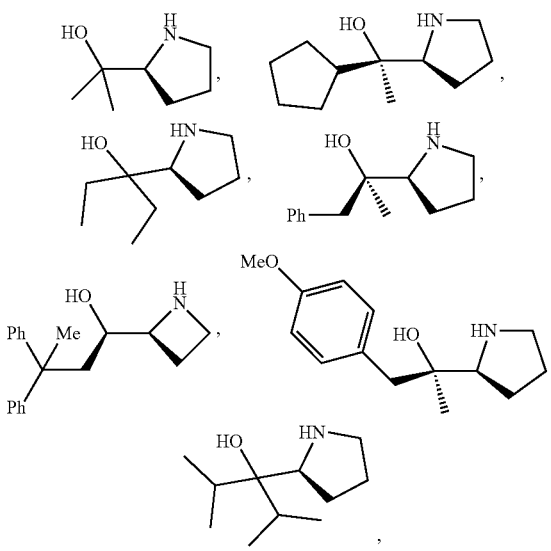

or a salt thereof. In some embodiments, a provided compound is

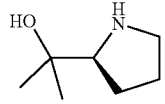

or a salt thereof. In some embodiments, a provided compound is

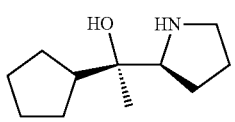

or a salt thereof. In some embodiments, a provided compound is

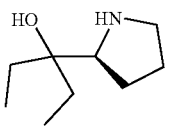

or a salt thereof. In some embodiments, a provided compound is

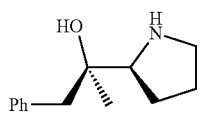

or a salt thereof. In some embodiments, a provided compound is

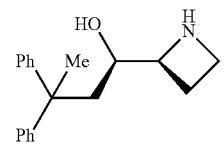 [SMILES: CC(C[C@@H](O)[C@@H]1CCN1)(c1ccccc1)c1ccccc1]

or a salt thereof. In some embodiments, a provided compound is

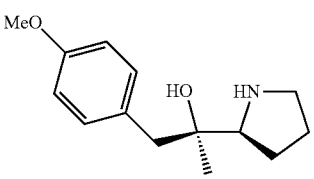 [SMILES: COc1ccc(C[C@@](C)(O)[C@@H]2CCCN2)cc1]

or a salt thereof. In some embodiments, a provided compound is

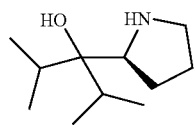

or a salt thereof.

In some embodiments, one of $R^1$ and $R^2$ is optionally substituted $C_{1-6}$ alkyl, and the other is optionally substituted phenyl. In some embodiments, $R^1$ is methyl, and $R^2$ is optionally substituted phenyl. In some embodiments, $R^1$ is methyl, and $R^2$ is phenyl. In some embodiments, $R^1$ is methyl, and $R^2$ is

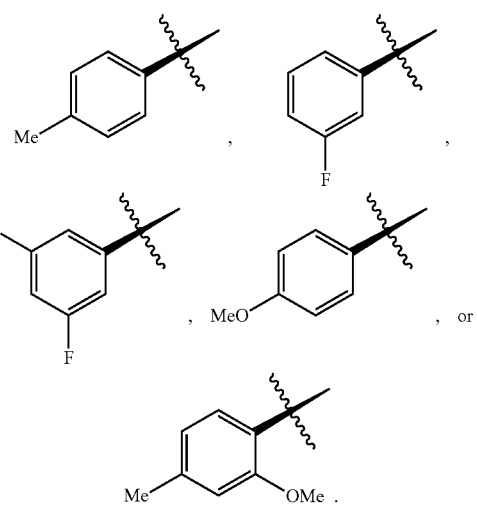

In some embodiments, a provided compound is selected from

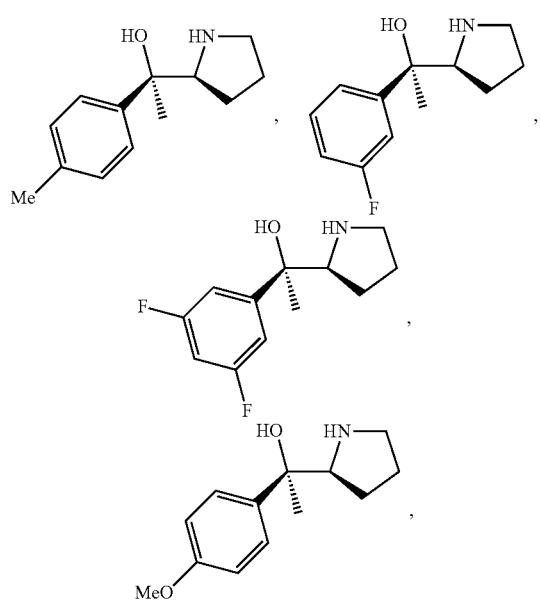

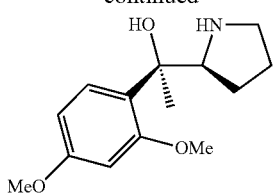

or salts thereof. In some embodiments, a provided compound is

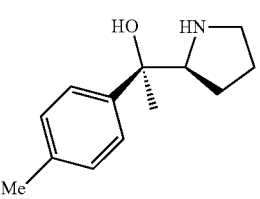

or a salt thereof. In some embodiments, a provided compound is

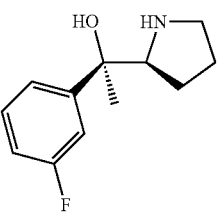

or a salt thereof. In some embodiments, a provided compound is

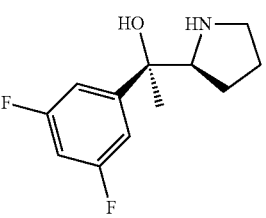 [SMILES: C[C@@](O)(c1cc(F)cc(F)c1)[C@@H]1CCCN1]

or a salt thereof. In some embodiments, a provided compound is

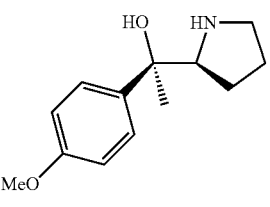 [SMILES: COc1ccc([C@@](C)(O)[C@@H]2CCCN2)cc1]

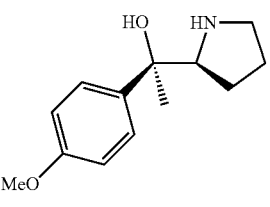 [SMILES: COc1ccc([C@@](C)(O)[C@@H]2CCCN2)cc1]

or a salt thereof. In some embodiments, a provided compound is

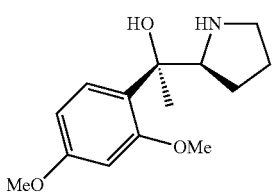 [SMILES: COc1ccc([C@@](C)(O)[C@@H]2CCCN2)c(OC)c1]

or a salt thereof.

In some embodiments, R¹ and R² are independently R, wherein R is an optionally substituted aryl group. In some embodiments, R¹ and R² are independently optionally substituted phenyl. In some embodiments, R¹ and R² are phenyl. In some embodiments, a provided compound is

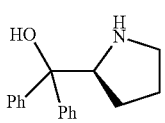

or a salt thereof.

In some embodiments, R¹ and R² are taken together with the carbon atom they are attached on to form an optionally substituted 3-20 membered monocyclic, bicyclic or polycyclic ring having 0-5 heteroatoms. In some embodiments, R¹ and R² are taken together with the carbon atom they are attached on to form an optionally substituted 3-7 membered monocyclic ring having no heteroatoms. In some embodiments, such a formed monocyclic ring is 3-membered; in some embodiments, 4-membered; in some embodiments, 5-membered; in some embodiments, 6-membered; in some embodiments 7-membered; in some embodiments, 8-membered; in some embodiments 9-membered; and in some embodiments 10-membered. In some embodiments, a formed ring is monocyclic. In some embodiments, a formed ring is bicyclic. In some embodiments, a formed ring is polycyclic. In some embodiments, a formed ring is aliphatic. In some embodiments, a formed ring comprises no unsaturation. In some embodiments, a formed ring is saturated, partially unsaturated, and/or partially aromatic, for example, a bicyclic or polycyclic ring comprising fused saturated, partially unsaturated, and/or aromatic moieties. In some embodiments, such a formed ring is substituted. In some embodiments, such a formed ring is not substituted. In some embodiments, the carbon to which R¹ and R² are attached is not chiral. In some embodiments, R¹ and R² are the same, and the carbon they are attached on is not chiral. In some embodiments, the ring formed by R¹ and R² taken together with the carbon atom they are attached on does not introduce asymmetry, and the carbon atom R¹ and R² attached on is not chiral. In some embodiments, R¹ and R² are different, and the carbon they are attached on is chiral. In some embodiments, the ring formed by R¹ and R² taken together with the carbon atom they are attached on introduces asymmetry, and the carbon atom R¹ and R² attached on is not chiral. In some embodiments, a provided compound is selected from

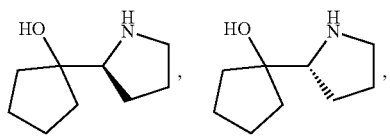

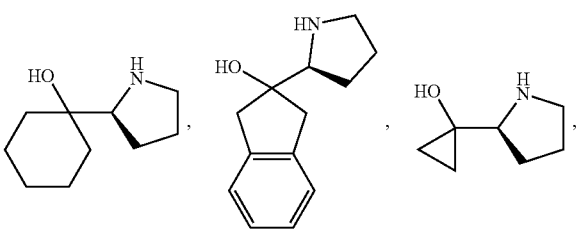

and salts thereof. In some embodiments, a provided compound is selected from

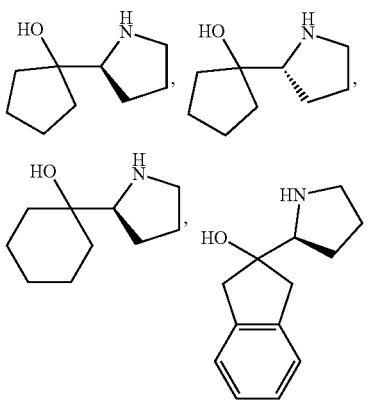

and salts thereof. In some embodiments, a provided compound is

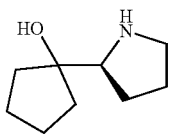

or a salt thereof. In some embodiments, a provided compound is

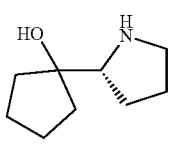

or a salt thereof. In some embodiments, a provided compound is

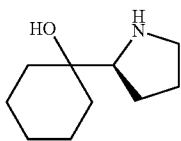 [SMILES: OC1([C@@H]2CCCN2)CCCCC1]

or a salt thereof. In some embodiments, a provided compound is

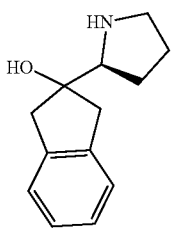 [SMILES: OC1([C@@H]2CCCN2)Cc2ccccc2C1]

or a salt thereof.

In some embodiments, $R^4$ and $R^5$ are taken together with their intervening atoms to form an optionally substituted 3-20 membered monocyclic, bicyclic or polycyclic ring having 1-5 heteroatoms. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, $R^3$ is —H, and $R^4$ and $R^5$ are taken together with their intervening atoms to form an optionally substituted 3-20 membered monocyclic, bicyclic or polycyclic ring having 1-5 heteroatoms. In some embodiments, $R^3$ is —H, and $R^4$ and $R^5$ are taken together with their intervening atoms to form an optionally substituted 3-20 membered monocyclic, bicyclic or polycyclic ring having a nitrogen atom (the one which $R^5$ is on). In some embodiments, $R^3$ is —H, and $R^4$ and $R^5$ are taken together with their intervening atoms to form an optionally substituted 4-7 membered monocyclic ring having a nitrogen atom (the one which $R^5$ is on). In some embodiments, $R^3$ is —H, and $R^4$ and $R^5$ are taken together with their intervening atoms to form an optionally substituted 4-membered monocyclic ring having a nitrogen atom (the one which $R^5$ is on). In some embodiments, $R^3$ is —H, and $R^4$ and $R^5$ are taken together with their intervening atoms to form an optionally substituted 5-membered monocyclic ring having a nitrogen atom (the one which $R^5$ is on). In some embodiments, $R^3$ is —H, and $R^4$ and $R^5$ are taken together with their intervening atoms to form an optionally substituted 6-membered monocyclic ring having a nitrogen atom (the one which $R^5$ is on). In some embodiments, $R^3$ is —H, and $R^4$ and $R^5$ are taken together with their intervening atoms to form an optionally substituted 7-membered monocyclic ring having a nitrogen atom (the one which $R^5$ is on). In some embodiments, $R^3$ is —H, and $R^4$ and $R^5$ are taken together with their intervening atoms to form an optionally substituted 8-membered monocyclic ring having a nitrogen atom (the one which $R^5$ is on). In some embodiments, $R^3$ is —H, and $R^4$ and $R^5$ are taken together with their intervening atoms to form an optionally substituted 9-membered monocyclic ring having a nitrogen atom (the one which $R^5$ is on). In some embodiments, $R^3$ is —H, and $R^4$ and $R^5$ are taken together with their intervening atoms to form an optionally substituted 10-membered monocyclic ring having a nitrogen atom (the one which $R^5$ is on). In some embodiments, a ring formed by $R^4$ and $R^5$ taken together with their intervening atoms is substituted. In some embodiments, a ring formed by $R^4$ and $R^5$ taken together with their intervening atoms is unsubstituted. In some embodiments, a ring formed by $R^4$ and $R^5$ taken together with their intervening atoms is monocyclic. In some embodiments, a ring formed by $R^4$ and $R^5$ taken together with their intervening atoms is bicyclic. In some embodiments, one of $R^1$ and $R^2$, and one of $R^3$ and $R^4$, are taken together with their intervening atoms to form an optionally substituted 3-20 membered monocyclic, bicyclic or polycyclic ring having 0-5 heteroatoms. In some embodiments, a formed ring is a 3-membered ring. In some embodiments, a formed ring is a 4-membered ring. In some embodiments, a formed ring is a 5-membered ring. In some embodiments, a formed ring is a 6-membered ring. In some embodiments, a formed ring is a 7-membered ring. In some embodiments, a formed ring is substituted. In some embodiments, a formed ring is unsubstituted. In some embodiments, a formed ring is monocyclic. In some embodiments, a formed ring is bicyclic. In some embodiments, a formed ring is polycyclic. In some embodiments, a formed ring has no additional heteroatoms in addition to an intervening atom. In some embodiments, a formed ring has additional ring heteroatoms in addition to an intervening atom. Example rings formed are extensively described in the present disclosure. In some embodiments, a provided compound is selected from

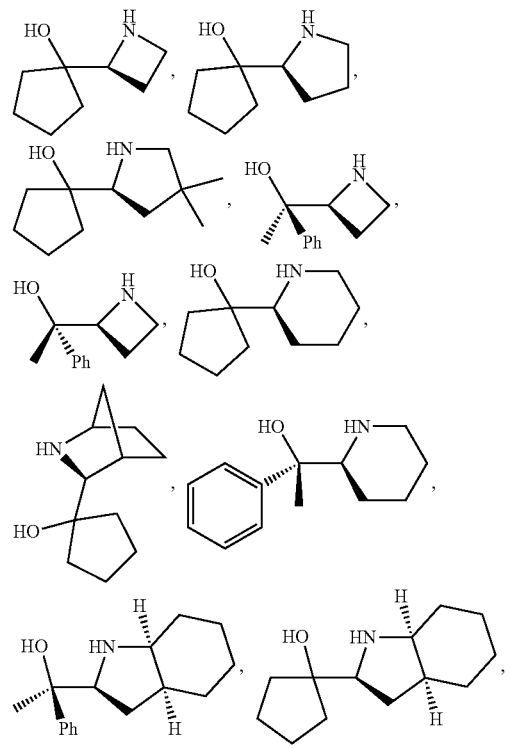

and salts thereof. In some embodiments, a provided compound is selected from

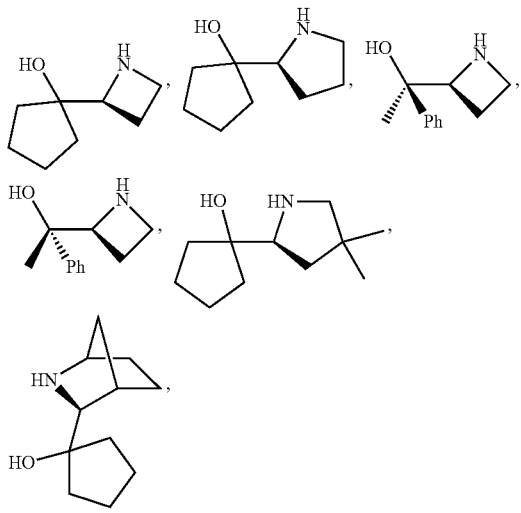

and salts thereof. In some embodiments, a provided compound is

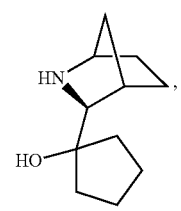

or a salt thereof. In some embodiments, a provided compound is

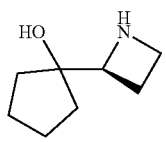

or a salt thereof. In some embodiments, a provided compound is

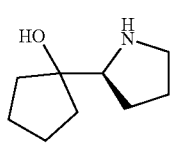

or a salt thereof. In some embodiments, a provided compound is

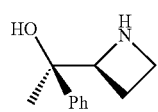

or a salt thereof. In some embodiments, a provided compound is

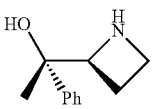

or a salt thereof. In some embodiments, a provided compound is

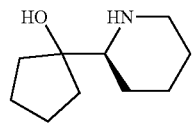 [SMILES: OC1([C@@H]2CCCCN2)CCCC1]

or a salt thereof. In some embodiments, a provided compound is

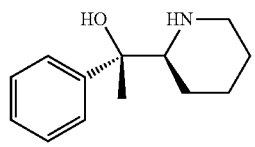

or a salt thereof. In some embodiments, a provided compound is

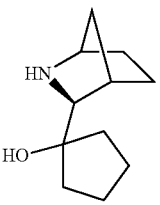

or a salt thereof. In some embodiments, a provided compound is

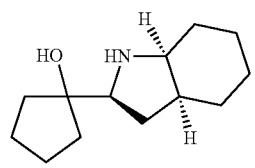 [SMILES: OC1([C@@H]2C[C@@H]3CCCC[C@@H]3N2)CCCC1]

or a salt thereof. In some embodiments, a provided compound is

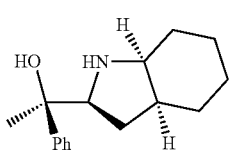 [SMILES: C[C@@](O)(c1ccccc1)[C@@H]1C[C@@H]2CCCC[C@@H]2N1]

a salt thereof.

In some embodiments, one or two of $R^1$ and $R^2$ are taken together with one or more of $R^3$, $R^4$, and $R^5$ and the intervening atoms to form an optionally substituted 3-20 membered monocyclic, bicyclic or polycyclic ring having 0-5 heteroatoms. In some embodiments, one or two of $R^1$ and $R^2$ are taken together with one or two of $R^3$ and $R^4$ and the intervening atoms to form an optionally substituted 3-20 membered monocyclic, bicyclic or polycyclic ring having 0-5 heteroatoms. In some embodiments, one or two of $R^1$ and $R^2$ are taken together with $R^5$ and the intervening atoms to form an optionally substituted 3-20 membered monocyclic, bicyclic or polycyclic ring having 1-5 heteroatoms. In some embodiments, one or two of $R^1$ and $R^2$ are taken together with $R^5$, one or two of $R^3$ and $R^4$, and the intervening atoms to form an optionally substituted 3-20 membered monocyclic, bicyclic or polycyclic ring having 1-5 heteroatoms. In some embodiments, one or two of $R^1$ and $R^2$ are taken together with $R^5$, one or two of $R^3$ and $R^4$, and the intervening atoms to form an optionally substituted 6-20 membered bicyclic or polycyclic ring having 1-5 heteroatoms. In some embodiments, one or two of $R^1$ and $R^2$ are taken together with $R^5$, one or two of $R^3$ and $R^4$, and the intervening atoms to form an optionally substituted 8-20 membered bicyclic or polycyclic ring having 1-5 heteroatoms. In some embodiments, one of $R^1$ and $R^2$ are taken together with $R^5$, one of $R^3$ and $R^4$, and the intervening atoms to form an optionally substituted 8-20 membered bicyclic or polycyclic ring having 1-5 heteroatoms. In some embodiments, one of $R^1$ and $R^2$ are taken together with $R^5$, one of $R^3$ and $R^4$, and the intervening atoms to form an optionally substituted 8-20 membered bicyclic ring having 1-5 heteroatoms. In some embodiments, a formed ring is 8-membered. In some embodiments, a formed ring is 9-membered.

In some embodiments, $R^5$ is taken with one of $R^1$ and $R^2$ and their intervening atoms to form an optionally substituted 3-20 membered monocyclic, bicyclic or polycyclic ring having 1-5 heteroatoms. In some embodiments, $R^5$ is taken with one of $R^3$ and $R^4$ and their intervening atoms to form an optionally substituted 3-20 membered monocyclic, bicyclic or polycyclic ring having 1-5 heteroatoms. Example rings formed are extensively described in the present disclosure. In some embodiments, a formed ring is 3-membered. In some embodiments, a formed ring is 4-membered. In some embodiments, a formed ring is 5-membered. In some embodiments, a formed ring is 6-membered. In some embodiments, $R^5$ is not taken with $R^1$, $R^2$, $R^3$, or $R^4$ to form an optionally substituted ring. In some embodiments, $R^5$ is optionally substituted $C_{1-6}$ aliphatic. In some embodiments, $R^5$ is optionally substituted $C_{1-6}$ alkyl. In some embodiments, $R^5$ is unsubstituted $C_{1-6}$ alkyl. In some embodiments, $R^5$ is methyl. In some embodiments, $R^5$ is ethyl. In some embodiments, $R^5$ is isopropyl.

In some embodiments, a provided compound is

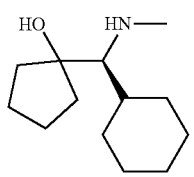

or a salt thereof. In some embodiments, a provided compound is

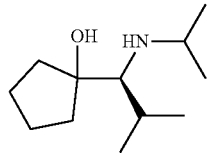

or a salt thereof. In some embodiments, a provided compound is

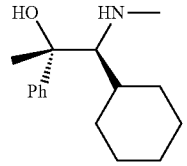 [SMILES: CN[C@@H](C1CCCCC1)[C@@](C)(O)c1ccccc1]

or a salt thereof.

In some embodiments, L is -L'-C($R^3$)($R^4$)—. In some embodiments, a provided compound has the structure of formula I-b:

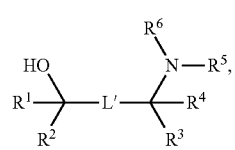

I-b or a salt thereof, wherein each variable is independently as described in the present disclosure. In some embodiments, a compound of formula I has the structure of formula I-b.

In some embodiments, L' is a covalent bond. In some embodiments, L' is —C($R^3$)($R^4$)—. In some embodiments, a provided compound has the structure of formula I-c:

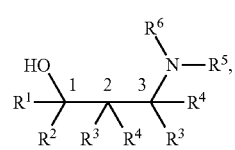

I-c or a salt thereof, wherein each variable is independently as described in the present disclosure. In some embodiments, a compound of formula I has the structure of formula I-c.

In some embodiments, one or $R^3$ and $R^4$ on C2 are taken together with $R^5$ to form with their intervening atoms to form an optionally substituted 3-20 membered monocyclic, bicyclic or polycyclic ring having a nitrogen atom (the one which $R^5$ is on). In some embodiments, one or $R^3$ and $R^4$ on C3 are taken together with $R^5$ to form with their intervening atoms to form an optionally substituted 3-20 membered monocyclic, bicyclic or polycyclic ring having a nitrogen atom (the one which $R^5$ is on). In some embodiments, one of $R^3$ and $R^4$ on C2, and one of $R^3$ and $R^4$ on C3, are taken together with their intervening atoms to form an optionally substituted 3-20 membered monocyclic, bicyclic or polycyclic ring having 0-5 heteroatoms. In some embodiments, $R^3$ and $R^4$ on the same carbon atom are taken together with the carbon atom to form an optionally substituted 3-20 membered monocyclic, bicyclic or polycyclic ring having 0-5 heteroatoms. In some embodiments, $R^3$ and $R^4$ on C2 are taken together with C2 to form an optionally substituted 3-20 membered monocyclic, bicyclic or polycyclic ring having 0-5 heteroatoms. In some embodiments, $R^3$ and $R^4$ on C3 are taken together with C3 to form an optionally substituted 3-20 membered monocyclic, bicyclic or polycyclic ring having 0-5 heteroatoms. Example such ring moieties, e.g., formed by $R^3/R^4$ and $R^5$, by $R^3/R^4$ and $R^3/R^4$, etc., are extensively described in the present disclosure, and can be e.g., 4-membered, 5-membered, 6-membered, 7-membered, monocyclic, bicyclic, polycyclic, substituted, unsubstituted, with additional ring heteroatoms (other than the intervening atom(s)), without additional ring heteroatoms, combinations thereof, etc.

In some embodiments, $R^3$ on C2 is hydrogen. In some embodiments, $R^4$ on C2 is hydrogen. In some embodiments, $R^3$ on C3 is hydrogen. In some embodiments, $R^4$ on C3 is hydrogen. In some embodiments, both $R^3$ and $R^4$ on C2 are hydrogen. In some embodiments, both $R^3$ and $R^4$ on C3 are hydrogen. In some embodiments, both $R^3$ and $R^4$ on C2, and one of $R^3$ and $R^4$ on C3, are hydrogen. In some embodiments, both $R^3$ and $R^4$ on C3, and one of $R^3$ and $R^4$ on C2, are hydrogen.

In some embodiments, a provided compound is

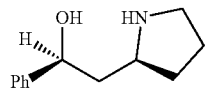

or a salt thereof.

In some embodiments, L is -Cy-. In some embodiments, a provided compound has the structure of formula I-d:

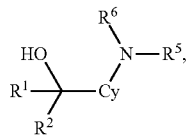

I-d or a salt thereof, wherein each variable is independently as described in the present disclosure. In some embodiments, a compound of formula I has the structure of formula I-d. In some embodiments, -Cy- is 1,2-bivalent. In some embodiments, -Cy- is optionally substituted cycloalkylene. In some embodiments, -Cy- is optionally substituted

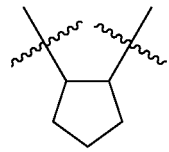

In some embodiments, -Cy- is optionally substituted

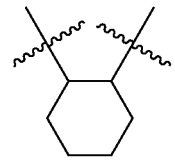

In some embodiments, one of $R^1$ and $R^2$, and one of $R^3$ and $R^4$, are R and are taken together with their intervening atoms to form an optionally substituted 3-20 membered ring having 1-10 heteroatoms as described in the present disclosure, e.g., Ring A as described herein. In some embodiments, a provided compound has the structure of formula I-e:

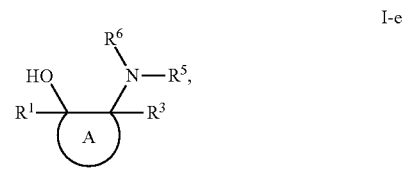

I-e or a salt thereof, wherein each variable is independently as described in the present disclosure. In some embodiments, a compound of formula I has the structure of formula I-e.

In some embodiments, one of $R^1$ and $R^2$, and $R^4$ are taken together with their intervening atoms to form an optionally substituted 3-20 membered ring having 1-5 heteroatoms. In some embodiments, $R^3$ is —H, one of $R^1$ and $R^2$, and $R^4$ are taken together with their intervening atoms to form an optionally substituted 3-20 membered ring having 1-5 heteroatoms. In some embodiments, $R^2$ and $R^4$ are taken together with their intervening atoms to form an optionally substituted ring (e.g., formula I-e). In some embodiments, a formed ring, e.g., Ring A in formula I-e, is 3, 4, 5, 6, 7, 8, 9, or 10-membered. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, a formed ring is monocyclic. In some embodiments, a formed ring is bicyclic. In some embodiments, a formed ring is polycyclic. In some embodiments, a formed ring is saturated. In some embodiments, a formed ring is partially unsaturated. In some embodiments, a formed ring has no heteroatoms. In some embodiments, a formed ring is an optionally substituted 3-membered saturated aliphatic ring. In some embodiments, a formed ring is an optionally substituted 4-membered saturated aliphatic ring. In some embodiments, a formed ring is an optionally substituted 5-membered saturated aliphatic ring. In some embodiments, a formed ring is an optionally substituted 6-membered saturated aliphatic ring. In some embodiments, a formed ring is an optionally substituted 7-membered saturated aliphatic ring. In some embodiments, a formed ring is an optionally substituted 8-membered saturated aliphatic ring. In some embodiments, a formed ring is an optionally substituted 9-membered saturated aliphatic ring. In some embodiments, a formed ring is an optionally substituted 10-membered saturated aliphatic ring. In some embodiments, $R^1$ is not —H. In some embodiments, $R^1$ is optionally substituted $C_{1-6}$ aliphatic. In some embodiments, $R^1$ is —CH=CH$_2$.

In some embodiments, $R^3$ is —H, $R^1$ is optionally substituted $C_{1-6}$ aliphatic or phenyl, $R^5$ is optionally substituted $C_{1-6}$ aliphatic, and $R^6$ is —H. In some embodiments, $R^3$ is —H, $R^1$ and $R^5$ are taken together with their intervening atoms to form an optionally substituted ring, and $R^6$ is —H. In some embodiments, $R^3$ is —H, $R^1$ and $R^5$ are taken together with their intervening atoms to form an optionally substituted 5- or 6-membered ring, and $R^6$ is —H. In some embodiments, $R^3$ is —H, $R^1$ and $R^5$ are taken together with their intervening atoms to form an optionally substituted 5-membered saturated ring having no heteroatom in addition to the nitrogen to which $R^5$ is attached, and $R^6$ is —H. In some embodiments, $R^3$ is —H, $R^1$ and $R^5$ are taken together with their intervening atoms to form an optionally substituted 6-membered saturated ring having no heteroatom in addition to the nitrogen to which $R^5$ is attached, and $R^6$ is —H. In some embodiments, a ring formed by $R^1$ and $R^5$ taken together are unsubstituted.

In some embodiments, —OH and —N($R^5$)($R^6$) are trans. In some embodiments, —OH and —N($R^5$)($R^6$) are cis. In some embodiments, the carbon to which $R^1$ and —OH are attached is R. In some embodiments, the carbon to which $R^1$ and —OH are attached is S. In some embodiments, $R^1$ is hydrogen. In some embodiments, $R^1$ is not hydrogen. In some embodiments, $R^1$ is optionally substituted $C_{1-6}$ aliphatic or phenyl. In some embodiments, $R^1$ is methyl. In some embodiments, $R^1$ is phenyl. In some embodiments, $R^3$ is hydrogen. In some embodiments, $R^5$ is hydrogen. In some embodiments, $R^5$ is not hydrogen. In some embodiments, $R^5$ is optionally substituted $C_{1-6}$ aliphatic or phenyl. In some embodiments, $R^5$ is methyl. In some embodiments, $R^5$ is phenyl. In some embodiments, $R^6$ is hydrogen. In some embodiments, $R^6$ is not hydrogen. In some embodiments, as demonstrated by certain example data, compounds with trans —OH and —N($R^5$)($R^6$) can provide high yields and/or diastereoselectivity. In some embodiments, as demonstrated by certain example data, compounds with trans —OH and —N($R^5$)($R^6$) can provide both high yields and diastereoselectivity.

In some embodiments, a provided compound, e.g., a compound of formula I-e, is selected from

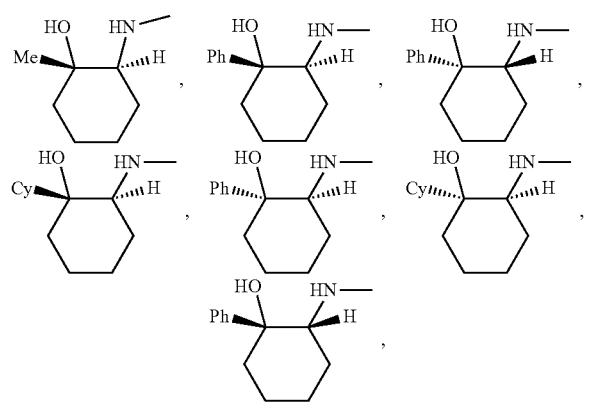

and salts thereof. In some embodiments, a provided compound is

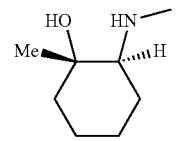

or a salt there of. In some embodiments, a provided compound is

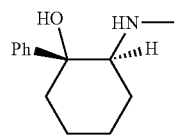

or a salt there of. In some embodiments, a provided compound is

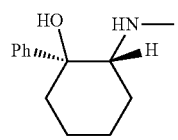

or a salt there of. In some embodiments, a provided compound is

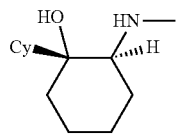

or a salt there of. In some embodiments, a provided compound is

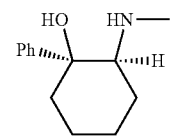

or a salt there of. In some embodiments, a provided compound is

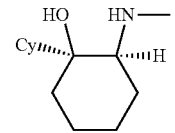

or a salt there of. In some embodiments, a provided compound is

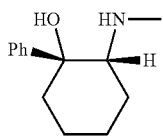

or a salt there of. In some embodiments, a provided compound is selected from

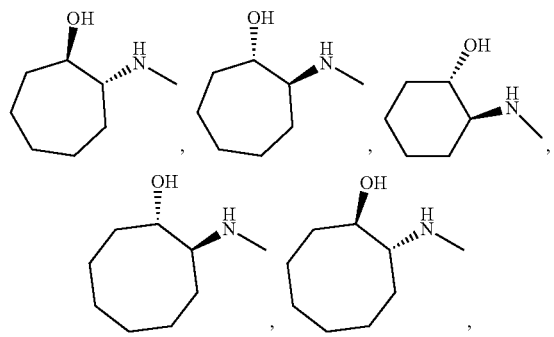

or salts thereof. In some embodiments, a provided compound is

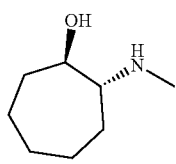

or a salt thereof. In some embodiments, a provided compound is

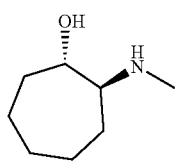

or a salt thereof. In some embodiments, a provided compound is

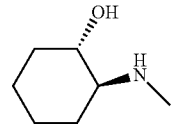

or a salt thereof. In some embodiments, a provided compound is

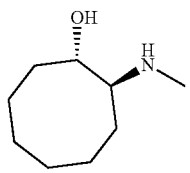

or a salt thereof. In some embodiments, a provided compound is

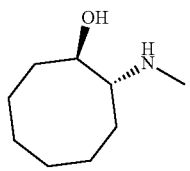

or a salt thereof. In some embodiments, a provided compound is

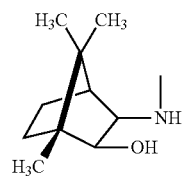

or a salt thereof. In some embodiments, a provided compound is

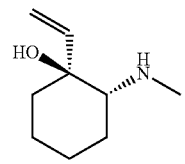

or a salt thereof.

In some embodiments, $R^1$ or $R^2$ are taken together with one of $R^5$ and $R^6$ (e.g., in formula I-d or I-e) and their intervening atoms to form an optionally substituted ring as described in the present disclosure. In some embodiments, a formed ring is monocyclic. In some embodiments, a formed ring is bicyclic. In some embodiments, a formed ring is polycyclic. In some embodiments, a formed ring is saturated. In some embodiments, a formed ring is partially unsaturated. In some embodiments, a formed ring is 3-10 membered. In some embodiments, a formed ring is 3, 4, 5, 6, or 7-membered. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring has 0-3 heteroatoms in addition to the nitrogen atom to which $R^5$ and $R^6$ is bonded. In some embodiments, a formed ring is monocyclic, 5-membered, saturated, and has no additional heteroatoms in addition to the nitrogen atom to which $R^5$ and $R^6$ is bonded. In some embodiments, a formed ring is monocyclic, 6-membered, saturated, and has no additional heteroatoms in addition to the nitrogen atom to which $R^5$ and $R^6$ is bonded. In some embodiments, a provided compound is

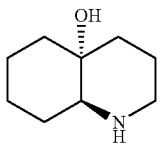 [SMILES: O[C@@]12CCCC[C@@H]1NCCC2]

or a salt thereof. In some embodiments, a provided compound is

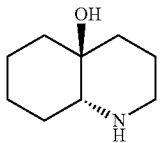

or a salt thereof.

In some embodiments, a provided compound has the structure of formula II:

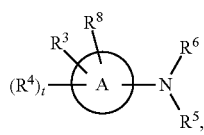

or a salt thereof, wherein:

Ring A is an optionally substituted 3-20 membered monocyclic, bicyclic or polycyclic ring having 0-10 heteroatoms independently selected from oxygen, nitrogen, sulfur, phosphorus and silicon;

each of $R^3$, $R^4$, and $R^5$ is independently —H, -$L^s$-R, halogen, —CN, —NO$_2$, -$L^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

t is 0-20;

$R^6$ is R';

$R^8$ is -L-$R^7$, -L-C($R^1$)($R^2$)—$R^7$, or -$L^s$-$R^7$;

$R^7$ is —OH or SH;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)$_3$]—;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, a provided compound has the structure of formula II-a:

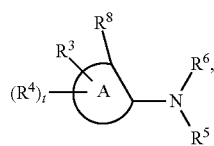

II-a or a salt thereof, wherein each variable is independently as described in the present disclosure. In some embodiments, a compound of formula II has the structure of formula II-a.

In some embodiments, a provided compound of structure II-a, has the structure of formula II-b:

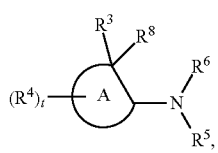

II-b or a salt thereof, wherein each variable is independently as described in the present disclosure. In some embodiments, a compound of formula II-a has the structure of formula II-b.

In some embodiments, a provided compound of structure II-a, has the structure of formula II-c:

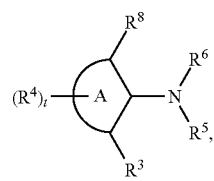

II-c or a salt thereof, wherein each variable is independently as described in the present disclosure. In some embodiments, a compound of formula II-a has the structure of formula II-c.

In some embodiments, $R^8$ is —OH. In some embodiments, $R^6$ is —H. In some embodiments, $R^5$ is optionally substituted alkyl. In some embodiments, $R^5$ is methyl. In some embodiments, t is 0. In some embodiments, $R^3$ is optionally substituted alkyl. In some embodiments, $R^3$ is methyl. In some embodiments, $R^3$ is optionally substituted phenyl. In some embodiments, $R^3$ is phenyl. In some embodiments, $R^3$ is optionally substituted $C_{3-10}$ cycloalkyl. In some embodiments, $R^3$ is optionally substituted cyclohexyl. In some embodiments, $R^3$ is cyclohexyl.

In some embodiments, Ring A is an optionally substituted 3-20 membered monocyclic, bicyclic or polycyclic ring having 0-10 heteroatoms independently selected from oxygen, nitrogen, sulfur, phosphorus and silicon. In some embodiments, Ring A is or comprises at least one monocyclic saturated or partially unsaturated monocyclic ring moiety, optionally as part of a bicyclic or polycyclic system. In some embodiments, Ring A is monocyclic. In some embodiments, Ring A is bicyclic or polycyclic comprising at least one monocyclic saturated or partially unsaturated monocyclic ring moiety, and optionally one or more aromatic monocyclic moieties. In some embodiments, Ring A is or comprises at least one saturated monocyclic ring moiety. In some embodiments, $R^8$ is connected to a $sp^3$ ring atom of Ring A. In some embodiments, $R^8$ is connected to a $sp^3$ carbon ring atom of Ring A. In some embodiments, $R^3$ is connected to a $sp^3$ ring atom of Ring A. In some embodiments, $R^3$ is connected to a $sp^3$ carbon ring atom of Ring A. In some embodiments, —N($R^5$)($R^6$) is connected to a $sp^3$ ring atom of Ring A. In some embodiments, —N($R^5$)($R^6$) is connected to a $sp^3$ carbon ring atom of Ring A.

In some embodiments, Ring A is optionally substituted $C_{3-10}$ cycloalkyl. In some embodiments, Ring A is optionally substituted cyclohexyl. In some embodiments, Ring A is cyclohexyl. In some embodiments, $R^8$ and —N($R^5$)($R^6$) are cis. In some embodiments, $R^8$ and —N($R^5$)($R^6$) are trans. In some embodiments, a provided compound of formula II is selected from

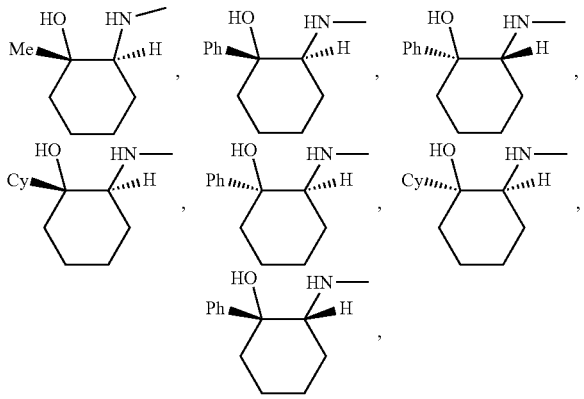

and salts thereof. In some embodiments, a provided compound is

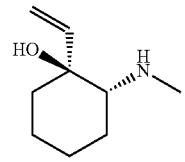

or a salt thereof.

In some embodiments, a provided compound is

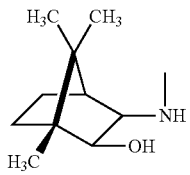

or a salt thereof.

In some embodiments, one of $R^3$ and $R^8$ and one of $R^5$ and $R^6$ are taken together with their intervening atoms to form an optionally substituted ring as described in the present disclosure. For example, in some embodiments, a formed ring is monocyclic. In some embodiments, a formed ring is bicyclic. In some embodiments, a formed ring is polycyclic. In some embodiments, a formed ring is saturated. In some embodiments, a formed ring is partially unsaturated. In some embodiments, a formed ring is 3-10 membered. In some embodiments, a formed ring is 3, 4, 5, 6, or 7-membered. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring has 0-3 heteroatoms in addition to the nitrogen atom to which $R^5$ and $R^6$ is bonded. In some embodiments, a formed ring is monocyclic, 5-membered, saturated, and has no additional heteroatoms in addition to the nitrogen atom to which $R^5$ and $R^6$ is bonded. In some embodiments, a formed ring is monocyclic, 6-membered, saturated, and has no additional heteroatoms in addition to the nitrogen atom to which $R^5$ and $R^6$ is bonded. In some embodiments, one of $R^3$ and $R^8$ and one of $R^5$ and $R^6$ are taken together with their intervening atoms to form an optionally substituted ring as described in the present disclosure, and the other of $R^3$ and $R^8$ is —OH. In some embodiments, a provided compound is a compound of II-b or a salt thereof. In some embodiments, a provided compound is a compound of II-c or a salt thereof. In some embodiments, $R^3$ and $R^5$ are R, and are taken together to form an optionally substituted ring as described in the present disclosure. In some embodiments, a provided compound of formula II is selected from

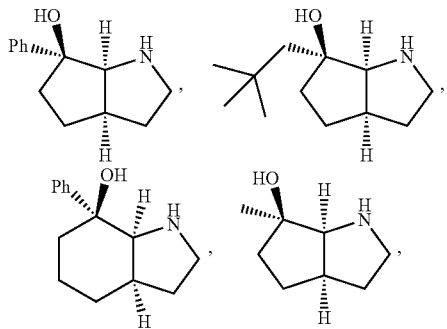

and salts thereof. In some embodiments, a provided compound of formula II (e.g., II-b) is selected from

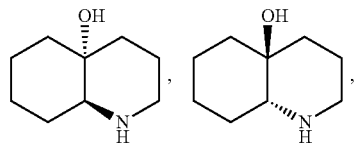

and salts thereof.

In some embodiments, a provided compound, e.g., a compound of formula I, has the structure of formula III:

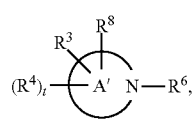

III or a salt thereof, wherein:

Ring A' is an optionally substituted 3-20 membered monocyclic, bicyclic or polycyclic ring having 1-10 heteroatoms independently selected from oxygen, nitrogen, sulfur, phosphorus and silicon, wherein Ring A' comprises a —N($R^6$)— moiety;

each of $R^3$ and $R^4$ is independently —H, -$L^s$-R, halogen, —CN, —NO$_2$, -$L^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

t is 0-20;

$R^6$ is R';

$R^8$ is -L-$R^7$, -L-C($R^1$)($R^2$)—$R^7$, or -$L^s$-$R^7$;

$R^7$ is —OH or SH;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)$_3$]—, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, a provided compound has the structure of formula III-a:

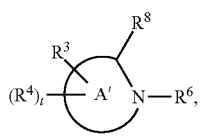

III-a or a salt thereof, wherein each variable is independently as described in the present disclosure. In some embodiments, a compound of formula III has the structure of formula III-a.

In some embodiments, a provided compound has the structure of formula III-b:

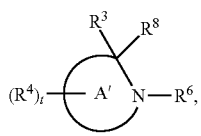

III-b or a salt thereof, wherein each variable is independently as described in the present disclosure. In some embodiments, a compound of formula III-a has the structure of formula III-b.

In some embodiments, $R^8$ is bonded to a carbon atom ($C^2$) next to the nitrogen atom in —$N(R^6)$—($N^1$) (e.g., formula III-a, formula III-b, etc.). In some embodiments, $R^8$ is bonded to a carbon atom next to $C^2$ ($C^3$). In some embodiments, $R^8$ is bonded to a carbon atom next to $C^3$ that is not $C^2$ ($C^4$). In some embodiments, $R^8$ is bonded to a carbon atom next to $C^4$ which is not $C^3$ ($C^5$). In some embodiments, $R^8$ is bonded to a carbon atom next to $C^5$ which is not $C^4$ ($C^6$).

In some embodiments, $R^8$ is —OH. In some embodiments, $R^6$ is —H. In some embodiments, $R^5$ is optionally substituted alkyl. In some embodiments, $R^5$ is methyl. In some embodiments, t is 0. In some embodiments, $R^3$ is optionally substituted alkyl. In some embodiments, $R^3$ is methyl. In some embodiments, $R^3$ is optionally substituted phenyl. In some embodiments, $R^3$ is phenyl. In some embodiments, $R^3$ is optionally substituted $C_{3-10}$ cycloalkyl. In some embodiments, $R^3$ is optionally substituted cyclohexyl. In some embodiments, $R^3$ is cyclohexyl.

In some embodiments, Ring A' is an optionally substituted 3-20 membered monocyclic, bicyclic or polycyclic ring having 1-5 heteroatoms independently selected from oxygen, nitrogen, sulfur, phosphorus and silicon, wherein Ring A' comprises a —$N(R^6)$— moiety. In some embodiments, Ring A' is Ring A as described in the present disclosure, wherein Ring A comprises a nitrogen ring atom. In some embodiments, Ring A' is or comprises at least one monocyclic saturated or partially unsaturated monocyclic ring moiety, optionally as part of a bicyclic or polycyclic system. In some embodiments, Ring A' is monocyclic. In some embodiments, Ring A' is bicyclic or polycyclic comprising at least one monocyclic saturated or partially unsaturated monocyclic ring moiety, and optionally one or more aromatic monocyclic moieties. In some embodiments, Ring A' is or comprises at least one saturated monocyclic ring moiety. In some embodiments, $R^8$ is connected to a sp$^3$ ring atom of Ring A'. In some embodiments, $R^8$ is connected to a sp$^3$ carbon ring atom of Ring A'. In some embodiments, $R^3$ is connected to a sp$^3$ ring atom of Ring A'. In some embodiments, $R^3$ is connected to a sp$^3$ carbon ring atom of Ring A'. In some embodiments, the nitrogen to which $R^6$ is attached is sp$^3$.

In some embodiments, a provided compound of formula III is selected from

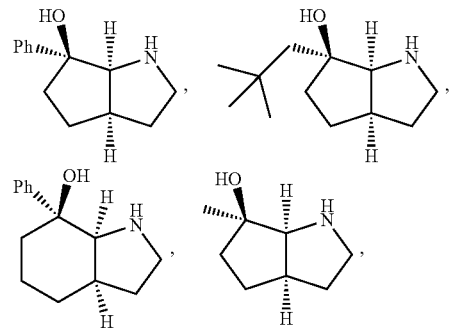

and salts thereof. In some embodiments, In some embodiments, a provided compound of formula III is selected from compounds listed in Table 4 below and salts thereof.

TABLE 1

Example compounds.

| Compound No. | Structure |
|---|---|
| WV-CA-001 | ![structure] |
| WV-CA-002 | ![structure] |
| WV-CA-002-S | ![structure] |

TABLE 1-continued

Example compounds.

| Compound No. | Structure |
|---|---|
| WV-CA-003 | 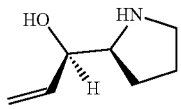 |
| WV-CA-004 | 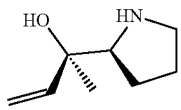 |
| WV-CA-005-D | 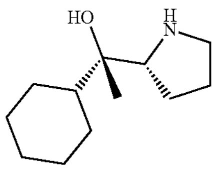 |
| WV-CA-005-L | 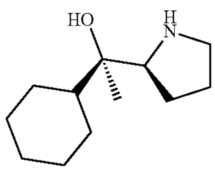 |
| WV-CA-006 | 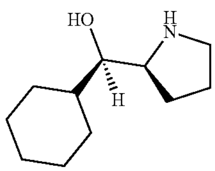 [SMILES: O[C@H](C1CCCCC1)[C@@H]1CCCN1] |
| WV-CA-011 | 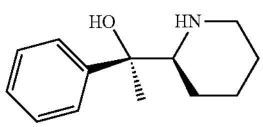 |
| WV-CA-011-S | 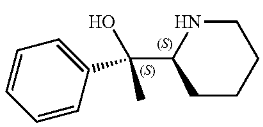 |
| WV-CA-012 | 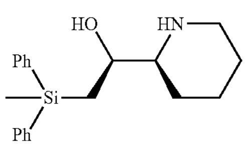 [SMILES: C[Si](C[C@@H](O)[C@@H]1CCCCN1)(c1ccccc1)c1ccccc1] |
| WV-CA-012-R | 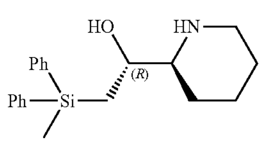 |
| WV-CA-013 | 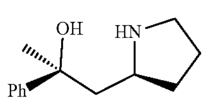 |
| WV-CA-014 | 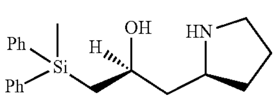 [SMILES: C[Si](C[C@@H](O)C[C@@H]1CCCN1)(c1ccccc1)c1ccccc1] |
| WV-CA-014-R | 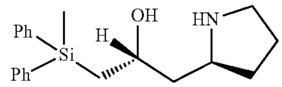 [SMILES: C[Si](C[C@H](O)C[C@@H]1CCCN1)(c1ccccc1)c1ccccc1] |
| WV-CA-015 | 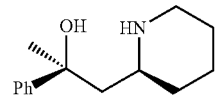 [SMILES: C[C@](O)(C[C@@H]1CCCCN1)c1ccccc1] |
| WV-CA-016 | 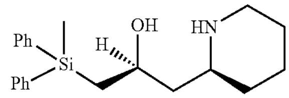 [SMILES: C[Si](C[C@@H](O)C[C@@H]1CCCCN1)(c1ccccc1)c1ccccc1] |
| WV-CA-021 | 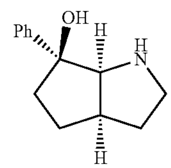 [SMILES: O[C@]1(c2ccccc2)CC[C@@H]2CCN[C@@H]21] |
| WV-CA-022 | 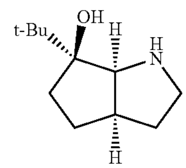 [SMILES: CC(C)(C)[C@@]1(O)CC[C@@H]2CCN[C@@H]21] |
| WV-CA-023 | 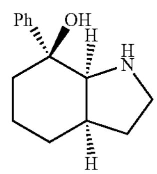 [SMILES: O[C@]1(c2ccccc2)CCC[C@@H]2CCN[C@@H]21] |
| WV-CA-040 | 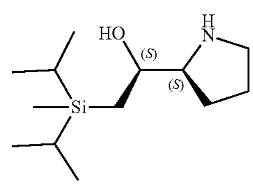 |
| WV-CA-041-D | 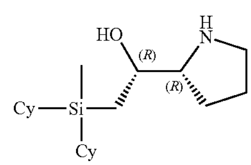 |
| WV-CA-041-L | 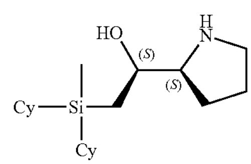 |
| WV-CA-042 | 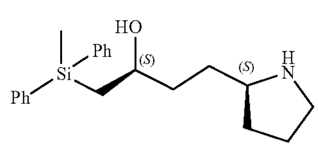 |

TABLE 1-continued

Example compounds.

| Compound No. | Structure |
|---|---|
| WV-CA-043 | 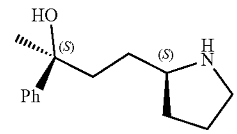 |
| WV-CA-044-R + S | 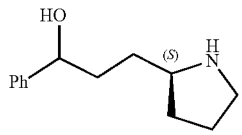 |
| WV-CA-045 | 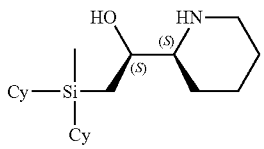 |
| WV-CA-046 | 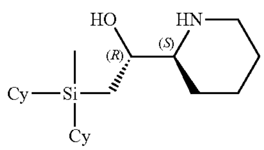 |
| WV-CA-048 | 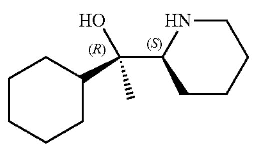 |
| WV-CA-049 | 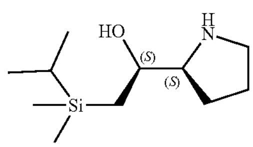 |
| WV-CA-050 | 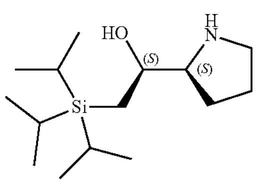 |
| WV-CA-051 | 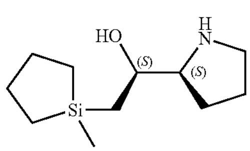 |
| WV-CA-052 | 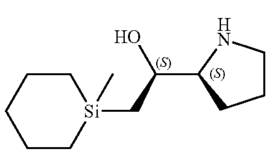 |
| WV-CA-053 | 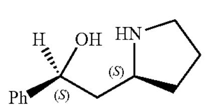 |
| WV-CA-054 | 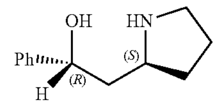 |
| WV-CA-056 | 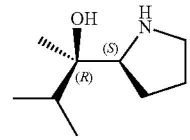 |
| WV-CA-056-S | 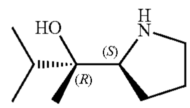 |
| WV-CA-057 | 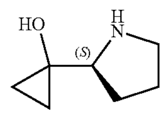 |
| WV-CA-058 | 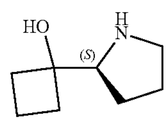 |
| WV-CA-059 | 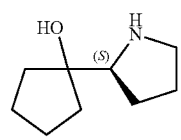 |
| WV-CA-059-R | 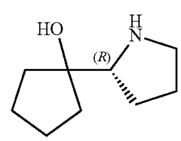 |
| WV-CA-060 | 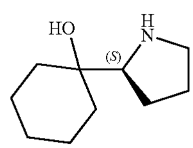 |
| WV-CA-062 | 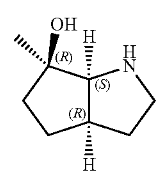 |
| WV-CA-063-S | 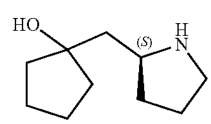 |
| WV-CA-064-S | 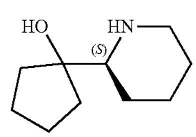 |

TABLE 1-continued

Example compounds.

| Compound No. | Structure |
|---|---|
| WV-CA-065-S | 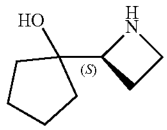 |
| WV-CA-067 | 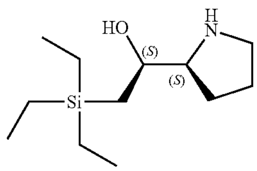 |
| WV-CA-068-S | 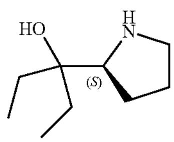 |
| WV-CA-069-S | 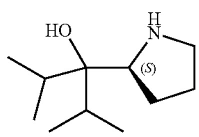 |
| WV-CA-072-S | 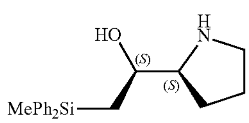 |
| WV-CA-073-S | 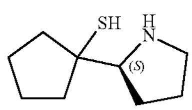 |
| WV-CA-074-M | 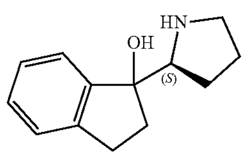 |
| WV-CA-074-R | 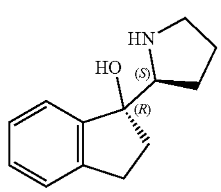 |
| WV-CA-074-S | 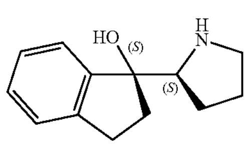 |
| WV-CA-076 | |
| WV-CA-077 | |
| WV-CA-078 | |
| WV-CA-079 | |
| WV-CA-080 | |
| WV-CA-081 | |
| WV-CA-082 | |
| WV-CA-083 | |
| WV-CA-084 | |

TABLE 1-continued

Example compounds.

| Compound No. | Structure |
|---|---|
| WV-CA-088 | 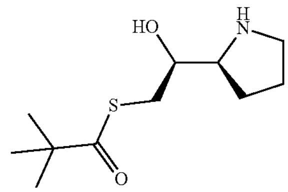 |
| WV-CA-089 | 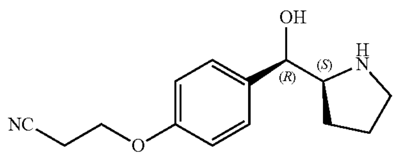 |
| WV-CA-090 | 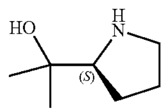 |
| WV-CA-091 | 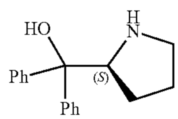 |
| WV-CA-093 | 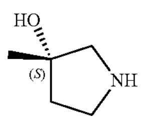 |
| WV-CA-094 | 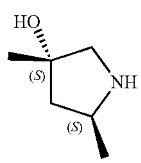 |
| WV-CA-096 | 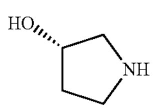 |
| WV-CA-097 | 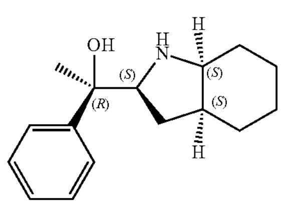 |
| WV-CA-098 | 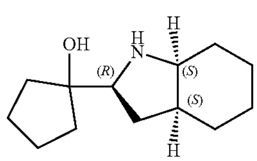 |
| WV-CA-099 | 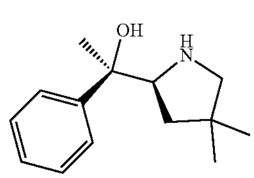 [SMILES: CC1(C)CN[C@H]([C@](C)(O)c2ccccc2)C1] |
| WV-CA-100-D | 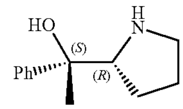 |
| WV-CA-100-L | 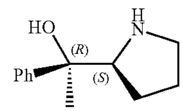 |
| WV-CA-101 | 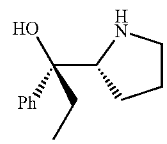 |
| WV-CA-102 | 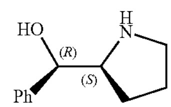 |
| WV-CA-103 | 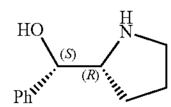 |
| WV-CA-104 | 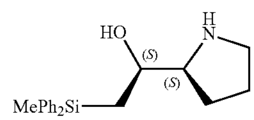 |
| WV-CA-105 | 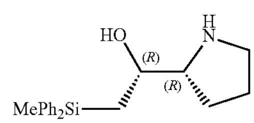 |
| WV-CA-106 | 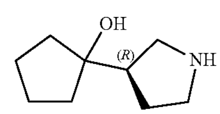 |
| WV-CA-107 | 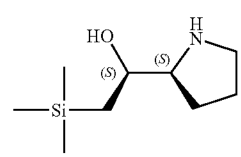 |
| WV-CA-108 | 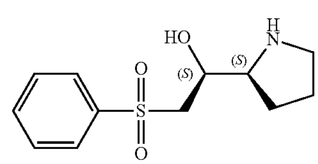 |
| WV-CA-109 | 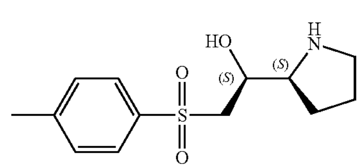 |

TABLE 1-continued

Example compounds.

| Compound No. | Structure |
|---|---|
| WV-CA-109a | [structure] |
| WV-CA-110 | [structure] |
| WV-CA-111 | [structure] |
| WV-CA-112 | [structure] |
| WV-CA-113 | [structure] |
| WV-CA-116 | [structure] |
| WV-CA-117 | [structure] |
| WV-CA-118 | [structure] |
| WV-CA-118-S | [structure] |
| WV-CA-119 | [structure] |
| WV-CA-120 | [structure] |
| WV-CA-121 | [structure] |
| WV-CA-122 | [structure] |
| WV-CA-123 | [structure] |
| WV-CA-124 | [structure] |
| WV-CA-125 | [structure] |
| WV-CA-126 | [structure] |
| WV-CA-127 | [structure] |
| WV-CA-128 | [structure] |

TABLE 1-continued

Example compounds.

| Compound No. | Structure |
|---|---|
| WV-CA-129 | (structure) |
| WV-CA-130 | (structure) |
| WV-CA-131 | (structure) |
| WV-CA-132 | (structure) |
| WV-CA-133 | (structure) |
| WV-CA-134 | (structure) |
| WV-CA-145 | (structure) |
| WV-CA-146 | (structure) |
| WV-CA-147 | (structure) |
| WV-CA-148 | (structure) |
| WV-CA-149 | (structure) |
| WV-CA-150 | (structure) |
| WV-CA-151 | (structure) |
| WV-CA-152 | (structure) |
| WV-CA-153 | (structure) |
| WV-CA-154 | (structure) |

TABLE 1-continued
Example compounds.
| Compound No. | Structure |
|---|---|
| WV-CA-155 | 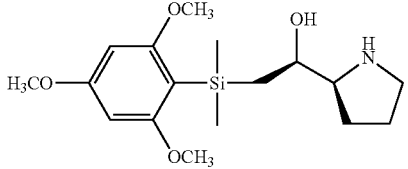 [SMILES: COc1cc(OC)c([Si](C)(C)C[C@@H](O)[C@@H]2CCCN2)c(OC)c1] |
| WV-CA-156 | 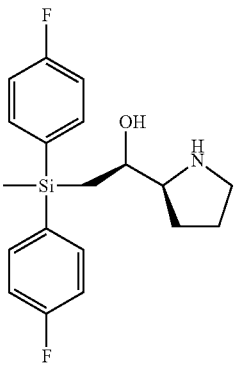 [SMILES: C[Si](C[C@@H](O)[C@@H]1CCCN1)(c1ccc(F)cc1)c1ccc(F)cc1] |
| WV-CA-157 | 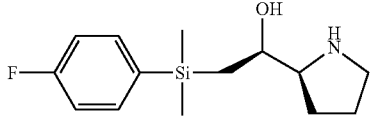 |
| WV-CA-163 |  |
| WV-CA-164 | 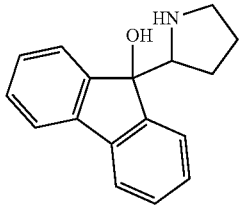 [SMILES: OC1(C2CCCN2)c2ccccc2-c2ccccc21] |
| WV-CA-165 | 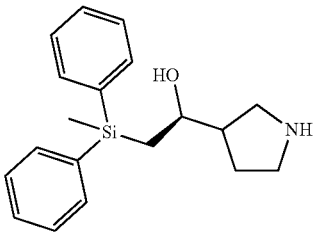 [SMILES: C[Si](C[C@@H](O)C1CCNC1)(c1ccccc1)c1ccccc1] |
| WV-CA-423 | 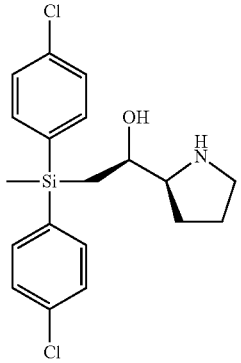 [SMILES: C[Si](C[C@@H](O)[C@@H]1CCCN1)(c1ccc(Cl)cc1)c1ccc(Cl)cc1] |
| WV-CA-424 | 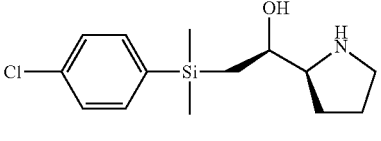 [SMILES: C[Si](C)(C[C@@H](O)[C@@H]1CCCN1)c1ccc(Cl)cc1] |
| WV-CA-165 | 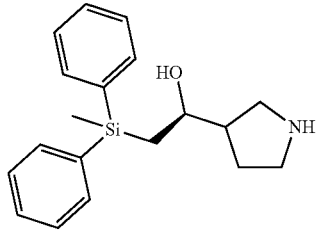 [SMILES: C[Si](C[C@@H](O)C1CCNC1)(c1ccccc1)c1ccccc1] |
| WV-CA-166 | 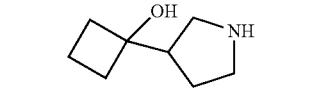 |
| WV-CA-167 | 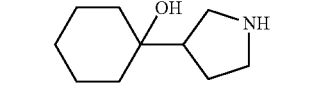 [SMILES: OC1(C2CCNC2)CCCCC1] |
| WV-CA-172 | 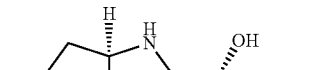 |
| WV-CA-173 | 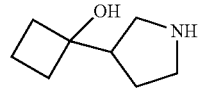 |
| WV-CA-174 | 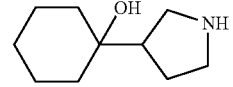 |
| WV-CA-175 | 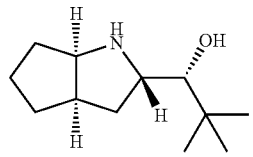 |

TABLE 1-continued

Example compounds.

| Compound No. | Structure |
|---|---|
| WV-CA-176 | (structure) |
| WV-CA-180 | (structure) |
| WV-CA-181 | (structure) |
| WV-CA-182 | (structure) |
| WV-CA-183 | (structure) |
| WV-CA-188 | (structure) |
| WV-CA-201 | (structure) |
| WV-CA-202 | (structure) |
| WV-CA-203 | (structure) |
| WV-CA-204 | (structure) |
| WV-CA-204a | (structure) |
| WV-CA-206 | (structure) |
| WV-CA-209 | (structure) |
| WV-CA-225 | (structure) |
| WV-CA-226 | (structure) |
| WV-CA-227 | (structure) |
| WV-CA-229 | (structure) |
| WV-CA-231 | (structure) |

TABLE 1-continued

Example compounds.

| Compound No. | Structure |
|---|---|
| WV-CA-233 | (structure) |
| WV-CA-234 | (structure) |
| WV-CA-301 | (structure) |
| WV-CA-304 | (structure) |
| WV-CA-306 | (structure) |
| WV-CA-307 | (structure) |
| WV-CA-308 | (structure) |
| WV-CA-309 | (structure) |
| WV-CA-310 | (structure) |
| WV-CA-311 | (structure) |
| WV-CA-312 | (structure) |
| WV-CA-313 | (structure) |
| WV-CA-314 | (structure) |
| WV-CA-315 | (structure) |
| WV-CA-316 | (structure) |
| WV-CA-317 | (structure) |
| WV-CA-318 | (structure) |
| WV-CA-319 | (structure) |
| WV-CA-320 | (structure) |

TABLE 1-continued

Example compounds.

| Compound No. | Structure |
|---|---|
| WV-CA-321 | 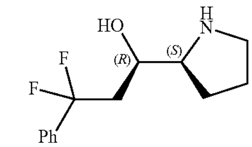 |
| WV-CA-322 | 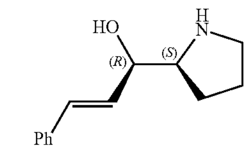 |
| WV-CA-323 | 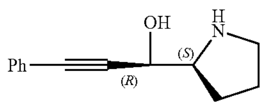 |
| WV-CA-324 | 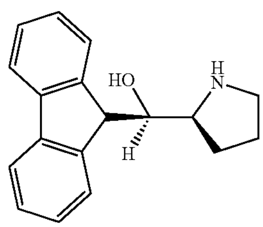 [SMILES: O[C@H](C1c2ccccc2-c2ccccc21)[C@@H]1CCCN1] |
| WV-CA-325 | 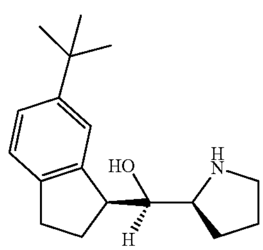 [SMILES: CC(C)(C)c1ccc2c(c1)[C@@H]([C@@H](O)[C@@H]1CCCN1)CC2] |
| WV-CA-326 | 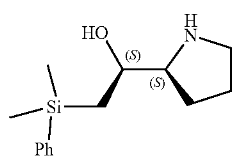 |
| WV-CA-327 | 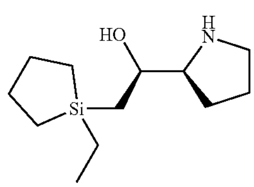 |
| WV-CA-328 | 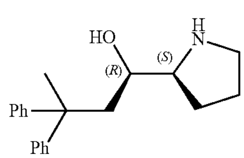 |
| WV-CA-329 | 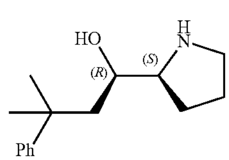 |
| WV-CA-330 | |
| WV-CA-331 | |
| WV-CA-332 | |
| WV-CA-333 | |
| WV-CA-334 | |
| WV-CA-335 | |
| WV-CA-336 | |
| WV-CA-337 | |
| WV-CA-338 | |

TABLE 1-continued

Example compounds.

| Compound No. | Structure |
|---|---|
| WV-CA-339 | (structure: cyclohexyl-CH(OH)-piperidine) |
| WV-CA-340 | (structure: Ph-CH2-CF(OH)-pyrrolidine, (S,S)) |
| WV-CA-341 | (structure: bicyclic pyrrolidine with Ph, OH substituents) |
| WV-CA-342 | (structure: bicyclic pyrrolidine with iPr, OH substituents) |
| WV-CA-343 | (structure: MeS-CH2-CH(OH)-pyrrolidine, (R,S)) |
| WV-CA-344 | (structure: MeHN-S(O)(Me)-CH2-CH(OH)-pyrrolidine, (S,R)) |
| WV-CA-344a | (structure: HN=S(O)(Me)-CH2-CH(OH)-pyrrolidine, (S,R)) |
| WV-CA-345 | (structure: (MeO)2P-CH2-CH(OH)-pyrrolidine) |
| WV-CA-346 | (structure: HN=S(O)(Me)-CH2-CH(OH)-pyrrolidine, (S,R)) |
| WV-CA-347 | (structure: MeS(O)2-CH2-CH(OH)-pyrrolidine, (S,R)) |
| WV-CA-348 | (structure: MeS(O)-CH2-CH(OH)-pyrrolidine, (S,R)) |
| WV-CA-349 | (structure: MeS(O)-CH2-CH(OH)-pyrrolidine, (S,R)) |
| WV-CA-350 | (structure: Et,Me-C(OH)-pyrrolidine) |
| WV-CA-351 | (structure: Et-CH(OH)-pyrrolidine) |
| WV-CA-352 | (structure: Ph-CH2-C(Me)(OH)-pyrrolidine) |
| WV-CA-352a | (structure: Ph-CH2-C(Me)(OH)-pyrrolidine) |
| WV-CA-353 | (structure: Me2N-CH2-CH(OH)-pyrrolidine) |
| WV-CA-354 | (structure: Me2N-CH2CH2CH2-CH(OH)-pyrrolidine) |
| WV-CA-355 | (structure: (MeO)2B-CH2-CH(OH)-pyrrolidine) |
| WV-CA-356 | (structure: H2B-CH2-CH(OH)-pyrrolidine) |

TABLE 1-continued

Example compounds.

| Compound No. | Structure |
|---|---|
| WV-CA-357 | (structure) |
| WV-CA-358 | (structure) |
| WV-CA-359 | (structure) |
| WV-CA-360 | (structure) |
| WV-CA-361 | (structure) |
| WV-CA-363 | (structure) |
| WV-CA-364 | (structure) |
| WV-CA-365 | (structure) |
| WV-CA-366 | (structure) |
| WV-CA-367 | (structure) |
| WV-CA-368 | (structure) |
| WV-CA-369 | (structure) |
| WV-CA-370 | (structure) |
| WV-CA-371 | (structure) |
| WV-CA-372 | (structure) |
| WV-CA-373 | (structure) |
| WV-CA-374 | (structure) |
| WV-CA-375 | (structure) |

TABLE 1-continued

Example compounds.

| Compound No. | Structure |
|---|---|
| WV-CA-376 | (R,S)-(2,6-difluorophenyl)(pyrrolidin-2-yl)methanol |
| WV-CA-377 | (R,S)-(3,4-difluorophenyl)(pyrrolidin-2-yl)methanol |
| WV-CA-378 | (S,S)-fluoro(perfluorophenyl)(pyrrolidin-2-yl)methanol |
| WV-CA-379 | (R,S)-(perfluorophenyl)(pyrrolidin-2-yl)methanol |
| WV-CA-380 | (R,S)-deutero(perfluorophenyl)(pyrrolidin-2-yl)methanol |
| WV-CA-381 | (R,S)-1-(4-fluorophenyl)-1-(pyrrolidin-2-yl)ethanol |
| WV-CA-382 | (R,S)-phenyl(pyrrolidin-2-yl)(trifluoromethyl)methanol |
| WV-CA-383 | (S,S)-fluoro(pentadeuterophenyl)(pyrrolidin-2-yl)methanol |
| WV-CA-384 | (R,S)-2,2,2-trideutero-1-phenyl-1-(pyrrolidin-2-yl)ethanol |
| WV-CA-385 | (R,S)-fluoro(pentadeuterophenyl)(pyrrolidin-2-yl)methanol |
| WV-CA-385a | (S,S)-fluoro(pentadeuterophenyl)(pyrrolidin-2-yl)methanol |
| WV-CA-386 | (S)-bis(3,5-bis(trifluoromethyl)phenyl)(pyrrolidin-2-yl)methanol |
| WV-CA-394 | (S,S)-deutero(pyrrolidin-2-yl)(trifluoromethyl)methanol |
| WV-CA-395 | (S,S)-2,2,2-trideutero-1-(pyrrolidin-2-yl)-1-(trifluoromethyl)ethanol |
| WV-CA-396 | (S,S)-1-(pyrrolidin-2-yl)-1-(trifluoromethyl)methanol |
| WV-CA-397 | (S,S)-1-(pyrrolidin-2-yl)-1-(trifluoromethyl)ethanol |

TABLE 1-continued

Example compounds.

| Compound No. | Structure |
|---|---|
| WV-CA-398 | (structure) |
| WV-CA-398a | (structure) |
| WV-CA-399 | (structure) |
| WV-CA-400 | (structure) |
| WV-CA-408 | (structure) |
| WV-CA-409 | (structure) |
| WV-CA-410 | (structure) |
| WV-CA-419 | (structure) |
| WV-CA-420 | (structure) |
| WV-CA-421 | (structure) |

In some embodiments, a provided compound is an enantiomer of a compound selected from Table 1 or a salt thereof. In some embodiments, a provided compound is a diastereomer of a compound selected from Table 1 or a salt thereof.

TABLE 2

Example compounds.

| Compound No. | Structure |
|---|---|
| WV-CA-007 | (structure) |
| WV-CA-008 | (structure) |
| WV-CA-008-S | (structure) |
| WV-CA-009 | (structure) |
| WV-CA-010 | (structure) |

TABLE 2-continued

Example compounds.

| Compound No. | Structure |
|---|---|
| WV-CA-017 | |
| WV-CA-018 | |
| WV-CA-019 | |
| WV-CA-020 | |
| WV-CA-024 | |
| WV-CA-025 | |
| WV-CA-026 | |
| WV-CA-027 | |
| WV-CA-028 | |
| WV-CA-029 | |
| WV-CA-030 | 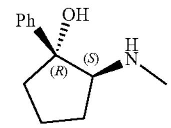 |
| WV-CA-031 | 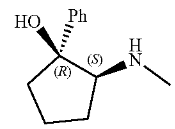 |
| WV-CA-032 | 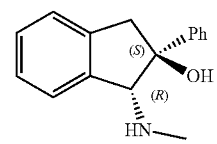 |
| WV-CA-033 | 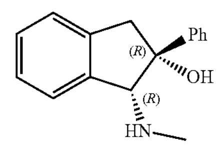 |
| WV-CA-034 | 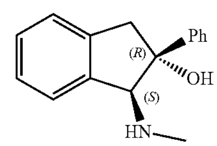 |
| WV-CA-035 | 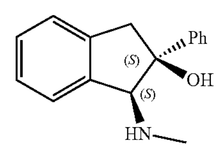 |
| WV-CA-036 | 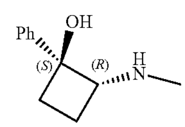 |
| WV-CA-037 | 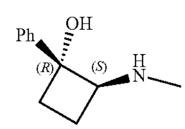 |
| WV-CA-038 | 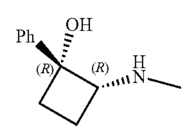 |
| WV-CA-039 | 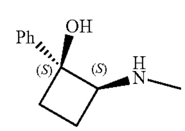 |
| WV-CA-047 | 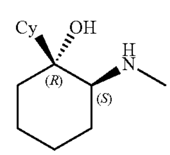 |

TABLE 2-continued

Example compounds.

| Compound No. | Structure |
|---|---|
| WV-CA-055 | (TIPS-CH2-C(OH)H-CH(NHMe)-Cy) |
| WV-CA-061 | (1S-Cy,1-OH-cyclohexyl, 2S-NHMe) |
| WV-CA-066-R | (1R-OH-cyclopentyl fused, 2S-NHMe) |
| WV-CA-070 | (1R-OH,1-Me-cyclohexyl, 2S-NHMe) |
| WV-CA-070-S | (1S-OH,1-Me-cyclohexyl, 2S-NHMe) |
| WV-CA-071S | (1-OH-cyclopentyl, S-CH(Cy)(NHMe)) |
| WV-CA-075-S | (1S-OH,1-Me-cyclohexyl, 2S-NHiPr) |
| WV-CA-092 | (1-OH-cyclopentyl, S-CH(iPr)(NHiPr)) |
| WV-CA-114 | (MePh2Si-CH2-C(S)(OH)H-C(S)H(NHMe)(iPr)) |
| WV-CA-115 | (R-C(OH)(Ph)-S-CH(NHMe)(tBu)) |

TABLE 2-continued

Example compounds.

| Compound No. | Structure |
|---|---|
| WV-CA-135 | (cyclodecane with OH and NHMe) |
| WV-CA-136 | (cyclodecane with OH and NHMe) |
| WV-CA-137 | (cyclodecane with OH and NHMe) |
| WV-CA-138 | (cyclodecane with OH and NHMe) |
| WV-CA-139 | (cyclodecane with OH and NHMe) |
| WV-CA-140 | (cyclodecane with OH and NHMe) |
| WV-CA-141 | (cyclodecane with OH and NHMe) |
| WV-CA-142 | (cyclodecane with OH and NHMe) |
| WV-CA-158 | (2-Me-2-OH-thiacyclohexane-3-NHMe) |

TABLE 2-continued

Example compounds.

| Compound No. | Structure |
|---|---|
| WV-CA-159 | |
| WV-CA-160 | |
| WV-CA-161 | |
| WV-CA-162 | |
| WV-CA-168 | |
| WV-CA-169 | |
| WV-CA-170 | |
| WV-CA-171 | |
| WV-CA-205 | |
| WV-CA-207 | 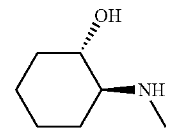 |
| WV-CA-208 | 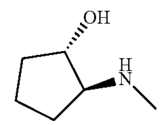 |
| WV-CA-210 | 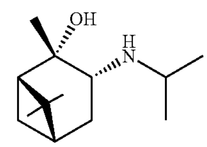 |
| WV-CA-211 | 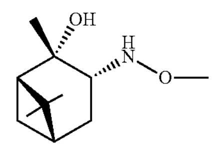 |
| WV-CA-216 | 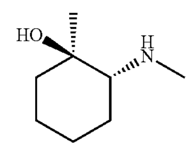 |
| WV-CA-217 | 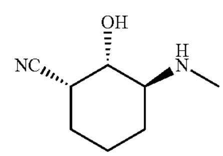 |
| WV-CA-218 | 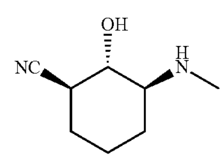 |
| WV-CA-219 | 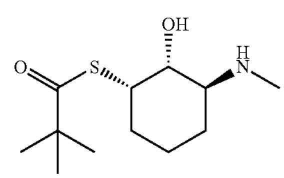 [SMILES: CN[C@H]1CCC[C@H](SC(=O)C(C)(C)C)[C@@H]1O] |
| WV-CA-220 | 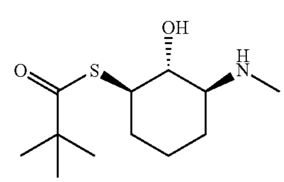 [SMILES: CN[C@H]1CCC[C@@H](SC(=O)C(C)(C)C)[C@@H]1O] |
| WV-CA-221 | 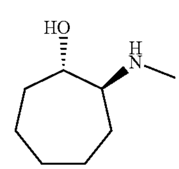 |

TABLE 2-continued

Example compounds.

| Compound No. | Structure |
|---|---|
| WV-CA-222 | |
| WV-CA-223 | |
| WV-CA-224 | |
| WV-CA-228 | |
| WV-CA-232 | |
| WV-CA-235 | |
| WV-CA-302 | |
| WV-CA-303 | |
| WV-CA-305 | 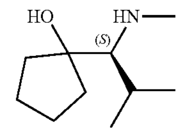 |
| WV-CA-362 | 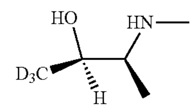 |
| WV-CA-387 | 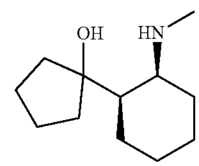 |
| WV-CA-388 | 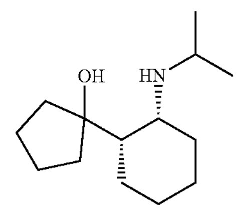 [SMILES: CC(C)N[C@@H]1CCCC[C@@H]1C1(O)CCCC1] |
| WV-CA-389 | 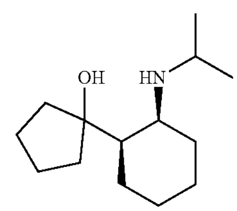 [SMILES: CC(C)N[C@H]1CCCC[C@H]1C1(O)CCCC1] |
| WV-CA-390 | 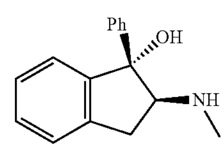 [SMILES: CN[C@H]1Cc2ccccc2[C@@]1(O)c1ccccc1] |
| WV-CA-391 | 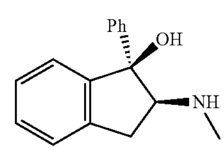 |
| WV-CA-392 | 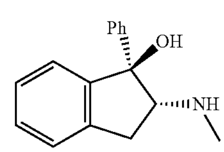 [SMILES: CN[C@@H]1Cc2ccccc2[C@]1(O)c1ccccc1] |
| WV-CA-393 | 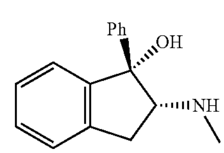 [SMILES: CN[C@@H]1Cc2ccccc2[C@@]1(O)c1ccccc1] |

TABLE 2-continued

Example compounds.

| Compound No. | Structure |
|---|---|
| WV-CA-401 | 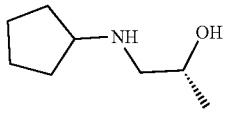 |
| WV-CA-402 | 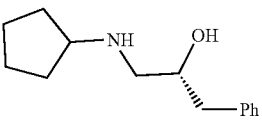 [SMILES: O[C@@H](CNC1CCCC1)Cc1ccccc1] |
| WV-CA-404 | 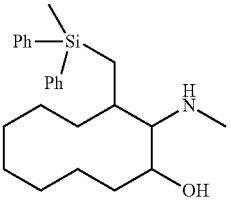 [SMILES: CNC1C(O)CCCCCCCC1C[Si](C)(c1ccccc1)c1ccccc1] |
| WV-CA-405 | 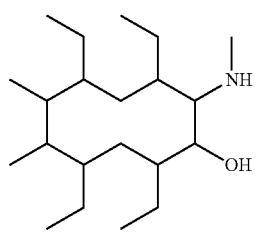 |
| WV-CA-406 | 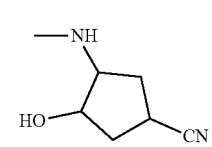 |
| WV-CA-407 | 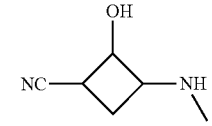 |
| WV-CA-411 | 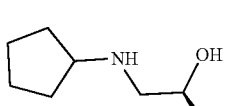 |
| WV-CA-412 | 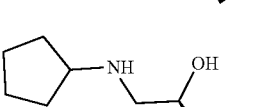 |
| WV-CA-413 | 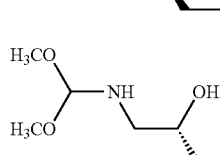 |
| WV-CA-414 | 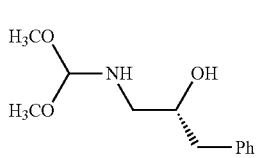 |
| WV-CA-415 | 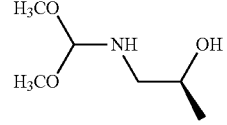 |
| WV-CA-416 | 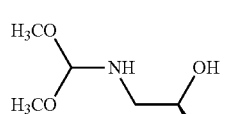 |
| WV-CA-417 | 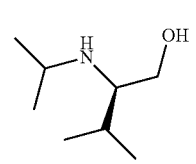 |
| WV-CA-418 | 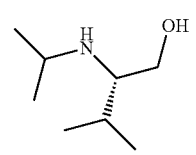 |

In some embodiments, a provided compound is an enantiomer of a compound selected from Table 2 or a salt thereof. In some embodiments, a provided compound is a diastereomer of a compound selected from Table 2 or a salt thereof.

TABLE 3

Example compounds.

| Compound No. | Structure |
|---|---|
| WV-CA-085 | 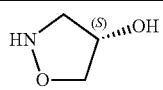 |
| WV-CA-086 | 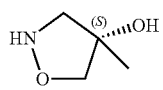 |
| WV-CA-087 | 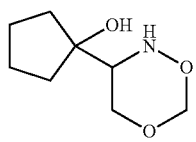 |
| WV-CA-087a | 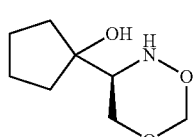 |
| WV-CA-087b | 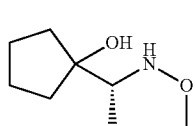 |

TABLE 3-continued

Example compounds.

| Compound No. | Structure |
|---|---|
| WV-CA-095 | (structure) |
| WV-CA-143 | (structure) |
| WV-CA-144 | (structure) |
| WV-CA-177 | (structure) |
| WV-CA-178 | (structure) |
| WV-CA-179 | (structure) |
| WV-CA-184 | (structure) |
| WV-CA-185 | (structure) |
| WV-CA-186 | (structure) |
| WV-CA-187 | (structure) |
| WV-CA-189 | (structure) |
| WV-CA-190 | (structure) |
| WV-CA-191 | (structure) |
| WV-CA-192 | (structure) |
| WV-CA-193 | (structure) |
| WV-CA-194 | (structure) |
| WV-CA-195 | (structure) |
| WV-CA-196 | (structure) |
| WV-CA-197 | (structure) |
| WV-CA-198 | (structure) |
| WV-CA-199 | (structure) |
| WV-CA-200 | (structure) |

TABLE 3-continued
Example compounds.
| Compound No. | Structure |
|---|---|
| WV-CA-212 | 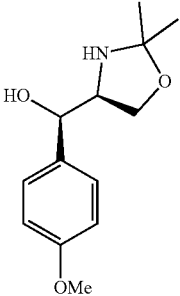 |
| WV-CA-213 | 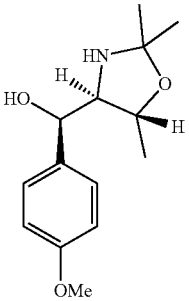 [SMILES: COc1ccc([C@@H](O)[C@H]2NC(C)(C)O[C@@H]2C)cc1] |
| WV-CA-214 | 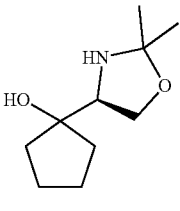 |
| WV-CA-215 | 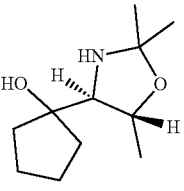 |
| WV-CA-403 | 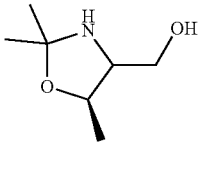 |
| WV-CA-422 | 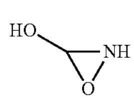 |
In some embodiments, a provided compound is an enantiomer of a compound selected from Table 3 or a salt thereof. In some embodiments, a provided compound is a diastereomer of a compound selected from Table 3 or a salt thereof.
TABLE 4
Example compounds
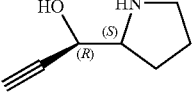
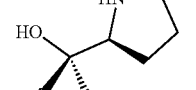
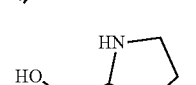
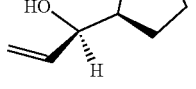
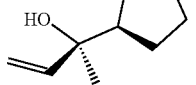
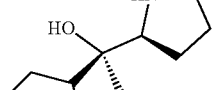
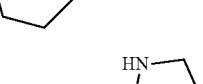
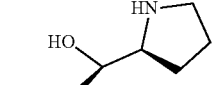
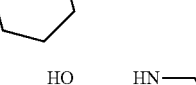

TABLE 4-continued

Example compounds

TABLE 4-continued

Example compounds

TABLE 4-continued
Example compounds
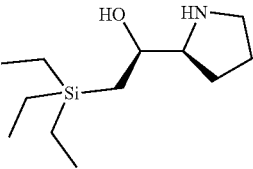
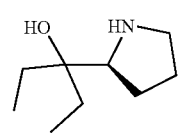
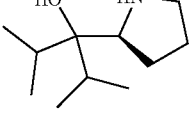
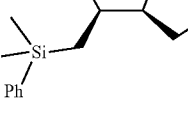
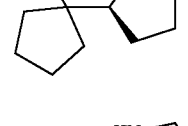
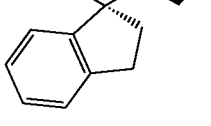
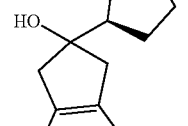
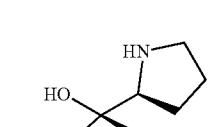
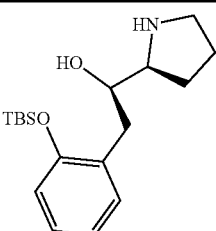
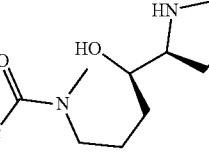
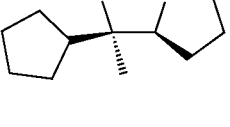
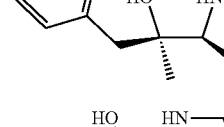
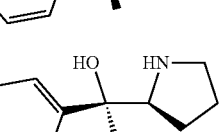
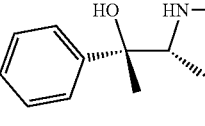
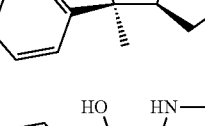
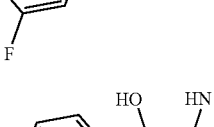
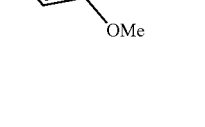

TABLE 4-continued
Example compounds
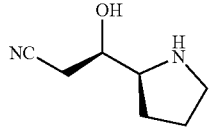
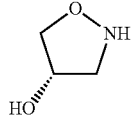
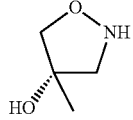
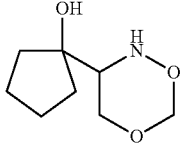 [SMILES: OC1(C2COCON2)CCCC1]
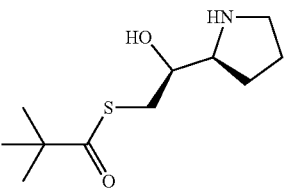
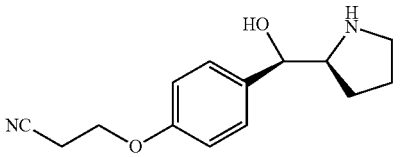 [SMILES: N#CCCOc1ccc([C@@H](O)[C@@H]2CCCN2)cc1]
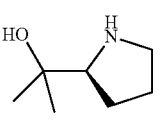
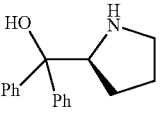
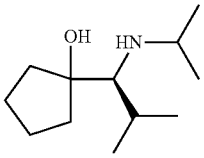
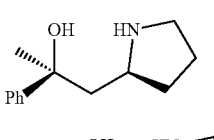
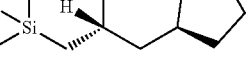
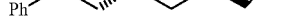
TABLE 4-continued
Example compounds
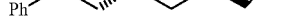
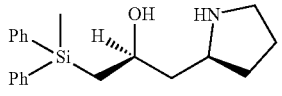 [SMILES: C[Si](C[C@@H](O)C[C@@H]1CCCN1)(c1ccccc1)c1ccccc1]
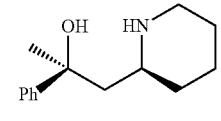 [SMILES: C[C@](O)(C[C@@H]1CCCCN1)c1ccccc1]
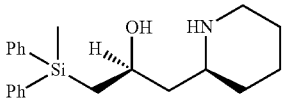 [SMILES: C[Si](C[C@@H](O)C[C@@H]1CCCCN1)(c1ccccc1)c1ccccc1]
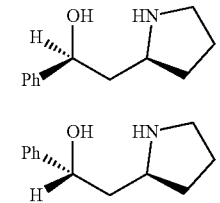
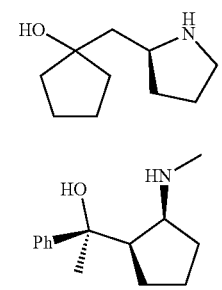
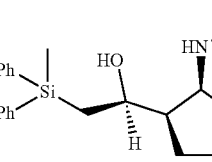
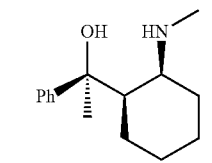
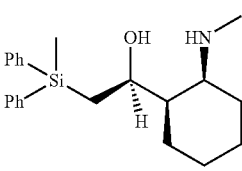 [SMILES: CN[C@H]1CCCC[C@H]1[C@H](O)C[Si](C)(c1ccccc1)c1ccccc1]
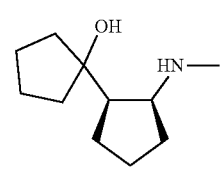

TABLE 4-continued

Example compounds

TABLE 4-continued

Example compounds

TABLE 4-continued

Example compounds

TABLE 4-continued

Example compounds

TABLE 4-continued
Example compounds
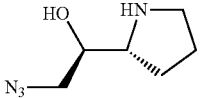
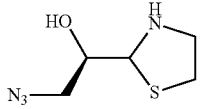
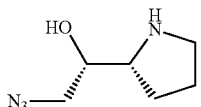
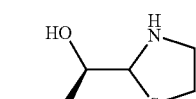
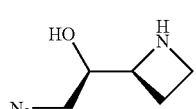
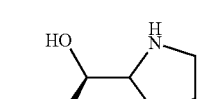
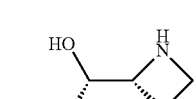
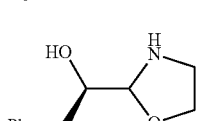
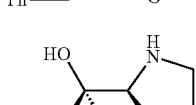
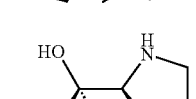
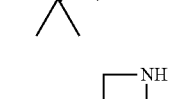
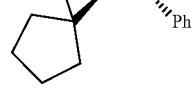
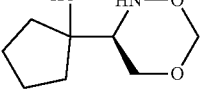
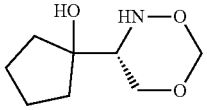
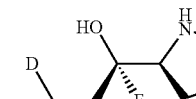
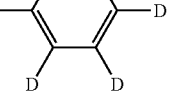
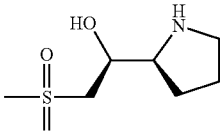
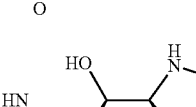
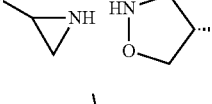
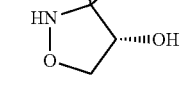
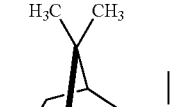
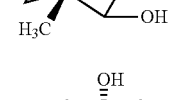
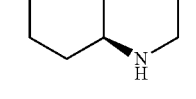
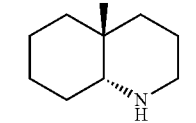

TABLE 4-continued
Example compounds
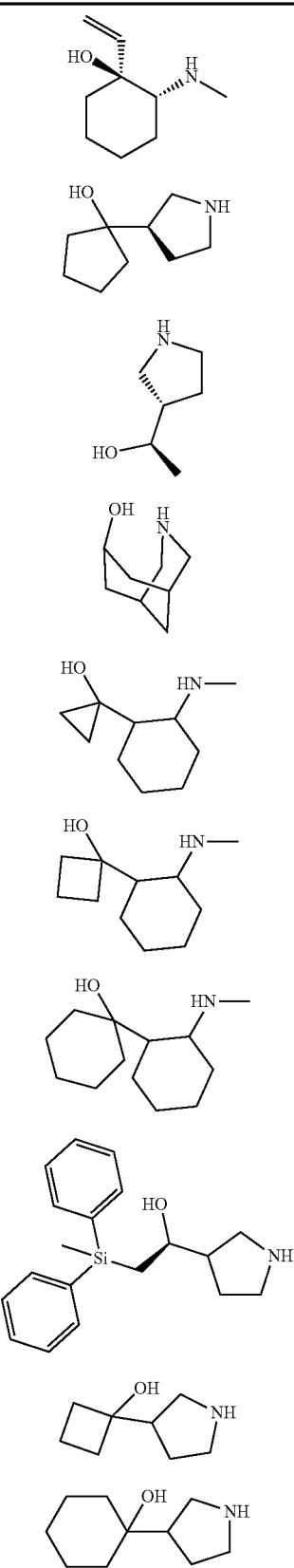
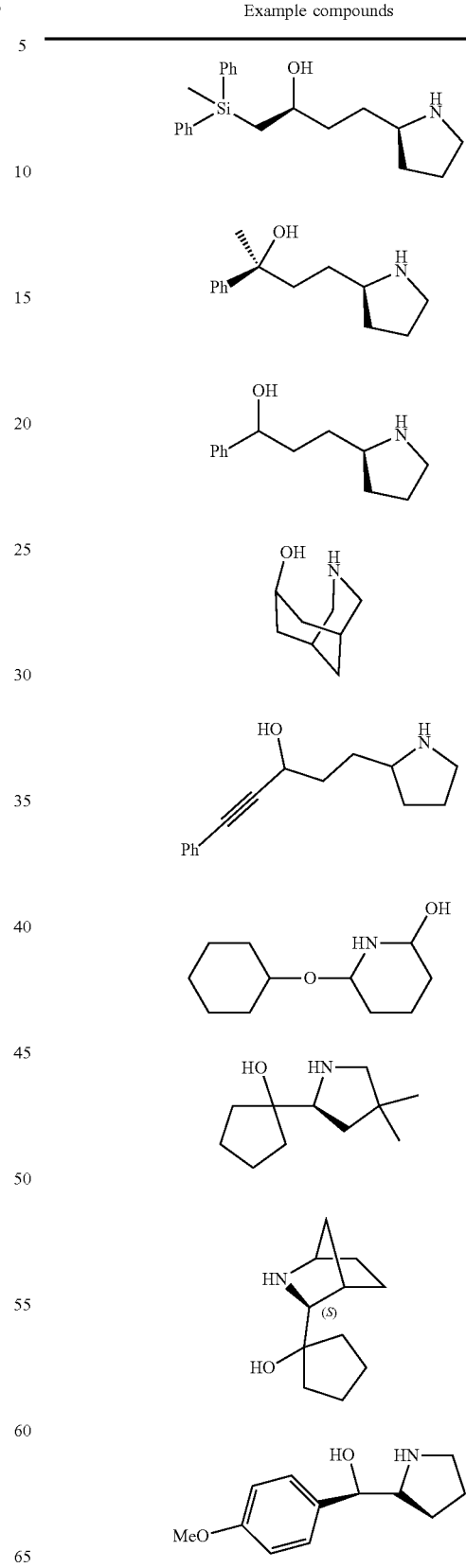

TABLE 4-continued
Example compounds
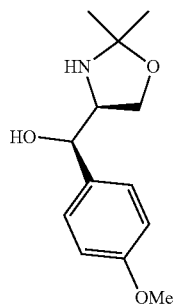 [SMILES: COc1ccc([C@@H](O)[C@@H]2COC(C)(C)N2)cc1]
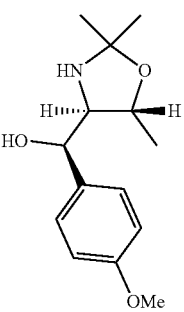 [SMILES: COc1ccc([C@@H](O)[C@H]2NC(C)(C)O[C@@H]2C)cc1]
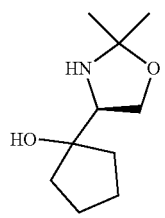
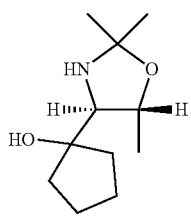
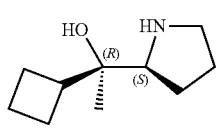
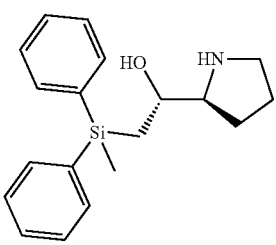 [SMILES: C[Si](C[C@H](O)[C@@H]1CCCN1)(c1ccccc1)c1ccccc1]
TABLE 4-continued
Example compounds
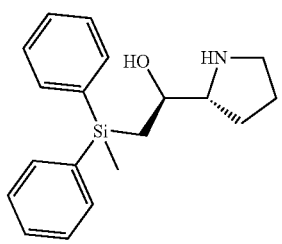 [SMILES: C[Si](C[C@@H](O)[C@H]1CCCN1)(c1ccccc1)c1ccccc1]
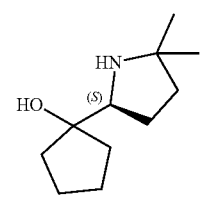
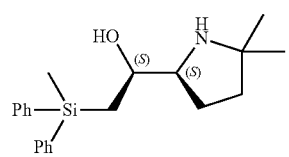
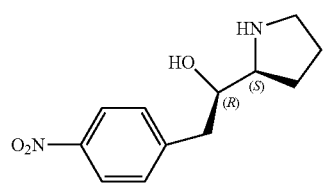
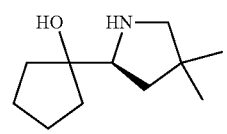
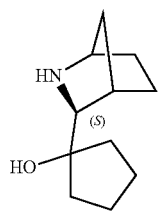
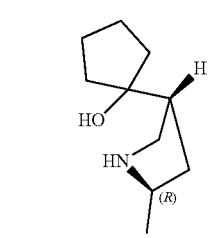

TABLE 4-continued
Example compounds
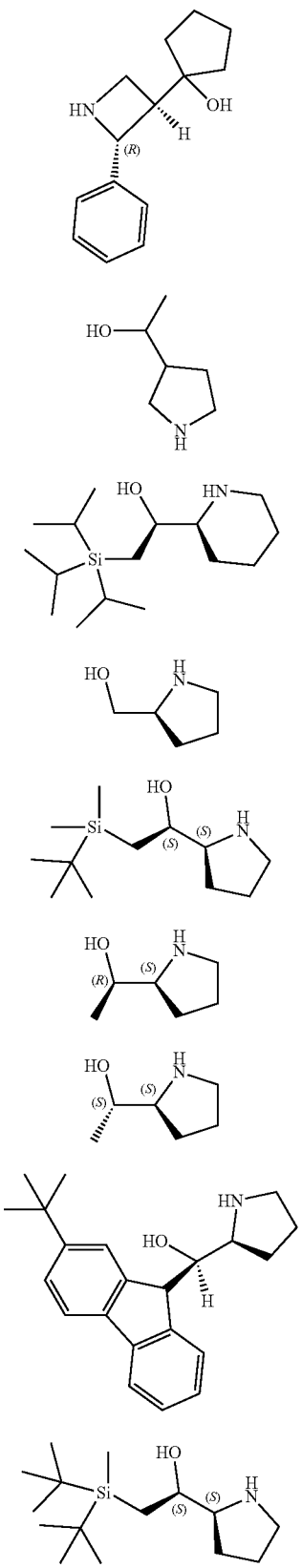
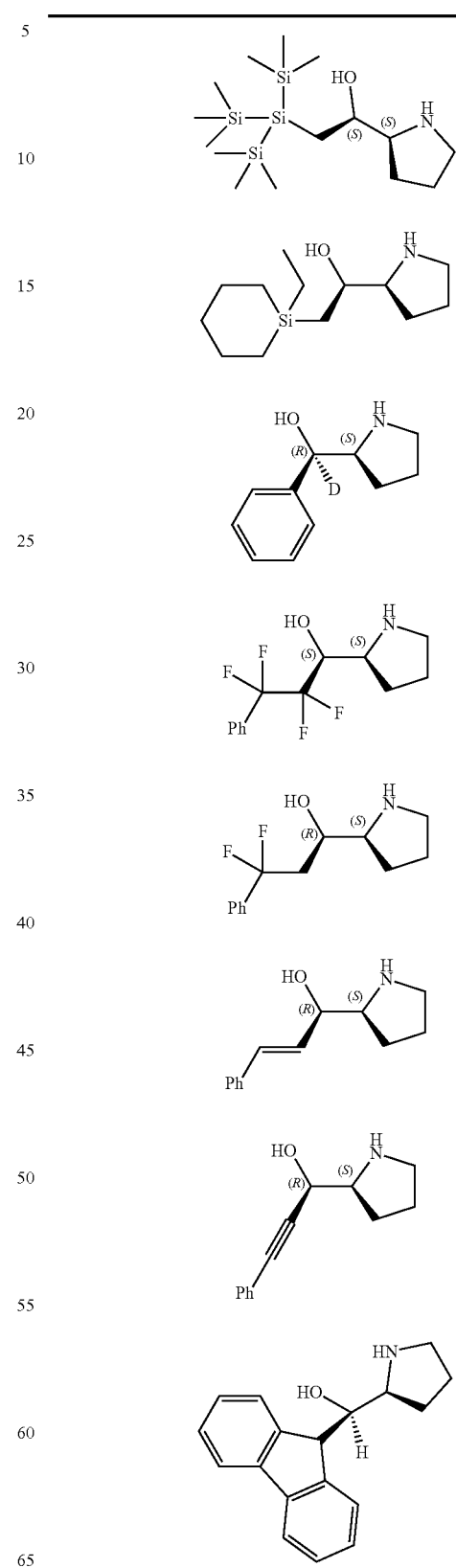

TABLE 4-continued

Example compounds

TABLE 4-continued

Example compounds

TABLE 4-continued

Example compounds

TABLE 4-continued

Example compounds

TABLE 4-continued

Example compounds

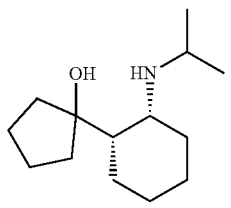 [SMILES: CC(C)N[C@@H]1CCCC[C@@H]1C1(O)CCCC1]

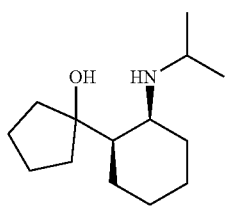 [SMILES: CC(C)N[C@H]1CCCC[C@H]1C1(O)CCCC1]

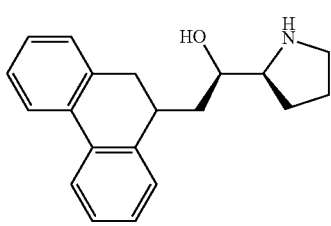 [SMILES: O[C@H](CC1Cc2ccccc2-c2ccccc21)[C@@H]1CCCN1]

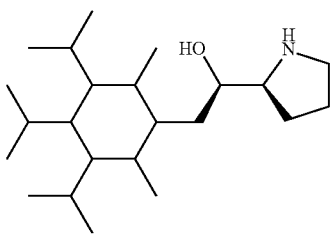 [SMILES: CC(C)C1C(C)C(C[C@@H](O)[C@@H]2CCCN2)C(C)C(C(C)C)C1C(C)C]

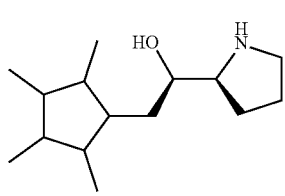 [SMILES: CC1C(C)C(C)C(C[C@@H](O)[C@@H]2CCCN2)C1C]

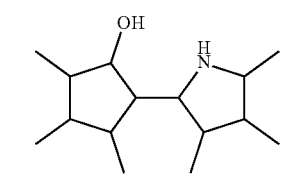

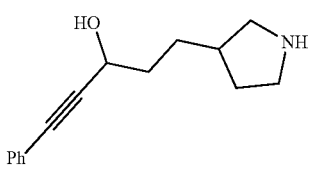 [SMILES: OC(C#Cc1ccccc1)CCC1CCNC1]

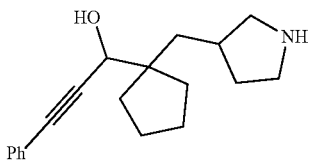 [SMILES: OC(C#Cc1ccccc1)C1(CC2CCNC2)CCCC1]

TABLE 4-continued

Example compounds

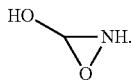

In some embodiments, a provided compound is an enantiomer of a compound selected from Table 4 or a salt thereof. In some embodiments, a provided compound is a diastereomer of a compound selected from Table 4 or a salt thereof.

In some embodiments, provided compounds, e.g., compounds of formula I, I-a, I-a-1, I-a-2, I-b, I-c, I-d, I-e, II, II-a, II-b, III, III-a, or III-b, or salts thereof, comprises one or more chiral elements. In some embodiments, provided compounds of formula I, I-a, I-a-1, I-a-2, I-b, I-c, I-d, I-e, II, II-a, II-b, III, III-a, or III-b, or salts thereof, are chiral. In some embodiments, provided chiral compounds, compounds of formula I, I-a, I-a-1, I-a-2, I-b, I-c, I-d, I-e, II, II-a, II-b, III, III-a, or III-b, or salts thereof, are of a purity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of a stereopurity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of a diastereomeric purity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of a enantiomeric purity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of diastereomeric and enantiomeric purity described in the present disclosure. In some embodiments, the present disclosure provides compounds, e.g., compounds of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, VI-e, VIII, or salts thereof, that are made from compounds of formula I, I-a, I-a-1, I-a-2, I-b, I-c, I-d, I-e, II, II-a, II-b, III, III-a, or III-b, or salts thereof, and comprise chiral elements of compounds of formula I, I-a, I-a-1, I-a-2, I-b, I-c, I-d, I-e, II, II-a, II-b, III, III-a, or III-b.

For example, in some embodiments, the present disclosure provides a compound having the structure of formula IV:

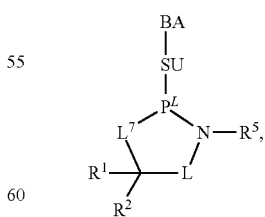

IV or a salt thereof, wherein:

$P^L$ is $P(=W)$, P, or $P \rightarrow B(R')_3$;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

each of $R^1$, $R^2$, $R^3$, $R^4$, and $R^5$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

L$^7$ is —O— or —S—;

at least one of $R^1$, $R^2$, $R^3$ and $R^4$ is not —H;

BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety;

SU is -L$^s$-O— or

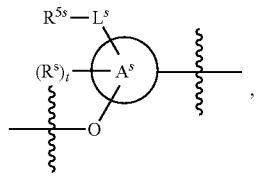

wherein SU is connected to the phosphorus atom through the oxygen atom;

each R$^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

t is 0-20;

Ring A$^s$ is an optionally substituted 3-20 membered monocyclic, bicyclic or polycyclic ring having 0-10 heteroatoms independently selected from oxygen, nitrogen, sulfur, phosphorus and silicon;

R$^{5s}$ is R$^s$;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, P$^L$ is P(=W). In some embodiments, P$^L$ is P. In some embodiments, P$^L$ is P→B(R')$_3$. In some embodiments, P of P$^L$ is chiral. In some embodiments, P of P$^L$ is Rp. In some embodiments, P of P$^L$ is Sp.

In some embodiments, SU is -L$^s$-O—. In some embodiments, SU is

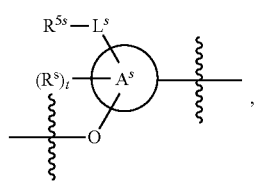

wherein each variable is independently as described in the present disclosure. In some embodiments, SU is

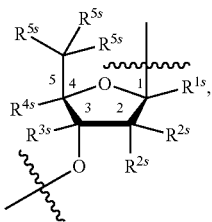

each of $R^{1s}$, $R^{2s}$, $R^{3s}$, $R^{4s}$ and $R^{5s}$ is independently $R^s$. In some embodiments, SU is

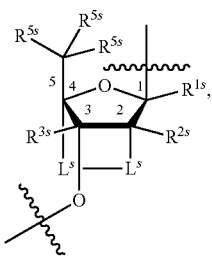

wherein each variable is independently as described in the present disclosure. In some embodiments, SU is

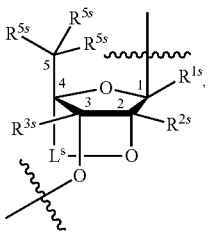

wherein each variable is independently as described in the present disclosure. In some embodiments, SU is

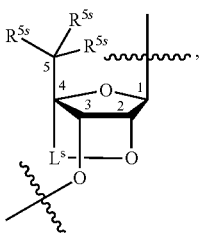

wherein each variable is independently as described in the present disclosure. In some embodiments, SU is

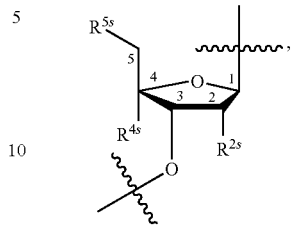

wherein each variable is independently as described in the present disclosure. In some embodiments, SU is

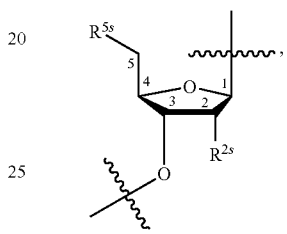

wherein each variable is independently as described in the present disclosure.

In some embodiments, a provided compound, e.g., a compound of formula IV, has the structure of formula IV-a:

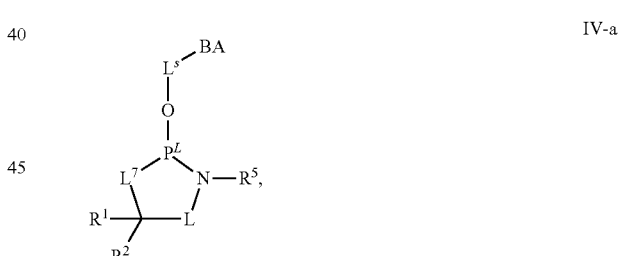

or a salt thereof, wherein each variable is independently as described in the present disclosure. In some embodiments, a provided compound of formula IV has the structure of formula IV-a. In some embodiments, $L^s$-Cy-. In some embodiments, $L^s$ is an optionally substituted monocyclic or bicyclic 3-20 membered heterocyclyl ring having 1-5 heteroatoms. In some embodiments, $L^s$ is an optionally substituted monocyclic or bicyclic 5-20 membered heterocyclyl ring having 1-5 heteroatoms, wherein at least one heteroatom is oxygen. In some embodiments, $L^s$ is an optionally substituted bivalent tetrahydrofuran ring. In some embodiments, $L^s$ is an optionally substituted furanose moiety. In some embodiments, the BA in formula IV-a is bonded to C1, and the —O— in formula IV-a is bonded to C3, of the furanose moiety.

In some embodiments, a provided compound, e.g., a compound of formula IV, has the structure of formula IV-b:

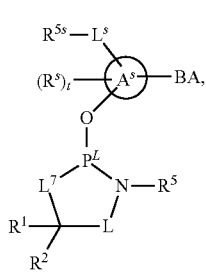

IV-b or a salt thereof, wherein each variable is independently as described in the present disclosure. In some embodiments, a provided compound of formula IV has the structure of formula IV-b.

In some embodiments, a provided compound, e.g., a compound of formula IV, has the structure of formula IV-c-1:

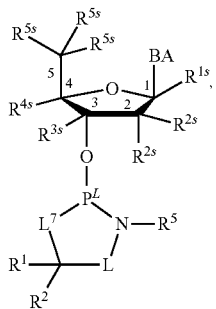

IV-c-1 or a salt thereof, wherein each variable is independently as described in the present disclosure. In some embodiments, a provided compound of formula IV has the structure of formula IV-c-1.

In some embodiments, a provided compound, e.g., a compound of formula IV, has the structure of formula IV-c-2:

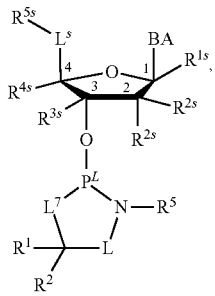

IV-c-2 or a salt thereof, wherein each variable is independently as described in the present disclosure. In some embodiments, a provided compound of formula IV has the structure of formula IV-c-2.

In some embodiments, a provided compound, e.g., a compound of formula IV, has the structure of formula IV-d:

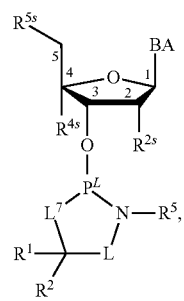

IV-d or a salt thereof, wherein each variable is independently as described in the present disclosure. In some embodiments, a provided compound of formula IV has the structure of formula IV-d.

In some embodiments, a provided compound, e.g., a compound of formula IV, has the structure of formula IV-e:

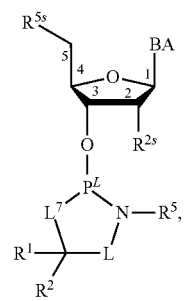

IV-e or a salt thereof, wherein each variable is independently as described in the present disclosure. In some embodiments, a provided compound of formula IV has the structure of formula IV-e.

In some embodiments, a compound of formula IV, IV-a, IV-b, IV-c-1, IV-c-2, IV-d, or IV-e, can be prepared from a compound of formula I, I-a, I-a-1, I-a-2, I-b, I-c, I-d, I-e, II, II-a, II-b, III, III-a, III-b, etc. In some embodiments,

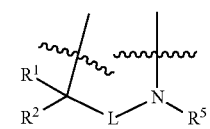

is as described for formula I, I-a, I-a-1, I-a-2, I-b, I-c, I-d, I-e, II, II-a, II-b, III, III-a, III-b, etc. In some embodiments, a compound of formula IV, IV-a, IV-b, IV-c-1, IV-c-2, IV-d, or IV-e has a structure such that

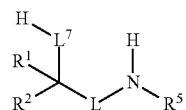

is a compound having the structure of I, I-a, I-a-1, I-a-2, I-b, I-c, I-d, or I-e, or a salt thereof.

In some embodiments, the present disclosure provides a compound having the structure of formula IVa:

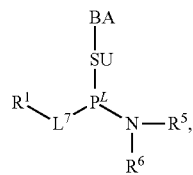

IVa or a salt thereof, wherein each variable is independently as described in the present disclosure. In some embodiments, the present disclosure provides a compound having the structure of formula IVa-a:

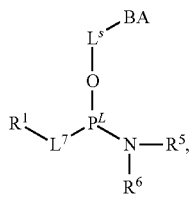

IVa-a or a salt thereof, wherein each variable is independently as described in the present disclosure. In some embodiments, a compound of formula IVa is a compound of formula IVa-a. In some embodiments, the present disclosure provides a compound having the structure of formula IVa-b:

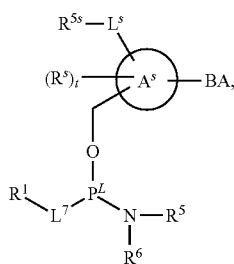

IVa-b or a salt thereof, wherein each variable is independently as described in the present disclosure. In some embodiments, a compound of formula IVa is a compound of formula IVa-b. In some embodiments, the present disclosure provides a compound having the structure of formula IVa-c-1:

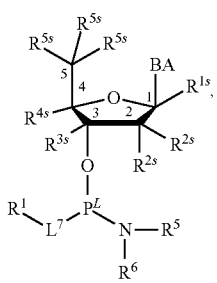

IVa-c-1 or a salt thereof, wherein each variable is independently as described in the present disclosure. In some embodiments, a compound of formula IVa is a compound of formula IVa-c-1. In some embodiments, the present disclosure provides a compound having the structure of formula IVa-c-2:

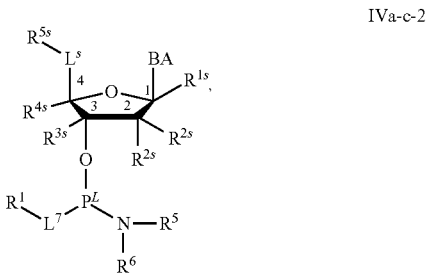

IVa-c-2 or a salt thereof, wherein each variable is independently as described in the present disclosure. In some embodiments, a compound of formula IVa is a compound of formula IVa-c-2. In some embodiments, the present disclosure provides a compound having the structure of formula IVa-d:

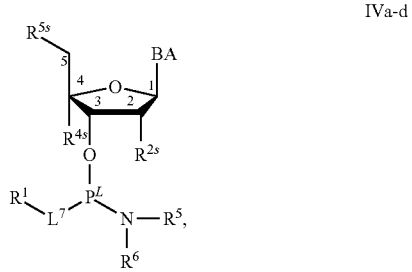

IVa-d or a salt thereof, wherein each variable is independently as described in the present disclosure. In some embodiments, a compound of formula IVa is a compound of formula IVa-d. In some embodiments, the present disclosure provides a compound having the structure of formula IVa-e:

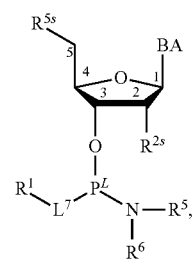

IVa-e or a salt thereof, wherein each variable is independently as described in the present disclosure. In some embodiments, a compound of formula IVa is a compound of formula IVa-e. In some embodiments, $L^7$ is —O—. In some embodiments, each of $R^1$, $R^5$ and $R^6$ is independently optionally substituted $C_{1-6}$ alkyl. In some embodiments, $R^5$ and $R^6$ are the same. In some embodiments, $P^L$ is P. In some embodiments, -$L^7$-$R^1$ contains no chiral elements. In some embodiments, —N($R^5$)($R^6$) contains no chiral elements. In some embodiments, -$L^7$-$R^1$ and —N($R^5$)($R^6$) contains no chiral elements. In some embodiments, -L⁷-R¹ is —O—CH₂CH₂—CN. In some embodiments, —N(R⁵)(R⁶) is —N(i-Pr)₂. In some embodiments, a compound of formula IVa, IVa-a, IVa-b, IVa-c-1, IVa-c-2, IVa-d, or IVa-e, or a salt thereof, is a phosphoramidite for non-chirally controlled oligonucleotide synthesis, e.g., oligonucleotide synthesis using traditional phosphoramidite chemistry. In some embodiments, R¹ and R⁵ are R and are taken together with their intervening atoms to form a ring as described in the present disclosure. In some embodiments, a formed ring contain a chiral element, and a compound of formula IVa, IVa-a, IVa-b, IVa-c-1, IVa-c-2, IVa-d, or IVa-e, or a salt thereof can be utilized for chirally controlled oligonucleotide synthesis.

In some embodiments, the present disclosure provides a compound having the structure of formula V:

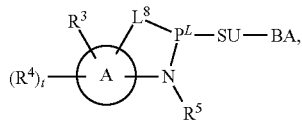

V or a salt thereof, wherein:
P$^L$ is P(=W), P, or P→B(R')₃;
Ring A is an optionally substituted 3-20 membered monocyclic, bicyclic or polycyclic ring having 0-10 heteroatoms independently selected from oxygen, nitrogen, sulfur, phosphorus and silicon;
each of R¹, R², R³, R⁴, and R⁵ is independently —H, -L$^s$-R, halogen, —CN, —NO₂, -L$^s$-Si(R)₃, —OR, —SR, or —N(R)₂;
each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms independently selected from oxygen, nitrogen, sulfur, phosphorus and silicon, —C(R')₂—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)₂—, —S(O)₂N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')₃]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')₃]O—, and one or more carbon atoms are optionally and independently replaced with Cy$^L$;
each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each R' is independently —R, —C(O)R, —C(O)OR, or —S(O)₂R;
t is 0-20;
L⁸ is -L-O—, -L-C(R¹)(R²)—O—, or -L$^s$-O—;
L is a covalent bond, or optionally substituted C$_{1-6}$ alkylene, wherein one or more methylene units are optionally and independently replaced with -L'-;
L' is a covalent bond, optionally substituted bivalent C$_{1-3}$ alkylene, —C(R³)(R⁴)—, —C(R³)(R⁴)—C(R³)(R⁴)—, -Cy-, or —C(R³)[C(R⁴)₃]—;
BA is an optionally substituted group selected from C$_{3-30}$ cycloaliphatic, C$_{6-30}$ aryl, C$_{5-30}$ heteroaryl having 1-10 heteroatoms independently selected from oxygen, nitrogen, sulfur, phosphorus and silicon, C$_{3-30}$ heterocyclyl having 1-10 heteroatoms independently selected from oxygen, nitrogen, sulfur, phosphorus and silicon, a natural nucleobase moiety, and a modified nucleobase moiety;
SU is -L$^s$-O— or

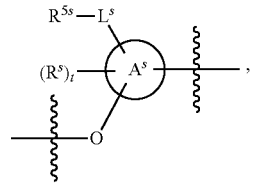

wherein SU is connected to the phosphorus atom through the oxygen atom;
R$^{5s}$ is R$^s$;
each R$^s$ is independently —H, halogen, —CN, —N₃, —NO, —NO₂, -L$^s$-R', -L$^s$-Si(R)₃, -L$^s$-OR', -L$^s$-SR', -L$^s$-N(R')₂, —O-L$^s$-R', —O-L$^s$-Si(R)₃, —O-L$^s$-OR', —O-L$^s$-SR', or —O-L$^s$-N(R')₂;
Ring A$^s$ is an optionally substituted 3-20 membered monocyclic, bicyclic or polycyclic ring having 0-10 heteroatoms independently selected from oxygen, nitrogen, sulfur, phosphorus and silicon;
each R' is independently —R, —C(O)R, —C(O)OR, or —S(O)₂R;
each R is independently —H, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, C$_{6-30}$ aryl, C$_{6-30}$ arylaliphatic, C$_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, $P^L$ is P(=W). In some embodiments, $P^L$ is P. In some embodiments, $P^L$ is P→B(R')$_3$. In some embodiments, P of $P^L$ is chiral. In some embodiments, P of $P^L$ is Rp. In some embodiments, P of $P^L$ is Sp.

In some embodiments, a provided compound, e.g., a compound of formula V, has the structure of formula V-a:

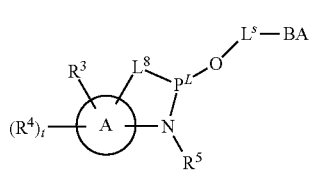

V-a or a salt thereof, wherein each variable is independently as described in the present disclosure. In some embodiments, a provided compound of formula V has the structure of formula V-a.

In some embodiments, a provided compound, e.g., a compound of formula V, has the structure of formula V-b:

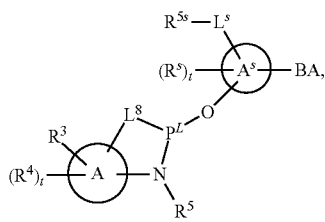

V-b or a salt thereof, wherein each variable is independently as described in the present disclosure. In some embodiments, a provided compound of formula V has the structure of formula V-b.

In some embodiments, a provided compound, e.g., a compound of formula V, has the structure of formula V-c-1:

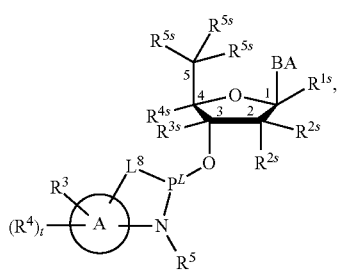

V-c-1 or a salt thereof, wherein each variable is independently as described in the present disclosure. In some embodiments, a provided compound of formula V has the structure of formula V-c-1.

In some embodiments, a provided compound, e.g., a compound of formula V, has the structure of formula V-c-2:

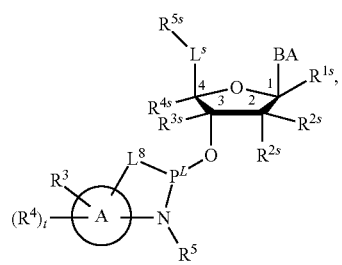

V-c-2 or a salt thereof, wherein each variable is independently as described in the present disclosure. In some embodiments, a provided compound of formula V has the structure of formula V-c-2.

In some embodiments, a provided compound, e.g., a compound of formula V, has the structure of formula V-d:

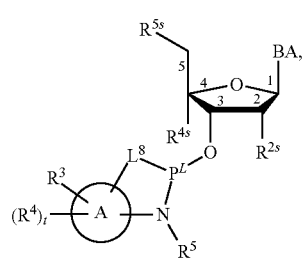

V-d or a salt thereof, wherein each variable is independently as described in the present disclosure. In some embodiments, a provided compound of formula V has the structure of formula V-d.

In some embodiments, a provided compound, e.g., a compound of formula V, has the structure of formula V-e:

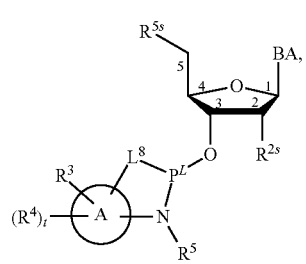

V-e or a salt thereof, wherein each variable is independently as described in the present disclosure. In some embodiments, a provided compound of formula V has the structure of formula V-e.

In some embodiments, a compound of formula V, V-a, V-b, V-c-1, V-c-2, V-d, or V-e, can be prepared from a compound of formula I, I-a, I-a-1, I-a-2, I-b, I-c, I-d, I-e, II, II-a, II-b, III, III-a, III-b, etc. In some embodiments,

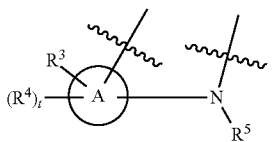

is as described for formula I, I-a, I-a-1, I-a-2, I-b, I-c, I-d, I-e, II, II-a, II-b, III, III-a, III-b, etc. In some embodiments, a compound of formula IV, IV-a, IV-b, IV-c-1, IV-c-2, IV-d, or IV-e has a structure such that

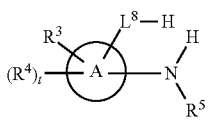

is a compound having the structure of II, II-a, or II-b.

In some embodiments, the present disclosure provides a compound having the structure of formula VI:

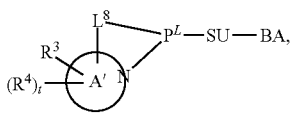

VI or a salt thereof, wherein each variable is independently as described in the present disclosure.

In some embodiments, a provided compound, e.g., a compound of formula VI, has the structure of formula VI-a:

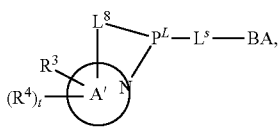

VI-a or a salt thereof, wherein Ring A' is Ring A comprising a ring nitrogen atom which is bond to P of $P^L$, and each variable is independently as described in the present disclosure. In some embodiments, a provided compound of formula VI has the structure of formula VI-a.

In some embodiments, a provided compound, e.g., a compound of formula VI, has the structure of formula VI-b:

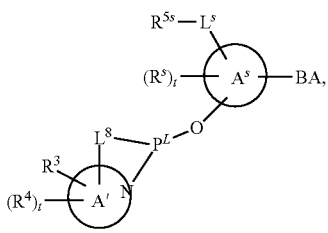

VI-b or a salt thereof, wherein each variable is independently as described in the present disclosure. In some embodiments, a provided compound of formula VI has the structure of formula VI-b.

In some embodiments, a provided compound, e.g., a compound of formula VI, has the structure of formula VI-c-1:

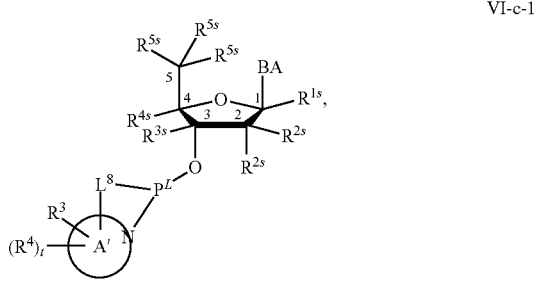

VI-c-1 or a salt thereof, wherein each variable is independently as described in the present disclosure. In some embodiments, a provided compound of formula VI has the structure of formula VI-c-1.

In some embodiments, a provided compound, e.g., a compound of formula VI, has the structure of formula VI-c-2:

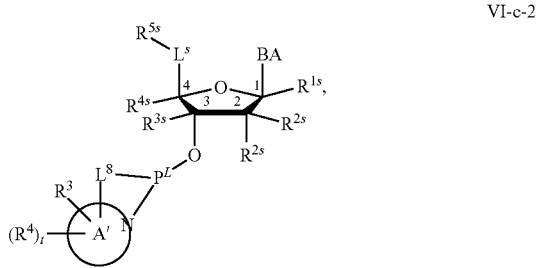

VI-c-2 or a salt thereof, wherein each variable is independently as described in the present disclosure. In some embodiments, a provided compound of formula VI has the structure of formula VI-c-2.

In some embodiments, a provided compound, e.g., a compound of formula VI, has the structure of formula VI-d:

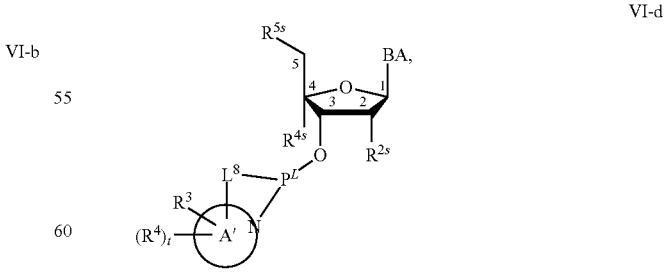

VI-d or a salt thereof, wherein each variable is independently as described in the present disclosure. In some embodiments, a provided compound of formula VI has the structure of formula VI-d.

In some embodiments, a provided compound, e.g., a compound of formula VI, has the structure of formula VI-e:

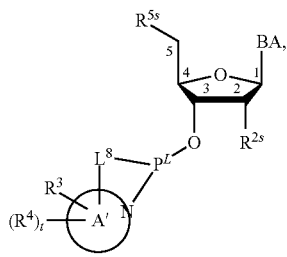

VI-e or a salt thereof, wherein each variable is independently as described in the present disclosure. In some embodiments, a provided compound of formula VI has the structure of formula VI-e.

In some embodiments, a compound of formula VI, VI-a, VI-b, VI-c-1, VI-c-2, VI-d, or VI-e, can be prepared from a compound of formula I, I-a, I-a-1, I-a-2, I-b, I-c, I-d, I-e, II, II-a, II-b, III, III-a, III-b, etc. In some embodiments,

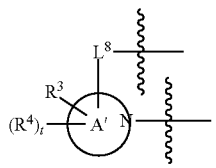

is as described for formula I, I-a, I-a-1, I-a-2, I-b, I-c, I-d, I-e, II, II-a, II-b, III, III-a, III-b, etc. In some embodiments, a compound of formula VI, VI-a, VI-b, VI-c-1, VI-c-2, VI-d, or VI-e has a structure such that

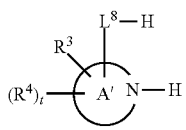

is a compound having the structure of III, III-a, or III-b.

In some embodiments, the present disclosure provides synthetic methods, comprising providing a provided compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof. In some embodiments, the present disclosure provides synthetic methods, comprising providing a provided compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, the present disclosure provides methods for stereoselective synthesis, comprising providing a provided compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, the present disclosure provides methods for stereoselective synthesis, comprising providing a provided compound of formula I, I-a, I-a-1, I-a-2, I-b, I-c, I-d, I-e, II, II-a, II-b, III, III-a, or III-b, or a salt thereof, is a chiral auxiliary. In some embodiments, the present disclosure provides methods for preparation of a phosphoramidite, comprising providing a provided compound of formula I, I-a, I-a-1, I-a-2, I-b, I-c, I-d, I-e, II, II-a, II-b, III, III-a, or III-b, or a salt thereof. In some embodiments, the present disclosure provides methods for stereoselective preparation of a phosphoramidite, comprising providing a provided compound of formula I, I-a, I-a-1, I-a-2, I-b, I-c, I-d, I-e, II, II-a, II-b, III, III-a, or III-b. In some embodiments, a phosphoramidite has the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof. In some embodiments, a phosphoramidite has the structure of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, the present disclosure provides methods for preparing nucleic acids, comprising providing a compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, VI-e, etc. In some embodiments, the present disclosure provides methods for preparing nucleic acids, comprising providing a compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, VI-e, etc. In some embodiments, the present disclosure provides methods for stereoselective (chirally controlled) preparation of nucleic acids, comprising providing a compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, VI-e, etc. In some embodiments, the present disclosure provides methods for stereoselective (chirally controlled) preparation of nucleic acids, comprising providing a compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, VI-e, etc. In some embodiments, provided compounds of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, VI-e, etc. is useful for oligonucleotide synthesis. In some embodiments, provided compounds of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, are phosphoramidites for oligonucleotide synthesis. In some embodiments, provided compounds are particularly useful for chirally controlled synthesis of oligonucleotides comprising one or more chiral internucleotidic linkages, wherein at least one chiral internucleotidic linkage is formed with chiral control. In some embodiments, the present disclosure provides methods for oligonucleotide synthesis, comprising providing a provided compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof. In some embodiments, the present disclosure provides methods for oligonucleotide synthesis, comprising providing a provided compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, a provided method is a chiral controlled method for preparing oligonucleotides comprising one or more chiral internucleotidic linkages, wherein at least one chiral internucleotidic linkage is formed with chiral control. In some embodiments, provided technologies (reagents, methods, etc.) provide chirally controlled oligonucleotide compositions of the oligonucleotides which comprise one or more chiral internucleotidic linkages, wherein at least one chiral internucleotidic linkage has diastereomeric purity of at least 80%, 85%, 86%, 87%, 88%, 89%, 90%, 91%, 92%, 93%, 94%, 95%, 96%, 97%, 98%, 99% within the composition. In some embodiments, provided technologies provide chirally controlled oligonucleotide compositions of the oligonucleotides which comprise one or more chiral internucleotidic linkages, wherein each chiral internucleotidic linkage has diastereomeric purity of at least 80%, 85%, 86%, 87%, 88%, 89%, 90%, 91%, 92%, 93%, 94%, 95%, 96%, 97%, 98%, 99% within the composition. In some embodiments, provided technologies provides oligonucleotides with diastereomeric purity of at least 80%, 85%, 86%, 87%, 88%, 89%, 90%, 91%, 92%, 93%, 94%, 95%, 96%, 97%, 98%, 99% at at least one chiral internucleotidic linkage. In some embodiments, provided technologies provides oligonucleotides with diastereomeric purity of at least 80%, 85%, 86%, 87%, 88%, 89%, 90%, 91%, 92%, 93%, 94%, 95%, 96%, 97%, 98%, 99% at each chiral internucleotidic linkage. In some embodiments, provided oligonucleotides comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 chiral internucleotidic linkages. In some embodiments, provided oligonucleotides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 15, 16, 17, 18, 19, 20, 21, 22, 23, 24, 25, 26, 27, 28, 29, 30, 35, 40, 45, or 50 nucleobases. In some embodiments, provided oligonucleotides comprise 5-200, 5-150, 5-100, 5-50, 5-40, 5-35, 5-30, 5-25, 10-200, 10-150, 10-100, 10-50, 10-40, 10-35, 10-30, 10-25, 15-200, 15-150, 15-100, 15-50, 15-40, 15-35, 15-30, or 15-25 nucleobases. In some embodiments, provided methods comprise oligonucleotide synthesis using solid supports. In some embodiments, provided oligonucleotides are connected to solid supports. In some embodiments, provided oligonucleotides are cleaved from solid support. In some embodiments, provided oligonucleotides comprise at least two chemically different types of internucleotidic linkages. In some embodiments, provided oligonucleotides comprise at least two chemically different types of chiral internucleotidic linkages, each of which is independently Rp or Sp. In some embodiments, the chemically different types of chiral internucleotidic linkages are all Sp. In some embodiments, the chemically different types of chiral internucleotidic linkages are all Rp. In some embodiments, some of the chemically different types of chiral internucleotidic linkages are Rp while the others are Sp. In some embodiments, some of the chemically different types of chiral internucleotidic linkages are Rp, some are Sp, while the others are not chirally controlled.

In some embodiments, a provided method is a method described in US/2011/0294124, US/2015/0211006, US/2017/0037399, WO/2017/015555, and WO/2017/062862, methods of each of which are incorporated herein by reference, wherein a chiral auxiliary in the method is replaced with a compound of formula I, I-a, I-a-1, I-a-2, I-b, I-c, I-d, I-e, II, II-a, II-b, III, III-a, III-b, and/or a phosphoramidite comprising a chiral phosphorus in the method is replaced with a compound of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof.

As readily appreciated by a person having ordinary skill in the art, provided technologies are capable of providing oligonucleotides of various base sequences with precise control of chemical modifications (e.g., base modifications, sugar modifications, internucleotidic linkage modifications, etc.) and/or chiral internucleotidic linkage stereochemistry. In some embodiments, provided methods are useful for preparing oligonucleotides and compositions thereof described in US/2015/0211006, US/2017/0037399, WO/2017/015555, and WO/2017/062862, each of which is incorporated herein by reference. In some embodiments, the present disclosure provides oligonucleotides which are intermediate for preparing oligonucleotides and compositions thereof described in US/2011/0294124, US/2015/0211006, US/2017/0037399, WO/2017/015555, and WO/2017/062862, for example, after completion of base sequence but before cleavage from solid support.

In some embodiments, an internucleotidic linkage formed using provided technologies are one described in US/2015/0211006, US/2017/0037399, WO/2017/015555, and WO/2017/062862, each of which is incorporated herein by reference. In some embodiments, an internucleotidic linkage is a chiral internucleotidic linkage in that it comprises a chiral linkage phosphorus. In some embodiments, an internucleotidic linkage has the structure of formula VII:

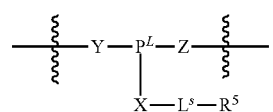

VII or a salt form thereof, wherein:
$P^L$ is P(=W), P, or P→B(R')$_3$;
W is O, S or Se;
each of $R^1$ and $R^5$ is independently —H, -$L^s$-R, halogen, —CN, —NO$_2$, -$L^s$-Si(R)$_3$, —OR, —SR, or —N(R)$_2$;
each of X, Y and Z is independently —O—, —S—, —N(-$L^s$-$R^1$)—, or $L^s$;
each $L^s$ is independently a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon; or H—X—$L^s$-$R^5$ has the structure of formula I, I-a, I-a-1, I-a-2, I-b, I-c, I-d, I-e, II, II-a, II-b, III, III-a, III-b, or a salt thereof.

In some embodiments, an internucleotidic linkage of formula VII is a chiral internucleotidic linkage. In some embodiments, P in $P^L$ is a chiral linkage phosphorus. In some embodiments, a chiral linkage phosphorus is Rp. In some embodiments, a chiral linkage phosphorus is Sp. In some embodiments, $P^L$ is P(=W). In some embodiments, $P^L$ is P. In some embodiments, $P^L$ is P→B(R')$_3$.

In some embodiments, an internucleotidic linkage of formula VII having the structure of formula VII-a-1:

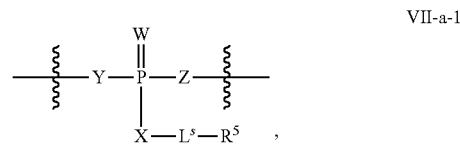

or a salt form thereof, wherein each other variable is independently as described in the present disclosure.

In some embodiments, an internucleotidic linkage of formula VII or VII-a-1 having the structure of formula VII-a-2:

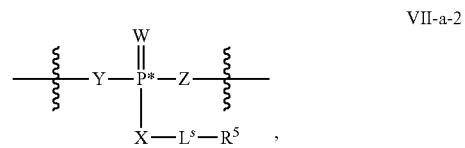

or a salt form thereof, wherein P* is an asymmetric phosphorus atom, and each other variable is independently as described in the present disclosure.

In some embodiments, an internucleotidic linkage has the structure of formula VII-b:

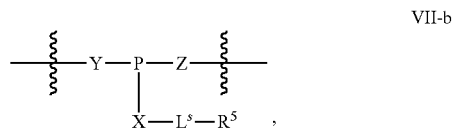

or a salt form thereof, wherein each variable is independently as described in the present disclosure. In some embodiments, an internucleotidic linkage of formula VII has the structure of formula VII-b.

In some embodiments, an internucleotidic linkage of formula VII having the structure of formula VII-c:

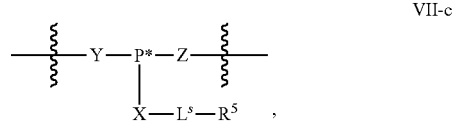

or a salt form thereof, wherein P* is an asymmetric phosphorus atom, and each other variable is independently as described in the present disclosure.

In some embodiments, an internucleotidic linkage has the structure of formula VII-d:

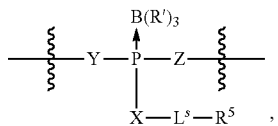

or a salt form thereof, wherein each variable is independently as described in the present disclosure.

In some embodiments, an internucleotidic linkage of formula VII-e having the structure of:

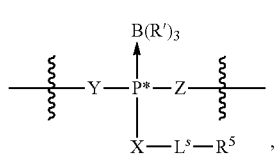

or a salt form thereof, wherein P* is an asymmetric phosphorus atom, and each other variable is independently as described in the present disclosure.

In some embodiments, W is O. In some embodiments, W is S. In some embodiments, —X-$L^s$-$R^5$ is —SR. In some embodiments, —X-$L^s$-$R^5$ is —SH. In some embodiments, —X-$L^s$-$R^5$ is —SR, wherein R is not hydrogen. In some embodiments, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof. In some embodiments, $R^7$ is —OH, and $R^6$ is —H or —R. In some embodiments, $R^6$ is —H. In some embodiments, $R^6$ is —R, wherein R is not hydrogen. In some embodiments, R is a capping group. Suitable capping groups for oligonucleotide synthesis are well known by a personal having ordinary skill in the art, for example, those described in US/2015/0211006, US/2017/0037399, WO/2017/015555, and WO/2017/062862, each of which is incorporated herein by reference. In some embodiments, $R^6$ is —C(O)R. As described in the present disclosure, in some embodiments, immediately after coupling, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof, wherein $R^5$ is —H, and a linkage may have the structure of formula VII, VII-a-1, VII-a-2, VII-b, VII-c, VII-d, or VII-e, or a salt form thereof. In some embodiments, after capping, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof, wherein $R^5$ is a capping group, for example, a group having the structure of —C(O)R, and a linkage may have the structure of formula VII, VII-a-1, VII-a-2, VII-b, VII-c, VII-d, or VII-e, or a salt form thereof. In some embodiments, the nitrogen atom to which $R^5$ is attached is capped with a R—C(O)— group, forming a group of —N($R^5$)(—C(O)—R). In some embodiments, after additional chemical modification steps, a linkage may have the structure of formula VII, VII-a-1, VII-a-2, VII-b, VII-c, VII-d, or VII-e, or a salt form thereof.

In some embodiments, the present disclosure provides oligonucleotides comprising one or more internucleotidic linkages having the structure of formula VII, VII-a-1, VII-a-2, VII-b, VII-c, VII-d, or VII-e, or a salt form thereof. In some embodiments, provided oligonucleotides comprise 1-100, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70 80, 90, 100 or more internucleotidic linkages having the structure of formula VII, VII-a-1, VII-a-2, VII-b, VII-c, VII-d, or VII-e, or a salt form thereof. In some embodiments, provided oligonucleotides comprise one or more such internucleotidic linkages. In some embodiments, provided oligonucleotides comprise two or more such internucleotidic linkages. In some embodiments, provided oligonucleotides comprise three or more such internucleotidic linkages. In some embodiments, provided oligonucleotides comprise four or more such internucleotidic linkages. In some embodiments, provided oligonucleotides comprise five or more such internucleotidic linkages. In some embodiments, provided oligonucleotides comprise six or more such internucleotidic linkages. In some embodiments, provided oligonucleotides comprise seven or more such internucleotidic linkages. In some embodiments, provided oligonucleotides comprise eight or more such internucleotidic linkages. In some embodiments, provided oligonucleotides comprise nine or more such internucleotidic linkages. In some embodiments, provided oligonucleotides comprise ten or more such internucleotidic linkages. In some embodiments, provided oligonucleotides comprise 11 or more such internucleotidic linkages. In some embodiments, provided oligonucleotides comprise 12 or more such internucleotidic linkages. In some embodiments, provided oligonucleotides comprise 13 or more such internucleotidic linkages. In some embodiments, provided oligonucleotides comprise 14 or more such internucleotidic linkages. In some embodiments, provided oligonucleotides comprise 15 or more such internucleotidic linkages. In some embodiments, provided oligonucleotides comprise 16 or more such internucleotidic linkages. In some embodiments, provided oligonucleotides comprise 17 or more such internucleotidic linkages. In some embodiments, provided oligonucleotides comprise 18 or more such internucleotidic linkages. In some embodiments, provided oligonucleotides comprise 19 or more such internucleotidic linkages. In some embodiments, provided oligonucleotides comprise 20 or more such internucleotidic linkages. In some embodiments, provided oligonucleotides comprise 21 or more such internucleotidic linkages. In some embodiments, provided oligonucleotides comprise 25 or more such internucleotidic linkages. In some embodiments, such an internucleotidic linkage is chiral. In some embodiments, as described in the present disclosure, each —X-$L^s$-$R^5$ is independently of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof. In some embodiments, provided oligonucleotides have the structure of formula VIII or a salt thereof.

In some embodiments, a provided oligonucleotide comprises at least two types of internucleotidic linkages, each independently having the structure of formula VII, VII-a-1, VII-a-2, VII-b, VII-c, VII-d, or VII-e, or a salt form thereof. In some embodiments, a provided oligonucleotide comprise at least two types of chiral internucleotidic linkages, each independently having the structure of formula VII, VII-a-1, VII-a-2, VII-b, VII-c, VII-d, or VII-e, or a salt form thereof. In some embodiments, the two types may have the same or different phosphorus configuration (Rp or Sp), or one or both can be stereorandom (e.g., formed not through chirally controlled synthesis). In some embodiments, a stereorandom linkage has diastereomeric purity less than 85%, 80%, 75%, 70%, 65%, 60%, or 55%. In some embodiments, P* is not stereorandom, and is either Rp or Sp. In some embodiments, in one type W is S and in the other type W is O. In some embodiments, in one type W is S and in the other type W is O, and for both types —X-$L^s$-$R^5$ is independently of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof. In some embodiments, one type is a natural phosphate linkage (—O—P(O)(OH)—O—, which may exist as —O—P(O)(O⁻)—O—, for example, at certain pH and/or when provided as a salt), and the other is a phosphorothioate linkage (—O—P(O)(SH)—O—, which may exist as —O—P(O)(S⁻)—O—, for example, at certain pH and/or when provided as a salt).

In some embodiments, a provided compound, e.g., an oligonucleotide, has the structure of formula VIII:

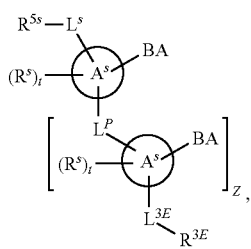

VIII or a salt thereof, wherein:
$R^{5s}$ is independently R' or —OR';
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each Ring $A^s$ is independently an optionally substituted 3-20 membered monocyclic, bicyclic or polycyclic ring having 0-10 heteroatoms independently selected from oxygen, nitrogen, sulfur, phosphorus and silicon;
each $R^s$ is independently —H, halogen, —CN, —N$_3$, —NO, —NO$_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;
each t is independently 0-20;
each BA is independently an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety;
each $L^P$ is independently an internucleotidic linkage;
z is 1-1000;
$L^{3E}$ is -$L^s$- or -$L^s$-$L^s$-;
$R^{3E}$ is —R', -$L^s$-R', —OR', or a solid support;
each R' is independently —R, —C(O)R, —C(O)OR, or —S(O)$_2$R;
each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each $L^P$ independently has the structure of VII, VII-a-1, VII-a-2, VII-b, VII-c, VII-d, or VII-e, or a salt form thereof. In some embodiments, each $L^P$ independently has the structure of VII, VII-a-1, VII-a-2, VII-b, VII-c, VII-d, or VII-e, and in each $L^P$, —X-$L^s$-$R^5$ independently has a structure such that H—X-$L^s$-$R^5$ is a compound of formula I, I-a, I-a-1, I-a-2, I-b, I-c, I-d, I-e, II, II-a, II-b, III, III-a, or III-b, or a salt thereof.

In some embodiments, at least one $L^P$ comprises W, wherein W is S. In some embodiments, at least 2, 3, 4, 5, 6, 7, 8, 9, 10, 11, 12, 13, 14, 15, 16, 17, 18, 19, 20 $L^P$ comprises W, wherein W is S. In some embodiments, at least one $L^P$ comprises W, wherein W is O. In some embodiments, at least 2, 3, 4, 5, 6, 7, 8, 9, 10, 11, 12, 13, 14, 15, 16, 17, 18, 19, 20 $L^P$ comprises W, wherein W is O. In some embodiments, $L^P$ independently comprises —X-$L^s$-$R^5$ wherein H—X-$L^s$-$R^5$ has the structure of formula I, I-a, I-a-1, I-a-2, I-b, I-c, I-d, I-e, II, II-a, II-b, III, III-a, or III-b, or a salt thereof.

In some embodiments, a provided compound is a compound selected from Table 1 or a salt thereof. In some embodiments, a provided compound is a stereoisomer of a compound selected from Table 1 or a salt thereof. In some embodiments, a provided compound is a diastereomer of a compound selected from Table 1 or a salt thereof. In some embodiments, a provided compound is an enantiomer of a compound selected from Table 1 or a salt thereof.

In some embodiments, a provided compound is a compound selected from Table 2 or a salt thereof. In some embodiments, a provided compound is a stereoisomer of a compound selected from Table 2 or a salt thereof. In some embodiments, a provided compound is a diastereomer of a compound selected from Table 2 or a salt thereof. In some embodiments, a provided compound is an enantiomer of a compound selected from Table 2 or a salt thereof.

In some embodiments, a provided compound is a compound selected from Table 3 or a salt thereof. In some embodiments, a provided compound is a stereoisomer of a compound selected from Table 3 or a salt thereof. In some embodiments, a provided compound is a diastereomer of a compound selected from Table 3 or a salt thereof. In some embodiments, a provided compound is an enantiomer of a compound selected from Table 3 or a salt thereof.

In some embodiments, a provided compound is a compound selected from Table 4 or a salt thereof. In some embodiments, a provided compound is a stereoisomer of a compound selected from Table 4 or a salt thereof. In some embodiments, a provided compound is a diastereomer of a compound selected from Table 4 or a salt thereof. In some embodiments, a provided compound is an enantiomer of a compound selected from Table 4 or a salt thereof.

In some embodiments, a provided compound has a purity of 60%-100%. In some embodiments, a provided compound has a purity of at least 60%, 65%, 70%, 75%, 80%, 85%, 90%, 91%, 92%, 93%, 94%, 95%, 96%, 97%, 98%, or 99%. In some embodiments, a provided compound has a purity of at least 60%. In some embodiments, a provided compound has a purity of at least 70%. In some embodiments, a provided compound has a purity of at least 80%. In some embodiments, a provided compound has a purity of at least 85%. In some embodiments, a provided compound has a purity of at least 90%. In some embodiments, a provided compound has a purity of at least 91%. In some embodiments, a provided compound has a purity of at least 92%. In some embodiments, a provided compound has a purity of at least 93%. In some embodiments, a provided compound has a purity of at least 94%. In some embodiments, a provided compound has a purity of at least 95%. In some embodiments, a provided compound has a purity of at least 96%. In some embodiments, a provided compound has a purity of at least 97%. In some embodiments, a provided compound has a purity of at least 98%. In some embodiments, a provided compound has a purity of at least 99%. In some embodiments, a provided compound has a purity of at least 99.5%.

In some embodiments, a provided compound, e.g., a chiral auxiliary, a phosphoramidite, an oligonucleotide, etc., has a diastereomeric purity of at least 60%, 65%, 70%, 75%, 80%, 85%, 90%, 91%, 92%, 93%, 94%, 95%, 96%, 97%, 98%, or 99%. In some embodiments, a provided compound has a diastereomeric purity of at least 60%. In some embodiments, a provided compound has a diastereomeric purity of at least 70%. In some embodiments, a provided compound has a diastereomeric purity of at least 80%. In some embodiments, a provided compound has a diastereomeric purity of at least 85%. In some embodiments, a provided compound has a diastereomeric purity of at least 90%. In some embodiments, a provided compound has a diastereomeric purity of at least 91%. In some embodiments, a provided compound has a diastereomeric purity of at least 92%. In some embodiments, a provided compound has a diastereomeric purity of at least 93%. In some embodiments, a provided compound has a diastereomeric purity of at least 94%. In some embodiments, a provided compound has a diastereomeric purity of at least 95%. In some embodiments, a provided compound has a diastereomeric purity of at least 96%. In some embodiments, a provided compound has a diastereomeric purity of at least 97%. In some embodiments, a provided compound has a diastereomeric purity of at least 98%. In some embodiments, a provided compound has a diastereomeric purity of at least 99%. In some embodiments, a provided compound has a diastereomeric purity of at least 99.5%.

In some embodiments, a chiral element, e.g., a chiral center (carbon, phosphorus, etc.) of a provided compound has a diastereomeric purity of 60%-100%. In some embodiments, a chiral element, e.g., a chiral center (carbon, phosphorus, etc.) of a provided compound has a diastereomeric purity of at least 60%, 65%, 70%, 75%, 80%, 85%, 90%, 91%, 92%, 93%, 94%, 95%, 96%, 97%, 98%, or 99%. In some embodiments, a chiral element is a chiral carbon. In some embodiments, a chiral element is a chiral phosphorus (e.g., a linkage phosphorus atom in a chiral internucleotidic linkage). In some embodiments, a chiral element has a diastereomeric purity of at least 60%. In some embodiments, a chiral center has a diastereomeric purity of at least 70%. In some embodiments, a chiral center has a diastereomeric purity of at least 80%. In some embodiments, a chiral center has a diastereomeric purity of at least 85%. In some embodiments, a chiral center has a diastereomeric purity of at least 90%. In some embodiments, a chiral center has a diastereomeric purity of at least 91%. In some embodiments, a chiral center has a diastereomeric purity of at least 92%. In some embodiments, a chiral center has a diastereomeric purity of at least 93%. In some embodiments, a chiral center has a diastereomeric purity of at least 94%. In some embodiments, a chiral center has a diastereomeric purity of at least 95%. In some embodiments, a chiral center has a diastereomeric purity of at least 96%. In some embodiments, a chiral center has a diastereomeric purity of at least 97%. In some embodiments, a chiral center has a diastereomeric purity of at least 98%. In some embodiments, a chiral center has a diastereomeric purity of at least 99%. In some embodiments, a chiral center has a diastereomeric purity of at least 99.5%.

In some embodiments, at least 1, 2, 3, 4, 5, 6, 7, 8, 9 or more chiral elements of a provided compound each independently have a diastereomeric purity as described herein. In some embodiments, at least 1, 2, 3, 4, 5, 6, 7, 8, 9 or more chiral carbon centers of a provided compound each independently have a diastereomeric purity as described herein. In some embodiments, at least 1, 2, 3, 4, 5, 6, 7, 8, 9 or more chiral phosphorus centers of a provided compound each independently have a diastereomeric purity as described herein.

In some embodiments, at least 5%-100% of all chiral elements of a provided compound each independently have a diastereomeric purity as described herein. In some embodiments, at least 5%, 10%, 15%, 20%, 25%, 30%, 40%, 45%, 50%, 55%, 60%, 65%, 70%, 75%, 80%, 85%, 90%, 95%, or 100% of all chiral elements of a provided compound each independently have a diastereomeric purity as described herein. In some embodiments, at least 5%-100% of all chiral phosphorus centers of a provided compound each independently have a diastereomeric purity as described herein. In some embodiments, at least 5%, 10%, 15%, 20%, 25%, 30%, 40%, 45%, 50%, 55%, 60%, 65%, 70%, 75%, 80%, 85%, 90%, 95%, or 100% of all chiral phosphorus centers of a provided compound each independently have a diastereomeric purity as described herein.

In some embodiments, each chiral element independently has a diastereomeric purity as described herein. In some embodiments, each chiral center independently has a diastereomeric purity as described herein. In some embodiments, each chiral carbon center independently has a diastereomeric purity as described herein. In some embodiments, each chiral phosphorus center independently has a diastereomeric purity as described herein.

In some embodiments, a provided compound has an enantiomeric purity of 60%-100%. In some embodiments, a provided compound has an enantiomeric purity of at least 60%, 65%, 70%, 75%, 80%, 85%, 90%, 91%, 92%, 93%, 94%, 95%, 96%, 97%, 98%, or 99%. In some embodiments, a provided compound has an enantiomeric purity of at least 60%. In some embodiments, a provided compound has an enantiomeric purity of at least 70%. In some embodiments, a provided compound has an enantiomeric purity of at least 80%. In some embodiments, a provided compound has an enantiomeric purity of at least 85%. In some embodiments, a provided compound has an enantiomeric purity of at least 90%. In some embodiments, a provided compound has an enantiomeric purity of at least 91%. In some embodiments, a provided compound has an enantiomeric purity of at least 92%. In some embodiments, a provided compound has an enantiomeric purity of at least 93%. In some embodiments, a provided compound has an enantiomeric purity of at least 94%. In some embodiments, a provided compound has an enantiomeric purity of at least 95%. In some embodiments, a provided compound has an enantiomeric purity of at least 96%. In some embodiments, a provided compound has an enantiomeric purity of at least 97%. In some embodiments, a provided compound has an enantiomeric purity of at least 98%. In some embodiments, a provided compound has an enantiomeric purity of at least 99%. In some embodiments, a provided compound has an enantiomeric purity of at least 99.5%.

In some embodiments, a chiral element, e.g., a chiral center (carbon, phosphorus, etc.) of a provided compound has an enantiomeric purity of 60%-100%. In some embodiments, a chiral element, e.g., a chiral center (carbon, phosphorus, etc.) of a provided compound has an enantiomeric purity of at least 60%, 65%, 70%, 75%, 80%, 85%, 90%, 91%, 92%, 93%, 94%, 95%, 96%, 97%, 98%, or 99%. In some embodiments, a chiral element is a chiral carbon. In some embodiments, a chiral element is a chiral phosphorus (e.g., a linkage phosphorus atom in a chiral internucleotidic linkage). In some embodiments, a chiral element has an enantiomeric purity of at least 60%. In some embodiments, a chiral center has an enantiomeric purity of at least 70%. In some embodiments, a chiral center has an enantiomeric purity of at least 80%. In some embodiments, a chiral center has an enantiomeric purity of at least 85%. In some embodiments, a chiral center has an enantiomeric purity of at least 90%. In some embodiments, a chiral center has an enantiomeric purity of at least 91%. In some embodiments, a chiral center has an enantiomeric purity of at least 92%. In some embodiments, a chiral center has an enantiomeric purity of at least 93%. In some embodiments, a chiral center has an enantiomeric purity of at least 94%. In some embodiments, a chiral center has an enantiomeric purity of at least 95%. In some embodiments, a chiral center has an enantiomeric purity of at least 96%. In some embodiments, a chiral center has an enantiomeric purity of at least 97%. In some embodiments, a chiral center has an enantiomeric purity of at least 98%. In some embodiments, a chiral center has an enantiomeric purity of at least 99%. In some embodiments, a chiral center has an enantiomeric purity of at least 99.5%.

In some embodiments, at least 1, 2, 3, 4, 5, 6, 7, 8, 9 or more chiral elements of a provided compound each independently have an enantiomeric purity as described herein. In some embodiments, at least 1, 2, 3, 4, 5, 6, 7, 8, 9 or more chiral carbon centers of a provided compound each independently have an enantiomeric purity as described herein. In some embodiments, at least 1, 2, 3, 4, 5, 6, 7, 8, 9 or more chiral phosphorus centers of a provided compound each independently have an enantiomeric purity as described herein.

In some embodiments, at least 5%-100% of all chiral elements of a provided compound each independently have an enantiomeric purity as described herein. In some embodiments, at least 5%, 10%, 15%, 20%, 25%, 30%, 40%, 45%, 50%, 55%, 60%, 65%, 70%, 75%, 80%, 85%, 90%, 95%, or 100% of all chiral elements of a provided compound each independently have an enantiomeric purity as described herein. In some embodiments, at least 5%-100% of all chiral phosphorus centers of a provided compound each independently have an enantiomeric purity as described herein. In some embodiments, at least 5%, 10%, 15%, 20%, 25%, 30%, 40%, 45%, 50%, 55%, 60%, 65%, 70%, 75%, 80%, 85%, 90%, 95%, or 100% of all chiral phosphorus centers of a provided compound each independently have an enantiomeric purity as described herein.

In some embodiments, each chiral element independently has an enantiomeric purity as described herein. In some embodiments, each chiral center independently has an enantiomeric purity as described herein. In some embodiments, each chiral carbon center independently has an enantiomeric purity as described herein. In some embodiments, each chiral phosphorus center independently has an enantiomeric purity as described herein.

In some embodiments, the present disclosure provides methods for stereoselective formation of chiral elements, e.g., chiral centers. In some embodiments, the present disclosure provides methods for stereoselective preparation of a phosphoramidite, comprising providing a compound of formula I, I-a, I-a-1, I-a-2, I-b, I-c, I-d, I-e, II, II-a, II-b, III, III-a, III-b, or a salt thereof. In some embodiments, a phosphoramidite has the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof. In some embodiments, a phosphoramidite has the structure of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, provided compounds, e.g., a chiral auxiliary having the structure of formula I, I-a, I-a-1, I-a-2, I-b, I-c, I-d, I-e, II, II-a, II-b, III, III-a, III-b, or a salt thereof, or a phosphoramidite having the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, etc., are useful for oligonucleotide preparation. In some embodiments, the present disclosure provides technologies (e.g., compounds, methods, etc.) for oligonucleotide synthesis. In some embodiments, the present disclosure provides methods for oligonucleotide synthesis, comprising providing a compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof. In some embodiments, the present disclosure provides methods for oligonucleotide synthesis, comprising providing a compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, the present disclosure provides methods for chirally controlled oligonucleotide synthesis, comprising providing a compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof. In some embodiments, the present disclosure provides methods for chirally controlled oligonucleotide synthesis, comprising providing a compound of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. Example prepared oligonucleotides are extensively described in the present disclosure. In some embodiments, example oligonucleotides have the structure of formula VIII or a salt thereof.

In some embodiments, the present disclosure provides methods, e.g., methods for preparing chiral auxiliaries, phosphoramidites, oligonucleotides, etc., with high stereoselectivity. In some embodiments, the present disclosure provides methods with high diastereoselectivity. In some embodiments, the present disclosure provides methods with high enantioselectivity. In some embodiments, the present disclosure provides methods with both high diastereoselectivity and high enantioselectivity. In some embodiments, a selectivity is about 60%-100%. In some embodiments, a selectivity is at least 60%, 65%, 70%, 75%, 80%, 85%, 90%, 91%, 92%, 93%, 94%, 95%, 96%, 97%, 98%, or 99%. In some embodiments, a diastereoselectivity is at least 60%, 65%, 70%, 75%, 80%, 85%, 90%, 91%, 92%, 93%, 94%, 95%, 96%, 97%, 98%, or 99%. In some embodiments, a enantioselectivity is at least 60%, 65%, 70%, 75%, 80%, 85%, 90%, 91%, 92%, 93%, 94%, 95%, 96%, 97%, 98%, or 99%. In some embodiments, both a diastereoselectivity and an enantioselectivity are at least 60%, 65%, 70%, 75%, 80%, 85%, 90%, 91%, 92%, 93%, 94%, 95%, 96%, 97%, 98%, or 99%. In some embodiments, a selectivity is at least 60%. In some embodiments, a selectivity is at least 70%. In some embodiments, a selectivity is at least 80%. In some embodiments, a selectivity is at least 85%. In some embodiments, a selectivity is at least 90%. In some embodiments, a selectivity is at least 91%. In some embodiments, a selectivity is at least 92%. In some embodiments, a selectivity is at least 93%. In some embodiments, a selectivity is at least 94%. In some embodiments, a selectivity is at least 95%. In some embodiments, a selectivity is at least 96%. In some embodiments, a selectivity is at least 97%. In some embodiments, a selectivity is at least 98%. In some embodiments, a selectivity is at least 99%. In some embodiments, a selectivity is at least 99.5%.

In some embodiments, provided methods provide high yields. In some embodiments, a yield is 50%-100%. In some embodiments, a yield is at least 60%, 65%, 70%, 75%, 80%, 85%, 90%, 91%, 92%, 93%, 94%, 95%, 96%, 97%, 98% or 99%. In some embodiments, a yield is at least 60%. In some embodiments, a yield is at least 65%. In some embodiments, a yield is at least 70%. In some embodiments, a yield is at least 75%. In some embodiments, a yield is at least 80%. In some embodiments, a yield is at least 85%. In some embodiments, a yield is at least 90%. In some embodiments, a yield is at least 91%. In some embodiments, a yield is at least 92%. In some embodiments, a yield is at least 93%. In some embodiments, a yield is at least 94%. In some embodiments, a yield is at least 95%. In some embodiments, a yield is at least 96%. In some embodiments, a yield is at least 97%. In some embodiments, a yield is at least 98%. In some embodiments, a yield is at least 99%.

In some embodiments, provided methods provide high yields as described herein, and also high stereoselectivity as described herein. In some embodiments, provided methods provides yields of 70%, 75%, 80%, 85%, 90%, 91%, 92%, 93%, 94%, 95%, 96%, 97%, 98%, 99% or more, and diastereoselectivity of 95%, 96%, 97%, 98%, 99%, or more. In some embodiments, provided methods provides yields of 70% or more, and diastereoselectivity of 95% or more. In some embodiments, provided methods provides yields of 75% or more, and diastereoselectivity of 95% or more. In some embodiments, provided methods provides yields of 80% or more, and diastereoselectivity of 95% or more. In some embodiments, provided methods provides yields of 85% or more, and diastereoselectivity of 95% or more. In some embodiments, provided methods provides yields of 90% or more, and diastereoselectivity of 95% or more. In some embodiments, provided methods provides yields of 95% or more, and diastereoselectivity of 95% or more. In some embodiments, provided methods provides yields of 70% or more, and diastereoselectivity of 97% or more. In some embodiments, provided methods provides yields of 75% or more, and diastereoselectivity of 97% or more. In some embodiments, provided methods provides yields of 80% or more, and diastereoselectivity of 97% or more. In some embodiments, provided methods provides yields of 85% or more, and diastereoselectivity of 97% or more. In some embodiments, provided methods provides yields of 90% or more, and diastereoselectivity of 97% or more. In some embodiments, provided methods provides yields of 95% or more, and diastereoselectivity of 97% or more. In some embodiments, provided methods provides yields of 70% or more, and diastereoselectivity of 98% or more. In some embodiments, provided methods provides yields of 75% or more, and diastereoselectivity of 98% or more. In some embodiments, provided methods provides yields of 80% or more, and diastereoselectivity of 98% or more. In some embodiments, provided methods provides yields of 85% or more, and diastereoselectivity of 98% or more. In some embodiments, provided methods provides yields of 90% or more, and diastereoselectivity of 98% or more. In some embodiments, provided methods provides yields of 95% or more, and diastereoselectivity of 98% or more.

In some embodiments, the present disclosure provides technologies for assessing performance of a compound, e.g., yield, purity, stereoselectivity, etc., for stereoselective synthesis. In some embodiments, the present disclosure provides technologies for assessing chiral auxiliaries, e.g., those of formula I, I-a, I-a-1, I-a-2, I-b, I-c, I-d, I-e, II, II-a, II-b, III, III-a, III-b, or a salt thereof, or chiral phosphoramidites, e.g., those of IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof, for stereoselective preparation of oligonucleotides, e.g., chirally controlled formation of predetermined chirally controlled internucleotidic linkages. In some embodiments, the present disclosure recognizes that many systems cannot sufficiently differentiate performances of one or more chiral auxiliaries. Among other things, the present disclosure provides technologies, e.g., reaction systems comprising solid supports, linkers, and target oligonucleotides (e.g., dimeric, pentameric, etc.) as demonstrated in the present disclosure for assessing chiral auxiliaries. In some embodiments, such reaction systems are significantly more demanding than typical oligonucleotide synthesis cycles in that they typically provide low yields and/or selectivity when compared to typical oligonucleotide synthesis cycles. In some embodiments, a target oligonucleotide is a dC dimer on solid support.

In some embodiments, provided compounds, e.g., chiral auxiliaries, oligonucleotides, etc, may exist as salts. In some embodiments, a salt is a pharmaceutically acceptable salt. In some embodiments, each hydrogen ion that may be donated to a base (e.g., under conditions of an aqueous solution, a pharmaceutical composition, etc.) is replaced by a non-$H^+$ cation. For example, in some embodiments, a pharmaceutically acceptable salt of an oligonucleotide is an all-metal ion salt, for example, wherein each hydrogen ion (for example, of —OH, —SH, etc.) of each internucleotidic linkage (e.g., a natural phosphate linkage, a phosphorothioate diester linkage, etc.) is replaced by a metal ion. In some embodiments, a provided salt is an all-sodium salt. In some embodiments, a provided pharmaceutically acceptable salt is an all-sodium salt. In some embodiments, a provided salt is an all-sodium salt, wherein each internucleotidic linkage which is a natural phosphate linkage (acid form —O—P(O)(OH)—O—), if any, exists as its sodium salt form (—O—P(O)(ONa)—O—), and each internucleotidic linkage which is a phosphorothioate diester linkage (acid form —O—P(O)(SH)—O—), if any, exists as its sodium salt form (—O—P(O)(SNa)—O—).

In some embodiments, the present disclosure provides an oligonucleotide composition comprising a plurality of oligonucleotides which share:
1) a common base sequence;
2) a common pattern of backbone linkages;
3) common stereochemistry independently at at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 chiral internucleotidic linkages ("chirally controlled internucleotidic linkages");
which composition is chirally controlled in that level of the plurality of oligonucleotides in the composition is predetermined.

In some embodiments, the present disclosure provides an oligonucleotide composition comprising a plurality of oligonucleotides, wherein oligonucleotides of the plurality are of a particular oligonucleotide type defined by:
1) base sequence;
2) pattern of backbone linkages;
3) pattern of backbone chiral centers; and
4) pattern of backbone phosphorus modifications;
which composition is chirally controlled in that level of the plurality of oligonucleotides in the composition is predetermined.

In some embodiments, the present disclosure provides an oligonucleotide composition comprising a plurality of oligonucleotides which share:
1) a common base sequence;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, an oligonucleotide composition comprising a plurality of oligonucleotides is chirally controlled in that oligonucleotides of the plurality share a common stereochemistry independently at one or more chiral internucleotidic linkages. In some embodiments, oligonucleotides of the plurality share a common stereochemistry configuration at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or more chiral internucleotidic linkages, each of which is independently Rp or Sp In some embodiments, oligonucleotides of the plurality share a common stereochemistry configuration at each chiral internucleotidic linkages. In some embodiments, a chiral internucleotidic linkage where a predetermined level of oligonucleotides of a composition share a common stereochemistry configuration (independently Rp or Sp) is referred to as a chirally controlled internucleotidic linkage. In some embodiments, a predetermined level of oligonucleotides of a provided composition, e.g., a first plurality of oligonucleotides of certain example compositions, comprise 1-50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or more chirally controlled internucleotidic linkages. In some embodiments, at least 5 internucleotidic linkages are chirally controlled; in some embodiments, at least 10 internucleotidic linkages are chirally controlled; in some embodiments, at least 15 internucleotidic linkages are chirally controlled; in some embodiments, each chiral internucleotidic linkage is chirally controlled. In some embodiments, 0.1%-100% of chiral internucleotidic linkages are chirally controlled. In some embodiments, 0.1%-100%, for example, at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of chiral internucleotidic linkages are chirally controlled.

In some embodiments, a predetermined level of oligonucleotides is 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition. In some embodiments, a predetermined level of oligonucleotides is 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition that are of or comprise a common base sequence. In some embodiments, all oligonucleotides in a provided composition that are of or comprise a common base sequence are 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition. In some embodiments, a predetermined level of oligonucleotides is 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition that are of or comprise a common base sequence, base modifications, sugar modification and/or modified internucleotidic linkage, if any. In some embodiments, all oligonucleotides in a provided composition that are of or comprise a common base sequence, base modifications, sugar modifications and/or modified internucleotidic linkages are 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition. In some embodiments, a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition that are of or comprise a common base sequence, pattern of base modification, pattern of sugar modification, and/or pattern of modified internucleotidic linkage. In some embodiments, all oligonucleotides in a provided composition that are of or comprise a common base sequence, pattern of base modification, pattern of sugar modification, and/or pattern of modified internucleotidic linkage are 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition. In some embodiments, a predetermined level of oligonucleotides is 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in a provided composition that share a common base sequence, a common pattern of base modification, a common pattern of sugar modification, and/or a common pattern of modified internucleotidic linkages. In some embodiments, all oligonucleotides in a provided composition that share a common base sequence, a common pattern of base modification, a common pattern of sugar modification, and/or a common pattern of modified internucleotidic linkages are 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of all oligonucleotides in the composition.

In some embodiments, a predetermined level is 0.1%-100%. In some embodiments, a predetermined level is at least 1%. In some embodiments, a predetermined level is at least 5%. In some embodiments, a predetermined level is at least 10%. In some embodiments, a predetermined level is at least 20%. In some embodiments, a predetermined level is at least 30%. In some embodiments, a predetermined level is at least 40%. In some embodiments, a predetermined level is at least 50%. In some embodiments, a predetermined level is at least 60%. In some embodiments, a predetermined level is at least 65%. In some embodiments, a predetermined level is at least 70%. In some embodiments, a predetermined level is at least 75%. In some embodiments, a predetermined level is at least 80%. In some embodiments, a predetermined level is at least 85%. In some embodiments, a predetermined level is at least 90%. In some embodiments, a predetermined level is at least 91%. In some embodiments, a predetermined level is at least 92%. In some embodiments, a predetermined level is at least 93%. In some embodiments, a predetermined level is at least 94%. In some embodiments, a predetermined level is at least 95%. In some embodiments, a predetermined level is at least 96%. In some embodiments, a predetermined level is at least 97%. In some embodiments, a predetermined level is at least 98%. In some embodiments, a predetermined level is at least 99%. In some embodiments, a predetermined level is at least $5*(\frac{1}{2}^g)$, wherein g is the number of chirally controlled internucleotidic linkages. In some embodiments, a predetermined level is at least $10*(\frac{1}{2}^g)$, wherein g is the number of chirally controlled internucleotidic linkages. In some embodiments, a predetermined level is at least $100*(\frac{1}{2}^g)$, wherein g is the number of chirally controlled internucleotidic linkages. In some embodiments, a predetermined level is at least $(0.80)^g$, wherein g is the number of chirally controlled internucleotidic linkages. In some embodiments, a predetermined level is at least $(0.80)^g$, wherein g is the number of chirally controlled internucleotidic linkages. In some embodiments, a predetermined level is at least $(0.80)^g$, wherein g is the number of chirally controlled internucleotidic linkages. In some embodiments, a predetermined level is at least $(0.85)^g$, wherein g is the number of chirally controlled internucleotidic linkages. In some embodiments, a predetermined level is at least $(0.90)^g$, wherein g is the number of chirally controlled internucleotidic linkages. In some embodiments, a predetermined level is at least $(0.95)^g$, wherein g is the number of chirally controlled internucleotidic linkages. In some embodiments, a predetermined level is at least $(0.96)^g$, wherein g is the number of chirally controlled internucleotidic linkages. In some embodiments, a predetermined level is at least $(0.97)^g$, wherein g is the number of chirally controlled internucleotidic linkages. In some embodiments, a predetermined level is at least $(0.98)^g$, wherein g is the number of chirally controlled internucleotidic linkages. In some embodiments, a predetermined level is at least $(0.99)^g$, wherein g is the number of chirally controlled internucleotidic linkages. In some embodiments, to determine level of oligonucleotides having g chirally controlled internucleotidic linkages in a composition, product of diastereopurity of each of the g chirally controlled internucleotidic linkages: (diastereopurity of chirally controlled internucleotidic linkage 1)*(diastereopurity of chirally controlled internucleotidic linkage 2)* . . . *(diastereopurity of chirally controlled internucleotidic linkage g) is utilized as the level, wherein diastereopurity of each chirally controlled internucleotidic linkage is independently represented by diastereopurity of a dimer comprising the same internucleotidic linkage and nucleosides flanking the internucleotidic linkage and prepared under comparable methods as the oligonucleotides (e.g., comparable or preferably identical oligonucleotide preparation cycles, including comparable or preferably identical reagents and reaction conditions). In some embodiments, levels of oligonucleotides and/or diastereopurity can be determined by analytical methods, e.g., chromatographic, spectrometric, spectroscopic methods or any combinations thereof.

In some embodiments, as described in the present disclosure, oligonucleotides of provided compositions, e.g., oligonucleotides of a plurality and/or predetermined levels, comprise one or more internucleotidic linkages having the structure of formula VII, VII-a-1, VII-a-2, VII-b, VII-c, VII-d, or VII-e, or a salt form thereof In some embodiments, oligonucleotides comprise 1-100, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70 80, 90, 100 or more internucleotidic linkages having the structure of formula VII, VII-a-1, VII-a-2, VII-b, VII-c, VII-d, or VII-e, or a salt for thereof. In some embodiments, as described in the present disclosure, each —X-L$^s$-R$^5$ is independently of such a structure that H—X-L$^s$-R$^5$ has the structure of formula I, I-a, I-a-1, I-a-2, I-b, I-c, I-d, I-e, II, II-a, II-b, III, III-a, or III-b, or a salt thereof. In some embodiments, oligonucleotides have the structure of formula VIII or a salt thereof. In some embodiments, oligonucleotides have the structure of formula VIII or a salt thereof, wherein each L$^P$ independently has the structure of formula VII, VII-a-1, VII-a-2, VII-b, VII-c, VII-d, or VII-e, or a salt form thereof. In some embodiments, oligonucleotides have the structure of formula VIII or a salt thereof, wherein each L$^P$ independently has the structure of formula VII, VII-a-1, VII-a-2, VII-b, VII-c, VII-d, or VII-e, or a salt for thereof, and wherein for each L$^P$ having the structure of formula VII, VII-a-1, VII-a-2, VII-b, VII-c, VII-d, or VII-e, or a salt form thereof, each —X-L$^s$-R$^5$ is independently of such a structure that H—X-L$^s$-R$^5$ has the structure of formula I, I-a, I-a-1, I-a-2, I-b, I-c, I-d, I-e, II, II-a, II-b, III, III-a, or III-b, or a salt thereof.

BRIEF DESCRIPTION OF THE DRAWING

FIG. 1 showed example pKa measurement data.

DETAILED DESCRIPTION OF CERTAIN EMBODIMENTS

1. Definitions

As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation, or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Aryl: The term "aryl" used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. In some embodiments, also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like, where a radical or point of attachment is on an aryl ring.

Chiral control: As used herein, "chiral control" refers to control of the stereochemical designation of a chiral linkage phosphorus in a chiral internucleotidic linkage within an oligonucleotide. In some embodiments, a control is achieved through a chiral element that is absent from the sugar and base moieties of an oligonucleotide, for example, in some embodiments, a control is achieved through use of one or more chiral auxiliaries during oligonucleotide preparation as exemplified in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in a chiral internucleotidic linkage within an oligonucleotide is controlled.

Chirally controlled oligonucleotide composition: The terms "chirally controlled oligonucleotide composition", "chirally controlled nucleic acid composition", and the like, as used herein, refers to a composition that comprises a plurality of oligonucleotides (or nucleic acids) which share 1) a common base sequence, 2) a common pattern of backbone linkages, and 3) a common pattern of backbone phosphorus modifications, wherein the plurality of oligonucleotides (or nucleic acids) share the same stereochemistry at one or more chiral internucleotidic linkages (chirally controlled internucleotidic linkages), and the level of the plurality of oligonucleotides (or nucleic acids) in the composition is pre-determined (e.g., through chirally controlled oligonucleotide preparation to form one or more chiral internucleotidic linkages). In some embodiments, the plurality of oligonucleotides in a chirally controlled oligonucleotide composition share the same base sequence, the same, if any, nucleobase, sugar, and internucleotidic linkage modifications, and the same stereochemistry (Rp or Sp) independently at linkage phosphorus chiral centers of one or more chirally controlled internucleotidic linkages, though stereochemistry of certain linkage phosphorus chiral centers may differ. In some embodiments, about 0.1%-100%, (e.g., about 1%-100%, 5%-100%, 10%-100%, 20%-100%, 30%-100%, 40%-100%, 50%-100%, 60%-100%, 70%-100%, 80%-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 0.1%-100%, (e.g., about 1%-100%, 5%-100%, 10%-100%, 20%-100%, 30%-100%, 40%-100%, 50%-100%, 60%-100%, 70%-100%, 80%-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence are oligonucleotides of the plurality. In some embodiments, about 0.1%-100%, (e.g., about 1%-100%, 5%-100%, 10%-100%, 20%-100%, 30%-100%, 40%-100%, 50%-100%, 60%-100%, 70%-100%, 80%-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, a predetermined level is be about 0.1%-100%, (e.g., about 1%-100%, 5%-100%, 10%-100%, 20%-100%, 30%-100%, 40%-100%, 50%-100%, 60%-100%, 70%-100%, 80%-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a composition, or of all oligonucleotides in a composition that share a common base sequence (e.g., of a plurality of oligonucleotide or an oligonucleotide type), or of all oligonucleotides in a composition that share a common base sequence, a common pattern of backbone linkages, and a common pattern of backbone phosphorus modifications, or of all oligonucleotides in a composition that share a common base sequence, a common patter of base modifications, a common pattern of sugar modifications, a common pattern of internucleotidic linkage types, and/or a common pattern of internucleotidic linkage modifications, are oligonucleotides of the plurality. In some embodiments, the plurality of oligonucleotides share the same stereochemistry at about 1-50 (e.g., about 1-10, 1-20, 5-10, 5-20, 10-15, 10-20, 10-25, 10-30, or about 1, 2, 3, 4, 5, 6, 7, 8, 9, 10, 11, 12, 13, 14, 15, 16, 17, 18, 19, or 20, or at least 1, 2, 3, 4, 5, 6, 7, 8, 9, 10, 11, 12, 13, 14, 15, 16, 17, 18, 19, or 20) chiral internucleotidic linkages. In some embodiments, the plurality of oligonucleotides share the same stereochemistry at about 0.1%-100% (e.g., about 1%-100%, 5%-100%, 10%-100%, 20%-100%, 30%-100%, 40%-100%, 50%-100%, 60%-100%, 70%-100%, 80%-100%, 90-100%, 95-100%, 50%-90%, about 5%, 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%, 25%, 30%, 35%, 40%, 45%, 50%, 55%, 60%, 65%, 70%, 75%, 80%, 85%, 90%, 95%, or 99%) of chiral internucleotidic linkages. In some embodiments, each chiral internucleotidic linkage is a chiral controlled internucleotidic linkage, and the composition is a completely chirally controlled oligonucleotide composition. In some embodiments, not all chiral internucleotidic linkages are chiral controlled internucleotidic linkages, and the composition is a partially chirally controlled oligonucleotide composition. In some embodiments, a chirally controlled oligonucleotide composition comprises predetermined levels of individual oligonucleotide or nucleic acids types. For instance, in some embodiments a chirally controlled oligonucleotide composition comprises one oligonucleotide type at a predetermined level. In some embodiments, a chirally controlled oligonucleotide composition comprises more than one oligonucleotide type, each independently at a predetermined level. In some embodiments, a chirally controlled oligonucleotide composition comprises multiple oligonucleotide types, each independently at a predetermined level. In some embodiments, a chirally controlled oligonucleotide composition is a composition of oligonucleotides of an oligonucleotide type, which composition comprises a predetermined level of a plurality of oligonucleotides of the oligonucleotide type.

Cycloaliphatic: The term "cycloaliphatic," as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic" may also include aliphatic rings that are fused to one or more aromatic or nonaromatic rings, such as decahydronaphthyl or tetrahydronaphthyl, where a radical or point of attachment is on an aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, or a $C_9$-$C_{16}$ tricyclic hydrocarbon that is completely saturated or that contains one or more units of unsaturation, but which is not aromatic.

Halogen: The term "halogen" means F, Cl, Br, or I.

Heteroaliphatic: The term "heteroaliphatic" is given its ordinary meaning in the art and refers to aliphatic groups as described herein in which one or more carbon atoms are replaced with one or more heteroatoms (e.g., oxygen, nitrogen, sulfur, silicon, phosphorus, and the like).

Heteroalkyl: The term "heteroalkyl" is given its ordinary meaning in the art and refers to alkyl groups as described herein in which one or more carbon atoms is replaced with a heteroatom (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-," used alone or as part of a larger moiety, e.g., "heteroaralkyl," or "heteroaralkoxy," refer to monocyclic, bicyclic or polycyclic ring systems having, for example, a total of five to thirty, ring members, wherein at least one ring in the system is aromatic and at least one aromatic ring atom is a heteroatom. In some embodiments, a heteroatom is nitrogen, oxygen or sulfur. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or $14\pi$ electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where a radical or point of attachment is on a heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon or hydrogen. In some embodiments, a heteroatom is oxygen, sulfur, nitrogen, phosphorus, boron or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.). In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur.

Heterocyclyl: As used herein, the terms "heterocycle," "heterocyclyl," "heterocyclic radical," and "heterocyclic ring" are used interchangeably and refer to a monocyclic, bicyclic or polycyclic ring moiety (e.g., 3-30 membered) that is saturated or partially unsaturated and has one or more heteroatom ring atoms. In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where a radical or point of attachment is on a heteroaliphatic ring. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Linkage phosphorus: As defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester of an internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is the phosphorus of $P^L$ of Formula VII. In some embodiments, a linkage phosphorus atom is chiral. In some embodiments, a linkage phosphorus is a chiral (e.g., in natural phosphate linkage).

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications (e.g., pattern of "—X-L-$R^5$" groups in formula VII). In some embodiments, oligonucleotides of a common designated "type" are structurally, including stereochemically, identical to one another.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other known methods such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, pharmaceutically acceptable salts include, but are not limited to, nontoxic base addition salts, such as those formed by acidic groups of provided compounds (e.g., phosphate linkage groups of oligonucleotides, phosphorothioate linkage groups of oligonucleotides, etc.) with bases. Representative alkali or alkaline earth metal salts include salts of sodium, lithium, potassium, calcium, magnesium, and the like. In some embodiments, pharmaceutically acceptable salts are ammonium salts (e.g., —N(R)$_3^+$). In some embodiments, pharmaceutically acceptable salts are sodium salts. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Predetermined: By predetermined (or pre-determined) is meant deliberately selected, for example as opposed to randomly occurring or achieved without control. Those of ordinary skill in the art, reading the present specification, will appreciate that the present disclosure provides technologies that permit selection of particular chemistry and/or stereochemistry features to be incorporated into oligonucleotide compositions, and further permits controlled preparation of oligonucleotide compositions having such chemistry and/or stereochemistry features. Such provided compositions are "predetermined" as described herein. A composition that may contain certain oligonucleotides because they happen to have been generated through a process that are not controlled to intentionally generate the particular chemistry and/or stereochemistry features is not a "predetermined" composition. In some embodiments, a predetermined composition is one that can be intentionally reproduced (e.g., through repetition of a controlled process). In some embodiments, a predetermined level of a plurality of oligonucleotides in a composition means that the absolute amount, and/or the relative amount (ratio, percentage, etc.) of the plurality of oligonucleotides in the composition is controlled. In some embodiments, a predetermined level of a plurality of oligonucleotides in a composition is achieved through chirally controlled oligonucleotide preparation.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Siphenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In some embodiments, example substituents are described below.

Suitable monovalent substituents are halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)$ R°; —$(CH_2)_{0-4}N(R°)C(O)N(R°)_2$; —$N(R°)C(S)N(R°)_2$; —$(CH_2)_{0-4}N(R°)C(O)OR°$; —$N(R°)N(R°)C(O)R°$; —$N(R°)N(R°)C(O)N(R°)_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSi(R°)_3$; —$(CH_2)_{0-4}OC(O)R°$; —OC(O)$(CH_2)_{0-4}SR°$, —SC(S)SR°; —$(CH_2)_{0-4}SC(O)R°$; —$(CH_2)_{0-4}C(O)N(R°)_2$; —C(S) N(R°)_2; —C(S)SR°; —SC(S)SR°, —$(CH_2)_{0-4}OC(O)$ N(R°)_2; —C(O)N(OR°)R°; —C(O)C(O)R°; —$C(O)CH_2C(O)R°$; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2N(R°)_2$; —$(CH_2)_{0-4}S(O)R°$; —$N(R°)S(O)_2N(R°)_2$; —$N(R°)S(O)_2R°$; —N(OR°)R°; —C(NH)N(R°)_2; —Si(R°)_3; —OSi(R°)_3; —P(R°)_2; —P(OR°)_2; —P(R°)(OR°); —OP(R°)_2; —OP(OR°)_2; —OP(R°)(OR°); —P[N(R°)_2]_2; —P(R°)[N(R°)_2]; —P(OR°)[N(R°)_2]; —OP[N(R°)_2]_2; —OP(R°)[N(R°)_2]; —OP(OR°)[N(R°)_2]; —N(R°)P(R°)_2; —N(R°)P(OR°)_2; —N(R°)P(R°)(OR°); —N(R°)P[N(R°)_2]_2; —N(R°)P(R°)[N(R°)_2]; —N(R°)P(OR°)[N(R°)_2]; —B(R°)_2; —B(R°)(OR°); —B(OR°)_2; —OB(R°)_2; —OB(R°)(OR°); —OB(OR°)_2; —P(O)(R°)_2;

—P(O)(R°)(OR°); —P(O)(R°)(SR°); —P(O)(R°)[N(R°)$_2$]; —P(O)(OR°)$_2$; —P(O)(SR°)$_2$; —P(O)(OR°)[N(R°)$_2$]; —P(O)(SR°)[N(R°)$_2$]; —P(O)(OR°)(SR°); —P(O)[N(R°)$_2$]$_2$; —OP(O)(R°)$_2$; —OP(O)(R°)(OR°); —OP(O)(R°)(SR°); —OP(O)(R°)[N(R°)$_2$]; —OP(O)(OR°)$_2$; —OP(O)(SR°)$_2$; —OP(O)(OR°)[N(R°)$_2$]; —OP(O)(SR°)[N(R°)$_2$]; —OP(O)(OR°)(SR°); —OP(O)[N(R°)$_2$]$_2$; —SP(O)(R°)$_2$; —SP(O)(R°)(OR°); —SP(O)(R°)(SR°); —SP(O)(R°)[N(R°)$_2$]; —SP(O)(OR°)$_2$; —SP(O)(SR°)$_2$; —SP(O)(OR°)[N(R°)$_2$]; —SP(O)(SR°)[N(R°)$_2$]; —SP(O)(OR°)(SR°); —SP(O)[N(R°)$_2$]$_2$; —N(R°)P(O)(R°)$_2$; —N(R°)P(O)(R°)(OR°); —N(R°)P(O)(R°)(SR°); —N(R°)P(O)(R°)[N(R°)$_2$]; —N(R°)P(O)(OR°)$_2$; —N(R°)P(O)(SR°)$_2$; —N(R°)P(O)(OR°)[N(R°)$_2$]; —N(R°)P(O)(SR°)[N(R°)$_2$]; —N(R°)P(O)(OR°)(SR°); —N(R°)P(O)[N(R°)$_2$]$_2$; —P(R°)$_2$[B(R°)$_3$]; —P(OR°)$_2$[B(R°)$_3$]; —P(NR°)$_2$[B(R°)$_3$]; —P(R°)(OR°)[B(R°)$_3$]; —P(R°)[N(R°)$_2$][B(R°)$_3$]; —P(OR°)[N(R°)$_2$][B(R°)$_3$]; —OP(R°)$_2$[B(R°)$_3$]; —OP(OR°)$_2$[B(R°)$_3$]; —OP(NR°)$_2$[B(R°)$_3$]; —OP(R°)(OR°)[B(R°)$_3$]; —OP(R°)[N(R°)$_2$][B(R°)$_3$]; —OP(OR°)[N(R°)$_2$][B(R°)$_3$]; —N(R°)P(R°)$_2$[B(R°)$_3$]; —N(R°)P(OR°)$_2$[B(R°)$_3$]; —N(R°)P(NR°)$_2$[B(R°)$_3$]; —N(R°)P(R°)(OR°)[B(R°)$_3$]; —N(R°)P(R°)[N(R°)$_2$][B(R°)$_3$]; —N(R°)P(OR°)[N(R°)$_2$][B(R°)$_3$]; —P(OR')[B(R')$_3$]—; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-20}$ aliphatic, C$_{1-20}$ heteroaliphatic having 1-5 heteroatoms independently selected from nitrogen, oxygen, sulfur, silicon and phosphorus, —CH$_2$—(C$_{6-14}$ aryl), —O(CH$_2$)$_{0-1}$(C$_{6-14}$ aryl), —CH$_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of R°, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on R° (or the ring formed by taking two independent occurrences of R° together with their intervening atoms), are independently halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents are the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* are halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

In some embodiments, suitable substituents on a substitutable nitrogen are —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Unsaturated: The term "unsaturated" as used herein, means that a moiety has one or more units of unsaturation.

Unless otherwise specified, salts, such as pharmaceutically acceptable acid or base addition salts, stereoisomeric forms, and tautomeric forms, of provided compound are included.

2. Detailed Description of Certain Embodiments

As appreciated by a person having ordinary skill in the art, stereoselective synthesis is a significant challenge. Among other things, the present disclosure recognizes that for stereoselective (chirally controlled) preparation of oligonucleotides, certain demanding conditions require technologies that are capable of providing higher yields, higher stereoselectivity, higher product purity, lower cost, and/or broader chemical compatibility. Among other things, the present disclosure provides such technologies on demand. In some embodiments, the present disclosure provides compounds useful as chiral auxiliaries for stereoselective synthesis, e.g., chirally controlled formation of chiral internucleotidic linkages. In some embodiments, the present disclosure provides compounds useful as reactants for stereoselective synthesis, e.g., certain provided compounds are useful as monomer phosphoramidites for preparing chirally controlled oligonucleotide compositions. In some embodiments, the present disclosure provides methods for preparing chiral compounds, e.g., oligonucleotides comprising one or more chiral internucleotidic linkages. In some embodiments, provided methods are useful for chirally controlled preparation of chirally controlled oligonucleotide compositions. In some embodiments, the present disclosure provides compounds and compositions from provided methods, e.g., chirally controlled preparation of oligonucleotides. In some embodiments, the present disclosure provides chirally controlled oligonucleotide compositions. In some embodiments, the present disclosure provides oligonucleotides, which comprise one or more chiral internucleotidic linkages, in high diastereomeric purity.

In some embodiments, the present disclosure provides conditions for assessing performance of a compound in stereoselective synthesis. For example, as illustrated in the Examples (e.g., solid supports, linkers, nucleosides, positioning, any combinations thereof, etc.), in some embodiments, the present disclosure provides conditions for assessing performance of a compound as a chiral auxiliary, a monomer phosphoramidite, etc. in chirally controlled formation of chiral internucleotidic linkages. In some embodiments, provided conditions are particularly useful in that they are more demanding than those in typical chirally controlled formation of chiral internucleotidic linkages, so that the performance of chiral auxiliaries can be differentiated, even though such chiral auxiliaries may demonstrate much less or no difference in certain typical chirally controlled formation of chiral internucleotidic linkages.

In some embodiments, for formation of challenging internucleotidic linkages, provided technologies deliver unexpectedly high yields while maintaining very high stereoselectivity, generally the same or comparable to the best results reported so far. As demonstrated by the Examples, in some embodiments, the present disclosure provides technologies that deliver high stereoselectivity (e.g., at least 90:10, 91:9, 92:8, 93:7, 94:6, 95:5, 96:4, 97:3, 98:2, or 99:1). In some embodiments, the present disclosure provides technologies that deliver high yields. In some embodiments, provided technologies provides alternative chemical capability. In some embodiments, provided technologies provide low cost. In some embodiments, provided technologies provides alternative preparation methods. Among other things, the present disclosure provides enormous flexibility for chirally controlled preparation of oligonucleotides: a person of ordinary skill in the art can choose from a variety of provided technologies to address specific preparations in accordance with the present disclosure. For example, if an oligonucleotide comprises multiple chiral internucleotidic linkages and high yields and purities are required, he or she can choose technologies that provide the highest purity and yields; if an oligonucleotide has only one or very few chiral internucleotidic linkages and purification is readily achievable, he or she may choose technologies delivering high stereoselectivity with relatively low yield (or higher yield with relatively low stereoselectivity) but of lower overall cost.

In some embodiments, the present disclosure provides technologies that are compatible with various chemical conditions, so that provided technologies can be used for many types of reactions and/or conditions. In some embodiments, the present disclosure provides chiral auxiliaries that can be cleaved under acidic conditions. In some embodiments, the present disclosure provides chiral auxiliaries that can be cleaved under basic conditions. In some embodiments, the present disclosure provides chiral auxiliaries that can be cleaved using, for example, a fluorine source (e.g., HF, HF-Et$_3$N, HF-Pyridine, TBAF, etc.).

In some embodiments, the present disclosure provides compounds that are useful as auxiliaries for synthesis, for example, preparation of oligonucleotides. In some embodiments, the present disclosure provides compounds that are useful as chiral auxiliaries for synthesis, for example, chirally controlled preparation of oligonucleotides.

In some embodiments, a provided compound is a compound that has the structure of formula I, I-a, I-a-1, I-a-2, I-b, I-c, I-d, I-e, II, II-a, II-b, III, III-a, or III-b, or a salt thereof. In some embodiments, a provided compound is a stereoisomer of a compound of formula I, I-a, I-a-1, I-a-2, I-b, I-c, I-d, I-e, II, II-a, II-b, III, III-a, or III-b, or a salt thereof. In some embodiments, a provided compound is a diastereomer of a compound of formula I, I-a, I-a-1, I-a-2, I-b, I-c, I-d, I-e, II, II-a, II-b, III, III-a, or III-b, or a salt thereof. In some embodiments, a provided compound is an enantiomer of a compound of formula I, I-a, I-a-1, I-a-2, I-b, I-c, I-d, I-e, II, II-a, II-b, III, III-a, or III-b, or a salt thereof. In some embodiments, a provided compound is a chiral auxiliary in that it is asymmetric, and can be used for stereoselective synthesis, e.g., chirally controlled formation of chiral internucleotidic linkages.

In some embodiments, the present disclosure provides compounds that are useful as building blocks for synthesis, for example, as monomer phosphoramidites for chirally controlled preparation of oligonucleotides.

In some embodiments, a provided compound is a compound that has the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof. In some embodiments, a provided compound is a compound that has the structure of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, a provided compound is a stereoisomer of a compound of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, a provided compound is a diastereomer of a compound of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, a provided compound is an enantiomer of a compound of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof. In some embodiments, a provided compound is a chiral auxiliary in that it is asymmetric, and can be used for stereoselective synthesis, e.g., chirally controlled formation of chiral internucleotidic linkages.

In some embodiments, the present disclosure provides oligonucleotides. In some embodiments, the present disclosure provides oligonucleotides of certain diastereomeric purity. In some embodiments, the present disclosure provides chirally controlled oligonucleotide composition. In some embodiments, a provided oligonucleotide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 chiral internucleotidic linkages. In some embodiments, a provided oligonucleotide comprises at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 chiral internucleotidic linkages. In some embodiments, a provided oligonucleotide comprises at least 5, 6, 7, 8, 9, 10, 11, 12, 13, 14, 15, 16, 17, 18, 19, 20, 21, 22, 23, 24, 25, 26, 27, 28, 29, or 30 chiral internucleotidic linkages. In some embodiments, a provided oligonucleotide comprises at least 10, 11, 12, 13, 14, 15, 16, 17, 18, 19, 20, 21, 22, 23, 24, 25, 26, 27, 28, 29, or 30 chiral internucleotidic linkages. In some embodiments, a provided oligonucleotide comprises at least 15, 16, 17, 18, 19, 20, 21, 22, 23, 24, 25, 26, 27, 28, 29, or 30 chiral internucleotidic linkages. In some embodiments, a provided oligonucleotide comprises at least 1 chiral internucleotidic linkage. In some embodiments, a provided oligonucleotide comprises at least 2 chiral internucleotidic linkages. In some embodiments, a provided oligonucleotide comprises at least 3 chiral internucleotidic linkages. In some embodiments, a provided oligonucleotide comprises at least 4 chiral internucleotidic linkages. In some embodiments, a provided oligonucleotide comprises at least 5 chiral internucleotidic linkages. In some embodiments, a provided oligonucleotide comprises at least 6 chiral internucleotidic linkages. In some embodiments, a provided oligonucleotide comprises at least 7 chiral internucleotidic linkages. In some embodiments, a provided oligonucleotide comprises at least 8 chiral internucleotidic linkages. In some embodiments, a provided oligonucleotide comprises at least 9 chiral internucleotidic linkages. In some embodiments, a provided oligonucleotide comprises at least 10 chiral internucleotidic linkages. In some embodiments, a provided oligonucleotide comprises at least 11 chiral internucleotidic linkages. In some embodiments, a provided oligonucleotide comprises at least 12 chiral internucleotidic linkages. In some embodiments, a provided oligonucleotide comprises at least 13 chiral internucleotidic linkages. In some embodiments, a provided oligonucleotide comprises at least 14 chiral internucleotidic linkages. In some embodiments, a provided oligonucleotide comprises at least 15 chiral internucleotidic linkages. In some embodiments, a provided oligonucleotide comprises at least 16 chiral internucleotidic linkages. In some embodiments, a provided oligonucleotide comprises at least 17 chiral internucleotidic linkages. In some embodiments, a provided oligonucleotide comprises at least 18 chiral internucleotidic linkages. In some embodiments, a provided oligonucleotide comprises at least 19 chiral internucleotidic linkages. In some embodiments, a provided oligonucleotide comprises at least 20 chiral internucleotidic linkages. In some embodiments, a provided oligonucleotide comprises at least 21 chiral internucleotidic linkages. In some embodiments, a provided oligonucleotide comprises at least 22 chiral internucleotidic linkages. In some embodiments, a provided oligonucleotide comprises at least 23 chiral internucleotidic linkages. In some embodiments, a provided oligonucleotide comprises at least 24 chiral internucleotidic linkages. In some embodiments, a provided oligonucleotide comprises at least 25 chiral internucleotidic linkages. In some embodiments, a provided oligonucleotide comprises at least 26 chiral internucleotidic linkages. In some embodiments, a provided oligonucleotide comprises at least 27 chiral internucleotidic linkages. In some embodiments, a provided oligonucleotide comprises at least 28 chiral internucleotidic linkages. In some embodiments, a provided oligonucleotide comprises at least 29 chiral internucleotidic linkages. In some embodiments, a provided oligonucleotide comprises at least 30 chiral internucleotidic linkages. In some embodiments, a chiral internucleotidic linkage has the structure of formula VII or a salt form thereof (e.g., —OP(O)(S⁻)O— is a salt form of —OP(O)(SH)O—). In some embodiments, a chiral internucleotidic linkage has the structure of formula VII-a or a salt form thereof. In some embodiments, a chiral internucleotidic linkage has the structure of formula VII-b or a salt form thereof. In some embodiments, a chiral internucleotidic linkage has the structure of formula VII-c or a salt form thereof. In some embodiments, a chiral internucleotidic linkage has the structure of formula VII-d or a salt form thereof. In some embodiments, a chiral internucleotidic linkage has the structure of formula VII-e or a salt form thereof. In some embodiments, H—X-L-$R^s$ is a compound of formula I, I-a, I-a-1, I-a-2, I-b, I-c, I-d, I-e, II, II-a, II-b, III, III-a, or III-b, or a salt thereof.

In some embodiments, $R^1$ is —H, -$L^s$-R, halogen, —CN, —$NO_2$, -$L^s$-Si(R)$_3$, —OR, —SR, or —N(R)$_2$. In some embodiments, $R^1$ is —H. In some embodiments, $R^1$ is -$L^s$-R, wherein each of $L^s$ and R is independently as described in the present disclosure. In some embodiments, $R^1$ is R, for example, an R embodiment as described in the present disclosure. In some embodiments, $R^1$ is halogen. In some embodiments, $R^1$ is —F. In some embodiments, $R^1$ is —Cl. In some embodiments, $R^1$ is —Br. In some embodiments, $R^1$ is —I. In some embodiments, $R^1$ is —CN. In some embodiments, $R^1$ is —$NO_2$. In some embodiments, $R^1$ is -$L^s$-Si(R)$_3$, wherein each of $L^s$ and R is independently as described in the present disclosure. In some embodiments, $R^1$ is —$CH_2$—Si(R)$_3$, wherein the —$CH_2$— group is optionally substituted, and each R is independently as described in the present disclosure. In some embodiments, $R^1$ is —$CH_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from $C_{1-6}$ alkyl and phenyl. In some embodiments, at least one R of —Si(R)$_3$ is optionally substituted $C_{1-6}$ alkyl, and at least one R of —Si(R)$_3$ is optionally substituted phenyl. In some embodiments, two R of —Si(R)$_3$ are independently optionally substituted $C_{1-6}$ alkyl, and one R of —Si(R)$_3$ is optionally substituted phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^1$ is —OR, wherein R is as described in the present disclosure. In some embodiments, $R^1$ is —SR wherein R is as described in the present disclosure. In some embodiments, $R^1$ is —N(R)$_2$, wherein each R is independently as described in the present disclosure.

In some embodiments, $R^2$ is —H, -$L^s$-R, halogen, —CN, —$NO_2$, -$L^s$-Si(R)$_3$, —OR, —SR, or —N(R)$_2$. In some embodiments, $R^2$ is —H. In some embodiments, $R^2$ is -$L^s$-R, wherein each of $L^s$ and R is independently as described in the present disclosure. In some embodiments, $R^2$ is R, for example, an R embodiment as described in the present disclosure. In some embodiments, $R^2$ is halogen. In some embodiments, $R^2$ is —F. In some embodiments, $R^2$ is —Cl. In some embodiments, $R^2$ is —Br. In some embodiments, $R^2$ is —I. In some embodiments, $R^2$ is —CN. In some embodiments, $R^2$ is —$NO_2$. In some embodiments, $R^2$ is -$L^s$-Si(R)$_3$, wherein each of $L^s$ and R is independently as described in the present disclosure. In some embodiments, $R^2$ is —$CH_2$—Si(R)$_3$, wherein the —$CH_2$— group is optionally substituted, and each R is independently as described in the present disclosure. In some embodiments, $R^2$ is —$CH_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from $C_{1-6}$ alkyl and phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^2$ is —OR, wherein R is as described in the present disclosure. In some embodiments, $R^2$ is —SR wherein R is as described in the present disclosure. In some embodiments, $R^2$ is —$N(R)_2$, wherein each R is independently as described in the present disclosure. In some embodiments, $R^2$ is the same or different from $R^1$, and is a group selected from any groups described for $R^1$ in the present disclosure.

In some embodiments, at least one of $R^1$ and $R^2$ is not hydrogen. In some embodiments, $R^1$ is hydrogen and $R^2$ is not hydrogen. In some embodiments, $R^1$ is not hydrogen and $R^2$ is hydrogen. In some embodiments, neither of $R^1$ and $R^2$ is hydrogen.

In some embodiments, one of $R^1$ and $R^2$ is —H, and the other is R, wherein R is as described in the present disclosure and is not hydrogen. In some embodiments, one of $R^1$ and $R^2$ is —H, and the other is R, wherein R is optionally substituted $C_{1-6}$ aliphatic as described in the present disclosure. In some embodiments, one of $R^1$ and $R^2$ is —H, and the other is R, wherein R is optionally substituted $C_{1-4}$ aliphatic. In some embodiments, one of $R^1$ and $R^2$ is —H, and the other is R, wherein R is optionally substituted $C_{1-3}$ aliphatic. In some embodiments, one of $R^1$ and $R^2$ is —H, and the other is R, wherein R is optionally substituted $C_{1-2}$ aliphatic. In some embodiments, one of $R^1$ and $R^2$ is —H, and the other is R, wherein R is optionally substituted $C_{1-6}$ alkenyl. In some embodiments, one of $R^1$ and $R^2$ is —H, and the other R, wherein R is vinyl. In some embodiments, one of $R^1$ and $R^2$ is —H, and the other is R, wherein R is optionally substituted $C_{1-6}$ alkynyl. In some embodiments, one of $R^1$ and $R^2$ is —H, and the other is R, wherein R is ethynyl. In some embodiments, one of $R^1$ and $R^2$ is —H, and the other is R, wherein R is optionally substituted benzyl. In some embodiments, one of $R^1$ and $R^2$ is —H, and the other is R, wherein R is benzyl wherein the phenyl group of the benzyl is optionally substituted. In some embodiments, $R^1$ is —H and $R^2$ is benzyl. In some embodiments, a provided compound is

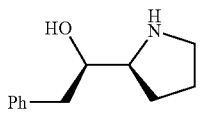

or a salt thereof. In some embodiments, a provided compound is a diastereomer of

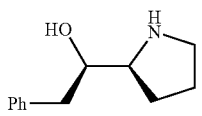

or a salt thereof. In some embodiments, a provided compound is an enantiomer of

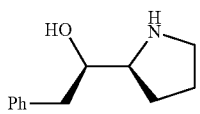

or a salt thereof.

In some embodiments, one of $R^1$ and $R^2$ is R, wherein R is as described in the present disclosure and comprises a ring moiety. In some embodiments, R is an optionally substituted group selected from $C_{3-20}$ cycloaliphatic, $C_{6-20}$ aryl, 5-20 membered heteroaryl having 1-5 heteroatoms, and 3-20 membered heterocyclyl having 1-5 heteroatoms, wherein each heteroatom is independently selected from nitrogen, oxygen, sulfur, phosphorus and silicon. In some embodiments, R is an optionally substituted group selected from $C_{3-20}$ cycloaliphatic, $C_{6-20}$ aryl, 5-20 membered heteroaryl having 1-5 heteroatoms, and 3-20 membered heterocyclyl having 1-5 heteroatoms, wherein each heteroatom is independently selected from nitrogen, oxygen, and sulfur. In some embodiments, R is optionally substituted $C_{3-20}$ cycloaliphatic. In some embodiments, R is optionally substituted $C_{3-10}$ cycloaliphatic. In some embodiments, R is optionally substituted $C_{3-10}$ cycloalkyl. In some embodiments, R is optionally substituted $C_{4-10}$ cycloalkyl. In some embodiments, R is optionally substituted cyclopropyl. In some embodiments, R is optionally substituted cyclobutyl. In some embodiments, R is optionally substituted cyclopentyl. In some embodiments, R is optionally substituted cyclohexyl. In some embodiments, R is optionally substituted cycloheptyl. In some embodiments, R is cyclopropyl. In some embodiments, R is cyclobutyl. In some embodiments, R is cyclopentyl. In some embodiments, R is cyclohexyl. In some embodiments, R is cycloheptyl. In some embodiments, R is optionally substituted $C_{6-20}$ aryl. In some embodiments, R is optionally substituted $C_{6-20}$ aryl. In some embodiments, R is phenyl. In some embodiments, R is optionally substituted phenyl. In some embodiments, R is optionally substituted 5-20 membered heteroaryl having 1-5 heteroatoms. In some embodiments, R is optionally substituted 5-membered heteroaryl having 1-5 heteroatoms. In some embodiments, R is optionally substituted 6-membered heteroaryl having 1-5 heteroatoms. In some embodiments, R is optionally substituted 3-20 membered heterocyclyl having 1-5 heteroatoms. In some embodiments, the other of $R^1$ and $R^2$ is R wherein R is not hydrogen. In some embodiments, R is optionally substituted $C_{1-6}$ aliphatic. In some embodiments, R is optionally substituted $C_{1-6}$ alkyl. In some embodiments, R is $C_{1-6}$ alkyl. In some embodiments, R is methyl. In some embodiments, R is substituted methyl. In some embodiments, R is ethyl. In some embodiments, R is substituted ethyl. In some embodiments, one of $R^1$ and $R^2$ is R comprising a cyclic moiety as described in the present disclosure, and the other is an alkyl group as described in the present disclosure.

In some embodiments, one of $R^1$ and $R^2$ is R, wherein R is optionally substituted $C_{1-6}$ alkyl, and the other is R, wherein R is optionally substituted $C_{1-6}$ alkenyl. In some embodiments, one of $R^1$ and $R^2$ is optionally substituted methyl or ethyl, and the other is vinyl. In some embodiments, one of $R^1$ and $R^2$ is methyl, and the other is vinyl.

In some embodiments, one of $R^1$ and $R^2$ is R, wherein R is optionally substituted $C_{1-6}$ alkyl, and the other is R, wherein R is optionally substituted $C_{1-6}$ alkynyl. In some embodiments, one of $R^1$ and $R^2$ is optionally substituted methyl or ethyl, and the other is ethynyl. In some embodiments, one of $R^1$ and $R^2$ is methyl, and the other is ethynyl.

In some embodiments, each of $R^1$ and $R^2$ is independently R, wherein R is optionally substituted $C_{1-20}$ aliphatic. In some embodiments, R is unsubstituted $C_{1-20}$ aliphatic. In some embodiments, R is optionally substituted $C_{1-20}$ alkyl. In some embodiments, R is optionally substituted $C_{1-6}$ alkyl. In some embodiments, R is linear $C_{1-6}$ alkyl. In some embodiments, one of $R^1$ and $R^2$ is optionally substituted $C_{1-6}$ alkyl, and the other is optionally substituted $C_{1-6}$ alkyl. In some embodiments, $R^1$ and $R^2$ are the same. In some embodiments, $R^1$ and $R^2$ are different.

In some embodiments, each of $R^1$ and $R^2$ is independently R, wherein R is optionally substituted $C_{1-6}$ alkyl. In some embodiments, $R^1$ and $R^2$ are the same. Among other things, the present disclosure demonstrates that compounds with $R^1$ and $R^2$ being the same, or phosphoramidites prepared therefrom, can deliver high stereoselectivity, yields and/or purity when utilized in chirally controlled oligonucleotide preparation. In some embodiments, $R^1$ and $R^2$ are the same optionally substituted $C_{1-2}$ alkyl, and $R^1$ and $R^2$ comprise no more than two carbon atoms. In some embodiments, both $R^1$ and $R^1$ are methyl. In some embodiments, both $R^1$ and $R^1$ are ethyl. In some embodiments, both $R^1$ and $R^1$ are isopropyl. In some embodiments, one of $R^1$ and $R^2$ is optionally substituted $C_{1-3}$ linear alkyl, and the other is optionally substituted $C_{3-10}$ cycloalkyl. In some embodiments, one of $R^1$ and $R^2$ is optionally substituted $C_{1-3}$ linear alkyl, and the other is optionally substituted $C_{5-6}$ cycloalkyl. In some embodiments, $R^1$ is methyl. In some embodiments, $R^2$ is cyclopentyl. In some embodiments, $R^2$ is cyclohexyl. In some embodiments, one of $R^1$ and $R^2$ is optionally substituted $C_{1-3}$ linear alkyl, and the other is optionally substituted benzyl. In some embodiments, $R^1$ is methyl and $R^2$ is optionally substituted benzyl. In some embodiments, $R^2$ is benzyl. In some embodiments, $R^2$ is p-$CH_3O$—$C_6H_4$—$CH_2$—. In some embodiments, $R^1$ is selected from methyl, ethyl, cyclohexyl, and benzyl which is optionally substituted at the phenyl. In some embodiments, $R^2$ is selected from methyl, ethyl, cyclohexyl, and benzyl which is optionally substituted at the phenyl. In some embodiments, each of $R^1$ and $R^2$ is independently selected from methyl, ethyl, cyclohexyl, and benzyl which is optionally substituted at the phenyl.

In some embodiments, a provided compound is

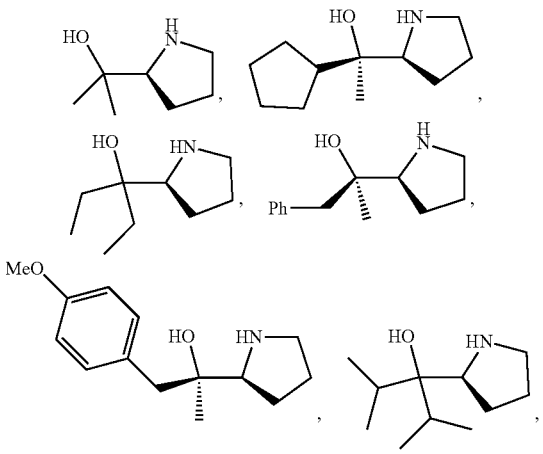

or a salt thereof. In some embodiments, a provided compound is a diastereomer of

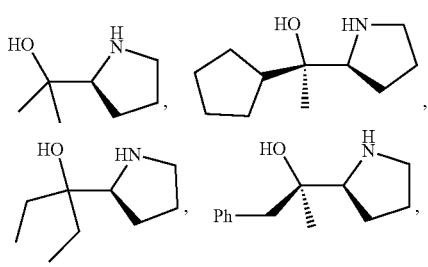

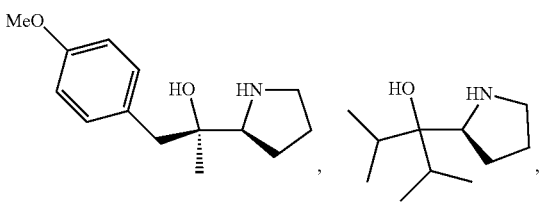

or a salt thereof. In some embodiments, a provided compound is an enantiomer of

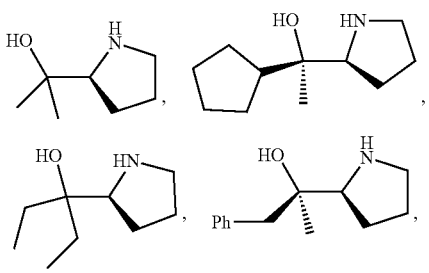

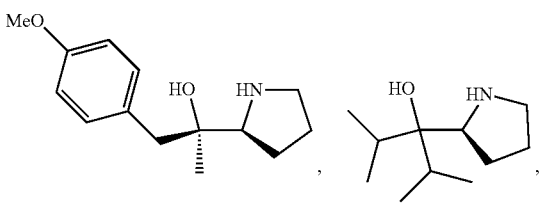

or a salt thereof. In some embodiments, a provided compound is

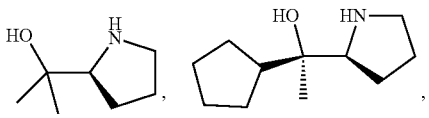

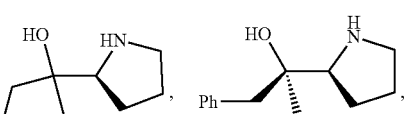

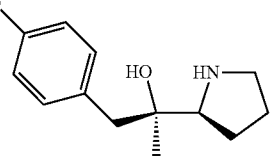

or a salt thereof. In some embodiments, a provided compound is a diastereomer of

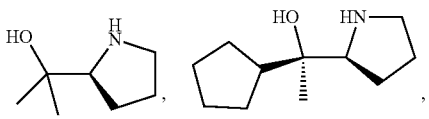

-continued

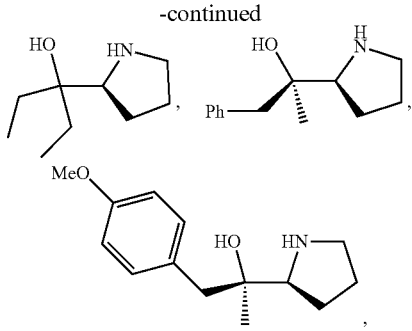

or a salt thereof. In some embodiments, a provided compound is an enantiomer of

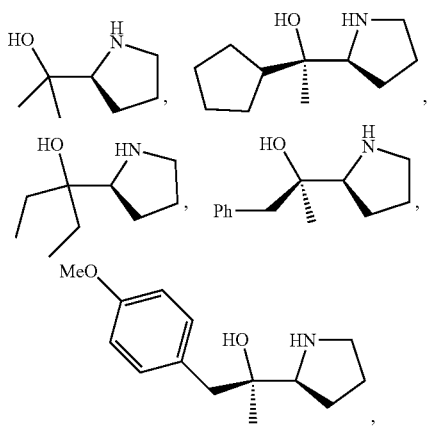

or a salt thereof. In some embodiments, a provided compound is

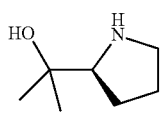

or a salt thereof. In some embodiments, a provided compound is

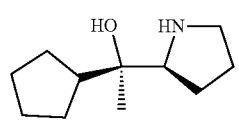

or a salt thereof. In some embodiments, a provided compound is

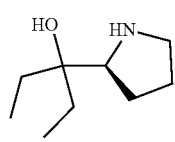

or a salt thereof. In some embodiments, a provided compound is

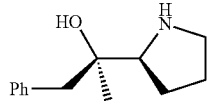

or a salt thereof. In some embodiments, a provided compound is

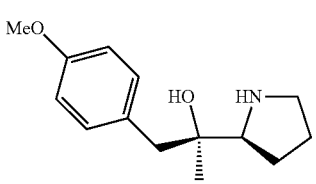

or a salt thereof. In some embodiments, a provided compound is

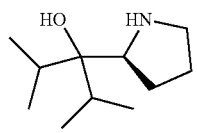

or a salt thereof. In some embodiments, a provided compound is a diastereomer of

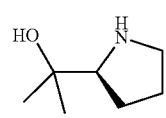

or a salt thereof. In some embodiments, a provided compound is a diastereomer of

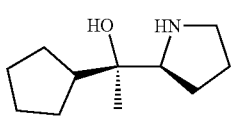

or a salt thereof. In some embodiments, a provided compound is a diastereomer of

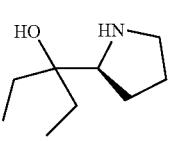

or a salt thereof. In some embodiments, a provided compound is a diastereomer of

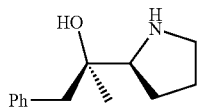

or a salt thereof. In some embodiments, a provided compound is a diastereomer of

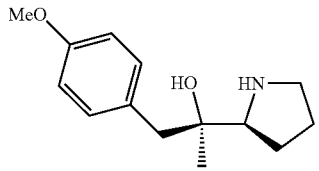 [SMILES: COc1ccc(C[C@@](C)(O)[C@@H]2CCCN2)cc1]

or a salt thereof. In some embodiments, a provided compound is a diastereomer of

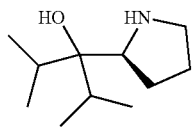

or a salt thereof. In some embodiments, a provided compound is an enantiomer of

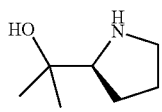

or a salt thereof. In some embodiments, a provided compound is an enantiomer of

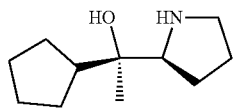

or a salt thereof. In some embodiments, a provided compound is an enantiomer of

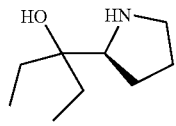

or a salt thereof. In some embodiments, a provided compound is an enantiomer of

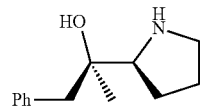

Ph or a salt thereof. In some embodiments, a provided compound is an enantiomer of

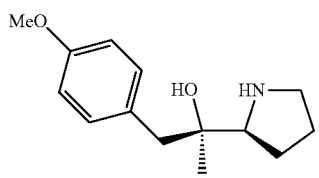 [SMILES: COc1ccc(C[C@@](C)(O)[C@@H]2CCCN2)cc1]

or a salt thereof. In some embodiments, a provided compound is an enantiomer of

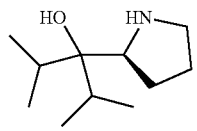

or a salt thereof.

In some embodiments, one of $R^1$ and $R^2$ is R, wherein R is optionally substituted $C_{1-6}$ alkyl, and the other is R, wherein R is an optionally substituted group selected from $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, one of $R^1$ and $R^2$ is R, wherein R is optionally substituted $C_{1-6}$ alkyl, and the other is R, wherein R is an optionally substituted group selected from $C_{3-20}$ cycloaliphatic, $C_{6-20}$ aryl, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, one of $R^1$ and $R^2$ is R, wherein R is optionally substituted $C_{1-6}$ alkyl, and the other is R, wherein R is an optionally substituted group selected from $C_{3-20}$ cycloaliphatic, $C_{6-20}$ aryl, 5-20 membered heteroaryl having 1-10 heteroatoms independently selected from oxygen, nitrogen, and sulfur, and 3-20 membered heterocyclyl having 1-10 heteroatoms independently selected from oxygen, nitrogen, and sulfur. In some embodiments, one of $R^1$ and $R^2$ is R, wherein R is optionally substituted $C_{1-6}$ alkyl, and the other is R, wherein R is an optionally substituted group selected from $C_{6-20}$ aryl, and 5-20 membered heteroaryl having 1-10 heteroatoms independently selected from oxygen, nitrogen, and sulfur. In some embodiments, one of $R^1$ and $R^2$ is R, wherein R is optionally substituted $C_{1-6}$ alkyl, and the other is R, wherein R is optionally substituted $C_{6-20}$ aryl. In some embodiments, one of $R^1$ and $R^2$ is R, wherein R is optionally substituted $C_{1-6}$ alkyl, and the other is R, wherein R is optionally substituted phenyl. In some embodiments, R as optionally substituted $C_{1-6}$ alkyl is methyl. In some embodiments, R as optionally substituted phenyl is

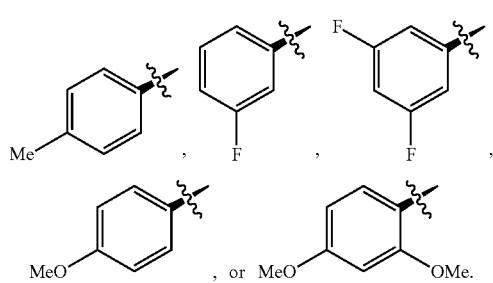

In some embodiments, $R^1$ is methyl, and $R^2$ is optionally substituted phenyl. In some embodiments, $R^1$ is methyl, and $R^2$ is phenyl. In some embodiments, $R^1$ is methyl, and $R^2$ is

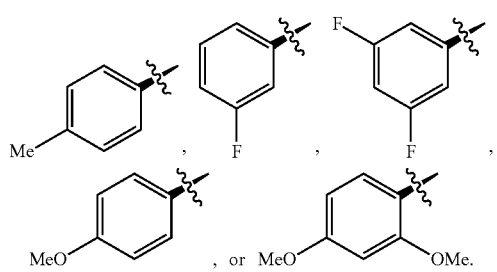

In some embodiments, a provided compound is selected from

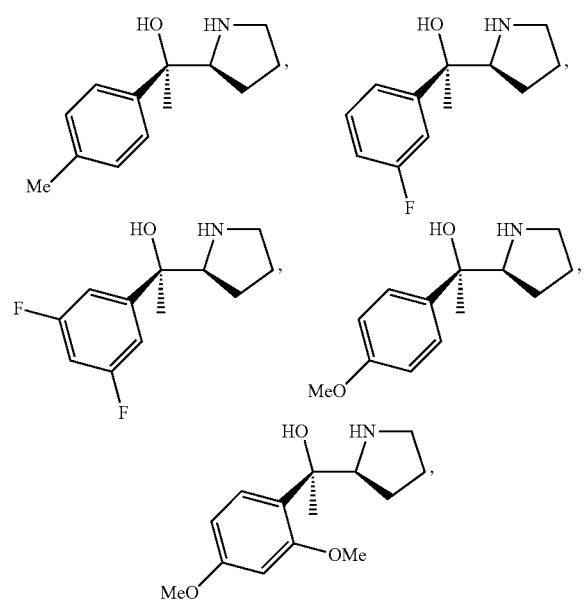

or salts thereof. In some embodiments, a provided compound is

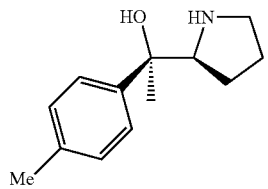

or a salt thereof. In some embodiments, a provided compound is

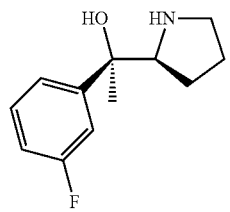

or a salt thereof. In some embodiments, a provided compound is

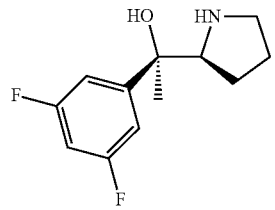 [SMILES: C[C@@](O)(c1cc(F)cc(F)c1)[C@@H]1CCCN1]

or a salt thereof. In some embodiments, a provided compound is

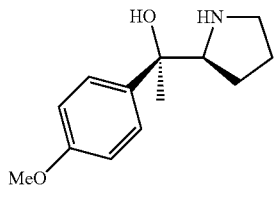 [SMILES: COc1ccc([C@@](C)(O)[C@@H]2CCCN2)cc1]

or a salt thereof. In some embodiments, a provided compound is

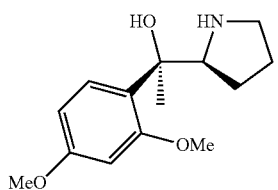 [SMILES: COc1ccc([C@@](C)(O)[C@@H]2CCCN2)c(OC)c1]

or a salt thereof. In some embodiments, a provided compound is a diastereomer of

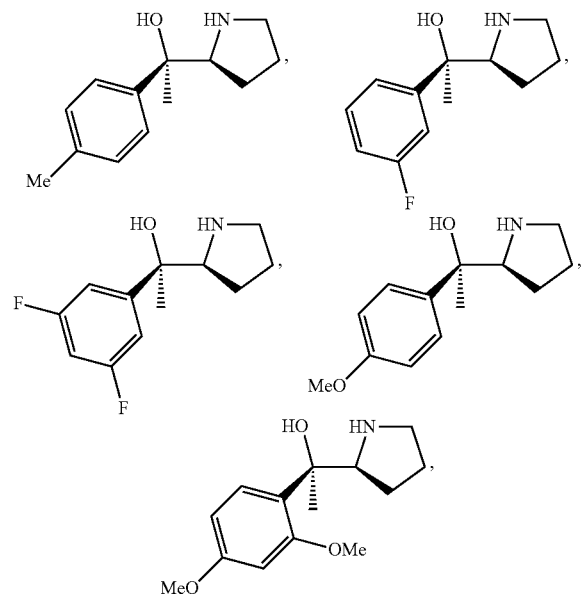

or a salt thereof. In some embodiments, a provided compound is a diastereomer of

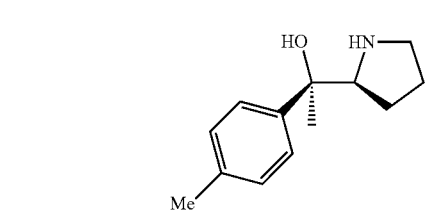

or a salt thereof. In some embodiments, a provided compound is a diastereomer of

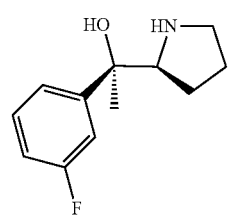

or a salt thereof. In some embodiments, a provided compound is a diastereomer of

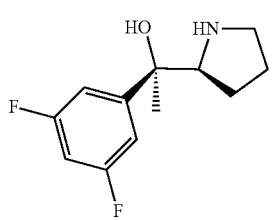 [SMILES: C[C@@](O)(c1cc(F)cc(F)c1)[C@@H]1CCCN1]

or a salt thereof. In some embodiments, a provided compound is a diastereomer of

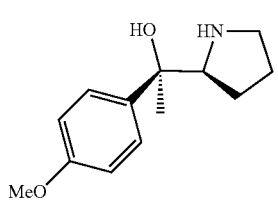 [SMILES: COc1ccc([C@@](C)(O)[C@@H]2CCCN2)cc1]

or a salt thereof. In some embodiments, a provided compound is a diastereomer of

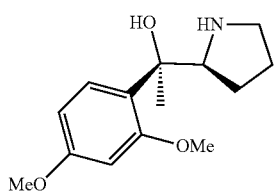 [SMILES: COc1ccc([C@@](C)(O)[C@@H]2CCCN2)c(OC)c1]

or a salt thereof. In some embodiments, a provided compound is an enantiomer of

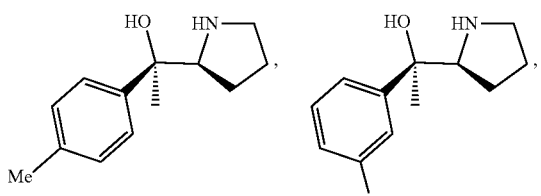

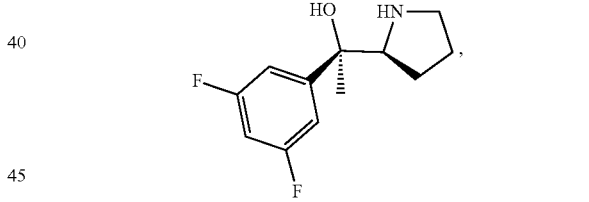

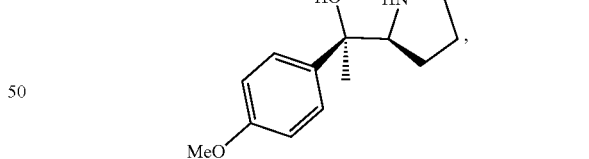

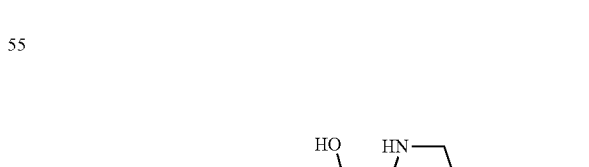

or a salt thereof. In some embodiments, a provided compound is an enantiomer of

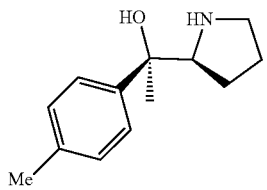

or a salt thereof. In some embodiments, a provided compound is an enantiomer of

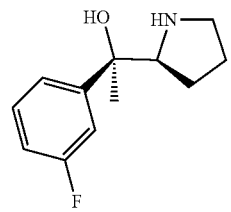

or a salt thereof. In some embodiments, a provided compound is an enantiomer of

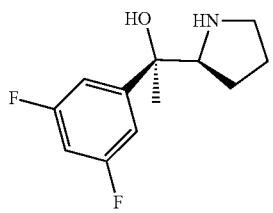 [SMILES: C[C@@](O)(c1cc(F)cc(F)c1)[C@@H]1CCCN1]

or a salt thereof. In some embodiments, a provided compound is an enantiomer of

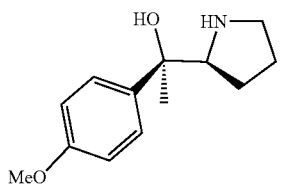 [SMILES: COc1ccc([C@@](C)(O)[C@@H]2CCCN2)cc1]

or a salt thereof. In some embodiments, a provided compound is an enantiomer of

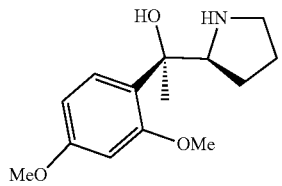 [SMILES: COc1ccc([C@@](C)(O)[C@@H]2CCCN2)c(OC)c1]

or a salt thereof.

In some embodiments, $R^1$ and $R^2$ are independently R, wherein R is as described in the present disclosure. In some embodiments, R is an optionally substituted group selected from $C_{3-20}$ cycloaliphatic, $C_{6-20}$ aryl, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, R is an optionally substituted group selected from $C_{3-20}$ cycloaliphatic, $C_{6-20}$ aryl, 5-20 membered heteroaryl having 1-10 heteroatoms independently selected from oxygen, nitrogen, and sulfur, and 3-20 membered heterocyclyl having 1-10 heteroatoms independently selected from oxygen, nitrogen, and sulfur. In some embodiments, R is an optionally substituted group selected from $C_{3-20}$ cycloaliphatic, and 3-20 membered heterocyclyl having 1-10 heteroatoms independently selected from oxygen, nitrogen, sulfur, phosphorus and silicon. In some embodiments, R is an optionally substituted group selected from $C_{6-20}$ aryl, and 5-20 membered heteroaryl having 1-10 heteroatoms independently selected from oxygen, nitrogen, sulfur, phosphorus and silicon. In some embodiments, R is an optionally substituted group selected from $C_{3-20}$ cycloaliphatic and $C_{6-20}$ aryl. In some embodiments, R is an optionally substituted group selected from 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, R is optionally substituted $C_{3-20}$ cycloaliphatic. In some embodiments, R is optionally substituted $C_{3-20}$ cycloalkyl. In some embodiments, R is optionally substituted $C_{1-20}$ heteroaliphatic having 1-10 heteroatoms independently selected from oxygen, nitrogen, sulfur, phosphorus and silicon. In some embodiments, R is optionally substituted $C_{6-20}$ aryl. In some embodiments, R is optionally substituted 5-20 membered heteroaryl having 1-10 heteroatoms independently selected from oxygen, nitrogen, sulfur, phosphorus and silicon. In some embodiments, R is optionally substituted 3-20 membered heterocyclyl having 1-10 heteroatoms independently selected from oxygen, nitrogen, sulfur, phosphorus and silicon. In some embodiments, R is optionally substituted phenyl. In some embodiments, R is phenyl. In some embodiments, $R^1$ and $R^2$ are optionally substituted phenyl. In some embodiments, $R^1$ and $R^2$ are phenyl. In some embodiments, a provided compound is

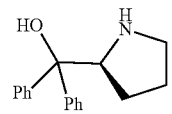 [SMILES: OC(c1ccccc1)(c1ccccc1)[C@@H]1CCCN1]

or a salt thereof. In some embodiments, a provided compound is a diastereomer of

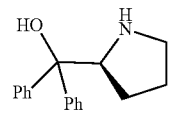

or a salt thereof. In some embodiments, a provided compound is an enantiomer of

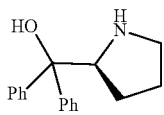

Ph or a salt thereof.

In some embodiments, the carbon atom to which $R^1$ and $R^2$ are attached is not chiral. In some embodiments, $R^1$ and $R^2$ are the same. In some embodiments, $R^1$ and $R^2$ are the same and neither are hydrogen. In some embodiments, $R^1$ and $R^2$ are methyl. In some embodiments, $R^1$ and $R^2$ are ethyl. In some embodiments, $R^1$ and $R^2$ are optionally substituted phenyl. In some embodiments, $R^1$ and $R^2$ are phenyl. In some embodiments, $R^1$ and $R^2$ are R, wherein the two R groups are taken together to form an optionally substituted ring as described in the present disclosure. In some embodiments, a formed ring does not contain any chiral elements. In some embodiments, a formed ring is an optionally substituted 5-membered cycloaliphatic ring. In some embodiments, a formed ring is optionally substituted

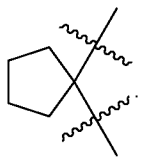

In some embodiments, a formed ring is

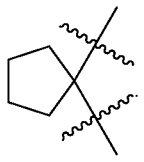

In some embodiments, a formed ring is optionally substituted

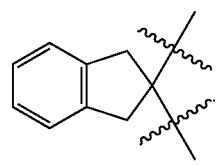 [SMILES: *C1(*)Cc2ccccc2C1]

In some embodiments, a formed ring is

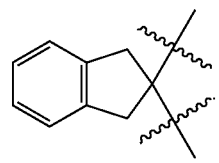 [SMILES: *C1(*)Cc2ccccc2C1]

In some embodiments, a formed ring is an optionally substituted 6-membered cycloaliphatic ring. In some embodiments, a formed ring is optionally substituted

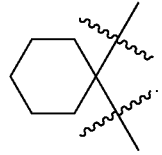 [SMILES: *C1(*)CCCCC1]

In some embodiments, a formed ring is

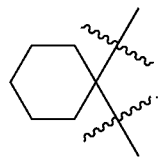 [SMILES: *C1(*)CCCCC1]

Among other things, the present disclosure demonstrated that provided compounds in which the carbon atom to which $R^1$ and $R^2$ are attached is not chiral can provide surprisingly high stereoselectivity when they are used in chirally controlled oligonucleotide synthesis. In some embodiments, such compounds provides high yields.

In some embodiments, $R^3$ is —H, -$L^s$-R, halogen, —CN, —NO$_2$, -$L^s$-Si(R)$_3$, —OR, —SR, or —N(R)$_2$. In some embodiments, $R^3$ is —H. In some embodiments, $R^3$ is -$L^s$-R, wherein each of $L^s$ and R is independently as described in the present disclosure. In some embodiments, $R^3$ is R, for example, an R embodiment as described in the present disclosure. In some embodiments, $R^3$ is halogen. In some embodiments, $R^3$ is —F. In some embodiments, $R^3$ is —Cl. In some embodiments, $R^3$ is —Br. In some embodiments, $R^3$ is —I. In some embodiments, $R^3$ is —CN. In some embodiments, $R^3$ is —NO$_2$. In some embodiments, $R^3$ is -$L^s$-Si(R)$_3$, wherein each of $L^s$ and R is independently as described in the present disclosure. In some embodiments, $R^3$ is —CH$_2$—Si(R)$_3$, wherein the —CH$_2$— group is optionally substituted, and each R is independently as described in the present disclosure. In some embodiments, $R^3$ is —CH$_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from $C_{1-6}$ alkyl and phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^3$ is —OR, wherein R is as described in the present disclosure. In some embodiments, $R^3$ is —SR wherein R is as described in the present disclosure. In some embodiments, $R^3$ is —N(R)$_2$, wherein each R is independently as described in the present disclosure. In some embodiments, $R^2$ is the same or different from $R^1$, and is a group selected from any groups described for $R^1$ in the present disclosure.

In some embodiments, $R^4$ is —H, -$L^s$-R, halogen, —CN, —NO$_2$, -$L^s$-Si(R)$_3$, —OR, —SR, or —N(R)$_2$. In some embodiments, $R^4$ is —H. In some embodiments, $R^4$ is -$L^s$-R, wherein each of $L^s$ and R is independently as described in the present disclosure. In some embodiments, $R^4$ is R, for example, an R embodiment as described in the present disclosure. In some embodiments, $R^4$ is halogen. In some embodiments, $R^4$ is —F. In some embodiments, $R^4$ is —Cl. In some embodiments, $R^4$ is —Br. In some embodiments, $R^4$ is —I. In some embodiments, $R^4$ is —CN. In some embodiments, $R^4$ is —NO$_2$. In some embodiments, $R^4$ is -L$^s$-Si(R)$_3$, wherein each of L$^s$ and R is independently as described in the present disclosure. In some embodiments, $R^4$ is —CH$_2$—Si(R)$_3$, wherein the —CH$_2$— group is optionally substituted, and each R is independently as described in the present disclosure. In some embodiments, $R^4$ is —CH$_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from C$_{1-6}$ alkyl and phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^4$ is —OR, wherein R is as described in the present disclosure. In some embodiments, $R^4$ is —SR wherein R is as described in the present disclosure. In some embodiments, $R^4$ is —N(R)$_2$, wherein each R is independently as described in the present disclosure. In some embodiments, $R^2$ is the same or different from $R^1$, and is a group selected from any groups described for $R^1$ in the present disclosure.

In some embodiments, at least one of $R^1$, $R^2$, $R^3$ and $R^4$ is not —H. In some embodiments, a provided compound of formula I, I-a, I-a-1, I-a-2, I-b, I-c, I-d, or I-e comprises one or more chiral elements. In some embodiments, $R^3$ and $R^4$ are not —H, and the carbon to which they are attached is a chiral center. In some embodiments, at least one of $R^1$ and $R^2$ is not hydrogen, and $R^1$ and $R^2$ are different, and the carbon to which they are attached is a chiral center. In some embodiments, at least one of $R^1$ and $R^2$ is not hydrogen, and $R^1$ and $R^2$ are the same, and the carbon to which they are attached is not a chiral center. Among other things, the present disclosure demonstrates that provided compounds, in which the carbon atoms to which $R^1$ and $R^2$ are attached are not chiral, can deliver surprisingly high stereoselectivity when used as chiral auxiliaries in oligonucleotide synthesis.

In some embodiments, $R^5$ is —H, -L$^s$-R, halogen, —CN, —NO$_2$, -L$^s$-Si(R)$_3$, —OR, —SR, or —N(R)$_2$. In some embodiments, $R^5$ is —H. In some embodiments, $R^5$ is -L$^s$-R, wherein each of L$^s$ and R is independently as described in the present disclosure. In some embodiments, $R^5$ is R, for example, an R embodiment as described in the present disclosure. In some embodiments, $R^5$ is halogen. In some embodiments, $R^5$ is —F. In some embodiments, $R^5$ is —Cl. In some embodiments, $R^5$ is —Br. In some embodiments, $R^5$ is —I. In some embodiments, $R^5$ is —CN. In some embodiments, $R^5$ is —NO$_2$. In some embodiments, $R^5$ is -L$^s$-Si(R)$_3$, wherein each of L$^s$ and R is independently as described in the present disclosure. In some embodiments, $R^5$ is —CH$_2$—Si(R)$_3$, wherein the —CH$_2$— group is optionally substituted, and each R is independently as described in the present disclosure. In some embodiments, $R^5$ is —CH$_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from C$_{1-6}$ alkyl and phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^5$ is —OR, wherein R is as described in the present disclosure. In some embodiments, $R^5$ is —SR wherein R is as described in the present disclosure. In some embodiments, $R^5$ is —N(R)$_2$, wherein each R is independently as described in the present disclosure. In some embodiments, $R^2$ is the same or different from $R^1$, and is a group selected from any groups described for $R^1$ in the present disclosure.

In some embodiments, $R^5$, and one or both of $R^1$ and $R^2$, are R and are taken together with their intervening atoms to form an optionally substituted, 3-20 membered monocyclic, bicyclic or polycyclic ring having 1-5 heteroatoms. In some embodiments, $R^5$ and $R^1$ are R and are taken together with their intervening atoms to form an optionally substituted, 3-20 membered monocyclic, bicyclic or polycyclic ring having 1-5 heteroatoms. In some embodiments, one of $R^1$ and $R^2$, and $R^5$, are R and are taken together with their intervening atoms to form an optionally substituted, 3-20 membered monocyclic, bicyclic or polycyclic ring having 1-5 heteroatoms. As extensively described in the present disclosure, a formed ring by two R groups taken together can be of various sizes, monocyclic, bicyclic or polycyclic, and contain various numbers of heteroatoms. In some embodiments, a ring is a 3-membered ring. In some embodiments, a ring is a 4-membered ring. In some embodiments, a ring is a 5-membered ring. In some embodiments, a ring is a 6-membered ring. In some embodiments, a formed ring contains no ring heteroatom in addition to the nitrogen to which $R^5$ is attached. In some embodiments, a ring is a saturated ring. In some embodiments, a ring is monocyclic. In some embodiments, a ring contains additional ring heteroatoms other than the intervening heteroatoms. In some embodiments, a ring is a 3-membered ring containing one ring heteroatom. In some embodiments, a ring is a 3-membered ring containing two ring heteroatoms. In some embodiments, a ring is a 3-membered ring containing one carbon, one nitrogen, and one oxygen ring atom.

In some embodiments, two or more of $R^1$, $R^2$, $R^3$, $R^4$, and $R^5$ are independently R, and the R groups are optionally and independently taken together to form rings as described in the present disclosure. In some embodiments, $R^1$ and $R^2$ are R, and the two R groups are taken together to form an optionally substituted ring as described in the present disclosure. In some embodiments, one of $R^1$ and $R^2$, and one of $R^3$ and $R^4$, are R, and the two R groups are taken together to form an optionally substituted ring as described in the present disclosure. In some embodiments, one of $R^3$ and $R^4$, and $R^5$, are R, and the two R groups are taken together to form an optionally substituted ring as described in the present disclosure.

In some embodiments, a formed ring, e.g., by $R^1$ and $R^2$, or one of $R^1$ and $R^2$ and one of $R^3$ and $R^4$, is an optionally substituted 3-20 membered monocyclic, bicyclic or polycyclic ring having 0-5 heteroatoms. In some embodiments, a formed ring is monocyclic. In some embodiments, a formed ring is bicyclic. In some embodiments, a formed ring is polycyclic. In some embodiments, a formed ring is aliphatic. In some embodiments, a formed ring comprises no unsaturation. In some embodiments, a formed ring is partially unsaturated. In some embodiments, a formed ring comprises one or more saturated monocyclic ring moieties. In some embodiments, a formed ring comprises one or more monocyclic partially unsaturated ring moieties. In some embodiments, a formed ring comprises one or more monocyclic aromatic ring moieties. In some embodiments, a formed ring comprises one or more saturated, partially unsaturated, and/or aromatic ring moieties, for example, a bicyclic or polycyclic ring comprising fused saturated, partially unsaturated, and/or aromatic monocyclic moieties. In some embodiments, a formed ring is optionally substituted. In some embodiments, a formed ring is substituted. In some embodiments, a formed ring is not substituted. In some embodiments, a formed ring comprises no chiral elements. In some embodiments, a formed ring comprises one or more chiral elements. In some embodiments, a formed ring comprises one or more chiral elements and is chiral. In some embodiments, a chiral element is a chiral center. In some embodiments, a formed ring is an optionally substituted 3-10 membered monocyclic ring having no heteroatoms. In some embodiments, a formed monocyclic ring is 3-membered; in some embodiments, 4-membered; in some embodiments, 5-membered; in some embodiments, 6-membered; in some embodiments 7-membered; in some embodiments, 8-membered; in some embodiments 9-membered; and in some embodiments 10-membered. In some embodiments, a formed ring is a 3-membered saturated cycloaliphatic ring. In some embodiments, a formed ring is an optionally substituted 5-membered saturated cycloaliphatic ring. In some embodiments, a formed ring is an optionally substituted 5-membered saturated cycloaliphatic ring containing no chiral elements. In some embodiments, a formed ring is an unsubstituted 5-membered saturated cycloaliphatic ring containing no chiral elements. In some embodiments, a 5-membered ring described herein is fused to another optionally substituted ring, which can be saturated, partially unsaturated or aryl. In some embodiments, a 5-membered ring described herein is fused to an optionally substituted aryl ring. In some embodiments, a 5-membered ring described herein is fused to an optionally substituted phenyl ring. In some embodiments, a 5-membered ring described herein is fused to a phenyl ring. In some embodiments, fusion is at C3 and C4 (C1 being the carbon atom to which $R^1$ and $R^2$ are attached). In some embodiments, a formed ring is optionally substituted

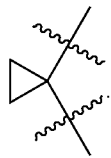 [SMILES: *C1(*)CC1]

In some embodiments, a formed ring is

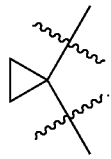 [SMILES: *C1(*)CC1]

In some embodiments, a formed ring is optionally substituted

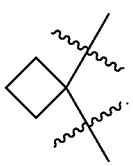 [SMILES: *C1(*)CCC1]

In some embodiments, a formed ring is

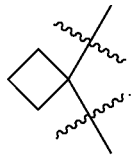

In some embodiments, a formed ring is optionally substituted

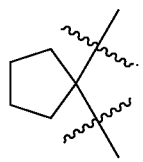 [SMILES: *C1(*)CCCC1]

In some embodiments, a formed ring is

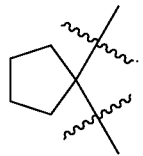 [SMILES: *C1(*)CCCC1]

In some embodiments, a formed ring is optionally substituted

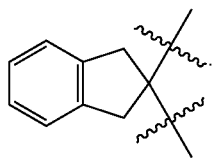 [SMILES: *C1(*)Cc2ccccc2C1]

In some embodiments, a formed ring is

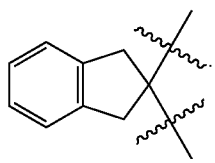 [SMILES: *C1(*)Cc2ccccc2C1]

In some embodiments, a formed ring is an optionally substituted 6-membered saturated cycloaliphatic ring. In some embodiments, a formed ring is an optionally substituted 6-membered saturated cycloaliphatic ring containing no chiral elements. In some embodiments, a formed ring is an unsubstituted 6-membered saturated cycloaliphatic ring containing no chiral elements. In some embodiments, one or more ring moieties may be fused to the 6-membered ring, for example, as described above for the 5-membered ring. Ring embodiments described herein are applicable to other variables two of which can be R and can be taken together to form an optionally substituted ring. In some embodiments, a formed ring is optionally substituted

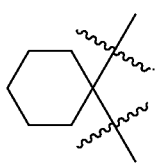

In some embodiments, a formed ring is

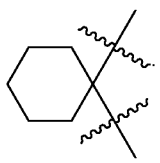

In some embodiments, a provided compound is

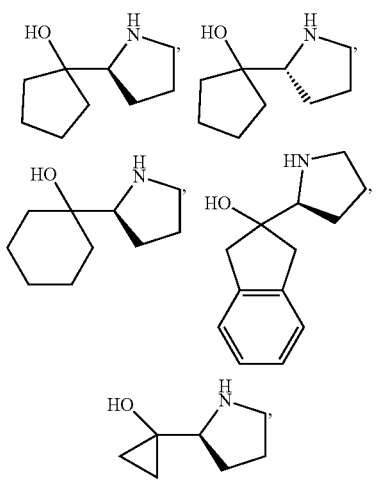

or a salt thereof. In some embodiments, a provided compound is selected from

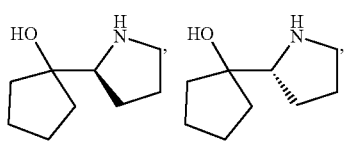

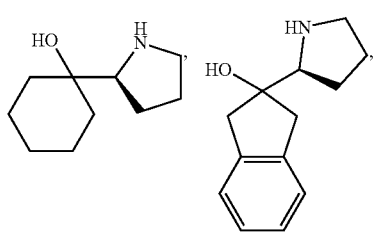

and salts thereof. In some embodiments, a provided compound is

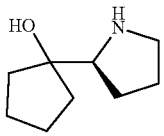 [SMILES: OC1([C@@H]2CCCN2)CCCC1]

or a salt thereof. In some embodiments, a provided compound is

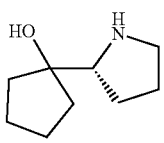 [SMILES: OC1([C@H]2CCCN2)CCCC1]

or a salt thereof. In some embodiments, a provided compound is

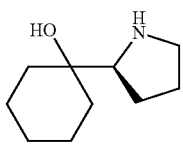 [SMILES: OC1([C@@H]2CCCN2)CCCCC1]

or a salt thereof. In some embodiments, a provided compound is

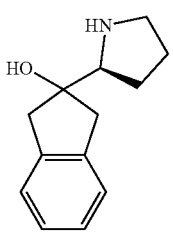 [SMILES: OC1([C@@H]2CCCN2)Cc2ccccc2C1]

or a salt thereof. In some embodiments, a provided compound is a diastereomer of

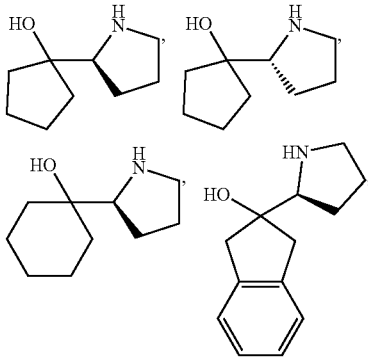

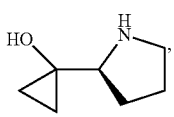

or a salt thereof. In some embodiments, a provided compound is a diastereomer of selected from

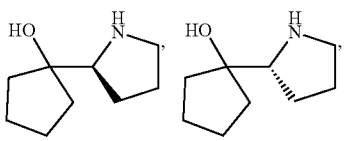

and salts thereof. In some embodiments, a provided compound is a diastereomer of

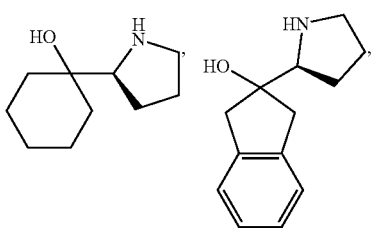

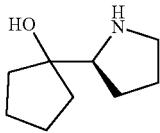

or a salt thereof. In some embodiments, a provided compound is a diastereomer of

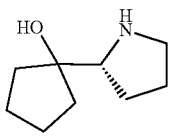

or a salt thereof. In some embodiments, a provided compound is a diastereomer of

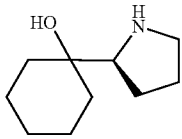 [SMILES: OC1([C@@H]2CCCN2)CCCCC1]

or a salt thereof. In some embodiments, a provided compound is a diastereomer of

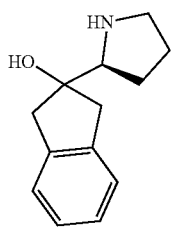 [SMILES: OC1([C@@H]2CCCN2)Cc2ccccc2C1]

or a salt thereof. In some embodiments, a provided compound is an enantiomer of

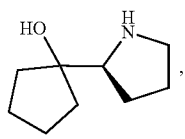

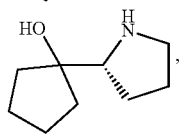

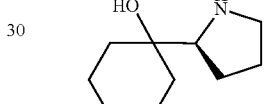

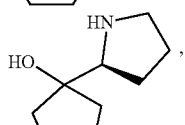

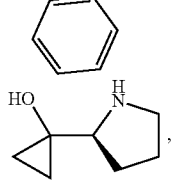

or a salt thereof. In some embodiments, a provided compound is an enantiomer of selected from

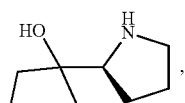

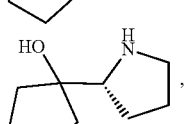

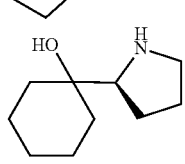

-continued

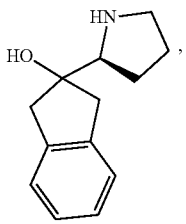

and salts thereof. In some embodiments, a provided compound is an enantiomer of

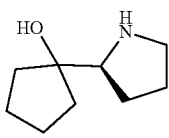

or a salt thereof. In some embodiments, a provided compound is an enantiomer of

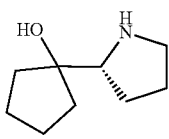

or a salt thereof. In some embodiments, a provided compound is an enantiomer of

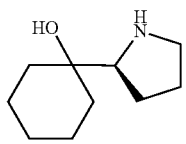 [SMILES: OC1([C@@H]2CCCN2)CCCCC1]

or a salt thereof. In some embodiments, a provided compound is an enantiomer of

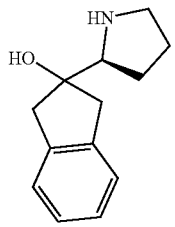 [SMILES: OC1([C@@H]2CCCN2)Cc2ccccc2C1]

or a salt thereof.

In some embodiments, one of $R^1$ and $R^2$, and one of $R^3$ and $R^4$, are R, (e.g., one of $R^1$ and $R^2$, and one of $R^3$ and $R^4$, of formula I-a) and the two R groups are taken together to form an optionally substituted ring as described in the present disclosure. In some embodiments, $R^1$ and $R^3$ are R, and the two R groups are taken together to form an optionally substituted ring as described in the present disclosure. In some embodiments, $R^1$ and $R^4$ are R, and the two R groups are taken together to form an optionally substituted ring as described in the present disclosure. In some embodiments, $R^2$ and $R^3$ are R and the two R groups are taken together to form an optionally substituted ring as described in the present disclosure. In some embodiments, $R^2$ and $R^4$ are R, and the two R groups are taken together to form an optionally substituted ring as described in the present disclosure. In some embodiments, a provided compound has the structure of formula I-e or a salt thereof. As described in the present disclosure, in some embodiments, a formed ring is an optionally substituted $C_{3-20}$ cycloaliphatic ring. In some embodiments, a formed ring is an optionally substituted $C_{3-10}$ cycloaliphatic ring. In some embodiments, a formed ring is an optionally substituted $C_{5-7}$ cycloaliphatic ring. In some embodiments, a formed ring is an optionally substituted $C_5$ cycloaliphatic ring. In some embodiments, a formed ring is an optionally substituted $C_6$ cycloaliphatic ring. In some embodiments, a formed ring is an optionally substituted $C_7$ cycloaliphatic ring. In some embodiments, a formed ring is an optionally substituted $C_8$ cycloaliphatic ring. In some embodiments, a formed ring is an optionally substituted $C_9$ cycloaliphatic ring. In some embodiments, a formed ring is an optionally substituted $C_{10}$ cycloaliphatic ring. As described in the present disclosure, in some embodiments, a formed ring can be monocyclic, bicyclic, or polycyclic, and can comprise one or more saturated, partially saturated and/or aromatic monocyclic moieties. In some embodiments, a formed ring is an optionally substituted $C_{3-20}$ saturated, monocyclic cycloaliphatic ring. In some embodiments, a formed ring is an optionally substituted $C_{3-10}$ saturated, monocyclic cycloaliphatic ring. In some embodiments, a formed ring is an optionally substituted $C_{5-7}$ saturated, monocyclic cycloaliphatic ring. In some embodiments, a formed ring is an optionally substituted $C_5$ saturated, monocyclic cycloaliphatic ring. In some embodiments, a formed ring is an optionally substituted $C_6$ saturated, monocyclic cycloaliphatic ring. In some embodiments, a formed ring is an optionally substituted $C_7$ saturated, monocyclic cycloaliphatic ring. In some embodiments, a formed ring is an optionally substituted $C_8$ saturated, monocyclic cycloaliphatic ring. In some embodiments, a formed ring is an optionally substituted $C_9$ saturated, monocyclic cycloaliphatic ring. In some embodiments, a formed ring is an optionally substituted $C_{10}$ saturated, monocyclic cycloaliphatic ring. In some embodiments, one of $R^1$ and $R^2$, and one of $R^3$ and $R^4$, are R, and the two R groups are taken together to form an optionally substituted ring as described in the present disclosure; $R^5$ is R, wherein R is an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon; $R^6$ is —H; and $R^7$ is —OH. In some embodiments, one of $R^1$ and $R^2$, and one of $R^3$ and $R^4$, are R, and the two R groups are taken together to form an optionally substituted ring as described in the present disclosure; $R^5$ is R, wherein R is an optionally substituted $C_{1-20}$ aliphatic; $R^6$ is —H; and $R^7$ is —OH. In some embodiments, one of $R^1$ and $R^2$, and one of $R^3$ and $R^4$, are R, and the two R groups are taken together to form an optionally substituted ring as described in the present disclosure; $R^5$ is R, wherein R is an optionally substituted $C_{1-6}$ alkyl; $R^6$ is —H; and $R^7$ is —OH. In some embodiments, one of $R^1$ and $R^2$, and one of $R^3$ and $R^4$, are R, and the two R groups are taken together to form an optionally substituted ring as described in the present disclosure; $R^5$ is R, wherein R is methyl; $R^6$ is —H; and $R^7$ is —OH. Among other things, the present disclosure demonstrated that provided compounds, wherein the N atom to which $R^5$ and $R^6$ are attached is not within a ring, can provide surprisingly high stereoselectivity and/or yield when used in chirally controlled preparation of oligonucleotides.

In some embodiments, a provided compound, e.g., a compound of formula I-e, is

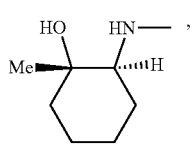

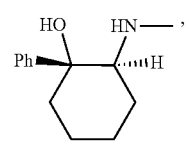

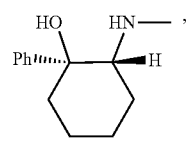

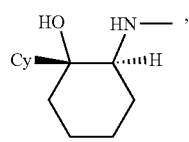

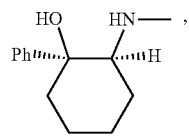

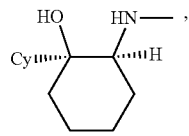

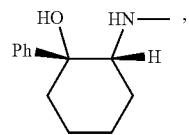

and thereof. In some embodiments, a provided compound is

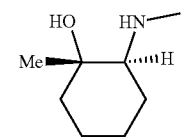

or a salt there of. In some embodiments, a provided compound is

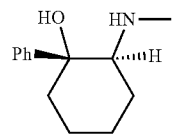

or a salt there of. In some embodiments, a provided compound is

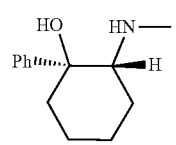

or a salt there of. In some embodiments, a provided compound is

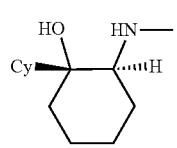

or a salt there of. In some embodiments, a provided compound is

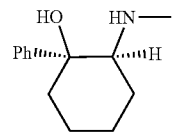

or a salt there of. In some embodiments, a provided compound is

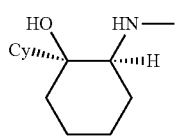

or a salt there of. In some embodiments, a provided compound is

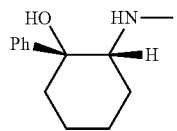

or a salt there of. In some embodiments, a provided compound is

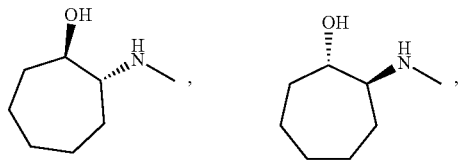

or a salt thereof. In some embodiments, a provided compound is

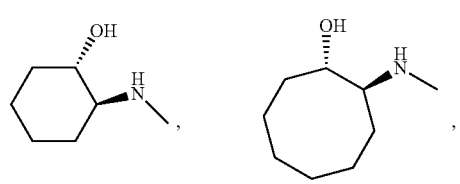

or a salt thereof. In some embodiments, a provided compound is

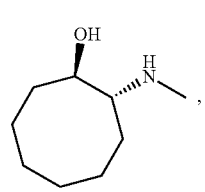

or a salt thereof. In some embodiments, a provided compound is

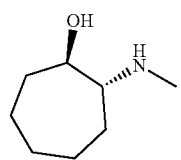

or a salt thereof. In some embodiments, a provided compound is

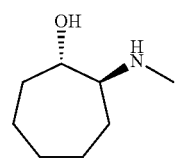

or a salt thereof. In some embodiments, a provided compound is

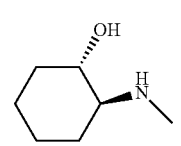

or a salt thereof. In some embodiments, a provided compound is

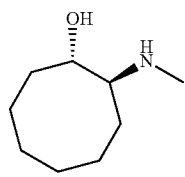

or a salt thereof. In some embodiments, a provided compound is

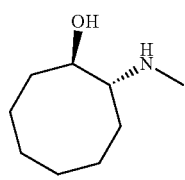

or a salt thereof.

In some embodiments, a provided compound, e.g., a compound of formula I-e, is

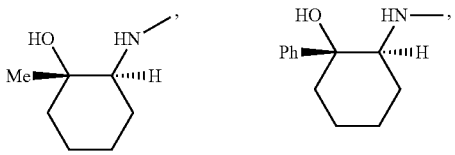

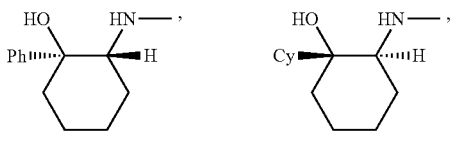

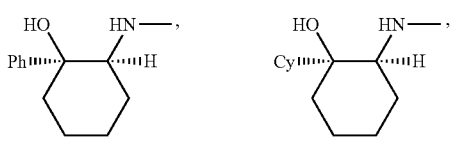

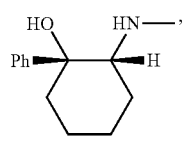

and thereof. In some embodiments, a provided compound is a diastereomer of

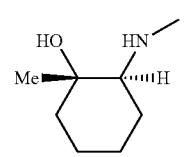

or a salt there of. In some embodiments, a provided compound is a diastereomer of


or a salt there of. In some embodiments, a provided compound is a diastereomer of

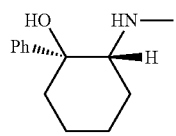

or a salt there of. In some embodiments, a provided compound is a diastereomer of

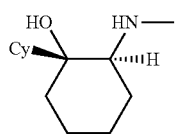

or a salt there of. In some embodiments, a provided compound is a diastereomer of


or a salt there of. In some embodiments, a provided compound is a diastereomer of

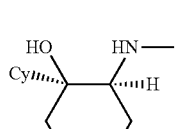

or a salt there of. In some embodiments, a provided compound is a diastereomer of

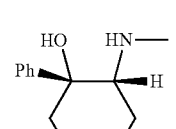

or a salt there of. In some embodiments, a provided compound is a diastereomer of

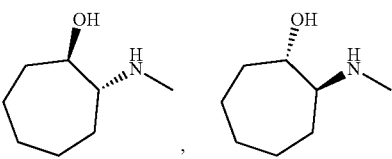

or a salt there of. In some embodiments, a provided compound is a diastereomer of

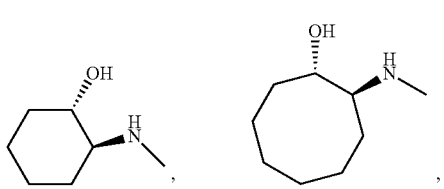

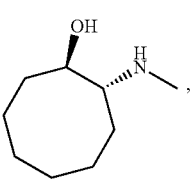

or a salt thereof. In some embodiments, a provided compound is a diastereomer of

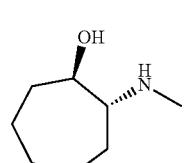

or a salt thereof. In some embodiments, a provided compound is a diastereomer of

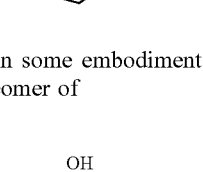

or a salt thereof. In some embodiments, a provided compound is a diastereomer of

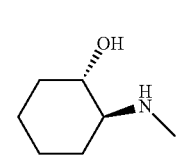

or a salt thereof. In some embodiments, a provided compound is a diastereomer of

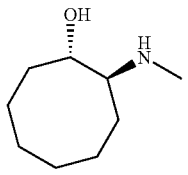

or a salt thereof. In some embodiments, a provided compound is a diastereomer of

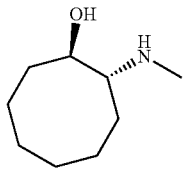

or a salt thereof.

In some embodiments, a provided compound, e.g., a compound of formula I-e, is

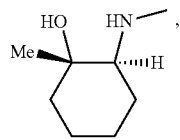 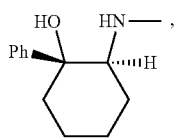

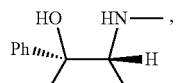 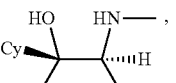

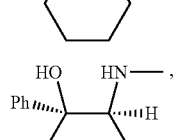 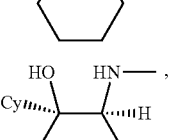

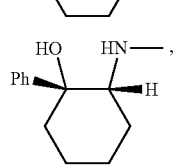

and thereof. In some embodiments, a provided compound is an enantiomer of

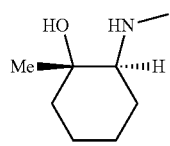

or a salt there of. In some embodiments, a provided compound is an enantiomer of

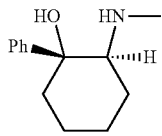

or a salt there of. In some embodiments, a provided compound is an enantiomer of

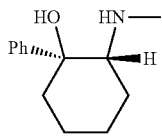

or a salt there of. In some embodiments, a provided compound is an enantiomer of

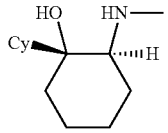

or a salt there of. In some embodiments, a provided compound is an enantiomer of

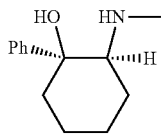

or a salt there of. In some embodiments, a provided compound is an enantiomer of

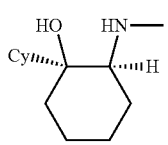

or a salt there of. In some embodiments, a provided compound is an enantiomer of

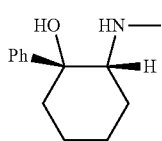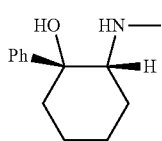

or a salt there of. In some embodiments, a provided compound is an enantiomer of

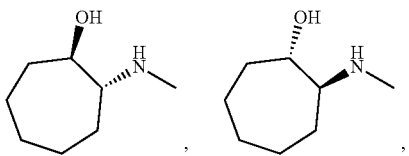

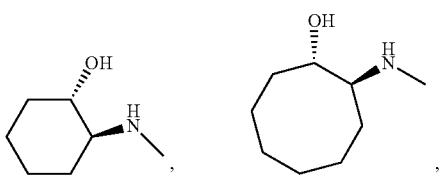

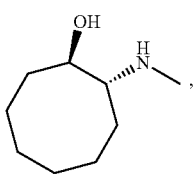

or a salt thereof. In some embodiments, a provided compound is an enantiomer of

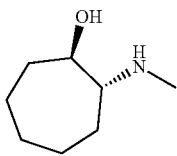

or a salt thereof. In some embodiments, a provided compound is an enantiomer of

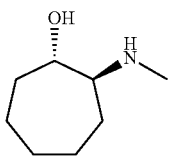

or a salt thereof. In some embodiments, a provided compound is an enantiomer of

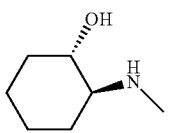

or a salt thereof. In some embodiments, a provided compound is an enantiomer of

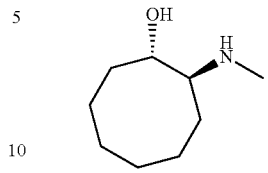

or a salt thereof. In some embodiments, a provided compound is an enantiomer of

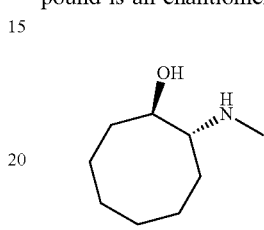

or a salt thereof.

In some embodiments, $R^3$ and $R^4$ are R, and the two R groups are taken together to form an optionally substituted ring as described in the present disclosure.

In some embodiments, $R^3$ and $R^5$ are R, and the two R groups are taken together to form an optionally substituted ring as described in the present disclosure. In some embodiments, $R^4$ and $R^5$ are R, and the two R groups are taken together to form an optionally substituted ring as described in the present disclosure. In some embodiments, $R^4$ and $R^5$ are R, and the two R groups are taken together to form an optionally substituted ring as described in the present disclosure; $R^6$ is —H; and $R^7$ is —OH.

In some embodiments, a formed ring is an optionally substituted 3-20 membered monocyclic, bicyclic or polycyclic ring having 1-5 heteroatoms. In some embodiments, a formed ring is an optionally substituted 4-6 membered monocyclic ring having no more than one heteroatom. In some embodiments, a formed ring is an optionally substituted 4-6 membered saturated monocyclic ring having only one ring heteroatom, which only ring heteroatom is the nitrogen to which $R^5$ is attached. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, $R^3$ is —H, and $R^4$ and $R^5$ are R, which are taken together with their intervening atoms to form an optionally substituted 3-20 membered monocyclic, bicyclic or polycyclic ring having 1-5 heteroatoms. In some embodiments, $R^3$ is —H, and $R^4$ and $R^5$ are R, which are taken together with their intervening atoms to form an optionally substituted 3-20 membered monocyclic, bicyclic or polycyclic ring having a nitrogen atom (the one which $R^5$ is on). In some embodiments, $R^3$ is —H, and $R^4$ and $R^5$ are R, which are taken together with their intervening atoms to form an optionally substituted 4-7 membered monocyclic ring having a nitrogen atom (the one which $R^5$ is on). In some embodiments, $R^3$ is —H, and $R^4$ and $R^5$ are R, which are taken together with their intervening atoms to form an optionally substituted 4-membered monocyclic ring having a nitrogen atom (the one which R⁵ is on). In some embodiments, R³ is —H, and R⁴ and R⁵ are R, which are taken together with their intervening atoms to form an optionally substituted 5-membered monocyclic ring having a nitrogen atom (the one which R⁵ is on). In some embodiments, R³ is —H, and R⁴ and R⁵ are R, which are taken together with their intervening atoms to form an optionally substituted 6-membered monocyclic ring having a nitrogen atom (the one which R⁵ is on). In some embodiments, R³ is —H, and R⁴ and R⁵ are R, which are taken together with their intervening atoms to form an optionally substituted 7-membered monocyclic ring having a nitrogen atom (the one which R⁵ is on). In some embodiments, R³ is —H, and R⁴ and R⁵ are R, which are taken together with their intervening atoms to form an optionally substituted 8-membered monocyclic ring having a nitrogen atom (the one which R⁵ is on). In some embodiments, R³ is —H, and R⁴ and R⁵ are R, which are taken together with their intervening atoms to form an optionally substituted 9-membered monocyclic ring having a nitrogen atom (the one which R⁵ is on). In some embodiments, R³ is —H, and R⁴ and R⁵ are R, which are taken together with their intervening atoms to form an optionally substituted 10-membered monocyclic ring having a nitrogen atom (the one which R⁵ is on). In some embodiments, a formed ring is substituted. In some embodiments, a formed ring is unsubstituted. In some embodiments, formed ring is monocyclic. In some embodiments, a formed ring is bicyclic. In some embodiments, a formed ring has no additional heteroatoms in addition to an intervening atom. In some embodiments, a formed ring has additional ring heteroatoms in addition to an intervening atom. In some embodiments, a formed ring is an optionally substituted saturated, monocyclic, 4-membered ring having no more than one ring heteroatom, wherein the only ring heteroatom is nitrogen. In some embodiments, a formed ring is an optionally substituted saturated, monocyclic, 5-membered ring having no more than one ring heteroatom, wherein the only ring heteroatom is nitrogen. In some embodiments, a formed ring is an optionally substituted saturated, monocyclic, 6-membered ring having no more than one ring heteroatom, wherein the only ring heteroatom is nitrogen. In some embodiments, a formed ring is an optionally substituted saturated, monocyclic, 7-membered ring having no more than one ring heteroatom, wherein the only ring heteroatom is nitrogen. In some embodiments, a formed ring is an optionally substituted saturated, monocyclic, 8-membered ring having no more than one ring heteroatom, wherein the only ring heteroatom is nitrogen. In some embodiments, a formed ring is an optionally substituted saturated, monocyclic, 9-membered ring having no more than one ring heteroatom, wherein the only ring heteroatom is nitrogen. In some embodiments, a formed ring is an optionally substituted saturated, monocyclic, 10-membered ring having no more than one ring heteroatom, wherein the only ring heteroatom is nitrogen. In some embodiments, a formed ring is of such a structure that

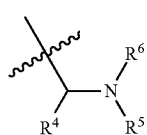

(R⁶ is —H), is, in some embodiments,

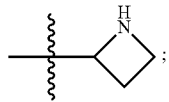 [SMILES: *C1CCN1]

in some embodiments,

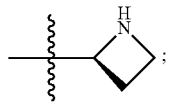 [SMILES: *[C@@H]1CCN1]

in some embodiments,

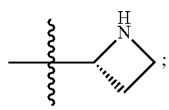

in some embodiments,

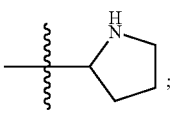 [SMILES: *C1CCCN1]

in some embodiments,

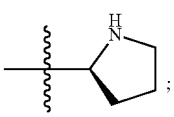 [SMILES: *[C@@H]1CCCN1]

in some embodiments,

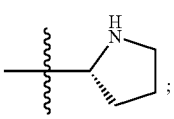

in some embodiments,

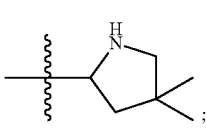 [SMILES: *C1CC(C)(C)CN1]

in some embodiments,

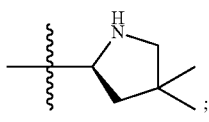 [SMILES: *[C@@H]1CC(C)(C)CN1]

in some embodiments,
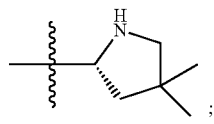 [SMILES: *[C@H]1CC(C)(C)CN1];
in some embodiments,
;
in some embodiments,
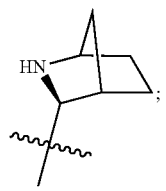 [SMILES: *[C@H]1NC2CCC1C2];
in some embodiments,
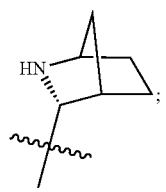 [SMILES: *[C@@H]1NC2CCC1C2];
in some embodiments,
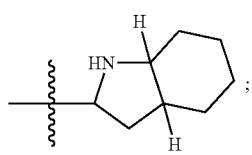 [SMILES: *C1CC2CCCCC2N1];
in some embodiments,
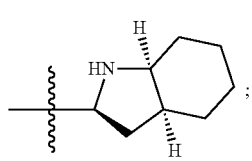 [SMILES: *[C@@H]1C[C@@H]2CCCC[C@@H]2N1];
in some embodiments,
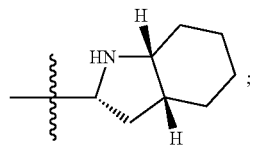 [SMILES: *[C@H]1C[C@H]2CCCC[C@H]2N1];
in some embodiments,
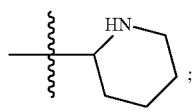;
in some embodiments,
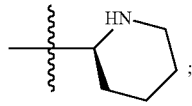;
in some embodiments,
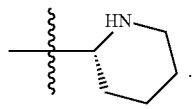 [SMILES: *[C@H]1CCCCN1].
In some embodiments, a provided compound is
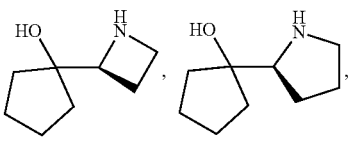,
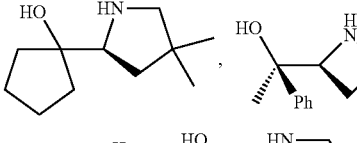,
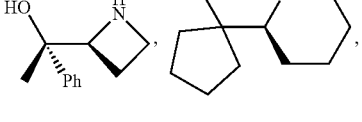,
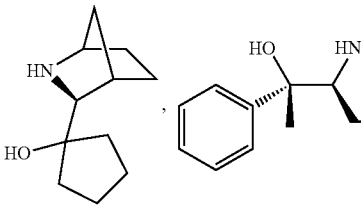, -continued

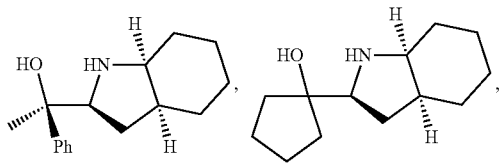

or a salt thereof. In some embodiments, a provided compound is

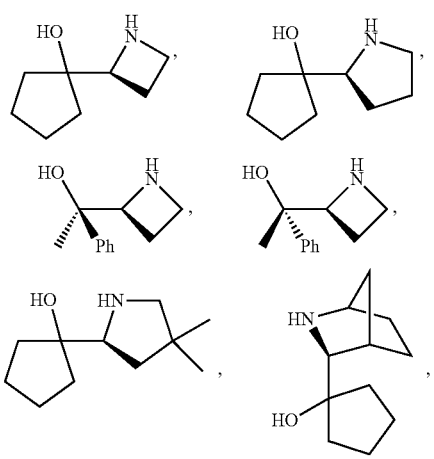

or a salt thereof. In some embodiments, a provided compound is

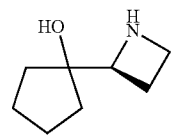

or a salt thereof. In some embodiments, a provided compound is

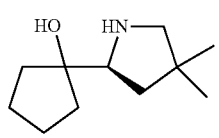

or a salt thereof. In some embodiments, a provided compound is

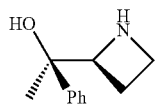

or a salt thereof. In some embodiments, a provided compound is

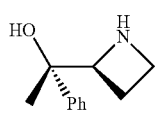

or a salt thereof. In some embodiments, a provided compound is

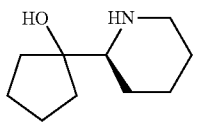 [SMILES: OC1([C@@H]2CCCCN2)CCCC1]

or a salt thereof. In some embodiments, a provided compound is

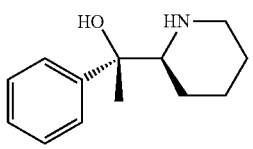

or a salt thereof. In some embodiments, a provided compound is

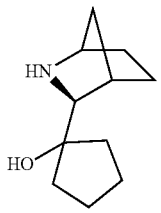

or a salt thereof. In some embodiments, a provided compound is

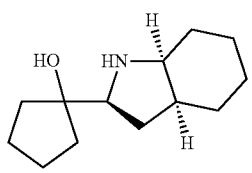 [SMILES: OC1([C@@H]2C[C@@H]3CCCC[C@@H]3N2)CCCC1]

or a salt thereof. In some embodiments, a provided compound is

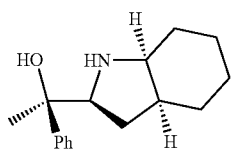 [SMILES: C[C@@](O)(c1ccccc1)[C@@H]1C[C@@H]2CCCC[C@@H]2N1]

or a salt thereof.

In some embodiments, a provided compound is a diastereomer of

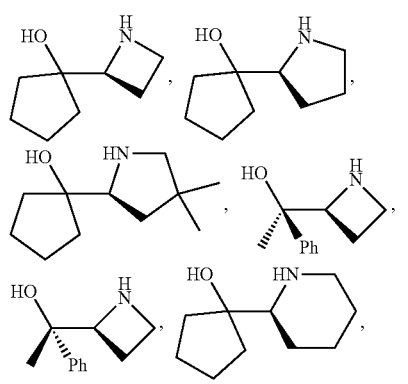

or a salt thereof. In some embodiments, a provided compound is a diastereomer of

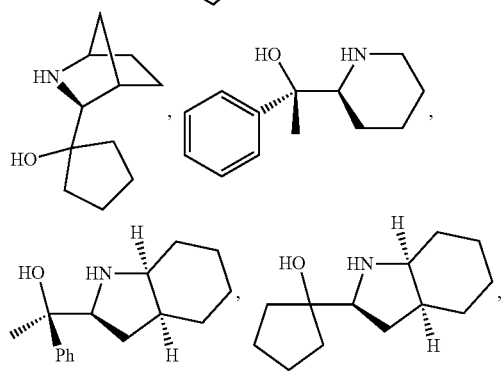

or a salt thereof. In some embodiments, a provided compound is a diastereomer of

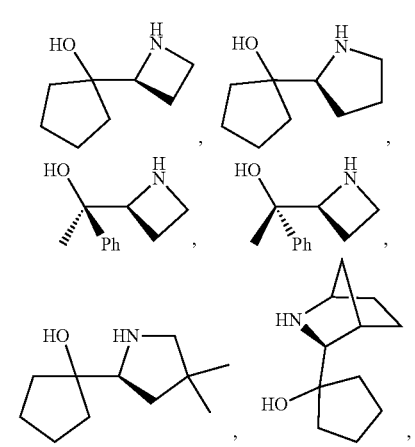

or a salt thereof. In some embodiments, a provided compound is a diastereomer of

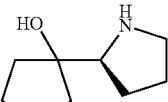

or a salt thereof. In some embodiments, a provided compound is a diastereomer of

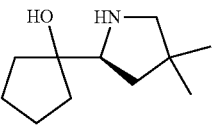

or a salt thereof. In some embodiments, a provided compound is a diastereomer of

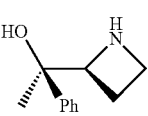

or a salt thereof. In some embodiments, a provided compound is a diastereomer of

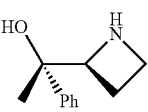

or a salt thereof. In some embodiments, a provided compound is a diastereomer of

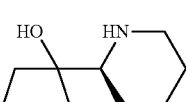

or a salt thereof. In some embodiments, a provided compound is a diastereomer of

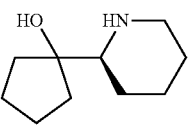 [SMILES: OC1([C@@H]2CCCCN2)CCCC1]

or a salt thereof. In some embodiments, a provided compound is a diastereomer of

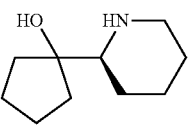 [SMILES: OC1([C@@H]2CCCCN2)CCCC1]

or a salt thereof. In some embodiments, a provided compound is a diastereomer of

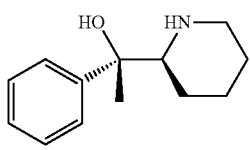

or a salt thereof. In some embodiments, a provided compound is a diastereomer of

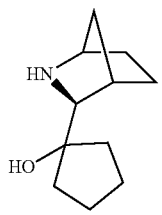

or a salt thereof. In some embodiments, a provided compound is a diastereomer of

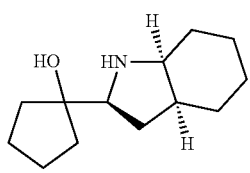 [SMILES: OC1([C@@H]2C[C@@H]3CCCC[C@@H]3N2)CCCC1]

or a salt thereof. In some embodiments, a provided compound is a diastereomer of

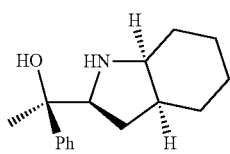

or a salt thereof.

In some embodiments, a provided compound is an enantiomer of

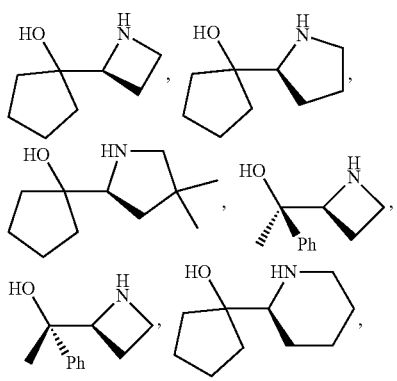

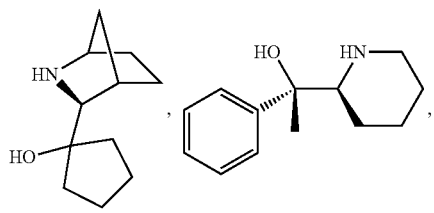

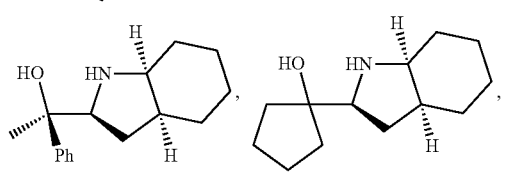

or a salt thereof. In some embodiments, a provided compound is an enantiomer of

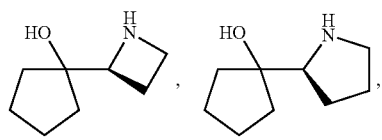

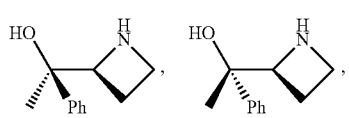

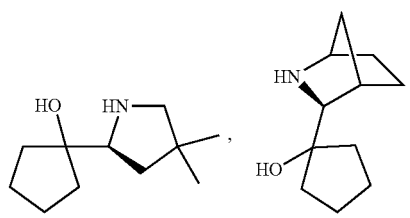

or a salt thereof. In some embodiments, a provided compound is an enantiomer of

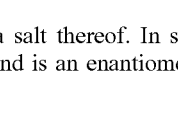

or a salt thereof. In some embodiments, a provided compound is an enantiomer of

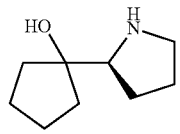

or a salt thereof. In some embodiments, a provided compound is an enantiomer of

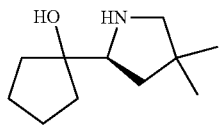

or a salt thereof. In some embodiments, a provided compound is an enantiomer of

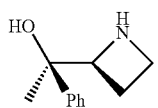

or a salt thereof. In some embodiments, a provided compound is an enantiomer of

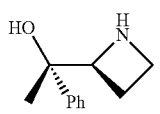

or a salt thereof. In some embodiments, a provided compound is an enantiomer of

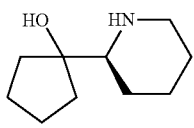 [SMILES: OC1([C@@H]2CCCCN2)CCCC1]

or a salt thereof. In some embodiments, a provided compound is an enantiomer of

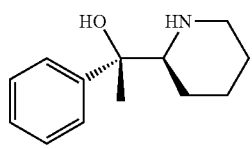

or a salt thereof. In some embodiments, a provided compound is an enantiomer of

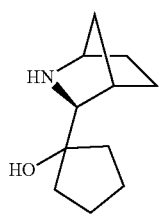 [SMILES: OC1([C@H]2NC3CCC2C3)CCCC1]

or a salt thereof. In some embodiments, a provided compound is an enantiomer of

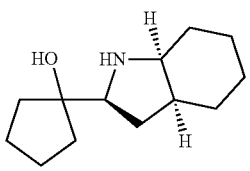 [SMILES: OC1([C@@H]2C[C@@H]3CCCC[C@@H]3N2)CCCC1]

or a salt thereof. In some embodiments, a provided compound is an enantiomer of

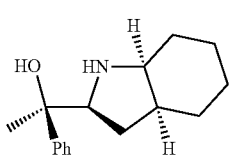 [SMILES: C[C@@](O)(c1ccccc1)[C@@H]1C[C@@H]2CCCC[C@@H]2N1]

or a salt thereof.

In some embodiments, $R^5$, and one or both of $R^1$ and $R^2$, are R, which are taken together with their intervening atoms to form an optionally substituted, 3-20 membered monocyclic, bicyclic or polycyclic ring having 1-5 heteroatoms. In some embodiments, one of $R^1$ and $R^2$, and $R^5$, are R, and the R groups are taken together with their intervening atoms to form an optionally substituted, 3-20 membered monocyclic, bicyclic or polycyclic ring having 1-5 heteroatoms. As extensively described in the present disclosure, a formed ring can be of various sizes, monocyclic, bicyclic or polycyclic, and contain various numbers and/or types of heteroatoms. In some embodiments, a ring is a 3-membered ring. In some embodiments, a ring is a 4-membered ring. In some embodiments, a ring is a 5-membered ring. In some embodiments, a ring is a 6-membered ring. In some embodiments, a ring is monocyclic. In some embodiments, a ring contains additional ring heteroatoms other than the intervening heteroatoms. In some embodiments, a ring is a 3-membered ring containing one ring heteroatom. In some embodiments, a ring is a 3-membered ring containing two ring heteroatoms. In some embodiments, a ring is a 3-membered ring containing one carbon, one nitrogen, and one oxygen ring atom.

In some embodiments, $R^6$ is R', wherein R' is as described in the present disclosure. In some embodiments, $R^6$ is —H, for example, when a provided compound has the structure of I, I-a, I-a-1, I-a-2, I-b, I-c, I-d, I-e, II, II-a, II-b, III, III-a, or III-b, or a salt thereof. In some embodiments, $R^6$ is a suitable capping group used in oligonucleotide synthesis, many of which are widely known and can be utilized in accordance with the present disclosure. In some embodiments, $R^6$ is —C(O)R, wherein R is as described in the present disclosure. In some embodiments, $R^6$ is a capping group when in a provided structure in oligonucleotide synthesis, for example, structure of formula VII, or VIII, or a salt thereof. In some embodiments, a capping group has the structure of —C(O)R, wherein R is as described in the present disclosure. In some embodiments, $R^6$ is —C(O)R, wherein R is as described in the present disclosure. In some embodiments, R is methyl. In some embodiments, R is —$CF_3$.

In some embodiments, $R^6$ is —H. In some embodiments, $R^6$ is —H, and $R^4$ and $R^5$ are R, and the R groups are taken together with their intervening atoms to form an optionally substituted 3-20 membered heterocyclyl ring having 1-5 heteroatoms as described in the present disclosure. In some embodiments, $R^6$ is —H, and $R^4$ and $R^5$ are R, and the R groups are taken together with their intervening atoms to form an optionally substituted 4-6 membered heterocyclyl ring having 1-5 heteroatoms as described in the present disclosure. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered.

In some embodiments, $R^7$ is —OH. In some embodiments, $R^7$ is —SH. In some embodiments, the present disclosure provides a compound of formula I, I-a, I-a-1, I-a-2, I-b, I-c, I-d, I-e, II, II-a, II-b, III, III-a, or III-b, or a salt thereof, wherein $R^7$ is —OH. In some embodiments, the present disclosure provides a compound of formula I, I-a, I-a-1, I-a-2, I-b, I-c, I-d, I-e, II, II-a, II-b, III, III-a, or III-b, or a salt thereof, wherein $R^7$ is —SH.

In some embodiments, $R^8$ is -L-$R^7$, -L-C($R^1$)($R^2$)—$R^7$, or -$L^s$-$R^7$, wherein each variable is independently as described in the present disclosure. In some embodiments, $R^8$ is $R^7$ as described in the present disclosure. In some embodiments, $R^8$ is —OH. In some embodiments, $R^8$ is —SH. In some embodiments, $R^8$ is -L-$R^7$, wherein each of L and $R^7$ is independently as described in the present disclosure. In some embodiments, $R^8$ is -L-OH, wherein $L^s$ is as described in the present disclosure. In some embodiments, $R^8$ is -L-SH, wherein $L^s$ is as described in the present disclosure. In some embodiments, $R^8$ is -L-C(R')($R^2$)—$R^7$, wherein each variable is independently as described in the present disclosure. In some embodiments, $R^8$ is —C($R^1$)($R^2$)—$R^7$, wherein each variable is independently as described in the present disclosure. In some embodiments, $R^8$ is —CH$_2$—$R^7$, wherein $R^7$ is as described in the present disclosure. In some embodiments, $R^8$ is —CH$_2$OH. In some embodiments, $R^8$ is —CH$_2$SH. In some embodiments, $R^8$ is -$L^s$-$R^7$, wherein each variable is independently as described in the present disclosure. In some embodiments, $R^8$ is -$L^s$-OH, wherein $L^s$ is as described in the present disclosure. In some embodiments, $R^8$ is -$L^s$-SH, wherein $L^s$ is as described in the present disclosure.

In some embodiments, $R^4$ and $R^5$ are R, which are taken together with their intervening atoms to form an optionally substituted 4-10 membered heterocyclyl ring with the intervening nitrogen atom as the only ring heteroatom. In some embodiments, $R^4$ and $R^5$ are R, which are taken together with their intervening atoms to form an optionally substituted 4-10 membered saturated monocyclic heterocyclyl ring with the intervening nitrogen atom as the only ring heteroatom. In some embodiments, $R^4$ and $R^5$ are R, which are taken together with their intervening atoms to form an optionally substituted 4-10 membered saturated bicyclic heterocyclyl ring with the intervening nitrogen atom as the only ring heteroatom. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is an optionally substituted pyrrolidine moiety. In some embodiments, $R^7$ is —OH. In some embodiments, $R^7$ is —SH.

In some embodiments, a provided compound of formula I, I-a, I-a-1, I-a-2, I-b, I-c, I-d, I-e, II, II-a, II-b, III, III-a, or III-b comprises no more than one chiral elements. In some embodiments, a provided compound of formula I, I-a, I-a-1, I-a-2, I-b, I-c, I-d, I-e, II, II-a, II-b, III, III-a, or III-b comprises no more than one chiral elements, wherein the only one chiral element is chiral carbon atom. In some embodiments, a provided compound of formula I, I-a, I-a-1, I-a-2, I-b, I-c, I-d, I-e, II, II-a, II-b, III, III-a, or III-b comprises no more than one chiral elements, wherein the only one chiral element is chiral carbon atom to which $R^3$ and $R^4$ are attached. In some embodiments, $R^1$ and $R^2$ are the same. In some embodiments, $R^1$ and $R^2$ are the same, and are optionally substituted straight chain $C_{1-3}$ alkyl. In some embodiments, $R^1$ and $R^2$ are the same, and are optionally substituted straight chain $C_{1-3}$ alkyl wherein no substituent comprises a carbon atom. In some embodiments, $R^1$ and $R^2$ are the same, and are optionally substituted straight chain $C_{1-2}$ alkyl. In some embodiments, $R^1$ and $R^2$ are the same, and are optionally substituted straight chain $C_{1-2}$ alkyl wherein no substituent comprises a carbon atom. In some embodiments, $R^1$ and $R^2$ are methyl. In some embodiments, $R^1$ and $R^2$ are ethyl. In some embodiments, $R^1$ and $R^2$ are n-propyl. In some embodiments, $R^1$ and $R^2$ are taken together to form an optionally substituted ring as described in the present disclosure. In some embodiments, $R^1$ and $R^2$ are taken together to form an optionally substituted ring where the ring contains no chiral elements.

In some embodiments, L is a covalent bond, or optionally substituted $C_{1-6}$ alkylene, wherein one or more methylene units are optionally and independently replaced with -L'-, wherein L' is as described in the present disclosure. In some embodiments, L is a covalent bond. In some embodiments, L is optionally substituted $C_{1-6}$ alkylene, wherein one or more methylene units are optionally and independently replaced with -L'-, wherein L' is as described in the present disclosure. In some embodiments, L is optionally substituted $C_{1-6}$ alkylene, wherein one or more methylene units are independently replaced with -L'-, wherein each L' is independently as described in the present disclosure.

In some embodiments, L is a covalent bond. In some embodiments, a provided compound, e.g., a compound of formula I, has the structure of

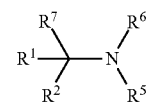

or a salt thereof.

In some embodiments, L is —C($R^3$)($R^4$)—. In some embodiments, a provided compound has the structure of formula I-a:

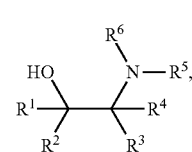

or a salt thereof, wherein each variable is independently as described in the present disclosure. In some embodiments, a compound of formula I has the structure of formula I-a. In some embodiments, a provided compound has the structure of

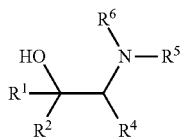

or a salt thereof, wherein each variable is independently as described in the present disclosure, and wherein $R^4$ and $R^5$ are not hydrogen. In some embodiments, a provided compound has the structure of

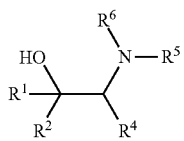

or a salt thereof, wherein each variable is independently as described in the present disclosure, and wherein $R^4$ and $R^5$ are R and are taken together to form an optionally substituted ring as described in the present disclosure. In some embodiments, $R^1$ and $R^2$ are different. In some embodiments, $R^1$ and $R^2$ are the same. In some embodiments, $R^1$ and $R^2$ are the same and are hydrogen. In some embodiments, $R^1$ and $R^2$ are the same and are not hydrogen. In some embodiments, $R^1$ and $R^2$ are the same and are optionally substituted $C_{1-6}$ aliphatic. In some embodiments, $R^1$ and $R^2$ are the same and are optionally substituted $C_{1-6}$ alkyl.

In some embodiments, a provided compound has the structure of formula (I-a-1):

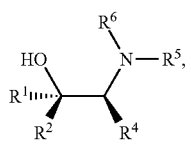

I-a-1 or a salt thereof, wherein each variable is independently as described in the present disclosure, and wherein $R^4$ and $R^5$ are not hydrogen, and $R^2$ has a larger size than $R^1$. In some embodiments, a compound of formula I-a has the structure of formula I-a-1. In some embodiments, $R^4$ and $R^5$ are R and are taken together to form an optionally substituted ring as described in the present disclosure. In some embodiments, $R^1$ and $R^2$ are different. In some embodiments, $R^1$ and $R^2$ are the same. In some embodiments, $R^1$ and $R^2$ are the same and are hydrogen. In some embodiments, $R^1$ and $R^2$ are the same and are not hydrogen. In some embodiments, $R^1$ and $R^2$ are the same and are optionally substituted $C_{1-6}$ aliphatic. In some embodiments, $R^1$ and $R^2$ are the same and are optionally substituted $C_{1-6}$ alkyl.

In some embodiments, a provided compound has the structure of formula (I-a-2):

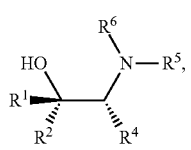

I-a-2 or a salt thereof, wherein each variable is independently as described in the present disclosure, and wherein $R^4$ and $R^5$ are not hydrogen, and $R^2$ has a larger size than $R^1$. In some embodiments, a compound of formula I-a has the structure of formula I-a-2. In some embodiments, $R^4$ and $R^5$ are R and are taken together to form an optionally substituted ring as described in the present disclosure. In some embodiments, $R^1$ and $R^2$ are different. In some embodiments, $R^1$ and $R^2$ are the same. In some embodiments, $R^1$ and $R^2$ are the same and are hydrogen. In some embodiments, $R^1$ and $R^2$ are the same and are not hydrogen. In some embodiments, $R^1$ and $R^2$ are the same and are optionally substituted $C_{1-6}$ aliphatic. In some embodiments, $R^1$ and $R^2$ are the same and are optionally substituted $C_{1-6}$ alkyl.

In some embodiments, L is -L'—C($R^3$)($R^4$)—, wherein each variable is independently as described in the present disclosure. In some embodiments, a provided compound has the structure of formula I-b:

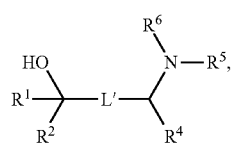

I-b or a salt thereof, wherein each variable is independently as described in the present disclosure. In some embodiments, a compound of formula I has the structure of formula I-b.

In some embodiments, L' is a covalent bond. In some embodiments, L' is optionally substituted bivalent $C_{1-3}$ alkylene. In some embodiments, L' is —C($R^3$)($R^4$)—, wherein each of $R^3$ and $R^4$ is independently as described in the present disclosure. In some embodiments, L' is —C($R^3$)($R^4$)—C($R^3$)($R^4$)—, wherein each of $R^3$ and $R^4$ is independently as described in the present disclosure. In some embodiments, L' is -Cy- as described in the present disclosure. In some embodiments, L' is —C($R^3$)[C($R^4$)$_3$]—, wherein each of $R^3$ and $R^4$ is independently as described in the present disclosure.

In some embodiments, L' is a covalent bond. In some embodiments, L' is optionally substituted bivalent $C_{1-3}$ alkylene. In some embodiments, L' is —C($R^3$)($R^4$)—. In some embodiments, a provided compound has the structure of formula I-c:

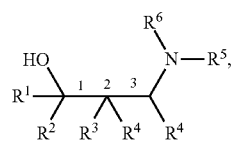

I-c or a salt thereof, wherein each variable is independently as described in the present disclosure. In some embodiments, a compound of formula I has the structure of formula I-c, or a salt thereof. In some embodiments, a compound of formula I-b has the structure of formula I-c, or a salt thereof. In some embodiments, each of $R^1$ and $R^2$ is independently R, wherein R is as described in the present disclosure. In some embodiments, one of $R^1$ and $R^2$ is —H, and the other is R, wherein R is as described in the present disclosure and is not —H. In some embodiments, each of $R^1$ and $R^2$ is independently R, wherein R is as described in the present disclosure and is not —H. In some embodiments, each of $R^1$ and $R^2$ is independently R, wherein the two R groups are taken together to form an optionally substituted ring as described in the present disclosure. In some embodiments, one of $R^1$ and $R^2$ is —H, and the other is optionally substituted phenyl. In some embodiments, one of $R^1$ and $R^2$ is —H, and the other is phenyl. In some embodiments, each of $R^3$ and $R^4$ attached to C2 in formula I-c is independently R, wherein R is as described in the present disclosure. In some embodiments, each of $R^3$ and $R^4$ attached to C2 is —H. In some embodiments, each of $R^3$ and $R^4$ attached to C3 is independently R, wherein R is as described in the present disclosure. In some embodiments, one of $R^3$ and $R^4$ attached to C3 is hydrogen. In some embodiments, one of $R^3$ and $R^4$ attached to C3 R, $R^5$ is R, and the two R groups are taken together to form an optionally substituted ring as described in the present disclosure.

In some embodiments, a formed ring is an optionally substituted heterocyclyl moiety as described in the present disclosure. In some embodiments, a formed ring is an optionally substituted, monocyclic, and saturated 4, 5, or 6-membered heterocyclyl ring having one nitrogen ring atom and no more than one heteroatom as described in the present disclosure. In some embodiments, a formed ring is an optionally substituted trivalent azetidinyl moiety as described in the present disclosure. In some embodiments, a formed ring is an optionally substituted trivalent pyrrolidinyl moiety as described in the present disclosure. In some embodiments, a formed ring is an optionally substituted trivalent piperidinyl moiety as described in the present disclosure. In some embodiments, one of $R^3$ and $R^4$ attached to C2 is R, one of $R^3$ and $R^4$ attached to C3 is R, and the two R groups are taken together to form an optionally substituted ring as described in the present disclosure. In some embodiments, a formed ring is an optionally substituted cycloaliphatic ring. In some embodiments, a formed ring an optionally substituted saturated cycloaliphatic ring. In some embodiments, a formed ring is 3, 4, 5, 6, 7, 8, 9, or 10-membered. In some embodiments, a formed ring is an optionally substituted 5-membered, saturated, monocyclic cycloaliphatic ring. In some embodiments, a provided compound is

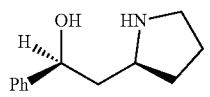 [SMILES: O[C@@H](C[C@@H]1CCCN1)c1ccccc1]

or a salt thereof. In some embodiments, a provided compound is a diastereomer of

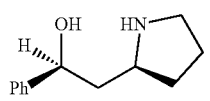 [SMILES: O[C@@H](C[C@@H]1CCCN1)c1ccccc1]

or a salt thereof. In some embodiments, a provided compound is an enantiomer of

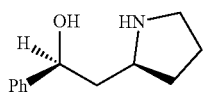

or a salt thereof. In some embodiments, a provided compound is

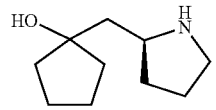

or a salt thereof. In some embodiments, a provided compound is a diastereomer of

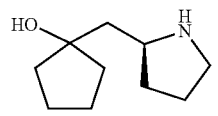

or a salt thereof. In some embodiments, a provided compound is an enantiomer of

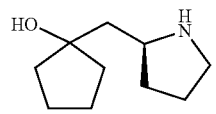

or a salt thereof. In some embodiments, a provided compound is

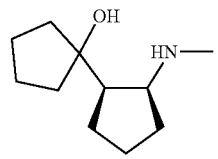

or a salt thereof. In some embodiments, a provided compound is a diastereomer of

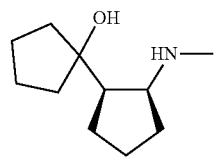

or a salt thereof. In some embodiments, a provided compound is an enantiomer of

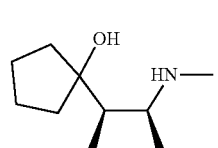

or a salt thereof.

In some embodiments, L' is —C($R^3$)($R^4$)—C($R^3$)($R^4$)—, wherein each variable is independently as described in the present disclosure. In some embodiments, L' is -Cy-. In some embodiments, L' is —C($R^3$)[C($R^4$)$_3$]—.

In some embodiments, each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon. In some embodiments, -Cy- is an optionally substituted ring as described in the present disclosure, for example, for R and $Cy^L$, but is bivalent.

In some embodiments, -Cy- is monocyclic. In some embodiments, -Cy- is bicyclic. In some embodiments, -Cy- is polycyclic. In some embodiments, -Cy- is saturated. In some embodiments, -Cy- is partially unsaturated. In some embodiments, -Cy- is aromatic. In some embodiments, -Cy- comprises a saturated cyclic moiety. In some embodiments, -Cy- comprises a partially unsaturated cyclic moiety. In some embodiments, -Cy- comprises an aromatic cyclic moiety. In some embodiments, -Cy- comprises a combination of a saturated, a partially unsaturated, and/or an aromatic cyclic moiety. In some embodiments, -Cy- is 3-membered. In some embodiments, -Cy- is 4-membered. In some embodiments, -Cy- is 5-membered. In some embodiments, -Cy- is 6-membered. In some embodiments, -Cy- is 7-membered. In some embodiments, -Cy- is 8-membered. In some embodiments, -Cy- is 9-membered. In some embodiments, -Cy- is 10-membered. In some embodiments, -Cy- is 11-membered. In some embodiments, -Cy- is 12-membered. In some embodiments, -Cy- is 13-membered. In some embodiments, -Cy- is 14-membered. In some embodiments, -Cy- is 15-membered. In some embodiments, -Cy- is 16-membered. In some embodiments, -Cy- is 17-membered. In some embodiments, -Cy- is 18-membered. In some embodiments, -Cy- is 19-membered. In some embodiments, -Cy- is 20-membered.

In some embodiments, -Cy- is an optionally substituted bivalent $C_{3-20}$ cycloaliphatic ring. In some embodiments, -Cy- is an optionally substituted bivalent, saturated $C_{3-20}$ cycloaliphatic ring. In some embodiments, -Cy- is an optionally substituted bivalent, partially unsaturated $C_{3-20}$ cycloaliphatic ring. In some embodiments, -Cy- comprises an aromatic moiety. In some embodiments, -Cy- is optionally substituted

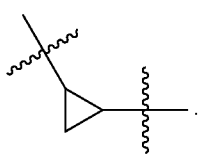 [SMILES: *C1CC1*]

In some embodiments, -Cy- is optionally substituted

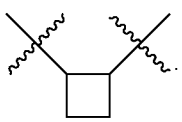 [SMILES: *C1CCC1*]

In some embodiments, -Cy- is optionally substituted

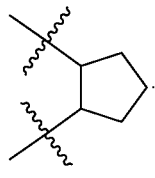 [SMILES: *C1CCCC1*]

In some embodiments, -Cy- is optionally substituted

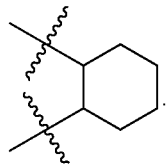 [SMILES: *C1CCCCC1*]

In some embodiments, -Cy- is optionally substituted

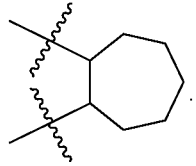 [SMILES: *C1CCCCCC1*]

In some embodiments, -Cy- is optionally substituted

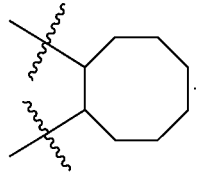 [SMILES: *C1CCCCCCC1*]

In some embodiments, -Cy-H is optionally substituted cycloaliphatic as described in the present disclosure, for example, cycloaliphatic embodiments for R.

In some embodiments, -Cy- is an optionally substituted $C_{6-20}$ aryl ring. In some embodiments, -Cy- is optionally substituted phenylene. In some embodiments, -Cy- is optionally substituted 1,2-phenylene. In some embodiments, -Cy- is optionally substituted 1,3-phenylene. In some embodiments, -Cy- is optionally substituted 1,4-phenylene. In some embodiments, -Cy- is an optionally substituted bivalent naphthalene ring. In some embodiments, -Cy-H is optionally substituted aryl as described in the present disclosure, for example, aryl embodiments for R.

In some embodiments, -Cy- is an optionally substituted bivalent 5-20 membered heteroaryl ring having 1-10 heteroatoms independently selected from oxygen, nitrogen, sulfur, phosphorus and silicon. In some embodiments, -Cy- is an optionally substituted bivalent 5-20 membered heteroaryl ring having 1-10 heteroatoms independently selected from oxygen, nitrogen, and sulfur. In some embodiments, -Cy- is an optionally substituted bivalent 5-6 membered heteroaryl ring having 1-4 heteroatoms independently selected from oxygen, nitrogen, sulfur. In some embodiments, -Cy- is an optionally substituted bivalent 5-6 membered heteroaryl ring having 1-3 heteroatoms independently selected from oxygen, nitrogen, sulfur. In some embodiments, -Cy- is an optionally substituted bivalent 5-6 membered heteroaryl ring having 1-2 heteroatoms independently selected from oxygen, nitrogen, sulfur. In some embodiments, -Cy- is an optionally substituted bivalent 5-6 membered heteroaryl ring having one heteroatom independently selected from oxygen, nitrogen, sulfur. In some embodiments, -Cy-H is optionally substituted heteroaryl as described in the present disclosure, for example, heteroaryl embodiments for R.

In some embodiments, -Cy- is an optionally substituted bivalent 3-20 membered heterocyclyl ring having 1-10 heteroatoms independently selected from oxygen, nitrogen, sulfur, phosphorus and silicon. In some embodiments, -Cy- is an optionally substituted bivalent 3-20 membered heterocyclyl ring having 1-10 heteroatoms independently selected from oxygen, nitrogen, and sulfur. In some embodiments, -Cy- is an optionally substituted bivalent 3-6 membered heterocyclyl ring having 1-4 heteroatoms independently selected from oxygen, nitrogen, sulfur. In some embodiments, -Cy- is an optionally substituted bivalent 5-6 membered heterocyclyl ring having 1-4 heteroatoms independently selected from oxygen, nitrogen, sulfur. In some embodiments, -Cy- is an optionally substituted bivalent 5-6 membered heterocyclyl ring having 1-3 heteroatoms independently selected from oxygen, nitrogen, sulfur. In some embodiments, -Cy- is an optionally substituted bivalent 5-6 membered heterocyclyl ring having 1-2 heteroatoms independently selected from oxygen, nitrogen, sulfur. In some embodiments, -Cy- is an optionally substituted bivalent 5-6 membered heterocyclyl ring having one heteroatom independently selected from oxygen, nitrogen, sulfur. In some embodiments, -Cy- is an optionally substituted saturated bivalent heterocyclyl group. In some embodiments, -Cy- is an optionally substituted partially unsaturated bivalent heterocyclyl group. In some embodiments, -Cy-H is optionally substituted heterocyclyl as described in the present disclosure, for example, heterocyclyl embodiments for R.

In some embodiments, -Cy- is an optionally substituted bivalent 3-30 membered carbocyclylene. In some embodiments, -Cy- is an optionally substituted bivalent 6-30 membered arylene. In some embodiments, -Cy- is an optionally substituted bivalent 5-30 membered heteroarylene having 1-10 heteroatoms independently selected from oxygen, nitrogen and sulfur. In some embodiments, -Cy- is an optionally substituted bivalent 3-30 membered heterocyclylene having 1-10 heteroatoms independently selected from oxygen, nitrogen, sulfur, phosphorus and silicon. In some embodiments, -Cy- is an optionally substituted bivalent 5-30 membered heteroarylene having 1-5 heteroatoms independently selected from oxygen, nitrogen and sulfur. In some embodiments, -Cy- is an optionally substituted bivalent 3-30 membered heterocyclylene having 1-5 heteroatoms independently selected from oxygen, nitrogen, sulfur, phosphorus and silicon.

In some embodiments, each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$.

In some embodiments, $L^s$ is a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$. In some embodiments, $L^s$ is a covalent bond, or a bivalent, optionally substituted, linear or branched $C_{1-30}$ aliphatic group, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$. In some embodiments, $L^s$ is a covalent bond, or a bivalent, optionally substituted, linear or branched $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N (R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L$^s$ is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, and one or more carbon atoms are optionally and independently replaced with Cy$^L$. In some embodiments, L$^s$ is a covalent bond, or a bivalent, optionally substituted, linear or branched group selected from a C$_{1-10}$ aliphatic group and a C$_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—, and one or more carbon atoms are optionally and independently replaced with Cy$^L$. In some embodiments, L$^s$ is a covalent bond, or a bivalent, optionally substituted, linear or branched group selected from a C$_{1-10}$ aliphatic group and a C$_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—.

In some embodiments, L$^s$ is a covalent bond. In some embodiments, L$^s$ is optionally substituted bivalent C$_{1-30}$ aliphatic. In some embodiments, L$^s$ is optionally substituted bivalent C$_{1-30}$ heteroaliphatic having 1-10 heteroatoms independently selected from boron, oxygen, nitrogen, sulfur, phosphorus and silicon.

In some embodiments, aliphatic moieties, e.g. those of L$^s$, R, etc., either monovalent or bivalent or multivalent, and can contain any number of carbon atoms (before any optional substitution) within its range, e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, etc. In some embodiments, heteroaliphatic moieties, e.g. those of L$^s$, R, etc., either monovalent or bivalent or multivalent, and can contain any number of carbon atoms (before any optional substitution) within its range, e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, etc.

In some embodiments, a methylene unit is replaced with -Cy-, wherein -Cy- is as described in the present disclosure. In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —O—. In some embodiments, a methylene unit is replaced with —S—. In some embodiments, a methylene unit is replaced with —N(R')—. In some embodiments, a methylene unit is replaced with —C(O)—. In some embodiments, a methylene unit is replaced with —S(O)—. In some embodiments, a methylene unit is replaced with —S(O)$_2$—. In some embodiments, a methylene unit is replaced with —P(O)(OR')—. In some embodiments, a methylene unit is replaced with —P(O)(SR')—. In some embodiments, a methylene unit is replaced with —P(O)(R')—. In some embodiments, a methylene unit is replaced with —P(O)(NR')—. In some embodiments, a methylene unit is replaced with —P(S)(OR')—. In some embodiments, a methylene unit is replaced with —P(S)(SR')—. In some embodiments, a methylene unit is replaced with —P(S)(R')—. In some embodiments, a methylene unit is replaced with —P(S)(NR')—. In some embodiments, a methylene unit is replaced with —P(R')—. In some embodiments, a methylene unit is replaced with —P(OR')—. In some embodiments, a methylene unit is replaced with —P(SR')—. In some embodiments, a methylene unit is replaced with —P(NR')—. In some embodiments, a methylene unit is replaced with —P(OR')[B(R')$_3$]—. In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, each of which may independently be an internucleotidic linkage.

In some embodiments, L$^s$, e.g., when connected to R$^s$, is —CH$_2$—. In some embodiments, L$^s$ is —C(R)$_2$—, wherein at least one R is not hydrogen. In some embodiments, L$^s$ is —CHR—. In some embodiments, R is hydrogen. In some embodiments, L$^s$ is —CHR—, wherein R is not hydrogen. In some embodiments, C of —CHR— is chiral. In some embodiments, L$^s$ is —(R)—CHR—, wherein C of —CHR— is chiral. In some embodiments, L$^s$ is —(S)—CHR—, wherein C of —CHR— is chiral. In some embodiments, R is optionally substituted C$_{1-6}$ aliphatic. In some embodiments, R is optionally substituted C$_{1-6}$ alkyl. In some embodiments, R is optionally substituted C$_{1-5}$ aliphatic. In some embodiments, R is optionally substituted C$_{1-5}$ alkyl. In some embodiments, R is optionally substituted C$_{1-4}$ aliphatic. In some embodiments, R is optionally substituted C$_{1-4}$ alkyl. In some embodiments, R is optionally substituted C$_{1-3}$ aliphatic. In some embodiments, R is optionally substituted C$_{1-3}$ alkyl. In some embodiments, R is optionally substituted C$_2$ aliphatic. In some embodiments, R is optionally substituted methyl. In some embodiments, R is C$_{1-6}$ aliphatic. In some embodiments, R is C$_{1-6}$ alkyl. In some embodiments, R is C$_{1-5}$ aliphatic. In some embodiments, R is C$_{1-5}$ alkyl. In some embodiments, R is C$_{1-4}$ aliphatic. In some embodiments, R is C$_{1-4}$ alkyl. In some embodiments, R is C$_{1-3}$ aliphatic. In some embodiments, R is C$_{1-3}$ alkyl. In some embodiments, R is C$_2$ aliphatic. In some embodiments, R is methyl. In some embodiments, R is C$_{1-6}$ haloaliphatic. In some embodiments, R is C$_{1-6}$ haloalkyl. In some embodiments, R is $C_{1-5}$ haloaliphatic. In some embodiments, R is $C_{1-5}$ haloalkyl. In some embodiments, R is $C_{1-4}$ haloaliphatic. In some embodiments, R is $C_{1-4}$ haloalkyl. In some embodiments, R is $C_{1-3}$ haloaliphatic. In some embodiments, R is $C_{1-3}$ haloalkyl. In some embodiments, R is $C_2$ haloaliphatic. In some embodiments, R is methyl substituted with one or more halogen. In some embodiments, R is —$CF_3$. In some embodiments, $L^s$ is optionally substituted —CH═CH—. In some embodiments, $L^s$ is optionally substituted (E)-CH═CH—. In some embodiments, $L^s$ is optionally substituted (Z)—CH═CH—. In some embodiments, $L^s$ is —C≡C—.

In some embodiments, $L^s$ comprises at least one phosphorus atom. In some embodiments, at least one methylene unit of $L^s$ is replaced with —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—.

In some embodiments, $L^s$ is -Cy-. In some embodiments, -Cy- is optionally substituted monocyclic or bicyclic 3-20 membered heterocyclyl ring having 1-5 heteroatoms. In some embodiments, -Cy- is optionally substituted monocyclic or bicyclic 5-20 membered heterocyclyl ring having 1-5 heteroatoms, wherein at least one heteroatom is oxygen. In some embodiments, -Cy- is optionally substituted bivalent tetrahydrofuran ring. In some embodiments, -Cy- is an optionally substituted furanose moiety.

In some embodiments, $Cy^L$ is an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon.

In some embodiments, $Cy^L$ is monocyclic. In some embodiments, $Cy^L$ is bicyclic. In some embodiments, $Cy^L$ is polycyclic.

In some embodiments, $Cy^L$ is saturated. In some embodiments, $Cy^L$ is partially unsaturated. In some embodiments, $Cy^L$ is aromatic. In some embodiments, $Cy^L$ is or comprises a saturated ring moiety. In some embodiments, $Cy^L$ is or comprises a partially unsaturated ring moiety. In some embodiments, $Cy^L$ is or comprises an aromatic ring moiety.

In some embodiments, $Cy^L$ is an optionally substituted $C_{3-20}$ cycloaliphatic ring as described in the present disclosure (for example, those described for R but tetravalent). In some embodiments, a ring is an optionally substituted saturated $C_{3-20}$ cycloaliphatic ring. In some embodiments, a ring is an optionally substituted partially unsaturated $C_{3-20}$ cycloaliphatic ring. A cycloaliphatic ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. In some embodiments, a ring is an optionally substituted cyclopropyl moiety. In some embodiments, a ring is an optionally substituted cyclobutyl moiety. In some embodiments, a ring is an optionally substituted cyclopentyl moiety. In some embodiments, a ring is an optionally substituted cyclohexyl moiety. In some embodiments, a ring is an optionally substituted cycloheptyl moiety. In some embodiments, a ring is an optionally substituted cyclooctanyl moiety. In some embodiments, a cycloaliphatic ring is a cycloalkyl ring. In some embodiments, a cycloaliphatic ring is monocyclic. In some embodiments, a cycloaliphatic ring is bicyclic. In some embodiments, a cycloaliphatic ring is polycyclic. In some embodiments, a ring is a cycloaliphatic moiety as described in the present disclosure for R with more valences.

In some embodiments, $Cy^L$ is an optionally substituted 6-20 membered aryl ring. In some embodiments, a ring is an optionally substituted tetravalent phenyl moiety. In some embodiments, a ring is a tetravalent phenyl moiety. In some embodiments, a ring is an optionally substituted naphthalene moiety. A ring can be of different size as described in the present disclosure. In some embodiments, an aryl ring is 6-membered. In some embodiments, an aryl ring is 10-membered. In some embodiments, an aryl ring is 14-membered. In some embodiments, an aryl ring is monocyclic. In some embodiments, an aryl ring is bicyclic. In some embodiments, an aryl ring is polycyclic. In some embodiments, a ring is an aryl moiety as described in the present disclosure for R with more valences.

In some embodiments, $Cy^L$ is an optionally substituted 5-20 membered heteroaryl ring having 1-10 heteroatoms independently selected from oxygen, nitrogen, sulfur, phosphorus and silicon. In some embodiments, $Cy^L$ is an optionally substituted 5-20 membered heteroaryl ring having 1-10 heteroatoms independently selected from oxygen, nitrogen, and sulfur. In some embodiments, as described in the present disclosure, heteroaryl rings can be of various sizes and contain various numbers and/or types of heteroatoms. In some embodiments, a heteroaryl ring contains no more than one heteroatom. In some embodiments, a heteroaryl ring contains more than one heteroatom. In some embodiments, a heteroaryl ring contains no more than one type of heteroatom. In some embodiments, a heteroaryl ring contains more than one type of heteroatoms. In some embodiments, a heteroaryl ring is 5-membered. In some embodiments, a heteroaryl ring is 6-membered. In some embodiments, a heteroaryl ring is 8-membered. In some embodiments, a heteroaryl ring is 9-membered. In some embodiments, a heteroaryl ring is 10-membered. In some embodiments, a heteroaryl ring is monocyclic. In some embodiments, a heteroaryl ring is bicyclic. In some embodiments, a heteroaryl ring is polycyclic. In some embodiments, a heteroaryl ring is a nucleobase moiety, e.g., A, T, C, G, U, etc. In some embodiments, a ring is a heteroaryl moiety as described in the present disclosure for R with more valences.

In some embodiments, $Cy^L$ is a 3-20 membered heterocyclyl ring having 1-10 heteroatoms independently selected from oxygen, nitrogen, sulfur, phosphorus and silicon. In some embodiments, $Cy^L$ is a 3-20 membered heterocyclyl ring having 1-10 heteroatoms independently selected from oxygen, nitrogen, and sulfur. In some embodiments, a heterocyclyl ring is saturated. In some embodiments, a heterocyclyl ring is partially unsaturated. A heterocyclyl ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. Heterocyclyl rings can contain various numbers and/or types of heteroatoms. In some embodiments, a heterocyclyl ring contains no more than one heteroatom. In some embodiments, a heterocyclyl ring contains more than one heteroatom. In some embodiments, a heterocyclyl ring contains no more than one type of heteroatom. In some embodiments, a heterocyclyl ring contains more than one type of heteroatoms. In some embodiments, a heterocyclyl ring is monocyclic. In some embodiments, a heterocyclyl ring is bicyclic. In some embodiments, a heterocyclyl ring is polycyclic. In some embodiments, a ring is a heterocyclyl moiety as described in the present disclosure for R with more valences.

As readily appreciated by a person having ordinary skill in the art, many suitable ring moieties are extensively described in and can be used in accordance with the present disclosure, for example, those described for R (which may have more valences for $Cy^L$).

In some embodiments, $Cy^L$ is a sugar moiety in a nucleic acid. In some embodiments, $Cy^L$ is an optionally substituted furanose moiety. In some embodiments, $Cy^L$ is a pyranose moiety. In some embodiments, $Cy^L$ is an optionally substituted furanose moiety found in DNA. In some embodiments, $Cy^L$ is an optionally substituted furanose moiety found in RNA. In some embodiments, $Cy^L$ is an optionally substituted 2'-deoxyribofuranose moiety. In some embodiments, $Cy^L$ is an optionally substituted ribofuranose moiety. In some embodiments, substitutions provide sugar modifications as described in the present disclosure. In some embodiments, an optionally substituted 2'-deoxyribofuranose moiety and/or an optionally substituted ribofuranose moiety comprise substitution at a 2'-position. In some embodiments, a 2'-position is a 2'-modification as described in the present disclosure. In some embodiments, a 2'-modification is —F. In some embodiments, a 2'-modification is —OR, wherein R is as described in the present disclosure. In some embodiments, R is not hydrogen. In some embodiments, $Cy^L$ is a modified sugar moiety, such as a sugar moiety in LNA. In some embodiments, $Cy^L$ is a modified sugar moiety, such as a sugar moiety in ENA. In some embodiments, $Cy^L$ is a terminal sugar moiety of an oligonucleotide, connecting an internucleotidic linkage and a nucleobase. In some embodiments, $Cy^L$ is a terminal sugar moiety of an oligonucleotide, for example, when that terminus is connected to a solid support optionally through a linker. In some embodiments, $Cy^L$ is a sugar moiety connecting two internucleotidic linkages and a nucleobase. Example sugars and sugar moieties are extensively described in the present disclosure.

In some embodiments, $Cy^L$ is a nucleobase moiety. In some embodiments, a nucleobase is a natural nucleobase, such as A, T, C, G, U, etc. In some embodiments, a nucleobase is a modified nucleobase. In some embodiments, $Cy^L$ is optionally substituted nucleobase moiety selected from A, T, C, G, U, and 5 mC. Example nucleobases and nucleobase moieties are extensively described in the present disclosure.

In some embodiments, two $Cy^L$ moieties are bonded to each other, wherein one $Cy^L$ is a sugar moiety and the other is a nucleobase moiety. In some embodiments, such a sugar moiety and nucleobase moiety forms a nucleoside moiety. In some embodiments, a nucleoside moiety is natural. In some embodiments, a nucleoside moiety is modified. In some embodiments, $Cy^L$ is an optionally substituted natural nucleoside moiety selected from adenosine, 5-methyluridine, cytidine, guanosine, uridine, 5-methylcytidine, 2'-deoxyadenosine, thymidine, 2'-deoxycytidine, 2'-deoxyguanosine, 2'-deoxyuridine, and 5-methyl-2'-deoxycytidine. Example nucleosides and nucleosides moieties are extensive described in the present disclosure.

In some embodiments, for example in $L^s$, $Cy^L$ is an optionally substituted nucleoside moiety bonded to an internucleotidic linkage, for example, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, —OP(OR')[B(R')$_3$]O—, etc., which may form an optionally substituted nucleotidic unit. Example nucleotides and nucleosides moieties are extensive described in the present disclosure.

In some embodiments, R' is —R, —C(O)R, —C(O)OR, or —S(O)$_2$R, wherein R is as described in the present disclosure. In some embodiments, R' is R, wherein R is as described in the present disclosure. In some embodiments, R' is —C(O)R, wherein R is as described in the present disclosure. In some embodiments, R' is —C(O)OR, wherein R is as described in the present disclosure. In some embodiments, R' is —S(O)$_2$R, wherein R is as described in the present disclosure. In some embodiments, R' is hydrogen. In some embodiments, R' is not hydrogen. In some embodiments, R' is R, wherein R is optionally substituted $C_{1-20}$ aliphatic as described in the present disclosure. In some embodiments, R' is R, wherein R is optionally substituted $C_{1-20}$ heteroaliphatic as described in the present disclosure. In some embodiments, R' is R, wherein R is optionally substituted $C_{6-20}$ aryl as described in the present disclosure. In some embodiments, R' is R, wherein R is optionally substituted $C_{6-20}$ arylaliphatic as described in the present disclosure. In some embodiments, R' is R, wherein R is optionally substituted $C_{6-20}$ arylheteroaliphatic as described in the present disclosure. In some embodiments, R' is R, wherein R is optionally substituted 5-20 membered heteroaryl as described in the present disclosure. In some embodiments, R' is R, wherein R is optionally substituted 3-20 membered heterocyclyl as described in the present disclosure. In some embodiments, two or more R' are R, and are optionally and independently taken together to form an optionally substituted ring as described in the present disclosure.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon.

In some embodiments, R is hydrogen. In some embodiments, R is not hydrogen. In some embodiments, R is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, R is hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, and sulfur, a 4-7 membered saturated or partially unsaturated heterocyclic ring having 1-3 heteroatoms independently selected from nitrogen, oxygen, and sulfur, a 7-10 membered bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, R is optionally substituted $C_{1-30}$ aliphatic. In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is —(CH$_2$)$_2$CN.

In some embodiments, R is optionally substituted $C_{3-30}$ cycloaliphatic. In some embodiments, R is optionally substituted $C_{3-20}$ cycloaliphatic. In some embodiments, R is optionally substituted $C_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, when R is or comprises a ring structure, e.g., cycloaliphatic, cycloheteroaliphatic, aryl, heteroaryl, etc., the ring structure can be monocyclic, bicyclic or polycyclic. In some embodiments, R is or comprises a monocyclic structure. In some embodiments, R is or comprises a bicyclic structure. In some embodiments, R is or comprises a polycyclic structure.

In some embodiments, R is optionally substituted $C_{1-30}$ heteroaliphatic having 1-10 heteroatoms independently selected from oxygen, nitrogen, sulfur, phosphorus and silicon. In some embodiments, R is optionally substituted $C_{1-20}$ heteroaliphatic having 1-10 heteroatoms. In some embodiments, R is optionally substituted $C_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is optionally substituted $C_{1-30}$ heteroaliphatic comprising 1-10 groups independently selected from

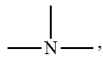

—N=, =N, —N, —S—, —S(O)—, —S(O)$_2$—, —O—, =O,

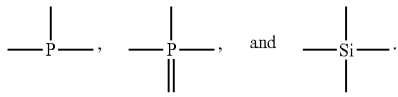

In some embodiments, R is optionally substituted $C_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur. In some embodiments, R is an optionally substituted 5-6 membered monocyclic heteroaryl ring having 1-3 heteroatoms independently selected from nitrogen, sulfur, and oxygen. In some embodiments, R is a substituted 5-6 membered monocyclic heteroaryl ring having 1-3 heteroatoms independently selected from nitrogen, oxygen, and sulfur. In some embodiments, R is an unsubstituted 5-6 membered monocyclic heteroaryl ring having 1-3 heteroatoms independently selected from nitrogen, sulfur, and oxygen.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Example R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Example R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur.

Example R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Example R groups include but are not limited to optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having 1 heteroatom independently selected from nitrogen, oxygen, and sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, and sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is an optionally substituted 5,6-fused heteroaryl ring having three heteroatoms independently selected from nitrogen, oxygen, and sulfur. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl.

In certain embodiments, R is an optionally substituted 6,6-fused heteroaryl ring having 1-4 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having 1 heteroatom independently selected from nitrogen, oxygen, and sulfur. In some embodiments, R is an optionally substituted quinolinyl. In some embodiments, R is an optionally substituted isoquinolinyl. In some embodiments, R is an optionally substituted 6,6-fused heteroaryl ring having 2 heteroatoms independently selected from nitrogen, oxygen, and sulfur. In some embodiments, R is optionally substituted quinazoline or a quinoxaline.

In some embodiments, R is 3-30 membered heterocyclic ring having 1-10 heteroatoms independently selected from oxygen, nitrogen, sulfur, phosphorus and silicon. In some embodiments, R is 3-30 membered heterocyclic ring having 1-10 heteroatoms independently selected from oxygen, nitrogen, and sulfur. In some embodiments, R is 3-30 membered heterocyclic ring having 1-5 heteroatoms independently selected from oxygen, nitrogen, sulfur, phosphorus and silicon. In some embodiments, R is 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 3-membered saturated or partially unsaturated heterocyclic ring having 1-2 heteroatoms independently selected from nitrogen, oxygen, and sulfur. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 7-membered saturated or partially unsaturated heterocyclic ring having 1-2 heteroatoms independently selected from nitrogen, oxygen, and sulfur.

In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms.

In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 5-membered partially unsaturated heterocyclic ring having 2 heteroatoms independently selected from nitrogen, oxygen, and sulfur. In some embodiments, R is an optionally substituted 5-membered partially unsaturated heterocyclic ring having no more than 1 heteroatom. In some embodiments, R is an optionally substituted 5-membered partially unsaturated heterocyclic ring having no more than 1 heteroatom, wherein the heteroatom is nitrogen. In some embodiments, R is an optionally substituted 5-membered partially unsaturated heterocyclic ring having no more than 1 heteroatom, wherein the heteroatom is oxygen. In some embodiments, R is an optionally substituted 5-membered partially unsaturated heterocyclic ring having no more than 1 heteroatom, wherein the heteroatom is sulfur. In some embodiments, R is an optionally substituted 5-membered partially unsaturated heterocyclic ring having 2 oxygen atoms. In some embodiments, R is an optionally substituted 5-membered partially unsaturated heterocyclic ring having 2 nitrogen atoms.

In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 6-membered partially unsaturated heterocyclic ring having 2 heteroatoms independently selected from nitrogen, oxygen, and sulfur. In some embodiments, R is an optionally substituted 6-membered partially unsaturated heterocyclic ring having no more than 1 heteroatom. In some embodiments, R is an optionally substituted 6-membered partially unsaturated heterocyclic ring having no more than 1 heteroatom, wherein the heteroatom is nitrogen. In some embodiments, R is an optionally substituted 6-membered partially unsaturated heterocyclic ring having no more than 1 heteroatom, wherein the heteroatom is oxygen. In some embodiments, R is an optionally substituted 6-membered partially unsaturated heterocyclic ring having no more than 1 heteroatom, wherein the heteroatom is sulfur. In some embodiments, R is an optionally substituted 6-membered partially unsaturated heterocyclic ring having 2 oxygen atoms. In some embodiments, R is an optionally substituted 6-membered partially unsaturated heterocyclic ring having 2 nitrogen atoms.

In certain embodiments, R is a 3-7 membered saturated or partially unsaturated heterocyclic ring having 1-2 heteroatoms independently selected from nitrogen, oxygen, and sulfur. In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl.

In certain embodiments, R is an optionally substituted 5-6 membered partially unsaturated monocyclic ring having 1-2 heteroatoms independently selected from nitrogen, oxygen, and sulfur. In certain embodiments, R is an optionally substituted tetrahydropyridinyl, dihydrothiazolyl, dihydrooxazolyl, or oxazolinyl group.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, and sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In certain embodiments, R is an optionally substituted 6,6-fused heteroaryl ring having 1-5 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having one heteroatom selected from nitrogen, oxygen, and sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, and sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, and sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, and sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, and sulfur.

In some embodiments, R is optionally substituted $C_{6-30}$ arylaliphatic. In some embodiments, R is optionally substituted $C_{6-20}$ arylaliphatic. In some embodiments, R is optionally substituted $C_{6-10}$ arylaliphatic. In some embodiments, an aryl moiety of the arylaliphatic has 6, 10, or 14 aryl carbon atoms. In some embodiments, an aryl moiety of the arylaliphatic has 6 aryl carbon atoms. In some embodiments, an aryl moiety of the arylaliphatic has 10 aryl carbon atoms. In some embodiments, an aryl moiety of the arylaliphatic has 14 aryl carbon atoms. In some embodiments, an aryl moiety is optionally substituted phenyl.

In some embodiments, R is optionally substituted $C_{6-30}$ arylheteroaliphatic having 1-10 heteroatoms independently selected from oxygen, nitrogen, sulfur, phosphorus and silicon. In some embodiments, R is optionally substituted $C_{6-30}$ arylheteroaliphatic having 1-10 heteroatoms independently selected from oxygen, nitrogen, and sulfur. In some embodiments, R is optionally substituted $C_{6-20}$ arylheteroaliphatic having 1-10 heteroatoms independently selected from oxygen, nitrogen, sulfur, phosphorus and silicon. In some embodiments, R is optionally substituted $C_{6-20}$ arylheteroaliphatic having 1-10 heteroatoms independently selected from oxygen, nitrogen, and sulfur. In some embodiments, R is optionally substituted $C_{6-10}$ arylheteroaliphatic having 1-5 heteroatoms independently selected from oxygen, nitrogen, sulfur, phosphorus and silicon. In some embodiments, R is optionally substituted $C_{6-10}$ arylheteroaliphatic having 1-5 heteroatoms independently selected from oxygen, nitrogen, and sulfur.

In some embodiments, two R groups are optionally and independently taken together to form a covalent bond. In some embodiments, —C=O is formed. In some embodiments, —C=C— is formed. In some embodiments, —C≡C— is formed.

In some embodiments, two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-10 membered monocyclic, bicyclic or polycyclic ring having, in addition to the atom, 0-5 heteroatoms independently selected from oxygen, nitrogen, sulfur, phosphorus and silicon. In some embodiments, two or more R groups on the same atom are optionally and independently taken together with the atom to form an optionally substituted, 3-6 membered monocyclic, bicyclic or polycyclic ring having, in addition to the atom, 0-3 heteroatoms independently selected from oxygen, nitrogen, sulfur, phosphorus and silicon. In some embodiments, two or more R groups on the same atom are optionally and independently taken together with the atom to form an optionally substituted, 3-5 membered monocyclic, bicyclic or polycyclic ring having, in addition to the atom, 0-3 heteroatoms independently selected from oxygen, nitrogen, sulfur, phosphorus and silicon.

In some embodiments, two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-5 heteroatoms independently selected from oxygen, nitrogen, sulfur, phosphorus and silicon. In some embodiments, two or more R groups on two or more atoms are optionally and independently taken together with their intervening atoms to form an optionally substituted, 3-6 membered monocyclic, bicyclic or polycyclic ring having, in addition to the intervening atoms, 0-3 heteroatoms independently selected from oxygen, nitrogen, sulfur, phosphorus and silicon. In some embodiments, two or more R groups on two or more atoms are optionally and independently taken together with their intervening atoms to form an optionally substituted, 3-5 membered monocyclic, bicyclic or polycyclic ring having, in addition to the intervening atoms, 0-3 heteroatoms independently selected from oxygen, nitrogen, sulfur, phosphorus and silicon.

In some embodiments, heteroatoms in R groups, or in the structures formed by two or more R groups taken together, are selected from oxygen, nitrogen, and sulfur. In some embodiments, a formed ring is 3, 4, 5, 6, 7, 8, 9, 10, 11, 12, 13, 14, 15, 16, 17, 18, 19, or 20-membered. In some embodiments, a formed ring is saturated. In some embodiments, a formed ring is partially saturated. In some embodiments, a formed ring is aromatic. In some embodiments, a formed ring comprises a saturated, partially saturated, or aromatic ring moiety. In some embodiments, a formed ring comprises 5, 6, 7, 8, 9, 10, 11, 12, 13, 14, 15, 16, 17, 18, 19, or 20 aromatic ring atoms. In some embodiments, a formed contains no more than 5, 6, 7, 8, 9, 10, 11, 12, 13, 14, 15, 16, 17, 18, 19, or 20 aromatic ring atoms. In some embodiments, aromatic ring atoms are selected from carbon, nitrogen, oxygen and sulfur.

In some embodiments, a ring formed by two or more R groups (or two or more groups selected from R and variables that can be R) taken together is a $C_{3-30}$ cycloaliphatic, $C_{6-30}$ aryl, 5-30 membered heteroaryl having 1-10 heteroatoms independently selected from oxygen, nitrogen, sulfur, phosphorus and silicon, or 3-30 membered heterocyclyl having 1-10 heteroatoms independently selected from oxygen, nitrogen, sulfur, phosphorus and silicon, ring as described for R, but bivalent or multivalent.

In some embodiments, $P^L$ is P(=W). In some embodiments, $P^L$ is P. In some embodiments, $P^L$ is P→B(R')$_3$. In some embodiments, P of $P^L$ is chiral. In some embodiments, P of $P^L$ is Rp. In some embodiments, P of $P^L$ is Sp. In some embodiments, a linkage of formula VII is a phosphate linkage or a salt form thereof. In some embodiments, a linkage of formula VII is a phosphorothioate linkage or a salt form thereof.

In some embodiments, $L^7$ is —O— or —S—. In some embodiments, $L^7$ is —O—. In some embodiments, $L^7$ is —S—.

In some embodiments, $L^8$ is -L-O—, -L-C(R$^1$)(R$^2$)—O—, or -L$^s$-O—, wherein each variable is independently as described in the present disclosure. In some embodiments, $L^8$ is -L-O, wherein L is as described in the present disclosure. In some embodiments, $L^8$ is -L-C(R$^1$)(R$^2$)—O—, wherein each variable is independently as described in the present disclosure. In some embodiments, $L^8$ is -L$^s$-O—, wherein L$^s$ is as described in the present disclosure.

In some embodiments, provided compounds, e.g., compounds of formula I, I-a, I-a-1, I-a-2, I-b, I-c, I-d, I-e, II, II-a, II-b, III, III-a, or III-b, or salts thereof, may be utilized to prepare other compounds which incorporate their chiral elements. In some embodiments, provide compounds of formula I, I-a, I-a-1, I-a-2, I-b, I-c, I-d, I-e, II, II-a, II-b, III, III-a, or III-b, or salts thereof, are incorporated into other compounds, e.g., compounds of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or salts thereof, as chiral auxiliaries so that such other compounds can be further utilized for stereoselective synthesis of, e.g., oligonucleotides (e.g., of formula VIII) comprising internucleotidic linkages having the structure of formula VII, VII-a-1, VII-a-2, VII-b, VII-c, VII-d, or VII-e, or a salt form thereof. In some embodiments, provided compounds, e.g., compounds of formula I, I-a, I-a-1, I-a-2, I-b, I-c, I-d, I-e, II, II-a, II-b, III, III-a, or III-b, or salts thereof, optionally activated, react with nucleosides or derivatives thereof to provide phosphoramidites for oligonucleotide preparation. In some embodiments, provided phosphoramidites have the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof. In some embodiments, provided phosphoramidites have the structure of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or salts thereof. In some embodiments, provided compounds, e.g., phosphoramidites of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof have purities, diastereopurities, and/or enantiopurities as described in the present disclosure. In some embodiments, provided compounds, e.g., phosphoramidites of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or salts thereof have purities, diastereopurities, and/or enantiopurities as described in the present disclosure.

In some embodiments, BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, a natural nucleobase moiety, and a modified nucleobase moiety. In some embodiments, BA is optionally substituted $C_{5-30}$ heteroaryl having 1-10 heteroatoms independently selected from oxygen, nitrogen, and sulfur. In some embodiments, BA is optionally substituted natural nucleobases and tautomers thereof. In some embodiments, BA is protected natural nucleobases and tautomers thereof. Various nucleobase protecting groups for oligonucleotide synthesis are known and can be utilized in accordance with the present disclosure. In some embodiments, BA is an optionally substituted nucleobase selected from adenine, cytosine, guanosine, thymine, and uracil, and tautomers thereof. In some embodiments, BA is an optionally protected nucleobase selected from adenine, cytosine, guanosine, thymine, and uracil, and tautomers thereof.

In some embodiments, BA is optionally substituted $C_{3-30}$ cycloaliphatic. In some embodiments, BA is optionally substituted $C_{6-30}$ aryl. In some embodiments, BA is optionally substituted $C_{3-30}$ heterocyclyl. In some embodiments, BA is optionally substituted $C_{5-30}$ heteroaryl. In some embodiments, BA is an optionally substituted natural base moiety. In some embodiments, BA is an optionally substituted modified base moiety. BA is an optionally substituted group selected from $C_{3-30}$ cycloaliphatic, $C_{6-30}$ aryl, $C_{3-30}$ heterocyclyl, and $C_{5-30}$ heteroaryl. In some embodiments, BA is an optionally substituted group selected from $C_{3-30}$ cycloaliphatic, $C_{6-30}$ aryl, $C_{3-30}$ heterocyclyl, $C_{5-30}$ heteroaryl, and a natural nucleobase moiety.

In some embodiments, BA is connected to SU through an aromatic ring. In some embodiments, BA is connected to SU through a heteroatom. In some embodiments, BA is connected to SU through a ring heteroatom of an aromatic ring. In some embodiments, BA is connected to SU through a ring nitrogen atom of an aromatic ring.

In some embodiments, BA is a natural nucleobase moiety. In some embodiments, BA is an optionally substituted natural nucleobase moiety. In some embodiments, BA is a substituted natural nucleobase moiety. In some embodiments, BA is natural nucleobase A, T, C, U, or G. In some embodiments, BA is an optionally substituted group selected from natural nucleobases A, T, C, U, and G.

In some embodiments, BA is an optionally substituted group, which group is formed by removing a —H from

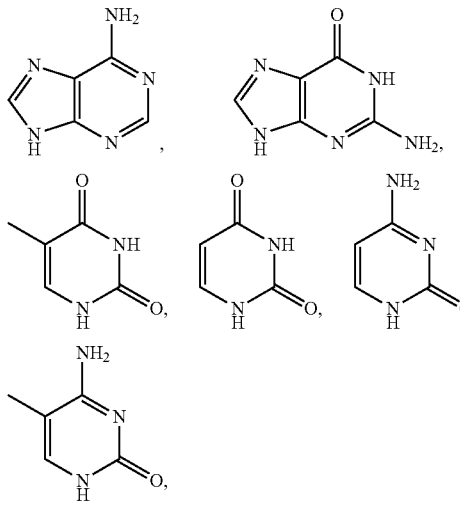

or a tautomer thereof. In some embodiments, BA is an optionally substituted group, which group is formed by removing a —H from

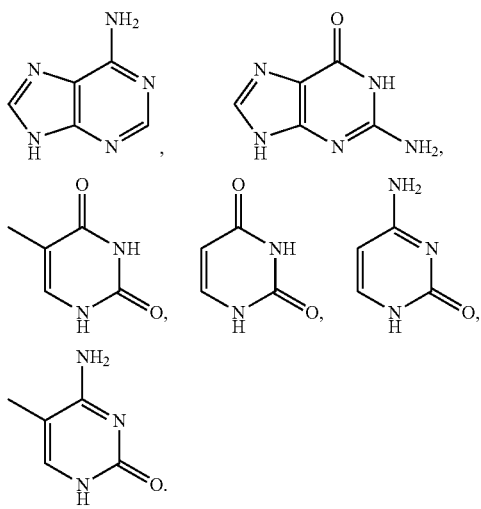

In some embodiments, BA is an optionally substituted group which group is selected from

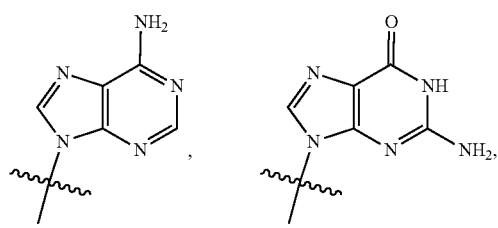

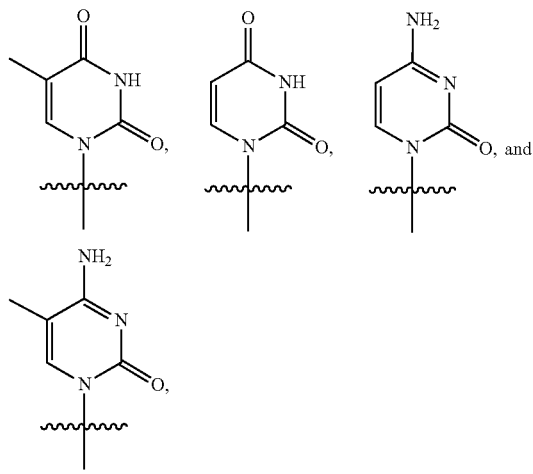

and tautomeric forms thereof. In some embodiments, BA is an optionally substituted group which group is selected from

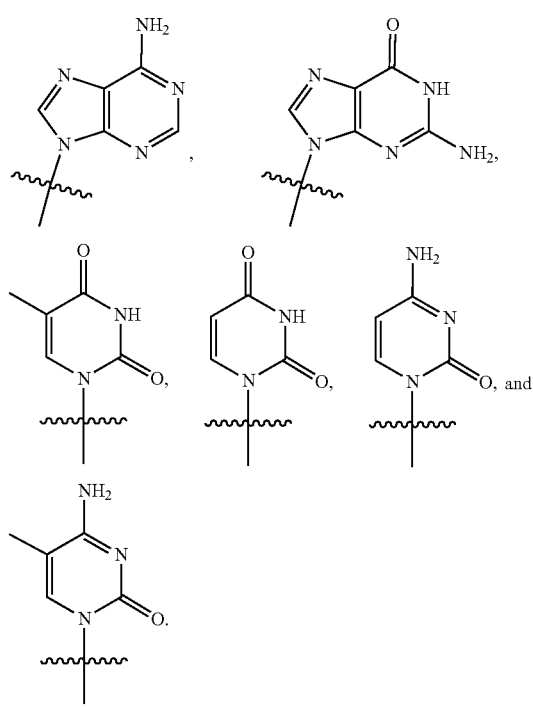

In some embodiments, BA is an optionally substituted group, which group is formed by removing a —H from

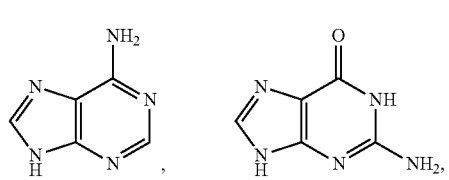

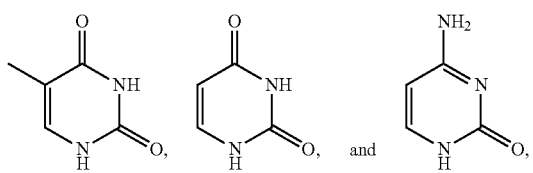

and tautomers thereof. In some embodiments, BA is an optionally substituted group, which group is formed by removing a —H from


In some embodiments, BA is an optionally substituted group which group is selected from

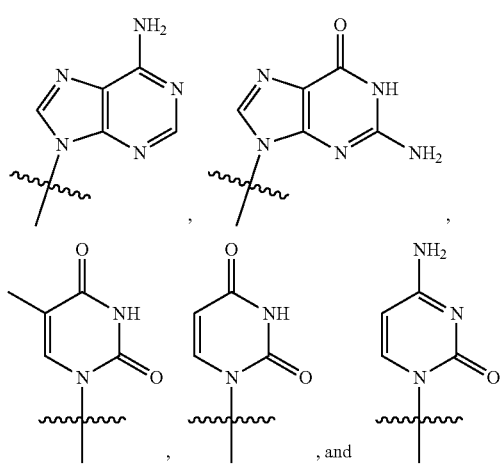

and tautomeric forms thereof. In some embodiments, BA is an optionally substituted group which group is selected from

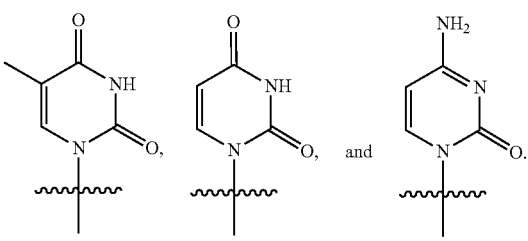

In some embodiments, BA is optionally substituted

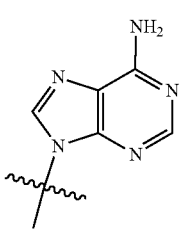

or a tautomeric form thereof. In some embodiments, BA is optionally substituted

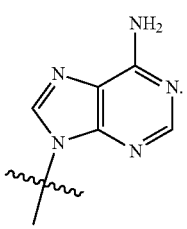 [SMILES: *n1cnc2c(N)ncnc21]

In some embodiments, BA is optionally substituted

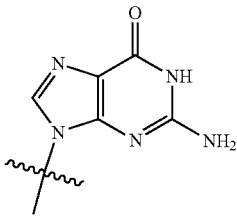 [SMILES: *n1cnc2c(=O)[nH]c(N)nc21]

or a tautomeric form thereof. In some embodiments, BA is optionally substituted

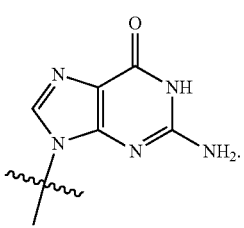

In some embodiments, BA is optionally substituted

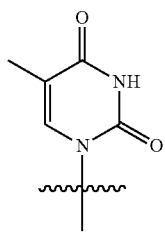

or a tautomeric form thereof. In some embodiments, BA is optionally substituted

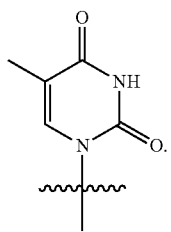

In some embodiments, BA is optionally substituted

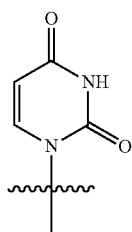

or a tautomeric form thereof. In some embodiments, BA is optionally substituted

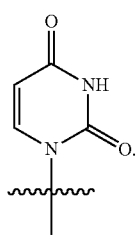

In some embodiments, BA is optionally substituted

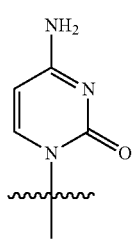 [SMILES: *n1ccc(N)nc1=O]

or a tautomeric form thereof. In some embodiments, BA is optionally substituted

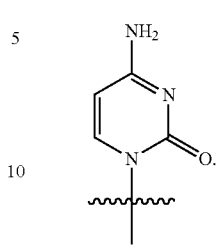

In some embodiments, BA is

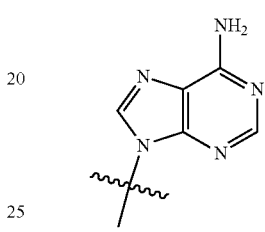

In some embodiments, BA is

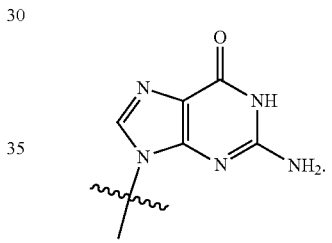

In some embodiments, BA is

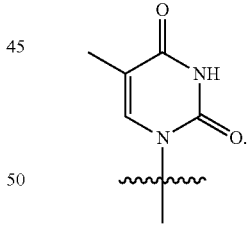

In some embodiments, BA is

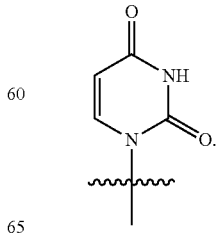

In some embodiments, BA is

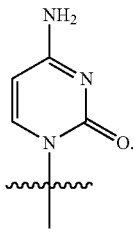 [SMILES: *n1ccc(N)nc1=O]

In some embodiments, BA of the 5'-end nucleoside unit of a provided oligonucleotide, e.g., an oligonucleotide of formula VIII, is an optionally substituted group, which group is formed by removing a —H from

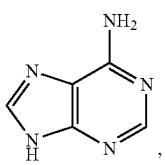

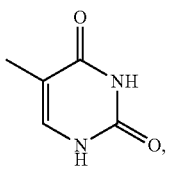

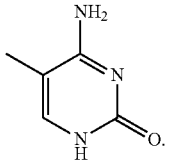

In some embodiments, BA of the 5'-end nucleoside unit is an optionally substituted group which group is selected from

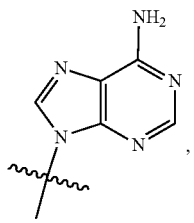

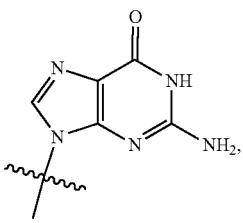

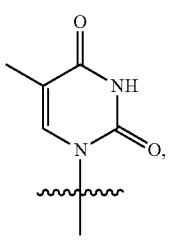

In some embodiments, BA of the 5'-end nucleoside unit is an optionally substituted group, which group is formed by removing a —H from

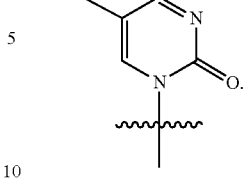

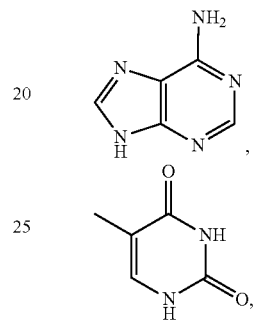

In some embodiments, BA of the 5'-end nucleoside unit is an optionally substituted group which group is selected from

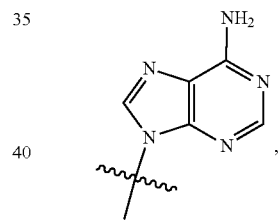

In some embodiments, BA of the 5'-end nucleoside unit is optionally substituted

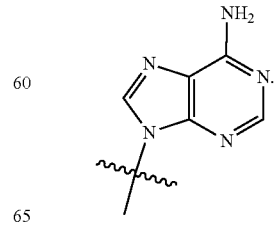

In some embodiments, BA of the 5'-end nucleoside unit is optionally substituted

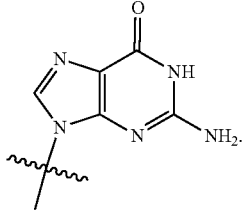

In some embodiments, BA of the 5'-end nucleoside unit is optionally substituted

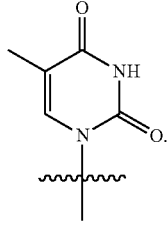

In some embodiments, BA of the 5'-end nucleoside unit is optionally substituted

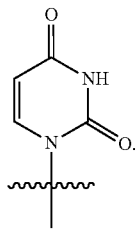

In some embodiments, BA of the 5'-end nucleoside unit is optionally substituted

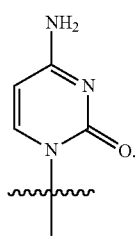 [SMILES: *n1ccc(N)nc1=O]

In some embodiments, BA of the 5'-end nucleoside unit is

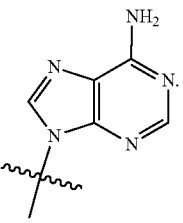

In some embodiments, BA of the 5'-end nucleoside unit is

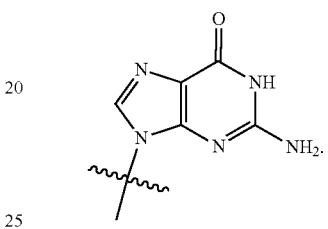

In some embodiments, BA of the 5'-end nucleoside unit is

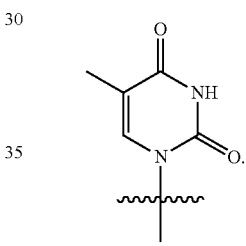

In some embodiments, BA of the 5'-end nucleoside unit is

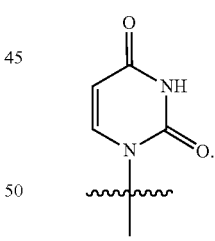

In some embodiments, BA of the 5'-end nucleoside unit is

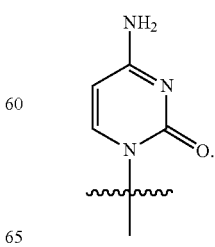

In some embodiments, BA is
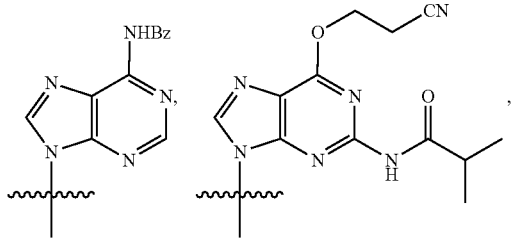
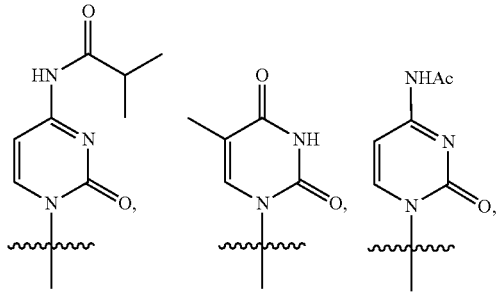
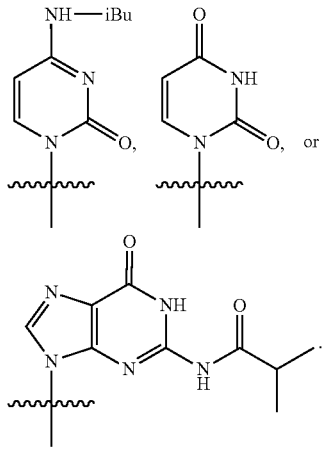
In some embodiments, BA is
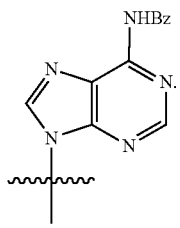
In some embodiments, BA is
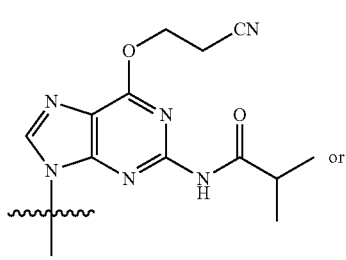
In some embodiments, BA is
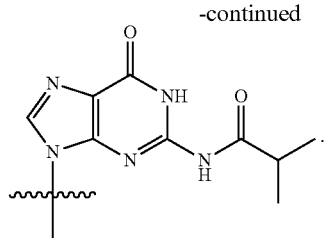
In some embodiments, BA is
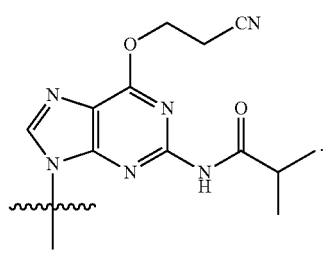 [SMILES: *n1cnc2c(OCCC#N)nc(NC(=O)C(C)C)nc21]
In some embodiments, BA is
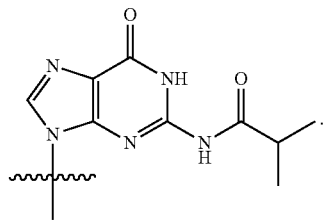 [SMILES: *n1cnc2c(=O)[nH]c(NC(=O)C(C)C)nc21]
In some embodiments, BA is
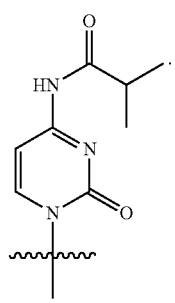 [SMILES: *n1ccc(NC(=O)C(C)C)nc1=O]
In some embodiments, BA is
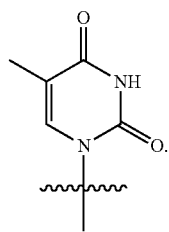 [SMILES: *n1cc(C)c(=O)[nH]c1=O]

In some embodiments, BA is

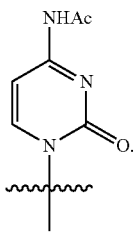

In some embodiments, BA is

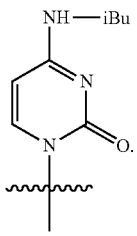

In some embodiments, BA is

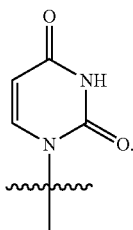 [SMILES: *n1ccc(=O)[nH]c1=O]

In some embodiments, a protection group is —Ac. In some embodiments, a protection group is -Bz. In some embodiments, a protection group is -iBu for nucleobase.

In some embodiments, BA is an optionally substituted purine base residue. In some embodiments, BA is a protected purine base residue. In some embodiments, BA is an optionally substituted adenine residue. In some embodiments, BA is a protected adenine residue. In some embodiments, BA is an optionally substituted guanine residue. In some embodiments, BA is a protected guanine residue. In some embodiments, BA is an optionally substituted cytosine residue. In some embodiments, BA is a protected cytosine residue. In some embodiments, BA is an optionally substituted thymine residue. In some embodiments, BA is a protected thymine residue. In some embodiments, BA is an optionally substituted uracil residue. In some embodiments, BA is a protected uracil residue. In some embodiments, BA is an optionally substituted 5-methylcytosine residue. In some embodiments, BA is a protected 5-methylcytosine residue.

In some embodiments, BA is a protected base residue as used in oligonucleotide preparation. In some embodiments, BA is a base residue illustrated in US 2011/0294124, US 2015/0211006, US 2015/0197540, and WO 2015/107425, each of which is incorporated herein by reference.

Those skilled in the art appreciate that a variety of modified nucleobases are suitable for use in accordance with the present disclosure in, for example, compounds of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, VI-e, or VIII, or salts thereof. Example modified bases include but are not limited to those limited in WO/2011/005761, WO/2013/012758, WO/2014/012081, WO/2015/107425, WO/2010/064146, WO/2014/010250, WO/2011/108682, WO/2012/039448, and WO/2012/073857, modified nucleobases of each of which are hereby incorporated by reference.

In some embodiments, BA is a substituted/protected nucleobase so that the phosphoramidite is properly protected with one or more protecting groups and can be used for oligonucleotide synthesis. Suitable protecting groups for nucleobases are widely known, including those useful for oligonucleotide synthesis, and can be utilized in accordance with the present disclosure. In some embodiments, a protecting group is acetyl (Ac), phenylacetyl, benzoyl (Bz), isobutyryl (iBu), phenoxyacetyl (Pac), isopropyl-Pac, tert-butyl-Pac, alkyl-Pac, dimethylformamidine (DMF), or dialkylformamidine. In some embodiments, a protecting group is phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). For additional suitable protecting groups, see Green and Wuts, Protective Groups in Organic Synthesis, 2nd Ed., John Wiley & Sons, New York, 1991, and WO/2011/005761, WO/2013/012758, WO/2014/012081, WO/2015/107425, WO/2010/064146, WO/2014/010250, WO/2011/108682, WO/2012/039448, and WO/2012/073857.

In some embodiments, SU is -L$^s$-O— or

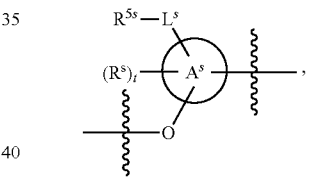

wherein SU is connected to the phosphorus atom through the oxygen atom. In some embodiments, SU is sugar moiety. In some embodiments, SU is a sugar moiety as used in oligonucleotides. In some embodiments, SU is a modified sugar moiety as used in oligonucleotides.

In some embodiments, SU is a sugar moiety or modified sugar moiety in natural or unnatural nucleosides, nucleotides, and/or oligonucleotides.

In some embodiments, SU is -L$^s$-O—, wherein SU is connected to the phosphorus atom through the oxygen atom.

In some embodiments, SU is -L$^s$-O—. In some embodiments, L$^s$ is -Cy-. In some embodiments, L$^s$ is optionally substituted 3-30 membered carbocyclylene. In some embodiments, L$^s$ is optionally substituted 6-30 membered arylene. In some embodiments, L$^s$ is optionally substituted 5-30 membered heteroarylene having 1-10 heteroatoms independently selected from oxygen, nitrogen and sulfur. In some embodiments, L$^s$ is optionally substituted 5-30 membered heteroarylene having 1-5 heteroatoms independently selected from oxygen, nitrogen and sulfur. In some embodiments, L$^s$ is optionally substituted 3-30 membered heterocyclylene having 1-10 heteroatoms independently selected from oxygen, nitrogen, sulfur, phosphorus and silicon. In some embodiments, L$^s$ is optionally substituted 3-30 membered heterocyclylene having 1-5 heteroatoms independently selected from oxygen, nitrogen, sulfur, phosphorus and silicon. In some embodiments, $L^s$ is optionally substituted 5-30 membered heterocyclylene having 1-10 heteroatoms independently selected from oxygen, nitrogen, sulfur, phosphorus and silicon. In some embodiments, $L^s$ is optionally substituted 5-30 membered heterocyclylene having 1-5 heteroatoms independently selected from oxygen, nitrogen, sulfur, phosphorus and silicon. In some embodiments, $L^s$ is optionally substituted 5-10 membered heterocyclylene having one oxygen atom. In some embodiments, $L^s$ is optionally substituted 5-membered heterocyclylene having one oxygen atom. In some embodiments, $L^s$ is optionally substituted 6-membered heterocyclylene having one oxygen atom. In some embodiments, $L^s$ is optionally substituted 5-10 membered bicyclic heterocyclylene having one or two oxygen atoms. In some embodiments, $L^s$ is optionally substituted 7-10 membered bicyclic heterocyclylene having one or two oxygen atoms. In some embodiments, $L^s$ is optionally substituted 7-10 membered bicyclic heterocyclylene having two oxygen atoms. In some embodiments, $L^s$ is optionally substituted 7-membered bicyclic heterocyclylene having two oxygen atoms.

In some embodiments, SU is a sugar moiety used in oligonucleotide synthesis. A person of ordinary skill in the art understands that phosphoramidites with a variety of sugar moieties can benefit from improved yields and/or purity when provided technologies are utilized for their preparation. In some embodiments, SU is an optionally substituted saturated monocyclic, bicyclic or polycyclic saturated aliphatic ring wherein one or more methylene units are replaced with —O—. In some embodiments, SU is a ribose or deoxyribose moiety found in natural DNA or RNA molecules.

In some embodiments, SU is

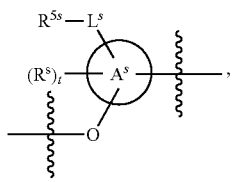

wherein each variable is independently as described in the present disclosure, and wherein SU is connected to the phosphorus atom through the oxygen atom.

In some embodiments, Ring $A^s$ is

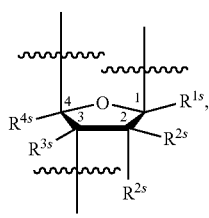

BA is connected at C1, and each of $R^{1s}$, $R^{2s}$, $R^{3s}$, $R^{4s}$ and $R^{5s}$ is independently $R^s$. In some embodiments, Ring $A^s$ is

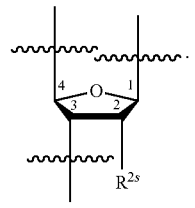

In some embodiments, Ring $A^s$ is

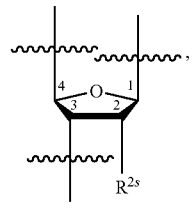

wherein $R^{2s}$ is not —OH. In some embodiments, Ring $A^s$ is

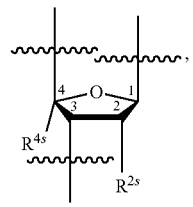

wherein $R^{2s}$ and $R^{4s}$ are R, and the two R groups are taken together with their intervening atoms to form an optionally substituted ring. In some embodiments, Ring $A^s$ is optionally substituted

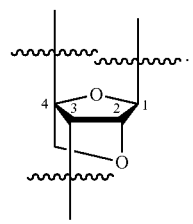 [SMILES: *C1[C@@H]2OC[C@]1(*)O[C@H]2*]

In some embodiments, Ring $A^s$ is

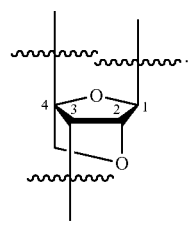 [SMILES: *C1[C@@H]2OC[C@]1(*)O[C@H]2*]

In some embodiments, Ring $A^s$ is

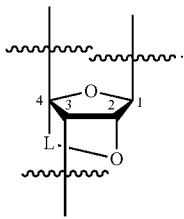

In some embodiments, SU is

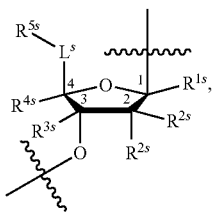

wherein each variable is independently as described in the present disclosure. In some embodiments, SU is

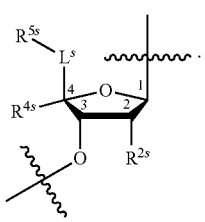

In some embodiments, SU is

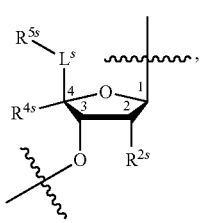

wherein $R^{4s}$ and $R^{2s}$ are taken together to form an optionally substituted ring. In some embodiments, SU is

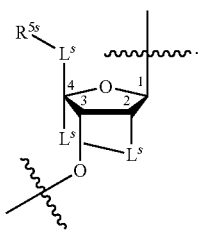

In some embodiments, SU is

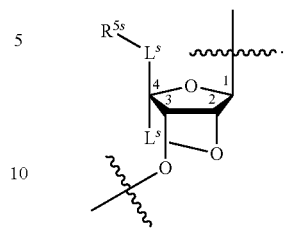

In some embodiments, SU is

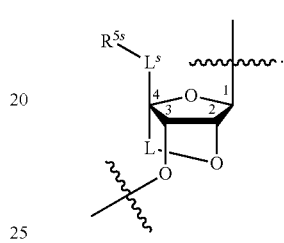

In some embodiments, SU is

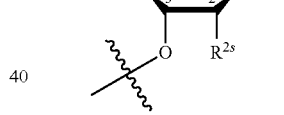

In some embodiments, $L^s$ is optionally substituted —O—CH$_2$—. In some embodiments, $L^s$ is optionally substituted —O—CH$_2$—, wherein the oxygen atom connects to $R^{5s}$. In some embodiments, $L^s$ is optionally substituted —O—C(R)$_2$—, wherein the oxygen atom connects to $R^{5s}$. In some embodiments, $L^s$ is optionally substituted —O—CHR—, wherein the oxygen atom connects to $R^{5s}$. In some embodiments, SU is

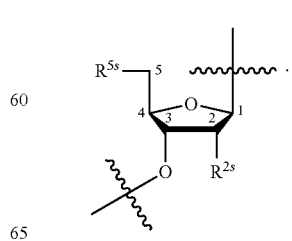

In some embodiments, SU is a modified sugar having the structure of:

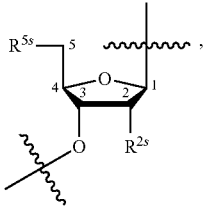

wherein $R^{5s}$ is —OR'; and $R^{2s}$ is —F, —CN, —N$_3$, —NO, —NO$_2$, —R', —OR', —SR', —N(R')$_2$, —O-L-OR', —O-L-SR', or —O-L-N(R')$_2$. In some embodiments, $R^{2s}$ and $R^{4s}$ are taken together to form an optionally substituted ring, and -L$^s$-connects C2 with C1, C2, C3, C4 or C5. In some embodiments, $R^{2s}$ is —H. In some embodiments, $R^{2s}$ is —F. In some embodiments, $R^{2s}$ is —OMe. In some embodiments, $R^{2s}$ is —OCH$_2$CH$_2$OMe.

In some embodiments, SU is

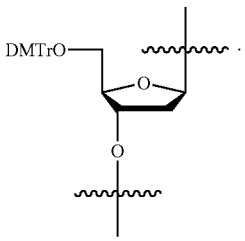

In some embodiments, SU is

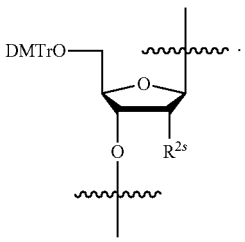

In some embodiments, SU is

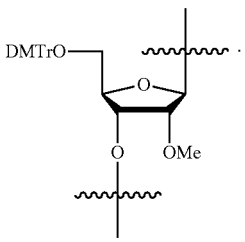

In some embodiments, SU is

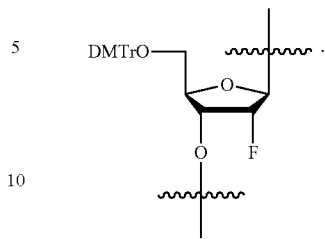

In some embodiments, SU is

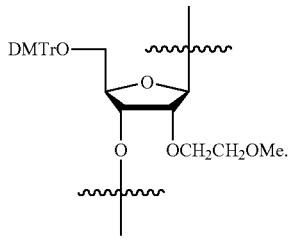

In some embodiments, a sugar moiety in a provided compound, e.g., a phosphoramidite of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof, an oligonucleotide of formula VIII or a salt thereof, is a modified sugar moiety as described in the present disclosure.

In some embodiments, one or more hydroxyl group in a sugar moiety is optionally and independently replaced with halogen, —R'—N(R')$_2$, —OR', or —SR', wherein each R' is independently as defined above and described herein.

In some embodiments, each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$.

In some embodiments, $R^s$ is R'. In some embodiments, $R^s$ is R. In some embodiments, $R^s$ is optionally substituted C$_{1-30}$ heteroaliphatic. In some embodiments, $R^s$ comprises one or more silicon atoms. In some embodiments, $R^s$ is —CH$_2$Si(Ph)$_2$CH$_3$.

In some embodiments, $R^s$ is -L$^s$-R'. In some embodiments, $R^s$ is -L$^s$-R' wherein -L$^s$- is a bivalent, optionally substituted C$_{1-30}$ heteroaliphatic group. In some embodiments, $R^s$ is —CH$_2$Si(Ph)$_2$CH$_3$.

In some embodiments, $R^s$ is —F. In some embodiments, $R^s$ is —Cl. In some embodiments, $R^s$ is —Br. In some embodiments, $R^s$ is —I. In some embodiments, $R^s$ is —CN. In some embodiments, $R^s$ is —N$_3$. In some embodiments, $R^s$ is —NO. In some embodiments, $R^s$ is —NO$_2$. In some embodiments, $R^s$ is -L$^s$-Si(R)$_3$. In some embodiments, $R^s$ is —Si(R)$_3$. In some embodiments, $R^s$ is -L$^s$-R'. In some embodiments, $R^s$ is —R'. In some embodiments, $R^s$ is -L$^s$-OR'. In some embodiments, $R^s$ is —OR'. In some embodiments, $R^s$ is -L$^s$-SR'. In some embodiments, $R^s$ is —SR'. In some embodiments, $R^s$ is -L$^s$-N(R')$_2$. In some embodiments, $R^s$ is —N(R')$_2$. In some embodiments, $R^s$ is —O-L$^s$-R'. In some embodiments, $R^s$ is —O-L$^s$-Si(R)$_3$. In some embodiments, $R^s$ is —O-L$^s$-OR'. In some embodiments, $R^s$ is —O-L$^s$-SR'. In some embodiments, $R^s$ is —O-L$^s$-N(R')$_2$. In some embodiments, $R^s$ is a 2'-modification as described in the present disclosure. In some embodiments, $R^s$ is —OR, wherein R is as described in the present disclosure. In some embodiments, $R^s$ is —OR, wherein R is optionally substituted $C_{1-6}$ aliphatic. In some embodiments, $R^s$ is —OMe. In some embodiments, $R^s$ is —OCH$_2$CH$_2$OMe.

In some embodiments, t is 0-20. In some embodiments, t is 1-20. In some embodiments, t is 1-5. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20.

In some embodiments, each of $R^{1s}$, $R^{2s}$, $R^{3s}$, $R^{4s}$, and $R^{5s}$ is independently $R^s$, wherein $R^s$ is as described in the present disclosure.

In some embodiments, $R^{1s}$ is $R^s$ at a 1'-position (BA is at 1'-position). In some embodiments, $R^s$ at a 1'-position is —F. In some embodiments, $R^s$ at a 1'-position is —Cl. In some embodiments, $R^s$ at a 1'-position is —Br. In some embodiments, $R^s$ at a 1'-position is —I. In some embodiments, $R^s$ at a 1'-position is —CN. In some embodiments, $R^s$ at a 1'-position is —N$_3$. In some embodiments, $R^s$ at a 1'-position is —NO. In some embodiments, $R^s$ at a 1'-position is —NO$_2$. In some embodiments, $R^s$ at a 1'-position is -L-R'. In some embodiments, $R^s$ at a 1'-position is —R'. In some embodiments, $R^s$ at a 1'-position is -L-OR'. In some embodiments, $R^s$ at a 1'-position is —OR'. In some embodiments, $R^s$ at a 1'-position is -L-SR'. In some embodiments, $R^s$ at a 1'-position is —SR'. In some embodiments, $R^s$ at a 1'-position is L-L-N(R')$_2$. In some embodiments, $R^s$ at a 1'-position is —N(R')$_2$. In some embodiments, $R^s$ at a 1'-position is —OR', wherein R' is optionally substituted $C_{1-6}$ aliphatic. In some embodiments, $R^s$ at a 1'-position is —OR', wherein R' is optionally substituted $C_{1-6}$ alkyl. In some embodiments, $R^s$ at a 1'-position is —OMe. In some embodiments, $R^s$ at a 1'-position is -MOE. In some embodiments, $R^s$ at a 1'-position is hydrogen. In some embodiments, $R^s$ at one 1'-position is hydrogen, and $R^s$ at the other 1'-position is not hydrogen as described herein. In some embodiments, $R^s$ at both 1'-positions are hydrogen. In some embodiments, $R^s$ at one 1'-position is hydrogen, and the other 1'-position is connected to an internucleotidic linkage. In some embodiments, $R^{1s}$ is —F. In some embodiments, $R^{1s}$ is —Cl. In some embodiments, $R^{1s}$ is —Br. In some embodiments, $R^{1s}$ is —I. In some embodiments, $R^{1s}$ is —CN. In some embodiments, $R^{1s}$ is —N$_3$. In some embodiments, $R^{1s}$ is —NO. In some embodiments, $R^{1s}$ is —NO$_2$. In some embodiments, $R^{1s}$ is -L-R'. In some embodiments, $R^{1s}$ is —R'. In some embodiments, $R^{1s}$ is -L-OR'. In some embodiments, $R^{1s}$ is —OR'. In some embodiments, $R^{1s}$ is -L-SR'. In some embodiments, $R^{1s}$ is —SR'. In some embodiments, $R^{1s}$ is -L-N(R')$_2$. In some embodiments, $R^{1s}$ is —N(R')$_2$. In some embodiments, $R^{1s}$ is —OR', wherein R' is optionally substituted $C_{1-6}$ aliphatic. In some embodiments, $R^{1s}$ is —OR', wherein R' is optionally substituted $C_{1-6}$ alkyl. In some embodiments, $R^{1s}$ is —OH. In some embodiments, $R^{1s}$ is —OMe. In some embodiments, $R^{1s}$ is -MOE. In some embodiments, $R^{1s}$ is hydrogen. In some embodiments, one $R^{1s}$ at a 1'-position is hydrogen, and the other $R^{1s}$ at the other 1'-position is not hydrogen as described herein. In some embodiments, $R^{1s}$ at both 1'-positions are hydrogen. In some embodiments, $R^{1s}$ is —O-L$^s$-OR'. In some embodiments, $R^{1s}$ is —O-L$^s$-OR', wherein L$^s$ is optionally substituted $C_{1-6}$ alkylene, and R' is optionally substituted $C_{1-6}$ aliphatic. In some embodiments, $R^{1s}$ is —O-(optionally substituted $C_{1-6}$ alkylene)-OR'. In some embodiments, $R^{1s}$ is —O-(optionally substituted $C_{1-6}$ alkylene)-OR', wherein R' is optionally substituted $C_{1-6}$ alkyl. In some embodiments, $R^{1s}$ is —OCH$_2$CH$_2$OMe.

In some embodiments, $R^{2s}$ is $R^s$ at a 2'-position (BA is at 1'-position). In some embodiments, $R^s$ at a 2'-position is —F. In some embodiments, $R^s$ at a 2'-position is —Cl. In some embodiments, $R^s$ at a 2'-position is —Br. In some embodiments, $R^s$ at a 2'-position is —I. In some embodiments, $R^s$ at a 2'-position is —CN. In some embodiments, $R^s$ at a 2'-position is —N$_3$. In some embodiments, $R^s$ at a 2'-position is —NO. In some embodiments, $R^s$ at a 2'-position is —NO$_2$. In some embodiments, $R^s$ at a 2'-position is -L-R'. In some embodiments, $R^s$ at a 2'-position is —R'. In some embodiments, $R^s$ at a 2'-position is -L-OR'. In some embodiments, $R^s$ at a 2'-position is —OR'. In some embodiments, $R^s$ at a 2'-position is -L-SR'. In some embodiments, $R^s$ at a 2'-position is —SR'. In some embodiments, $R^s$ at a 2'-position is L-L-N(R')$_2$. In some embodiments, $R^s$ at a 2'-position is —N(R')$_2$. In some embodiments, $R^s$ at a 2'-position is —OR', wherein R' is optionally substituted $C_{1-6}$ aliphatic. In some embodiments, $R^s$ at a 2'-position is —OR', wherein R' is optionally substituted $C_{1-6}$ alkyl. In some embodiments, $R^s$ at a 2'-position is —OMe. In some embodiments, $R^s$ at a 2'-position is -MOE. In some embodiments, $R^s$ at a 2'-position is hydrogen. In some embodiments, $R^s$ at one 2'-position is hydrogen, and $R^s$ at the other 2'-position is not hydrogen as described herein. In some embodiments, $R^s$ at both 2'-positions are hydrogen. In some embodiments, $R^s$ at one 2'-position is hydrogen, and the other 2'-position is connected to an internucleotidic linkage. In some embodiments, $R^{2s}$ is —F. In some embodiments, $R^{2s}$ is —Cl. In some embodiments, $R^{2s}$ is —Br. In some embodiments, $R^{2s}$ is —I. In some embodiments, $R^{2s}$ is —CN. In some embodiments, $R^{2s}$ is —N$_3$. In some embodiments, $R^{2s}$ is —NO. In some embodiments, $R^{2s}$ is —NO$_2$. In some embodiments, $R^{2s}$ is -L-R'. In some embodiments, $R^{2s}$ is —R'. In some embodiments, $R^{2s}$ is -L-OR'. In some embodiments, $R^{2s}$ is —OR'. In some embodiments, $R^{2s}$ is -L-SR'. In some embodiments, $R^{2s}$ is —SR'. In some embodiments, $R^{2s}$ is -L-N(R')$_2$. In some embodiments, $R^{2s}$ is —N(R')$_2$. In some embodiments, $R^{2s}$ is —OR', wherein R' is optionally substituted $C_{1-6}$ aliphatic. In some embodiments, $R^{2s}$ is —OR', wherein R' is optionally substituted $C_{1-6}$ alkyl. In some embodiments, $R^{2s}$ is —OH. In some embodiments, $R^{2s}$ is —OMe. In some embodiments, $R^{2s}$ is -MOE. In some embodiments, $R^{2s}$ is hydrogen. In some embodiments, one $R^{2s}$ at a 2'-position is hydrogen, and the other $R^{2s}$ at the other 2'-position is not hydrogen as described herein. In some embodiments, $R^{2s}$ at both 2'-positions are hydrogen. In some embodiments, $R^{2s}$ is —O-L$^s$-OR'. In some embodiments, $R^{2s}$ is —O-L$^s$-OR', wherein L$^s$ is optionally substituted $C_{1-6}$ alkylene, and R' is optionally substituted $C_{1-6}$ aliphatic. In some embodiments, $R^{2s}$ is —O-(optionally substituted $C_{1-6}$ alkylene)-OR'. In some embodiments, $R^{2s}$ is —O-(optionally substituted $C_{1-6}$ alkylene)-OR', wherein R' is optionally substituted $C_{1-6}$ alkyl. In some embodiments, $R^{2s}$ is —OCH$_2$CH$_2$OMe.

In some embodiments, $R^{3s}$ is $R^s$ at a 3'-position (BA is at 1'-position). In some embodiments, $R^s$ at a 3'-position (BA is at 1'-position) is —F. In some embodiments, $R^s$ at a 3'-position is —Cl. In some embodiments, $R^s$ at a 3'-position is —Br. In some embodiments, $R^s$ at a 3'-position is —I. In some embodiments, $R^s$ at a 3'-position is —CN. In some embodiments, $R^s$ at a 3'-position is —$N_3$. In some embodiments, $R^s$ at a 3'-position is —NO. In some embodiments, $R^s$ at a 3'-position is —$NO_2$. In some embodiments, $R^s$ at a 3'-position is -L-R'. In some embodiments, $R^s$ at a 3'-position is —R'. In some embodiments, $R^s$ at a 3'-position is -L-OR'. In some embodiments, $R^s$ at a 3'-position is —OR'. In some embodiments, $R^s$ at a 3'-position is -L-SR'. In some embodiments, $R^s$ at a 3'-position is —SR'. In some embodiments, $R^s$ at a 3'-position is -L-N(R')$_2$. In some embodiments, $R^s$ at a 3'-position is —N(R')$_2$. In some embodiments, $R^s$ at a 3'-position is —OR', wherein R' is optionally substituted $C_{1-6}$ aliphatic. In some embodiments, $R^s$ at a 3'-position is —OR', wherein R' is optionally substituted $C_{1-6}$ alkyl. In some embodiments, $R^s$ at a 3'-position is —OMe. In some embodiments, $R^s$ at a 3'-position is -MOE. In some embodiments, $R^s$ at a 3'-position is hydrogen. In some embodiments, $R^s$ at one 3'-position is hydrogen, and $R^s$ at the other 3'-position is not hydrogen as described herein. In some embodiments, $R^s$ at both 3'-positions are hydrogen. In some embodiments, $R^s$ at one 3'-position is hydrogen, and the other 3'-position is connected to an internucleotidic linkage. In some embodiments, $R^{3s}$ is —F. In some embodiments, $R^{3s}$ is —Cl. In some embodiments, $R^{3s}$ is —Br. In some embodiments, $R^{3s}$ is —I. In some embodiments, $R^{3s}$ is —CN. In some embodiments, $R^{3s}$ is —$N_3$. In some embodiments, $R^{3s}$ is —NO. In some embodiments, $R^{3s}$ is —$NO_2$. In some embodiments, $R^{3s}$ is -L-R'. In some embodiments, $R^{3s}$ is —R'. In some embodiments, $R^{3s}$ is -L-OR'. In some embodiments, $R^{3s}$ is —OR'. In some embodiments, $R^{3s}$ is -L-SR'. In some embodiments, $R^{3s}$ is —SR'. In some embodiments, $R^{3s}$ is L-L-N(R')$_2$. In some embodiments, $R^{3s}$ is —N(R')$_2$. In some embodiments, $R^{3s}$ is —OR', wherein R' is optionally substituted $C_{1-6}$ aliphatic. In some embodiments, $R^{3s}$ is —OR', wherein R' is optionally substituted $C_{1-6}$ alkyl. In some embodiments, $R^{3s}$ is —OH. In some embodiments, $R^{3s}$ is —OMe. In some embodiments, $R^{3s}$ is -MOE. In some embodiments, $R^{3s}$ is hydrogen.

In some embodiments, $R^{4s}$ is $R^s$ at a 4'-position (BA is at 1'-position). In some embodiments, $R^s$ at a 4'-position (BA is at 1'-position) is —F. In some embodiments, $R^s$ at a 4'-position is —Cl. In some embodiments, $R^s$ at a 4'-position is —Br. In some embodiments, $R^s$ at a 4'-position is —I. In some embodiments, $R^s$ at a 4'-position is —CN. In some embodiments, $R^s$ at a 4'-position is —$N_3$. In some embodiments, $R^s$ at a 4'-position is —NO. In some embodiments, $R^s$ at a 4'-position is —$NO_2$. In some embodiments, $R^s$ at a 4'-position is -L-R'. In some embodiments, $R^s$ at a 4'-position is —R'. In some embodiments, $R^s$ at a 4'-position is -L-OR'. In some embodiments, $R^s$ at a 4'-position is —OR'. In some embodiments, $R^s$ at a 4'-position is -L-SR'. In some embodiments, $R^s$ at a 4'-position is —SR'. In some embodiments, $R^s$ at a 4'-position is -L-N(R')$_2$. In some embodiments, $R^s$ at a 4'-position is —N(R')$_2$. In some embodiments, $R^s$ at a 4'-position is —OR', wherein R' is optionally substituted $C_{1-6}$ aliphatic. In some embodiments, $R^s$ at a 4'-position is —OR', wherein R' is optionally substituted $C_{1-6}$ alkyl. In some embodiments, $R^s$ at a 4'-position is —OMe. In some embodiments, $R^s$ at a 4'-position is -MOE. In some embodiments, $R^s$ at a 4'-position is hydrogen. In some embodiments, $R^s$ at one 4'-position is hydrogen, and $R^s$ at the other 4'-position is not hydrogen as described herein. In some embodiments, $R^s$ at both 4'-positions are hydrogen. In some embodiments, $R^s$ at one 4'-position is hydrogen, and the other 4'-position is connected to an internucleotidic linkage. In some embodiments, $R^{4s}$ is —F. In some embodiments, $R^{4s}$ is —Cl. In some embodiments, $R^{4s}$ is —Br. In some embodiments, $R^{4s}$ is —I. In some embodiments, $R^{4s}$ is —CN. In some embodiments, $R^{4s}$ is —$N_3$. In some embodiments, $R^{4s}$ is —NO. In some embodiments, $R^{4s}$ is —$NO_2$. In some embodiments, $R^{4s}$ is -L-R'. In some embodiments, $R^{4s}$ is —R'. In some embodiments, $R^{4s}$ is -L-OR'. In some embodiments, $R^{4s}$ is —OR'. In some embodiments, $R^{4s}$ is -L-SR'. In some embodiments, $R^{4s}$ is —SR'. In some embodiments, $R^{4s}$ is L-L-N(R')$_2$. In some embodiments, $R^{4s}$ is —N(R')$_2$. In some embodiments, $R^{4s}$ is —OR', wherein R' is optionally substituted $C_{1-6}$ aliphatic. In some embodiments, $R^{4s}$ is —OR', wherein R' is optionally substituted $C_{1-6}$ alkyl. In some embodiments, $R^{4s}$ is —OH. In some embodiments, $R^{4s}$ is —OMe. In some embodiments, $R^{4s}$ is -MOE. In some embodiments, $R^{4s}$ is hydrogen.

In some embodiments, $R^{5s}$ is R'. In some embodiments, $R^{5s}$ is —F. In some embodiments, $R^{5s}$ is —Cl. In some embodiments, $R^{5s}$ is —Br. In some embodiments, $R^{5s}$ is —I. In some embodiments, $R^{5s}$ is —CN. In some embodiments, $R^{5s}$ is —$N_3$. In some embodiments, $R^{5s}$ is —NO. In some embodiments, $R^{5s}$ is —$NO_2$. In some embodiments, $R^{5s}$ is -L-R'. In some embodiments, $R^{5s}$ is —R'. In some embodiments, $R^{5s}$ is -L-OR'. In some embodiments, $R^{5s}$ is —OR'. In some embodiments, $R^{5s}$ is -L-SR'. In some embodiments, $R^{5s}$ is —SR'. In some embodiments, $R^{5s}$ is L-L-N(R')$_2$. In some embodiments, $R^{5s}$ is —N(R')$_2$. In some embodiments, $R^{5s}$ is —OR', wherein R' is optionally substituted $C_{1-6}$ aliphatic. In some embodiments, $R^{5s}$ is —OR', wherein R' is optionally substituted $C_{1-6}$ alkyl. In some embodiments, $R^{5s}$ is —OH. In some embodiments, $R^{5s}$ is —OMe. In some embodiments, $R^{5s}$ is -MOE. In some embodiments, $R^{5s}$ is hydrogen.

In some embodiments, $R^{5s}$ is optionally substituted

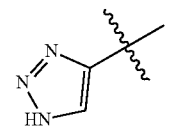

In some embodiments, $R^{5s}$ is optionally substituted

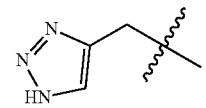

In some embodiments, $R^{5s}$ is a protected hydroxyl group suitable for oligonucleotide synthesis. In some embodiments, $R^{5s}$ is —OR', wherein R' is optionally substituted $C_{1-6}$ aliphatic. In some embodiments, $R^{5s}$ is DMTrO—. Example protecting groups are widely known for use in accordance with the present disclosure. For additional examples, see Greene, T. W.; Wuts, P. G. M. Protective Groups in Organic Synthesis, 2nd ed.; Wiley: New York, 1991, and WO/2011/005761, WO/2013/012758, WO/2014/012081, WO/2015/107425, WO/2010/064146, WO/2014/010250, WO/2011/108682, WO/2012/039448, and WO/2012/073857, protecting groups of each of which are hereby incorporated by reference.

In some embodiments, -$L^s$-$R^{5s}$ is $R^E$. In some embodiments, —C($R^{5s}$)$_3$ is $R^E$. In some embodiments, provided oligonucleotides, e.g., oligonucleotides comprising one or more internucleotidic linkages each independently of formula VII, VII-a-1, VII-a-2, VII-b, VII-c, VII-d, or VII-e, or a salt form thereof, oligonucleotides of formula VIII or salts thereof, etc. comprise $R^E$. In some embodiments, 5'-end nucleoside comprise $R^E$. In some embodiments, the present disclosure encompasses the recognition that incorporation of $R^E$ may significantly improve properties and/or activities of oligonucleotides, for example, in RNAi.

In some embodiments, $R^E$ is R. In some embodiments, $R^E$ is —H. In some embodiments, $R^E$ is —OR'. In some embodiments, $R^E$ is —OH. In some embodiments, $R^E$ is —OR', wherein R' is optionally substituted $C_{1-6}$ aliphatic. In some embodiments, $R^E$ is —OR', wherein R' is optionally substituted $C_{1-6}$ alkyl. In some embodiments, R' is methyl. In some embodiments, R' is ethyl. In some embodiments, R' is n-propyl. In some embodiments, $R^E$ is —CH$_2$OCH$_3$. In some embodiments, $R^E$ is —CH$_2$F. In some embodiments, $R^E$ is —CH$_2$OH.

In some embodiments, $R^E$ is —CH$_2$OP(O)(OR)$_2$ or a salt form thereof, wherein each R is independently as described in the present disclosure. In some embodiments, $R^E$ is —CH$_2$OP(O)(OH)$_2$ or a salt form thereof. In some embodiments, $R^E$ is —CH$_2$OP(O)(OR)(SR) or a salt form thereof, wherein each R is independently as described in the present disclosure. In some embodiments, $R^E$ is —CH$_2$OP(O)(SH)(OH) or a salt form thereof. In some embodiments, $R^E$ is —CH=CHP(O)(OR)$_2$ or a salt form thereof, wherein each R is independently as described in the present disclosure. In some embodiments, $R^E$ is -(E)-CH=CHP(O)(OR)$_2$ or a salt form thereof, wherein each R is independently as described in the present disclosure. In some embodiments, $R^E$ is -(E)-CH=CHP(O)(OH)$_2$.

In some embodiments, $R^E$ is —CH(R)—OR'. In some embodiments, $R^E$ is —(R)—CH(R)—OR'. In some embodiments, $R^E$ is —(S)—CH(R)—OR'. In some embodiments, R is not hydrogen. In some embodiments, R is optionally substituted $C_{1-6}$ aliphatic. In some embodiments, R is optionally substituted $C_{1-6}$ alkyl. In some embodiments, R is optionally substituted $C_{1-3}$ aliphatic. In some embodiments, R is optionally substituted $C_{1-3}$ alkyl. In some embodiments, R is linear. In some embodiments, R is unsubstituted. In some embodiments, R is substituted. In some embodiments, R is unsubstituted linear $C_{1-3}$ alkyl. In some embodiments, R is linear $C_{1-3}$ haloalkyl. In some embodiments, R is methyl. In some embodiments, R is ethyl. In some embodiments, R' is a hydroxyl protecting group. In some embodiments, R' is —C(O)R. In some embodiments, R' is DMTr.

In some embodiments, $R^E$ is —CH(R')—OH, wherein R' is as described in the present disclosure. In some embodiments, $R^E$ is —CH(R')—OP(O)(R)$_2$ or a salt form thereof, wherein each R' and R is independently as described in the present disclosure. In some embodiments, $R^E$ is —CH(R')—OP(O)(OR)$_2$ or a salt form thereof, wherein each R' and R is independently as described in the present disclosure. In some embodiments, $R^E$ is —CH(R')—OP(O)(OH)$_2$ or a salt form thereof. In some embodiments, $R^E$ is —CH(R')—OP(O)(OR)(SR) or a salt form thereof. In some embodiments, $R^E$ is —CH(R')—OP(O)(OH)(SH) or a salt form thereof. In some embodiments, $R^E$ is —(R)—CH(R')—OH, wherein R' is as described in the present disclosure. In some embodiments, $R^E$ is —(R)—CH(R')—OP(O)(R)$_2$ or a salt form thereof, wherein each R' and R is independently as described in the present disclosure. In some embodiments, $R^E$ is —(R)—CH(R')—OP(O)(OR)$_2$ or a salt form thereof, wherein each R' and R is independently as described in the present disclosure. In some embodiments, $R^E$ is —(R)—CH(R')—OP(O)(OH)$_2$ or a salt form thereof. In some embodiments, $R^E$ is —(R)—CH(R')—OP(O)(OR)(SR) or a salt form thereof. In some embodiments, $R^E$ is —(R)—CH(R')—OP(O)(OH)(SH) or a salt form thereof. In some embodiments, $R^E$ is —(S)—CH(R')—OH, wherein R' is as described in the present disclosure. In some embodiments, $R^E$ is —(S)—CH(R')—OP(O)(R)$_2$ or a salt form thereof, wherein each R' and R is independently as described in the present disclosure. In some embodiments, $R^E$ is —(S)—CH(R')—OP(O)(OR)$_2$ or a salt form thereof, wherein each R' and R is independently as described in the present disclosure. In some embodiments, $R^E$ is —(S)—CH(R')—OP(O)(OH)$_2$ or a salt form thereof. In some embodiments, $R^E$ is —(S)—CH(R')—OP(O)(OR)(SR) or a salt form thereof. In some embodiments, $R^E$ is —(S)—CH(R')—OP(O)(OH)(SH) or a salt form thereof. In some embodiments, R' is optionally substituted $C_1$, $C_2$, $C_3$, or $C_4$ aliphatic. In some embodiments, R' is $C_1$, $C_2$, $C_3$, or $C_4$ aliphatic or haloaliphatic. In some embodiments, R' is optionally substituted —CH$_3$. In some embodiments, R' is —CH$_3$.

In some embodiments, $R^E$ is -L$^s$-P(O)(XR)$_2$ or a salt form thereof, wherein each X is independently —O—, —S—, or —N(R')—. In some embodiments, $R^E$ is -L$^s$-P(O)(XR)$_2$ or a salt form thereof, wherein each X is independently —O—, —S—, or a covalent bond. In some embodiments, $R^E$ is -L$^s$-P(O)(OR)$_2$ or a salt form thereof. In some embodiments, $R^E$ is -L$^s$-P(O)(OR)(SR) or a salt form thereof. In some embodiments, $R^E$ is -L$^s$-P(O)(OR)(R) or a salt form thereof. In some embodiments, L$^s$ is a covalent bond, or a bivalent, optionally substituted, linear or branched $C_{1-6}$ aliphatic, wherein one or more methylene units are optionally and independently replaced with —O—, —S— or —N(R')—. In some embodiments, $R^E$ is —X-L$^s$-R. In some embodiments, $R^E$ is —X-L$^s$-R$^5$. In some embodiments, R$^5$ is optionally substituted 5-20 membered heteroaryl having 1-5 heteroatoms. In some embodiments, R$^5$ is optionally substituted 5-membered heteroaryl having 1-4 heteroatoms. In some embodiments, $R^E$ is optionally substituted

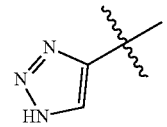

In some embodiments, $R^E$ is

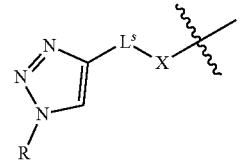

In some embodiments, $R^E$ is

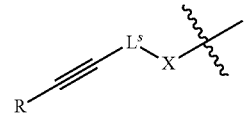

or a salt form thereof. In some embodiments, $R^E$ is

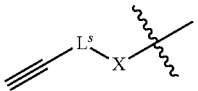

In some embodiments, X in $R^E$ is —C(R)$_2$—. In some embodiments, X is —O—. In some embodiments, X is —S—. In some embodiments, X is —N(R)—. In some embodiments, $L^s$ comprises an optionally substituted, bivalent or multivalent

group. In some embodiments, $L^s$ comprises an optionally substituted

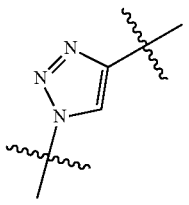 [SMILES: *c1cn(*)nn1]

group. In some embodiments, $L^s$ comprises a

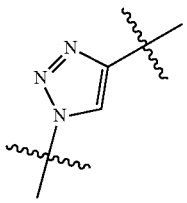 [SMILES: *c1cn(*)nn1]

group. In some embodiments, R is independently —H, or an optionally substituted group selected from $C_{1-10}$ alkyl, $C_{1-10}$ allyl, and $C_{6-14}$ aryl. In some embodiments, R is —H. In some embodiments, $R^E$ is optionally substituted

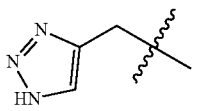

In some embodiments, $R^E$ is

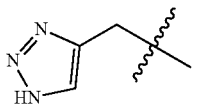

In some embodiments, $R^E$ is —CHR—O—$R^s$, wherein R is —H or optionally substituted $C_{1-4}$ aliphatic, and $R^s$ is hydroxyl protecting group. In some embodiments, R is methyl and $R^s$ is DMTr. In some embodiments, $R^E$ is —(R)—CH(Me)-ODMTr. In some embodiments, $R^E$ is —(S)—CH(Me)-ODMTr. In some embodiments, $R^E$ is -$L^s$-P(O)(OR)$_2$. In some embodiments, $R^E$ is -$L^s$-P(O)(OR)$_2$, wherein each R is independently optionally substituted $C_{1-6}$ aliphatic. In some embodiments, -$L^s$- is -(E)-CH=CH—. In some embodiments, $R^E$ is -(E)-CH=CH—P(O)(OR)$_2$. In some embodiments, $R^E$ is -(E)-CH=CH—P(O)(OR)$_2$, wherein each R is independently optionally substituted $C_{1-6}$ aliphatic. In some embodiments, $R^E$ is -(E)-CH=CH—P(O)(OMe)$_2$.

In some embodiments, s is 0-20. In some embodiments, s is 1-20. In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is 11. In some embodiments, s is 12. In some embodiments, s is 13. In some embodiments, s is 14. In some embodiments, s is 15. In some embodiments, s is 16. In some embodiments, s is 17. In some embodiments, s is 18. In some embodiments, s is 19. In some embodiments, s is 20.

In some embodiments, each Ring $A^s$ is independently an optionally substituted 3-20 membered monocyclic, bicyclic or polycyclic ring having 0-10 heteroatoms independently selected from oxygen, nitrogen, sulfur, phosphorus and silicon. In some embodiments, Ring A is an optionally substituted ring, which ring is as described in the present disclosure. In some embodiments, a ring is

In some embodiments, a ring is

In some embodiments, Ring A is or comprises a ring of a sugar moiety. In some embodiments, Ring A is or comprises a ring of a modified sugar moiety.

In some embodiments, provided compounds comprise one or more bivalent or multivalent optionally substituted rings, e.g., Ring A, Ring $A^s$, Ring A', -Cy-, $Cy^L$, those formed by two or more R groups (R and (combinations of) variables that can be R) taken together, etc. In some embodiments, a ring is a cycloaliphatic, aryl, heteroaryl, or heterocyclyl group as described for R but bivalent or multivalent. As appreciated by those skilled in the art, ring moieties described for one variable, e.g., Ring A, can also be applicable to other variables, e.g., Ring A', -Cy-, $Cy^L$, etc., if requirements of the other variables, e.g., number of heteroatoms, valence, etc., are satisfied. Example rings are extensively described in the present disclosure.

In some embodiments, a ring, e.g., in Ring A, Ring $A^s$, R, etc. which is optionally substituted, is a 3-20 membered monocyclic, bicyclic or polycyclic ring having 0-10 heteroatoms independently selected from oxygen, nitrogen, sulfur, phosphorus and silicon. In some embodiments, a ring is a 3-20 membered monocyclic, bicyclic or polycyclic ring having 1-10 heteroatoms independently selected from oxygen, nitrogen, sulfur, phosphorus and silicon, wherein the ring comprises a —N(R$^6$)— moiety.

In some embodiments, a ring can be of any size within its range, e.g., 3, 4, 5, 6, 7, 8, 9, 10, 11, 12, 13, 14, 15, 16, 17, 18, 19, or 20-membered.

In some embodiments, a ring is monocyclic. In some embodiments, a ring is saturated and monocyclic. In some embodiments, a ring is monocyclic and partially saturated. In some embodiments, a ring is monocyclic and aromatic.

In some embodiments, a ring is bicyclic. In some embodiments, a ring is polycyclic. In some embodiments, a bicyclic or polycyclic ring comprises two or more monocyclic ring moieties, each of which can be saturated, partially saturated, or aromatic, and each which can contain no or 1-10 heteroatoms. In some embodiments, a bicyclic or polycyclic ring comprises a saturated monocyclic ring. In some embodiments, a bicyclic or polycyclic ring comprises a saturated monocyclic ring containing no heteroatoms. In some embodiments, a bicyclic or polycyclic ring comprises a saturated monocyclic ring comprising one or more heteroatoms. In some embodiments, a bicyclic or polycyclic ring comprises a partially saturated monocyclic ring. In some embodiments, a bicyclic or polycyclic ring comprises a partially saturated monocyclic ring containing no heteroatoms. In some embodiments, a bicyclic or polycyclic ring comprises a partially saturated monocyclic ring comprising one or more heteroatoms. In some embodiments, a bicyclic or polycyclic ring comprises an aromatic monocyclic ring. In some embodiments, a bicyclic or polycyclic ring comprises an aromatic monocyclic ring containing no heteroatoms. In some embodiments, a bicyclic or polycyclic ring comprises an aromatic monocyclic ring comprising one or more heteroatoms. In some embodiments, a bicyclic or polycyclic ring comprises a saturated ring and a partially saturated ring, each of which independently contains one or more heteroatoms. In some embodiments, a bicyclic ring comprises a saturated ring and a partially saturated ring, each of which independently comprises no, or one or more heteroatoms. In some embodiments, a bicyclic ring comprises an aromatic ring and a partially saturated ring, each of which independently comprises no, or one or more heteroatoms. In some embodiments, a polycyclic ring comprises a saturated ring and a partially saturated ring, each of which independently comprises no, or one or more heteroatoms. In some embodiments, a polycyclic ring comprises an aromatic ring and a partially saturated ring, each of which independently comprises no, or one or more heteroatoms. In some embodiments, a polycyclic ring comprises an aromatic ring and a saturated ring, each of which independently comprises no, or one or more heteroatoms. In some embodiments, a polycyclic ring comprises an aromatic ring, a saturated ring, and a partially saturated ring, each of which independently comprises no, or one or more heteroatoms. In some embodiments, a ring comprises at least one heteroatom. In some embodiments, a ring comprises at least one nitrogen atom. In some embodiments, a ring comprises at least one oxygen atom. In some embodiments, a ring comprises at least one sulfur atom.

As appreciated by those skilled in the art in accordance with the present disclosure, a ring is typically optionally substituted. In some embodiments, a ring is unsubstituted. In some embodiments, a ring is substituted. In some embodiments, a ring is substituted on one or more of its carbon atoms. In some embodiments, a ring is substituted on one or more of its heteroatoms. In some embodiments, a ring is substituted on one or more of its carbon atoms, and one or more of its heteroatoms. In some embodiments, two or more substituents can be located on the same ring atom. In some embodiments, all available ring atoms are substituted. In some embodiments, not all available ring atoms are substituted. In some embodiments, in provided structures where rings are indicated to be connected to other structures (e.g., Ring A$^s$ in

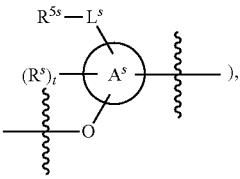),

"optionally substituted" is to mean that, besides those structures already connected, remaining substitutable ring positions, if any, are optionally substituted (e.g., in

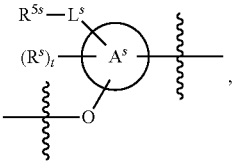,

Ring A$^s$ may optionally have one or more substituents besides R$^{5s}$-L$^s$-, t R$^s$, —O—, and -).

In some embodiments, a ring is a bivalent or multivalent $C_{3-30}$ cycloaliphatic ring. In some embodiments, a ring is a bivalent or multivalent $C_{3-20}$ cycloaliphatic ring. In some embodiments, a ring is a bivalent or multivalent $C_{3-10}$ cycloaliphatic ring. In some embodiments, a ring is a bivalent or multivalent 3-30 membered saturated or partially unsaturated carbocyclic ring. In some embodiments, a ring is a bivalent or multivalent 3-7 membered saturated or partially unsaturated carbocyclic ring. In some embodiments, a ring is a bivalent or multivalent 3-membered saturated or partially unsaturated carbocyclic ring. In some embodiments, a ring is a bivalent or multivalent 4-membered saturated or partially unsaturated carbocyclic ring. In some embodiments, a ring is a bivalent or multivalent 5-membered saturated or partially unsaturated carbocyclic ring. In some embodiments, a ring is a bivalent or multivalent 6-membered saturated or partially unsaturated carbocyclic ring. In some embodiments, a ring is a bivalent or multivalent 7-membered saturated or partially unsaturated carbocyclic ring. In some embodiments, a ring is a bivalent or multivalent cyclohexyl ring. In some embodiments, a ring is a bivalent or multivalent cyclopentyl ring. In some embodiments, a ring is a bivalent or multivalent cyclobutyl ring. In some embodiments, a ring is a bivalent or multivalent cyclopropyl ring.

In some embodiments, a ring is a bivalent or multivalent $C_{6-30}$ aryl ring. In some embodiments, a ring is a bivalent or multivalent phenyl ring.

In some embodiments, a ring is a bivalent or multivalent 8-10 membered bicyclic saturated, partially unsaturated or aryl ring. In some embodiments, a ring is a bivalent or multivalent 8-10 membered bicyclic saturated ring. In some embodiments, a ring is a bivalent or multivalent 8-10 membered bicyclic partially unsaturated ring. In some embodiments, a ring is a bivalent or multivalent 8-10 membered bicyclic aryl ring. In some embodiments, a ring is a bivalent or multivalent naphthyl ring.

In some embodiments, a ring is a bivalent or multivalent 5-30 membered heteroaryl ring having 1-10 heteroatoms independently selected from oxygen, nitrogen, sulfur, phosphorus and silicon. In some embodiments, a ring is a bivalent or multivalent 5-30 membered heteroaryl ring having 1-10 heteroatoms independently selected from oxygen, nitrogen, and sulfur. In some embodiments, a ring is a bivalent or multivalent 5-30 membered heteroaryl ring having 1-5 heteroatoms independently selected from oxygen, nitrogen, sulfur, phosphorus and silicon. In some embodiments, a ring is a bivalent or multivalent 5-30 membered heteroaryl ring having 1-5 heteroatoms independently selected from oxygen, nitrogen, and sulfur.

In some embodiments, a ring is a bivalent or multivalent 5-6 membered monocyclic heteroaryl ring having 1-4 heteroatoms independently selected from nitrogen, oxygen, and sulfur. In some embodiments, a ring is a bivalent or multivalent 5-6 membered monocyclic heteroaryl ring having 1-3 heteroatoms independently selected from nitrogen, sulfur, and oxygen.

In some embodiments, a ring is a bivalent or multivalent 5-membered monocyclic heteroaryl ring having 1-4 heteroatoms independently selected from nitrogen, oxygen or sulfur. In some embodiments, a ring is a bivalent or multivalent 6-membered monocyclic heteroaryl ring having 1-4 heteroatoms independently selected from nitrogen, oxygen, and sulfur.

In some embodiments, a ring is a bivalent or multivalent 5-membered monocyclic heteroaryl ring having one heteroatom selected from nitrogen, oxygen, and sulfur. In some embodiments, a ring is a bivalent or multivalent pyrrolyl, furanyl, or thienyl ring.

In some embodiments, a ring is a bivalent or multivalent 5-membered heteroaryl ring having two heteroatoms independently selected from nitrogen, oxygen, and sulfur. In certain embodiments, a ring is a bivalent or multivalent 5-membered heteroaryl ring having one nitrogen atom, and an additional heteroatom selected from sulfur or oxygen. In some embodiments, a ring is a bivalent or multivalent pyrazolyl, imidazolyl, thiazolyl, isothiazolyl, oxazolyl or isoxazolyl ring.

In some embodiments, a ring is a bivalent or multivalent 5-membered heteroaryl ring having three heteroatoms independently selected from nitrogen, oxygen, and sulfur. In some embodiments, a ring is a bivalent or multivalent triazolyl, oxadiazolyl or thiadiazolyl ring.

In some embodiments, a ring is a bivalent or multivalent 5-membered heteroaryl ring having four heteroatoms independently selected from nitrogen, oxygen, and sulfur. In some embodiments, a ring is a bivalent or multivalent tetrazolyl, oxatriazolyl and thiatriazolyl ring.

In some embodiments, a ring is a bivalent or multivalent 6-membered heteroaryl ring having 1-4 nitrogen atoms. In some embodiments, a ring is a bivalent or multivalent 6-membered heteroaryl ring having 1-3 nitrogen atoms. In other embodiments, a ring is a bivalent or multivalent 6-membered heteroaryl ring having 1-2 nitrogen atoms. In some embodiments, a ring is a bivalent or multivalent 6-membered heteroaryl ring having four nitrogen atoms. In some embodiments, a ring is a bivalent or multivalent 6-membered heteroaryl ring having three nitrogen atoms. In some embodiments, a ring is a bivalent or multivalent 6-membered heteroaryl ring having two nitrogen atoms. In certain embodiments, a ring is a bivalent or multivalent 6-membered heteroaryl ring having one nitrogen atom. In some embodiments, a ring is a bivalent or multivalent pyridinyl, pyrimidinyl, pyrazinyl, pyridazinyl, triazinyl, or tetrazinyl ring.

In certain embodiments, a ring is a bivalent or multivalent 8-10 membered bicyclic heteroaryl ring having 1-4 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In other embodiments, a ring is a bivalent or multivalent 5,6-fused heteroaryl ring having 1-2 heteroatoms independently selected from nitrogen, oxygen, and sulfur. In certain embodiments, a ring is a bivalent or multivalent 5,6-fused heteroaryl ring having 1 heteroatom independently selected from nitrogen, oxygen, and sulfur. In some embodiments, a ring is a bivalent or multivalent indolyl ring. In some embodiments, a ring is a bivalent or multivalent azabicyclo [3.2.1]octanyl ring. In certain embodiments, a ring is a bivalent or multivalent 5,6-fused heteroaryl ring having 2 heteroatoms independently selected from nitrogen, oxygen, and sulfur. In some embodiments, a ring is a bivalent or multivalent azaindolyl ring. In some embodiments, a ring is a bivalent or multivalent benzimidazolyl ring. In some embodiments, a ring is a bivalent or multivalent benzothiazolyl ring. In some embodiments, a ring is a bivalent or multivalent benzoxazolyl ring. In some embodiments, a ring is a bivalent or multivalent indazolyl ring. In certain embodiments, a ring is a bivalent or multivalent 5,6-fused heteroaryl ring having 3 heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In some embodiments, a ring is a bivalent or multivalent 5,6-fused heteroaryl ring having 1-3 heteroatoms independently selected from nitrogen, oxygen, and sulfur. In some embodiments, a ring is a bivalent or multivalent 5,6-fused heteroaryl ring having two heteroatoms independently selected from nitrogen, oxygen, and sulfur. In some embodiments, a ring is a bivalent or multivalent 5,6-fused heteroaryl ring having three heteroatoms independently selected from nitrogen, oxygen, and sulfur. In some embodiments, a ring is a bivalent or multivalent 5,6-fused heteroaryl ring having four heteroatoms independently selected from nitrogen, oxygen, and sulfur. In some embodiments, a ring is a bivalent or multivalent 5,6-fused heteroaryl ring having five heteroatoms independently selected from nitrogen, oxygen, and sulfur.

In certain embodiments, a ring is a bivalent or multivalent 5,6-fused heteroaryl ring having one heteroatom independently selected from nitrogen, oxygen, and sulfur. In some embodiments, a ring is a bivalent or multivalent indolyl ring. In some embodiments, a ring is a bivalent or multivalent benzofuranyl ring. In some embodiments, a ring is a bivalent or multivalent benzo[b]thienyl ring. In certain embodiments, a ring is a bivalent or multivalent 5,6-fused heteroaryl ring having two heteroatoms independently selected from nitrogen, oxygen, and sulfur. In some embodiments, a ring is a bivalent or multivalent azaindolyl ring. In some embodiments, a ring is a bivalent or multivalent benzimidazolyl ring. In some embodiments, a ring is a bivalent or multivalent benzothiazolyl ring. In some embodiments, a ring is a bivalent or multivalent benzoxazolyl ring. In some embodiments, a ring is a bivalent or multivalent indazolyl ring. In certain embodiments, a ring is a bivalent or multivalent 5,6-fused heteroaryl ring having three heteroatoms independently selected from nitrogen, oxygen, and sulfur. In some embodiments, a ring is a bivalent or multivalent oxazolopyridiyl, thiazolopyridinyl or imidazopyridinyl ring. In certain embodiments, a ring is a bivalent or multivalent 5,6-fused heteroaryl ring having four heteroatoms independently selected from nitrogen, oxygen, and sulfur. In some embodiments, a ring is a bivalent or multivalent purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl ring. In certain embodiments, a ring is a bivalent or multivalent 5,6-fused heteroaryl ring having five heteroatoms independently selected from nitrogen, oxygen, and sulfur.

In some embodiments, a ring is a bivalent or multivalent 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl ring. In some embodiments, a ring is a bivalent or multivalent dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl ring.

In certain embodiments, a ring is a bivalent or multivalent 6,6-fused heteroaryl ring having 1-4 heteroatoms independently selected from nitrogen, oxygen, and sulfur. In some embodiments, a ring is a bivalent or multivalent 6,6-fused heteroaryl ring having 1-2 heteroatoms independently selected from nitrogen, oxygen, and sulfur. In other embodiments, a ring is a bivalent or multivalent 6,6-fused heteroaryl ring having 1 heteroatom independently selected from nitrogen, oxygen, and sulfur. In some embodiments, a ring is a bivalent or multivalent quinolinyl ring. In some embodiments, a ring is a bivalent or multivalent isoquinolinyl ring. In some embodiments, a ring is a bivalent or multivalent 6,6-fused heteroaryl ring having 2 heteroatoms independently selected from nitrogen, oxygen, and sulfur. In some embodiments, a ring is a bivalent or multivalent quinazoline or a quinoxaline.

In some embodiments, a ring is a bivalent or multivalent 3-30 membered heterocyclic ring having 1-10 heteroatoms independently selected from oxygen, nitrogen, sulfur, phosphorus and silicon. In some embodiments, a ring is a bivalent or multivalent 3-30 membered heterocyclic ring having 1-10 heteroatoms independently selected from oxygen, nitrogen, and sulfur. In some embodiments, a ring is a bivalent or multivalent 3-30 membered heterocyclic ring having 1-5 heteroatoms independently selected from oxygen, nitrogen, sulfur, phosphorus and silicon. In some embodiments, a ring is a bivalent or multivalent 3-30 membered heterocyclic ring having 1-5 heteroatoms independently selected from oxygen, nitrogen, and sulfur.

In some embodiments, a ring is a bivalent or multivalent 3-7 membered saturated or partially unsaturated heterocyclic ring having 1-3 heteroatoms independently selected from nitrogen, oxygen, and sulfur. In some embodiments, a ring is a bivalent or multivalent a substituted 3-7 membered saturated or partially unsaturated heterocyclic ring having 1-3 heteroatoms independently selected from nitrogen, oxygen, and sulfur. In some embodiments, a ring is a bivalent or multivalent an unsubstituted 3-7 membered saturated or partially unsaturated heterocyclic ring having 1-3 heteroatoms independently selected from nitrogen, oxygen, and sulfur. In certain embodiments, a ring is a bivalent or multivalent 5-7 membered partially unsaturated monocyclic ring having 1-3 heteroatoms independently selected from nitrogen, oxygen, and sulfur. In certain embodiments, a ring is a bivalent or multivalent 5-6 membered partially unsaturated monocyclic ring having 1-3 heteroatoms independently selected from nitrogen, oxygen, and sulfur. In certain embodiments, a ring is a bivalent or multivalent 5-membered partially unsaturated monocyclic ring having 1-3 heteroatoms independently selected from nitrogen, oxygen, and sulfur. In certain embodiments, a ring is a bivalent or multivalent 6-membered partially unsaturated monocyclic ring having 1-3 heteroatoms independently selected from nitrogen, oxygen, and sulfur. In certain embodiments, a ring is a bivalent or multivalent 7-membered partially unsaturated monocyclic ring having 1-3 heteroatoms independently selected from nitrogen, oxygen, and sulfur. In some embodiments, a ring is a bivalent or multivalent 3-membered heterocyclic ring having one heteroatom selected from nitrogen, oxygen or sulfur. In some embodiments, a ring is a bivalent or multivalent 4-membered heterocyclic ring having 1-3 heteroatoms independently selected from nitrogen, oxygen, and sulfur. In some embodiments, a ring is a bivalent or multivalent 5-membered heterocyclic ring having 1-3 heteroatoms independently selected from nitrogen, oxygen, and sulfur. In some embodiments, a ring is a bivalent or multivalent 6-membered heterocyclic ring having 1-3 heteroatoms independently selected from nitrogen, oxygen, and sulfur. In some embodiments, a ring is a bivalent or multivalent 7-membered heterocyclic ring having 1-3 heteroatoms independently selected from nitrogen, oxygen, and sulfur.

In some embodiments, a ring is a bivalent or multivalent 3-membered saturated or partially unsaturated heterocyclic ring having 1-2 heteroatoms independently selected from nitrogen, oxygen, and sulfur. In some embodiments, a ring is a bivalent or multivalent 4-membered saturated or partially unsaturated heterocyclic ring having 1-2 heteroatoms independently selected from nitrogen, oxygen, and sulfur. In some embodiments, a ring is a bivalent or multivalent 5-membered saturated or partially unsaturated heterocyclic ring having 1-2 heteroatoms independently selected from nitrogen, oxygen, and sulfur. In some embodiments, a ring is a bivalent or multivalent 6-membered saturated or partially unsaturated heterocyclic ring having 1-2 heteroatoms independently selected from nitrogen, oxygen, and sulfur. In some embodiments, a ring is a bivalent or multivalent 7-membered saturated or partially unsaturated heterocyclic ring having 1-2 heteroatoms independently selected from nitrogen, oxygen, and sulfur.

In some embodiments, a ring is a bivalent or multivalent 4-membered saturated or partially unsaturated heterocyclic ring having 1-2 heteroatoms independently selected from nitrogen, oxygen, and sulfur. In some embodiments, a ring is a bivalent or multivalent 4-membered partially unsaturated heterocyclic ring having 2 heteroatoms independently selected from nitrogen, oxygen, and sulfur. In some embodiments, a ring is a bivalent or multivalent 4-membered partially unsaturated heterocyclic ring having no more than 1 heteroatom. In some embodiments, a ring is a bivalent or multivalent 4-membered partially unsaturated heterocyclic ring having no more than 1 heteroatom, wherein the heteroatom is nitrogen. In some embodiments, a ring is a bivalent or multivalent 4-membered partially unsaturated heterocyclic ring having no more than 1 heteroatom, wherein the heteroatom is oxygen. In some embodiments, a ring is a bivalent or multivalent 4-membered partially unsaturated heterocyclic ring having no more than 1 heteroatom, wherein the heteroatom is sulfur. In some embodiments, a ring is a bivalent or multivalent 4-membered partially unsaturated heterocyclic ring having 2 oxygen atoms. In some embodiments, a ring is a bivalent or multivalent 4-membered partially unsaturated heterocyclic ring having 2 nitrogen atoms. In some embodiments, a ring is a bivalent or multivalent 4-membered saturated or partially unsaturated heterocyclic ring having 1-2 heteroatoms independently selected from nitrogen, oxygen, and sulfur. In some embodiments, a ring is a bivalent or multivalent 4-membered partially unsaturated heterocyclic ring having 2 heteroatoms independently selected from nitrogen, oxygen, and sulfur. In some embodiments, a ring is a bivalent or multivalent 4-membered partially unsaturated heterocyclic ring having no more than 1 heteroatom. In some embodiments, a ring is a bivalent or multivalent 4-membered partially unsaturated heterocyclic ring having no more than 1 heteroatom, wherein the heteroatom is nitrogen. In some embodiments, a ring is a bivalent or multivalent 4-membered partially unsaturated heterocyclic ring having no more than 1 heteroatom, wherein the heteroatom is oxygen. In some embodiments, a ring is a bivalent or multivalent 4-membered partially unsaturated heterocyclic ring having no more than 1 heteroatom, wherein the heteroatom is sulfur. In some embodiments, a ring is a bivalent or multivalent 4-membered partially unsaturated heterocyclic ring having 2 oxygen atoms. In some embodiments, a ring is a bivalent or multivalent 4-membered partially unsaturated heterocyclic ring having 2 nitrogen atoms.

In some embodiments, a ring is a bivalent or multivalent 5-membered saturated or partially unsaturated heterocyclic ring having 1-2 heteroatoms independently selected from nitrogen, oxygen, and sulfur. In some embodiments, a ring is a bivalent or multivalent 5-membered partially unsaturated heterocyclic ring having 2 heteroatoms independently selected from nitrogen, oxygen, and sulfur. In some embodiments, a ring is a bivalent or multivalent 5-membered partially unsaturated heterocyclic ring having no more than 1 heteroatom. In some embodiments, a ring is a bivalent or multivalent 5-membered partially unsaturated heterocyclic ring having no more than 1 heteroatom, wherein the heteroatom is nitrogen. In some embodiments, a ring is a bivalent or multivalent 5-membered partially unsaturated heterocyclic ring having no more than 1 heteroatom, wherein the heteroatom is oxygen. In some embodiments, a ring is a bivalent or multivalent 5-membered partially unsaturated heterocyclic ring having no more than 1 heteroatom, wherein the heteroatom is sulfur. In some embodiments, a ring is a bivalent or multivalent 5-membered partially unsaturated heterocyclic ring having 2 oxygen atoms. In some embodiments, a ring is a bivalent or multivalent 5-membered partially unsaturated heterocyclic ring having 2 nitrogen atoms.

In some embodiments, a ring is a bivalent or multivalent 6-membered saturated or partially unsaturated heterocyclic ring having 1-2 heteroatoms independently selected from nitrogen, oxygen, and sulfur. In some embodiments, a ring is a bivalent or multivalent 6-membered partially unsaturated heterocyclic ring having 2 heteroatoms independently selected from nitrogen, oxygen, and sulfur. In some embodiments, a ring is a bivalent or multivalent 6-membered partially unsaturated heterocyclic ring having no more than 1 heteroatom. In some embodiments, a ring is a bivalent or multivalent 6-membered partially unsaturated heterocyclic ring having no more than 1 heteroatom, wherein the heteroatom is nitrogen. In some embodiments, a ring is a bivalent or multivalent 6-membered partially unsaturated heterocyclic ring having no more than 1 heteroatom, wherein the heteroatom is oxygen. In some embodiments, a ring is a bivalent or multivalent 6-membered partially unsaturated heterocyclic ring having no more than 1 heteroatom, wherein the heteroatom is sulfur. In some embodiments, a ring is a bivalent or multivalent 6-membered partially unsaturated heterocyclic ring having 2 oxygen atoms. In some embodiments, a ring is a bivalent or multivalent 6-membered partially unsaturated heterocyclic ring having 2 nitrogen atoms.

In certain embodiments, a ring is a bivalent or multivalent a 3-7 membered saturated or partially unsaturated heterocyclic ring having 1-2 heteroatoms independently selected from nitrogen, oxygen, and sulfur. In certain embodiments, a ring is a bivalent or multivalent oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl ring.

In certain embodiments, a ring is a bivalent or multivalent 5-6 membered partially unsaturated monocyclic ring having 1-2 heteroatoms independently selected from nitrogen, oxygen, and sulfur. In certain embodiments, a ring is a bivalent or multivalent tetrahydropyridinyl, dihydrothiazolyl, dihydrooxazolyl, or oxazolinyl group.

In some embodiments, a ring is a bivalent or multivalent 7-10 membered bicyclic saturated or partially unsaturated heterocyclic ring having 1-5 heteroatoms independently selected from nitrogen, oxygen, and sulfur. In some embodiments, a ring is a bivalent or multivalent indolinyl ring. In some embodiments, a ring is a bivalent or multivalent isoindolinyl ring. In some embodiments, a ring is a bivalent or multivalent 1, 2, 3, 4-tetrahydroquinolinyl ring. In some embodiments, a ring is a bivalent or multivalent 1, 2, 3, 4-tetrahydroisoquinolinyl ring. In some embodiments, a ring is a bivalent or multivalent azabicyclo[3.2.1]octanyl ring.

In some embodiments, a ring is a bivalent or multivalent 8-10 membered bicyclic heteroaryl ring having 1-5 heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In some embodiments, a ring is a bivalent or multivalent 5,6-fused heteroaryl ring having 1-3 heteroatoms independently selected from nitrogen, oxygen, and sulfur. In some embodiments, a ring is a bivalent or multivalent 5,6-fused heteroaryl ring having two heteroatoms independently selected from nitrogen, oxygen, and sulfur. In some embodiments, a ring is a bivalent or multivalent 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl ring. In some embodiments, a ring is a bivalent or multivalent 5,6-fused heteroaryl ring having three heteroatoms independently selected from nitrogen, oxygen, and sulfur. In some embodiments, a ring is a bivalent or multivalent dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl ring. In some embodiments, a ring is a bivalent or multivalent 5,6-fused heteroaryl ring having four heteroatoms independently selected from nitrogen, oxygen, and sulfur. In some embodiments, a ring is a bivalent or multivalent 5,6-fused heteroaryl ring having five heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In other embodiments, a ring is a bivalent or multivalent 5,6-fused heteroaryl ring having 1-2 heteroatoms independently selected from nitrogen, oxygen, and sulfur. In certain embodiments, a ring is a bivalent or multivalent 5,6-fused heteroaryl ring having one heteroatom independently selected from nitrogen, oxygen, and sulfur. In some embodiments, a ring is a bivalent or multivalent indolyl ring. In some embodiments, a ring is a bivalent or multivalent benzofuranyl ring. In some embodiments, a ring is a bivalent or multivalent benzo[b]thienyl ring. In certain embodiments, a ring is a bivalent or multivalent 5,6-fused heteroaryl ring having two heteroatoms independently selected from nitrogen, oxygen, and sulfur. In some embodiments, a ring is a bivalent or multivalent azaindolyl ring. In some embodiments, a ring is a bivalent or multivalent benzimidazolyl ring. In some embodiments, a ring is a bivalent or multivalent benzothiazolyl ring. In some embodiments, a ring is a bivalent or multivalent benzoxazolyl ring. In some embodiments, a ring is a bivalent or multivalent indazolyl ring. In certain embodiments, a ring is a bivalent or multivalent 5,6-fused heteroaryl ring having three heteroatoms independently selected from nitrogen, oxygen, and sulfur. In some embodiments, a ring is a bivalent or multivalent oxazolopyridiyl, thiazolopyridinyl or imidazopyridinyl ring. In certain embodiments, a ring is a bivalent or multivalent 5,6-fused heteroaryl ring having four heteroatoms independently selected from nitrogen, oxygen, and sulfur. In some embodiments, a ring is a bivalent or multivalent purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl ring. In certain embodiments, a ring is a bivalent or multivalent 5,6-fused heteroaryl ring having five heteroatoms independently selected from nitrogen, oxygen, and sulfur.

In certain embodiments, a ring is a bivalent or multivalent 6,6-fused heteroaryl ring having 1-5 heteroatoms independently selected from nitrogen, oxygen, and sulfur. In some embodiments, a ring is a bivalent or multivalent 6,6-fused heteroaryl ring having 1-2 heteroatoms independently selected from nitrogen, oxygen, and sulfur. In other embodiments, a ring is a bivalent or multivalent 6,6-fused heteroaryl ring having one heteroatom selected from nitrogen, oxygen, and sulfur. In some embodiments, a ring is a bivalent or multivalent quinolinyl ring. In some embodiments, a ring is a bivalent or multivalent isoquinolinyl ring. In some embodiments, a ring is a bivalent or multivalent 6,6-fused heteroaryl ring having two heteroatoms independently selected from nitrogen, oxygen, and sulfur. In some embodiments, a ring is a bivalent or multivalent quinazolinyl, phthalazinyl, quinoxalinyl or naphthyridinyl ring. In some embodiments, a ring is a bivalent or multivalent 6,6-fused heteroaryl ring having three heteroatoms independently selected from nitrogen, oxygen, and sulfur. In some embodiments, a ring is a bivalent or multivalent pyridopyrimidinyl, pyridopyridazinyl, pyridopyrazinyl, or benzotriazinyl ring. In some embodiments, a ring is a bivalent or multivalent 6,6-fused heteroaryl ring having four heteroatoms independently selected from nitrogen, oxygen, and sulfur. In some embodiments, a ring is a bivalent or multivalent pyridotriazinyl, pteridinyl, pyrazinopyrazinyl, pyrazinopyridazinyl, pyridazinopyridazinyl, pyrimidopyridazinyl or pyrimidopyrimidinyl ring. In some embodiments, a ring is a bivalent or multivalent 6,6-fused heteroaryl ring having five heteroatoms independently selected from nitrogen, oxygen, and sulfur.

In some embodiments, a ring formed by two or more groups taken together, which is typically optionally substituted, is a monocyclic saturated 5-7 membered ring having no additional heteroatoms in addition to intervening heteroatoms, if any. In some embodiments, a ring formed by two or more groups taken together is a monocyclic saturated 5-membered ring having no additional heteroatoms in addition to intervening heteroatoms, if any. In some embodiments, a ring formed by two or more groups taken together is a monocyclic saturated 6-membered ring having no additional heteroatoms in addition to intervening heteroatoms, if any. In some embodiments, a ring formed by two or more groups taken together is a monocyclic saturated 7-membered ring having no additional heteroatoms in addition to intervening heteroatoms, if any.

In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, and sulfur. In some embodiments, a ring formed by two or more groups taken together is a bicyclic and saturated 8-10 membered bicyclic ring having no additional heteroatoms in addition to intervening heteroatoms, if any. In some embodiments, a ring formed by two or more groups taken together is a bicyclic and saturated 8-membered bicyclic ring having no additional heteroatoms in addition to intervening heteroatoms, if any. In some embodiments, a ring formed by two or more groups taken together is a bicyclic and saturated 9-membered bicyclic ring having no additional heteroatoms in addition to intervening heteroatoms, if any. In some embodiments, a ring formed by two or more groups taken together is a bicyclic and saturated 10-membered bicyclic ring having no additional heteroatoms in addition to intervening heteroatoms, if any. In some embodiments, a ring formed by two or more groups taken together is bicyclic and comprises a 5-membered ring fused to a 5-membered ring. In some embodiments, a ring formed by two or more groups taken together is bicyclic and comprises a 5-membered ring fused to a 6-membered ring. In some embodiments, the 5-membered ring comprises one or more intervening nitrogen, phosphorus and oxygen atoms as ring atoms. In some embodiments, a ring formed by two or more groups taken together comprises a ring system having the backbone structure of

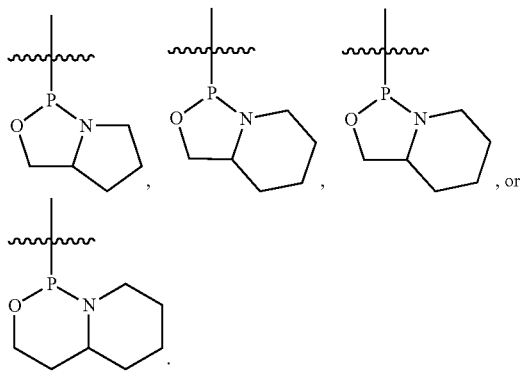

In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, and sulfur.

In some embodiments, a ring formed by two or more groups taken together is monocyclic, bicyclic or polycyclic and comprises a 5-10 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-9 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-8 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-7 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-6 membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 6-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 7-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 8-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 9-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 10-membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 6-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 7-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 8-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 9-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 10-membered ring whose ring atoms consist of carbon atoms and the intervening nitrogen, phosphorus and oxygen atoms.

In some embodiments, a ring formed by two or more groups taken together comprises a ring system having the backbone structure of

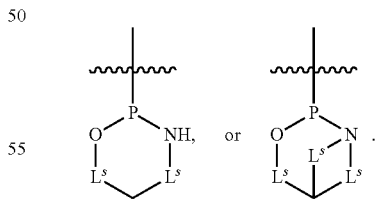

In some embodiments, rings described herein are unsubstituted. In some embodiments, rings described herein are substituted. In some embodiments, substituents are selected from those described in example compounds provided in the present disclosure.

In some embodiments, the present disclosure provides methods for preparing a compound, comprising providing a compound having a structure of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or a salt thereof. In some embodiments, the present disclosure provides methods for preparing a compound, comprising providing a compound having a structure of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, V, V-a, V-b, V-c-1, V-c-2, V-d, V-e, VI, VI-a, VI-b, VI-c, VI-c-1, VI-c-2, VI-d, or VI-e, or a salt thereof. In some embodiments, the present disclosure provides methods for stereoselective preparation of a compound, comprising providing a compound having a structure of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or a salt thereof. In some embodiments, the present disclosure provides methods for stereoselective preparation of a compound, comprising providing a compound having a structure of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, V, V-a, V-b, V-c-1, V-c-2, V-d, V-e, VI, VI-a, VI-b, VI-c, VI-c-1, VI-c-2, VI-d, or VI-e, or a salt thereof. In some embodiments, a method is for preparation of a compound comprising one or more moieties each independently having the structure of formula VII, VII-a-1, VII-a-2, VII-b, VII-c, VII-d, or VII-e, or a salt form thereof. In some embodiments, a method is for preparation of an oligonucleotide comprising one or more moieties each independently having the structure of formula VII, VII-a-1, VII-a-2, VII-b, VII-c, VII-d, or VII-e, or a salt form thereof. In some embodiments, a method is for preparing a compound of formula VIII or a salt thereof. In some embodiments, a method is for preparing an oligonucleotide of formula VIII or a salt thereof. In some embodiments, provided methods are stereoselective, e.g., diastereoselective or enantioselective. In some embodiments, formation of structures, e.g., those of formula VII, VII-a-1, VII-a-2, VII-b, VII-c, VII-d, or VII-e, or a salt form thereof, can be controlled and the present disclosure provides chirally controlled compositions of compounds. In some embodiments, the present disclosure provides chirally controlled oligonucleotide composition and preparation methods therefor. In some embodiments, pluralities of oligonucleotides in provided chirally controlled oligonucleotide compositions have the structure of formula VIII or a salt thereof.

In some embodiments, provided compounds, e.g., phosphoramidites of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or salts thereof, can be utilized for preparing chirally controlled oligonucleotide compositions, such as those described in WO/2010/064146, WO/2011/005761, WO/2013/012758, WO/2014/010250, US2013/0178612, WO/2014/012081, WO/2015/107425, WO/2017/015555, and WO/2017/062862, the compositions of each of which are incorporated herein by reference. In some embodiments, provided compounds, e.g., compounds having structures of formula I, I-a, I-a-1, I-a-2, I-b, I-c, I-d, I-e, II, II-a, II-b, III, III-a, III-b, IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or salts thereof, can be utilized in oligonucleotide synthetic schemes and/or cycles described in WO/2010/064146, WO/2011/005761, WO/2013/012758, WO/2014/010250, US2013/0178612, WO/2014/012081, WO/2015/107425, WO/2017/015555, and WO/2017/062862, the schemes and cycles of each of which are incorporated herein by reference, in accordance with the present disclosure.

In some embodiments, when used in oligonucleotide synthesis, provided technologies, (e.g., compounds, methods, etc.) can deliver diastereoselectivity greater than about 80%, 90%, 91%, 92%, 93%, 94%, 95%, 96%, 97%, 98% or 99% at the newly formed P-chiral center (delivering greater than about 50%, 60%, 70%, 80%, 90%, 91%, 92%, 93%, 94%, 95%, 96%, 97%, 98% or 99% diastereopurity), optionally with greater than about 80%, 90%, 91%, 92%, 93%, 94%, 95%, 96%, 97%, 98% or 99% yield. In some embodiments, diastereoselectivity at, and/or diastereopurity of, chiral linkage phosphorus of a chiral internucleotidic linkage in an oligonucleotide may be measured or represented through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage. For example, diastereopurity of the underlined linkage in NNNNNNNG*SGNNNNNNN can be assessed from coupling two G moieties under the same or comparable conditions, e.g., monomers, chiral auxiliaries, solvents, activators, temperatures, etc. In some embodiments, diastereopurity (and/or diastereoselectivity) of the linkage of a dimer (G*SG) is used as diastereopurity (and/or diastereoselectivity) of a corresponding linkage in an oligonucleotide (NNNNNNNG*SGNNNNNNN). In some embodiments, diastereopurity of a compound comprising multiple chiral elements is product of diastereomeric purity of all its chiral elements. In some embodiments, diastereopurity (i.e., diastereomeric purity) of a provided oligonucleotide is product of diastereomeric purity of all its chiral linkage phosphorus in its chiral internucleotidic linkages.

In some embodiments, provided technologies (reagents, methods, etc.) provide chirally controlled oligonucleotide compositions of the oligonucleotides which comprise one or more chiral internucleotidic linkages, wherein at least one chiral internucleotidic linkage is a chirally controlled internucleotidic linkage and has diastereomeric purity of at least 80%, 85%, 86%, 87%, 88%, 89%, 90%, 91%, 92%, 93%, 94%, 95%, 96%, 97%, 98%, 99% within the composition.

In some embodiments, the chiral linkage phosphorus of each chirally controlled internucleotidic linkage, as a chiral element, independently has a diastereomeric purity as described in the present disclosure.

In some embodiments, a diastereomeric purity of a chiral element (e.g., a chiral center, such as a carbon chiral center, a phosphorus chiral center (e.g., a chiral linkage phosphorus in a chirally controlled internucleotidic linkage), etc.) is 80%-100%. In some embodiments, a diastereomeric purity is at least 80%. In some embodiments, a diastereomeric purity is at least 81%. In some embodiments, a diastereomeric purity is at least 82%. In some embodiments, a diastereomeric purity is at least 83%. In some embodiments, a diastereomeric purity is at least 84%. In some embodiments, a diastereomeric purity is at least 85%. In some embodiments, a diastereomeric purity is at least 86%. In some embodiments, a diastereomeric purity is at least 87%. In some embodiments, a diastereomeric purity is at least 88%. In some embodiments, a diastereomeric purity is at least 89%. In some embodiments, a diastereomeric purity is at least 90%. In some embodiments, a diastereomeric purity is at least 91%. In some embodiments, a diastereomeric purity is at least 92%. In some embodiments, a diastereomeric purity is at least 93%. In some embodiments, a diastereomeric purity is at least 94%. In some embodiments, a diastereomeric purity is at least 95%. In some embodiments, a diastereomeric purity is at least 96%. In some embodiments, a diastereomeric purity is at least 97%. In some embodiments, a diastereomeric purity is at least 98%. In some embodiments, a diastereomeric purity is at least 99%. In some embodiments, a diastereomeric purity is at least 99.5%.

In some embodiments, provided oligonucleotides comprise 1-30 non-natural internucleotidic linkages (not —O—P(O)(OH)—O— or salt forms thereof). In some embodiments, provided oligonucleotides comprise 2-30 non-natural internucleotidic linkages. In some embodiments, provided oligonucleotides comprise 5-30 non-natural internucleotidic linkages. In some embodiments, provided oligonucleotides comprise 10-30 non-natural internucleotidic linkages. In some embodiments, provided oligonucleotides comprise 1 chirally controlled internucleotidic linkage. In some embodiments, provided oligonucleotides comprise 2 non-natural internucleotidic linkages. In some embodiments, provided oligonucleotides comprise 3 non-natural internucleotidic linkages. In some embodiments, provided oligonucleotides comprise 4 non-natural internucleotidic linkages. In some embodiments, provided oligonucleotides comprise 5 non-natural internucleotidic linkages. In some embodiments, provided oligonucleotides comprise 6 non-natural internucleotidic linkages. In some embodiments, provided oligonucleotides comprise 7 non-natural internucleotidic linkages. In some embodiments, provided oligonucleotides comprise 8 non-natural internucleotidic linkages. In some embodiments, provided oligonucleotides comprise 9 non-natural internucleotidic linkages. In some embodiments, provided oligonucleotides comprise 10 non-natural internucleotidic linkages. In some embodiments, provided oligonucleotides comprise 11 non-natural internucleotidic linkages. In some embodiments, provided oligonucleotides comprise 12 non-natural internucleotidic linkages. In some embodiments, provided oligonucleotides comprise 13 non-natural internucleotidic linkages. In some embodiments, provided oligonucleotides comprise 14 non-natural internucleotidic linkages. In some embodiments, provided oligonucleotides comprise 15 non-natural internucleotidic linkages. In some embodiments, provided oligonucleotides have 16 non-natural internucleotidic linkages. In some embodiments, provided oligonucleotides have 17 non-natural internucleotidic linkages. In some embodiments, provided oligonucleotides have 18 non-natural internucleotidic linkages. In some embodiments, provided oligonucleotides have 19 non-natural internucleotidic linkages. In some embodiments, provided oligonucleotides have 20 non-natural internucleotidic linkages. In some embodiments, about 1-100% of all internucleotidic linkages are non-natural internucleotidic linkages. In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, each non-natural internucleotidic linkage independently has the structure of formula VII, VII-a-1, VII-a-2, VII-b, VII-c, VII-d, or VII-e, or a salt form thereof, wherein the structure of formula VII, VII-a-1, VII-a-2, VII-b, VII-c, VII-d, or VII-e, or a salt form thereof, is not a natural phosphate linkage (not —O—P(O)(OH)—O— or a salt form thereof). In some embodiments, a portion of or all of non-natural internucleotidic linkages in provided oligonucleotides or one or more segments thereof (e.g., 5'-wing regions, core wings, 3'-wing regions) are consecutive. In some embodiments, all non-natural internucleotidic linkages in provided oligonucleotides or one or more segments thereof (e.g., 5'-wing regions, core wings, 3'-wing regions) are consecutive.

In some embodiments, provided oligonucleotides comprise 1-30 chiral internucleotidic linkages. In some embodiments, provided oligonucleotides comprise 2-30 chiral internucleotidic linkages. In some embodiments, provided oligonucleotides comprise 5-30 chiral internucleotidic linkages. In some embodiments, provided oligonucleotides comprise 10-30 chiral internucleotidic linkages. In some embodiments, provided oligonucleotides comprise 1 chirally controlled internucleotidic linkage. In some embodiments, provided oligonucleotides comprise 2 chiral internucleotidic linkages. In some embodiments, provided oligonucleotides comprise 3 chiral internucleotidic linkages. In some embodiments, provided oligonucleotides comprise 4 chiral internucleotidic linkages. In some embodiments, provided oligonucleotides comprise 5 chiral internucleotidic linkages. In some embodiments, provided oligonucleotides comprise 6 chiral internucleotidic linkages. In some embodiments, provided oligonucleotides comprise 7 chiral internucleotidic linkages. In some embodiments, provided oligonucleotides comprise 8 chiral internucleotidic linkages. In some embodiments, provided oligonucleotides comprise 9 chiral internucleotidic linkages. In some embodiments, provided oligonucleotides comprise 10 chiral internucleotidic linkages. In some embodiments, provided oligonucleotides comprise 11 chiral internucleotidic linkages. In some embodiments, provided oligonucleotides comprise 12 chiral internucleotidic linkages. In some embodiments, provided oligonucleotides comprise 13 chiral internucleotidic linkages. In some embodiments, provided oligonucleotides comprise 14 chiral internucleotidic linkages. In some embodiments, provided oligonucleotides have 15 chiral internucleotidic linkages. In some embodiments, provided oligonucleotides have 16 chiral internucleotidic linkages. In some embodiments, provided oligonucleotides have 17 chiral internucleotidic linkages. In some embodiments, provided oligonucleotides have 18 chiral internucleotidic linkages. In some embodiments, provided oligonucleotides have 19 chiral internucleotidic linkages. In some embodiments, provided oligonucleotides have 20 chiral internucleotidic linkages. In some embodiments, about 1-100% of all internucleotidic linkages are chiral internucleotidic linkages. In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, each chiral internucleotidic linkage independently has the structure of formula VII, VII-a-1, VII-a-2, VII-b, VII-c, VII-d, or VII-e, or a salt form thereof, wherein the structure of formula VII, VII-a-1, VII-a-2, VII-b, VII-c, VII-d, or VII-e, or a salt form thereof, is not a natural phosphate linkage (not —O—P(O)(OH)—O— or a salt form thereof). In some embodiments, a portion of or all of chiral internucleotidic linkages in provided oligonucleotides or one or more segments thereof (e.g., 5'-wing regions, core wings, 3'-wing regions) are consecutive. In some embodiments, all chiral internucleotidic linkages in provided oligonucleotides or one or more segments thereof (e.g., 5'-wing regions, core wings, 3'-wing regions) are consecutive.

In some embodiments, provided oligonucleotides comprise 1-30 chirally controlled internucleotidic linkages. In some embodiments, provided oligonucleotides comprise 2-30 chirally controlled internucleotidic linkages. In some embodiments, provided oligonucleotides comprise 5-30 chirally controlled internucleotidic linkages. In some embodiments, provided oligonucleotides comprise 10-30 chirally controlled internucleotidic linkages. In some embodiments, provided oligonucleotides comprise 1 chirally controlled internucleotidic linkage. In some embodiments, provided oligonucleotides comprise 2 chirally controlled internucleotidic linkages. In some embodiments, provided oligonucleotides comprise 3 chirally controlled internucleotidic linkages. In some embodiments, provided oligonucleotides comprise 4 chirally controlled internucleotidic linkages. In some embodiments, provided oligonucleotides comprise 5 chirally controlled internucleotidic linkages. In some embodiments, provided oligonucleotides comprise 6 chirally controlled internucleotidic linkages. In some embodiments, provided oligonucleotides comprise 7 chirally controlled internucleotidic linkages. In some embodiments, provided oligonucleotides comprise 8 chirally controlled internucleotidic linkages. In some embodiments, provided oligonucleotides comprise 9 chirally controlled internucleotidic linkages. In some embodiments, provided oligonucleotides comprise 10 chirally controlled internucleotidic linkages. In some embodiments, provided oligonucleotides comprise 11 chirally controlled internucleotidic linkages. In some embodiments, provided oligonucleotides comprise 12 chirally controlled internucleotidic linkages. In some embodiments, provided oligonucleotides comprise 13 chirally controlled internucleotidic linkages. In some embodiments, provided oligonucleotides comprise 14 chirally controlled internucleotidic linkages. In some embodiments, provided oligonucleotides have 15 chirally controlled internucleotidic linkages. In some embodiments, provided oligonucleotides have 16 chirally controlled internucleotidic linkages. In some embodiments, provided oligonucleotides have 17 chirally controlled internucleotidic linkages. In some embodiments, provided oligonucleotides have 18 chirally controlled internucleotidic linkages. In some embodiments, provided oligonucleotides have 19 chirally controlled internucleotidic linkages. In some embodiments, provided oligonucleotides have 20 chirally controlled internucleotidic linkages. In some embodiments, about 1-100% of all internucleotidic linkages are chirally controlled internucleotidic linkages. In some embodiments, about 1-100% of all chiral internucleotidic linkages (comprising chiral linkage phosphorus) are chirally controlled internucleotidic linkages. In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, each chiral internucleotidic linkage is chirally controlled. In some embodiments, a portion of or all of chirally controlled internucleotidic linkages in provided oligonucleotides or one or more segments thereof (e.g., 5'-wing regions, core wings, 3'-wing regions) are consecutive. In some embodiments, all chirally controlled internucleotidic linkages in provided oligonucleotides or one or more segments thereof (e.g., 5'-wing regions, core wings, 3'-wing regions) are consecutive.

In some embodiments, provided oligonucleotides comprise 1-30 natural phosphate linkages (not —O—P(O)(OH)—O— or salt forms thereof). In some embodiments, provided oligonucleotides, in addition to natural phosphate linkages, or chiral internucleotidic linkages, or chirally controlled internucleotidic linkages as described herein, further comprise 1-30 natural phosphate linkages (not —O—P(O)(OH)—O— or salt forms thereof). In some embodiments, provided oligonucleotides comprise 2-30 natural phosphate linkages. In some embodiments, provided oligonucleotides comprise 5-30 natural phosphate linkages. In some embodiments, provided oligonucleotides comprise 10-30 natural phosphate linkages. In some embodiments, provided oligonucleotides comprise 1 chirally controlled internucleotidic linkage. In some embodiments, provided oligonucleotides comprise 2 natural phosphate linkages. In some embodiments, provided oligonucleotides comprise 3 natural phosphate linkages. In some embodiments, provided oligonucleotides comprise 4 natural phosphate linkages. In some embodiments, provided oligonucleotides comprise 5 natural phosphate linkages. In some embodiments, provided oligonucleotides comprise 6 natural phosphate linkages. In some embodiments, provided oligonucleotides comprise 7 natural phosphate linkages. In some embodiments, provided oligonucleotides comprise 8 natural phosphate linkages. In some embodiments, provided oligonucleotides comprise 9 natural phosphate linkages. In some embodiments, provided oligonucleotides comprise 10 natural phosphate linkages. In some embodiments, provided oligonucleotides comprise 11 natural phosphate linkages. In some embodiments, provided oligonucleotides comprise 12 natural phosphate linkages. In some embodiments, provided oligonucleotides comprise 13 natural phosphate linkages. In some embodiments, provided oligonucleotides comprise 14 natural phosphate linkages. In some embodiments, provided oligonucleotides have 15 natural phosphate linkages. In some embodiments, provided oligonucleotides have 16 natural phosphate linkages. In some embodiments, provided oligonucleotides have 17 natural phosphate linkages. In some embodiments, provided oligonucleotides have 18 natural phosphate linkages. In some embodiments, provided oligonucleotides have 19 natural phosphate linkages. In some embodiments, provided oligonucleotides have 20 natural phosphate linkages. In some embodiments, about 1-100% of all internucleotidic linkages are natural phosphate linkages. In some embodiments, about 1-99% of all internucleotidic linkages are natural phosphate linkages, and about 1-99% of all internucleotidic linkages are non-natural internucleotidic linkages (e.g., internucleotidic linkages of formula VII, VII-a-1, VII-a-2, VII-b, VII-c, VII-d, or VII-e, or a salt form thereof and are non-natural internucleotidic linkages). In some embodiments, about 1-99% of all internucleotidic linkages are natural phosphate linkages, and about 1-99% of all internucleotidic linkages are chiral internucleotidic linkages (e.g., internucleotidic linkages of formula VII, VII-a-1, VII-a-2, VII-b, VII-c, VII-d, or VII-e, or a salt form thereof and are chiral). In some embodiments, about 1-99% of all internucleotidic linkages are natural phosphate linkages, and about 1-99% of all internucleotidic linkages are chirally controlled oligonucleotide composition internucleotidic linkages (e.g., internucleotidic linkages of formula VII, VII-a-1, VII-a-2, VII-b, VII-c, VII-d, or VII-e, or a salt form thereof and are chirally controlled). In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, each non-natural internucleotidic linkage independently has the structure of formula VII, VII-a-1, VII-a-2, VII-b, VII-c, VII-d, or VII-e, or a salt form thereof, wherein the structure of formula VII, VII-a-1, VII-a-2, VII-b, VII-c, VII-d, or VII-e, or a salt form thereof, is a non-natural internucleotidic linkage (not —O—P(O)(OH)—O— or a salt form thereof). In some embodiments, each chiral linkage independently has the structure of formula VII, VII-a-1, VII-a-2, VII-b, VII-c, VII-d, or VII-e, or a salt form thereof, wherein the structure of formula VII, VII-a-1, VII-a-2, VII-b, VII-c, VII-d, or VII-e, or a salt form thereof, is not a natural phosphate linkage (not —O—P(O)(OH)—O— or a salt form thereof). In some embodiments, each chirally controlled phosphate linkage independently has the structure of formula VII, VII-a-1, VII-a-2, VII-b, VII-c, VII-d, or VII-e, or a salt form thereof, wherein the structure of formula VII, VII-a-1, VII-a-2, VII-b, VII-c, VII-d, or VII-e, or a salt form thereof, is not a natural phosphate linkage (not —O—P(O)(OH)—O— or a salt form thereof). In some embodiments, a portion of or all of natural phosphate linkages in provided oligonucleotides or one or more segments thereof (e.g., 5'-wing regions, core wings, 3'-wing regions) are consecutive. In some embodiments, all natural phosphate linkages in provided oligonucleotides or one or more segments thereof (e.g., 5'-wing regions, core wings, 3'-wing regions) are consecutive.

In some embodiments, a non-natural internucleotidic linkage is a phosphorothioate linkage or a salt form thereof (—O—P(O)(SH)—O— or a salt form thereof). In some embodiments, a chiral internucleotidic linkage is a phosphorothioate linkage or a salt form thereof (—O—P(O)(SH)—O— or a salt form thereof). In some embodiments, a chirally controlled internucleotidic linkage is a phosphorothioate linkage or a salt form thereof (—O—P(O)(SH)—O— or a salt form thereof).

In some embodiments, provided oligonucleotides comprise 5-200, 5-150, 5-100, 5-50, 5-40, 5-35, 5-30, 5-25, 10-200, 10-150, 10-100, 10-50, 10-40, 10-35, 10-30, 10-25, 15-200, 15-150, 15-100, 15-50, 15-40, 15-35, 15-30, or 15-25 nucleobases. In some embodiments, provided oligonucleotides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 15, 16, 17, 18, 19, 20, 21, 22, 23, 24, 25, 26, 27, 28, 29, 30, 35, 40, 45, or 50 nucleobases. In some embodiments, provided oligonucleotides comprise at least 15 nucleobases. In some embodiments, provided oligonucleotides comprise at least 16 nucleobases. In some embodiments, provided oligonucleotides comprise at least 17 nucleobases. In some embodiments, provided oligonucleotides comprise at least 18 nucleobases. In some embodiments, provided oligonucleotides comprise at least 19 nucleobases. In some embodiments, provided oligonucleotides comprise at least 20 nucleobases. In some embodiments, provided oligonucleotides comprise at least 21 nucleobases. In some embodiments, provided oligonucleotides comprise at least 22 nucleobases. In some embodiments, provided oligonucleotides comprise at least 23 nucleobases. In some embodiments, provided oligonucleotides comprise at least 24 nucleobases. In some embodiments, provided oligonucleotides comprise at least 25 nucleobases. In some embodiments, a nucleobase is optionally substituted adenine, cytosine, guanosine, thymine, or uracil, or a tautomer thereof.

In some embodiments, provided methods comprise oligonucleotide synthesis using solid supports. In some embodiments, provided oligonucleotides are connected to solid supports. In some embodiments, provided oligonucleotides are cleaved from solid support. In some embodiments, provided oligonucleotides comprise at least two chemically different types of internucleotidic linkages. In some embodiments, provided oligonucleotides comprise at least two chemically different types of chiral internucleotidic linkages, each of which is independently Rp or Sp. In some embodiments, the chemically different types of chiral internucleotidic linkages are all Sp. In some embodiments, the chemically different types of chiral internucleotidic linkages are all Rp. In some embodiments, some of the chemically different types of chiral internucleotidic linkages are Rp while the others are Sp. In some embodiments, some of the chemically different types of chiral internucleotidic linkages are Rp, some are Sp, while the others are not chirally controlled.

In some embodiments, an internucleotidic linkage formed using provided technologies is one described in US/2015/0211006, US/2017/0037399, WO/2017/015555, and WO/2017/062862, each of which is incorporated herein by reference. In some embodiments, an internucleotidic linkage is a chiral internucleotidic linkage in that it comprises a chiral linkage phosphorus. In some embodiments, a linkage structure in a provided compound has the structure of formula VII, VII-a-1, VII-a-2, VII-b, VII-c, VII-d, or VII-e, or a salt form thereof. In some embodiments, an internucleotidic linkage in a provided compound has the structure of formula VII, VII-a-1, VII-a-2, VII-b, VII-c, VII-d, or VII-e, or a salt form thereof. In some embodiments, a chiral internucleotidic linkage in a provided compound has the structure of formula VII, VII-a-1, VII-a-2, VII-b, VII-c, VII-d, or VII-e, or a salt form thereof. In some embodiments, a chirally controlled internucleotidic linkage in a provided compound has the structure of formula VII, VII-a-1, VII-a-2, VII-b, VII-c, VII-d, or VII-e, or a salt form thereof.

In some embodiments, as described in the present disclosure, —X-$L^s$-$R^5$ is of such structure that H—X-$L^s$-$R^5$ has the structure of formula I, I-a, I-a-1, I-a-2, I-b, I-c, I-d, I-e, II, II-a, II-b, III, III-a, III-b, or a salt thereof.

In some embodiments, an internucleotidic linkage of formula VII, VII-a-1, VII-a-2, VII-b, VII-c, VII-d, or VII-e, or a salt form thereof, is a chiral internucleotidic linkage. In some embodiments, P in $P^L$ is a chiral linkage phosphorus. In some embodiments, a chiral linkage phosphorus is Rp. In some embodiments, a chiral linkage phosphorus is Sp. In some embodiments, $P^L$ is P(=W). In some embodiments, $P^L$ is P(=O). In some embodiments, $P^L$ is P(=S). In some embodiments, $P^L$ is P. In some embodiments, $P^L$ is P→B(R')$_3$.

In some embodiments, Y is —O— and Z is —O—, and X is —O— or —S—. In some embodiments, X and Y and Z are —O—. In some embodiments, X is —S—, and Y and Z are —O—.

In some embodiments, W is O. In some embodiments, W is O, and X and Y and Z are —O—. In some embodiments, W is O, X is —S—, and Y and Z are —O—. In some embodiments, W is S. In some embodiments, W is S, and X and Y and Z are —O—. In some embodiments, W is S, X is —S—, and Y and Z are —O—.

In some embodiments, Z is $L^s$, wherein a terminal methylene unit of $L^s$ which is bonded to $P^L$ is replaced with —O—, —S—, or —N(R')—. In some embodiments, Z is —O—C(R')$_2$—. In some embodiments, Z is —O—C(R')$_2$—, wherein —O— is bonded to $P^L$ and —C(R')$_2$— is bonded to a ring atom of Ring $A^s$. In some embodiments, Z is —S—C(R')$_2$—. In some embodiments, Z is —S—C(R')$_2$—, wherein —S— is bonded to $P^L$ and —C(R')$_2$— is bonded to a ring atom of Ring $A^s$. In some embodiments, Z is —N(R')—C(R')$_2$—. In some embodiments, Z is —N(R')—C(R')$_2$—, wherein —N(R')— is bonded to $P^L$ and —C(R')$_2$— is bonded to a ring atom Ring $A^s$. In some embodiments, Y is bonded to Ring $A^s$ and is —O—. In some embodiments, Y is bonded to Ring $A^s$ and is —S—. In some embodiments, Y is bonded to Ring $A^s$ and is —N(R')—. In some embodiments, a ring atom, e.g., of Ring $A^s$, that is bonded to Y or Z is a carbon atom.

In some embodiments, —X-$L^s$-$R^5$ is —OR. In some embodiments, —X-$L^s$-$R^5$ is —OH. In some embodiments, —X-$L^s$-$R^5$ is —OR, wherein R is not hydrogen. In some embodiments, W is O and —X-$L^s$-$R^5$ is —OR. In some embodiments, W is O and —X-$L^s$-$R^5$ is —OH. In some embodiments, W is O and —X-$L^s$-$R^5$ is —OR, wherein R is not hydrogen.

In some embodiments, —X-$L^s$-$R^5$ is —SR. In some embodiments, —X-$L^s$-$R^5$ is —SH. In some embodiments, —X-$L^s$-$R^5$ is —SR, wherein R is not hydrogen. In some embodiments, W is O and —X-$L^s$-$R^5$ is —SR. In some embodiments, W is O and —X-$L^s$-$R^5$ is —SH. In some embodiments, W is O and —X-$L^s$-$R^5$ is —SR, wherein R is not hydrogen.

In some embodiments, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof. In some embodiments, $R^7$ is —OH, and $R^6$ is —H or —R. In some embodiments, $R^6$ is —H. In some embodiments, $R^6$ is —R, wherein R is not hydrogen. In some embodiments, R is a capping group. Suitable capping groups for oligonucleotide synthesis are well known by a personal having ordinary skill in the art, for example, those described in US/2015/0211006, US/2017/0037399, WO/2017/015555, and WO/2017/062862, each of which is incorporated herein by reference. In some embodiments, $R^6$ is —C(O)R. As described in the present disclosure, in some embodiments, immediately after coupling, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof, wherein $R^6$ is —H in formula I, I-a, I-a-1, I-a-2, I-b, I-c, I-d, I-e, II, II-a, II-b, III, III-a, or III-b, and a linkage may have the structure of formula VII, VII-a-1, VII-a-2, VII-b, VII-c, VII-d, or VII-e, or a salt form thereof. In some embodiments, after capping, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof, wherein $R^6$ is a capping group, for example, a group having the structure of —C(O)R, and a linkage may have the structure of formula VII, VII-a-1, VII-a-2, VII-b, VII-c, VII-d, or VII-e, or a salt form thereof. In some embodiments, the nitrogen atom to which $R^5$ is attached is capped with a R—C(O)— group, forming a group of —N($R^5$)(—C(O)—R). In some embodiments, a capping group is —C(O)—CH$_3$. In some embodiments, a capping group is —C(O)—CF$_3$. In some embodiments, after additional chemical modification steps, a linkage may have the structure of formula VII, VII-a-1, VII-a-2, VII-b, VII-c, VII-d, or VII-e, or a salt form thereof.

In some embodiments, the present disclosure provides oligonucleotides comprising one or more internucleotidic linkages having the structure of formula VII, VII-a-1, VII-a-2, VII-b, VII-c, VII-d, or VII-e, or a salt form thereof as described in the present disclosure (e.g., in some embodiments, an internucleotidic linkage having the structure of formula VII, VII-a-1, VII-a-2, VII-b, VII-c, VII-d, or VII-e, or a salt form thereof, is a non-natural internucleotidic linkage; in some embodiments, an internucleotidic linkage having the structure of formula VII, VII-a-1, VII-a-2, VII-b, VII-c, VII-d, or VII-e, or a salt form thereof, is a chiral linkage; in some embodiments, an internucleotidic linkage having the structure of formula VII, VII-a-1, VII-a-2, VII-b, VII-c, VII-d, or VII-e, or a salt form thereof, is a chirally controlled internucleotidic linkage; in some embodiments, an internucleotidic linkage having the structure of formula VII, VII-a-1, VII-a-2, VII-b, VII-c, VII-d, or VII-e, or a salt form thereof, is a phosphorothioate linkage, etc.). In some embodiments, provided oligonucleotides comprise 1-100, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70 80, 90, 100 or more internucleotidic linkages having the structure of formula VII, VII-a-1, VII-a-2, VII-b, VII-c, VII-d, or VII-e, or a salt form thereof. In some embodiments, provided oligonucleotides comprise one or more such internucleotidic linkages. In some embodiments, provided oligonucleotides comprise two or more such internucleotidic linkages. In some embodiments, provided oligonucleotides comprise three or more such internucleotidic linkages. In some embodiments, provided oligonucleotides comprise four or more such internucleotidic linkages. In some embodiments, provided oligonucleotides comprise five or more such internucleotidic linkages. In some embodiments, provided oligonucleotides comprise six or more such internucleotidic linkages. In some embodiments, provided oligonucleotides comprise seven or more such internucleotidic linkages. In some embodiments, provided oligonucleotides comprise eight or more such internucleotidic linkages. In some embodiments, provided oligonucleotides comprise nine or more such internucleotidic linkages. In some embodiments, provided oligonucleotides comprise ten or more such internucleotidic linkages. In some embodiments, provided oligonucleotides comprise 11 or more such internucleotidic linkages. In some embodiments, provided oligonucleotides comprise 12 or more such internucleotidic linkages. In some embodiments, provided oligonucleotides comprise 13 or more such internucleotidic linkages. In some embodiments, provided oligonucleotides comprise 14 or more such internucleotidic linkages. In some embodiments, provided oligonucleotides comprise 15 or more such internucleotidic linkages. In some embodiments, provided oligonucleotides comprise 16 or more such internucleotidic linkages. In some embodiments, provided oligonucleotides comprise 17 or more such internucleotidic linkages. In some embodiments, provided oligonucleotides comprise 18 or more such internucleotidic linkages. In some embodiments, provided oligonucleotides comprise 19 or more such internucleotidic linkages. In some embodiments, provided oligonucleotides comprise 20 or more such internucleotidic linkages. In some embodiments, provided oligonucleotides comprise 21 or more such internucleotidic linkages. In some embodiments, provided oligonucleotides comprise 25 or more such internucleotidic linkages. In some embodiments, such an internucleotidic linkage is chiral. In some embodiments, as described in the present disclosure, each —X-L$^s$-R$^5$ is independently of such a structure that H—X-L$^s$-R$^5$ has the structure of formula I, I-a, I-a-1, I-a-2, I-b, I-c, I-d, I-e, II, II-a, II-b, III, III-a, or III-b, or a salt thereof. In some embodiments, provided oligonucleotides have the structure of formula X or a salt thereof.

In some embodiments, a provided oligonucleotide comprises at least two types of internucleotidic linkages, each independently having the structure of formula VII, VII-a-1, VII-a-2, VII-b, VII-c, VII-d, or VII-e, or a salt thereof. In some embodiments, a provided oligonucleotide comprise at least two types of chiral internucleotidic linkages, each independently having the structure of formula VII, VII-a-1, VII-a-2, VII-b, VII-c, VII-d, or VII-e, or a salt thereof. In some embodiments, the two types may have the same or different phosphorus configuration (Rp or Sp), or one or both can be stereorandom (e.g., formed not through chirally controlled synthesis). In some embodiments, a stereorandom linkage has diastereomeric purity less than 90%, 85%, 80%, 75%, 70%, 65%, 60%, or 55%. In some embodiments, P* is not stereorandom, and is either Rp or Sp. In some embodiments, in one type W is S and in the other type W is O. In some embodiments, in one type W is S and in the other type W is O, and for both types —X-L$^s$-R$^5$ is independently of such a structure that H—X-L$^s$-R$^5$ has the structure of formula I, I-a, I-a-1, I-a-2, I-b, I-c, I-d, I-e, II, II-a, II-b, III, III-a, or III-b, or a salt thereof. In some embodiments, one type is a natural phosphate linkage (—O—P(O)(OH)—O—, which may exist as —O—P(O)(O$^-$)—O—, for example, at certain pH and/or when provided as a salt), and the other is a phosphorothioate linkage (—O—P(O)(SH)—O—, which may exist as —O—P(O)(S$^-$)—O—, for example, at certain pH and/or when provided as a salt).

In some embodiments, the present disclosure provides compounds having the structure of formula X, or salts thereof. In some embodiments, the present disclosure provides oligonucleotides having the structure of formula X, or salts thereof.

In some embodiments, each L$^P$ is independently an internucleotidic linkage. In some embodiments, each L$^P$ independently has the structure of formula VII, VII-a-1, VII-a-2, VII-b, VII-c, VII-d, or VII-e, or a salt form thereof. In some embodiments, each L$^P$ independently has the structure of formula VII, VII-a-1, VII-a-2, VII-b, VII-c, VII-d, or VII-e, or a salt form thereof, wherein each —X-L$^s$-R$^5$ is independently of a structure that H—X-L$^s$-R$^5$ is a compound of formula I, I-a, I-a-1, I-a-2, I-b, I-c, I-d, I-e, II, II-a, II-b, III, III-a, or III-b, or a salt thereof. In some embodiments, each L$^P$ independently has the structure of formula VII, VII-a-1, or VII-a-2, or a salt form thereof, wherein each —X-L$^s$-R$^5$ is independently of a structure that H—X-L$^s$-R$^5$ is a compound of formula I, I-a, I-a-1, I-a-2, I-b, I-c, I-d, I-e, II, II-a, II-b, III, III-a, or III-b, or a salt thereof, and W is O or S. In some embodiments, each L$^P$ independently has the structure of formula VII, VII-a-1, or VII-a-2, or a salt form thereof, wherein each —X-L$^s$-R$^5$ is independently of a structure that H—X-L$^s$-R$^5$ is a compound of formula I, I-a, I-a-1, I-a-2, I-b, I-c, I-d, I-e, II, II-a, II-b, III, III-a, or III-b, or a salt thereof, and W is O or S, and X is O. In some embodiments, each L$^P$ independently has the structure of formula VII, VII-a-1, or VII-a-2, or a salt form thereof, wherein each —X-L$^s$-R$^5$ is independently of a structure that H—X-L$^s$-R$^5$ is a compound of formula I, I-a, I-a-1, I-a-2, I-b, I-c, I-d, I-e, II, II-a, II-b, III, III-a, or III-b, or a salt thereof, and W is O or S, and X and Y and Z are —O—. In some embodiments, L$^P$ has the structure of formula VII or a salt thereof. In some embodiments, L$^P$ has the structure of formula VII or a salt thereof, wherein W is O or S, and X and Y and Z are —O—. In some embodiments, L$^P$ has the structure of formula VII-a-1 or a salt thereof. In some embodiments, L$^P$ has the structure of formula VII-a-1 or a salt thereof, wherein W is O or S, and X and Y and Z are —O—. In some embodiments, L$^P$ has the structure of formula VII-a-2 or a salt thereof. In some embodiments, L$^P$ has the structure of formula VII-a-2 or a salt thereof, wherein W is O or S, and X and Y and Z are —O—. In some embodiments, L$^P$ has the structure of formula VII-b or a salt thereof. In some embodiments, L$^P$ has the structure of formula VII-b or a salt thereof, wherein X and Y and Z are —O—. In some embodiments, L$^P$ has the structure of formula VII-c or a salt thereof. In some embodiments, L$^P$ has the structure of formula VII-c or a salt thereof, wherein X and Y and Z are —O—. In some embodiments, L$^P$ has the structure of formula VII-d or a salt thereof. In some embodiments, L$^P$ has the structure of formula VII-d or a salt thereof, wherein X and Y and Z are —O—. In some embodiments, L$^P$ has the structure of formula VII-e or a salt thereof. In some embodiments, L$^P$ has the structure of formula VII-e or a salt thereof, wherein X and Y and Z are —O—. In some embodiments, L is natural phosphate linkage. In some embodiments, L is a phosphorothioate linkage or a salt form thereof. In some embodiments, each L is independently a natural phosphate linkage or a phosphorothioate linkage, or a salt thereof.

In some embodiments, at least one L$^P$ comprises W, wherein W is S. In some embodiments, about 1-20 L$^P$ comprises W, wherein W is S. In some embodiments, at least 2, 3, 4, 5, 6, 7, 8, 9, 10, 11, 12, 13, 14, 15, 16, 17, 18, 19, 20 L$^P$ comprises W, wherein W is S. In some embodiments, at least one L$^P$ comprises W, wherein W is O. In some embodiments, about 1-20 L$^P$ comprises W, wherein W is O. In some embodiments, at least 2, 3, 4, 5, 6, 7, 8, 9, 10, 11, 12, 13, 14, 15, 16, 17, 18, 19, 20 L$^P$ comprises W, wherein W is O.

In some embodiments, z is 1. In some embodiments, z is 2. In some embodiments, z is 3. In some embodiments, z is 4. In some embodiments, z is 5. In some embodiments, z is 6. In some embodiments, z is 7. In some embodiments, z is 8. In some embodiments, z is 9. In some embodiments, z is 10. In some embodiments, z is 11. In some embodiments, z is 12. In some embodiments, z is 13. In some embodiments, z is 14. In some embodiments, z is 15. In some embodiments, z is 16. In some embodiments, z is 17. In some embodiments, z is 18. In some embodiments, z is 19. In some embodiments, z is 20. In some embodiments, z is 21. In some embodiments, z is 22. In some embodiments, z is 23. In some embodiments, z is 24. In some embodiments, z is 25. In some embodiments, z is 26. In some embodiments, z is 27. In some embodiments, z is 28. In some embodiments, z is 29. In some embodiments, z is 30. In some embodiments, z is at least 2. In some embodiments, z is at least 3. In some embodiments, z is at least 4. In some embodiments, z is at least 5. In some embodiments, z is at least 6. In some embodiments, z is at least 7. In some embodiments, z is at least 8. In some embodiments, z is at least 9. In some embodiments, z is at least 10. In some embodiments, z is at least 11. In some embodiments, z is at least 12. In some embodiments, z is at least 13. In some embodiments, z is at least 14. In some embodiments, z is at least 15. In some embodiments, z is at least 16. In some embodiments, z is at least 17. In some embodiments, z is at least 18. In some embodiments, z is at least 19. In some embodiments, z is at least 20. In some embodiments, z is at least 21. In some embodiments, z is at least 22. In some embodiments, z is at least 23. In some embodiments, z is at least 24. In some embodiments, z is at least 25. In some embodiments, z is at least 26. In some embodiments, z is at least 27. In some embodiments, z is at least 28. In some embodiments, z is at least 29. In some embodiments, z is at least 30.

In some embodiments, $L^{3E}$ is -$L^s$- or -$L^s$-$L^s$-. In some embodiments, $L^{3E}$ is -$L^s$-. In some embodiments, $L^{3E}$ is -$L^s$-$L^s$-. In some embodiments, $L^{3E}$ is a covalent bond. In some embodiments, $L^{3E}$ is a linker used in oligonucleotide synthesis. In some embodiments, $L^{3E}$ is a linker used in solid phase oligonucleotide synthesis. Various types of linkers are known and can be utilized in accordance with the present disclosure. In some embodiments, a linker is a succinate linker (—O—C(O)—CH$_2$—CH$_2$—C(O)—). In some embodiments, a linker is an oxalyl linker (—O—C(O)—C(O)—). In some embodiments, $L^{3E}$ is a succinyl-piperidine linker (SP) linker. In some embodiments, $L^{3E}$ is a succinyl linker. In some embodiments, $L^{3E}$ is a Q-linker.

In some embodiments, $R^{3E}$ is —R', -$L^s$-R', —OR', or a solid support. In some embodiments, $R^{3E}$ is —R'. In some embodiments, $R^{3E}$ is -$L^s$-R'. In some embodiments, $R^{3E}$ is —OR'. In some embodiments, $R^{3E}$ is a solid support. In some embodiments, $R^{3E}$ is —H. In some embodiments, -$L^3$-$R^{3E}$ is —H. In some embodiments, $R^{3E}$ is —OH. In some embodiments, -$L^3$-$R^{3E}$ is —OH. In some embodiments, $R^{3E}$ is optionally substituted $C_{1-6}$ aliphatic. In some embodiments, $R^{3E}$ is optionally substituted $C_{1-6}$ alkyl. In some embodiments, $R^{3E}$ is —OR'. In some embodiments, $R^{3E}$ is —OH. In some embodiments, $R^{3E}$ is —OR', wherein R' is not hydrogen. In some embodiments, $R^{3E}$ is —OR', wherein R' is optionally substituted $C_{1-6}$ alkyl. In some embodiments, $R^{3E}$ is a 3'-end cap (e.g., those used in RNAi technologies).

In some embodiments, $R^{3E}$ is a solid support. In some embodiments, $R^{3E}$ is a solid support for oligonucleotide synthesis. Various types of solid support are known and can be utilized in accordance with the present disclosure. In some embodiments, a solid support is HCP. In some embodiments, a solid support is CPG.

In some embodiments, each chiral linkage phosphorus independently has a diastereomeric purity as described in the present disclosure. In some embodiments, a provided compound has a purity, diastereomeric purity, and/or enantiomeric purity as described in the present disclosure. In some embodiments, a provided compound has a purity as described in the present disclosure. In some embodiments, a provided compound has a diastereomeric purity as described in the present disclosure. In some embodiments, a provided compound has an enantiomeric purity as described in the present disclosure. In some embodiments, a provided compound has a diastereomeric purity and an enantiomeric purity as described in the present disclosure.

In some embodiments, the present disclosure provides oligonucleotides comprising one or more internucleotidic linkages of formula VII, VII-a-1, VII-a-2, VII-b, VII-c, VII-d, or VII-e, or a salt form thereof (e.g., oligonucleotides of formula VIII or salts thereof, wherein one or more $L^P$ is of formula VII, VII-a-1, VII-a-2, VII-b, VII-c, VII-d, or VII-e, or a salt form thereof), wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof. In some embodiments, the present disclosure provides oligonucleotides of formula VIII or salts thereof, wherein one or more $L^P$ is of formula VII, VII-a-1, VII-a-2, VII-b, VII-c, VII-d, or VII-e, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof. In some embodiments, provided oligonucleotides comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or more such internucleotidic linkages (each of which independently of formula VII, VII-a-1, VII-a-2, VII-b, VII-c, VII-d, or VII-e, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof). In some embodiments, the present disclosure provides compositions of such oligonucleotides. In some embodiments, levels of such oligonucleotides in provided compositions are pre-determined, which predetermined levels are independently as described in the present disclosure.

In some embodiments, provided oligonucleotides comprises 1-50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or more such internucleotidic linkages (each of which independently of formula VII, VII-a-1, VII-a-2, VII-b, VII-c, VII-d, or VII-e, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof). In some embodiments, a provided oligonucleotides comprises 1 such internucleotidic linkage. In some embodiments, a provided oligonucleotide comprises 2 such internucleotidic linkages. In some embodiments, a provided oligonucleotide comprises 3 such internucleotidic linkages. In some embodiments, a provided oligonucleotide comprises 4 such internucleotidic linkages. In some embodiments, a provided oligonucleotide comprises 5 such internucleotidic linkages. In some embodiments, a provided oligonucleotide comprises 6 such internucleotidic linkages. In some embodiments, a provided oligonucleotide comprises 7 such internucleotidic linkages. In some embodiments, a provided oligonucleotide comprises 8 such internucleotidic linkages. In some embodiments, a provided oligonucleotide comprises 9 such internucleotidic linkages. In some embodiments, a provided oligonucleotide comprises 10 such internucleotidic linkages. In some embodiments, a provided oligonucleotide comprises 15 such internucleotidic linkages. In some embodiments, a provided oligonucleotide comprises 20 such internucleotidic linkages. In some embodiments, a provided oligonucleotide comprises no more than 2 such internucleotidic linkages. In some embodiments, a provided oligonucleotide comprises no more than 3 such internucleotidic linkages. In some embodiments, a provided oligonucleotide comprises no more than 4 such internucleotidic linkages. In some embodiments, a provided oligonucleotide comprises no more than 5 such internucleotidic linkages. In some embodiments, a provided oligonucleotide comprises no more than 6 such internucleotidic linkages. In some embodiments, a provided oligonucleotide comprises no more than 7 such internucleotidic linkages. In some embodiments, a provided oligonucleotide comprises no more than 8 such internucleotidic linkages. In some embodiments, a provided oligonucleotide comprises no more than 9 such internucleotidic linkages. In some embodiments, a provided oligonucleotide comprises no more than 10 such internucleotidic linkages. In some embodiments, a provided oligonucleotide comprises no more than 15 such internucleotidic linkages. In some embodiments, a provided oligonucleotide comprises no more than 20 such internucleotidic linkages. In some embodiments, 0.1%-100% of internucleotidic linkages of provided oligonucleotides are such internucleotidic linkages (each of which independently of formula VII, VII-a-1, VII-a-2, VII-b, VII-c, VII-d, or VII-e, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof). In some embodiments, 0.1%-100%, for example, at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of internucleotidic linkages are such internucleotidic linkages. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, such an internucleotidic linkage is chiral. In some embodiments, each of such internucleotidic linkages is chiral. In some embodiments, such an internucleotidic linkage is chiral and chirally controlled. In some embodiments, each of such internucleotidic linkages is chiral and is independently chirally controlled. In some embodiments, such an internucleotidic linkage is a phosphorothioate linkage or a salt form thereof. In some embodiments, each of such internucleotidic linkages is a phosphorothioate linkage or a salt form thereof. In some embodiments, such an internucleotidic linkage is a phosphorothioate linkage or a salt form thereof and is chirally controlled. In some embodiments, each of such internucleotidic linkages is a phosphorothioate linkage or a salt form thereof and independently chirally controlled.

In some embodiments, a provided oligonucleotide has a diastereomeric purity as described in the present disclosure. In some embodiments, the present disclosure provides chirally controlled oligonucleotide compositions.

In some embodiments, the present disclosure provides an oligonucleotide composition comprising a plurality of oligonucleotides which share:
1) a common base sequence;
2) a common pattern of backbone linkages;
3) common stereochemistry independently at about 1-50 (e.g., about 5-50, about 10-50, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50, etc.) chiral internucleotidic linkages ("chirally controlled internucleotidic linkages");
which composition is chirally controlled in that level of the plurality of oligonucleotides in the composition is predetermined.

In some embodiments, the present disclosure provides an oligonucleotide composition comprising a plurality of oligonucleotides, wherein oligonucleotides of the plurality are of a particular oligonucleotide type defined by:
1) base sequence;
2) pattern of backbone linkages;
3) pattern of backbone chiral centers; and
4) pattern of backbone phosphorus modifications;
which composition is chirally controlled in that level of the plurality of oligonucleotides in the composition is predetermined.

In some embodiments, the present disclosure provides an oligonucleotide composition comprising a plurality of oligonucleotides which share:
1) a common base sequence;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, oligonucleotides of a plurality in chirally controlled oligonucleotide compositions share a common stereochemistry independently at one or more chiral internucleotidic linkages (chirally controlled internucleotidic linkages). In some embodiments, oligonucleotides of the plurality share a common stereochemistry configuration at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or more chiral internucleotidic linkages, each of which is independently Rp or Sp In some embodiments, oligonucleotides of the plurality share a common stereochemistry configuration at each chiral internucleotidic linkages. In some embodiments, a chiral internucleotidic linkage where a predetermined level of oligonucleotides of a composition share a common stereochemistry configuration (independently Rp or Sp) is referred to as a chirally controlled internucleotidic linkage. In some embodiments, a predetermined level of oligonucleotides of a provided composition, e.g., a first plurality of oligonucleotides of certain example compositions, comprise 1-50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or more chirally controlled internucleotidic linkages. In some embodiments, at least 5 internucleotidic linkages are chirally controlled; in some embodiments, at least 10 internucleotidic linkages are chirally controlled; in some embodiments, at least 15 internucleotidic linkages are chirally controlled; in some embodiments, each chiral internucleotidic linkage is chirally controlled. In some embodiments, 0.1%-100% of chiral internucleotidic linkages are chirally controlled. In some embodiments, 0.1%-100%, for example, at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% of chiral internucleotidic linkages are chirally controlled. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, a chirally controlled internucleotidic linkage is of formula VII, VII-a-1, VII-a-2, VII-b, VII-c, VII-d, or VII-e, or a salt form thereof. In some embodiments, each chirally controlled internucleotidic linkage is independently of formula VII, VII-a-1, VII-a-2, VII-b, VII-c, VII-d, or VII-e, or a salt form thereof. In some embodiments, a chirally controlled internucleotidic linkage is a chirally controlled phosphorothioate linkage or a salt form thereof. In some embodiments, each chirally controlled internucleotidic linkage is a chirally controlled phosphorothioate linkage or a salt form thereof.

In some embodiments, a predetermined level of oligonucleotides is 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a provided composition. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, a predetermined level of oligonucleotides is 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a provided composition that are of or comprise a common base sequence. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, all oligonucleotides in a provided composition that are of or comprise a common base sequence are 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in the composition. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, a predetermined level of oligonucleotides is 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a provided composition that are of or comprise a common base sequence, base modifications, sugar modifications and/or modified internucleotidic linkages, if any. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%.

In some embodiments, a predetermined level of oligonucleotides is 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a provided composition that possess identical constitution (identity and connectivity (and corresponding bond multiplicities) of the atoms in a molecular entity) as a plurality of oligonucleotides. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, all oligonucleotides in a provided composition that are of or comprise a common base sequence, base modifications, sugar modifications and/or modified internucleotidic linkages are 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in the composition. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, a predetermined level of oligonucleotides is about 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a provided composition that are of or comprise a common base sequence, pattern of base modification, pattern of sugar modification, and/or pattern of modified internucleotidic linkage. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, all oligonucleotides in a provided composition that are of or comprise a common base sequence, pattern of base modification, pattern of sugar modification, and/or pattern of modified internucleotidic linkage are 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in the composition. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, a predetermined level of oligonucleotides is 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a provided composition that share a common base sequence, a common pattern of base modification, a common pattern of sugar modification, and/or a common pattern of modified internucleotidic linkages. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, all oligonucleotides in a provided composition that share a common base sequence, a common pattern of base modification, a common pattern of sugar modification, and/or a common pattern of modified internucleotidic linkages are 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in the composition. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%. In some embodiments, all oligonucleotides in a provided composition that possess identical constitution are 0.1%-100%, for example, at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in the composition. In some embodiments, a percentage is about 1%-10%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 40%. In some embodiments, a percentage is about 50%. In some embodiments, a percentage is about 60%. In some embodiments, a percentage is about 70%. In some embodiments, a percentage is about 80%. In some embodiments, a percentage is about 90%. In some embodiments, a percentage is about 95%. In some embodiments, a percentage is about 100%.

In some embodiments, a predetermined level is 0.1%-100%. In some embodiments, a predetermined level is at least 1%. In some embodiments, a predetermined level is at least 5%. In some embodiments, a predetermined level is at least 10%. In some embodiments, a predetermined level is at least 20%. In some embodiments, a predetermined level is at least 30%. In some embodiments, a predetermined level is at least 40%. In some embodiments, a predetermined level is at least 50%. In some embodiments, a predetermined level is at least 60%. In some embodiments, a predetermined level is at least 10%. In some embodiments, a predetermined level is at least 70%. In some embodiments, a predetermined level is at least 80%. In some embodiments, a predetermined level is at least 85%. In some embodiments, a predetermined level is at least 90%. In some embodiments, a predetermined level is at least 91%. In some embodiments, a predetermined level is at least 92%. In some embodiments, a predetermined level is at least 93%. In some embodiments, a predetermined level is at least 94%. In some embodiments, a predetermined level is at least 95%. In some embodiments, a predetermined level is at least 96%. In some embodiments, a predetermined level is at least 97%. In some embodiments, a predetermined level is at least 98%. In some embodiments, a predetermined level is at least 99%. In some embodiments, a predetermined level is at least $5*(1/2^g)$, wherein g is the number of chirally controlled internucleotidic linkages. In some embodiments, a predetermined level is at least $10*(1/2^g)$, wherein g is the number of chirally controlled internucleotidic linkages. In some embodiments, a predetermined level is at least $100*(1/2^g)$, wherein g is the number of chirally controlled internucleotidic linkages. In some embodiments, a predetermined level is at least $(0.80)^g$, wherein g is the number of chirally controlled internucleotidic linkages. In some embodiments, a predetermined level is at least $(0.80)^g$, wherein g is the number of chirally controlled internucleotidic linkages. In some embodiments, a predetermined level is at least $(0.80)^g$, wherein g is the number of chirally controlled internucleotidic linkages. In some embodiments, a predetermined level is at least $(0.85)^g$, wherein g is the number of chirally controlled internucleotidic linkages. In some embodiments, a predetermined level is at least $(0.90)^g$, wherein g is the number of chirally controlled internucleotidic linkages. In some embodiments, a predetermined level is at least $(0.95)^g$, wherein g is the number of chirally controlled internucleotidic linkages. In some embodiments, a predetermined level is at least $(0.96)^g$, wherein g is the number of chirally controlled internucleotidic linkages. In some embodiments, a predetermined level is at least $(0.97)^g$, wherein g is the number of chirally controlled internucleotidic linkages. In some embodiments, a predetermined level is at least $(0.98)^g$, wherein g is the number of chirally controlled internucleotidic linkages. In some embodiments, a predetermined level is at least $(0.99)^g$, wherein g is the number of chirally controlled internucleotidic linkages. In some embodiments, to determine level of oligonucleotides having g chirally controlled internucleotidic linkages in a composition, product of diastereopurity of each of the g chirally controlled internucleotidic linkages: (diastereopurity of chirally controlled internucleotidic linkage 1)*(diastereopurity of chirally controlled internucleotidic linkage 2)* . . . *(diastereopurity of chirally controlled internucleotidic linkage g) is utilized as the level, wherein diastereopurity of each chirally controlled internucleotidic linkage is independently represented by diastereopurity of a dimer comprising the same internucleotidic linkage and nucleosides flanking the internucleotidic linkage and prepared under comparable methods as the oligonucleotides (e.g., comparable or preferably identical oligonucleotide preparation cycles, including comparable or preferably identical reagents and reaction conditions). In some embodiments, levels of oligonucleotides and/or diastereopurity can be determined by analytical methods, e.g., chromatographic, spectrometric, spectroscopic methods or any combinations thereof.

In some embodiments, provided features, e.g., purity (e.g., overall purity, diastereomeric purity, enantiomeric purity, etc.), selectivity (e.g., overall selectivity, region-selectivity, diastereomeric selectivity, enantiomeric selectivity, etc.), levels (e.g., predetermined levels (of oligonucleotides, chiral auxiliaries, etc.), levels of activities, etc.), etc., are described as percentages or ranges of percentages. A percentage can be any percentage within provided ranges. For example, in some embodiments, depending on the ranges if any, a percentage is about 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%. In some embodiments, depending on the ranges if any, a percentage is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%. In some embodiments, a percentage is at least 1%. In some embodiments, a percentage is at least 2%. In some embodiments, a percentage is at least 3%. In some embodiments, a percentage is at least 140%. In some embodiments, a percentage is at least 5%. In some embodiments, a percentage is at least 10%. In some embodiments, a percentage is at least 15%. In some embodiments, a percentage is at least 20%. In some embodiments, a percentage is at least 25%. In some embodiments, a percentage is at least 30%. In some embodiments, a percentage is at least 35%. In some embodiments, a percentage is at least 40%. In some embodiments, a percentage is at least 45%. In some embodiments, a percentage is at least 50%. In some embodiments, a percentage is at least 55%. In some embodiments, a percentage is at least 60%. In some embodiments, a percentage is at least 65%. In some embodiments, a percentage is at least 70%. In some embodiments, a percentage is at least 75%. In some embodiments, a percentage is at least 80%. In some embodiments, a percentage is at least 85%. In some embodiments, a percentage is at least 90%. In some embodiments, a percentage is at least 91%. In some embodiments, a percentage is at least 92%. In some embodiments, a percentage is at least 93%. In some embodiments, a percentage is at least 94%. In some embodiments, a percentage is at least 95%. In some embodiments, a percentage is at least 96%. In some embodiments, a percentage is at least 97%. In some embodiments, a percentage is at least 98%. In some embodiments, a percentage is at least 99%. In some embodiments, a percentage is about 1%. In some embodiments, a percentage is about 2%. In some embodiments, a percentage is about 3%. In some embodiments, a percentage is about 140%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 35%. In some embodiments, a percentage is about 40%. In some embodiments, a percentage is about 45%. In some embodiments, a percentage is about 50%. In some embodiments, a percentage is about 55%. In some embodiments, a percentage is about 60%. In some embodiments, a percentage is about 65%. In some embodiments, a percentage is about 70%. In some embodiments, a percentage is about 75%. In some embodiments, a percentage is about 80%. In some embodiments, a percentage is about 85%. In some embodiments, a percentage is about 90%. In some embodiments, a percentage is about 91%. In some embodiments, a percentage is about 92%. In some embodiments, a percentage is about 93%. In some embodiments, a percentage is about 94%. In some embodiments, a percentage is about 95%. In some embodiments, a percentage is about 96%. In some embodiments, a percentage is about 97%. In some embodiments, a percentage is about 98%. In some embodiments, a percentage is about 99%. In some embodiments, a percentage is less than 1%. In some embodiments, a percentage is less than 2%. In some embodiments, a percentage is less than 3%. In some embodiments, a percentage is less than 140%. In some embodiments, a percentage is less than 5%. In some embodiments, a percentage is less than 10%. In some embodiments, a percentage is less than 15%. In some embodiments, a percentage is less than 20%. In some embodiments, a percentage is less than 25%. In some embodiments, a percentage is less than 30%. In some embodiments, a percentage is less than 35%. In some embodiments, a percentage is less than 40%. In some embodiments, a percentage is less than 45%. In some embodiments, a percentage is less than 50%. In some embodiments, a percentage is less than 55%. In some embodiments, a percentage is less than 60%. In some embodiments, a percentage is less than 65%. In some embodiments, a percentage is less than 70%. In some embodiments, a percentage is less than 75%. In some embodiments, a percentage is less than 80%. In some embodiments, a percentage is less than 85%. In some embodiments, a percentage is less than 90%. In some embodiments, a percentage is less than 91%. In some embodiments, a percentage is less than 92%. In some embodiments, a percentage is less than 93%. In some embodiments, a percentage is less than 94%. In some embodiments, a percentage is less than 95%. In some embodiments, a percentage is less than 96%. In some embodiments, a percentage is less than 97%. In some embodiments, a percentage is less than 98%. In some embodiments, a percentage is less than 99%.

In some embodiments, provided oligonucleotides comprise or are of a 5'-wing region-core region-3'-wing region structure. In some embodiments, provided oligonucleotides comprise or are of a 5'-wing region-core region structure. In some embodiments, provided oligonucleotides comprise or are of a core region-3'-wing region structure. In some embodiments, provided oligonucleotides comprise of a 5'-wing region-core region-3'-wing region structure. In some embodiments, provided oligonucleotides comprise of a 5'-wing region-core region structure. In some embodiments, provided oligonucleotides comprise of a core region-3'-wing region structure. In some embodiments, provided oligonucleotides are of a 5'-wing region-core region-3'-wing region structure. In some embodiments, provided oligonucleotides are of a 5'-wing region-core region structure. In some embodiments, provided oligonucleotides are of a core region-3'-wing region structure. In some embodiments, a wing-core-wing (i.e., X-Y-X) motif is represented numerically as, e.g., 5-10-4, meaning 5'-wing region is 5 bases in length, the core region is 10 bases in length, and the 3'-wing region is 4-bases in length. In some embodiments, a wing-core-wing motif is any of, e.g. 2-16-2, 3-14-3, 4-12-4, 5-10-5, 2-9-6, 3-9-3, 3-9-4, 3-9-5, 4-7-4, 4-9-3, 4-9-4, 4-9-5, 4-10-5, 4-11-4, 4-11-5, 5-7-5, 5-8-6, 8-7-5, 7-7-6, 5-9-3, 5-9-5, 5-10-4, 5-10-5, 6-7-6, 6-8-5, and 6-9-2, etc. In certain embodiments, a wing-core-wing motif is 5-10-5. In certain embodiments, a wing-core-wing motif is 7-7-6. In certain embodiments, a wing-core-wing motif is 8-7-5. In some embodiments, a wing-core motif is 5-15, 6-14, 7-13, 8-12, 9-12, etc. In some embodiments, a core-wing motif is 5-15, 6-14, 7-13, 8-12, 9-12, etc.

In some embodiments, a wing region comprises a sugar modification absent from a core region. In some embodiments, a wing region comprises a 2'-modification. In some embodiments, each nucleotide unit of a wing region independently comprises a 2'-modification. In some embodiments, each nucleotide unit of a wing region independently comprises the same 2'-modification. In some embodiments, each nucleotide unit of a 5'-wing region independently comprises the same 2'-modification. In some embodiments, each nucleotide unit of a 3'-wing region independently comprises the same 2'-modification. In some embodiments, 2'-modifications of the 5'-wing region are the same. In some embodiments, 2'-modifications of the 5'-wing region are the different. In some embodiments, a 2'-modification is 2'-OR, wherein R' is not hydrogen. In some embodiments, a 2'-modification is 2'-OR, wherein R' is optionally substituted $C_{1-6}$ aliphatic. In some embodiments, a 2'-modification is 2'-OR, wherein R' is optionally substituted $C_{1-6}$ alkyl. In some embodiments, a 2'-modification is 2'-OMe. In some embodiments, a 2'-modification is 2'-$OCH_2CH_2OMe$.

In some embodiments, a wing region comprises one or more natural phosphate linkages as described in the present disclosure. In some embodiments, each of the 5'- and 3'-wing regions independently comprises one or more natural phosphate linkages as described in the present disclosure. In some embodiments, a wing region comprises two or more consecutive natural phosphate linkages. In some embodiments, a 5'-wing region comprises two or more consecutive natural phosphate linkages. In some embodiments, a 3'-wing region comprises two or more consecutive natural phosphate linkages. In some embodiments, a wing region comprises 1-20, e.g., 1, 2, 3, 4, 5, 6, 7, 8, 9, 10, 11, 12, 13, 14, 15, 16, 17, 18, 19 or 20 natural phosphate linkages. In some embodiments, a wing region comprises 2-20, e.g., 2, 3, 4, 5, 6, 7, 8, 9, 10, 11, 12, 13, 14, 15, 16, 17, 18, 19 or 20 natural phosphate linkages. In some embodiments, a wing region comprises at least 1, 2, 3, 4, 5, 6, 7, 8, 9, 10, 11, 12, 13, 14, 15, 16, 17, 18, 19 or 20 natural phosphate linkages. In some embodiments, a wing region comprises at least 2, 3, 4, 5, 6, 7, 8, 9, 10, 11, 12, 13, 14, 15, 16, 17, 18, 19 or 20 natural phosphate linkages. In some embodiments, a wing region comprises about 2, 3, 4, 5, 6, 7, 8, 9, 10, 11, 12, 13, 14, 15, 16, 17, 18, 19 or 20 natural phosphate linkages. In some embodiments, a wing region comprises 1 natural phosphate linkages. In some embodiments, a wing region comprises 2 natural phosphate linkages. In some embodiments, a wing region comprises 3 natural phosphate linkages. In some embodiments, a wing region comprises 4 natural phosphate linkages. In some embodiments, a wing region comprises 5 natural phosphate linkages. In some embodiments, a wing region comprises 6 natural phosphate linkages. In some embodiments, a wing region comprises 7 natural phosphate linkages. In some embodiments, a wing region comprises 8 natural phosphate linkages. In some embodiments, a wing region comprises 9 natural phosphate linkages. In some embodiments, a wing region comprises 10 natural phosphate linkages. In some embodiments, a wing region comprises 2 and no more than 2 natural phosphate linkages. In some embodiments, a wing region comprises 1 and no more than 1 natural phosphate linkage. In some embodiments, a wing region comprises 3 and no more than 3 natural phosphate linkages. In some embodiments, a wing region comprises 4 and no more than 4 natural phosphate linkages. In some embodiments, a wing region comprises 5 and no more than 5 natural phosphate linkages. In some embodiments, a wing region comprises 6 and no more than 6 natural phosphate linkages. In some embodiments, a wing region comprises 7 and no more than 7 natural phosphate linkages. In some embodiments, a wing region comprises 8 and no more than 8 natural phosphate linkages. In some embodiments, a wing region comprises 9 and no more than 9 natural phosphate linkages. In some embodiments, a wing region comprises 10 and no more than 10 natural phosphate linkages. In some embodiments, a wing region comprises about 2, 3, 4, 5, 6, 7, 8, 9, 10, 11, 12, 13, 14, 15, 16, 17, 18, 19 or 20 consecutive natural phosphate linkages. In some embodiments, a wing region comprises 2 consecutive natural phosphate linkages. In some embodiments, a wing region comprises 3 consecutive natural phosphate linkages. In some embodiments, a wing region comprises 4 consecutive natural phosphate linkages. In some embodiments, a wing region comprises 5 consecutive natural phosphate linkages. In some embodiments, a wing region comprises 6 consecutive natural phosphate linkages. In some embodiments, a wing region comprises 7 consecutive natural phosphate linkages. In some embodiments, a wing region comprises 8 consecutive natural phosphate linkages. In some embodiments, a wing region comprises 9 consecutive natural phosphate linkages. In some embodiments, a wing region comprises 10 consecutive natural phosphate linkages. In some embodiments, a wing region comprises 2 and no more than 2 consecutive natural phosphate linkages. In some embodiments, a wing region comprises 3 and no more than 3 consecutive natural phosphate linkages. In some embodiments, a wing region comprises 4 and no more than 4 consecutive natural phosphate linkages. In some embodiments, a wing region comprises 5 and no more than 5 consecutive natural phosphate linkages. In some embodiments, a wing region comprises 6 and no more than 6 consecutive natural phosphate linkages. In some embodiments, a wing region comprises 7 and no more than 7 consecutive natural phosphate linkages. In some embodiments, a wing region comprises 8 and no more than 8 consecutive natural phosphate linkages. In some embodiments, a wing region comprises 9 and no more than 9 consecutive natural phosphate linkages. In some embodiments, a wing region comprises 10 and no more than 10 consecutive natural phosphate linkages. In some embodiments, a 5'-wing region comprises one or more natural phosphate linkages as described herein. In some embodiments, a 5'-wing region comprises two or more natural phosphate linkages as described herein. In some embodiments, a 3'-wing region comprises one or more natural phosphate linkages as described herein. In some embodiments, a 3'-wing region comprises two or more natural phosphate linkages as described herein. In some embodiments, each of the 5'- and the 3'-wing regions independently comprises one or more natural phosphate linkages as described herein. In some embodiments, each of the 5'- and the 3'-wing regions independently comprises two or more consecutive natural phosphate linkages as described herein.

Additionally or alternatively, in some embodiments, a wing region comprises one or more non-natural internucleotidic linkages as described in the present disclosure. In some embodiments, each of the 5'- and 3'-wing regions independently comprises one or more non-natural internucleotidic linkages as described in the present disclosure. In some embodiments, a wing region comprises two or more consecutive non-natural internucleotidic linkages. In some embodiments, a 5'-wing region comprises two or more consecutive non-natural internucleotidic linkages. In some embodiments, a 3'-wing region comprises two or more consecutive non-natural internucleotidic linkages. In some embodiments, a wing region comprises 1-20, e.g., 1, 2, 3, 4, 5, 6, 7, 8, 9, 10, 11, 12, 13, 14, 15, 16, 17, 18, 19 or 20 non-natural internucleotidic linkages. In some embodiments, a wing region comprises 2-20, e.g., 2, 3, 4, 5, 6, 7, 8, 9, 10, 11, 12, 13, 14, 15, 16, 17, 18, 19 or 20 non-natural internucleotidic linkages. In some embodiments, a wing region comprises at least 1, 2, 3, 4, 5, 6, 7, 8, 9, 10, 11, 12, 13, 14, 15, 16, 17, 18, 19 or 20 non-natural internucleotidic linkages. In some embodiments, a wing region comprises at least 2, 3, 4, 5, 6, 7, 8, 9, 10, 11, 12, 13, 14, 15, 16, 17, 18, 19 or 20 non-natural internucleotidic linkages. In some embodiments, a wing region comprises about 2, 3, 4, 5, 6, 7, 8, 9, 10, 11, 12, 13, 14, 15, 16, 17, 18, 19 or 20 non-natural internucleotidic linkages. In some embodiments, a wing region comprises 1 non-natural internucleotidic linkages. In some embodiments, a wing region comprises 2 non-natural internucleotidic linkages. In some embodiments, a wing region comprises 3 non-natural internucleotidic linkages. In some embodiments, a wing region comprises 4 non-natural internucleotidic linkages. In some embodiments, a wing region comprises 5 non-natural internucleotidic linkages. In some embodiments, a wing region comprises 6 non-natural internucleotidic linkages. In some embodiments, a wing region comprises 7 non-natural internucleotidic linkages. In some embodiments, a wing region comprises 8 non-natural internucleotidic linkages. In some embodiments, a wing region comprises 9 non-natural internucleotidic linkages. In some embodiments, a wing region comprises 10 non-natural internucleotidic linkages. In some embodiments, a wing region comprises 2 and no more than 2 non-natural internucleotidic linkages. In some embodiments, a wing region comprises 1 and no more than 1 non-natural internucleotidic linkage. In some embodiments, a wing region comprises 3 and no more than 3 non-natural internucleotidic linkages. In some embodiments, a wing region comprises 4 and no more than 4 non-natural internucleotidic linkages. In some embodiments, a wing region comprises 5 and no more than 5 non-natural internucleotidic linkages. In some embodiments, a wing region comprises 6 and no more than 6 non-natural internucleotidic linkages. In some embodiments, a wing region comprises 7 and no more than 7 non-natural internucleotidic linkages. In some embodiments, a wing region comprises 8 and no more than 8 non-natural internucleotidic linkages. In some embodiments, a wing region comprises 9 and no more than 9 non-natural internucleotidic linkages. In some embodiments, a wing region comprises 10 and no more than 10 non-natural internucleotidic linkages. In some embodiments, a wing region comprises about 2, 3, 4, 5, 6, 7, 8, 9, 10, 11, 12, 13, 14, 15, 16, 17, 18, 19 or 20 consecutive non-natural internucleotidic linkages. In some embodiments, a wing region comprises 2 consecutive non-natural internucleotidic linkages. In some embodiments, a wing region comprises 3 consecutive non-natural internucleotidic linkages. In some embodiments, a wing region comprises 4 consecutive non-natural internucleotidic linkages. In some embodiments, a wing region comprises 5 consecutive non-natural internucleotidic linkages. In some embodiments, a wing region comprises 6 consecutive non-natural internucleotidic linkages. In some embodiments, a wing region comprises 7 consecutive non-natural internucleotidic linkages. In some embodiments, a wing region comprises 8 consecutive non-natural internucleotidic linkages. In some embodiments, a wing region comprises 9 consecutive non-natural internucleotidic linkages. In some embodiments, a wing region comprises 10 consecutive non-natural internucleotidic linkages. In some embodiments, a wing region comprises 2 and no more than 2 consecutive non-natural internucleotidic linkages. In some embodiments, a wing region comprises 3 and no more than 3 consecutive non-natural internucleotidic linkages. In some embodiments, a wing region comprises 4 and no more than 4 consecutive non-natural internucleotidic linkages. In some embodiments, a wing region comprises 5 and no more than 5 consecutive non-natural internucleotidic linkages. In some embodiments, a wing region comprises 6 and no more than 6 consecutive non-natural internucleotidic linkages. In some embodiments, a wing region comprises 7 and no more than 7 consecutive non-natural internucleotidic linkages. In some embodiments, a wing region comprises 8 and no more than 8 consecutive non-natural internucleotidic linkages. In some embodiments, a wing region comprises 9 and no more than 9 consecutive non-natural internucleotidic linkages. In some embodiments, a wing region comprises 10 and no more than 10 consecutive non-natural internucleotidic linkages. In some embodiments, a 5'-wing region comprises one or more non-natural internucleotidic linkages as described herein. In some embodiments, a 5'-wing region comprises two or more non-natural internucleotidic linkages as described herein. In some embodiments, a 3'-wing region comprises one or more non-natural internucleotidic linkages as described herein. In some embodiments, a 3'-wing region comprises two or more non-natural internucleotidic linkages as described herein. In some embodiments, each of the 5'- and the 3'-wing regions independently comprises one or more non-natural internucleotidic linkages as described herein. In some embodiments, each of the 5'- and the 3'-wing regions independently comprises two or more consecutive non-natural internucleotidic linkages as described herein.

In some embodiments, a 5'-wing region comprises one and no more than one non-natural internucleotidic linkage.

In some embodiments, a 5'-wing region comprises one and no more than one non-natural internucleotidic linkage, and the non-natural internucleotidic linkage is linking the first and the second nucleoside of the 5'-wing region. In some embodiments, a 3'-wing region comprises two and no more than two non-natural internucleotidic linkages. In some embodiments, a 3'-wing region comprises two and no more than two non-natural internucleotidic linkages, wherein one non-natural internucleotidic linkage is linking the last and the second last nucleoside of the 3'-wing region, and the other is linking the last nucleoside of a core region and the first nucleoside of the 3'-wing region. In some embodiments, a non-natural internucleotidic linkage is of formula VII, VII-a-1, VII-a-2, VII-b, VII-c, VII-d, or VII-e, or a salt form thereof. In some embodiments, a non-natural internucleotidic linkage is a chiral internucleotidic linkage. In some embodiments, a non-natural internucleotidic linkage is a chirally controlled internucleotidic linkage. In some embodiments, of formula VII, VII-a-1, VII-a-2, VII-b, VII-c, VII-d, or VII-e, or a salt form thereof, —X-$L^s$-$R^5$ is of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof. In some embodiments, of formula VII, VII-a-1, VII-a-2, VII-b, VII-c, VII-d, or VII-e, or a salt form thereof, X, Y, and Z are —O—, and —X-$L^s$-$R^5$ is of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof. In some embodiments, of formula VII, VII-a-1, VII-a-2, or VII-b, or a salt form thereof, W is O or S, X, Y, and Z are —O—, and —X-$L^s$-$R^5$ is of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof. In some embodiments, of formula VII, VII-a-1, VII-a-2, or VII-b, or a salt form thereof, W is S, X, Y, and Z are —O—, and —X-$L^s$-$R^5$ is of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof. In some embodiments, a chirally controlled internucleotidic linkage is a wing region is Rp. In some embodiments, a chirally controlled internucleotidic linkage is a wing region is Sp. In some embodiments, each chirally controlled internucleotidic linkage in a 5'-wing region is Sp. In some embodiments, each chirally controlled internucleotidic linkage in a 3'-wing region is Sp. In some embodiments, each chirally controlled internucleotidic linkage in a wing region is Sp.

In some embodiments, a core region comprises a sugar modification absent from a core region. In some embodiments, a core region comprises a 2'-modification different from any one those in a wing region. In some embodiments, a core region comprises no 2'-modification. In some embodiments, a core region comprises no 2'-substitution (at 2' position is —$CH_2$—).

In some embodiments, a core region comprises one or more natural phosphate linkages as described in the present disclosure. In some embodiments, a core region comprises two or more consecutive natural phosphate linkages. In some embodiments, a core region comprises 1-20, e.g., 1, 2, 3, 4, 5, 6, 7, 8, 9, 10, 11, 12, 13, 14, 15, 16, 17, 18, 19 or 20 natural phosphate linkages. In some embodiments, a core region comprises 2-20, e.g., 2, 3, 4, 5, 6, 7, 8, 9, 10, 11, 12, 13, 14, 15, 16, 17, 18, 19 or 20 natural phosphate linkages. In some embodiments, a core region comprises at least 1, 2, 3, 4, 5, 6, 7, 8, 9, 10, 11, 12, 13, 14, 15, 16, 17, 18, 19 or 20 natural phosphate linkages. In some embodiments, a core region comprises at least 2, 3, 4, 5, 6, 7, 8, 9, 10, 11, 12, 13, 14, 15, 16, 17, 18, 19 or 20 natural phosphate linkages. In some embodiments, a core region comprises about 2, 3, 4, 5, 6, 7, 8, 9, 10, 11, 12, 13, 14, 15, 16, 17, 18, 19 or 20 natural phosphate linkages. In some embodiments, a core region comprises 1 natural phosphate linkages. In some embodiments, a core region comprises 2 natural phosphate linkages. In some embodiments, a core region comprises 3 natural phosphate linkages. In some embodiments, a core region comprises 4 natural phosphate linkages. In some embodiments, a core region comprises 5 natural phosphate linkages. In some embodiments, a core region comprises 6 natural phosphate linkages. In some embodiments, a core region comprises 7 natural phosphate linkages. In some embodiments, a core region comprises 8 natural phosphate linkages. In some embodiments, a core region comprises 9 natural phosphate linkages. In some embodiments, a core region comprises 10 natural phosphate linkages. In some embodiments, a core region comprises 2 and no more than 2 natural phosphate linkages. In some embodiments, a core region comprises 1 and no more than 1 natural phosphate linkage. In some embodiments, a core region comprises 3 and no more than 3 natural phosphate linkages. In some embodiments, a core region comprises 4 and no more than 4 natural phosphate linkages. In some embodiments, a core region comprises 5 and no more than 5 natural phosphate linkages. In some embodiments, a core region comprises 6 and no more than 6 natural phosphate linkages. In some embodiments, a core region comprises 7 and no more than 7 natural phosphate linkages. In some embodiments, a core region comprises 8 and no more than 8 natural phosphate linkages. In some embodiments, a core region comprises 9 and no more than 9 natural phosphate linkages. In some embodiments, a core region comprises 10 and no more than 10 natural phosphate linkages. In some embodiments, a core region comprises about 2, 3, 4, 5, 6, 7, 8, 9, 10, 11, 12, 13, 14, 15, 16, 17, 18, 19 or 20 consecutive natural phosphate linkages. In some embodiments, a core region comprises 2 consecutive natural phosphate linkages. In some embodiments, a core region comprises 3 consecutive natural phosphate linkages. In some embodiments, a core region comprises 4 consecutive natural phosphate linkages. In some embodiments, a core region comprises 5 consecutive natural phosphate linkages. In some embodiments, a core region comprises 6 consecutive natural phosphate linkages. In some embodiments, a core region comprises 7 consecutive natural phosphate linkages. In some embodiments, a core region comprises 8 consecutive natural phosphate linkages. In some embodiments, a core region comprises 9 consecutive natural phosphate linkages. In some embodiments, a core region comprises 10 consecutive natural phosphate linkages. In some embodiments, a core region comprises 2 and no more than 2 consecutive natural phosphate linkages. In some embodiments, a core region comprises 3 and no more than 3 consecutive natural phosphate linkages. In some embodiments, a core region comprises 4 and no more than 4 consecutive natural phosphate linkages. In some embodiments, a core region comprises 5 and no more than 5 consecutive natural phosphate linkages. In some embodiments, a core region comprises 6 and no more than 6 consecutive natural phosphate linkages. In some embodiments, a core region comprises 7 and no more than 7 consecutive natural phosphate linkages. In some embodiments, a core region comprises 8 and no more than 8 consecutive natural phosphate linkages. In some embodiments, a core region comprises 9 and no more than 9 consecutive natural phosphate linkages. In some embodiments, a core region comprises 10 and no more than 10 consecutive natural phosphate linkages.

Additionally or alternatively, in some embodiments, a core region comprises one or more non-natural internucleotidic linkages as described in the present disclosure. In some embodiments, a core region comprises no natural phosphate linkages. In some embodiments, a core region comprises 1-20, e.g., 1, 2, 3, 4, 5, 6, 7, 8, 9, 10, 11, 12, 13, 14, 15, 16, 17, 18, 19 or 20 non-natural internucleotidic linkages. In some embodiments, a core region comprises 2-20, e.g., 2, 3, 4, 5, 6, 7, 8, 9, 10, 11, 12, 13, 14, 15, 16, 17, 18, 19 or 20 non-natural internucleotidic linkages. In some embodiments, a core region comprises at least 1, 2, 3, 4, 5, 6, 7, 8, 9, 10, 11, 12, 13, 14, 15, 16, 17, 18, 19 or 20 non-natural internucleotidic linkages. In some embodiments, a core region comprises at least 2, 3, 4, 5, 6, 7, 8, 9, 10, 11, 12, 13, 14, 15, 16, 17, 18, 19 or 20 non-natural internucleotidic linkages. In some embodiments, a core region comprises about 2, 3, 4, 5, 6, 7, 8, 9, 10, 11, 12, 13, 14, 15, 16, 17, 18, 19 or 20 non-natural internucleotidic linkages. In some embodiments, a core region comprises 1 non-natural internucleotidic linkages. In some embodiments, a core region comprises 2 non-natural internucleotidic linkages. In some embodiments, a core region comprises 3 non-natural internucleotidic linkages. In some embodiments, a core region comprises 4 non-natural internucleotidic linkages. In some embodiments, a core region comprises 5 non-natural internucleotidic linkages. In some embodiments, a core region comprises 6 non-natural internucleotidic linkages. In some embodiments, a core region comprises 7 non-natural internucleotidic linkages. In some embodiments, a core region comprises 8 non-natural internucleotidic linkages. In some embodiments, a core region comprises 9 non-natural internucleotidic linkages. In some embodiments, a core region comprises 10 non-natural internucleotidic linkages. In some embodiments, a core region comprises 2 and no more than 2 non-natural internucleotidic linkages. In some embodiments, a core region comprises 1 and no more than 1 non-natural internucleotidic linkage. In some embodiments, a core region comprises 3 and no more than 3 non-natural internucleotidic linkages. In some embodiments, a core region comprises 4 and no more than 4 non-natural internucleotidic linkages. In some embodiments, a core region comprises 5 and no more than 5 non-natural internucleotidic linkages. In some embodiments, a core region comprises 6 and no more than 6 non-natural internucleotidic linkages. In some embodiments, a core region comprises 7 and no more than 7 non-natural internucleotidic linkages. In some embodiments, a core region comprises 8 and no more than 8 non-natural internucleotidic linkages. In some embodiments, a core region comprises 9 and no more than 9 non-natural internucleotidic linkages. In some embodiments, a core region comprises 10 and no more than 10 non-natural internucleotidic linkages. In some embodiments, a core region comprises about 2, 3, 4, 5, 6, 7, 8, 9, 10, 11, 12, 13, 14, 15, 16, 17, 18, 19 or 20 consecutive non-natural internucleotidic linkages. In some embodiments, a core region comprises 2 consecutive non-natural internucleotidic linkages. In some embodiments, a core region comprises 3 consecutive non-natural internucleotidic linkages. In some embodiments, a core region comprises 4 consecutive non-natural internucleotidic linkages. In some embodiments, a core region comprises 5 consecutive non-natural internucleotidic linkages. In some embodiments, a core region comprises 6 consecutive non-natural internucleotidic linkages. In some embodiments, a core region comprises 7 consecutive non-natural internucleotidic linkages. In some embodiments, a core region comprises 8 consecutive non-natural internucleotidic linkages. In some embodiments, a core region comprises 9 consecutive non-natural internucleotidic linkages. In some embodiments, a core region comprises 10 consecutive non-natural internucleotidic linkages. In some embodiments, a core region comprises 2 and no more than 2 consecutive non-natural internucleotidic linkages. In some embodiments, a core region comprises 3 and no more than 3 consecutive non-natural internucleotidic linkages. In some embodiments, a core region comprises 4 and no more than 4 consecutive non-natural internucleotidic linkages. In some embodiments, a core region comprises 5 and no more than 5 consecutive non-natural internucleotidic linkages. In some embodiments, a core region comprises 6 and no more than 6 consecutive non-natural internucleotidic linkages. In some embodiments, a core region comprises 7 and no more than 7 consecutive non-natural internucleotidic linkages. In some embodiments, a core region comprises 8 and no more than 8 consecutive non-natural internucleotidic linkages. In some embodiments, a core region comprises 9 and no more than 9 consecutive non-natural internucleotidic linkages. In some embodiments, a core region comprises 10 and no more than 10 consecutive non-natural internucleotidic linkages. As described in the present disclosure, in some embodiments, a non-natural internucleotidic linkage is of formula VII, VII-a-1, VII-a-2, VII-b, VII-c, VII-d, or VII-e, or a salt form thereof. In some embodiments, a non-natural internucleotidic linkage is a chiral internucleotidic linkage. In some embodiments, a non-natural internucleotidic linkage is a chirally controlled internucleotidic linkage. In some embodiments, of formula VII, VII-a-1, VII-a-2, VII-b, VII-c, VII-d, or VII-e, or a salt form thereof, $-X-L^s-R^5$ is of a structure that $H-X-L^s-R^5$ is a compound of formula I, I-a, I-a-1, I-a-2, I-b, I-c, I-d, I-e, II, II-a, II-b, III, III-a, or III-b, or a salt thereof. In some embodiments, of formula VII, VII-a-1, VII-a-2, VII-b, VII-c, VII-d, or VII-e, or a salt form thereof, X, Y, and Z are —O—, and $-X-L^s-R^5$ is of a structure that $H-X-L^s-R^5$ is a compound of formula I, I-a, I-a-1, I-a-2, I-b, I-c, I-d, I-e, II, II-a, II-b, III, III-a, or III-b, or a salt thereof. In some embodiments, of formula VII, VII-a-1, VII-a-2, or VII-b, or a salt form thereof, W is O or S, X, Y, and Z are —O—, and $-X-L^s-R^5$ is of a structure that $H-X-L^s-R^5$ is a compound of formula I, I-a, I-a-1, I-a-2, I-b, I-c, I-d, I-e, II, II-a, II-b, III, III-a, or III-b, or a salt thereof. In some embodiments, of formula VII, VII-a-1, VII-a-2, or VII-b, or a salt form thereof, W is S, X, Y, and Z are —O—, and $-X-L^s-R^5$ is of a structure that $H-X-L^s-R^5$ is a compound of formula I, I-a, I-a-1, I-a-2, I-b, I-c, I-d, I-e, II, II-a, II-b, III, III-a, or III-b, or a salt thereof. In some embodiments, a chirally controlled internucleotidic linkage is a core region is Rp. In some embodiments, a chirally controlled internucleotidic linkage is a core region is Sp. In some embodiments, pattern of backbone chiral centers of a core region (unless otherwise specified, including stereochemistry of linkage phosphorus of internucleotidic linkage linking the first nucleoside of the core region with its 5'-nucleoside, and internucleotidic linkage linking the last nucleoside of the core region with its 3'-nucleoside) comprises a pattern described herein.

In some embodiments, a pattern of backbone chiral centers of oligonucleotides or segments thereof, e.g., core regions, provides increased stability. In some embodiments, a pattern of backbone chiral centers provides surprisingly increased activity. In some embodiments, a pattern of backbone chiral centers provides increased stability and activity. In some embodiments, a pattern of backbone chiral centers provides surprisingly increased binding to certain proteins. In some embodiments, a pattern of backbone chiral centers provides surprisingly enhanced delivery. In some embodiments, a pattern of backbone chiral centers comprises or is (Sp)m(Rp)n, (Rp)n(Sp)m, (Np)p(Rp)n(Sp)m, or (Sp)p(Rp)n(Sp)m (unless otherwise specified, from 5' to 3'), wherein n is 1-10, and each of p and m is independently 0-50. In some embodiments, a pattern of backbone chiral centers comprises or is (Sp)m(Rp)n, (Rp)n(Sp)m, (Np)p(Rp)n(Sp)m, or (Sp)p(Rp)n(Sp)m (unless otherwise specified, from 5' to 3'), wherein n is 1-10, and each of p and m is independently 1-50. In some embodiments, a pattern of backbone chiral centers comprises (Sp)m(Rp)n, (Rp)n(Sp)m, (Np)p(Rp)n(Sp)m, or (Sp)p(Rp)n(Sp)m. In some embodiments, a pattern of backbone chiral centers is (Sp)m(Rp)n, (Rp)n(Sp)m, (Np)p(Rp)n(Sp)m, or (Sp)p(Rp)n(Sp)m. In some embodiments, a pattern of backbone chiral centers comprises or is a repeating pattern comprising or being of (Sp)m(Rp)n, (Rp)n(Sp)m, (Np)p(Rp)n(Sp)m, or (Sp)p(Rp)n(Sp)m. In some embodiments, a pattern of backbone chiral centers comprises or is a repeating pattern of (Sp)m(Rp)n, (Rp)n(Sp)m, (Np)p(Rp)n(Sp)m, or (Sp)p(Rp)n(Sp)m (from 5' to 3').

In some embodiments, a pattern of backbone chiral centers comprises or is (Rp)n(Sp)m, (Np)p(Rp)n(Sp)m, or (Sp)p(Rp)n(Sp)m, wherein m>2. In some embodiments, a pattern of backbone chiral centers comprises or is (Rp)n(Sp)m, (Np)p(Rp)n(Sp)m, or (Sp)p(Rp)n(Sp)m, wherein n is 1, p>1, and m>2. In some embodiments, m>3. In some embodiments, m>4.

In some embodiments, a pattern of backbone chiral centers comprises or is (Rp)n(Sp)m, (Sp)p(Rp)n, (Np)p(Rp)n(Sp)m, (Sp)p(Sp)m or (Sp)p(Rp)n(Sp)m. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprises one or more 2'-modifications as described herein. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprises one or more 2'-F modifications as described herein. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprises one or more 2'-OR modifications as described herein. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprises one or more 2'-OR modifications, wherein R is not —H. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and each nucleoside unit between internucleotidic linkages having the pattern of (Rp)n(Sp)m, (Sp)p(Rp)n, (Np)p(Rp)n(Sp)m, or (Sp)p(Rp)n(Sp)m comprises no 2'-modifications. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and each nucleoside unit between internucleotidic linkages having the pattern of (Rp)n(Sp)m, (Sp)p(Rp)n, (Np)p(Rp)n(Sp)m, or (Sp)p(Rp)n(Sp)m comprises no 2'-substitutions (—CH$_2$— at 2'-position). In some embodiments, a pattern of backbone chiral centers comprises or is (Rp)n(Sp)m. In some embodiments, a pattern of backbone chiral centers comprises or is (Sp)p(Rp)n. In some embodiments, a pattern of backbone chiral centers comprises (Np)p(Rp)n(Sp)m. In some embodiments, a pattern of backbone chiral centers is (Rp)n(Sp)m. In some embodiments, a pattern of backbone chiral centers is (Sp)p(Rp)n. In some embodiments, a pattern of backbone chiral centers is (Np)p(Rp)n(Sp)m. In some embodiments, a pattern of backbone chiral centers comprises or is (Sp)p(Sp)m, optionally with n achiral phosphate diester internucleotidic linkages and/or stereorandom (non-chirally controlled) chiral internucleotidic linkages between the section having (Sp)p and the section having (Sp)m. In some embodiments, there are n achiral phosphate diester internucleotidic linkages in between. In some embodiments, there are n stereorandom chiral internucleotidic linkages in between. In some embodiments, a pattern of backbone chiral centers comprises or is (Sp)p(Rp)n(Sp)m.

In some embodiments, an oligonucleotide, or a region thereof, comprises a pattern, or a repeating pattern, of backbone chiral centers of (Sp)m(Rp)n, (Rp)n(Sp)m, (Np)p(Rp)n(Sp)m, or (Sp)p(Rp)n(Sp)m (structurally starting from the first, and ending at the last, internucleotidic linkage of the internucleotidic linkages which have the pattern, or the repeating pattern, of (Sp)m(Rp)n, (Rp)n(Sp)m, (Np)p(Rp)n(Sp)m, or (Sp)p(Rp)n(Sp)m, respectively; a "(repeating) (Sp)m(Rp)n region", a "(repeating) (Rp)n(Sp)m region", a "(repeating) (Np)p(Rp)n(Sp)m region", or a "(repeating) (Sp)p(Rp)n(Sp)m region", respectively, depending on repeating or not). For example, a (Sp)p(Rp)n(Sp)m region (Sp)7(Rp)1(Sp)3) in WV-2555:

```
                                              (SEQ ID NO: 1))
mA * SmGmCmUmU * SC * ST * ST * SG * ST * SC

* SC * RA * SG * SC * SmUmUmUmA * SmU
``` comprises no 2'-OR sugar modifications. In some embodiments, each sugar moieties in the region is —CH$_2$— at the 2'-position. In some embodiments, each sugar moieties in the region is an unmodified, natural, 2'-deoxyribose moiety of DNA. In some embodiments, a region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m is flanked by a 5'-wing region, which structurally ends with a nucleoside moiety (which nucleoside moiety, at its 3'-end, is connected to the first internucleotidic linkage of the region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m).

```
(For example, a flaking 5'-wing region
in WV-2555:
mA * SmGmCmUmU * SC * ST * ST * SG *

ST * SC * SC * RA * SG * SC * SmUmUm

UmA * SmU (SEQ ID NO: 1)).
```

In some embodiments, a region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m is flanked by a 3'-wing region, which structurally starts with a nucleoside moiety (which nucleoside moiety, at its 5'-end, is connected to the last internucleotidic linkage of the region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m).

For example, a flaking 3'-wing region in WV-2555:

(SEQ ID NO: 1)
mA * SmGmCmUmU * SC * ST * ST * SG * ST * SC

* SC * RA * SG * SC * **SmUmUmUmA * SmU**).

In some embodiments, a region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m is flanked by a 5'-end and a 3'-wing regions. In some embodiments, the flanking 5'-wing region and/or the 3'-wing region comprise a non-natural internucleotidic linkage. In some embodiments, the flanking 5'-wing region and/or the 3'-wing region comprise a chiral internucleotidic linkage. In some embodiments, the flanking 5'-wing region and/or the 3'-wing region comprise a chirally controlled internucleotidic linkage. In some embodiments, the flanking 5'-wing region and/or the 3'-wing region comprise a modified internucleotidic linkage comprising a Sp linkage phosphorus. In some embodiments, the flanking 5'-wing region and/or the 3'-wing region comprise a Sp phosphorothioate linkage. In some embodiments, the flanking 5'-wing region and/or the 3'-wing region comprise one or more natural phosphate linkages. In some embodiments, the flanking 5'-wing region and/or the 3'-wing region comprise one or more consecutive natural phosphate linkages. In some embodiments, the flanking 5'-end comprises only one modified internucleotidic linkage which is the 5'-end internucleotidic linkage, and one or more consecutive natural phosphate linkages (for example, in WV-2555:

(for example, in WV-2555:
**mA * SmGmCmUmU** * SC * ST * ST * SG * ST * SC

* SC * RA * SG * SC * SmUmUmUmA * SmU (SOOOSSSSSSSRSSSOOOS)(SEQ ID NO: 1)).

In some embodiments, the flanking 3'-end comprises only one modified internucleotidic linkage which is the 3'-end internucleotidic linkage, and one or more consecutive natural phosphate linkages (for example, in WV-2555:

(for example, in WV-2555:
mA * SmGmCmUmU * SC * ST * ST * SG * ST * SC

* SC * RA * SG * SC * **SmUmUmUmA * SmU**

(SOOOSSSSSSSRSSSOOOS)(SEQ ID NO: 1)).

In some embodiments, the flanking 5'-wing region and/or the 3'-wing region comprise 2'-modified sugar units. In some embodiments, each sugar unit in the 5'-wing region and/or the 3'-wing region is independently modified. In some embodiments, each sugar unit in the 5'-wing region and/or the 3'-wing region independently comprises a 2'-modification (for example, m, 2'-OMe in WV-2555: mA*SmGmCmUmU*SC*ST*ST*SG*ST*SC*SC*RA* SG*SC*SmUmUmUmA*SmU (SEQ ID NO: 1)). In some embodiments, each sugar unit in the 5'-wing region and/or the 3'-wing region comprises the same 2'-modification. In some embodiments, a 2'-modification is 2'-OR, wherein R is optionally substituted $C_{1-6}$ aliphatic. In some embodiments, a 2'-modification is 2'-OMe. In some embodiments, a 2'-modification is 2'-MOE. In some embodiments, a 2'-modification is a LNA modification (which comprises a type of C2-C4 bridge).

In some embodiments, n is 1-10. In some embodiments, n is 1, 2, 3, 4, 5, 6, 7 or 8. In some embodiments, n is 1. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, n is 1. In some embodiments, m is at least 2, 3, 4, 5, 6, 7, 8, 9, 10, 11, 12, 13, 14, or 15. In some embodiments, m is 2, 3, 4, 5, 6, 7, 8, 9, 10, 11, 12, 13, 14, or 15. In some embodiments, p is at least 2, 3, 4, 5, 6, 7, 8, 9, 10, 11, 12, 13, 14, or 15. In some embodiments, m is at least 2. In some embodiments, p is at least 2. In some embodiments, n is 1. In some embodiments, m is at least 2, p is at least 2, n is 1. In some embodiments, p is 2, 3, 4, 5, 6, 7, 8, 9, 10, 11, 12, 13, 14, or 15. In some embodiments, each of m and p is independently at least 2, 3, 4, 5, 6, 7, 8, 9, 10, 11, 12, 13, 14, or 15. In some embodiments, each of m and p is independently 2, 3, 4, 5, 6, 7, 8, 9, 10, 11, 12, 13, 14, or 15. In some embodiments, at least one of m and p is at least 5, 6, 7, 8, 9, 10, 11, 12, 13, 14, or 15. In some embodiments, m is at least 5, 6, 7, 8, 9, 10, 11, 12, 13, 14, or 15. In some embodiments, p is at least 5, 6, 7, 8, 9, 10, 11, 12, 13, 14, or 15.

In some embodiments, p is 0-50. In some embodiments, p is 1-50. In some embodiments, p is 1. In some embodiments, p is 2-50. In some embodiments, p is 2, 3, 4, 5, 6, 7 or 8. In some embodiments, p is 3, 4, 5, 6, 7 or 8. In some embodiments, p is 4, 5, 6, 7 or 8. In some embodiments, p is 5, 6, 7 or 8. In some embodiments, p is 6, 7 or 8. In some embodiments, p is 7 or 8. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, p is 9. In some embodiments, p is 10. In some embodiments, p is 11. In some embodiments, p is 12. In some embodiments, p is 13. In some embodiments, p is 14. In some embodiments, p is 15. In some embodiments, p is 16. In some embodiments, p is 17. In some embodiments, p is 18. In some embodiments, p is 19. In some embodiments, p is 20. In some embodiments, p is 21. In some embodiments, p is 22. In some embodiments, p is 23. In some embodiments, p is 24. In some embodiments, p is 25. In some embodiments, p is at least 2. In some embodiments, p is at least 3. In some embodiments, p is at least 4. In some embodiments, p is at least 5. In some embodiments, p is at least 6. In some embodiments, p is at least 7. In some embodiments, p is at least 8. In some embodiments, p is at least 9. In some embodiments, p is at least 10. In some embodiments, p is at least 11. In some embodiments, p is at least 12. In some embodiments, p is at least 13. In some embodiments, p is at least 14. In some embodiments, p is at least 15. In some embodiments, p is at least 16. In some embodiments, p is at least 17. In some embodiments, p is at least 18. In some embodiments, p is at least 19. In some embodiments, p is at least 20. In some embodiments, p is at least 21. In some embodiments, p is at least 22. In some embodiments, p is at least 23. In some embodiments, p is at least 24. In some embodiments, p is at least 25.

In some embodiments, m is 0-50. In some embodiments, m is 1-50. In some embodiments, m is 1. In some embodiments, m is 2-50. In some embodiments, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20. In some embodiments, m is 21. In some embodiments, m is 22. In some embodiments, m is 23. In some embodiments, m is 24. In some embodiments, m is 25. In some embodiments, m is at least 2. In some embodiments, m is at least 3. In some embodiments, m is at least 4. In some embodiments, m is at least 5. In some embodiments, m is at least 6. In some embodiments, m is at least 7. In some embodiments, m is at least 8. In some embodiments, m is at least 9. In some embodiments, m is at least 10. In some embodiments, m is at least 11. In some embodiments, m is at least 12. In some embodiments, m is at least 13. In some embodiments, m is at least 14. In some embodiments, m is at least 15. In some embodiments, m is at least 16. In some embodiments, m is at least 17. In some embodiments, m is at least 18. In some embodiments, m is at least 19. In some embodiments, m is at least 20. In some embodiments, m is at least 21. In some embodiments, m is at least 22. In some embodiments, m is at least 23. In some embodiments, m is at least 24. In some embodiments, m is at least 25. In some embodiments, m is at least greater than 25.

In some embodiments, at least one of m and p is greater than 2. In some embodiments, at least one of m and p is greater than 3. In some embodiments, at least one of m and p is greater than 4. In some embodiments, at least one of m and p is greater than 5. In some embodiments, at least one of m and p is greater than 6. In some embodiments, at least one of m and p is greater than 7. In some embodiments, at least one of m and p is greater than 8. In some embodiments, at least one of m and p is greater than 9. In some embodiments, at least one of m and p is greater than 10. In some embodiments, at least one of m and p is greater than 11. In some embodiments, at least one of m and p is greater than 12. In some embodiments, at least one of m and p is greater than 13. In some embodiments, at least one of m and p is greater than 14. In some embodiments, at least one of m and p is greater than 15. In some embodiments, at least one of m and p is greater than 16. In some embodiments, at least one of m and p is greater than 17. In some embodiments, at least one of m and p is greater than 18. In some embodiments, at least one of m and p is greater than 19. In some embodiments, at least one of m and p is greater than 20. In some embodiments, at least one of m and p is greater than 21. In some embodiments, at least one of m and p is greater than 22. In some embodiments, at least one of m and p is greater than 23. In some embodiments, at least one of m and p is greater than 24. In some embodiments, at least one of m and p is greater than 25.

In some embodiments, each of m and p is greater than 2. In some embodiments, each of m and p is greater than 3. In some embodiments, each of m and p is greater than 4. In some embodiments, each of m and p is greater than 5. In some embodiments, each of m and p is greater than 6. In some embodiments, each of m and p is greater than 7. In some embodiments, each of m and p is greater than 8. In some embodiments, each of m and p is greater than 9. In some embodiments, each of m and p is greater than 10. In some embodiments, each of m and p is greater than 11. In some embodiments, each of m and p is greater than 12. In some embodiments, each of m and p is greater than 13. In some embodiments, each of m and p is greater than 14. In some embodiments, each of m and p is greater than 15. In some embodiments, each of m and p is greater than 16. In some embodiments, each of m and p is greater than 17. In some embodiments, each of m and p is greater than 18. In some embodiments, each of m and p is greater than 19. In some embodiments, each of m and p is greater than 20.

In some embodiments, the sum of m and p is greater than 3. In some embodiments, the sum of m and p is greater than 4. In some embodiments, the sum of m and p is greater than 5. In some embodiments, the sum of m and p is greater than 6. In some embodiments, the sum of m and p is greater than 7. In some embodiments, the sum of m and p is greater than 8. In some embodiments, the sum of m and p is greater than 9. In some embodiments, the sum of m and p is greater than 10. In some embodiments, the sum of m and p is greater than 11. In some embodiments, the sum of m and p is greater than 12. In some embodiments, the sum of m and p is greater than 13. In some embodiments, the sum of m and p is greater than 14. In some embodiments, the sum of m and p is greater than 15. In some embodiments, the sum of m and p is greater than 16. In some embodiments, the sum of m and p is greater than 17. In some embodiments, the sum of m and p is greater than 18. In some embodiments, the sum of m and p is greater than 19. In some embodiments, the sum of m and p is greater than 20. In some embodiments, the sum of m and p is greater than 21. In some embodiments, the sum of m and p is greater than 22. In some embodiments, the sum of m and p is greater than 23. In some embodiments, the sum of m and p is greater than 24. In some embodiments, the sum of m and p is greater than 25.

In some embodiments, n is 1, and at least one of m and p is greater than 1. In some embodiments, n is 1 and each of m and p is independently greater than 1. In some embodiments, m>n and p>n. In some embodiments, (Sp)m(Rp)n(Sp)p is $(Sp)_2Rp(Sp)_2$. In some embodiments, (Sp)p(Rp)n(Sp)m is $(Sp)_2Rp(Sp)_2$. In some embodiments, (Sp)p(Rp)n(Sp)m is $SpRp(Sp)_2$. In some embodiments, (Np)p(Rp)n(Sp)m is (Np)tRp(Sp)m. In some embodiments, (Np)p(Rp)n(Sp)m is $(Np)_2Rp(Sp)m$. In some embodiments, (Np)p(Rp)n(Sp)m is $(Rp)_2Rp(Sp)m$. In some embodiments, (Np)p(Rp)n(Sp)m is $(Sp)_2Rp(Sp)m$. In some embodiments, (Np)p(Rp)n(Sp)m is RpSpRp(Sp)m. In some embodiments, (Np)p(Rp)n(Sp)m is SpRpRp(Sp)m.

In some embodiments, (Sp)p(Rp)n(Sp)m is SpRpSpSp. In some embodiments, (Sp)p(Rp)n(Sp)m is $(Sp)_2Rp(Sp)_2$. In some embodiments, (Sp)p(Rp)n(Sp)m is $(Sp)_3Rp(Sp)_3$. In some embodiments, (Sp)p(Rp)n(Sp)m is $(Sp)_4Rp(Sp)_4$. In some embodiments, (Sp)p(Rp)n(Sp)m is $(Sp)tRp(Sp)_5$. In some embodiments, (Sp)p(Rp)n(Sp)m is $SpRp(Sp)_5$. In some embodiments, (Sp)p(Rp)n(Sp)m is $(Sp)_2Rp(Sp)_5$. In some embodiments, (Sp)p(Rp)n(Sp)m is $(Sp)_3Rp(Sp)_5$. In some embodiments, (Sp)p(Rp)n(Sp)m is $(Sp)_4Rp(Sp)_5$. In some embodiments, (Sp)p(Rp)n(Sp)m is $(Sp)_5Rp(Sp)_5$.

In some embodiments, (Sp)m(Rp)n(Sp)p is $(Sp)_2Rp(Sp)_2$. In some embodiments, (Sp)m(Rp)n(Sp)p is $(Sp)_3Rp(Sp)_3$. In some embodiments, (Sp)m(Rp)n(Sp)p is $(Sp)_4Rp(Sp)_4$. In some embodiments, (Sp)m(Rp)n(Sp)p is $(Sp)mRp(Sp)_5$. In some embodiments, (Sp)m(Rp)n(Sp)p is $(Sp)_2Rp(Sp)_5$. In some embodiments, (Sp)m(Rp)n(Sp)p is $(Sp)_3Rp(Sp)_5$. In some embodiments, (Sp)m(Rp)n(Sp)p is (Sp)$_4$Rp(Sp)$_5$. In some embodiments, (Sp)m(Rp)n(Sp)p is (Sp)$_5$Rp(Sp)$_5$.

In some embodiments, provided oligonucleotides are blockmers. In some embodiments, provided oligonucleotide are altmers. In some embodiments, provided oligonucleotides are altmers comprising alternating blocks. In some embodiments, a blockmer or an altmer can be defined by chemical modifications (including presence or absence), e.g., base modifications, sugar modification, internucleotidic linkage modifications, stereochemistry, etc., or patterns thereof. Example chemical modifications, stereochemistry and patterns thereof for a block and/or an alternating unit include but are not limited to those described in this disclosure, such as those described for an oligonucleotide, etc. In some embodiments, a blockmer comprises a pattern of . . . SS . . . RR . . . SS . . . RR . . . . In some embodiments, an altmer comprises a pattern of SRSRSRSR.

In some embodiments, a provided pattern of backbone chiral centers comprises repeating (Sp)m(Rp)n, (Rp)n(Sp)m, (Np)p(Rp)n(Sp)m, or (Sp)p(Rp)n(Sp)m units. In some embodiments, a repeating unit is (Sp)m(Rp)n. In some embodiments, a repeating unit is SpRp. In some embodiments, a repeating unit is SpSpRp. In some embodiments, a repeating unit is SpRpRp. In some embodiments, a repeating unit is RpRpSp. In some embodiments, a repeating unit is (Rp)n(Sp)m. In some embodiments, a repeating unit is (Np)p(Rp)n(Sp)m. In some embodiments, a repeating unit is (Sp)p(Rp)n(Sp)m.

In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages in provided oligonucleotides or segments thereof (e.g., 5'-wing regions, core regions, 3'-wing regions, portions thereof, etc.) are natural phosphate linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages in provided oligonucleotides are natural phosphate linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of one or more regions are natural phosphate linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of a 5'-wing region are natural phosphate linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of a 3'-wing region are natural phosphate linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of the 5'- and the 3'-wing regions of provided oligonucleotides are natural phosphate linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of the 5'-wing and the core regions of provided oligonucleotides are natural phosphate linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of the core and the 3'-wing regions of provided oligonucleotides are natural phosphate linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of the 5'- and the 3'-wing, and the core regions of provided oligonucleotides are natural phosphate linkages. In some embodiments, at least 5% of the internucleotidic linkages are natural phosphate linkages. In some embodiments, at least 10% of the internucleotidic linkages are natural phosphate linkages. In some embodiments, at least 15% of the internucleotidic linkages are natural phosphate linkages. In some embodiments, at least 20% of the internucleotidic linkages are natural phosphate linkages. In some embodiments, at least 25% of the internucleotidic linkages are natural phosphate linkages. In some embodiments, at least 30% of the internucleotidic linkages are natural phosphate linkages. In some embodiments, at least 35% of the internucleotidic linkages are natural phosphate linkages. In some embodiments, at least 40% of the internucleotidic linkages are natural phosphate linkages. In some embodiments, at least 45% of the internucleotidic linkages are natural phosphate linkages. In some embodiments, at least 50% of the internucleotidic linkages are natural phosphate linkages. In some embodiments, at least 55% of the internucleotidic linkages are natural phosphate linkages. In some embodiments, at least 60% of the internucleotidic linkages are natural phosphate linkages. In some embodiments, at least 65% of the internucleotidic linkages are natural phosphate linkages. In some embodiments, at least 66% of the internucleotidic linkages are natural phosphate linkages. In some embodiments, at least 67% of the internucleotidic linkages are natural phosphate linkages. In some embodiments, at least 70% of the internucleotidic linkages are natural phosphate linkages. In some embodiments, at least 75% of the internucleotidic linkages are natural phosphate linkages. In some embodiments, at least 80% of the internucleotidic linkages are natural phosphate linkages. In some embodiments, at least 85% of the internucleotidic linkages are natural phosphate linkages. In some embodiments, at least 90% of the internucleotidic linkages are natural phosphate linkages. In some embodiments, at least 95% of the internucleotidic linkages are natural phosphate linkages. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. internucleotidic linkages are natural phosphate linkages. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. internucleotidic linkages of a 5'-wing region, core region, and/or 3'-wing region are natural phosphate linkages. In some embodiments, at least 1 internucleotidic linkage is natural phosphate linkage. In some embodiments, at least 2 internucleotidic linkages are natural phosphate linkages. In some embodiments, at least 3 internucleotidic linkages are natural phosphate linkages. In some embodiments, at least 4 internucleotidic linkages are natural phosphate linkages. In some embodiments, at least 5 internucleotidic linkages are natural phosphate linkages. In some embodiments, at least 6 internucleotidic linkages are natural phosphate linkages. In some embodiments, at least 7 internucleotidic linkages are natural phosphate linkages. In some embodiments, at least 8 internucleotidic linkages are natural phosphate linkages. In some embodiments, at least 9 internucleotidic linkages are natural phosphate linkages. In some embodiments, at least 10 internucleotidic linkages are natural phosphate linkages. In some embodiments, at least 11 internucleotidic linkages are natural phosphate linkages. In some embodiments, at least 12 internucleotidic linkages are natural phosphate linkages. In some embodiments, at least 13 internucleotidic linkages are natural phosphate linkages. In some embodiments, at least 14 internucleotidic linkages are natural phosphate linkages. In some embodiments, at least 15 internucleotidic linkages are natural phosphate linkages. In some embodiments, at least 16 internucleotidic linkages are natural phosphate linkages. In some embodiments, at least 17 internucleotidic linkages are natural phosphate linkages. In some embodiments, at least 18 internucleotidic linkages are natural phosphate linkages. In some embodiments, at least 19 internucleotidic linkages are natural phosphate linkages. In some embodiments, at least 20 internucleotidic linkages are natural phosphate linkages. In some embodiments, at least 21 internucleotidic linkages are natural phosphate linkages. In some embodiments, at least 25 internucleotidic linkages are natural phosphate linkages. In some embodiments, at least 30 internucleotidic linkages are natural phosphate linkages. In some embodiments, at least 2 consecutive internucleotidic linkages are natural phosphate linkages. In some embodiments, at least 3 consecutive internucleotidic linkages are natural phosphate linkages. In some embodiments, at least 4 consecutive internucleotidic linkages are natural phosphate linkages. In some embodiments, at least 5 consecutive internucleotidic linkages are natural phosphate linkages. In some embodiments, at least 6 consecutive internucleotidic linkages are natural phosphate linkages. In some embodiments, at least 7 consecutive internucleotidic linkages are natural phosphate linkages. In some embodiments, at least 8 consecutive internucleotidic linkages are natural phosphate linkages. In some embodiments, at least 9 consecutive internucleotidic linkages are natural phosphate linkages. In some embodiments, at least 10 consecutive internucleotidic linkages are natural phosphate linkages. In some embodiments, at least 11 consecutive internucleotidic linkages are natural phosphate linkages. In some embodiments, at least 12 consecutive internucleotidic linkages are natural phosphate linkages. In some embodiments, at least 13 consecutive internucleotidic linkages are natural phosphate linkages. In some embodiments, at least 14 consecutive internucleotidic linkages are natural phosphate linkages. In some embodiments, at least 15 consecutive internucleotidic linkages are natural phosphate linkages. In some embodiments, at least 16 consecutive internucleotidic linkages are natural phosphate linkages. In some embodiments, at least 17 consecutive internucleotidic linkages are natural phosphate linkages. In some embodiments, at least 18 consecutive internucleotidic linkages are natural phosphate linkages. In some embodiments, at least 19 consecutive internucleotidic linkages are natural phosphate linkages. In some embodiments, at least 20 consecutive internucleotidic linkages are natural phosphate linkages. In some embodiments, at least 21 consecutive internucleotidic linkages are natural phosphate linkages. In some embodiments, at least 25 consecutive internucleotidic linkages are natural phosphate linkages. In some embodiments, at least 30 consecutive internucleotidic linkages are natural phosphate linkages. In some embodiments, only one internucleotidic linkage of a provided oligonucleotide, or a segment thereof (e.g., 5'-wing region, core region, 3'-wing region, portions thereof, etc.) is natural phosphate linkage. In some embodiments, only one internucleotidic linkage of a provided oligonucleotide is natural phosphate linkage. In some embodiments, only one internucleotidic linkage of a 5'-wing region is natural phosphate linkage. In some embodiments, only one internucleotidic linkage of a 3'-wing region is natural phosphate linkage. In some embodiments, only one internucleotidic linkage of a 5'-wing region is natural phosphate linkage, and only one internucleotidic linkage of a 3'-wing region is natural phosphate linkage.

In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages in provided oligonucleotides or segments thereof (e.g., 5'-wing regions, core regions, 3'-wing regions, portions thereof, etc.) are non-natural internucleotidic linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages in provided oligonucleotides are non-natural internucleotidic linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of one or more regions are non-natural internucleotidic linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of a 5'-wing region are non-natural internucleotidic linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of a 3'-wing region are non-natural internucleotidic linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of the 5'- and the 3'-wing regions of provided oligonucleotides are non-natural internucleotidic linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of the 5'-wing and the core regions of provided oligonucleotides are non-natural internucleotidic linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of the core and the 3'-wing regions of provided oligonucleotides are non-natural internucleotidic linkages. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages of the 5'- and the 3'-wing, and the core regions of provided oligonucleotides are non-natural internucleotidic linkages. In some embodiments, at least 5% of the internucleotidic linkages are non-natural internucleotidic linkages. In some embodiments, at least 10% of the internucleotidic linkages are non-natural internucleotidic linkages. In some embodiments, at least 15% of the internucleotidic linkages are non-natural internucleotidic linkages. In some embodiments, at least 20% of the internucleotidic linkages are non-natural internucleotidic linkages. In some embodiments, at least 25% of the internucleotidic linkages are non-natural internucleotidic linkages. In some embodiments, at least 30% of the internucleotidic linkages are non-natural internucleotidic linkages. In some embodiments, at least 35% of the internucleotidic linkages are non-natural internucleotidic linkages. In some embodiments, at least 40% of the internucleotidic linkages are non-natural internucleotidic linkages. In some embodiments, at least 45% of the internucleotidic linkages are non-natural internucleotidic linkages. In some embodiments, at least 50% of the internucleotidic linkages are non-natural internucleotidic linkages. In some embodiments, at least 55% of the internucleotidic linkages are non-natural internucleotidic linkages. In some embodiments, at least 60% of the internucleotidic linkages are non-natural internucleotidic linkages. In some embodiments, at least 65% of the internucleotidic linkages are non-natural internucleotidic linkages. In some embodiments, at least 66% of the internucleotidic linkages are non-natural internucleotidic linkages. In some embodiments, at least 67% of the internucleotidic linkages are non-natural internucleotidic linkages. In some embodiments, at least 70% of the internucleotidic linkages are non-natural internucleotidic linkages. In some embodiments, at least 75% of the internucleotidic linkages are non-natural internucleotidic linkages. In some embodiments, at least 80% of the internucleotidic linkages are non-natural internucleotidic linkages. In some embodiments, at least 85% of the internucleotidic linkages are non-natural internucleotidic linkages. In some embodiments, at least 90% of the internucleotidic linkages are non-natural internucleotidic linkages. In some embodiments, at least 95% of the internucleotidic linkages are non-natural internucleotidic linkages. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. internucleotidic linkages are non-natural internucleotidic linkages. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. internucleotidic linkages of a 5'-wing region, core region, and/or 3'-wing region are non-natural internucleotidic linkages. In some embodiments, at least 1 internucleotidic linkage is non-natural internucleotidic linkage. In some embodiments, at least 2 internucleotidic linkages are non-natural internucleotidic linkages. In some embodiments, at least 3 internucleotidic linkages are non-natural internucleotidic linkages. In some embodiments, at least 4 internucleotidic linkages are non-natural internucleotidic linkages. In some embodiments, at least 5 internucleotidic linkages are non-natural internucleotidic linkages. In some embodiments, at least 6 internucleotidic linkages are non-natural internucleotidic linkages. In some embodiments, at least 7 internucleotidic linkages are non-natural internucleotidic linkages. In some embodiments, at least 8 internucleotidic linkages are non-natural internucleotidic linkages. In some embodiments, at least 9 internucleotidic linkages are non-natural internucleotidic linkages. In some embodiments, at least 10 internucleotidic linkages are non-natural internucleotidic linkages. In some embodiments, at least 11 internucleotidic linkages are non-natural internucleotidic linkages. In some embodiments, at least 12 internucleotidic linkages are non-natural internucleotidic linkages. In some embodiments, at least 13 internucleotidic linkages are non-natural internucleotidic linkages. In some embodiments, at least 14 internucleotidic linkages are non-natural internucleotidic linkages. In some embodiments, at least 15 internucleotidic linkages are non-natural internucleotidic linkages. In some embodiments, at least 16 internucleotidic linkages are non-natural internucleotidic linkages. In some embodiments, at least 17 internucleotidic linkages are non-natural internucleotidic linkages. In some embodiments, at least 18 internucleotidic linkages are non-natural internucleotidic linkages. In some embodiments, at least 19 internucleotidic linkages are non-natural internucleotidic linkages. In some embodiments, at least 20 internucleotidic linkages are non-natural internucleotidic linkages. In some embodiments, at least 21 internucleotidic linkages are non-natural internucleotidic linkages. In some embodiments, at least 25 internucleotidic linkages are non-natural internucleotidic linkages. In some embodiments, at least 30 internucleotidic linkages are non-natural internucleotidic linkages. In some embodiments, at least 2 consecutive internucleotidic linkages are non-natural internucleotidic linkages. In some embodiments, at least 3 consecutive internucleotidic linkages are non-natural internucleotidic linkages. In some embodiments, at least 4 consecutive internucleotidic linkages are non-natural internucleotidic linkages. In some embodiments, at least 5 consecutive internucleotidic linkages are non-natural internucleotidic linkages. In some embodiments, at least 6 consecutive internucleotidic linkages are non-natural internucleotidic linkages. In some embodiments, at least 7 consecutive internucleotidic linkages are non-natural internucleotidic linkages. In some embodiments, at least 8 consecutive internucleotidic linkages are non-natural internucleotidic linkages. In some embodiments, at least 9 consecutive internucleotidic linkages are non-natural internucleotidic linkages. In some embodiments, at least 10 consecutive internucleotidic linkages are non-natural internucleotidic linkages. In some embodiments, at least 11 consecutive internucleotidic linkages are non-natural internucleotidic linkages. In some embodiments, at least 12 consecutive internucleotidic linkages are non-natural internucleotidic linkages. In some embodiments, at least 13 consecutive internucleotidic linkages are non-natural internucleotidic linkages. In some embodiments, at least 14 consecutive internucleotidic linkages are non-natural internucleotidic linkages. In some embodiments, at least 15 consecutive internucleotidic linkages are non-natural internucleotidic linkages. In some embodiments, at least 16 consecutive internucleotidic linkages are non-natural internucleotidic linkages. In some embodiments, at least 17 consecutive internucleotidic linkages are non-natural internucleotidic linkages. In some embodiments, at least 18 consecutive internucleotidic linkages are non-natural internucleotidic linkages. In some embodiments, at least 19 consecutive internucleotidic linkages are non-natural internucleotidic linkages. In some embodiments, at least 20 consecutive internucleotidic linkages are non-natural internucleotidic linkages. In some embodiments, at least 21 consecutive internucleotidic linkages are non-natural internucleotidic linkages. In some embodiments, at least 25 consecutive internucleotidic linkages are non-natural internucleotidic linkages. In some embodiments, at least 30 consecutive internucleotidic linkages are non-natural internucleotidic linkages. In some embodiments, only one internucleotidic linkage of a provided oligonucleotide, or a segment thereof (e.g., 5'-wing region, core region, 3'-wing region, portions thereof, etc.) is non-natural internucleotidic linkage. In some embodiments, only one internucleotidic linkage of a provided oligonucleotide is non-natural internucleotidic linkage. In some embodiments, only one internucleotidic linkage of a 5'-wing region is non-natural internucleotidic linkage. In some embodiments, only one internucleotidic linkage of a 3'-wing region is non-natural internucleotidic linkage. In some embodiments, only one internucleotidic linkage of a 5'-wing region is non-natural internucleotidic linkage, and only one internucleotidic linkage of a 3'-wing region is non-natural internucleotidic linkage. In some embodiments, a non-natural internucleotidic linkage is independently of formula VII, VII-a-1, VII-a-2, VII-b, VII-c, VII-d, or VII-e, or a salt form thereof, as described in the present disclosure. In some embodiments, a non-natural internucleotidic linkage is chiral. In some embodiments, a non-natural internucleotidic linkage is chiral and is independently of formula VII, VII-a-1, VII-a-2, VII-b, VII-c, VII-d, or VII-e, or a salt form thereof, as described in the present disclosure.

In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral linkage phosphorus in chiral internucleotidic linkages in provided oligonucleotides or segments thereof (e.g., 5'-wing regions, core regions, 3'-wing regions, portions thereof, etc.) are chirally controlled and are Sp (1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages are Sp). In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of provided oligonucleotides are Sp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of one or more regions are Sp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of a 5'-wing region are Sp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of a 3'-wing region are Sp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of the 5'- and the 3'-wing regions of provided oligonucleotides are Sp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of the 5'-wing and the core regions of provided oligonucleotides are Sp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of the core and the 3'-wing regions of provided oligonucleotides are Sp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of the 5'- and the 3'-wing, and the core regions of provided oligonucleotides are Sp. In some embodiments, at least 5% of the chiral internucleotidic linkages are Sp. In some embodiments, at least 10% of the chiral internucleotidic linkages are Sp. In some embodiments, at least 15% of the chiral internucleotidic linkages are Sp. In some embodiments, at least 20% of the chiral internucleotidic linkages are Sp. In some embodiments, at least 25% of the chiral internucleotidic linkages are Sp. In some embodiments, at least 30% of the chiral internucleotidic linkages are Sp. In some embodiments, at least 35% of the chiral internucleotidic linkages are Sp. In some embodiments, at least 40% of the chiral internucleotidic linkages are Sp. In some embodiments, at least 45% of the chiral internucleotidic linkages are Sp. In some embodiments, at least 50% of the chiral internucleotidic linkages are Sp. In some embodiments, at least 55% of the chiral internucleotidic linkages are Sp. In some embodiments, at least 60% of the chiral internucleotidic linkages are Sp. In some embodiments, at least 65% of the chiral internucleotidic linkages are Sp. In some embodiments, at least 66% of the chiral internucleotidic linkages are Sp. In some embodiments, at least 67% of the chiral internucleotidic linkages are Sp. In some embodiments, at least 70% of the chiral internucleotidic linkages are Sp. In some embodiments, at least 75% of the chiral internucleotidic linkages are Sp. In some embodiments, at least 80% of the chiral internucleotidic linkages are Sp. In some embodiments, at least 85% of the chiral internucleotidic linkages are Sp. In some embodiments, at least 90% of the chiral internucleotidic linkages are Sp. In some embodiments, at least 95% of the chiral internucleotidic linkages are Sp. In some embodiments, each chiral internucleotidic linkages is Sp. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. chiral internucleotidic linkages are Sp. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. chiral internucleotidic linkages of a 5'-wing region, core region, and/or 3'-wing region are Sp. In some embodiments, at least 1 chiral internucleotidic linkage is Sp. In some embodiments, at least 2 chiral internucleotidic linkages are Sp. In some embodiments, at least 3 chiral internucleotidic linkages are Sp. In some embodiments, at least 4 chiral internucleotidic linkages are Sp. In some embodiments, at least 5 chiral internucleotidic linkages are Sp. In some embodiments, at least 6 chiral internucleotidic linkages are Sp. In some embodiments, at least 7 chiral internucleotidic linkages are Sp. In some embodiments, at least 8 chiral internucleotidic linkages are Sp. In some embodiments, at least 9 chiral internucleotidic linkages are Sp. In some embodiments, at least 10 chiral internucleotidic linkages are Sp. In some embodiments, at least 11 chiral internucleotidic linkages are Sp. In some embodiments, at least 12 chiral internucleotidic linkages are Sp. In some embodiments, at least 13 chiral internucleotidic linkages are Sp. In some embodiments, at least 14 chiral internucleotidic linkages are Sp. In some embodiments, at least 15 chiral internucleotidic linkages are Sp. In some embodiments, at least 16 chiral internucleotidic linkages are Sp. In some embodiments, at least 17 chiral internucleotidic linkages are Sp. In some embodiments, at least 18 chiral internucleotidic linkages are Sp. In some embodiments, at least 19 chiral internucleotidic linkages are Sp. In some embodiments, at least 20 chiral internucleotidic linkages are Sp. In some embodiments, at least 21 chiral internucleotidic linkages are Sp. In some embodiments, at least 25 chiral internucleotidic linkages are Sp. In some embodiments, at least 30 chiral internucleotidic linkages are Sp. In some embodiments, at least 2 consecutive chiral internucleotidic linkages are Sp. In some embodiments, at least 3 consecutive chiral internucleotidic linkages are Sp. In some embodiments, at least 4 consecutive chiral internucleotidic linkages are Sp. In some embodiments, at least 5 consecutive chiral internucleotidic linkages are Sp. In some embodiments, at least 6 consecutive chiral internucleotidic linkages are Sp. In some embodiments, at least 7 consecutive chiral internucleotidic linkages are Sp. In some embodiments, at least 8 consecutive chiral internucleotidic linkages are Sp. In some embodiments, at least 9 consecutive chiral internucleotidic linkages are Sp. In some embodiments, at least 10 consecutive chiral internucleotidic linkages are Sp. In some embodiments, at least 11 consecutive chiral internucleotidic linkages are Sp. In some embodiments, at least 12 consecutive chiral internucleotidic linkages are Sp. In some embodiments, at least 13 consecutive chiral internucleotidic linkages are Sp. In some embodiments, at least 14 consecutive chiral internucleotidic linkages are Sp. In some embodiments, at least 15 consecutive chiral internucleotidic linkages are Sp. In some embodiments, at least 16 consecutive chiral internucleotidic linkages are Sp. In some embodiments, at least 17 consecutive chiral internucleotidic linkages are Sp. In some embodiments, at least 18 consecutive chiral internucleotidic linkages are Sp. In some embodiments, at least 19 consecutive chiral internucleotidic linkages are Sp. In some embodiments, at least 20 consecutive chiral internucleotidic linkages are Sp. In some embodiments, at least 21 consecutive chiral internucleotidic linkages are Sp. In some embodiments, at least 25 consecutive chiral internucleotidic linkages are Sp. In some embodiments, at least 30 consecutive chiral internucleotidic linkages are Sp. In some embodiments, only one internucleotidic linkage of a provided oligonucleotide, or a segment thereof (e.g., 5'-wing region, core region, 3'-wing region, portions thereof, etc.) is Sp. In some embodiments, only one internucleotidic linkage of a provided oligonucleotide is Sp. In some embodiments, only one internucleotidic linkage of a 5'-wing region is Sp. In some embodiments, only one internucleotidic linkage of a 3'-wing region is Sp. In some embodiments, only one internucleotidic linkage of a 5'-wing region is Sp, and only one internucleotidic linkage of a 3'-wing region is Sp. In some embodiments, one internucleotidic linkage of a 5'-wing region is Sp, and only one internucleotidic linkage of a 3'-wing region is Sp, and only one internucleotidic linkage of a core region is Rp. In some embodiments, each chiral internucleotidic linkage is independently of formula VII, VII-a-1, VII-a-2, VII-b, VII-c, VII-d, or VII-e, or a salt form thereof, as described in the present disclosure.

In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral linkage phosphorus in chiral internucleotidic linkages in provided oligonucleotides or segments thereof (e.g., 5'-wing regions, core regions, 3'-wing regions, portions thereof, etc.) are chirally controlled and are Rp (1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages are Rp). In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of provided oligonucleotides are Rp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of one or more regions are Rp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of a 5'-wing region are Rp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of a 3'-wing region are Rp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of the 5'- and the 3'-wing regions of provided oligonucleotides are Rp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of the 5'-wing and the core regions of provided oligonucleotides are Rp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of the core and the 3'-wing regions of provided oligonucleotides are Rp. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of chiral internucleotidic linkages of the 5'- and the 3'-wing, and the core regions of provided oligonucleotides are Rp. In some embodiments, at least 5% of the chiral internucleotidic linkages are Rp. In some embodiments, at least 10% of the chiral internucleotidic linkages are Rp. In some embodiments, at least 15% of the chiral internucleotidic linkages are Rp. In some embodiments, at least 20% of the chiral internucleotidic linkages are Rp. In some embodiments, at least 25% of the chiral internucleotidic linkages are Rp. In some embodiments, at least 30% of the chiral internucleotidic linkages are Rp. In some embodiments, at least 35% of the chiral internucleotidic linkages are Rp. In some embodiments, at least 40% of the chiral internucleotidic linkages are Rp. In some embodiments, at least 45% of the chiral internucleotidic linkages are Rp. In some embodiments, at least 50% of the chiral internucleotidic linkages are Rp. In some embodiments, at least 55% of the chiral internucleotidic linkages are Rp. In some embodiments, at least 60% of the chiral internucleotidic linkages are Rp. In some embodiments, at least 65% of the chiral internucleotidic linkages are Rp. In some embodiments, at least 66% of the chiral internucleotidic linkages are Rp. In some embodiments, at least 67% of the chiral internucleotidic linkages are Rp. In some embodiments, at least 70% of the chiral internucleotidic linkages are Rp. In some embodiments, at least 75% of the chiral internucleotidic linkages are Rp. In some embodiments, at least 80% of the chiral internucleotidic linkages are Rp. In some embodiments, at least 85% of the chiral internucleotidic linkages are Rp. In some embodiments, at least 90% of the chiral internucleotidic linkages are Rp. In some embodiments, at least 95% of the chiral internucleotidic linkages are Rp. In some embodiments, each chiral internucleotidic linkages is Rp. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. chiral internucleotidic linkages are Rp. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. chiral internucleotidic linkages of a 5'-wing region, core region, and/or 3'-wing region are Rp. In some embodiments, at least 1 chiral internucleotidic linkage is Rp. In some embodiments, at least 2 chiral internucleotidic linkages are Rp. In some embodiments, at least 3 chiral internucleotidic linkages are Rp. In some embodiments, at least 4 chiral internucleotidic linkages are Rp. In some embodiments, at least 5 chiral internucleotidic linkages are Rp. In some embodiments, at least 6 chiral internucleotidic linkages are Rp. In some embodiments, at least 7 chiral internucleotidic linkages are Rp. In some embodiments, at least 8 chiral internucleotidic linkages are Rp. In some embodiments, at least 9 chiral internucleotidic linkages are Rp. In some embodiments, at least 10 chiral internucleotidic linkages are Rp. In some embodiments, at least 11 chiral internucleotidic linkages are Rp. In some embodiments, at least 12 chiral internucleotidic linkages are Rp. In some embodiments, at least 13 chiral internucleotidic linkages are Rp. In some embodiments, at least 14 chiral internucleotidic linkages are Rp. In some embodiments, at least 15 chiral internucleotidic linkages are Rp. In some embodiments, at least 16 chiral internucleotidic linkages are Rp. In some embodiments, at least 17 chiral internucleotidic linkages are Rp. In some embodiments, at least 18 chiral internucleotidic linkages are Rp. In some embodiments, at least 19 chiral internucleotidic linkages are Rp. In some embodiments, at least 20 chiral internucleotidic linkages are Rp. In some embodiments, at least 21 chiral internucleotidic linkages are Rp. In some embodiments, at least 25 chiral internucleotidic linkages are Rp. In some embodiments, at least 30 chiral internucleotidic linkages are Rp. In some embodiments, at least 2 consecutive chiral internucleotidic linkages are Rp. In some embodiments, at least 3 consecutive chiral internucleotidic linkages are Rp. In some embodiments, at least 4 consecutive chiral internucleotidic linkages are Rp. In some embodiments, at least 5 consecutive chiral internucleotidic linkages are Rp. In some embodiments, at least 6 consecutive chiral internucleotidic linkages are Rp. In some embodiments, at least 7 consecutive chiral internucleotidic linkages are Rp. In some embodiments, at least 8 consecutive chiral internucleotidic linkages are Rp. In some embodiments, at least 9 consecutive chiral internucleotidic linkages are Rp. In some embodiments, at least 10 consecutive chiral internucleotidic linkages are Rp. In some embodiments, at least 11 consecutive chiral internucleotidic linkages are Rp. In some embodiments, at least 12 consecutive chiral internucleotidic linkages are Rp. In some embodiments, at least 13 consecutive chiral internucleotidic linkages are Rp. In some embodiments, at least 14 consecutive chiral internucleotidic linkages are Rp. In some embodiments, at least 15 consecutive chiral internucleotidic linkages are Rp. In some embodiments, at least 16 consecutive chiral internucleotidic linkages are Rp. In some embodiments, at least 17 consecutive chiral internucleotidic linkages are Rp. In some embodiments, at least 18 consecutive chiral internucleotidic linkages are Rp. In some embodiments, at least 19 consecutive chiral internucleotidic linkages are Rp. In some embodiments, at least 20 consecutive chiral internucleotidic linkages are Rp. In some embodiments, at least 21 consecutive chiral internucleotidic linkages are Rp. In some embodiments, at least 25 consecutive chiral internucleotidic linkages are Rp. In some embodiments, at least 30 consecutive chiral internucleotidic linkages are Rp. In some embodiments, only one internucleotidic linkage of a provided oligonucleotide, or a segment thereof (e.g., 5'-wing region, core region, 3'-wing region, portions thereof, etc.) is Rp. In some embodiments, only one internucleotidic linkage of a provided oligonucleotide is Rp. In some embodiments, only one internucleotidic linkage of a 5'-wing region is Rp. In some embodiments, only one internucleotidic linkage of a 3'-wing region is Rp. In some embodiments, only one internucleotidic linkage of a 5'-wing region is Rp, and only one internucleotidic linkage of a 3'-wing region is Rp. In some embodiments, only one internucleotidic linkage of a core region is Rp. In some embodiments, each chiral internucleotidic linkage is independently of formula VII, VII-a-1, VII-a-2, VII-b, VII-c, VII-d, or VII-e, or a salt form thereof, as described in the present disclosure.

In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties in provided oligonucleotides or segments thereof (e.g., 5'-wing regions, core regions, 3'-wing regions, portions thereof, etc.) comprise modifications (1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties are modified). In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of provided oligonucleotides are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of one or more regions are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of a 5'-wing region are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of a 3'-wing region are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'- and the 3'-wing regions of provided oligonucleotides are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'-wing and the core regions of provided oligonucleotides are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the core and the 3'-wing regions of provided oligonucleotides are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'- and the 3'-wing, and the core regions of provided oligonucleotides are modified. In some embodiments, at least 5% of the sugar moieties are modified. In some embodiments, at least 10% of the sugar moieties are modified. In some embodiments, at least 15% of the sugar moieties are modified. In some embodiments, at least 20% of the sugar moieties are modified. In some embodiments, at least 25% of the sugar moieties are modified. In some embodiments, at least 30% of the sugar moieties are modified. In some embodiments, at least 35% of the sugar moieties are modified. In some embodiments, at least 40% of the sugar moieties are modified. In some embodiments, at least 45% of the sugar moieties are modified. In some embodiments, at least 50% of the sugar moieties are modified. In some embodiments, at least 55% of the sugar moieties are modified. In some embodiments, at least 60% of the sugar moieties are modified. In some embodiments, at least 65% of the sugar moieties are modified. In some embodiments, at least 66% of the sugar moieties are modified. In some embodiments, at least 67% of the sugar moieties are modified. In some embodiments, at least 70% of the sugar moieties are modified. In some embodiments, at least 75% of the sugar moieties are modified. In some embodiments, at least 80% of the sugar moieties are modified. In some embodiments, at least 85% of the sugar moieties are modified. In some embodiments, at least 90% of the sugar moieties are modified. In some embodiments, at least 95% of the sugar moieties are modified. In some embodiments, each sugar moieties is modified. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. sugar moieties are modified. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. sugar moieties of a 5'-wing region, core region, and/or 3'-wing region are modified. In some embodiments, at least 1 sugar moiety is modified. In some embodiments, at least 2 sugar moieties are modified. In some embodiments, at least 3 sugar moieties are modified. In some embodiments, at least 4 sugar moieties are modified. In some embodiments, at least 5 sugar moieties are modified. In some embodiments, at least 6 sugar moieties are modified. In some embodiments, at least 7 sugar moieties are modified. In some embodiments, at least 8 sugar moieties are modified. In some embodiments, at least 9 sugar moieties are modified. In some embodiments, at least 10 sugar moieties are modified. In some embodiments, at least 11 sugar moieties are modified. In some embodiments, at least 12 sugar moieties are modified. In some embodiments, at least 13 sugar moieties are modified. In some embodiments, at least 14 sugar moieties are modified. In some embodiments, at least 15 sugar moieties are modified. In some embodiments, at least 16 sugar moieties are modified. In some embodiments, at least 17 sugar moieties are modified. In some embodiments, at least 18 sugar moieties are modified. In some embodiments, at least 19 sugar moieties are modified. In some embodiments, at least 20 sugar moieties are modified. In some embodiments, at least 21 sugar moieties are modified. In some embodiments, at least 25 sugar moieties are modified. In some embodiments, at least 30 sugar moieties are modified. In some embodiments, at least 2 consecutive sugar moieties are modified. In some embodiments, at least 3 consecutive sugar moieties are modified. In some embodiments, at least 4 consecutive sugar moieties are modified. In some embodiments, at least 5 consecutive sugar moieties are modified. In some embodiments, at least 6 consecutive sugar moieties are modified. In some embodiments, at least 7 consecutive sugar moieties are modified. In some embodiments, at least 8 consecutive sugar moieties are modified. In some embodiments, at least 9 consecutive sugar moieties are modified. In some embodiments, at least 10 consecutive sugar moieties are modified. In some embodiments, at least 11 consecutive sugar moieties are modified. In some embodiments, at least 12 consecutive sugar moieties are modified. In some embodiments, at least 13 consecutive sugar moieties are modified. In some embodiments, at least 14 consecutive sugar moieties are modified. In some embodiments, at least 15 consecutive sugar moieties are modified. In some embodiments, at least 16 consecutive sugar moieties are modified. In some embodiments, at least 17 consecutive sugar moieties are modified. In some embodiments, at least 18 consecutive sugar moieties are modified. In some embodiments, at least 19 consecutive sugar moieties are modified. In some embodiments, at least 20 consecutive sugar moieties are modified. In some embodiments, at least 21 consecutive sugar moieties are modified. In some embodiments, at least 25 consecutive sugar moieties are modified. In some embodiments, at least 30 consecutive sugar moieties are modified. In some embodiments, only one sugar moiety of a provided oligonucleotide, or a segment thereof (e.g., 5'-wing region, core region, 3'-wing region, portions thereof, etc.) is modified. In some embodiments, only one internucleotidic linkage of a provided oligonucleotide is modified. In some embodiments, only one internucleotidic linkage of a 5'-wing region is modified. In some embodiments, only one internucleotidic linkage of a 3'-wing region is modified. In some embodiments, only one internucleotidic linkage of a 5'-wing region is modified, and only one internucleotidic linkage of a 3'-wing region is modified. In some embodiments, only one internucleotidic linkage of a core region is modified.

In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties in provided oligonucleotides or segments thereof (e.g., 5'-wing regions, core regions, 3'-wing regions, portions thereof, etc.) comprise modifications (1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties are modified). In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of provided oligonucleotides are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of one or more regions are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of a 5'-wing region are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of a 3'-wing region are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'- and the 3'-wing regions of provided oligonucleotides are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'-wing and the core regions of provided oligonucleotides are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the core and the 3'-wing regions of provided oligonucleotides are modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'- and the 3'-wing, and the core regions of provided oligonucleotides are modified. In some embodiments, at least 5% of the sugar moieties are modified. In some embodiments, at least 10% of the sugar moieties are modified. In some embodiments, at least 15% of the sugar moieties are modified. In some embodiments, at least 20% of the sugar moieties are modified. In some embodiments, at least 25% of the sugar moieties are modified. In some embodiments, at least 30% of the sugar moieties are modified. In some embodiments, at least 35% of the sugar moieties are modified. In some embodiments, at least 40% of the sugar moieties are modified. In some embodiments, at least 45% of the sugar moieties are modified. In some embodiments, at least 50% of the sugar moieties are modified. In some embodiments, at least 55% of the sugar moieties are modified. In some embodiments, at least 60% of the sugar moieties are modified. In some embodiments, at least 65% of the sugar moieties are modified. In some embodiments, at least 66% of the sugar moieties are modified. In some embodiments, at least 67% of the sugar moieties are modified. In some embodiments, at least 70% of the sugar moieties are modified. In some embodiments, at least 75% of the sugar moieties are modified. In some embodiments, at least 80% of the sugar moieties are modified. In some embodiments, at least 85% of the sugar moieties are modified. In some embodiments, at least 90% of the sugar moieties are modified. In some embodiments, at least 95% of the sugar moieties are modified. In some embodiments, each sugar moieties is modified. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. sugar moieties are modified. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. sugar moieties of a 5'-wing region, core region, and/or 3'-wing region are modified. In some embodiments, at least 1 sugar moiety is modified. In some embodiments, at least 2 sugar moieties are modified. In some embodiments, at least 3 sugar moieties are modified. In some embodiments, at least 4 sugar moieties are modified. In some embodiments, at least 5 sugar moieties are modified. In some embodiments, at least 6 sugar moieties are modified. In some embodiments, at least 7 sugar moieties are modified. In some embodiments, at least 8 sugar moieties are modified. In some embodiments, at least 9 sugar moieties are modified. In some embodiments, at least 10 sugar moieties are modified. In some embodiments, at least 11 sugar moieties are modified. In some embodiments, at least 12 sugar moieties are modified. In some embodiments, at least 13 sugar moieties are modified. In some embodiments, at least 14 sugar moieties are modified. In some embodiments, at least 15 sugar moieties are modified. In some embodiments, at least 16 sugar moieties are modified. In some embodiments, at least 17 sugar moieties are modified. In some embodiments, at least 18 sugar moieties are modified. In some embodiments, at least 19 sugar moieties are modified. In some embodiments, at least 20 sugar moieties are modified. In some embodiments, at least 21 sugar moieties are modified. In some embodiments, at least 25 sugar moieties are modified. In some embodiments, at least 30 sugar moieties are modified. In some embodiments, at least 2 consecutive sugar moieties are modified. In some embodiments, at least 3 consecutive sugar moieties are modified. In some embodiments, at least 4 consecutive sugar moieties are modified. In some embodiments, at least 5 consecutive sugar moieties are modified. In some embodiments, at least 6 consecutive sugar moieties are modified. In some embodiments, at least 7 consecutive sugar moieties are modified. In some embodiments, at least 8 consecutive sugar moieties are modified. In some embodiments, at least 9 consecutive sugar moieties are modified. In some embodiments, at least 10 consecutive sugar moieties are modified. In some embodiments, at least 11 consecutive sugar moieties are modified. In some embodiments, at least 12 consecutive sugar moieties are modified. In some embodiments, at least 13 consecutive sugar moieties are modified. In some embodiments, at least 14 consecutive sugar moieties are modified. In some embodiments, at least 15 consecutive sugar moieties are modified. In some embodiments, at least 16 consecutive sugar moieties are modified. In some embodiments, at least 17 consecutive sugar moieties are modified. In some embodiments, at least 18 consecutive sugar moieties are modified. In some embodiments, at least 19 consecutive sugar moieties are modified. In some embodiments, at least 20 consecutive sugar moieties are modified. In some embodiments, at least 21 consecutive sugar moieties are modified. In some embodiments, at least 25 consecutive sugar moieties are modified. In some embodiments, at least 30 consecutive sugar moieties are modified. In some embodiments, only one sugar moiety of a provided oligonucleotide, or a segment thereof (e.g., 5'-wing region, core region, 3'-wing region, portions thereof, etc.) is modified. In some embodiments, only one sugar moiety of a provided oligonucleotide is modified. In some embodiments, only one sugar moiety of a 5'-wing region is modified. In some embodiments, only one sugar moiety of a 3'-wing region is modified. In some embodiments, only one sugar moiety of a 5'-wing region is modified, and only one sugar moiety of a 3'-wing region is modified. In some embodiments, only one sugar moiety of a core region is modified. In some embodiments, each sugar moiety of a 5'-wing region is independently modified. In some embodiments, each sugar moiety of a 3'-wing region is independently modified. In some embodiments, each sugar moiety of a 5'-wing region and a 3'-wing region is independently modified. In some embodiments, a modification in a wing region is a 2'-modification. In some embodiments, each modification in a wing region is independently a 2'-modification. In some embodiments, each modification in a wing region is the same and is a 2'-modification. In some embodiments, each modification in a wing region is the same and is a 2'-OR modification as described in the present disclosure. In some embodiments, each modification in a wing region is the same and is 2'-OR, wherein R is optionally substituted $C_{1-6}$ aliphatic. In some embodiments, each modification in a wing region is the same and is 2'-OR, wherein R is optionally substituted $C_{1-6}$ alkyl. In some embodiments, each modification in a wing region is the same and is 2'-OR, wherein R is 2'-OMe. In some embodiments, each modification in a wing region is the same and is 2'-OR, wherein R is 2'-MOE. In some embodiments, each modification in a wing region is the same and is a LNA-type 2'-modification. In some embodiments, each modification in a wing region is the same and is (C2-O—CH$_2$—C4), (C2-O—C(R)$_2$—C4), (C2-O—(R)—CHR—C4), or (C2-O—(S)—CHR—C4) as described in the present disclosure (e.g., infra).

Various types of sugar modifications are known and can be utilized in accordance with the present disclosure. In some embodiments, a sugar modification is a 2'-modification. In some embodiments, a 2'-modification is 2'-F. In some embodiments, a 2'-modification is 2'-OR, wherein R is not hydrogen. In some embodiments, a 2'-modification is 2'-OR, wherein R is optionally substituted $C_{1-6}$ aliphatic. In some embodiments, a 2'-modification is 2'-OR, wherein R is optionally substituted $C_{1-6}$ alkyl. In some embodiments, a 2'-modification is 2'-OMe. In some embodiments, a 2'-modification is 2'-MOE. In some embodiments, a 2'-modification is a LNA sugar modification (C2-O—CH$_2$—C4). In some embodiments, a 2'-modification is (C2-O—C(R)$_2$—C4), wherein each R is independently as described in the present disclosure. In some embodiments, a 2'-modification is (C2-O—CHR—C4), wherein R is as described in the present disclosure. In some embodiments, a 2'-modification is (C2-O—(R)—CHR—C4), wherein R is as described in the present disclosure and is not hydrogen. In some embodiments, a 2'-modification is (C2-O—(S)—CHR—C4), wherein R is as described in the present disclosure and is not hydrogen. In some embodiments, R is optionally substituted $C_{1-6}$ aliphatic. In some embodiments, R is optionally substituted $C_{1-6}$ alkyl. In some embodiments, R is unsubstituted $C_{1-6}$ alkyl. In some embodiments, R is methyl. In some embodiments, R is ethyl. In some embodiments, a 2'-modification is (C2-O—CHR—C4), wherein R is optionally substituted $C_{1-6}$ aliphatic. In some embodiments, a 2'-modification is (C2-O—CHR—C4), wherein R is optionally substituted $C_{1-6}$ alkyl. In some embodiments, a 2'-modification is (C2-O—CHR—C4), wherein R is methyl. In some embodiments, a 2'-modification is (C2-O—CHR—C4), wherein R is ethyl. In some embodiments, a 2'-modification is (C2-O—(R)—CHR—C4), wherein R is optionally substituted $C_{1-6}$ aliphatic. In some embodiments, a 2'-modification is (C2-O—(R)—CHR—C4), wherein R is optionally substituted $C_{1-6}$ alkyl. In some embodiments, a 2'-modification is (C2-O—(R)—CHR—C4), wherein R is methyl. In some embodiments, a 2'-modification is (C2-O—(R)—CHR—C4), wherein R is ethyl. In some embodiments, a 2'-modification is (C2-O—(S)—CHR—C4), wherein R is optionally substituted $C_{1-6}$ aliphatic. In some embodiments, a 2'-modification is (C2-O—(S)—CHR—C4), wherein R is optionally substituted $C_{1-6}$ alkyl. In some embodiments, a 2'-modification is (C2-O—(S)—CHR—C4), wherein R is methyl. In some embodiments, a 2'-modification is (C2-O—(S)—CHR—C4), wherein R is ethyl. In some embodiments, a 2'-modification is C2-O—(R)—CH(CH$_2$CH$_3$)—C4. In some embodiments, a 2'-modification is C2-O—(S)—CH(CH$_2$CH$_3$)—C4.

In some embodiments, a core region comprises one or more modified sugar moieties. In some embodiments, a core region comprises two or more modified sugar moieties. In some embodiments, a core region comprises three or more modified sugar moieties. In some embodiments, a core region comprises four or more modified sugar moieties. In some embodiments, a core region comprises five or more modified sugar moieties. In some embodiments, a core region comprises six or more modified sugar moieties. In some embodiments, a core region comprises seven or more modified sugar moieties. In some embodiments, a core region comprises eight or more modified sugar moieties. In some embodiments, a core region comprises nine or more modified sugar moieties. In some embodiments, a core region comprises ten or more modified sugar moieties. In some embodiments, a core region comprises 11 or more modified sugar moieties. In some embodiments, a core region comprises 12 or more modified sugar moieties. In some embodiments, a core region comprises 13 or more modified sugar moieties. In some embodiments, a core region comprises 14 or more modified sugar moieties. In some embodiments, a core region comprises 15 or more modified sugar moieties. In some embodiments, a core region comprises 16 or more modified sugar moieties. In some embodiments, a core region comprises 17 or more modified sugar moieties. In some embodiments, a core region comprises 18 or more modified sugar moieties. In some embodiments, a core region comprises 19 or more modified sugar moieties. In some embodiments, a core region comprises 20 or more modified sugar moieties. In some embodiments, a core region comprises 21 or more modified sugar moieties. In some embodiments, a core region comprises 22 or more modified sugar moieties. In some embodiments, a core region comprises 23 or more modified sugar moieties. In some embodiments, a core region comprises 24 or more modified sugar moieties. In some embodiments, a core region comprises 25 or more modified sugar moieties. In some embodiments, a core region comprises 30 or more modified sugar moieties. In some embodiments, a core region comprises 35 or more modified sugar moieties. In some embodiments, a modified sugar moiety comprises a modification as described in the present disclosure. In some embodiments, a modified sugar moiety comprises a 2'-modification as described in the present disclosure (e.g., 2'-OMe, 2'-MOE, 2'-LNA type (C2-O—C(R)$_2$—C4, etc.). In some embodiments, each sugar moiety is a core region is not 2'-substituted (—CH$_2$— at 2'-position).

In some embodiments, a wing region, e.g., a 5'-wing region, a 3'-wing region, etc., comprises one or more modified sugar moieties. In some embodiments, a wing region comprises two or more modified sugar moieties. In some embodiments, a wing region comprises three or more modified sugar moieties. In some embodiments, a wing region comprises four or more modified sugar moieties. In some embodiments, a wing region comprises five or more modified sugar moieties. In some embodiments, a wing region comprises six or more modified sugar moieties. In some embodiments, a wing region comprises seven or more modified sugar moieties. In some embodiments, a wing region comprises eight or more modified sugar moieties. In some embodiments, a wing region comprises nine or more modified sugar moieties. In some embodiments, a wing region comprises ten or more modified sugar moieties. In some embodiments, a wing region comprises 11 or more modified sugar moieties. In some embodiments, a wing region comprises 12 or more modified sugar moieties. In some embodiments, a wing region comprises 13 or more modified sugar moieties. In some embodiments, a wing region comprises 14 or more modified sugar moieties. In some embodiments, a wing region comprises 15 or more modified sugar moieties. In some embodiments, a wing region comprises 16 or more modified sugar moieties. In some embodiments, a wing region comprises 17 or more modified sugar moieties. In some embodiments, a wing region comprises 18 or more modified sugar moieties. In some embodiments, a wing region comprises 19 or more modified sugar moieties. In some embodiments, a wing region comprises 20 or more modified sugar moieties. In some embodiments, a wing region comprises 21 or more modified sugar moieties. In some embodiments, a wing region comprises 22 or more modified sugar moieties. In some embodiments, a wing region comprises 23 or more modified sugar moieties. In some embodiments, a wing region comprises 24 or more modified sugar moieties. In some embodiments, a wing region comprises 25 or more modified sugar moieties. In some embodiments, a wing region comprises 30 or more modified sugar moieties. In some embodiments, a wing region comprises 35 or more modified sugar moieties. In some embodiments, each sugar moiety in a wing region is independently modified. In some embodiments, each sugar moiety in a 5'-wing region is independently modified. In some embodiments, each sugar moiety in a 3'-wing region is independently modified. In some embodiments, each sugar moiety in a 5'-wing region and a 3'-wing region is independently modified.

In some embodiments, a wing comprises one or more 2'-modified sugar moieties. In some embodiments, a wing comprises two or more 2'-modified sugar moieties. In some embodiments, a wing comprises three or more 2'-modified sugar moieties. In some embodiments, a wing comprises four or more 2'-modified sugar moieties. In some embodiments, a wing comprises five or more 2'-modified sugar moieties. In some embodiments, a wing comprises six or more 2'-modified sugar moieties. In some embodiments, a wing comprises seven or more 2'-modified sugar moieties. In some embodiments, a wing comprises eight or more 2'-modified sugar moieties. In some embodiments, a wing comprises nine or more 2'-modified sugar moieties. In some embodiments, a wing comprises ten or more 2'-modified sugar moieties. In some embodiments, a wing comprises 11 or more 2'-modified sugar moieties. In some embodiments, a wing comprises 12 or more 2'-modified sugar moieties. In some embodiments, a wing comprises 13 or more 2'-modified sugar moieties. In some embodiments, a wing comprises 14 or more 2'-modified sugar moieties. In some embodiments, a wing comprises 15 or more 2'-modified sugar moieties. In some embodiments, a wing comprises 16 or more 2'-modified sugar moieties. In some embodiments, a wing comprises 17 or more 2'-modified sugar moieties. In some embodiments, a wing comprises 18 or more 2'-modified sugar moieties. In some embodiments, a wing comprises 19 or more 2'-modified sugar moieties. In some embodiments, a wing comprises 20 or more 2'-modified sugar moieties. In some embodiments, a wing comprises 21 or more 2'-modified sugar moieties. In some embodiments, a wing comprises 22 or more 2'-modified sugar moieties. In some embodiments, a wing comprises 23 or more 2'-modified sugar moieties. In some embodiments, a wing comprises 24 or more 2'-modified sugar moieties. In some embodiments, a wing comprises 25 or more 2'-modified sugar moieties. In some embodiments, a wing comprises 30 or more 2'-modified sugar moieties. In some embodiments, a wing comprises 35 or more 2'-modified sugar moieties. In some embodiments, a wing comprises two 2'-modified sugar moieties. In some embodiments, a wing comprises three 2'-modified sugar moieties. In some embodiments, a wing comprises four 2'-modified sugar moieties. In some embodiments, a wing comprises five 2'-modified sugar moieties. In some embodiments, a wing comprises six 2'-modified sugar moieties. In some embodiments, a wing comprises seven 2'-modified sugar moieties. In some embodiments, a wing comprises eight 2'-modified sugar moieties. In some embodiments, a wing comprises nine 2'-modified sugar moieties. In some embodiments, a wing comprises ten 2'-modified sugar moieties. In some embodiments, a wing comprises 11 2'-modified sugar moieties. In some embodiments, a wing comprises 12 2'-modified sugar moieties. In some embodiments, a wing comprises 13 2'-modified sugar moieties. In some embodiments, a wing comprises 14 2'-modified sugar moieties. In some embodiments, a wing comprises 15 2'-modified sugar moieties. In some embodiments, a wing comprises 16 2'-modified sugar moieties. In some embodiments, a wing comprises 17 2'-modified sugar moieties. In some embodiments, a wing comprises 18 2'-modified sugar moieties. In some embodiments, a wing comprises 19 2'-modified sugar moieties. In some embodiments, a wing comprises 20 2'-modified sugar moieties. In some embodiments, a wing comprises 21 2'-modified sugar moieties. In some embodiments, a wing comprises 22 2'-modified sugar moieties. In some embodiments, a wing comprises 23 2'-modified sugar moieties. In some embodiments, a wing comprises 24 2'-modified sugar moieties. In some embodiments, a wing comprises 25 2'-modified sugar moieties. In some embodiments, a wing comprises 30 2'-modified sugar moieties. In some embodiments, a wing comprises 35 2'-modified sugar moieties. In some embodiments, a wing comprises two or more consecutive 2'-modified sugar moieties. In some embodiments, a wing comprises three or more consecutive 2'-modified sugar moieties. In some embodiments, a wing comprises four or more consecutive 2'-modified sugar moieties. In some embodiments, a wing comprises five or more consecutive 2'-modified sugar moieties. In some embodiments, a wing comprises six or more consecutive 2'-modified sugar moieties. In some embodiments, a wing comprises seven or more consecutive 2'-modified sugar moieties. In some embodiments, a wing comprises eight or more consecutive 2'-modified sugar moieties. In some embodiments, a wing comprises nine or more consecutive 2'-modified sugar moieties. In some embodiments, a wing comprises ten or more consecutive 2'-modified sugar moieties. In some embodiments, a wing comprises 11 or more consecutive 2'-modified sugar moieties. In some embodiments, a wing comprises 12 or more consecutive 2'-modified sugar moieties. In some embodiments, a wing comprises 13 or more consecutive 2'-modified sugar moieties. In some embodiments, a wing comprises 14 or more consecutive 2'-modified sugar moieties. In some embodiments, a wing comprises 15 or more consecutive 2'-modified sugar moieties. In some embodiments, a wing comprises 16 or more consecutive 2'-modified sugar moieties. In some embodiments, a wing comprises 17 or more consecutive 2'-modified sugar moieties. In some embodiments, a wing comprises 18 or more consecutive 2'-modified sugar moieties. In some embodiments, a wing comprises 19 or more consecutive 2'-modified sugar moieties. In some embodiments, a wing comprises 20 or more consecutive 2'-modified sugar moieties. In some embodiments, a wing comprises 21 or more consecutive 2'-modified sugar moieties. In some embodiments, a wing comprises 22 or more consecutive 2'-modified sugar moieties. In some embodiments, a wing comprises 23 or more consecutive 2'-modified sugar moieties. In some embodiments, a wing comprises 24 or more consecutive 2'-modified sugar moieties. In some embodiments, a wing comprises 25 or more consecutive 2'-modified sugar moieties. In some embodiments, a wing comprises 30 or more consecutive 2'-modified sugar moieties. In some embodiments, a wing comprises 35 or more consecutive 2'-modified sugar moieties. In some embodiments, a wing comprises two consecutive 2'-modified sugar moieties. In some embodiments, a wing comprises three consecutive 2'-modified sugar moieties. In some embodiments, a wing comprises four consecutive 2'-modified sugar moieties. In some embodiments, a wing comprises five consecutive 2'-modified sugar moieties. In some embodiments, a wing comprises six consecutive 2'-modified sugar moieties. In some embodiments, a wing comprises seven consecutive 2'-modified sugar moieties. In some embodiments, a wing comprises eight consecutive 2'-modified sugar moieties. In some embodiments, a wing comprises nine consecutive 2'-modified sugar moieties. In some embodiments, a wing comprises ten consecutive 2'-modified sugar moieties. In some embodiments, a wing comprises 11 consecutive 2'-modified sugar moieties. In some embodiments, a wing comprises 12 consecutive 2'-modified sugar moieties. In some embodiments, a wing comprises 13 consecutive 2'-modified sugar moieties. In some embodiments, a wing comprises 14 consecutive 2'-modified sugar moieties. In some embodiments, a wing comprises 15 consecutive 2'-modified sugar moieties. In some embodiments, a wing comprises 16 consecutive 2'-modified sugar moieties. In some embodiments, a wing comprises 17 consecutive 2'-modified sugar moieties. In some embodiments, a wing comprises 18 consecutive 2'-modified sugar moieties. In some embodiments, a wing comprises 19 consecutive 2'-modified sugar moieties. In some embodiments, a wing comprises 20 consecutive 2'-modified sugar moieties. In some embodiments, a wing comprises 21 consecutive 2'-modified sugar moieties. In some embodiments, a wing comprises 22 consecutive 2'-modified sugar moieties. In some embodiments, a wing comprises 23 consecutive 2'-modified sugar moieties. In some embodiments, a wing comprises 24 consecutive 2'-modified sugar moieties. In some embodiments, a wing comprises 25 consecutive 2'-modified sugar moieties. In some embodiments, a wing comprises 30 consecutive 2'-modified sugar moieties. In some embodiments, a wing comprises 35 consecutive 2'-modified sugar moieties. In some embodiments, each sugar moiety in a wing region is independently 2'-modified. In some embodiments, each sugar moiety in a 5'-wing region is independently 2'-modified. In some embodiments, each sugar moiety in a 3'-wing region is independently 2'-modified. In some embodiments, each sugar moiety in a 5'-wing region and a 3'-wing region is independently 2'-modified. In some embodiments, a 2'-modified sugar moiety comprises a 2'-modification as described in the present disclosure (e.g., 2'-F, 2'-OMe, 2'-MOE, 2'-LNA type (C2-O—C(R)$_2$—C4, etc.). In some embodiments, each sugar moiety is a core region is not 2'-substituted (—CH$_2$— at 2'-position). In some embodiments, a 2'-modification is 2'-F. In some embodiments, each 2'-modification is 2'-F. In some embodiments, a 2'-modification is 2'-OR, wherein R is optionally substituted $C_{1-6}$ aliphatic. In some embodiments, each 2'-modification is independently 2'-OR, wherein R is optionally substituted $C_{1-6}$ aliphatic. In some embodiments, a 2'-modification is 2'-OR, wherein R is optionally substituted $C_{1-6}$ alkyl. In some embodiments, each 2'-modification is independently 2'-OR, wherein R is optionally substituted $C_{1-6}$ alkyl. In some embodiments, a 2'-modification is 2'-OMe. In some embodiments, each 2'-modification is 2'-OMe. In some embodiments, a 2'-modification is 2'-MOE. In some embodiments, each 2'-modification is 2'-MOE. In some embodiments, a 2'-modification is 2'-LNA type (C2-O—C(R)$_2$—C4, —C(R)$_2$—being —CH$_2$—, —CHR—, —(R)—CHR—, —(S)—CHR—, etc.). In some embodiments, each 2'-modification is independently 2'-LNA type. In some embodiments, a 2'-modification is C2-O—C(R)$_2$—C4, wherein each R is independently as described in the present disclosure. In some embodiments, each 2'-modification is independently C2-O—C(R)$_2$—C4, wherein each R is independently as described in the present disclosure. In some embodiments, a 2'-modification is C2-O—CH$_2$—C4. In some embodiments, each 2'-modification is C2-O—CH$_2$—C4. In some embodiments, a 2'-modification is C2-O—CHR—C4, wherein R is as described in the present disclosure. In some embodiments, each 2'-modification is independently C2-O—CHR—C4, wherein R is as described in the present disclosure. In some embodiments, a 2'-modification is C2-O—(R)—CHR—C4, wherein R is as described in the present disclosure. In some embodiments, each 2'-modification is independently C2-O—(R)—CHR—C4, wherein R is as described in the present disclosure. In some embodiments, a 2'-modification is C2-O—(S)—CHR—C4, wherein R is as described in the present disclosure. In some embodiments, each 2'-modification is independently C2-O—(S)—CHR—C4, wherein R is as described in the present disclosure. In some embodiments, R is optionally substituted $C_{1-6}$ aliphatic. In some embodiments, R is optionally substituted $C_{1-6}$ alkyl. In some embodiments, R is unsubstituted alkyl. In some embodiments, R is methyl. In some embodiments, R is ethyl. In some embodiments, a 2'-modification is C2-O—(R)—CH(CH$_2$CH$_3$)—C4. In some embodiments, each 2'-modification is C2-O—(R)—CH(CH$_2$CH$_3$)—C4. In some embodiments, a 2'-modification is C2-O—(S)—CH(CH$_2$CH$_3$)—C4. In some embodiments, each 2'-modification is C2-O—(S)—CH(CH$_2$CH$_3$)—C4. In some embodiments, each wing region sugar moiety contains the same 2'-modification, if it contains a 2'-modification.

In some embodiments, a core region comprises one or more modified sugar moieties. In some embodiments, a core region comprises two or more modified sugar moieties. In some embodiments, a core region comprises three or more modified sugar moieties. In some embodiments, a core region comprises four or more modified sugar moieties. In some embodiments, a core region comprises five or more modified sugar moieties. In some embodiments, a core region comprises six or more modified sugar moieties. In some embodiments, a core region comprises seven or more modified sugar moieties. In some embodiments, a core region comprises eight or more modified sugar moieties. In some embodiments, a core region comprises nine or more modified sugar moieties. In some embodiments, a core region comprises ten or more modified sugar moieties. In some embodiments, a core region comprises 11 or more modified sugar moieties. In some embodiments, a core region comprises 12 or more modified sugar moieties. In some embodiments, a core region comprises 13 or more modified sugar moieties. In some embodiments, a core region comprises 14 or more modified sugar moieties. In some embodiments, a core region comprises 15 or more modified sugar moieties. In some embodiments, a core region comprises 16 or more modified sugar moieties. In some embodiments, a core region comprises 17 or more modified sugar moieties. In some embodiments, a core region comprises 18 or more modified sugar moieties. In some embodiments, a core region comprises 19 or more modified sugar moieties. In some embodiments, a core region comprises 20 or more modified sugar moieties. In some embodiments, a core region comprises 21 or more modified sugar moieties. In some embodiments, a core region comprises 22 or more modified sugar moieties. In some embodiments, a core region comprises 23 or more modified sugar moieties. In some embodiments, a core region comprises 24 or more modified sugar moieties. In some embodiments, a core region comprises 25 or more modified sugar moieties. In some embodiments, a core region comprises 30 or more modified sugar moieties. In some embodiments, a core region comprises 35 or more modified sugar moieties. In some embodiments, a modified sugar moiety comprises a modification as described in the present disclosure. In some embodiments, a modified sugar moiety comprises a 2'-modification as described in the present disclosure (e.g., 2'-OMe, 2'-MOE, 2'-LNA type (C2-O—C(R)$_2$—C4, etc.). In some embodiments, each sugar moiety is a core region is not 2'-substituted (—CH$_2$— at 2'-position).

In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties in provided oligonucleotides or segments thereof (e.g., 5'-wing regions, core regions, 3'-wing regions, portions thereof, etc.) comprise no modifications (1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties are not modified). In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of provided oligonucleotides are not modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of one or more regions are not modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of a 5'-wing region are not modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of a 3'-wing region are not modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'- and the 3'-wing regions of provided oligonucleotides are not modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'-wing and the core regions of provided oligonucleotides are not modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the core and the 3'-wing regions of provided oligonucleotides are not modified. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'- and the 3'-wing, and the core regions of provided oligonucleotides are not modified. In some embodiments, at least 5% of the sugar moieties are not modified. In some embodiments, at least 10% of the sugar moieties are not modified. In some embodiments, at least 15% of the sugar moieties are not modified. In some embodiments, at least 20% of the sugar moieties are not modified. In some embodiments, at least 25% of the sugar moieties are not modified. In some embodiments, at least 30% of the sugar moieties are not modified. In some embodiments, at least 35% of the sugar moieties are not modified. In some embodiments, at least 40% of the sugar moieties are not modified. In some embodiments, at least 45% of the sugar moieties are not modified. In some embodiments, at least 50% of the sugar moieties are not modified. In some embodiments, at least 55% of the sugar moieties are not modified. In some embodiments, at least 60% of the sugar moieties are not modified. In some embodiments, at least 65% of the sugar moieties are not modified. In some embodiments, at least 66% of the sugar moieties are not modified. In some embodiments, at least 67% of the sugar moieties are not modified. In some embodiments, at least 70% of the sugar moieties are not modified. In some embodiments, at least 75% of the sugar moieties are not modified. In some embodiments, at least 80% of the sugar moieties are not modified. In some embodiments, at least 85% of the sugar moieties are not modified. In some embodiments, at least 90% of the sugar moieties are not modified. In some embodiments, at least 95% of the sugar moieties are not modified. In some embodiments, each sugar moieties is not modified. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. sugar moieties are not modified. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. sugar moieties of a 5'-wing region, core region, and/or 3'-wing region are not modified. In some embodiments, at least 1 sugar moiety is not modified. In some embodiments, at least 2 sugar moieties are not modified. In some embodiments, at least 3 sugar moieties are not modified. In some embodiments, at least 4 sugar moieties are not modified. In some embodiments, at least 5 sugar moieties are not modified. In some embodiments, at least 6 sugar moieties are not modified. In some embodiments, at least 7 sugar moieties are not modified. In some embodiments, at least 8 sugar moieties are not modified. In some embodiments, at least 9 sugar moieties are not modified. In some embodiments, at least 10 sugar moieties are not modified. In some embodiments, at least 11 sugar moieties are not modified. In some embodiments, at least 12 sugar moieties are not modified. In some embodiments, at least 13 sugar moieties are not modified. In some embodiments, at least 14 sugar moieties are not modified. In some embodiments, at least 15 sugar moieties are not modified. In some embodiments, at least 16 sugar moieties are not modified. In some embodiments, at least 17 sugar moieties are not modified. In some embodiments, at least 18 sugar moieties are not modified. In some embodiments, at least 19 sugar moieties are not modified. In some embodiments, at least 20 sugar moieties are not modified. In some embodiments, at least 21 sugar moieties are not modified. In some embodiments, at least 25 sugar moieties are not modified. In some embodiments, at least 30 sugar moieties are not modified. In some embodiments, at least 2 consecutive sugar moieties are not modified. In some embodiments, at least 3 consecutive sugar moieties are not modified. In some embodiments, at least 4 consecutive sugar moieties are not modified. In some embodiments, at least 5 consecutive sugar moieties are not modified. In some embodiments, at least 6 consecutive sugar moieties are not modified. In some embodiments, at least 7 consecutive sugar moieties are not modified. In some embodiments, at least 8 consecutive sugar moieties are not modified. In some embodiments, at least 9 consecutive sugar moieties are not modified. In some embodiments, at least 10 consecutive sugar moieties are not modified. In some embodiments, at least 11 consecutive sugar moieties are not modified. In some embodiments, at least 12 consecutive sugar moieties are not modified. In some embodiments, at least 13 consecutive sugar moieties are not modified. In some embodiments, at least 14 consecutive sugar moieties are not modified. In some embodiments, at least 15 consecutive sugar moieties are not modified. In some embodiments, at least 16 consecutive sugar moieties are not modified. In some embodiments, at least 17 consecutive sugar moieties are not modified. In some embodiments, at least 18 consecutive sugar moieties are not modified. In some embodiments, at least 19 consecutive sugar moieties are not modified. In some embodiments, at least 20 consecutive sugar moieties are not modified. In some embodiments, at least 21 consecutive sugar moieties are not modified. In some embodiments, at least 25 consecutive sugar moieties are not modified. In some embodiments, at least 30 consecutive sugar moieties are not modified. In some embodiments, only one sugar moiety of a provided oligonucleotide, or a segment thereof (e.g., 5'-wing region, core region, 3'-wing region, portions thereof, etc.) is not modified. In some embodiments, only one sugar moiety of a provided oligonucleotide is not modified. In some embodiments, only one sugar moiety of a 5'-wing region is not modified. In some embodiments, only one sugar moiety of a 3'-wing region is not modified. In some embodiments, only one sugar moiety of a 5'-wing region is not modified, and only one sugar moiety of a 3'-wing region is not modified. In some embodiments, only one sugar moiety of a core region is not modified.

In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties in provided oligonucleotides or segments thereof (e.g., 5'-wing regions, core regions, 3'-wing regions, portions thereof, etc.) comprise no substitutions at 2'-position (—$CH_2$— at 2'-position; 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties are not 2'-substituted). In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of provided oligonucleotides are not 2'-substituted. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of one or more regions are not 2'-substituted. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of a 5'-wing region are not 2'-substituted. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of a 3'-wing region are not 2'-substituted. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'- and the 3'-wing regions of provided oligonucleotides are not 2'-substituted. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'-wing and the core regions of provided oligonucleotides are not 2'-substituted. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the core and the 3'-wing regions of provided oligonucleotides are not 2'-substituted. In some embodiments, 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of sugar moieties of the 5'- and the 3'-wing, and the core regions of provided oligonucleotides are not 2'-substituted. In some embodiments, at least 5% of the sugar moieties are not 2'-substituted. In some embodiments, at least 10% of the sugar moieties are not 2'-substituted. In some embodiments, at least 15% of the sugar moieties are not 2'-substituted. In some embodiments, at least 20% of the sugar moieties are not 2'-substituted. In some embodiments, at least 25% of the sugar moieties are not 2'-substituted. In some embodiments, at least 30% of the sugar moieties are not 2'-substituted. In some embodiments, at least 35% of the sugar moieties are not 2'-substituted. In some embodiments, at least 40% of the sugar moieties are not 2'-substituted. In some embodiments, at least 45% of the sugar moieties are not 2'-substituted. In some embodiments, at least 50% of the sugar moieties are not 2'-substituted. In some embodiments, at least 55% of the sugar moieties are not 2'-substituted. In some embodiments, at least 60% of the sugar moieties are not 2'-substituted. In some embodiments, at least 65% of the sugar moieties are not 2'-substituted. In some embodiments, at least 66% of the sugar moieties are not 2'-substituted. In some embodiments, at least 67% of the sugar moieties are not 2'-substituted. In some embodiments, at least 70% of the sugar moieties are not 2'-substituted. In some embodiments, at least 75% of the sugar moieties are not 2'-substituted. In some embodiments, at least 80% of the sugar moieties are not 2'-substituted. In some embodiments, at least 85% of the sugar moieties are not 2'-substituted. In some embodiments, at least 90% of the sugar moieties are not 2'-substituted. In some embodiments, at least 95% of the sugar moieties are not 2'-substituted. In some embodiments, each sugar moieties is not 2'-substituted. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. sugar moieties are not 2'-substituted. In some embodiments, at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. sugar moieties of a 5'-wing region, core region, and/or 3'-wing region are not 2'-substituted. In some embodiments, at least 1 sugar moiety is not 2'-substituted. In some embodiments, at least 2 sugar moieties are not 2'-substituted. In some embodiments, at least 3 sugar moieties are not 2'-substituted. In some embodiments, at least 4 sugar moieties are not 2'-substituted. In some embodiments, at least 5 sugar moieties are not 2'-substituted. In some embodiments, at least 6 sugar moieties are not 2'-substituted. In some embodiments, at least 7 sugar moieties are not 2'-substituted. In some embodiments, at least 8 sugar moieties are not 2'-substituted. In some embodiments, at least 9 sugar moieties are not 2'-substituted. In some embodiments, at least 10 sugar moieties are not 2'-substituted. In some embodiments, at least 11 sugar moieties are not 2'-substituted. In some embodiments, at least 12 sugar moieties are not 2'-substituted. In some embodiments, at least 13 sugar moieties are not 2'-substituted. In some embodiments, at least 14 sugar moieties are not 2'-substituted. In some embodiments, at least 15 sugar moieties are not 2'-substituted. In some embodiments, at least 16 sugar moieties are not 2'-substituted. In some embodiments, at least 17 sugar moieties are not 2'-substituted. In some embodiments, at least 18 sugar moieties are not 2'-substituted. In some embodiments, at least 19 sugar moieties are not 2'-substituted. In some embodiments, at least 20 sugar moieties are not 2'-substituted. In some embodiments, at least 21 sugar moieties are not 2'-substituted. In some embodiments, at least 25 sugar moieties are not 2'-substituted. In some embodiments, at least 30 sugar moieties are not 2'-substituted. In some embodiments, at least 2 consecutive sugar moieties are not 2'-substituted. In some embodiments, at least 3 consecutive sugar moieties are not 2'-substituted. In some embodiments, at least 4 consecutive sugar moieties are not 2'-substituted. In some embodiments, at least 5 consecutive sugar moieties are not 2'-substituted. In some embodiments, at least 6 consecutive sugar moieties are not 2'-substituted. In some embodiments, at least 7 consecutive sugar moieties are not 2'-substituted. In some embodiments, at least 8 consecutive sugar moieties are not 2'-substituted. In some embodiments, at least 9 consecutive sugar moieties are not 2'-substituted. In some embodiments, at least 10 consecutive sugar moieties are not 2'-substituted. In some embodiments, at least 11 consecutive sugar moieties are not 2'-substituted. In some embodiments, at least 12 consecutive sugar moieties are not 2'-substituted. In some embodiments, at least 13 consecutive sugar moieties are not 2'-substituted. In some embodiments, at least 14 consecutive sugar moieties are not 2'-substituted. In some embodiments, at least 15 consecutive sugar moieties are not 2'-substituted. In some embodiments, at least 16 consecutive sugar moieties are not 2'-substituted. In some embodiments, at least 17 consecutive sugar moieties are not 2'-substituted. In some embodiments, at least 18 consecutive sugar moieties are not 2'-substituted. In some embodiments, at least 19 consecutive sugar moieties are not 2'-substituted. In some embodiments, at least 20 consecutive sugar moieties are not 2'-substituted. In some embodiments, at least 21 consecutive sugar moieties are not 2'-substituted. In some embodiments, at least 25 consecutive sugar moieties are not 2'-substituted. In some embodiments, at least 30 consecutive sugar moieties are not 2'-substituted. In some embodiments, only one sugar moiety of a provided oligonucleotide, or a segment thereof (e.g., 5'-wing region, core region, 3'-wing region, portions thereof, etc.) is not 2'-substituted. In some embodiments, only one sugar moiety of a provided oligonucleotide is not 2'-substituted. In some embodiments, only one sugar moiety of a 5'-wing region is not 2'-substituted. In some embodiments, only one sugar moiety of a 3'-wing region is not 2'-substituted. In some embodiments, only one sugar moiety of a 5'-wing region is not 2'-substituted, and only one sugar moiety of a 3'-wing region is not 2'-substituted. In some embodiments, only one sugar moiety of a core region is not 2'-substituted. In some embodiments, each sugar moiety of a core region is not 2'-substituted.

Nucleobases

In some embodiments, a nucleobase in provided oligonucleotides is a natural nucleobase (e.g., adenine, cytosine, guanosine, thymine, or uracil) or a modified nucleobase derived from a natural nucleobase. Examples include, but are not limited to, uracil, thymine, adenine, cytosine, and guanine, and tautomeric forms thereof, having their respective amino groups protected by protecting groups, e.g., one or more of —R, —C(O)R, etc. Example protecting groups are widely known in the art and can be utilized in accordance with the present disclosure. In some embodiments, a protected nucleobase and/or derivative is selected from nucleobases with one or more acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Example modified nucleobases are also disclosed in Chiu and Rana, *RNA,* 2003, 9, 1034-1048, Limbach et al. *Nucleic Acids Research,* 1994, 22, 2183-2196 and Revankar and Rao, *Comprehensive Natural Products Chemistry,* vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a modified base is optionally substituted adenine, cytosine, guanine, thymine, or uracil. In some embodiments, a modified nucleobase is independently adenine, cytosine, guanine, thymine or uracil, modified by one or more modifications by which:

(1) a nucleobase is modified by one or more optionally substituted groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

(2) one or more atoms of a nucleobase are independently replaced with a different atom selected from carbon, nitrogen or sulfur;

(3) one or more double bonds in a nucleobase are independently hydrogenated; or (4) one or more optionally substituted aryl or heteroaryl rings are independently inserted into a nucleobase.

Compounds represented by the following general formulae are also contemplated as modified nucleobases:

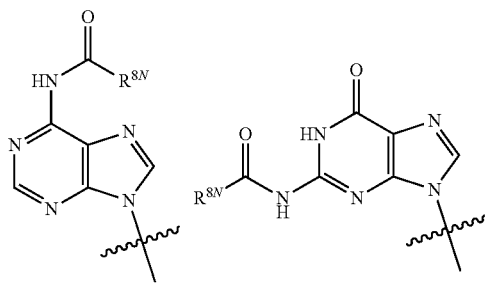

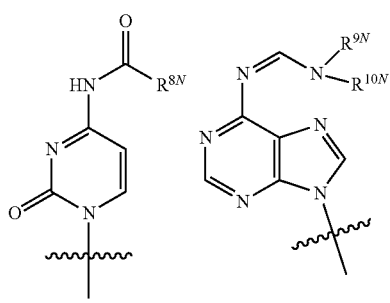

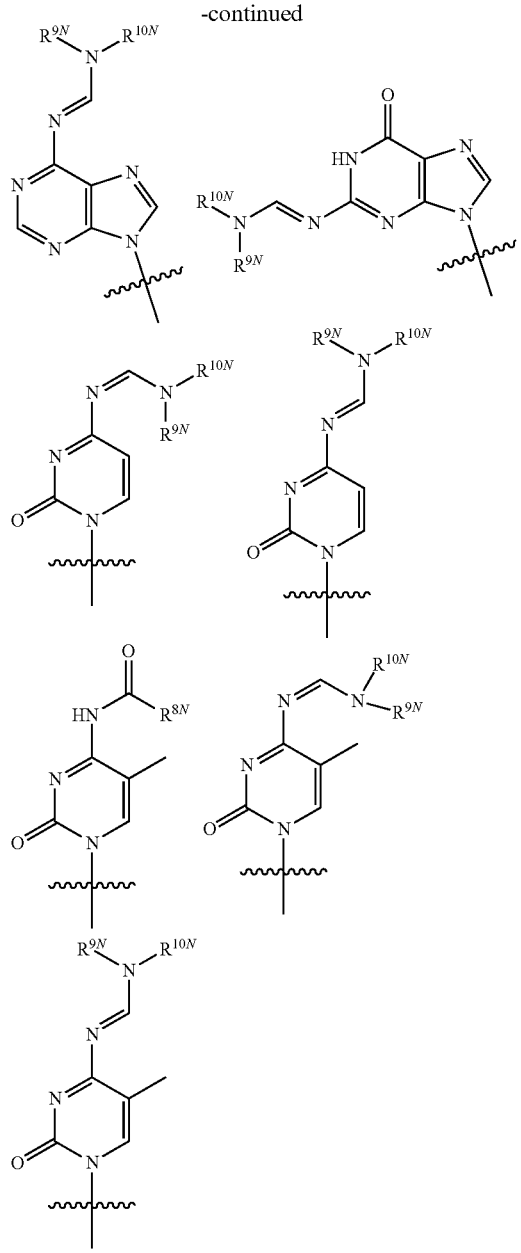

-continued wherein $R^{8N}$ is an optionally substituted, linear or branched group selected from aliphatic, aryl, aralkyl, aryloxylalkyl, carbocyclyl, heterocyclyl and heteroaryl, each having 1 to 30 carbon atoms, and 1-10 heteroatoms if applicable, including, by way of example only, a methyl, isopropyl, phenyl, benzyl, or phenoxymethyl group; and each of $R^{9N}$ and $R^{10N}$ is independently an optionally substituted group selected from linear or branched aliphatic, carbocyclyl, aryl, heterocyclyl and heteroaryl, each having 1 to 30 carbon atoms, and 1-10 heteroatoms Modified nucleobases also include expanded-size nucleobases in which one or more aryl rings, such as phenyl rings, have been added. Nucleic base replacements described in the Glen Research catalog (www.glenresearch.com); Krueger A T et al, *Acc. Chem. Res.,* 2007, 40, 141-150; Kool, E T, *Acc. Chem. Res.,* 2002, 35, 936-943; Benner S. A., et al., *Nat. Rev. Genet.,* 2005, 6, 553-543; Romesberg, F. E., et al., *Curr. Opin. Chem. Biol.,* 2003, 7, 723-733; Hirao, I., *Curr. Opin.*

Chem. Biol., 2006, 10, 622-627, are contemplated as useful for the synthesis of certain provided compounds in the present disclosure. Some examples of these expanded-size nucleobases are shown below:

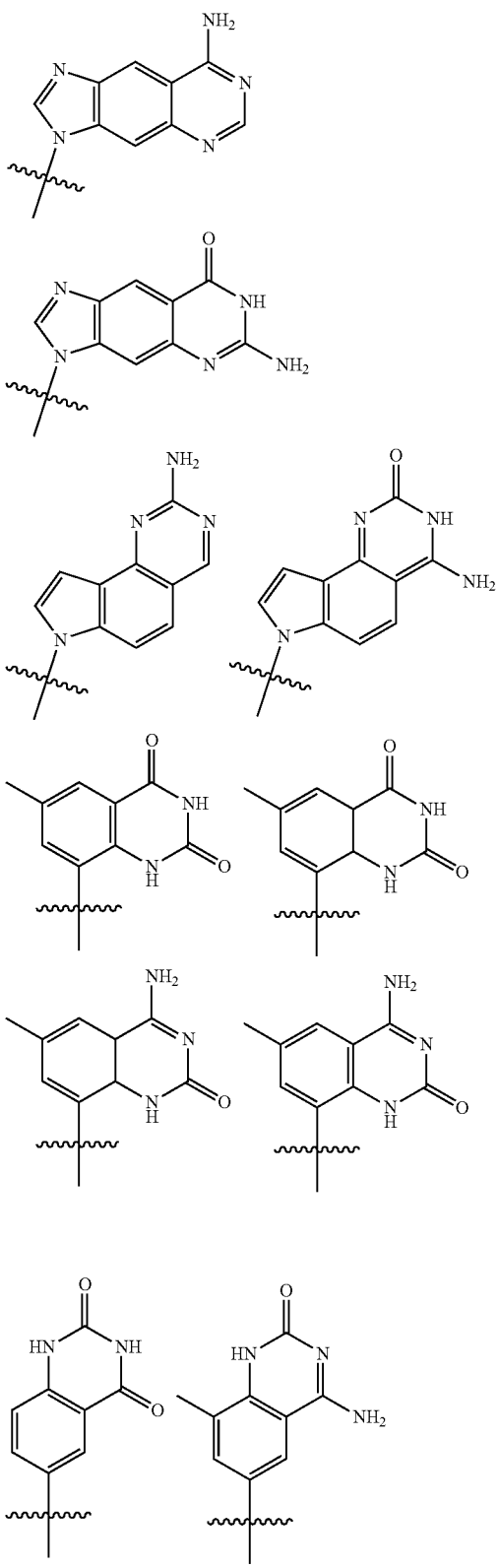

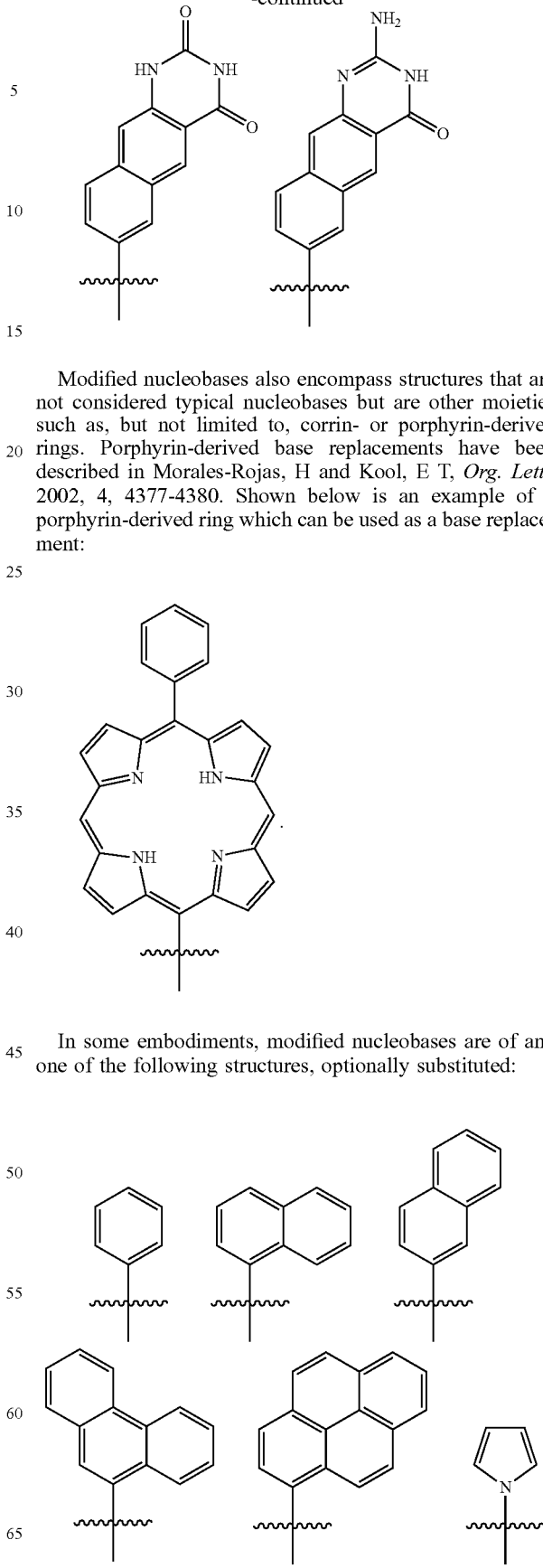

Modified nucleobases also encompass structures that are not considered typical nucleobases but are other moieties such as, but not limited to, corrin- or porphyrin-derived rings. Porphyrin-derived base replacements have been described in Morales-Rojas, H and Kool, E T, Org. Lett., 2002, 4, 4377-4380. Shown below is an example of a porphyrin-derived ring which can be used as a base replacement:

In some embodiments, modified nucleobases are of any one of the following structures, optionally substituted:

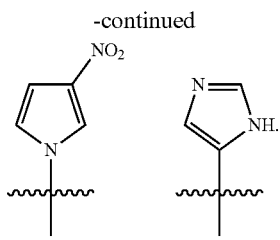

In some embodiments, a modified nucleobase is fluorescent. Examples of such fluorescent modified nucleobases include phenanthrene, pyrene, stilbene, isoxanthine, isozanthopterin, terphenyl, terthiophene, benzoterthiophene, coumarin, lumazine, tethered stilbene, benzo-uracil, and naphtho-uracil, as shown below:

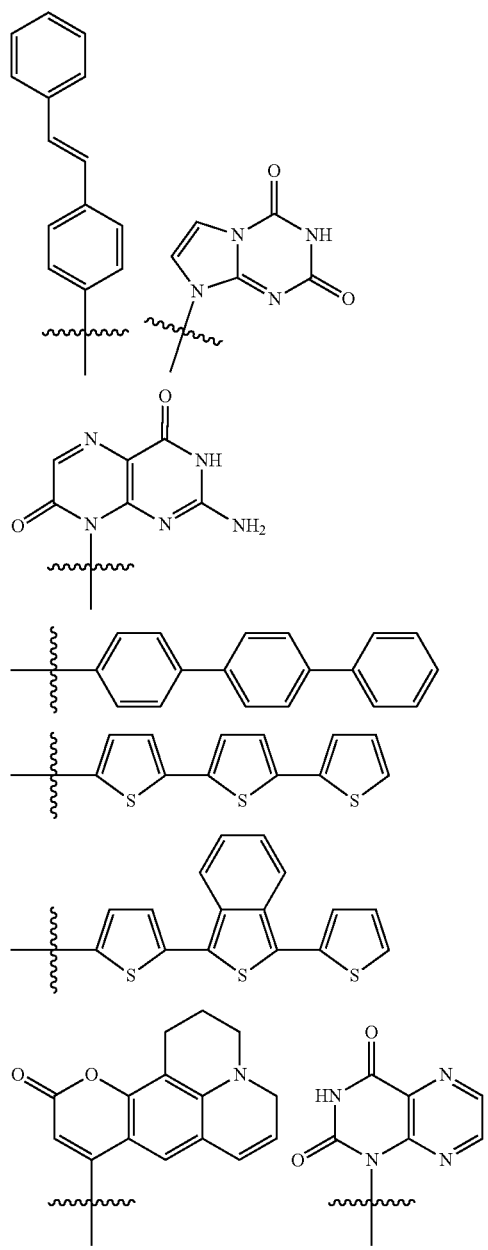

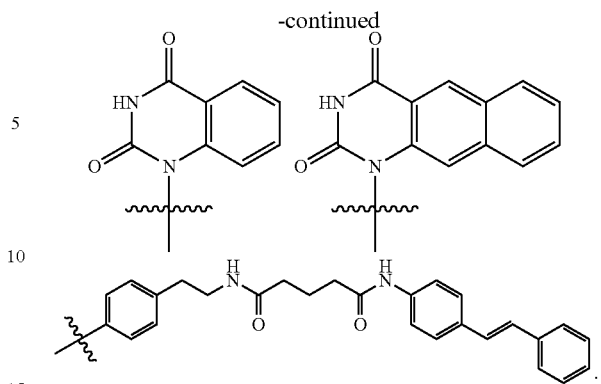

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One example of such a universal base is 3-nitropyrrole.

In some embodiments, other nucleosides can also be used in technologies disclosed in the present disclosure and may include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In some embodiments, nucleosides include 5'-modified bicyclic nucleoside analogs that have either (R) or (S)-chirality at the 5'-position and include the analogs described in US Patent Application Publication No. 20070287831.

In some embodiments, a nucleobase or modified nucleobase comprises one or more biomolecule binding moieties such as e.g., antibodies, antibody fragments, biotin, avidin, streptavidin, receptor ligands, or chelating moieties. In other embodiments, a nucleobase or modified nucleobase is 5-bromouracil, 5-iodouracil, or 2,6-diaminopurine. In some embodiments, a nucleobase or modified nucleobase is modified by substitution with a fluorescent or biomolecule binding moiety. In some embodiments, the substituent on a nucleobase or modified nucleobase is a fluorescent moiety. In some embodiments, the substituent on a nucleobase or modified nucleobase is biotin or avidin.

Representative U.S. patents that teach preparation of certain of noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, modified nucleobases, sugars, and internucleotidic linkages of each of which are incorporated by reference.

In some embodiments, a base is optionally substituted A, T, C, G or U, wherein one or more —$NH_2$ are independently and optionally replaced with —$C(-L-R^1)_3$, one or more —NH— are independently and optionally replaced with —$C(-L-R^1)_2$—, one or more =N— are independently and optionally replaced with —$C(-L-R^1)$—, one or more =CH— are independently and optionally replaced with =N—, and one or more =O are independently and optionally replaced with =S, =$N(-L-R^1)$, or =$C(-L-R^1)_2$, wherein two or more -L-$R^1$ are optionally taken together with their intervening atoms to form a 3-30 membered bicyclic or polycyclic ring having 0-10 heteroatom atoms. In some embodiments, a modified base is optionally substituted A, T, C, G or U, wherein one or more —$NH_2$ are independently and optionally replaced with —$C(-L-R^1)_3$, one or more —NH— are independently and optionally replaced with —$C(-L-R^1)_2$—, one or more =N— are independently and optionally replaced with —$C(-L-R^1)$—, one or more =CH— are independently and optionally replaced with =N—, and one or more =O are independently and optionally replaced with =S, =$N(-L-R^1)$, or =$C(-L-R^1)_2$, wherein two or more -L-$R^1$ are optionally taken together with their intervening atoms to form a 3-30 membered bicyclic or polycyclic ring having 0-10 heteroatom atoms, wherein the modified base is different than the natural A, T, C, G and U. In some embodiments, a base is optionally substituted A, T, C, G or U. In some embodiments, a modified base is substituted A, T, C, G or U, wherein the modified base is different than the natural A, T, C, G and U.

In some embodiments, a modified nucleotide or nucleotide analog is any modified nucleotide or nucleotide analog described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; and WO 2016/079181.

Example nucleobases are also described in US 20110294124, US 20120316224, US 20140194610, US 20150211006, US 20150197540, WO 2015107425, PCT/US2016/043542, and PCT/US2016/043598, nucleobases of each of which are incorporated herein by reference.

Sugars

In some embodiments, provided compounds, e.g., oligonucleotides, comprise one or more modified sugar moieties.

In some embodiments, linkage phosphorus in nucleotides can be linked to various positions of a sugar or modified sugar. For example, in some embodiments, linkage phosphorus can be linked to the 2', 3', 4' or 5' hydroxyl moiety of a sugar or modified sugar. Nucleotides that incorporate modified nucleobases as described herein are also contemplated in this context. In some embodiments, nucleotides or modified nucleotides comprising an unprotected —OH moiety are used in accordance with the present disclosure.

Various types of modified sugars can be utilized in accordance with the present disclosure. In some embodiments, a modified sugar contains one or more substituents at the 2' position selected from: —F; —$CF_3$, —CN, —$N_3$, —NO, —$NO_2$, —OR', —SR', or —$N(R')_2$, wherein each R' is independently as defined above and described herein; —O—($C_1$-$C_{10}$ alkyl), —S—($C_1$-$C_{10}$ alkyl), —NH—($C_1$-$C_{10}$ alkyl), or —N($C_1$-$C_{10}$ alkyl)$_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)$_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl)$_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl)$_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein the alkyl, alkylene, alkenyl and alkynyl may be substituted or unsubstituted, and each independently contain or are of, e.g., 1-30, 1-20, 1-10, 1-9, 1-8, 1-7, 1-6, 1-5, 1-4, 1-3, 1-2, or 1, carbon. In some embodiments, examples of substituents include, and are not limited to, —O($CH_2$)$_n$$OCH_3$, and —O($CH_2$)$_n$$NH_2$, wherein n is from 1 to about 10, MOE, DMAOE, DMAEOE. In some embodiments, a modified sugar is selected from those described in WO 2001/088198; and Martin et al., *Helv. Chim. Acta,* 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of 2', 3', 4', 5', and/or 6'-positions (if any) of sugar or modified sugar moieties, including 3'-positions of a sugar moiety on a 3'-terminal nucleotide and/or 5' positions of a 5'-terminal nucleotide. In some embodiments, a RNA comprises a sugar which has, at the 2' position, a 2'-OH, or 2'-OR$^1$, wherein R$^1$ is optionally substituted C$_{1-6}$ alkyl. In some embodiments, a 2'-modification is 2'-F.

In some embodiments, the 2'-OH of a ribose is replaced with a substituent selected from: —H, —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted, and each independently contain or are of, e.g., 1-30, 1-20, 1-10, 1-9, 1-8, 1-7, 1-6, 1-5, 1-4, 1-3, 1-2, or 1, carbon. In some embodiments, a 2'-OH is replaced with —H (deoxyribose). In some embodiments, a 2'-OH is replaced with —F. In some embodiments, a 2'-OH is replaced with —OR', wherein R' is as described in the present disclosure and is not hydrogen. In some embodiments, a 2'-OH is replaced with —OMe. In some embodiments, a 2'-OH is replaced with —OCH$_2$CH$_2$OMe.

Modified sugars also include sugars of locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L$^s$- as defined herein. In some embodiments, -L$^s$- is —O—C(R)$_2$—, wherein each R is independently as described in the present disclosure. In some embodiments, -L$^s$- is —O—CHR—, wherein R is as described in the present disclosure. In some embodiments, -L$^s$- is —O—(R)—CHR—, wherein R is as described in the present disclosure. In some embodiments, -L$^s$- is —O—(S)—CHR—, wherein R is as described in the present disclosure. In some embodiments, -L$^s$- is —O—CH$_2$—, wherein —CH$_2$— is optionally substituted. In some embodiments, -L$^s$- is —O—CH$_2$—. In some embodiments, -L$^s$- is —O—CH(Et)-. In some embodiments, -L$^s$- is —O—(R)—CH(Et)-. In some embodiments, -L$^s$- is —O—(S)—CH(Et)-. In some embodiments, -L$^s$- is between C2 and C4 of a sugar moiety.

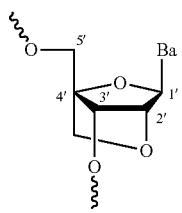

C2—OCH$_2$—C4 in e.g., LNA

In some embodiments, a modified sugar is a sugar of ENA or modified ENA (such as those described in, e.g., Seth et al., J Am Chem Soc. 2010 Oct. 27; 132(42): 14942-14950). In some embodiments, a modified sugar is any of those found in an XNA (xenonucleic acid), for instance, arabinose, anhydrohexitol, threose, 2'fluoroarabinose, or cyclohexene.

In some embodiments, modified sugars are sugar mimetics such as cyclobutyl or cyclopentyl moieties in place of pentofuranosyl. Representative United States patents that teach preparation of such modified sugar structures include, but are not limited to, U.S. Pat. Nos. 4,981,957; 5,118,800; 5,319,080; and 5,359,044. In some embodiments, modified sugars are sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc).

Non-limiting examples of modified sugars include glycerol, which form glycerol nucleic acid (GNA) analogues. One example of a GNA analogue is shown below and is described in Zhang, R et al., *J. Am. Chem. Soc.*, 2008, 130, 5846-5847; Zhang L, et al., *J. Am. Chem. Soc.*, 2005, 127, 4174-4175 and Tsai C H et al., *PNAS*, 2007, 14598-14603 (X=O$^-$):

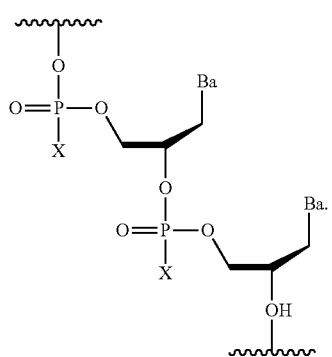

Another example of a GNA derived analogue, flexible nucleic acid (FNA) based on the mixed acetal aminal of formyl glycerol, is described in Joyce G F et al., *PNAS*, 1987, 84, 4398-4402 and Heuberger B D and Switzer C, *J. Am. Chem. Soc.*, 2008, 130, 412-413, and is shown below:

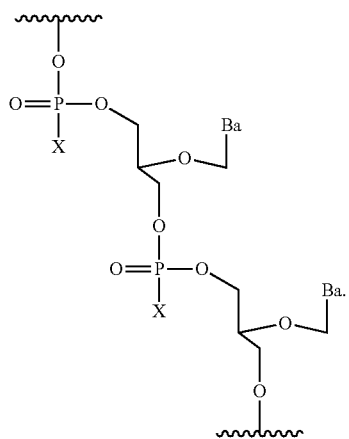

Additional non-limiting examples of modified sugars include hexopyranosyl (6' to 4'), pentopyranosyl (4' to 2'), pentopyranosyl (4' to 3'), or tetrafuranosyl (3' to 2') sugars.

In some embodiments, a hexopyranosyl (6' to 4') sugar moiety is one in the following formulae:

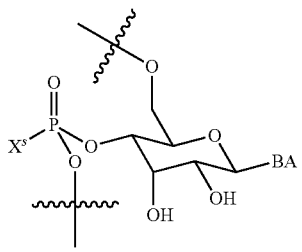

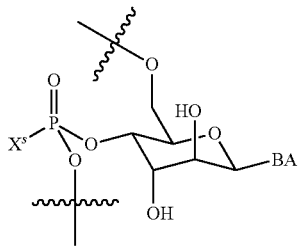

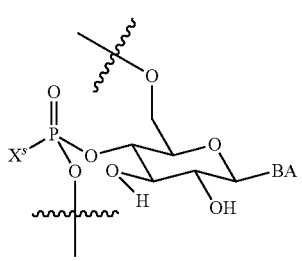

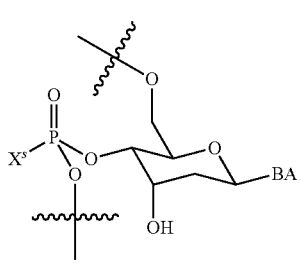

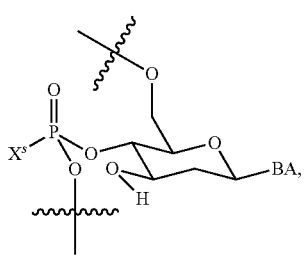

wherein $X^s$ corresponds to the P-modification group "—X-L-R$^5$" described herein and BA is as defined herein.

In some embodiments, a pentopyranosyl (4' to 2') sugar moiety is one in the following formulae:

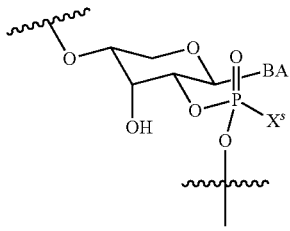

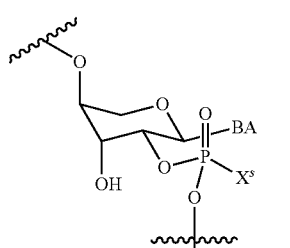

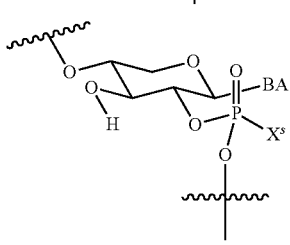

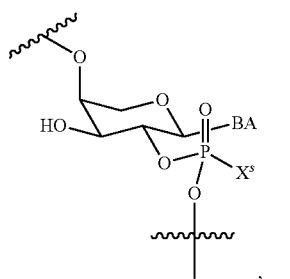

wherein $X^s$ corresponds to the P-modification group "—X-L-R$^5$" described herein and BA is as defined herein.

In some embodiments, a pentopyranosyl (4' to 3') sugar moiety is one in the following formulae:

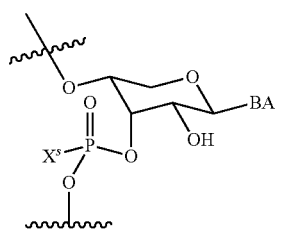

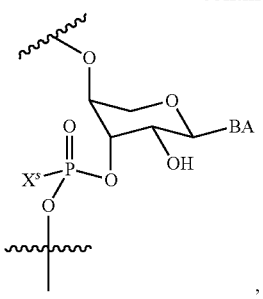

wherein $X^s$ corresponds to the P-modification group "—X-L-$R^5$" described herein and BA is as defined herein.

In some embodiments, a tetrafuranosyl (3' to 2') sugar moiety is one in the following formulae:

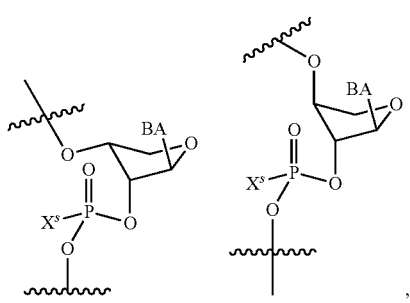

wherein $X^s$ corresponds to the P-modification group "—X-L-$R^5$" described herein and BA is as defined herein.

In some embodiments, a modified sugar moiety is one in the following formulae:

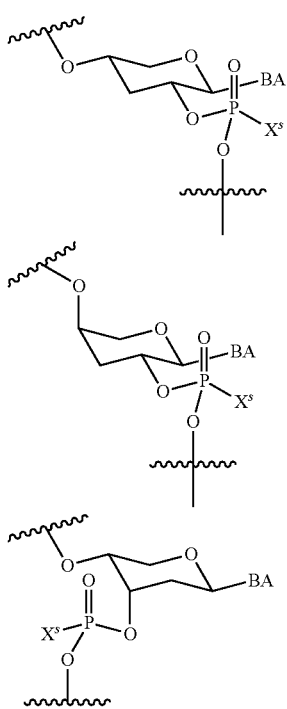

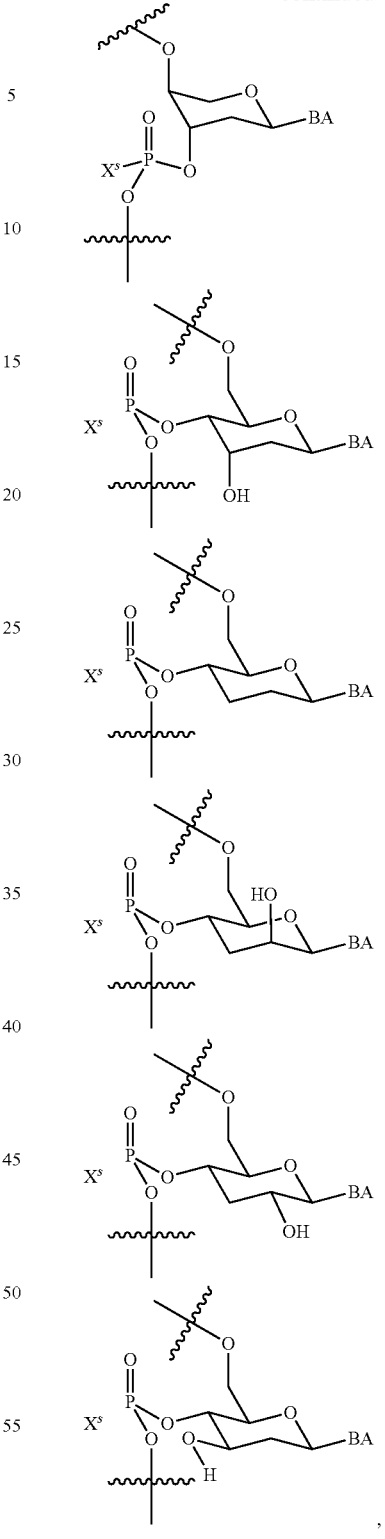

wherein $X^s$ corresponds to a P-modification group "—X-L-$R^5$" described herein and BA is as defined herein.

In some embodiments, one or more hydroxyl group in a sugar moiety is optionally and independently replaced with halogen, R'—N(R')$_2$, —OR', or —SR', wherein each R' is independently as defined above and described herein.

In some embodiments, a modified sugar moiety is one illustrated below, wherein $X^s$ corresponds to the P-modification group "—X-L-$R^5$" described herein, BA is as defined herein, and $X^1$ is selected from —S—, —Se—, —CH$_2$—, —NMe-, —NEt- or —NiPr—:
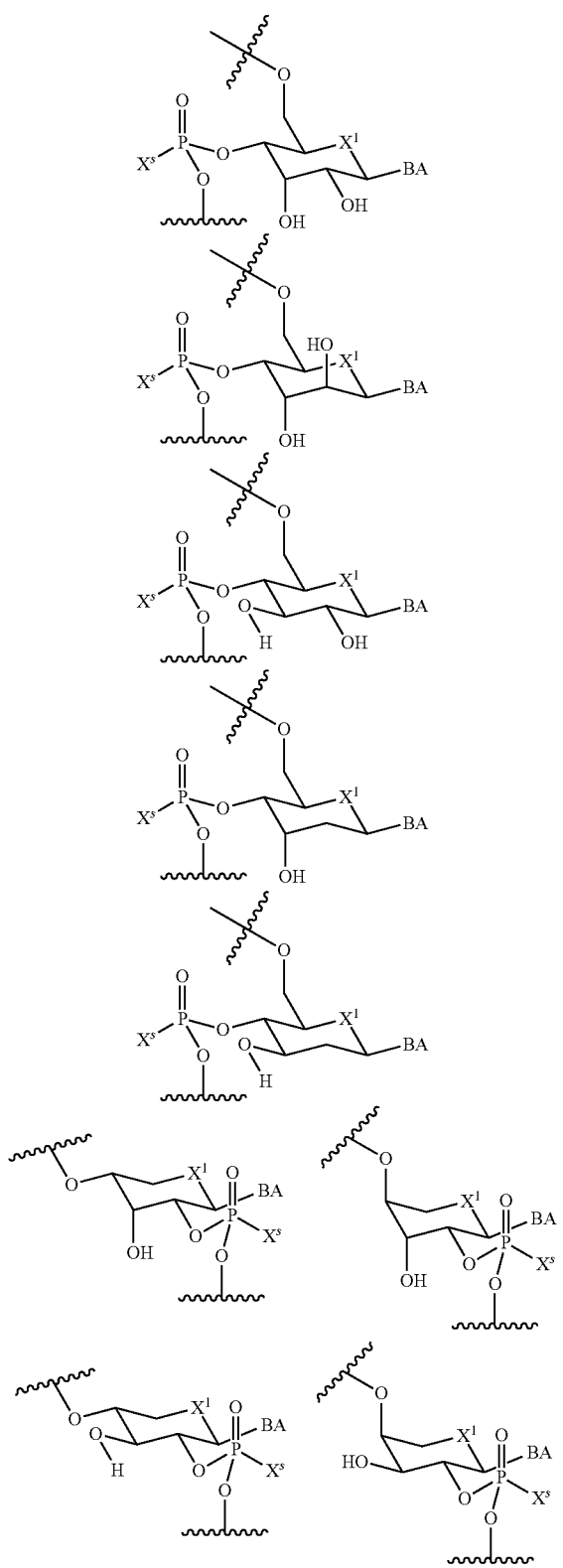
-continued
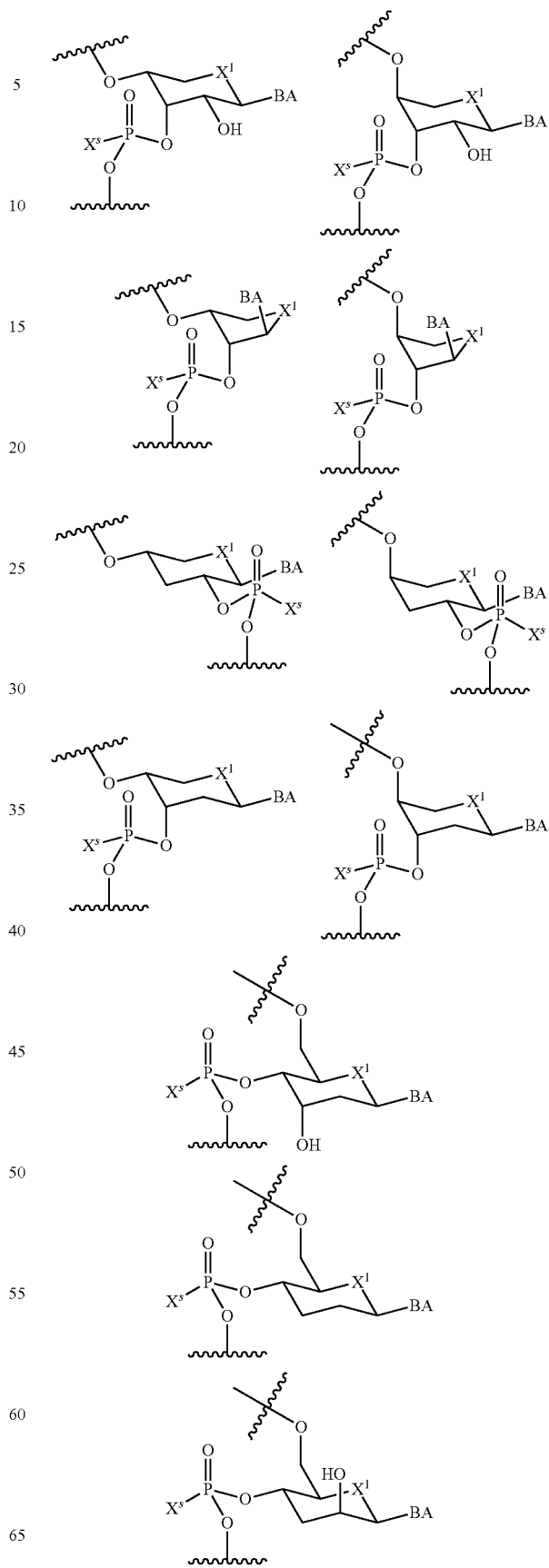

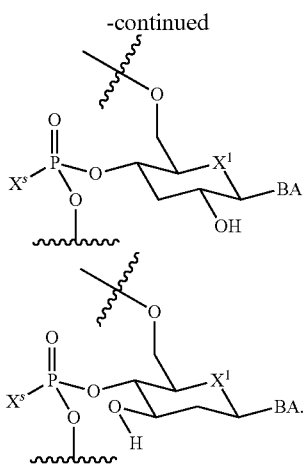

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in a chirally controlled oligonucleotide composition are modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyridimin residues are modified). In some embodiments, both purine and pyrimidine residues are modified.

Modified sugars can be prepared and/or reacted with and/or incorporated into provided compounds by methods known in the art in accordance with the present disclosure, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in Chemical Synthesis: Gnosis to Prognosis, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Helv. Chim. Acta 1996, 79, 1930-1938), "LNA" (Wengel, J. Acc. Chem. Res. 1999, 32, 301-310). In some embodiments, a modified sugar is any of those described in PCT Publication No. WO2012/030683. In some embodiments, a modified sugar is any modified sugar described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; and WO 2016/079181.

In some embodiments, a modified sugar moiety is an optionally substituted pentose or hexose moiety. In some embodiments, a modified sugar moiety is an optionally substituted pentose moiety. In some embodiments, a modified sugar moiety is an optionally substituted hexose moiety. In some embodiments, a modified sugar moiety is an optionally substituted ribose or hexitol moiety. In some embodiments, a modified sugar moiety is an optionally substituted ribose moiety. In some embodiments, a modified sugar moiety is an optionally substituted hexitol moiety.

In some embodiments, an example modified internucleotidic linkage and/or sugar moiety is selected from, e.g, those in:

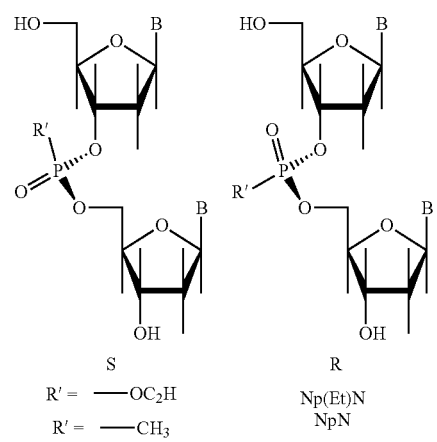

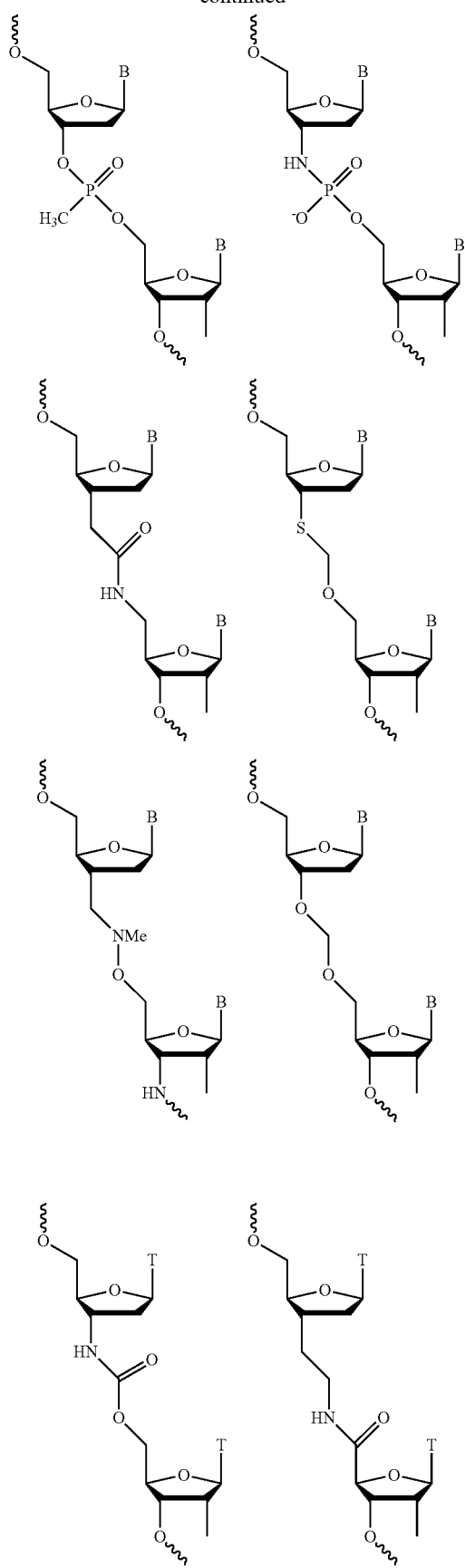
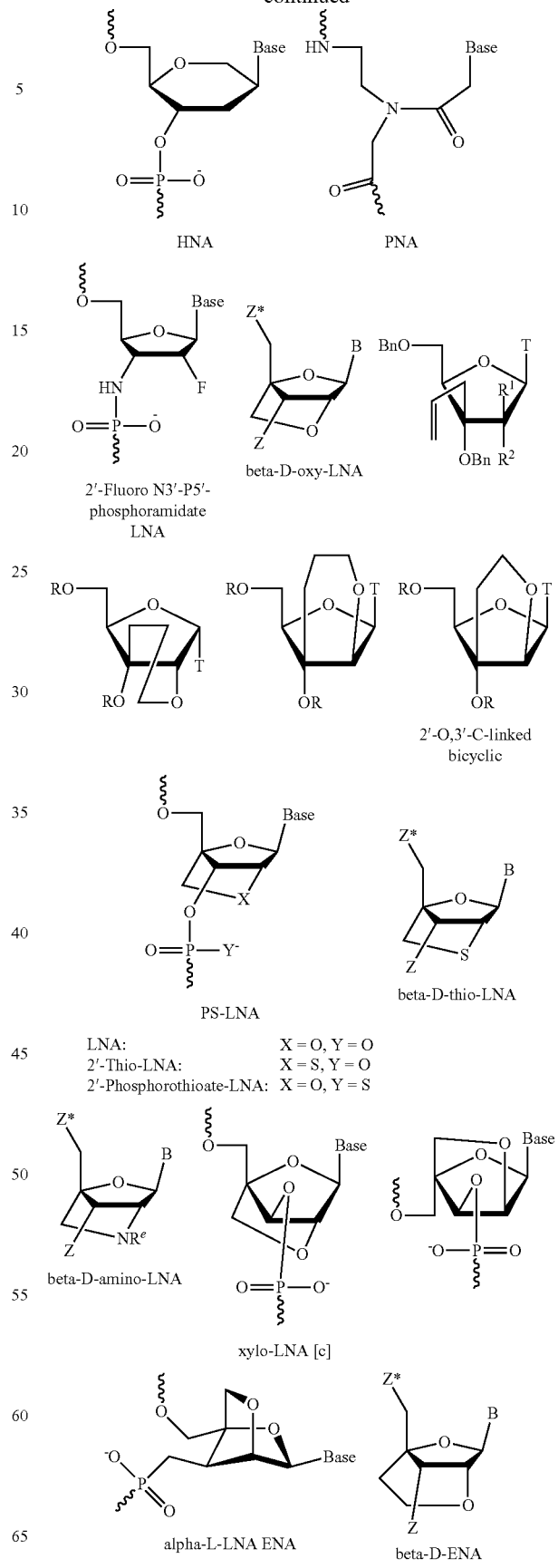

-continued

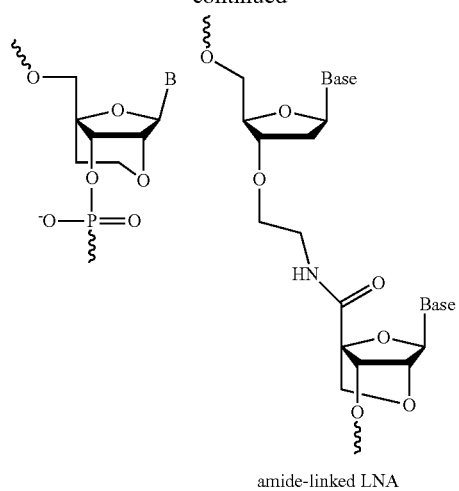

amide-linked LNA

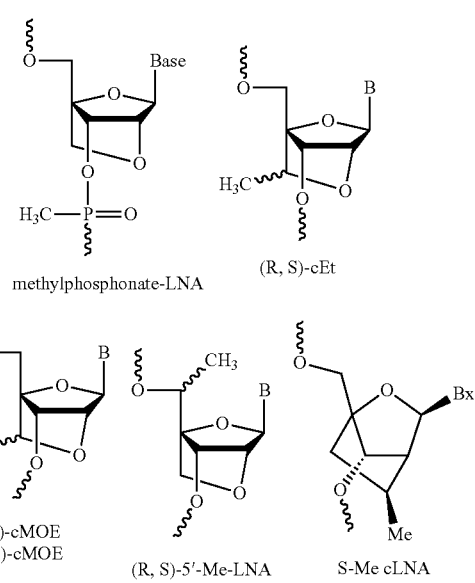

methylphosphonate-LNA (R, S)-cEt

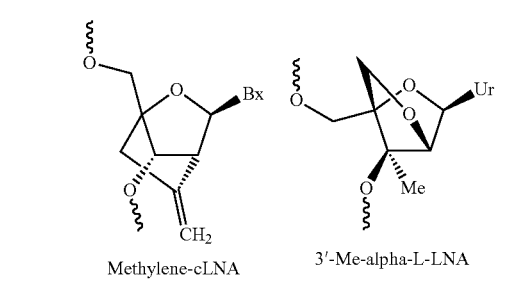

(R,S)-cMOE
(R, S)-cMOE   (R, S)-5′-Me-LNA   S-Me cLNA

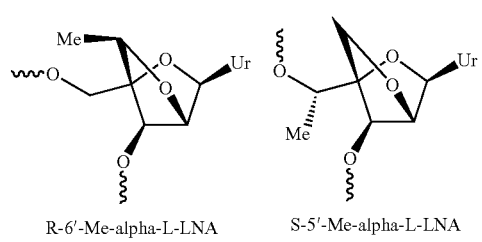

Methylene-cLNA   3′-Me-alpha-L-LNA

R-6′-Me-alpha-L-LNA   S-5′-Me-alpha-L-LNA

-continued

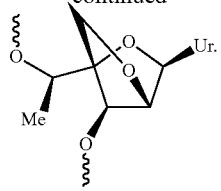

R-5′-Me-alpha-L-LNA

In some embodiments, $R^1$ is R as described in the present disclosure. In some embodiments, $R^2$ is R as described in the present disclosure. In some embodiments, $R^e$ is R as described in the present disclosure. In some embodiments, $R^e$ is H, —CH$_3$, -Bn, —COCF$_3$, benzoyl, benzyl, pyren-1-ylcarbonyl, pyren-1-ylmethyl, or 2-aminoethyl. In some embodiments, an example modified internucleotidic linkage and/or sugar moiety is selected from those described in Ts'o et al. Ann. N. Y. Acad. Sci. 1988, 507, 220; Gryaznov, S.; Chen, J.-K. J. Am. Chem. Soc. 1994, 116, 3143; Mesmaeker et al. Angew. Chem., Int. Ed. Engl. 1994, 33, 226; Jones et al. J. Org. Chem. 1993, 58, 2983; Vasseur et al. J. Am. Chem. Soc. 1992, 114, 4006; Van Aerschot et al. 1995 Angew. Chem. Int. Ed. Engl. 34: 1338; Hendrix et al. 1997 Chem. Eur. J. 3: 110; Koshkin et al. 1998 Tetrahedron 54: 3607-3630; Hyrup et al. 1996 Bioorg. Med. Chem. 4: 5; Nielsen et al. 1997 Chem. Soc. Rev. 73; Schultz et al. 1996 Nucleic Acids Res. 24: 2966; Obika et al. 1997 Tetrahedron Lett. 38 (50): 8735-8; Obika et al. 1998 Tetrahedron Lett. 39: 5401-5404; Singh et al. 1998 Chem. Comm. 1247-1248; Kumar et al. 1998 Bioo. Med. Chem. Let. 8: 2219-2222; Nielsen et al. 1997 J. Chem. Soc. Perkins Transl. 1: 3423-3433; Singh et al. 1998 J. Org. Chem. 63: 6078-6079; Seth et al. 2010 J. Org. Chem. 75: 1569-1581; Singh et al. 1998 J. Org. Chem. 63: 10035-39; Sorensen 2003 Chem. Comm. 2130-2131; Petersen et al. 2003 TRENDS Biotech. 21: 74-81; Rajwanshi et al. 1999 Chem. Commun. 1395-1396; Jepsen et al. 2004 Oligo. 14: 130-146; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Koizumi et al. 2003 Nuc. Acids Res. 12: 3267-3273; Lauritsen et al. 2002 Chem. Comm. 5: 530-531; Lauritsen et al. 2003 Bioo. Med. Chem. Lett. 13: 253-256; WO 2007090071; Seth et al., Nucleic Acids Symposium Series (2008), 52(1), 553-554; Seth et al. 2009 J. Med. Chem. 52: 10-13; Seth et al. 2012 Mol. Ther-Nuc. Acids. 1, e47; Pallan et al. 2012 Chem. Comm. 48: 8195-8197; Seth et al. 2010 J. Med. Chem. 53: 8309-8318; Seth et al. 2012 Bioo. Med. Chem. Lett. 22: 296-299; WO 2016/079181; U.S. Pat. Nos. 6,326,199; 6,066,500; and 6,440,739, base and sugar modifications of each of which is herein incorporated by reference.

Synthesis on Solid Support

In some embodiments, synthesis of provided oligonucleotides is performed on solid support. In some embodiments, reactive groups present on a solid support are protected. In some embodiments, reactive groups present on a solid support are unprotected. In some embodiments, during oligonucleotide synthesis a solid support is treated with various reagents in several synthesis cycles to achieve stepwise elongation of a growing oligonucleotide chain with individual nucleotide units. A nucleoside unit at the end of an oligonucleotide chain which is directly linked to a solid support is typically referred to as the first nucleoside linked to a solid support. In some embodiments, a first nucleoside linked to a solid support is bound to a solid support via a linker moiety, a diradical forming a bond at one end with a solid support, e.g., of a CPG, a polymer or other solid support, and at the other end with a nucleoside. In some embodiments, a linker stays intact during synthesis cycles performed to assemble the oligonucleotide chain and is cleaved after the chain assembly to liberate the oligonucleotide from the support.

In some embodiments, a solid supports for solid-phase nucleic acid synthesis is a support described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262,530; and Koster U.S. Pat. No. 4,725,677 (reissued as RE34,069). In some embodiments, a solid support is an organic polymer support. In some embodiments, a solid support is an inorganic polymer support. In some embodiments, an organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In some embodiments, an inorganic polymer support is silica, alumina, controlled pore glass (CPG), which is a silica-gel support, or aminopropyl CPG. In some embodiments, a solid support is selected from fluorous solid supports (see e.g., WO/2005/070859), and long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.*, 1983, 105, 661-663; G. R. Gough, M. J. Bruden and P. T. Gilham, *Tetrahedron Lett.*, 1981, 22, 4177-4180). Membrane supports and polymeric membranes (see e.g. Innovation and Perspectives in Solid Phase Synthesis, Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis. In addition to attachment of a functional group to membrane, use of a linker or spacer group attached to the membrane is also used in some embodiments to minimize steric hindrance between the membrane and the synthesized chain.

Example suitable solid supports also include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research*, 1991, 19, 1527), TentaGel Support—an aminopolyethyleneglycol derivatized support (see, e.g., Wright, et al., *Tetrahedron Lett.*, 1993, 34, 3373), and Poros-a copolymer of polystyrene/divinylbenzene.

Surface activated polymers have been demonstrated for use in synthesis of natural and modified nucleic acids and proteins on several solid supports mediums. In some embodiments, a solid support material is any polymer suitably uniform in porosity, having sufficient amine content, and sufficient flexibility to undergo any attendant manipulations without losing integrity. Examples of suitable selected materials include nylon, polypropylene, polyester, polytetrafluoroethylene, polystyrene, polycarbonate, and nitrocellulose. In some embodiments, other materials can serve as a solid support, depending on design in accordance with the present disclosure. In some embodiments, in consideration of some designs, for example, a coated metal, in particular gold or platinum can be selected (see e.g., US publication No. 20010055761). In some embodiments, for example, a nucleoside is anchored to a solid support which is functionalized with hydroxyl or amino residues. In some embodiments, a solid support is derivatized to provide an acid labile trialkoxytrityl group, such as a trimethoxytrityl group (TMT). Without being bound by theory, it is expected that presence of a trialkoxytrityl protecting group may permit initial detritylation under conditions commonly used on DNA synthesizers. In some embodiments, for a faster release of oligonucleotide material in solution with aqueous ammonia, a diglycolate linker is optionally introduced onto the support.

In some embodiments, a provided oligonucleotide is synthesized from 3' to 5' direction. In some embodiments, a provided oligonucleotide is synthesized from 5' to 3' direction. In some embodiments, a nucleic acid is attached to a solid support through its 5' end of the growing nucleic acid, thereby presenting its 3' group for reaction, i.e. using 5'-nucleoside phosphoramidites or in an enzymatic reaction (e.g. ligation and polymerization using nucleoside 5'-triphosphates). In some embodiments, in a 5' to 3' synthesis iterative steps of the present disclosure remain unchanged (e.g. capping and modification on the chiral phosphorus).

Linking Moiety

In some embodiments, a linking moiety or linker is optionally used to connect a solid support to a first nucleoside linked to a solid support, or a compound comprising a free nucleophilic moiety. In some embodiments, suitable linkers are known such as short moieties which serve to connect a solid support to functional groups (e.g., hydroxyl groups) of initial nucleoside molecules in solid phase synthetic techniques, and can be utilized in accordance with the present disclosure. In some embodiments, a linking moiety is a succinamic acid linker, or a succinate linker (—CO—CH$_2$—CH$_2$—CO—), or an oxalyl linker (—CO—CO—). In some embodiments, a linker is a succinamic acid linker. In some embodiments, a linker is a succinate linker. In some embodiments, a linker is an oxalyl linker. In some embodiments, a linking moiety and a nucleoside are bonded together through an ester bond. In some embodiments, a linking moiety and a nucleoside are bonded together through an amide bond. In some embodiments, a linking moiety connects a nucleoside to another nucleotide or nucleic acid. Example suitable linkers are disclosed in, for example, *Oligonucleotides And Analogues A Practical Approach*, Ekstein, F. Ed., IRL Press, N.Y., 1991, Chapter 1 and Solid-Phase Supports for Oligonucleotide Synthesis, Pon, R. T., *Curr. Prot. Nucleic Acid Chem.*, 2000, 3.1.1-3.1.28.

In some embodiments, a linking moiety is a phosphodiester linkage. In some embodiments, a linking moiety is an H-phosphonate moiety. In some embodiments, a linking moiety is a modified phosphorus linkage as described herein. In some embodiments, a universal linker (UnyLinker) is used to attach a nucleoside, nucleotide, oligonucleotide and/or nucleic acid to a solid support (Ravikumar et al., *Org. Process Res. Dev.*, 2008, 12 (3), 399-410). In some embodiments, other universal linkers are used (Pon, R. T., *Curr. Prot. Nucleic Acid Chem.*, 2000, 3.1.1-3.1.28). In some embodiments, various orthogonal linkers (such as disulfide linkers) are used (Pon, R. T., *Curr. Prot. Nucleic Acid Chem.*, 2000, 3.1.1-3.1.28).

Among other things, the present disclosure recognizes that a linker can be chosen or designed to be compatible with a set of reaction conditions employed in synthesis. In some embodiments, to avoid degradation of oligonucleotides and to avoid desulfurization, auxiliary groups are selectively removed before de-protection. In some embodiments, DPSE group can selectively be removed by F⁻. In some embodiments, the present disclosure provides linkers that are stable under a DPSE de-protection condition, e.g., 0.1M TBAF in MeCN, 0.5M HF-Et$_3$N in THF or MeCN, etc. In some embodiments, a provided linker is a SP linker. In some embodiments, the present disclosure demonstrates that a SP linker is stable under a DPSE de-protection condition, e.g., 0.1M TBAF in MeCN, 0.5M HF-Et$_3$N in THF or MeCN, etc. In some embodiments, a SP linker is also stable, e.g., under anhydrous basic conditions, such as om1M DBU in MeCN. In some embodiments, a linker is succinyl linker. In some embodiments, a linker is Q-linker. In some embodiments, a linker is oxalyl linker. Example use of certain linkers are depicted below:

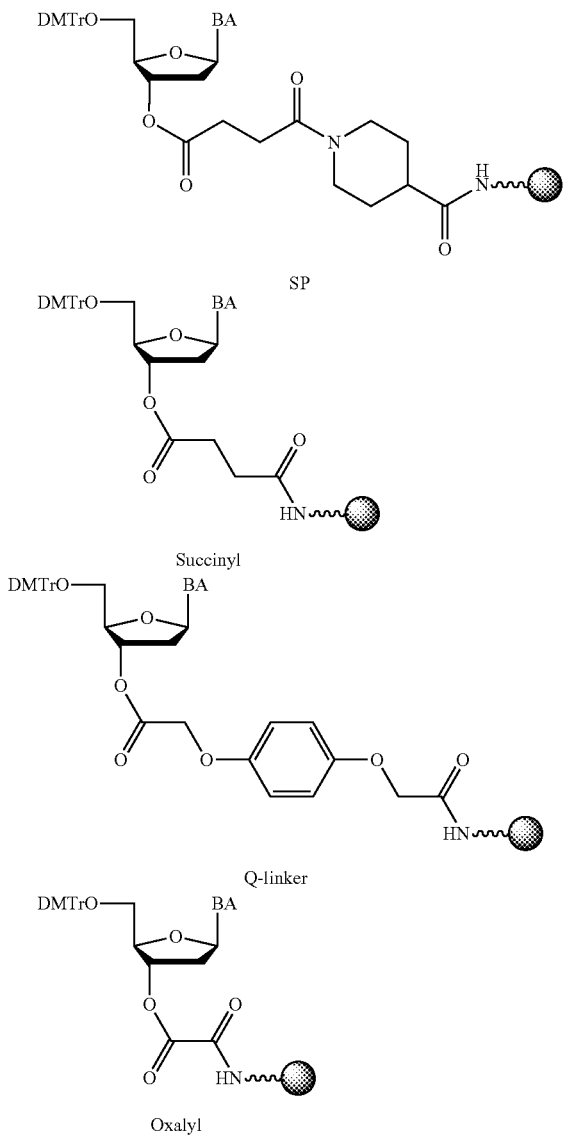

Example Preparation of Provided Compounds and Compositions Thereof

In some embodiments, provided compounds, e.g., compounds of formula I, I-a, I-a-1, I-a-2, I-b, I-c, I-d, I-e, II, II-a, II-b, III, III-a, III-b, or stereoisomers (diastereomers and enantiomers) thereof, are chiral, and are useful in stereoselective organic synthesis to provide chirally controlled formation of chiral elements. Among other things, provided compounds, e.g., compounds of formula I, I-a, I-a-1, I-a-2, I-b, I-c, I-d, I-e, II, II-a, II-b, III, III-a, or III-b, are useful as chiral auxiliaries for chirally controlled preparation of oligonucleotides comprising one or more chiral internucleotidic linkages. In some embodiments, the present disclosure demonstrates that technologies (compounds, methods, etc.) of the present disclosure can provide high yields and stereochemical control, and are particularly useful for constructing challenging internucleotidic linkages. In some embodiments, provided compounds (or activated forms thereof) react with nucleosides or derivatives thereof, to form chiral monomer phosphoramidites which can be utilized to form chiral internucleotidic linkage with chiral control of the linkage phosphorus chiral center. Suitable technologies (e.g., procedures, reagents, conditions, etc.) for preparation of chiral monomer phosphoramidites and their uses in chirally controlled oligonucleotide synthesis are widely known (e.g., US/2015/0211006, US/2017/0037399, WO/2017/015555, and WO/2017/062862, each of which is incorporated herein by reference) and can be used in accordance with the present disclosure. In some embodiments, a provided phosphoramidite is one formed by a chiral auxiliary described in the present disclosure, e.g., a compound of I, I-a, I-a-1, I-a-2, I-b, I-c, I-d, I-e, II, II-a, II-b, III, III-a, or III-b, with a nucleoside described in the present disclosure and/or a nucleoside described in US/2015/0211006, US/2017/0037399, WO/2017/015555, and WO/2017/062862, each of which is incorporated herein by reference, under a suitable condition. In some embodiments, a provided phosphoramidite is of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or a salt thereof. In some embodiments, a provided phosphoramidite is of formula IV, IV-a, IV-b, IV-c-1, IV-c-2, IV-d, IV-e, V, V-a, V-b, V-c-1, V-c-2, V-d, V-e, VI, VI-a, VI-b, VI-c, VI-c-1, VI-c-2, VI-d, or VI-e, or a salt thereof.

In some embodiments, the present disclosure provides oligonucleotides and compositions thereof. In some embodiments, the present disclosure provides technologies for preparing provided oligonucleotides and oligonucleotide compositions, e.g., chirally controlled oligonucleotide compositions and non-chirally controlled oligonucleotide compositions. As those skilled in the art appreciate, provided compounds, e.g., those of formula I, I-a, I-a-1, I-a-2, I-b, I-c, I-d, I-e, II, II-a, II-b, III, III-a, or III-b, or salts thereof, those of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or salts thereof, etc., can be combined with various known technologies in accordance with the present disclosure to provide oligonucleotides and compositions thereof. In some embodiments, example technologies, e.g., reagents, conditions, solvents, oligonucleotide synthesis cycles, etc. that can be combined with provided compounds in accordance with the present disclosure are selected from those described in US Patent Publication Nos. US/2015/0211006 and US/2017/0037399, and PCT Application Nos. WO/2017/015555 and WO/2017/062862, technologies, e.g., reagents, conditions, solvents, oligonucleotide synthesis cycles, etc., of each of which are incorporated herein by reference.

In some embodiments, the present disclosure provides methods for preparing a compound, e.g., a compound of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or a salt thereof, a compound of formula VIII or a salt thereof, an oligonucleotide comprising one or more internucleotidic linkages each independently of formula VII, VII-a-1, VII-a-2, VII-b, VII-c, VII-d, or VII-e, or a salt form thereof, etc., comprising providing a compound of formula I, I-a, I-a-1, I-a-2, I-b, I-c, I-d, I-e, II, II-a, II-b, III, III-a, or III-b, or a salt thereof.

In some embodiments, the present disclosure provides methods for preparing oligonucleotides, comprising coupling, optionally capping, optionally modifying, optionally deblocking, and repeating one or more of these steps to provide an oligonucleotide.

In some embodiments, the present disclosure provides a method for preparing an oligonucleotide, comprising steps of:
(1) coupling;
(2) optionally capping;
(3) optionally modifying;
(4) optionally deblocking; and
(5) optionally repeating (1) to (4) until the desired oligonucleotide length is achieved.

In some embodiments, the present disclosure provides a method for preparing an oligonucleotide, comprising steps of:
(1) coupling;
(2) optionally capping;
(3) modifying;
(4) optionally deblocking; and
(5) optionally repeating (1) to (4) until the desired oligonucleotide length is achieved.

In some embodiments, the present disclosure provides a method for preparing an oligonucleotide, comprising steps of:
(1) coupling;
(2) optionally capping;
(3) modifying;
(4) optionally deblocking; and
(5) repeating (1) to (4) until the desired oligonucleotide length is achieved.

In some embodiments, the present disclosure provides a method for preparing an oligonucleotide, comprising steps of:
(1) coupling;
(2) optionally capping;
(4) optionally deblocking; and
(5) repeating (1) to (4) until the desired oligonucleotide length is achieved; and (6) modifying.

In some embodiments, coupling comprises providing a compound of formula I, I-a, I-a-1, I-a-2, I-b, I-c, I-d, I-e, II, II-a, II-b, III, III-a, or III-b, or a salt thereof. In some embodiments, coupling comprises providing a compound of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or a salt thereof. In some embodiments, coupling comprises providing a compound of formula IV, IV-a, IV-b, IV-c-1, IV-c-2, IV-d, IV-e, V, V-a, V-b, V-c-1, V-c-2, V-d, V-e, VI, VI-a, VI-b, VI-c, VI-c-1, VI-c-2, VI-d, or VI-e, or a salt thereof. In some embodiments, coupling forms an internucleotidic linkage of formula VII, VII-a-1, VII-a-2, VII-b, VII-c, VII-d, or VII-e, or a salt form thereof. In some embodiments, coupling provides a compound of formula VIII or a salt thereof, or an oligonucleotide comprising one or more internucleotidic linkages each independently of formula VII, VII-a-1, VII-a-2, VII-b, VII-c, VII-d, or VII-e, or a salt form thereof. In some embodiments, coupling provides purity, stereoselectivity, and/or yields as described in the present disclosure. Various coupling reagents and/or conditions are known and can be utilized in accordance with the present disclosure, e.g., those described in US Patent Publication Nos. US/2015/0211006 and US/2017/0037399, and PCT Application Nos. WO/2017/015555 and WO/2017/062862, coupling technologies, e.g., reagents, conditions, solvents, etc., of each of which are incorporated herein by reference.

In some embodiments, provided methods comprise one or more capping steps. In some embodiments, capping blocks unreacted 5'-hydroxyl groups. In some embodiments, capping blocks an amino group in internucleotidic linkage of formula VII, VII-a-1, VII-a-2, VII-b, VII-c, VII-d, or VII-e, or a salt form thereof, converting —X-$L^s$-$R^5$ from a structure wherein H—X-$L^s$-$R^5$ is a compound of formula I, I-a, I-a-1, I-a-2, I-b, I-c, I-d, I-e, II, II-a, II-b, III, III-a, or III-b, or a salt thereof wherein $R^6$ is —H to a structure wherein H—X-$L^s$-$R^5$ is a compound of formula I, I-a, I-a-1, I-a-2, I-b, I-c, I-d, I-e, II, II-a, II-b, III, III-a, or III-b, or a salt thereof wherein $R^6$ is not —H (e.g., —C(O)R, which can be introduced using an activated form of acid R—COOH). In some embodiments, capping provides a compound of formula VIII or a salt thereof, or an oligonucleotide comprising one or more internucleotidic linkages each independently of formula VII, VII-a-1, VII-a-2, VII-b, VII-c, VII-d, or VII-e, or a salt form thereof, wherein —X-$L^s$-$R^5$ is a structure that H—X-$L^s$-$R^5$ is a compound of formula I, I-a, I-a-1, I-a-2, I-b, I-c, I-d, I-e, II, II-a, II-b, III, III-a, or III-b, or a salt thereof wherein $R^6$ is not —H (e.g., —C(O)R). In some embodiments, capping provides purity, stereoselectivity, and/or yields as described in the present disclosure. Various capping reagents and/or conditions are known and can be utilized in accordance with the present disclosure, e.g., those described in US Patent Publication Nos. US/2015/0211006 and US/2017/0037399, and PCT Application Nos. WO/2017/015555 and WO/2017/062862, capping technologies, e.g., reagents, conditions, solvents, etc., of each of which are incorporated herein by reference.

In some embodiments, provided methods comprise one or more modifying steps. In some embodiments, modifying is oxidation introducing =O to a linkage phosphorus. In some embodiments, modifying is sulfurization introducing =S to a linkage phosphorus. In some embodiments, modifying introducing =Se to a linkage phosphorus. In some embodiments, modifying introducing $B(R')_3$ to a linkage phosphorus. In some embodiments, capping provides a compound of formula VIII or a salt thereof, or an oligonucleotide comprising one or more internucleotidic linkages each independently of formula VII-a-1, VII-a-2, VII-d, or VII-e, or a salt form thereof, wherein —X-$L^s$-$R^5$ is a structure that H—X-$L^s$-$R^5$ is a compound of formula I, I-a, I-a-1, I-a-2, I-b, I-c, I-d, I-e, II, II-a, II-b, III, III-a, or III-b, or a salt thereof wherein $R^6$ is not —H (e.g., —C(O)R). In some embodiments, capping provides a compound of formula VIII or a salt thereof, or an oligonucleotide comprising one or more internucleotidic linkages each independently of formula VII-a-1, VII-a-2, VII-d, or VII-e, or a salt form thereof, wherein X in —X-$L^s$-$R^5$ is —S—, and modifying introduces =O to a modified linkage phosphorus. In some embodiments, chiral auxiliaries are removed during modifying. In some embodiments, chiral auxiliaries remain attached during modifying. In some embodiments, modifying provides purity, stereoselectivity, and/or yields as described in the present disclosure. In some embodiments, oligonucleotides are modified after desired lengths are achieved. In some embodiments, oligonucleotides are modified during cycles. Various modifying reagents and/or conditions are known and can be utilized in accordance with the present disclosure, e.g., those described in US Patent Publication Nos. US/2015/0211006 and US/2017/0037399, and PCT Application Nos. WO/2017/015555 and WO/2017/062862, modifying technologies, e.g., reagents, conditions, solvents, etc., of each of which are incorporated herein by reference.

In some embodiments, provided methods comprise one or more deblocking steps. In some embodiments, de-blocking removes protecting groups of 5'-OH of full-length oligonucleotides so that they can be used for next step, but keeps intact capping groups on 5'-OH of shorter oligonucleotides which, e.g., are formed from incomplete coupling steps. In some embodiments, chiral auxiliaries are removed during deblocking. In some embodiments, deblocking provides purity, stereoselectivity, and/or yields as described in the present disclosure. Various deblocking reagents and/or conditions are known and can be utilized in accordance with the present disclosure, e.g., those described in US Patent Publication Nos. US/2015/0211006 and US/2017/0037399, and PCT Application Nos. WO/2017/015555 and WO/2017/062862, deblocking technologies, e.g., reagents, conditions, solvents, etc., of each of which are incorporated herein by reference.

In some embodiments, provided methods comprises one or more de-protecting and/or cleaving steps. In some embodiments, after synthesis oligonucleotides are de-protected, e.g., removing protected groups from one or more nucleobases, sugars, and/or internucleotidic linkages, and/or cleaved from a synthetic support, e.g., solid support, used for oligonucleotide synthesis. Various supports are known in the art and can be utilized in accordance with the present disclosure. Among other things, the present disclosure provides compounds and methods that are compatible with various de-protection and cleavage conditions, thereby providing enormous flexibility for oligonucleotide synthesis to achieve desired results. Many de-protection and cleavage conditions are known and can be utilized in accordance with the present disclosure, e.g., those described in US Patent Publication Nos. US/2015/0211006 and US/2017/0037399, and PCT Application Nos. WO/2017/015555 and WO/2017/062862, de-protecting and cleavage technologies, e.g., reagents, conditions, solvents, etc., of each of which are incorporated herein by reference. In some embodiments, de-protecting and/or cleavage provide purity, stereoselectivity, and/or yields as described in the present disclosure.

In some embodiments, provided methods provide purity, stereoselectivity, and/or yields as described in the present disclosure. As demonstrated by certain example data, technologies of the present disclosure, among other things, can provide high yields, purity, and/or stereoselectivity, particularly for challenging internucleotidic linkages.

For example, in some embodiments, one or more cycles for oligonucleotide synthesis are as depicted in Cycle A. In some embodiments, one or more cycles for oligonucleotide synthesis are depicted as in Cycle B. As readily appreciated by those skilled in the art, absolute stereochemistry of linkage phosphorus can be achieved as desired through selection of chiral auxiliary and/or phosphoramidite compounds in accordance with the present disclosure.

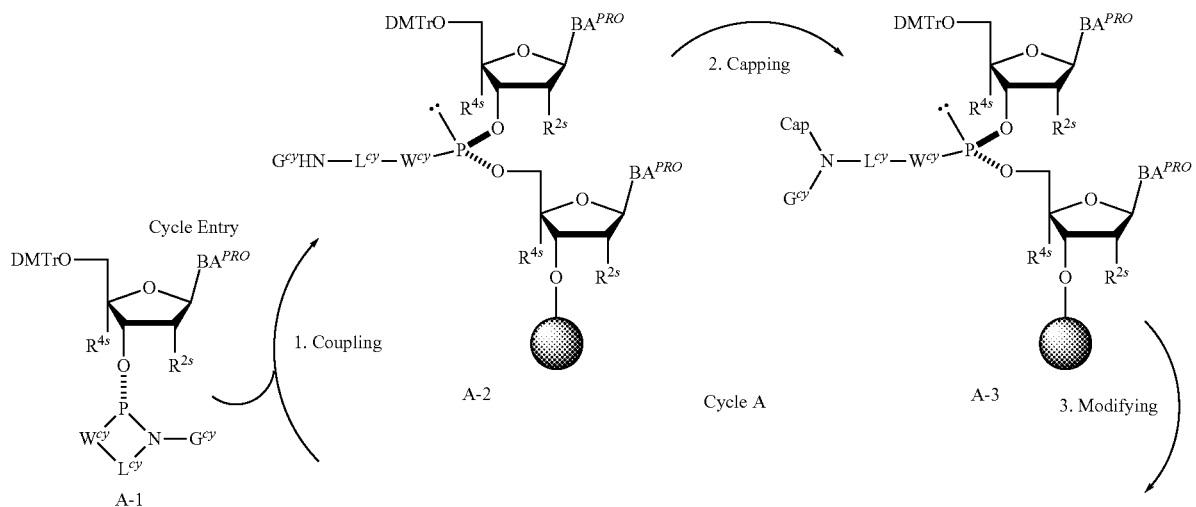

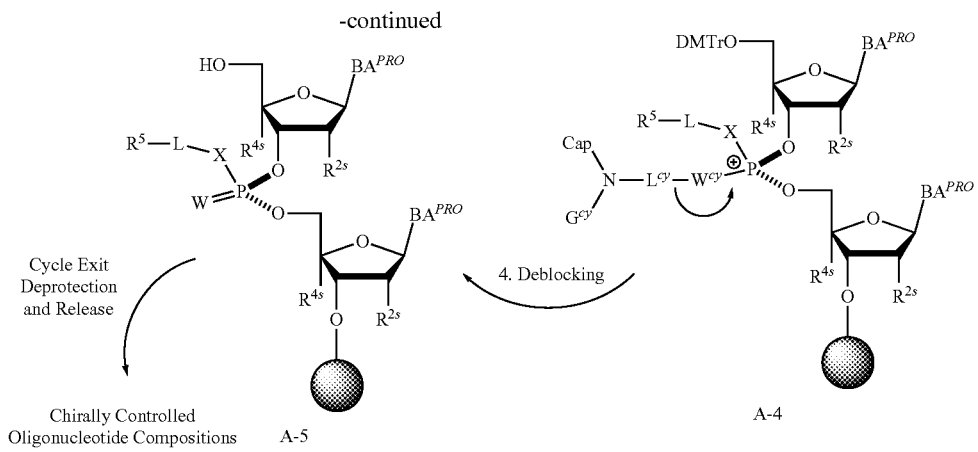

A-5 Chirally Controlled Oligonucleotide Compositions

A-4

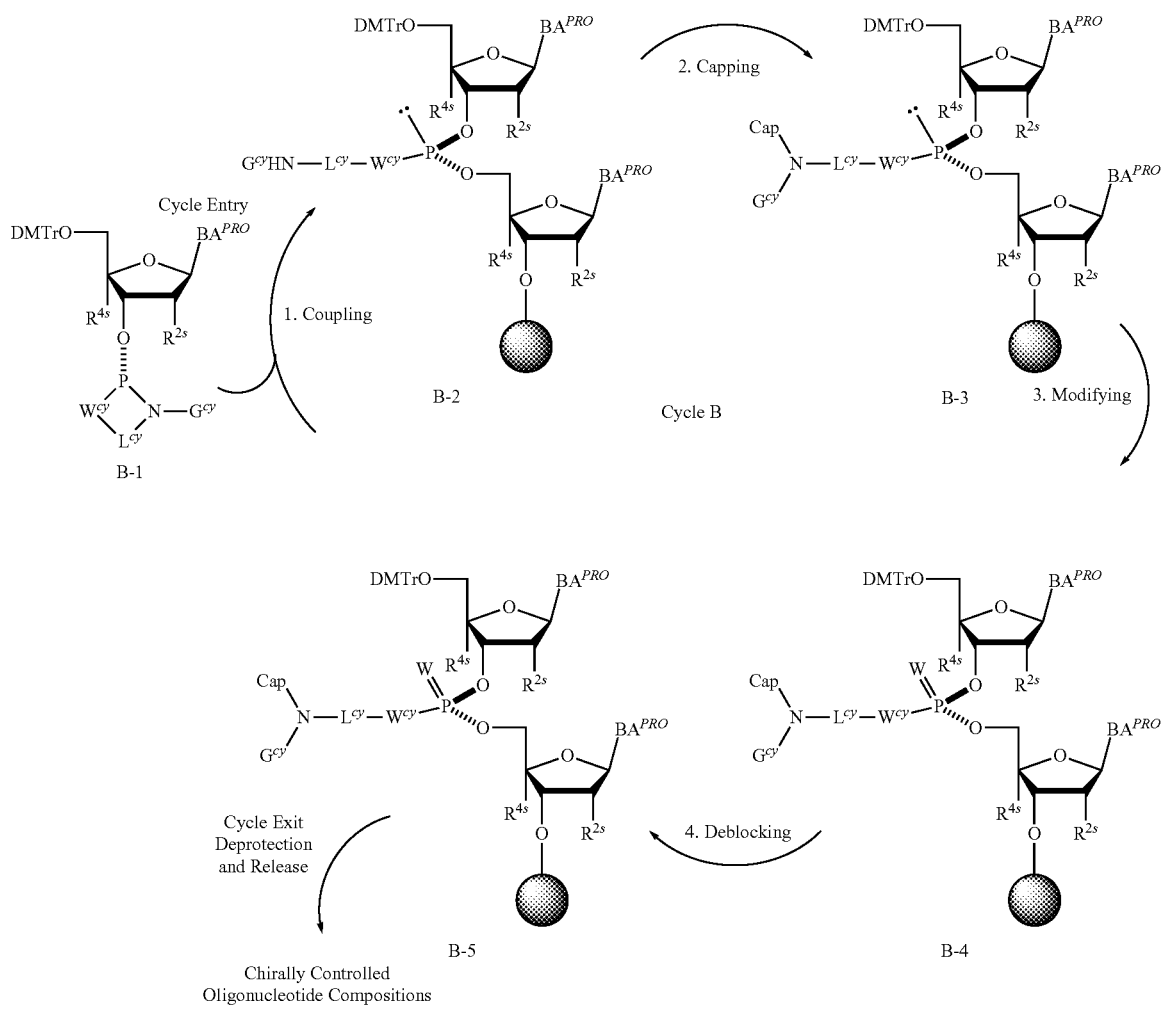

In some embodiments, —$W^{cy}$-$L^{cy}$-$NG^{cy}$- is of a structure that H—$W^{cy}$-$L^{cy}$-$NHG^{cy}$ is a compound of formula I, I-a, I-a-1, I-a-2, I-b, I-c, I-d, I-e, II, II-a, II-b, III, III-a, or III-b, or a salt thereof. In some embodiments, each $BA^{PRO}$ is independently protected nucleobase, e.g., protected adenine, cytosine, guanosine, thymine, or uracil, or a tautomeric form thereof. In some embodiments, each $R^{2s}$ and $R^{4s}$ is independently as described in the present disclosure. In some embodiments, $R^{4s}$ and $R^{2s}$ are hydrogen. In some embodiments, $R^{4s}$ is hydrogen, and $R^{2s}$ is a 2'-modification as described in the present disclosure. In some embodiments, $R^{4s}$ is hydrogen, and $R^{2s}$ is 2'-OR, wherein R is not hydrogen. In some embodiments, $R^{4s}$ is hydrogen, and $R^{2s}$ is a 2'-F. In some embodiments, $R^{4s}$ is hydrogen, and $R^{2s}$ is a 2'-OMe. In some embodiments, $R^{4s}$ is hydrogen, and $R^{2s}$ is a 2'-MOE. In some embodiments, $R^{4s}$ and $R^{2s}$ are taken together to form a LNA-type modification (e.g., C2-O—C(R)$_2$—C4, C2-O—CH$_2$—C4, C2-O—(R)—CHR—C4, C2-O—(S)—CHR—C4, etc., wherein each R is independently as described in the present disclosure) as described in the present disclosure. In some embodiments, —W$^{cy}$-L$^{cy}$-NG$^{cy}$(Cap)- is of a structure that H—W$^{cy}$-L$^{cy}$-NG$^{cy}$(Cap) is a compound of formula I, I-a, I-a-1, I-a-2, I-b, I-c, I-d, I-e, II, II-a, II-b, III, III-a, or III-b, or a salt thereof. In some embodiments, -Cap is $R^6$. In some embodiments, -Cap is $R^6$, wherein $R^6$ is —C(O)—R. In some embodiments, R is methyl. In some embodiments, R is —CF$_3$. In some embodiments, compounds of formula A-1 and/or B-1 are compounds of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or salts thereof. In some embodiments, compounds of formula A-1 and/or B-1 are compounds of formula IV, IV-a, IV-b, IV-c-1, IV-c-2, IV-d, IV-e, V, V-a, V-b, V-c-1, V-c-2, V-d, V-e, VI, VI-a, VI-b, VI-c, VI-c-1, VI-c-2, VI-d, or VI-e, or salts thereof. In some embodiments, compounds of formula A-2, A-3, A-4, A-5, B-2, B-3, B-4, and/or B-5, are compounds of formula VIII or salts thereof. In some embodiments, W is O or S. In some embodiments, a modification reaction is a sulfurization reaction. In some embodiments, a modification reaction is an oxidation reaction. In some embodiments, provided methods comprise one or more cycles with sulfurization reactions and one or more cycles with oxidation reactions, so that oligonucleotides comprising one or more internucleotidic linkages with W being S and one or more internucleotidic linkages with W being O are prepared as designed.

In some embodiments, in one or more cycles of oligonucleotide synthesis, instead of using Cycle A (and a compound of formula A-1) or Cycle B (and a compound of formula B-1), a traditional phosphoramidite for non-chirally controlled oligonucleotide synthesis can be used, particularly if an internucleotidic linkage to be incorporated in a final product is an achiral internucleotidic linkage such as a natural phosphate linkage. In some embodiments, provided technologies are compatible with traditional non-chirally controlled phosphoramidite oligonucleotide synthesis technologies. In some embodiments, synthetic cycles for provided oligonucleotides comprise one or more Cycles A. In some embodiments, synthetic cycles for provided oligonucleotides comprise one or more Cycles B. In some embodiments, synthetic cycles for provided oligonucleotides comprise one or more Cycles A. In some embodiments, synthetic cycles for provided oligonucleotides comprise one or more Cycles A. and one or more Cycles B. In some embodiments, synthetic cycles for provided oligonucleotides further comprises one or more traditional non-chirally controlled phosphoramidite chemistry cycle to incorporate a non-chirally controlled phosphoramidite linkage, e.g., a natural phosphate linkage, a non-chirally controlled phosphorothioate linkage, etc. In some embodiments, provided methods comprise one or more Cycles A. In some embodiments, provided methods comprise one or more Cycles B. In some embodiments, provided methods comprise one or more Cycles A. In some embodiments, provided methods comprise one or more Cycles A. and one or more Cycles B. In some embodiments, synthetic cycles further comprise one or more traditional non-chirally controlled phosphoramidite chemistry cycles to incorporate one or more non-chirally controlled phosphoramidite linkages, e.g., natural phosphate linkages, and/or non-chirally controlled phosphorothioate linkages, etc. As appreciated by those skilled in the art, provided technologies (e.g., reagents, methods, etc.) provide enormous flexibilities and capabilities so that oligonucleotides of various sequences and lengths, and/or comprising various modifications, e.g., to nucleases, sugars, and/or internucleotidic linkages, etc., can be readily prepared with high yields and/or chiral control in accordance with the present disclosure. In some embodiments, provided oligonucleotides comprise two or more types of internucleotidic linkages. In some embodiments, provided oligonucleotides comprise one or more natural phosphate linkages and one or more chiral internucleotidic linkages. In some embodiments, the chiral internucleotidic linkages are the same. In some embodiments, the chiral internucleotidic linkages are different. In some embodiments, the chiral internucleotidic linkages are chirally controlled. In some embodiments, the chiral internucleotidic linkages are of formula VII, VII-a-1, VII-a-2, VII-b, VII-c, VII-d, or VII-e, or salt forms thereof. In some embodiments, the chiral internucleotidic linkages are phosphorothioate linkages or salt forms thereof. In some embodiments, the chiral internucleotidic linkages are phosphorothioate linkages or salt forms thereof, and are chirally controlled.

In some embodiments, an example of Cycle B is Cycle C, which includes, among other things, certain example reagents and DPSE chiral auxiliary. In some embodiments, provided methods comprise one or more modifying steps comprising oxidation instead of sulfurization (e.g., in Cycle C), so that (=O) can be incorporated as designed. In some embodiments, provided methods comprise one or more traditional non-chirally controlled phosphoramidite chemistry cycles (e.g., using protected nucleoside —P(OCH$_2$CH$_2$CN)[N(i-Pr)$_2$] as phosphoramidites) to incorporate one or more non-chirally controlled phosphoramidite linkages, e.g., natural phosphate linkages, and/or non-chirally controlled phosphorothioate linkages, etc. Among other things, the present disclosure provides cycles for forming chirally controlled internucleotidic linkages which are compatible with traditional phosphoramidite chemistry for oligonucleotide synthesis, so oligonucleotides comprising both chirally controlled internucleotidic linkages (e.g., chirally controlled phosphorothioate linkages), non-chirally controlled chiral internucleotidic linkages (e.g., non-chirally controlled phosphorothioate linkages), and/or natural phosphate linkages, can be readily prepared with high yields, selectivity, and/or low cost. In some embodiments, one or more natural phosphate linkages or non-chirally controlled chiral internucleotidic linkages may be optionally introduced by one or more chemical methods that are other than phosphoramidite-based oligonucleotide synthesis but are compatible with and/or adaptable to oligonucleotide synthesis. A variety of oligonucleotides, such as those comprising both PO and PS linkages, e.g., those described in US/2011/0294124, US/2015/0211006, US/2017/0037399, WO/2017/015555, and WO/2017/062862, etc., can be readily prepared in accordance with the present disclosure.

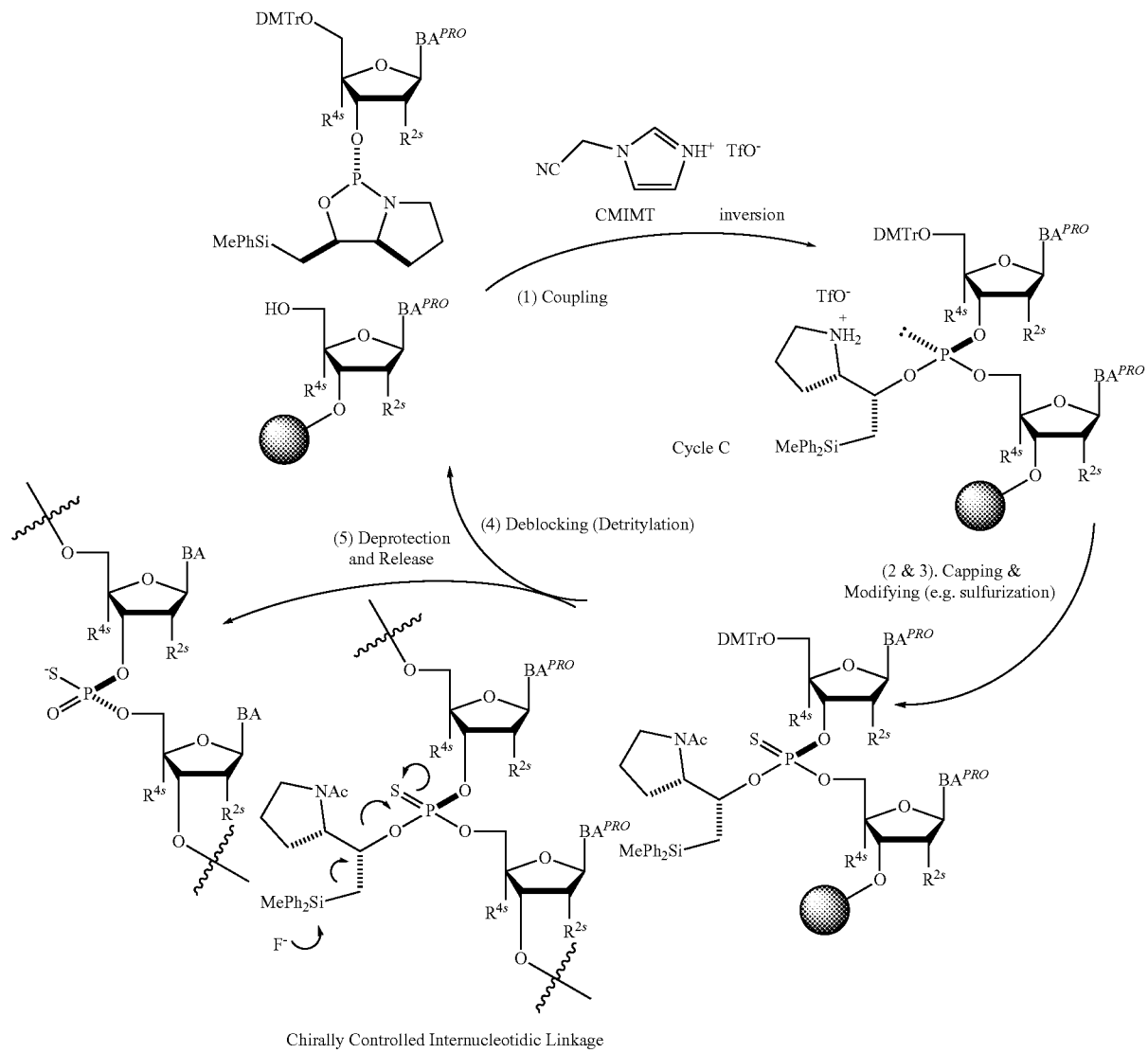

Chirally Controlled Internucleotidic Linkage

Various known reagents and conditions may be utilized in accordance with the present disclosure for using provided compounds to prepare oligonucleotide compositions, e.g., those in US/2011/0294124, US/2015/0211006, US/2017/0037399, WO/2017/015555, and WO/2017/062862, reagents and conditions of each of which are incorporated herein by reference.

In some embodiments, activating reagents are employed during coupling steps. In some embodiments, example activating reagents are selected from 4,5-dicyanoimidazole (DCI), 4,5-dichloroimidazole, 1-phenylimidazolium triflate (PhIMT), benzimidazolium triflate (BIT), benztriazole, 3-nitro-1,2,4-triazole (NT), tetrazole, 5-ethylthiotetrazole (ETT), 5-benzylthiotetrazole (BTT), 5-(4-nitrophenyl)tetrazole, N-cyanomethylpyrrolidinium triflate (CMPT), N-cyanomethylpiperidinium triflate, N-cyanomethyldimethylammonium triflate, and N-cyanomethylimidazolium triflate (CMIMT). In some embodiments, provided phosphoramidites, e.g., those of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or salts thereof, are used in coupling steps to grow oligonucleotide chains. In some embodiments, non-chirally pure phosphoramidites, e.g., those of formula IVa, IVa-a, IVa-b, IVa-c-1, IVa-c-2, IVa-d, or IVa-e, wherein -$L^7$-$R^1$ and —N($R^5$)($R^6$) contains no chiral elements, or salts thereof, can be used for cycles comprising oxidation steps, or other steps that do not require chiral control. In some embodiments, β-cyanoethylphosphoramidites protected with DMTr is used. In some embodiments, a phosphoramidite being used has the structure of

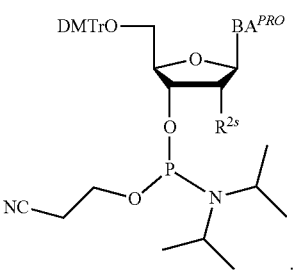

Among other things, provided technologies (e.g., compounds, methods, etc.) provide high stereoselectivity, yields, and/or purity as described in the present disclosure for coupling steps (e.g., 95%, 96%, 97%, 98%, 99% or more diastereoselectivity, 70%, 75%, 80%, 85%, 90%, 91%, 92%, 93%, 94%, 95%, 96%, 97%, 98%, 99% or more yield, etc.).

In some embodiments, a final oligonucleotide is larger than a dimer, and unreacted —OH moieties during synthesis is capped with a blocking group and chiral auxiliary in the compound may also be capped with a blocking group to form a capped condensed intermediate. Among other things, provided technologies (e.g., compounds, methods, etc.) provide high stereoselectivity, yields, and/or purity as described in the present disclosure for coupling steps (e.g., 95%, 96%, 97%, 98%, 99% or more diastereoselectivity, 70%, 75%, 80%, 85%, 90%, 91%, 92%, 93%, 94%, 95%, 96%, 97%, 98%, 99% or more yield, etc.).

In some embodiments, during modifying steps, an oligonucleotide is modified by reaction with an electrophile. In some embodiments, a modifying step is performed using an oxygen electrophile, sulfur electrophile, a selenium electrophile or a boronating agent. In some embodiments, a modifying step comprises sulfurization. In some embodiments, a modifying step comprises oxidation. In some embodiments, a modifying step comprises boronation. Among other things, provided technologies (e.g., compounds, methods, etc.) provide high stereoselectivity, yields, and/or purity as described in the present disclosure for coupling steps (e.g., 95%, 96%, 97%, 98%, 99% or more diastereoselectivity, 70%, 75%, 80%, 85%, 90%, 91%, 92%, 93%, 94%, 95%, 96%, 97%, 98%, 99% or more yield, etc.).

In some embodiments, a sulfur electrophile is a compound having one of the following formulae:

$$S_8, Z^{z1}-S-S-Z^{z2}, \text{ or } Z^{z1}-S-V^{z1}-Z^{z2}; \quad \text{(Formula Z—B)}$$

wherein $Z^{z1}$ and $Z^{z2}$ are independently optionally substituted alkyl, aminoalkyl, cycloalkyl, heterocyclyl, cycloalkylalkyl, heterocycloalkyl, aryl, heteroaryl, alkyloxy, aryloxy, heteroaryloxy, acyl, amide, imide, or thiocarbonyl, or $Z^{z1}$ and $Z^{z2}$ are taken together to form an optionally substituted 3 to 8 membered ring having one or more heteroatoms, $V^z$ is $SO_2$, O, or $NR^f$; and $R^f$ is hydrogen, or optionally substituted alkyl, alkenyl, alkynyl, or aryl.

In some embodiments, a sulfur electrophile is selected from:

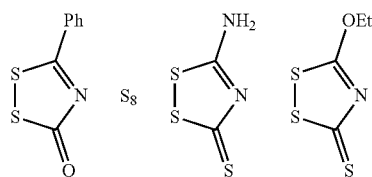

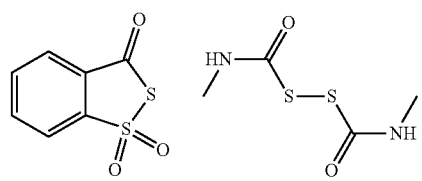

In some embodiments, a sulfurization reagent is 3-phenyl-1,2,4-dithiazolin-5-one.

Additional example sulfuring reagents are depicted below:

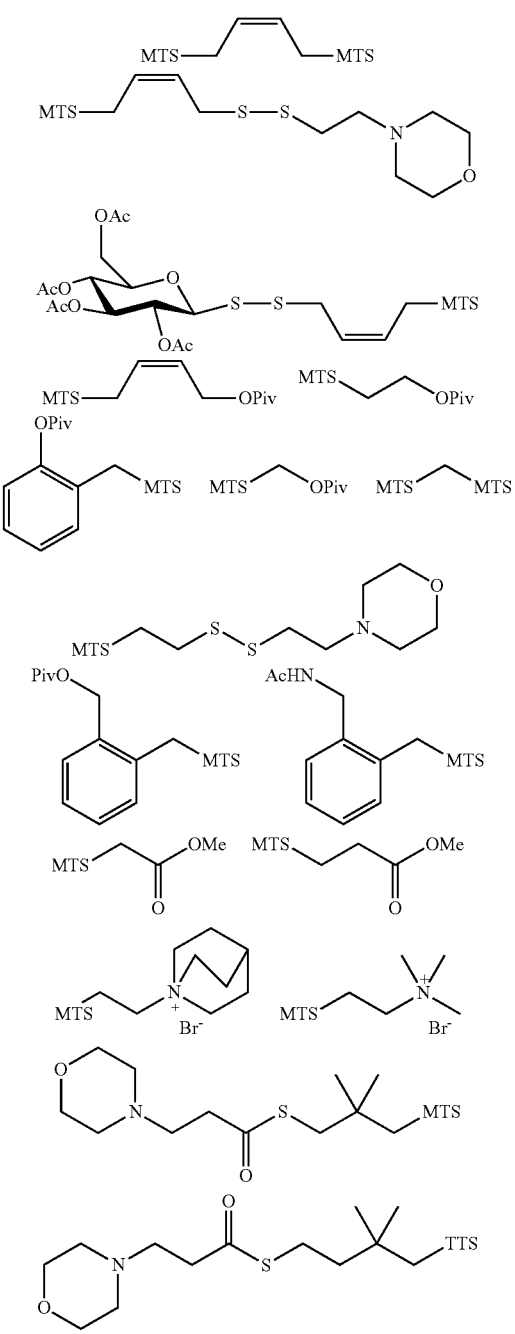

377
-continued

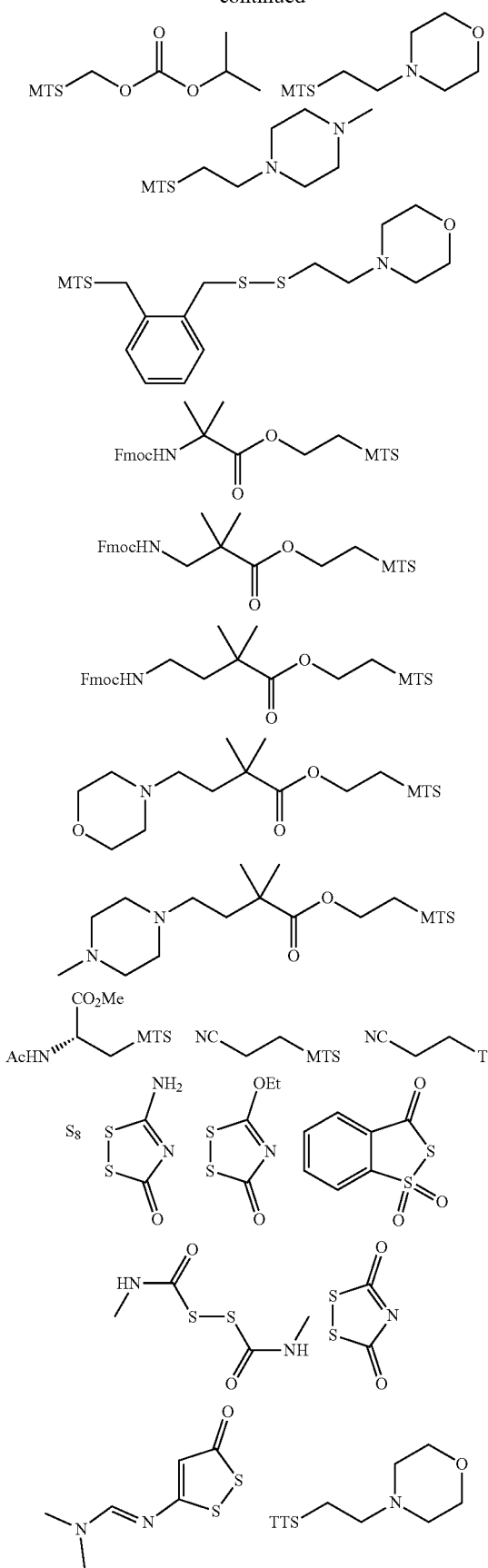

378
-continued

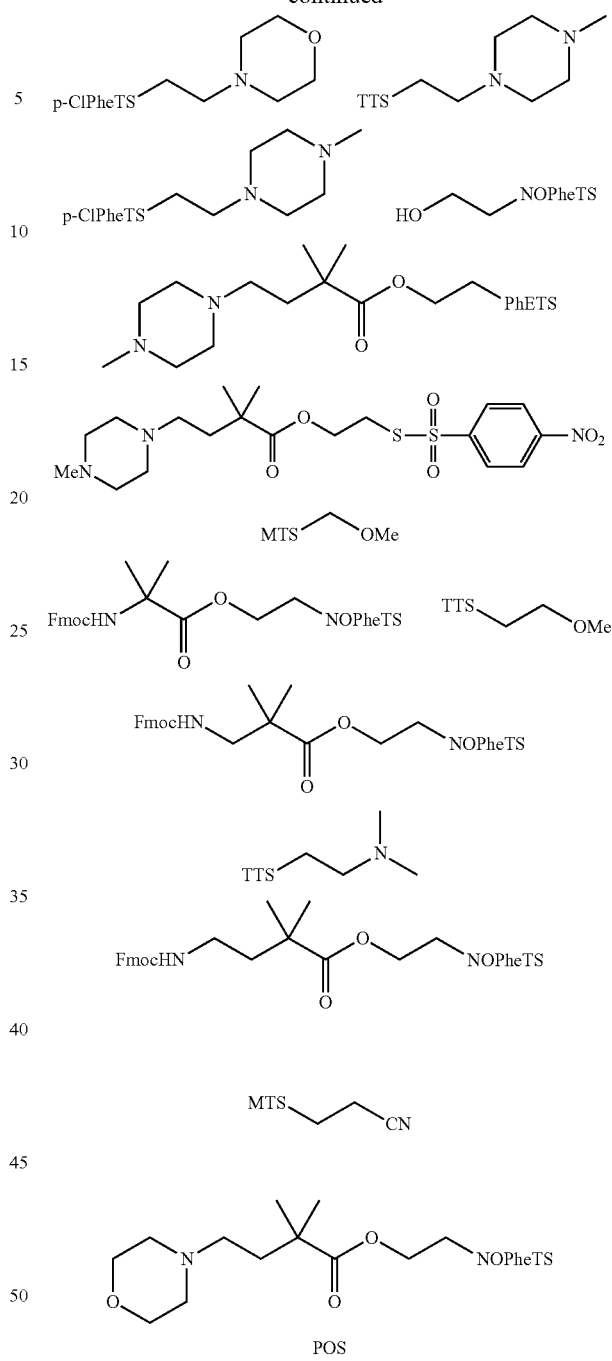

In some embodiments, a phosphorothioate is directly formed through sulfurization by a sulfurization reagents, e.g., 3-phenyl-1,2,4-dithiazolin-5-one. In some embodiments, after a direct installation of a phosphorothioate, a chiral auxiliary group remains attached to the internucleotidic phosphorus atom. In some embodiments, an additional de-protecting step is required to remove the chiral auxiliary (e.g., for DPSE-type chiral auxiliary, using TBAF, HF-Et$_3$N, etc.). In some embodiments, a phosphorothioate precursor is used to synthesize chirally controlled oligonucleotides comprising phosphorothioate linkages. In some embodiments, such a phosphorothioate precursor is

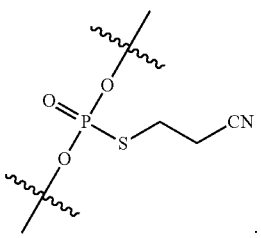 [SMILES: *OP(=O)(O*)SCCC#N]

In some embodiments,

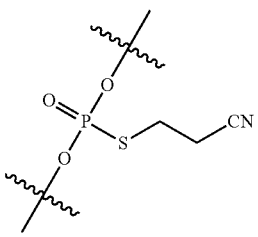 [SMILES: *OP(=O)(O*)SCCC#N]

is converted into phosphorothioate diester linkages during standard deprotection/release procedure after cycle exit. In some embodiments, a phosphorothioate precursor is a phosphorus protecting group as described herein, e.g., 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, 4-[N-methyl-N-(2,2,2-trifluoroacetyl)amino]butyl, etc.

In some embodiments, the selenium electrophile is a compound having one of the following formulae:

$$Se, Z^{z3}\text{—}Se\text{—}Se\text{—}Z^{z4}, \text{ or } Z^{z3}\text{—}Se\text{—}V^{z}\text{—}Z^{z4}; \quad \text{(Formula Z-G)}$$

wherein $Z^{z3}$ and $Z^{z4}$ are independently optionally substituted alkyl, aminoalkyl, cycloalkyl, heterocyclyl, cycloalkylalkyl, heterocycloalkyl, aryl, heteroaryl, alkyloxy, aryloxy, heteroaryloxy, acyl, amide, imide, or thiocarbonyl, or $Z^{z3}$ and $Z^{z4}$ are taken together to form an optionally substituted 3 to 8 membered ring having one or more heteroatoms; $V^z$ is $SO_2$, S, O, or $NR^f$; and $R^f$ is hydrogen, or optionally substituted alkyl, alkenyl, alkynyl, or aryl.

In some embodiments, the selenium electrophile is selected from:

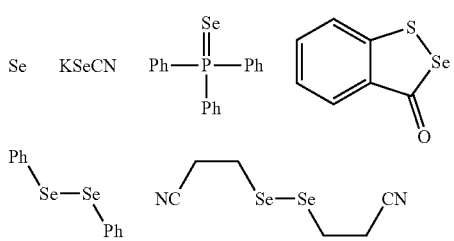

In some embodiments, a boronating agent is borane-N,N-diisopropylethylamine ($BH_3$ DIPEA), borane-pyridine ($BH_3$ Py), borane-2-chloropyridine ($BH_3$ CPy), borane-aniline ($BH_3$ An), borane-tetrahydrofurane ($BH_3$ THF), or borane-dimethylsulfide ($BH_3$ $Me_2S$).

In some embodiments, after a modifying step, a chiral auxiliary group falls off from a growing oligonucleotide chain. In some embodiments, after a modifying step, a chiral auxiliary group remains connected to an internucleotidic phosphorus atom. In some embodiments of the method, a modifying step is an oxidation step. In some embodiments, a modifying step is an oxidation step.

In some embodiments, a step of coupling is preceded by a step of deblocking. For instance, in some embodiments, the 5' hydroxyl group of a growing oligonucleotide is blocked and must be deblocked in order to subsequently react with a nucleoside coupling partner. In some embodiments, acidification is used to remove a blocking group.

Various deprotection/cleavage reagents and conditions are known and can be utilized in accordance with the present disclosure, e.g., those described in US/2011/0294124, US/2015/0211006, US/2017/0037399, WO/2017/015555, and WO/2017/062862 and are incorporated herein by reference.

Provided methods may comprise use of a temperature higher and/or lower than room temperature. In some embodiments, provided methods, e.g., in a reaction forming a phosphoramidite, comprise use of a lowered temperature, such as a temperature equal to or lower than about −78, −75, −70, −65, −60, −55, −50, −45, −40, −35, −30, −25, −20, −15, −10, −5, 0, 5, 10, 15, or 20° C. In some embodiments, provided methods, e.g., in a reaction forming a phosphoramidite, comprise use of an elevated temperature, such as a temperature equal to or more than about 25, 30, 35, 40, 45, 50, 55, 60, 65, 70, 75, 80, 85, 90, 95, 100, 110, 120, 130, 140 or 150° C. In some embodiments, provided methods comprise a temperature increase from a lowered temperature to another lowered temperature. In some embodiments, provided methods comprise a temperature increase from a lowered temperature to room temperature. In some embodiments, provided methods comprise a temperature increase from room temperature to an elevated temperature. In some embodiments, provided methods comprise a temperature increase from a lowered temperature to an elevated temperature. In some embodiments, provided methods comprise a temperature decrease from an elevated temperature to another elevated temperature. In some embodiments, provided methods comprise a temperature decrease from an elevated temperature to room temperature. In some embodiments, provided methods comprise a temperature decrease from room temperature to a lowered temperature. In some embodiments, provided methods comprise a temperature decrease from an elevated temperature to a lowered temperature.

Various solvents are suitable for use in provided methods. In some embodiments, reactions for forming phosphoramidites are performed in a solvent comprising ether. In some embodiments, reactions for forming phosphoramidites are performed in a solvent comprising THF. In some embodiments, reactions for forming phosphoramidites are performed in THF. Suitable solvents are widely known (e.g., those in US/2011/0294124, US/2015/0211006, US/2017/0037399, WO/2017/015555, and WO/2017/062862, solvents of each of which are incorporated herein by reference) and can be utilized in accordance with the present disclosure.

In some embodiments, one or more steps are performed under an inert gas. In some embodiments, formation of phosphoramidites is performed under an inert gas. In some embodiments, one or more steps of oligonucleotide synthesis cycle is performed under an inert gas. In some embodiments, an inert gas is argon. In some embodiments, an inert gas is nitrogen.

In some embodiments, one or more steps are performed under increased pressure. In some embodiments, one or more steps are performed under vacuum. In some embodiments, filtration is performed under vacuum.

In some embodiments, provided methods comprise purifying phosphoramidites using chromatography. In some embodiments, a chromatography is HPLC. In some embodiments, a chromatography is silica gel column chromatograph. In some embodiments, silica gel is pre-treated with a solvent with a modifier, e.g., a amine base. In some embodiments, a mobile phase comprises 0.1%-10% base. In some embodiments, a mobile phase comprises 1% base. In some embodiments, a mobile phase comprises 5% base. In some embodiments, a base is $N(R)_3$. In some embodiments, a base is $Et_3N$. In some embodiments, phosphoramidites may be directly used without purification.

In some embodiments, a provided compound, e.g., a compound of formula I, I-a, I-a-1, I-a-2, I-b, I-c, I-d, I-e, II, II-a, II-b, III, III-a, or III-b, or a salt thereof, a compound of formula IV, IV-a, IV-b, IV-c-1, IV-c-2, IV-d, IV-e, IVa, IVa-a, IVa-b, IVa-c-1, IVa-c-2, IVa-e, V, V-a, V-b, V-c-1, V-c-2, V-d, V-e, VI, VI-a, VI-b, VI-c, VI-c-1, VI-c-2, VI-d, or VI-e, or a salt thereof, etc., has a purity which is about or more than 50%, 60%, 70%, 75%, 80%, 85%, 90%, 91%, 92%, 93%, 94%, 95%, 96%, 97%, 98%, or 99%. In some embodiments, a purity is about 50% or more. In some embodiments, a purity is about 55% or more. In some embodiments, a purity is about 60% or more. In some embodiments, a purity is about 65% or more. In some embodiments, a purity is about 70% or more. In some embodiments, a purity is about 75% or more. In some embodiments, a purity is about 80% or more. In some embodiments, a purity is about 85% or more. In some embodiments, a purity is about 90% or more. In some embodiments, a purity is about 91% or more. In some embodiments, a purity is about 92% or more. In some embodiments, a purity is about 93% or more. In some embodiments, a purity is about 94% or more. In some embodiments, a purity is about 95% or more. In some embodiments, a purity is about 96% or more. In some embodiments, a purity is about 97% or more. In some embodiments, a purity is about 98% or more. In some embodiments, a purity is about 99% or more. In some embodiments, a purity is about 99.5% or more.

As demonstrated herein, provided technologies can surprisingly improve yields and/or purity. In some embodiments, the absolute improvement is about 5%, 10%, 15%, 20%, 25%, 30%, 35%, 40%, 45%, 50%, 55%, 60%, 65%, 70%, 75%, 80%, 85%, 90%, 95% or more. In some embodiments, the absolute improvement is greater than about 5%, 10%, 15%, 20%, 25%, 30%, 35%, 40%, 45%, 50%, 55%, 60%, 65%, 70%, 75%, 80%, 85%, 90%, 95% or more. In some embodiments, yield from a provided technology is greater than about 80%, while yield from a corresponding technology is less than about 60% (corresponding to an absolute improvement of greater than 20%). In some embodiments, the improvement relative to a corresponding technology is greater than about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 400%, 500%, 600%, 700%, 800%, 900% or more.

In some embodiments, a reagent in a provided method is dried before use. Various drying methods in the art can be utilized in accordance with the present disclosure. In some embodiments, a reagent is dried through azeotrope. In some embodiments, a reagent is dried under high vacuum. In some embodiments, a reagent is dried using a desiccant, e.g., $MgSO_4$, $CaH_2$, etc. In some embodiments, a reagent is dried by a combination of methods.

In some embodiments, technologies of the present disclosure can provide oligonucleotides and compositions thereof, including chirally controlled oligonucleotide compositions thereof, described in US/2011/0294124, US/2015/0211006, US/2017/0037399, WO/2017/015555, and WO/2017/062862, oligonucleotides and compositions thereof of each of which are incorporated herein by reference. In some embodiments, the present disclosure provides intermediate oligonucleotides (e.g., those of growing chain, those before cleavage from solid support, deprotection of nucleobases, and/or removal of chiral auxiliaries, etc.) to oligonucleotides and oligonucleotides compositions of US/2011/0294124, US/2015/0211006, US/2017/0037399, WO/2017/015555, and WO/2017/062862. In some embodiments, such intermediate oligonucleotides are of formula VIII or salts thereof. In some embodiments, such intermediate oligonucleotides are oligonucleotides as described in the present disclosure comprising one or more internucleotidic linkages each of which is independently of formula VII, VII-a-1, VII-a-2, VII-b, VII-c, VII-d, or VII-e, or a salt form thereof, wherein each $-X-L^s-R^5$ is independently of a structure that $H-X-L^s-R^5$ is a compound of formula I, I-a, I-a-1, I-a-2, I-b, I-c, I-d, I-e, II, II-a, II-b, III, III-a, or III-b, or a salt thereof.

In some embodiments, as readily appreciated by a person having ordinary skill in the art, in provided oligonucleotide compositions oligonucleotides may exist as salts. In some embodiments, provided oligonucleotide compositions are pharmaceutical compositions. In some embodiments, provided oligonucleotides exist as pharmaceutically acceptable salts.

In some embodiments, one or more lipid moieties, one or more targeting moieties, and/or one or more carbohydrate moieties may be independently and optionally incorporated into oligonucleotides. In some embodiments, provided oligonucleotides comprise one or more lipid moieties, one or more targeting moieties, and/or one or more carbohydrate moieties. Example lipid moieties, targeting moieties, and carbohydrate moieties are widely known (e.g., those in US/2015/0211006, US/2017/0037399, WO/2017/015555, and WO/2017/062862, lipid moieties, targeting moieties, and carbohydrate moieties of each of which are incorporated herein by reference) and can be utilized in accordance with the present disclosure.

In some embodiments, the present disclosure provides multimers of provided oligonucleotides. In some embodiments, the present disclosure provides multimers of provided oligonucleotides, each of which independently has the structure of formula VIII or a salt thereof. In some embodiments, provided multimers are of oligonucleotides of the same structure. In some embodiments, provided multimers are of oligonucleotides of different structures.

Unless otherwise stated, structures depicted herein are also meant to include all isomeric (e.g., enantiomeric, diastereomeric, and geometric (or conformational)) forms of the structures. Unless otherwise stated, all tautomeric forms of compounds of the present disclosure are included. Additionally, unless otherwise stated, structures depicted herein are also meant to include compounds that differ only in the presence of one or more isotopically enriched atoms. For example, compounds having present structures except for replacement of hydrogen with deuterium and/or tritium, or replacement of carbon by $^{11}$C, $^{13}$C, and/or $^{14}$C are included. Such compounds are useful, for example, as analytical tools or probes in biological assays. Unless otherwise specified, compounds, e.g., oligonucleotides, etc. include salts thereof.

In some embodiments, provided compounds are isotope labelled. In some embodiments, labeled compounds are useful for diagnosis, detection, modulation of one or more properties, modulation of activities, etc. In some embodiments, an isotope label is selected from $^2$H, $^3$H, $^{11}$C, $^{13}$C, $^{14}$C, $^{15}$N, $^{18}$O, $^{32}$P, $^{35}$S, etc. In some embodiments, an isotope label is selected from $^2$H, $^3$H, $^{11}$C, $^{13}$C, $^{14}$C, $^{15}$N, $^{18}$O, $^{32}$P, and $^{35}$S. In some embodiments, an isotope is a stable isotope. In some embodiments, an isotope is selected from $^2$H, $^{13}$C, $^{15}$N, and $^{18}$O. In some embodiments, an isotope is radioactive. In some embodiments, an isotope is selected from $^3$H, $^{32}$P, and $^{35}$S. In some embodiments, a provided compound comprises a $^2$H label. In some embodiments, a provided compound comprises a $^3$H label. In some embodiments, a provided compound comprises a $^{11}$C label. In some embodiments, a provided compound comprises a $^{13}$C label. In some embodiments, a provided compound comprises a $^{14}$C label. In some embodiments, a provided compound comprises a $^{15}$N label. In some embodiments, a provided compound comprises a $^{18}$O label. In some embodiments, a provided compound comprises a $^{32}$P label. In some embodiments, a provided compound comprises a $^{35}$S label. In some embodiments, a provided compound comprises one and no more than one type of isotope label. In some embodiments, a provided compound comprises two or more types of isotope labels. In some embodiments, a provided compound comprises one or more types of isotope labels, each of which is independently enriched at least 1.5, 2, 3, 4, 5, 6, 7, 8, 9, 10, 50, 100, 1,000, 5,000, 10,000 or more folds or natural level. In some embodiments, a label is of an atom % of at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 99.5%. In some embodiments, a label is of an atom % of at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 99.5%. In some embodiments, essentially all atoms at one or more position are labelled (atom % greater than 99%).

As used herein and in the claims, singular forms "a", "an", and "the" include the plural reference unless the context clearly indicates otherwise. Thus, for example, a reference to "a compound" includes a plurality of such compounds.

Certain embodiments (Embodiments 1-1347) of the present disclosure are described below:

1. A compound having the structure of formula I:

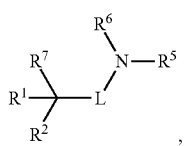

I or a salt thereof, wherein:
  L is a covalent bond, or optionally substituted $C_{1-6}$ alkylene, wherein one or more methylene units are optionally and independently replaced with -L'-;
  each L' is independently a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;
  each of R$^1$, R$^2$, R$^3$, R$^4$, and R$^5$ is independently —H, -L$^s$-R, halogen, —CN, —NO$_2$, -L$^s$-Si(R)$_3$, —OR, —SR, or —N(R)$_2$;
  each L$^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
  each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
  each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
  each R' is independently —R, —C(O)R, —CO$_2$R, or —SO$_2$R;
  R$^6$ is R';
  R$^7$ is —OH or SH;
  at least one of R$^1$, R$^2$, R$^3$ and R$^4$ is not —H;
  each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
  two R groups are optionally and independently taken together to form a covalent bond, or:
  two or more R groups on the same atom are optionally and independently taken together with the atom to form an optionally substituted, 3-30 membered, monocyclic, bicyclic or polycyclic ring having, in addition to the atom, 0-10 heteroatoms; or
  two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

2. The compound of embodiment 1, wherein the compound has the structure of formula I-a:

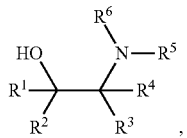

I-a or a salt thereof.

3. The compound of any one of the preceding embodiments, wherein the compound has the structure of formula

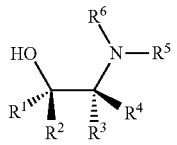

or a salt thereof.

4. The compound of any one of the preceding embodiments, wherein the compound has the structure of formula

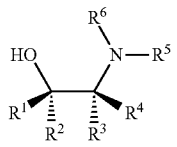

or a salt thereof.

5. The compound of any one of the preceding embodiments, wherein the compound has the structure of formula

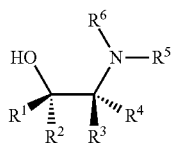

or a salt thereof.

6. The compound of any one of the preceding embodiments, wherein the compound has the structure of formula

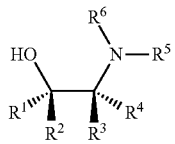

or a salt thereof.

7. The compound of any one of embodiments 1-2, wherein the compound has the structure of formula I-a-1:

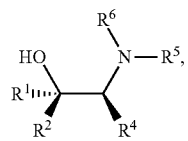

I-a-1 or a salt thereof.

8. The compound of any one of embodiments 1-2, wherein the compound has the structure of formula I-a-2:

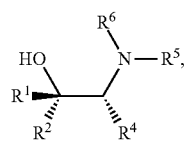

I-a-2 or a salt thereof.

9. The compound of any one of embodiments 1-6, wherein:
$R^1$ is not —H;
one of $R^3$ and $R^4$ is not —H, and is taken together with $R^5$ and the intervening atoms to form an optionally substituted 3-20 membered monocyclic, bicyclic or polycyclic ring having 1-5 heteroatoms.

10. The compound of any one of the preceding embodiments, wherein $R^4$ and $R^5$ are taken together with the intervening atoms to form an optionally substituted 3-20 membered monocyclic, bicyclic or polycyclic ring having 1-5 heteroatoms.

11. The compound of embodiment 10, wherein the ring is 3-10 membered.

12. The compound of embodiment 11, wherein the ring is 4-9 membered.

13. The compound of embodiment 11, wherein the ring is 4-membered.

14. The compound of embodiment 11, wherein the ring is 5-membered.

15. The compound of embodiment 11, wherein the ring is 6-membered.

16. The compound of embodiment 11, wherein the ring is 7-membered.

17. The compound of embodiment 11, wherein the ring is 8-membered.

18. The compound of embodiment 11, wherein the ring is 9-membered.

19. The compound of any one of embodiments 10-18, wherein the ring is monocyclic.

20. The compound of any one of embodiments 10-19, wherein the ring is bicyclic.

21. The compound of any one of embodiments 10-19, wherein the ring is polycyclic.

22. The compound of any one of embodiments 10-19, wherein the ring is saturated.

23. The compound of any one of embodiments 10-19, wherein the ring is substituted.

24. The compound of any one of embodiments 10-19, wherein the ring is unsubstituted.

25. The compound of any one of embodiments 10-24, wherein the ring comprises no more heteroatoms other than the nitrogen to which $R^5$ is attached.

26. The compound of any one of embodiments 10-24, wherein the ring comprises one or more heteroatoms in addition to the nitrogen to which $R^5$ is attached.

27. The compound of any one of embodiments 10-24, wherein the ring comprises one or more oxygen atom in addition to the nitrogen to which $R^5$ is attached.

28. The compound of embodiment 20 or 25, wherein —C($R^3$)($R^4$)—N($R^5$)($R^6$) is

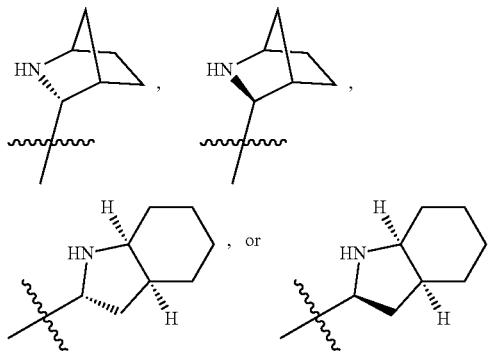

29. The compound of embodiment 25, wherein —C($R^3$)($R^4$)—N($R^5$)($R^6$) is

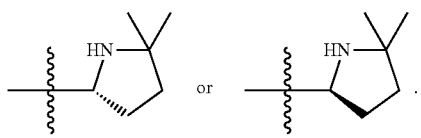

30. The compound of embodiment 25, wherein —C($R^3$)($R^4$)—N($R^5$)($R^6$) is

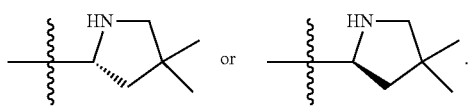

31. The compound of embodiment 25, wherein —C($R^3$)($R^4$)—N($R^5$)($R^6$) is

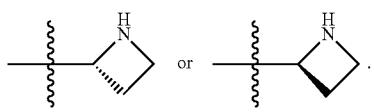 [SMILES: *[C@H]1CCN1 ; *[C@@H]1CCN1]

32. The compound of embodiment 25, wherein —C($R^3$)($R^4$)—N($R^5$)($R^6$) is

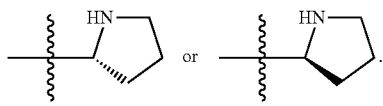 [SMILES: *[C@H]1CCCN1 ; *[C@@H]1CCCN1]

33. The compound of embodiment 27, wherein —C($R^3$)($R^4$)—N($R^5$)($R^6$) is

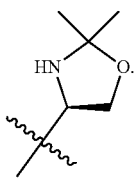 [SMILES: *[C@@H]1COC(C)(C)N1]

34. The compound of embodiment 1, wherein L is L', wherein L' is optionally substituted $C_2$ alkylene.

35. The compound any one of embodiments 1-34, wherein $R^1$ is —H.

36. The compound any one of embodiments 1-34, wherein $R^1$ is $C_{1-3}$ alkyl.

37. The compound any one of embodiments 1-34, wherein $R^1$ is methyl.

38. The compound any one of embodiments 1-37, wherein $R^2$ is R, wherein R is not hydrogen.

39. The compound of any one of embodiments 1-38, wherein $R^2$ is optionally substituted $C_{1-30}$ aliphatic.

40. The compound of any one of embodiments 1-39, wherein $R^2$ is optionally substituted $C_{3-30}$ cycloaliphatic.

41. The compound of any one of embodiments 1-39, wherein $R^2$ is optionally substituted $C_{3-30}$ cycloalkyl.

42. The compound of any one of embodiments 1-42, wherein $R^2$ is cyclopentyl.

43. The compound of any one of embodiments 1-38, wherein $R^2$ is optionally substituted $C_{1-30}$ heteroaliphatic having 1-10 heteroatoms.

44. The compound of any one of embodiments 1-38, wherein $R^2$ is optionally substituted $C_{6-30}$ aryl.

45. The compound of embodiment 44, wherein $R^2$ is optionally substituted phenyl.

46. The compound of embodiment 45, wherein $R^2$ is substituted phenyl.

47. The compound of embodiment 46, wherein a substituent of the substituted phenyl is an electron-donating group.

48. The compound of embodiment 46, wherein a substituent of the substituted phenyl is an electron-withdrawing group.

49. The compound of embodiment 46, wherein a substituent of the substituted phenyl is $C_{1-6}$ alkyl.

50. The compound of embodiment 49, wherein a substituent of the substituted phenyl is p-methyl.

51. The compound of embodiment 46, wherein a substituent of the substituted phenyl is halogen.

52. The compound of embodiment 51, wherein a substituent of the substituted phenyl is —F.

53. The compound of embodiment 52, wherein a substituent of the substituted phenyl is m-F.

54. The compound of embodiment 52, wherein two substituents of the substituted phenyl are m-F.

55. The compound of embodiment 46, wherein a substituent of the substituted phenyl is p-OMe.

56. The compound of embodiment 46, wherein a substituent of the substituted phenyl is p-OMe, and a substituent is o-OMe.

57. The compound of any one of embodiments 1-38, wherein $R^2$ is optionally substituted $C_{6-30}$ arylaliphatic.

58. The compound of embodiment 57, wherein $R^2$ is optionally substituted benzyl.

59. The compound of embodiment 58, wherein $R^2$ is benzyl.

60. The compound of embodiment 58, wherein $R^2$ is substituted benzyl.

61. The compound of embodiment 58, wherein $R^2$ is p-OMeC$_6$H$_4$—CH$_2$—.
62. The compound of any one of embodiments 1-38, wherein $R^2$ is optionally substituted C$_{6-30}$ arylheteroaliphatic having 1-10 heteroatoms.
63. The compound of any one of embodiments 1-38, wherein $R^2$ is optionally substituted 5-30 membered heteroaryl having 1-10 heteroatoms.
64. The compound of embodiment 59, wherein $R^2$ is optionally substituted monocyclic 5-membered heteroaryl.
65. The compound of embodiment 59, wherein $R^2$ is optionally substituted monocyclic 6-membered heteroaryl.
66. The compound of embodiment 59, wherein $R^2$ is optionally substituted bicyclic 9-membered heteroaryl.
67. The compound of embodiment 59, wherein $R^2$ is optionally substituted bicyclic 10-membered heteroaryl.
68. The compound of embodiment 59, wherein $R^2$ is optionally substituted 3-30 membered heterocyclyl having 1-10 heteroatoms.
69. The compound any one of embodiments 1-34, wherein $R^1$ and $R^2$ are taken together with their intervening atoms to form an optionally substituted 3-20 membered monocyclic, bicyclic or polycyclic ring having 0-5 heteroatoms.
70. The compound of embodiment 69, wherein $R^1$ and $R^2$ are taken together with their intervening atoms to form an optionally substituted 3-15 membered monocyclic, bicyclic or polycyclic ring having 0-5 heteroatoms.
71. The compound of embodiment 70, wherein the ring is 3-10 membered.
72. The compound of any one of embodiments 69-71, wherein the ring is 10-membered.
73. The compound of any one of embodiments 69-71, wherein the ring is 9-membered.
74. The compound of any one of embodiments 69-71, wherein the ring is 8-membered.
75. The compound of any one of embodiments 69-71, wherein the ring is 7-membered.
76. The compound of any one of embodiments 69-71, wherein the ring is 3-6 membered.
77. The compound of any one of embodiments 69-71, wherein the ring is 6-membered.
78. The compound of any one of embodiments 69-71, wherein the ring is 5-membered.
79. The compound of any one of embodiments 69-71, wherein the ring is 4-membered.
80. The compound of any one of embodiments 69-71, wherein the ring is 3-membered.
81. The compound of any one of embodiments 69-80, wherein the ring is monocyclic.
82. The compound of any one of embodiments 69-79, wherein the ring is bicyclic.
83. The compound of any one of embodiments 69-79, wherein the ring is polycyclic.
84. The compound of any one of embodiments 69-74, wherein the ring is bicyclic or polycyclic, and comprises an aromatic monocyclic ring.
85. The compound of any one of embodiments 69-84, wherein the ring comprises no heteroatom.
86. The compound of any one of embodiments 69-84, wherein the ring comprises one or more heteroatoms.
87. The compound of embodiment 77, wherein the ring is

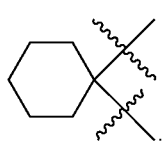 [SMILES: *C1(*)CCCCC1]

.

88. The compound of embodiment 78, wherein the ring is

.

89. The compound of embodiment 79, wherein the ring is

.

90. The compound of embodiment 80, wherein the ring is

.

91. The compound of embodiment 84, wherein $R^1$ and $R^2$ are taken together with their intervening atoms to form an optionally substituted ring having the structure of

.

92. The compound of any one of embodiments 69-91, wherein the ring is substituted.
93. The compound of any one of embodiments 69-91, wherein the ring is unsubstituted.
94. The compound of any one of embodiments 69-93, wherein the ring comprises no chiral elements.
95. The compound any one of embodiments 1-34, wherein $R^1$ and $R^2$ are the same.
96. The compound of embodiment 95, wherein $R^1$ and $R^2$ are optionally substituted C$_{1-6}$ aliphatic.
97. The compound of embodiment 95, wherein $R^1$ and $R^2$ are optionally substituted C$_{1-6}$ alkyl.
98. The compound of embodiment 95, wherein $R^1$ and $R^2$ are optionally substituted C$_{1-3}$ alkyl.
99. The compound of embodiment 95, wherein $R^1$ and $R^2$ are C$_{1-3}$ haloalkyl.
100. The compound of embodiment 95, wherein $R^1$ and $R^2$ are C$_{1-2}$ haloalkyl.
101. The compound of embodiment 95, wherein $R^1$ and $R^2$ are C$_{1-3}$ alkyl.
102. The compound of embodiment 95, wherein $R^1$ and $R^2$ are C$_{1-2}$ alkyl.
103. The compound of any one of embodiments 97-102, wherein the alkyl or haloalkyl is linear.
104. The compound of embodiment 95, wherein $R^1$ and $R^2$ are methyl.

105. The compound of embodiment 95, wherein $R^1$ and $R^2$ are ethyl.

106. The compound of embodiment 1, wherein the compound is of formula I-b:

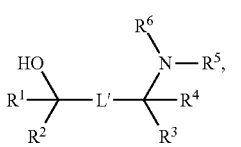

I-b or a salt thereof.

107. The compound of embodiment 106, wherein L' is optionally substituted methylene.

108. The compound of embodiment 106, wherein L' is —$CH_2$—.

109. The compound of embodiment 1, wherein L is —$C(R^3)(R^4)$—$C(R^3)(R^4)$—, wherein the two $R^3$ in L are taken together with their intervening atoms to form an optionally substituted 3-20 membered monocyclic, bicyclic or polycyclic ring having 0-5 heteroatoms.

110. The compound of embodiment 109, wherein the two $R^3$ in L are taken together with their intervening atoms to form an optionally substituted 5-6 membered monocyclic, bicyclic or polycyclic ring having 0-5 heteroatoms.

111. The compound of embodiment 109, wherein the two $R^3$ in L are taken together with their intervening atoms to form an optionally substituted 5-6 membered saturated carbocyclic ring.

112. The compound of embodiment 1, wherein the compound is of formula I-c:

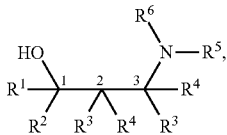

I-c or a salt thereof.

113. The compound of embodiment 112, wherein one or $R^3$ and $R^4$ on C2 are taken together with $R^5$ to form with their intervening atoms to form an optionally substituted 3-20 membered monocyclic, bicyclic or polycyclic ring having a nitrogen atom (the one which $R^5$ is on).

114. The compound of embodiment 112, wherein one or $R^3$ and $R^4$ on C3 are taken together with $R^5$ to form with their intervening atoms to form an optionally substituted 3-20 membered monocyclic, bicyclic or polycyclic ring having a nitrogen atom (the one which $R^5$ is on).

115. The compound of embodiment 112, one of $R^3$ and $R^4$ on C2, and one of $R^3$ and $R^4$ on C3, are taken together with their intervening atoms to form an optionally substituted 3-20 membered monocyclic, bicyclic or polycyclic ring having 0-5 heteroatoms.

116. The compound of embodiment 112, $R^3$ and $R^4$ on the same carbon atom are taken together with the carbon atom to form an optionally substituted 3-20 membered monocyclic, bicyclic or polycyclic ring having 0-5 heteroatoms.

117. The compound of embodiment 112, $R^3$ and $R^4$ on C2 are taken together with C2 to form an optionally substituted 3-20 membered monocyclic, bicyclic or polycyclic ring having 0-5 heteroatoms.

118. The compound of embodiment 112, $R^3$ and $R^4$ on C3 are taken together with C3 to form an optionally substituted 3-20 membered monocyclic, bicyclic or polycyclic ring having 0-5 heteroatoms.

119. The compound of any one of embodiments 112-118, wherein the formed ring is monocyclic.

120. The compound of any one of embodiments 112-118, wherein the formed ring is bicyclic.

121. The compound of any one of embodiments 112-120, wherein the formed ring is 3-10 membered.

122. The compound of any one of embodiments 112-120, wherein the formed ring is 4-6 membered.

123. The compound of any one of embodiments 112-120, wherein the formed ring is 4-membered.

124. The compound of any one of embodiments 112-120, wherein the formed ring is 5-membered.

125. The compound of any one of embodiments 112-120, wherein the formed ring is 6-membered.

126. The compound of embodiment 112, wherein $R^3$ on C2 is hydrogen.

127. The compound of embodiment 112 or 126, wherein $R^4$ on C2 is hydrogen.

128. The compound of any one of embodiments 112 and 126, wherein $R^3$ on C3 is hydrogen.

129. The compound of embodiment 128, wherein $R^4$ on C3 is hydrogen.

130. The compound of embodiment 112, wherein both $R^3$ and $R^4$ on C2, and one of $R^3$ and $R^4$ on C3, are hydrogen.

131. The compound of embodiment 112, wherein both $R^3$ and $R^4$ on C3, and one of $R^3$ and $R^4$ on C2, are hydrogen.

132. The compound of embodiment 1, wherein the compound is of formula I-d:

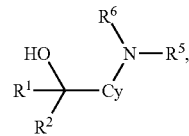

I-d or a salt thereof.

133. The compound of embodiment 132, wherein -Cy- is 1,2-bivalent.

134. The compound of embodiment 132 or 133, wherein -Cy- is optionally substituted cycloalkylene.

135. The compound of any one of embodiments 132-134, wherein -Cy- is optionally substituted

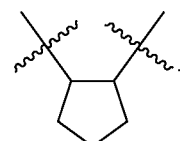

136. The compound of any one of embodiments 132-134, wherein -Cy- is

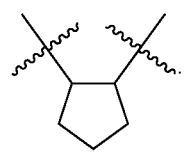 [SMILES: *C1CCCC1*]

137. The compound of any-one of embodiments 132-134, wherein -Cy- is optionally substituted

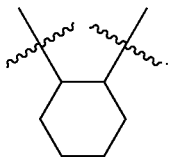 [SMILES: *C1CCCCC1*]

138. The compound of any one of embodiments 132-134, wherein -Cy- is

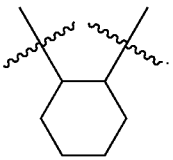 [SMILES: *C1CCCCC1*]

139. The compound of embodiment 1, wherein L is —C($R^3$)[C($R^4$)$_3$].
140. The compound of embodiment 139, wherein L is —C($R^3$)[C($R^4$)$_3$]—, wherein one $R^4$ and one of $R^1$ and $R^2$ are taken together with their intervening atoms to form an optionally substituted 3-20 membered monocyclic, bicyclic or polycyclic ring having 0-5 heteroatoms, and one $R^4$ and $R^5$ are taken together with their intervening atoms to form an optionally substituted 3-20 membered monocyclic, bicyclic or polycyclic ring having 0-5 heteroatoms.
141. The compound of embodiment 139, wherein one of $R^1$ and $R^2$ and one of $R^3$ and $R^4$ are taken together with their intervening atoms to form an optionally substituted 3-20 membered monocyclic, bicyclic or polycyclic ring having 0-5 heteroatoms, and one $R^4$ and $R^5$ are taken together with their intervening atoms to form an optionally substituted 3-20 membered monocyclic, bicyclic or polycyclic ring having 0-5 heteroatoms.
142. The compound of embodiment 141, wherein one of $R^1$ and $R^2$ and one of $R^3$ and $R^4$ are taken together with their intervening atoms to form an optionally substituted 4-6 membered monocyclic saturated carbocyclic ring.
143. The compound of embodiment 142, wherein one of $R^1$ and $R^2$ and one of $R^3$ and $R^4$ are taken together with their intervening atoms to form an optionally substituted 4-membered monocyclic saturated carbocyclic ring.
144. The compound of embodiment 142, wherein one of $R^1$ and $R^2$ and one of $R^3$ and $R^4$ are taken together with their intervening atoms to form an optionally substituted 5-membered monocyclic saturated carbocyclic ring.
145. The compound of embodiment 142, wherein one of $R^1$ and $R^2$ and one of $R^3$ and $R^4$ are taken together with their intervening atoms to form an optionally substituted 6-membered monocyclic saturated carbocyclic ring.
146. The compound of embodiment 141, wherein one of $R^1$ and $R^2$ and one of $R^3$ and $R^4$ are taken together with their intervening atoms to form an optionally substituted monocyclic, bicyclic or polycyclic ring comprising an aromatic ring.
147. The compound of embodiment 141 or 146, wherein one of $R^1$ and $R^2$ and one of $R^3$ and $R^4$ are taken together with their intervening atoms to form an optionally substituted monocyclic, bicyclic or polycyclic ring comprising a partially saturated ring.

148. The compound of embodiment 141, wherein $R^1$ and $R^4$ are taken together to form a ring.
149. The compound of embodiment 141, wherein $R^1$ and $R^3$ are taken together to form a ring.
150. The compound of any one of embodiments 139-149, wherein one of $R^3$ and $R^4$, and $R^5$, are taken together with their intervening atoms to form an optionally substituted 3-20 membered monocyclic, bicyclic or polycyclic ring having 1-5 heteroatoms.
151. The compound of embodiment 150, wherein one of $R^3$ and $R^4$, and $R^5$, are taken together with their intervening atoms to form an optionally substituted 3-20 membered monocyclic, bicyclic or polycyclic ring having one or more oxygen atoms in addition to the nitrogen to which $R^5$ is attached.
152. The compound of embodiment 150, wherein one of $R^3$ and $R^4$, and $R^5$, are taken together with their intervening atoms to form an optionally substituted 3-20 membered monocyclic, bicyclic or polycyclic ring having only one heteroatom which is the nitrogen to which $R^5$ is attached.
153. The compound of embodiment 150-152, wherein the formed ring is 3-10 membered.
154. The compound of embodiment 150-152, wherein the formed ring is 4-6 membered.
155. The compound of embodiment 150-152, wherein the formed ring is 4-membered.
156. The compound of embodiment 150-152, wherein the formed ring is 5-membered.
157. The compound of embodiment 150-152, wherein the formed ring is 6-membered.
158. The compound of any one of embodiments 1-157, wherein one of $R^1$ and $R^2$, and $R^5$, are taken together with their intervening atoms to form an optionally substituted 3-20 membered monocyclic, bicyclic or polycyclic ring having 1-5 heteroatoms.
159. The compound of embodiment 158, wherein one of $R^1$ and $R^2$, and $R^5$, are taken together with their intervening atoms to form an optionally substituted 5-membered monocyclic saturated ring.
160. The compound of embodiment 158, wherein one of $R^1$ and $R^2$, and $R^5$, are taken together with their intervening atoms to form an optionally substituted 6-membered monocyclic saturated ring.
161. The compound of embodiments 158-160, wherein one of $R^1$ and $R^2$, and $R^5$, are taken together with their intervening atoms to form an optionally substituted ring having one oxygen atom and one nitrogen atom.
162. The compound of any one of embodiments 158-161, wherein one of $R^3$ and $R^4$ is not —H.
163. The compound of any one of embodiments 158-161, wherein $R^3$ and $R^4$ are —H.
164. The compound of embodiment 1, wherein the compound is of formula I-e:

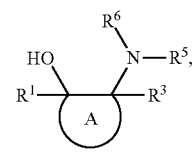

or a salt thereof.

165. The compound of embodiment 164, wherein —OH and —N(R$^5$)(R$^6$) are trans.
166. The compound of embodiment 164, wherein —OH and —N(R$^5$)(R$^6$) are cis.
167. The compound of any one of embodiments 164-166, wherein R$^3$ is —H.
168. The compound of any one of embodiments 164-167, wherein Ring A is 3-10 membered.
169. The compound of any one of embodiments 164-168, wherein Ring A is 4-8 membered.
170. The compound of any one of embodiments 164-169, wherein Ring A is 4-membered.
171. The compound of any one of embodiments 164-169, wherein Ring A is 5-membered.
172. The compound of any one of embodiments 164-169, wherein Ring A is 6-membered.
173. The compound of any one of embodiments 164-169, wherein Ring A is 7-membered.
174. The compound of any one of embodiments 164-169, wherein Ring A is 8-membered.
175. The compound of any one of embodiments 168-174, wherein Ring A is monocyclic.
176. The compound of any one of embodiments 168-174, wherein Ring A is bicyclic.
177. The compound of any one of embodiments 168-174, wherein Ring A is polycyclic.
178. The compound of any one of embodiments 168-177, wherein Ring A is cycloaliphatic.
179. The compound of any one of embodiments 168-178, wherein Ring A is saturated.
180. The compound of any one of embodiments 168-178, wherein Ring A is not substituted.
181. The compound of any one of embodiments 164-180, wherein R$^1$ is not —H.
182. The compound of any one of embodiments 164-181, wherein R$^1$ is optionally substituted C$_{1-6}$ aliphatic.
183. The compound of any one of embodiments 164-182, wherein R$^1$ is optionally substituted C$_{1-6}$ alkyl.
184. The compound of any one of embodiments 164-183, wherein R$^1$ is cyclohexyl.
185. The compound of any one of embodiments 164-183, wherein R$^1$ is methyl.
186. The compound of any one of embodiments 164-181, wherein R$^1$ is optionally substituted phenyl.
187. The compound of any one of embodiments 164-181, wherein R$^1$ is phenyl.
188. The compound of any one of embodiments 164-167, wherein R$^1$ is —H.
189. The compound of any one of embodiments 168-180, wherein the carbon to which R$^1$ is attached is chiral and has R configuration.
190. The compound of any one of embodiments 168-180, wherein the carbon to which R$^1$ is attached is chiral and has S configuration.
191. The compound of any one of embodiments 164-190, wherein R$^5$ is not —H.
192. The compound of any one of embodiments 164-191, wherein R$^5$ is optionally substituted C$_{1-6}$ aliphatic.
193. The compound of any one of embodiments 164-192, wherein R$^5$ is optionally substituted C$_{1-6}$ alkyl.
194. The compound of any one of embodiments 164-193, wherein R$^5$ is methyl.
195. The compound of any one of embodiments 164-180, wherein R$^1$ and R$^5$ are taken together with their intervening atoms to form an optionally substituted 3-10 membered ring having 1-5 heteroatoms.
196. The compound of embodiment 195, wherein the ring formed by R$^1$ and R$^5$ taken together with their intervening atoms is substituted.
197. The compound of embodiment 195, wherein the ring formed by R$^1$ and R$^5$ taken together with their intervening atoms is unsubstituted.
198. The compound of any one of embodiments 195-197, wherein the ring formed by R$^1$ and R$^5$ taken together with their intervening atoms is saturated.
199. The compound of any one of embodiments 195-198, wherein the ring formed by R$^1$ and R$^5$ taken together with their intervening atoms is 3-membered.
200. The compound of any one of embodiments 195-198, wherein the ring formed by R$^1$ and R$^5$ taken together with their intervening atoms is 4-membered.
201. The compound of any one of embodiments 195-198, wherein the ring formed by R$^1$ and R$^5$ taken together with their intervening atoms is 5-membered.
202. The compound of any one of embodiments 195-198, wherein the ring formed by R$^1$ and R$^5$ taken together with their intervening atoms is 6-membered.
203. The compound of any one of embodiments 195-202, wherein the ring formed by R$^1$ and R$^5$ taken together with their intervening atoms contains no other heteroatoms other than the nitrogen to which R$^5$ is attached.
204. The compound of any one of embodiments 195-203, wherein the ring formed by R$^1$ and R$^5$ taken together with their intervening atoms is monocyclic.
205. The compound of any one of embodiments 195-203, wherein the ring formed by R$^1$ and R$^5$ taken together with their intervening atoms is bicyclic.
206. The compound of any one of embodiments 195-203, wherein the ring formed by R$^1$ and R$^5$ taken together with their intervening atoms is polycyclic.
207. A compound having the structure of formula II:

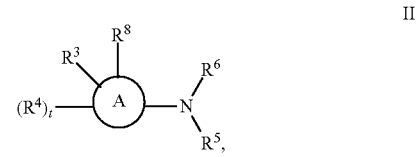

or a salt thereof, wherein:
 Ring A is an optionally substituted 3-20 membered monocyclic, bicyclic or polycyclic ring having 0-10 heteroatoms;
 each of R$^3$, R$^4$, and R$^5$ is independently —H, -L$^s$-R, halogen, —CN, —NO$_2$, -L$^s$-Si(R)$_3$, —OR, —SR, or —N(R)$_2$;
 each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')₃]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')₃]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)₂R;

t is 0-20;

$R^6$ is R';

$R^8$ is -L-$R^7$, -L-C($R^1$)($R^2$)—$R^7$, or -$L^s$-$R^7$;

$R^7$ is —OH or SH;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)₃]—;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

208. The compound of embodiment 207, wherein the compound is of formula II-a:

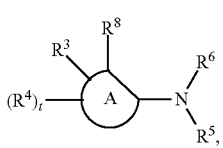

or a salt thereof.

209. The compound of embodiment 207, wherein the compound is of formula II-b:

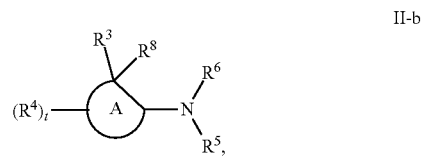

or a salt thereof.

210. The compound of embodiment 207, wherein the compound is of formula II-c:

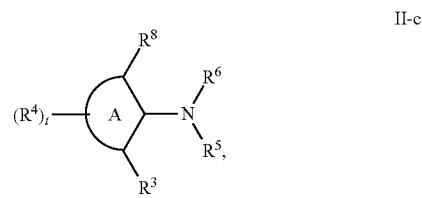

or a salt thereof.

211. The compound of any one of embodiments 207-210, wherein $R^8$ is —OH.

212. The compound of any one of embodiments 207-210, wherein $R^8$ is -L-C($R^1$)($R^2$)—OH.

213. The compound of embodiment 212, wherein L is a covalent bond.

214. The compound of embodiment 212, wherein L is optionally substituted —CH₂—.

215. The compound of any one of embodiments 207-214, wherein $R^8$ is connected to a sp³ ring atom of Ring A.

216. The compound of any one of embodiments 207-215, wherein $R^8$ and —N($R^5$)($R^6$) are trans.

217. The compound of any one of embodiments 207-215, wherein $R^8$ and —N($R^5$)($R^6$) are cis.

218. The compound of any one of embodiments 207-217, wherein t is 0.

219. The compound of any one of embodiments 207-218, wherein $R^3$ is optionally substituted $C_{1-6}$ aliphatic.

220. The compound of any one of embodiments 207-219, wherein $R^3$ is optionally substituted $C_{1-6}$ alkyl.

221. The compound of any one of embodiments 207-220, wherein $R^3$ is cyclohexyl.

222. The compound of any one of embodiments 207-220, wherein $R^3$ is methyl.

223. The compound of any one of embodiments 207-218, wherein $R^3$ is optionally substituted phenyl.

224. The compound of any one of embodiments 207-218, wherein $R^3$ is phenyl.

225. The compound of any one of embodiments 207-218, wherein $R^3$ is —H.

226. The compound of any one of embodiments 207-218, wherein $R^3$ and $R^6$ are taken together with their intervening atoms to form an optionally substituted 3-10 membered ring having 1-5 heteroatoms.

227. The compound of embodiment 226, wherein the formed ring is 4-membered.

228. The compound of embodiment 226, wherein the formed ring is 5-membered.

229. The compound of embodiment 226, wherein the formed ring is 6-membered.

230. The compound of embodiment 226, wherein the formed ring is 7-membered.
231. The compound of any one of embodiments 226-230, wherein the formed ring is monocyclic.
232. The compound of any one of embodiments 226-231, wherein the formed ring is saturated.
233. The compound of any one of embodiments 226-232, wherein the formed ring contains no other heteroatoms other than the nitrogen atom to which $R^6$ is attached.
234. The compound of any one of embodiments 207-233, wherein $R^3$ is connected to a $sp^3$ ring atom of Ring A.
235. The compound of any one of embodiments 207-229, wherein Ring A is 3-10 membered.
236. The compound of any one of embodiments 207-235, wherein Ring A is 4-8 membered.
237. The compound of any one of embodiments 207-236, wherein Ring A is 4-membered.
238. The compound of any one of embodiments 207-236, wherein Ring A is 5-membered.
239. The compound of any one of embodiments 207-236, wherein Ring A is 6-membered.
240. The compound of any one of embodiments 207-236, wherein Ring A is 7-membered.
241. The compound of any one of embodiments 207-236, wherein Ring A is 8-membered.
242. The compound of any one of embodiments 207-241, wherein Ring A is monocyclic.
243. The compound of any one of embodiments 207-241, wherein Ring A is bicyclic.
244. The compound of any one of embodiments 207-241, wherein Ring A is polycyclic.
245. The compound of any one of embodiments 207-244, wherein Ring A is cycloaliphatic.
246. The compound of any one of embodiments 207-245, wherein Ring A is saturated.
247. The compound of any one of embodiments 207-245, wherein Ring A is substituted.
248. The compound of any one of embodiments 207-246, wherein Ring A is not substituted.
249. The compound of any one of embodiments 207-248, wherein the carbon to which $R^8$ is attached is chiral and has R configuration.
250. The compound of any one of embodiments 207-241, wherein the carbon to which $R^8$ is attached is chiral and has S configuration.
251. The compound of any one of embodiments 207-250, wherein $R^5$ is not —H.
252. The compound of any one of embodiments 207-251, wherein $R^5$ is optionally substituted $C_{1-6}$ aliphatic.
253. The compound of any one of embodiments 207-252, wherein $R^5$ is optionally substituted $C_{1-6}$ alkyl.
254. The compound of any one of embodiments 207-253, wherein $R^5$ is methyl.
255. The compound of any one of embodiments 207-250, wherein $R^5$ is —H.
256. The compound of any one of embodiments 207-255, wherein —N($R^5$)($R^6$) is connected to a $sp^3$ ring atom of Ring A.
257. A compound having the structure of formula III:

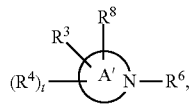

III or a salt thereof, wherein:
Ring A' is an optionally substituted 3-20 membered monocyclic, bicyclic or polycyclic ring having 1-10 heteroatoms, wherein Ring A' comprises a —N($R^6$)— moiety;
each of $R^3$ and $R^4$ is independently —H, -$L^s$-R, halogen, —CN, —$NO_2$, -$L^s$-Si(R)$_3$, —OR, —SR, or —N(R)$_2$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;
t is 0-20;
$R^6$ is R';
$R^8$ is -L-$R^7$, -L-C($R^1$)($R^2$)—$R^7$, or -$L^s$-$R^7$;
$R^7$ is —OH or SH;
L is a covalent bond, or optionally substituted $C_{1-6}$ alkylene, wherein one or more methylene units are optionally and independently replaced with -L'-;
L' is a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)$_3$]—;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their inter- 258. The compound of embodiment 257, wherein Ring A' is monocyclic.

259. The compound of embodiment 257, wherein Ring A' is bicyclic.

260. The compound of embodiment 257, wherein Ring A' is polycyclic.

261. The compound of any one of embodiments 257-260, wherein Ring A' is cycloaliphatic.

262. The compound of any one of embodiments 257-261, wherein Ring A' is saturated.

263. The compound of any one of embodiments 257-262, wherein Ring A' is not substituted.

264. The compound of any one of embodiments 257-263, wherein Ring A' contains no more heteroatoms other than the nitrogen to which $R^6$ is attached.

265. The compound of any one of embodiments 257-263, wherein Ring A' is 3-10 membered.

266. The compound of any one of embodiments 257-265, wherein Ring A' is 4-8 membered.

267. The compound of any one of embodiments 257-266, wherein Ring A' is 8-membered.

268. The compound of any one of embodiments 257-266, wherein Ring A' is 7-membered.

269. The compound of any one of embodiments 257-266, wherein Ring A' is 6-membered.

270. The compound of any one of embodiments 257-266, wherein Ring A' is 5-membered.

271. The compound of any one of embodiments 257-266, wherein Ring A' is 4-membered.

272. The compound of any one of embodiments 257-271, wherein $R^8$ is bonded to a carbon atom ($C^2$) next to the nitrogen atom in —$N(R^6)$—($N^1$).

273. The compound of any one of embodiments 257-271, wherein $R^8$ is bonded to $C^3$ (the nitrogen atom in —$N(R^6)$— is $N^1$.

274. The compound of any one of embodiments 257-271, wherein $R^8$ is bonded to $C^4$ (the nitrogen atom in —$N(R^6)$— is $N^1$.

275. The compound of any one of embodiments 257-270, wherein $R^5$ is bonded to $C^3$ (the nitrogen atom in —$N(R^6)$— is $N^1$.

276. The compound of any one of embodiments 257-269, wherein $R^5$ is bonded to $C^6$ (the nitrogen atom in —$N(R^6)$— is $N^1$.

277. The compound of any one of embodiments 257-276, wherein the compound is of formula III-a:

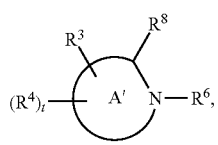

or a salt thereof.

278. The compound of any one of embodiments 257-276, wherein the compound is of formula III-b:

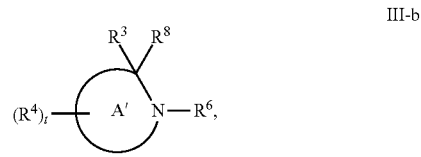

or a salt thereof.

279. The compound of any one of embodiments 257-278, wherein $R^8$ is —OH.

280. The compound of any one of embodiments 257-278, wherein $R^8$ is -L-C($R^1$)($R^2$)—OH.

281. The compound of embodiment 280, wherein L is a covalent bond.

282. The compound of embodiment 280, wherein L is optionally substituted —$CH_2$—.

283. The compound of any one of embodiments 257-282, wherein $R^8$ is connected to a $sp^3$ ring atom of Ring A.

284. The compound of any one of embodiments 257-283, wherein the carbon to which $R^8$ is attached is chiral and has R configuration.

285. The compound of any one of embodiments 257-283, wherein the carbon to which $R^8$ is attached is chiral and has S configuration.

286. The compound of any one of embodiments 257-285, wherein $R^8$ and —$N(R^5)(R^6)$ are trans.

287. The compound of any one of embodiments 257-285, wherein $R^8$ and —$N(R^5)(R^6)$ are cis.

288. The compound of any one of embodiments 257-287, wherein t is 0.

289. The compound of any one of embodiments 257-288, wherein $R^3$ is optionally substituted $C_{1-6}$ aliphatic.

290. The compound of any one of embodiments 257-289, wherein $R^3$ is optionally substituted $C_{1-6}$ alkyl.

291. The compound of any one of embodiments 257-290, wherein $R^3$ is cyclohexyl.

292. The compound of any one of embodiments 257-290, wherein $R^3$ is methyl.

293. The compound of any one of embodiments 257-288, wherein $R^3$ is optionally substituted phenyl.

294. The compound of any one of embodiments 257-288, wherein $R^3$ is phenyl.

295. The compound of any one of embodiments 257-288, wherein $R^3$ is —H.

296. The compound of any one of embodiments 257-295, wherein $R^3$ is connected to a $sp^3$ ring atom of Ring A.

297. The compound of any one of the preceding embodiments, wherein $R^6$ is —H.

298. A compound, or a diastereomer of a compound, or an enantiomer of a compound, of Table 1, or a salt thereof.

299. A compound, or a diastereomer of a compound, or an enantiomer of a compound, of Table 2, or a salt thereof.

300. A compound, or a diastereomer of a compound, or an enantiomer of a compound, of Table 3, or a salt thereof.

301. A compound, or a diastereomer of a compound, or an enantiomer of a compound, of Table 4, or a salt thereof.

302. The compound of any one of embodiments 1-296, wherein $R^6$ is not H.

303. The compound of embodiment 302, wherein $R^6$ is a nitrogen protecting group.

304. The compound of embodiment 302, wherein $R^6$ is a capping group in oligonucleotide synthesis.

305. The compound of any one of embodiments 302-304, wherein $R^6$ is —R'.

306. The compound of any one of embodiments 302-305, wherein $R^6$ is —C(O)R.

307. The compound of embodiment 307, wherein R is —CH$_3$.

308. The compound of embodiment 307, wherein R is —CF$_3$.

309. A compound having the structure of formula IV:

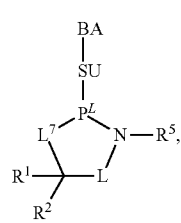

IV or a salt thereof, wherein:
$P^L$ is P(=W), P, or P→B(R')$_3$;
L is a covalent bond, or optionally substituted C$_{1-6}$ alkylene, wherein one or more methylene units are optionally and independently replaced with -L'-;
L' is a covalent bond, optionally substituted bivalent C$_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;
each of $R^1$, $R^2$, $R^3$, $R^4$, and $R^5$ is independently —H, -L$^s$-R, halogen, —CN, —NO$_2$, -L$^s$-Si(R)$_3$, —OR, —SR, or —N(R)$_2$;
each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;

$L^7$ is —O— or —S—;
at least one of $R^1$, $R^2$, $R^3$ and $R^4$ is not —H;
BA is an optionally substituted group selected from C$_{3-30}$ cycloaliphatic, C$_{6-30}$ aryl, C$_{5-30}$ heteroaryl having 1-10 heteroatoms, C$_{3-30}$ heterocyclyl having 1-10 heteroatoms, a natural nucleobase moiety, and a modified nucleobase moiety;
SU is -L$^s$-O— or

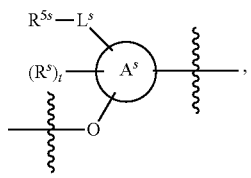

wherein SU is connected to the phosphorus atom through the oxygen atom;
each R$^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;
t is 0-20;
Ring A$^s$ is an optionally substituted 3-20 membered monocyclic, bicyclic or polycyclic ring having 0-10 heteroatoms;
$R^{5s}$ is R$^s$;
each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

310. The compound of embodiment 309, wherein SU is -L$^s$-O—.

311. The compound of embodiment 310, wherein L$^s$ of SU comprises an optionally substituted group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms.

312. The compound of embodiment 310, wherein L$^s$ of SU comprises an optionally substituted 3-20 membered heterocyclyl ring having 1-10 heteroatoms.

313. The compound of embodiment 310, wherein L$^s$ of SU comprises an optionally substituted 5-6 membered heterocyclyl ring having an oxygen atom.

314. The compound of embodiment 310, wherein L$^s$ of SU comprises an optionally substituted 5-membered heterocyclyl ring having an oxygen atom.

315. The compound of embodiment 310, wherein $L^s$ of SU comprises an optionally substituted 6-membered heterocyclyl ring having an oxygen atom.

316. A compound having the structure of formula IV-a:

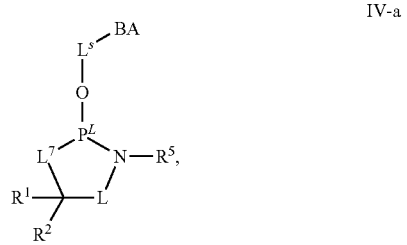

IV-a or a salt thereof, wherein:
$P^L$ is P(=W), P, or P→B(R')$_3$;
L is a covalent bond, or optionally substituted $C_{1-6}$ alkylene, wherein one or more methylene units are optionally and independently replaced with -L'-;
L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;
each of $R^1$, $R^2$, $R^3$, $R^4$, and $R^5$ is independently —H, -L$^s$-R, halogen, —CN, —NO$_2$, -L$^s$-Si(R)$_3$, —OR, —SR, or —N(R)$_2$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;
$L^7$ is —O— or —S—;
at least one of $R^1$, $R^2$, $R^3$ and $R^4$ is not —H;
BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

317. The compound of embodiment 316, wherein $L^s$ in -L$^s$-BA comprises an optionally substituted 3-20 membered heterocyclyl ring having 1-10 heteroatoms.

318. The compound of embodiment 316, wherein $L^s$ in -L$^s$-BA comprises an optionally substituted 5-6 membered heterocyclyl ring having an oxygen atom.

319. The compound of embodiment 316, wherein $L^s$ in -L$^s$-BA comprises an optionally substituted 5-membered heterocyclyl ring having an oxygen atom.

320. The compound of embodiment 316, wherein $L^s$ in -L$^s$-BA comprises an optionally substituted 6-membered heterocyclyl ring having an oxygen atom.

321. The compound of embodiment 309, wherein SU is

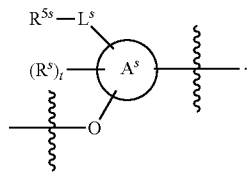

322. A compound having the structure of formula IV-b:

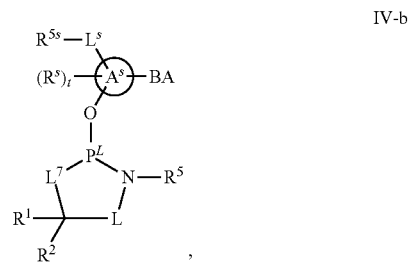

IV-b or a salt thereof, wherein:
$P^L$ is P(=W), P, or P→B(R')$_3$;
L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R³)(R⁴)—, —C(R³)(R⁴)—C(R³)(R⁴)—, -Cy-, or —C(R³)[C(R⁴)₃]—;

each of R¹, R², R³, R⁴, and R⁵ is independently —H, -L$^s$-R, halogen, —CN, —NO₂, -L$^s$-Si(R)₃, —OR, —SR, or —N(R)₂;

each L$^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')₂—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)₂—, —S(O)₂N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')₃]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')₃]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)₂R;

L⁷ is —O— or —S—;

at least one of R¹, R², R³ and R⁴ is not —H;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each R$^s$ is independently —H, halogen, —CN, —N₃, —NO, —NO₂, -L$^s$-R', -L$^s$-Si(R)₃, -L$^s$-OR', -L$^s$-SR', -L$^s$-N(R')₂, —O-L$^s$-R', —O-L$^s$-Si(R)₃, —O-L$^s$-OR', —O-L$^s$-SR', or —O-L$^s$-N(R')₂;

t is 0-20;

Ring A$^s$ is an optionally substituted 3-20 membered monocyclic, bicyclic or polycyclic ring having 0-10 heteroatoms;

R$^{5s}$ is R$^s$;

each R' is independently —R, —C(O)R, —C(O)OR, or —S(O)₂R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

323. The compound of any one of embodiments 321-322, wherein Ring A$^s$ is

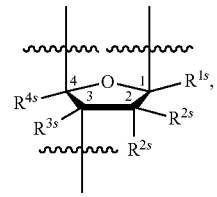

wherein each of R$^{1s}$, R$^{2s}$, R$^{3s}$, R$^{4s}$ and R$^{5s}$ is independently R$^s$.

324. The compound of embodiment 323, wherein Ring A$^s$ is

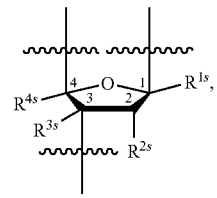

wherein each of R$^{1s}$, R$^{2s}$, R$^{3s}$, R$^{4s}$ and R$^{5s}$ is independently R$^s$.

325. A compound having the structure of formula IV-c-1:

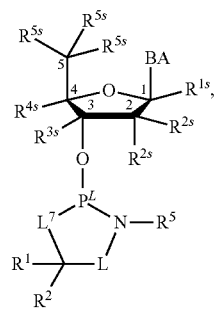

IV-c-1 or a salt thereof, wherein:

P$^L$ is P(=W), P, or P→B(R')₃;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R³)(R⁴)—, —C(R³)(R⁴)—C(R³)(R⁴)—, -Cy-, or —C(R³)[C(R⁴)₃]—;

each of R¹, R², R³, R⁴, and R⁵ is independently —H, -L$^s$-R, halogen, —CN, —NO₂, -L$^s$-Si(R)₃, —OR, —SR, or —N(R)₂;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

$L^7$ is —O— or —S—;

at least one of $R^1$, $R^2$, $R^3$ and $R^4$ is not —H;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{1s}$, $R^{2s}$, $R^{3s}$, $R^{4s}$ and $R^{5s}$ is independently $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

326. A compound having the structure of formula IV-c-2:

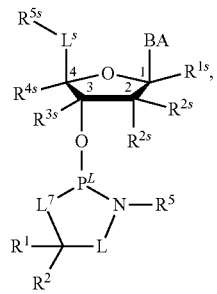

IV-c-2 or a salt thereof, wherein:

$P^L$ is P(=W), P, or P→B(R')$_3$;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

each of $R^1$, $R^2$, $R^3$, $R^4$, and $R^5$ is independently —H, -L$^s$-R, halogen, —CN, —NO$_2$, -L$^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

L⁷ is —O— or —S—;
at least one of $R^1$, $R^2$, $R^3$ and $R^4$ is not —H;
BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;
each of $R^{1s}$, $R^{2s}$, $R^{3s}$, $R^{4s}$ and $R^{5s}$ is independently $R^s$;
each $R^s$ is independently —H, halogen, —CN, —N₃, —NO, —NO₂, -Lˢ-R', -Lˢ-Si(R)₃, -Lˢ-OR', -Lˢ-SR', -Lˢ-N(R')₂, —O-Lˢ-R', —O-Lˢ-Si(R)₃, —O-Lˢ-OR', —O-Lˢ-SR', or —O-Lˢ-N(R')₂;
each R' is independently —R, —C(O)R, —C(O)OR, or —S(O)₂R;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

327. The compound of any one of embodiments 323-326, wherein $R^{1s}$ is —H.

328. The compound of any one of embodiments 323-327, wherein $R^{3s}$ is —H.

329. The compound of any one of embodiments 323-328, wherein

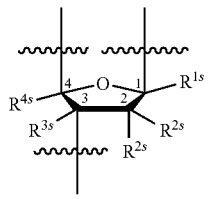

330. A compound having the structure of formula IV-d:

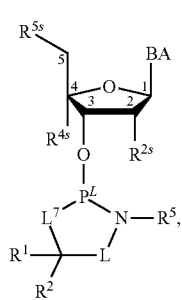

IV-d or a salt thereof, wherein:
$P^L$ is P(=W), P, or P→B(R')₃;
L is a covalent bond, or optionally substituted $C_{1-6}$ alkylene, wherein one or more methylene units are optionally and independently replaced with -L'-;
L' is a covalent bond, optionally substituted bivalent $C_{1-3}$ alkylene, —C(R³)(R⁴)—, —C(R³)(R⁴)—C(R³)(R⁴)—, -Cy-, or —C(R³)[C(R⁴)₃]—;
each of $R^1$, $R^2$, $R^3$, $R^4$, and $R^5$ is independently —H, -Lˢ-R, halogen, —CN, —NO₂, -Lˢ-Si(R)₃, —OR, —SR, or —N(R)₂;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')₂—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)₂—, —S(O)₂N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')₃]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')₃]O—, and one or more carbon atoms are optionally and independently replaced with $Cy^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)₂R;
L⁷ is —O— or —S—;
at least one of $R^1$, $R^2$, $R^3$ and $R^4$ is not —H;
BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;
each of $R^{2s}$, $R^{4s}$ and $R^{5s}$ is independently $R^s$;
each $R^s$ is independently —H, halogen, —CN, —N₃, —NO, —NO₂, -Lˢ-R', -Lˢ-Si(R)₃, -Lˢ-OR', -Lˢ-SR', -Lˢ-N(R')₂, —O-Lˢ-R', —O-Lˢ-Si(R)₃, —O-Lˢ-OR', —O-Lˢ-SR', or —O-Lˢ-N(R')₂;
each R' is independently —R, —C(O)R, —C(O)OR, or —S(O)₂R;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

331. The compound of any one of embodiments 323-330, wherein $R^{4s}$ is —H.

332. The compound of any one of embodiments 323-331, wherein

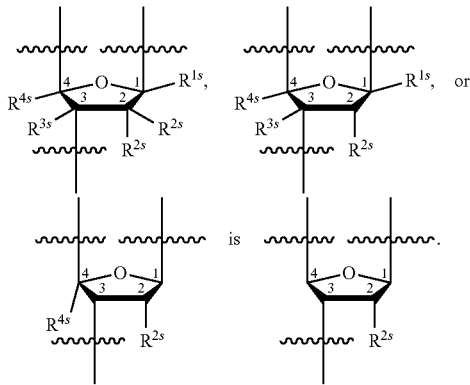

is

333. A compound having the structure of formula IV-e:

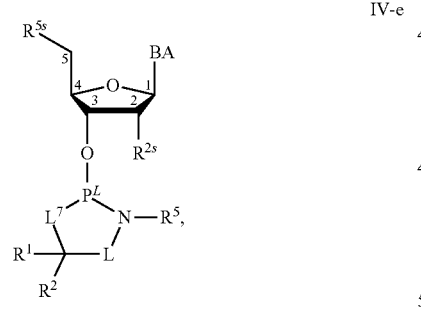

IV-e or a salt thereof, wherein:

$P^L$ is P(=W), P, or P→B(R')$_3$;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

each of $R^1$, $R^2$, $R^3$, $R^4$, and $R^5$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms; each R' is independently —R, —C(O)R, —C(O)OR, or —S(O)$_2$R;

$L^7$ is —O— or —S—;

at least one of $R^1$, $R^2$, $R^3$ and $R^4$ is not —H;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{2s}$ and $R^{5s}$ is independently $R^s$; each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

334. The compound of any one of embodiments 323-333, wherein $R^{2s}$ is —H.

335. The compound of any one of embodiments 323-333, wherein $R^{2s}$ is —F.

336. The compound of any one of embodiments 323-333, wherein $R^{2s}$ is —OR.

337. The compound of any one of embodiments 323-333, wherein $R^{2s}$ is —OR, wherein R is not —H.

338. The compound of any one of embodiments 323-333, wherein $R^{2s}$ is —OR, wherein R is optionally substituted $C_{1-6}$ aliphatic.

339. The compound of any one of embodiments 323-333, wherein $R^{2s}$ is —OR, wherein R is optionally substituted $C_{1-6}$ alkyl.

340. The compound of any one of embodiments 323-333, wherein $R^{2s}$ is —OMe.

341. The compound of any one of embodiments 323-333, wherein $R^{2s}$ is -MOE.

342. The compound of embodiment 323-330, wherein

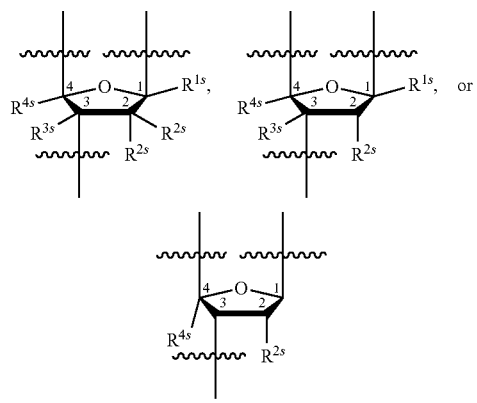

is optionally substituted

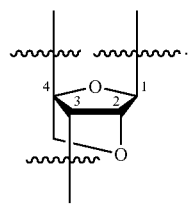 [SMILES: *C1[C@@H]2OC[C@]1(*)O[C@H]2*]

343. The compound of embodiment 342, wherein

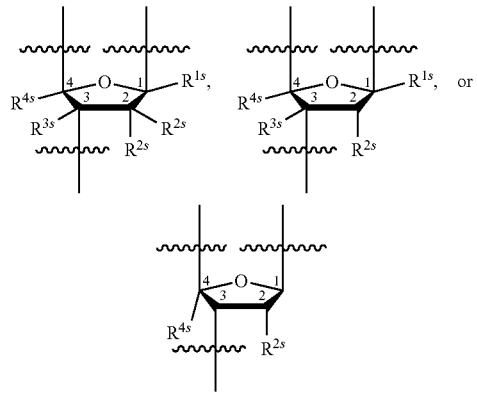

is unsubstituted

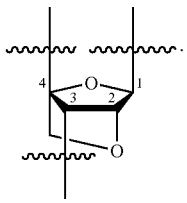 [SMILES: *C1[C@@H]2OC[C@]1(*)O[C@H]2*]

344. The compound of embodiment 342, wherein

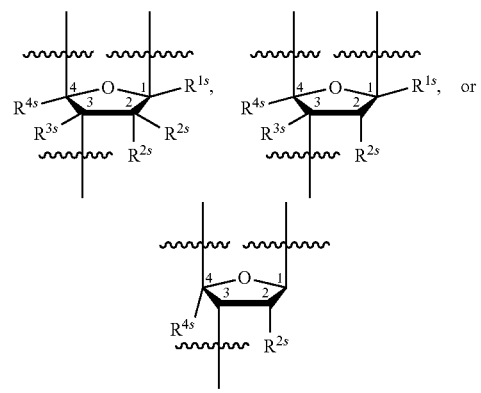

is substituted

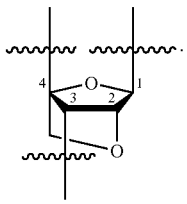

345. The compound of embodiment 323-330, wherein

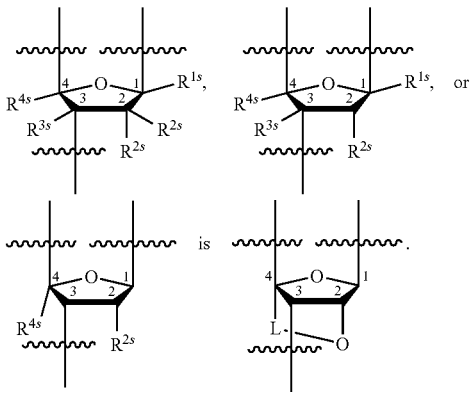

346. The compound of embodiment 345, wherein L is —CHR—.

347. The compound of embodiment 345, wherein L is —(R)—CHR—.

348. The compound of embodiment 345, wherein L is —(S)—CHR—.
349. The compound of any one of embodiments 346-348, wherein R of —CHR— is optionally substituted $C_{1-6}$ aliphatic.
350. The compound of any one of embodiments 346-348, wherein R of —CHR— is optionally substituted $C_{1-6}$ alkyl.
351. The compound of any one of embodiments 346-348, wherein R of —CHR— is optionally substituted $C_{1-3}$ alkyl.
352. The compound of any one of embodiments 346-348, wherein R of —CHR— is H.
353. The compound of any one of embodiments 346-348, wherein R of —CHR— is methyl.
354. The compound of any one of embodiments 346-348, wherein R of —CHR— is ethyl.
355. The compound of any one of embodiments 309-354, wherein

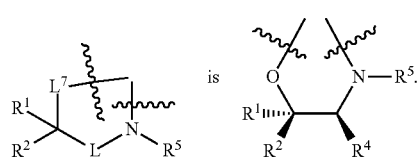

356. The compound of any one of embodiments 309-354, wherein

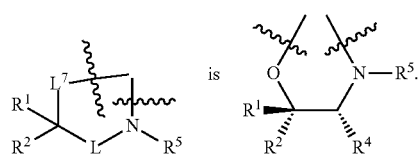

357. The compound of any one of embodiments 355-356, wherein $R^4$ and $R^5$ are taken together with the intervening atoms to form an optionally substituted 3-20 membered monocyclic, bicyclic or polycyclic ring having 1-5 heteroatoms.
358. The compound of embodiment 357, wherein the ring is 3-10 membered.
359. The compound of embodiment 357, wherein the ring is 4-9 membered.
360. The compound of embodiment 357, wherein the ring is 4-membered.
361. The compound of embodiment 357, wherein the ring is 5-membered.
362. The compound of embodiment 357, wherein the ring is 6-membered.
363. The compound of embodiment 357, wherein the ring is 7-membered.
364. The compound of embodiment 357, wherein the ring is 8-membered.
365. The compound of embodiment 357, wherein the ring is 9-membered.
366. The compound of any one of embodiments 357-365, wherein the ring is monocyclic.
367. The compound of any one of embodiments 357-365, wherein the ring is bicyclic.
368. The compound of any one of embodiments 357-365, wherein the ring is polycyclic.
369. The compound of any one of embodiments 357-368, wherein the ring is saturated.
370. The compound of any one of embodiments 357-369, wherein the ring is substituted.
371. The compound of any one of embodiments 357-369, wherein the ring is unsubstituted.
372. The compound of any one of embodiments 357-371, wherein the ring comprises no more heteroatoms other than the nitrogen to which $R^5$ is attached.
373. The compound of any one of embodiments 357-371, wherein the ring comprises one or more heteroatoms in addition to the nitrogen to which $R^5$ is attached.
374. The compound of any one of embodiments 357-371, wherein the ring comprises one or more oxygen atom in addition to the nitrogen to which $R^5$ is attached.
375. The compound of any one of embodiments 355-357, wherein —C($R^3$)($R^4$)—N($R^5$($R^6$) is

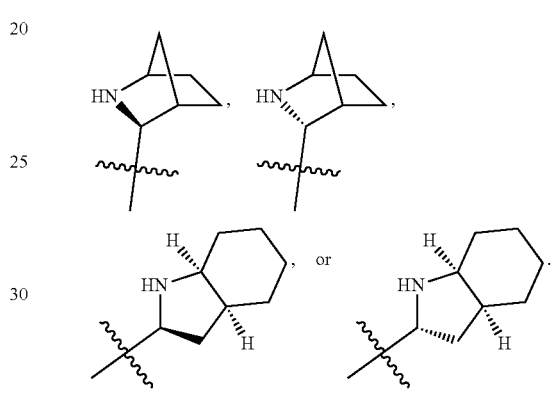

376. The compound of any one of embodiments 355-357, wherein —C($R^3$)($R^4$)—N($R^5$($R^6$) is

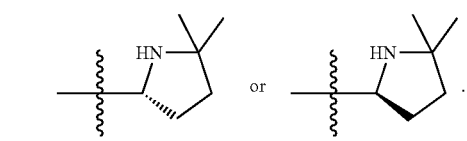

377. The compound of any one of embodiments 355-357, wherein —C($R^3$)($R^4$)—N($R^5$($R^6$) is

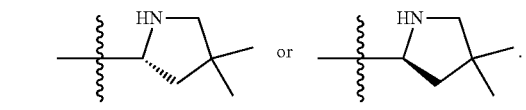

378. The compound of any one of embodiments 355-357, wherein —C($R^3$)($R^4$)—N($R^5$($R^6$) is

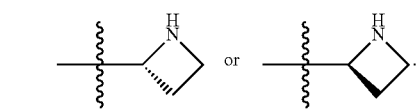 [SMILES: *[C@H]1CCN1 ; *[C@@H]1CCN1]

379. The compound of any one of embodiments 355-357, wherein —C(R³)(R⁴)—N(R⁵(R⁶) is

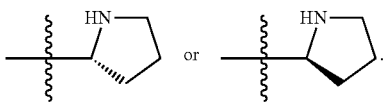 [SMILES: *[C@H]1CCCN1 ; *[C@@H]1CCCN1]

380. The compound of any one of embodiments 355-357, wherein —C(R³)(R⁴)—N(R⁵(R⁶) is

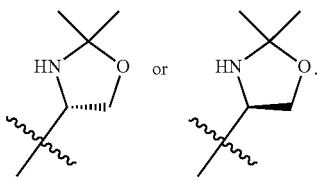

381. The compound of any one of embodiments 355-380, wherein $R^1$ is —H.
382. The compound of any one of embodiments 355-380, wherein $R^1$ is $C_{1-3}$ alkyl.
383. The compound of any one of embodiments 355-380, wherein $R^1$ is methyl.
384. The compound of any one of embodiments 355-383, wherein $R^2$ is R, wherein R is not hydrogen.
385. The compound of any one of embodiments 355-383, wherein $R^2$ is optionally substituted $C_{1-30}$ aliphatic.
386. The compound of any one of embodiments 355-385, wherein $R^2$ is optionally substituted $C_{3-30}$ cycloaliphatic.
387. The compound of any one of embodiments 355-386, wherein $R^2$ is optionally substituted $C_{3-30}$ cycloalkyl.
388. The compound of any one of embodiments 355-386, wherein $R^2$ is cyclopentyl.
389. The compound of any one of embodiments 355-383, wherein $R^2$ is optionally substituted $C_{1-30}$ heteroaliphatic having 1-10 heteroatoms.
390. The compound of any one of embodiments 355-383, wherein $R^2$ is optionally substituted $C_{6-30}$ aryl.
391. The compound of embodiment 390, wherein $R^2$ is optionally substituted phenyl.
392. The compound of embodiment 391, wherein $R^2$ is substituted phenyl.
393. The compound of embodiment 391, wherein a substituent of the substituted phenyl is an electron-donating group.
394. The compound of embodiment 391, wherein a substituent of the substituted phenyl is an electron-withdrawing group.
395. The compound of embodiment 393, wherein a substituent of the substituted phenyl is $C_{1-6}$ alkyl.
396. The compound of embodiment 393, wherein a substituent of the substituted phenyl is p-methyl.
397. The compound of embodiment 391, wherein a substituent of the substituted phenyl is halogen.
398. The compound of embodiment 397, wherein a substituent of the substituted phenyl is —F.
399. The compound of embodiment 398, wherein a substituent of the substituted phenyl is m-F.
400. The compound of embodiment 398, wherein two substituents of the substituted phenyl are m-F.
401. The compound of embodiment 393, wherein a substituent of the substituted phenyl is p-OMe.
402. The compound of embodiment 401, wherein a substituent of the substituted phenyl is p-OMe, and a substituent is o-OMe.
403. The compound of any one of embodiments 355-383, wherein $R^2$ is optionally substituted $C_{6-30}$ arylaliphatic.
404. The compound of any one of embodiments 355-383, wherein $R^2$ is optionally substituted benzyl.
405. The compound of any one of embodiments 355-383, wherein $R^2$ is benzyl.
406. The compound of embodiment 405, wherein $R^2$ is substituted benzyl.
407. The compound of embodiment 406, wherein $R^2$ is p-OMeC$_6$H$_4$—CH$_2$—.
408. The compound of any one of embodiments 355-383, wherein $R^2$ is optionally substituted $C_{6-30}$ arylheteroaliphatic having 1-10 heteroatoms.
409. The compound of any one of embodiments 355-383, wherein $R^2$ is optionally substituted 5-30 membered heteroaryl having 1-10 heteroatoms.
410. The compound of embodiment 409, wherein $R^2$ is optionally substituted monocyclic 5-membered heteroaryl.
411. The compound of embodiment 409, wherein $R^2$ is optionally substituted monocyclic 6-membered heteroaryl.
412. The compound of embodiment 409, wherein $R^2$ is optionally substituted bicyclic 9-membered heteroaryl.
413. The compound of embodiment 409, wherein $R^2$ is optionally substituted bicyclic 10-membered heteroaryl.
414. The compound of any one of embodiments 355-383, wherein $R^2$ is optionally substituted 3-30 membered heterocyclyl having 1-10 heteroatoms.
415. The compound of any one of embodiments 355-380, wherein $R^1$ and $R^2$ are taken together with their intervening atoms to form an optionally substituted 3-20 membered monocyclic, bicyclic or polycyclic ring having 0-5 heteroatoms.
416. The compound of embodiment 415, wherein $R^1$ and $R^2$ are taken together with their intervening atoms to form an optionally substituted 3-15 membered monocyclic, bicyclic or polycyclic ring having 0-5 heteroatoms.
417. The compound of embodiment 415, wherein the ring is 3-10 membered.
418. The compound of any one of embodiments 415-417, wherein the ring is 10-membered.
419. The compound of any one of embodiments 415-417, wherein the ring is 9-membered.
420. The compound of any one of embodiments 415-417, wherein the ring is 8-membered.
421. The compound of any one of embodiments 415-417, wherein the ring is 7-membered.
422. The compound of any one of embodiments 415-417, wherein the ring is 3-6 membered.
423. The compound of any one of embodiments 415-417, wherein the ring is 6-membered.
424. The compound of any one of embodiments 415-417, wherein the ring is 5-membered.
425. The compound of any one of embodiments 415-417, wherein the ring is 4-membered.
426. The compound of any one of embodiments 415-417, wherein the ring is 3-membered.
427. The compound of any one of embodiments 415-426, wherein the ring is monocyclic.
428. The compound of any one of embodiments 415-426, wherein the ring is bicyclic.
429. The compound of any one of embodiments 415-426, wherein the ring is polycyclic.

430. The compound of any one of embodiments 415-417, wherein the ring is bicyclic or polycyclic, and comprises an aromatic monocyclic ring.

431. The compound of any one of embodiments 415-430, wherein the ring comprises no heteroatom.

432. The compound of any one of embodiments 415-430, wherein the ring comprises one or more heteroatoms.

433. The compound of embodiment 423, wherein the ring is

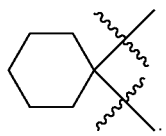 [SMILES: *C1(*)CCCCC1]

434. The compound of embodiment 424, wherein the ring is

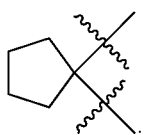

435. The compound of embodiment 425, wherein the ring is

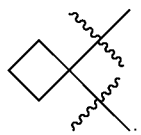 [SMILES: *C1(*)CCC1]

436. The compound of embodiment 426, wherein the ring is

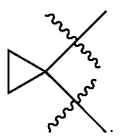

437. The compound of embodiment 419, wherein $R^1$ and $R^2$ are taken together with their intervening atoms to form an optionally substituted ring having the structure of

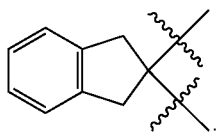 [SMILES: *C1(*)Cc2ccccc2C1]

438. The compound of any one of embodiments 415-437, wherein the ring is substituted.

439. The compound of any one of embodiments 415-437, wherein the ring is unsubstituted.

440. The compound of any one of embodiments 415-439, wherein the ring comprises no chiral elements.

441. The compound of any one of embodiments 309-354, wherein

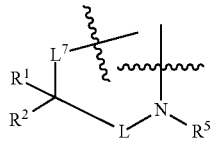

is of such a structure that

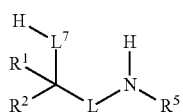

is a compound of any one of embodiments 1-301 or a salt thereof.

442. The compound of any one of embodiments 309-354, wherein

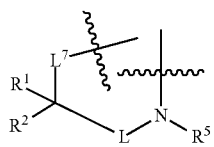

is of such a structure that

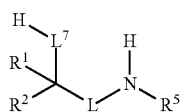

is a compound of any one of embodiments 1-206 or a salt thereof.

443. A compound having the structure of formula IVa:

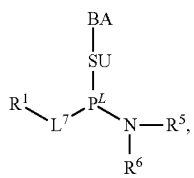

IVa or a salt thereof, wherein:
$P^L$ is P(=W), P, or P→B(R')$_3$;
each of $R^1$ and $R^5$ is independently —H, -L$^s$-R, halogen, —CN, —NO$_2$, -L$^s$-Si(R)$_3$, —OR, —SR, or —N(R)$_2$;
each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

R$^6$ is R';

L$^7$ is —O— or —S—;

BA is an optionally substituted group selected from C$_{3-30}$ cycloaliphatic, C$_{6-30}$ aryl, C$_{5-30}$ heteroaryl having 1-10 heteroatoms, C$_{3-30}$ heterocyclyl having 1-10 heteroatoms, a natural nucleobase moiety, and a modified nucleobase moiety;

SU is -L$^s$-O— or

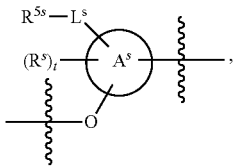

, wherein SU is connected to the phosphorus atom through the oxygen atom;

each R$^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

t is 0-20;

Ring A$^s$ is an optionally substituted 3-20 membered monocyclic, bicyclic or polycyclic ring having 0-10 heteroatoms;

R$^{5s}$ is R$^s$;

each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

444. The compound of embodiment 443, wherein SU is -L$^s$-O—.

445. The compound of embodiment 444, wherein L$^s$ of SU comprises an optionally substituted group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms.

446. The compound of embodiment 444, wherein L$^s$ of SU comprises an optionally substituted 3-20 membered heterocyclyl ring having 1-10 heteroatoms.

447. The compound of embodiment 444, wherein L$^s$ of SU comprises an optionally substituted 5-6 membered heterocyclyl ring having an oxygen atom.

448. The compound of embodiment 444, wherein L$^s$ of SU comprises an optionally substituted 5-membered heterocyclyl ring having an oxygen atom.

449. The compound of embodiment 444, wherein L$^s$ of SU comprises an optionally substituted 6-membered heterocyclyl ring having an oxygen atom.

450. A compound having the structure of formula IVa-a:

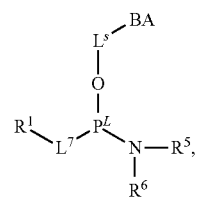

IVa-a or a salt thereof, wherein:

P$^L$ is P(=W), P, or P→B(R')$_3$;

each of R$^1$ and R$^5$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

$R^6$ is R';

$L^7$ is —O— or —S—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

451. The compound of embodiment 450, wherein $L^s$ in -$L^s$-BA comprises an optionally substituted 3-20 membered heterocyclyl ring having 1-10 heteroatoms.

452. The compound of embodiment 450, wherein $L^s$ in -$L^s$-BA comprises an optionally substituted 5-6 membered heterocyclyl ring having an oxygen atom.

453. The compound of embodiment 450, wherein $L^s$ in -$L^s$-BA comprises an optionally substituted 5-membered heterocyclyl ring having an oxygen atom.

454. The compound of embodiment 450, wherein $L^s$ in -$L^s$-BA comprises an optionally substituted 6-membered heterocyclyl ring having an oxygen atom.

455. The compound of embodiment 443, wherein SU is

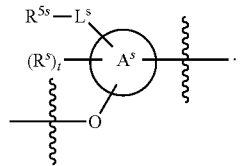

.

456. A compound having the structure of formula IVa-b:

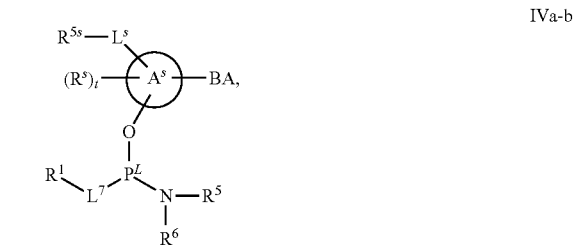

IVa-b or a salt thereof, wherein:

$P^L$ is P(=W), P, or P→B(R')$_3$;

each of $R^1$ and $R^5$ is independently —H, -$L^s$-R, halogen, —CN, —NO$_2$, -$L^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

$L^7$ is —O— or —S—;

$R^6$ is R';

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each $R^s$ is independently —H, halogen, —CN, —N$_3$, —NO, —NO$_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;

t is 0-20;

Ring $A^s$ is an optionally substituted 3-20 membered monocyclic, bicyclic or polycyclic ring having 0-10 heteroatoms;

$R^{5s}$ is $R^s$;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

457. The compound of any one of embodiments 455-456, wherein Ring $A^s$ is

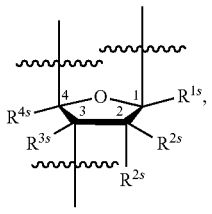

wherein each of $R^{1s}$, $R^{2s}$, $R^{3s}$, $R^{4s}$ and $R^{5s}$ is independently $R^s$.

458. The compound of embodiment 457, wherein Ring $A^s$ is

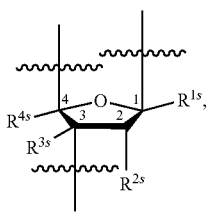

wherein each of $R^{1s}$, $R^{2s}$, $R^{3s}$, $R^{4s}$ and $R^{5s}$ is independently $R^s$.

459. A compound having the structure of formula IVa-c-1:

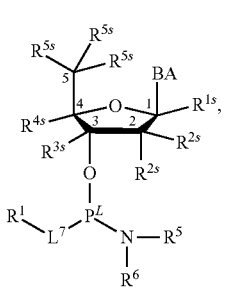

IVa-c-1 or a salt thereof, wherein:

$P^L$ is P(=W), P, or P→B(R')$_3$;

each of $R^1$ and $R^5$ is independently —H, -L$^s$-R, halogen, —CN, —NO$_2$, -L$^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

$L^7$ is —O— or —S—;

$R^6$ is R';

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{1s}$, $R^{2s}$, $R^{3s}$, $R^{4s}$ and $R^{5s}$ is independently $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

460. A compound having the structure of formula IVa-c-2:

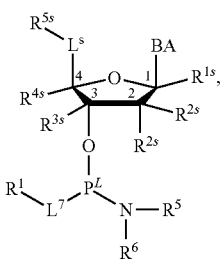

IVa-c-2 or a salt thereof, wherein:
$P^L$ is P(=W), P, or P→B(R')$_3$;
each of $R^1$ and $R^5$ is independently —H, -$L^s$-R, halogen, —CN, —NO$_2$, -$L^s$-Si(R)$_3$, —OR, —SR, or —N(R)$_2$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;
$L^7$ is —O— or —S—;
$R^6$ is R';
BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;
each of $R^{1s}$, $R^{2s}$, $R^{3s}$, $R^{4s}$ and $R^{5s}$ is independently R$^s$;
each R$^s$ is independently —H, halogen, —CN, —N$_3$, —NO, —NO$_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

461. The compound of any one of embodiments 457-460, wherein $R^{1s}$ is —H.

462. The compound of any one of embodiments 457-461, wherein $R^{3s}$ is —H.

463. The compound of any one of embodiments 457-462, wherein

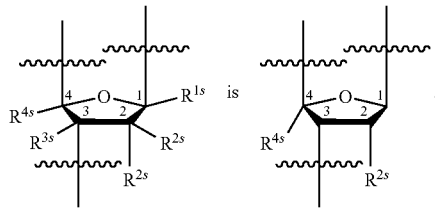

464. A compound having the structure of formula IVa-d:

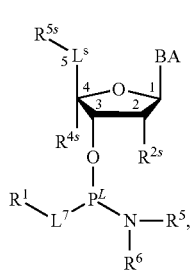

IVa-d or a salt thereof, wherein:
$P^L$ is P(=W), P, or P→B(R')$_3$;
each of $R^1$ and $R^5$ is independently —H, -$L^s$-R, halogen, —CN, —NO$_2$, -$L^s$-Si(R)$_3$, —OR, —SR, or —N(R)$_2$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

$R^6$ is R';

$L^7$ is —O— or —S—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{2s}$, $R^{4s}$ and $R^{5s}$ is independently $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

465. The compound of any one of embodiments 457-464, wherein $R^{4s}$ is —H.

466. The compound of any one of embodiments 457-465, wherein

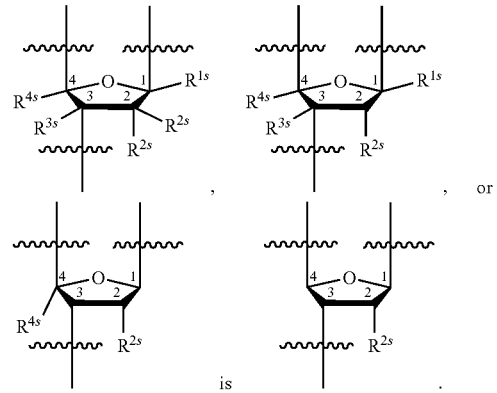

is .

467. A compound having the structure of formula IVa-e:

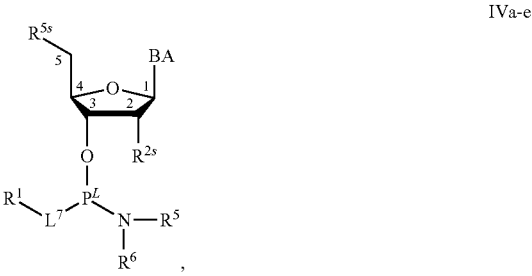

IVa-e or a salt thereof, wherein:
$P^L$ is P(=W), P, or P→B(R')$_3$;
each of $R^1$ and $R^5$ is independently —H, -L$^s$-R, halogen, —CN, —NO$_2$, -L$^s$-Si(R)$_3$, —OR, —SR, or —N(R)$_2$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)₂R;

$L^7$ is —O— or —S—;

$R^6$ is R';

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{2s}$ and $R^{5s}$ is independently $R^s$;

each $R^s$ is independently —H, halogen, —CN, —N₃, —NO, —NO₂, -$L^s$-R', -$L^s$-Si(R)₃, -$L^s$-OR', -$L^s$-SR', -$L^s$-N(R')₂, —O-$L^s$-R', —O-$L^s$-Si(R)₃, —O-$L^s$-OR', —O-$L^s$-SR', or —O-$L^s$-N(R')₂;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

468. The compound of any one of embodiments 457-467, wherein $R^{2s}$ is —H.

469. The compound of any one of embodiments 457-467, wherein $R^{2s}$ is —F.

470. The compound of any one of embodiments 457-467, wherein $R^{2s}$ is —OR.

471. The compound of any one of embodiments 457-467, wherein $R^{2s}$ is —OR, wherein R is not —H.

472. The compound of any one of embodiments 457-467, wherein $R^{2s}$ is —OR, wherein R is optionally substituted $C_{1-6}$ aliphatic.

473. The compound of any one of embodiments 457-467, wherein $R^{2s}$ is —OR, wherein R is optionally substituted $C_{1-6}$ alkyl.

474. The compound of any one of embodiments 457-467, wherein $R^{2s}$ is —OMe.

475. The compound of any one of embodiments 457-467, wherein $R^{2s}$ is -MOE.

476. The compound of any one of embodiments 457-464, wherein

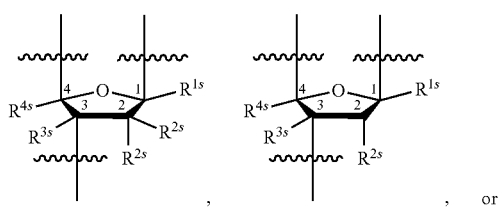

,                , or

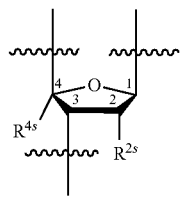

is optionally substituted

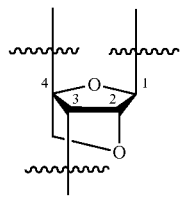

477. The compound of embodiment 476, wherein

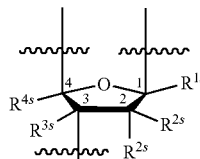 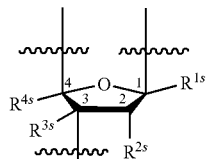

,                , or

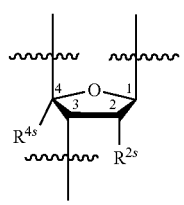

is unsubstituted

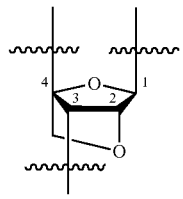

478. The compound of embodiment 476, wherein

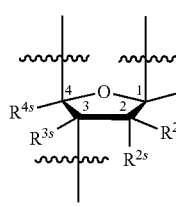 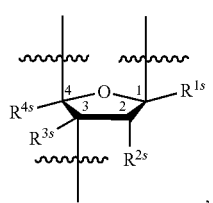

,                , or

-continued

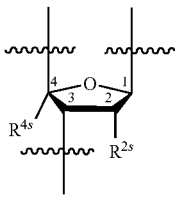

is substituted

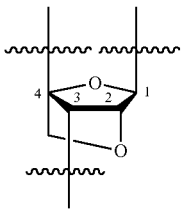

479. The compound of any one of embodiments 457-464, wherein

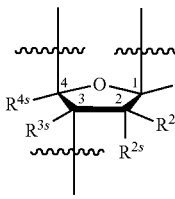 , 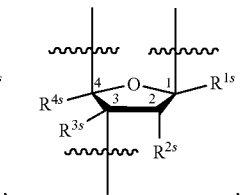 , or

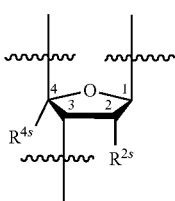 is .

wherein L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—; and each of R$^3$ and R$^4$ is independently —H, -L$^s$-R, halogen, —CN, —NO$_2$, -L$^s$-Si(R)$_3$, —OR, —SR, or —N(R)$_2$.

480. The compound of embodiment 479, wherein L is —CHR—.

481. The compound of embodiment 479, wherein L is —(R)—CHR—.

482. The compound of embodiment 479, wherein L is —(S)—CHR—.

483. The compound of any one of embodiments 479-482, wherein R of —CHR— is optionally substituted $C_{1-6}$ aliphatic.

484. The compound of any one of embodiments 479-482, wherein R of —CHR— is optionally substituted $C_{1-6}$ alkyl.

485. The compound of any one of embodiments 479-482, wherein R of —CHR— is optionally substituted $C_{1-3}$ alkyl.

486. The compound of any one of embodiments 479-482, wherein R of —CHR— is H.

487. The compound of any one of embodiments 479-482, wherein R of —CHR— is methyl.

488. The compound of any one of embodiments 479-482, wherein R of —CHR— is ethyl.

489. The compound of any one of embodiments 443-488, wherein R$^1$ optionally substituted $C_{1-6}$ aliphatic.

490. The compound of any one of embodiments 443-489, wherein R$^1$ optionally substituted $C_{1-6}$ aliphatic.

491. The compound of embodiment 490, wherein R$^1$ is optionally substituted ethyl.

492. The compound of embodiment 490, wherein R$^1$ is —CH$_2$CH$_2$CN.

493. The compound of any one of embodiments 309-492, wherein L$^7$ is —O—.

494. The compound of any one of embodiments 443-493, wherein each of R$^5$ and R$^6$ is independently optionally substituted $C_{1-6}$ aliphatic.

495. The compound of any one of embodiments 443-493, wherein each of R$^5$ and R$^6$ is independently optionally substituted $C_{1-6}$ alkyl.

496. The compound of any one of embodiments 443-493, wherein R$^5$ and R$^6$ are the same.

497. The compound of any one of embodiments 443-493, wherein R$^5$ and R$^6$ are isopropyl.

498. A compound having the structure of formula V:

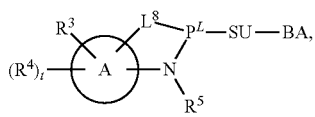

(V)

or a salt thereof, wherein:

P$^L$ is P(=W), P, or P→B(R')$_3$;

Ring A is an optionally substituted 3-20 membered monocyclic, bicyclic or polycyclic ring having 0-10 heteroatoms;

each of R$^1$, R$^2$, R$^3$, R$^4$, and R$^5$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S) (OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O) (SR')O—, —OP(O)(R')O—, —OP(O)(NR')O—, —OP (OR')O—, —OP(SR')O—, —OP(NR')O—, —OP(R') O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

each t is independently 0-20;

$L^8$ is -L-O—, -L-C(R$^1$)(R$^2$)—O—, or -L$^s$-O—;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

SU is -L$^s$-O— or

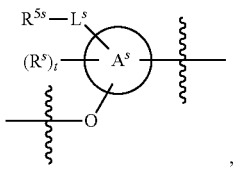

, wherein SU is connected to the phosphorus atom through the oxygen atom;

$R^{5s}$ is $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

Ring $A^s$ is an optionally substituted 3-20 membered monocyclic, bicyclic or polycyclic ring having 0-10 heteroatoms;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

499. The compound of embodiment 498, wherein SU is -L$^s$-O—.

500. The compound of embodiment 499, wherein L$^s$ of SU comprises an optionally substituted group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms.

501. The compound of embodiment 499, wherein L$^s$ of SU comprises an optionally substituted 3-20 membered heterocyclyl ring having 1-10 heteroatoms.

502. The compound of embodiment 499, wherein L$^s$ of SU comprises an optionally substituted 5-6 membered heterocyclyl ring having an oxygen atom.

503. The compound of embodiment 499, wherein L$^s$ of SU comprises an optionally substituted 5-membered heterocyclyl ring having an oxygen atom.

504. The compound of embodiment 499, wherein L$^s$ of SU comprises an optionally substituted 6-membered heterocyclyl ring having an oxygen atom.

505. A compound having the structure of formula V-a:

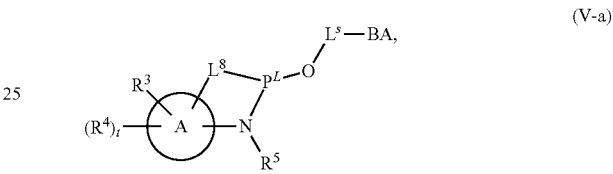

(V-a)

or a salt thereof, wherein:

$P^L$ is P(=W), P, or P→B(R')$_3$;

Ring A is an optionally substituted 3-20 membered monocyclic, bicyclic or polycyclic ring having 0-10 heteroatoms;

each of R$^1$, R$^2$, R$^3$, R$^4$, and R$^5$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

t is 0-20;

$L^8$ is -L-O—, -L-C(R$^1$)(R$^2$)—O—, or -L$^s$-O—;

L is a covalent bond, or optionally substituted C$_{1-6}$ alkylene, wherein one or more methylene units are optionally and independently replaced with -L'-;

L' is a covalent bond, optionally substituted bivalent C$_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from C$_{3-30}$ cycloaliphatic, C$_{6-30}$ aryl, C$_{5-30}$ heteroaryl having 1-10 heteroatoms, C$_{3-30}$ heterocyclyl having 1-10 heteroatoms, a natural nucleobase moiety, and a modified nucleobase moiety;

each R' is independently —R, —C(O)R, —C(O)OR, or —S(O)$_2$R;

each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

506. The compound of embodiment 505, wherein L$^s$ comprises an optionally substituted 3-20 membered heterocyclyl ring having 1-10 heteroatoms.

507. The compound of embodiment 505, wherein L$^s$ comprises an optionally substituted 5-6 membered heterocyclyl ring having an oxygen atom.

508. The compound of embodiment 505, wherein L$^s$ comprises an optionally substituted 5-membered heterocyclyl ring having an oxygen atom.

509. The compound of embodiment 505, wherein L$^s$ comprises an optionally substituted 6-membered heterocyclyl ring having an oxygen atom.

510. The compound of embodiment 498, wherein SU is

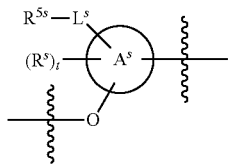

511. A compound having the structure of formula V-b:

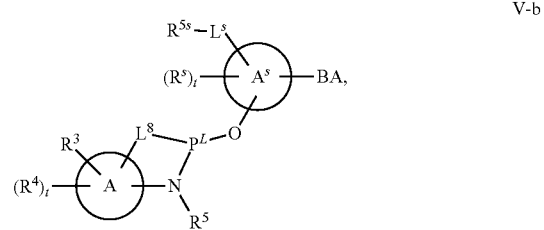

V-b or a salt thereof, wherein:

$P^L$ is P(=W), P, or P→B(R')$_3$;

Ring A is an optionally substituted 3-20 membered monocyclic, bicyclic or polycyclic ring having 0-10 heteroatoms;

each of R$^1$, R$^2$, R$^3$, R$^4$, and R$^5$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S) (OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O) (SR')O—, —OP(O)(R')O—, —OP(O)(NR')O—, —OP (OR')O—, —OP(SR')O—, —OP(NR')O—, —OP(R') O—, or —OP(OR')[B(R')$_3$]O—, and one or more carbon atoms are optionally and independently replaced with Cy$^L$;

each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

each t is independently 0-20;

$L^8$ is -L-O—, -L-C(R$^1$)(R$^2$)—O—, or -L$^s$-O—;

L is a covalent bond, or optionally substituted C$_{1-6}$ alkylene, wherein one or more methylene units are optionally and independently replaced with -L'-;

L' is a covalent bond, optionally substituted bivalent C$_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from C$_{3-30}$ cycloaliphatic, C$_{6-30}$ aryl, C$_{5-30}$ heteroaryl having 1-10 heteroatoms, C$_{3-30}$ heterocyclyl having 1-10 heteroatoms, a natural nucleobase moiety, and a modified nucleobase moiety;

$R^{5s}$ is $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

Ring A$^s$ is an optionally substituted 3-20 membered monocyclic, bicyclic or polycyclic ring having 0-10 heteroatoms;

each R' is independently —R, —C(O)R, —C(O)OR, or —S(O)$_2$R;

each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

512. The compound of any one of embodiments 510-511, wherein Ring A$^s$ is

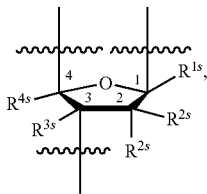

wherein each of $R^{1s}$, $R^{2s}$, $R^{3s}$, $R^{4s}$ and $R^{5s}$ is independently $R^s$.

513. The compound of embodiment 512, wherein Ring A$^s$ is

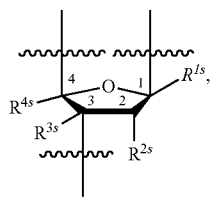

wherein each of $R^{1s}$, $R^{2s}$, $R^{3s}$, $R^{4s}$ and $R^{5s}$ is independently $R^s$.

514. A compound having the structure of formula V-c-1:

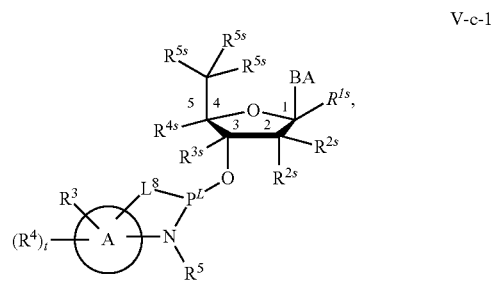

V-c-1 or a salt thereof, wherein:

$P^L$ is P(=W), P, or P→B(R')$_3$;

Ring A is an optionally substituted 3-20 membered monocyclic, bicyclic or polycyclic ring having 0-10 heteroatoms;

each of $R^1$, $R^2$, $R^3$, $R^4$, and $R^5$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

t is 0-20;

$L^8$ is -L-O—, -L-C(R$^1$)(R$^2$)—O—, or -L$^s$-O—;

L is a covalent bond, or optionally substituted C$_{1-6}$ alkylene, wherein one or more methylene units are optionally and independently replaced with -L'-;

L' is a covalent bond, optionally substituted bivalent C$_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from C$_{3-30}$ cycloaliphatic, C$_{6-30}$ aryl, C$_{5-30}$ heteroaryl having 1-10 heteroatoms, $C_{3-30}$ heterocyclyl having 1-10 heteroatoms, a natural nucleobase moiety, and a modified nucleobase moiety;

each of $R^{1s}$, $R^{2s}$, $R^{3s}$, $R^{4s}$ and $R^{5s}$ is independently $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

515. A compound having the structure of formula V-c-2:

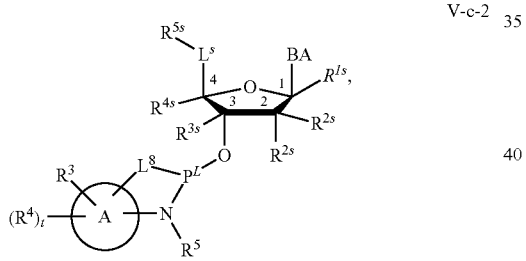

V-c-2 or a salt thereof, wherein:

P$^L$ is P(=W), P, or P→B(R')$_3$;

Ring A is an optionally substituted 3-20 membered monocyclic, bicyclic or polycyclic ring having 0-10 heteroatoms;

each of $R^1$, $R^2$, $R^3$, $R^4$, and $R^5$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

t is 0-20;

L$^8$ is -L-O—, -L-C(R$^1$)(R$^2$)—O—, or -L$^s$-O—;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{1s}$, $R^{2s}$, $R^{3s}$, $R^{4s}$ and $R^{5s}$ is independently $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

516. The compound of any one of embodiments 512-515, wherein $R^{1s}$ is —H.

517. The compound of any one of embodiments 512-516, wherein $R^{3s}$ is —H.

518. The compound of any one of embodiments 512-517, wherein

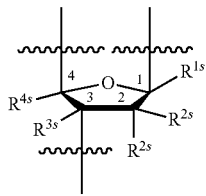

519. A compound having the structure of formula V-d:

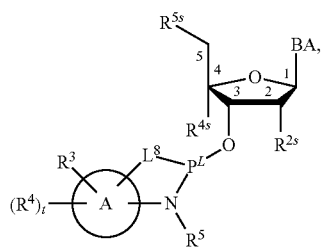

V-d or a salt thereof, wherein:
P$^L$ is P(=W), P, or P→B(R')$_3$;
Ring A is an optionally substituted 3-20 membered monocyclic, bicyclic or polycyclic ring having 0-10 heteroatoms;
each of R$^1$, R$^2$, R$^3$, R$^4$, and R$^5$ is independently —H, -L$^s$-R, halogen, —CN, —NO$_2$, -L$^s$-Si(R)$_3$, —OR, —SR, or —N(R)$_2$;
each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;
t is 0-20;
L$^8$ is -L-O—, -L-C(R$^1$)(R$^2$)—O—, or -L$^s$-O—;
L is a covalent bond, or optionally substituted C$_{1-6}$ alkylene, wherein one or more methylene units are optionally and independently replaced with -L'-;
L' is a covalent bond, optionally substituted bivalent C$_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;
BA is an optionally substituted group selected from C$_{3-30}$ cycloaliphatic, C$_{6-30}$ aryl, C$_{5-30}$ heteroaryl having 1-10 heteroatoms, C$_{3-30}$ heterocyclyl having 1-10 heteroatoms, a natural nucleobase moiety, and a modified nucleobase moiety;
each of R$^{2s}$, R$^{4s}$ and R$^{5s}$ is independently R$^s$;
each R$^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;
each R' is independently —R, —C(O)R, —C(O)OR, or —S(O)$_2$R;
each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

520. The compound of any one of embodiments 512-519, wherein R$^{4s}$ is —H.

521. The compound of any one of embodiments 512-519, wherein

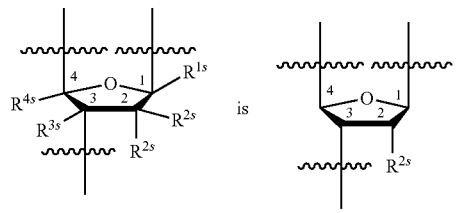

522. A compound having the structure of formula V-e:

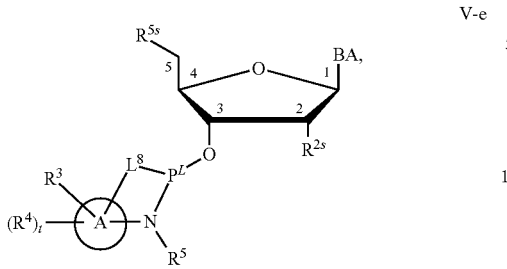

or a salt thereof, wherein:
P$^L$ is P(=W), P, or P→B(R')$_3$;
Ring A is an optionally substituted 3-20 membered monocyclic, bicyclic or polycyclic ring having 0-10 heteroatoms;
each of R$^1$, R$^2$, R$^3$, R$^4$, and R$^5$ is independently —H, -L$^s$-R, halogen, —CN, —NO$_2$, -L$^s$-Si(R)$_3$, —OR, —SR, or —N(R)$_2$;
each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C=C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;
t is 0-20;
L$^8$ is -L-O—, -L-C(R$^1$)(R$^2$)—O—, or -L$^s$-O—;
L is a covalent bond, or optionally substituted C$_{1-6}$ alkylene, wherein one or more methylene units are optionally and independently replaced with -L'-;
L' is a covalent bond, optionally substituted bivalent C$_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;
BA is an optionally substituted group selected from C$_{3-30}$ cycloaliphatic, C$_{6-30}$ aryl, C$_{5-30}$ heteroaryl having 1-10 heteroatoms, C$_{3-30}$ heterocyclyl having 1-10 heteroatoms, a natural nucleobase moiety, and a modified nucleobase moiety;
each of R$^{2s}$ and R$^{5s}$ is independently R$^s$;
each R$^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;
each R' is independently —R, —C(O)R, —C(O)OR, or —S(O)$_2$R;
each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

523. The compound of any one of embodiments 512-522, wherein R$^{2s}$ is —H.
524. The compound of any one of embodiments 512-522, wherein R$^{2s}$ is —F.
525. The compound of any one of embodiments 512-522, wherein R$^{2s}$ is —OR.
526. The compound of any one of embodiments 512-522, wherein R$^{2s}$ is —OR, wherein R is not —H.
527. The compound of any one of embodiments 512-522, wherein R$^{2s}$ is —OR, wherein R is optionally substituted C$_{1-6}$ aliphatic.
528. The compound of any one of embodiments 512-522, wherein R$^{2s}$ is —OR, wherein R is optionally substituted C$_{1-6}$ alkyl.
529. The compound of any one of embodiments 512-522, wherein R$^{2s}$ is —OMe.
530. The compound of any one of embodiments 512-522, wherein R$^{2s}$ is -MOE.
531. The compound of any one of embodiments 512-519, wherein

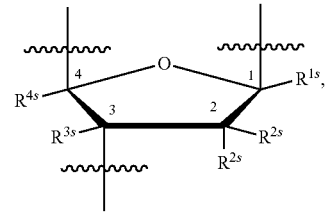

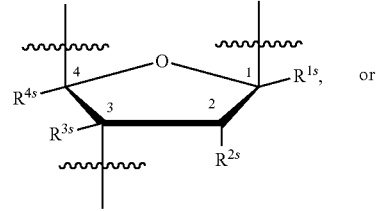

or

-continued
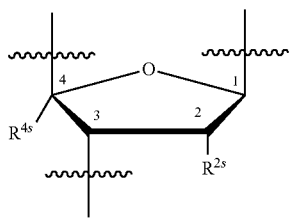
is optionally substituted
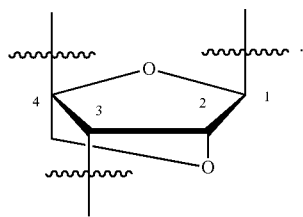 [SMILES: *C1[C@@H]2OC[C@]1(*)O[C@H]2*]
532. The compound of embodiment 531, wherein
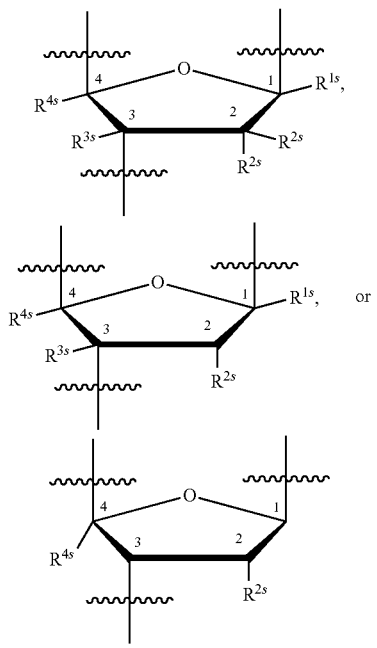
is unsubstituted.
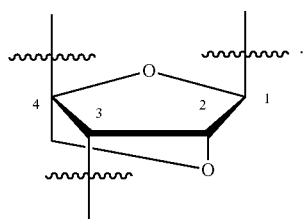 [SMILES: *C1[C@@H]2OC[C@]1(*)O[C@H]2*]
533. The compound of embodiment 531, wherein
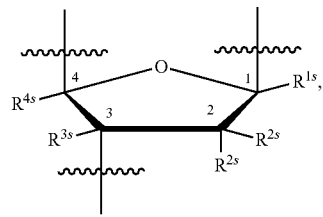
is substituted
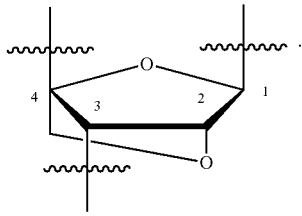 [SMILES: *C1[C@@H]2OC[C@]1(*)O[C@H]2*]
534. The compound of any one of embodiments 512-519, wherein
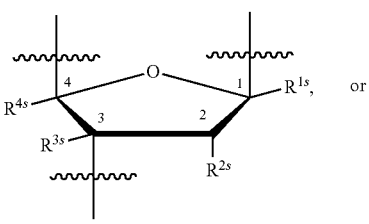

-continued

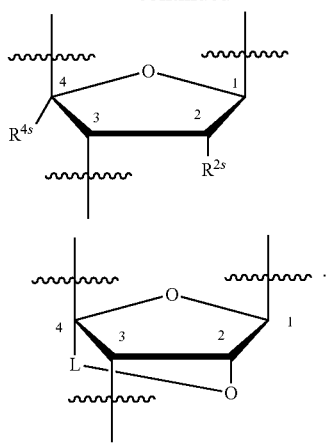

535. The compound of embodiment 534, wherein L is —CHR—.

536. The compound of embodiment 534, wherein L is —(R)—CHR—.

537. The compound of embodiment 534, wherein L is —(S)—CHR—.

538. The compound of any one of embodiments 535-537, wherein R is optionally substituted $C_{1-6}$ aliphatic.

539. The compound of any one of embodiments 535-537, wherein R is optionally substituted $C_{1-6}$ alkyl.

540. The compound of any one of embodiments 535-537, wherein R is optionally substituted $C_{1-3}$ alkyl.

541. The compound of any one of embodiments 535-537, wherein R is H.

542. The compound of any one of embodiments 535-537, wherein R is methyl.

543. The compound of any one of embodiments 535-537, wherein R is ethyl.

544. The compound of any one of embodiments 498-543, wherein

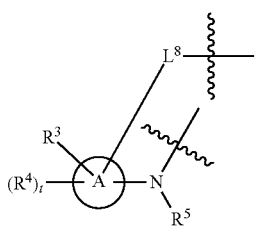

is of such a structure that

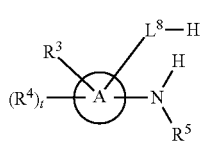

is a compound of any one of embodiments 1-301 or a salt thereof.

545. The compound of any one of embodiments 498-543, wherein

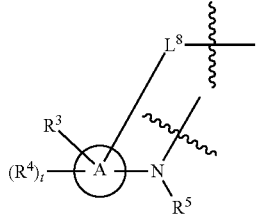

is of such a structure that

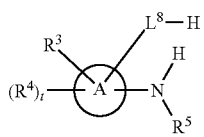

is a compound of any one of embodiments 207-256 or a salt thereof.

546. A compound having the structure of formula VI:

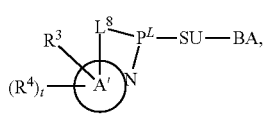

VI or a salt thereof, wherein:

$P^L$ is P(=W), P, or P→B(R')$_3$;

Ring A' is an optionally substituted 3-20 membered monocyclic, bicyclic or polycyclic ring having 1-10 heteroatoms, wherein Ring A' comprises a ring nitrogen bonded to P of $P^L$;

each of $R^1$, $R^2$, $R^3$ and $R^4$ is independently —H, -$L^s$-R, halogen, —CN, —NO$_2$, -$L^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

each t is independently 0-20;

$L^8$ is -L-O—, -L-C(R$^1$)(R$^2$)—O—, or -L$^s$-O—;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

SU is -L$^s$-O— or

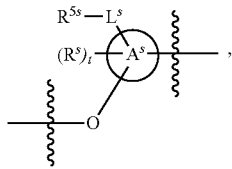

wherein SU is connected to the phosphorus atom through the oxygen atom;

$R^{5s}$ is $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

Ring $A^s$ is an optionally substituted 3-20 membered monocyclic, bicyclic or polycyclic ring having 0-10 heteroatoms;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or;

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

547. The compound of embodiment 546, wherein SU is -L$^s$-O—.

548. The compound of embodiment 547, wherein L$^s$ of SU comprises an optionally substituted group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms.

549. The compound of embodiment 548, wherein L$^s$ of SU comprises an optionally substituted 3-20 membered heterocyclyl ring having 1-10 heteroatoms.

550. The compound of embodiment 548, wherein L$^s$ of SU comprises an optionally substituted 5-6 membered heterocyclyl ring having an oxygen atom.

551. The compound of embodiment 548, wherein L$^s$ of SU comprises an optionally substituted 5-membered heterocyclyl ring having an oxygen atom.

552. The compound of embodiment 548, wherein L$^s$ of SU comprises an optionally substituted 6-membered heterocyclyl ring having an oxygen atom.

553. A compound having the structure of formula VI-a:

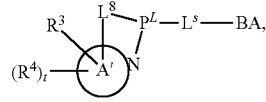

VI-a or a salt thereof, wherein:

$P^L$ is P(=W), P, or P→B(R')$_3$;

Ring A' is an optionally substituted 3-20 membered monocyclic, bicyclic or polycyclic ring having 1-10 heteroatoms, wherein Ring A' comprises a ring nitrogen bonded to P of $P^L$;

each of R$^1$, R$^2$, R$^3$ and R$^4$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

t is 0-20;

L$^8$ is -L-O—, -L-C(R$^1$)(R$^2$)—O—, or -L$^s$-O—;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

554. The compound of embodiment 553, wherein L$^s$ comprises an optionally substituted 3-20 membered heterocyclyl ring having 1-10 heteroatoms.

555. The compound of embodiment 553, wherein L$^s$ comprises an optionally substituted 5-6 membered heterocyclyl ring having an oxygen atom.

556. The compound of embodiment 553, wherein L$^s$ comprises an optionally substituted 5-membered heterocyclyl ring having an oxygen atom.

557. The compound of embodiment 553, wherein L$^s$ comprises an optionally substituted 6-membered heterocyclyl ring having an oxygen atom.

558. The compound of embodiment 546, wherein SU is

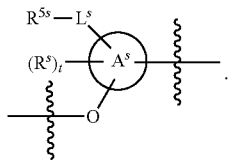

559. A compound having the structure of formula VI-b:

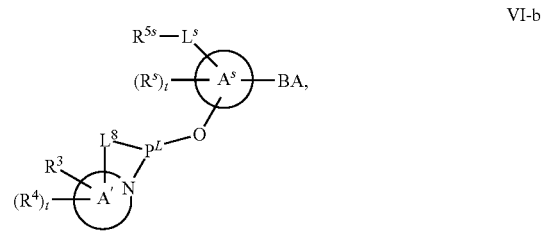

or a salt thereof, wherein:

P$^L$ is P(=W), P, or P→B(R')$_3$;

Ring A' is an optionally substituted 3-20 membered monocyclic, bicyclic or polycyclic ring having 1-10 heteroatoms, wherein Ring A' comprises a ring nitrogen bonded to P of P$^L$;

each of R$^1$, R$^2$, R$^3$ and R$^4$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

each t is independently 0-20;

L$^8$ is -L-O—, -L-C(R$^1$)(R$^2$)—O—, or -L$^s$-O—;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

$R^{5s}$ is $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

Ring $A^s$ is an optionally substituted 3-20 membered monocyclic, bicyclic or polycyclic ring having 0-10 heteroatoms;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

560. The compound of any one of embodiments 558-559, wherein Ring $A^s$ is

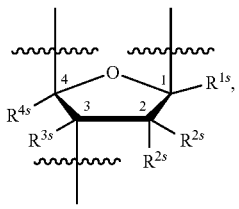

wherein each of $R^{1s}$, $R^{2s}$, $R^{3s}$, $R^{4s}$ and $R^{5s}$ is independently $R^s$.

561. The compound of embodiment 560, wherein Ring $A^s$ is

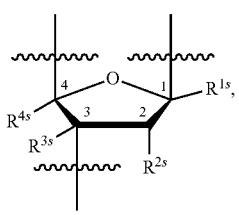

wherein each of $R^{1s}$, $R^{2s}$, $R^{3s}$, $R^{4s}$ and $R^{5s}$ is independently $R^s$.

562. A compound having the structure of formula VI-c-1:

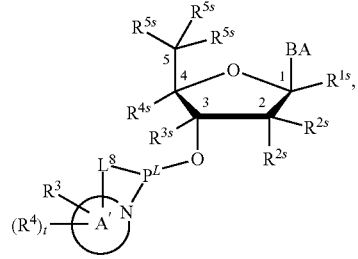

VI-c-1 or a salt thereof, wherein:

$P^L$ is P(=W), P, or P→B(R')$_3$;

Ring A' is an optionally substituted 3-20 membered monocyclic, bicyclic or polycyclic ring having 1-10 heteroatoms, wherein Ring A' comprises a ring nitrogen bonded to P of $P^L$;

each of $R^1$, $R^2$, $R^3$ and $R^4$ is independently —H, -L$^s$-R, halogen, —CN, —NO$_2$, -L$^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

t is 0-20;

$L^8$ is -L-O—, -L-C(R$^1$)(R$^2$)—O—, or -L$^s$-O—;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{1s}$, $R^{2s}$, $R^{3s}$, $R^{4s}$, and $R^{5s}$ is independently $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

563. A compound having the structure of formula VI-c-2:

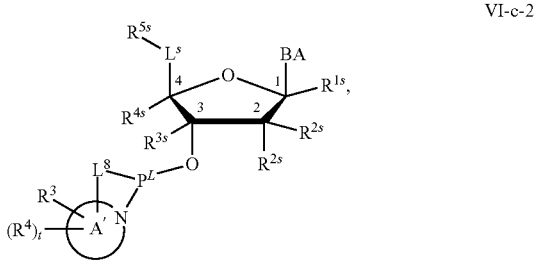

VI-c-2 or a salt thereof, wherein:

$P^L$ is P(=W), P, or P→B(R')$_3$;

Ring A' is an optionally substituted 3-20 membered monocyclic, bicyclic or polycyclic ring having 1-10 heteroatoms, wherein Ring A' comprises a ring nitrogen bonded to P of $P^L$;

each of $R^1$, $R^2$, $R^3$ and $R^4$ is independently —H, -L$^s$-R, halogen, —CN, —NO$_2$, -L$^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C=C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

t is 0-20;

$L^8$ is -L-O—, -L-C(R$^1$)(R$^2$)—O—, or -L$^s$-O—;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each of $R^{1s}$, $R^{2s}$, $R^{3s}$, $R^{4s}$, and $R^{5s}$ is independently $R^s$;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

564. The compound of any one of embodiments 560-563, wherein $R^{1s}$ is —H.

565. The compound of any one of embodiments 560-564, wherein $R^{3s}$ is —H.

566. The compound of any one of embodiments 560-565, wherein

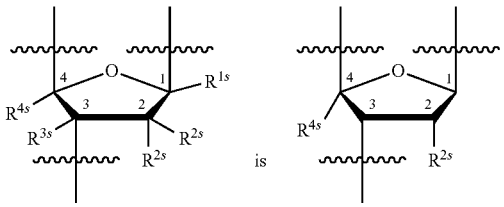

567. A compound having the structure of formula VI-d:

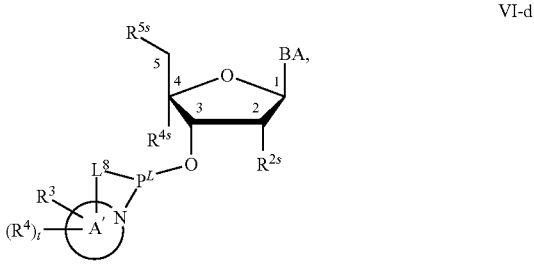

or a salt thereof, wherein:
P$^L$ is P(=W), P, or P→B(R')$_3$;
Ring A' is an optionally substituted 3-20 membered monocyclic, bicyclic or polycyclic ring having 1-10 heteroatoms, wherein Ring A' comprises a ring nitrogen bonded to P of P$^L$;
each of R$^1$, R$^2$, R$^3$ and R$^4$ is independently —H, -L$^s$-R, halogen, —CN, —NO$_2$, -L$^s$-Si(R)$_3$, —OR, —SR, or —N(R)$_2$;
each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;
t is 0-20;
L$^8$ is -L-O—, -L-C(R$^1$)(R$^2$)—O—, or -L$^s$-O—;
L is a covalent bond, or optionally substituted C$_{1-6}$ alkylene, wherein one or more methylene units are optionally and independently replaced with -L'-;
L' is a covalent bond, optionally substituted bivalent C$_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;
BA is an optionally substituted group selected from C$_{3-30}$ cycloaliphatic, C$_{6-30}$ aryl, C$_{5-30}$ heteroaryl having 1-10 heteroatoms, C$_{3-30}$ heterocyclyl having 1-10 heteroatoms, a natural nucleobase moiety, and a modified nucleobase moiety;
each of R$^{2s}$, R$^{4s}$, and R$^{5s}$ is R$^s$;
each R$^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;
each R' is independently —R, —C(O)R, —C(O)OR, or —S(O)$_2$R;
each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

568. The compound of any one of embodiments 560-567, wherein R$^{4s}$ is —H.

569. The compound of any one of embodiments 560-567, wherein

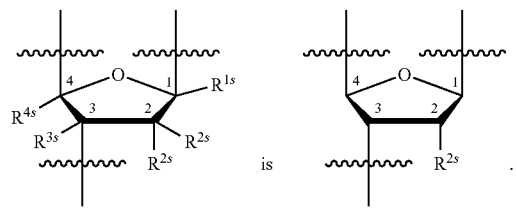

570. A compound having the structure of formula VI-e:

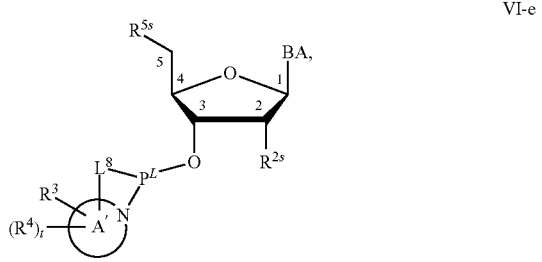

VI-e or a salt thereof, wherein:
$P^L$ is P(=W), P, or P→B(R')$_3$;
Ring A' is an optionally substituted 3-20 membered monocyclic, bicyclic or polycyclic ring having 1-10 heteroatoms, wherein Ring A' comprises a ring nitrogen bonded to P of $P^L$;
each of $R^1$, $R^2$, $R^3$ and $R^4$ is independently —H, $-L^s$-R, halogen, —CN, —NO$_2$, $-L^s$-Si(R)$_3$, —OR, —SR, or —N(R)$_2$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;
t is 0-20;
$L^8$ is $-L$-O—, $-L$-C(R$^1$)(R$^2$)—O—, or $-L^s$-O—;
L is a covalent bond, or optionally substituted $C_{1-6}$ alkylene, wherein one or more methylene units are optionally and independently replaced with -L'-;
L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

BA is an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;
each of $R^{2s}$ and $R^{5s}$ is independently $R^s$;
each $R^s$ is independently —H, halogen, —CN, —N$_3$, —NO, —NO$_2$, $-L^s$-R', $-L^s$-Si(R)$_3$, $-L^s$-OR', $-L^s$-SR', $-L^s$-N(R')$_2$, —O-$L^s$-R', —O-$L^s$-Si(R)$_3$, —O-$L^s$-OR', —O-$L^s$-SR', or —O-$L^s$-N(R')$_2$;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.
571. The compound of any one of embodiments 560-570, wherein $R^{2s}$ is —H.
572. The compound of any one of embodiments 560-570, wherein $R^{2s}$ is —F.
573. The compound of any one of embodiments 560-570, wherein $R^{2s}$ is —OR.
574. The compound of any one of embodiments 560-570, wherein $R^{2s}$ is —OR, wherein R is not —H.
575. The compound of any one of embodiments 560-570, wherein $R^{2s}$ is —OR, wherein R is optionally substituted $C_{1-6}$ aliphatic.
576. The compound of any one of embodiments 560-570, wherein $R^{2s}$ is —OR, wherein R is optionally substituted $C_{1-6}$ alkyl.
577. The compound of any one of embodiments 560-570, wherein $R^{2s}$ is —OMe.
578. The compound of any one of embodiments 560-570, wherein $R^{2s}$ is -MOE.
579. The compound of any one of embodiments 560-567, wherein

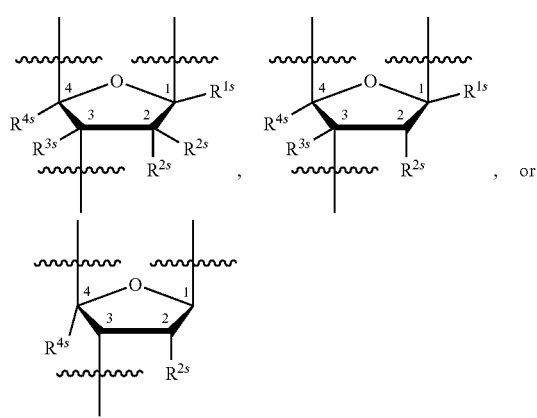

is optionally substituted

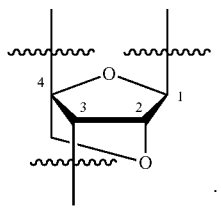 [SMILES: *[C@@H]1O[C@@]2(*)COC1[C@H]2*]

580. The compound of embodiment 579, wherein

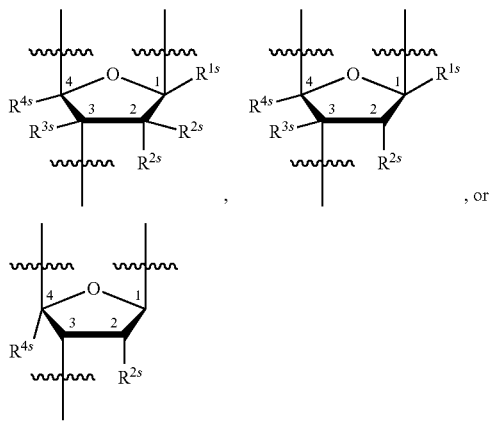

is unsubstituted

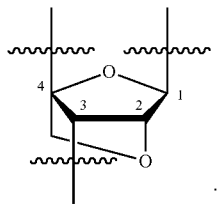 [SMILES: *[C@@H]1O[C@@]2(*)COC1[C@H]2*]

581. The compound of embodiment 579, wherein

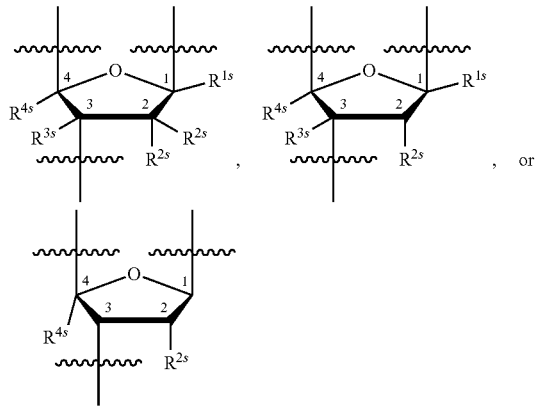

is substituted

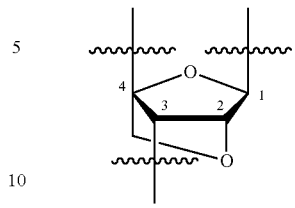

582. The compound of any one of embodiments 560-567, wherein

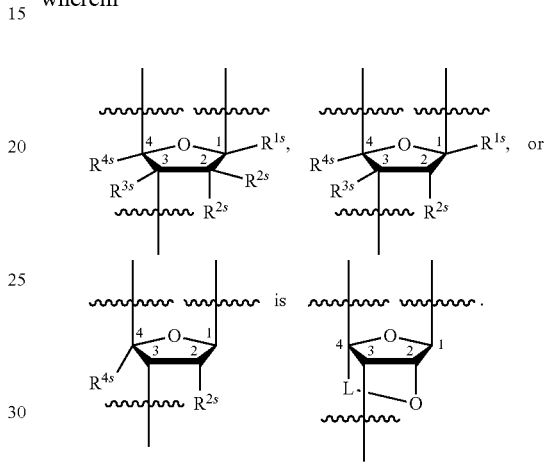

583. The compound of embodiment 582, wherein L is —CHR—.

584. The compound of embodiment 582, wherein L is —(R)—CHR—.

585. The compound of embodiment 582, wherein L is —(S)—CHR—.

586. The compound of any one of embodiments 583-585, wherein R is optionally substituted $C_{1-6}$ aliphatic.

587. The compound of any one of embodiments 583-585, wherein R is optionally substituted $C_{1-6}$ alkyl.

588. The compound of any one of embodiments 583-585, wherein R is optionally substituted $C_{1-3}$ alkyl.

589. The compound of any one of embodiments 583-585, wherein R is H.

590. The compound of any one of embodiments 583-585, wherein R is methyl.

591. The compound of any one of embodiments 583-585, wherein R is ethyl.

592. The compound of any one of embodiments 546-591, wherein

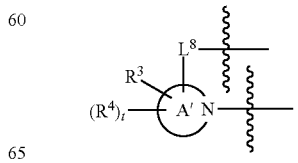

is of such a structure that

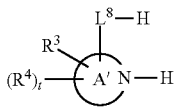

is a compound of any one of embodiments 1-301 or a salt thereof.
593. The compound of any one of embodiments 546-591, wherein

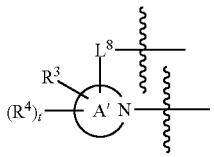

is of such a structure that

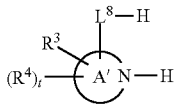

is a compound of any one of embodiments 257-301 or a salt thereof.
594. The compound of any one of embodiments 546-593, wherein $L^8$ is —O—.
595. The compound of any one of embodiments 309-594, wherein $P^L$ is P(=W).
596. The compound of embodiment 595, wherein W is O.
597. The compound of embodiment 595, wherein W is S.
598. The compound of any one of embodiments 309-594, wherein $P^L$ is P.
599. The compound of any one of embodiments 309-594, wherein $P^L$ is P→B(R')$_3$.
600. The compound of any one of embodiments 595-599, wherein P is asymmetric.
601. A compound having the structure of formula VIII:

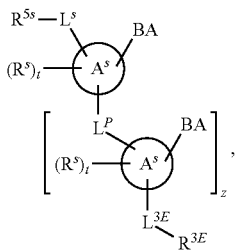

or a salt thereof, wherein:
$R^{5s}$ is $R^s$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each Ring $A^s$ is independently an optionally substituted 3-20 membered monocyclic, bicyclic or polycyclic ring having 0-10 heteroatoms;
each $R^s$ is independently —H, halogen, —CN, —N$_3$, —NO, —NO$_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;
each t is independently 0-20;
each BA is independently an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;
each $L^P$ is independently an internucleotidic linkage;
z is 1-1000;
$L^{3E}$ is -$L^s$- or -$L^s$-$L^s$-;
$R^{3E}$ is —R', -$L^s$-R', —OR', or a solid support;
each R' is independently —R, —C(O)R, —C(O)OR, or —S(O)$_2$R;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

602. A compound having the structure of formula VIII:

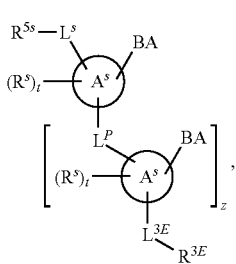

VIII or a salt thereof, wherein:

$R^{5s}$ is independently $R^s$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Ring $A^s$ is independently an optionally substituted 3-20 membered monocyclic, bicyclic or polycyclic ring having 0-10 heteroatoms;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each t is independently 0-20;

each BA is independently an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each $L^P$ is independently of formula VII:

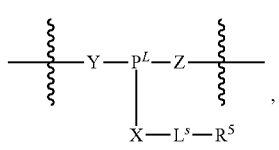

VII or a salt form thereof;

$P^L$ is P(=W), P, or P→B(R')$_3$;

W is O, S or Se;

each of $R^1$ and $R^5$ is independently —H, -L$^s$-R, halogen, —CN, —NO$_2$, -L$^s$-Si(R)$_3$, —OR, —SR, or —N(R)$_2$;

each of X, Y and Z is independently —O—, —S—, —N(-L$^s$-R$^1$)—, or L$^s$;

or for formula VII, H—X-L$^s$-R$^5$ has the structure of formula I, I-a, I-a-1, I-a-2, I-b, I-c, I-d, I-e, II, II-a, II-b, III, III-a, III-b, or a salt thereof;

z is 1-1000;

$L^{3E}$ is -L$^s$- or -L$^s$-L$^s$-;

$R^{3E}$ is —R', -L$^s$-R', —OR', or a solid support;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

603. The compound of embodiment 601, wherein one or more $L^P$ independently have the structure of formula VII:

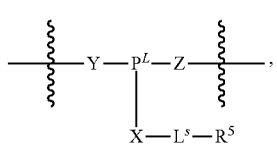

VII or a salt form thereof, wherein:

$P^L$ is P(=W), P, or P→B(R')$_3$;

W is O, S or Se;

each of $R^1$ and $R^5$ is independently —H, -L$^s$-R, halogen, —CN, —NO$_2$, -L$^s$-Si(R)$_3$, —OR, —SR, or —N(R)$_2$;

each of X, Y and Z is independently —O—, —S—, —N(-L$^s$-R$^1$)—, or L$^s$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms; or H—X-$L^s$-$R^5$ has the structure of formula I, I-a, I-a-1, I-a-2, I-b, I-c, I-d, I-e, II, II-a, II-b, III, III-a, III-b, or a salt thereof.

604. The compound of embodiment 603, wherein each $L^P$ independently has the structure of formula VII.

605. The compound of any one of embodiments 601-604, wherein a $L^P$ of formula VII has the structure of formula VII-a-1:

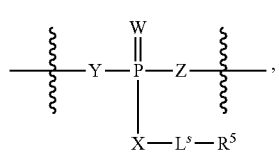

or a salt form thereof.

606. The compound of any one of embodiments 601-605, wherein a $L^P$ of formula VII has the structure of formula VII-a-2:

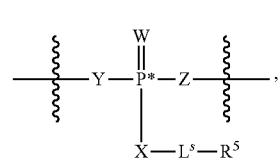

or a salt form thereof, wherein P* is an asymmetric phosphorus atom.

607. The compound of any one of embodiments 602-606, wherein a W is O.

608. The compound of any one of embodiments 602-607, wherein a W is S.

609. The compound of any one of embodiments 602-608, wherein a W is Se.

610. The compound of any one of embodiments 797-609, wherein for one or more $L^P$ independently of formula VII or salts form thereof, W is O, and for one or more $L^P$ independently of formula VII or salts form thereof, W is S.

611. The compound of any one of embodiments 601-604, wherein a $L^P$ of formula VII has the structure of formula VII-b:

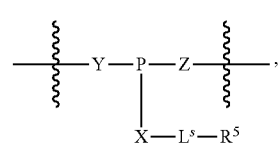

or a salt form thereof.

612. The compound of any one of embodiments 601-604 and 611, wherein a $L^P$ of formula VII has the structure of formula VII-c:

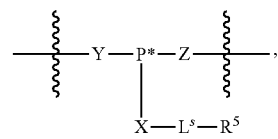

or a salt form thereof, wherein P* is an asymmetric phosphorus atom.

613. The compound of any one of embodiments 601-604, wherein a $L^P$ of formula VII has the structure of formula VII-d:

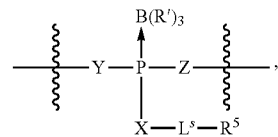

or a salt form thereof.

614. The compound of any one of embodiments 601-604 and 613, wherein a $L^P$ of formula VII has the structure of formula VII-e:

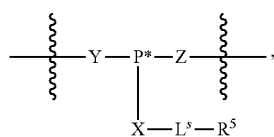

VII-e or a salt form thereof, wherein P* is an asymmetric phosphorus atom.

615. The compound of any one of embodiments 601-614, wherein Y is —O—.

616. The compound of any one of embodiments 601-615, wherein Z is $L^s$, wherein a terminal methylene unit of $L^s$ which is bonded to $P^L$ is replaced with —O—, —S—, or —N(R')—.

617. The compound of any one of embodiments 601-615, wherein Z is —O—C(R')$_2$—, wherein —O— is bonded to $P^L$ and —C(R')$_2$— is bonded to a ring atom of Ring $A^s$.

618. The compound of any one of embodiments 601-615, Z is —S—C(R')$_2$—, wherein —S— is bonded to $P^L$ and —C(R')$_2$— is bonded to a ring atom of Ring $A^s$.

619. The compound of any one of embodiments 601-615, Z is —N(R')—C(R')$_2$—, wherein —N(R')— is bonded to $P^L$ and —C(R')$_2$— is bonded to a ring atom Ring $A^s$.

620. The compound of any one of embodiments 617-619, wherein the ring atom is a carbon atom.

621. The compound of any one of embodiments 601-615, wherein Z is —O—.

622. The compound of any one of embodiments 601-621, wherein X is —O—.

623. The compound of any one of embodiments 601-622, wherein one or more —X-$L^s$-$R^5$ are each independently of such a structure that H—X-$L^s$-$R^5$ is a compound of any one of embodiments 1-308.

624. The compound of any one of embodiments 601-622, wherein each —X-$L^s$-$R^5$ is independently of such a structure that H—X-$L^s$-$R^5$ is a compound of any one of embodiments 1-308.

625. The compound of any one of embodiments 601-622, wherein one or more —X-$L^s$-$R^5$ are each independently of such a structure that H—X-$L^s$-$R^5$ is a compound of any one of embodiments 1-301.

626. The compound of any one of embodiments 601-622, wherein one or more —X-$L^s$-$R^5$ are each independently of such a structure that H—X-$L^s$-$R^5$ is a compound of any one of embodiments 302-308.

627. The compound of any one of embodiments 601-622, wherein each —X-$L^s$-$R^5$ is independently of such a structure that H—X-$L^s$-$R^5$ is a compound of any one of embodiments 1-301.

628. The compound of any one of embodiments 601-622, wherein each —X-$L^s$-$R^5$ is independently of such a structure that H—X-$L^s$-$R^5$ is a compound of any one of embodiments 302-308.

629. The compound of any one of embodiments 601-614, wherein X is —S—.

630. The compound of any one of embodiments 601-629, wherein z is 1-200.

631. The compound of any one of embodiments 601-629, wherein z is 5-200.

632. The compound of any one of embodiments 601-629, wherein z is 10-200

633. The compound of any one of embodiments 601-629, wherein z is 10-50.

634. The compound of any one of embodiments 601-633, wherein z is at least 11.

635. The compound of any one of embodiments 601-633, wherein z is at least 12.

636. The compound of any one of embodiments 601-633, wherein z is at least 13.

637. The compound of any one of embodiments 601-633, wherein z is at least 14.

638. The compound of any one of embodiments 601-633, wherein z is at least 15.

639. The compound of any one of embodiments 601-633, wherein z is at least 16.

640. The compound of any one of embodiments 601-633, wherein z is at least 17.

641. The compound of any one of embodiments 601-633, wherein z is at least 18.

642. The compound of any one of embodiments 601-633, wherein z is at least 19.

643. The compound of any one of embodiments 601-633, wherein z is at least 20.

644. The compound of any one of embodiments 601-643, wherein a Ring $A^s$ is

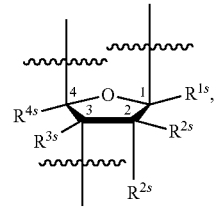

wherein each of $R^{1s}$, $R^{2s}$, $R^{3s}$, $R^{4s}$ and $R^{5s}$ is independently $R^s$.

645. The compound of any one of embodiments 601-643, wherein each Ring $A^s$ is independently

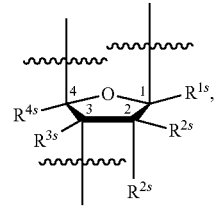

wherein each of $R^{1s}$, $R^{2s}$, $R^{3s}$, $R^{4s}$ and $R^{5s}$ is independently $R^s$.

646. The compound of any one of embodiments 644-645, wherein

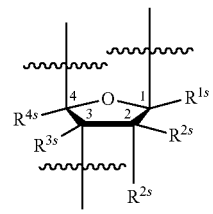 is 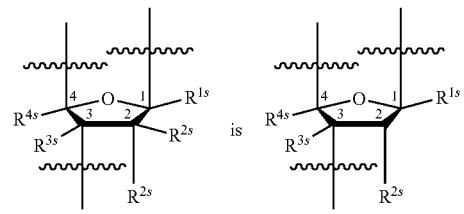.

647. The compound of any one of embodiments 644-646, wherein $R^{1s}$ is —H.

648. The compound of any one of embodiments 644-647, wherein $R^{3s}$ is —H.

649. The compound of any one of embodiments 644-646, wherein

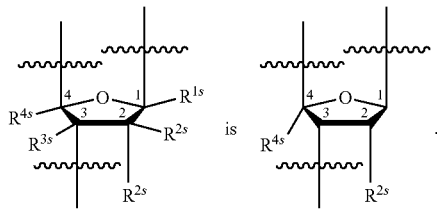 is .

650. The compound of any one of embodiments 644-649, wherein $R^{4s}$ is —H.

651. The compound of any one of embodiments 644-646, wherein

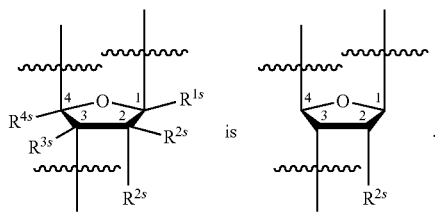 is .

652. The compound of any one of embodiments 644-651, wherein $R^{2s}$ is —H.

653. The compound of any one of embodiments 644-651, wherein $R^{2s}$ is —F.

654. The compound of any one of embodiments 644-651, wherein $R^{2s}$ is —OR.

655. The compound of any one of embodiments 644-651, wherein $R^{2s}$ is —OR, wherein R is not —H.

656. The compound of any one of embodiments 644-651, wherein $R^{2s}$ is —OR, wherein R is optionally substituted $C_{1-6}$ aliphatic.

657. The compound of any one of embodiments 644-651, wherein $R^{2s}$ is —OR, wherein R is optionally substituted $C_{1-6}$ alkyl.

658. The compound of any one of embodiments 644-651, wherein $R^{2s}$ is —OMe.

659. The compound of any one of embodiments 644-651, wherein $R^{2s}$ is -MOE.

660. The compound of any one of embodiments 644-649, wherein

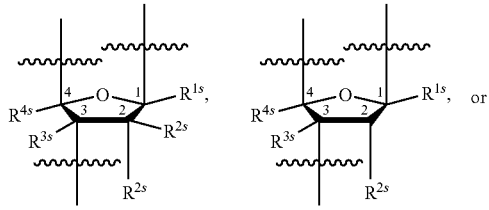

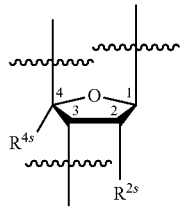

is optionally substituted

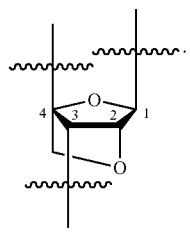 [SMILES: *C1[C@@H]2OC[C@]1(*)O[C@H]2*]

661. The compound of any one of embodiments 644-649, wherein

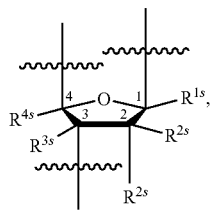, 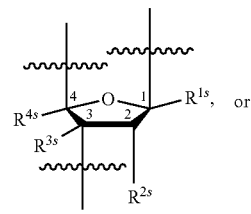

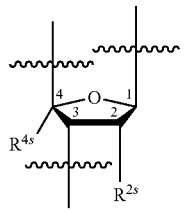

is unsubstituted

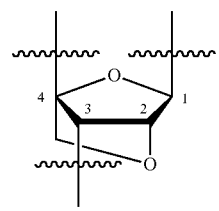

662. The compound of any one of embodiments 644-649, wherein

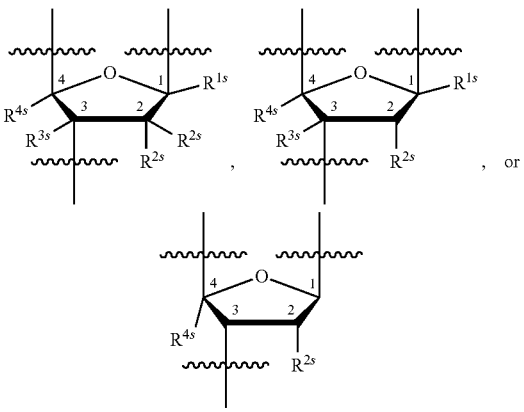

is substituted

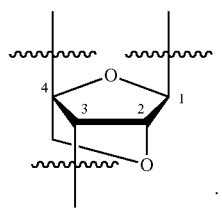 [SMILES: *[C@@H]1O[C@@]2(*)COC1[C@H]2*]

663. The compound of any one of embodiments 644-649, wherein

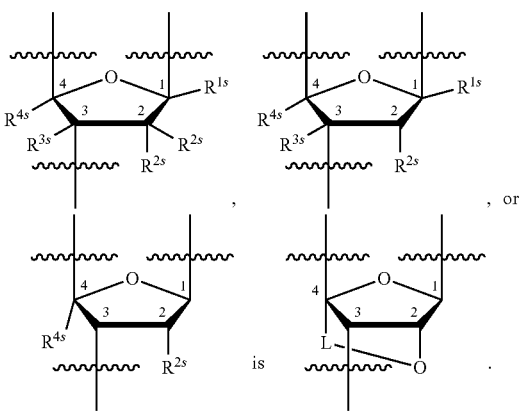

664. The compound of embodiment 663, wherein L is —CHR—.
665. The compound of embodiment 663, wherein L is —(R)—CHR—.
666. The compound of embodiment 663, wherein L is —(S)—CHR—.
667. The compound of any one of embodiments 664-666, wherein R is optionally substituted $C_{1-6}$ aliphatic.
668. The compound of any one of embodiments 664-666, wherein R is optionally substituted $C_{1-6}$ alkyl.
669. The compound of any one of embodiments 664-666, wherein R is optionally substituted $C_{1-3}$ alkyl.
670. The compound of any one of embodiments 664-666, wherein R is H.
671. The compound of any one of embodiments 664-666, wherein R is methyl.
672. The compound of any one of embodiments 664-666, wherein R is ethyl.
673. The compound of any one of embodiments 601-672, wherein $L^{3E}$ is -$L^s$-$L^s$-.
674. The compound of any one of embodiments 601-672, wherein $L^{3E}$ is -$L^s$-.
675. The compound of any one of embodiments 601-672, wherein $L^{3E}$ is —O-$L^s$-, wherein —O— is connected to Ring A, and $L^s$ is a linker as described in the present disclosure.
676. The compound of any one of embodiments 601-675, wherein $L^{3E}$ is

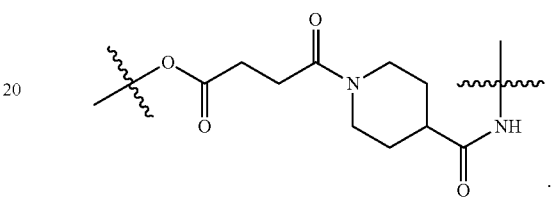

677. The compound of any one of embodiments 601-675, wherein $L^{3E}$ is

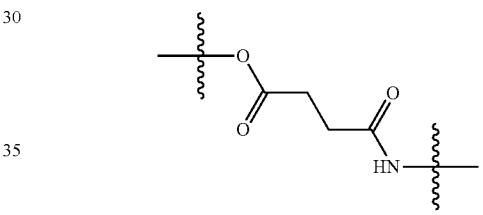

678. The compound of any one of embodiments 601-675, wherein $L^{3E}$ is

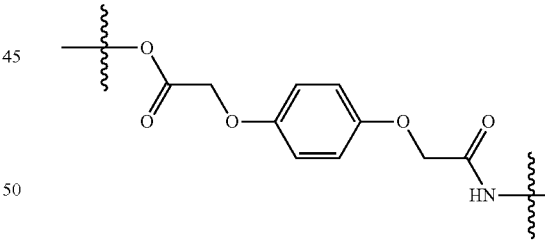

679. The compound of any one of embodiments 601-675, wherein $L^3$ is

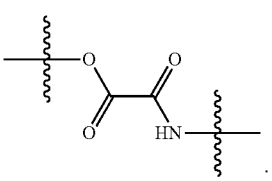 [SMILES: *NC(=O)C(=O)O*]

680. The compound of any one of embodiments 601-674, wherein $L^{3E}$ is a covalent bond.

681. The compound of any one of embodiments 601-675, wherein -L$^{3E}$-R$^{3E}$ is

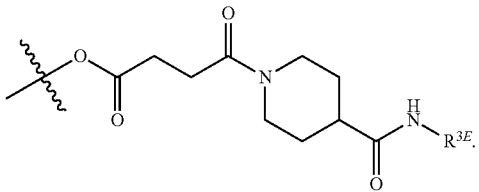

682. The compound of any one of embodiments 601-675, wherein -L$^{3E}$-R$^{3E}$ is

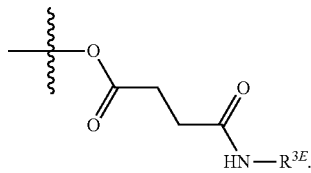

683. The compound of any one of embodiments 601-675, wherein -L$^{3E}$-R$^{3E}$ is

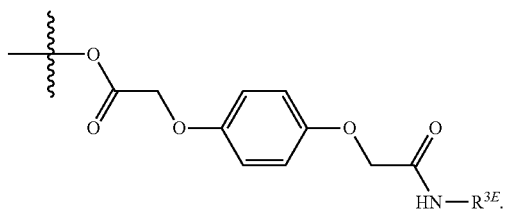

684. The compound of any one of embodiments 601-675, wherein -L$^{3E}$-R$^{3E}$ is

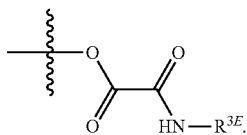

685. The compound of any one of embodiments 601-684, wherein R$^{3E}$ is —R'.
686. The compound of any one of embodiments 601-684, wherein R$^{3E}$ is -L$^s$-R'.
687. The compound of any one of embodiments 601-684, wherein R$^{3E}$ is —OR'.
688. The compound of any one of embodiments 685-687, wherein R' is hydrogen.
689. The compound of any one of embodiments 601-684, wherein R$^{3E}$ is a solid support.
690. The compound embodiment 689, wherein the solid support is a polymer.
691. The compound embodiment 689, wherein the solid support is HCP.
692. The compound embodiment 689, wherein the solid support is CPG.
693. The compound of any one of embodiments 309-692, wherein R$^{5s}$ is —H.
694. The compound of any one of embodiments 309-692, wherein R$^{5s}$ is —OH.
695. The compound of any one of embodiments 309-692, wherein R$^{5s}$ is —OR', wherein R is a hydroxyl protecting group.
696. The compound of any one of embodiments 309-692, wherein R$^{5s}$ is -ODMTr.
697. The compound of any one of embodiments 309-692, wherein the compound comprises R$^E$.
698. The compound of any one of embodiments 309-692, wherein —C(R$^{5s}$)$_3$ is R$^E$.
699. The compound of any one of embodiments 309-692, wherein or -L$^s$-R$^{5s}$ is R$^E$.
700. The compound of any one of embodiments 697-699, wherein R$^E$ is R.
701. The compound of any one of embodiments 697-699, wherein R$^E$ is —OR'.
702. The compound of any one of embodiments 697-699, wherein R$^E$ is —CH$_2$OH.
703. The compound of embodiment 699, wherein L$^s$ in the formula of R$^E$ is —CH=CH—.
704. The compound of embodiment 699, wherein L$^s$ in the formula of R$^E$ is -(E)-CH=CH—.
705. The compound of any one of embodiments 697-699, wherein R$^E$ is —CH$_2$OP(O)(OR)$_2$ or a salt form thereof.
706. The compound of any one of embodiments 697-699, wherein R$^E$ is —CH=CHP(O)(OR)$_2$ or a salt form thereof.
707. The compound of any one of embodiments 697-699, wherein R$^E$ is -(E)-CH=CHP(O)(OR)$_2$ or a salt form thereof.
708. The compound of any one of embodiments 705-707, wherein each R in the formula of R$^E$ is independently optionally substituted C$_{1-6}$ aliphatic.
709. The compound of embodiment 708, wherein each R in the formula of R$^E$ is independently optionally substituted C$_{1-6}$ alkyl.
710. The compound of embodiment 708, wherein each R in the formula of R$^E$ is methyl.
711. The compound of any one of embodiments 697-699, R$^E$ is —CH$_2$—OR'.
712. The compound of any one of embodiments 697-699, R$^E$ is —CH(R)—OR'.
713. The compound of any one of embodiments 697-699, R$^E$ is —(R)—CH(R)—OR'.
714. The compound of any one of embodiments 697-699, R$^E$ is —(S)—CH(R)—OR'.
715. The compound of any one of embodiments 711-714, wherein R' in the formula of R$^E$ is a hydroxyl protecting group.
716. The compound of any one of embodiments 711-715, wherein R' in the formula of R$^E$ is —C(O)R.
717. The compound of any one of embodiments 711-716, wherein —OR' in the formula of R$^E$ is —ODMTr.
718. The compound of any one of embodiments 711-714, wherein R' in the formula of R$^E$ is —H.
719. The compound of any one of embodiments 712-718, wherein R in the formula of R$^E$ is optionally substituted C$_{1-6}$ aliphatic.
720. The compound of embodiment 719, wherein R in the formula of R$^E$ is optionally substituted C$_{1-6}$ alkyl.
721. The compound of embodiment 719, wherein R in the formula of R$^E$ is optionally substituted C$_{1-3}$ aliphatic.
722. The compound of embodiment 719, wherein R in the formula of R$^E$ is optionally substituted C$_{1-3}$ alkyl.
723. The compound of embodiment 719, wherein R in the formula of R$^E$ is unsubstituted C$_{1-3}$ alkyl.

724. The compound of embodiment 719, wherein R in the formula of $R^E$ is unsubstituted linear $C_{1-3}$ alkyl.
725. The compound of embodiment 719, wherein R in the formula of $R^E$ is methyl.
726. The compound of embodiment 719, wherein R in the formula of $R^E$ is ethyl.
727. The compound of embodiment 719, wherein R in the formula of $R^E$ is $C_{1-3}$ haloaliphatic.
728. The compound of embodiment 719, wherein R in the formula of $R^E$ is $C_{1-3}$ haloalkyl.
729. The compound of embodiment 719, wherein R in the formula of $R^E$ is $C_1$ haloalkyl.
730. The compound of embodiment 719, wherein R in the formula of $R^E$ is $C_2$ haloaliphatic.
731. The compound of embodiment 719, wherein R in the formula of $R^E$ is $C_2$ haloalkyl.
732. The compound of embodiment 719, wherein R in the formula of $R^E$ is $C_3$ haloaliphatic.
733. The compound of embodiment 719, wherein R in the formula of $R^E$ is $C_3$ haloalkyl.
734. The compound of any one of embodiments 697-699, wherein $R^E$ is —CH(R')—OH.
735. The compound of any one of embodiments 697-699, wherein $R^E$ is —CH(R')—OP(O)(R)$_2$ or a salt form thereof.
736. The compound of any one of embodiments 697-699, wherein $R^E$ is —CH(R')—OP(O)(OR)(SR) or a salt form thereof.
737. The compound of any one of embodiments 734-736, wherein R' in the formula of $R^E$ is optionally substituted $C_{1-6}$ aliphatic.
738. The compound of embodiment 737, wherein R' in the formula of $R^E$ is optionally substituted $C_{1-6}$ alkyl.
739. The compound of embodiment 737, wherein R' in the formula of $R^E$ is optionally substituted $C_{1-3}$ aliphatic.
740. The compound of embodiment 737, wherein R' in the formula of $R^E$ is optionally substituted $C_{1-3}$ alkyl.
741. The compound of embodiment 737, wherein R' in the formula of $R^E$ is unsubstituted $C_{1-3}$ alkyl.
742. The compound of embodiment 737, wherein R' in the formula of $R^E$ is unsubstituted linear $C_{1-3}$ alkyl.
743. The compound of embodiment 737, wherein R' in the formula of $R^E$ is methyl.
744. The compound of embodiment 737, wherein R' in the formula of $R^E$ is ethyl.
745. The compound of embodiment 737, wherein R' in the formula of $R^E$ is $C_{1-3}$ haloaliphatic.
746. The compound of embodiment 737, wherein R' in the formula of $R^E$ is $C_{1-3}$ haloalkyl.
747. The compound of embodiment 737, wherein R' in the formula of $R^E$ is $C_1$ haloalkyl.
748. The compound of embodiment 737, wherein R' in the formula of $R^E$ is $C_2$ haloaliphatic.
749. The compound of embodiment 737, wherein R' in the formula of $R^E$ is $C_2$ haloalkyl.
750. The compound of embodiment 737, wherein R' in the formula of $R^E$ is $C_3$ haloaliphatic.
751. The compound of embodiment 737, wherein R' in the formula of $R^E$ is $C_3$ haloalkyl.
752. The compound of any one of embodiments 734-751, wherein —CH(R')— in the formula of $R^E$ is of R configuration.
753. The compound of any one of embodiments 734-751, wherein —CH(R')— in the formula of $R^E$ is of S configuration.
754. The compound of any one of embodiments 734-736, wherein R' in the formula of $R^E$ is —H.
755. The compound of any one of embodiments 735-754, wherein each R in the formula of $R^E$ is independently optionally substituted $C_{1-6}$ aliphatic.
756. The compound of embodiment 755, wherein each R in the formula of $R^E$ is independently optionally substituted $C_{1-6}$ alkyl.
757. The compound of embodiment 755, wherein each R in the formula of $R^E$ is methyl.
758. The compound of any one of embodiments 697-699, wherein $R^E$ is -$L^s$-P(O)(XR)$_2$ or a salt form thereof.
759. The compound of any one of embodiments 697-699, wherein $R^E$ is -$L^s$-P(O)(XR)$_2$ or a salt form thereof, wherein each X is independently —O—, —S—, or —N(R')—.
760. The compound of any one of embodiments 697-699, wherein $R^E$ is -$L^s$-P(O)(XR)$_2$ or a salt form thereof, wherein each X is independently —O—, —S—, or a covalent bond.
761. The compound of any one of embodiments 697-699, wherein $R^E$ is -$L^s$-P(O)(OR)$_2$ or a salt form thereof.
762. The compound of any one of embodiments 697-699, wherein $R^E$ is -$L^s$-P(O)(OR)(SR) or a salt form thereof.
763. The compound of any one of embodiments 697-699, wherein $R^E$ is -$L^s$-P(O)(OR)(R) or a salt form thereof.
764. The compound of any one of embodiments 758-763, wherein $L^s$ in the formula of $R^E$ is a covalent bond, or a bivalent, optionally substituted, linear or branched $C_{1-6}$ aliphatic, wherein one or more methylene units are optionally and independently replaced with —O—, —S— or —N(R')—.
765. The compound of any one of embodiments 758-764, wherein each R in the formula of $R^E$ is independently optionally substituted $C_{1-6}$ aliphatic.
766. The compound of embodiment 765, wherein each R in the formula of $R^E$ is independently optionally substituted $C_{1-6}$ alkyl.
767. The compound of embodiment 765, wherein each R in the formula of $R^E$ is methyl.
768. The compound of any one of embodiments 697-699, wherein $R^E$ is —X-$L^s$-$R^5$ or a salt form thereof.
769. The compound of embodiment 768, wherein $R^5$ in the formula of $R^E$ is optionally substituted 5-20 membered heteroaryl having 1-5 heteroatoms.
770. The compound of embodiment 768, wherein $R^5$ in the formula of $R^E$ is optionally substituted 5-membered heteroaryl having 1-4 heteroatoms.
771. The compound of embodiment 768, wherein $R^5$ in the formula of $R^E$ is optionally substituted

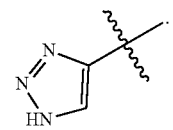

772. The compound of any one of embodiments 697-699, wherein $R^E$ is

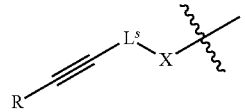

or a salt form thereof.

773. The compound of any one of embodiments 697-699, wherein $R^E$ is

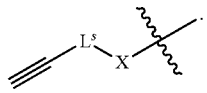

774. The compound of any one of embodiments 697-699, wherein $R^E$ is

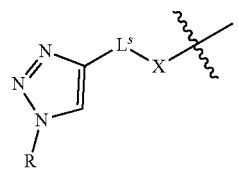

or a salt form thereof.

775. The compound of any one of embodiments 697-699, wherein $R^E$ is

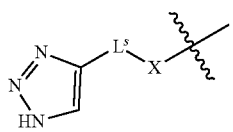

or a salt form thereof.

776. The compound of any one of embodiments 768-775, wherein X in the formula of $R^E$ is —O—.

777. The compound of any one of embodiments 768-775, wherein X in the formula of $R^E$ is —C(R)$_2$—.

778. The compound of any one of embodiments 768-775, wherein X in the formula of $R^E$ is optionally substituted —CH$_2$—.

779. The compound of any one of embodiments 768-775, wherein X in the formula of $R^E$ is —S—.

780. The compound of any one of embodiments 768-775, wherein X in the formula of $R^E$ is —N(R)—.

781. The compound of any one of embodiments 768-775, wherein X in the formula of $R^E$ is a covalent bond.

782. The compound of any one of embodiments 768-781, wherein $L^s$ in the formula of $R^E$ is optionally substituted bivalent $C_{1-10}$ aliphatic.

783. The compound of any one of embodiments 768-781, wherein $L^s$ in the formula of $R^E$ is optionally substituted $C_{1-10}$ alkylene.

784. The compound of any one of embodiments 768-781, wherein $L^s$ in the formula of $R^E$ is optionally substituted —CH$_2$—.

785. The compound of any one of embodiments 768-781, wherein $L^s$ in the formula of $R^E$ is unsubstituted —CH$_2$—.

786. The compound of any one of embodiments 768-781, wherein $L^s$ in the formula of $R^E$ is substituted —CH$_2$—.

787. The compound of any one of embodiments 309-786, wherein each BA is independently an optionally substituted group selected from $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety.

788. The compound of any one of embodiments 309-786, wherein each BA is independently an optionally substituted group selected from $C_{6-30}$ aryl, $C_{5-30}$ heteroaryl having 1-10 heteroatoms, $C_{3-30}$ heterocyclyl having 1-10 heteroatoms, and a natural nucleobase moiety.

789. The compound of any one of embodiments 309-786, wherein each BA is independently an optionally substituted group selected from $C_{6-30}$ aryl, $C_{5-30}$ heteroaryl having 1-10 heteroatoms, and a natural nucleobase moiety.

790. The compound of any one of embodiments 309-786, wherein each BA is independently optionally substituted $C_{5-30}$ heteroaryl having 1-10 heteroatoms, or optionally substituted adenine, cytosine, guanosine, thymine, or uracil, or optionally substituted tautomeric forms of adenine, cytosine, guanosine, thymine, and uracil.

791. The compound of any one of embodiments 309-786, wherein each BA is independently an optionally substituted group, which group is formed by removing a —H from

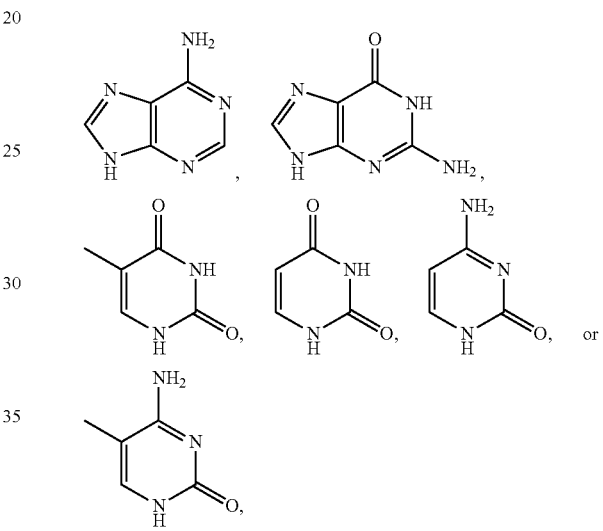

or a tautomer thereof.

792. The compound of any one of embodiments 309-786, wherein each BA is independently an optionally substituted group which group is selected from

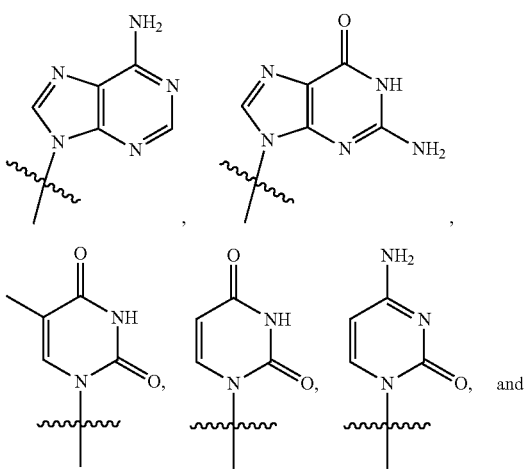

-continued

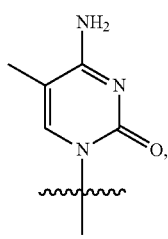

and tautomeric forms thereof.

793. The compound of any one of embodiments 309-786, wherein each BA is independently an optionally substituted group which group is selected from

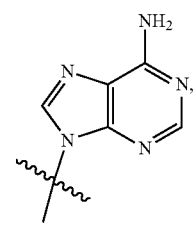 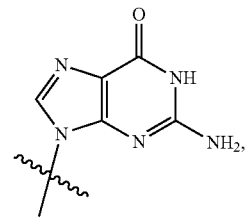

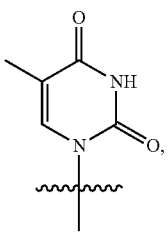 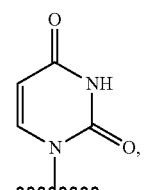 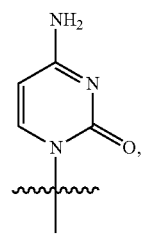 and

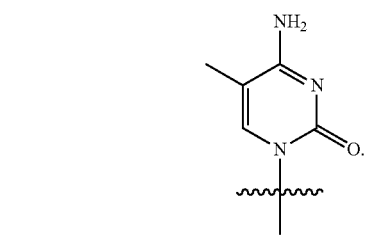

794. The compound of any one of embodiments 309-786, wherein each BA is independently

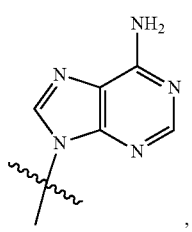 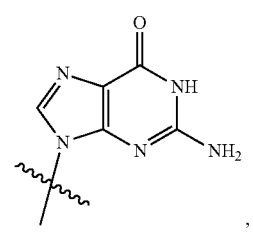,

-continued

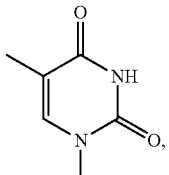 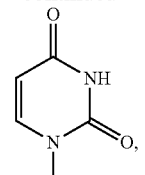 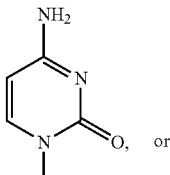 or

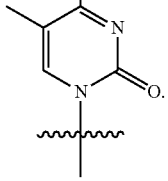

795. The compound of any one of embodiments 309-786, wherein each BA is independently

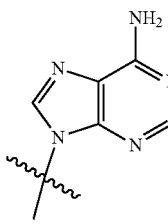 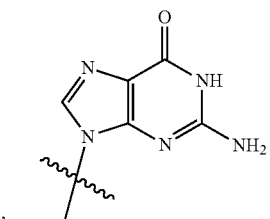,

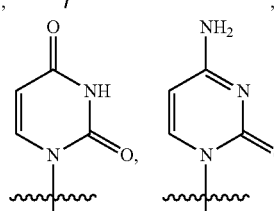 or

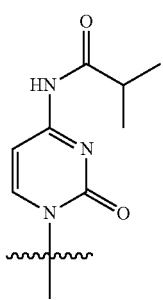 [SMILES: *n1ccc(NC(=O)C(C)C)nc1=O]

796. The compound of any one of embodiments 309-795, wherein a BA is

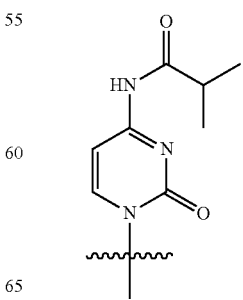

797. An oligonucleotide comprising one or more internucleotidic linkages independently of formula VII:

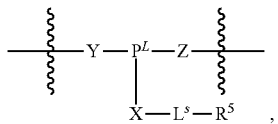

or a salt form thereof, wherein:
  $P^L$ is $P(=W)$, P, or $P \rightarrow B(R')_3$;
  W is O, S or Se;
  each of $R^1$ and $R^5$ is independently —H, $-L^s$-R, halogen, —CN, —NO$_2$, $-L^s$-Si(R)$_3$, —OR, —SR, or —N(R)$_2$;
  each of X, Y and Z is independently —O—, —S—, —N($-L^s$-$R^1$)—, or $L^s$;
  each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;
  each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
  each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
  each R' is independently —R, —C(O)R, —C(O)OR, or —S(O)$_2$R;
  each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
  two R groups are optionally and independently taken together to form a covalent bond, or:
  two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms; or
  H—X-$L^s$-$R^5$ has the structure of formula I, I-a, I-a-1, I-a-2, I-b, I-c, I-d, I-e, II, II-a, II-b, III, III-a, III-b, or a salt thereof.

798. The oligonucleotide of embodiment 797, wherein an internucleotidic linkage of formula VII has the structure of formula VII-a-1:

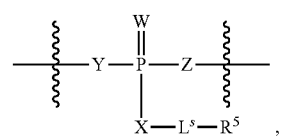

or a salt form thereof.

799. The oligonucleotide of embodiment 797 or 798, wherein an internucleotidic linkage of formula VII or VII-a-1 has the structure of formula VII-a-2:

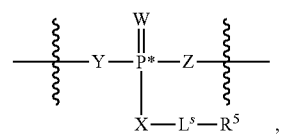

or a salt form thereof, wherein P* is an asymmetric phosphorus atom.

800. The oligonucleotide of any one of embodiments 797-799, wherein a W is O.

801. The oligonucleotide of any one of embodiments 797-800, wherein a W is S.

802. The oligonucleotide of any one of embodiments 797-801, wherein a W is Se.

803. The oligonucleotide of any one of embodiments 797-802, wherein for one or more internucleotidic linkages independently of formula VII or salts form thereof, W is O, and for one or more internucleotidic linkages independently of formula VII or salts form thereof, W is S.

804. The oligonucleotide of embodiment 797, wherein an internucleotidic linkage of formula VII has the structure of formula VII-b:

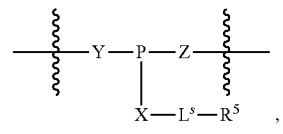

or a salt form thereof.

805. The oligonucleotide of embodiment 797 or 804, wherein an internucleotidic linkage of formula VII or VII-b has the structure of formula VII-c:

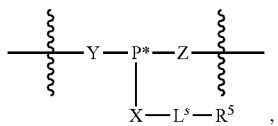

VII-c or a salt form thereof, wherein P* is an asymmetric phosphorus atom.
806. The oligonucleotide of embodiment 797, wherein an internucleotidic linkage of formula VII has the structure of formula VII-d:

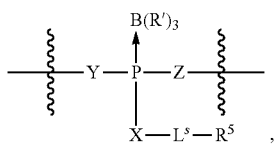

VII-d or a salt form thereof.
807. The oligonucleotide of embodiment 797 or 806, wherein an internucleotidic linkage of formula VII or VII-d has the structure of formula VII-e:

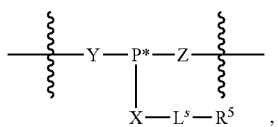

VII-e or a salt form thereof, wherein P* is an asymmetric phosphorus atom.
808. The oligonucleotide of any one of embodiments 797-807, wherein Y is —O—.
809. The oligonucleotide of any one of embodiments 797-808, wherein Z is —O—.
810. The oligonucleotide of any one of embodiments 797-809, wherein X is —O—.
811. The oligonucleotide of any one of embodiments 797-810, wherein each —X-$L^s$-$R^5$ is independently of such a structure that H—X-$L^s$-$R^5$ is a compound of any one of embodiments 1-308.
812. The oligonucleotide of any one of embodiments 797-810, wherein each —X-$L^s$-$R^5$ is independently of such a structure that H—X-$L^s$-$R^5$ is a compound of any one of embodiments 1-301.
813. The oligonucleotide of any one of embodiments 797-810, wherein each —X-$L^s$-$R^5$ is independently of such a structure that H—X-$L^s$-$R^5$ is a compound of any one of embodiments 302-308.
814. The oligonucleotide of any one of embodiments 797-809, wherein X is —S—.
815. The oligonucleotide of any one of embodiments 797-814, wherein the one or more is 1-50.
816. The oligonucleotide of any one of embodiments 797-814, wherein the one or more is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or more.
817. The oligonucleotide of any one of embodiments 797-816, wherein the one or more is 1 or more.
818. The oligonucleotide of any one of embodiments 797-816, wherein the one or more is 2 or more.
819. The oligonucleotide of any one of embodiments 797-816, wherein the one or more is 3 or more.
820. The oligonucleotide of any one of embodiments 797-816, wherein the one or more is 4 or more.
821. The oligonucleotide of any one of embodiments 797-816, wherein the one or more is 5 or more.
822. The oligonucleotide of any one of embodiments 797-816, wherein the one or more is 6 or more.
823. The oligonucleotide of any one of embodiments 797-816, wherein the one or more is 7 or more.
824. The oligonucleotide of any one of embodiments 797-816, wherein the one or more is 8 or more.
825. The oligonucleotide of any one of embodiments 797-816, wherein the one or more is 9 or more.
826. The oligonucleotide of any one of embodiments 797-816, wherein the one or more is 10 or more.
827. The oligonucleotide of any one of embodiments 797-816, wherein the one or more is 15 or more.
828. The oligonucleotide of any one of embodiments 797-816, wherein the one or more is 20 or more.
829. The oligonucleotide of any one of embodiments 797-828, wherein 0.1%-100% of internucleotidic linkages of the oligonucleotide are independently such internucleotidic linkages.
830. The oligonucleotide of embodiment 829, wherein the percentage is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%.
831. The oligonucleotide of embodiment 829, wherein the percentage is about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%.
832. The oligonucleotide of any one of embodiments 797-831, wherein each such internucleotidic linkage is independently chirally controlled.
833. The oligonucleotide of any one of embodiments 797-832, wherein the 5'-end nucleoside of the oligonucleotide comprises -$L^s$-$R^5$.
834. The oligonucleotide of any one of embodiments 797-832, wherein the 5'-end nucleoside of the oligonucleotide comprises —C($R^{5s}$)$_3$.
835. The oligonucleotide of any one of embodiments 797-834, wherein the oligonucleotide comprises $R^E$.
836. The oligonucleotide of any one of embodiments 797-834, wherein the 5'-end nucleoside of the oligonucleotide comprises $R^E$.
837. The oligonucleotide of embodiment 836, wherein $R^E$ replaces —CH$_2$OH of a natural nucleoside.
838. the 5'-end nucleoside of the oligonucleotide comprises $R^E$.
839. The oligonucleotide of embodiment 833, wherein $R^E$ is -$L^s$-R s.
840. The oligonucleotide of embodiment 834, wherein $R^E$ is —C($R^{5s}$)$_3$.
841. The oligonucleotide of any one of embodiments 835-840, wherein $R^E$ is R.
842. The oligonucleotide of any one of embodiments 835-840, wherein $R^E$ is —OR'.
843. The oligonucleotide of any one of embodiments 835-840, wherein $R^E$ is —CH$_2$OH.
844. The oligonucleotide of embodiment 839, wherein $L^s$ in the formula of $R^E$ is —CH=CH—.
845. The oligonucleotide of embodiment 839, wherein $L^s$ in the formula of $R^E$ is -(E)-CH=CH—.

846. The oligonucleotide of any one of embodiments 835-840, wherein $R^E$ is —CH$_2$OP(O)(OR)$_2$ or a salt form thereof.
847. The oligonucleotide of any one of embodiments 835-840, wherein $R^E$ is —CH=CHP(O)(OR)$_2$ or a salt form thereof.
848. The oligonucleotide of any one of embodiments 835-840, wherein $R^E$ is -(E)-CH=CHP(O)(OR)$_2$ or a salt form thereof.
849. The oligonucleotide of any one of embodiments 846-848, wherein each R in the formula of $R^E$ is independently optionally substituted $C_{1-6}$ aliphatic.
850. The oligonucleotide of embodiment 849, wherein each R in the formula of $R^E$ is independently optionally substituted $C_{1-6}$ alkyl.
851. The oligonucleotide of embodiment 849, wherein each R in the formula of $R^E$ is methyl.
852. The oligonucleotide of any one of embodiments 835-840, $R^E$ is —CH$_2$—OR'.
853. The oligonucleotide of any one of embodiments 835-840, $R^E$ is —CH(R)—OR'.
854. The oligonucleotide of any one of embodiments 835-840, $R^E$ is —(R)—CH(R)—OR'.
855. The oligonucleotide of any one of embodiments 835-840, $R^E$ is —(S)—CH(R)—OR'.
856. The oligonucleotide of any one of embodiments 852-855, wherein R' in the formula of $R^E$ is a hydroxyl protecting group.
857. The oligonucleotide of any one of embodiments 852-856, wherein R' in the formula of $R^E$ is —C(O)R.
858. The oligonucleotide of any one of embodiments 852-857, wherein —OR' in the formula of $R^E$ is —ODMTr.
859. The oligonucleotide of any one of embodiments 846-848, wherein R' in the formula of $R^E$ is —H.
860. The oligonucleotide of any one of embodiments 853-859, wherein R in the formula of $R^E$ is optionally substituted $C_{1-6}$ aliphatic.
861. The oligonucleotide of embodiment 860, wherein R in the formula of $R^E$ is optionally substituted $C_{1-6}$ alkyl.
862. The oligonucleotide of embodiment 860, wherein R in the formula of $R^E$ is optionally substituted $C_{1-3}$ aliphatic.
863. The oligonucleotide of embodiment 860, wherein R in the formula of $R^E$ is optionally substituted $C_{1-3}$ alkyl.
864. The oligonucleotide of embodiment 860, wherein R in the formula of $R^E$ is unsubstituted $C_{1-3}$ alkyl.
865. The oligonucleotide of embodiment 860, wherein R in the formula of $R^E$ is unsubstituted linear $C_{1-3}$ alkyl.
866. The oligonucleotide of embodiment 860, wherein R in the formula of $R^E$ is methyl.
867. The oligonucleotide of embodiment 860, wherein R in the formula of $R^E$ is ethyl.
868. The oligonucleotide of embodiment 860, wherein R in the formula of $R^E$ is $C_{1-3}$ haloaliphatic.
869. The oligonucleotide of embodiment 860, wherein R in the formula of $R^E$ is $C_{1-3}$ haloalkyl.
870. The oligonucleotide of embodiment 860, wherein R in the formula of $R^E$ is $C_1$ haloalkyl.
871. The oligonucleotide of embodiment 860, wherein R in the formula of $R^E$ is $C_2$ haloaliphatic.
872. The oligonucleotide of embodiment 860, wherein R in the formula of $R^E$ is $C_2$ haloalkyl.
873. The oligonucleotide of embodiment 860, wherein R in the formula of $R^E$ is $C_3$ haloaliphatic.
874. The oligonucleotide of embodiment 860, wherein R in the formula of $R^E$ is $C_3$ haloalkyl.
875. The oligonucleotide of any one of embodiments 835-840, wherein $R^E$ is —CH(R')—OH.
876. The oligonucleotide of any one of embodiments 835-840, wherein $R^E$ is —CH(R')—OP(O)(R)$_2$ or a salt form thereof.
877. The oligonucleotide of any one of embodiments 835-840, wherein $R^E$ is —CH(R')—OP(O)(OR)(SR) or a salt form thereof.
878. The oligonucleotide of any one of embodiments 875-877, wherein R' in the formula of $R^E$ is optionally substituted $C_{1-6}$ aliphatic.
879. The oligonucleotide of embodiment 878, wherein R' in the formula of $R^E$ is optionally substituted $C_{1-6}$ alkyl.
880. The oligonucleotide of embodiment 878, wherein R' in the formula of $R^E$ is optionally substituted $C_{1-3}$ aliphatic.
881. The oligonucleotide of embodiment 878, wherein R' in the formula of $R^E$ is optionally substituted $C_{1-3}$ alkyl.
882. The oligonucleotide of embodiment 878, wherein R' in the formula of $R^E$ is unsubstituted $C_{1-3}$ alkyl.
883. The oligonucleotide of embodiment 878, wherein R' in the formula of $R^E$ is unsubstituted linear $C_{1-3}$ alkyl.
884. The oligonucleotide of embodiment 878, wherein R' in the formula of $R^E$ is methyl.
885. The oligonucleotide of embodiment 878, wherein R' in the formula of $R^E$ is ethyl.
886. The oligonucleotide of embodiment 878, wherein R' in the formula of $R^E$ is $C_{1-3}$ haloaliphatic.
887. The oligonucleotide of embodiment 878, wherein R' in the formula of $R^E$ is $C_{1-3}$ haloalkyl.
888. The oligonucleotide of embodiment 878, wherein R' in the formula of $R^E$ is $C_1$ haloalkyl.
889. The oligonucleotide of embodiment 878, wherein R' in the formula of $R^E$ is $C_2$ haloaliphatic.
890. The oligonucleotide of embodiment 878, wherein R' in the formula of $R^E$ is $C_2$ haloalkyl.
891. The oligonucleotide of embodiment 878, wherein R' in the formula of $R^E$ is $C_3$ haloaliphatic.
892. The oligonucleotide of embodiment 878, wherein R' in the formula of $R^E$ is $C_3$ haloalkyl.
893. The oligonucleotide of any one of embodiments 875-892, wherein —CH(R')— in the formula of $R^E$ is of R configuration.
894. The oligonucleotide of any one of embodiments 875-892, wherein —CH(R')— in the formula of $R^E$ is of S configuration.
895. The oligonucleotide of any one of embodiments 875-877, wherein R' in the formula of $R^E$ is —H.
896. The oligonucleotide of any one of embodiments 876-895, wherein each R in the formula of $R^E$ is independently optionally substituted $C_{1-6}$ aliphatic.
897. The oligonucleotide of embodiment 896, wherein each R in the formula of $R^E$ is independently optionally substituted $C_{1-6}$ alkyl.
898. The oligonucleotide of embodiment 896, wherein each R in the formula of $R^E$ is methyl.
899. The oligonucleotide of any one of embodiments 835-840, wherein $R^E$ is -L$^s$-P(O)(XR)$_2$ or a salt form thereof.
900. The oligonucleotide of any one of embodiments 835-840, wherein $R^E$ is -L$^s$-P(O)(XR)$_2$ or a salt form thereof, wherein each X is independently —O—, —S—, or —N(R')—.
901. The oligonucleotide of any one of embodiments 835-840, wherein $R^E$ is -L$^s$-P(O)(XR)$_2$ or a salt form thereof, wherein each X is independently —O—, —S—, or a covalent bond.
902. The oligonucleotide of any one of embodiments 835-840, wherein $R^E$ is -L$^s$-P(O)(OR)$_2$ or a salt form thereof.
903. The oligonucleotide of any one of embodiments 835-840, wherein $R^E$ is -L$^s$-P(O)(OR)(SR) or a salt form thereof.

904. The oligonucleotide of any one of embodiments 835-840, wherein $R^E$ is -$L^s$-P(O)(OR)(R) or a salt form thereof.
905. The oligonucleotide of any one of embodiments 899-904, wherein $L^s$ in the formula of $R^E$ is a covalent bond, or a bivalent, optionally substituted, linear or branched $C_{1-6}$ aliphatic, wherein one or more methylene units are optionally and independently replaced with —O—, —S— or —N(R')—.
906. The oligonucleotide of any one of embodiments 899-905, wherein each R in the formula of $R^E$ is independently optionally substituted $C_{1-6}$ aliphatic.
907. The oligonucleotide of embodiment 906, wherein each R in the formula of $R^E$ is independently optionally substituted $C_{1-6}$ alkyl.
908. The oligonucleotide of embodiment 906, wherein each R in the formula of $R^E$ is methyl.
909. The oligonucleotide of any one of embodiments 835-840, wherein $R^E$ is —X-$L^s$-$R^5$ or a salt form thereof.
910. The oligonucleotide of embodiment 909, wherein $R^s$ in the formula of $R^E$ is optionally substituted 5-20 membered heteroaryl having 1-5 heteroatoms.
911. The oligonucleotide of embodiment 909, wherein $R^s$ in the formula of $R^E$ is optionally substituted 5-membered heteroaryl having 1-4 heteroatoms.
912. The oligonucleotide of embodiment 909, wherein $R^s$ in the formula of $R^E$ is optionally substituted

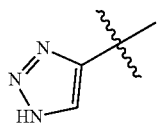

913. The oligonucleotide of any one of embodiments 835-840, wherein $R^E$ is

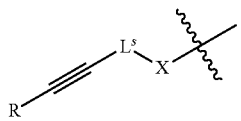

or a salt form thereof.
914. The oligonucleotide of any one of embodiments 835-840, wherein $R^E$ is

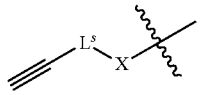

915. The oligonucleotide of any one of embodiments 835-840, wherein $R^E$ is

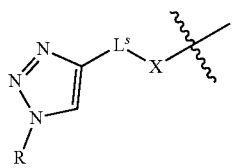

or a salt form thereof.

916. The oligonucleotide of any one of embodiments 835-840, wherein $R^E$ is

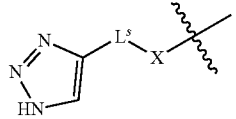

or a salt form thereof.
917. The oligonucleotide of any one of embodiments 909-916, wherein X in the formula of $R^E$ is —O—.
918. The oligonucleotide of any one of embodiments 909-916, wherein X in the formula of $R^E$ is —C(R)$_2$—.
919. The oligonucleotide of any one of embodiments 909-916, wherein X in the formula of $R^E$ is optionally substituted —CH$_2$—.
920. The oligonucleotide of any one of embodiments 909-916, wherein X in the formula of $R^E$ is —S—.
921. The oligonucleotide of any one of embodiments 909-916, wherein X in the formula of $R^E$ is —N(R)—.
922. The oligonucleotide of any one of embodiments 909-916, wherein X in the formula of $R^E$ is a covalent bond.
923. The oligonucleotide of any one of embodiments 909-922, wherein $L^s$ in the formula of $R^E$ is optionally substituted bivalent $C_{1-10}$ aliphatic.
924. The oligonucleotide of any one of embodiments 909-922, wherein $L^s$ in the formula of $R^E$ is optionally substituted $C_{1-10}$ alkylene.
925. The oligonucleotide of any one of embodiments 909-922, wherein $L^s$ in the formula of $R^E$ is optionally substituted —CH$_2$—.
926. The oligonucleotide of any one of embodiments 909-922, wherein $L^s$ in the formula of $R^E$ is unsubstituted —CH$_2$—.
927. The oligonucleotide of any one of embodiments 909-922, wherein $L^s$ in the formula of $R^E$ is substituted —CH$_2$—.
928. The oligonucleotide of any one of embodiments 797-927, wherein the oligonucleotide comprises 5-200 nucleobases.
929. The oligonucleotide of any one of embodiments 797-927, wherein the oligonucleotide comprises 5-100 nucleobases.
930. The oligonucleotide of any one of embodiments 797-927, wherein the oligonucleotide comprises 5-50 nucleobases.
931. The oligonucleotide of any one of embodiments 797-930, wherein the oligonucleotide comprises 5 or more nucleobases.
932. The oligonucleotide of any one of embodiments 797-930, wherein the oligonucleotide comprises 10 or more nucleobases.
933. The oligonucleotide of any one of embodiments 797-930, wherein the oligonucleotide comprises 15 or more nucleobases.
934. The oligonucleotide of any one of embodiments 797-930, wherein the oligonucleotide comprises 16 or more nucleobases.
935. The oligonucleotide of any one of embodiments 797-930, wherein the oligonucleotide comprises 17 or more nucleobases.
936. The oligonucleotide of any one of embodiments 797-930, wherein the oligonucleotide comprises 18 or more nucleobases.

937. The oligonucleotide of any one of embodiments 797-930, wherein the oligonucleotide comprises 19 or more nucleobases.
938. The oligonucleotide of any one of embodiments 797-930, wherein the oligonucleotide comprises 20 or more nucleobases.
939. The oligonucleotide of any one of embodiments 797-938, wherein the oligonucleotide comprises no more than 30 nucleobases.
940. The oligonucleotide of any one of embodiments 797-938, wherein the oligonucleotide comprises no more than 25 nucleobases.
941. The oligonucleotide of any one of embodiments 928-940, wherein the nucleobases are optionally substituted adenine, cytosine, guanosine, thymine, or uracil.
942. The oligonucleotide of any one of embodiments 797-941, wherein the oligonucleotide comprises a structure of 5'-wing region-core region-3'-wing region.
943. The oligonucleotide of any one of embodiments 797-941, wherein the oligonucleotide comprises a structure of 5'-wing region-core region.
944. The oligonucleotide of any one of embodiments 797-941, wherein the oligonucleotide comprises a structure of core region-3'-wing region.
945. The oligonucleotide of any one of embodiments 797-941, wherein the oligonucleotide is of a structure of 5'-wing region-core region-3'-wing region.
946. The oligonucleotide of any one of embodiments 797-941, wherein the oligonucleotide is of a structure of 5'-wing region-core region.
947. The oligonucleotide of any one of embodiments 797-941, wherein the oligonucleotide is of a structure of core region-3'-wing region.
948. The oligonucleotide of any one of embodiments 942-947, wherein: a 5'-wing region starts with a nucleoside unit at its 5'-end and ends with a nucleoside unit at its 3'-end;
a core region starts with an internucleotidic linkage that links the 3'-end nucleoside unit of a 5'-wing region and the 5'-end nucleoside of the core region if there is a 5'-wing region directly connected to the core region, or starts with a nucleoside unit at its 5'-end if there is no 5'-wing region directly connected to the core region, and ends with an internucleotidic linkage that links the 5'-end nucleoside unit of a 3'-wing region and the 3'-end nucleoside of the core region if there is a 3'-wing region directly connected to the core region, or ends with a nucleoside unit at its 3'-end if there is no 3'-wing region directly connected to the core region; and
a 3'-wing region starts with a nucleoside unit at its 5'-end and ends with a nucleoside unit at its 3'-end.
949. The oligonucleotide of any one of embodiments 942-948, wherein a 5'-wing region comprises one or more nucleobases.
950. The oligonucleotide of any one of embodiments 942-948, wherein a 5'-wing region comprises 1-20 nucleobases.
951. The oligonucleotide of any one of embodiments 942-948, wherein a 5'-wing region comprises 2 nucleobases.
952. The oligonucleotide of any one of embodiments 942-948, wherein a 5'-wing region comprises 3 nucleobases.
953. The oligonucleotide of any one of embodiments 942-948, wherein a 5'-wing region comprises 4 nucleobases.
954. The oligonucleotide of any one of embodiments 942-948, wherein a 5'-wing region comprises 5 nucleobases.
955. The oligonucleotide of any one of embodiments 942-948, wherein a 5'-wing region comprises 6 nucleobases.
956. The oligonucleotide of any one of embodiments 942-948, wherein a 5'-wing region comprises 7 nucleobases.
957. The oligonucleotide of any one of embodiments 942-948, wherein a 5'-wing region comprises 8 nucleobases.
958. The oligonucleotide of any one of embodiments 942-948, wherein a 5'-wing region comprises 9 nucleobases.
959. The oligonucleotide of any one of embodiments 942-948, wherein a 5'-wing region comprises 10 nucleobases.
960. The oligonucleotide of any one of embodiments 942-959, wherein a 5'-wing region comprises one or more chiral internucleotidic linkages.
961. The oligonucleotide of any one of embodiments 942-959, wherein a 5'-wing region comprises one and no more than one chiral internucleotidic linkage.
962. The oligonucleotide of any one of embodiments 960-961, wherein a chiral internucleotidic linkage is chirally controlled.
963. The oligonucleotide of embodiment 962, wherein a chiral linkage phosphorus of a chirally controlled internucleotidic linkage is of Sp configuration.
964. The oligonucleotide of any one of embodiments 962-963, wherein a chiral internucleotidic linkage is the first internucleotidic linkage of the 5'-wing region from the 5' to 3'.
965. The oligonucleotide of any one of embodiments 960-964, wherein a chiral internucleotidic linkage is of formula VII or a salt form thereof.
966. The oligonucleotide of any one of embodiments 960-965, wherein a chiral internucleotidic linkage is of formula VII-a-1 or a salt form thereof.
967. The oligonucleotide of any one of embodiments 960-965, wherein a chiral internucleotidic linkage is of formula VII-a-2 or a salt form thereof.
968. The oligonucleotide of any one of embodiments 966-967, wherein a W is O.
969. The oligonucleotide of any one of embodiments 966-967, wherein a W is S.
970. The oligonucleotide of any one of embodiments 960-965, wherein a chiral internucleotidic linkage is of formula VII-b or a salt form thereof.
971. The oligonucleotide of any one of embodiments 960-965, wherein a chiral internucleotidic linkage is of formula VII-c or a salt form thereof.
972. The oligonucleotide of any one of embodiments 960-965, wherein a chiral internucleotidic linkage is of formula VII-d or a salt form thereof.
973. The oligonucleotide of any one of embodiments 960-965, wherein a chiral internucleotidic linkage is of formula VII-e or a salt form thereof.
974. The oligonucleotide of any one of embodiments 960-968, wherein a chiral internucleotidic linkage is a —O—P(O)(SH)—O— internucleotidic linkage or a salt thereof.
975. The oligonucleotide of any one of embodiments 942-974, wherein a 5'-wing region comprises one or more —O—P(O)(OH)—O— internucleotidic linkages or salt forms thereof.
976. The oligonucleotide of any one of embodiments 942-974, wherein a 5'-wing region comprises 1-50 —O—P(O)(OH)—O— internucleotidic linkages or salt forms thereof.
977. The oligonucleotide of any one of embodiments 942-974, wherein a 5'-wing region comprises 1-20 —O—P(O)(OH)—O— internucleotidic linkages or salt forms thereof.
978. The oligonucleotide of any one of embodiments 942-974, wherein a 5'-wing region comprises 1-10 —O—P(O)(OH)—O— internucleotidic linkages or salt forms thereof.
979. The oligonucleotide of any one of embodiments 942-974, wherein a 5'-wing region comprises 1 —O—P(O)(OH)—O— internucleotidic linkages or salt forms thereof.

980. The oligonucleotide of any one of embodiments 942-974, wherein a 5'-wing region comprises 2 —O—P(O)(OH)—O— internucleotidic linkages or salt forms thereof.
981. The oligonucleotide of any one of embodiments 942-974, wherein a 5'-wing region comprises 3 —O—P(O)(OH)—O— internucleotidic linkages or salt forms thereof.
982. The oligonucleotide of any one of embodiments 942-974, wherein a 5'-wing region comprises 4 —O—P(O)(OH)—O— internucleotidic linkages or salt forms thereof.
983. The oligonucleotide of any one of embodiments 942-974, wherein a 5'-wing region comprises 5, 6, 7, 8, 9, or 10 —O—P(O)(OH)—O— internucleotidic linkages or salt forms thereof.
984. The oligonucleotide of any one of embodiments 975-983, wherein the —O—P(O)(OH)—O— internucleotidic linkages are consecutive.
985. The oligonucleotide of any one of embodiments 942-984, wherein one or more sugar moieties of the 5'-wing region are modified.
986. The oligonucleotide of embodiment 985, wherein each sugar moieties of the 5'-wing region is independently modified.
987. The oligonucleotide of embodiment 985, wherein each sugar moieties of the 5'-wing region is modified and comprises the same modification.
988. The oligonucleotides of any one of embodiments 985-987, wherein a modified sugar moiety comprises a 2'-modification.
989. The oligonucleotide of embodiment 988, wherein a 2'-modification is 2'-F.
990. The oligonucleotide of embodiment 988, wherein a 2'-modification is 2'-OR, wherein R is not hydrogen.
991. The oligonucleotide of embodiment 988, wherein a 2'-modification is 2'-OMe.
992. The oligonucleotide of embodiment 988, wherein a 2'-modification is 2'-MOE.
993. The oligonucleotide of embodiment 988, wherein a 2'-modification is C2-O—CH$_2$—C4, wherein —CH$_2$— is optionally substituted.
994. The oligonucleotide of embodiment 988, wherein a 2'-modification is C2-O—C(R)$_2$—C4.
995. The oligonucleotide of embodiment 988, wherein a 2'-modification is C2-O—CHR—C4.
996. The oligonucleotide of embodiment 988, wherein a 2'-modification is C2-O—(R)—CHR—C4.
997. The oligonucleotide of embodiment 988, wherein a 2'-modification is C2-O—(S)—CHR—C4.
998. The oligonucleotide of any one of embodiments 994-997, wherein each R is independently optionally substituted C$_{1-6}$ aliphatic.
999. The oligonucleotide of any one of embodiments 994-997, wherein each R is independently optionally substituted C$_{1-6}$ alkyl.
1000. The oligonucleotide of any one of embodiments 994-997, wherein R is methyl.
1001. The oligonucleotide of any one of embodiments 994-997, wherein R is ethyl.
1002. The oligonucleotide of any one of embodiments 942-1001, wherein a 3'-wing region comprises one or more nucleobases.
1003. The oligonucleotide of any one of embodiments 942-1001, wherein a 3'-wing region comprises 1-20 nucleobases.
1004. The oligonucleotide of any one of embodiments 942-1001, wherein a 3'-wing region comprises 2 nucleobases.
1005. The oligonucleotide of any one of embodiments 942-1001, wherein a 3'-wing region comprises 3 nucleobases.
1006. The oligonucleotide of any one of embodiments 942-1001, wherein a 3'-wing region comprises 4 nucleobases.
1007. The oligonucleotide of any one of embodiments 942-1001, wherein a 3'-wing region comprises 5 nucleobases.
1008. The oligonucleotide of any one of embodiments 942-1001, wherein a 3'-wing region comprises 6 nucleobases.
1009. The oligonucleotide of any one of embodiments 942-1001, wherein a 3'-wing region comprises 7 nucleobases.
1010. The oligonucleotide of any one of embodiments 942-1001, wherein a 3'-wing region comprises 8 nucleobases.
1011. The oligonucleotide of any one of embodiments 942-1001, wherein a 3'-wing region comprises 9 nucleobases.
1012. The oligonucleotide of any one of embodiments 942-1001, wherein a 3'-wing region comprises 10 nucleobases.
1013. The oligonucleotide of any one of embodiments 942-1012, wherein a 3'-wing region comprises one or more chiral internucleotidic linkages.
1014. The oligonucleotide of any one of embodiments 942-1013, wherein a 3'-wing region comprises one and no more than one chiral internucleotidic linkage.
1015. The oligonucleotide of any one of embodiments 1013-1014, wherein a chiral internucleotidic linkage is chirally controlled.
1016. The oligonucleotide of embodiment 1015, wherein a chiral linkage phosphorus of a chirally controlled internucleotidic linkage is of Sp configuration.
1017. The oligonucleotide of any one of embodiments 1013-1016, wherein a chiral internucleotidic linkage is the last internucleotidic linkage of the 3'-wing region from the 5' to 3'.
1018. The oligonucleotide of any one of embodiments 1013-1017, wherein a chiral internucleotidic linkage is of formula VII or a salt form thereof.
1019. The oligonucleotide of any one of embodiments 1013-1018, wherein a chiral internucleotidic linkage is of formula VII-a-1 or a salt form thereof.
1020. The oligonucleotide of any one of embodiments 1013-1018, wherein a chiral internucleotidic linkage is of formula VII-a-2 or a salt form thereof.
1021. The oligonucleotide of any one of embodiments 1019-1020, wherein a W is O.
1022. The oligonucleotide of any one of embodiments 1019-1020, wherein a W is S.
1023. The oligonucleotide of any one of embodiments 1013-1018, wherein a chiral internucleotidic linkage is of formula VII-b or a salt form thereof.
1024. The oligonucleotide of any one of embodiments 1013-1018, wherein a chiral internucleotidic linkage is of formula VII-c or a salt form thereof.
1025. The oligonucleotide of any one of embodiments 1013-1018, wherein a chiral internucleotidic linkage is of formula VII-d or a salt form thereof.
1026. The oligonucleotide of any one of embodiments 1013-1018, wherein a chiral internucleotidic linkage is of formula VII-e or a salt form thereof.

1027. The oligonucleotide of any one of embodiments 1013-1021, wherein a chiral internucleotidic linkage is a —O—P(O)(SH)—O— internucleotidic linkage or a salt thereof.

1028. The oligonucleotide of any one of embodiments 942-1027, wherein a 3'-wing region comprises one or more —O—P(O)(OH)—O— internucleotidic linkages or salt forms thereof.

1029. The oligonucleotide of any one of embodiments 942-1027, wherein a 3'-wing region comprises 1-50 —O—P(O)(OH)—O— internucleotidic linkages or salt forms thereof.

1030. The oligonucleotide of any one of embodiments 942-1027, wherein a 3'-wing region comprises 1-20 —O—P(O)(OH)—O— internucleotidic linkages or salt forms thereof.

1031. The oligonucleotide of any one of embodiments 942-1027, wherein a 3'-wing region comprises 1-10 —O—P(O)(OH)—O— internucleotidic linkages or salt forms thereof.

1032. The oligonucleotide of any one of embodiments 942-1027, wherein a 3'-wing region comprises 1 —O—P(O)(OH)—O— internucleotidic linkages or salt forms thereof.

1033. The oligonucleotide of any one of embodiments 942-1027, wherein a 3'-wing region comprises 2 —O—P(O)(OH)—O— internucleotidic linkages or salt forms thereof.

1034. The oligonucleotide of any one of embodiments 942-1027, wherein a 3'-wing region comprises 3 —O—P(O)(OH)—O— internucleotidic linkages or salt forms thereof.

1035. The oligonucleotide of any one of embodiments 942-1027, wherein a 3'-wing region comprises 4 —O—P(O)(OH)—O— internucleotidic linkages or salt forms thereof.

1036. The oligonucleotide of any one of embodiments 942-1027, wherein a 3'-wing region comprises 5, 6, 7, 8, 9, or 10 —O—P(O)(OH)—O— internucleotidic linkages or salt forms thereof.

1037. The oligonucleotide of any one of embodiments 1028-1036, wherein the —O—P(O)(OH)—O— internucleotidic linkages are consecutive.

1038. The oligonucleotide of any one of embodiments 942-1037, wherein one or more sugar moieties of the 3'-wing region are modified.

1039. The oligonucleotide of embodiment 1038, wherein each sugar moieties of the 3'-wing region is independently modified.

1040. The oligonucleotide of embodiment 1038, wherein each sugar moieties of the 3'-wing region is modified and comprises the same modification.

1041. The oligonucleotides of any one of embodiments 1038-1040, wherein a modified sugar moiety comprises a 2'-modification.

1042. The oligonucleotide of embodiment 1041, wherein a 2'-modification is 2'-F.

1043. The oligonucleotide of embodiment 1041, wherein a 2'-modification is 2'-OR, wherein R is not hydrogen.

1044. The oligonucleotide of embodiment 1041, wherein a 2'-modification is 2'-OMe.

1045. The oligonucleotide of embodiment 1041, wherein a 2'-modification is 2'-MOE.

1046. The oligonucleotide of embodiment 1041, wherein a 2'-modification is C2-O—CH$_2$—C4, wherein —CH$_2$— is optionally substituted.

1047. The oligonucleotide of embodiment 1041, wherein a 2'-modification is C2-O—C(R)$_2$—C4.

1048. The oligonucleotide of embodiment 1041, wherein a 2'-modification is C2-O—CHR—C4.

1049. The oligonucleotide of embodiment 1041, wherein a 2'-modification is C2-O—(R)—CHR—C4.

1050. The oligonucleotide of embodiment 1041, wherein a 2'-modification is C2-O—(S)—CHR—C4.

1051. The oligonucleotide of any one of embodiments 1047-1050, wherein each R is independently optionally substituted $C_{1-6}$ aliphatic.

1052. The oligonucleotide of any one of embodiments 1047-1050, wherein each R is independently optionally substituted $C_{1-6}$ alkyl.

1053. The oligonucleotide of any one of embodiments 1047-1050, wherein R is methyl.

1054. The oligonucleotide of any one of embodiments 1047-1050, wherein R is ethyl.

1055. The oligonucleotide of any one of embodiments 942-1054, wherein a core region comprises one or more nucleobases.

1056. The oligonucleotide of any one of embodiments 942-1054, wherein a core region comprises 1-20 nucleobases.

1057. The oligonucleotide of any one of embodiments 942-1054, wherein a core region comprises 2 nucleobases.

1058. The oligonucleotide of any one of embodiments 942-1054, wherein a core region comprises 3 nucleobases.

1059. The oligonucleotide of any one of embodiments 942-1054, wherein a core region comprises 4 nucleobases.

1060. The oligonucleotide of any one of embodiments 942-1054, wherein a core region comprises 5 nucleobases.

1061. The oligonucleotide of any one of embodiments 942-1054, wherein a core region comprises 6 nucleobases.

1062. The oligonucleotide of any one of embodiments 942-1054, wherein a core region comprises 7 nucleobases.

1063. The oligonucleotide of any one of embodiments 942-1054, wherein a core region comprises 8 nucleobases.

1064. The oligonucleotide of any one of embodiments 942-1054, wherein a core region comprises 9 nucleobases.

1065. The oligonucleotide of any one of embodiments 942-1054, wherein a core region comprises 10 nucleobases.

1066. The oligonucleotide of any one of embodiments 942-1054, wherein a core region comprises one or more chiral internucleotidic linkages.

1067. The oligonucleotide of embodiment 1066, wherein a core region comprises 2, 3, 4, 5, 6, 7, 8, 9, 10, 11, 12, 13, 14, 15, 16, 17, 18, 19, 20, 21, 22, 23, 24, or 25 chiral internucleotidic linkages.

1068. The oligonucleotide of embodiment 1066, wherein a core region comprises 5 chiral internucleotidic linkages.

1069. The oligonucleotide of any one ore embodiments 1066-1068, wherein a core region comprises 8 internucleotidic linkages.

1070. The oligonucleotide of any one ore embodiments 1066-1069, wherein a core region comprises 9 chiral internucleotidic linkages.

1071. The oligonucleotide of any one ore embodiments 1066-1070, wherein a core region comprises 10 chiral internucleotidic linkages.

1072. The oligonucleotide of any one ore embodiments 1066-1071, wherein a core region comprises 11 chiral internucleotidic linkages.

1073. The oligonucleotide of any one ore embodiments 1066-1072, wherein a core region comprises 12 chiral internucleotidic linkages.

1074. The oligonucleotide of any one ore embodiments 1066-1073, wherein a core region comprises 13 chiral internucleotidic linkages.
1075. The oligonucleotide of any one ore embodiments 1066-1074, wherein a core region comprises 14 chiral internucleotidic linkages.
1076. The oligonucleotide of any one ore embodiments 1066-1075, wherein a core region comprises 15 chiral internucleotidic linkages.
1077. The oligonucleotide of any one of embodiments 1066-1076, wherein a chiral internucleotidic linkage of a core region is chirally controlled.
1078. The oligonucleotide of any one of embodiments 1066-1077, wherein each of the chiral internucleotidic linkages of a core region is independently chirally controlled.
1079. The oligonucleotide of any one of embodiments 1066-1078, wherein a chiral linkage phosphorus of a chirally controlled internucleotidic linkage is of Sp configuration.
1080. The oligonucleotide of any one of embodiments 1066-1079, wherein a chiral linkage phosphorus of a chirally controlled internucleotidic linkage is of Rp configuration.
1081. The oligonucleotide of any one of embodiments 1066-1080, wherein no more than 1, 2, 3, 4, 5, 6, 7, 8, 9, or 10 chirally controlled internucleotidic linkages of a core region is of Rp configuration.
1082. The oligonucleotide of any one of embodiments 1066-1081, wherein one and no more than one chirally controlled internucleotidic linkage of a core region is of Rp configuration.
1083. The oligonucleotide of any one of embodiments 1066-1080, wherein no more than 1%-90% of chirally controlled internucleotidic linkages of a core region are of Rp configuration.
1084. The oligonucleotide of any one of embodiments 1066-1080, wherein no more than about 5%, 10%, 15%, 20%, 25%, 30%, 35%, 40%, 50%, 60%, 70%, 80%, 90% of chirally controlled internucleotidic linkages of a core region are of Rp configuration.
1085. The oligonucleotide of any one of embodiments 1083-1084, wherein no more than about $\frac{1}{20}$, $\frac{1}{19}$, $\frac{1}{18}$, $\frac{1}{17}$, $\frac{1}{16}$, $\frac{1}{15}$, $\frac{1}{14}$, $\frac{1}{13}$, $\frac{1}{12}$, $\frac{1}{11}$, $\frac{1}{10}$, $\frac{1}{9}$, $\frac{1}{8}$, $\frac{1}{7}$, $\frac{1}{6}$, $\frac{1}{5}$, $\frac{1}{4}$, $\frac{1}{3}$, $\frac{1}{2}$ of chirally controlled internucleotidic linkages of a core region are of Rp configuration.
1086. The oligonucleotide of any one of embodiments 1083-1085, wherein no more than about $\frac{1}{3}$ of chirally controlled internucleotidic linkages of a core region are of Rp configuration.
1087. The oligonucleotide of any one of embodiments 1083-1086, wherein no more than about $\frac{1}{5}$ of chirally controlled internucleotidic linkages of a core region are of Rp configuration.
1088. The oligonucleotide of any one of embodiments 1066-1087, wherein a chiral internucleotidic linkage is the first internucleotidic linkage of the core region from the 5' to 3'.
1089. The oligonucleotide of any one of embodiments 1066-1088, wherein a chiral internucleotidic linkage is not the first or the last internucleotidic linkage of the core region.
1090. The oligonucleotide of any one of embodiments 1066-1089, wherein a chiral internucleotidic linkage is the first internucleotidic linkage of the core region from the 5' to 3'.
1091. The oligonucleotide of any one of embodiments 1055-1090, wherein a chiral internucleotidic linkage is of formula VII or a salt form thereof.
1092. The oligonucleotide of any one of embodiments 1055-1091, wherein a chiral internucleotidic linkage is of formula VII-a-1 or a salt form thereof.
1093. The oligonucleotide of any one of embodiments 1055-1092, wherein a chiral internucleotidic linkage is of formula VII-a-2 or a salt form thereof.
1094. The oligonucleotide of any one of embodiments 1055-1093, wherein a W is O.
1095. The oligonucleotide of any one of embodiments 1055-1094, wherein a W is S.
1096. The oligonucleotide of any one of embodiments 1055-1095, wherein a chiral internucleotidic linkage is of formula VII-b or a salt form thereof.
1097. The oligonucleotide of any one of embodiments 1055-1096, wherein a chiral internucleotidic linkage is of formula VII-c or a salt form thereof.
1098. The oligonucleotide of any one of embodiments 1055-1097, wherein a chiral internucleotidic linkage is of formula VII-d or a salt form thereof.
1099. The oligonucleotide of any one of embodiments 1055-1098, wherein a chiral internucleotidic linkage is of formula VII-e or a salt form thereof.
1100. The oligonucleotide of any one of embodiments 1055-1099, wherein a chiral internucleotidic linkage is a —O—P(O)(SH)—O— internucleotidic linkage or a salt thereof.
1101. The oligonucleotide of any one of embodiments 1055-1100, wherein each internucleotidic linkage of a core region is not a —O—P(O)(OH)—O— internucleotidic linkage or a salt form thereof.
1102. The oligonucleotide of any one of embodiments 1055-1101, wherein each internucleotidic linkage of a core region is independently a chiral internucleotidic linkage.
1103. The oligonucleotide of any one of embodiments 1055-1102, wherein each internucleotidic linkage of a core region is independently a chirally controlled internucleotidic linkage.
1104. The oligonucleotide of any one of embodiments 1055-1103, wherein each internucleotidic linkage of a core region is independent an internucleotidic linkage of formula VII, VII-a-1, VII-a-2, VII-b, VII-c, VII-d, or VII-e, or a salt form thereof.
1105. The oligonucleotide of any one of embodiments 1055-1094 and 1100-1104, wherein each internucleotidic linkage of a core region is a —O—P(O)(SH)—O— internucleotidic linkage or a salt thereof.
1106. The oligonucleotide of any one of embodiments 942-1100, wherein a core region comprises one or more —O—P(O)(OH)—O— internucleotidic linkages or salt forms thereof.
1107. The oligonucleotide of embodiment 1106, wherein a core region comprises 1-50 —O—P(O)(OH)—O— internucleotidic linkages or salt forms thereof.
1108. The oligonucleotide of any one of embodiments 1106-1107, wherein a core region comprises 1-20 —O—P(O)(OH)—O— internucleotidic linkages or salt forms thereof.
1109. The oligonucleotide of any one of embodiments 1106-1107, wherein a core region comprises 1-10 —O—P(O)(OH)—O— internucleotidic linkages or salt forms thereof.
1110. The oligonucleotide of any one of embodiments 1106-1109, wherein a core region comprises 1 —O—P(O)(OH)—O— internucleotidic linkages or salt forms thereof.

1111. The oligonucleotide of any one of embodiments 1106-1110, wherein a core region comprises 2 —O—P(O)(OH)—O— internucleotidic linkages or salt forms thereof.
1112. The oligonucleotide of any one of embodiments 1106-1111, wherein a core region comprises 3 —O—P(O)(OH)—O— internucleotidic linkages or salt forms thereof.
1113. The oligonucleotide of any one of embodiments 1106-1112, wherein a core region comprises 4 —O—P(O)(OH)—O— internucleotidic linkages or salt forms thereof.
1114. The oligonucleotide of any one of embodiments 1106-1113, wherein a core region comprises 5, 6, 7, 8, 9, or 10 —O—P(O)(OH)—O— internucleotidic linkages or salt forms thereof.
1115. The oligonucleotide of any one of embodiments 1106-1114, wherein the —O—P(O)(OH)—O— internucleotidic linkages are consecutive.
1116. The oligonucleotide of any one of embodiments 942-1115, wherein one or more sugar moieties of a core region are modified.
1117. The oligonucleotide of embodiment 1116, wherein a modified sugar moiety comprises a 2'-modification.
1118. The oligonucleotide of embodiment 1117, wherein a 2'-modification is 2'-F.
1119. The oligonucleotide of embodiment 1117, wherein a 2'-modification is 2'-OR, wherein R is not hydrogen.
1120. The oligonucleotide of embodiment 1117, wherein a 2'-modification is 2'-OMe.
1121. The oligonucleotide of embodiment 1117, wherein a 2'-modification is 2'-MOE.
1122. The oligonucleotide of embodiment 1117, wherein a 2'-modification is C2-O—CH$_2$—C4, wherein —CH$_2$— is optionally substituted.
1123. The oligonucleotide of embodiment 1117, wherein a 2'-modification is C2-O—C(R)$_2$—C4.
1124. The oligonucleotide of embodiment 1117, wherein a 2'-modification is C2-O—CHR—C4.
1125. The oligonucleotide of embodiment 1117, wherein a 2'-modification is C2-O—(R)—CHR—C4.
1126. The oligonucleotide of embodiment 1117, wherein a 2'-modification is C2-O—(S)—CHR—C4.
1127. The oligonucleotide of any one of embodiments 1123-1126, wherein each R is independently optionally substituted C$_{1-6}$ aliphatic.
1128. The oligonucleotide of any one of embodiments 1123-1126, wherein each R is independently optionally substituted C$_{1-6}$ alkyl.
1129. The oligonucleotide of any one of embodiments 1123-1126, wherein R is methyl.
1130. The oligonucleotide of any one of embodiments 1123-1126, wherein R is ethyl.
1131. The oligonucleotide of any one of embodiments 1116-1130, wherein each sugar moieties of a core region is independently modified.
1132. The oligonucleotide of embodiment 1131, wherein each sugar moieties of the core region is modified and comprises the same modification.
1133. The oligonucleotide of any one of embodiments 942-1130, wherein one or more sugar moieties of the core region comprise no 2'-substitution (—CH$_2$— at 2'-position).
1134. The oligonucleotide of any one of embodiments 942-1115, wherein each sugar moiety of the core region comprises no 2'-substitution (—CH$_2$— at 2'-position).
1135. The oligonucleotide of any one of embodiments 797-1134, wherein the oligonucleotide comprises one or more chirally controlled internucleotidic linkages, which chirally controlled internucleotidic linkages have a pattern of backbone chiral centers of 5'-(Np)p(Rp)n(Sp)m-3', wherein each of p and m is independently 0-50, n is 1-10, and each Np is independently Rp or Sp.
1136. The oligonucleotide of any one of embodiments 797-1134, wherein the oligonucleotide comprises a region comprising one or more chirally controlled internucleotidic linkages, which chirally controlled internucleotidic linkages have a pattern of backbone chiral centers of 5'-(Np)p(Rp)n(Sp)m-3', wherein each of p and m is independently 0-50, n is 1-10, and each Np is independently Rp or Sp.
1137. The oligonucleotide of any one of embodiments 797-1134, wherein the oligonucleotide comprises a core region comprising one or more chirally controlled internucleotidic linkages, which chirally controlled internucleotidic linkages have a pattern of backbone chiral centers of 5'-(Np)p(Rp)n(Sp)m-3', wherein each of p and m is independently 0-50, n is 1-10, and each Np is independently Rp or Sp.
1138. The oligonucleotide of embodiment 1137, wherein the one or more chirally controlled internucleotidic linkages include all chirally controlled internucleotidic linkages of the core region.
1139. The oligonucleotide of embodiment 1136, wherein the one or more chirally controlled internucleotidic linkages include all chirally controlled internucleotidic linkages of the region.
1140. The oligonucleotide of embodiment 1135, wherein the one or more chirally controlled internucleotidic linkages include all chirally controlled internucleotidic linkages of the oligonucleotide.
1141. The oligonucleotide of any one of embodiments 1135-1137, wherein the oligonucleotide, the region, or the core region, comprises a repeating pattern of 5'-(Np)p(Rp)n(Sp)m-3'.
1142. The oligonucleotide of any one of embodiments 1135-1141, wherein the one or more chirally controlled internucleotidic linkages are consecutive.
1143. The oligonucleotide of any one of embodiments 1135-1142, wherein p is 1-50.
1144. The oligonucleotide of any one of embodiments 1135-1143, wherein p is 1, 2, 3, 4, 5, 6, 7, 8, 9, 10 or more.
1145. The oligonucleotide of any one of embodiments 1135-1144, wherein p is at least 2.
1146. The oligonucleotide of any one of embodiments 1135-1144, wherein p is at least 3.
1147. The oligonucleotide of any one of embodiments 1135-1144, wherein p is at least 4.
1148. The oligonucleotide of any one of embodiments 1135-1144, wherein p is at least 5.
1149. The oligonucleotide of any one of embodiments 1135-1144, wherein p is at least 6.
1150. The oligonucleotide of any one of embodiments 1135-1144, wherein p is at least 6.
1151. The oligonucleotide of any one of embodiments 1135-1144, wherein p is at least 8.
1152. The oligonucleotide of any one of embodiments 1135-1144, wherein p is at least 9.
1153. The oligonucleotide of any one of embodiments 1135-1144, wherein p is at least 10.
1154. The oligonucleotide of any one of embodiments 1135-1153, wherein n is 1.
1155. The oligonucleotide of any one of embodiments 1135-1153, wherein n is 2, 3, 4, 5, 6, 7, 8, 9, or 10.
1156. The oligonucleotide of any one of embodiments 1135-1155, wherein m is 1-50.
1157. The oligonucleotide of any one of embodiments 1135-1156, wherein m is 1, 2, 3, 4, 5, 6, 7, 8, 9, 10 or more.

1158. The oligonucleotide of any one of embodiments 1135-1157, wherein m is at least 2.
1159. The oligonucleotide of any one of embodiments 1135-1157, wherein m is at least 3.
1160. The oligonucleotide of any one of embodiments 1135-1157, wherein m is at least 4.
1161. The oligonucleotide of any one of embodiments 1135-1157, wherein m is at least 5.
1162. The oligonucleotide of any one of embodiments 1135-1157, wherein m is at least 6.
1163. The oligonucleotide of any one of embodiments 1135-1157, wherein m is at least 6.
1164. The oligonucleotide of any one of embodiments 1135-1157, wherein m is at least 8.
1165. The oligonucleotide of any one of embodiments 1135-1157, wherein m is at least 9.
1166. The oligonucleotide of any one of embodiments 1135-1157, wherein m is at least 10.
1167. The oligonucleotide of any one of embodiments 1135-1166, wherein a Np is Sp.
1168. The oligonucleotide of any one of embodiments 1135-1167, wherein a Np is Rp.
1169. The oligonucleotide of any one of embodiments 1135-1167, wherein each Np is Sp.
1170. The oligonucleotide of any one of embodiments 1135-1166, wherein each Np is Rp.
1171. The oligonucleotide of any one of embodiments 797-1170, wherein the oligonucleotide is a compound of any one of embodiments 601-796, or a salt thereof.
1172. The compound of any one of embodiments 601-796, wherein the compound is an oligonucleotide of any one of embodiments 797-1170, or a salt thereof.
1173. The compound or oligonucleotide of any one of embodiments 1-1172, wherein the compound or oligonucleotide has a purity of at least 50%, 60%, 70%, 80%, 85%, 90%, 91%, 92%, 93%, 94%, 95%, 96%, 97%, 98%, or 99%.
1174. The compound or oligonucleotide of any one of embodiments 1-1172, wherein the compound or oligonucleotide has a stereochemical purity of at least 60%, 70%, 80%, 85%, 90%, 91%, 92%, 93%, 94%, 95%, 96%, 97%, 98%, or 99%.
1175. The compound or oligonucleotide of any one of embodiments 1-1172, wherein the compound or oligonucleotide has a diastereomeric purity of at least 60%, 70%, 80%, 85%, 90%, 91%, 92%, 93%, 94%, 95%, 96%, 97%, 98%, or 99%.
1176. The compound or oligonucleotide of any one of embodiments 1-1172, wherein the compound or oligonucleotide has a enantiomeric purity of at least 60%, 70%, 80%, 85%, 90%, 91%, 92%, 93%, 94%, 95%, 96%, 97%, 98%, or 99%.
1177. The compound or oligonucleotide of any one of embodiments 1173-1176, wherein the percentage is at least 85%.
1178. The compound or oligonucleotide of embodiment 1177, wherein the percentage is at least 90%.
1179. The compound or oligonucleotide of embodiment 1177, wherein the percentage is at least 95%.
1180. The compound or oligonucleotide of embodiment 1177, wherein the percentage is at least 96%.
1181. The compound or oligonucleotide of embodiment 1177, wherein the percentage is at least 97%.
1182. The compound or oligonucleotide of embodiment 1177, wherein the percentage is at least 98%.
1183. The compound or oligonucleotide of embodiment 1177, wherein the percentage is at least 99%.

1184. A composition, comprising a compound or oligonucleotide of any one of the preceding embodiments.
1185. A composition, comprising a predetermined level of a compound or oligonucleotide of any one of embodiments 601-1184 or a salt thereof.
1186. An oligonucleotide composition comprising a plurality of oligonucleotides which share:
 1) a common base sequence;
 2) a common pattern of backbone linkages;
 3) common stereochemistry independently at about 1-50 chiral internucleotidic linkages ("chirally controlled internucleotidic linkages");
 which composition is chirally controlled in that level of the plurality of oligonucleotides in the composition is predetermined.
1187. An oligonucleotide composition comprising a plurality of oligonucleotides, wherein oligonucleotides of the plurality are of a particular oligonucleotide type defined by:
 1) base sequence;
 2) pattern of backbone linkages;
 3) pattern of backbone chiral centers; and
 4) pattern of backbone phosphorus modifications;
 which composition is chirally controlled in that level of the plurality of oligonucleotides in the composition is predetermined.
1188. An oligonucleotide composition comprising a plurality of oligonucleotides which share:
 1) a common base sequence;
 2) a common pattern of backbone linkages; and
 3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.
1189. The oligonucleotide composition any one of embodiments 1186-1189, wherein a plurality of oligonucleotides comprise about 5-50 chirally controlled internucleotidic linkages.
1190. The oligonucleotide composition any one of embodiments 1186-1189, wherein a plurality of oligonucleotides comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 chirally controlled internucleotidic linkages.
1191. The oligonucleotide composition any one of embodiments 1186-1190, wherein a plurality of oligonucleotides comprise at least 5 chirally controlled internucleotidic linkages.
1192. The oligonucleotide composition of embodiment 1191, wherein a plurality of oligonucleotides comprise at least 5 chirally controlled internucleotidic linkages.
1193. The oligonucleotide composition of embodiment 1191, wherein a plurality of oligonucleotides comprise at least 6 chirally controlled internucleotidic linkages.
1194. The oligonucleotide composition of embodiment 1191, wherein a plurality of oligonucleotides comprise at least 7 chirally controlled internucleotidic linkages.
1195. The oligonucleotide composition of embodiment 1191, wherein a plurality of oligonucleotides comprise at least 8 chirally controlled internucleotidic linkages.
1196. The oligonucleotide composition of embodiment 1191, wherein a plurality of oligonucleotides comprise at least 9 chirally controlled internucleotidic linkages.

1197. The oligonucleotide composition of embodiment 1191, wherein a plurality of oligonucleotides comprise at least 10 chirally controlled internucleotidic linkages.

1198. The oligonucleotide composition of any one of embodiments 1186-1197, wherein a chirally controlled oligonucleotide composition has the structure of formula VII or a salt form thereof.

1199. The oligonucleotide composition of any one of embodiments 1186-1198, wherein a chirally controlled oligonucleotide composition has the structure of formula VII-a-1 or a salt form thereof.

1200. The oligonucleotide composition of any one of embodiments 1186-1199, wherein a chirally controlled oligonucleotide composition has the structure of formula VII-a-2 or a salt form thereof.

1201. The oligonucleotide composition of any one of embodiments 1186-1200, wherein a W is O.

1202. The oligonucleotide composition of any one of embodiments 1186-1201, wherein a W is S.

1203. The oligonucleotide composition of any one of embodiments 1186-1202, wherein a chirally controlled oligonucleotide composition has the structure of formula VII-b or a salt form thereof.

1204. The oligonucleotide composition of any one of embodiments 1186-1203, wherein a chirally controlled oligonucleotide composition has the structure of formula VII-c or a salt form thereof.

1205. The oligonucleotide composition of any one of embodiments 1186-1204, wherein a chirally controlled oligonucleotide composition has the structure of formula VII-d or a salt form thereof.

1206. The oligonucleotide composition of any one of embodiments 1186-1205, wherein a chirally controlled oligonucleotide composition has the structure of formula VII-e or a salt form thereof.

1207. The oligonucleotide composition of any one of embodiments 1186-1206, wherein each chirally controlled oligonucleotide composition independently has the structure of formula VII or a salt form thereof.

1208. The oligonucleotide composition of any one of embodiments 1186-1207, wherein Y is —O—.

1209. The oligonucleotide composition of any one of embodiments 1186-1208, wherein Z is —O—.

1210. The oligonucleotide composition of any one of embodiments 1186-1209, wherein a X is —O—.

1211. The oligonucleotide composition of any one of embodiments 1186-1209, wherein each X is —O—.

1212. The oligonucleotide composition of any one of embodiments 1186-1210, wherein a X is —S—.

1213. The oligonucleotide composition of any one of embodiments 1186-1209, wherein each X is —S—.

1214. The oligonucleotide composition of any one of embodiments 1185-1213, wherein the plurality of oligonucleotides are compounds or oligonucleotides of any one of embodiments 601-1183 or salts thereof.

1215. The oligonucleotide composition of any one of embodiments 1185-1214, wherein the plurality of oligonucleotides are compounds of any one of embodiments 601-796 or salts thereof.

1216. The oligonucleotide composition of any one of embodiments 1185-1214, wherein the plurality of oligonucleotides are compounds of any one of embodiments 797-1183 or salts thereof.

1217. The oligonucleotide composition of any one of embodiments 1185-1216, wherein a predetermined level of oligonucleotides is 0.1%-100% of all oligonucleotides in a composition that possess the same constitution as that shared by a plurality of oligonucleotides.

1218. The oligonucleotide composition of any one of embodiments 1185-1217, wherein a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a composition that possess the same constitution as that shared by a plurality of oligonucleotides.

1219. The oligonucleotide composition of any one of embodiments 1185-1218, wherein all oligonucleotides that possess the same constitution as that shared by a plurality of oligonucleotides are 0.1%-100% of all oligonucleotides in the composition.

1220. The oligonucleotide composition of any one of embodiments 1185-1219, wherein a predetermined level of oligonucleotides is 0.1%-100% of all oligonucleotides in a composition that are of or comprise a common base sequence, and share the same base modifications, sugar modifications, and modified internucleotidic linkages, if any.

1221. The oligonucleotide composition of any one of embodiments 1185-1220, wherein a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a composition that are of or comprise a common base sequence, and share the same base modifications, sugar modifications, and modified internucleotidic linkages, if any.

1222. The oligonucleotide composition of any one of embodiments 1185-1221, wherein all oligonucleotides that are of or comprise a common base sequence, and share the same base modifications, sugar modifications, and modified internucleotidic linkages, if any, are 0.1%-100% of all oligonucleotides in the composition.

1223. The oligonucleotide composition of any one of embodiments 1185-1222, wherein a predetermined level of oligonucleotides is 0.1%-100% of all oligonucleotides in a composition that are of a common base sequence.

1224. The oligonucleotide composition of any one of embodiments 1185-1223, wherein a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a composition that are of a common base sequence.

1225. The oligonucleotide composition of any one of embodiments 1185-1224, wherein all oligonucleotides that are of a common base sequence are 0.1%-100% of all oligonucleotides in the composition.

1226. The oligonucleotide composition of any one of embodiments 1185-1225, wherein a predetermined level of oligonucleotides is 0.1%-100% of all oligonucleotides in a composition that are of or comprise a common base sequence.

1227. The oligonucleotide composition of any one of embodiments 1185-1226, wherein a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a composition that are of or comprise a common base sequence.

1228. The oligonucleotide composition of any one of embodiments 1185-1227, wherein all oligonucleotides that are of or comprise a common base sequence are 0.1%-100% of all oligonucleotides in the composition.

1229. The oligonucleotide composition of any one of embodiments 1185-1228, wherein a predetermined level of oligonucleotides is 0.1%-100% of all oligonucleotides in a composition.

1230. The oligonucleotide composition of any one of embodiments 1185-1229, wherein a predetermined level of oligonucleotides is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, of all oligonucleotides in a provided composition.

1231. The oligonucleotide composition of any one of embodiments 1217-1230, wherein a percent is about 1% or more.

1232. The oligonucleotide of any one of embodiments 1217-1230, wherein a percent is about 5% or more.

1233. The oligonucleotide composition of any one of embodiments 1217-1230, wherein a percent is about 10% or more.

1234. The oligonucleotide composition of any one of embodiments 1217-1230, wherein a percent is about 20% or more.

1235. The oligonucleotide composition of any one of embodiments 1217-1230, wherein a percent is about 30% or more.

1236. The oligonucleotide composition of any one of embodiments 1217-1230, wherein a percent is about 40% or more.

1237. The oligonucleotide composition of any one of embodiments 1217-1230, wherein a percent is about 50% or more.

1238. The oligonucleotide composition of any one of embodiments 1217-1230, wherein a percent is about 60% or more.

1239. The oligonucleotide composition of any one of embodiments 1217-1230, wherein a percent is about 70% or more.

1240. The oligonucleotide composition of any one of embodiments 1217-1230, wherein a percent is about 80% or more.

1241. The oligonucleotide composition of any one of embodiments 1217-1230, wherein a percent is about 90% or more.

1242. The oligonucleotide composition of any one of embodiments 1217-1230, wherein a percent is about 95% or more.

1243. The oligonucleotide composition of any one of embodiments 1217-1230, wherein a percent is about 97% or more.

1244. The oligonucleotide composition of any one of embodiments 1217-1230, wherein a percent is about 98% or more.

1245. The oligonucleotide composition of any one of embodiments 1217-1230, wherein a percent is about 99% or more.

1246. A method for stereoselective synthesis, comprising providing a compound of any one of embodiments 1-308.

1247. A method for stereoselective synthesis, comprising providing a compound of any one of embodiments 1-301.

1248. A method for stereoselective synthesis, comprising providing a compound of any one of embodiments 309-600.

1249. A method for stereoselective synthesis, comprising providing a compound of any one of embodiments 1-600.

1250. The method of any one of embodiments 1246-1249, wherein a product is an oligonucleotide.

1251. The method of any one of embodiments 1246-1249, wherein a product is an oligonucleotide comprising at least 5 nucleobases.

1252. The method of any one of embodiments 1246-1249, wherein a product is an oligonucleotide comprising at least 5 optionally substituted nucleobases each independently selected from A, T, C, G, U, and their tautomers.

1253. The method of any one of embodiments 1246-1249, wherein a product is a compound of any one of embodiments 309-600.

1254. The method of any one of embodiments 1246-1249, wherein a product is a compound of any one of embodiments 601-796.

1255. The method of any one of embodiments 1246-1249, wherein a product is an oligonucleotide of any one of embodiments 797-1183.

1256. The method of any one of embodiments 1246-1249, wherein a product is an oligonucleotide of the plurality of any oligonucleotide compositions of any one of embodiments 1186-1245.

1257. The method of any one of embodiments 1246-1249, wherein a product is formed with a yield of a percentage selected from 50%-100%.

1258. The method of any one of embodiments 1246-1257, wherein a product is formed with a stereoselectivity of a percentage selected from 60%-100%.

1259. The method of any one of embodiments 1246-1258, wherein a product is formed with a purity of a percentage selected from 60%-100%.

1260. A method for preparing an oligonucleotide, comprising one or more coupling steps, each of which independently comprises providing a compound of any one of embodiments 1-600.

1261. A method for preparing an oligonucleotide, comprising one or more coupling steps, each of which independently comprises providing a compound of any one of embodiments 1-301.

1262. A method for preparing an oligonucleotide, comprising one or more coupling steps, each of which independently comprises providing a compound of any one of embodiments 1-308.

1263. A method for preparing an oligonucleotide, comprising one or more coupling steps, each of which independently comprises providing a compound of any one of embodiments 309-600.

1264. The method of any one of embodiments 1260-1262, wherein an internucleotidic linkage formed is of formula VII, VII-a-1, VII-a-2, VII-b, VII-c, VII-d, or VII-e, or a salt form thereof.

1265. The method of any one of embodiments 1260-1262, wherein an internucleotidic linkage formed is of formula VII-b, VII-c, VII-d, or VII-e, or a salt form thereof.

1266. The method of any one of embodiments 1260-1265, further comprising a capping step.

1267. The method of any one of embodiments 1260-1266, further comprising a modifying step.

1268. The method of any one of embodiments 1260-1267, comprising a modifying step, which modifying step comprises an oxidation step converting P to P(=O).

1269. The method of any one of embodiments 1260-1268, comprising a modifying step, which modifying step comprises a sulfurization step converting P to P(=S).

1270. The method of any one of embodiments 1260-1269, comprising a modifying step, which modifying step provides an internucleotidic linkage of formula VII, VII-a-1, or VII-a-2, or a salt form thereof.

1271. The method of any one of embodiments 1260-1270, further comprising a deblocking step.

1272. The method of any one of embodiments 1260-1271, comprising repeating one or more coupling, capping, modifying, and/or deblocking steps until a desired oligonucleotide length is achieved.

1273. The method of any one of embodiments 1260-1272, further comprising removing nucleobase, sugar, and internucleotidic linkage protection groups.

1274. The method of any one of embodiments 1260-1273, further comprising removing chiral auxiliaries.

1275. The method of any one of embodiments 1260-1273, further comprising cleavage from solid support if oligonucleotide synthesis is performed on solid support.

1276. The method of any one of embodiments 1260-1275, wherein a product formed is a compound of any one of embodiments 601-796, or an oligonucleotide of any one of embodiments 797-1183.

1277. A method for preparing an oligonucleotide, comprising steps of:
  (1) coupling;
  (2) optionally capping;
  (3) optionally modifying;
  (4) optionally deblocking; and
  (5) optionally repeating (1) to (4) until the desired oligonucleotide length is achieved;
  wherein a coupling step comprises providing a compound of any one of embodiments 1-600.

1278. A method for preparing an oligonucleotide, comprising steps of:
  (1) coupling;
  (2) capping;
  (3) modifying;
  (4) deblocking; and
  (5) repeating (1) to (4) until the desired oligonucleotide length is achieved;
  wherein a coupling step comprises providing a compound of any one of embodiments 1-600.

1279. The method of any one of embodiments [00524]-1278, wherein a coupling step comprises providing a compound of any one of embodiments 1-308.

1280. The method of any one of embodiments [00524]-1278, wherein a coupling step comprises providing a compound of any one of embodiments 1-301.

1281. The method of any one of embodiments [00524]-1278, wherein a coupling step comprises providing a compound of any one of embodiments 309-600.

1282. The method of any one of embodiments 1260-1280, wherein an internucleotidic linkage formed in coupling is of formula VII, VII-a-1, VII-a-2, VII-b, VII-c, VII-d, or VII-e, or a salt form thereof.

1283. The method of any one of embodiments 1260-1280, wherein an internucleotidic linkage formed in coupling is of formula VII-b, or VII-c, or a salt form thereof.

1284. The method of any one of embodiments 1282-1283, wherein —X-$L^s$-$R^5$ is of a structure that H—X-$L^s$-$R^5$ is of a compound of any one of embodiments 1-301.

1285. The method of any one of embodiments 1260-1283, wherein an internucleotidic linkage provided after capping is of formula VII, VII-a-1, VII-a-2, VII-b, VII-c, VII-d, or VII-e, or a salt form thereof.

1286. The method of any one of embodiments 1260-1285, wherein an internucleotidic linkage provided after capping is of formula VII-b, or VII-c, or a salt form thereof.

1287. The method of any one of embodiments 1285-1286, wherein —X-$L^s$-$R^5$ is of a structure that H—X-$L^s$-$R^5$ is of a compound of any one of embodiments 302-308.

1288. The method of any one of embodiments [00524]-1287, comprising a modifying step, which modifying step comprises an oxidation step converting P to P(=O).

1289. The method of any one of embodiments [00524]-1288, comprising a modifying step, which modifying step comprises a sulfurization step converting P to P(=S).

1290. The method of any one of embodiments 1260-1269, comprising a modifying step, which modifying step provides an internucleotidic linkage of formula VII, VII-a-1, VII-a-2, VII-d, or VII-e, or a salt form thereof.

1291. The method of any one of embodiments 1260-1269, comprising a modifying step, which modifying step provides an internucleotidic linkage of formula VII-a-1, VII-a-2, VII-d, or VII-e, or a salt form thereof.

1292. The method of any one of embodiments 1260-1269, comprising a modifying step, which modifying step provides an internucleotidic linkage of formula VII-a-1, or VII-a-2, or a salt form thereof.

1293. The method of any one of embodiments 1260-1269, comprising a modifying step, which modifying step provides an internucleotidic linkage of formula VII-a-2, or a salt form thereof.

1294. The method of any one of embodiments 1290-1293, wherein —X-$L^s$-$R^5$ is of a structure that H—X-$L^s$-$R^5$ is of a compound of any one of embodiments 1-308.

1295. The method of any one of embodiments 1290-1293, wherein —X-$L^s$-$R^5$ is of a structure that H—X-$L^s$-$R^5$ is of a compound of any one of embodiments 302-308.

1296. The method of any one of embodiments 1290-1293, wherein X is —S—, and W is O in the internucleotidic linkage provided by the modifying step.

1297. The method of any one of embodiments 1260-1270, further comprising a deblocking step removing a 5'-OH protecting group.

1298. The method of embodiment 1296, wherein the deblocking step removes the 5'-OH protecting group.

1299. The method of any one of embodiments 1288-1298, comprising repeating one or more coupling, capping, modifying, and/or deblocking steps until a desired oligonucleotide length is achieved.

1300. The method of any one of embodiments 1288-1299, further comprising removing nucleobase, sugar, and internucleotidic linkage protection groups.

1301. The method of any one of embodiments 1288-1300, further comprising removing chiral auxiliaries.

1302. The method of any one of embodiments 1288-1301, further comprising cleavage from solid support if oligonucleotide synthesis is performed on solid support.

1303. The method of any one of embodiments 1288-1302, wherein a product formed is a compound of any one of embodiments 601-796, or an oligonucleotide of any one of embodiments 797-1183.

1304. The compound or oligonucleotide or method of any one of the preceding embodiments, wherein heteroatoms recited in the embodiments are independently selected from oxygen, nitrogen, sulfur, phosphorus, selenium, boron, and silicon.

1305. The compound or oligonucleotide or method of any one of the preceding embodiments, wherein heteroatoms recited in the embodiments are independently selected from oxygen, nitrogen, sulfur, phosphorus, boron, and silicon.

1306. The compound or oligonucleotide or method of any one of the preceding embodiments, wherein heteroatoms recited in the embodiments are independently selected from oxygen, nitrogen, sulfur, phosphorus, and silicon.

1307. The compound or oligonucleotide or method of any one of the preceding embodiments, wherein heteroatoms recited in the embodiments are independently selected from oxygen, nitrogen, sulfur, and silicon.

1308. The compound or oligonucleotide or method of any one of the preceding embodiments, wherein heteroatoms recited in the embodiments are independently selected from oxygen, nitrogen, sulfur, and phosphorus.

1309. The compound or oligonucleotide or method of any one of the preceding embodiments, wherein heteroatoms recited in the embodiments are independently selected from oxygen, nitrogen, and sulfur.

1310. The method of any one of embodiments 1246-1309, wherein a product is formed with a yield of a percentage selected from 50%-100%.

1311. The method of embodiment 1310, wherein a percentage is at least 50%, 55%, 60%, 65%, 70%, 75%, 80%, 85%, 90%, 91%, 92%, 93%, 94%, 95%, 96%, 97%, 98%, 99%.

1312. The method of embodiment 1310, wherein a percentage is at least 50%.

1313. The method of embodiment 1310, wherein a percentage is at least 55%.

1314. The method of embodiment 1310, wherein a percentage is at least 60%.

1315. The method of embodiment 1310, wherein a percentage is at least 65%.

1316. The method of embodiment 1310, wherein a percentage is at least 70%.

1317. The method of embodiment 1310, wherein a percentage is at least 75%.

1318. The method of embodiment 1310, wherein a percentage is at least 80%.

1319. The method of embodiment 1310, wherein a percentage is at least 85%.

1320. The method of embodiment 1310, wherein a percentage is at least 90%.

1321. The method of embodiment 1310, wherein a percentage is at least 95%.

1322. The method of any one of embodiments 1246-1321, wherein a product is formed with a stereoselectivity of a percentage selected from 60%-100%.

1323. The method of embodiment 1322, wherein a percentage is at least 60%, 65%, 70%, 75%, 80%, 85%, 90%, 91%, 92%, 93%, 94%, 95%, 96%, 97%, 98%, 99%.

1324. The method of embodiment 1322, wherein a percentage is at least 85%.

1325. The method of embodiment 1322, wherein a percentage is at least 90%.

1326. The method of embodiment 1322, wherein a percentage is at least 91%.

1327. The method of embodiment 1322, wherein a percentage is at least 92%.

1328. The method of embodiment 1322, wherein a percentage is at least 93%.

1329. The method of embodiment 1322, wherein a percentage is at least 94%.

1330. The method of embodiment 1322, wherein a percentage is at least 95%.

1331. The method of embodiment 1322, wherein a percentage is at least 96%.

1332. The method of embodiment 1322, wherein a percentage is at least 97%.

1333. The method of embodiment 1322, wherein a percentage is at least 98%.

1334. The method of embodiment 1322, wherein a percentage is at least 99%.

1335. The method of any one of embodiments 1246-1334, wherein a product is formed with a purity of a percentage selected from 60%-100%.

1336. The method of embodiment 1335, wherein a percentage is at least 50%, 55%, 60%, 65%, 70%, 75%, 80%, 85%, 90%, 91%, 92%, 93%, 94%, 95%, 96%, 97%, 98%, 99%.

1337. The method of embodiment 1335, wherein a percentage is at least 50%.

1338. The method of embodiment 1335, wherein a percentage is at least 55%.

1339. The method of embodiment 1335, wherein a percentage is at least 60%.

1340. The method of embodiment 1335, wherein a percentage is at least 65%.

1341. The method of embodiment 1335, wherein a percentage is at least 70%.

1342. The method of embodiment 1335, wherein a percentage is at least 75%.

1343. The method of embodiment 1335, wherein a percentage is at least 80%.

1344. The method of embodiment 1335, wherein a percentage is at least 85%.

1345. The method of embodiment 1335, wherein a percentage is at least 90%.

1346. The method of embodiment 1335, wherein a percentage is at least 95%.

1347. The compound or oligonucleotide or method of any one of the preceding embodiments, wherein the compound or oligonucleotide is isotope labelled.

EXEMPLIFICATION

Non-limiting examples were provided below. A person of ordinary skill in the art appreciates that other compounds and compositions, e.g., compounds of formula I, I-a, I-a-1, I-a-2, I-b, I-c, I-d, I-e, II, II-a, II-b, III, III-a, or III-b, or salts thereof, compounds of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or salts thereof, compounds of formula VIII or salts thereof, oligonucleotides comprising one or more internucleotidic linkages each independently of formula VII, VII-a-1, VII-a-2, VII-b, VII-c, VII-d, or VII-e, or a salt form thereof, compositions of provided compounds, compositions of provided oligonucleotides (including various chirally controlled compositions), etc. can be similarly prepared in accordance with the present disclosure.

Example 1. Example Deprotection Conditions

In some embodiments, the present disclosure provides a variety of conditions for use with provided compounds as chiral auxiliaries in oligonucleotide synthesis. Example deprotection conditions are described herein.

In some embodiments, AMA conditions were utilized. In some embodiments, AMA conditions were used for 2-mers (and can be utilized for other lengths, e.g., longer oligonucleotides, as described in the present disclosure). In some embodiments, example AMA conditions described below were utilized.

AMA Conditions (1 µmol scale): After synthesis, the resin was treated with AMA (conc. $NH_3$— 40% $MeNH_2$ (1:1, v/v)) (1 mL) for 45 min at 50° C. (if an oligonucleotide contains 2'F-nucleoside, 35° C. for 2 h can be beneficial and was typically used). The mixture was cooled to room temperature and the resin was removed by membrane filtration (washed with $H_2O$ for 2 mL). The filtrate was concentrated under reduced pressure until it becomes about 1 mL. The residue was diluted with 1 mL of H₂O and analyzed by RP-UPLC-MS.

In some embodiments, TBAF conditions were utilized. In some embodiments, AMA conditions were used for 5-mers (and can be utilized for other lengths, e.g., longer oligonucleotides, as described in the present disclosure). In some embodiments, example TBAF conditions described below were utilized.

TBAF Conditions (SP-linker, 1 μmol scale): After synthesis, the resin was treated with 0.1 TBAF in MeCN (1 mL) for 2 h (generally, 30 min is enough) at room temperature, washed with MeCN, dried, and add conc. NH₃ (1 mL) for 12 h at 55° C. The mixture was cooled to room temperature and the resin was removed by membrane filtration. The filtrate was concentrated under reduced pressure until it becomes about 1 mL. The residue was diluted with 1 mL of H₂O and analyzed by RP-UPLC-MS.

In some embodiments, TEA-HF conditions were utilized. In some embodiments, TEA-HF conditions were used for 5-mers (and can be utilized for other lengths, e.g., longer oligonucleotides, as described in the present disclosure). In some embodiments, example TEA-HF conditions described below were utilized.

TEA-HF Conditions (suc.-linker, 1 μmol scale): After synthesis, the resin was treated with 1 M TEA-HF in DMF-H₂O (3:1, v/v; 1 mL) for 2 h at 50° C. PS5G support is washed with MeCN, H₂O, and add AMA (conc. NH₃— 40% MeNH₂ (1:1, v/v)) (1 mL) for 45 min at 50° C. (if oligonucleotide contains 2'F-nucleoside, 35° C. for 2 h can be beneficial and was typically used). The mixture was cooled to room temperature and the resin was removed by membrane filtration (washed with H₂O for 2 mL). The filtrate was concentrated under reduced pressure until it becomes about 1 mL. The residue was diluted with 1 mL of H₂O and analyzed by RP-UPLC-MS. In some embodiments, TEA-HF provided better yields and/or purities compared to other conditions when certain chiral auxiliaries were used.

Among other things, the present disclosure provides compounds with diverse properties for use as chiral auxiliaries, and various deprotection conditions which can effectively remove certain types of chiral auxiliaries according to their properties while being compatible with the overall oligonucleotide preparation schemes, thereby providing enormous flexibility and options so that oligonucleotides can be prepared with desired yield, purity, and/or selectivity.

Example 2. Synthesis of WV-CA-002 and WV-CA-002-S

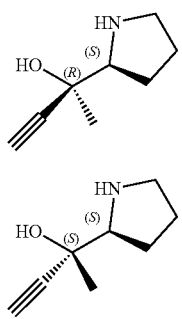

General Scheme.

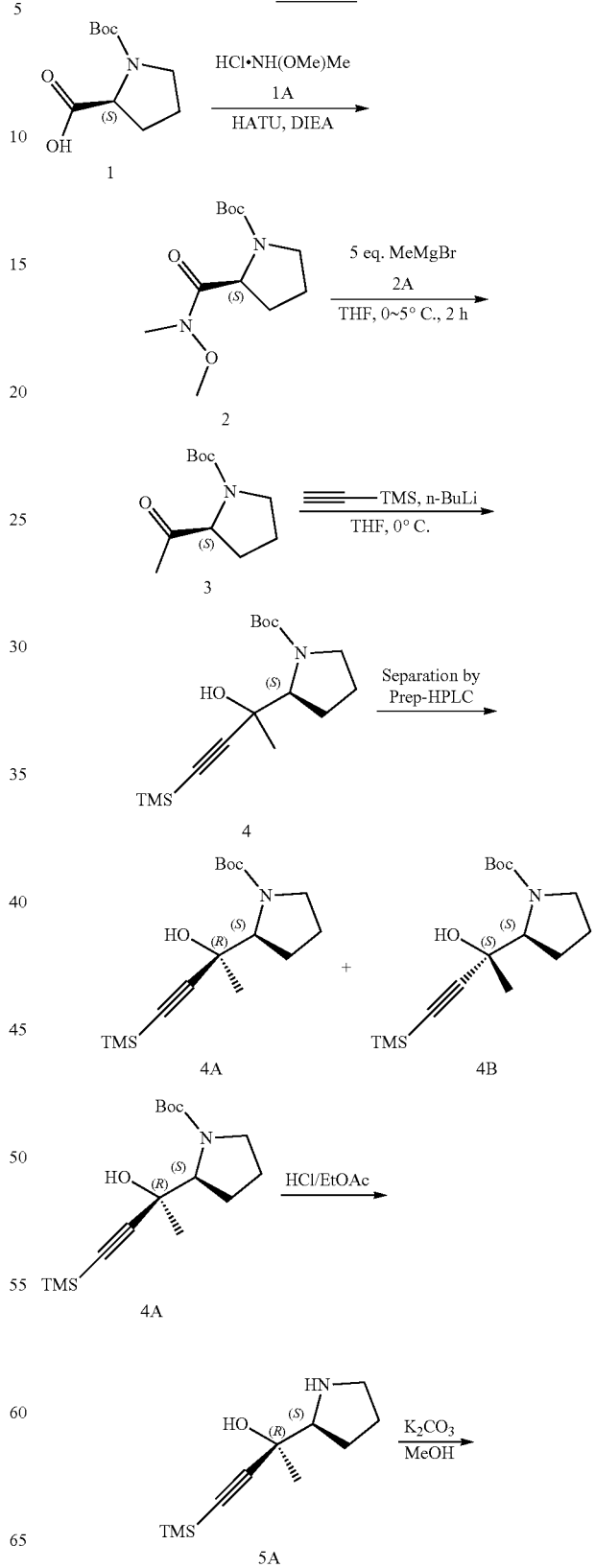

517

-continued

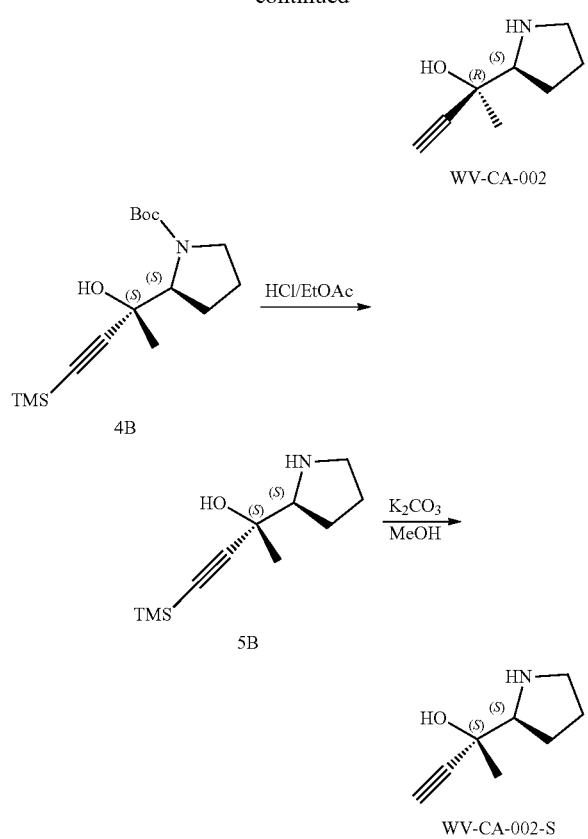

Scheme E1A

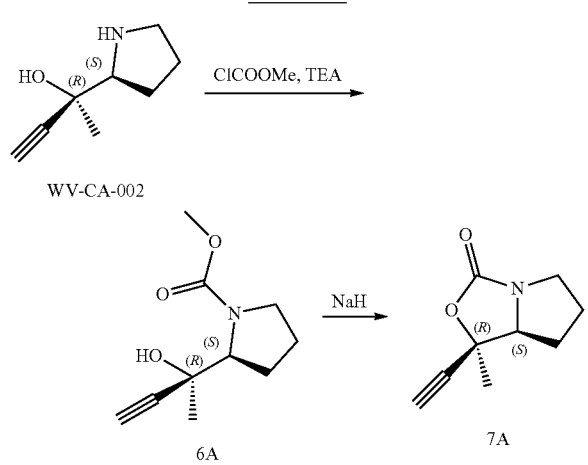

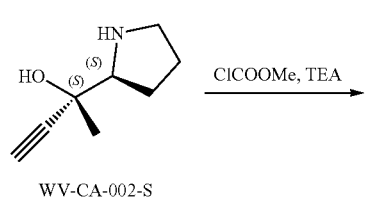

518

-continued

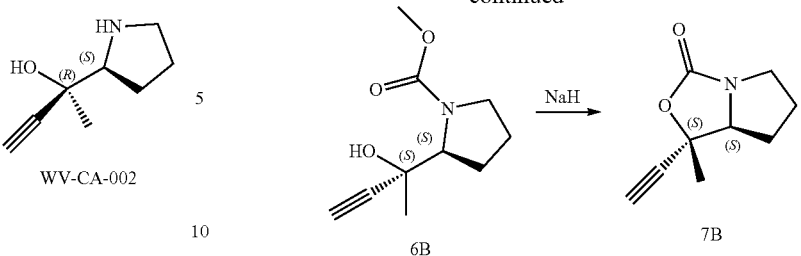

1. Preparation of Compound 2.

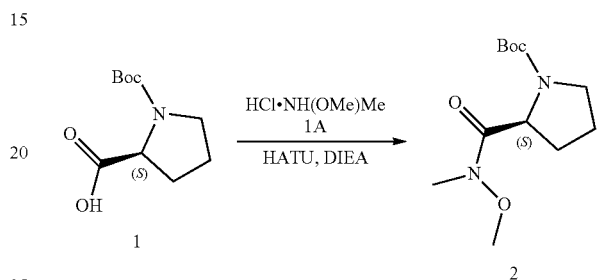

To a solution of compound 1 (40.00 g, 185.83 mmol), compound 1A (498.92 mg, 5.12 mmol) and HATU (77.72 g, 204.41 mmol) in DCM (400.00 mL) was slowly added DIEA (48.03 g, 371.66 mmol) and stirred at 20° C. for 12 hr. TLC showed the starting material was consumed. H$_2$O (100 mL) was added and extracted with DCM (1L*3). The combined organic layers were washed with brine (1 L), dried over anhydrous Na$_2$SO$_4$, filtered and concentrated to get the crude. The residue was purified by column chromatography on silica gel (Petroleum ether:Ethyl acetate=30:1 to 10:1) to get compound 2 as a colorless oil (28.00 g, 58.33%). $^1$H NMR (400 MHz, CDCl3): δ=4.71-4.49 (m, 1H), 3.82-3.64 (m, 3H), 3.60-3.31 (m, 2H), 3.17 (br. s., 3H), 2.77 (br. s., 2H), 2.23-1.76 (m, 5H), 1.41 (d, J=18.1 Hz, 9H). TLC (Petroleum ether:Ethyl acetate=1:1) R$_f$=0.43.

2. Preparation of Compound 3.

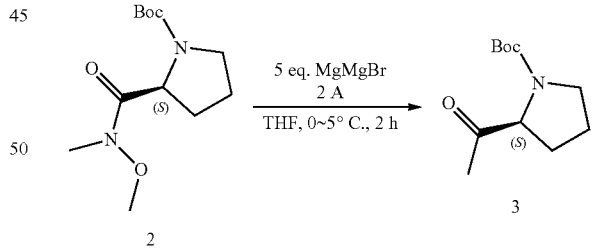

To a solution of compound 2 (28.00 g, 108.40 mmol) in Et$_2$O (500.00 mL) was added compound 2A (3 M, 144.53 mL) at 0° C. under N$_2$. The mixture was stirred at 0° C. for 3 hr. TLC showed the starting material was consumed. The mixture was poured into sat. NH$_4$Cl (1 L) at 0° C. slowly, and then extracted with EtOAc (500 mL*3). The combined organic layers were washed with brine (1 L), dried over anhydrous Na$_2$SO$_4$, filtered and concentrated to afford a crude. The residue was purified by column chromatography on silica gel (Petroleum ether:Ethyl acetate=3:1) to get the compound 3 as a yellow oil (20.00 g, 86.51%). TLC (Petroleum ether:Ethyl acetate=3:1) R$_f$=0.61.

3. Preparation of Compound 4A and Compound 4B.

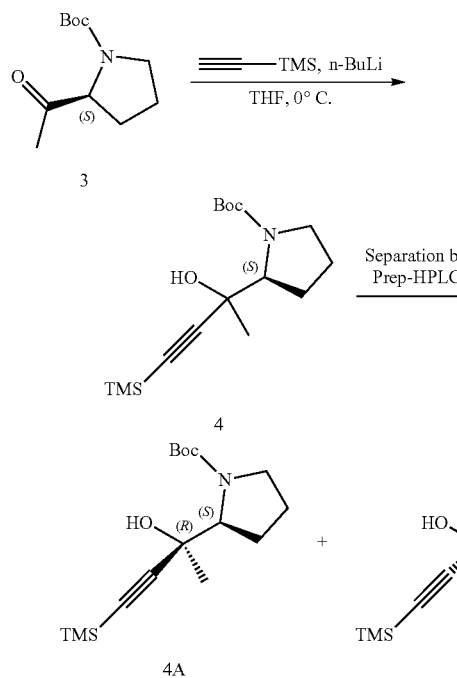

To a solution of ethynyl(trimethyl)silane (30.40 g, 309.47 mmol) in THF (200.00 mL) was added n-BuLi (3 M, 93.78 mL) at −30° C. The mixture was stirred at −30° C. for 1 hr, and then the mixture was added to a solution of compound 3 (20.00 g, 93.78 mmol) dissolved in THF (200.00 mL) at 0° C. The reaction was stirred at 0° C. for 3 hr. TLC showed the starting material was consumed. The mixture was poured into sat. NH$_4$Cl (2L) at 0° C., and extracted with EtOAc (1L*3). The combined organic layers were washed with brine (2 L) dried over Na$_2$SO$_4$, filtered and concentrated to get the crude. The residue was purified by column chromatography on silica gel (Petroleum ether:Ethyl acetate=10:1). The mixture was purified by Pre-HPLC (TFA) to get the compound 4A as light yellow solid (5.00 g, 17.12%) and compound 4B as light yellow solid (4.00 g, 13.69%). Compound 4A: $^1$H NMR (400 MHz, CDCl$_3$): δ=6.22 (br. s., 1H), 4.23-4.07 (m, 1H), 3.61 (br. s., 1H), 3.29 (td, J=6.8, 11.0 Hz, 1H), 2.26-2.15 (m, 1H), 2.02-1.68 (m, 3H), 1.47 (s, 9H), 1.35 (br. s., 3H), 0.24-0.07 (m, 9H). Compound 4B: $^1$H NMR (400 MHz, CDCl$_3$): δ=6.41 (br. s., 1H), 3.88 (t, J=7.5 Hz, 1H), 3.67 (t, J=7.3 Hz, 1H), 3.36-3.22 (m, 1H), 2.26-2.04 (m, 2H), 2.01-1.60 (m, 3H), 1.49 (s, 9H), 1.41 (s, 3H), 0.19-0.11 (m, 9H); TLC (Petroleum ether/Ethyl acetate=5:1) R$_f$=0.43.

4. Preparation of Compound 5A.

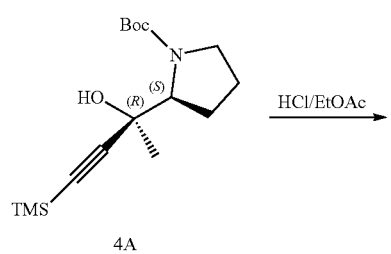

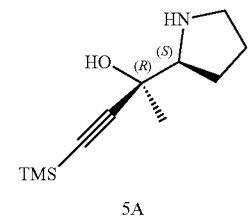

A solution of compound 4A (4.80 g, 15.41 mmol) in EtOAc was added to HCl/EtOAc (100.00 mL, 4N) at 5° C., and then the mixture was stirred at 20° C. for 0.5 hr. TLC showed the starting material was consumed. Concentrated the mixture to move most of the solvents and filtered the mixture, and the filter cake was dried to get the compound 5A as a white solid (3.80 g, 99.50%). TLC (Petroleum ether:Ethyl acetate=3:1) R$_f$=0.

5. Preparation of WV-CA-002.

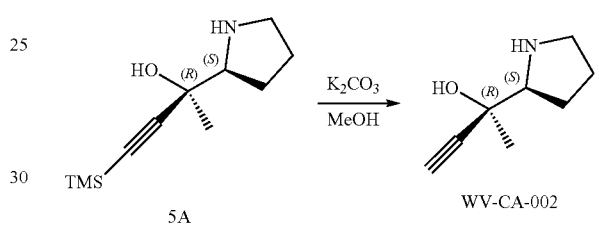

To a solution of compound 5A (3.80 g, 15.33 mmol) in MeOH (100.00 mL) was added K$_2$CO$_3$ (10.60 g, 76.66 mmol) at 20° C., and then the mixture was stirred at 20° C. for 12 hr. TLC showed the starting material was consumed. Concentrated the mixture to move most of the solvents and filtered the mixture, the cake was washed with DCM (50 mL*3), the combined organic was concentrated to get the crude. The residue was purified by column chromatography on silica gel (Dichloromethane:Methanol=30:1 to 5:1) to get WV-CA-002 as a yellow solid (560.00 mg, 26.19%). $^1$H NMR (400 MHz, CDCl$_3$): δ=3.30 (t, J=7.5 Hz, 1H), 3.10-2.97 (m, 2H), 2.41-2.30 (m, 1H), 1.89-1.56 (m, 4H), 1.43 (s, 3H). $^{13}$C NMR (101 MHz, CDCl$_3$): δ=88.61, 70.16, 67.63, 66.58, 46.50, 25.70, 25.10, 24.60. LCMS: (M+H+): 140.1. TLC (Dichloromethane:Methanol=10:1) R$_f$=0.33. LCMS purity: 99.81%. SFC purity=100.0%.

6. Preparation of Compound 5B.

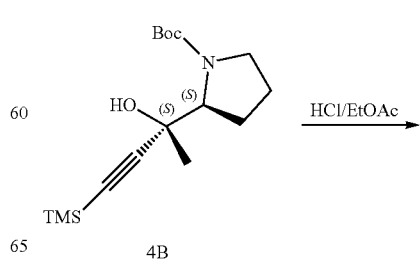

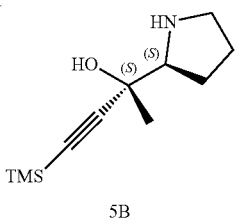

5B

A solution of compound 4B (3.80 g, 12.20 mmol) was added HCl/EtOAc (40.00 mL) at 5° C., then the mixture was stirred at 20° C. for 2 hr. TLC showed the start material was consumed. Concentrated the mixture to move most of the solvents and filtered the mixture, the filter cake was dried to get the compound 5B as a white solid (2.60 g, 85.99%). TLC (Petroleum ether/Ethyl acetate=3:1) $R_f$=0.

7. Preparation of WV-CA-002S.

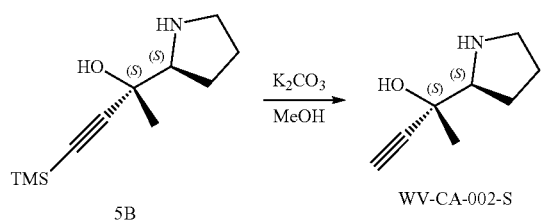

A solution of compound 5B (2.60 g, 10.49 mmol) in MeOH (40.00 mL) was added $K_2CO_3$ (7.25 g, 52.45 mmol) at 20° C., and then the mixture was stirred at 20° C. for 12 hr. TLC showed the starting material was consumed. The mixture was concentrated to remove most of the solvents and filtered, and the filter cake was washed with DCM (50 mL*3). The combined organic phase was concentrated to get the crude. The residue was purified by column chromatography on silica gel (Dichloromethane:Methanol=30:1 to 5:1) to afford WV-CA-002-S as a yellow solid (580.00 mg, 39.72%). $^1$H NMR (400 MHz, CDCl$_3$): δ=3.19 (t, J=7.3 Hz, 1H), 3.00 (dd, J=5.7, 7.5 Hz, 2H), 2.56-2.22 (m, 3H), 2.03-1.60 (m, 4H), 1.48-1.34 (m, 3H). $^{13}$C NMR (101 MHz, CDCl$_3$): δ=87.90, 72.01, 69.73, 67.47, 47.39, 27.84, 27.35, 27.21. LCMS: (M+H+): 140.1. TLC (Dichloromethane:Methanol=10:1) $R_f$=0.26. LCMS purity: 95.8%. SFC purity=93.3%.

8. Preparation of Compound 6A.

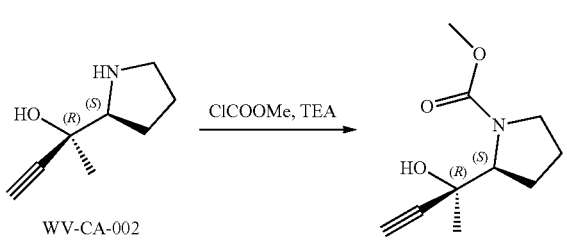

To a solution of WV-CA-002-S(20.00 mg, 143.69 μmol) and TEA (72.70 mg, 718.44 mol) in DCM (10.00 mL) was added methyl carbonochloridate (135.79 mg, 1.44 mmol). The mixture was stirred at 20° C. for 3 hr. TLC showed the starting material was consumed. The mixture was concen-trated to give a crude, which was used directly without further purification. TLC (Dichloromethane:Methanol=10:1) $R_f$=0.43.

9. Preparation of Compound 7A.

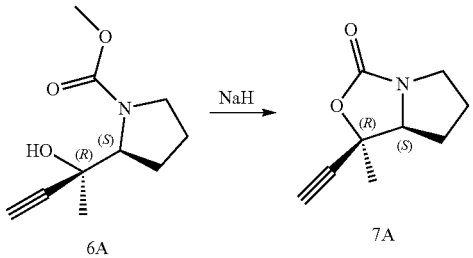

To a solution of compound 6A (28.00 mg, 141.97 μmol) in THF (5.00 mL) was added NaH (5.68 mg, 141.97 μmol, 60% purity). The mixture was stirred at 20° C. for 2 hr. TLC showed the starting material was consumed. Sat. NH$_4$Cl (5 mL) was added and extracted with EtOAc (5 mL*3). The combined organic layers were washed with brine, dried over Na$_2$SO$_4$, filtered and concentrated to get the crude. The residue was purified by Prep-TLC (Petroleum ether:Ethyl acetate=2:1). The stereochemistry structure cannot be confirmed by NOE. $^1$H NMR (400 MHz, CDCl$_3$): δ=3.97 (dd, J=5.3, 10.3 Hz, 1H), 3.67 (td, J=7.8, 11.5 Hz, 1H), 3.24 (ddd, J=3.5, 9.0, 11.5 Hz, 1H), 2.64 (s, 1H), 2.20-2.04 (m, 1H), 1.99-1.82 (m, 2H), 1.66 (s, 4H), 1.57-1.38 (m, 1H). TLC (Petroleum ether:Ethyl acetate=2:1) $R_f$=0.63.

10. Preparation of Compound 6B.

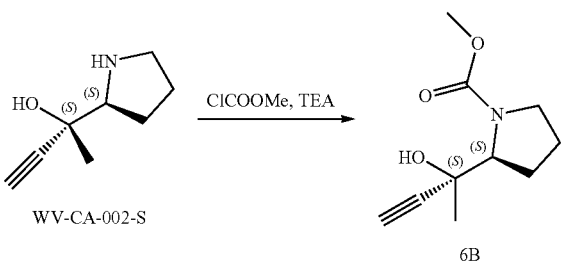

To a solution of WV-CA-002 (30.00 mg, 215.53 μmol) and TEA (65.43 mg, 646.59 mol) in DCM (5.00 mL) was added methyl carbonochloridate (101.84 mg, 1.08 mmol). The mixture was stirred at 20° C. for 2 hr. TLC the starting material was consumed. The mixture was concentrated to get the crude, which was used directly without any purification. TLC (DCM:MeOH=10:1) $R_f$=0.80.

11. Preparation of Compound 7B.

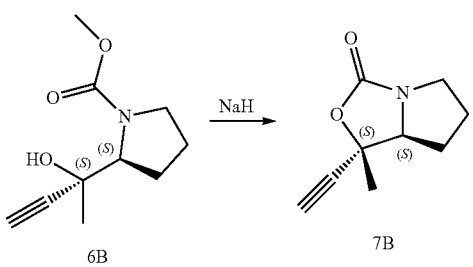

To a solution of compound 6B (28.00 mg, 141.97 μmol) in THF (5.00 mL) was added NaH (5.68 mg, 141.97 μmol, 60% purity). The mixture was stirred at 20° C. for 1 hr. TLC showed the starting material was consumed. Sat. NH₄Cl (5 mL) was added and extracted with EtOAc (10 mL*3). The combined organic layers were washed with brine, dried over Na₂SO₄, filtered and concentrated to get the crude. The residue was purified by Prep-TLC (Petroleum ether:Ethyl acetate=3:1). NOE showed the stereochemistry structure was corrected. ¹H NMR (400 MHz, CDCl₃): δ=1.64 (br. s., 2H) 1.77-1.84 (m, 4H) 1.86-2.19 (m, 5H) 2.66-2.78 (m, 1H) 3.10-3.27 (m, 1H) 3.62-3.80 (m, 1H). TLC (Petroleum ether:Ethyl acetate=2:1) R$_f$=0.43. LCMS: (M+H+): 140.1.

Example 3. Synthesis of WV-CA-002-dCiBu

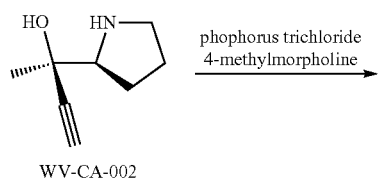

WV-CA-002

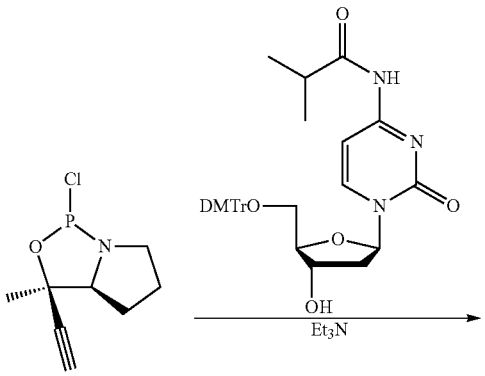

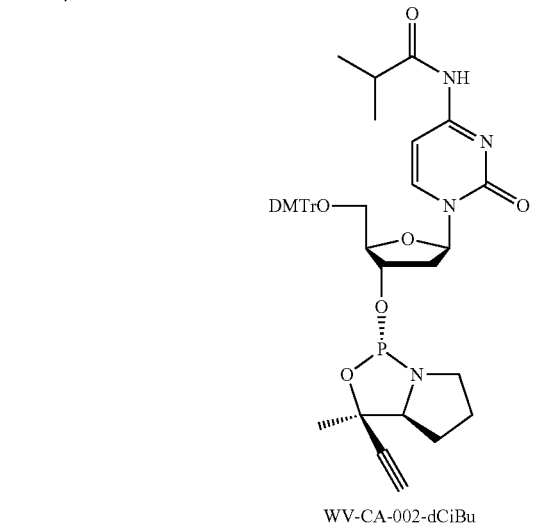

WV-CA-002-dCiBu

Using WV-CA-002 as starting material, the title compound (0.71 g, 50%) as a white solid was prepared analogously to WV-CA-008S-dCiBu. ¹H NMR (500 MHz, Chloroform-d) δ 8.56 (s, 1H), 8.27 (d, J=7.3 Hz, 1H), 7.43-7.37 (m, 2H), 7.32-7.23 (m, 7H), 7.02 (d, J=7.4 Hz, 1H), 6.87-6.81 (m, 4H), 6.29-6.23 (m, 1H), 4.91 (dq, J=11.2, 5.9 Hz, 1H), 4.20 (dt, J=5.7, 2.9 Hz, 1H), 3.92 (dt, J=6.2, 3.1 Hz, 1H), 3.80 (s, 6H), 3.56-3.44 (m, 3H), 2.93 (tt, J=7.9, 4.7 Hz, 1H), 2.76-2.67 (m, 1H), 2.61 (p, J=6.8 Hz, 1H), 2.45-2.36 (m, 2H), 2.03 (s, 1H), 2.00-1.94 (m, 1H), 1.50 (dd, J=9.1, 3.9 Hz, 1H), 1.44 (s, 3H), 1.25 (t, J=7.1 Hz, 1H), 1.19 (t, J=6.5 Hz, 6H); ³¹P NMR (202 MHz, CDCl₃) δ 149.88.

Example 4. Synthesis of WV-CA-003

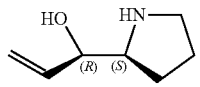

General Scheme.

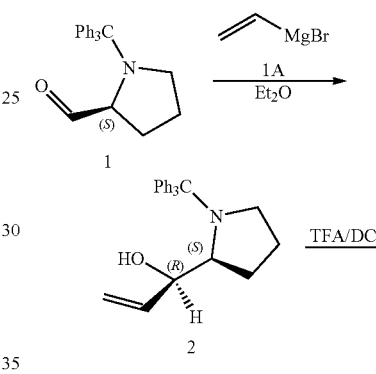

1. Preparation of Compound 2.

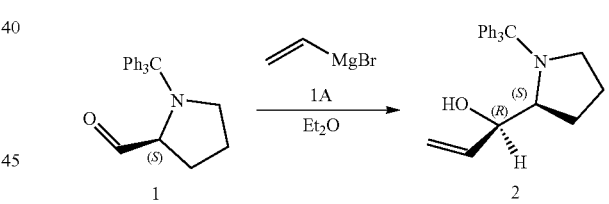

To a solution of compound 1 (10 g, 29.29 mmol, 1.00 eq) in Et₂O (200 mL) under N₂ was added compound 1A (1 M, 58.58 mL, 2.00 eq) at −70° C. The reaction was stirred at −70° C. for 5 hours. TLC (Petroleum Ether/Ethyl Acetate=5:1, R$_f$=0.45) showed that the material remained and there was a new point appeared. The reaction was quenched with a 2:1 mixture of a saturated aqueous NH₄Cl solution (400 mL) and NH₃ (25% in water, 200 mL). The organic layer was separated and the water phase was washed with DCM (500 mL*2). The organic layers were combined, washed with brine (300 mL), dried over Na₂SO₄. The organic layer was concentrated to give the compound 2 (10 g, 26.56 mmol, 90.68% yield, 98.14% purity) as a white solid. ¹H NMR (400 MHz, CDCl₃) δ 7.58 (d, J=8.0 Hz, 6H), 7.34-7.25 (m, 6H), 7.24-7.17 (m, 3H), 5.66 (s, 1H), 5.21 (s, 1H), 5.11-5.03 (m, 1H), 4.47 (brs, 1H), 3.51 (brs, 1H), 3.28-3.17 (m, 1H), 3.09-3.00 (m, 1H), 1.70-1.51 (m, 2H), 1.39-1.23 (m, 1H), 1.19-1.04 (m, 1H), 0.31-0.15 (m, 1H).

2. Preparation of Compound 3.

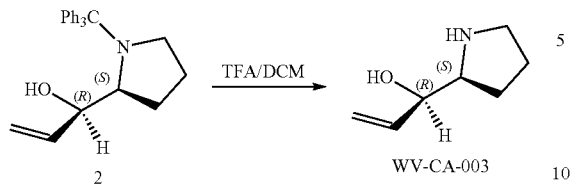

To a solution of compound 2 (5.60 g, 15.16 mmol, 1.00 eq) in DCM (50.00 mL) was added TFA (15.30 g, 134.19 mmol, 10.00 mL, 8.85 eq) at 0° C., the mixture was stirred at 0° C. for 4 hours. LCMS showed that the material was consumed and there was product's MS was detected. The reaction was concentrated to give a residue. The residue was diluted with water (80 mL) and extracted with MTBE (50 mL*3), the water phase was alkalized with NaOH (2N, 5 mL), then the water phase was concentrated to give the crude product. The crude product was purified by silica gel chromatography (DCM/MeOH from 30:1 to 15:1) to give the product. The solvent was removed and dried under reduced pressure to give WV-CA-003 (1.80 g, 13.50 mmol, 89.02% yield: 95.35% purity) as a red oil. $^1$H NMR (400 MHz, CDCl$_3$) δ 5.91 (ddd, J=16.8, 10.8, 5.5 Hz, 1H), 5.41 (d, J=17.1 Hz, 1H), 5.27 (d, J=10.5 Hz, 1H), 4.29 (t, J=5.0 Hz, 1H), 3.46-3.38 (m, 1H), 3.23-3.15 (m, 1H), 3.15-3.06 (m, 1H), 2.03-1.80 (m, 4H). LCMS: [M+H]$^+$: 128.1.

Example 5. Synthesis of WV-CA-003-dC$^{iBu}$

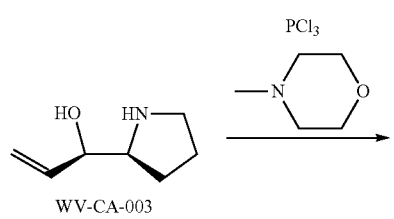

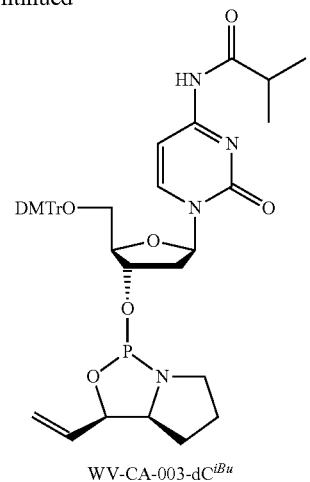

Using WV-CA-003 as starting material, the title compound (0.96 g, 52%) as a white solid was prepared analogously to WV-CA-008S-dC$^{iBu}$. $^1$H NMR (600 MHz, CDCl$_3$) δ 8.46 (brs, 1H), 8.22 (d, J=7.8 Hz, 1H), 7.38 (t, J=6.6 Hz, 2H), 7.31-7.19 (m, 7H), 7.07 (d, J=7.2 Hz, 1H), 6.84 (d, J=1.8 Hz, 2H), 6.82 (d, J=1.8 Hz, 2H), 6.23 (t, J=5.7 Hz, 1H), 5.80 (ddd, J=17.1, 10.5, 6.0 Hz, 1H), 5.36-5.30 (m, 1H), 5.24-5.20 (m, 1H), 5.00 (t, J=6.0 Hz, 1H), 4.78-4.73 (m, 1H), 4.16-4.12 (m, 1H), 3.79 (s, 6H), 3.63-3.57 (m, 1H), 3.53-3.41 (m, 1H), 3.14-3.07 (m, 1H), 2.74 (dt, J=13.2, 6.0 Hz, 1H), 2.56 (sep, J=6.9 Hz, 1H), 2.32-2.25 (m, 1H), 1.81-1.68 (m, 2H), 1.58-1.51 (m, 1H), 1.33-1.26 (m, 1H), 1.20 (d, J=6.6 Hz, 3H), 1.19 (d, J=6.0 Hz, 3H); $^{31}$P NMR (243 MHz, CDCl$_3$) δ 155.63.

Example 6. Synthesis of WV-CA-004

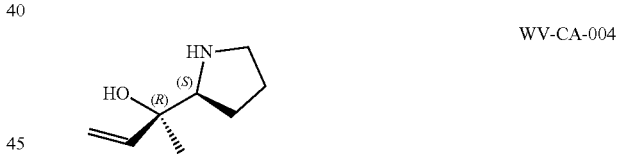

General Scheme.

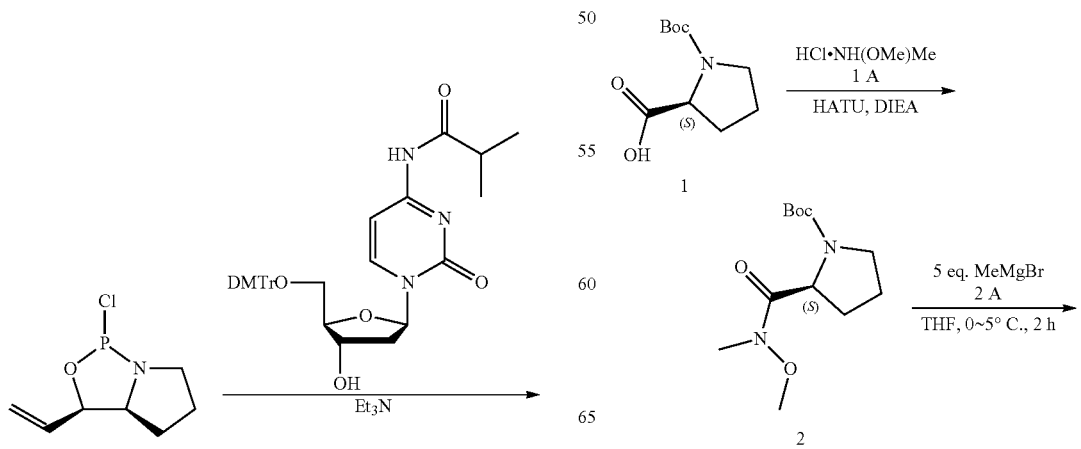

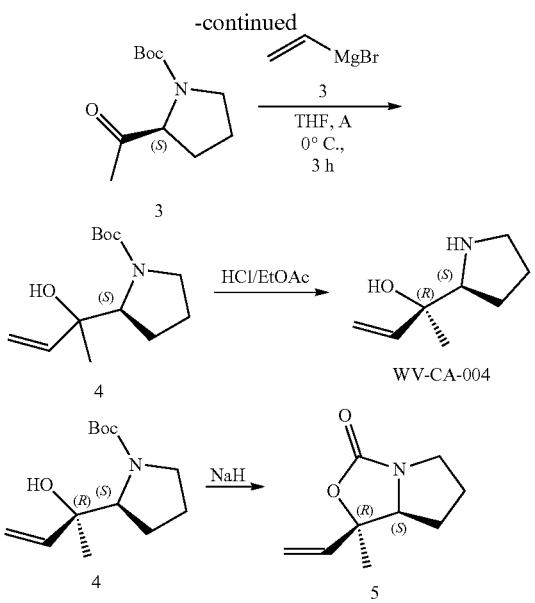

1. Preparation of Compound 2.

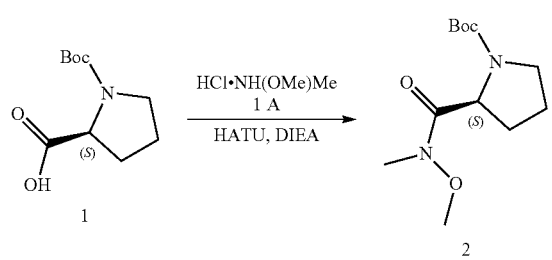

To a solution of compound 1 (40.00 g, 185.83 mmol) in DCM (400.00 mL) was added compound 1A (19.94 g, 204.41 mmol), DIPEA (48.03 g, 371.66 mmol) and HATU (91.86 g, 241.58 mmol) at 0° C., and the mixture was stirred at 25° C. for 15 hr. TLC showed that the material was consumed and a new spot appeared. The mixture was quenched with H₂O (600 mL), and extracted with DCM (500 mL*2). The organic layers were combined and dried over Na₂SO₄. The organic layer was filtered and concentrated. The residue was purified by silica gel chromatography (petroleum ether/ethyl acetate from 30:1 to 5:1) to give compound 2 as a white solid (25.00 g, 52.08%). TLC (petroleum ether/ethyl acetate=1:1) R$_f$=0.40.

2. Preparation of Compound 3.

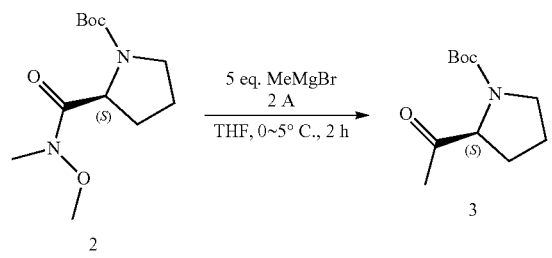

To a cooled solution of compound 2 (20.00 g, 77.43 mmol) in Et₂O (500.00 mL) at 0° C., was added compound 2 A (3 M, 129.05 mL). The mixture was stirred at 0~5° C. for 2 hr. TLC showed compound 2 was consumed, and a new spot with low polarity was formed on TLC. The resulting mixture was quenched with sat. NH₄Cl aq. (800 mL), extracted with EtOAc (300 mL*3). The combined layers were dried over anhydrous MgSO₄, filtered and concentrated. The crude product was purified by column chromatography on silica gel (Petroleum ether:Ethyl acetate=10:1, 5:1) to afford compound 3 as a colorless oil (12.00 g, 63.89%). ¹H NMR (400 MHz, CDCl₃): δ=4.16-4.32 (m, 1H), 3.45-3.55 (m, 2H), 1.88-2.21 (m, 4H), 1.45-1.79 (m, 9H). LCMS: (M+H+): 214.1. TLC (Petroleum ether:Ethyl acetate=1:1) R$_f$=0.77. LCMS purity: 87.9%.

3. Preparation of Compound 4.

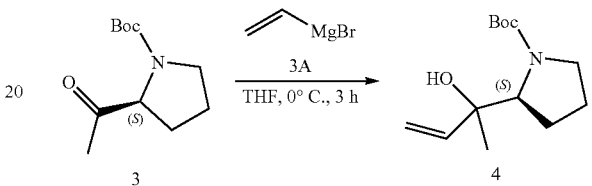

To a solution of compound 3 (11.00 g, 51.58 mmol) in THF (200.00 mL) was added compound 3A (1 M, 154.73 mL) at 0° C. The mixture was stirred at 0° C. for 2 hr. TLC and LCMS showed the starting material was consumed. The resulting mixture was quenched with sat. NH₄Cl (50 mL) at 0° C., and extracted with EA (100 mL*3). The combined organic layers were washed with brine dried over Na₂SO₄, filtered, and concentrated to get the crude. The residue was purified by column chromatography on silica gel (Petroleum ether:Ethyl acetate=80:1, 20:1) to get the compound 4 as a yellow oil (5.80 g, 46.59%). ¹H NMR (400 MHz, CDCl₃): δ=5.84-5.96 (m, 2H), 3.35-3.39 (d, J=16.0 Hz, 1H), 5.09-5.12 (d, J=12.0 Hz, 1H), 3.87-3.91 (t, 1H), 3.64 (s, 1H), 3.14-3.19 (m, 1H), 1.71-1.97 (m, 4H), 1.69 (s, 9H), 1.17 (s, 3H). LCMS: (M+Na+): 264.1. TLC (Petroleum ether/Ethyl acetate=3:1) R$_f$=0.62.

4. Preparation of WV-CA-004.

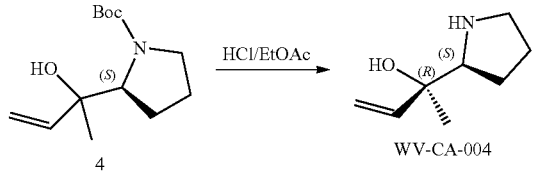

A solution of compound 4 (4.00 g, 16.57 mmol) was added HCl/EtOAc (150.00 mL, 4 N) at 0° C., then the mixture was stirred at 20° C. for 2 hr. TLC showed the starting material was consumed. The mixture was concentrated to move the most of the solvent and filtered the mixture. The filter cake was dissolved in water (3 mL) and added NaOH (2N) until pH=11, extracted with DCM (20 mL). The combined organic layers were washed with brine (15 mL), dried over Na₂SO₄, filtered and concentrated to get the product, which was purified by chiral-SFC (10% NH₃·H₂O), and then the residue was purified by Prep-TLC (DCM:MeOH=10:1) to afford WV-CA-004 as a white solid (900.00 mg, 38.46%). ¹H NMR (400 MHz, CDCl₃): δ=6.04-6.11 (m, 1H), 5.54-5.58 (d, J=16.0 Hz, 1H), 5.28-5.31 (d, J=12.0 Hz, 1H), 3.65-3.69 (m, 1H), 3.31-3.42 (m, 2H), 2.06-2.18 (m, 4H), 1.88-1.99 (br. s, 1H), 1.35 (s, 3H). $^{13}$C NMR (101 MHz, CDCl$_3$): δ=141.58, 115.50, 72.42, 67.40, 46.07, 25.38, 25.27, 24.40. LCMS: (M+H+): 142.2. TLC (Petroleum ether:Ethyl acetate=5:1) R$_f$=0. LCMS purity: 100.0%. SFC purity: 100.0%.

5. Preparation of Compound 5.

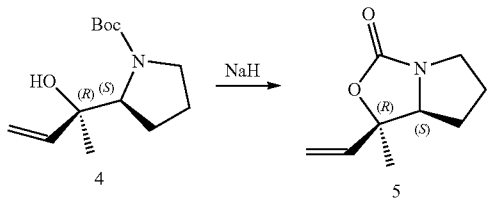

To a solution of compound 4 (30.00 mg, 124.31 μmol) in THF (2.00 mL) was added NaH (9.94 mg, 248.62 μmol, 60% purity). The mixture was stirred at 0° C. for 1 hr, TLC showed no reaction. Stirring was continued at 25° C. for 5 hr. TLC (Petroleum ether:Ethyl acetate=3:1) showed the reaction was completed. The resulting mixture was quenched with sat. NH$_4$Cl aq. (10 mL), extracted with EtOAc (10 mL*3). The combined organic layers were dried over anhydrous MgSO$_4$, filtered and concentrated to afford a crude, which was purified by Prep-TLC (Petroleum ether: Ethyl acetate=3:1) to afford the compound 5 as a colorless oil (15.00 mg, 64.95%). $^1$H NMR (400 MHz, CDCl$_3$): δ=5.09-6.04 (m, 1H), 5.40-5.42 (d, J=8.0 Hz, 1H), 5.18-5.21 (d, J=12.0 Hz, 1H), 3.63-3.69 (m, 2H), 3.15-3.18 (m, 1H), 1.59-2.12 (m, 5H), 1.46 (s, 3H). TLC (Petroleum ether:Ethyl acetate=5:1) R$_f$=0.21.

Example 7. Synthesis of WV-CA-005-D

WV-CA-005-D

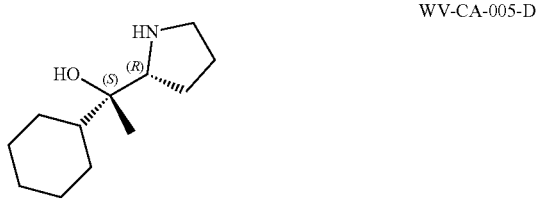

General Scheme.

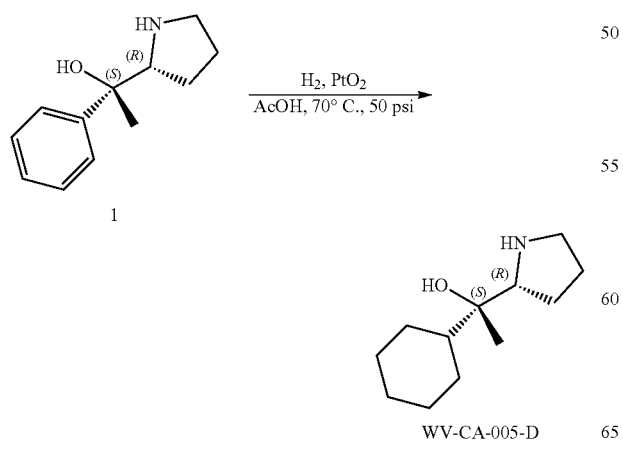

1. Preparation of Compound WV-CA-005-D.

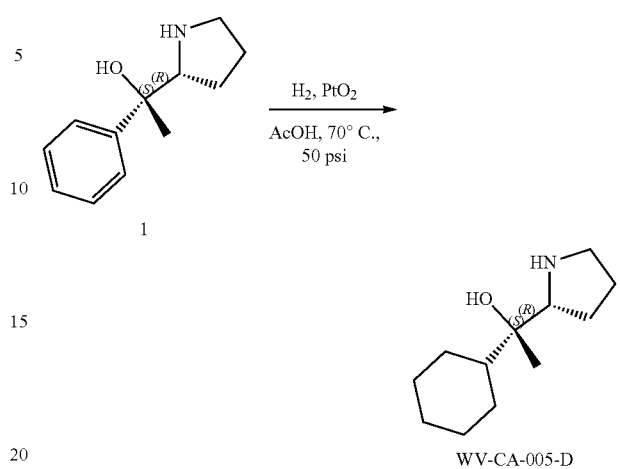

A mixture of compound 1 (30.00 g, 156.85 mmol) and H$_2$ (316.83 mg, 156.85 mmol) in AcOH (800.00 mL) was hydrogenated under 50 psi of hydrogen pressure for 12 hr at 70° C. LC-MS showed ~15% of compound 1 remained. Several new peaks were shown on LC-MS and ~50% of desired compound was detected. The mixture was filtered to recovered compound 1, and then to the mixture was added PtO$_2$ (7.12 g, 31.37 mmol). The mixture was hydrogenated under 50 psi of hydrogen pressure for 12 hr at 70° C. LC-MS showed ~5% of compound 1 remained. Several new peaks were shown on LC-MS and ~60% of desired compound was detected. The mixture was filtered to recovered compound 1, and then to the mixture was added PtO$_2$ (7.12 g, 31.37 mmol). The mixture was hydrogenated under 50 psi of hydrogen pressure for 12 hr at 70° C. LC-MS showed compound 1 was consumed completely and one main peak with desired MS was detected. The mixture was concentrated in vacuo. The reaction was quenched with sat. Na$_2$CO$_3$ (200 mL), and then extracted with DCM (100 mL*6). The combined organic phase was washed with brine (300 mL*1), dried over anhydrous Na$_2$SO$_4$, filtered and concentrated in vacuo. The residue was purified by column chromatography (SiO$_2$, Petroleum ether/Ethyl acetate=5/1 to DCM:Methanol=50/1 to 5/1). Compound WV-CA-005-D was obtained as a white solid (11.4 g, 51.70%). $^1$H NMR (400 MHz, CDCl$_3$): δ=0.99-0.91 (m, 1H), 1.28-1.05 (m, 7H), 1.47-1.38 (m, 1H), 1.58 (br d, J=13.15 Hz, 1H), 1.82-1.65 (m, 7H), 1.93 (br d, J=12.72 Hz, 1H), 3.10-2.92 (m, 2H), 3.19 (t, J=7.67 Hz, 1H). $^{13}$C NMR (125.7 MHz, CDCl$_3$): δ=73.31, 64.88, 46.28, 45.16, 27.98, 26.97, 26.79, 26.73, 26.58, 25.95, 24.64, 21.72. LCMS: (M+H+): 198.3. TLC (Dichloromethane/Methanol=5:1) R$_f$=0.01. SFC purity=100.0%.

Example 8. Synthesis of WV-CA-005D-dCiBu

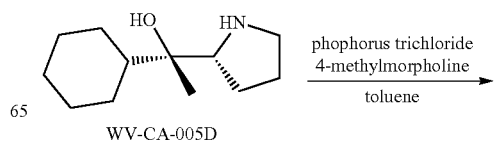

General Scheme.

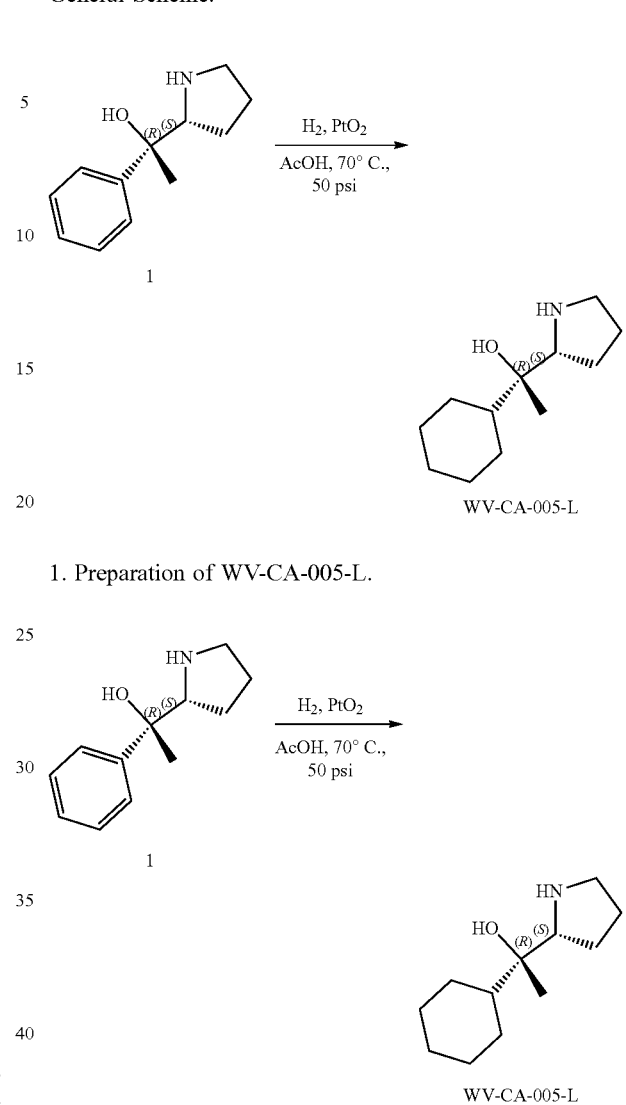

1. Preparation of WV-CA-005-L.

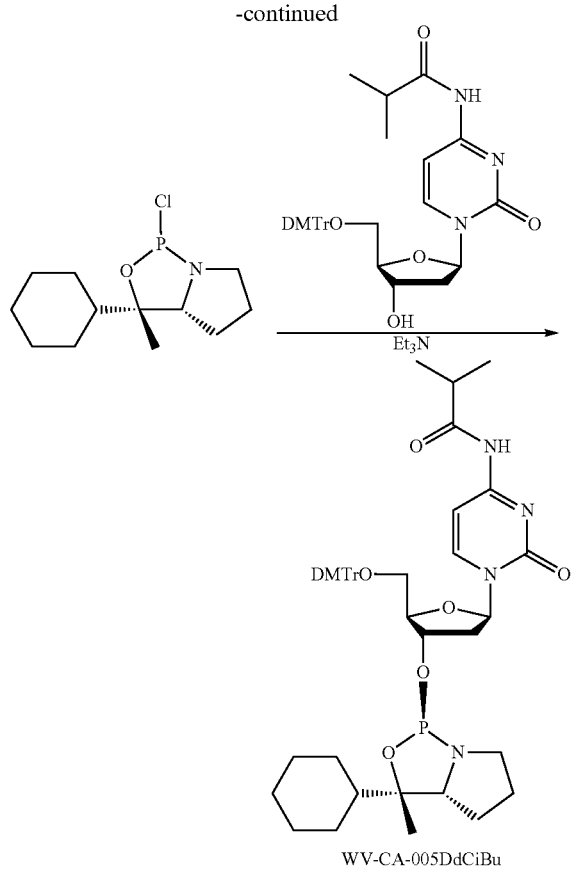

Using WV-CA-005D as starting material, the title compound (4.67 g, 71%) as a white solid was prepared analogously to WV-CA-008S-dCiBu. ¹H NMR (500 MHz, Chloroform-d) δ 8.56 (s, 1H), 8.37 (d, J=7.5 Hz, 1H), 7.40 (d, J=7.7 Hz, 2H), 7.33-7.20 (m, 7H), 7.11 (d, J=7.4 Hz, 1H), 6.84 (d, J=8.2 Hz, 4H), 6.19 (dd, J=6.6, 3.9 Hz, 1H), 4.84 (p, J=6.9 Hz, 1H), 4.12 (q, J=4.5, 2.9 Hz, 1H), 3.80 (s, 6H), 3.52-3.39 (m, 3H), 3.34 (td, J=9.6, 5.3 Hz, 1H), 3.09 (q, J=8.9 Hz, 1H), 2.65 (ddt, J=27.9, 13.8, 6.8 Hz, 2H), 2.52 (q, J=7.2 Hz, 1H), 2.35-2.26 (m, 1H), 1.94-1.01 m, 23H). ³¹P NMR (202 MHz, CDCl₃) δ 165.56.

Example 9. Synthesis of WV-CA-005-L

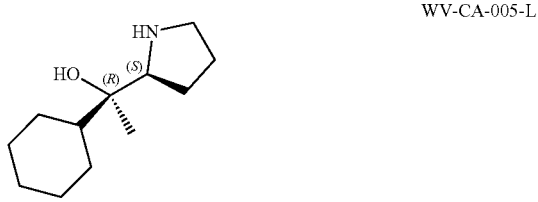

A mixture of compound 1 (30.00 g, 156.85 mmol) and PtO₂ (7.12 g, 31.37 mmol) in AcOH (800.00 mL) was hydrogenated under 50 psi of hydrogen pressure for 12 hr at 70° C. LC-MS and HNMR showed ~5% of compound 1 was remained. The mixture was concentrated in vacuo to get WV-CA-005-L (20.00 g, crude) as a yellow solid. The reaction was set up again. Two reactions were carried out in parallel. To a solution of compound 1 (9.00 g, 47.05 mmol) in AcOH (300.00 mL) was added PtO₂ (1.71 g, 7.53 mmol) under Ar atmosphere. The suspension was degassed and purged with H₂ for 3 times. The mixture was stirred under H₂ (50 psi) at 70° C. for 12 hr. HNMR showed the starting material was consumed. Two reactions were combined for workup. The mixture was concentrated to get the crude, and the residue was dissolved in water (20 mL), and Na₂CO₃ (aq.) was added until pH>11. The mixture was extracted with DCM (50 mL*3), and the combined organic layers were washed brine (100 mL), dried over Na₂SO₄, filtered and concentrated to get the crude, which was purified by silica (Dichloromethane/Methanol=30:1 to 10:1) to get WV-CA-005-L (10.00 g, 50.68 mmol) as a yellow solid. ¹H NMR (400 MHz, CDCl₃): δ=3.37 (brs, 2H), 3.22-3.12 (m, 1H), 3.05-2.90 (m, 2H), 1.94 (d, J=13.2 Hz, 1H), 1.83-1.62 (m, 7H), 1.62-1.55 (m, 1H), 1.44 (tt, J=2.9, 11.9 Hz, 1H), 1.29-1.09 (m, 4H), 1.07 (s, 3H), 1.00-0.86 (m, 1H). $^{13}$C NMR (125.7 MHz, CDCl$_3$): δ=73.30, 65.01, 46.23, 45.19, 27.98, 26.73 (dd, J=16.0, 20.6 Hz, 1C), 25.84, 24.64, 21.66. LCMS: (M+H+): 198.2. TLC (Dichloromethane/Methanol=10:1) R$_f$=0.15. SFC purity=100.0%.

Example 10. Synthesis of CA-005L-dCiBu

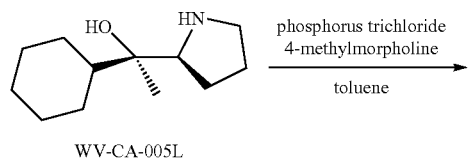

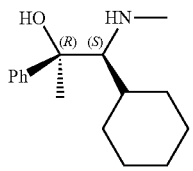

Example 11. Synthesis of WV-CA-008

General Scheme.

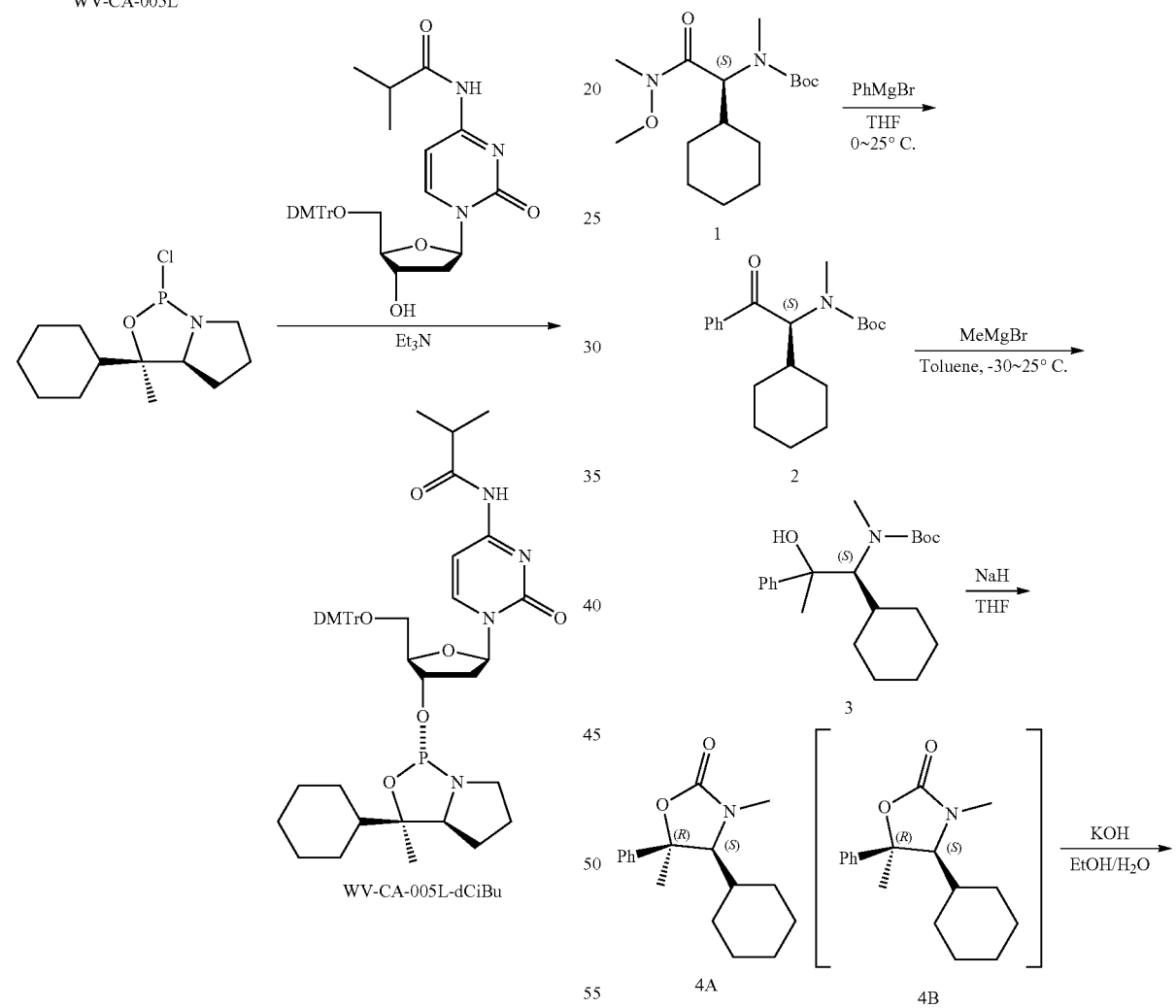

Using WV-CA-005L as starting material, the title compound (4.6 g, 70%) as a white solid was prepared analogously to WV-CA-008S-dCiBu. $^1$H NMR (500 MHz, Chloroform-d) δ 8.51 (s, 1H), 8.24 (d, J=7.5 Hz, 1H), 7.43-7.33 (m, 2H), 7.33-7.20 (m, 7H), 7.06 (d, J=7.4 Hz, 1H), 6.87-6.81 (m, 4H), 6.22 (dd, J=6.4, 4.8 Hz, 1H), 4.77 (dq, J=11.1, 5.9 Hz, 1H), 4.18 (brs, 1H), 3.80 (s, 6H), 3.56-3.46 (m, 2H), 3.32 (ddd, J=10.3, 7.6, 4.9 Hz, 1H), 3.14 (qd, J=11.1, 9.8, 4.7 Hz, 1H), 2.77-2.68 (m, 1H), 2.60 (hept, J=7.2 Hz, 1H), 2.29 (ddd, J=13.9, 6.5, 4.8 Hz, 1H), 1.99-1.01 (m, 25H). $^{31}$P NMR (202 MHz, CDCl3) δ 165.17.

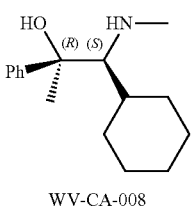

1. Preparation of Compound 2.

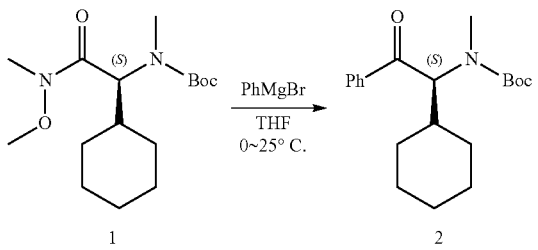

To a solution of compound 1 (22.40 g, 71.24 mmol) in THF (250 mL) was added bromo(phenyl)magnesium (3 M, 71.24 mL) at −20° C. The mixture was warmed to 25° C. slowly and stirred at 25° C. for 4 hr. TLC showed compound 1 was remained, and a new spot with strong UV absorption and lower polarity was observed. The resulting mixture was quenched with sat. NH$_4$Cl aq. (300 mL), extracted with EtOAc (150 mL*3). The combined organic layers were dried over anhydrous MgSO$_4$, filtered and concentrated to give a crude oil, which was purified by column chromatography on silica gel (Petroleum ether:Ethyl acetate=1:0, 100:1, 50:1) to afford compound 2 as a light-yellow oil (12.98 g, 46.23% yield, 84.1% purity). $^1$H NMR (400 MHz, CHLOROFORM-d, the rotamers ratio=2:1) δ=8.12 (d, J=7.7 Hz, 2H), 7.49-7.41 (m, 3H), 5.41 (d, J=10.6 Hz, 1H), 2.62 (s, 3H), 2.21-2.06 (m, 1H), 1.79 (br d, J=12.3 Hz, 1H), 1.73-1.58 (m, 3H), 1.44 (s, 9H), 1.38-0.77 (m, 6H); the rotamer: δ=8.02 (d, J=7.5 Hz, 2H), 7.60-7.51 (m, 3H), 5.16 (d, J=10.4 Hz, 1H), 2.67 (s, 3H), 2.21-2.06 (m, 1H), 1.79 (br d, J=12.3 Hz, 1H), 1.73-1.58 (m, 3H), 1.53 (s, 9H), 1.38-0.77 (m, 6H). TLC (Petroleum ether:Ethyl acetate=10:1), R$_f$=0.64.

2. Preparation of Compound 3

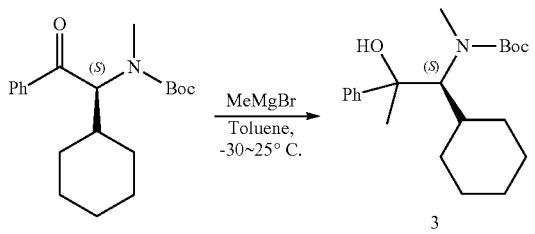

To a solution of compound 2 (11.00 g, 33.19 mmol) in toluene (250 mL) was added MeMgBr (3 M, 55.32 mL) at −20° C. The mixture was stirred at −20-25° C. for 3 hr. TLC and LCMS showed most of compound 2 was consumed. The reaction was quenched with sat. NH$_4$Cl aq. (200 mL), extracted with EtOAc (100 mL*3). The combined organic layers were dried over anhydrous Na$_2$SO$_4$, filtered, and concentrated to afford compound 3 as a crude light yellow solid (12.90 g), which was used into the next step without further purification. LCMS: (M+H$^+$): 348.2; (M+Na$^+$): 370.1. TLC (Petroleum ether:Ethyl acetate=5:1), R$_f$=0.5.

3. Preparation of Compound 4A

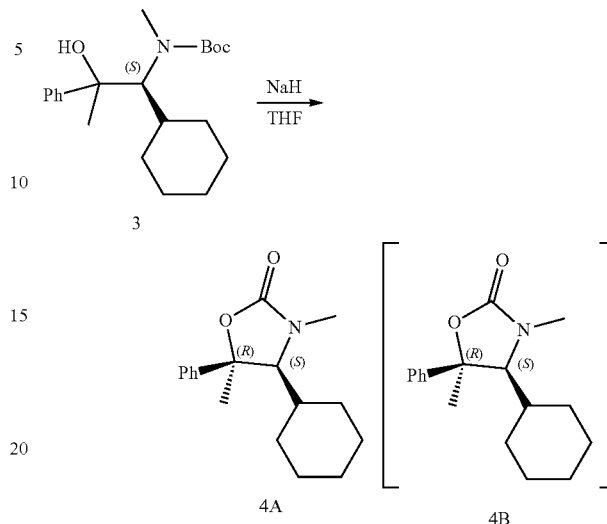

To a solution of compound 3 (11.50 g, 33.09 mmol) in THF (20.00 mL) was added NaH (3.97 g, 99.28 mmol, 60% purity). The mixture was stirred at 25° C. for 2 hr. TLC showed the reaction was completed. The resulting mixture was quenched with sat. NH$_4$Cl aq. (50 mL), extracted with EtOAc (50 mL*3). The separated aqueous layers were dried over anhydrous MgSO$_4$, filtered, and concentrated to afford a crude product, which was purified by column chromatography on silica gel (Petroleum ether:Ethyl acetate=50:1, 25:1, 10:1) to afford pure compound 4A (5.00 g, 55.27% yield), 1.2 g crude compound 4A and compound 4B (200 mg, 2.21% yield) as white solid. $^1$H NMR: (400 MHz, CHLOROFORM-d) δ=7.29-7.36 (m, 5H), 3.36 (s, 1H), 3.04 (s, 3H), 1.69 (s, 3H), 1.67-1.63 (m, 1H), 1.53-1.43 (m, 3H), 1.31-1.23 (m, 3H), 1.05-0.90 (m, 2H), 0.85-0.70 (m, 1H), 0.65-0.49 (m, 1H). LCMS: (M+H$^+$): 274.2. TLC (Petroleum ether:Ethyl acetate=10:1), R$_f$=0.1.

3. Preparation of WV-CA-008.

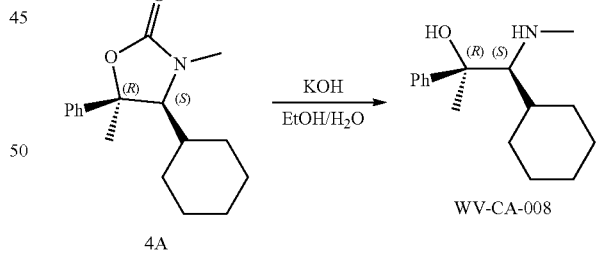

Compound 4A (5.90 g, 21.58 mmol) was dissolved in a KOH (35.40 g, 630.78 mmol) solution in EtOH-H$_2$O (1:1, v/v) (100 mL). The mixture was refluxed (90° C.) for 24 hr. LCMS showed compound 4A remained. To the reaction was additionally added KOH (30 g). Stirring was continued at 90° C. for 20 hr. LCMS showed compound 4A was consumed, and the reaction was completed. The resulting mixture was concentrated under reduced pressure. The residue was taken up in DCM (200 mL), dried over anhydrous MgSO$_4$, filtered and concentrated to afford the product as a crude, which was purified by column chromatography on silica gel (Dichloromethane:Methanol=100:1, 50:1, 10:1) to afford WV-CA-008 as a light yellow solid (1.80 g, 32.03% yield, 95% purity). $^1$H NMR (400 MHz, CHLOROFORM-d) δ=7.37 (d, J=7.5 Hz, 2H), 7.28 (t, J=7.5 Hz, 2H), 7.23-7.15 (m, 1H), 2.59 (s, 3H), 2.36-2.22 (m, 1H), 1.64 (d, J=12.8 Hz, 1H), 1.59-1.40 (m, 6H), 1.35-1.19 (m, 2H), 1.18-1.05 (m, 1H), 1.04-0.73 (m, 3H), 0.62 (m, 1H). $^{13}$C NMR (101 MHz, CHLOROFORM-d) δ=145.64, 127.72, 126.24, 125.38, 74.83, 73.81, 39.17, 38.85, 34.57, 28.55, 27.09, 26.28, 26.02. LCMS: (M+H$^+$): 274.2; 95% purity. HPLC purity=99.7%. Chiral SFC purity=100.0%.

Example 12. Synthesis of WV-CA-008-S

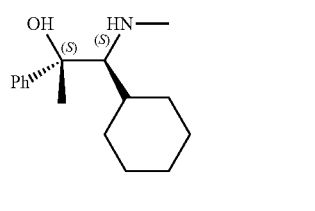

WV-CA-008-S

General Scheme.

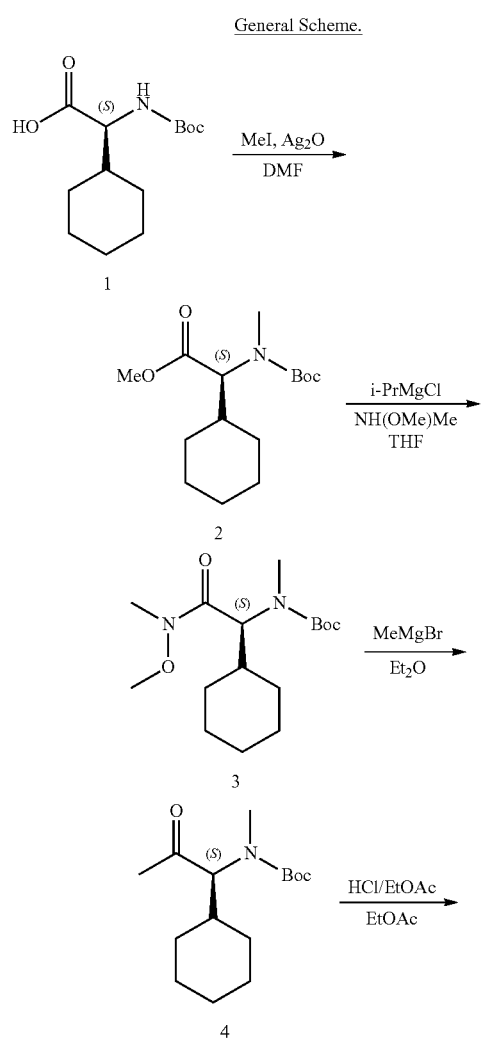

-continued

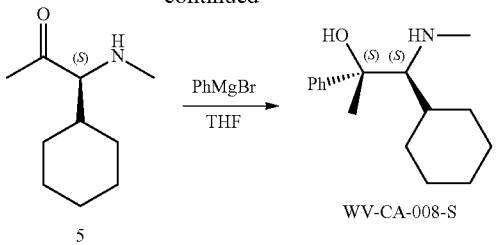

1. Preparation of Compound 2.

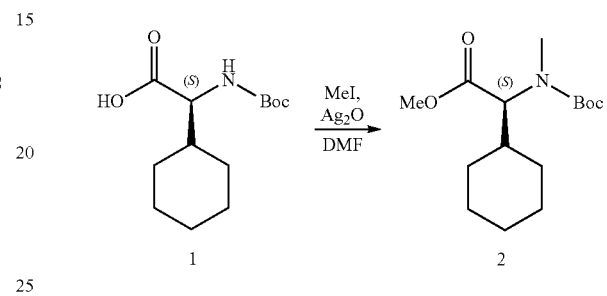

To a solution of compound 1 (20.00 g, 77.72 mmol) in dry DMF (200.00 mL) was added Ag$_2$O (72.04 g, 310.88 mmol) followed by MeI (88.25 g, 621.76 mmol, 38.71 mL) at 20° C. The dark suspension was stirred at 40° C. for 12 hr. TLC showed a new spot was formed. The reaction was detected on LCMS. The reaction was diluted by EtOAc (100 mL) and filtered through celite. The filtrate was washed with sat. NaHCO$_3$ aq. (300 mL*3), dry over Na$_2$SO$_4$, concentrated in vacuo to dryness. The residue was purified by column (Petroleum ether:Ethyl acetate=50/1 to 20/1) to give compound 2 as a colorless oil (13.00 g, 58.61% yield). LCMS: (M+Na+): 308.1. TLC (Petroleum ether:Ethyl acetate=10:1, Color Developing Reagent: I$_2$), R$_f$(material)=0.05, R$_f$(product)=0.50.

2. Preparation of Compound 3.

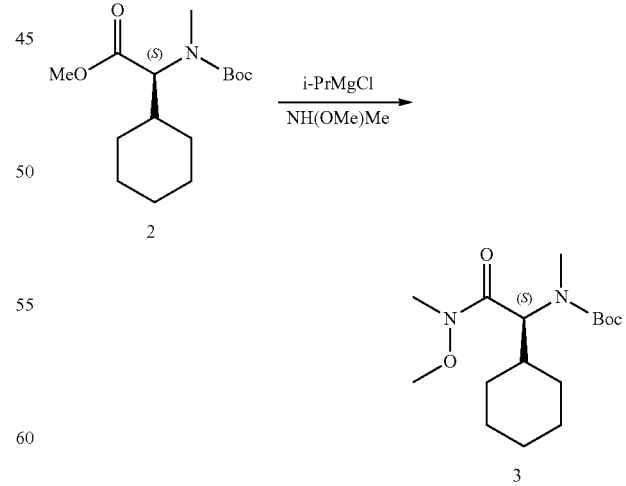

To a stirred solution of compound 2 (13.00 g, 45.55 mmol) and N-methoxymethanamine-hydrochloride (6.66 g, 68.33 mmol) in THF (100.00 mL) at 0° C. was slowly added chloro(isopropyl)magnesium (2 M, 68.33 mL) for 10 minutes under N$_2$. The reaction was turned colorless solution and stirred for another 170 minutes at 20° C. TLC showed compound 2 was consumed and a new spot was detected. The reaction mixture was quenched with sat. NH$_4$Cl aq. (100 mL), extracted with EtOAc (200 mL*3), dried over Na$_2$SO$_4$, filtered and concentrated in vacuo to dryness to give Compound 3 as a colorless oil (12.00 g, 83.79% yield). HPLC purity=95.4%. TLC (Petroleum ether:Ethyl acetate=10:1, Color Developing Reagent: I$_2$), R$_f$ (material) =0.50, R$_f$ (product)=0.10.

3. Preparation of Compound 4.

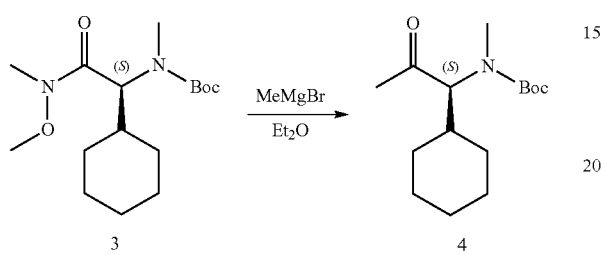

MeMgBr (3 M, 68.38 mL) was added drop-wise to a cooled solution of compound 3 (12.90 g, 41.03 mmol) in Et$_2$O (150.00 mL) at 0° C. The mixture was stirred at 20° C. for 3 hr. TLC showed compound 3 was consumed and one new spot was formed. The resulting mixture was quenched with sat. NH$_4$Cl aq. (200 mL), and extracted with EtOAc (200 mL*3). The combined layers were dried over anhydrous Na$_2$SO$_4$, filtered, and concentrated in vacuo to dryness to give compound 4 (10.50 g, crude) as a colorless oil, which was used directly in the next step. HPLC purity=90.2%. TLC (Petroleum ether:Ethyl acetate=10:1, Color Developing Reagent: I$_2$), R$_f$ (material)=0.10, R$_f$ (product)=0.43.

4. Preparation of Compound 5.

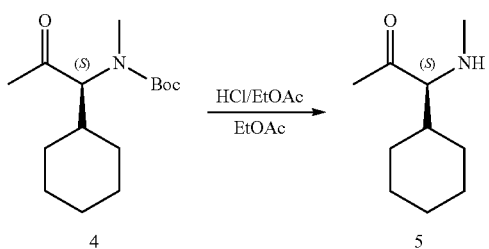

To a solution of compound 4 (10.50 g, 38.98 mmol) in EtOAc (10.00 mL) was added HCl/EtOAc (4 M, 119.96 mL) at 0° C. The mixture was stirred at 0~25° C. for 1 hr. TLC showed the reaction was completed. The reaction mixture was concentrated under reduced pressure at 25° C., and a large amount of white solid precipitated, which was filtered, and the filter cake was dried to give the crude product of compound 5 (6.30 g, crude, HCl salt), which was used in the next step without further purification. TLC (Petroleum ether: Ethyl acetate=3:1, Color Developing Reagent: I$_2$), R$_f$ (material)=0.66, R$_f$ (product)=0.01.

5. Preparation of WV-CA-008-S.

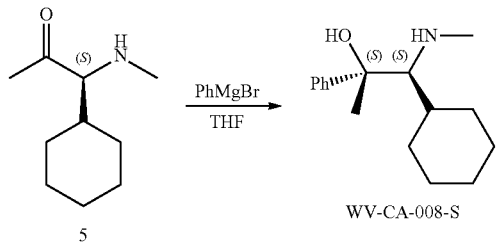

To a suspension of compound 5 (6.30 g, 30.62 mmol, HCl salt) in THF (150.00 mL) was added PhMgBr (3 M, 58.18 mL) at −60° C. The mixture was stirred at −60~0° C. for 3 hr. LCMS showed the reaction was completed. The resulting mixture was quenched with sat. NH4Cl aq. (200 mL), extracted with EtOAc (150 mL*3), dried over anhydrous MgSO$_4$, filtered and concentrated to afford a crude. The crude product was first purified by column chromatography on silica gel (Petroleum ether:Ethyl acetate=1:0, 20:1; 10:1; 5:1) to afford two parts of crude, which were dissolved in HCl/EtOAc (150 mL, 50 mL) respectively, stirred at 0~25° C. for 1 hr, concentrated at 25° C. under reduced pressure until white solid precipitated, filtered and dried to afford the product as a white HCl salt solid (6.3 g), which was combined with another batch (0.8 g) HCl salt and dissolved in water (60 mL), washed with DCM (30 mL). The separated aqueous layer was alkalized with NaOH aq. (2.5 M, 10 mL) to pH ~11, extracted with DCM (80 mL*3). The combined organic layers were washed with brine (60 mL), dried over anhydrous MgSO$_4$, filtered and concentrated under reduced pressure to afford WV-CA-008-S as a white solid (6.00 g, 79.21% yield, 100% purity). $^1$H NMR (400 MHz, CDCl$_3$): δ=7.45 (d, J=7.5 Hz, 2H), 7.29 (t, J=7.5 Hz, 2H), 7.21-7.14 (m, 1H), 2.46 (br. s., 1H), 2.08 (s, 3H), 1.94 (d, J=13.2 Hz, 1H), 1.79-1.60 (m, 4H), 1.46-1.36 (m, 4H), 1.25-0.91 (m, 5H). $^{13}$C NMR (400 MHz, CDCl$_3$): δ=149.38, 127.80, 126.19, 125.61, 74.44, 73.97, 39.20, 38.12, 33.38, 27.41, 26.96, 26.41, 24.58. LCMS: (M+H$^+$): 248.2; 100% purity. Chiral SFC: 100%. TLC (Petroleum ether:Ethyl acetate=1:1, Color Developing Reagent: I$_2$), R$_f$ (material)=0.96, R$_f$ (product)=0.28.

Example 13. Synthesis of WV-CA-008S-dCiBu

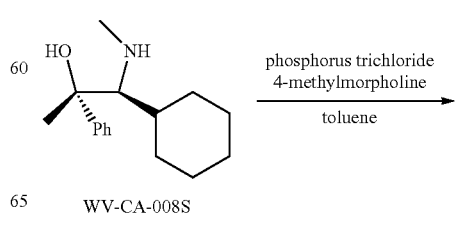

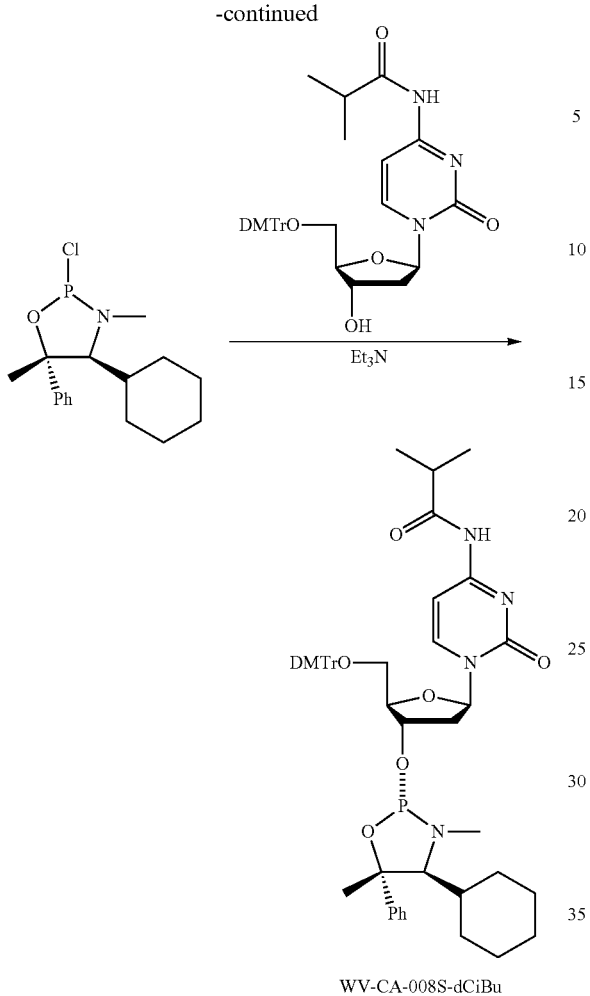

WV-CA-008S-dCiBu (1S, 2S)-1-cyclohexyl-1-(methylamino)-2-phenylpropan-2-ol (1.207 g, 4.88 mmol) was dried by azeotropic distillation with toluene (3×10 mL). A solution of this dried (1S,2S)-1-cyclohexyl-1-(methylamino)-2-phenylpropan-2-ol (1.207 g, 4.88 mmol) and 4-methylmorpholine (1.073 mL, 9.76 mmol) in ether (5 mL) was added to an ice-cold solution of trichlorophosphine (0.426 mL, 4.88 mmol) in ether (5 mL). Reaction mixture was warmed to room temperature, stirred at room temperature for 40 minutes and then filtered under argon. Solvent removal under argon afforded (4S,5S)-2-chloro-4-cyclohexyl-3,5-dimethyl-5-phenyl-1,3,2-oxazaphospholidine as an oil which was used for the next step directly. The nucleoside N-(1-((2R,4S,5R)-5-((bis(4-methoxyphenyl)(phenyl)methoxy)methyl)-4-hydroxytetrahydrofuran-2-yl)-2-oxo-1,2-dihydropyrimidin-4-yl)isobutyramide (1.951 g, 3.25 mmol) was dried by azeotropic distillation first by pyridine (20 mL×1), then by toluene (15 mL×3) and dried under vacuum for 24 hr. This dried compound was dissolved in dry THF (20 mL) followed by the addition of triethylamine (3.17 mL, 22.77 mmol) then cooled to −78° C. A THF solution (20 mL) of the above crude product (4S,5S)-2-chloro-4-cyclohexyl-3,5-dimethyl-5-phenyl-1,3,2-oxazaphospholidine was added dropwise over 10 minutes, then removed cooler bath and gradually warmed to room temperature and stirred at room temperature for 3 hr. The mixture at 0° C. was added sat. NaHCO₃ (50 mL), 1 N Na₂CO₃ (10 mL), and CHCl₃ (200 mL). The organic layer was separated, washed with sat. NaHCO₃ (2×). The combined water layer was re-extracted with CHCl₃ (100 mL), washed with sat. NaHCO₃. The CHCl₃ extract was dried over anhydrous Na₂SO₄, filtered and dried under rotary evaporation under 25° C. to afford the yellowish solid. The crude product was re-dissolved in 5% TEA in 60% EtOAc in hexane (10 mL) loaded onto a short plug of silica gel eluting with 5% TEA 40% EtOAc in hexane to 5% TEA 70% EtOAc in hexane to afford WV-CA-008S-dCiBu as a white solid (2.177 g, 76%). $^1$H NMR (500 MHz, Chloroform-d) δ 8.30 (d, J=7.5 Hz, 1H), 8.21 (s, 1H), 7.45-7.39 (m, 2H), 7.37-7.23 (m, 12H), 7.11 (d, J=7.4 Hz, 1H), 6.88-6.81 (m, 4H), 6.27 (dd, J=6.4, 4.7 Hz, 1H), 4.85 (dq, J=9.0, 5.9 Hz, 1H), 4.16-4.08 (m, 2H), 3.79 (s, 6H), 3.53 (dd, J=10.8, 2.9 Hz, 1H), 3.43 (dd, J=10.7, 3.5 Hz, 1H), 2.82-2.69 (m, 2H), 2.56 (h, J=7.0 Hz, 1H), 2.45 (d, J=11.6 Hz, 2H), 2.30 (ddd, J=14.0, 6.7, 4.8 Hz, 1H), 1.91-0.96 (m, 20H); $^{31}$P NMR (202 MHz, CDCl₃) δ 150.49.

Example 14. Synthesis of WV-CA-011

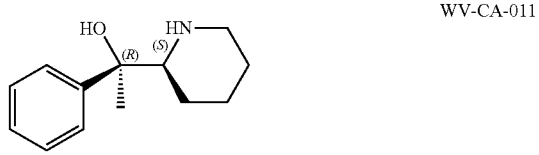

WV-CA-011

General Scheme.

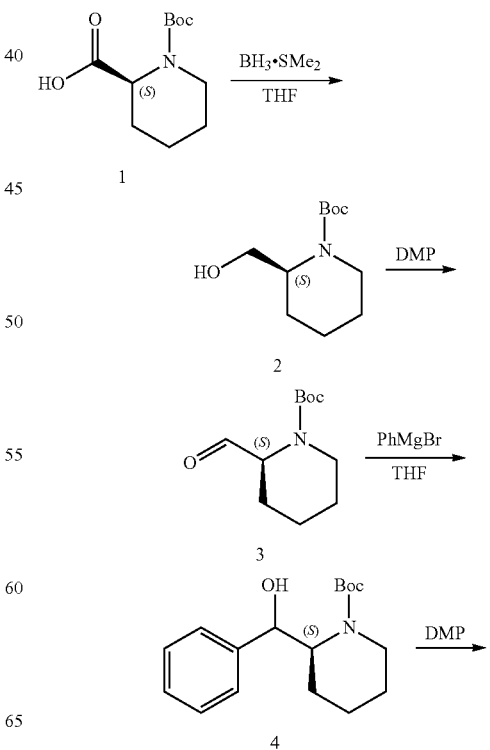

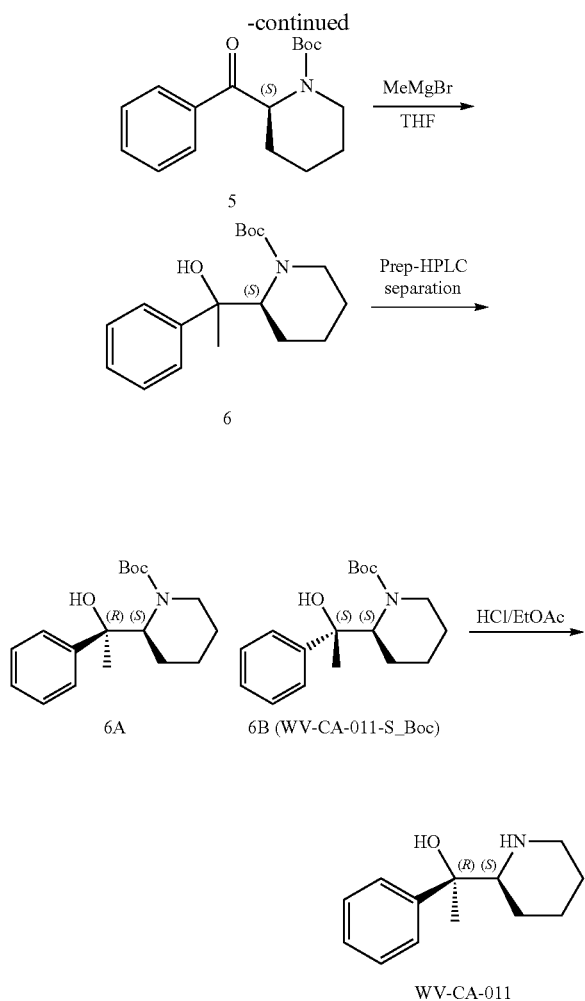

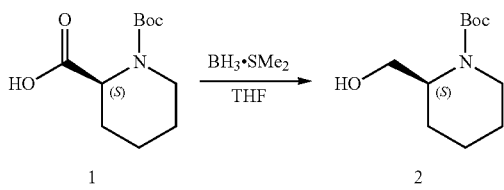

WV-CA-011

1. Preparation of Compound 2.

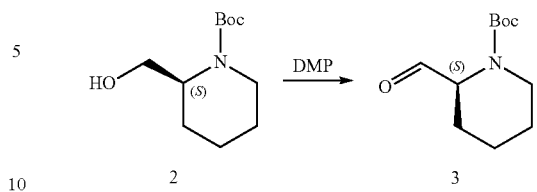

To a solution of BH$_3$-Me$_2$S (10 M, 44.49 mL) in THF (400 mL) was added a solution of compound 1 (51.00 g, 222.45 mmol) in THF (100 mL) at 0° C. The resultant solution was stirred for 1 hr. The reaction mixture was then warmed to 20° C. and stirred for additional 3 hr. TLC showed most of the starting material was consumed. The resulting mixture were cooled to 0° C., and then sat. NaHCO$_3$ aq. (500 mL) was added slowly to quench the reaction, and water (100 mL) was added, and then extracted with EtOAc (200 mL*3). The combined organic extracts were washed with sat. NaHCO$_3$ aq. (1 L) and brine (300 mL), dried over Na$_2$SO$_4$, filtered and concentrated to give compound 2 as a white solid (46.00 g, crude). The material was carried forward without additional purification. TLC (Petroleum ether/EtOAc=1:1) R$_f$=0.43.

2. Preparation of Compound 3.

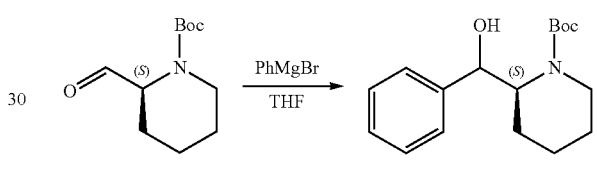

To a solution of compound 2 (46.00 g, 213.67 mmol) in DCM (500 mL) was added DMP (99.69 g, 235.04 mmol, 72.77 mL) in 5 portions to not allow the reaction to exceed 20° C. After the addition, the mixture was stirred at 20° C. for 1 hr. TLC showed the starting material was consumed. A solution of NaHCO$_3$/Na$_2$SO$_3$ (V/V=3:2, 2 L) was added and extracted with DCM (1 L*2). The combined organic layers were washed with brine (200 mL*2), dried over Na$_2$SO$_4$, filtered and concentrated to get the crude which was purified by silica gel chromatography (petroleum ether/EtOAc from 30:1 to 10:1) to get compound 3 as a yellow oil (33.00 g, 72.42%). TLC (petroleum ether/EtOAc=5:1) R$_f$=0.56.

3. Preparation of Compound 4.

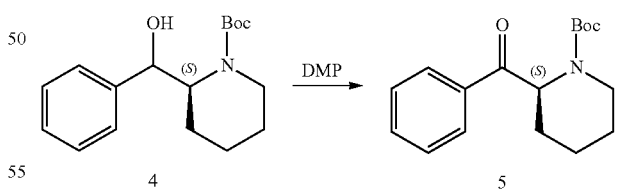

To a solution of compound 3 (33.00 g, 154.73 mmol) in THF (400 mL) was added bromo(phenyl)magnesium (3 M, 51.58 mL) at −60° C. The mixture was stirred at 0° C. for 1.5 hr. TLC showed the starting material was consumed. Sat. NH$_4$Cl (200 mL) was added and extracted with EtOAc (300 mL*2). The combined organic layers were washed with brine (500 mL), dried over Na$_2$SO$_4$, filtered and concentrated to get the crude. The residue was purified by MPLC (petroleum ether/EtOAc from 10:1 to 5:1) to get compound 4 as a yellow solid (28.00 g, 62.10%). TLC (petroleum ether/EtOAc=10:1) R$_f$=0.51.

4. Preparation of Compound 5.

To a solution of compound 4 (28.00 g, 96.09 mmol) in DCM (300 mL) was added DMP (44.83 g, 105.70 mmol) slowly at 0° C., and then the mixture was stirred at 20° C. for 1 hr. TLC showed the starting material was consumed. A solution of NaHCO$_3$/Na$_2$SO$_3$ (V/V=3/2, 2 L) was added and extracted with DCM (1 L*2). The combined organic layers were washed with brine (200 mL*2), dried over Na$_2$SO$_4$, filtered and concentrated to get compound 5 as a white solid (28.00 g, crude). The mixture was used directly without any purification. TLC (petroleum ether/EtOAc=5:1) R$_f$=0.65.

5. Preparation of Compound 6.

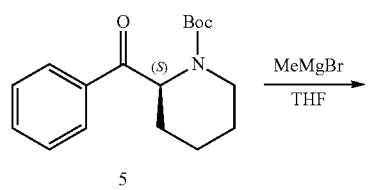

To a solution of compound 5 (28.00 g, 96.76 mmol) in THF (400 mL) was added bromo(methyl)magnesium (3 M, 96.76 mL) at 0° C. under N$_2$. The mixture was stirred at 0° C. for 2 hr. TLC showed most of starting material was consumed and a new spot was observed. Sat. NH$_4$Cl aq. (300 mL) was added and extracted with EtOAc (100 mL*3). The combined organic layers were washed with brine (500 mL), dried over Na$_2$SO$_4$, filtered and concentrated to get give a residue, which was purified by MPLC (petroleum ether/EtOAc=10:1 to 5:1) to get compound 6 as a yellow oil (16.00 g, 54.14%). 0.5 g of the crude product was purified by prep-HPLC (column: Waters Xbridge 150*25 5u; mobile phase: [Neu-ACN]; B %: 40%-60%, 12 min) to get compound 6A. TLC (petroleum ether/EtOAc=5:1) R$_f$=0.43 SFC purity: 68% ee.

5. Preparation of Compound 6A and 6B (WV-CA-011-S_Boc)

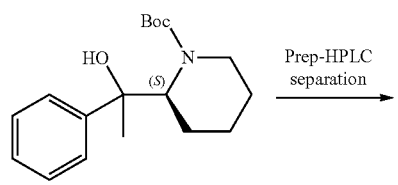

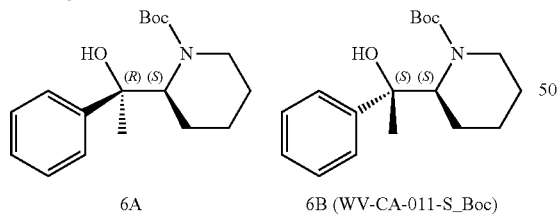

The crude of compound 6 was first purified by prep-HPLC (column: Phenomenex Gemini C18 250*50 mm*10 immobile phase: [water (10 mM NH4HCO$_3$)-ACN]; B %: 45%-70%, 30 min) to afford compound 6A as yellow solid (1.60 g, 10.67%) and 6B (WV-CA-011-S_Boc) as yellow solid (9.90 g, 66.01%). Compound 6A was further purified by chiral Prep-HPLC (column: OD (250 mm*30 mm, 5 m); mobile phase: [Base-IPA]; B %: 18%-18%, min)) to get the pure compound 6A as a white solid (780.00 mg, 52.02%). $^1$H NMR (400 MHz, CDCl$_3$): δ=7.49 (d, J=6.6 Hz, 2H), 7.35-7.27 (m, 2H), 7.22 (d, J=4.9 Hz, 1H), 5.32-5.15 (m, 1H), 4.04 (br. s, 1H), 3.69 (br. s, 1H), 3.19 (br. s, 1H), 1.76 (br. s, 1H), 1.66-1.46 (m, 3H), 1.38 (br. s, 9H). $^{13}$C NMR (101 MHz, CDCl$_3$): δ=157.84, 146.86, 127.71, 126.58, 125.79, 80.14, 78.33, 63.55, 42.11, 28.26, 24.68, 23.80, 23.36, 20.23. LCMS: (M (cyclic carbamate)+H$^+$): 232.1. LCMS purity=98.4%. SFC purity: 66.9%. 6A: SFC purity: 99.9%.

6. Preparation of WV-CA-011.

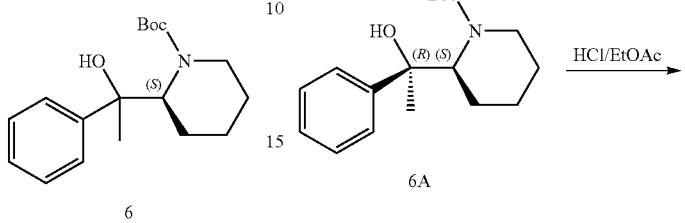

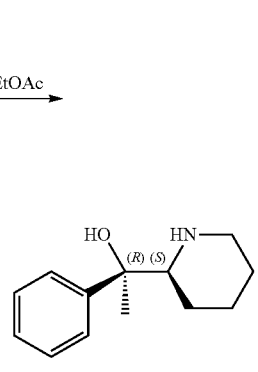

To a solution of compound 6A (760.00 mg, 2.49 mmol) in EtOAc (10 mL) was added HCl/EtOAc (100 mL, 4N) at 0° C., and then the mixture was stirred at 15° C. for 2 hr. TLC showed the starting material was consumed. The mixture was concentrated under the reduced pressure. Water (5 mL) was added and extracted with Petroleum ether/EtOAc (3:1, 10 mL*2). The combined organic extracts were washed water (3 mL). The aqueous phase was combined and added sat. Na$_2$CO$_3$ aq. until pH>11. The mixture was extracted with DCM (15 mL*3). The combined organic layers were washed with brine (30 mL), dried over Na$_2$SO$_4$, filtered and concentrated to get WV-CA-011 as a yellow oil (340 mg, 66.51%). δ=7.43-7.39 (m, 2H), 7.34 (t, J=7.5 Hz, 2H), 7.27-7.22 (m, 1H), 3.11 (td, J=2.0, 12.3 Hz, 1H), 2.72-2.56 (m, 2H), 1.76 (d, J=12.8 Hz, 1H), 1.57 (s, 3H), 1.51 (t, J=14.1 Hz, 2H), 1.38-1.09 (m, 2H), 1.05-0.87 (m, 1H). $^{13}$C NMR (101 MHz, CDCl$_3$): δ=145.14, 127.82, 126.50, 125.67, 74.67, 65.72, 47.04, 27.23, 26.71, 26.57, 24.7. LCMS: (M+H+): 206.1. TLC (Petroleum ether/EtOAc=5:1) R$_f$=0. LCMS purity=100.0%.

Example 15. Synthesis of WV-CA-011-S

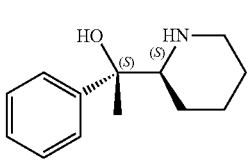

WV-CA-011-S

General Scheme.

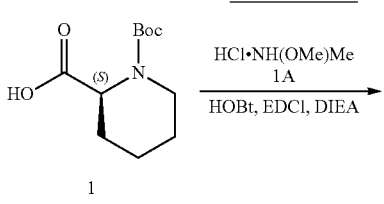

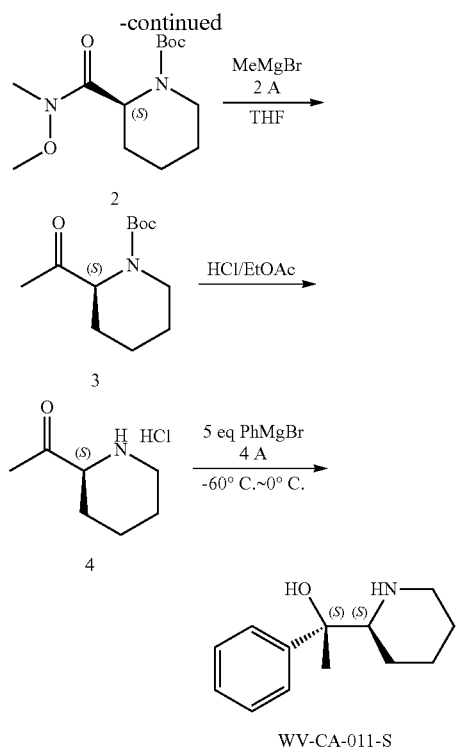

1. Preparation of Compound 2.

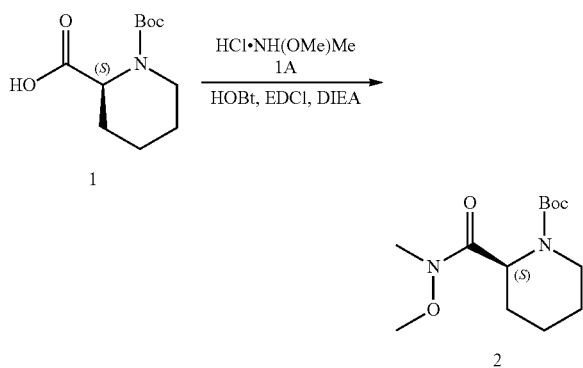

To a stirred solution of compound 1 (10.00 g, 43.62 mmol) and compound 1A (5.53 g, 56.71 mmol) in DMF (100.00 mL) was added HOBt (7.66 g, 56.71 mmol), EDCI (10.87 g, 56.71 mmol) and DIEA (11.27 g, 87.24 mmol) in the above order at 0° C. The reaction mixture was stirred for 2 hr at 0° C., and then the mixture was stirred at 20° C. for another 12 hr. TLC and LCMS showed the starting material was consumed. The reaction was quenched with water (100 mL) and extracted with EtOAc (100 mL*2), and the combined organic was washed with brine (200 mL*2), dried over Na₂SO₄, filtered and concentrated to get the crude. The residue was purified by silica gel chromatography (petroleum ether/ethyl acetate=3:1) to get compound 2 as a yellow oil (10.40 g, 87.55%). ¹H NMR (400 MHz, CDCl3): δ=4.91-5.05 (d, J=8.0 Hz, 1H), 3.89 (s, 1H), 3.75 (s, 3H), 3.47 (s, 1H), 3.17 (s, 3H), 1.96-1.99 (m, 1H), 1.57-1.68 (m, 3H), 1.43 (s, 9H). LCMS: (M+Na⁺): 295.1. TLC (Petroleum ether/Ethyl acetate=3:1) R$_f$=0.43.

2. Preparation of Compound 3.

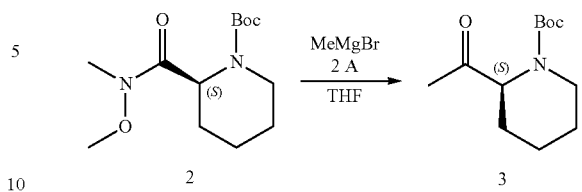

A solution of compound 2 (10.00 g, 36.72 mmol) in THF (100.00 mL) was added to 2A (3 M, 61.20 mL) at 0° C. After addition the mixture was stirred at 0° C. for 2 hrs. TLC showed the material remained and a new point appeared. The reaction was quenched with aqueous NH₄Cl (100 land extracted with EtOAc (100 mL*3). The combined organic layers were washed with brine (30 mL), dried over anhydrous Na₂SO₄, filtered and concentrated to get the crude. The crude product was purified by silica gel chromatography (petroleum ether/ethyl acetate=3:1) to get compound 3 as a yellow oil (7.50 g, 89.87%). LCMS: (M+Na⁺): 250.1. TLC (petroleum ether/ethyl acetate=3:1) R$_f$=0.47.

3. Preparation of Compound 4.

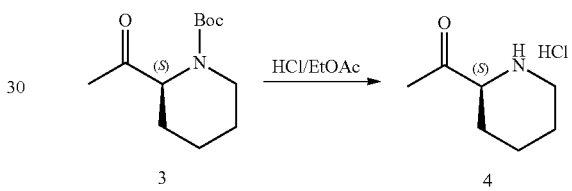

To a solution of compound 3 (7.50 g, 33.00 mmol) was added HCl/EtOAc (4 M, 99.99 mL) at 5° C., then the mixture was stirred at 20° C. for 1 hr. TLC showed the starting material was consumed. Concentrated the mixture to move most of the solvents and filtered, the filter cake was dried to get compound 4 (5.00 g, 92.58%) as a white solid. ¹H NMR: (400 MHz, MeOD) δ=4.07-4.10 (d, J=12.0 Hz, 1H), 3.41-3.44 (d, J=12.0 Hz, 1H), 3.01-3.01 (t, 1H), 2.61 (s, 3H), 2.43-2.47 (m, 1H), 1.90-1.99 (m, 2H), 1.57-1.68 (m, 3H). TLC (petroleum ether/ethyl acetate=3:1) R$_f$=0.

3. Preparation of WV-CA-011-S.

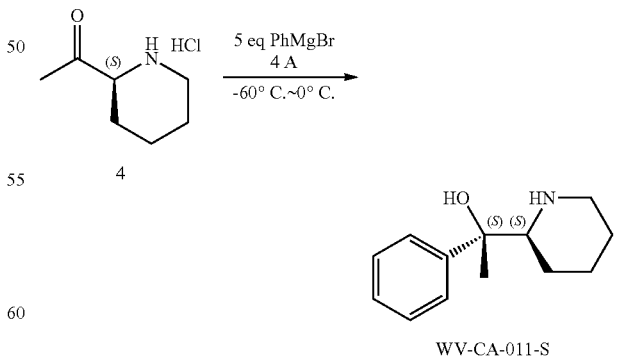

To a solution of compound 4A (3 M, 50.92 mL) in THF (100.00 mL) was added compound 4 (5.00 g, 30.55 mmol) at −60° C. for 0.5 hr, and then the mixture was stirred at 0° C. for 1 hr. LCMS showed the start material was consumed.

The mixture was poured into NH₄Cl (200 mL) and extracted with EtOAc (100 mL), and then the mixture was extracted with DCM/MeOH (10:1, 200 mL*3), the combined organic layers were dried over anhydrous Na₂SO₄, filtrated and concentrated to get the crude. The crude was added HCl/EtOAc (4 N, 100 mL) and stirred for 1 hr, and then concentrated to remove most of solvent, and water (20 mL) was added, extracted with DCM (30 mL*3). The aqueous phase was adjusted to pH=11 with NaOH (2N), and then extracted with DCM (50 mL*3). The combined organic layers were dried over anhydrous Na₂SO₄, filtrated and concentrated to get the crude mixture. The residue was purified by column chromatography on silica gel (DCM/MeOH, 50:1 to 30:1) to get WV-CA-011-S as a yellow solid (1.00 g, 15.94%). ¹H NMR (400 MHz, CDCl₃): δ=7.48-7.50 (m, 2H), 7.373-7.38 (m, 2H), 7.26-7.28 (m, 1H), 3.75 (br. s, 1H), 2.82-2.96 (m, 1H), 2.79-2.81 (m, 1H), 2.54-2.57 (t, 1H), 1.58-1.89 (m, 2H), 1.47-1.55 (m, 2H), 1.43 (s, 3H), 1.32-1.39 (m, 2H). ¹³C NMR (125.7 MHz, CDCl₃): δ=147.67, 128.20, 126.61, 125.11, 75.02, 63.94, 46.76, 25.83, 25.61, 25.22, 24.46. LCMS: (M+H⁺): 206.2. SFC purity=100.0%.

Example 16. Synthesis of WV-CA-011S-dCiBu

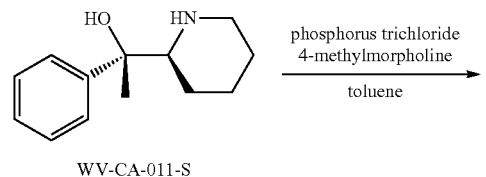

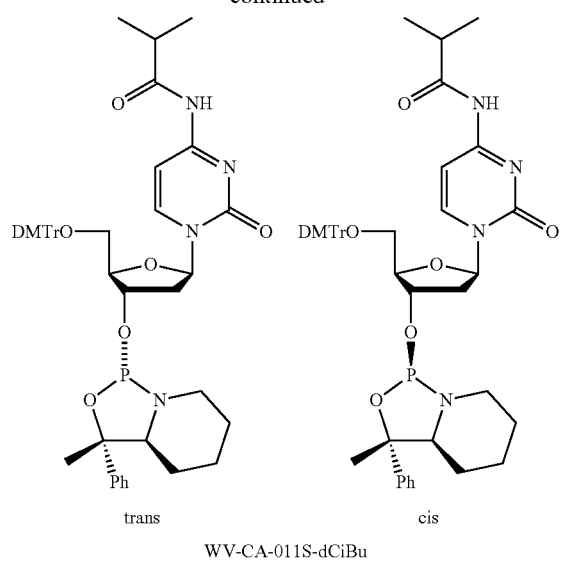

WV-CA-011S-dCiBu

Using WV-CA-011S as starting material, the title compound (1.498 g, 67.4%) as a white solid was prepared analogously to WV-CA-008S-dCiBu. ¹H NMR (500 MHz, Chloroform-d) δ 8.36 (d, J=7.4 Hz, 1H), 8.15 (s, 1H), 7.48-7.21 (m, 14H), 7.13 (d, J=7.5 Hz, 1H), 6.90-6.79 (m, 4H), 6.24 (dd, J=6.6, 4.0 Hz, 1H), 4.94 (dq, J=8.9, 6.5 Hz, 1H), 4.17-4.08 (m, 2H), 3.81 (s, 6H), 3.50 (td, J=12.8, 11.8, 3.0 Hz, 1H), 3.42 (dd, J=10.9, 3.3 Hz, 1H), 3.24-3.16 (m, 1H), 2.92 (ddd, J=11.2, 7.9, 2.8 Hz, 1H), 2.82-2.65 (m, 2H), 2.59-2.53 (m, 1H), 2.37 (ddd, J=13.9, 6.8, 4.1 Hz, 1H), 1.90-1.18 (m, 14H). ³¹P NMR (202 MHz, CDCl₃) δ 148.00 (95%, trans), 139.31 (5%, cis).

Example 17. Synthesis of WV-CA-012 and WV-CA-045 and WV-CA-046

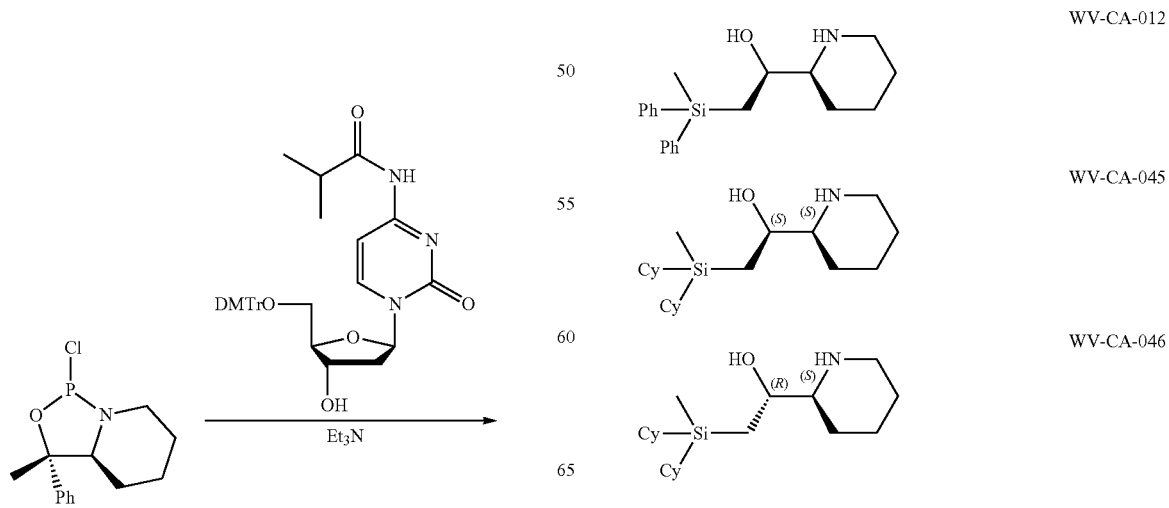

General Scheme.
Scheme 1

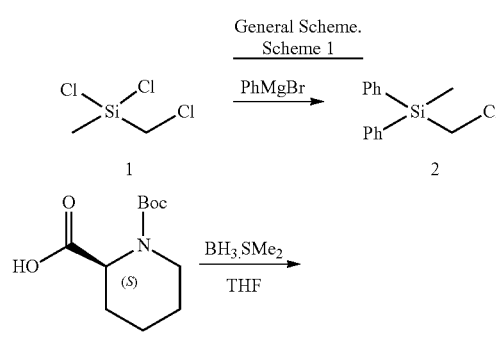

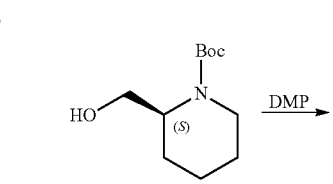

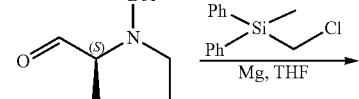

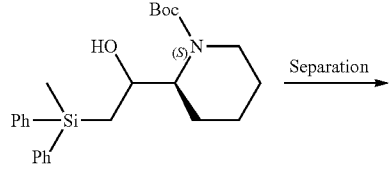

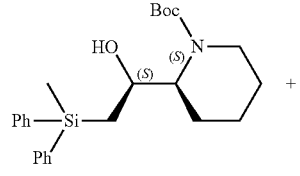

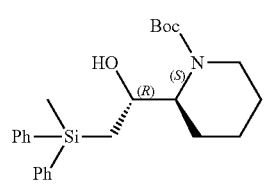

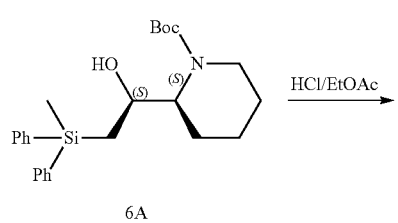

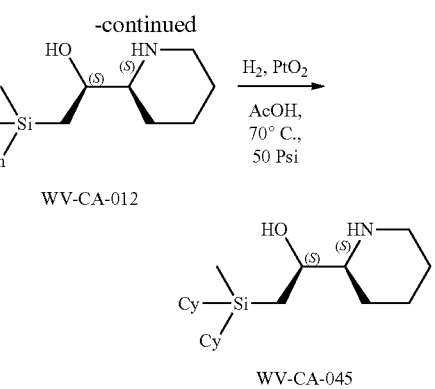

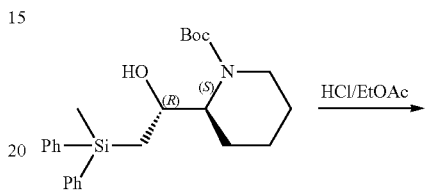

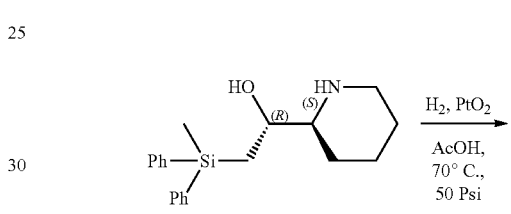

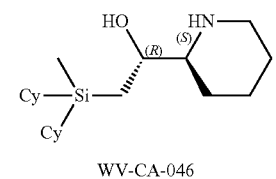

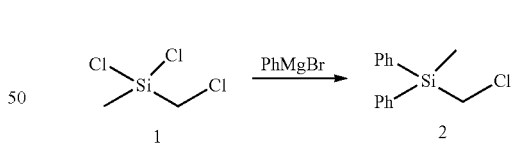

1. Preparation of Compound 2.

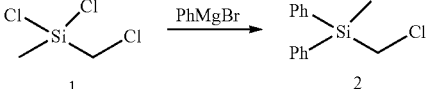

To a solution of bromo(phenyl)magnesium (3 M, 470.92 mL, 2.20 eq.) in THF (1.00 L) was added compound 1 (105.00 g, 642.16 mmol, 1.00 eq.) at 30° C.-60° C. After addition, the mixture was stirred 60° C. for 3 hr. TLC (Petroleum ether, $R_f$=0.7) showed the starting material was consumed. After the mixture was cooled to 30° C., saturated NH$_4$Cl (1000 mL) aqueous was added at 30-50° C., and then extracted with EtOAc (1000 mL*2). The combined organic layers were washed with brine (1 L), dried over Na$_2$SO$_4$, filtered and concentrated to get the crude. The residue was purified by silica gel chromatography (Petroleum ether) to get compound 2 (120.00 g, 486.20 mmol, 37.86% yield) and 160 g crude as a yellow oil.

2. Preparation of Compound 4

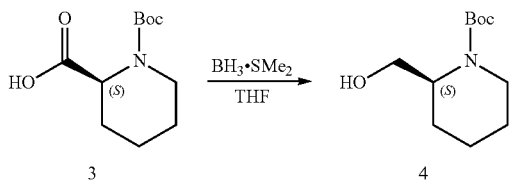

A solution of BH₃-Me₂S (10 M, 43.62 mL, 2.00 eq.) in THF (400.00 mL) was added to (2S)-1-tert-butoxycarbonylpiperidine-2-carboxylic acid (50.00 g, 218.08 mmol, 1.00 eq.) dissolved in THF (100 mL) at 0° C., and the resultant solution was stirred for 1 hr, the reaction mixture was then warmed to 20° C. and stirred for an additional 3 hr. TLC (Petroleum ether:Ethyl acetate=1:1) showed most of the starting material was consumed. The reaction mixture was cooled to 0° C. Sat. NaHCO₃ (500 mL) aqueous was added slowly to quench excess reagent, and water (100 mL) was added to dissolve the precipitated salts. The resulting mixture was then extracted with EtOAc (200 mL*3), and the combined organic extracts were washed with saturated aqueous NaHCO₃ (1000 mL*1) and brine (300 mL), dried Na₂SO₄, filtered and concentrated to give compound 4 (43.00 g, crude) as a white solid, which was used directly without additional purification.

3. Preparation of Compound 5.

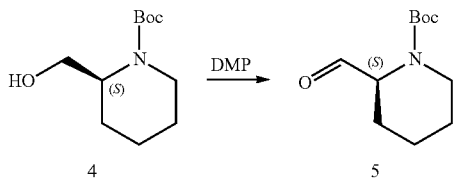

To a solution of compound 4 (28.00 g, 130.06 mmol, 1.00 eq.) in DCM (200.00 mL) was added DMP (60.68 g, 143.06 mmol, 44.29 mL, 1.10 eq.) in five portions under 20° C. The mixture was stirred at 20° C. for 1 hr. TLC (Petroleum ether:Ethyl acetate=3:1) showed the starting material was consumed. NaHCO₃:Na₂SO₃ (3:1, 2 L) was added and extracted with DCM (1000 mL*2). The combined organic layers were washed with brine (200 mL*2), dried over Na₂SO₄, filtered and concentrated to get the crude. The residue was purified by silica gel chromatography (Petroleum ether:Ethyl acetate=30:1 to 10:1) to afford compound 5 (17.00 g, 79.71 mmol, 61.29% yield) as a yellow oil.

4. Preparation of Grignard Reagent.

Mg (8.18 g, 336.29 mmol, 1.00 eq.) was taken up in THF (60.00 mL), and then a solution of compound 2 (83.00 g, 336.29 mmol, 1.00 eq.) in THF (240.00 mL) was added dropwise to the Mg suspension (activated with I₂ (one crystal), and 0.5 mL of 1, 2-dibromoethane, with stirring at 60° C.) keeping the temperature between 53-60° C. After completed the addition, the mixture was then stirred for 2 h at 60° C. until the Mg was disappeared, and then at 20° C. for additional 0.5 h. TLC (Petroleum ether:Ethyl acetate=50:1) showed the starting material was consumed and a new spot was found. The mixture was used directly without any purification.

5. Preparation of Compound 6A and compound 6B.

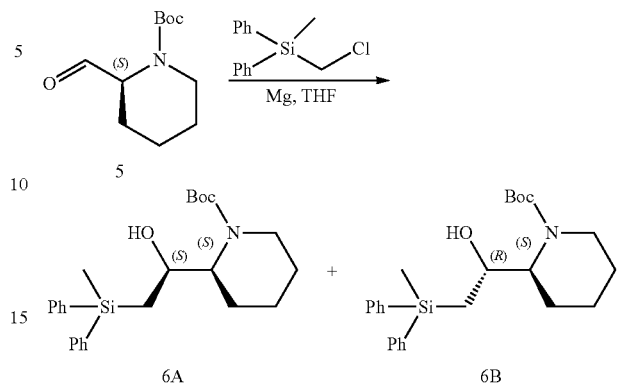

A solution of compound 5 (17.00 g, 79.71 mmol, 1.00 eq.) in THF (200.00 mL) was added dropwise the prepared Grignard reagent (1 M, 159.42 mL, 2.00 eq.) at 0° C. under N₂. After completed the addition, the mixture was stirred at 0° C. for 0.5 hr, and then the mixture was warm to 20° C. and stirred for 12 hr. TLC (Petroleum ether:Ethyl acetate=10:1) showed most of the starting material was consumed. Sat. NH₄Cl (500 mL) aq. was added and extracted with EtOAc (100 mL*3). The combined organic layers were washed with brine (100 mL), dried over Na₂SO₄, filtered and concentrated to get the crude. The residue was purified by silica gel chromatography ((Petroleum ether:Ethyl acetate, 100:1 to 10:1) to get compound 6A (4 g, crude) a yellow oil and compound 6B (2.60 g) as white solid, and 15 g mixture.

6. Preparation of WV-CA-012.

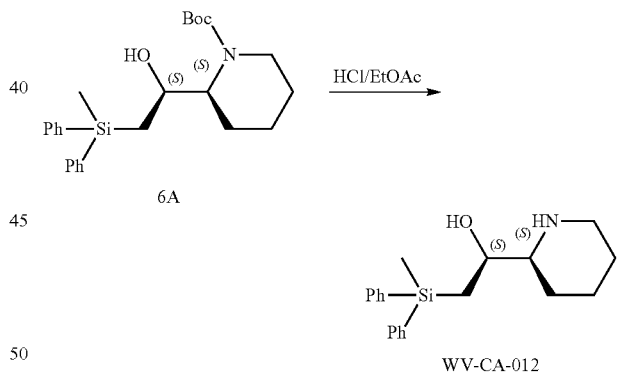

To a solution of compound 6A ((4.00 g, 9.40 mmol, 1.00 eq.) in HCl/EtOAc (4 M, 100.00 mL), the mixture was stirred at 20° C. for 3 hr. TLC (Petroleum ether:Ethyl acetate=5:1) showed the starting material was consumed. The mixture was concentrated to remove most of the solvent and filtered. The filter cake was dried to get the crude. The residue was dissolved in H₂O (5 mL) then aqueous Na₂CO₃ was added to adjust pH=11, extracted with DCM (20 mL*3), dried over Na₂SO₄, filtered and concentrated to get WV-CA-012 (1.60 g, 4.92 mmol, 52.29% yield) as a white solid. ¹H NMR (400 MHz, CDCl₃) δ 7.56 (dt, J=6.7, 2.3 Hz, 1H), 7.44-7.29 (m, 1H), 3.59-3.49 (m, 1H), 3.03 (d, J=11.5 Hz, 1H), 2.52-2.29 (m, 3H), 2.23 (brs, 1H), 1.77 (d, J=8.5 Hz, 1H), 1.67 (d, J=12.5 Hz, 1H), 1.59-1.51 (m, 1H), 1.46-1.23 (m, 5H), 1.07 (d, J=7.5 Hz, 1H), 0.68 (s, 3H).

7. Preparation of WV-CA-045.

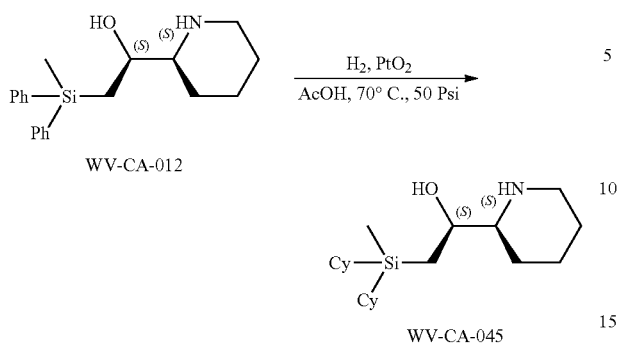

To a solution of WV-CA-012 (3.00 g, 9.22 mmol, 1.00 eq.) in AcOH (100.00 mL) was added PtO₂ (1.51 g, 6.64 mmol, 0.72 eq.). The mixture was stirred at 70° C. for 14 hr under 50 Psi of H₂. LCMS showed the starting material was remained, and then PtO₂ (1.50 g, 6.61 mmol, 0.72 eq.) was additionally added and the mixture was stirred for another 12 hr. LCMS showed the starting material was consumed. The mixture was filtered, and the filter cake was washed with AcOH (100 mL) and dried. The residue was dissolved in H₂O (15 mL), and aqueous Na₂CO₃ (aq.) was added until pH>10, extracted with DCM (20 mL*3), dried over Na₂SO₄, filtered and concentrated to get the crude. The residue was purified by silica gel chromatography (DCM:MeOH=30:1 to 10:1) to afford WV-CA-045 (1.30 g, 3.85 mmol, 41.76% yield) as a yellow oil. ¹H NMR (400 MHz, CDCl₃) δ 3.53-3.39 (m, 1H), 3.11 (d, J=11.5 Hz, 1H), 2.64-2.50 (m, 1H), 2.32-2.23 (m, 1H), 1.90-1.51 (m, 5H), 1.40-1.07 (m, 4H), 0.86-0.59 (m, 1H), −0.04 (s, 3H).

8. Preparation of WV-CA-045.

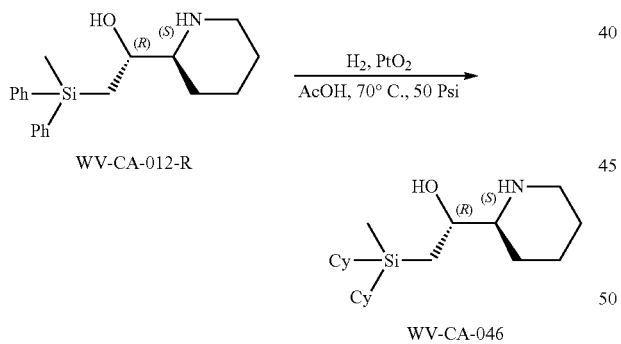

To a solution of WV-CA-012-R (3.20 g, 9.83 mmol, 1.00 eq.) in AcOH (100.00 mL) was added PtO₂ (1.6 g). The mixture was stirred at 70° C. for 14 hr under 50 Psi of H₂. LCMS showed the starting material was remained, and then PtO₂ (1.6 g) was additionally added, and the mixture was stirred for another 12 hr. LCMS showed the starting material was consumed. The mixture was filtered, and the filter cake was washed with AcOH (100 mL) and dried. The residue was dissolved in H₂O (15 mL) and then aqueous Na₂CO₃ (aq.) was added until pH>10, extracted with DCM (20 mL*3), dried over Na₂SO₄, filtered and concentrated to get the crude. The residue was purified by silica gel chromatography (DCM:MeOH=30:1 to 10:1) to afford WV-CA-046 (1.20 g, 3.55 mmol, 36.16% yield) as a yellow oil. ¹H NMR (400 MHz, CDCl₃) δ 3.73-3.61 (m, 1H), 3.12 (d, J=11.5 Hz, 1H), 2.74-2.64 (m, 1H), 2.52-2.43 (m, 1H), 1.91-1.53 (m, 18H), 1.45-1.07 (m, 14H), 0.81-0.65 (m, 4H), −0.04 (s, 3H).

Example 18. Synthesis of WV-CA-012-R

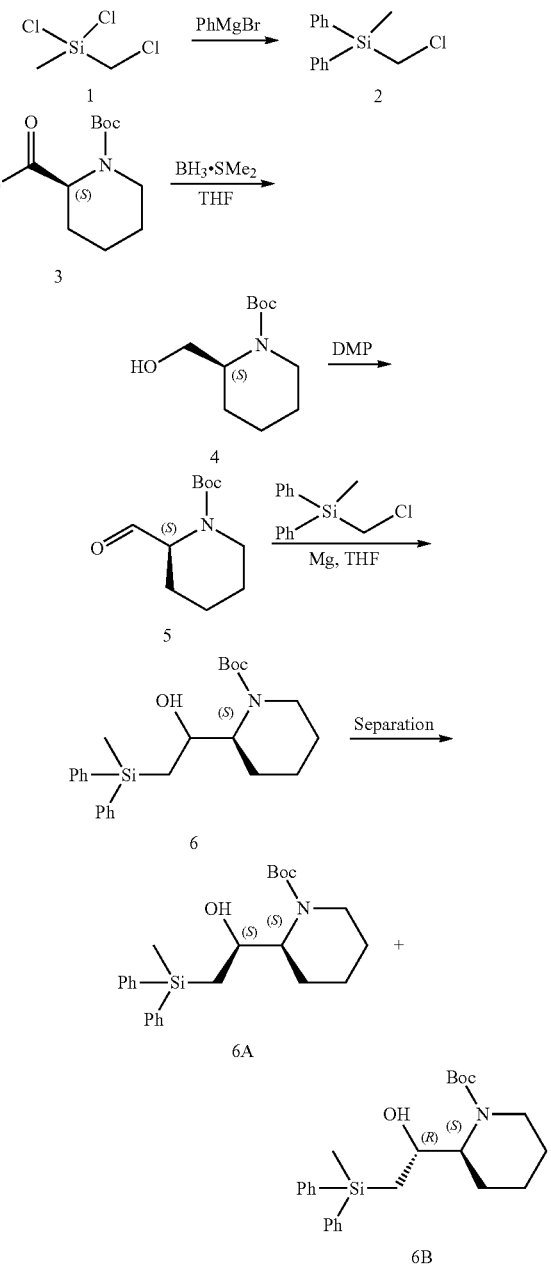

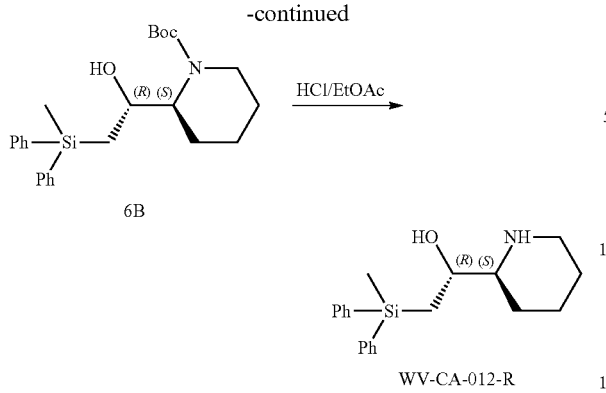

6B

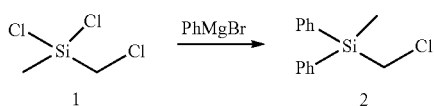

WV-CA-012-R

1. Preparation of Compound 2.

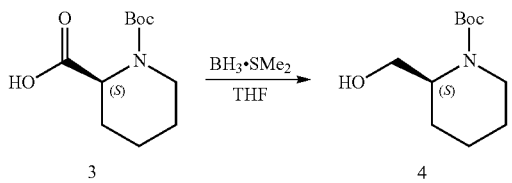

To a solution of bromo(phenyl)magnesium (3 M, 224.25 mL) in THF (270.00 mL) was added dropwise compound 1 (50.00 g, 305.79 mmol) at 30° C.-60° C. After addition, the mixture was stirred 60° C. for 3 hr. TLC showed the starting material was consumed. After the mixture was cooled to 30° C. aqueous NH$_4$Cl (800 mL) was added at 30-50° C. then extracted with EtOAc (200 mL*2), the combine organic was washed with brine (1 L), dried over Na$_2$SO$_4$, filtered and concentrated to get the crude. The residue was purified by silica gel chromatography (Petroleum ether) to get compound 2 as a yellow oil (70.00 g, 92.75%). $^1$H NMR (400 MHz, CDCl$_3$): δ=7.69-7.56 (m, 4H), 7.54-7.35 (m, 6H), 3.30 (s, 2H), 0.81-0.69 (m, 3H). TLC (Petroleum ether: EtOAc=1:0) R$_f$=0.7.

2. Preparation of Compound 4.

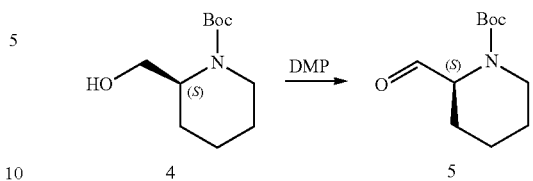

A solution of BH$_3$-Me$_2$S (10 M, 8.72 mL) in THF (100.00 mL) was added compound 3 (10.00 g, 43.62 mmol) dissolved in THF (20 mL) at 0° C. and the resultant solution was stirred for 1 hr, and then the reaction mixture was warmed to 20° C. and stirred for an additional 3 hr. TLC and LCMS showed most of the starting material was consumed. The reaction contents were cooled to 0° C., sat. aqueous NaHCO$_3$ (100 mL) was added slowly to quench excess reagent, and water (100 mL) was added to dissolve the precipitated salts. The crude reaction contents were then extracted with EtOAc (4*50 mL), and the combined organic extracts were washed with sat. aqueous NaHCO$_3$ (1×100 mL) and brine (300 mL), dried Na$_2$SO$_4$, filtered and concentrated to give the crude. This material was carried forward without additional purification to get compound 4 as a white solid (8.50 g, 90.51%). TLC (Petroleum ether/Ethyl acetate=1:1) Rf=0.43. LCMS: (M+Na+): 238.3.

3. Preparation of Compound 5.

To a solution of compound 4 (8.50 g, 39.48 mmol) in DCM (100.00 mL) was added DMP (18.42 g, 43.43 mmol) in 5 portions to not allow the temperature exceed to 20° C., and then the mixture was stirred at 20° C. for 1 hr. TLC showed the starting material was consumed. NaHCO$_3$: Na$_2$SO$_3$ (1:1, 200 mL) was added and extracted with DCM (100 mL*2), the combined organic was washed with brine (200 mL*2), dried over Na$_2$SO$_4$, filtered and concentrated to get the crude. The residue was purified by silica gel chromatography (Petroleum ether:Ethyl acetate=5:1) to get compound 5 as a white solid (8.00 g, 95.01%). TLC (Petroleum ether/Ethyl acetate=3:1) R$_f$=0.56.

4. Preparation of Grignard Reagent.

Mg (1.97 g, 81.03 mmol) was taken up in THF (8.00 mL) then a solution of compound 2 (20.00 g, 81.03 mmol) in THF (25.00 mL) was added to the Mg suspension (activated with I$_2$ (one crystal), and 0.5 mL of 1,2-dibromoethane) with stirring at 60° C.) in a dropwise keeping the temperature between 53-60° C. After complete addition, the mixture was then stirred for 2 h at 60° C. until the Mg was disappeared then at 20° C. for 0.5 hr. TLC (Petroleum ether:Ethyl acetate=50:1) showed the starting material was consumed and a new spot was found. The mixture was used directly without any purification.

5. Preparation of Compound 6A and Compound 6B.

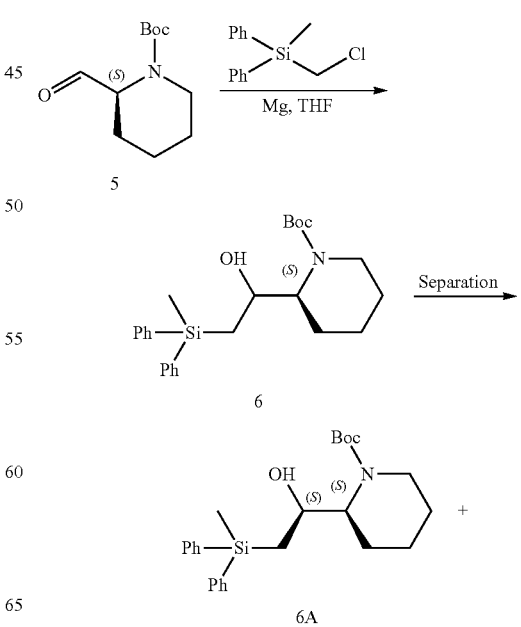

-continued

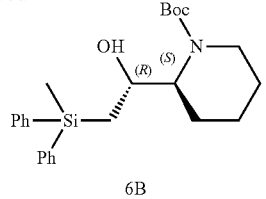

6B

A solution of compound 5 (8.00 g, 37.51 mmol) in THF (100.00 mL) was added the prepared Grignard reagent (1 M, 63.39 mL) at 0° C. under $N_2$. After complete addition, the mixture was stirred at 0° C. for 0.5 hr, then the mixture was warmed to 20° C. for 12 hr. TLC showed most of the starting material was consumed. $NH_4Cl$ (50 mL) was added and extracted with EtOAc (50 mL*3), the combined organic was washed with brine (100 mL) dried over $Na_2SO_4$, filtrated and concentrated to get the crude. The residue was purified by silica gel chromatography ((Petroleum ether:Ethyl acetate, from 100:1 to 10:1) to get compound 6A as a yellow oil (2.50 g, 5.87 mmol, crude) and compound 6B a white solid (1.30 g, 8.14%). Compound 6A: $^1$H NMR (400 MHz, $CDCl_3$): δ=7.61-7.51 (m, 4H), 7.40-7.31 (m, 6H), 4.10-3.91 (m, 2H), 2.80 (m, 1H), 1.83-1.49 (m, 7H), 1.44 (s, 9H), 1.35-1.15 (m, 3H), 0.70 (s, 3H). TLC (Petroleum ether/Ethyl acetate=10:1) $R_f$=0.55. Compound 6B: $^1$H NMR (400 MHz, $CDCl_3$): δ=7.58-7.51 (m, 4H), 7.38 (m, 6H), 4.14-4.06 (m, 1H), 3.98-3.89 (m, 2H), 2.59 (t, J=12.3 Hz, 1H), 1.95 (d, J=4.0 Hz, 1H), 1.59-1.49 (m, 7H), 1.47 (s, 9H), 1.45-1.26 (m, 3H), 0.67 (s, 3H). TLC (Petroleum ether/Ethyl acetate=10:1) $R_f$=0.31.

6. Preparation of WV-CA-012-R.

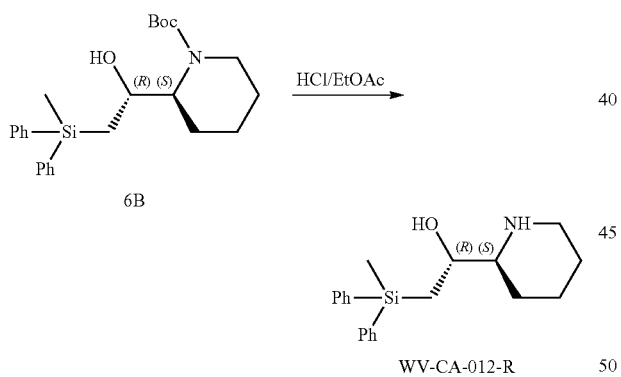

WV-CA-012-R

To a solution of compound 6B (1.30 g, 3.05 mmol) in HCl/EtOAc (80.00 mL), the mixture was stirred at 20° C. for 3 hr. TLC showed the start material was consumed. The mixture was concentrated to move most of solvent and filtered, the cake was dried to get the crude. The residue was dissolved in $H_2O$ (5 mL) then aqueous $Na_2CO_3$ was added adjust the PH=11, extracted with DCM (20 mL*3), dried over $Na_2SO_4$, filtered and concentrated to get WV-CA-012-R as a yellow solid (900.00 mg, 90.46%). $^1$H NMR (400 MHz, $CDCl_3$): δ=7.60-7.52 (m, 4H), 7.43-7.31 (m, 6H), 3.78-3.62 (m, 1H), 3.06 (d, J=11.5 Hz, 1H), 2.60 (dt, J=2.8, 11.9 Hz, 1H), 2.46-2.37 (m, 1H), 1.92-1.50 (m, 4H), 1.46-1.15 (m, 5H), 0.66 (s, 1H). $^{13}$C NMR (125.7 MHz, CDCl3): δ=134.54, 134.46, 129.18, 127.84, 71.82, 62.35, 46.95, 26.42, 25.41, 24.31, 18.21. LCMS: (M+H+): 326.2. TLC (Petroleum ether/Ethyl acetate=5:1) $R_f$=0. LCMS purity=99.79%. SFC purity=97.79%.

Example 19. Synthesis of WV-CA-012-dA$^{bz}$

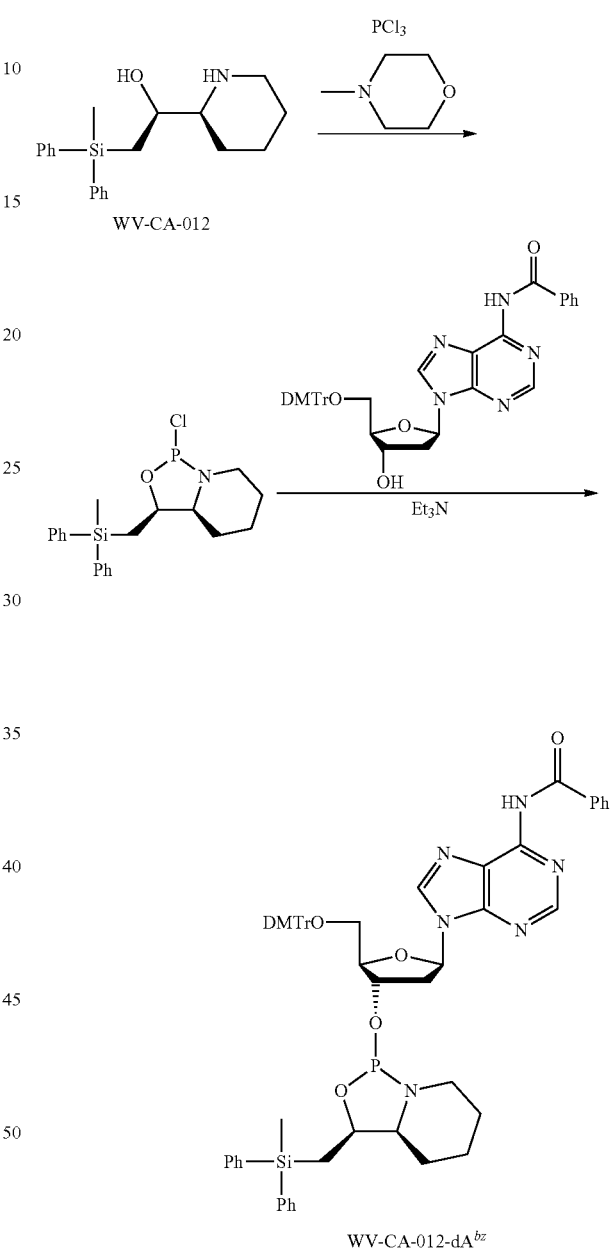

Using WV-CA-012 as starting material, the title compound (1.55 g, 70%) as a white solid was prepared analogously to WV-CA-008S-dC$^{iBu}$. $^1$H NMR (600 MHz, $CDCl_3$) δ 9.12 (brs, 1H), 8.70 (s, 1H), 8.09 (s, 1H), 8.07-8.00 (m, 2H), 7.60-7.15 (m, 22H), 6.79-6.70 (m, 4H), 6.35-6.26 (m, 1H), 5.01-4.89 (m, 1H), 4.15-3.98 (m, 2H), 3.76-3.72 (m, 6H), 3.35-3.09 (m, 3H), 2.78-2.62 (m, 1H), 2.55-2.47 (m, 1H), 2.24-2.02 (m, 1H), 1.82-1.65 (m, 2H), 1.56-1.39 (m, 2H), 1.35-1.16 (m, 3H), 1.05-0.86 (m, 2H), 0.66-0.63 (m, 3H); $^{31}$P NMR (243 MHz, $CDCl_3$) δ 139.60 (minor), 136.83 (minor), 131.47 (major).

Example 20. Synthesis of WV-CA-045-dA$^{bz}$

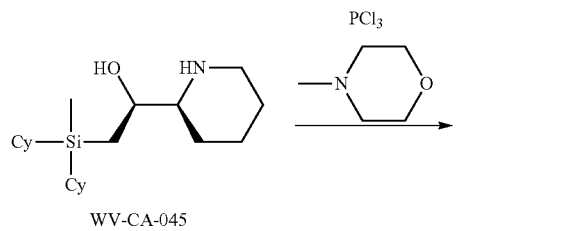

Using WV-CA-045 as starting material, the title compound (0.84 g, 48%) as a white solid was prepared analogously to WV-CA-008S-dC$^{iBu}$ 1H NMR (600 MHz, CDCl$_3$) δ 9.05 (brs, 1H), 8.72 (s, 1H), 8.19 (s, 1H), 8.00 (d, J=7.8 Hz, 2H), 7.57 (t, J=3.9 Hz, 1H), 7.50 (t, J=7.8 Hz, 2H), 7.38 (d, J=7.8 Hz, 2H), 7.29-7.16 (m, 7H), 6.79-6.75 (m, 4H), 6.48 (t, J=6.6 Hz, 1H), 5.03-4.98 (m, 1H), 4.24-4.21 (m, 1H), 4.12-4.08 (m, 1H), 3.75 (s, 6H), 3.43-3.24 (m, 3H), 2.94-2.87 (m, 1H), 2.79-2.73 (m, 1H), 2.57-2.53 (m, 1H), 2.49-2.44 (m, 1H), 1.89-1.83 (m, 1H), 1.71-0.65 (m, 28H), −0.02 (s, 1H), −0.08 (s, 1H), −0.11 (s, 2H). $^{31}$P NMR (243 MHz, CDCl$_3$) δ 141.21 (major), 137.22 (minor), 135.30 (minor).

Example 21. Synthesis of WV-CA-046-dA$^{bz}$

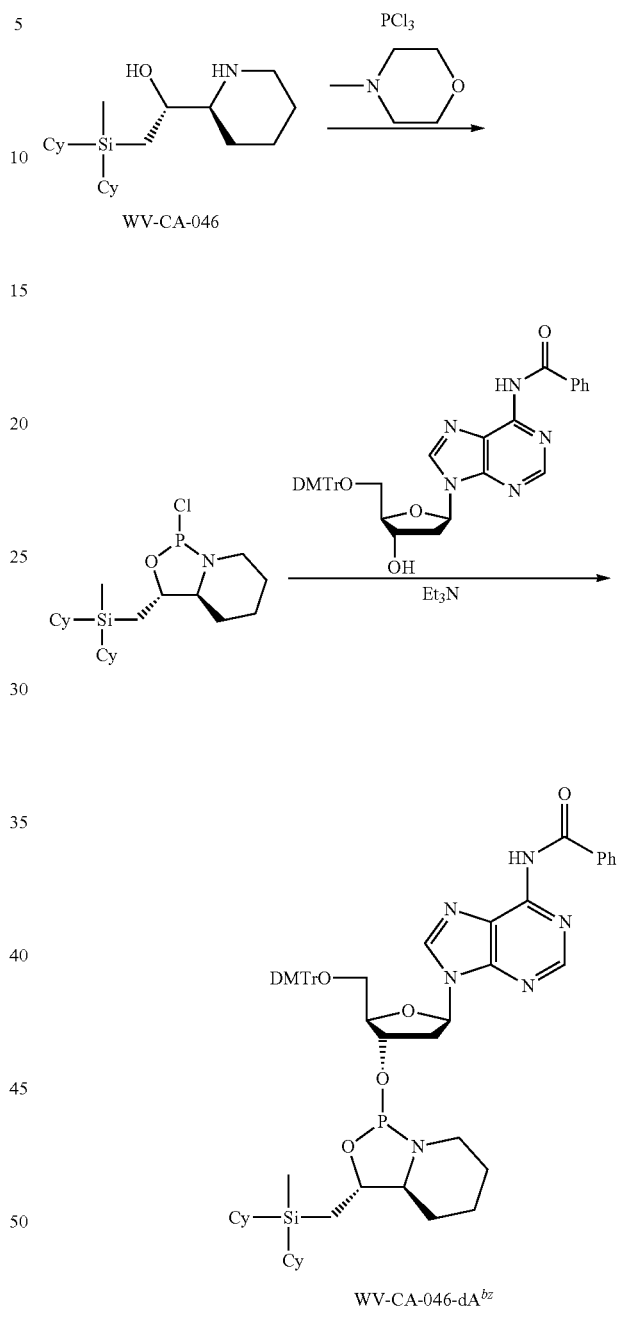

WV-CA-046-dA$^{bz}$

Using WV-CA-046 as starting material, the title compound (0.78 g, 44%) as a white solid was prepared analogously to WV-CA-008S-dC$^{iBu}$ 1H NMR (600 MHz, CDCl$_3$) δ 9.01 (brs, 1H), 8.70 (s, 1H), 8.17 (s, 1H), 8.00 (d, J=6.6 Hz, 2H), 7.56 (t, J=4.5 Hz, 1H), 7.49 (t, J=7.8 Hz, 2H), 7.38 (d, J=7.8 Hz, 2H), 7.30-7.16 (m, 7H), 6.79-6.75 (m, 4H), 6.49 (dd, J=7.8, 6.0 Hz, 1H), 4.98-4.93 (m, 1H), 4.73-4.67 (m, 1H), 4.24-4.20 (m, 1H), 3.75 (s, 6H), 3.40-3.30 (m, 3H), 3.06-3.00 (m, 1H), 2.93-2.86 (m, 1H), 2.76-2.69 (m, 1H), 2.62-2.55 (m, 1H), 1.93-1.87 (m, 1H), 1.71-0.64 (m, 28H), −0.07--0.11 (m, 4H). $^{31}$P NMR (243 MHz, CDCl$_3$) δ 145.52 (minor), 141.96 (minor), 136.80 (major).

Example 22. Synthesis of WV-CA-014 and WV-CA-014-R
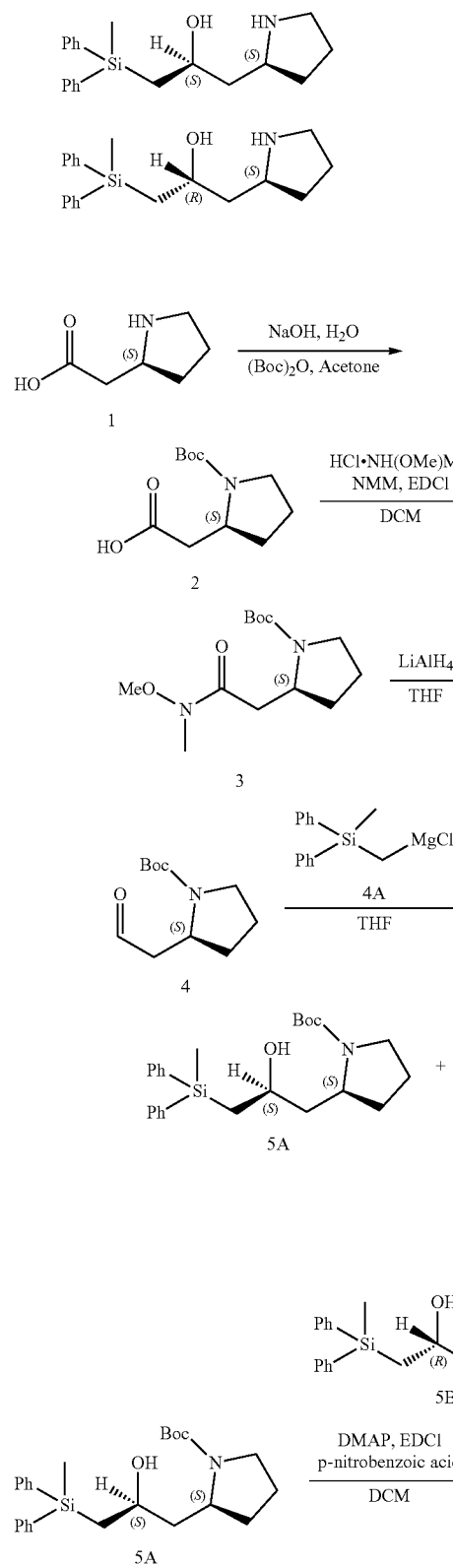
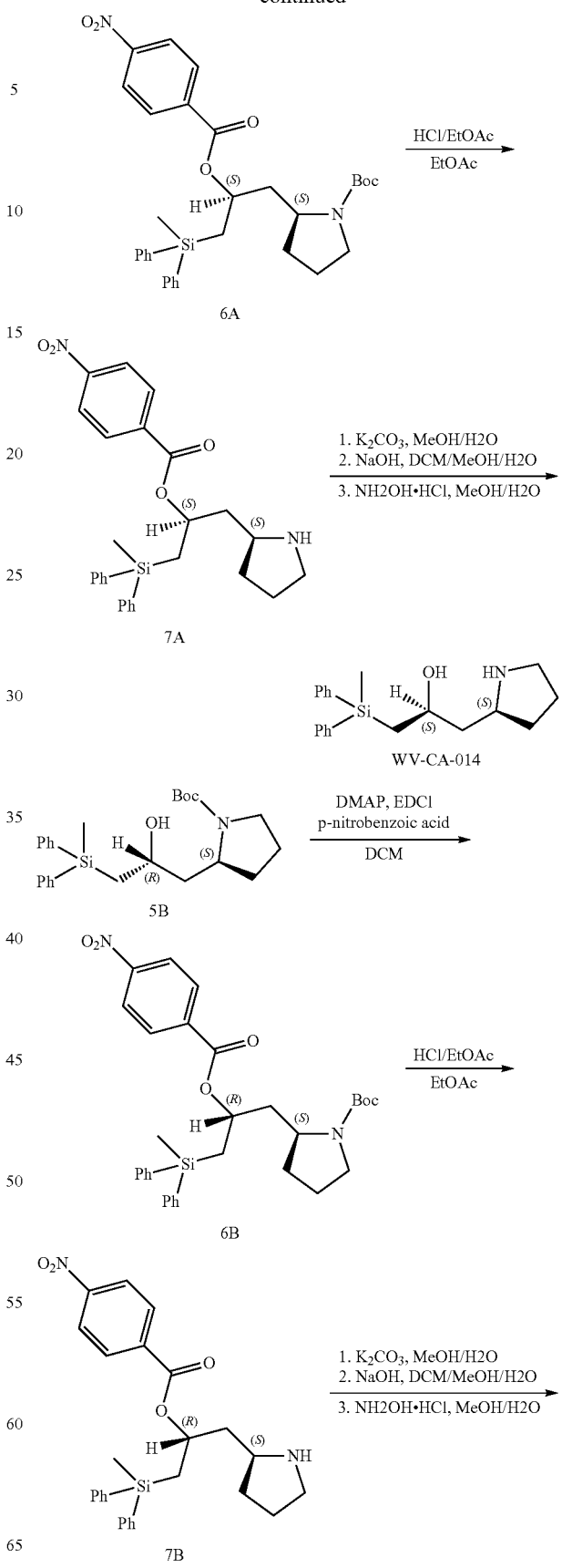

1. WV-CA-014.
1.1 Preparation of Compound 2.

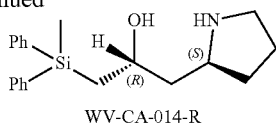
WV-CA-014-R

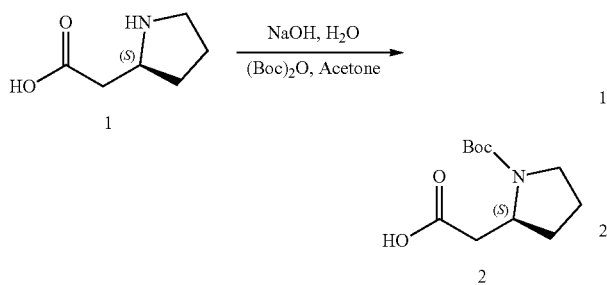

Compound 1 (20.00 g, 120.76 mmol, HCl salt) was dissolved in H₂O (200 mL), and pH was adjusted to around 10 at 0° C. with NaOH aq. (2 M, 150.95 mL). The solution was diluted with acetone (400 mL), and di-tert-butyl dicarbonate (39.53 g, 181.14 mmol) was added at 0° C. with stirring. After 0.5 hr the temperature was warmed to 25° C. and stirred for 4 hr. TLC and LCMS (a sample was added 1 M HCl, 0.1 mL; extracted with EtOAc, 0.2 mL) showed the reaction was completed. The reaction was concentrated to remove acetone. The aqueous phase left was acidified with 1 M HCl (100 mL) to pH ~3, extracted with EtOAc (200 mL*3), washed with brine (80 mL), dried, filtered and concentrated to afford compound 2 as a yellow solid (39.00 g, crude). ¹H NMR (400 MHz, CHLOROFORM-d) δ=3.35 (br s, 2H), 2.90 (br s, 1H), 2.37 (br s, 1H), 2.20-2.06 (m, 1H), 1.90-1.73 (m, 3H), 1.49-1.44 (m, 10H). LCMS: (M+Na+): 253.2.

TLC (Ethyl acetate:Dichloromethane=10:1) R$_f$=0.43.
1.2 Preparation of Compound 3.

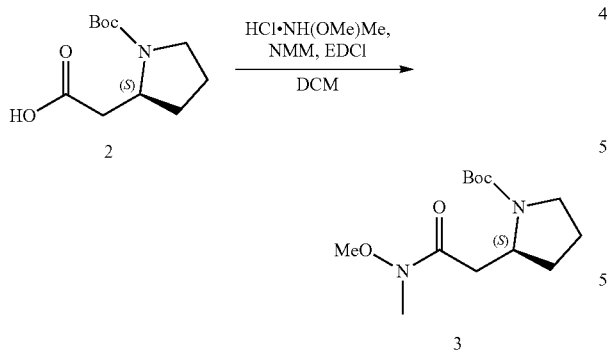

Compound 2 (38.50 g, 167.92 mmol) was dissolved in anhydrous DCM (400 mL) cooled to 0° C. To this solution was added N-methoxymethanamine hydrochloride (19.66 g, 201.51 mmol) and N-methylmorpholine (20.38 g, 201.51 mmol) followed by EDCI (38.63 g, 201.51 mmol) at 0° C. The reaction mixture was then allowed to warm to 25° C. and stirred for 3 hr. TLC and LCMS (quenched with 1 M HCl) showed the reaction was completed. The reaction was again cooled to 0° C., quenched by the addition of an ice cold 2M HCl (50 mL), and stirred at the temperature for 5 minutes. The reaction was diluted with water (100 mL) and extracted with DCM (100 mL*3). The combined organic layers were washed with sat. NaHCO₃ aq. (100 mL*1), dried over Na₂SO₄, filtered and concentrated in vacuo to dryness. The residue was purified by column chromatography (Petroleum ether/EtOAc=50/1 to 1/1) to afford compound 3 as a colorless oil (28.00 g, 61.22%). LCMS: (M+Na+): 295.1.
TLC (Dichloromethane:Methanol=20:1) R$_f$=0.61.
1.3 Preparation of Compound 4.

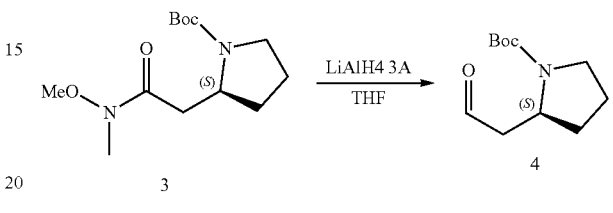

In a three-necked bottle with insert thermometer, to a solution of compound 3 (17.50 g, 67.75 mmol) in THF (200 mL) was added LiAlH₄ (2.83 g, 74.53 mmol) at −40° C. The suspension reaction slowly warm to 0° C. for 2 hr. TLC showed compound 3 was consumed completely and one new spot was detected. The reaction was quenched with sat. MgSO₄ aq. (20 mL). The suspension was diluted with EtOAc (200 mL) and filtered. The filter cake was washed with EtOAc (200 mL). The combined organic filtrate was concentrated in vacuo to afford compound 4 as a yellow oil (11 g, crude). TLC (Petroleum ether/EtOAc=5/1) R$_f$=0.43.
1.4 Preparation of Compound 5A.

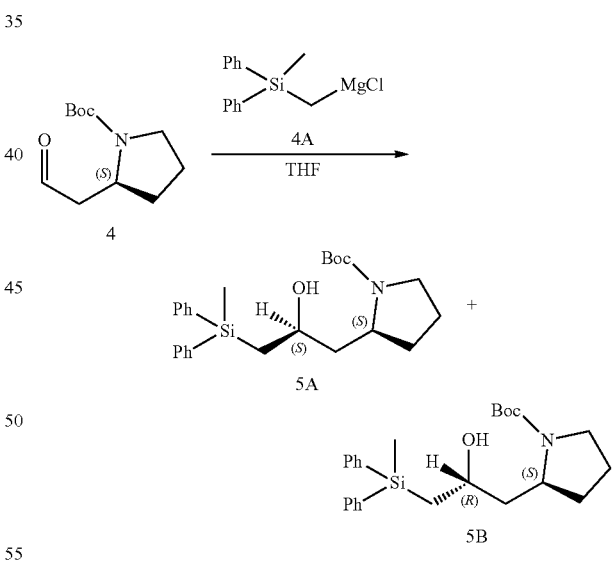

Compound 4A (41.95 g, 154.74 mmol) was added dropwise to the solution of compound 4 (11.00 g, 51.58 mmol) in THF (150 mL) a −40° C. under N₂. The reaction was stirred at −20~0° C. for 3 hr. TLC and LCMS showed about 90% compound 4 was consumed and one main peak with desired MS was detected. The reaction mixture was quenched by the addition of sat. NH₄Cl (aq., 20 mL) at −40° C., diluted with EtOAc (150 mL), and extracted with EtOAc (200 mL*3). The combined organic layers were washed with H₂O (100 mL), dried over Na₂SO₄, filtered and concentrated under reduced pressure to give a residue, which was purified by column chromatography (SiO₂, Petroleum ether/EtOAc=100/1 to 3/1) to afford compound 5A as yellow oil (4.00 g, 18.22%) and compound 5B as yellow oil (5.00 g, 22.77%). Compound 5A: $^1$H NMR (400 MHz, CHLOROFORM-d) δ=7.65-7.61 (m, 2H), 7.60-7.56 (m, 3H), 7.46-7.40 (m, 3H), 7.39-7.36 (m, 4H), 4.21-4.08 (m, 1H), 3.31-3.13 (m, 2H), 1.95-1.66 (m, 2H), 1.61-1.45 (m, 3H), 1.43 (s, 9H), 1.05-0.85 (m, 1H), 0.67 (s, 4H). LCMS: (M+Na+): 448.1. TLC (Petroleum ether/EtOAc=5:1) $R_{f1}$=0.5. Compound 0.5B: LCMS: (M+Na+): 448.1. TLC (Petroleum ether/EtOAc=5:1) $R_{f2}$=0.33.

1.5 Preparation of Compound 6A.

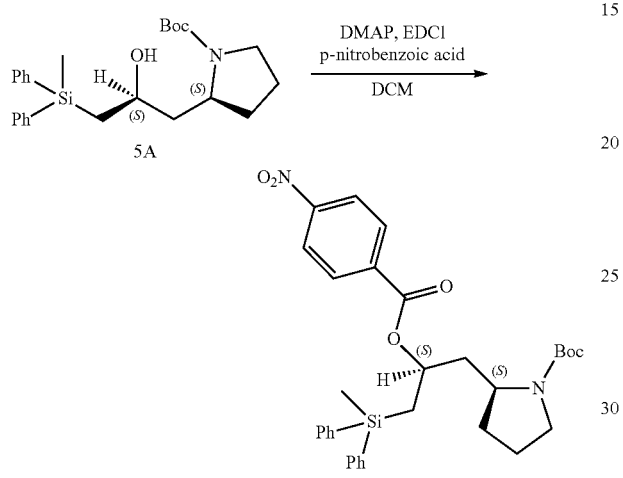

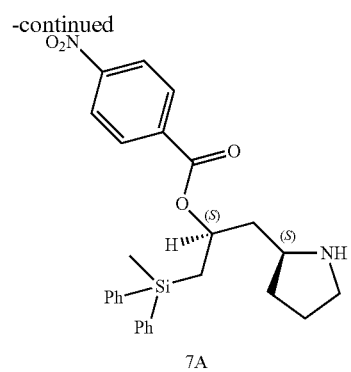

To a stirred solution compound 5A (4.00 g, 9.40 mmol) in DCM (150 mL) were added DMAP (9.19 g, 75.20 mmol), EDCI (18.02 g, 94.00 mmol) and p-nitrobenzoic acid (10.99 g, 65.80 mmol) at 0° C. The mixture was stirred at 20° C. for 17 hr. LCMS and TLC showed compound 5A was consumed completely and two main spots with lower polarity were detected. The reaction mixture was quenched with sat. NH₄Cl aq. (100 mL) and extracted with DCM (100 mL*3). The combined organic layers were dried over Na₂SO₄, filtered, and concentrated under reduced pressure to give a residue, which was purified by column chromatography (SiO₂, Petroleum ether/EtOAc=30/1 to 15/1) to give compound 6A as yellow oil (2.8 g, 51.8%). LCMS: (M+Na+): 597.3. TLC (Petroleum ether:EtOAc=5:1) $R_f$=0.5.

1.6 Preparation of Compound 7A.

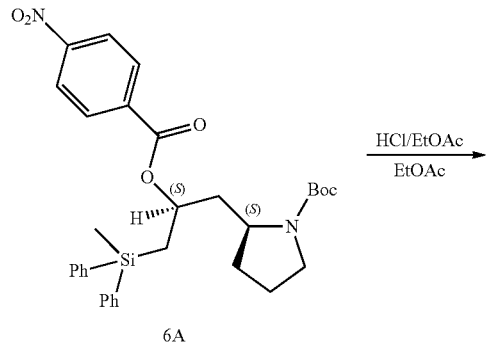

To a solution of compound 6A (2.80 g, 4.87 mmol, 1.00 eq.) in EtOAc (10 mL) was added HCl/EtOAc (150 mL). The mixture was stirred at 20° C. for 0.5 hr. TLC and LCMS showed compound 6A was consumed completely, and one major new spot with larger polarity was detected. The reaction mixture was concentrated under reduced pressure to give compound 7A as a yellow oil (2.50 g, crude, HCl salt). LCMS: (M+Na+): 475.2. TLC (Petroleum ether:EtOAc=5:1) $R_f$=0.

1.7 Preparation of Compound WV-CA-014.

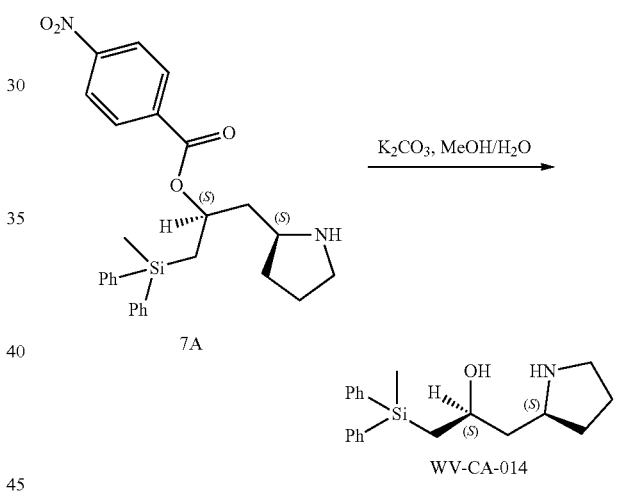

To a solution of compound 7A (2.50 g, 4.89 mmol, HCl salt) in MeOH (50.00 mL) was added K₂CO₃ (6.76 g, 48.90 mmol) and H₂O (150 mL). The mixture was stirred at 20° C.-40° C. for 36 hr. LCMS and TLC showed 36% of compound 7A was consumed and one main peak with desired MS. The mixture was concentrated under reduced pressure to give a residue, which was triturated with DCM and filtered. The filtrate was concentrated under reduced pressure to give a residue. The residue was purified by column chromatography (SiO₂, DCM:MeOH=200:1 to 10:1) to give compound WA-CA-014 was obtained as a yellow oil (350.00 mg, 22.09%). Compound 7A (1.40 g, crude) was the starting material as a yellow oil. $^1$H NMR (400 MHz, CHLOROFORM-d) δ=7.62-7.49 (m, 4H), 7.43-7.30 (m, 6H), 4.13-3.92 (m, 1H), 3.41-3.19 (m, 1H), 3.03-2.81 (m, 2H), 1.96 (s, 1H), 1.92-1.70 (m, 2H), 1.64 (s, 1H), 1.54-1.41 (m, 3H), 1.38-1.24 (m, 2H), 0.66 (s, 3H). $^{13}$C NMR (101 MHz, CHLOROFORM-d): δ=140.81, 140.51, 137.76, 137.71, 132.28, 130.99, 72.84, 62.52, 48.50, 46.62, 35.57, 28.10, 27.95. LCMS (M+H⁺): 326.1, 96.2% purity. Chiral SFC purity: 98.8%. TLC (DCM:Methanol=10:1) $R_f$=0.11.

2. WV-CA-014-R

2.1 Preparation of Compound 6B.

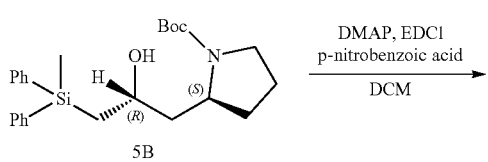

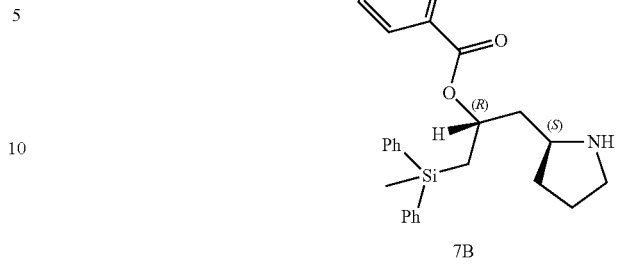

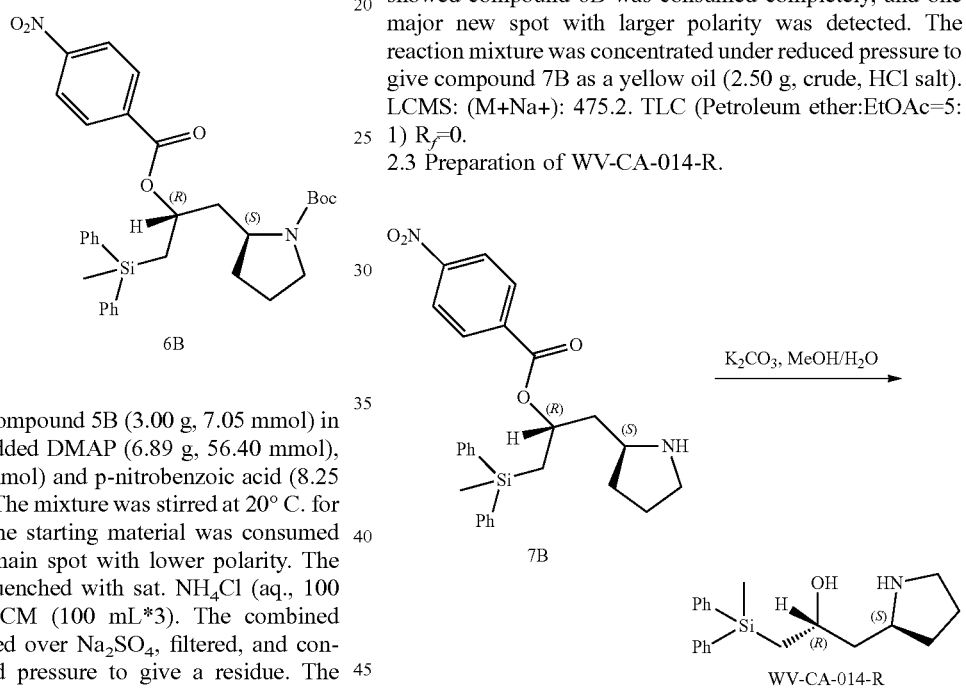

To a stirred solution compound 5B (3.00 g, 7.05 mmol) in DCM (150 mL) were added DMAP (6.89 g, 56.40 mmol), EDCI (13.51 g, 70.50 mmol) and p-nitrobenzoic acid (8.25 g, 49.35 mmol) at 0° C. The mixture was stirred at 20° C. for 17 hr. LCMS showed the starting material was consumed and TLC showed one main spot with lower polarity. The reaction mixture was quenched with sat. $NH_4Cl$ (aq., 100 mL), extracted with DCM (100 mL*3). The combined organic layers were dried over $Na_2SO_4$, filtered, and concentrated under reduced pressure to give a residue. The residue was purified by column chromatography ($SiO_2$, Petroleum ether/EtOAc=30/1 to 15/1) to give compound 6B as a yellow oil (2.80 g, 69.10%). LCMS: (M+Na+): 597.3.

TLC (Petroleum ether:EtOAc=5/1) $R_f$=0.5.

2.2 Preparation of Compound 7B.

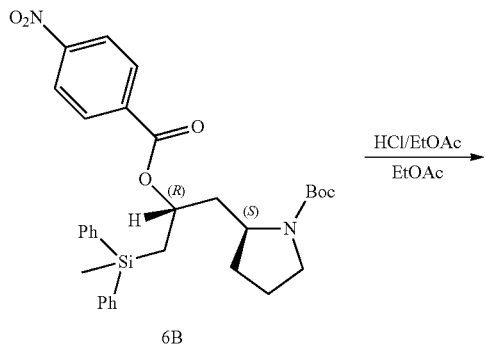

To a solution of compound 6B (2.80 g, 4.87 mmol) in EtOAc (10 mL) was added HCl/EtOAc (150 mL). The mixture was stirred at 20° C. for 0.5 hr. TLC and LCMS showed compound 6B was consumed completely, and one major new spot with larger polarity was detected. The reaction mixture was concentrated under reduced pressure to give compound 7B as a yellow oil (2.50 g, crude, HCl salt). LCMS: (M+Na+): 475.2. TLC (Petroleum ether:EtOAc=5:1) $R_f$=0.

2.3 Preparation of WV-CA-014-R.

To a solution of compound 7B (2.50 g, 4.89 mmol, HCl salt) in MeOH (50 mL) was added $K_2CO_3$ (6.76 g, 48.90 mmol) and $H_2O$ (150 mL). The mixture was stirred at 20° C.-40° C. for 36 hr. LCMS and TLC showed 42% of compound 7B was consumed and one main peak with desired MS. The mixture was concentrated under reduced pressure to give a residue, which was triturated with DCM and filtered. The filtrate was concentrated under reduced pressure to give a residue, which was purified by column chromatography ($SiO_2$, DCM:MeOH=200:1 to 10:1) to give compound WV-CA-014-R was obtained as a colorless oil (290.00 mg, 16.90%). $^1$H NMR (400 MHz, CHLOROFORM-d) δ=7.54 (br. s., 1H), 7.35 (br. s., 1H), 4.24-4.06 (m, 1H), 3.47 (d, J=6.8 Hz, 1H), 3.09-2.85 (m, 2H), 1.93 (s, 2H), 1.89-1.60 (m, 6H), 1.56 (dd, J=7.5, 14.6 Hz, 1H), 1.49-1.33 (m, 2H), 0.63 (s, 3H). $^{13}$C NMR (101 MHz, CHLOROFORM-d): 140.80, 140.56, 138.12, 138.02, 132.71, 131.39, 69.85, 59.76, 48.38, 44.13, 33.90, 27.50, 26.69. LCMS: (M+H$^+$): 326.1, 94.2% purity. Chiral SFC purity: 100.0%. TLC (DCM:Methanol=10:1) $R_f$=0.11.

Example 23. Synthesis of WV-CA-024, 025, 026, 027
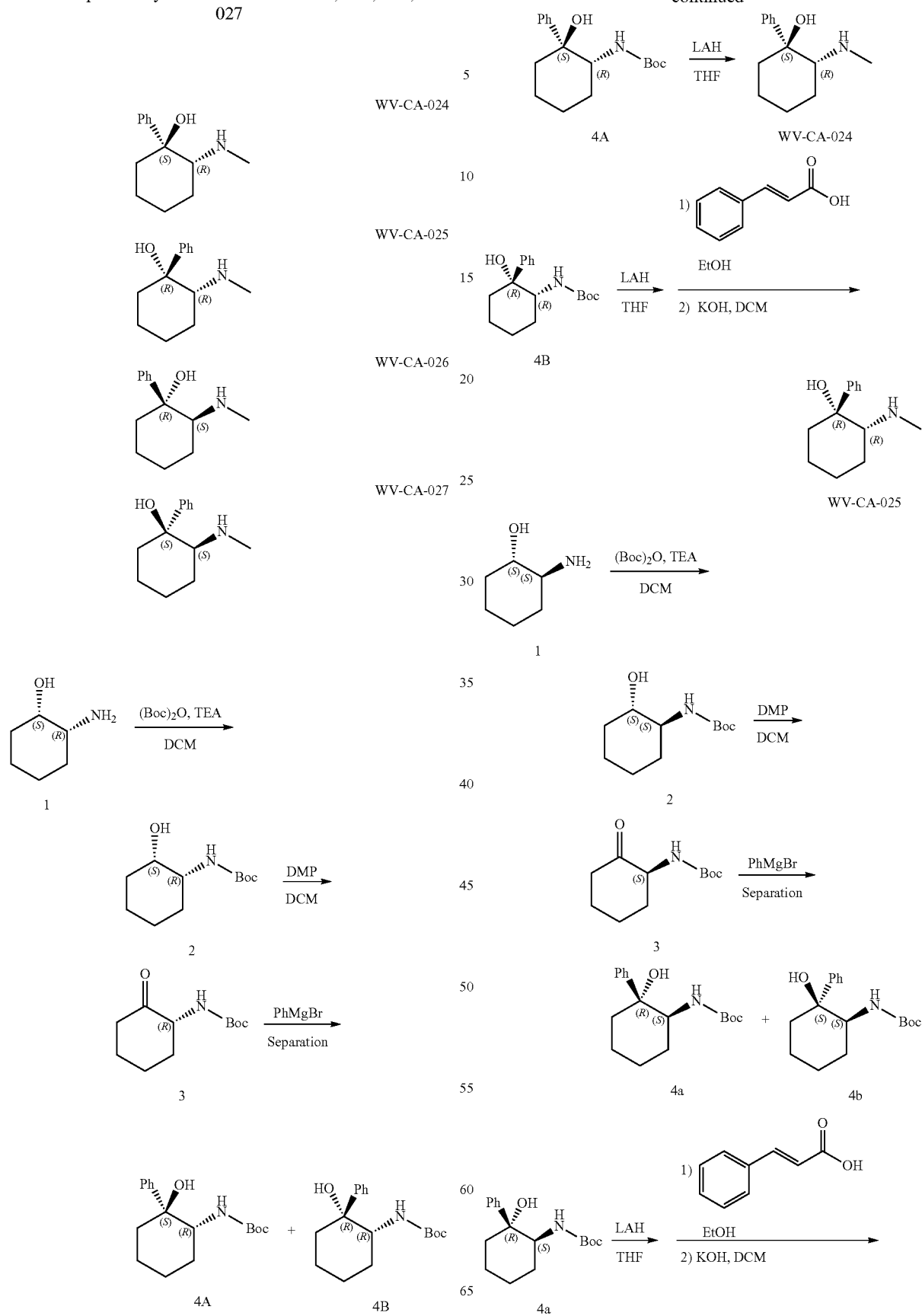

-continued

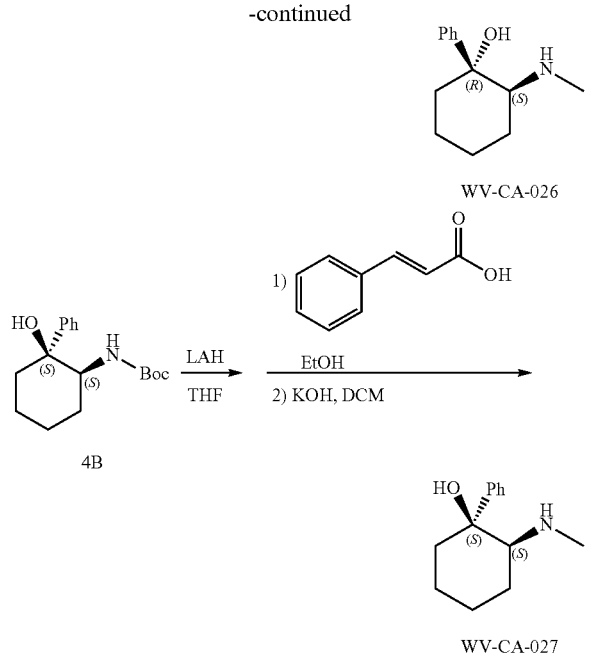

WV-CA-026

WV-CA-027

1. Preparation of Compound 2.

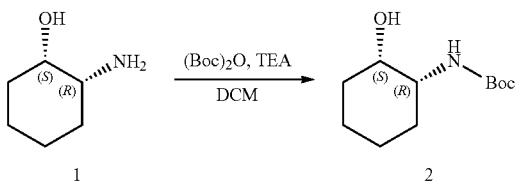

To a solution of compound 1 (30.00 g, 197.85 mmol) in DCM (300.00 mL) was added TEA (60.06 g, 593.55 mmol) and di-tert-butyl dicarbonate (43.18 g, 197.85 mmol). The mixture was stirred at 25° C. for 12 hr. TLC showed the reaction was completed. The resulting mixture was washed with water (300 mL*2), and brine (200 mL). The organic layer was dried over anhydrous MgSO$_4$, filtered, and concentrated to afford the product as a white solid. The crude product Compound 2 was used into the next step without further purification (40.00 g, crude). TLC (Petroleum ether: Ethyl acetate=2:1) R$_f$=0.70.

2. Preparation of Compound 3.

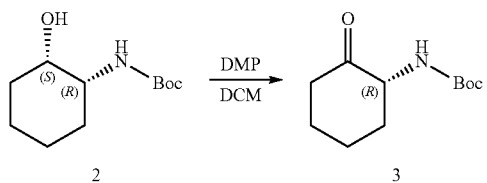

To a solution of compound 2 (35.50 g, 164.89 mmol) in DCM (300.00 mL) was added DMP (80.43 g, 189.62 mmol) at 0° C. The mixture was stirred at 0~25° C. for 1 hr. TLC showed the reaction was completed. The reaction was quenched with sat. Na$_2$SO$_3$ aq. and sat. NaHCO$_3$ aq. (V/V=1:1, 800 mL), extracted with DCM (300 mL*3). The combined organic layers were dried over anhydrous MgSO$_4$, filtered, and concentrated to afford a crude, which was purified by column chromatography on silica gel (Petroleum ether:Ethyl acetate=10:1, 5:1) to afford compound 3 colorless oil (33.5 g). TLC (Petroleum ether:Ethyl acetate=3:1) R$_f$=0.69.

3. Preparation of Compound 4A&4b.

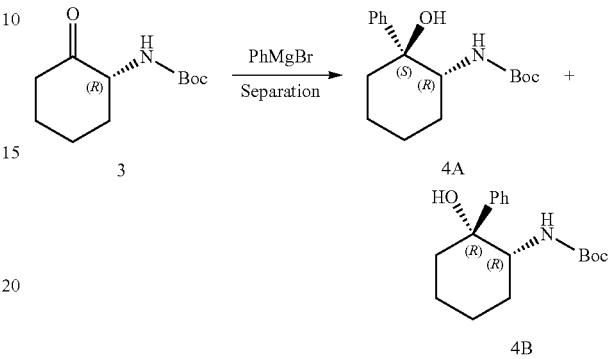

To a solution of compound 3 (33.50 g, 157.08 mmol) in THF (100.00 mL) was slowly added PhMgBr (3 M, 261.80 mL) at −40° C. The mixture was stirred at −40~0° C. for 3 hr. LCMS showed the reaction was completed. The reaction was quenched with sat. NH$_4$Cl aq. (100 mL), extracted with EtOAc (200 mL*3). The combined organic layers were washed with brine (200 mL), dried over anhydrous Na$_2$SO$_4$, filtered and concentrated to afford a crude. The crude product was purified by column (PE/EA=50/1 to 3/1), and MPLC, washed with PE/EA=10/1 to afford two isomers compound 4B (6.5 g) and compound 4A (4 g) as white solid. Compound 4A: $^1$H NMR (400 MHz, CDCl$_3$): δ=7.49 (d, J=7.9 Hz, 2H), 7.25 (br t, J=7.4 Hz, 2H), 7.17 (br d, J=6.6 Hz, 1H), 3.83 (br s, 1H), 3.30 (d, J=0.7 Hz, 9H), 2.36-2.08 (m, 3H), 1.89-1.46 (m, 8H), 1.19 (s, 8H). Compound 4B: $^1$H NMR (400 MHz, CDCl$_3$): δ=7.46 (br d, J=7.5 Hz, 2H), 7.27 (br t, J=7.6 Hz, 2H), 7.21-7.12 (m, 1H), 5.74 (br d, J=8.6 Hz, 1H), 3.89-3.70 (m, 1H), 1.88-1.66 (m, 6H), 1.58-1.39 (m, 2H), 1.21 (s, 9H). LCMS: (M+Na+): 314.1. TLC (Petroleum ether:Ethyl acetate=3:1) R$_f$ 4A=0.50; R$_f$ 4B=0.45.

4. Preparation of Compound WV-CA-024.

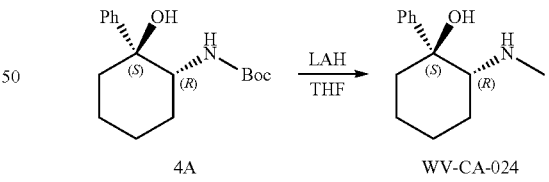

To a solution of compound 4A (3.20 g, 10.98 mmol) in THF (50.00 mL) was added LiAlH$_4$ (2.08 g, 54.91 mmol) at 20° C. The suspension reaction was stirred at 65° C. for 24 hr. LCMS showed desired product was observed. TLC showed 4A was consumed completely and one new spot was detected. The reaction was quenched with sat. MgSO$_4$ aq. (10 mL). The suspension was diluted with EtOAc (50 mL). The residue was filtered, and the filter cake was washed with EtOAc (150 mL) and MeOH (100 mL). The organic phase was concentrated in vacuo to dryness. The residue was purified by column (PE/EA=10/1 to 1/1), which was further purified by Prep-HPLC to give WV-CA-024 as a yellow solid (660.00 mg, 29.23%). $^1$H NMR (400 MHz, CDCl$_3$): δ=7.56 (d, J=7.6 Hz, 2H), 7.39-7.35 (m, 2H), 7.30-7.27 (m, 1H), 2.71 (d, J=3.2 Hz, 1H), 2.47-2.44 (m, 1H), 2.17 (s, 3H), 2.00-1.45 (m, 9H). $^{13}$C NMR (101 MHz, CDCl$_3$): δ=146.45, 128.33, 127.36, 126.09, 64.73, 34.52, 32.68, 24.50, 21.52, 19.69. LCMS: (M+H+): 206.2. TLC (Petroleum ether:Ethyl acetate=1:1) R$_f$=0.10. SFC purity=100.0%.

5. Preparation of Compound WV-CA-025.

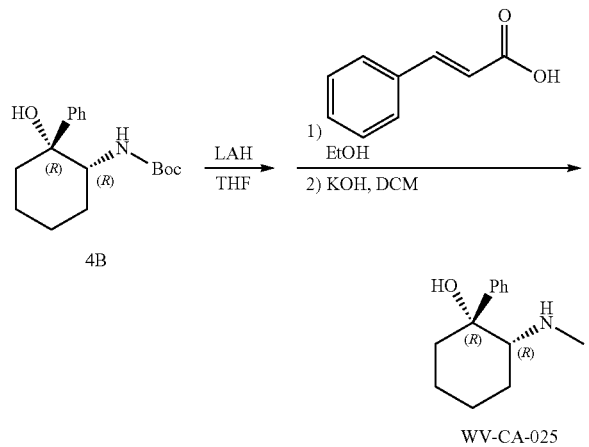

WV-CA-025

To a solution of compound 4B (6.80 g, 23.34 mmol) in THF (100.00 mL) was added LiAlH$_4$ (4.43 g, 116.70 mmol) at 0° C. The suspension reaction was stirred at 75° C. for 96 hr. TLC showed a little 4B remained, and one new spot of desired product was detected. The reaction was quenched with sat. MgSO$_4$ aq. (10 mL). The reaction mixture was filtered, and the filter cake was washed with EtOAc (50 mL*2) and MeOH (50 mL*2). The filtrate was dried over Na$_2$SO$_4$, concentrated in vacuo to dryness. The residue was purified by column (PE/EA=20/1 to 1/1) to give a crude of WV-CA-025 as colorless oil (3.50 g, 73.05%). To the crude WV-CA-025 (2.30 g, 11.20 mmol) in EtOH (10.00 mL) was added (E)-3-phenylprop-2-enoic acid (1.66 g, 11.20 mmol). The mixture was heated at 80° C. for 30 minutes. The mixture was cooled to 25° C. slowly. After 1 hr standing, still no solid precipitated. Concentrated under reduced pressure, to the residue was added 20 mL EtOAc heated to reflux (80° C.) until the mixture became clear, and then cool to 25° C. slowly. After 1 hr standing, a large amount of solid precipitated, which was filtered and dried to give a cinnamic salt (2.5 g). To a suspension of cinnamic salt in DCM (30 mL) was added KOH aq. (2M, 8 mL), and stirred at 25° C. for 0.5 hr. The separated aqueous layer was extracted with DCM (20 mL*2). The combined organic layers were washed with brine (40 mL), dried over anhydrous MgSO$_4$, filtered and concentrated to afford WV-CA-025 as colorless oil, which solidified to a white solid (1.20 g, 50.46%). $^1$H NMR (400 MHz, CDCl$_3$): δ=7.44 (d, J=7.6 Hz, 2H), 7.28-7.25 (m, 2H), 7.17-7.13 (m, 1H), 2.81-2.77 (m, 1H), 2.07 (s, 3H), 1.85-1.15 (m, 8H). $^{13}$C NMR (101 MHz, CDCl$_3$): δ=146.45, 128.33, 127.36, 126.09, 64.73, 34.52, 32.68, 24.50, 21.52, 19.69. LCMS: (M+H+): 206.2. TLC (Petroleum ether:Ethyl acetate=1:1) R$_f$=0.10. SFC purity=99.5%

6. Preparation of Compound 2.

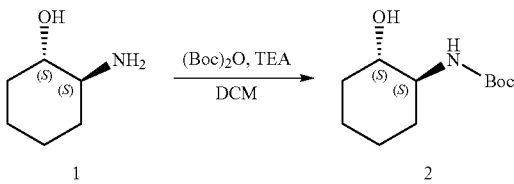

To a solution of compound 1 (30.00 g, 206.48 mmol) in DCM (300.00 mL) was added TEA (52.72 g, 520.97 mmol) and di-tert-butyl dicarbonate (56.85 g, 260.48 mmol). The mixture was stirred at 25° C. for 12 hr. TLC showed the reaction was completed. The resulting mixture was washed with water (300 mL*2), and brine (200 mL). The organic layer was dried over anhydrous MgSO$_4$, filtered, and concentrated to afford the product as a white solid. The crude product Compound. 2 was used into the next step without further purification (53.00 g, crude). $^1$H NMR (400 MHz, CHLOROFORM-d) δ=4.61 (br s, 1H), 3.28 (br s, 3H), 2.02-1.89 (m, 2H), 1.74-1.60 (m, 2H), 1.43 (d, J=1.1 Hz, 9H), 1.33-1.04 (m, 5H). LCMS: (M+H+): 150.1. TLC (Petroleum ether:Ethyl acetate=2:1) R$_f$=0.70.

7. Preparation of Compound 3.

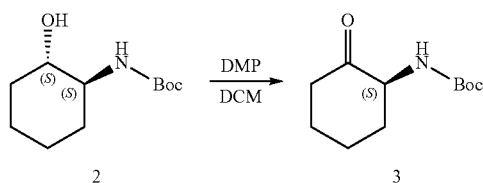

To a solution of compound 2 (48.00 g, 222.96 mmol) in DCM (500.00 mL) was added DMP (104.02 g, 245.26 mmol) at 0° C. The mixture was stirred at 0~25° C. for 1 hr. TLC showed the reaction was completed. The reaction was quenched with sat. Na$_2$SO$_3$ aq. and sat. NaHCO$_3$ aq. (V/V=2:3, 1000 mL), extracted with DCM (100 mL*3). The combined organic layers were dried over anhydrous MgSO$_4$, filtered, and concentrated to afford a crude, which was purified by column chromatography on silica gel (Petroleum ether:Ethyl acetate=25:1, 15:1) to afford compound 3 as a colorless oil (47.00 g). TLC (Petroleum ether:Ethyl acetate=3:1) R$_f$=0.69.

8. Preparation of Compound 4a & 4b.

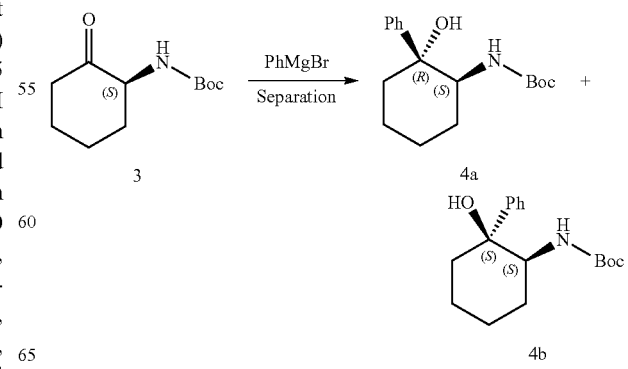

To a solution of compound 3 (47.00 g, 220.38 mmol) in THF (200.00 mL) was slowly added PhMgBr (3 M, 261.80 mL) at −40° C. The mixture was stirred at −40~0° C. for 3 hr. LCMS showed the reaction was completed. TLC showed compound 3 was consumed and two new spots of P1 and P2 was detected. The reaction was quenched with sat. NH₄Cl aq. (200 mL), extracted with EtOAc (200 mL*3). The combined organic layers were washed with brine (200 mL), dried over anhydrous Na₂SO₄, filtered and concentrated to afford a crude. The crude product was purified by column (PE/EA=50/1 to 3/1), and MPLC, and washed with PE/EA=10/1 to afford two isomers compound 4b as white solid (10 g) and compound 4a as white solid (6 g). ¹H NMR (400 MHz, CHLOROFORM-d) δ=7.45 (d, J=7.7 Hz, 2H), 7.30 (t, J=7.7 Hz, 2H), 7.25-7.17 (m, 2H), 4.76 (br d, J=7.7 Hz, 1H), 3.87-3.71 (m, 1H), 2.62-2.27 (m, 1H), 2.15-2.05 (m, 1H), 1.94-1.56 (m, 10H), 1.48-1.39 (m, 4H), 1.20 (d, J=0.9 Hz, 10H). ¹H NMR (400 MHz, CHLOROFORM-d) δ=7.54-7.48 (m, 2H), 7.34-7.28 (m, 2H), 7.25-7.20 (m, 1H), 4.47 (br d, J=8.8 Hz, 1H), 3.92 (br s, 1H), 2.21-2.02 (m, 1H), 1.86-1.74 (m, 2H), 1.69-1.54 (m, 4H), 1.51-1.38 (m, 1H), 1.26-1.14 (m, 1H), 1.26-1.14 (m, 8H). TLC (Petroleum ether:Ethyl acetate=3:1) $R_{f\ 4a}$=0.50; $R_{f\ 4b}$=0.45.

9. Preparation of Compound WV-CA-026.

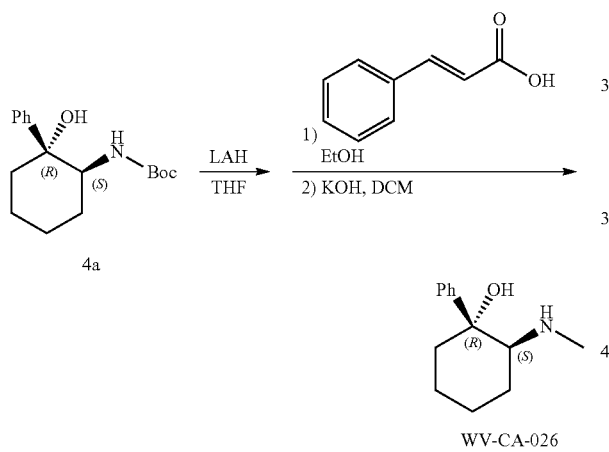

To a solution of compound 4a (5.50 g, 18.88 mmol) in THF (50.00 mL) was added LiAlH₄ (3.58 g, 94.38 mmol) at 0° C. The suspension reaction was stirred at 75° C. for 16 hr. TLC showed compound 4a was consumed completely and one new spot was detected. The reaction was quenched with sat. MgSO₄ aq. (10 mL). The suspension was diluted with EA (50 mL). The residue was filtered, washed with EA (150 mL) and MeOH (100 mL). The organic phase was concentrated in vacuo to dryness. The residue was purified by column (PE/EA=10/1 to 1/1) to give a crude of WV-CA-026 as colorless oil (2.70 g, 69.66%). To a mixture of the crude WV-CA-026 in EtOH (15.00 mL) was added (E)-3-phenyl-prop-2-enoic acid (1.95 g, 13.15 mmol). The mixture was heated at 90° C. for 30 minutes. The mixture was concentrated in vacuo to dryness. The white crude solid was dissolved in EA (20 mL) at 80° C. for 0.5 hr until the mixture became clear, the solution was cooled to 25° C. (r.t.) slowly. A large amount of solid precipitated, which was filtered, and concentrated in vacuo to dryness to give a white solid. To a solution of the white solid in DCM (20.00 mL) was added drop-wise 2 M KOH aq. (20.00 mL) at 20° C. until pH ~13. The mixture was stirred at 20° C. for 0.5 hr, and extracted with DCM (30 mL*2). The organic phase was washed with brine. The aqueous phase was back extracted with DCM (30 mL*2). The organic layers were combined, dried over Na₂SO₄, and concentrated in vacuo to dryness to give WV-CA-026 as white solid (2.00 g, 82.00%). ¹H NMR (400 MHz, CDCl₃): δ=7.56 (d, J=7.6 Hz, 2H), 7.39-7.35 (m, 2H), 7.30-7.27 (m, 1H), 2.71 (d, J=3.2 Hz, 1H), 2.47-2.44 (m, 1H), 2.16 (s, 3H), 2.00-1.45 (m, 9H). ¹³C NMR (125.7 MHz, CDCl₃): δ=146.45, 128.33, 127.36, 126.09, 64.73, 34.52, 32.68, 24.50, 21.52, 19.69. LCMS: (M+H+): 206.2. TLC (Petroleum ether:Ethyl acetate=1:1) $R_f$=0.10. SFC purity=98.9%.

10. Preparation of Compound WV-CA-027.

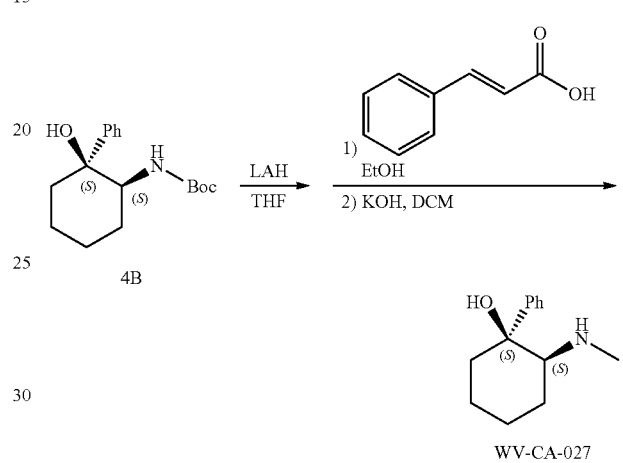

To a solution of compound 4B (9.50 g, 32.60 mmol) in THF (100.00 mL) was added LiAlH₄ (6.19 g, 163.00 mmol) at 0° C. The suspension reaction was stirred at 75° C. for 168 hr. TLC showed compound 4B was consumed completely and one new spot was detected. The reaction was quenched with sat. MgSO₄ aq. (10 mL). The suspension was diluted with EA (50 mL). The residue was filtered, washed with EA (100 mL) and MeOH (100 mL). The organic phase was concentrated in vacuo to dryness. The residue was purified by column (PE/EA=10/1 to 1/1) to give a crude of WV-CA-027 as colorless oil (3.50 g, 52.30%).

To a mixture of the crude WV-CA-027 in EtOH (15.00 mL) was added (E)-3-phenylprop-2-enoic acid (2.19 g, 14.76 mmol). The mixture was heated at 90° C. for 30 minutes. The mixture was concentrated in vacuo to dryness. The white crude solid was dissolved in EA (20 mL) at 80° C. for 0.5 hr until the mixture became clear. The solution was cooled to 25° C. slowly. A large amount of solid precipitated, which was filtered, concentrated in vacuo to dryness to give a white solid. To a solution of the solid in DCM (20.00 mL) was added drop-wise 2 M KOH aq. (20.00 mL) at 20° C. until pH ~13. The reaction was stirred at 20° C. for 0.5 hr. The mixture was extracted with DCM (30 mL*2). The organic phase was washed with brine. The aqueous phase was back extracted with DCM (30 mL*2). The organic layers were combined, dried over Na₂SO₄, and concentrated in vacuo to dryness to give WV-CA-027 as colorless oil (2.00 g, 76.51%). ¹H NMR (400 MHz, CDCl₃): δ=7.56 (d, J=7.6 Hz, 2H), 7.39-7.35 (m, 2H), 7.30-7.27 (m, 1H), 2.71 (d, J=3.2 Hz, 1H), 2.47-2.44 (m, 1H), 2.17 (s, 3H), 2.00-1.45 (m, 9H). ¹³C NMR (125.7 MHz, CDCl₃): δ==146.45, 128.33, 127.36, 126.09, 64.73, 34.52, 32.68, 24.50, 21.52, 19.69. LCMS: (M+H$^+$): 206.2. TLC (Petroleum ether:Ethyl acetate=1:1) R$_f$=0.10. SFC purity=99.4%.

Example 24. Synthesis of WV-CA-024-dCiBu

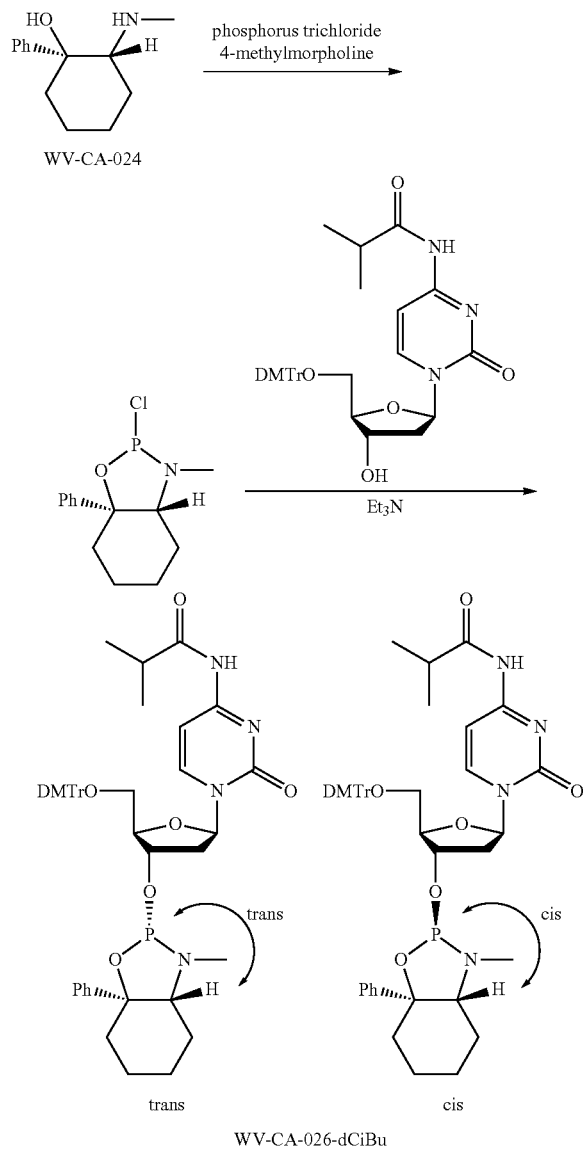

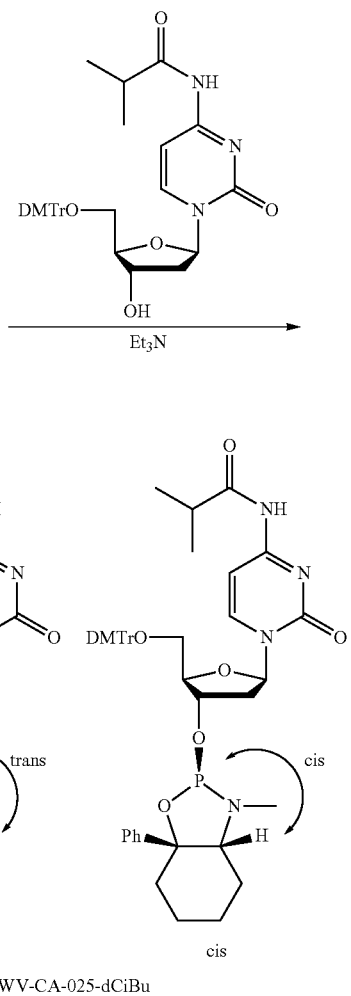

Using WV-CA-024 as starting material, the title compound (0.75 g, 44%) as a white solid was prepared analogously to WV-CA-008S-dCiBu. $^{31}$P NMR (202 MHz, CDCl$_3$) δ 163.87 (85%, trans), 141.81 (15%, cis).

Example 25. Synthesis of WV-CA-025-dCiBu

Using WV-CA-025 as starting material, the title compound (1.80 g, 69%) as a white solid was prepared analogously to WV-CA-008S-dCiBu. $^1$H NMR (500 MHz, Chloroform-d) δ 8.41 (s, 1H), 8.31 (d, J=7.5 Hz, 1H), 7.53-7.31 (m, 8H), 7.34-7.26 (m, 4H), 7.28-7.20 (m, 2H), 7.09 (d, J=7.5 Hz, 1H), 6.89-6.80 (m, 4H), 6.23 (dd, J=6.4, 4.7 Hz, 1H), 4.90 (dq, J=8.8, 5.9 Hz, 1H), 4.21 (dt, J=5.8, 3.1 Hz, 1H), 3.77 (s, 6H), 3.58 (dd, J=10.9, 3.4 Hz, 1H), 3.49 (dd, J=10.8, 2.9 Hz, 1H), 3.24 (ddd, J=12.9, 8.6, 5.9 Hz, 1H), 2.72-2.54 (m, 5H), 2.42-2.26 (m, 1H), 2.16 (dt, J=14.5, 4.9 Hz, 1H), 1.89-1.13 (m, 13H). $^{31}$P NMR (202 MHz, CDCl$_3$) δ 152.18 (95%, trans), 141.20 (5%, cis).

Example 26. Synthesis of WV-CA-026-dCiBu

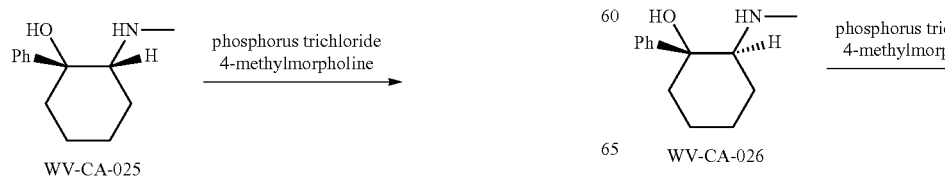

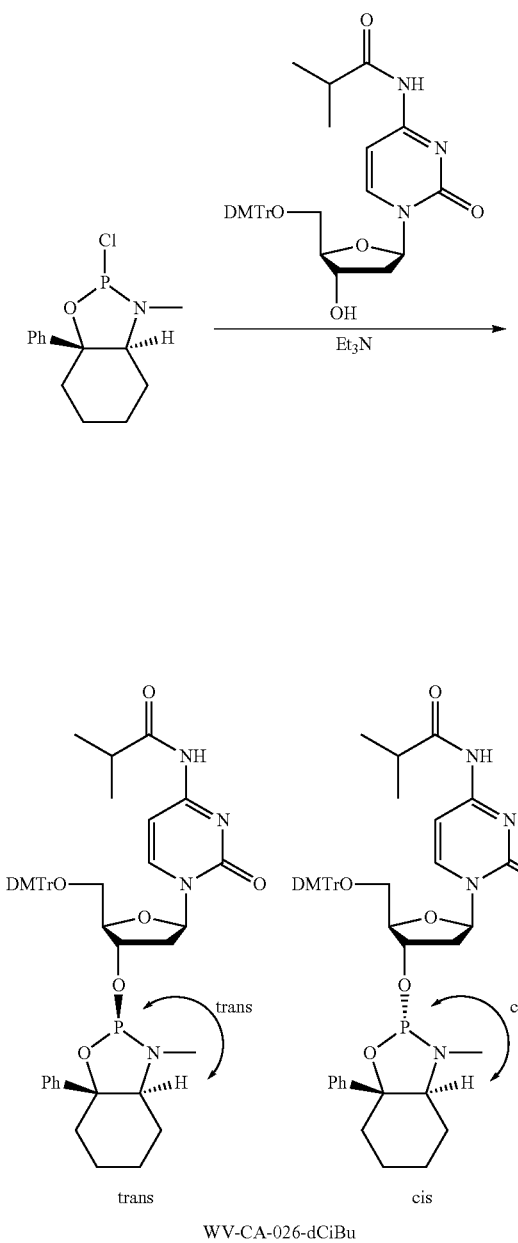

Using WV-CA-026 as starting material, the title compound (0.904 g, 39%) as a white solid was prepared analogously to WV-CA-008S-dCiBu. $^{31}$P NMR (202 MHz, CDCl$_3$) δ 164.93 (90%, trans), 147.17 (10%, cis).

Example 27. Synthesis of WV-CA-027-dCiBu

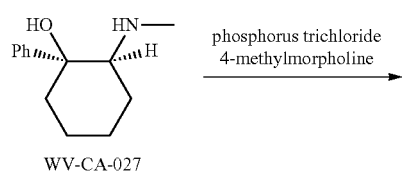

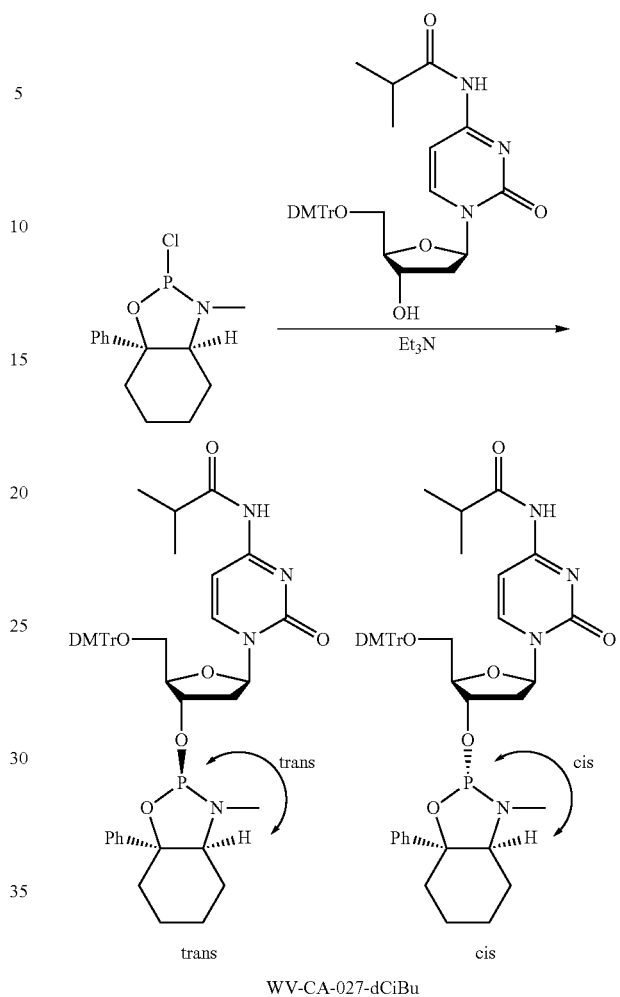

Using WV-CA-027 as starting material, the title compound (1.778 g, 77%) as a white solid was prepared analogously to WV-CA-008S-dCiBu. $^1$H NMR (500 MHz, Chloroform-d) δ 8.36 (d, J=7.4 Hz, 1H), 8.24 (s, 1H), 7.43 (t, J=7.8 Hz, 4H), 7.40-7.20 (m, 10H), 7.13 (d, J=7.3 Hz, 1H), 6.85 (d, J=8.3 Hz, 4H), 6.27 (t, J=5.7 Hz, 1H), 4.86 (p, J=6.5 Hz, 1H), 4.15-4.10 (m, 1H), 3.79 (s, 6H), 3.52 (d, J=10.9 Hz, 1H), 3.41 (dd, J=10.8, 3.2 Hz, 1H), 3.23 (dt, J=13.5, 6.8 Hz, 1H), 2.74 (dt, J=13.6, 6.6 Hz, 1H), 2.58 (p, J=7.0 Hz, 1H), 2.39 (d, J=12.0 Hz, 4H), 2.22 (dd, J=12.2, 7.4 Hz, 1H), 1.98-1.19 (m, 13H). $^{31}$P NMR (202 MHz, CDCl$_3$) δ 152.16 (95.5%, trans), 141.81 (4.5%, cis).

Example 28. Synthesis of WV-CA-031 and 031-dCiBu

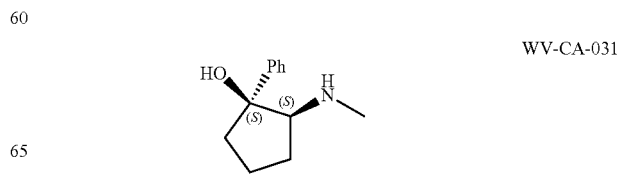

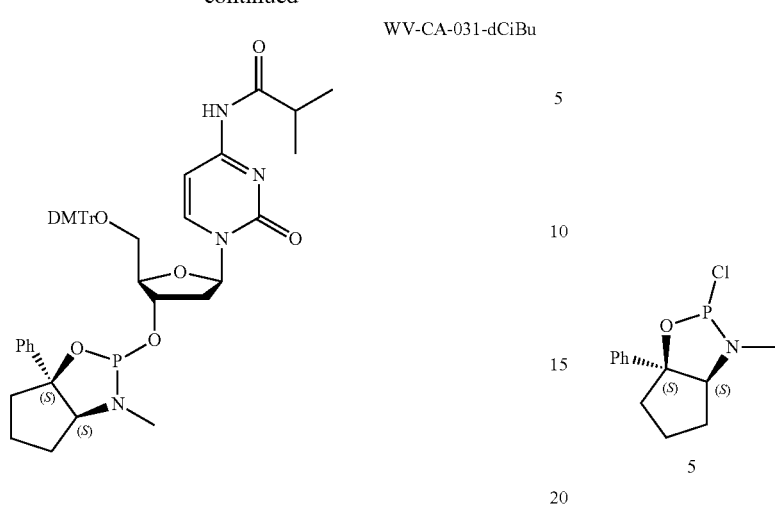

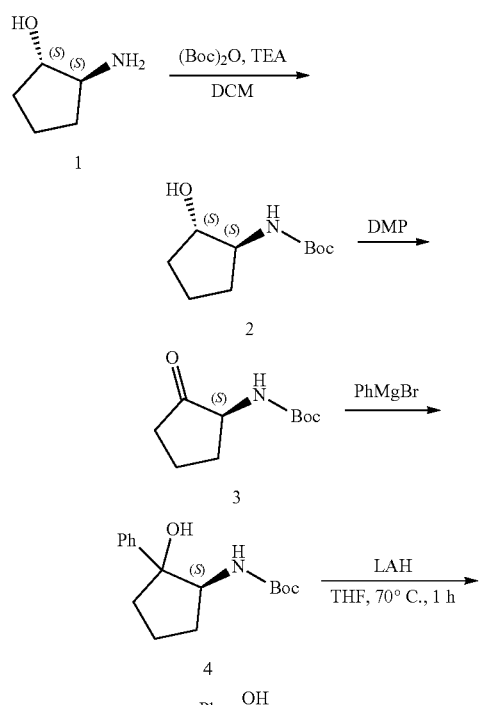

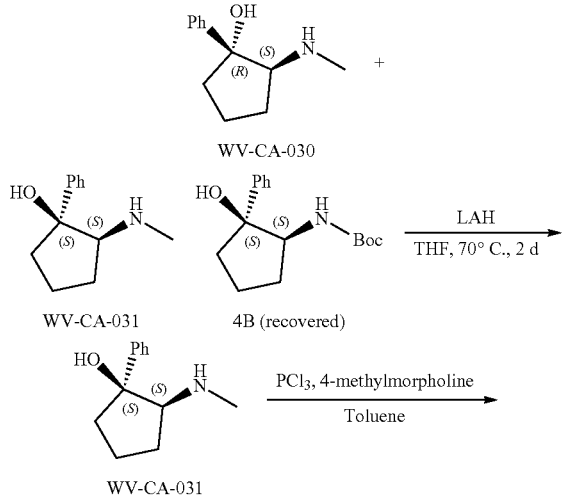

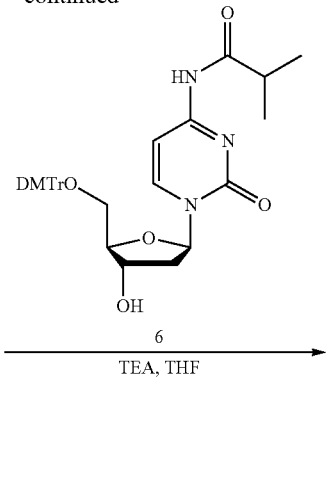

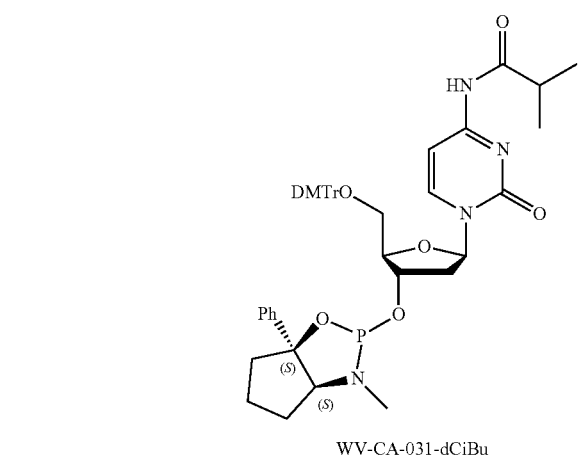

1. Preparation of Compound 2.

To a solution of compound 1 (65.40 g, 475.26 mmol, HCl salt) in DCM (500.00 mL) was added TEA (144.27 g, 1.43 mol, 197.63 mL) and (Boc)₂O (108.91 g, 499.02 mmol, 114.64 mL) at 0° C. The mixture was stirred at 25° C. for 12 hr. TLC and LCMS showed the reaction was completed. The resulting mixture was washed with water (300 mL*2) and brine (150 mL). The organic layer was dried over anhydrous MgSO₄, filtered, and concentrated to afford compound 2 as a white solid (91.70 g, crude), which was used into the next step without further purification. LCMS: (M+Na+): 224.1. TLC (Eluent: Petroleum ether:Ethyl acetate=2:1) R$_f$=0.7.

2. Preparation of Compound 3.

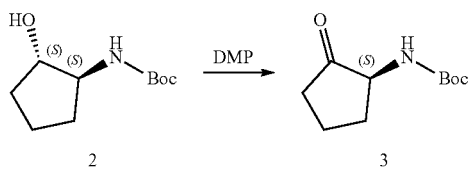

To a solution of compound 2 (70.00 g, 347.81 mmol) in DCM (1.00 L) was added DMP (162.27 g, 382.59 mmol) in portions at 0° C. The mixture was stirred at 0~25° C. for 2 hr. TLC indicated compound 2 was consumed, and one major new spot with lower polarity was detected. The reaction was quenched with sat. $Na_2SO_3$ aq. and sat. $NaHCO_3$ aq. (V/V=2:3, 1800 mL). The separated aqueous layer was extracted with DCM (500 mL*2). The combined organic layers were dried over anhydrous $Na_2SO_4$, filtered and concentrated to afford a light yellow crude oil (78 g). The crude product was purified by column chromatography on silica gel (Petroleum ether:Ethyl acetate=25:1, 15:1) to afford the product as crude colorless oil (48 g, 53.33%). HPLC purity: 77.2%. Chiral SFC purity: 82.12%. TLC (Petroleum ether:Ethyl acetate=3:1) $R_f$=0.64.

3. Preparation of Compound 4.

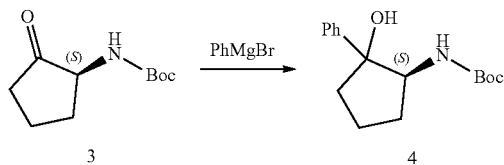

In a three-necked bottle with insert thermometer, to a solution of compound 3 (66.00 g, 331.24 mmol) in THF (400.00 mL) was added bromo(phenyl)magnesium (3 M, 350.00 mL) at −40~−20° C. (internal temperature) for 1 hr under $N_2$. The mixture was stirred at −40~0° C. for another 3 hr. LCMS showed the reaction was completed. TLC showed compound 3 was consumed, one new spot of two diastereomers was detected. The reaction was poured into sat. $NH_4Cl$ aq. (200 mL) at 0° C., extracted with EtOAc (200 mL*3). The combined organic layers were washed with brine (200 mL), dried over anhydrous $Na_2SO_4$, filtered and concentrated to afford crude product. The crude product was purified by column (PE/EA=50/1 to 10/1). The mixture product of compound 4 was obtained as yellow gum (55.00 g, 59.87%). LCMS: (M+Na+): 300.1. HPLC purity: 51.44%. TLC (Petroleum ether:Ethyl acetate=1:1) $R_f$=0.50.

4. Preparation of Compound 4B (Recover).

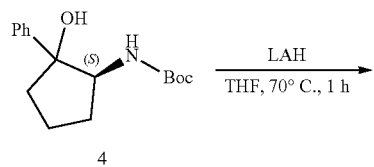

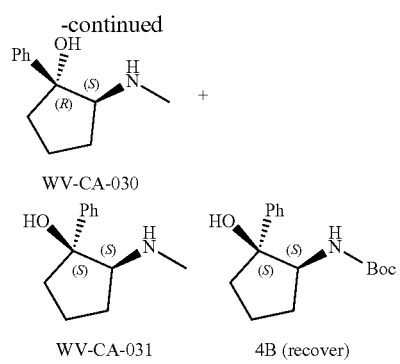

To a mixture solution of compound 4 (50.00 g, 180.27 mmol) in THF (50.00 mL) was added $LiAlH_4$ (13.68 g, 360.54 mmol) in portions at 0° C. The mixture was stirred at 75° C. for 1 hr. TLC showed compound 4 was consumed, WV-CA-030, 031 and compound 4B was detected. The reaction was quenched with sat. $MgSO_4$ aq. (50 mL). The reaction was filtered, and the filter cake was washed with EtOAc (100 mL*2) and MeOH (100 mL*2). The filtrate was dried over $Na_2SO_4$, and concentrated in vacuo to dryness. The residue was purified by column (Petroleum ether:Ethyl acetate=50:1, 1:1 to DCM:Methanol=100:1). The mixture residue of WV-CA-030, 031 was purified by Prep-HPLC (column: Phenomenex Luna C18 250*50 mm*10 m; mobile phase: [water (0.1% TFA)-ACN]; B %: 1%-30%, 20 min) to obtain compound WV-CA-030 was obtained as white solid (4.00 g, 11.60%). Compound WV-CA-031 was obtained as colorless oil (130.00 mg, 0.38%). and Compound 4B (recovered) as colorless oil (6.00 g, 12.00%). Compound WV-CA-030: $^1$H NMR (400 MHz, CHLOROFORM-d) δ=7.55-7.46 (m, 2H), 7.43-7.24 (m, 3H), 3.04-2.85 (m, 1H), 2.49 (td, J=8.9, 13.0 Hz, 1H), 2.18-2.08 (m, 4H), 2.01-1.82 (m, 4H), 1.79-1.54 (m, 1H). TLC (ethyl acetate:Petroleum ether=1:1) $R_f$=0.1. Compound WV-CA-031: $^1$H NMR (400 MHz, CHLOROFORM-d) δ=7.51 (d, J=7.2 Hz, 2H), 7.35-7.29 (m, 2H), 7.23-7.17 (m, 1H), 3.17 (t, J=8.5 Hz, 1H), 2.17-1.90 (m, 7H), 1.83-1.70 (m, 1H), 1.67-1.47 (m, 2H). TLC (ethyl acetate:Petroleum ether=1:1) $R_f$=0.1.

5. Preparation of Compound WV-CA-031.

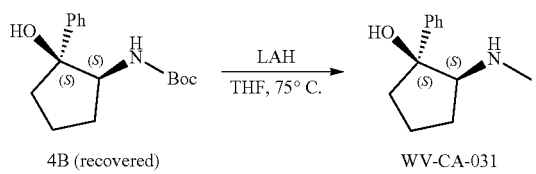

To a mixture solution of compound 4B (recovered) (6.00 g, 21.63 mmol) in THF (60.00 mL) was added $LiAlH_4$ (4.10 g, 108.15 mmol) in portions at 0° C. The mixture was stirred at 75° C. for 16 hr. TLC showed compound 4B was consumed, and compound WV-CA-031 was detected. The reaction was quenched with sat. $MgSO_4$ aq. (6 mL). The reaction was filtered, and the filter cake was washed with EA (100 mL*2) and MeOH (100 mL*2). The filtrate was dried over $Na_2SO_4$, concentrated in vacuo to dryness. The residue was purified by column (Petroleum ether:Ethyl acetate=10:1 to 1:1 and MeOH:TEA=100:1). The residue (2 g) was purified on Prep-HPLC (column: Phenomenex Luna C18 250*50 mm*10 m; mobile phase: [water (0.1% TFA)-ACN]; B %: 1%-25%, 20 min) to obtain compound WV-CA-031 as colorless oil (1.48 g, 33.75% yield). $^1$H NMR (400 MHz, CHLOROFORM-d) δ=7.53 (d, J=7.3 Hz, 2H), 7.34 (t, J=6.9 Hz, 2H), 7.29-7.18 (m, 1H), 3.24 (t, J=8.3 Hz, 1H), 2.21-1.61 (m, 10H). $^{13}$C NMR (101 MHz, CHLOROFORM-d): δ=146.86, 128.24, 128.6, 126.34, 124.89, 80.00, 70.65, 41.99, 35.06, 30.71, 21.61. LCMS: (M+H+): 192.1, 94.4% purity. Chiral SFC purity: 78.68%. TLC (Eluent: Ethyl acetate:Petroleum ether=1:1) $R_f$=0.10.

6. Preparation of Compound 5.

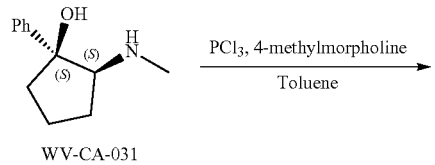

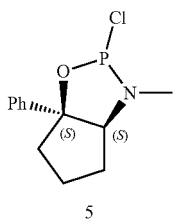

Compound WV-CA-031 (500.00 mg, 2.61 mmol) was dried by azeotropic distillation on a rotary evaporator with toluene (20 mL*3). To a solution of PCl$_3$ (358.43 mg, 2.61 mmol) in toluene (5 mL) was added a solution of compound WV-CA-031 (500.00 mg, 2.61 mmol, 1.00 eq.) and 4-methylmorpholine (528.00 mg, 5.22 mmol) in toluene (5 mL) at 0° C. The mixture was stirred at 15~20° C. for 1 hr. The resulting mixture was filtered (flushed with Ar) and concentrated to afford a residue as colorless oil. The crude product compound 5 was obtained as a yellow oil (660.00 mg, crude), which was used into the next step without further purification.

7. Preparation of Compound WV-CA-031-dCiBu.

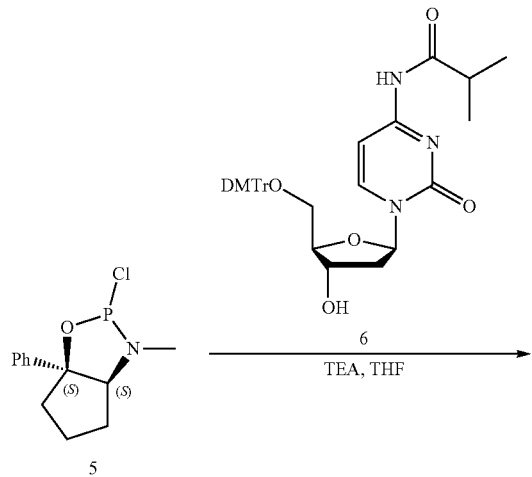

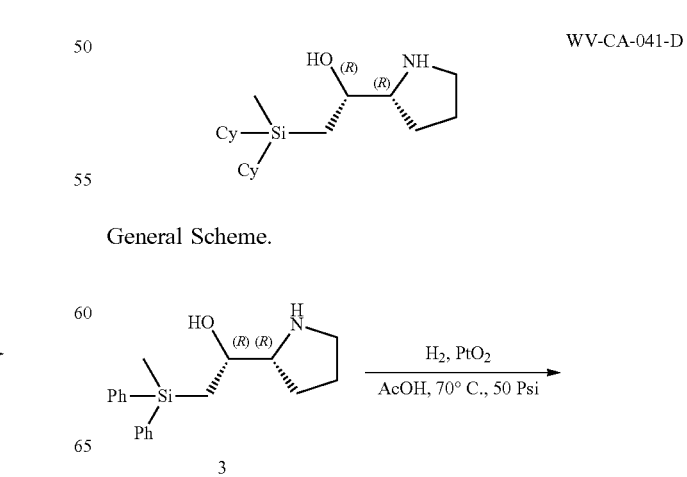

Compound 6 (1.03 g, 1.72 mmol) was dried by azeotropic distillation on a rotary evaporator with pyridine (20 mL) and toluene (20 mL*5). The dried compound 6 (1.03 g, 1.72 mmol) was dissolved in THF (15 mL), and then Et$_3$N (1.22 g, 12.04 mmol) was added. The mixture was cooled to −70° C. A solution of compound 5 (660.00 mg, 2.58 mmol) in THF (15 mL) was added dropwise at −70° C., then warm to 23° C. over 0.5 hr and stirred for another 1.5 hr. TLC showed one major spot was same polarity with the starting material. The resulting mixture was diluted with DCM (100 mL), washed with sat. NaHCO$_3$ aq. (30 mL*3). The organic layer was dried over anhydrous MgSO$_4$, filtered, and concentrated to afford a white foam. The residue was purified by MPLC (SiO$_2$, Petroleum ether:Ethyl acetate=1:3, 5% TEA) to give compound WV-CA-031-dCiBu a white solid (400.00 mg, 28.40%). $^1$H NMR (400 MHz, CHLOROFORM-d) δ=8.30 (d, J=7.5 Hz, 1H), 8.20-8.08 (m, 3H), 7.50-6.98 (m, 41H), 6.84-6.74 (m, 7H), 6.16 (dd, J=4.3, 6.3 Hz, 1H), 5.98 (t, J=5.8 Hz, 1H), 4.88-4.76 (m, 1H), 4.63-4.38 (m, 1H), 4.09-3.97 (m, 4H), 3.75-3.59 (m, 14H), 3.56-3.18 (m, 6H), 2.81 (d, J=8.0 Hz, 2H), 2.71-2.26 (m, 11H), 2.21-1.50 (m, 1H), 2.21-1.50 (m, 34H), 1.40-0.75 (m, 27H). $^{31}$P NMR (162 MHz, CHLOROFORM-d) δ=148.34, 148.03, 144.19, 143.19. TLC (Petroleum ether:Ethyl acetate=1:3, 5% TEA) $R_f$=0.25.

Example 29. Synthesis of WV-CA-041-D

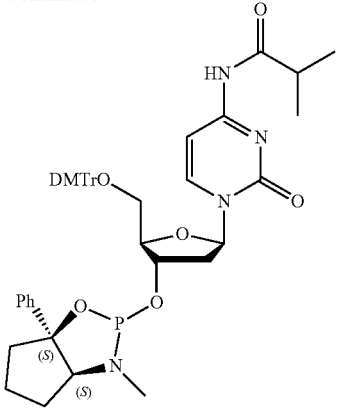

General Scheme.

-continued

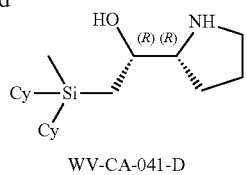

WV-CA-041-D

-continued

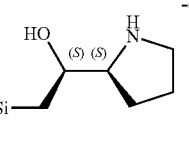

1. Preparation of Compound WV-CA-041-D.

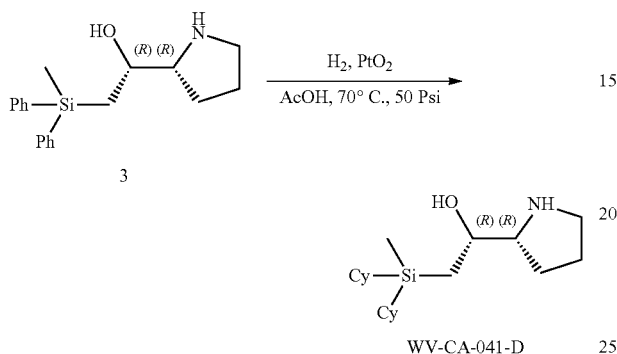

WV-CA-041-D

A mixture of compound 3 (1.00 g, 3.21 mmol) and PtO$_2$ (0.6 g, 2.64 mmol) in AcOH (150 mL) was hydrogenated under 50 psi of hydrogen pressure for 21 hr at 70° C. The reaction was cooled to 25° C. and then filtered, to the reaction was additionally added PtO$_2$ (0.6 g) and the mixture was stirred under 50 psi of hydrogen pressure for 23 hr at 70° C. LCMS showed that most of the intermediate remained and only a little product was detected. The reaction was cooled to 25° C. and then filtered, to the reaction was additionally added PtO$_2$ (1.5 g) and the mixture was stirred under 50 psi of hydrogen pressure for 24 hr at 70° C. LCMS showed that the intermediate was consumed and the product was detected. Three batches were combined. The reaction was cooled to 25° C. and then filtered. The filtrate was concentrated to give a residue. The residue was dissolved with DCM (100 mL) and neutralized with Na$_2$CO$_3$ (1 M, 100 mL), and the mixture was stirred at 10° C. for 2 hr. The organic layer was separated and the water phase was extracted with DCM (100 mL*2). The combined organic layers were dried over Na$_2$SO$_4$, filtered, and the filtrate was concentrated to give a residue, which was purified by silica gel chromatography (DCM:MeOH=50:1 to 10:1) to give the product. The solvent was removed under reduced pressure to give the final compound WV-CA-041-D as a colorless oil (850 mg, 27.3%). $^1$H NMR (400 MHz, CDCl3) δ=3.80-3.83 (m, 1H), 3.12-3.14 (m, 1H), 2.95-3.02 (m, 2H), 1.68-1.73 (m, 14H), 1.21-1.27 (m, 10H), 0.69-0.82 (m, 4H), 0.02 (s, 3H). $^{13}$C NMR (400 MHz, CDCl3) δ=69.495, 64.495, 46.932, 28.307, 27.989, 27.056, 25.781, 24.325, 23.733, 15.919, −7.675. LCMS: (M+H$^+$): 324.3.

Example 30. Synthesis of WV-CA-041-L

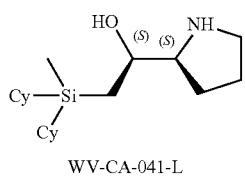

WV-CA-041-L

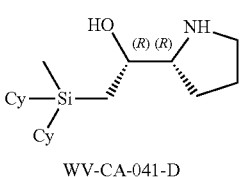

WV-CA-041-L

A mixture of compound 3 (1.00 g, 3.21 mmol) and PtO$_2$ (0.6 g, 2.64 mmol) in AcOH (150 mL) was hydrogenated under 50 psi of hydrogen pressure for 21 hr at 70° C. LCMS showed that the material was consumed and only intermediate was detected. The reaction was cooled to 25° C. and then filtered. To the reaction was additionally added PtO$_2$ (0.6 g) and the mixture was stirred under 50 psi of hydrogen pressure for 23 hr at 70° C. LCMS showed that most of the intermediate remained and only a little product was detected. The reaction was cooled to 25° C. and then filtered. To the reaction was additionally added PtO$_2$ (1.5 g) and the mixture was stirred under 50 psi of hydrogen pressure for 24 hr at 70° C. LCMS showed that the intermediate was consumed and there was product detected. Three batches were combined. The reaction was cooled to 25° C. and then filtered. The filtrate was concentrated to give a residue. The residue was dissolved with DCM (100 mL) and neutralized with Na$_2$CO$_3$ (1M, 100 mL), and the mixture was stirred at 10° C. for 2 hr. The organic layer was separated and the water phase was extracted with DCM (100 mL*2). The combined organic layers were dried over Na$_2$SO$_4$, filtered, and the filtrate was concentrated to give a residue. The residue was purified by silica gel chromatography (DCM: MeOH=50:1 to 10:1) to give the product. The solvent was removed under reduced pressure to give the final compound WV-CA-041-L as colorless oil (880 mg, 28.2%). $^1$H NMR (400 MHz, CDCl3) δ=3.79-3.83 (m, 1H), 3.10-3.12 (m, 1H), 2.94-3.00 (m, 2H), 1.69-1.71 (m, 14H), 1.19-1.26 (m, 10H), 0.67-0.82 (m, 4H), 0.04 (s, 3H). $^{13}$C NMR (400 MHz, CDCl3) δ=69.429, 64.712, 46.877, 28.328, 28.073, 28.000, 27.060, 25.747, 24.435, 23.808, 16.013, −7.720. LCMS: (M+H$^+$): 324.3.

Example 31. Synthesis of WV-CA-042

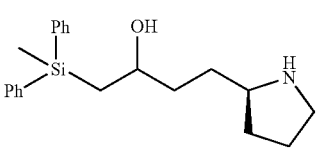

WV-CA-042

General Scheme.

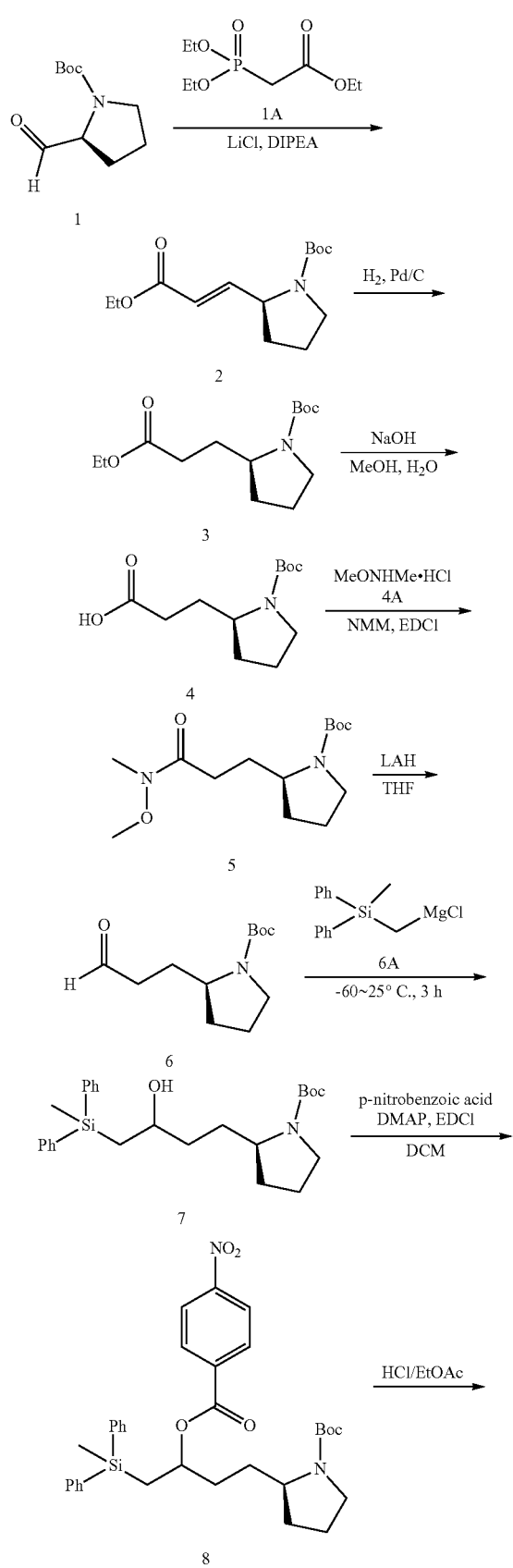

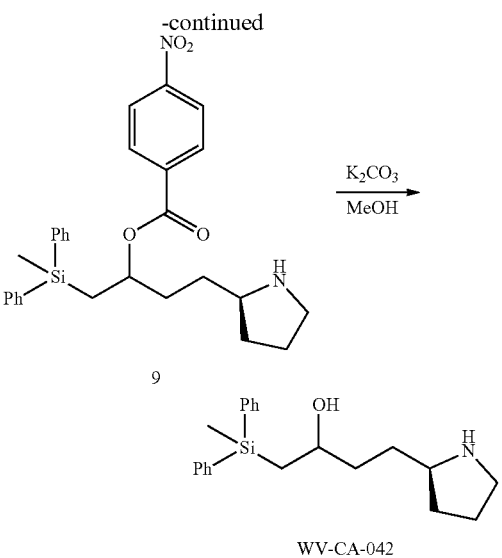

1. Preparation of Compound 2.

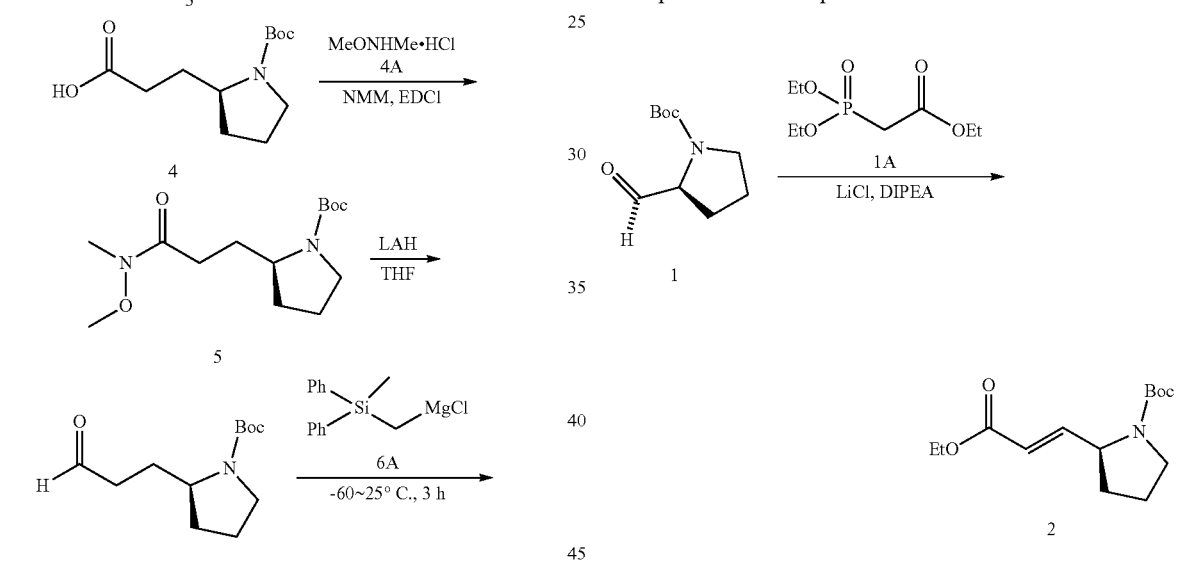

Compound 1 (87.50 g, 439.15 mmol) was dissolved in ACN (1.50 L). Following addition of LiCl (22.34 g, 526.98 mmol) and DIPEA (68.11 g, 526.98 mmol), compound 1A (118.14 g, 526.98 mmol) were added to the reaction mixture at 25° C. The reaction was stirred at 25° C. for 16 hr. TLC showed the reaction was completed. The resulting mixture was concentrated to afford a residue. To the residue was added EtOAc (1 L) and water (1 L). The aqueous layer was extracted with EtOAc (800 mL*3). The combined organic layers were washed with water (800 mL), dried over $MgSO_4$, filtered, and concentrated in vacuo to afford a crude oil (141 g). The crude product was combined with another part of crude product, and purified by column chromatography on silica gel (Petroleum ether:Ethyl acetate=10:1, 5:1) to afford compound 2 as a light brown oil (118.00 g, 99.76%). $^1$H NMR (400 MHz, $CDCl_3$): δ=6.82 (br. s, 1H), 5.94-5.58 (m, 1H), 5.27 (br. s, 1H), 4.62-3.92 (m, 3H), 3.59-3.18 (m, 2H), 2.32 (br. s, 1H), 2.04 (d, J=2.6 Hz, 2H), 1.95-1.57 (m, 4H), 1.43 (d, J=11.5 Hz, 9H), 1.32-1.16 (m, 4H). TLC (petroleum ether/ethyl acetate=5:1) $R_f$=0.51.

2. Preparation of Compound 3.

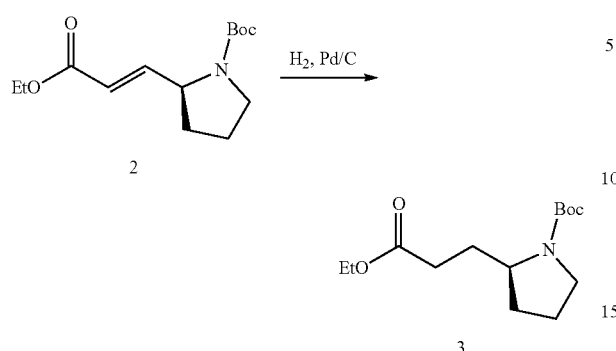

To a solution of compound 2 (80.00 g, 297.02 mmol, 1.00 eq.) in MeOH (800.00 mL) was added Pd/C (2.6 g) under $H_2$ atmosphere. The suspension was degassed and purged with $H_2$ 3 times. The mixture was stirred under $H_2$ (15 Psi) at 20° C. for 3 hr. TLC showed the starting material was consumed. The resulting mixture was filtered, and concentrated to get compound 3 as a yellow oil (63.00 g, crude). The mixture was used directly without further purification. $^1$H NMR (400 MHz, CDCl$_3$): δ=4.12 (q, J=7.0 Hz, 2H), 3.79 (br. s, 1H), 3.51-3.16 (m, 2H), 2.30 (br. s, 2H), 2.06-1.57 (m, 6H), 1.46 (s, 9H), 1.25 (t, J=7.3 Hz, 3H). LCMS: (M+H$^+$): 272.3. TLC (Petroleum ether/Ethyl acetate=10:1) $R_f$=0.56.

3. Preparation of Compound 4.

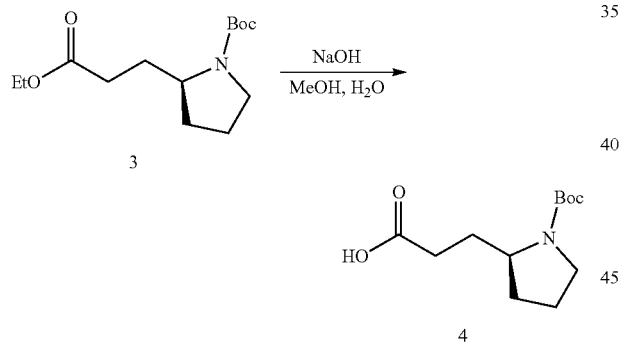

To a mixture of compound 3 (80.80 g, 297.77 mmol) in MeOH (400.00 mL) and $H_2O$ (400.00 mL) was added NaOH (59.55 g, 1.49 mol). The mixture was stirred at 25° C. for 5 hr. TLC showed the reaction was completed. The resulting mixture was concentrated under reduced pressure to remove MeOHR. The resulting aqueous phase was diluted with water (30 mL) and washed with DCM (30 mL*2). The aqueous layer was adjusted to pH 3 with 1M HCl (40 mL), and extracted with EtOAc (50 mL*3). The combined organic layers were washed with brine, dried over anhydrous MgSO$_4$, filtered and concentrated to afford compound 4 as a colorless oil (71.50 g, crude). The mixture was used directly without further purification. $^1$H NMR (400 MHz, CDCl$_3$): δ=4.08-3.76 (m, 1H), 3.34 (d, J=6.5 Hz, 2H), 2.40 (br. s., 2H), 2.04-1.57 (m, 7H), 1.54-1.39 (m, 10H). LCMS: (M−Boc+H+): 144.2. TLC (Petroleum ether/Ethyl acetate=3:1) $R_f$=0.02.

4. Preparation of Compound 5.

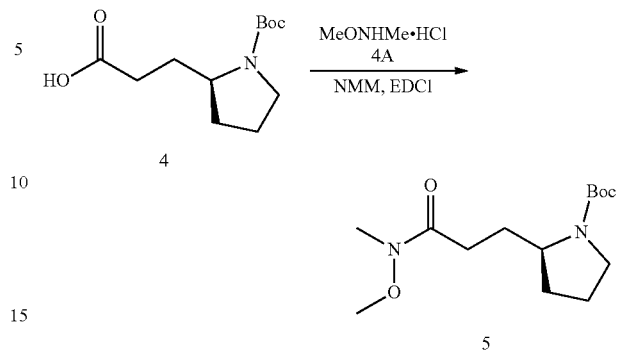

Compound 4 (72.80 g, 299.22 mmol) was dissolved in anhydrous DCM (800 mL) under $N_2$ atmosphere and cooled to 0° C. To this solution was added compound 4A (35.02 g, 359.06 mmol) and NMM (36.32 g, 359.06 mmol) followed by EDCI (68.83 g, 359.06 mmol). The reaction mixture was then allowed to come to 25° C. and stirred for 3 hr. TLC showed the reaction was completed. The reaction was cooled to 0° C., quenched by the addition of an ice cold 2 M HCl solution (1200 mL) and stirred at this temperature for 5 minutes. The reaction was diluted with water (300 mL) and extracted with DCM (600 mL*3). The combined organic layers were washed with brine (500 mL), sat. NaHCO$_3$ aq. (400 mL), dried over MgSO$_4$, filtered and concentrated to afford compound 5 as a light-yellow oil (82.60 g, crude). The mixture was used directly without any further purification. $^1$H NMR (400 MHz, CDCl$_3$): δ=3.85 (d, J=12.5 Hz, 1H), 3.70 (s, 3H), 3.53-3.23 (m, 2H), 3.19 (s, 3H), 2.45 (s, 2H), 2.03-1.60 (m, 6H), 1.46 (s, 9H). LCMS: (M+Na$^+$): 309.1. TLC (Dichloromethane:Methanol=20:1) $R_f$=0.67.

5. Preparation of Compound 6.

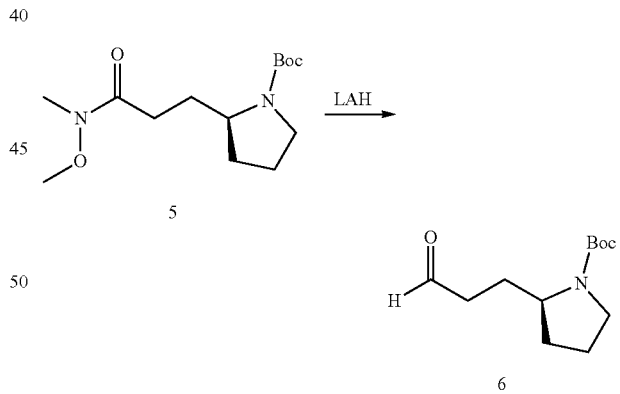

To a solution of compound 5 (10.00 g, 34.92 mmol) in THF (100 mL) was added LiAlH$_4$ (5.10 g, 134.39 mmol) at −10° C. The mixture was stirred at −10~0° C. for 2 hr. TLC showed the reaction was completed. The resulting mixture was quenched and adjusted to pH 5-6 with 5% KHSO$_4$ aq. (350 mL), extracted with EtOAc (250 mL*3). The combined organic layers were washed with brine (200 mL), dried over anhydrous MgSO$_4$, filtered and concentrated to afford compound 6 as a light-yellow oil (7.90 g, crude), which was unstable, and used immediately for the next step. TLC (petroleum ether/Ethyl acetate=3:1) $R_f$=0.51.

6. Preparation of Compound 7.

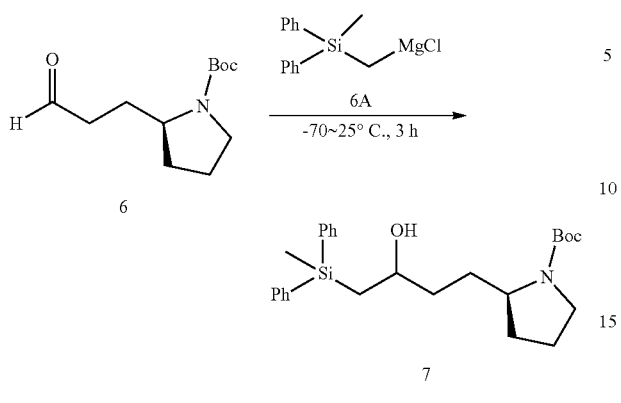

To a solution of compound 6 (16.00 g, 70.39 mmol) in THF (200.00 mL) was added compound 6A (1 M, 140.78 mL) at −70° C. The mixture was warmed to 25° C. slowly over 2 hr, and stirred at 25° C. for 1 hr. TLC and LCMS showed the starting material was consumed. Sat. NH$_4$Cl aq. (500 mL) was dropped slowly at 0° C., and then extracted with EtOAc (300 mL*3). The combined organic layers were washed with brine (150 mL), dried over Na$_2$SO$_4$, filtered and concentrated to get the crude. The residue was purified by column chromatography on silica gel (Petroleum ether/Ethyl acetate from 100/1 to 10/1) to get compound 7 as a yellow oil (10.00 g, 32.31%). LCMS: (M+Na$^+$): 462.2. TLC (Petroleum ether/Ethyl acetate=5:1) R$_f$=0.43.

7. Preparation of Compound 8.

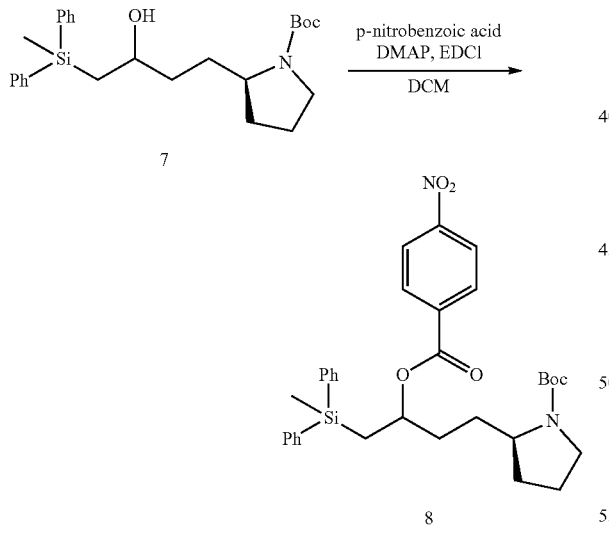

To a solution of compound 7 (5.00 g, 11.37 mmol) in DCM (100 mL) was added DMAP (11.11 g, 90.96 mmol), EDCI (17.44 g, 90.96 mmol) and 4-nitrobenzoic acid (13.30 g, 79.59 mmol) at 0° C. The mixture was stirred at 20° C. for 12 hr. TLC showed the starting material was consumed. Sat. NH$_4$Cl aq. (150 mL) was added and extracted with DCM (180 mL*3). The combined organic layers were washed with brine (200 mL), dried over Na$_2$SO$_4$, filtered and concentrated to give a residue, which was purified by silica gel chromatography (Petroleum ether/Ethyl acetate=8:1) to get compound 8 as a yellow oil (6.30 g, 91.62%). TLC (Petroleum ether:Ethyl acetate=5:1) R$_f$=0.57.

8. Preparation of Compound 9.

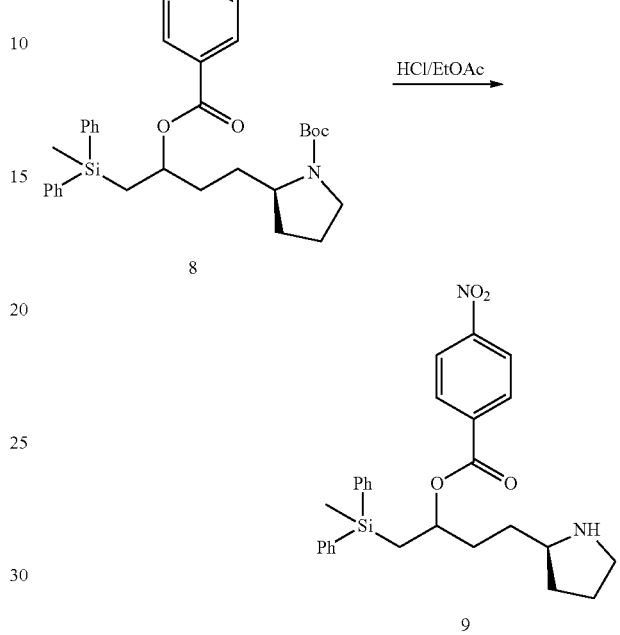

A solution of compound 8 (6.30 g, 10.42 mmol) in HCl/EtOAc (4N, 100 mL) was stirred at 20° C. for 0.5 hr. TLC showed the starting material was consumed. The resulting mixture was concentrated to get compound 9 as a yellow oil (5.00 g, crude), which was used directly without further purification. TLC (Petroleum ether:Ethyl acetate=5:1) R$_f$=0.

9. Preparation of WV-CA-042.

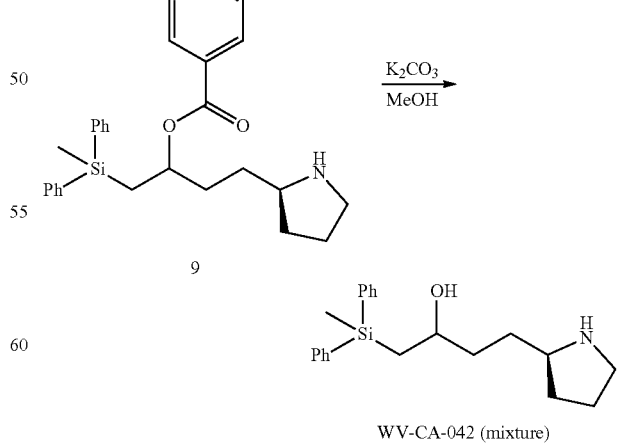

To a solution of compound 9 (5.00 g, 8.49 mmol) in MeOH (60.00 mL) and H$_2$O (10 mL) was added K$_2$CO$_3$ (3.52 g, 25.47 mmol). The mixture was stirred at 20° C. for 12 hr. LCMS showed the starting material was remained, and then K$_2$CO$_3$ (3.52 g, 25.47 mmol) was added. The mixture was stirred at 50° C. for 4 hr. LCMS and TLC showed the starting material was consumed. The resulting mixture was concentrated to remove the solvent, and then the mixture was dissolved in DCM:MeOH=10:1 (100 mL), filtered, and the filtrate was concentrated to get a residue, which was purified by silica gel chromatography (DCM:MeOH=30:1 to 10:1) to get WV-CA-042 as a yellow oil (1.60 g, 54.87%). $^1$H NMR (400 MHz, CDCl$_3$): δ=7.60-7.51 (m, 4H), 7.40-7.30 (m, 6H), 4.69 (br. s, 1H), 3.93-3.70 (m, 1H), 3.17-2.83 (m, 3H), 1.94-1.20 (m, 11H), 0.69-0.59 (m, 3H). $^{13}$C NMR (101 MHz, CDCl$_3$): δ=140.72, 137.94, 137.90, 137.85, 132.41, 132.35, 131.12, 131.10, 72.93, 71.61, 63.20, 61.94, 49.01, 48.92, 42.35, 40.40, 36.18, 35.56, 34.48, 34.02, 28.73, 28.64, 27.80, 27.19, 0.09. LCMS: (M+H+): 340.1. TLC (Dichloromethane:Methanol=10:1) R$_f$=0.39. LCMS purity: 98.8%.

Example 32. Synthesis of WV-CA-043

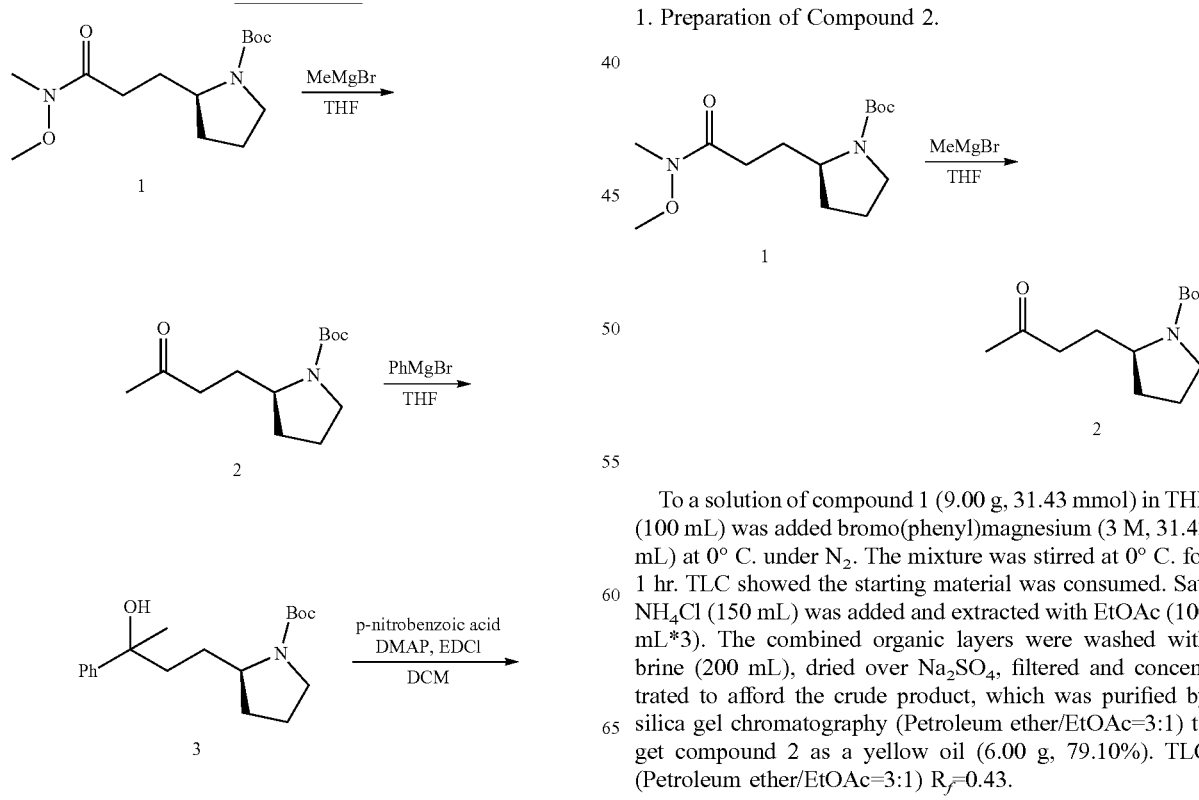

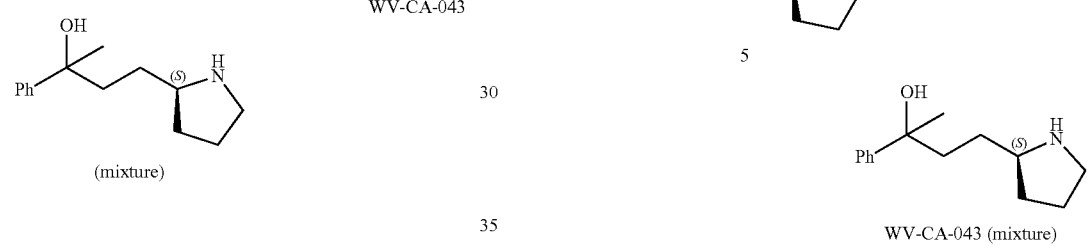

1. Preparation of Compound 2.

To a solution of compound 1 (9.00 g, 31.43 mmol) in THF (100 mL) was added bromo(phenyl)magnesium (3 M, 31.43 mL) at 0° C. under N$_2$. The mixture was stirred at 0° C. for 1 hr. TLC showed the starting material was consumed. Sat. NH$_4$Cl (150 mL) was added and extracted with EtOAc (100 mL*3). The combined organic layers were washed with brine (200 mL), dried over Na$_2$SO$_4$, filtered and concentrated to afford the crude product, which was purified by silica gel chromatography (Petroleum ether/EtOAc=3:1) to get compound 2 as a yellow oil (6.00 g, 79.10%). TLC (Petroleum ether/EtOAc=3:1) R$_f$=0.43.

2. Preparation of Compound 3.

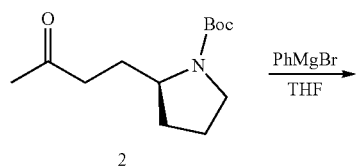

To a solution of compound 2 (6.00 g, 24.86 mmol) in THF (100 mL) was added bromo(phenyl)magnesium (3 M, 41.44 mL) at 0° C. The mixture was stirred at 20° C. for 1 hr. TLC showed the starting material was consumed. Sat. NH$_4$Cl aq. (100 mL) was added and extracted with EtOAc (100 mL*2). The combined organic layers were washed with brine (100 mL), dried over Na$_2$SO$_4$, filtered and concentrated to give a residue, which was purified by silica gel chromatography (Petroleum ether/EtOAc=3:1) to give compound 3 as a yellow oil (5.50 g, 69.26%). TLC (Petroleum ether/EtOAc=3:1) R$_f$=0.49.

3. Preparation of Compound 4.

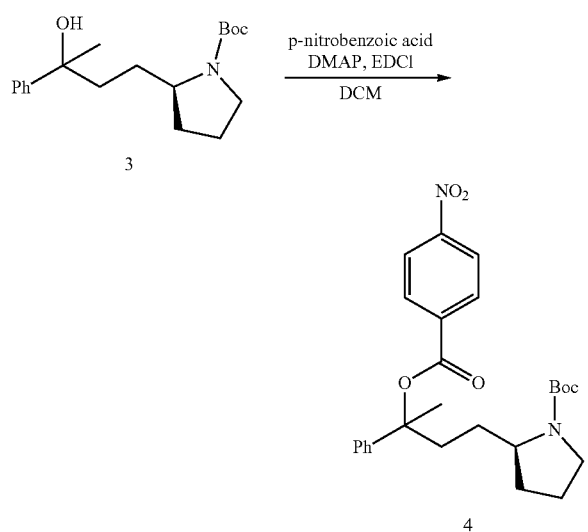

To a stirred solution of compound 3 (5.50 g, 17.22 mmol) in DCM (100 mL) were added DMAP (16.83 g, 137.76 mmol), EDCI (26.41 g, 137.76 mmol), and 4-nitrobenzoic acid (20.14 g, 120.54 mmol) at 0° C. The mixture was stirred at 20° C. for 12 hr. TLC showed the starting material was consumed. Sat. NH$_4$Cl (100 mL) was added and extracted with DCM (50 mL*2). The combined organic layers were washed with brine (80 mL), dried over Na$_2$SO$_4$, filtered and concentrated to get a residue, which was purified by silica gel chromatography (Petroleum ether/EtOAc=5:1) to get compound 4 as a yellow oil (7.20 g, 89.24%). TLC (Petroleum ether/EtOAc=3:1) R$_f$=0.65.

4. Preparation of Compound 5.

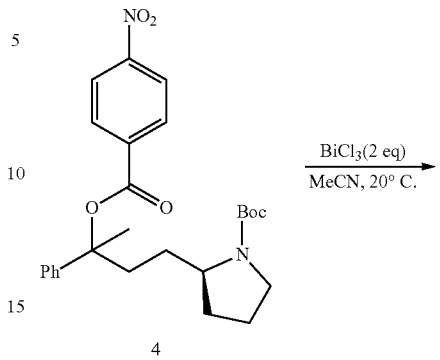

To a solution of compound 4 (3.00 g, 6.81 mmol) in MeCN (60.00 mL) was added trichlorobismuthane (4.29 g, 13.62 mmol). The mixture was stirred at 20° C. for 2 hr. TLC showed most of the starting material was consumed, and the desired product was found. Two batches were combined together for workup. The mixture was poured into an EDTA aq. (200 mL) and extracted with DCM (200 mL*2) The combined organic layers were washed with brine (100 mL), dried over Na$_2$SO$_4$, filtered and concentrated to get the crude product, which was purified by column chromatography on silica gel (Dichloromethane/Methanol, from 50:1 to 10:1) to get compound 5 as a yellow oil (1.30 g, 56.08%). $^1$H NMR (400 MHz, CDCl$_3$): δ=8.32-7.95 (m, 5H), 7.42-7.18 (m, 6H), 3.28-2.82 (m, 3H), 2.47-2.13 (m, 2H), 2.06-1.96 (s, 3H), 1.93-1.29 (m, 6H). TLC (Petroleum ether/EtOAc=3:1) R$_f$=0.01.

5. Preparation of WV-CA-043.

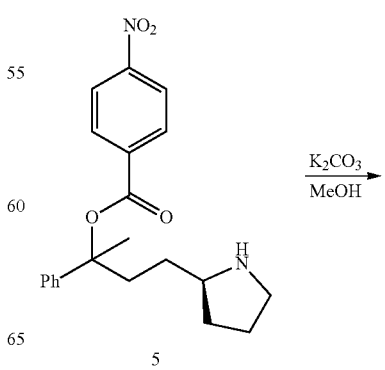

601

-continued

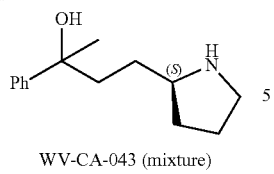

WV-CA-043 (mixture)

To a solution of compound 5 (2.60 g, 7.06 mmol) in the mixture of MeOH (30 mL) and H₂O (6 mL) was added K₂CO₃ (2.93 g, 21.18 mmol). The mixture was stirred at 50° C. for 12 hr. LCMS showed the starting material was consumed. The mixture was concentrated to afford the product as a crude, which was dissolve in DCM (200 mL), filtered and the filtrate was concentrated to give a residue, which was purified by prep-HPLC (column: Phenomenex Luna C18 250*50 mm*10 m; mobile phase: [water (0.1% TFA)-ACN]; B %: 1%-20%, 20 minutes) to get WV-CA-043 as a light yellow solid (900 mg, 58.12%). ¹H NMR (400 MHz, CDCl₃): δ=7.50-7.42 (m, 3H), 7.33 (t, J=7.7 Hz, 3H), 7.24-7.15 (m, 2H), 3.11-2.95 (m, 2H), 2.93-2.82 (m, 2H), 2.73 (td, J=7.1, 11.8 Hz, 1H), 2.25 (ddd, J=3.1, 7.9, 14.6 Hz, 1H), 2.03-1.97 (m, 1H), 1.94-1.41 (m, 15H), 1.22-1.00 (m, 2H). ¹³C NMR (101 MHz, CDCl₃): δ=149.73, 149.38, 127.90, 125.85, 125.73, 125.36, 125.11, 73.21, 72.72, 60.06, 58.04, 45.89, 45.56, 42.19, 39.98, 32.69, 32.40, 31.35, 30.60, 30.30, 29.23, 25.78, 25.49. LCMS: (M+H+): 220.1. LCMS purity=100.0%.

Example 33. Synthesis of WV-CA-044

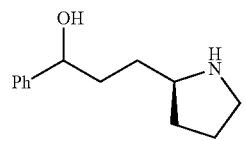

WV-CA-044

General Scheme.

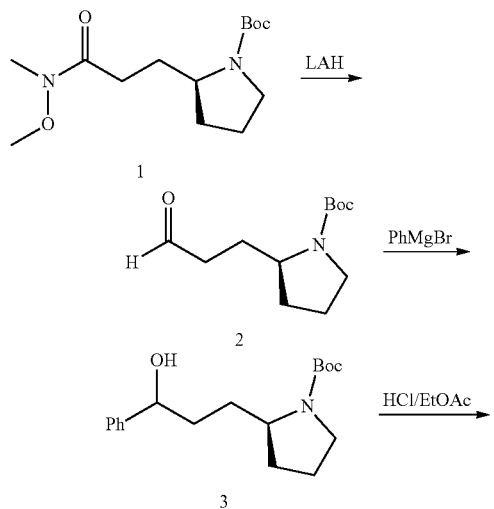

602

-continued

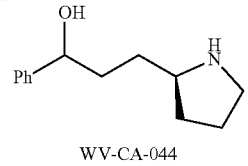

WV-CA-044

1. Preparation of Compound 2.

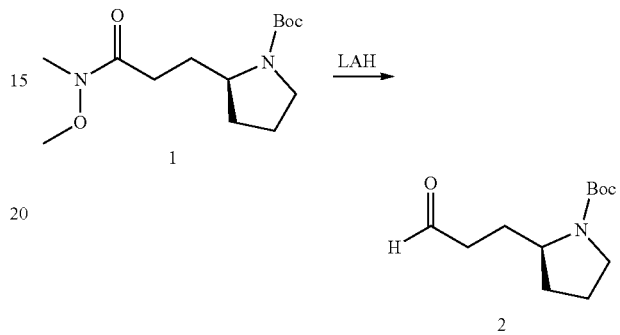

To a solution of compound 1 (10.00 g, 34.92 mmol) in THF (100 mL) was added LiAlH₄ (5.10 g, 134.39 mmol) at −10° C. The mixture was stirred at −10~0° C. for 2 hr. TLC showed the reaction was completed. The resulting mixture was quenched and adjusted to pH 5-6 with 5% KHSO₄ aq. (350 mL), and extracted with EtOAc (250 mL*3). The combined organic layers were washed with brine (200 mL), dried over anhydrous MgSO₄, filtered and concentrated to afford compound 2 (7.90 g, crude), which was unstable, and used immediately for the next step. TLC (Petroleum ether/Ethyl acetate=3:1) R_f=0.51.

2. Preparation of Compound 3.

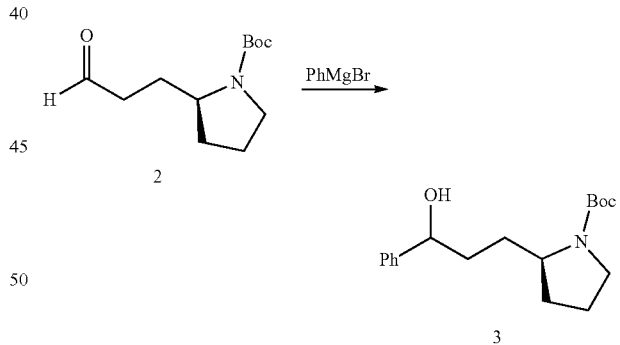

To a solution of bromo(phenyl)magnesium (3 M, 23.17 mL) in THF (100 mL) was added compound 2 (7.90 g, 34.76 mmol) at −70° C. The mixture was allowed to warm to 25° C. slowly over 2 hr, and stirred at 25° C. for 1 hr. TLC showed compound 2 was consumed, and desired product was observed. The resulting mixture was quenched with sat. NH₄Cl aq. (100 mL), extracted with EtOAc (150 mL*3). The combined organic layers were dried over anhydrous MgSO₄, filtered and concentrated to afford the product as a crude light yellow gum. The crude product was purified by column chromatography on silica gel (Petroleum ether/Ethyl acetate=5:1) to afford compound 3 (7.8 g, crude), HPLC showed only 70% was desired product, and then the residue was re-purified by MPLC (Petroleum ether/Ethyl acetate, 10:1, 5:1) to get compound 3 as a yellow oil (5.00 g, 71.43%). TLC (Petroleum ether/Ethyl acetate=3:1) $R_f$=0.50. HPLC purity=86.7%.

3. Preparation of Compound WV-CA-044.

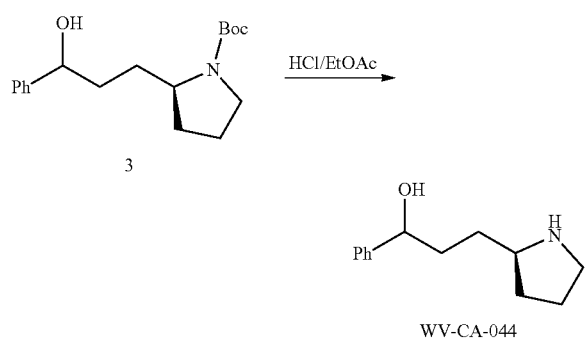

To a solution of compound 3 (5.00 g, 16.37 mmol) in EtOAc (5 mL) was added HCl/EtOAc (4 M, 100.00 mL) slowly at 0° C. The mixture was stirred at 0° C. for 0.5 hr. TLC showed the starting material was consumed. The mixture was concentrated to get the crude, and sat. $Na_2CO_3$ aq. was added until pH>10, and then extracted with DCM (15 mL*2). The combined organic layers were washed with sat. $Na_2CO_3$ aq. (30 mL) and brine (30 mL), dried over $Na_2SO_4$, filtered and concentrated to get a residue, which was purified by MPLC (DCM/MeOH=10:1) to get WV-CA-044 as a yellow solid (1.20 g, 35.71%).

$^1$H NMR (400 MHz, $CDCl_3$): δ=7.44-7.16 (m, 4H), 4.78 (t, J=5.5 Hz, 1H), 4.66 (dd, J=2.9, 8.6 Hz, 1H), 3.26-3.07 (m, 1H), 3.04-2.88 (m, 2H), 2.02-1.48 (m, 7H), 1.46-1.31 (m, 1H). $^{13}$C NMR (101 MHz, $CDCl_3$): δ=145.99, 128.12, 126.73, 125.75, 74.33, 72.88, 59.49, 58.42, 45.96, 38.18, 36.21, 35.23, 32.13, 31.17, 31.10, 25.73. LCMS: (M+H+): 206.2. TLC (Petroleum ether/Ethyl acetate=3:1) $R_f$=0.01. LCMS purity: 100.0%.

Example 34. Synthesis of WV-CA-047

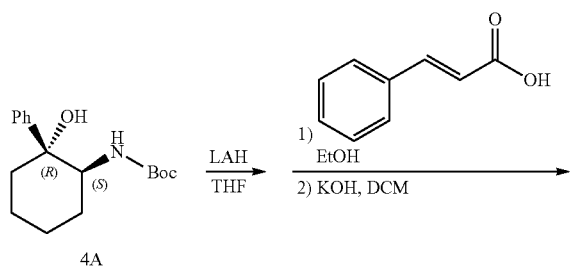

1. Preparation of Compound WV-CA-026.

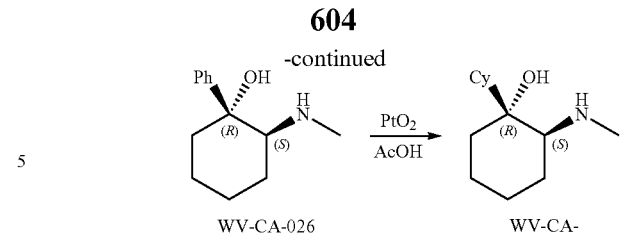

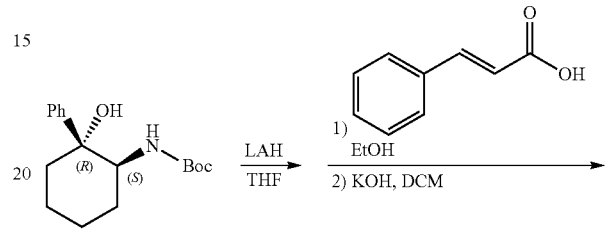

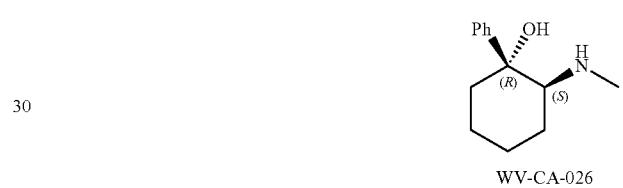

To a solution of compound 4A (6.00 g, 20.59 mmol) in THF (60.00 mL) was added $LiAlH_4$ (3.91 g, 102.95 mmol) at 0° C. The suspension reaction was stirred at 75° C. for 12 hr. TLC showed compound 4A was consumed completely and one new spot was detected. The reaction was quenched with sat. $MgSO_4$ aq. (6 mL). The suspension was diluted with EtOAc (50 mL). The residue was filtered, and washed with EtOAc (150 mL) and MeOH (100 mL). The organic phase was concentrated in vacuo to dryness to give the crude of WV-CA-026 as yellow solid (4.0 g, crude). To a crude of WV-CA-026 (4.0 g, crude) in EtOH (15.00 mL) was added (E)-3-phenylprop-2-enoic acid (2.89 g, 19.48 mmol). The mixture was heated at 90° C. for 30 minutes. The mixture was concentrated in vacuo to dryness. The white crude solid was dissolved in EtOAc (20 mL) at 80° C. for 0.5 hr until the mixture became clear. The solution was allowed to cool to 25° C. (r.t.) slowly. A large amount of solid precipitated, filtered, and concentrated in vacuo to dryness. To a suspension of cinnamic acid salt in DCM (20 mL) was added dropwise 2M KOH aq. (20.00 mL) at 20° C. with pH of ~13. The mixture was stirred at 20° C. for 0.5 h, and then extracted with DCM (30 mL*2). The organic phase was washed with brine. The aqueous phase was back extracted with DCM (30 mL*2). The combined organic layers were dried over $Na_2SO_4$, filtered and concentrated in vacuo to afford WV-CA-026 as a colorless oil (2.00 g, 57.36%). $^1$H NMR (400 MHz, $CDCl_3$): δ=7.56 (d, J=7.6 Hz, 2H), 7.39-7.35 (m, 2H), 7.30-7.27 (m, 1H), 2.71 (d, J=3.2 Hz, 1H), 2.47-2.44 (m, 1H), 2.17 (s, 3H), 2.00-1.45 (m, 9H). TLC (Petroleum ether:Ethyl acetate=1:1) $R_f$=0.10. HPLC purity=97.7%. SFC purity=99.6%.

2. Preparation of Compound WV-CA-047.

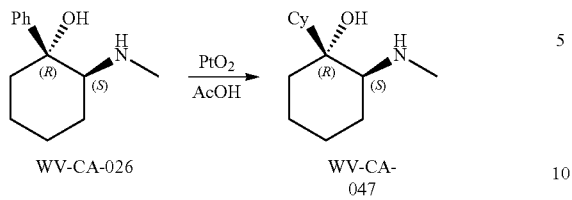

To a solution of WV-CA-026 (2.00 g, 9.74 mmol) in AcOH (100.00 mL) was added PtO$_2$ (1.00 g, 2.20 mmol) under N$_2$. The suspension was degassed under vacuum and purged with H$_2$ three times. The mixture was stirred under H$_2$ (50 psi) at 70° C. for 16 hr. LCMS and HPLC showed the reactant was consumed and one new spot was detected. The reaction was filtered, and the filter cake was washed with AcOH (80 mL*3). The solvent was removed under reduced pressure. The residue was dissolved in H$_2$O (50 mL), and was adjusted to pH 12 with sat. Na$_2$CO$_3$ aq. (40 mL). The aqueous phase was extracted with EtOAc (50 mL*3). The combined organic layers were dried over Na$_2$SO$_4$, filtered and concentrated in vacuo to give WV-CA-047 as a yellow solid (1.80 g, 87.47%). $^1$H NMR (400 MHz, CDCl$_3$): δ=7.50 (d, J=3.6 Hz, 1H), 2.39 (s, 2H), 1.81-1.11 (m, 21H). $^{13}$C NMR (125.7 MHz, CDCl$_3$): δ=74.35, 42.51, 34.65, 31.20, 26.78, 26.54, 25.91, 25.56, 23.45, 21.42, 19.99. LCMS: (M+H$^+$): 212.2.

Example 35. Synthesis of WV-CA-047-dCiBu

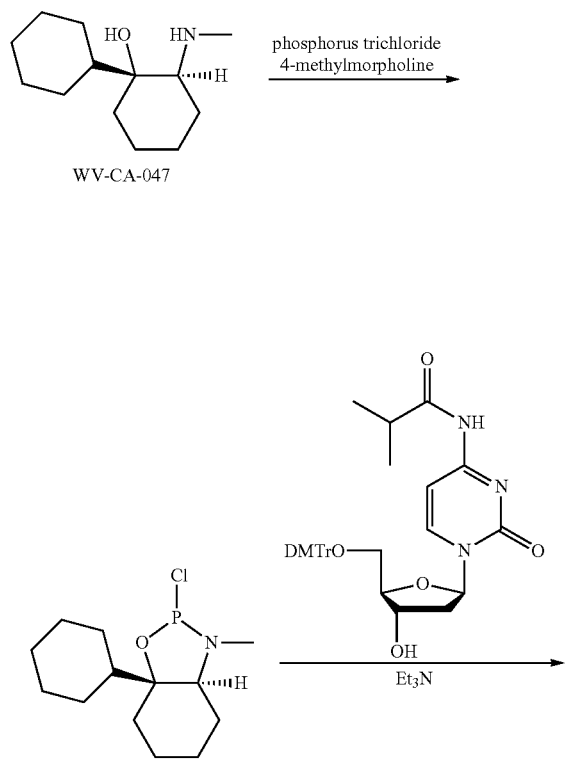

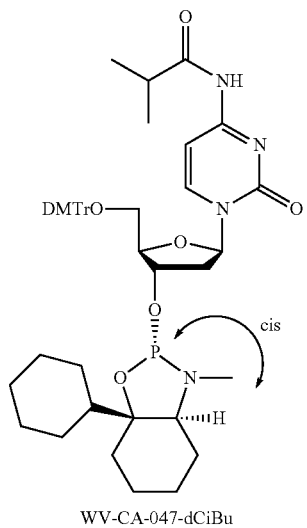

Using WV-CA-047 as starting material, the title compound (0.70 g, 18%) as a white solid was prepared analogously to WV-CA-008S-dCiBu. $^{31}$P NMR (202 MHz, CDCl$_3$) δ 143.94 (100%, cis).

Example 36. Synthesis of WV-CA-050

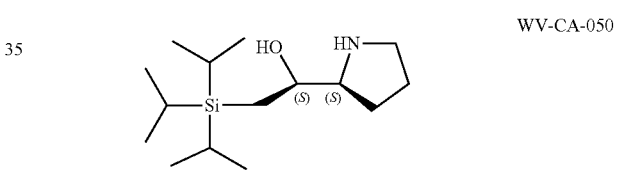

General Scheme.
Scheme 1

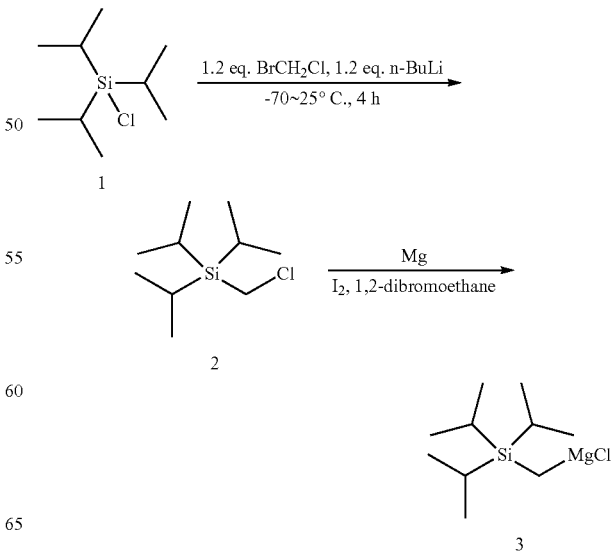

1. Preparation of Compound 2.

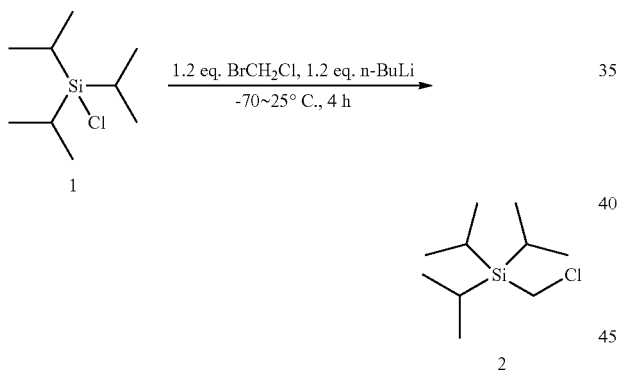

Into a 3 L three necked flask equipped with a low-temperature thermometer were placed compound 1 (125.00 g, 648.34 mmol, 138.89 mL, 1.00 eq.) and bromo(chloro)methane (100.66 g, 778.01 mmol, 1.20 eq.) in dry THF (1.30 L). To this mixture, maintained between −70 and −60° C. under $N_2$ was added on the cold wall of the flask for 1.5 h, n-BuLi (2.5 M, 311.20 mL, 1.20 eq.). The solution was warmed to 25° C. (r.t.) during 2.5 h. The reaction was continued stirred for another 1 h at 25° C. (r.t.). The reaction was detected on GC-MS. The reaction was added sat. $NH_4Cl$ (500 mL) and extracted with EtOAc (500 mL*3). The combined organic layers were washed with water (100 mL) and dried over $Na_2SO_4$. The solvent was removed in vacuo to dryness afford 300 g crude product. The crude product was distilled under reduced pressure, by using a 20-cm Vigreux column, at 160° C. (oil temperature) with water pump to removed remaining reactant (110° C. gas temperature). The residue was further distilled without Vigreux column, at 160° C. with water pump to get compound 2 (115.00 g, 511.53 mmol, 39.45% yield, 92% purity) as a colorless oil. $^1$H NMR (400 MHz, $CDCl_3$) δ 3.03-2.88 (m, 2H), 1.25-1.14 (m, 5H), 1.13-1.07 (m, 23H).

2. Preparation of Compound 3.

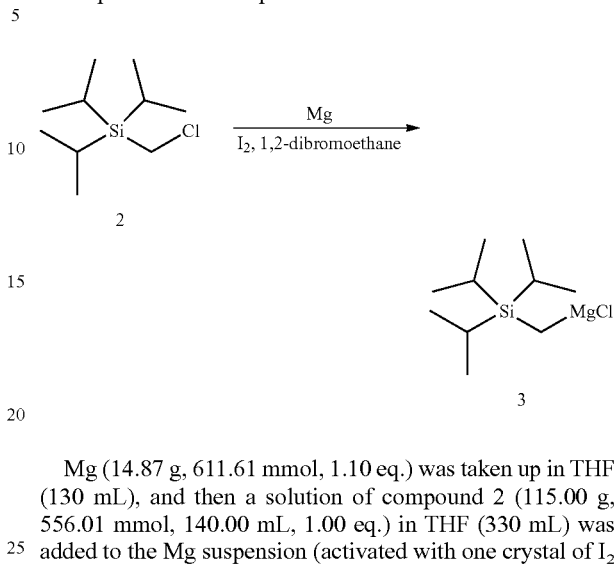

Mg (14.87 g, 611.61 mmol, 1.10 eq.) was taken up in THF (130 mL), and then a solution of compound 2 (115.00 g, 556.01 mmol, 140.00 mL, 1.00 eq.) in THF (330 mL) was added to the Mg suspension (activated with one crystal of $I_2$ and 1,2-dibromoethane) with stirring at 70~80° C. in a dropwise fashion over 1 h, keeping the temperature between 70~80° C. under $N_2$. The reaction was stirred at 70° C. for 3 h until Mg was consumed completely, and then the reaction suspension was cooled to 25° C. for 1 h, and the mixture was used directly for next step.

3. Preparation of Compound 4.

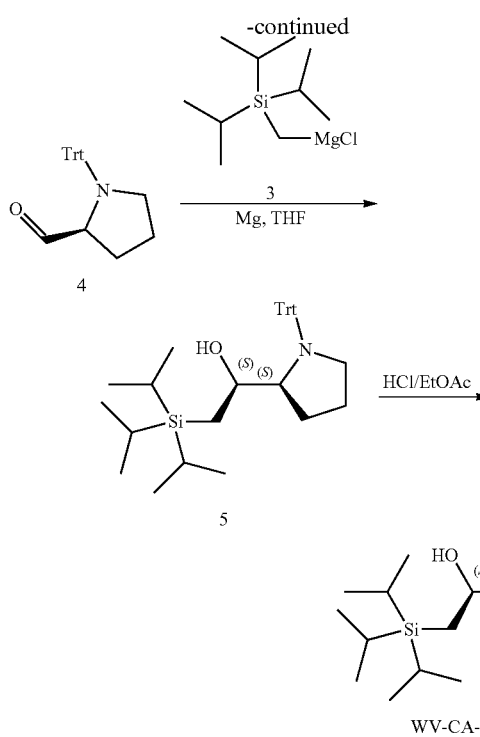

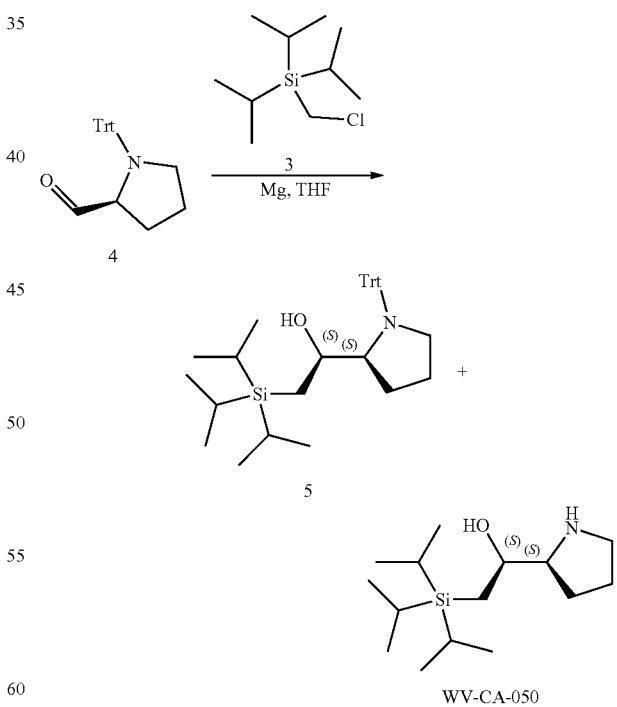

Compound 3 (1 M, 556.47 mL, 3.80 eq.) was added drop-wise to the solution of compound 4 (50.00 g, 146.44 mmol, 1.00 eq.) in THF (250 mL) at −40~−30° C. for 1 h under $N_2$, and then the reaction was warmed to 25° C. (r.t.) for 0.5 h. The reaction was stirred at 25° C. for 3 h. TLC

609

(Petroleum Ether:Ethyl Acetate=10:1, $R_f$=0.18) and LCMS showed compound 3 was remained a little, two new spots were detected. The reaction was added to sat. NH₄Cl (1 L) at 0° C., extracted by EtOAc (500 mL*3), dried over Na₂SO₄, filtered and concentrated in vacuo to dryness. The residue was purified by column chromatography on silica gel (Petroleum Ether/Ethyl Acetate=100/1 to 50/1; MeOH) to obtained compound 5 (18.50 g, 36.00 mmol, 12.29% yield) as yellow gum and a crude of WA-CA-050 (25.00 g, crude) as yellow oil, which was purified by silica gel chromatography (DCM:MeOH=50:1 to 10:1) to give WV-CA-050 (10 g) as a yellow oil.

4. Preparation of WV-CA-050.

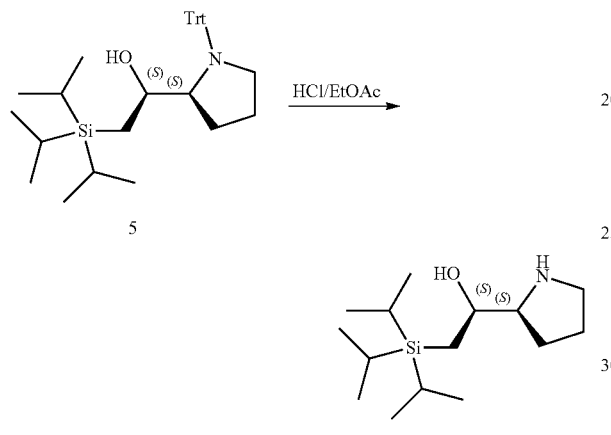

A solution of compound 5 (17.00 g, 33.08 mmol, 1.00 eq.) in HCl/EtOAc (200 mL) (cold, 5° C.), was stirred at 25° C. for 1 h. TLC (Petroleum Ether/Ethyl Acetate=5:1) showed the reactant was consumed and desired product was detected. The residue was dissolved in water (20 mL). To the mixture was added Na₂CO₃(aq) until pH>11. The mixture was extracted with DCM (100 mL*3). The combined organic layers were dried over Na₂SO₄, filtered, and concentrated to give a residue, which was purified by silica gel chromatography (DCM:MeOH=50:1 to 10:1) to give WV-CA-050 (6.20 g, 22.84 mmol, 69.03% yield) as a yellow oil, which was combined with another batch of the product (10 g) to give WV-CA-050 (16.12 g) as a yellow oil. ¹H NMR (400 MHz, CDCl₃) δ 4.03-3.86 (m, 1H), 3.65 (brs, 2H), 3.21 (d, J=2.0 Hz, 1H), 3.08-2.91 (m, 2H), 1.84-1.67 (m, 4H), 1.14-0.98 (m, 20H), 0.89-0.77 (m, 1H), 0.76-0.65 (m, 1H).

Example 37. Synthesis of WV-CA-050-dA$^{bz}$

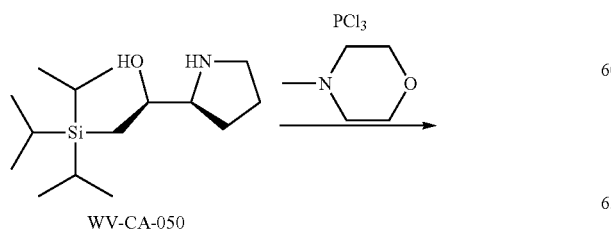

610

-continued

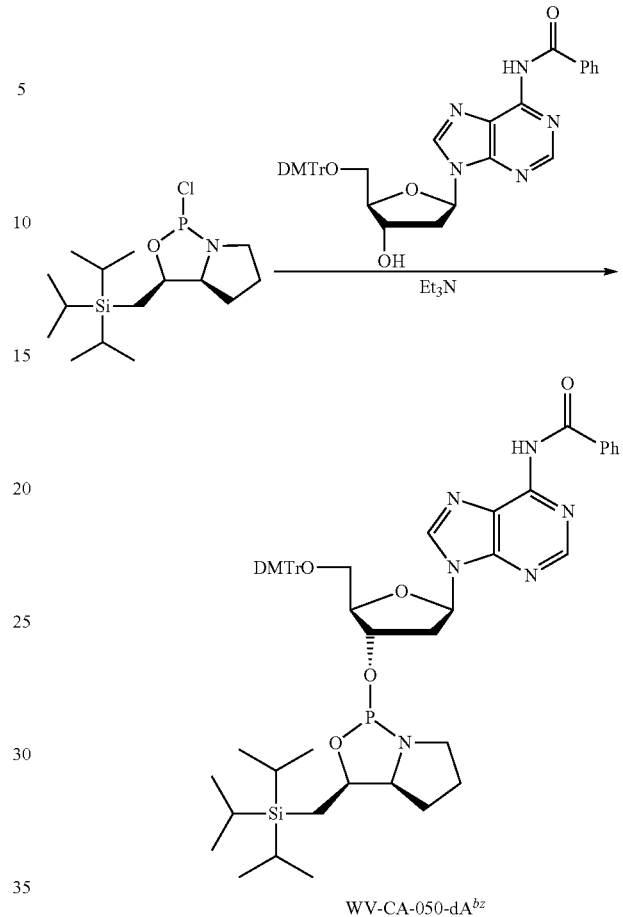

Using WV-CA-050 as starting material, the title compound (4.72 g, 62%) as a white solid was prepared analogously to WV-CA-008S-dC$^{iBu}$. ¹H NMR (600 MHz, CDCl₃) δ 8.68 (s, 1H), 8.15 (s, 1H), 8.00 (d, J=7.2 Hz, 2H), 7.57 (t, J=7.2 Hz, 1H), 7.49 (t, J=7.8 Hz, 2H), 7.38 (d, J=6.6 Hz, 2H), 7.29-7.15 (m, 7H), 6.77 (d, J=1.2 Hz, 2H), 6.76 (d, J=1.2 Hz, 2H), 6.51 (dd, J=7.5, 6.0 Hz, 1H), 4.97-4.87 (m, 2H), 4.29-4.25 (m, 1H), 3.75 (s, 6H), 3.61-3.51 (m, 1H), 3.49-3.42 (m, 1H), 3.38 (dd, J=10.2, 3.6 Hz, 1H), 3.33 (dd, J=10.5, 4.8 Hz, 1H), 3.19-3.11 (m, 1H), 2.95-2.87 (m, 1H), 2.70-2.64 (m, 1H), 1.93-1.85 (m, 1H), 180-1.72 (m, 1H), 1.62-1.55 (m, 1H), 1.32-1.23 (m, 1H), 1.10-0.96 (m, 23H). ³¹P NMR (202 MHz, CDCl₃) δ 155.42.

Example 38. Synthesis of WV-CA-051 and WV-CA-051-dA$^{bz}$

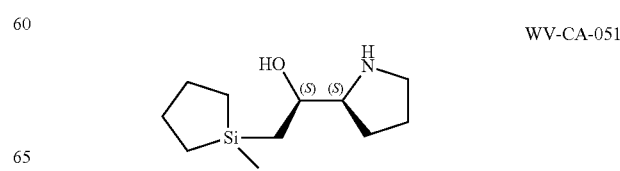

General Scheme.

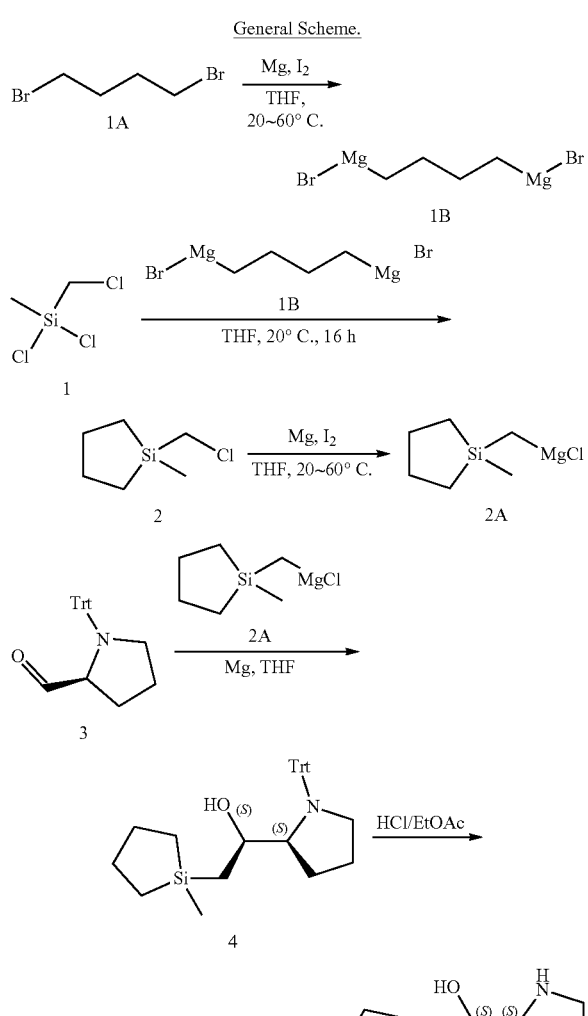

1. Preparation of Compound 1B.

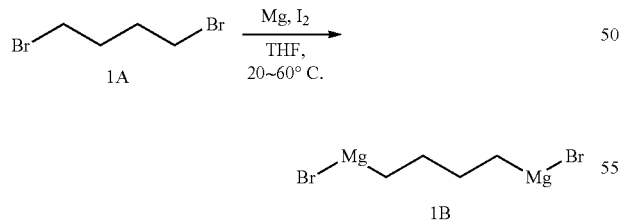

To a suspension of Mg (27.02 g, 1.11 mol) and I₂ (10.00 mg, 39.40 µmol) in THF (600 mL) was added compound 1A (120.00 g, 555.79 mmol) (first 10% volume, when the reaction was initiated, and then added dropwise the left over 2 hr at 20~60° C.) in THF (150 mL). The mixture was stirred at 20~60° C. for another 2 hr. Most of Mg was consumed. The reaction was completed. The Grignard reagent in THF was used directly in next step.

2. Preparation of Compound 2.

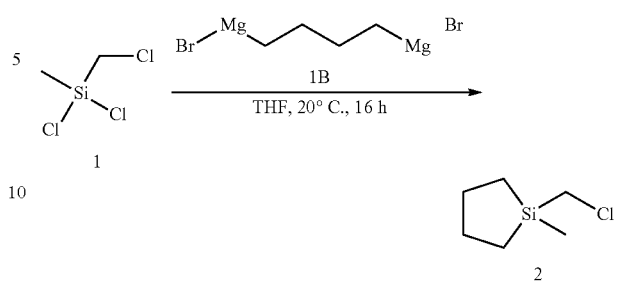

A mixture of compound 1B (147.00 g, 555.72 mmol) in THF was added to compound 1 (90.00 g, 550.43 mmol) in THF (50 mL) dropwise at 0~20° C. The mixture was stirred at 20° C. for 16 hr. GCMS showed the reaction was completed, and one main peak was observed. The reaction mixture was poured into sat. NH₄Cl aq. (1000 mL), extracted with EtOAc (1000 mL*3). The combined organic layers were dried over anhydrous MgSO₄, filtered and concentrated to afford a crude oil (61 g). The crude product was distilled under reduced pressure with water pump at 78-80° C. to afford compound 2 as a colorless oil (31 g). ¹H NMR (400 MHz, CDCl₃): δ=2.86 (s, 2H), 1.68-1.56 (m, 4H), 0.83-0.68 (m, 2H), 0.66-0.50 (m, 2H), 0.24 (s, 3H). GCMS: (M+): 148.

3. Preparation of Compound 2A.

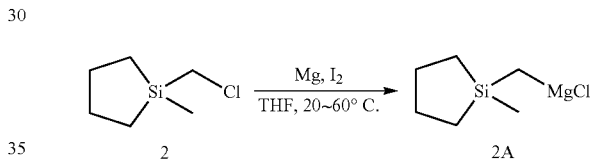

Mg (817.36 mg, 33.62 mmol) was taken up in THF (3.50 mL), and then a solution of compound 2 (5.00 g, 33.62 mmol) in THF (14 mL) was added dropwise to the Mg suspension (activated with I₂ (one crystal), and 1,2-dibromoethane (249.00 mg, 1.33 mmol) with stirring at 60° C. keeping the temperature between 53-60° C. After completed the addition, the mixture was then stirred for 1.5 hr at 60° C. until Mg was disappeared, and then at 20° C. for 0.5 hr. The mixture was used directly without any purification.

4. Preparation of Compound 4.

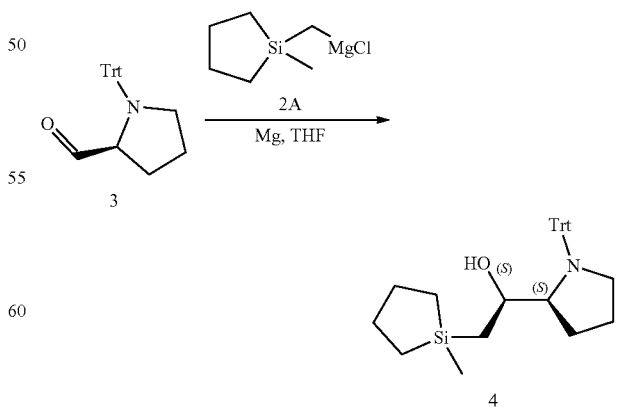

A solution of compound 2A (1.5 M, 19.52 mL) was added to compound 3 (5.00 g, 14.64 mmol) dissolved in THF (25 mL) at −30° C. After the addition, the mixture was stirred at 15° C. for 1 hr. TLC showed the starting material was consumed. The mixture was quenched with sat. NH₄Cl (aq., 50 mL), and then the mixture was extracted with EtOAc (50 mL*2). The combined organic layers were washed with brine (30 mL), dried over Na₂SO₄, filtered and concentrated to give compound 4 as a crude yellow oil (6.50 g), which was used directly without any purification. TLC (Petroleum ether:EtOAc=5:1) $R_f$=0.25.

5. Preparation of WV-CA-051.

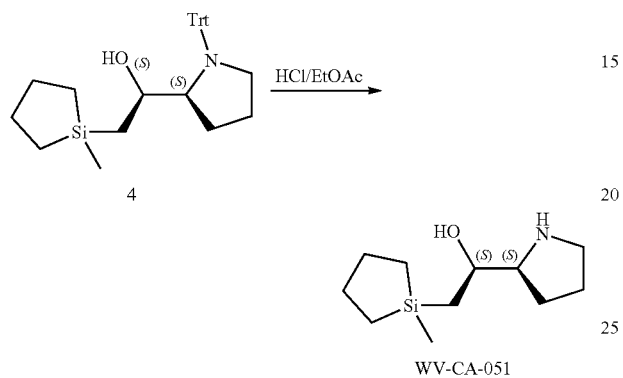

To a mixture of compound 4 (6.10 g, 13.39 mmol) dissolved in EtOAc (10 mL) was added HCl/EtOAc (100 mL, 4N) at 0° C. The mixture was stirred at 15° C. for 1.5 hr. TLC showed the starting material was consumed. The mixture was concentrated under reduced pressure to remove most of the solvent and filtered. The filter cake was dissolved in water (10 mL), and to the mixture was added sat. Na₂CO₃ aq. until pH=11. The mixture was extracted with DCM (20 mL*3), and the combined organic layers were washed with brine (20 mL), dried over Na₂SO₄, filtered and concentrated to get the crude. ¹H NMR showed the product was not freed completely, and then the mixture was dissolved in KOH (2M, 50 mL) and stirred for 5 minutes. The mixture was extracted with DCM (20 mL*3), and the combined organic layers were washed with brine, dried over Na₂SO₄, filtered and concentrated to afford WV-CA-051 as a white solid (1.71 g, 58.24%). ¹H NMR (400 MHz, CDCl₃): δ=3.78 (ddd, J=3.3, 5.8, 8.9 Hz, 1H), 3.06 (dt, J=3.3, 7.6 Hz, 1H), 3.01-2.81 (m, 2H), 2.70 (br. s., 2H), 1.79-1.45 (m, 8H), 0.92 (dd, J=8.4, 14.6 Hz, 1H), 0.82-0.72 (m, 1H), 0.67-0.41 (m, 4H), 0.11 (s, 3H). ¹³C NMR (101 MHz, CDCl₃): δ=69.72, 64.15, 46.93, 27.16, 25.82, 23.93, 20.60, 12.91, 2.39. LCMS: (M+H⁺): 214.1. TLC (Petroleum ether:EtOAc=5:1) $R_f$=0.01. LCMS purity: 97.3%.

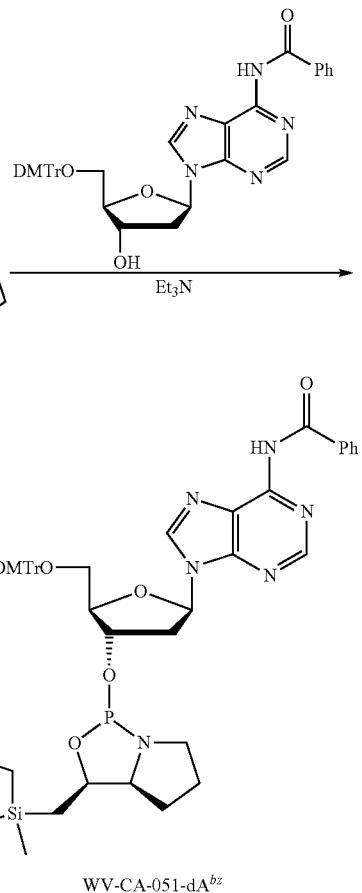

Using WV-CA-051 as starting material, the title compound (1.21 g, 41%) as a white solid was prepared analogously to WV-CA-008S-dC$^{iBu}$. ¹H NMR (600 MHz, CDCl₃) δ 8.90 (brs, 1H), 8.68 (s, 1H), 8.14 (s, 1H), 8.00 (d, J=7.8 Hz, 2H), 7.58 (t, J=7.8 Hz, 1H), 7.50 (t, J=7.5 Hz, 2H), 7.39 (d, J=7.2 Hz, 2H), 7.29-7.16 (m, 8H), 6.79-6.75 (m, 4H), 6.51 (dd, J=7.8, 6.0 Hz, 1H), 4.98-4.93 (m, 1H), 4.85-4.80 (m, 1H), 4.30-4.26 (m, 1H), 3.75 (s, 6H), 3.60-3.52 (m, 1H), 3.51-3.45 (m, 1H), 3.39 (dd, J=10.2, 4.8 Hz, 1H), 3.34 (dd, J=10.5, 4.2 Hz, 1H), 3.20~3.12 (m, 1H), 2.96-2.90 (m, 1H), 2.69-2.63 (m, 1H), 1.91-1.84 (m, 1H), 1.80-1.72 (m, 1H), 1.58-1.47 (m, 5H), 1.29-1.21 (m, 1H), 1.11 (dd, J=14.4, 9.0 Hz, 1H), 0.97 (dd, J=14.4, 6.0 Hz, 1H), 0.63-0.56 (m, 2H), 0.54-0.45 (m, 2H), 0.10 (s, 3H). ³¹P NMR (243 MHz, CDCl₃) δ 154.96.

Example 39. Synthesis of WV-CA-052

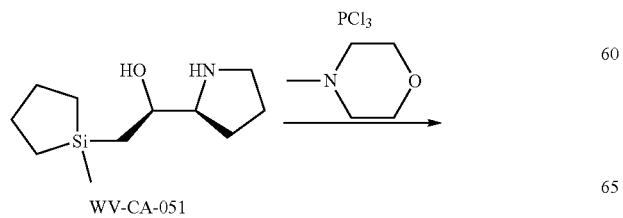

General Scheme.
Scheme 1

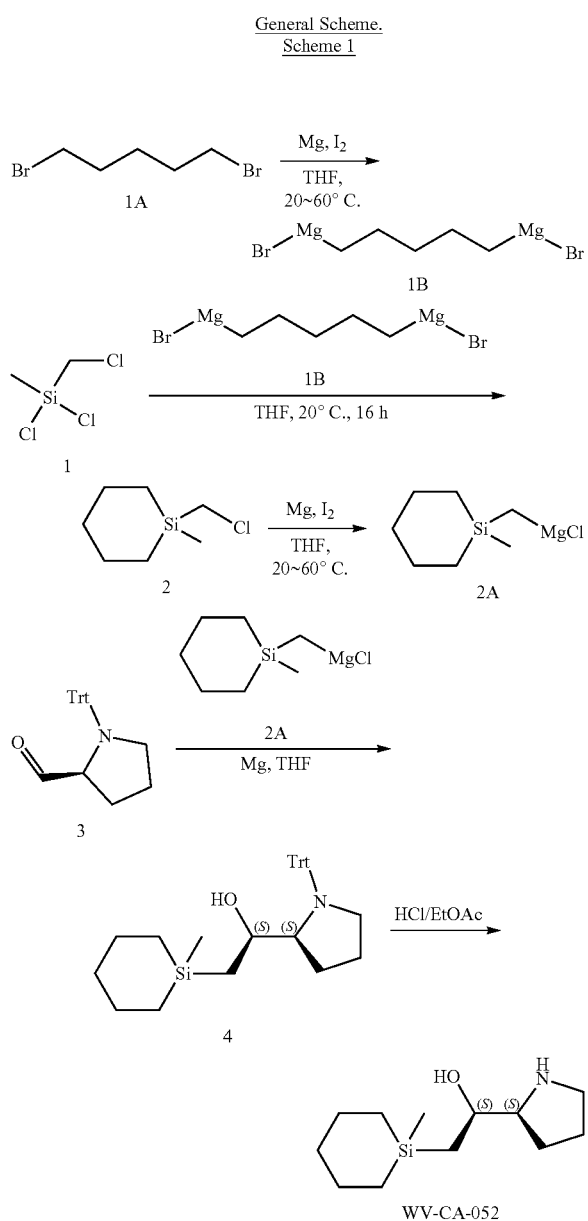

1. Preparation of Compound B.

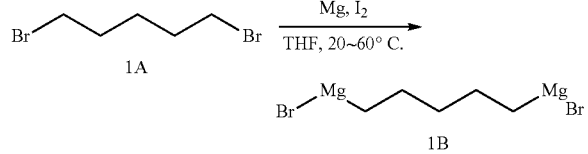

To a suspension of Mg (27.07 g, 1.11 mol, 2.00 eq.) in THF (600 mL) was added dropwise compound 1A (128.00 g, 556.67 mmol, 75.29 mL, 1.00 eq.) (activated with one crystal of 12) in THF (150 mL) over 1 h. The mixture was stirred at 20~60° C. for 3 hr. Mg was disappeared. The reaction was completed. The Grignard reagent in THF was used directly in next step.

2. Preparation of Compound 2.

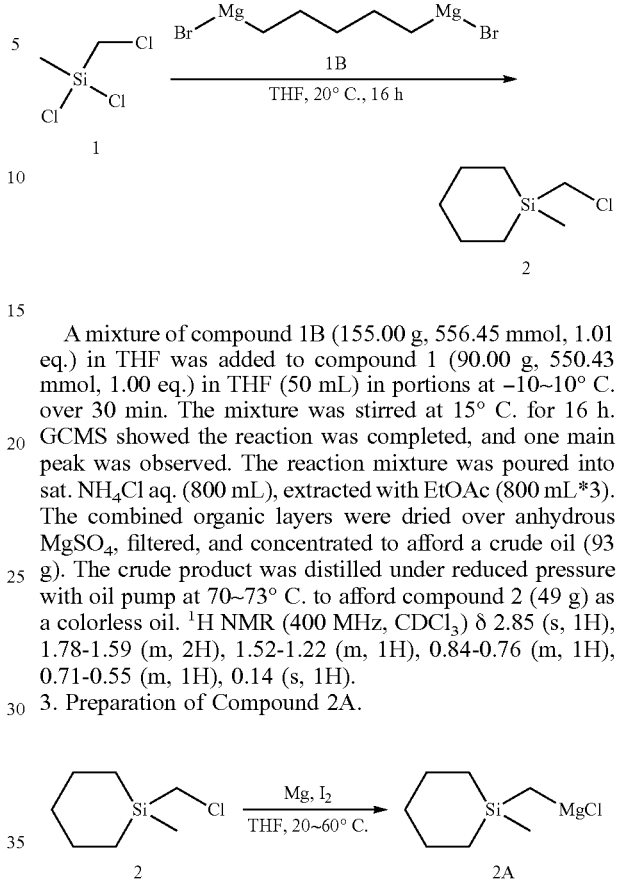

A mixture of compound 1B (155.00 g, 556.45 mmol, 1.01 eq.) in THF was added to compound 1 (90.00 g, 550.43 mmol, 1.00 eq.) in THF (50 mL) in portions at −10~10° C. over 30 min. The mixture was stirred at 15° C. for 16 h. GCMS showed the reaction was completed, and one main peak was observed. The reaction mixture was poured into sat. NH$_4$Cl aq. (800 mL), extracted with EtOAc (800 mL*3). The combined organic layers were dried over anhydrous MgSO$_4$, filtered, and concentrated to afford a crude oil (93 g). The crude product was distilled under reduced pressure with oil pump at 70~73° C. to afford compound 2 (49 g) as a colorless oil. $^1$H NMR (400 MHz, CDCl$_3$) δ 2.85 (s, 1H), 1.78-1.59 (m, 2H), 1.52-1.22 (m, 1H), 0.84-0.76 (m, 1H), 0.71-0.55 (m, 1H), 0.14 (s, 1H).

3. Preparation of Compound 2A.

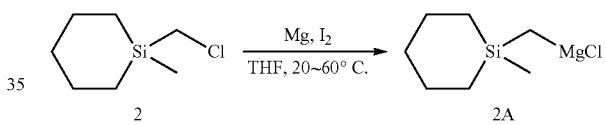

To a suspension of Mg (817.36 mg, 33.62 mmol, 1.00 eq.) in THF (5 mL) (activated with one crystal of I$_2$ and 1,2-dibromoethane (28.86 mg, 153.65 μmol, 11.59 μL, 5.00e-3 eq.)) was added dropwise a solution of compound 2 (5.00 g, 30.73 mmol, 1.00 eq.) in THF (15 mL) keeping the temperature between 50~70° C. After completed the addition, the mixture was then stirred for 1 h at 70° C. until the Mg was disappeared, and then stirred at 20° C. for 1 h. The Grignard reagent in THF was used directly in next step.

4. Preparation of Compound 4.

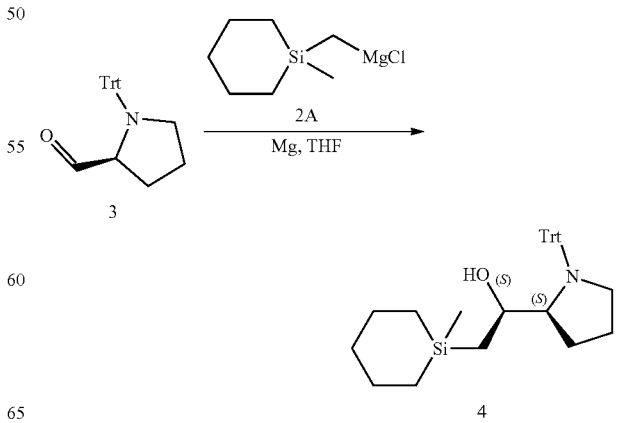

To a solution of compound 2A (5.50 g, 29.38 mmol, 2.28 eq.) in THF was added a solution of compound 3 (4.40 g, 12.89 mmol, 1.00 eq.) in THF (20 mL) at −40° C. The mixture was stirred at 15° C. for 1.5 h. TLC (Petroleum Ether:EtOAc=10:1) showed the reaction was completed. The resulting mixture was quenched with sat. NH₄Cl aq. (80 mL), extracted with EtOAc (60 mL*3). The combined organic layers were dried over anhydrous MgSO₄, filtered, and concentrated to afford the crude product compound 4 (7.68 g, crude) as a light-yellow oil, which was used into the next step without further purification.

5. Preparation of WV-CA-052.

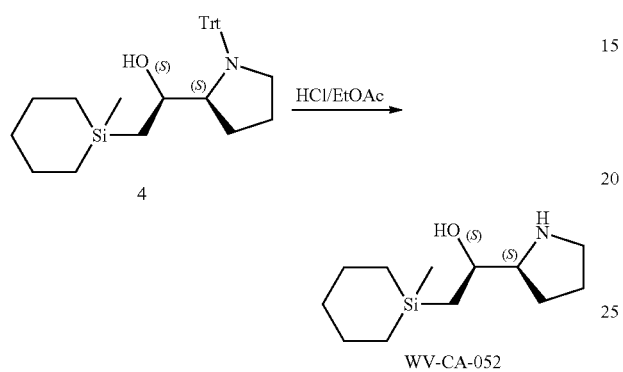

To a solution of compound 4 (6.32 g, 13.45 mmol, 1.00 eq.) in EtOAc (20 mL) was added HCl/EtOAc (100.00 mL, 4N) at 0° C. The mixture was stirred at 0~15° C. for 2 h. TLC (Petroleum Ether:EtOAc=10:1) showed the reaction was completed. The resulting mixture was concentrated under reduced pressure at 30° C. until solid precipitated. The mixture was filtered, rinsed with EtOAc (15 mL), and dried to give the HCl salt as a white solid (2 g). NMR showed the HCl salt of the product was clean enough. The HCl salt was dissolved in DCM (10 mL), adjust to pH 11 with sat. Na₂CO₃ aq. The separated aqueous layer was extracted with DCM (10 mL*2), the combined organic layers were washed with brine (5 mL), dried over anhydrous MgSO₄, filtered and concentrated to afford the product as a light-yellow gum. ¹H NMR showed part of HCl salt was freed. To the crude gum was added KOH aq. (2M, 10 mL). After stirred at 20° C. for 5 min, the mixture was extracted with DCM (20 mL*3). The combined extracts were washed with brine (10 mL). The separated organic layer was dried over anhydrous MgSO₄, filtered, and concentrated to afford WV-CA-052 (1.20 g, 5.27 mmol, 39.15% yield, 99.79% purity) as a light-yellow gum. ¹H NMR (400 MHz, CDCl₃) δ 3.77 (ddd, J=8.7, 6.1, 3.3 Hz, 1H), 3.07 (dt, J=7.6, 3.3 Hz, 1H), 3.02-2.82 (m, 2H), 2.62 (brs, 1H), 1.84-1.52 (m, 9H), 1.50-1.24 (m, 3H), 0.92-0.79 (m, 1H), 0.77-0.50 (m, 6H), 0.06 (s, 3H).

Example 40. Synthesis of WV-CA-052-dA$^{bz}$

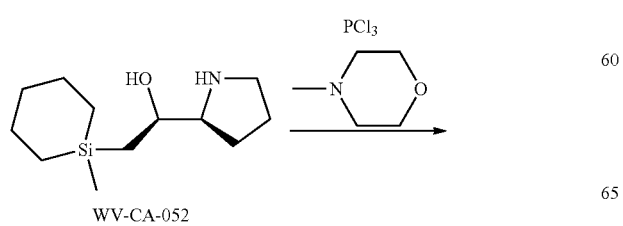

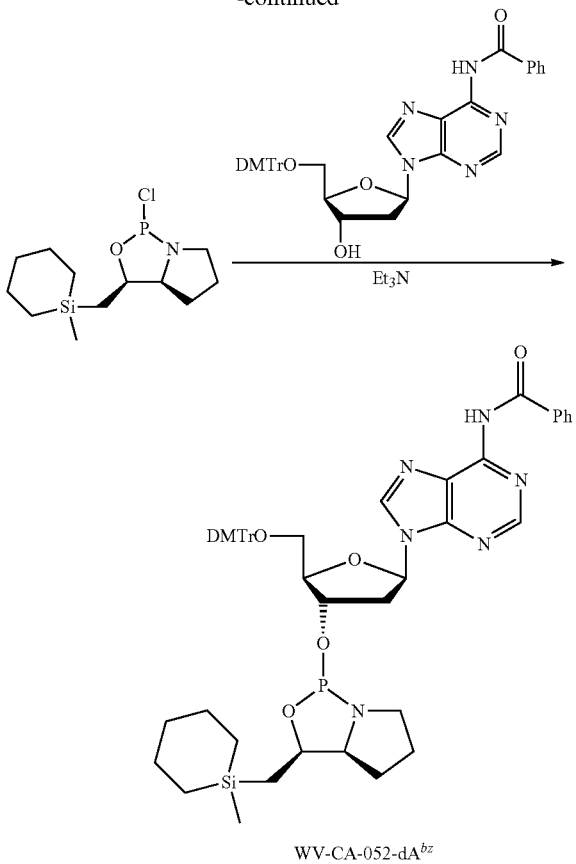

Using WV-CA-052 as starting material, the title compound (0.74 g, 39%) as a white solid was prepared analogously to WV-CA-008S-dC$^{iBu}$. ¹H NMR (600 MHz, CDCl₃) δ 8.69 (s, 1H), 8.14 (s, 1H), 8.00 (d, J=7.2 Hz, 2H), 7.57 (t, J=7.2 Hz, 1H), 7.49 (t, J=7.8 Hz, 2H), 7.38 (d, J=6.6 Hz, 2H), 7.29-7.16 (m, 7H), 6.77 (d, J=1.8 Hz, 2H), 6.76 (d, J=1.8 Hz, 2H), 6.51 (dd, J=7.2, 6.0 Hz, 1H), 4.99-4.94 (m, 1H), 4.85-4.79 (m, 1H), 4.30-4.26 (m, 1H), 3.75 (s, 6H), 3.60-3.52 (m, 1H), 3.49-3.42 (m, 1H), 3.39 (dd, J=10.2, 4.2 Hz, 1H), 3.35 (dd, J=10.2, 4.8 Hz, 1H), 3.20~3.12 (m, 1H), 2.96-2.89 (m, 1H), 2.69-2.62 (m, 1H), 1.91-1.83 (m, 1H), 1.79-1.62 (m, 3H), 1.59-1.50 (m, 3H), 1.45-1.38 (m, 1H), 1.30-1.21 (m, 2H), 1.06 (dd, J=14.4, 9.0 Hz, 1H), 0.91 (dd, J=14.4, 6.6 Hz, 1H), 0.63-0.56 (m, 4H), 0.04 (s, 3H). ³¹P NMR (243 MHz, CDCl₃) δ 154.90.

Example 41. Synthesis of WV-CA-053 and WV-CA-054

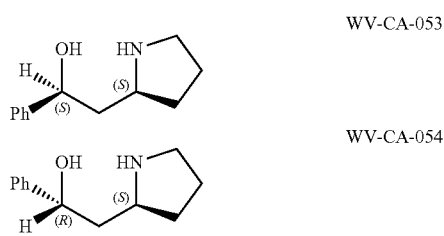

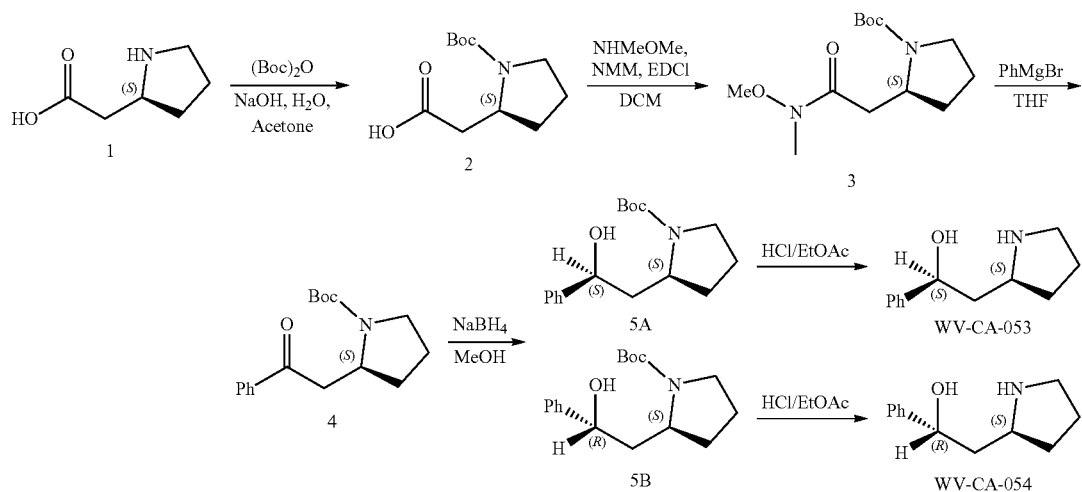

1. Preparation of Compound 2.

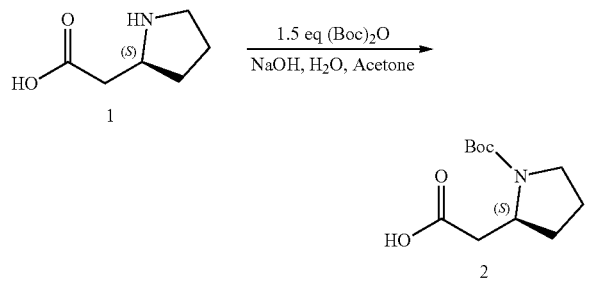

Compound 1 (20.00 g, 120.76 mmol, HCl salt) was dissolved in H₂O (200 mL), and the pH was adjusted to around 10 at 0° C. with NaOH aq. (2 M, 150 mL). Then the solution was diluted with acetone (400 mL) and (Boc)₂O (39.53 g, 181.14 mmol) was added at 0° C. with stirring. After 0.5 hr the temperature was warmed to 25° C. and stirred for 4 hr. TLC and showed the reaction was completed. The reaction was concentrated to remove acetone. The aqueous phase left was acidified with 1 M HCl (100 mL) to pH ~3, extracted with EtOAc (200 mL*3), washed with brine (80 mL), dried over anhydrous MgSO₄, filtered and concentrated to afford compound 2 as a yellow solid (39.00 g, crude), which was used directly without any purification. TLC (Ethyl acetate:Dichloromethane=10:1) $R_f$=0.43. ¹H NMR (400 MHz, CHLOROFORM-d) δ=3.35 (s, 2H), 2.37 (s, 1H), 2.08 (d, J=7.9 Hz, 1H), 1.91-1.71 (m, 3H), 1.52 (s, 15H), 1.46 (s, 10H).

2. Preparation of Compound 3.

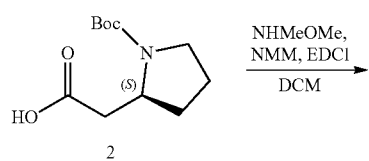

-continued

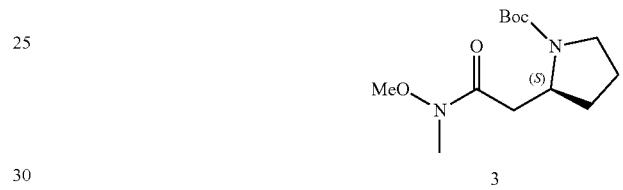

Compound 2 (38.50 g, 167.92 mmol) was dissolved in anhydrous DCM (400 mL) cooled to 0° C. To this solution was added N, O-dimethyl hydroxylamine (19.66 g, 201.51 mmol, HCl salt) and 4-methylmorpholine (20.38 g, 201.51 mmol) followed by 3-(ethyliminomethyleneamino)-N, N-dimethylpropan-1-amine-hydrochloride (38.63 g, 201.51 mmol) at 0° C. The reaction mixture was then allowed to come to 25° C. and stirred for 3 hr. TLC showed the reaction was completed. The reaction was cooled to 0° C. and quenched by the addition of an ice cold 2 M HCl solution (50 mL) and was stirred at this temperature for 5 minutes. The reaction was diluted with water (100 mL) and extracted with DCM (100 mL*3). The combined organic layers were washed with sat. NaHCO₃ (aq., 100 mL), dried over Na₂SO₄, filtered and concentrated in vacuo to dryness. The residue was purified by column (Petroleum ether:Ethyl acetate=50/1 to 1/1). Compound 3 was obtained as colorless oil (28.00 g, 61.22%). ¹H NMR (400 MHz, CHLOROFORM-d) δ=4.21 (s, 1H), 3.69 (s, 3H), 3.36 (s, 2H), 3.18 (s, 3H), 2.44 (s, 1H), 2.06 (d, J=8.3 Hz, 1H), 1.88-1.73 (m, 3H), 1.47 (s, 9H). TLC (Dichloromethane:Methanol=20:1) $R_f$=0.61.

3. Preparation of Compound 4.

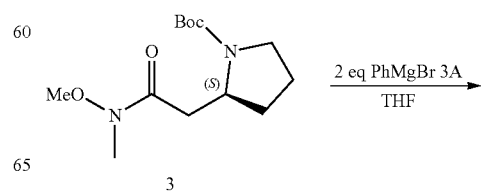

-continued

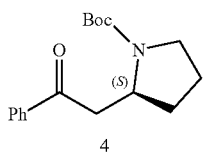

To a solution of compound 3 (10.00 g, 36.72 mmol) in THF (100 mL) was added compound 3A (3M, 24.48 mL) at −20° C. The mixture was stirred at −20~0° C. for 3 hr. TLC showed compound 3 was consumed, and a new spot with strong ultraviolet absorption and lower polarity was observed. The reaction mixture was quenched by addition NH$_4$Cl (aq., 100 mL), diluted with EtOAc (100 mL) and extracted with EtOAc (100 mL*3). The combined organic layers were washed with H$_2$O (100 mL), dried over Na$_2$SO$_4$, filtered and concentrated under reduced pressure to give a residue, which was combined with another part of crude product, and purified by column chromatography on silica gel (Petroleum ether/Ethyl acetate=20/1 to 5:1). Compound 4 was obtained as a yellow oil (11.74 g, 92.70%). LCMS: (M+H$^+$): 190.2. TLC (Petroleum ether/Ethyl acetate=5:1) R$_f$=0.43.

4. Preparation of Compound 5A and 5B.

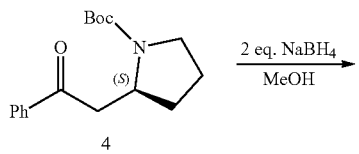

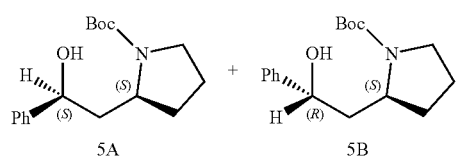

To a solution of compound 4 (6.45 g, 22.29 mmol) in MeOH (200 mL) was slowly added NaBH$_4$ (1.69 g, 44.58 mmol). The mixture was stirred at 0° C. for 2 hr. TLC showed compound 4 was consumed, and two major new spot with larger polarity were detected. The reaction mixture was quenched by the addition of sat. NH$_4$Cl aq. (200 mL), and then diluted with ethyl acetate (100 mL) and extracted with ethyl acetate (100 mL*3). The combined organic layers were washed with H$_2$O (100 mL), dried over, filtered, and concentrated under reduced pressure to give a residue. The residue was purified by column chromatography on silica gel (Petroleum ether/Ethyl acetate=50/1 to 5/1). Compound 5A was obtained as a white solid (4.00 g, 61.60%). $^1$H NMR (400 MHz, CHLOROFORM-d) δ=7.48-7.38 (m, 2H), 7.35 (t, J=7.5 Hz, 2H), 7.30-7.17 (m, 1H), 4.67 (d, J=7.0 Hz, 1H), 4.33 (br. s., 1H), 3.42 (d, J=7.0 Hz, 2H), 2.11-1.85 (m, 3H), 1.82-1.57 (m, 3H), 1.56-1.46 (m, 9H). LCMS: (M+H$^+$): 314.1. TLC (petroleum ether:ethyl acetate=5:1) R$_{f1}$=0.39. Compound 5B was obtained as a white solid (1.50 g, 23.10%). $^1$H NMR (400 MHz, CHLOROFORM-d) δ=7.42-7.30 (m, 1H), 7.27 (d, J=5.5 Hz, 1H), 4.79 (s, 1H), 4.13 (s, 1H), 3.34 (d, J=4.5 Hz, 2H), 2.16 (s, 1H), 2.09-1.93 (m, 1H), 1.93-1.81 (m, 2H), 1.73 (s, 2H), 1.49 (s, 9H). LCMS: (M+H$^+$): 314.1. TLC (petroleum ether:ethyl acetate=5:1) R$_{f2}$=0.24.

5. Preparation of WV-CA-053.

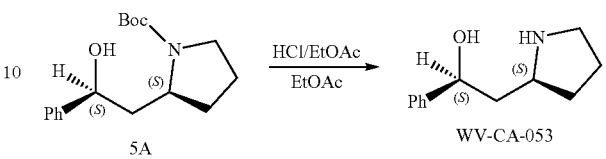

To a solution of compound 5A (1.50 g, 5.15 mmol) in Ethyl acetate (3 mL) was added HCl/EtOAc (50 mL, 4N). The mixture was stirred at 25° C. for 2 hr. LCMS showed compound 5A consumed completely, and one main peak with desired MS was detected. The reaction mixture was concentrated under reduced pressure to give a residue. To a solution of the residue in H$_2$O (10 mL) was slowly added Na$_2$CO$_3$ (aq.) until pH ~11, extracted with EtOAc (30 mL*3). The combined organic layers dried over Na$_2$SO$_4$, filtered, and concentrated under reduced pressure to give a residue. The residue was purified by prep-HPLC (water (0.1% TFA)-ACN). Compound WV-CA-053 was obtained as a white solid (400 mg, 40.61%). $^1$H NMR (400 MHz, CHLOROFORM-d) δ=7.43-7.38 (m, 2H), 7.38-7.31 (m, 2H), 7.28-7.23 (m, 1H), 4.90 (dd, J=1.6, 10.4 Hz, 1H), 3.60 (tdd, J=4.0, 7.4, 11.2 Hz, 1H), 3.04 (ddd, J=4.5, 7.7, 11.9 Hz, 1H), 2.91 (td, J=7.5, 11.8 Hz, 1H), 2.03-1.91 (m, 1H), 1.90-1.79 (m, 1H), 1.75-1.63 (m, 2H), 1.63-1.51 (m, 1H), 1.48-1.35 (m, 1H). $^{13}$C NMR (101 MHz, CHLOROFORM-d): δ=145.36, 128.20, 126.94, 125.61, 76.69, 74.88, 59.31, 45.72, 43.41, 32.81, 25.81. LCMS: (M+H+): 192.1, 97.5% purity. Chiral SFC purity: 96.1%.

6. Preparation of WV-CA-054.

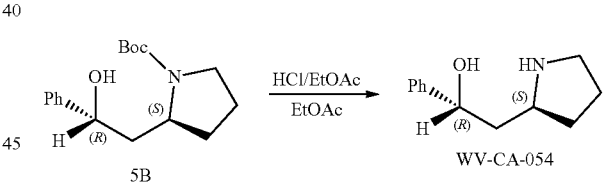

To a solution of compound 5B (1.50 g, 5.15 mmol) in EtOAc (3 mL) was added HCl/EtOAc (50 mL). The mixture was stirred at 25° C. for 2 hr. LCMS showed compound 5B was consumed completely and one main peak with desired MS was detected. The reaction mixture was reduced pressure to give a residue. To a solution of the residue in H$_2$O (10 mL) was slowly added Na$_2$CO$_3$ (aq.) until pH ~11, extracted with EtOAc (30 mL*3). The combined organic layers dried over Na$_2$SO$_4$, filtered, and concentrated under reduced pressure to give a residue. The residue was purified by prep-HPLC (water (10 Mm NH$_4$HCO$_3$)-ACN). Compound WV-CA-054 was obtained as a white solid (500 mg, 50.29%). $^1$H NMR (400 MHz, CHLOROFORM-d) δ=7.45-7.32 (m, 3H), 7.32-7.20 (m, 2H), 5.08 (s, 1H), 3.43 (s, 1H), 3.16-2.72 (m, 2H), 2.10-1.81 (m, 4H), 1.79-1.47 (m, 2H). $^{13}$C NMR (101 MHz, CHLOROFORM-d): δ=145.32, 128.15, 126.64, 125.59, 76.69, 72.14, 55.82, 46.01, 41.06, 30.82, 25.79. LCMS: (M+H$^+$): 192.1, 98.9% purity. Chiral SFC purity: 100.0%.

Example 42. Synthesis of WV-CA-053-dCiBu

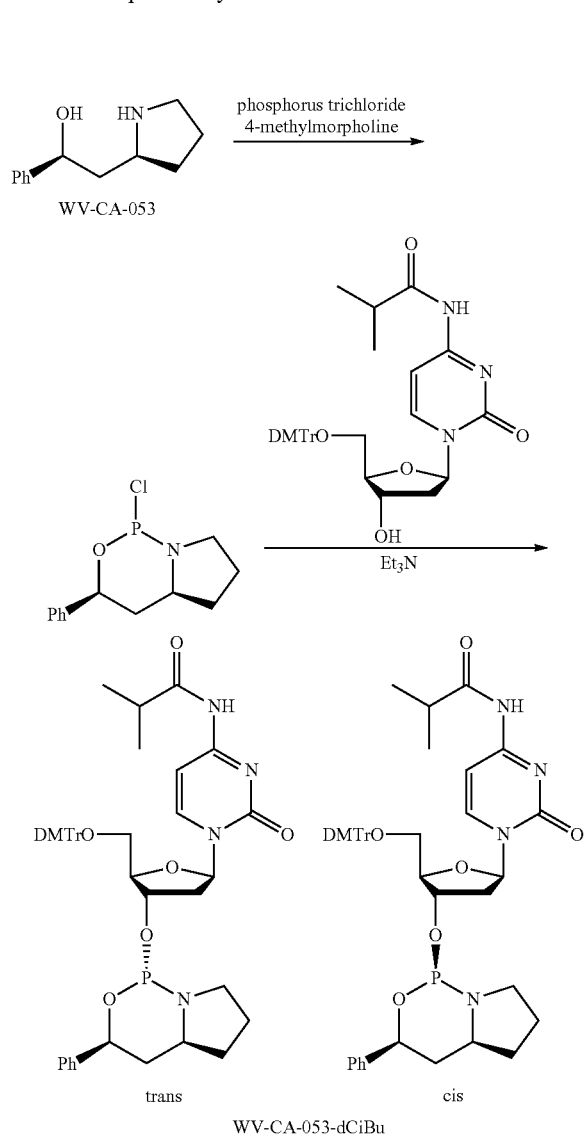

Using WV-CA-053 as starting material, the title compound (0.80 g, 43%) as a white solid was prepared analogously to WV-CA-008S-dCiBu. $^{31}$P NMR (202 MHz, CDCl$_3$) δ 137.19 (28%), 133.84 (72%).

Example 43. Synthesis of WV-CA-056

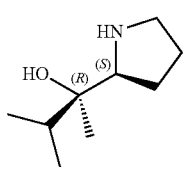

WV-CA-056

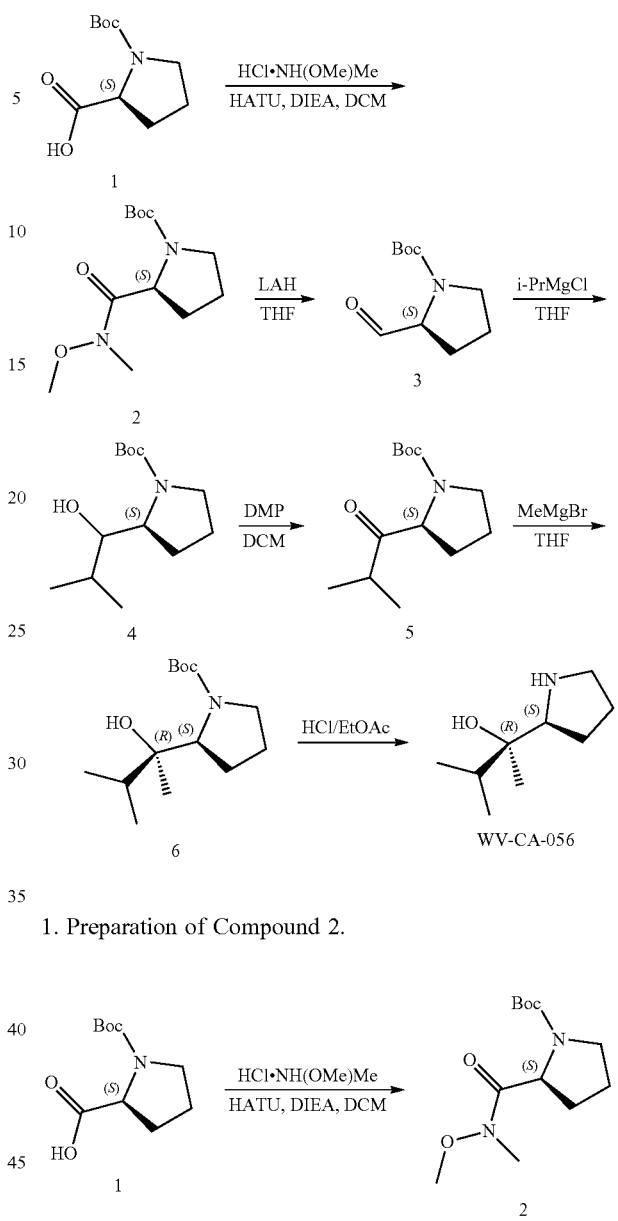

1. Preparation of Compound 2.

To a solution of compound 1 (100.00 g, 464.58 mmol), N-methoxymethanamine hydrochloride (49.85 g, 511.04 mmol) and HATU (194.31 g, 511.04 mmol) in DCM (1.00 L) was slowly added DIEA (120.08 g, 929.16 mmol, 162.27 mL). The mixture was stirred at 20° C. for 16 hr. TLC showed the starting material was consumed completely. Water (1 L) was added and extracted with DCM (1 L*3). The combined organic layers were washed with brine (1 L), dried over Na$_2$SO$_4$, filtered and concentrated to get the crude, which was purified by column chromatography (SiO$_2$, Petroleum ether/EtOAc=50/1 to 1:1) to give compound 2 as a yellow oil (91.00 g, 75.83%). $^1$H NMR (400 MHz, CHLOROFORM-d) δ=4.75-4.49 (m, 1H), 3.79-3.66 (m, 3H), 3.60-3.35 (m, 2H), 3.17 (s, 3H), 2.23-2.08 (m, 1H), 2.03-1.73 (m, 3H), 1.41 (d, J=17.9 Hz, 9H). TLC (Petroleum ether:EtOAc=5:1) R$_f$=0.38.

2. Preparation of Compound 3.

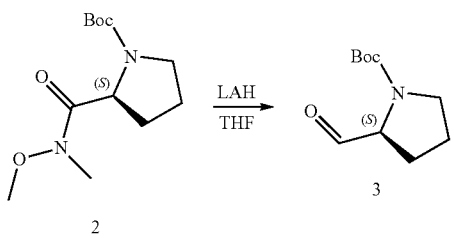

To a solution of compound 2 (60.00 g, 232.28 mmol) in THF (300 mL) was slowly added LiAlH₄ (9.70 g, 255.51 mmol) at −15° C. The mixture was stirred at −15-0° C. for 1 hr. TLC showed compound 2 was consumed completely, and one new spot was detected. The reaction was quenched with sat. MgSO₄ aq. (20 mL). The suspension was diluted with EtOAc (300 mL) and filtered. The filter cake was washed with EtOAc (600 mL). The combined organic filtrate was concentrated in vacuo to afford compound 3 as a yellow oil (40.00 g, crude). TLC (Petroleum ether:EtOAc=5:1) $R_f$=0.35.

3. Preparation of Compound 4.

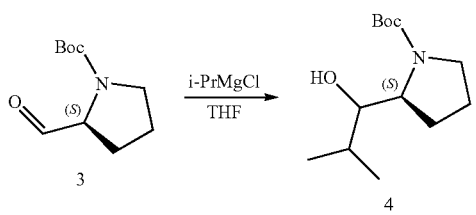

To a solution of compound 3 (80.00 g, 401.51 mmol) in THF (1.50 L) was added i-PrMgCl (2 M, 401.51 mL) at −10° C. The mixture was stirred at −10-10° C. for 4 hr. TLC showed the starting material was consumed. The reaction mixture was quenched by the addition of sat. NH₄Cl aq. (500 mL) at 0° C., and then extracted with EtOAc (1 L*3), dried over Na₂SO₄, filtered and concentrated under reduced pressure to give a residue, which was purified by column chromatography (SiO₂, Petroleum ether/EtOAc=30/1 to 10:1) to give compound 4 was obtained as a yellow oil (24.00 g, 24.56%). LCMS: (M+Na+): 266.1. TLC (Petroleum ether:EtOAc=5:1) $R_f$=0.48.

4. Preparation of Compound 5.

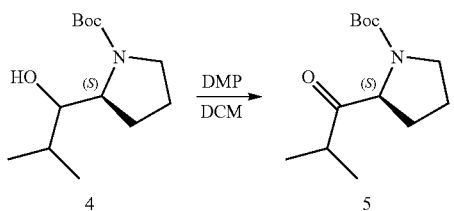

To a solution of compound 4 (10.50 g, 43.15 mmol) in DCM (500 mL) was added DMP (20.13 g, 47.46 mmol, 14.69 mL) at 0° C. The mixture was stirred at 15° C. for 2 hr. TLC showed the starting material was consumed. The mixture was quenched by the addition of sat. Na₂SO₃ aq. (500 mL) at 0° C., washed with sat. NaHCO₃ aq. (300 mL), and extracted with DCM (500 mL*3). The combined organic layers were dried over Na₂SO₄, filtered, and concentrated under reduced pressure to give a residue. The residue was purified by column chromatography (SiO₂, Petroleum ether/EtOAc=100/1 to 10/1) to give compound 5 was obtained as a colorless oil (7.45 g, 71.54%). ¹H NMR (400 MHz, Chloroform-d) δ=4.57-4.37 (m, 1H), 3.62-3.36 (m, 2H), 2.89-2.69 (m, 1H), 2.30-2.03 (m, 1H), 1.94-1.69 (m, 3H), 1.50-1.32 (m, 9H), 1.19-1.01 (m, 6H). LCMS: (M+H+): 264.1. HPLC purity=95.9%. Chiral SFC purity=100.0%. TLC (Petroleum ether:EtOAc=5:1) $R_f$=0.42.

5. Preparation of Compound 6.

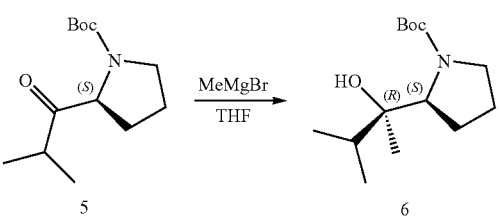

To a solution of compound 5 (32.00 g, 132.60 mmol) in THF (500 mL) was added MeMgBr (3 M, 88.40 mL) at −10° C. The mixture was stirred at −10-10° C. for 2 hr. TLC and LCMS showed the starting material was consumed, and one new spot with larger polarity and one new spot with lower polarity were detected. The reaction mixture was quenched by the addition of sat. NH₄Cl aq. (200 mL) at 0° C., and then diluted with EtOAc (500 mL) and extracted with EtOAc (500 mL*3), dried over Na₂SO₄, filtered and concentrated under reduced pressure to give a residue, which was purified by column chromatography (SiO₂, Petroleum ether/EtOAc=50/1 to 5:1) to give compound 6 was obtained as a yellow oil (27.00 g, 79.12%). ¹H NMR (400 MHz, CHLOROFORM-d) δ=4.02 (t, J=6.4 Hz, 1H), 3.76-3.58 (m, 1H), 3.19 (dd, J=3.5, 7.0 Hz, 1H), 2.03-1.55 (m, 6H), 1.46 (s, 10H), 1.06 (s, 4H), 0.95 (d, J=6.8 Hz, 3H), 0.89 (d, J=6.8 Hz, 4H). LCMS: (M+H+): 258.1. HPLC purity: 81.4%. Chiral SFC purity: 100.0%. TLC (Petroleum ether:EtOAc=5:1) $R_f$=0.31.

6. Preparation of Compound WA-CA-056.

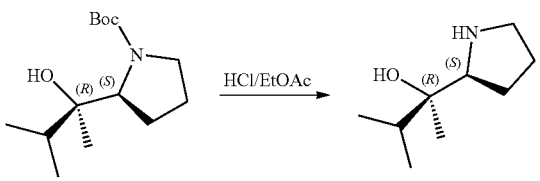

To a solution of compound 6 (26.90 g, 104.52 mmol) in EtOAc (40 mL) was added HCl/EtOAc (400 Ml, 4N). The mixture was stirred at 15° C. for 2 hr. TLC showed the starting material was consumed completely. The mixture was concentrated under reduced pressure until around 80 mL of the solvent left, filtered to give a residue, which was dissolved in water (30 mL), and added sat. Na₂CO₃ (aq.) to pH 10-11, and then extracted with DCM (300 mL*3), dried over Na₂SO₄, filtered and concentrated under reduced pressure to give compound WV-CA-056 as a yellow oil (12.50 g, 76.05%). ¹H NMR (400 MHz, CHLOROFORM-d)

δ=3.13 (t, J=7.6 Hz, 1H), 3.04-2.86 (m, 2H), 1.87-1.56 (m, 5H), 1.05-0.95 (m, 6H), 0.83 (d, J=7.1 Hz, 3H). ¹³C NMR (101 MHz, CHLOROFORM-d): δ=73.73, 64.69, 46.42, 34.13, 26.11, 24.55, 20.14, 17.58, 17.15. LCMS: (M+H⁺): 158.2, 100.0% purity. TLC (Petroleum ether:EtOAc=5:1) $R_f$=0.

Example 44. Synthesis of WV-CA-056-dCiBu

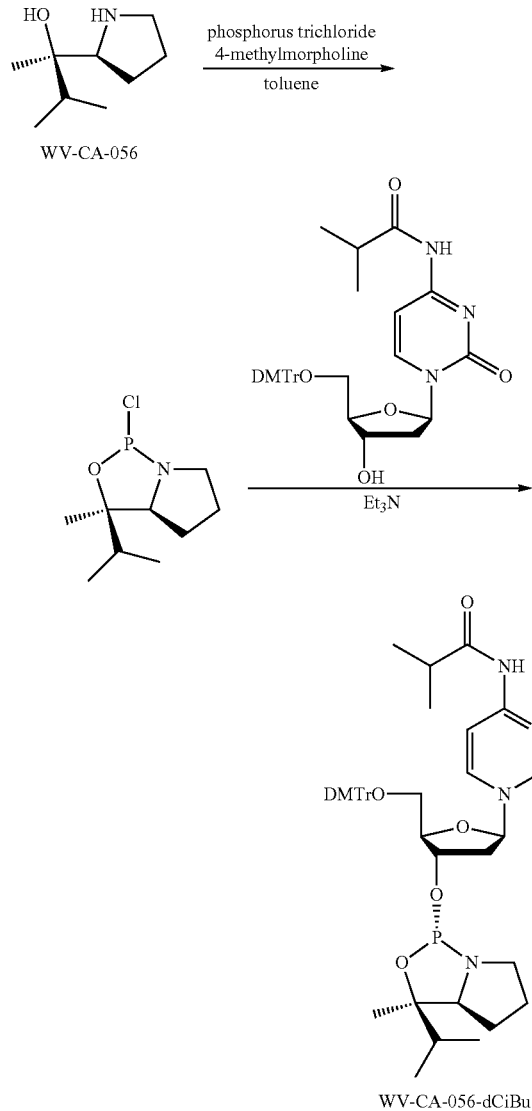

WV-CA-056-dCiBu

Using WV-CA-056 as starting material, the title compound (4.59 g, 79%) as a white solid was prepared analogously to WV-CA-008S-dCiBu. ¹H NMR (500 MHz, Chloroform-d) δ 8.73 (s, 1H), 8.24 (d, J=7.5 Hz, 1H), 7.39 (d, J=7.6 Hz, 2H), 7.32-7.19 (m, 7H), 7.03 (d, J=7.5 Hz, 1H), 6.83 (dd, J=8.8, 2.2 Hz, 4H), 6.23 (t, J=5.6 Hz, 1H), 4.77 (dq, J=10.9, 5.8 Hz, 1H), 4.18 (q, J=3.5 Hz, 1H), 3.79 (s, 6H), 3.53-3.10 (m, 4H), 2.77-2.68 (m, 1H), 2.63 (hept, J=6.5 Hz, 1H), 2.33-2.24 (m, 1H), 1.91-0.86 (m, 21H). ³¹P NMR (202 MHz, CDCl₃) δ 166.14.

Example 45. Synthesis of WV-CA-056-S

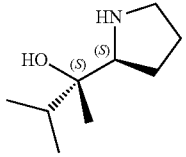

WV-CA-056-S

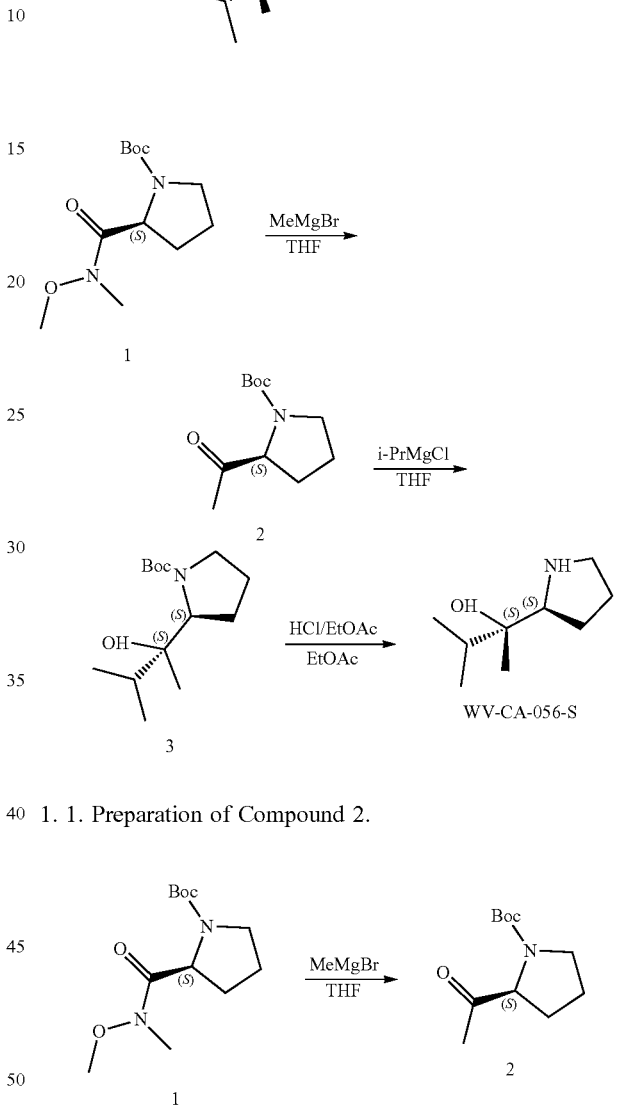

1.1. Preparation of Compound 2.

To a solution of compound 1 (17.00 g, 65.81 mmol) in THF (300 mL) was added dropwise methyl magnesium bromide (3 M, 87.75 mL) at 0° C. The mixture was stirred at 0° C. for 3 hr. TLC showed compound 1 was consumed and one major new spot with lower polarity was detected. The mixture was quenched by the addition of sat. NH₄Cl aq. (300 mL) at 0° C., and extracted with EtOAc (300 mL*3). The combined organic layers were dried over anhydrous Na₂SO₄, filtered and concentrated under reduced pressure to give a residue. The residue was purified by column chromatography (SiO₂, Petroleum ether:Ethyl acetate=10:1 to 5:1) to afford compound 2 as a yellow oil (11.40 g, 81.22%). ¹H NMR (400 MHz, CHLOROFORM-d) δ=4.19 (dd, J=5.2, 8.1 Hz, 1H), 3.66-3.36 (m, 2H), 2.29-2.05 (m, 4H), 1.95-

1.75 (m, 3H), 1.53-1.34 (m, 9H). HPLC purity: 94.1%. SFC purity: 100.0%. TLC (Petroleum ether:Ethyl acetate=5:1) $R_f$=0.43.

2. Preparation of Compound 3.

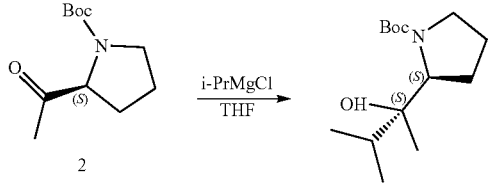

To a solution of compound 2 (11.50 g, 53.92 mmol) in THF (300 mL) was added dropwise isopropyl-magnesium chloride (2 M, 80.88 mL). The mixture was stirred at 0~5° C. for 4 hr. TLC showed compound 2 was consumed completely, and one larger and two lower polarity new spots were detected. The reaction mixture was quenched by the addition of sat. NH$_4$Cl aq. (200 mL) at 0° C., and then diluted with EtOAc (100 mL) and extracted with EtOAc (300 mL*3), dried over anhydrous Na$_2$SO$_4$, filtered and concentrated under reduced pressure to give a residue (20 g). The residue was purified by column chromatography (SiO$_2$, Petroleum ether:Ethyl acetate=30:1 to 5:1) to give compound 3 was obtained as a white solid (3.20 g, 23.05%). $^1$H NMR (400 MHz, CHLOROFORM-d) δ=5.61-5.45 (m, 1H), 4.20~4.03 (m, 1H), 3.76-3.51 (m, 1H), 3.24-3.05 (m, 1H), 2.07-1.93 (m, 1H), 1.79 (d, J=5.5 Hz, 1H), 1.73-1.49 (m, 3H), 1.48-1.38 (m, 9H), 0.99 (s, 3H), 0.94 (d, J=6.8 Hz, 6H). HPLC purity: 69.7%. SFC purity: 100.0%. TLC (Petroleum ether:Ethyl acetate=5:1) $R_f$=0.53.

3. Preparation of Compound WA-CA-056-S.

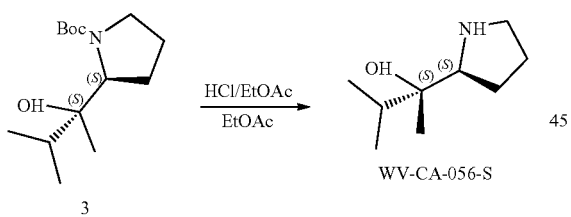

To a solution of compound 3 (3.00 g, 11.66 mmol) in EtOAc (5 mL) was added HCl/EtOAc (50 mL, 4 N). The mixture was stirred at 20° C. for 2 hr. TLC showed compound 3 was consumed completely and one major new spot with larger polarity was detected. The mixture was concentrated under reduced pressure to give a residue, which was dissolved in H$_2$O (5 mL) and added sat. Na$_2$CO$_3$ aq. to adjust pH 10-11, and then extracted with EtOAc (5 mL*3), dried over anhydrous Na$_2$SO$_4$, filtered and concentrated under reduced pressure to give compound WV-CA-056-S as a white solid (1.40 g, 76.36%). $^1$H NMR (400 MHz, CHLOROFORM-d) δ=3.22 (s, 1H), 3.02-2.79 (m, 2H), 1.84-1.56 (m, 5H), 0.97-0.90 (m, 6H), 0.84 (d, J=7.1 Hz, 3H). $^{13}$C NMR (101 MHz, CDCl$_3$): δ=73.86, 62.72, 46.78, 35.92, 26.11, 18.15, 17.25, 16.98. LCMS: (M+H+): 158.1, 100.0% purity. TLC (Petroleum ether:Ethyl acetate=3:1) $R_f$=0.

Example 46. Synthesis of WV-CA-056S-dCiBu

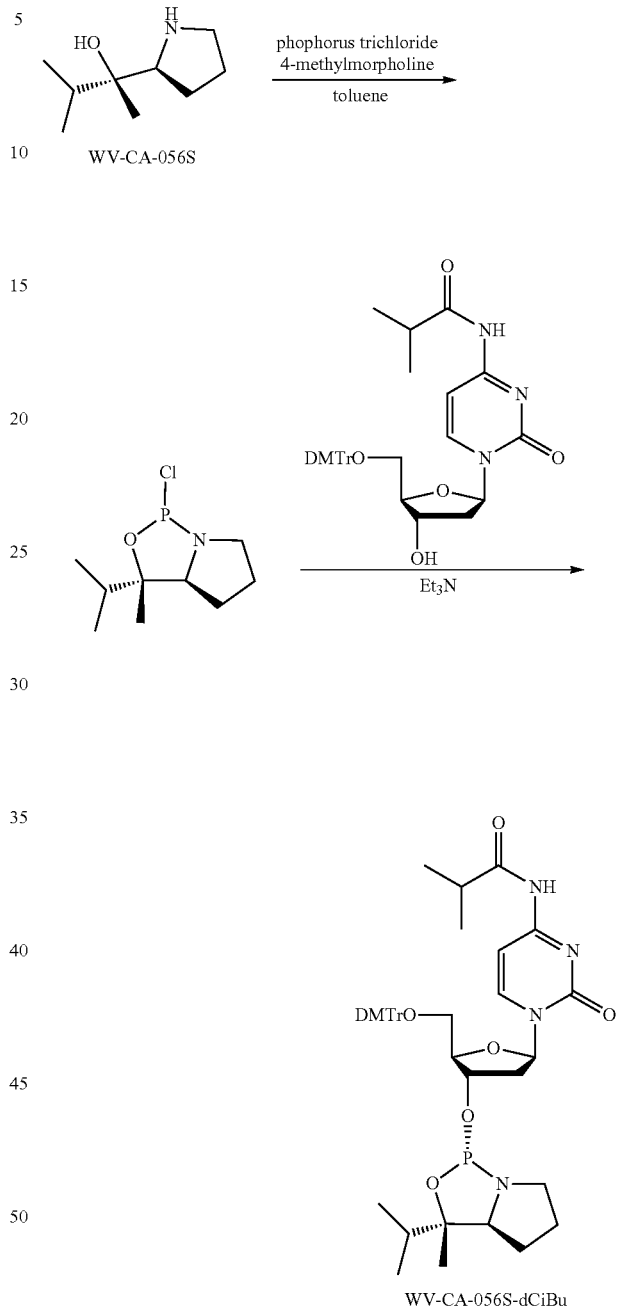

Using WV-CA-056S as starting material, the title compound (2.0 g, 60%) as a white solid was prepared analogously to WV-CA-008S-dCiBu. $^1$H NMR (500 MHz, Chloroform-d) δ 8.89 (s, 1H), 8.24 (d, J=7.5 Hz, 1H), 7.38 (d, J=7.3 Hz, 2H), 7.27 (dh, J=14.4, 8.3, 7.2 Hz, 7H), 7.07 (d, J=7.5 Hz, 1H), 6.90-6.80 (m, 4H), 6.24 (t, J=5.7 Hz, 1H), 4.75 (dq, J=10.5, 5.4 Hz, 1H), 4.16-4.10 (m, 1H), 3.79 (s, 6H), 3.57-3.37 (m, 4H), 2.86-2.76 (m, 1H), 2.67 (dq, J=13.7, 7.0, 6.4 Hz, 2H), 2.27-2.17 (m, 1H), 1.87-1.67 (m, 2H), 1.54 (tt, J=11.6, 5.6 Hz, 1H), 1.21 (dt, J=29.0, 7.1 Hz, 8H), 1.07-0.89 (m, 6H), 0.83 (d, J=6.9 Hz, 3H); $^{31}$P NMR (202 MHz, CDCl$_3$) δ 147.25.

Example 47. Synthesis of WV-CA-057

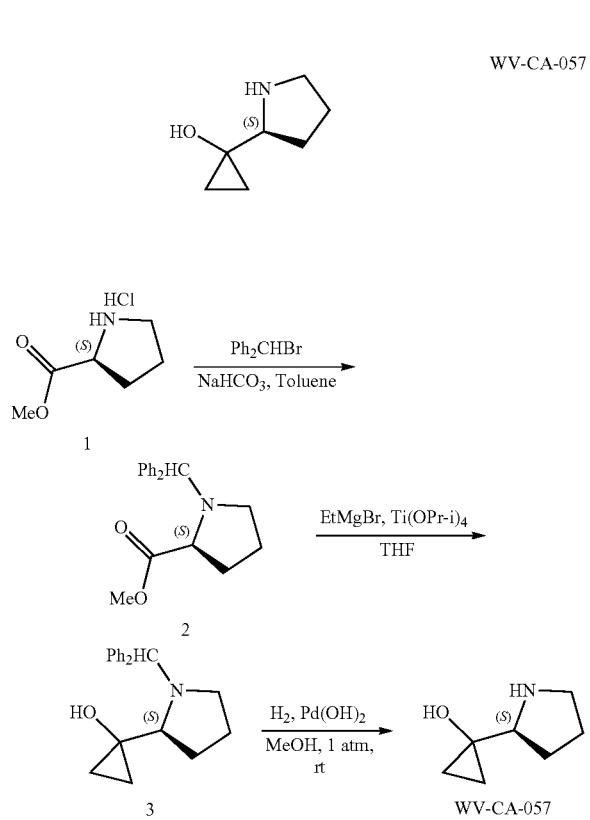

1. Preparation of Compound 2.

A mixture of compound 1 (90.00 g, 543.41 mmol), [bromo(phenyl)methyl]-benzene (147.72 g, 597.75 mmol) and NaHCO$_3$ (114.13 g, 1.36 mol) in toluene (1 L) was degassed and purged with N$_2$ for 3 times, and then the mixture was stirred at 120° C. for 12 hr under N$_2$ atmosphere. TLC showed the starting material was consumed. Two batches were combined for workup. The mixture was cooled to 20° C., and then water (1 L) was added. The organic layer was separated, and the aqueous layer was extracted with EtOAc (100 mL*2). The combined organic layers were dried over Na$_2$SO$_4$, filtered, and concentrated to give a residue, which was purified by silica gel chromatography (Petroleum ether/EtOAc, from 300:1 to 50:1) to get compound 2 as a yellow oil (50.00 g, 31.15%). $^1$H NMR (400 MHz, CDCl$_3$): δ=7.45 (t, J=6.4 Hz, 4H), 7.26 (q, J=7.5 Hz, 4H), 7.22-7.13 (m, 2H), 4.77 (s, 1H), 3.53-3.39 (m, 4H), 3.05-2.93 (m, 1H), 2.70-2.54 (m, 1H), 2.22-2.04 (m, 1H), 1.98-1.73 (m, 3H). TLC (Petroleum ether/EtOAc=5:1) R$_f$=0.43.

2. Preparation of Compound 3.

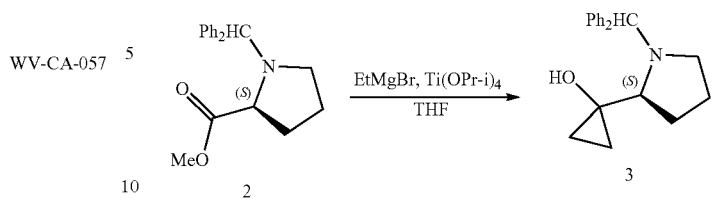

A solution of bromo(ethyl)magnesium (3 M, 152.35 mL) was added over a period of 1 h at 15° C. to a solution of compound 2 (45.00 g, 152.35 mmol) and Ti(Oi-Pr)$_4$ (8.66 g, 30.47 mmol) in THF (450 mL). The mixture was stirred at 15° C. for 12 hr. TLC showed the starting material was consumed. Two batches were combined for workup. The mixture was cooled to 0° C. and poured the mixture to an ice water (1 L). The mixture was stirred at 0° C. for 0.5 hr. The mixture was filtered, and the cake was washed with EtOAc (2 L). To the combined filtrate was added water (300 mL). The organic layer was separated, and the aqueous layer was extracted with EtOAc (1 L*2). The combined organic layers were washed with brine (200 mL), dried over Na$_2$SO$_4$, filtered and concentrated to afford a crude, which was purified by silica gel chromatography (Petroleum ether/EtOAc from 100:1 to 50:1) to give compound 3 as a yellow oil (30.5 g, 68.23%). TLC (Petroleum ether/EtOAc=5:1) R$_f$=0.43.

3. Preparation of WV-CA-057.

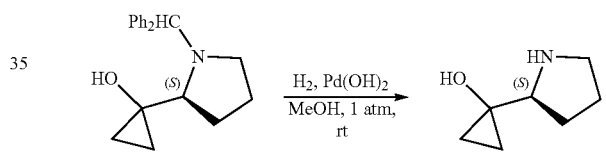

To a solution of compound 3 (30.00 g, 102.25 mmol) in MeOH (600 mL) was added Pd(OH)$_2$ (14.93 g, 106.34 mmol). The mixture was stirred at 15° C. under 20 psi of H$_2$ for 1.5 hr. LCMS showed compound 3 was consumed. Two batches were combined for workup. The catalyst was filtered off, and the filtrate was evaporated under reduced pressure. To the residue was added hexane (100 mL) at 15° C. The precipitate solid was filtered, and the filter cake was washed with hexane (200 mL*2), and dried to get WV-CA-057 as a yellow solid (7.75 g, 59.60%). $^1$H NMR (400 MHz, CDCl$_3$): δ=3.74 (br. s., 2H), 3.04-2.95 (m, 1H), 2.94-2.66 (m, 2H), 1.88-1.57 (m, 4H), 0.72 (m, 2H), 0.50-0.41 (m, 2H). $^{13}$C NMR (101 MHz, CDCl$_3$): δ=64.79, 55.52, 46.72, 27.24, 25.70, 12.92, 10.16. LCMS: (M+H+): 128.1. LCMS purity: 99.6%.

Example 48. Synthesis of WV-CA-057-dCiBu

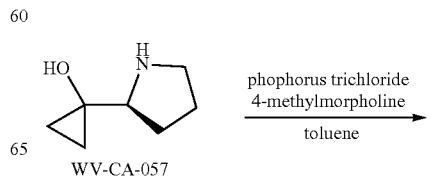

-continued

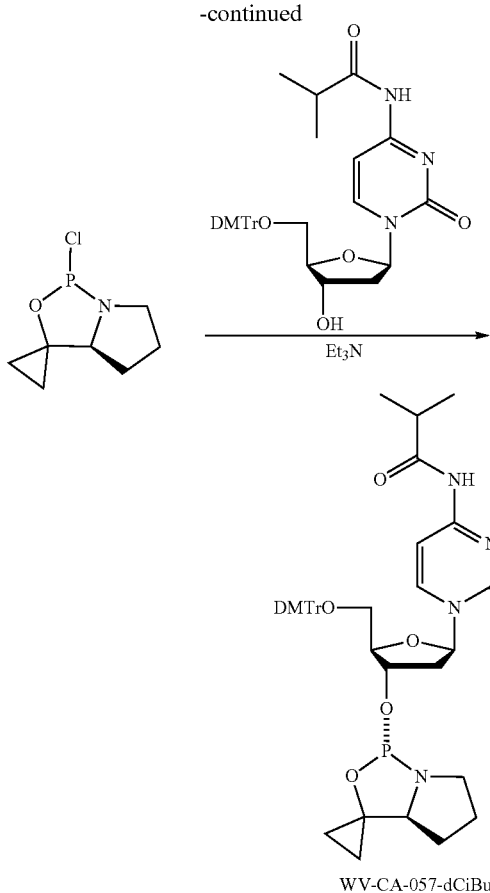

WV-CA-057-dCiBu

Using WV-CA-057 as starting material, the title compound (2.70 g, 45%) as a white solid was prepared analogously to WV-CA-008S-dCiBu. $^1$H NMR (500 MHz, Chloroform-d) δ 8.62 (s, 1H), 8.23 (d, J=7.4 Hz, 1H), 7.38 (d, J=7.6 Hz, 2H), 7.31-7.20 (m, 7H), 7.09 (d, J=7.5 Hz, 1H), 6.83 (d, J=8.3 Hz, 4H), 6.26 (t, J=5.7 Hz, 1H), 4.83 (dq, J=10.4, 5.2 Hz, 1H), 4.21-4.12 (m, 1H), 3.79 (s, 6H), 3.57-3.45 (m, 2H), 3.39 (td, J=10.0, 9.5, 4.6 Hz, 2H), 3.01 (tt, J=10.1, 6.4 Hz, 1H), 2.80-2.71 (m, 1H), 2.62 (h, J=6.8 Hz, 1H), 2.27 (dt, J=13.4, 6.0 Hz, 1H), 1.77-1.69 (m, 2H), 1.39 (dt, J=12.8, 6.7 Hz, 1H), 1.22 (dt, J=25.7, 6.8 Hz, 8H), 0.98-0.85 (m, 2H), 0.59 (s, 2H); $^{31}$P NMR (202 MHz, CDCl$_3$) δ 155.05.

Example 49. Synthesis of WV-CA-059

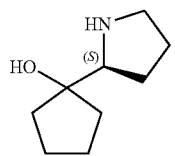

WV-CA-059

-continued

General Scheme.

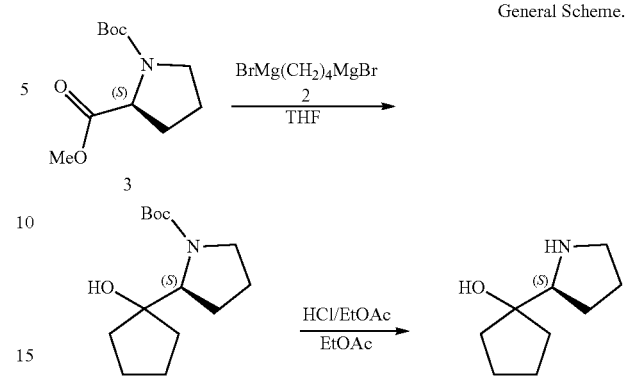

1. Preparation of Compound 2.

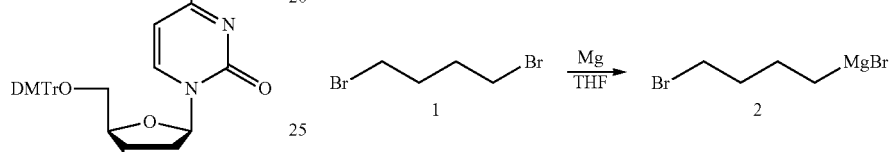

To a suspension of Mg (18.01 g, 741.04 mmol) in THF (400 mL) was added drop-wise a solution of 1,4-dibromobutane (80.00 g, 370.52 mmol) in THF (100 mL) (activated with one crystal of I$_2$). The mixture was stirred at 20~60° C. for 3. Mg was disappeared. The reaction was completed. The Grignard reagent in THF was used directly in next step.

2. Preparation of Compound 4.

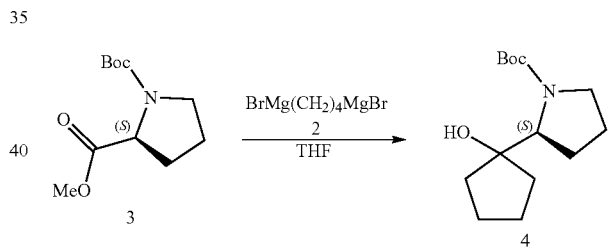

To a mixture of compound 2 (98.00 g, 370.31 mmol) in THF was added dropwise compound 3 (30.00 g, 130.85 mmol) in THF (100 mL) at 0° C. The mixture was stirred at 10~20° C. for 16 hr. Most of compound 3 was consumed, and desired product was observed by LCMS. The resulting mixture was quenched with sat. NH$_4$Cl aq. (500 mL), extracted with EtOAc (250 mL*3). The combined organic layers were dried over anhydrous Na$_2$SO$_4$, filtered, and concentrated to afford a crude white solid. The crude product was purified by column chromatography on silica gel (Petroleum ether:Ethyl acetate=100:1, 50:1, 10:1) to afford the product (14.3 g) and a crude, which was recrystallized in Petroleum ether/Ethyl acetate (100 mL/5 mL) to afford another part of purified product (11.3 g). Compound 4 was obtained as a light yellow solid (25.60 g, 68.96%). $^1$H NMR (400 MHz, CDCl$_3$): δ=5.06 (br. s, 1H), 4.01 (br. s, 1H), 3.64 (br. s, 1H), 3.28-3.07 (m, 1H), 2.13-1.34 (m, 16H). LCMS: (M+H$^+$): 182.0. TLC (Petroleum ether:Ethyl acetate=3:1) R$_f$=0.65. SFC purity=100.0%.

3. Preparation of Compound WV-CA-059.

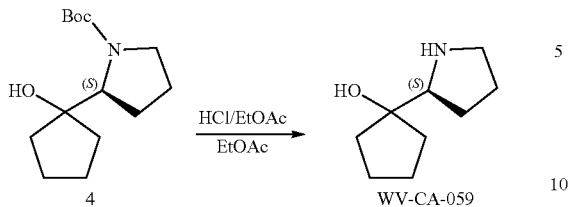

To a solution of compound 4 (34.00 g, 133.15 mmol) in EtOAc (50 mL) was added HCl/EtOAc (500 mL, 4 N) at 15° C. The reaction was stirred at 20° C. for 4 hr. TLC showed compound 4 was consumed completely. The resulting mixture was concentrated in vacuo. The suspension was filtered and the filter cake was washed with EtOAc (30 mL*2). The white solid filter cake was dried in vacuo. To the solid was added a solution of $Na_2CO_3$ (~10 g) in $H_2O$ (~20 mL), and the mixture was stirred for 0.5 hr, and then concentrated in vacuo with oil pump. To the residue was added DCM (50 mL). The filtered organic phase was dried over $Na_2SO_4$, concentrated in vacuo to give the crude product of WV-CA-059 (17.7 g). The crude product was dissolved in DCM (177 mL), added KOH (2M, 20 mL) to adjust pH=12~13 and stirred of 0.5 hr. The separated aqueous phase was extracted with DCM (50 mL*2). The combined organic phase was dried over $Na_2SO_4$, and concentrated in vacuo to dryness to give compound WV-CA-059 as light yellow solid (13.55 g, 65.55%). $^1$H NMR (400 MHz, $CDCl_3$): δ=3.09-3.05 (m, 1H), 3.01-2.93 (m, 2H), 2.46 (br, 1H), 1.75-1.48 (m, 12H). $^1$H NMR (400 MHz, MeOD): δ=3.02-2.93 (m, 1H), 2.92-2.84 (m, 1H), 2.76-2.65 (m, 1H), 1.95-1.39 (m, 13H). $^{13}$C NMR (125.7 MHz, $CDCl_3$): δ=81.85, 65.99, 46.97, 39.99, 35.99, 26.26, 25.95, 24.04. $^{13}$C NMR (125.7 MHz, MeOH): δ=83.57, 68.48, 48.08, 39.53, 39.82, 28.07, 27.21, 25.13, 24.89. LCMS: (M+H$^+$): 156.1. TLC (Dichloromethane/Methanol=10:1) $R_f$=0.10.

Example 50. Synthesis of WV-CA-059-dCiBu

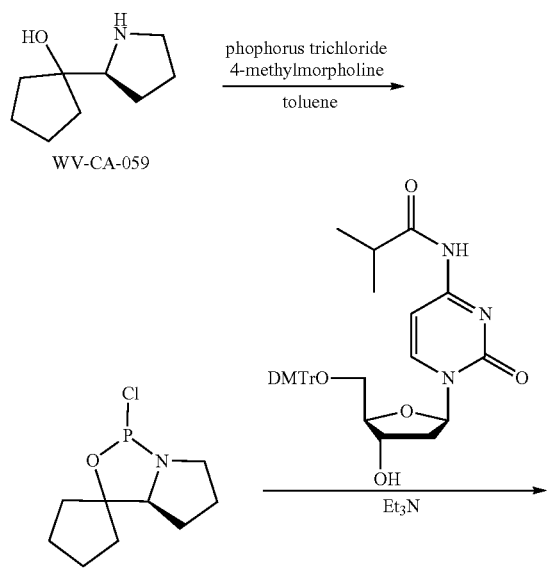

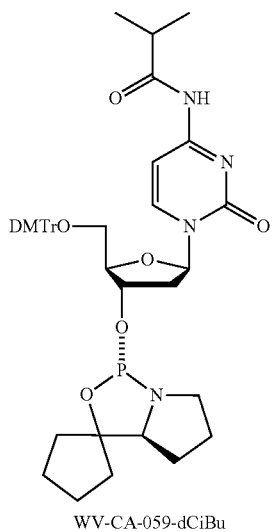

Using WV-CA-059 as starting material, the title compound (4.0 g, 64%) as a white solid was prepared analogously to WV-CA-008S-dCiBu. $^1$H NMR (400 MHz, Chloroform-d) δ 8.25 (d, J=7.4 Hz, 1H), 8.05 (s, 1H), 7.43-7.36 (m, 2H), 7.34-7.19 (m, 7H), 7.04 (d, J=7.4 Hz, 1H), 6.87-6.80 (m, 4H), 6.24 (t, J=5.6 Hz, 1H), 4.78 (dq, J=10.8, 5.7 Hz, 1H), 4.20-4.12 (m, 1H), 3.80 (s, 7H), 3.57-3.40 (m, 4H), 3.08 (tt, J=10.0, 6.9 Hz, 1H), 2.75 (dt, J=13.8, 6.0 Hz, 1H), 2.53 (p, J=6.9 Hz, 1H), 2.29 (dt, J=13.8, 5.9 Hz, 1H), 2.04-1.17 (m, 18H). $^{31}$P NMR (202 MHz, $CDCl_3$) δ 158.39.

Example 51. Synthesis of WV-CA-059R

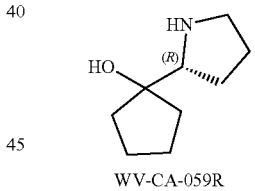

General Scheme.

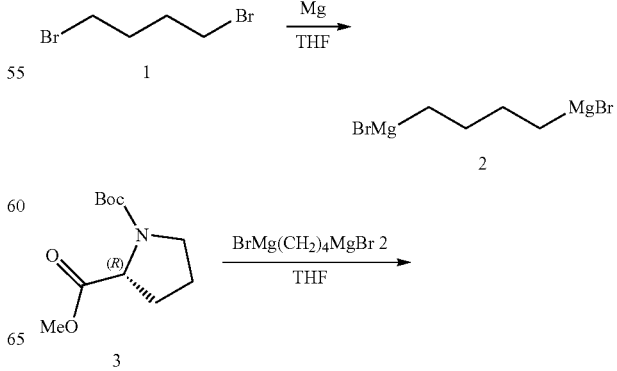

-continued

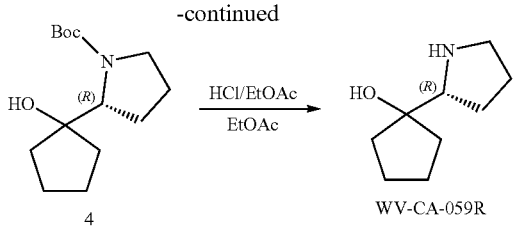

1. Preparation of Compound 2.

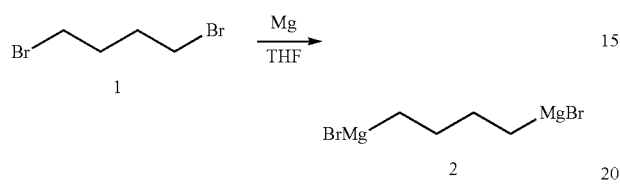

To a suspension of Mg (27.02 g, 1.11 mol) and I₂ (30.00 mg, 118.20 µmol) in THF (700 mL) was added compound 1 (120.00 g, 555.79 mmol) (first 10% volume, when the reaction was initiated, and then added dropwise the left over 2 hr at 20~60° C.) in THF (100 mL). The mixture was stirred at 20~60° C. for another 2 hr. Most of Mg was consumed. The reaction was almost completed. The Grignard reagent in THF was used directly in next step.

2. Preparation of Compound 4.

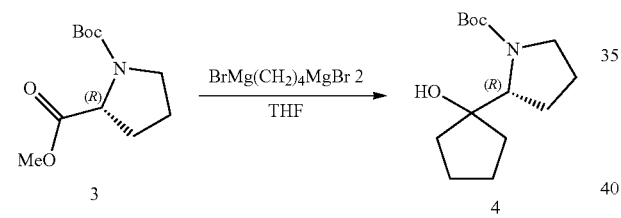

To a mixture of compound 2 (147.00 g, 556.11 mmol) in THF (previous step) was added dropwise compound 3 (42.50 g, 185.37 mmol) in THF (120 mL) at 0° C. The mixture was stirred at 10~20° C. for 16 hr. TLC showed compound 3 was consumed. The resulting mixture was quenched with sat. NH₄Cl aq. (1000 mL), extracted with EtOAc (800 mL*3). The combined organic layers were dried over anhydrous Na₂SO₄, filtered, and concentrated until a large amount of solid precipitated. The mixture was filtered, and the filter cake was rinsed with petroleum ether (100 mL), and dried to give the product as a white solid (22 g). The crude product was purified by column chromatography on silica gel (Petroleum ether:EtOAc=20:1, 10:1) to afford the product as a white solid (13 g). Twice purification got compound 4 as a white solid (35.00 g, 73.94%). TLC (Petroleum ether:EtOAc=5:1, eluted two times) $R_f$=0.35. Batch 1 (22 g): ¹H NMR (400 MHz, CHLOROFORM-d) δ=5.01 (br s, 1H), 4.01 (br s, 1H), 3.64 (br s, 1H), 3.18 (td, J=7.8, 10.9 Hz, 1H), 2.09-1.94 (m, 1H), 1.92-1.74 (m, 3H), 1.73-1.61 (m, 3H), 1.61-1.47 (m, 5H), 1.46-1.40 (m, 9H). LCMS: (M+Na+): 278.2, 85.1% purity. SFC purity: 100.0%. Batch 2 (13 g): ¹H NMR (400 MHz, CHLOROFORM-d) δ=5.01 (br s, 1H), 4.01 (br s, 1H), 3.64 (br s, 1H), 3.18 (td, J=7.8, 10.9 Hz, 1H), 2.09-1.94 (m, 1H), 1.92-1.74 (m, 3H), 1.73-1.61 (m, 3H), 1.61-1.47 (m, 5H), 1.46-1.40 (m, 9H). HPLC purity: 100.0%. SFC purity: 100.0%.

3. Preparation of Compound WV-CA-059R.

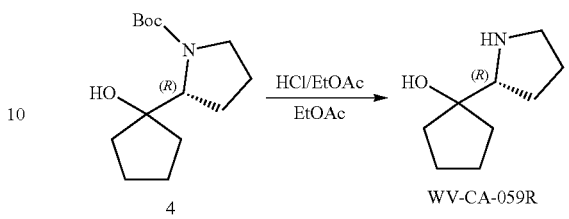

To a solution of compound 4 (18.00 g, 70.49 mmol) in EtOAc (50 mL) was added HCl/EtOAc (450 mL, 4 N). The mixture was stirred at 15° C. for 4 hr. TLC indicated the starting material was consumed completely. The mixture was concentrated under reduced pressure, and filtered to give a residue, which was dissolved in water (30 mL), adjusted to pH 11-12 with KOH (aq.), and then extracted with DCM (100 mL*3), dried over Na₂SO₄, filtered and concentrated under reduced pressure to give WV-CA-059R as a white solid (8.00 g, 73.11%). ¹H NMR (400 MHz, CHLOROFORM-d) δ=3.11-2.99 (m, 1H), 2.99-2.82 (m, 2H), 2.48 (br. s., 1H), 1.88-1.50 (m, 10H), 1.50-1.33 (m, 2H). ¹³C NMR (101 MHz, CDCl₃): δ=76.72, 66.04, 46.99, 40.01, 36.03, 26.29, 25.97, 24.07. LCMS: (M+H⁺): 156.1, 100.0% purity. TLC (Petroleum ether:EtOAc=5:1) $R_f$=0.

Example 52. Synthesis of WV-CA-059R-dCiBu

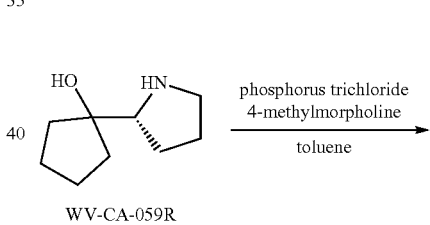

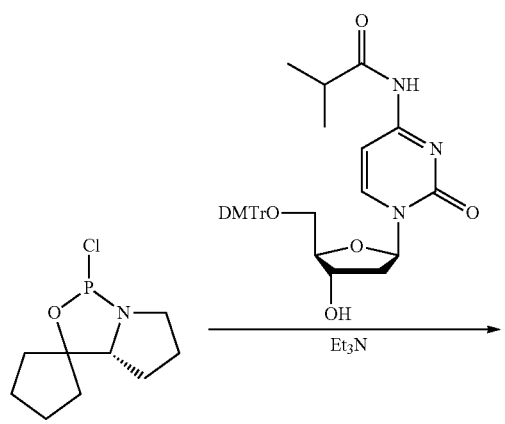

639
-continued

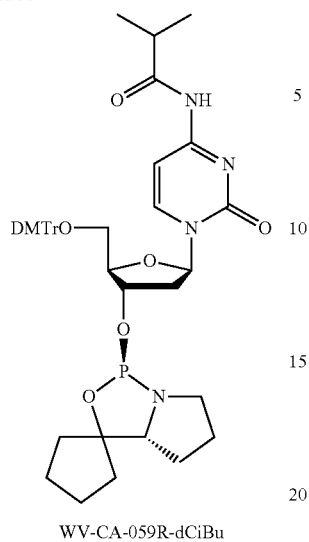

WV-CA-059R-dCiBu

Using WV-CA-059R as starting material, the title compound (3.90 g, 62.3%) as a white solid was prepared analogously to WV-CA-008S-dCiBu. $^1$H NMR (500 MHz, Chloroform-d) δ 8.90 (s, 1H), 8.36 (d, J=7.5 Hz, 1H), 7.43-7.37 (m, 2H), 7.32-7.20 (m, 7H), 7.12 (d, J=7.4 Hz, 1H), 6.83 (dd, J=8.7, 1.9 Hz, 4H), 6.19 (dd, J=6.6, 4.1 Hz, 1H), 4.83 (dq, J=12.5, 6.6 Hz, 1H), 4.15-4.10 (m, 1H), 3.78 (s, 6H), 3.47 (dddd, J=35.4, 21.3, 9.5, 4.2 Hz, 3H), 3.13-3.03 (m, 1H), 2.66 (dt, J=13.4, 6.7 Hz, 2H), 2.30 (ddd, J=13.8, 6.5, 4.1 Hz, 1H), 2.10 (dd, J=11.2, 5.2 Hz, 1H), 1.83-1.13 (m, 18H). $^{31}$P NMR (202 MHz, CDCl$_3$) δ 158.98.

Example 53. Synthesis of WV-CA-059-C(OMe)Ac

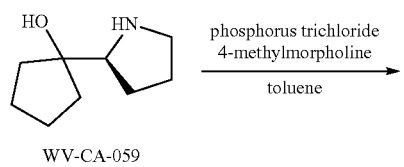

WV-CA-059

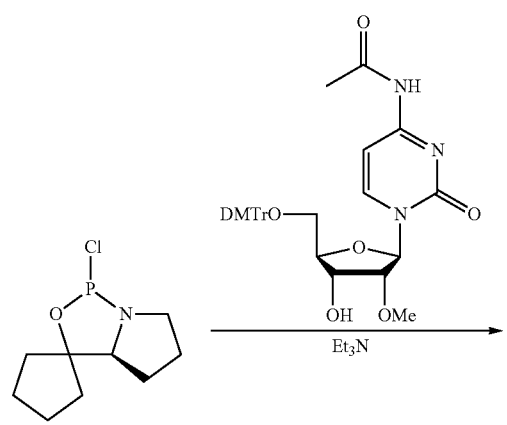

640
-continued

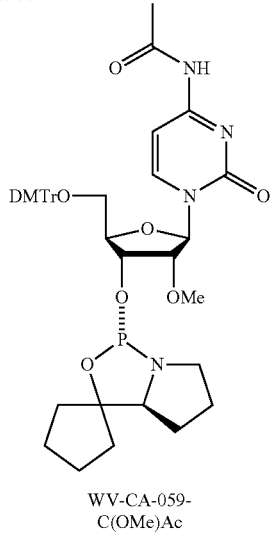

WV-CA-059-
C(OMe)Ac

Using WV-CA-059 and N-(1-((2R,3R,4R,5R)-5-((bis(4-methoxyphenyl)(phenyl)methoxy)methyl)-4-hydroxy-3-methoxytetrahydrofuran-2-yl)-2-oxo-1,2-dihydropyrimidin-4-yl)acetamide as starting material, the title compound (4.48 g, 71.4%) as a white solid was prepared analogously to WV-CA-008S-dCiBu. $^1$H NMR (500 MHz, Chloroform-d) δ 10.32 (s, 1H), 8.55 (d, J=7.5 Hz, 1H), 7.40 (d, J=7.1 Hz, 2H), 7.34-7.22 (m, 7H), 6.92 (d, J=7.5 Hz, 1H), 6.84 (d, J=8.5 Hz, 5H), 5.98 (s, 1H), 4.69-4.60 (m, 1H), 4.28 (dt, J=9.2, 2.4 Hz, 1H), 4.11 (q, J=7.2 Hz, 1H), 3.88 (d, J=4.7 Hz, 1H), 3.79 (s, 6H), 3.64 (s, 3H), 3.65-3.59 (m, 1H), 3.58-3.44 (m, 3H), 2.99 (td, J=10.0, 9.4, 5.2 Hz, 1H), 2.24 (s, 3H), 1.97-1.24 (m, 12H). $^{31}$P NMR (202 MHz, CDCl$_3$) δ 156.89.

Example 54. Synthesis of WV-CA-060

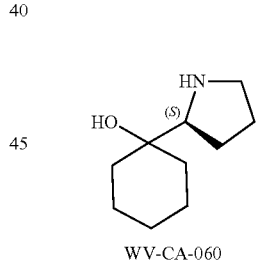

WV-CA-060

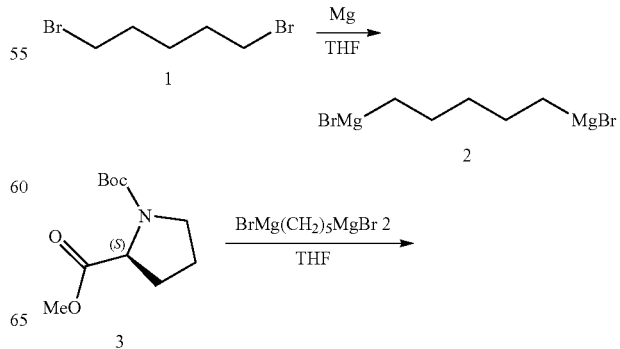

-continued

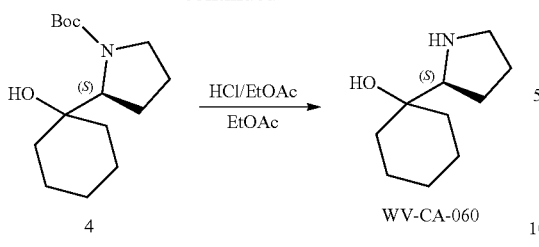

1. Preparation of Compound 2.

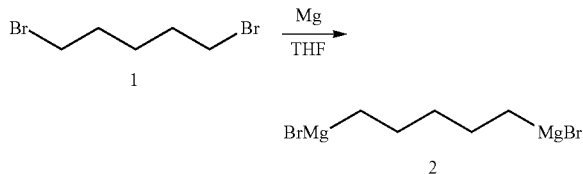

To a suspension of Mg (27.07 g, 1.11 mol) in THF (600 mL) was added dropwise 1,5-dibromopentane (128.00 g, 556.67 mmol) (activated with one crystal of $I_2$) in THF (150 mL) over 1 hr. The mixture was stirred at 20~60° C. for 3 hr. Mg was disappeared. The reaction was completed. The Grignard reagent in THF was used directly in next step.

2. Preparation of Compound 4.

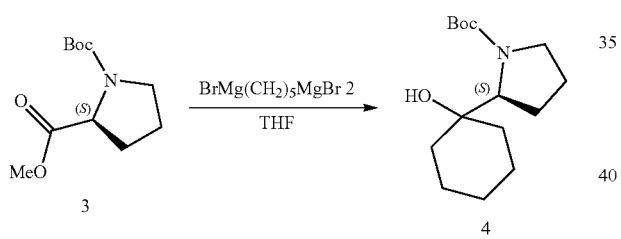

A mixture of compound 2 (154.73 g, 555.47 mmol) in THF was diluted with THF (200 mL), and compound 3 (45.00 g, 196.28 mmol) in THF (150 mL) was added dropwise at 0° C. The mixture was first stirred at 0° C. for 1 hr. And then stirring was continued at 20° C. for 15 hr. Part of compound 3 was consumed, and desired product was observed by LCMS. The resulting mixture was quenched with sat. $NH_4Cl$ aq. (1200 mL), extracted with EtOAc (800 mL*3). The combined organic layers were dried over anhydrous $Na_2SO_4$, filtered, and concentrated to afford a crude light yellow oil. The crude was purified by column chromatography on silica gel (Petroleum ether:Ethyl acetate=50:1, 10:1, 5:1) to afford a light yellow oil (54 g), and then combined with the crude from 8 g, to which was added petroleum ether (40 mL), and laid aside overnight at 12° C. (rt.). The crystallized solid was filtered and further purified by column chromatography on silica gel (Petroleum ether:Ethyl acetate=50:1, 10:1) to afford compound 4 as a white solid (25.50 g, 45.82% yield). $^1$H NMR (400 MHz, $CDCl_3$): δ=3.79-3.77 (m, 1H), 3.64-3.62 (m, 1H), 3.21-3.17 (m, 1H), 1.90-1.18 (m, 24H). LCMS: (M+H+): 195.8. TLC (Petroleum ether:Ethyl acetate=1:1) $R_f$=0.65. SFC purity=100.0%.

3. Preparation of Compound WV-CA-060.

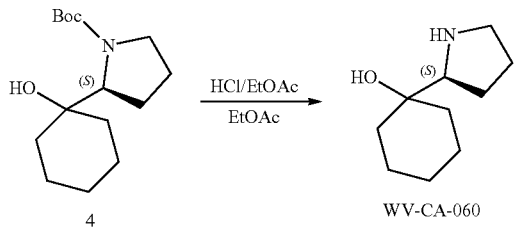

To a solution of compound 4 (30.00 g, 100.23 mmol) in EtOAc (50 mL) was added HCl/EtOAc (500 mL, 4 N) at 15° C. The reaction was stirred at 20° C. for 4 hr. TLC showed compound 4 was consumed completely. The reaction was concentrated in vacuo. The suspension was filtered and washed with EtOAc (30 mL*2). The white solid was dried in vacuo. To the white solid in DCM (200 mL) was added KOH (2 N, 120.08 mL) at 15° C. to adjust pH=12-13 and stirred of 0.5 hr. The reaction solution was extracted with DCM (100 mL*3). The combined organic phase was dried over $MgSO_4$, filtered, and concentrated in vacuo to dryness to afford compound WV-CA-060 as white solid (16.38 g, 97.11%). $^1$H NMR (400 MHz, $CDCl_3$): δ=2.98-2.92 (m, 1H), 2.92-2.88 (m, 2H), 2.35 (br, 1H), 1.74-1.48 (m, 11H), 1.26-1.19 (m, 3H). $^1$H NMR (400 MHz, MeOH): δ=3.01-2.90 (m, 1H), 2.86 (dd, J=7.1, 8.4 Hz, 1H), 2.77-2.67 (m, 1H), 1.79-1.13 (m, 14H). $^{13}$C NMR (125.7 MHz, $CDCl_3$): δ=70.53, 66.80, 46.67, 37.16, 33.86, 26.06, 25.88, 24.56, 21.93. $^{13}$C NMR (125.7 MHz, MeOH): δ=6=71.09, 66.99, 46.25, 35.27, 34.75, 25.55, 25.37, 25.12, 21.49, 21.43. LCMS: (M+H+): 170.1. TLC (Petroleum ether:Ethyl acetate=3:1) $R_f$=0.00.

Example 55. Synthesis of WV-CA-060-dCiBu

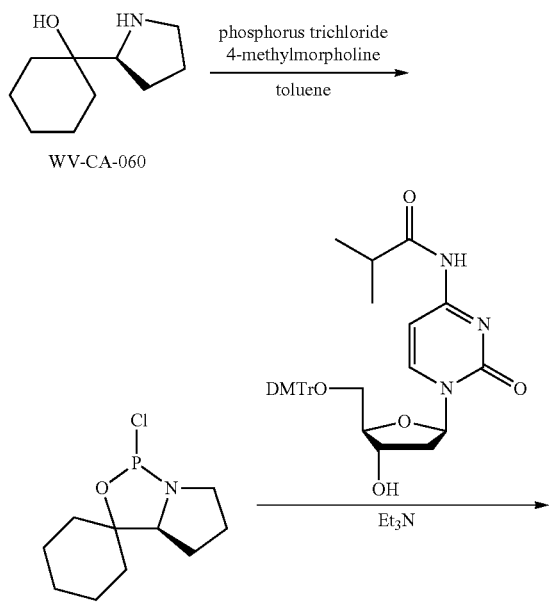

-continued

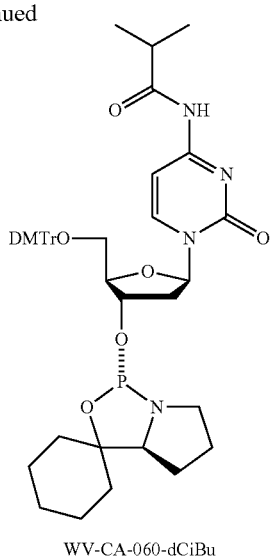

WV-CA-060-dCiBu

Using WV-CA-060 as starting material, the title compound (4.0 g, 64%) as a white solid was prepared analogously to WV-CA-008S-dCiBu. $^1$H NMR (500 MHz, Chloroform-d) δ 8.52 (s, 1H), 8.23 (d, J=7.4 Hz, 1H), 7.40 (d, J=7.6 Hz, 2H), 7.33-7.20 (m, 7H), 7.06 (d, J=7.5 Hz, 1H), 6.87-6.81 (m, 4H), 6.24 (t, J=5.7 Hz, 1H), 4.77 (dq, J=10.8, 5.4 Hz, 1H), 4.20-4.12 (m, 1H), 3.80 (s, 6H), 3.52-3.37 (m, 4H), 3.07-2.97 (m, 1H), 2.73 (dt, J=13.8, 5.8 Hz, 1H), 2.60 (h, J=6.9 Hz, 1H), 2.30-2.21 (m, 1H), 1.82-1.37 (m, 12H), 1.28-1.17 (m, 8H). $^{31}$P NMR (202 MHz, CDCl$_3$) δ 156.34.

Example 56. Synthesis of WV-CA-061

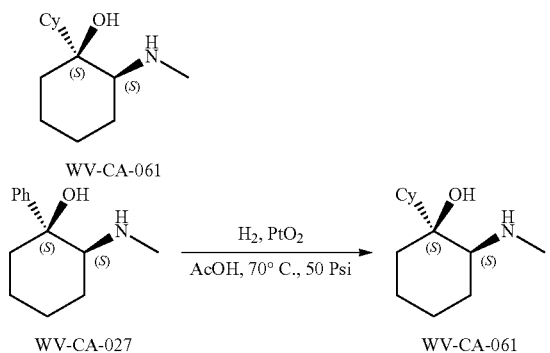

A mixture of WV-CA-027 (900.00 mg, 4.38 mmol) and PtO$_2$ (500.00 mg, 2.20 mmol) in AcOH (50 mL) was hydrogenated under 50 psi of hydrogen pressure for 21 hr at 70° C. $^1$H NMR showed about 4.9% of the starting material was remained. The reaction was cooled to 25° C. and then filtered, to the reaction was additionally added PtO$_2$ (500.00 mg, 2.20 mmol) and the mixture was stirred under 50 psi of hydrogen pressure for 23 hr at 70° C. $^1$HNMR showed 3% of the starting material remained. The reaction was cooled to 25° C. and then filtered, to the reaction was additionally added PtO$_2$ (500.00 mg, 2.20 mmol) and the mixture was stirred under 50 psi of hydrogen pressure for 23 hr at 70° C. $^1$H NMR showed the starting material was consumed. The mixture was concentrated under reduced pressure to remove the solvent, and then water (5 mL) was added and sat. Na$_2$CO$_3$ (aq.) was added until pH>11, extracted with DCM (15 mL*3). The combined organic layers were washed with brine (30 mL), dried over anhydrous Na$_2$SO$_4$, filtered and concentrated to afford WV-CA-061 as a yellow oil (630.00 mg, 68.06%). $^1$H NMR (400 MHz, CDCl$_3$): δ=2.49 (dd, J=4.2, 9.3 Hz, 1H), 2.46-2.38 (m, 3H), 1.93-1.73 (m, 3H), 1.72-1.61 (m, 3H), 1.60-1.00 (m, 13H). $^{13}$C NMR (101 MHz, CDCl$_3$): δ=73.83, 59.69, 43.51, 35.09, 29.58, 27.61, 27.04, 26.74, 26.57, 26.11, 23.46, 21.15. LCMS: (M+H+): 212.1. LCMS purity=100.0%.

Example 57. Synthesis of WV-CA-061-dCiBu

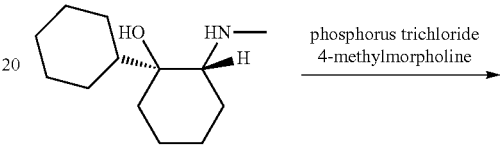

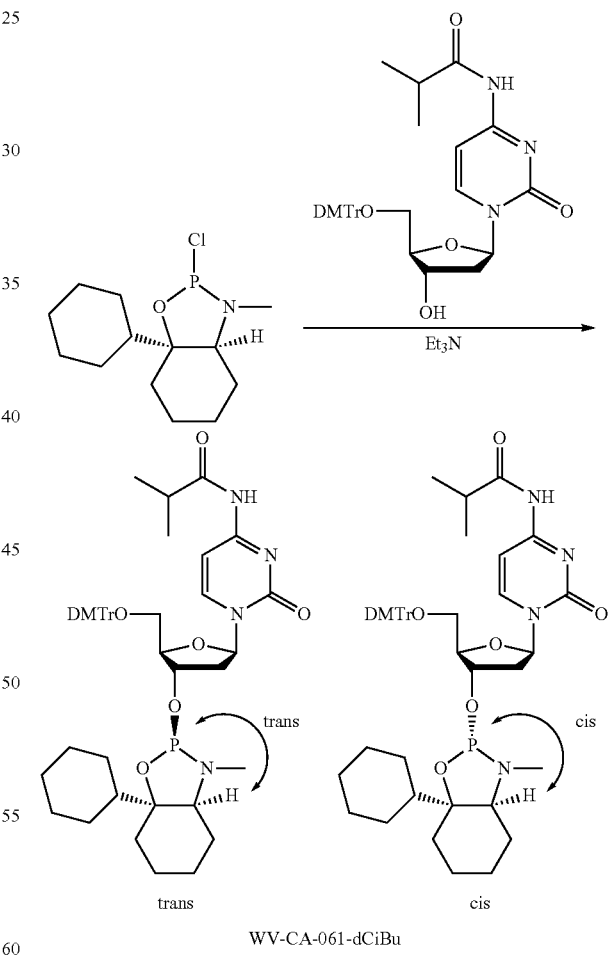

WV-CA-061-dCiBu

Using WV-CA-061 as starting material, the title compound (0.77 g, 48%) as a white solid was prepared analogously to WV-CA-008S-dCiBu. $^{31}$P NMR (202 MHz, CDCl$_3$) δ 150.69 (81%, trans), 144.74 (19%, cis).

Example 58. Synthesis of WV-CA-062

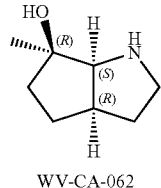
WV-CA-062

General Scheme.

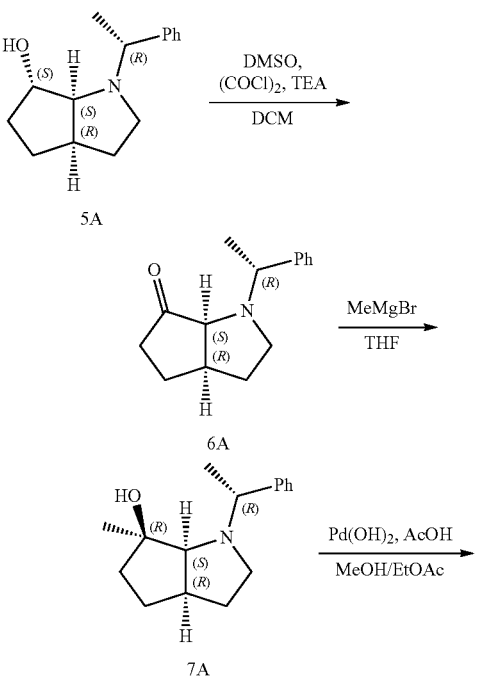

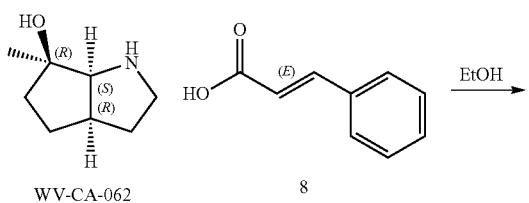

1. Preparation of Compound 6A.

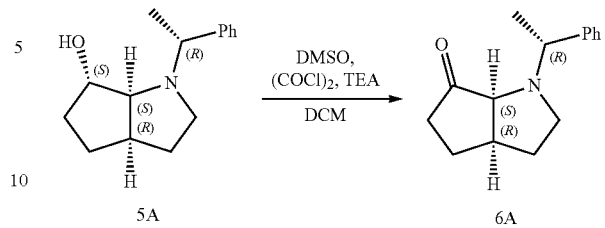

A solution of DMSO (12.67 g, 162.10 mmol, 12.67 mL) in dry DCM (7.00 mL) was added dropwise to a stirred solution of oxalyl chloride (12.35 g, 97.26 mmol, 8.52 mL) in dry DCM (70.00 mL) at −78° C. The mixture was stirred for 10 minutes at this temperature. A solution of compound 5A (7.50 g, 32.42 mmol) in dry DCM (70.00 mL) was added dropwise to the reaction mixture at −78° C. After stirring for another 50 minutes, Et$_3$N (49.21 g, 486.30 mmol, 67.41 mL) was added dropwise to the reaction mixture at −78° C. The resulting mixture was stirred for an additional 30 minutes. TLC showed the starting material was consumed. Water (50 mL) was added and extracted with DCM (100 mL*3) and the combined organic was washed brine (50 mL), dried over Na$_2$SO$_4$, filtered and concentrated to get the crude. The residue was purified by silica (Petroleum ether/Ethyl acetate=10:1, 5% TEA) to get the compound 6A as a yellow oil (4.60 g, 61.87% yield). $^1$H NMR (400 MHz, CHLOROFORM-d): δ=7.37-7.25 (m, 4H), 7.23-7.16 (m, 1H), 4.03 (q, J=6.6 Hz, 1H), 3.24 (br d, J=7.7 Hz, 1H), 2.83 (br t, J=6.5 Hz, 1H), 2.65-2.53 (m, 2H), 2.44-2.32 (m, 1H), 2.22-2.11 (m, 1H), 2.08-1.91 (m, 2H), 1.78 (tdd, J=3.3, 9.6, 13.0 Hz, 1H), 1.53 (qd, J=6.7, 12.9 Hz, 1H), 1.43 (d, J=6.6 Hz, 3H). TLC (Petroleum ether/Ethyl acetate=3:1) R$_f$=0.43.

2. Preparation of Compound 7A.

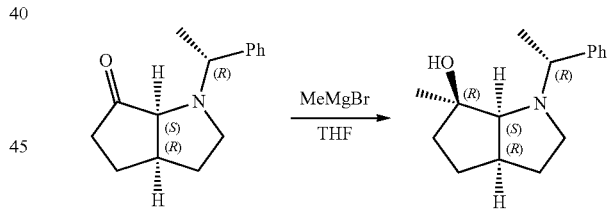

A solution of compound 6A (4.60 g, 20.06 mmol) dissolved in THF (20.00 mL) was added dropwise to a stirred solution of bromo(methyl)magnesium (3 M, 33.43 mL) in dry THF (30.00 mL) at −78° C. The mixture was stirred at −78° C. for 1 hr. TLC showed the starting material was consumed. Water (15 mL) was added and extracted with Ethyl acetate (15 mL*2), the combined organic was washed with brine (15 mL), dried over Na$_2$SO$_4$, filtered and concentrated to get the crude. The residue was purified by MPLC (Petroleum ether/Ethyl acetate=10:1, 5% TEA) to get compound 7B as a yellow oil (4.00 g, 81.27% yield). $^1$H NMR: (400 MHz, CDCl$_3$): δ=7.44-7.17 (m, 5H), 4.80 (br s, 1H), 3.94 (q, J=6.6 Hz, 1H), 3.02 (d, J=9.6 Hz, 1H), 2.91-2.74 (m, 2H), 2.69-2.48 (m, 1H), 1.86-1.69 (m, 2H), 1.65-1.39 (m, 8H), 1.00 (s, 3H). SFC purity: 96.1%. HPLC purity: 97.0%. TLC (Petroleum ether/Ethyl acetate=3:1) R$_f$=0.36.

3. Preparation of WV-CA-062.

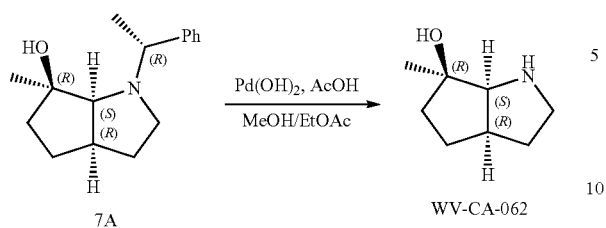

To a solution of compound 7A (5.00 g, 20.38 mmol) in the mixture of MeOH (80.00 mL) and AcOH (10 mL) was added Pd(OH)$_2$ (2.86 g, 20.38 mmol) under N$_2$ atmosphere. The suspension was degassed and purged with H$_2$ for 3 times. The mixture was stirred under H$_2$ (50 Psi) at 50° C. for 24 hr. $^1$H NMR showed the starting material was consumed. The mixture was filtered and the filtrate was concentrated to get the crude. The residue was dissolved in water (10 mL), and KOH (2 M, aq.) was added until pH>11 and extracted with DCM (20 mL*5). The combined organic was dried over Na$_2$SO$_4$, filtered, and concentrated to get WV-CA-062 as a yellow oil (2.20 g, 76.45% yield). $^1$H NMR: (400 MHz, CHLOROFORM-d): δ=3.27-3.13 (m, 3H), 3.01 (td, J=6.5, 10.4 Hz, 1H), 2.89 (td, J=6.6, 10.5 Hz, 1H), 2.69-2.54 (m, 1H), 1.83-1.63 (m, 3H), 1.57-1.31 (m, 3H), 1.16 (s, 3H). $^{13}$C NMR: (101 MHz, CHLOROFORM-d): δ=75.92, 70.67, 48.31, 42.61, 40.47, 34.54, 29.30, 27.00. LCMS: (M+H$^+$): 142.1; LCMS purity=99.8%.

4. Purification of WV-CA-062.

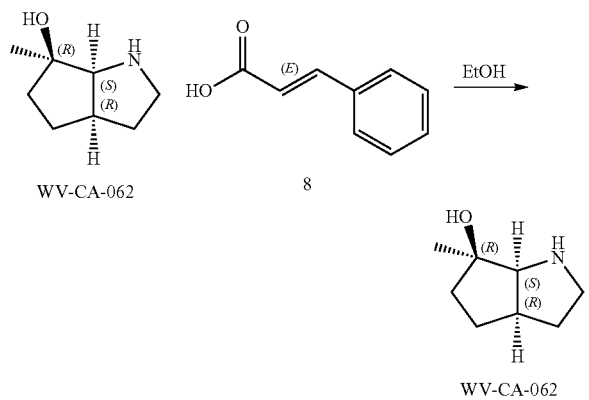

To a solution, WV-CA-062 (2.20 g, 15.58 mmol) in EtOH (30.00 mL) was added compound 8 (2.31 g, 15.58 mmol) and reflux at 90° C. for 0.5 hr, and then the mixture was dried in rotary evaporation to give the yellow solid, to which was added ethyl acetate (35 mL), and slowly dropped MeOH until the yellow solid become liquid at 90° C. for 2 hr. The mixture was stewed for 72 h, we got 1.5 g salt. The mixture was filtered and the cake was washed with ethyl acetate (10 mL) and the cake was dissolved in water (10 mL), and to the mixture was added sat. Na$_2$CO$_3$ (aq.) until pH>11. The mixture was extracted with DCM (15 mL*3). The combined organic was washed with brine (20 mL) then Na$_2$CO$_3$ (15 mL), dried over Na$_2$SO$_4$, filtered and concentrated to get WV-CA-062 as a yellow oil (850.00 mg, 38.64% yield). $^1$H NMR: (400 MHz, CHLOROFORM-d): δ=3.40-3.17 (m, 3H), 3.00 (td, J=6.4, 10.4 Hz, 1H), 2.94-2.81 (m, 1H), 2.70-2.51 (m, 1H), 1.86-1.62 (m, 3H), 1.56-1.32 (m, 3H), 1.18 (s, 3H). $^{13}$C NMR: (101 MHz, CHLOROFORM-d): δ=75.93, 70.71, 48.35, 42.65, 40.50, 34.62, 29.34, 27.05. LCMS: (M+H$^+$): 142.0; LCMS purity=99.4%.

Example 59. Synthesis of WV-CA-062S

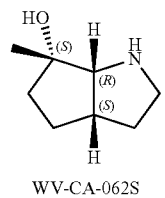

WV-CA-062S

1. Preparation of Compound 2.

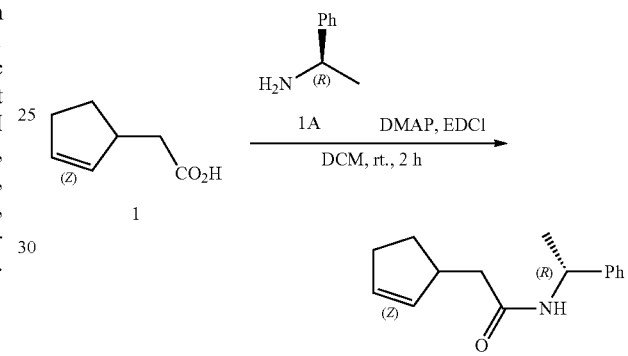

EDCI (125.37 g, 653.98 mmol), DMAP (7.26 g, 59.45 mmol), compound 1 (75.00 g, 594.53 mmol) and compound 1A (72.05 g, 594.53 mmol) were added sequentially to DCM (1.50 L). The mixture was stirred at 15° C. for 12 hr. TLC showed the starting material was consumed. Two reactions were combined for workup. The resulting mixture was washed with 1 M HCl (600 mL), 1M NaOH (600 mL), and brine (200 mL*2), dried over anhydrous MgSO$_4$, filtered and concentrated to afford compound 2 as a white solid (120.00 g, 88.02%). The mixture was used directly without any purification. $^1$H NMR (400 MHz, CDCl$_3$): δ=7.38-7.18 (m, 5H), 5.84-5.69 (m, 2H), 5.69-5.56 (m, 1H), 5.13 (quin, J=7.2 Hz, 1H), 2.40-1.99 (m, 6H), 1.52-1.41 (m, 4H). TLC (Petroleum ether/Ethyl acetate=3:1) R$^f$=0.25.

2. Preparation of Compound 3.

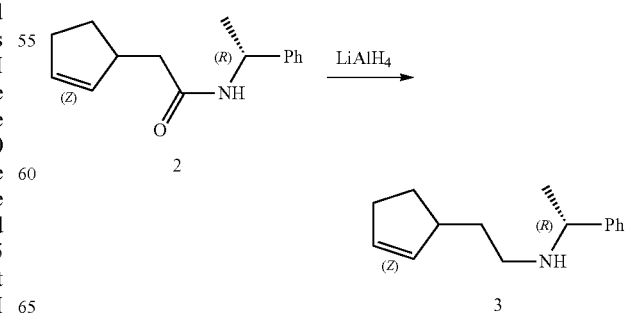

To a solution of compound 2 (123.00 g, 536.37 mmol) in THF (2.00 L) was added LAH (40.71 g, 1.07 mol) at 0° C., then the mixture was stirred at 80° C. for 12 hr. LCMS and TLC showed that the material was consumed. The reaction was quenched by careful addition of 41 mL of $H_2O$, 41 mL of NaOH (15%, w/v) and 123 mL of $H_2O$ in sequence. The insoluble solid was removed by filtration, and washed with EtOAc (150 mL*2). The combined extracts were dried over anhydrous $Na_2SO_4$. The organic was concentrated the mixture to get the crude. The residue was purified by silica gel chromatography (Petroleum ether/Ethyl acetate=10:1, 0:1) to get compound 3 as a yellow oil (98.00 g, 84.85%). $^1$H NMR (400 MHz, CDCl$_3$) δ=7.41-7.18 (m, 5H), 5.75-5.56 (m, 2H), 3.76 (q, J=6.6 Hz, 1H), 2.74-2.59 (m, 1H), 2.59-2.38 (m, 2H), 2.36-2.12 (m, 2H), 2.06-1.90 (m, 1H), 1.63-1.41 (m, 2H), 1.39-1.27 (m, 4H), 1.24-1.10 (m, 1H). LCMS: (M+H+): 215.9. TLC (petroleum ether/ethyl acetate=1:1) $R_f$=0.43.

4. Preparation of Compound 4.

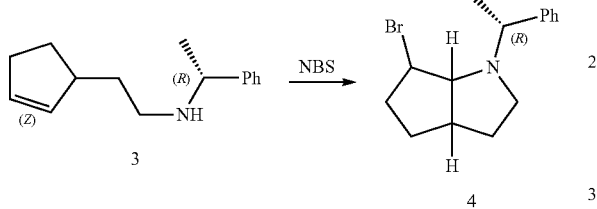

To a solution of compound 3 (47.00 g, 218.27 mmol) in Hexane (1.00 L) was added NBS (58.27 g, 327.41 mmol) at 0° C. The mixture was stirred at 0° C. for 1 hr, TLC showed part of compound 3 remained. And then the mixture was filtered. The filtrate was diluted with DCM (1.00 L) too which CuBr (3.13 g, 21.83 mmol) was added at 0° C. After stirred at 0~15° C. for 2 hr. TLC showed the starting material was consumed. Two reactions were combined for workup. The mixture was concentrated to get the crude. The mixture was purified by MPLC (Petroleum ether/Ethyl acetate=10:1 to 5:1) to provide compound 4 as yellow oil (40.00 g, 62.29%). TLC (Petroleum ether/Ethyl acetate=5:1, plate 1) $R_f$=0.58. TLC (Petroleum ether/Ethyl acetate=5:1) $R_f$=0.38.

5. Preparation of Compounds 5A and 5B.

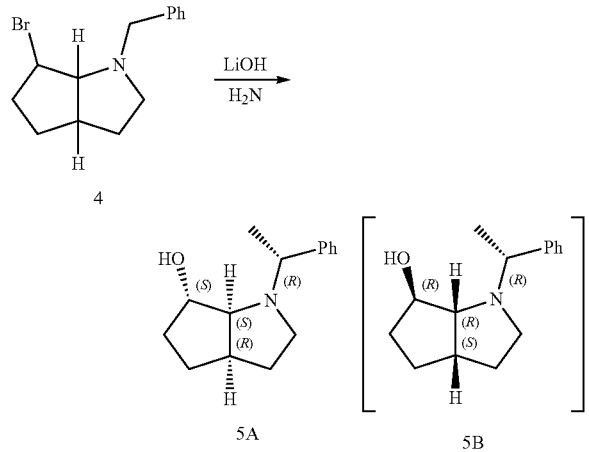

A mixture of compound 4 (40.00 g, 135.95 mmol) in the mixture of LiOH (750.00 mL) and DME (750.00 mL), the mixture was stirred at 90° C. for 3 hr. TLC showed the starting material was consumed. Two reactions were combined for workup. DCM (500 mL) was added and the organic layer was separated and the aqueous layer was extracted with DCM (200 mL*3), dried over $Na_2SO_4$, filtered and concentrated to get the crude. The mixture was purified by MPLC (Petroleum ether/Ethyl acetate=10:1 to 5:1, 5 times) to get compound 5A as yellow oil (6.00 g, 19.08%) and compound 5B as yellow oil (6.6 g, 20.99%) and the mixture 5 g. 5A: TLC (Petroleum ether/Ethyl acetate=1:1) $R_f$=0.42. SFC purity=100.0%.

5B: TLC (Petroleum ether/Ethyl acetate=1:1) $R_f$=0.39. SFC purity=100.0%.

6. Preparation of Compound 6B.

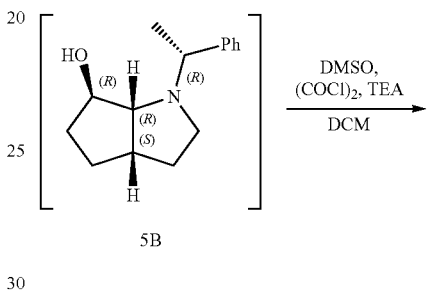

A solution of DMSO (10.98 g, 140.50 mmol) in dry DCM (5.00 mL) was added drop wise to a stirred solution of OXALYL CHLORIDE (10.70 g, 84.30 mmol, 7.38 mL) in dry DCM (48.00 mL) at −78° C. The mixture was stirred for 10 minutes at this temperature. A solution of compound 5B (6.50 g, 28.10 mmol) in dry DCM (48.00 mL) was added dropwise to the reaction mixture at −78° C. After stirring for another 50 minutes, $Et_3N$ (56.87 g, 562.00 mmol) was added dropwise to the reaction mixture at −78° C. The resulting mixture was stirred for an additional 30 minutes. TLC showed the starting material was consumed. Water (50 mL) was added and extracted with DCM (100 mL*3) and the combined organic was washed brine (50 mL), dried over $Na_2SO_4$, filtered and concentrated to get the crude. The residue was purified by MPLC (Petroleum ether/Ethyl acetate=10:1, 5% TEA) to get compound 6B as a yellow oil (5.10 g, 79.14%). $^1$H NMR (400 MHz, CDCl$_3$) δ=7.35-7.16 (m, 5H), 3.93 (q, J=6.9 Hz, 1H), 2.91-2.81 (m, 2H), 2.72 (dquin, J=3.3, 8.0 Hz, 1H), 2.59-2.39 (m, 2H), 2.19-2.08 (m, 1H), 1.99-1.87 (m, 2H), 1.82-1.68 (m, 1H), 1.64-1.48 (m, 2H), 1.43 (d, J=6.8 Hz, 3H). TLC (Petroleum ether/Ethyl acetate=3:1) $R_f$=0.43.

7. Preparation of WV-CA-079-dCiBu.

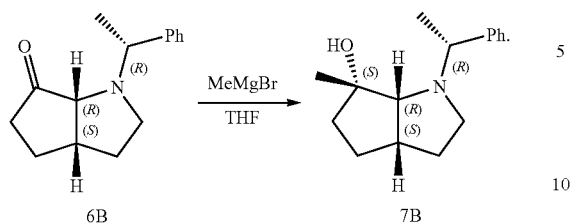

A solution of compound 6B (5.10 g, 22.24 mmol) dissolved in THF (50.00 mL) was added dropwise to a stirred solution of bromo(methyl)magnesium (3 M, 37.07 mL, in dry THF (50.00 mL) at −78° C. The mixture was stirred at −78° C. for 1 hr. TLC showed the starting material was consumed. Water (55 mL) was added and extracted with Ethyl acetate (50 mL*2), the combined organic was washed with brine (50 mL), dried over $Na_2SO_4$, filtered and concentrated to get the crude. The residue was purified by MPLC (Petroleum ether/Ethyl acetate=10:1) to get compound 7B as a yellow oil (4.50 g, 82.47%). $^1$H NMR (400 MHz, CDCl3) δ=7.41-7.13 (m, 5H), 3.75 (q, J=6.9 Hz, 1H), 3.01-2.80 (m, 2H), 2.60-2.32 (m, 2H), 1.85-1.32 (m, 11H), 1.27 (s, 3H). TLC (Petroleum ether/Ethyl acetate=3:1) $R_f$=0.36. SFC purity=100.0%.

8. Preparation of WV-CA-062S.

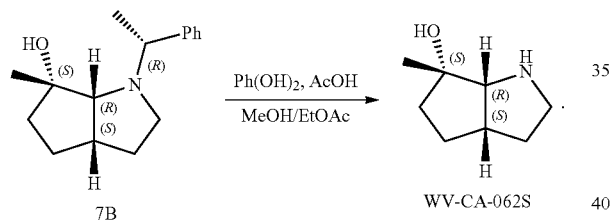

To a solution of compound 7B (4.60 g, 18.75 mmol) in MEOH (100.00 mL) and HOAc (10.00 mL) was added $Pd(OH)_2$ (2.63 g, 18.75 mmol) under $N_2$ atmosphere. The suspension was degassed and purged with $H_2$ for 3 times. The mixture was stirred under $H_2$ (50 Psi) at 50° C. for 24 hr. HNMR showed the starting material was consumed. The mixture was filtered and the filter layer was concentrated to get the crude. The residue was dissolved in water (30 mL) and KOH (2N) was added until pH>11 and the mixture was stirred for 0.5 hr, and then the mixture was extracted with DCM (50 mL*5), the combined organic was dried over $Na_2SO_4$, filtered, and concentrated to get the WV-CA-062S as a yellow oil (1.70 g, 64.21%). $^1$H NMR (400 MHz, CDCl$_3$): δ=3.24 (d, J=8.6 Hz, 1H), 3.12 (br s, 2H), 3.02 (td, J=6.4, 10.5 Hz, 1H), 2.89 (td, J=6.6, 10.4 Hz, 1H), 2.62 (dtd, J=5.5, 8.2, 13.5 Hz, 1H), 1.87-1.63 (m, 3H), 1.59-1.34 (m, 3H), 1.19 (s, 3H). $^{13}$C NMR (101 MHz, CDCl$_3$) δ=75.91, 70.70, 48.37, 42.65, 40.51, 34.60, 29.32, 27.03. LCMS: (M+H+): 142.1. LCMS purity=99.4%.

Example 60. Synthesis of WV-CA-063S and WV-CA-063S-dCiBu

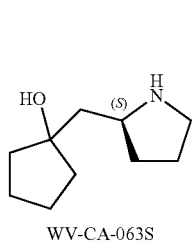

WV-CA-063S

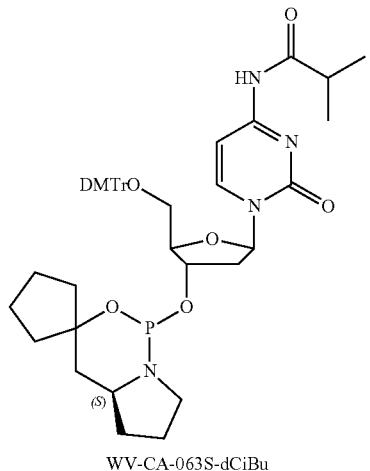

WV-CA-063S-dCiBu

General Scheme.

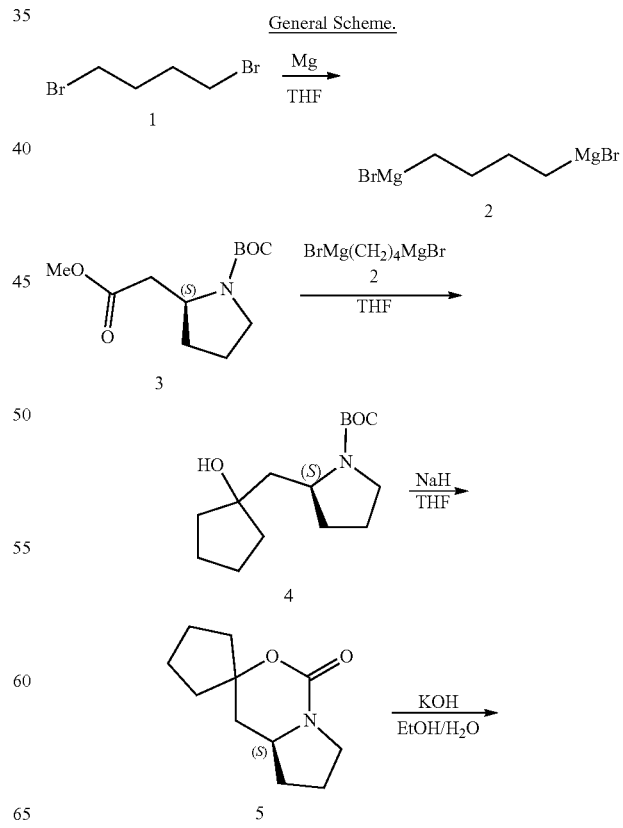

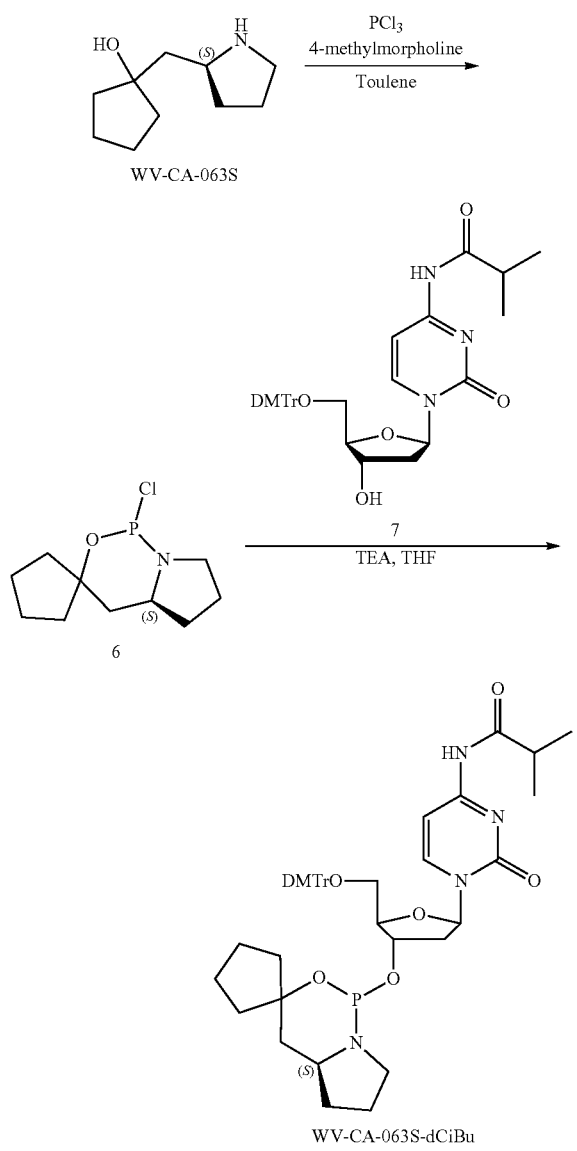

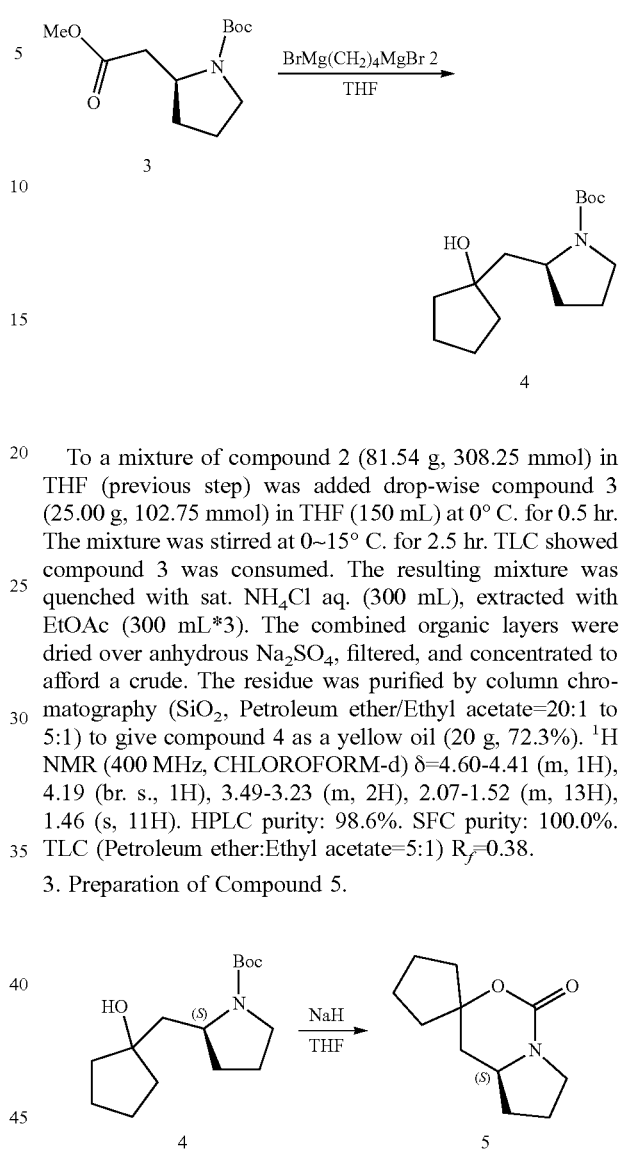

1. Preparation of Compound 2.

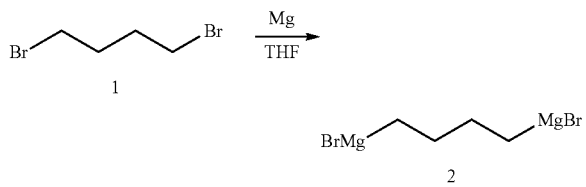

To a suspension of Mg (22.63 g, 930.93 mmol) and I₂ (300.00 mg, 1.18 mmol) in THF (150 mL) was added compound 1 (67.00 g, 310.31 mmol, 37.43 mL) in THF (200 mL) (first 10% volume, when the reaction was initiated, and then added drop-wise the left over 2 hr at 20~60° C.). The mixture was stirred at 20~60° C. for another 2 hr. Most of Mg was consumed. The reaction was almost completed. The Grignard reagent in THF was used directly in the next step.

2. Preparation of Compound 4.

To a mixture of compound 2 (81.54 g, 308.25 mmol) in THF (previous step) was added drop-wise compound 3 (25.00 g, 102.75 mmol) in THF (150 mL) at 0° C. for 0.5 hr. The mixture was stirred at 0~15° C. for 2.5 hr. TLC showed compound 3 was consumed. The resulting mixture was quenched with sat. NH₄Cl aq. (300 mL), extracted with EtOAc (300 mL*3). The combined organic layers were dried over anhydrous Na₂SO₄, filtered, and concentrated to afford a crude. The residue was purified by column chromatography (SiO₂, Petroleum ether/Ethyl acetate=20:1 to 5:1) to give compound 4 as a yellow oil (20 g, 72.3%). ¹H NMR (400 MHz, CHLOROFORM-d) δ=4.60-4.41 (m, 1H), 4.19 (br. s., 1H), 3.49-3.23 (m, 2H), 2.07-1.52 (m, 13H), 1.46 (s, 11H). HPLC purity: 98.6%. SFC purity: 100.0%. TLC (Petroleum ether:Ethyl acetate=5:1) $R_f$=0.38.

3. Preparation of Compound 5.

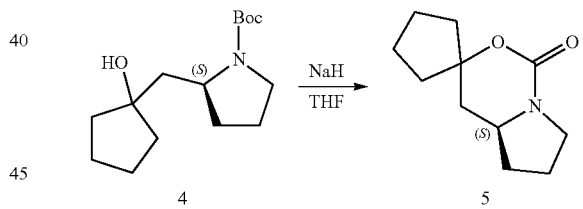

To a solution of compound 4 (20.00 g, 74.24 mmol) in THF (200.00 mL) was added NaH (5.94 g, 148.48 mmol, 60% purity) at 0° C. The mixture was stirred at 40° C. for 20 hr. TLC showed compound 4 was consumed and one major point with larger polarity was detected. The reaction mixture was drop-wise into ice-cold NH₄Cl (200 mL) at 0° C., and then diluted with ethyl acetate (200 mL) and extracted with ethyl acetate (200 mL*3). The combined organic layers were dried over Na₂SO₄, filtered, and concentrated under reduced pressure to give a residue. The residue was purified by column chromatography (SiO₂, Petroleum ether:Ethyl acetate=3:1 to 1:1). Compound 5 was obtained as a yellow oil (10.00 g, 68.98%). ¹H NMR (400 MHz, CHLOROFORM-d) δ=3.67-3.39 (m, 1H), 2.23-2.07 (m, 1H), 2.05-1.33 (m, 13H). TLC (Petroleum ether/Ethyl acetate=3:1) $R_f$=0.18.

4. Preparation of WV-CA-063S.

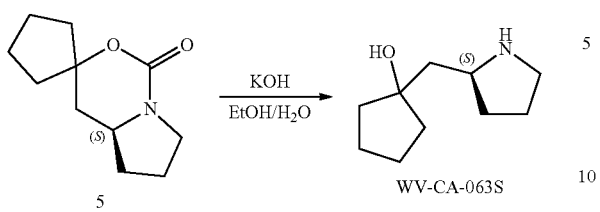

To a solution of compound 5 (10.00 g, 51.21 mmol) in H$_2$O (10.00 mL) and EtOH (10.00 mL) was added KOH (12.00 g, 213.87 mmol). The mixture was reflux at 90° C. for 72 hr. TLC showed compound 5 was partly remained and one major spot was detected. The reaction mixture was added DCM (100 mL), extracted with DCM (100 mL*3). The combined organic layers were dried over Na$_2$SO$_4$, filtered, and concentrated under reduced pressure to give a residue. The residue was purified by column chromatography (SiO$_2$, Petroleum ether:Ethyl acetate=5:1 to 1:1; DCM: MeOH=50:1 to 5:1). Compound WV-CA-063S was obtained as a yellow solid (6.70 g, 77.30%). $^1$H NMR (400 MHz, CHLOROFORM-d) δ=4.46 (br. s., 1H), 3.45 (br. s., 1H), 2.99-2.74 (m, 2H), 1.98-1.26 (m, 14H). $^{13}$C NMR (101 MHz, CDCl$_3$): δ=81.69, 56.90, 45.67, 43.74, 41.48, 38.73, 32.95, 25.75, 23.94, 23.53. LCMS (M+H+): 170.1, 100% purity. TLC (Dichloromethane:Methanol=10:1) R$_f$=0.04.

5. Preparation of Compound 6.

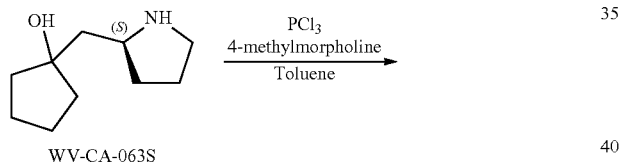

Compound WV-CA-063S (1.00 g, 5.91 mmol) was dried by azeotropic distillation on a rotary evaporator with toluene (20 mL*3). To a solution of PCl$_3$ (811.36 mg, 5.91 mmol) in toluene (20 mL) was added a solution of WV-CA-063S (1.00 g, 5.91 mmol) and 4-methylmorpholine (1.20 g, 11.82 mmol, 1.30 mL) in toluene (20 mL) at 0° C. The mixture was stirred at 15~20° C. for 1 hr. The resulting mixture was filtered (flushed with Ar) and concentrated to afford a residue as a colorless oil. The crude product compound 6 was obtained as a yellow oil (1.25 g, crude), which was used into the next step without further purification.

6. Preparation of WV-CA-063S-dCiBu.

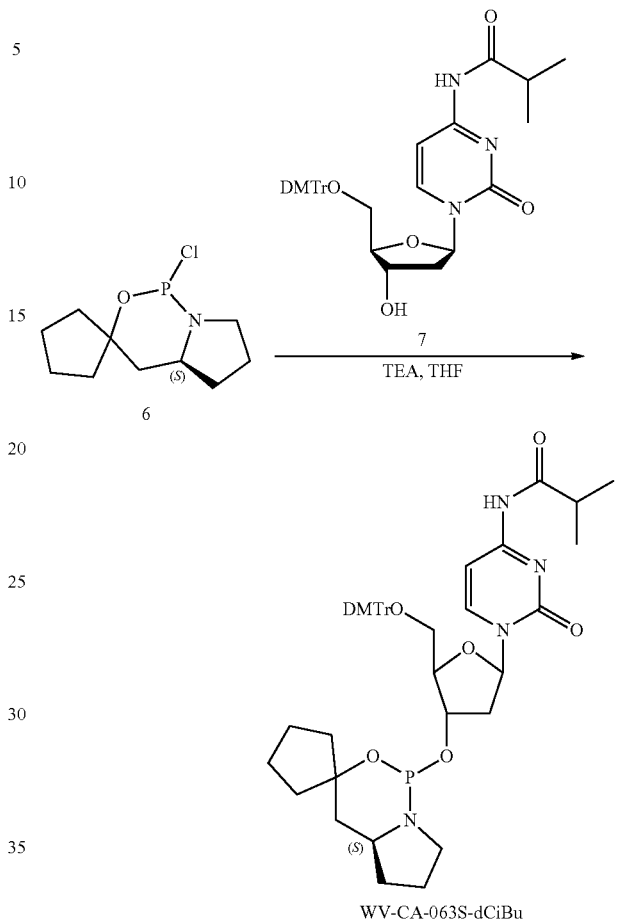

Compound 7 (2.14 g, 3.57 mmol) was dried by azeotropic distillation on a rotary evaporator with pyridine (20 mL) and toluene (20 mL*5). The dried compound 7 (2.14 g, 3.57 mmol) was dissolved in THF (25 mL), and then Et$_3$N (2.53 g, 24.97 mmol, 3.46 mL) was added. The mixture was cooled to −70° C. A solution of compound 6 (1.25 g, 5.35 mmol) in THF (25 mL) was added drop-wise at −70° C., then warmed to 23° C. over 0.5 hr and stirred for another 1.5 hr. TLC showed two new major spots and the starting material was consumed. The resulting mixture was diluted with DCM (100 mL), washed with sat. NaHCO$_3$ aq. (30 mL*3). The organic layer was dried over anhydrous MgSO$_4$, filtered, and concentrated to afford a white foam. The residue was purified by MPLC (SiO$_2$, Petroleum ether:Ethyl acetate=2:1 to 1:3, 5% TEA). Compound WV-CA-063S-dCiBu was obtained as a white solid (1.10 g, 38.70%). $^1$H NMR (400 MHz, CHLOROFORM-d) δ=9.12 (br s, 1H), 8.38 (d, J=7.5 Hz, 1H), 8.24 (d, J=7.5 Hz, 1H), 7.48-7.39 (m, 2H), 7.35-7.27 (m, 5H), 7.30-7.19 (m, 1H), 7.17-7.10 (m, 1H), 6.85 (dd, J=1.4, 8.8 Hz, 4H), 6.31-6.21 (m, 1H), 4.73 (br d, J=4.3 Hz, 1H), 4.23 (br d, J=3.5 Hz, 1H), 3.84-3.76 (m, 6H), 3.56-3.25 (m, 5H), 2.94 (quin, J=7.5 Hz, 1H), 2.82-2.55 (m, 2H), 2.40-2.14 (m, 3H), 1.82-1.42 (m, 13H), 1.22-1.21 (m, 1H), 1.22-1.17 (m, 5H). $^{31}$P NMR (162 MHz, CHLOROFORM-d) δ=135.20 (s, 1P), 134.04 (s, 1P). TLC (Petroleum ether:Ethyl acetate=1:3, 5% TEA) R$_{f1}$=0.28; R$_{f2}$=0.23.

Example 61. Synthesis of WV-CA-064S

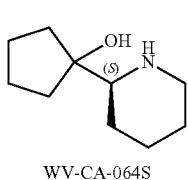

WV-CA-064S

General Scheme.

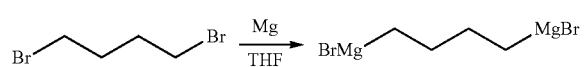

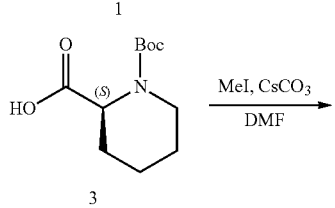

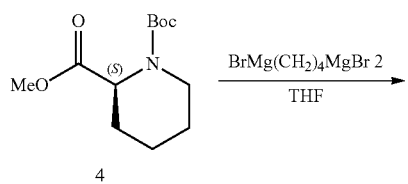

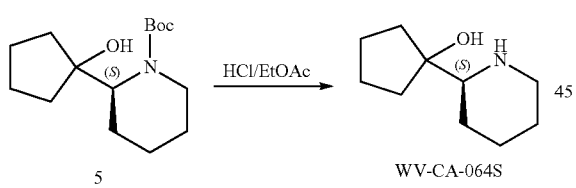

1. Preparation of Compound 2.

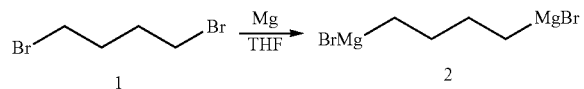

To a suspension of magnesium (28.18 g, 1.16 mol) in THF (660 mL) was added dropwise compound 1 (125.12 g, 579.50 mmol) (activated with one crystal of $I_2$) in THF (100 mL) for 1 hr at 20~60° C. during the addition. The yellow solution was stirred at 20° C. for 1 hr, and the solution was turned to white suspension. Most of Mg was consumed. The reaction was completed. The Grignard reagent in THF was used directly in next step.

2. Preparation of Compound 4.

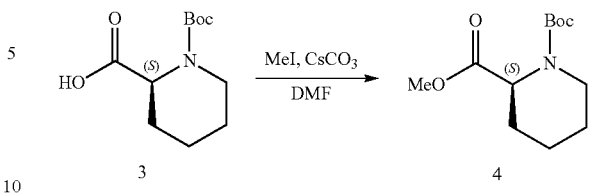

To a solution of compound 3 (50.00 g, 218.08 mmol) in DMF (400 mL) was added MeI (46.43 g, 327.12 mmol) and $Cs_2CO_3$ (35.53 g, 109.04 mmol). The mixture was stirred at 15° C. for 16 hr. TLC showed the starting material was consumed and one new spot with lower polarity was detected. The mixture was diluted with $H_2O$ (400 mL) and extracted with EtOAc (400 mL*3). The combined organic layers were washed with $H_2O$ (400 mL*2), dried over $Na_2SO_4$, filtered and concentrated under reduced pressure to give a residue, which was purified by column chromatography ($SiO_2$, Petroleum ether:EtOAc=100/1 to 10:1) to give compound 4 as a colorless oil (48.00 g, 90.47%). $^1$H NMR (400 MHz, CHLOROFORM-d) δ=4.94-4.61 (m, 1H), 4.10-3.82 (m, 1H), 3.71 (s, 3H), 3.03-2.70 (m, 1H), 2.17 (d, J=10.4 Hz, 1H), 1.77-1.51 (m, 4H), 1.47-1.30 (m, 11H), 1.28-1.08 (m, 1H). TLC (Petroleum ether:EtOAc=5:1) $R_f$=0.61.

3. Preparation of Compound 5.

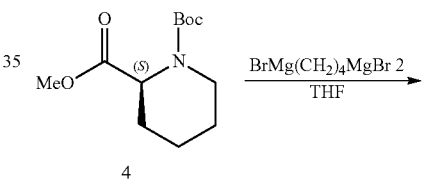

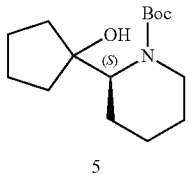

To a mixture of compound 2 (0.7 M, 810.30 mL) in THF (previous step) was added dropwise compound 4 (46.00 g, 189.07 mmol) in THF (200 mL) at −10° C. The mixture was stirred at 10~15° C. for 16 hr. TLC indicated the starting material was consumed and one major new spot with larger polarity was detected. The reaction mixture was slowly added to ice-cold sat. $NH_4Cl$ (100 mL), keeping the temperature at around 0° C., diluted with EtOAc (200 mL) and extracted with EtOAc (200 mL*3). The combined organic layers were dried over $Na_2SO_4$, filtered, and concentrated under reduced pressure to give a residue, the residue was purified by MPLC ($SiO_2$, Petroleum ether/EtOAc=50/1 to 5/1) to give compound 5 was obtained as a white solid (21.4 g, 42.02%). $^1$H NMR (400 MHz, CHLOROFORM-d) δ=4.19-2.88 (m, 3H), 1.92-1.41 (m, 20H). HPLC purity: 100.0%. SFC purity: 100.0%. TLC (Petroleum ether:EtOAc=10:1) $R_f$=0.24.

4. Preparation of Compound WV-CA-064S.

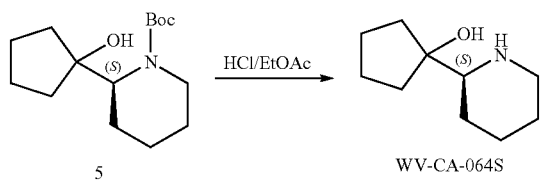

To a solution of compound 5 (25.50 g, 94.66 mmol) in EtOAc (50 mL) was added HCl/EtOAc (450 mL, 4 N). The mixture was stirred at 15° C. for 4 hr. TLC indicated the starting material was consumed completely. The mixture was concentrated under reduced pressure, and filtered to give a residue, which was dissolved in water (30 mL) and adjusted to pH 11-12 with KOH aq., and then extracted with DCM (70 mL*3), dried over Na$_2$SO$_4$, filtered and concentrated under reduced pressure to WV-CA-064S as a white solid (15.80 g, 98.61%). $^1$H NMR (400 MHz, CHLOROFORM-d) δ=3.14-3.02 (m, 1H), 2.95 (br. s., 1H), 2.69-2.56 (m, 1H), 2.39 (dd, J=2.6, 10.4 Hz, 1H), 1.88-1.70 (m, 3H), 1.63-1.27 (m, 11H). $^{13}$CNMR (101 MHz, CHLOROFORM-d) δ=83.24, 64.58, 47.11, 38.34, 35.62, 26.97, 26.27, 24.64, 23.90. LCMS: (M+H+): 170.1, 99.54% purity. TLC (Petroleum ether:EtOAc=5:1) R$_f$=0.

Example 62. Synthesis of WV-CA-064S-dCiBu

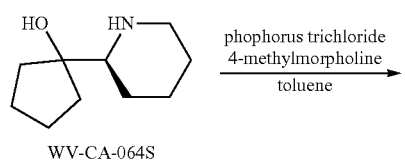

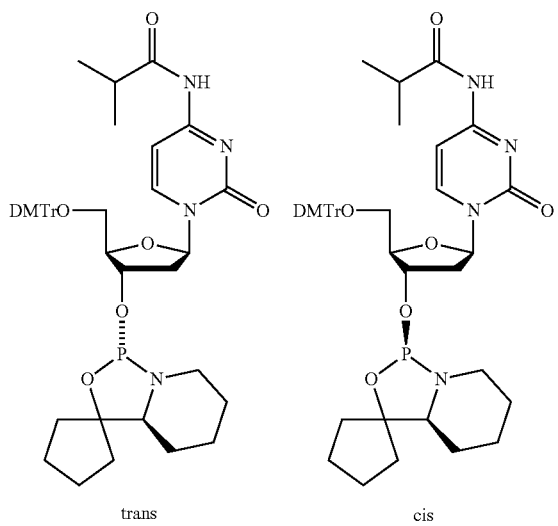

Using WV-CA-064S as starting material, the title compound (5.37 g, 84%) as a white solid was prepared analogously to WV-CA-008S-dCiBu. $^1$H NMR (500 MHz, Chloroform-d) δ 8.81 (s, 1H), 8.36 (d, J=7.4 Hz, 1H), 7.41 (d, J=7.8 Hz, 2H), 7.30 (t, J=8.5 Hz, 7H), 7.12 (d, J=7.4 Hz, 1H), 6.84 (d, J=8.3 Hz, 4H), 6.20 (t, J=5.1 Hz, 1H), 4.85 (q, J=7.5 Hz, 1H), 4.14-4.02 (m, 1H), 3.79 (s, 6H), 3.48-3.15 (m, 4H), 2.80-1.03 (m, 24H); $^{31}$P NMR (202 MHz, CDCl$_3$) δ 147.87 (93%, trans, 139.85 (7%, cis).

Example 63. Synthesis of WV-CA-065S and WV-CA-065-dCiBu

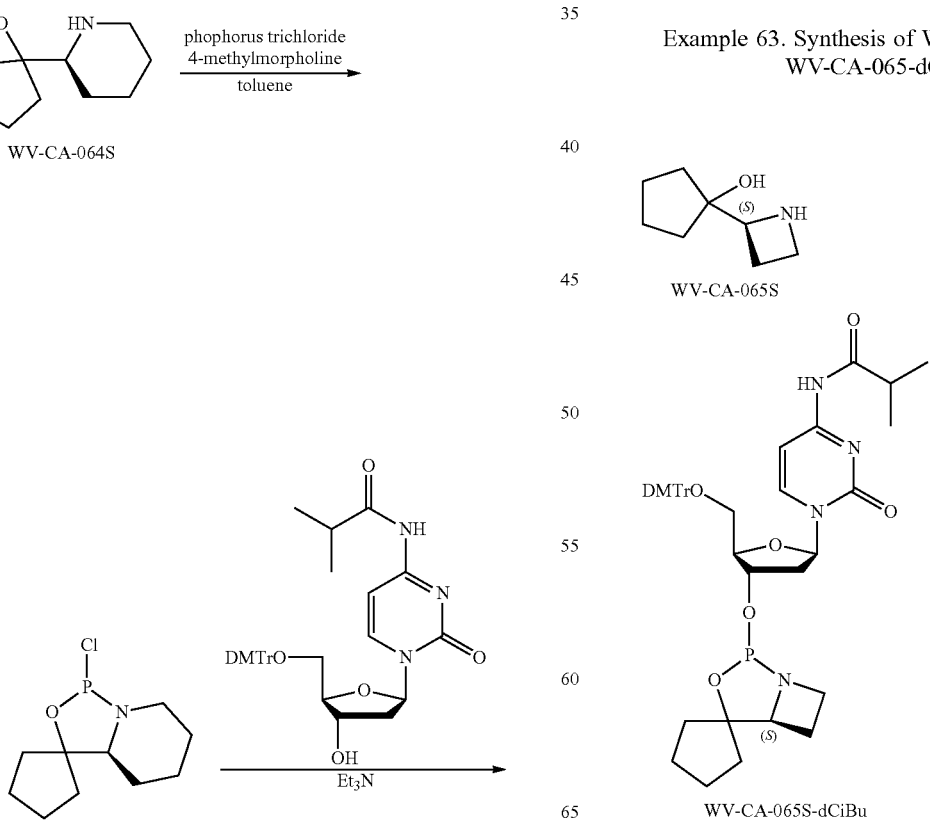

661

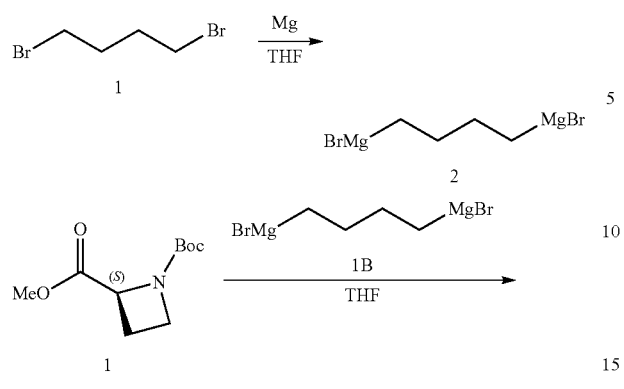

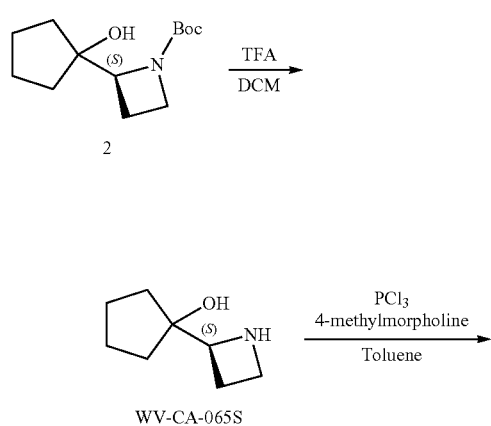

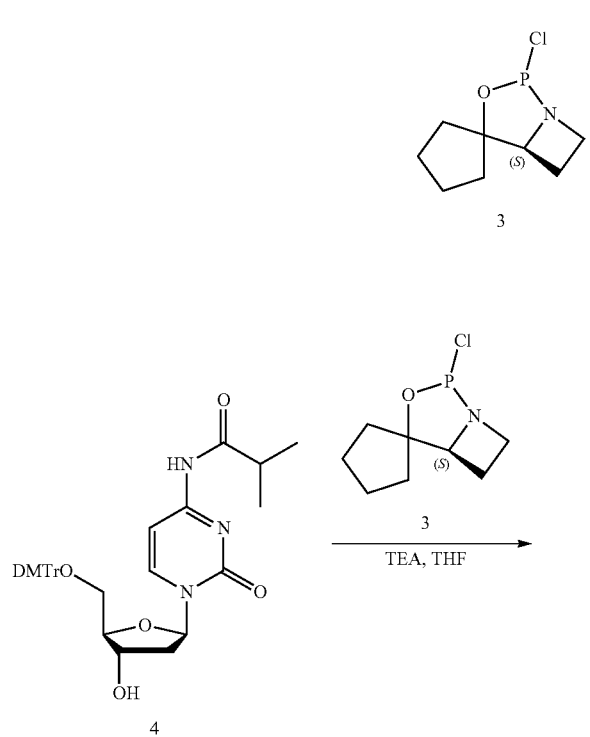

662

-continued

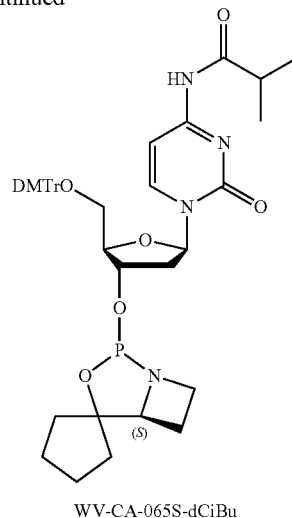

WV-CA-065S-dCiBu

1. Preparation of Compound 1B.

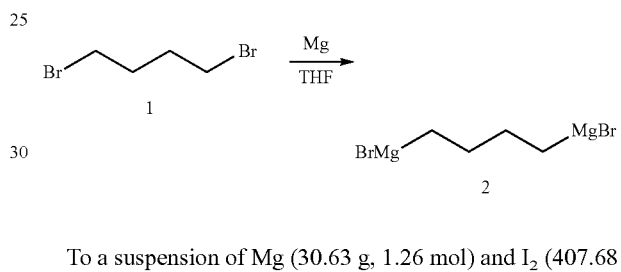

To a suspension of Mg (30.63 g, 1.26 mol) and $I_2$ (407.68 mg, 1.61 mmol) in THF (500 mL) was added compound 1A (136.00 g, 629.89 mmol) (first 10% volume, when the reaction was initiated, and then added dropwise the left over 2 hr at 20~60° C.) in THF (200 mL). The mixture was stirred at 20~60° C. for another 2 hr. Most of Mg was consumed. The reaction was almost completed. The Grignard reagent in THF was used directly in next step.

2. Preparation of Compound 2.

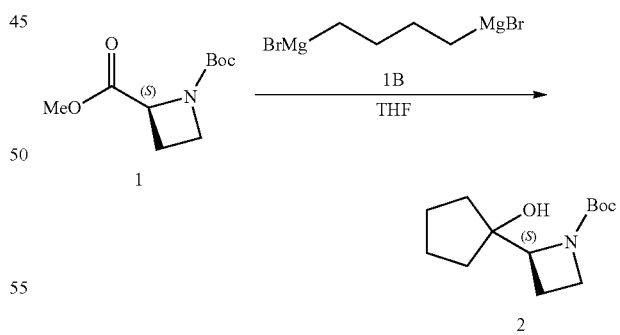

To a mixture of compound 1B in THF was added dropwise compound 1 (43.70 g, 203.02 mmol) in THF (200 mL) at 0° C. The mixture was stirred at 10~20° C. for 3 hr. TLC and showed compound 1 was consumed. The resulting mixture was quenched with sat. $NH_4Cl$ aq. (1500 mL), extracted with EtOAc (800 mL*3). The combined organic layers were dried over anhydrous $Na_2SO_4$, filtered, and concentrated to afford the crude. The crude was purified by MPLC (Petroleum ether/Ethyl acetate=10:1, 5:1) three times to afford the product (10 g) as a light-yellow oil. The crude (26 g) was purified by MPLC (Petroleum ether/Ethyl acetate=10:1, 5:1) (13 g*2) two times to afford the product (12 g). The crude product (8 g) was purified by MPLC (Petroleum ether/Ethyl acetate=10:1, 5:1) to afford another part of the product (6 g). Three parts of the product were combined to give compound 2 as a light-yellow oil (28.00 g, 57.15%). ¹H NMR (400 MHz, CDCl₃): δ=4.40 (br t, J=6.91 Hz, 1H), 3.63-3.88 (m, 2H), 2.08-2.23 (m, 1H), 1.63-1.60 (m, 3H), 1.79-1.44 (m, 16H). LCMS: (M+Na+): 264.1. TLC (Petroleum ether/Ethyl acetate=5:1, Eluted two times) R<sub>f</sub>=0.15.

3. Preparation of WV-CA-065S.

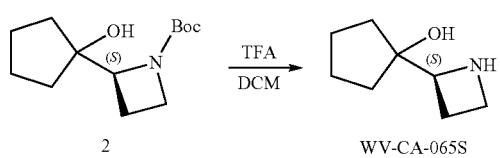

To a solution of compound 2 (27.00 g, 111.88 mmol) in the mixture of DCM (400.00 mL) and TFA (40.00 mL) at 0° C., the mixture was stirred at 0~15° C. for 1 hr. TLC showed the starting material was consumed. The mixture was concentrated to get the crude. Water (20 mL) was added and KOH (2 M) was added until pH>12, and then the mixture was extracted with DCM (50 mL*5). The combined organic layers were washed with brine (80 mL), dried over Na₂SO₄, filtered and concentrated to get the crude. The residue was purified by column chromatography (SiO₂, Dichloromethane/Methanol=20/1 to 8:1). Two batches of the final compound were 6.6 g by column at first, and NMR seemed clean. Combined two batches of final compound, and its ¹H NMR seems a bit dirty. The mixture was washed with petroleum ether to give 4.2 g product. After 36 hr, LCMS and ¹H NMR seemed even dirtier. The mixture was re-checked 2 months later, and LCMS and ¹H NMR seemed even dirtier. Such compounds can be used immediately or shortly after purification. ¹H NMR (400 MHz, CDCl₃): δ=5.56-5.41 (m, 2H), 4.12 (t, J=8.2 Hz, 1H), 3.79 (q, J=8.8 Hz, 1H), 3.51 (dt, J=4.5, 9.1 Hz, 1H), 2.63-2.43 (m, 1H), 2.20 (dtd, J=4.6, 8.6, 11.4 Hz, 1H), 1.93-1.25 (m, 8H). ¹³C NMR (101 MHz, CDCl₃) δ=80.76, 77.62, 76.71, 66.65, 42.31, 38.00, 35.00, 34.96, 34.83, 24.50, 24.10, 20.77, 19.44. LCMS: (M+H⁺): 142.1. TLC (Petroleum ether/Ethyl acetate=5:1). LCMS purity=68.7%.

4. Preparation of Compound 3.

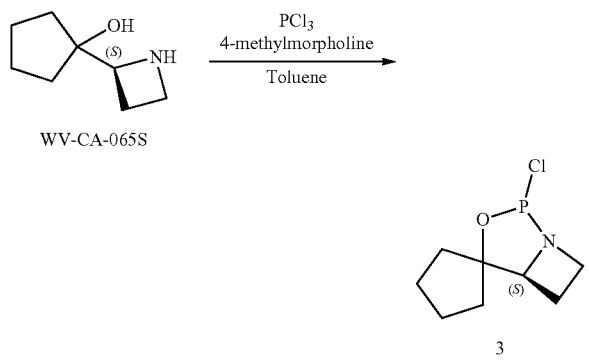

The compound WV-CA-065S was dried by azeotropic distillation on a rotary evaporator with toluene (20 mL*3). To a solution of PCl₃ (972.52 mg, 7.08 mmol) in toluene (10 mL) was added a solution of WV-CA-065S and 4-methylmorpholine (1.43 g, 14.16 mmol) in toluene (10 mL) at 0° C. The mixture was stirred at 15~20° C. for 1 hr. The phosphoryl chloride was not suitable for detection and no monitoring. The resulting mixture was filtered (flushed with Ar) and concentrated to afford the crude product compound 3 as yellow oil (1.46 g, crude). The crude was used into the next step without further purification.

5. Preparation of WV-CA-065S-dCiBu.

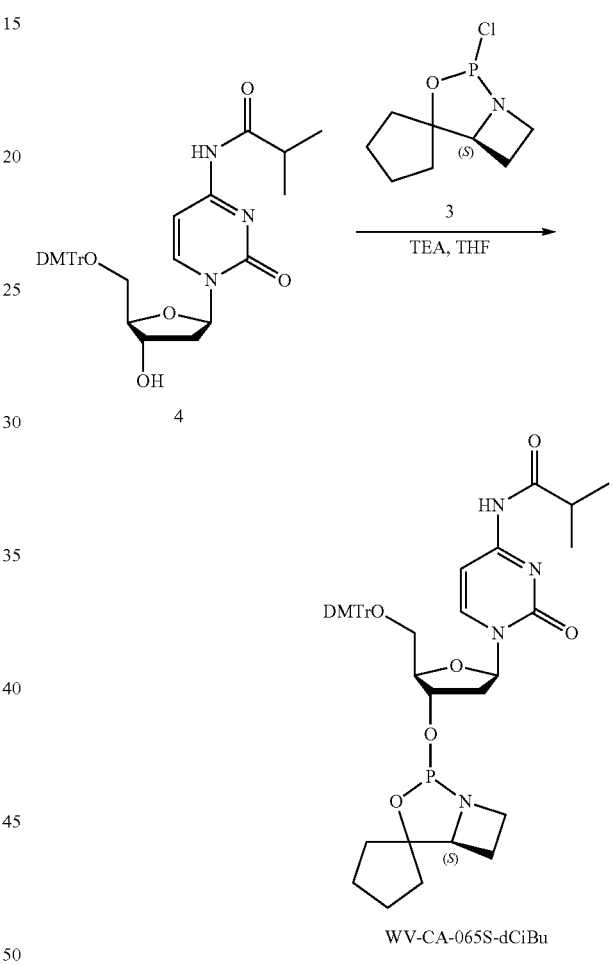

Compound 4 (2.50 g, 4.18 mmol) was dried by azeotropic distillation on a rotary evaporator with pyridine (20 mL) and toluene (20 mL*5). The dried compound 4 (2.50 g, 4.18 mmol) was dissolved in THF (15 mL), and then Et₃N (2.96 g, 29.24 mmol) was added. The mixture was cooled to −70° C. A THF (15 mL) solution of compound 3 (1.46 g, 7.10 mmol) was added dropwise at −70° C., then warm to 23° C. over 0.5 hr and stirred for another 1.5 hr. TLC showed part of compound 4 remained. The resulting mixture was diluted with DCM (100 mL), washed with sat. NaHCO₃ (30 mL*3). The organic layer was dried over anhydrous MgSO₄, filtered, and concentrated to afford a white foam. The residue was purified by MPLC (SiO₂, Petroleum ether/Ethyl acetate=0:1, 5% TEA) to get compound WV-CA-065S-dCiBu as a light yellow solid (1.60 g, 49.83%). ¹H NMR (400 MHz, CHLOROFORM-d) δ=8.41-8.30 (m, 1H), 8.16

(d, J=7.5 Hz, 1H), 7.38-6.97 (m, 9H), 6.86-6.67 (m, 4H), 6.14 (t, J=5.7 Hz, 1H), 4.67-4.56 (m, 1H), 4.31-4.18 (m, 1H), 4.13-3.96 (m, 1H), 4.13-3.96 (m, 2H), 3.81-3.61 (m, 11H), 3.55-3.26 (m, 5H), 2.70-2.47 (m, 3H), 2.32-2.09 (m, 1H), 2.32-2.09 (m, 3H), 1.86-1.19 (m, 6H). $^{31}$P NMR (162 MHz, CDCl$_3$) δ=162.32. TLC (Petroleum ether/Ethyl acetate=0:1, 5% TEA) R$_f$=0.24.
Example 64. Synthesis of WV-CA-066R and 066R-dCiBu
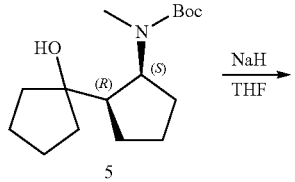
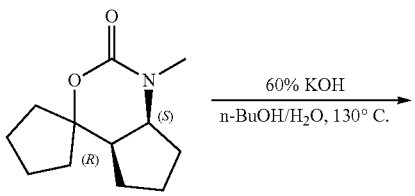
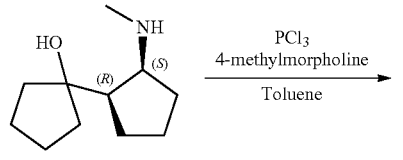
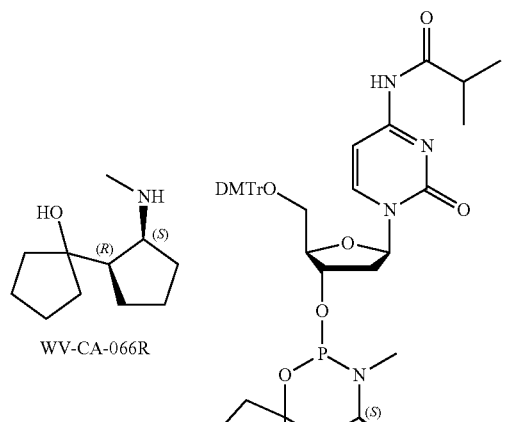
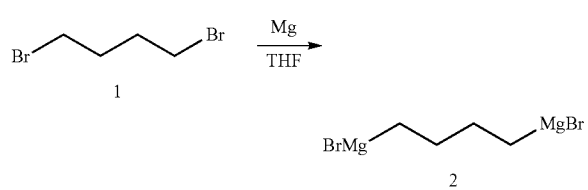
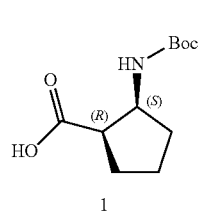
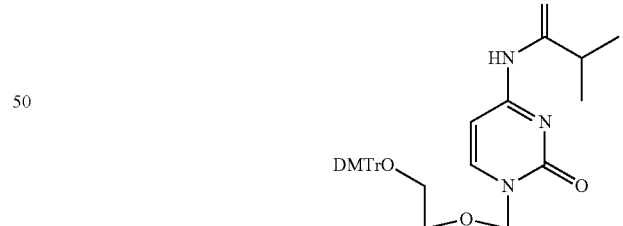
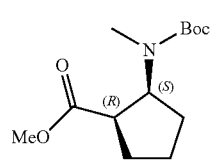
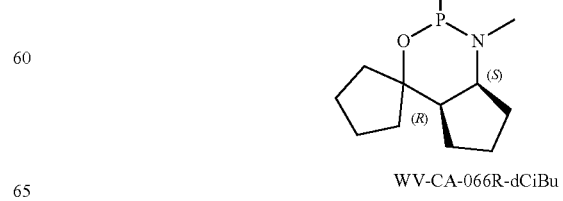

1. Preparation of Compound 2.

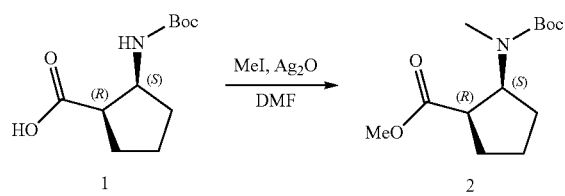

To a solution of compound 1 (22.00 g, 95.96 mmol) in DMF (300.00 mL) (HPLC grade purity) was added Ag$_2$O (88.95 g, 383.84 mmol) followed by MeI (108.96 g, 767.68 mmol) at 20° C. The dark suspension was stirred at 40° C. for 12 hr. TLC showed the starting material was consumed and a new spot was detected. The reaction was diluted by ethyl acetate (300 mL) and filtered through celite. The solution was washed with sat. NaHCO$_3$ aq. (200 mL*2), dried over Na$_2$SO$_4$, and concentrated in vacuo to dryness. The residue was purified by column chromatography (Petroleum ether:Ethyl acetate=100:1 to 10:1). Compound 2 was obtained as a colorless oil (24.00 g, 97.19%). $^1$H NMR (400 MHz, CHLOROFORM-d) δ=4.71-4.45 (m, 1H), 3.68-3.60 (m, 3H), 3.06 (q, J=7.9 Hz, 1H), 2.79-2.68 (m, 3H), 2.06-1.81 (m, 4H), 1.74-1.61 (m, 1H), 1.44 (d, J=10.6 Hz, 10H). HPLC purity: 91.2%. SFC purity: 26.9%. LCMS: (M+Na$^+$): 280.0. TLC (Petroleum ether:Ethyl acetate=5:1) R$_f$=0.5.

2. Preparation of Compound 4.

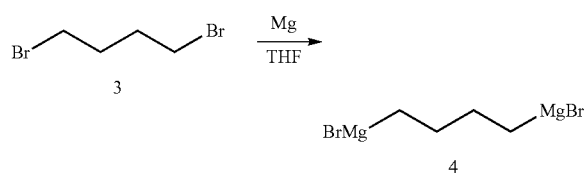

To a suspension of Mg (6.98 g, 287.16 mmol) in THF (150.00 mL) was added compound 3 (31.00 g, 143.58 mmol) (activated with one crystal of I$_2$) in THF (15.00 mL) for 2 hr at 20~60° C. during the addition. The yellow solution was stirred at 20° C. for 1 hr, and the solution was turned to off-white suspension. Mg was disappeared. The reaction was completed. The Grignard reagent in THF was used directly in the next step.

3. Preparation of Compound 5.

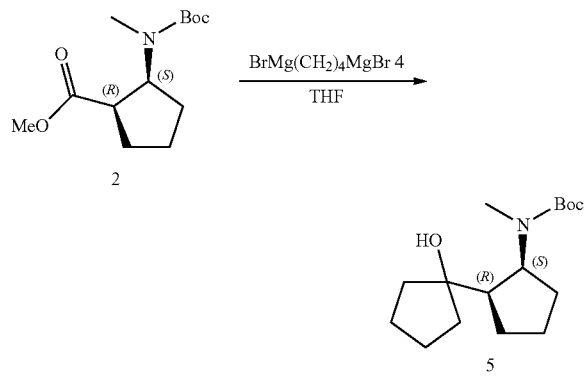

To a mixture of compound 4 (0.7 M, 199.84 mL) was added dropwise compound 2 (12.00 g, 46.63 mmol) in THF (30.00 mL) at −10° C. The mixture was stirred at 10~15° C. for 4 hr. TLC indicated the starting material was consumed and one major new spot with larger polarity was detected. The reaction mixture was slowly instilled in ice-cold NH$_4$Cl (100 mL), keeping temperature of the mixture at around 0° C., and then diluted with ethyl acetate (200 mL) and extracted with ethyl acetate (200 mL*3). Dried over Na$_2$SO$_4$, filtered, and concentrated under reduced pressure to give a residue. The residue was purified by column chromatography (SiO$_2$, Petroleum ether/Ethyl acetate=20/1 to 5:1). Compound 5 was obtained as a yellow oil (11.60 g, crude). $^1$H NMR (400 MHz, CHLOROFORM-d) δ=4.59 (br s, 1H), 4.50-4.37 (m, 1H), 4.26 (br s, 1H), 3.06 (s, 1H), 2.71 (d, J=14.8 Hz, 3H), 2.25-1.93 (m, 1H), 1.86-1.69 (m, 6H), 1.67-1.50 (m, 6H), 1.48-1.40 (m, 11H). TLC (Petroleum ether:Ethyl acetate=5:1) R$_f$=0.36.

4. Preparation of Compound 6.

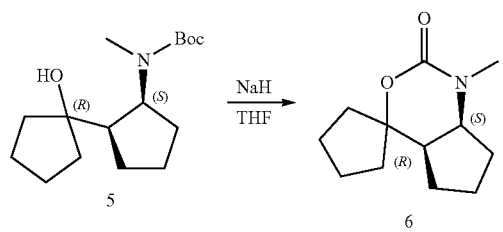

To a solution of compound 5 (10.00 g, 35.28 mmol) in THF (150.00 mL) was added NaH (2.82 g, 70.56 mmol, 60% purity). The mixture was stirred at 15° C. for 5 hr. HPLC indicated the starting material was consumed. The reaction mixture was quenched by the addition of H$_2$O (50 mL) at 0° C., and then diluted with ethyl acetate (100 mL) and extracted with ethyl acetate (100 mL*3). The combined organic layers were dried over Na$_2$SO$_4$, filtered, and concentrated under reduced pressure to give a residue. The residue was purified by MPLC (SiO$_2$, Petroleum ether/Ethyl acetate=50:1 to 1:1) to give compound 6 as a colorless oil (3.80 g, 51.47%). $^1$H NMR (400 MHz, CHLOROFORM-d) δ=3.71 (ddd, J=2.4, 4.9, 6.9 Hz, 1H), 2.95-2.86 (m, 3H), 2.24-2.15 (m, 1H), 2.04-1.46 (m, 14H). TLC (Petroleum ether:Ethyl acetate=3:1) R$_f$=0.24.

5. Preparation of WV-CA-066R.

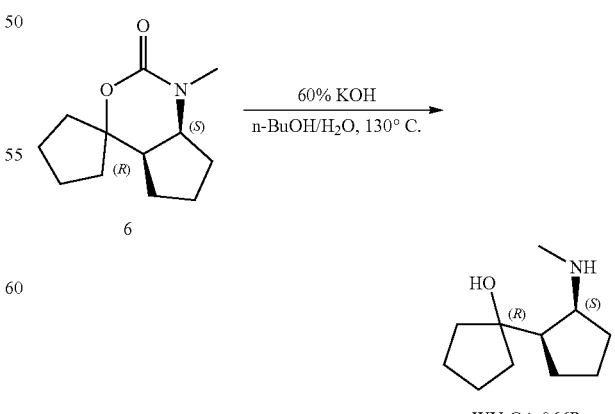

To a solution of compound 6 (3.80 g, 18.16 mmol) in n-BuOH (15.00 mL) and H₂O (15.00 mL) was added KOH (18.00 g, 320.80 mmol). The mixture was reflux at 130° C. for 110 hr. LCMS and TLC showed the starting material was partly remained and MS of desired compound was detected. The mixture was concentrated under reduced pressure to give a residue. The residue was washed with CH₂Cl₂ (100 mL*6), filtered and concentrated under reduced pressure to give a crude, which was purified by MPLC (SiO₂, Petroleum ether:Ethyl acetate=50:1 to 1:1, DCM:MeOH=50:1 to 10:1) to give compound WV-CA-066R was obtained as a yellow solid (1.00 g, 30.07%). ¹H NMR (400 MHz, CHLORO-FORM-d) δ=3.07-2.95 (m, 1H), 2.37 (s, 3H), 1.89-1.48 (m, 14H), 1.43-1.33 (m, 1H). ¹³C NMR (101 MHz, CHLORO-FORM-d) δ=82.20, 64.37, 51.94, 41.37, 39.49, 34.61, 30.80, 23.82, 23.79, 23.55, 21.24. LCMS: (M+H⁺): 184.2, 99.81% purity. TLC (Dichloromethane:Methanol=10:1) R$_f$=0.04.

6. Preparation of Compound 7.

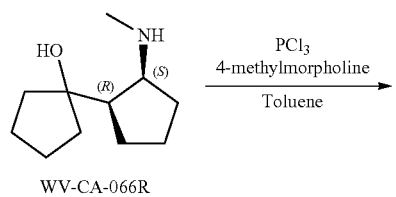

WV-CA-066R

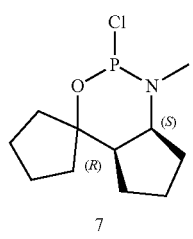

7

Compound WV-CA-066R (480.00 mg, 2.62 mmol) was dried by azeotropic distillation on a rotary evaporator with toluene (20 mL*3). To a solution of PCl₃ (359.64 mg, 2.62 mmol) in toluene (10 mL) was added a solution of WV-CA-066R (480.00 mg, 2.62 mmol) and 4-methylmorpholine (529.78 mg, 5.24 mmol) in toluene (10 mL) at 0° C. The mixture was stirred at 15~20° C. for 1 hr. The resulting mixture was filtered (flushed with Ar) and concentrated to afford a residue. The crude product compound 7 was obtained as yellow oil (640.00 mg, crude), which was used into the next step without further purification.

7. Preparation of WV-CA-066R-dCiBu

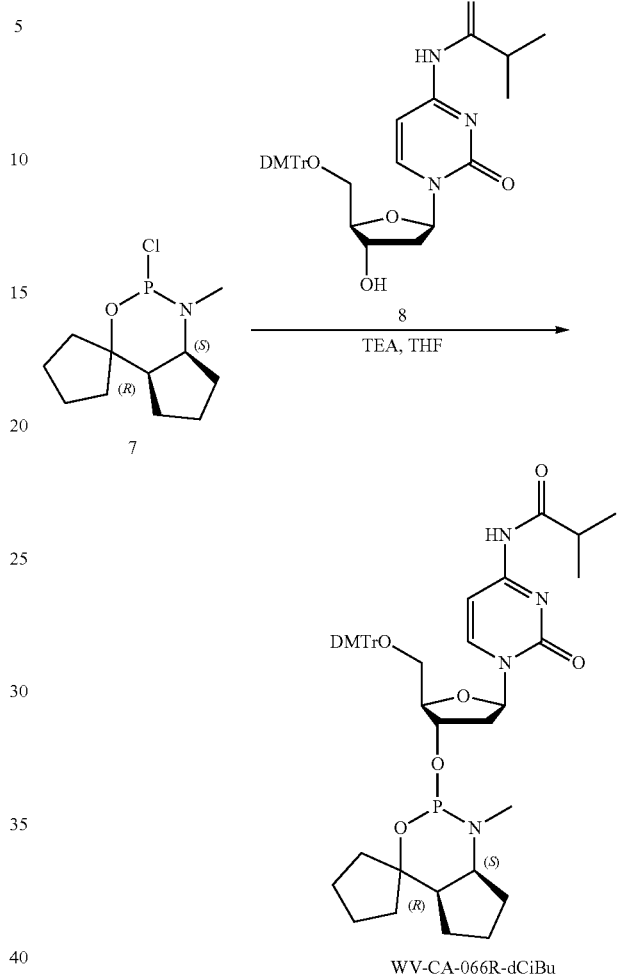

Compound 8 (1.11 g, 1.84 mmol) was dried by azeotropic distillation on a rotary evaporator with pyridine (20 mL) and toluene (20 mL*5). The dried compound 8 (1.11 g, 1.84 mmol) was dissolved in THF (15 mL), and then Et₃N (1.31 g, 12.90 mmol) was added. The mixture was cooled to −70° C. A solution of compound 7 (640.00 mg, 2.58 mmol) in THF (15 mL) was added drop-wise at −70° C., then warmed to 23° C. over 0.5 hr and stirred for another 1.5 hr. TLC showed two new major spots and the starting material was consumed. The resulting mixture was diluted with DCM (100 mL), washed with sat. NaHCO₃ aq. (30 mL*3). The organic layer was dried over anhydrous MgSO₄, filtered, and concentrated to afford a white foam. The residue was purified by MPLC (SiO₂, Petroleum ether:Ethyl acetate=1:3, 5% TEA). Compound WV-CA-066R-dCiBu was obtained as a yellow solid (300.00 mg, 20.08%). ¹H NMR (400 MHz, CHLOROFORM-d) δ=8.26 (br d, J=7.5 Hz, 1H), 8.16 (d, J=7.4 Hz, 1H), 7.36-7.09 (m, 10H), 7.06-6.97 (m, 1H), 6.78 (dd, J=1.6, 8.8 Hz, 4H), 6.23-6.12 (m, 1H), 4.69-4.56 (m, 1H), 4.17-4.10 (m, 1H), 4.09-3.90 (m, 1H), 3.73 (d, J=1.6 Hz, 6H), 3.66-3.49 (m, 1H), 3.47-3.19 (m, 3H), 2.67-2.47 (m, 4H), 2.44-2.32 (m, 4H), 2.23-2.10 (m, 3H), 2.09-1.93 (m, 5H), 1.80-1.75 (m, 3H), 1.72-1.43 (m, 19H), 1.25-1.06 (m, 10H), 0.89-0.73 (m, 2H), 0.10-−0.09 (m, 1H). ³¹P NMR (162 MHz, CHLOROFORM-d) δ=139.73 (s, 1P), 132.29 (s, 1P). TLC (Petroleum ether:Ethyl acetate=1:3, 5% TEA) $R_{f1}$=0.28; $R_{f2}$=0.23.

Example 65. Synthesis of WV-CA-067

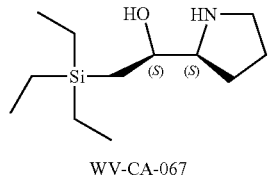

WV-CA-067

Scheme 1

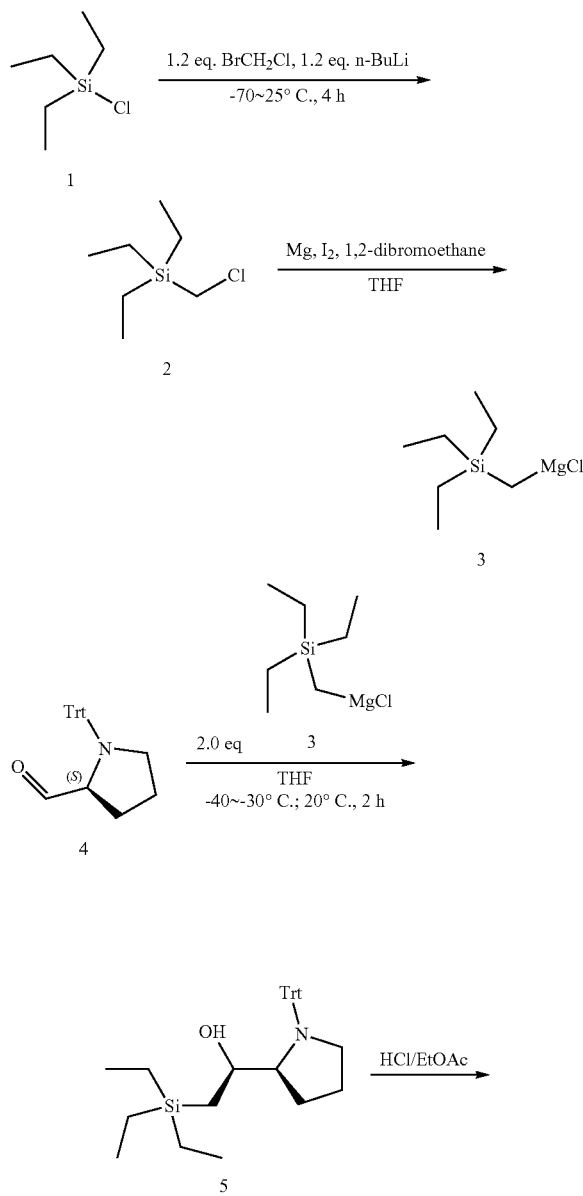

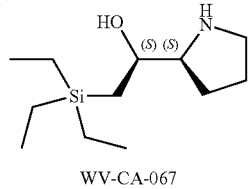

WV-CA-067

1. Preparation of Compound 2.

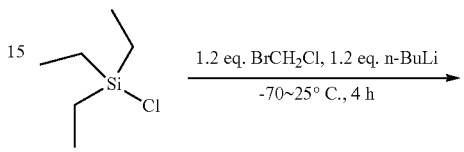

To a solution of compound 1 (100.00 g, 663.48 mmol, 112.36 mL, 1.00 eq.) and bromo(chloro)methane (103.01 g, 796.18 mmol, 53.10 mL, 1.20 eq.) in THF (1.00 L) was added dropwise n-BuLi (2.5 M, 318.47 mL, 1.20 eq.) slowly in 3 hr at −78° C. After the addition, the mixture was stirred at −78° C. for 0.5 h. GCMS showed the starting material was consumed. The mixture was poured into sat. NH$_4$Cl (aq, 2 L), and the organic layer was separated. The aqueous layer was extracted with EtOAc (1 L*2), dried over Na$_2$SO$_4$, filtered and concentrated to get the crude product, which was distilled under reduced pressure with water pump at 70~80° C. to afford compound 2 (89.00 g, 540.21 mmol, 40.71% yield) as a colorless oil.

2. Preparation of Compound 3.

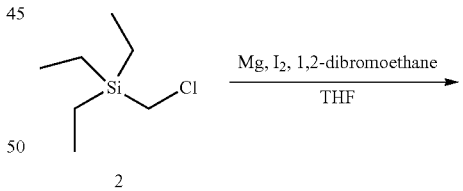

Mg (811.59 mg, 33.39 mmol, 1.10 eq.) was taken up in THF (100 mL), and then a solution of compound 2 (57.00 g, 345.98 mmol, 1.00 eq.) in THF (150 mL) was added dropwise to the Mg suspension (activated with I$_2$ (one crystal), and 1,2-dibromoethane (249.00 mg, 1.33 mmol, 100.00 μL, 3.83e-3 eq.)) with stirring at 70° C. over 1 hr, keeping the temperature between 50-70° C. After the addition, the mixture was then stirred for 2 hr at 70° C. until the Mg was disappeared, and then stirred at 20° C. for 0.5 h. The mixture in THF was used directly in next step.

3. Preparation of Compound 5.

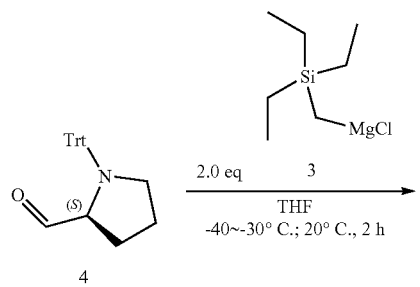

To a solution of compound 3 (1.52 M, 226.40 mL, 2.50 eq.) in THF was added dropwise a solution of compound 4 (47.00 g, 137.65 mmol, 1.00 eq.) in THF (200 mL) at −10° C. The mixture was stirred at −10~15° C. for 1 hr. TLC (Petroleum Ether/EtOAc=10:1, eluted three times) showed the reaction was completed. The resulting mixture was quenched with sat. NH$_4$Cl aq. (1 L). The mixture was extracted with EtOAc (800 mL*3). The combined organic layers were dried over anhydrous MgSO$_4$, filtered, and concentrated to get compound 5 (79.00 g, crude) as light yellow oil, which was used into the next step without further purification.

4. Preparation of Compound WV-CA-067.

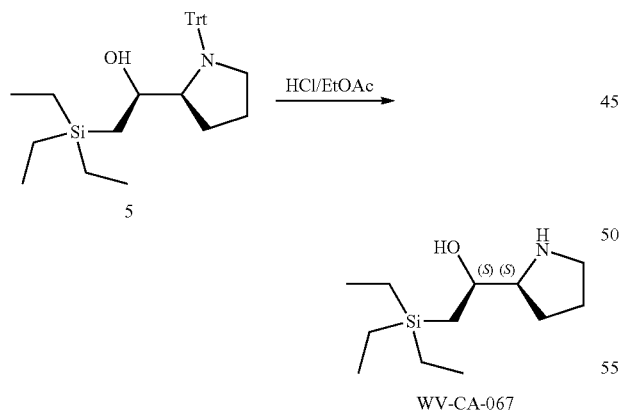

A mixture of compound 5 (79.00 g, 167.46 mmol, 1.00 eq.) dissolved in EtOAc (50 mL) was added HCl/EtOAc (400.00 mL) at 10° C., and the mixture was stirred at 10° C. for 0.5 hr. TLC (Petroleum Ether/EtOAc=5:1) showed the starting material was consumed. The residue was purified by column chromatography on silica gel (Petroleum ether, Petroleum Ether/EtOAc=10:1 to DCM/Methanol=10:1) to give the HCl salt of the product (40 g). The white solid salt was added H$_2$O (100 mL), adjusted to pH ~11 with KOH aq. (2 M), and then extracted with DCM (200 mL*3). The combined organic layers were washed with brine (500 mL), dried over Na$_2$SO$_4$, filtered and concentrated in vacuo to dryness. $^1$H NMR showed the product was not clean. The residue was further purified by silica gel chromatography (DCM/Methanol from 30:1 to 9:1) to get the WV-CA-067 (19.50 g, 84.82 mmol, 50.65% yield, 99.80% purity) as a yellow oil. $^1$H NMR (400 MHz, CDCl$_3$) δ 3.79 (ddd, J=8.7, 5.4, 3.5 Hz, 1H), 3.13 (dt, J=7.4, 3.1 Hz, 1H), 3.05-2.88 (m, 2H), 2.73 (brs, 2H), 1.82-1.62 (m, 4H), 0.96 (t, J=8.0 Hz, 9H), 0.87-0.77 (m, 1H), 0.73-0.65 (m, 1H), 0.58 (q, J=7.8 Hz, 6H).

Example 66. Synthesis of WV-CA-067-dA$^{bz}$

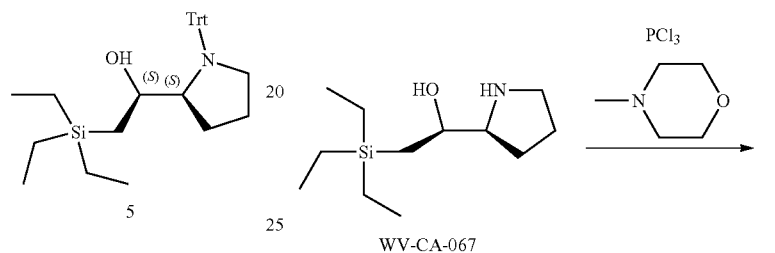

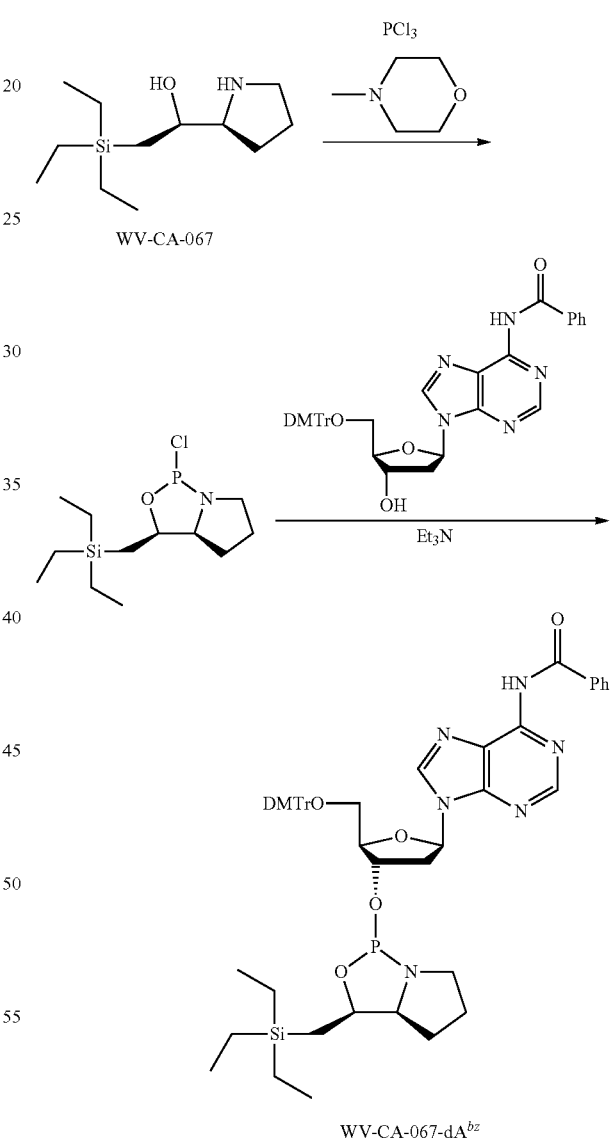

Using WV-CA-067 as starting material, the title compound (0.96 g, 52%) as a white solid was prepared analogously to WV-CA-008S-dC$^{iBu}$. $^1$H NMR (600 MHz, CDCl$_3$) δ 9.06 (brs, 1H), 8.67 (s, 1H), 8.14 (s, 1H), 8.00 (d, J=7.2 Hz, 2H), 7.57 (t, J=7.2 Hz, 1H), 7.48 (t, J=7.5 Hz, 2H), 7.38 (d, J=8.4 Hz, 2H), 7.29-7.15 (m, 7H), 6.79-6.74 (m, 4H), 6.51

(dd, J=7.8, 6.0 Hz, 1H), 4.99-4.93 (m, 1H), 4.84-4.78 (m, 1H), 4.30-4.24 (m, 1H), 3.75 (s, 6H), 3.60-3.52 (m, 1H), 3.49-3.42 (m, 1H), 3.39 (dd, J=10.2, 4.2 Hz, 1H), 3.35 (dd, J=10.8, 4.8 Hz, 1H), 3.20-3.11 (m, 1H), 2.95-2.88 (m, 1H), 2.69-2.62 (m, 1H), 1.91-1.83 (m, 1H), 1.78-1.70 (m, 1H), 1.57-1.51 (m, 1H), 1.30-1.22 (m, 1H), 1.01 (dd, J=14.4, 9.0 Hz, 1H), 0.95-0.80 (m, 10H), 0.61-0.46 (m, 6H). $^{31}$P NMR (243 MHz, CDCl$_3$) δ 154.80.

Example 67. Synthesis of WV-CA-068S

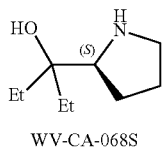

WV-CA-068S

General Scheme.

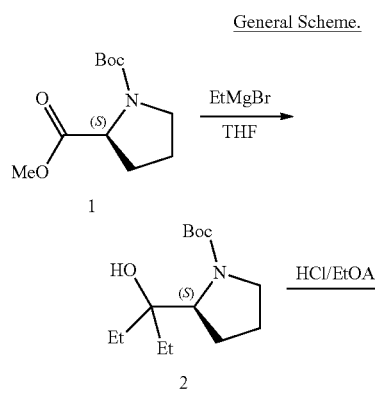

1. Preparation of Compound 2.

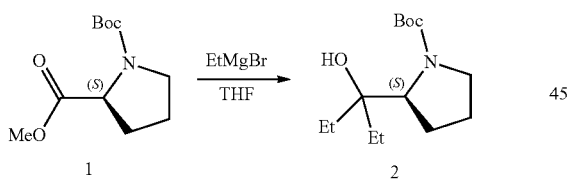

To a mixture of bromo(ethyl)magnesium (3M, 87.23 mL) was added dropwise compound 1 (20.00 g, 87.23 mmol) in THF (300 mL) at −10° C. The mixture was stirred at 10~15° C. for 16 hr. TLC and LCMS indicated the starting material was consumed, and one major new spot with lower polarity was detected. The reaction mixture was slowly added to ice-cold sat. NH$_4$Cl aq. (100 mL), keeping the temperature at around 0° C., and then diluted with EtOAc (200 mL) and extracted with EtOAc (200 mL*3), dried over Na$_2$SO$_4$, filtered and concentrated under reduced pressure to give a residue, which was purified by MPLC (SiO$_2$, Petroleum ether/EtOAc=50/1 to 5/1). Compound 2 was obtained as a colorless oil (13.00 g, 57.91%). $^1$H NMR (400 MHz, CHLOROFORM-d) δ=5.48-5.30 (m, 1H), 4.02 (dd, J=6.3, 8.3 Hz, 1H), 3.75-3.58 (m, 1H), 3.23-3.06 (m, 1H), 2.09-1.93 (m, 1H), 1.88-1.73 (m, 1H), 1.73-1.55 (m, 3H), 1.52-1.36 (m, 11H), 1.25 (tt, J=7.1, 14.1 Hz, 2H), 1.00-0.82 (m, 6H). LCMS: (M+Na+): 280.2. HPLC purity: 84.9%. SFC purity: 100.0%. TLC (Petroleum ether:EtOAc=5:1) R$_f$=0.45.

2. Preparation of WV-CA-068S.

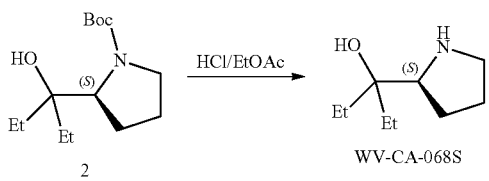

To a solution of compound 2 (12.80 g, 49.73 mmol) in EtOAc (5 mL) was added HCl/EtOAc (250 mL, 4 N). The mixture was stirred at 15° C. for 2 hr. TLC indicated the starting material was consumed completely. The mixture was concentrated under reduced pressure, and filtered to give a residue, which was dissolved in water (10 mL) and adjusted to pH 11-12 with KOH aq., and then extracted with DCM (100 mL*3), dried over Na$_2$SO$_4$, filtered and concentrated under reduced pressure to give WV-CA-068S as a white solid (4.80 g, 61.38%). $^1$H NMR (400 MHz, CHLOROFORM-d) δ=3.16-3.00 (m, 1H), 2.98-2.77 (m, 2H), 2.63-2.03 (m, 1H), 1.80-1.25 (m, 8H), 0.82 (t, J=7.5 Hz, 6H). $^{13}$CNMR (101 MHz, CHLOROFORM-d) δ=73.74, 63.26, 46.59, 29.44, 26.61, 26.15, 25.17, 8.01, 7.78. LCMS: (M+H$^+$): 158.1, 100.0%. TLC (Petroleum ether:EtOAc=5:1) R$_f$=0.

Example 68. Synthesis of WV-CA-068S-dCiBu

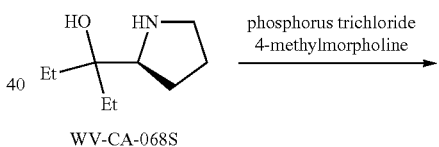

WV-CA-068S

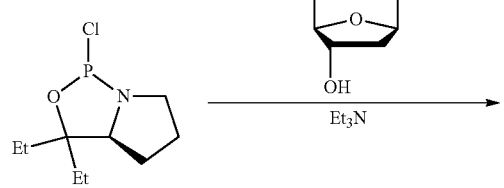

-continued
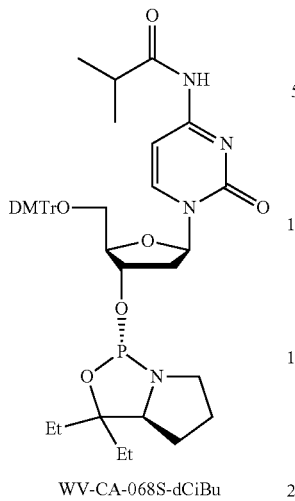
WV-CA-068S-dCiBu
General Scheme.
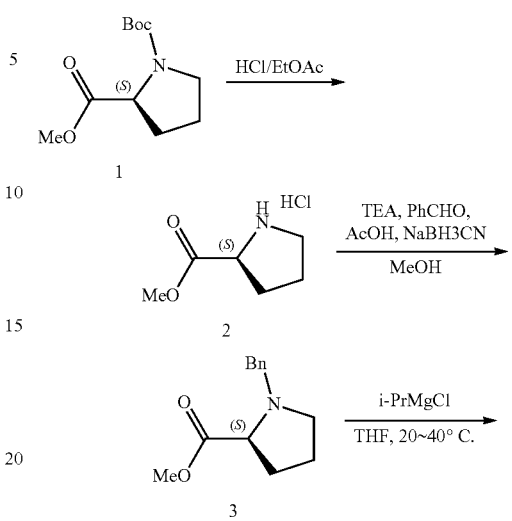
Using WV-CA-068S as starting material, the title compound (4.89 g, 78%) as a white solid was prepared analogously to WV-CA-008S-dCiBu. $^1$H NMR (500 MHz, Chloroform-d) δ 8.25 (t, J=12.0 Hz, 2H), 7.42-7.36 (m, 2H), 7.31-7.22 (m, 7H), 7.05 (d, J=7.4 Hz, 1H), 6.88-6.81 (m, 4H), 6.25 (t, J=5.7 Hz, 1H), 4.77 (dq, J=10.5, 5.4 Hz, 1H), 4.20-4.13 (m, 1H), 3.80 (s, 6H), 3.53-3.36 (m, 4H), 2.94 (dq, J=10.1, 7.0 Hz, 1H), 2.72 (dt, J=13.7, 5.9 Hz, 1H), 2.57 (p, J=6.2, 5.4 Hz, 1H), 2.26 (dt, J=13.5, 5.9 Hz, 1H), 1.90-1.57 (m, 5H), 1.51-1.43 (m, 3H), 1.23-1.16 (m, 6H), 0.89 (t, J=7.4 Hz, 3H), 0.80 (t, J=7.5 Hz, 3H). $^{31}$P NMR (202 MHz, CDCl$_3$) δ 152.71.
Example 69. Synthesis of WV-CA-069S and WV-CA-069S-dCiBu
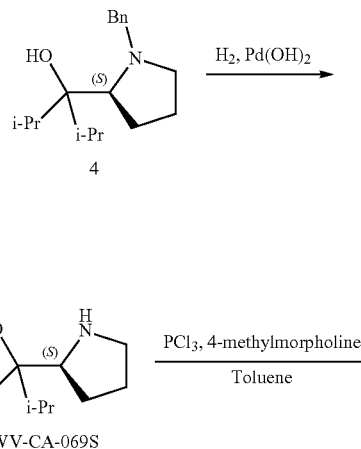
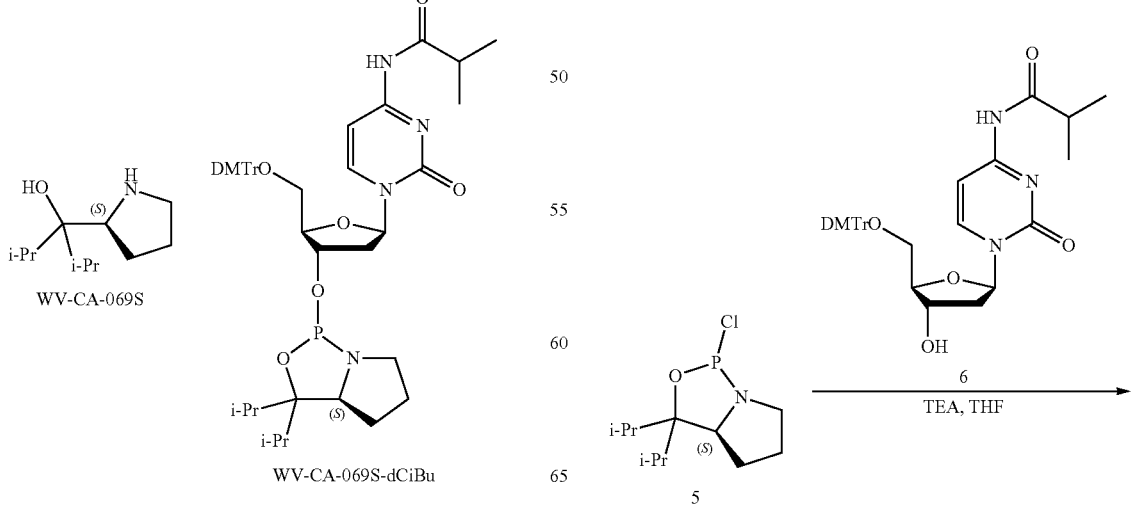

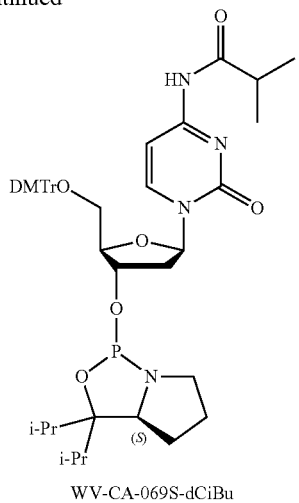

WV-CA-069S-dCiBu

1. Preparation of Compound 2.

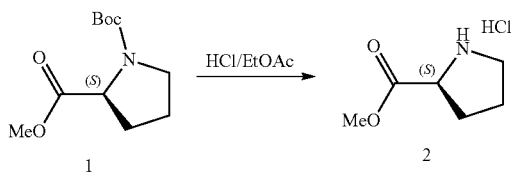

To a solution of compound 1 (40.00 g, 174.47 mmol) in EtOAc (50.00 mL) was added HCl/EtOAc (450.00 mL, 4 N). The mixture was stirred at 15° C. for 2 hr. TLC indicated the starting material was consumed completely. The mixture was concentrated under reduced pressure to give a residue. The crude product compound 2 (29.00 g, crude, HCl salt) was used into the next step without further purification. TLC (Petroleum ether:Ethyl acetate=5:1) $R_f$=0.

2. Preparation of Compound 3.

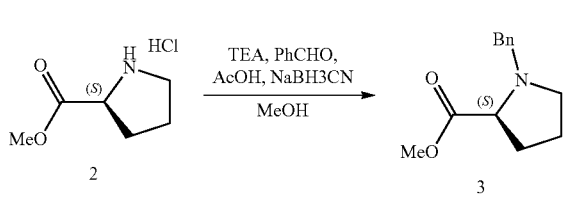

To a mixture of compound 2 (29.00 g, 175.10 mmol, HCl salt), Et$_3$N (17.72 g, 175.10 mmol) and benzaldehyde (20.44 g, 192.61 mmol) in MeOH (500.00 mL) was added AcOH (1.05 g, 17.51 mmol). The mixture was stirred at 15° C. for 0.5 hr, and then NaBH$_3$CN (33.01 g, 525.30 mmol) was added and stirring was continued at 15° C. for 16 hr. TLC and LCMS indicated the starting material was consumed. The resulting mixture was concentrated under reduced pressure. The residue was partitioned between water (200 mL) and EtOAc (300 mL). The separated aqueous layer was extracted with EtOAc (300 mL*3). The combined organic layers were dried over anhydrous Na$_2$SO$_4$, filtered, and concentrated to afford the product as a crude. The residue was purified by column chromatography (SiO$_2$, Petroleum ether/Ethyl acetate=100/1 to 1:1). Compound 3 was obtained as a colorless oil (29.00 g, 75.53%). $^1$H NMR (400 MHz, CHLOROFORM-d) δ=7.34-7.21 (m, 5H), 3.88 (d, J=12.8 Hz, 1H), 3.76-3.55 (m, 4H), 3.25 (dd, J=6.3, 8.9 Hz, 1H), 3.08-3.00 (m, 1H), 2.47-2.30 (m, 1H), 2.17-2.03 (m, 1H), 2.00-1.72 (m, 3H). LCMS: (M+H$^+$): 219.9. TLC (Petroleum ether:Ethyl acetate=3:1) $R_f$=0.40.

3. Preparation of Compound 4.

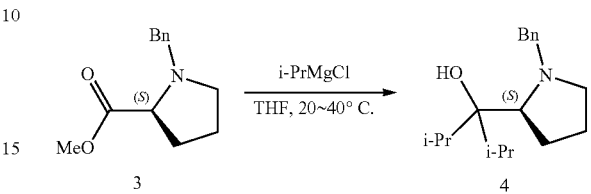

To a solution of compound 3 (29.00 g, 132.25 mmol) in THF (150.00 mL) was added i-PrMgCl (2 M, 231.44 mL) at 20~50° C. The mixture was stirred at 40° C. for 16 hr. TLC showed the starting material was consumed. The reaction mixture was slowly instilled in ice-cold NH$_4$Cl (200 mL), keeping temperature of the mixture at around 0° C., and then diluted with ethyl acetate (300 mL) and extracted with ethyl acetate (300 mL*3). The combined solution was dried over Na$_2$SO$_4$, filtered and concentrated under reduced pressure to give a residue. The residue was purified by column chromatography (SiO$_2$, Petroleum ether/Ethyl acetate=100:1 to 5:1, 4 times) to give compound 4 was obtained as a colorless oil (5.40 g, 14.82%). $^1$H NMR (400 MHz, CHLOROFORM-d) δ=7.34-7.21 (m, 5H), 4.05 (d, J=13.9 Hz, 1H), 3.50 (d, J=13.9 Hz, 1H), 3.34 (s, 1H), 3.14 (t, J=7.7 Hz, 1H), 2.84 (td, J=6.9, 11.0 Hz, 1H), 2.46 (td, J=5.7, 11.3 Hz, 1H), 2.18-1.96 (m, 2H), 1.94-1.73 (m, 4H), 1.09-0.88 (m, 12H). Chiral SFC purity: 96.5%. HPLC purity: 100.0%. TLC (Petroleum ether:Ethyl acetate=5:1) $R_{f1}$=0.45, $R_{f2}$=0.20.

4. Preparation of WV-CA-069S.

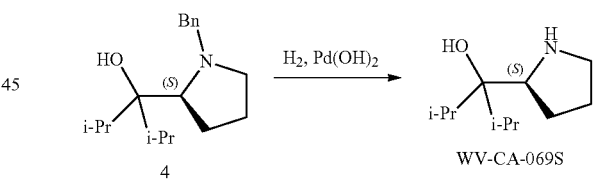

To a solution of compound 4 (5.20 g, 18.88 mmol) in EtOAc (30.00 mL) was added Pd(OH)$_2$ (530.30 mg, 3.78 mmol) under H$_2$. The mixture was stirred at 15° C. for 16 hr. TLC showed the starting material was partly remained and one major spot was detected. The mixture was filtered and removed solvent to give residue. The residue was purified by column chromatography (SiO$_2$, Petroleum ether/Ethyl acetate=100/1 to 10:1, Dichloromethane:Methanol=100:1 to 3:1) to give compound WV-CA-069S was obtained as a yellow oil (2.30 g, 65.74%). $^1$H NMR (400 MHz, CHLOROFORM-d) δ=3.44 (t, J=7.5 Hz, 1H), 3.01-2.83 (m, 2H), 2.07-1.85 (m, 2H), 1.82-1.58 (m, 4H), 1.05-0.90 (m, 12H). $^{13}$C NMR (101 MHz, CHLOROFORM-d) δ=75.49, 61.37, 46.09, 34.02, 33.78, 26.51, 26.08, 19.52, 19.50, 18.57, 18.33. LCMS: (M+H$^+$): 186.2; 99.16% purity. TLC (Petroleum ether:Ethyl acetate=1:1) $R_f$=0.06.

5. Preparation of Compound 5.

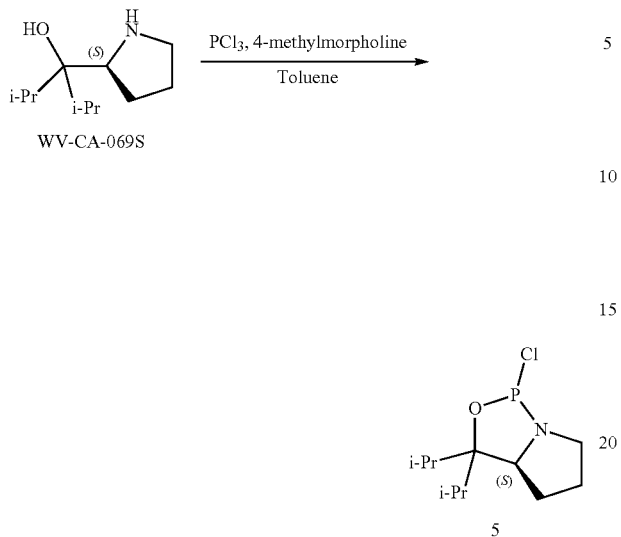

Compound WV-CA-069S (1.00 g, 5.40 mmol) was dried by azeotropic distillation on a rotary evaporator with toluene (20 mL*3). To a solution of PCl$_3$ (741.08 mg, 5.40 mmol) in toluene (10 mL) was added a solution of WV-CA-069S (1.00 g, 5.40 mmol) and 4-methylmorpholine (1.09 g, 10.80 mmol, 1.19 mL) in toluene (10 mL) at 0° C. The mixture was stirred at 15~20° C. for 1 hr. The resulting mixture was filtered (flushed with Ar) and concentrated to afford a residue as colorless oil. The crude product compound 5 (1.20 g, crude) was obtained as a yellow oil, which was used into the next step without further purification.

6. Preparation of WV-CA-069S-dCiBu.

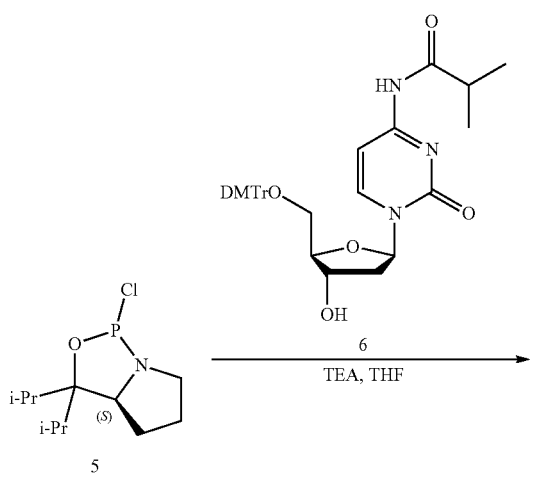

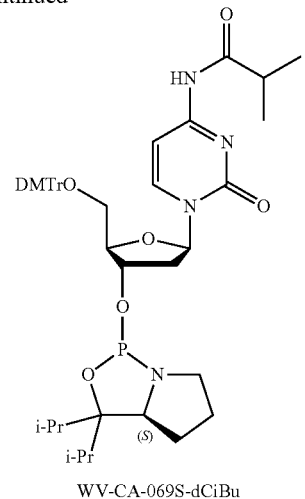

Compound 6 (1.92 g, 3.21 mmol) was dried by azeotropic distillation on a rotary evaporator with pyridine (20 mL) and toluene (20 mL*5). Compound 6 (1.92 g, 3.21 mmol) was dissolved in THF (15 mL), and then Et$_3$N (2.27 g, 22.47 mmol) was added. The mixture was cooled to −70° C. A solution of compound 5 (1.20 g, 4.81 mmol) in THF (15 mL) was added drop-wise at −70° C., then warmed to 23° C. over 0.5 hr and stirred for another 2.5 hr. TLC showed part of compound 6 remained. LCMS showed the compound was not stable in column; the compound can not to be detected. The resulting mixture was diluted with DCM (100 mL), and washed with sat. NaHCO$_3$ (aq., 30 mL*3). The organic layer was dried over anhydrous MgSO$_4$, filtered, and concentrated to afford a white foam. The residue was purified by MPLC (SiO$_2$, Ethyl acetate:Petroleum ether=3:1, 5% TEA). Compound WV-CA-069S-dCiBu was obtained as a light yellow solid (1.20 g, 45.99%). $^1$H NMR (400 MHz, CDCl$_3$): δ=8.26 (d, J=7.4 Hz, 1H), 7.47-7.41 (m, 2H), 7.37-7.30 (m, 6H), 7.29-7.23 (m, 2H), 7.09 (br d, J=7.4 Hz, 1H), 6.91-6.83 (m, 4H), 6.25 (t, J=5.7 Hz, 1H), 4.92-4.77 (m, 1H), 4.23-4.18 (m, 1H), 3.87-3.80 (m, 6H), 3.80-3.75 (m, 1H), 3.48 (d, J=3.1 Hz, 2H), 3.33-3.21 (m, 1H), 3.11-2.98 (m, 1H), 2.78-2.66 (m, 1H), 2.63-2.49 (m, 1H), 2.34-2.07 (m, 4H), 1.94-1.83 (m, 1H), 1.69 (dt, J=5.5, 8.1 Hz, 2H), 1.26-1.18 (m, 6H), 0.96 (dd, J=6.7, 12.0 Hz, 6H), 0.85 (dd, J=3.9, 6.3 Hz, 6H). $^{31}$P NMR (162 MHz, CHLOROFORM-d) δ=143.20 (s, 1P), 141.75 (s, 1P). TLC (Ethyl acetate:Petroleum ether=3:1, 5% TEA) R$_f$=0.24.

Example 70. Synthesis of WV-CA-070 & WV-CA-070-dCiBu

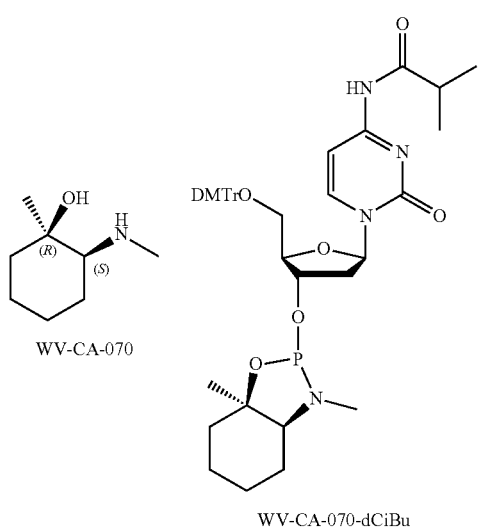

WV-CA-070-dCiBu

General Scheme.

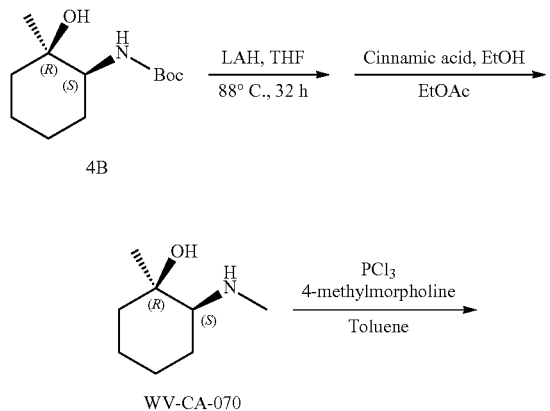

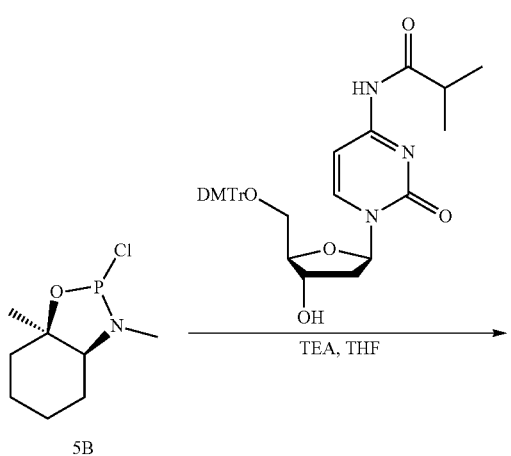

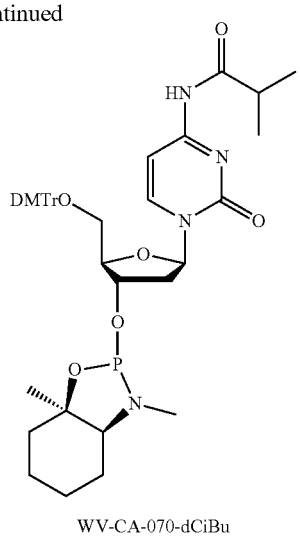

WV-CA-070-dCiBu

1. Preparation of Compound WV-CA-070.

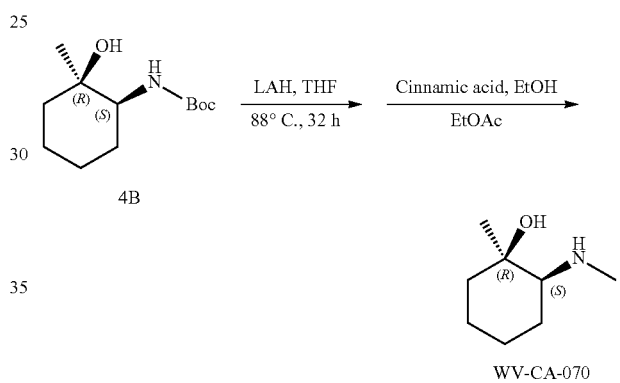

To a solution of compound 4B (8.00 g, 34.89 mmol) in THF (80 mL) was added LAH (3.97 g) in portions at 0° C. The mixture was stirred at 80° C. for 16 hr. TLC showed compound 4B was remained. LAH (2.65 g) was added to the reaction at 30° C. Then the reaction mixture was stirred at 88° C. for 16 hr. TLC showed compound 4B was consumed, and WV-CA-070 was detected. The reaction was slowly added sat. MgSO₄ (12 mL) at 0° C. The mixture was filtered through Celatom. The filter cake was washed with EtOAc (50 mL*3) and EtOAc (50 mL). The organic phase was dried over MgSO₄, filtered, and concentrated in vacuo to dryness to afford the crude of WV-CA-070 as colorless oil (4.50 g, crude), contained undissolved solid. To a solution of crude of WV-CA-070 (4.50 g, 31.42 mmol) in EtOH (20 mL) was added (E)-3-phenylprop-2-enoic acid (4.66 g, 31.42 mmol). The mixture was heated at 90° C. for 30 minutes. The mixture was concentrated in vacuo to dryness. The white crude solid of P1 was dissolved in EtOAc (20 mL) at 90° C. for 0.5 hr until the mixture became clear, the solution was cooled to 20° C. slowly. A large amount of solid precipitated, filtered. The filter cake was concentrated in vacuo to dryness to afford cinnamic acid salt of WV-CA-070 as white solid (7.00 g, 76.45%). To a solution of the cinnamic acid salt of WV-CA-070 (7.00 g, 24.02 mmol) in DCM (20 mL) was added drop-wise 2 M aqueous of KOH (20 mL) at 20° C. until pH ~13. The reaction was stirred at 20° C. for 0.5 hr. The reaction was extracted with DCM (30 mL*2). The combined organic phase was dried over Na$_2$SO$_4$, filtered, and concentrated in vacuo to dryness at 30° C. to afford WV-CA-070 as colorless oil (3.00 g, 87.20%). $^1$H NMR (400 MHz, CDCl$_3$): δ=2.45 (s, 1H), 2.22 (dd, J=4.0, 7.9 Hz, 1H), 1.71-1.24 (m, 9H), 1.20 (s, 3H). $^{13}$C NMR (125.7 MHz, CDCl$_3$): δ=70.04, 64.50, 37.05, 35.37, 27.07, 26.22, 22.70, 21.96. LCMS: (M+H+): 144.1. TLC (Petroleum ether:Ethyl acetate=1:1) R$_f$=0.04.

2. Preparation of Compound 5B.

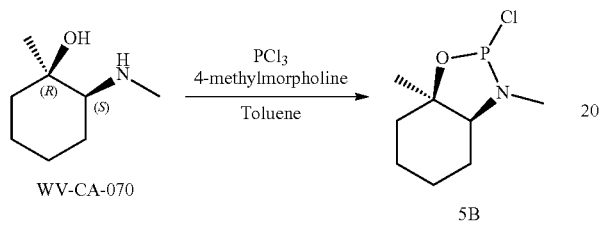

Compound WV-CA-070 (1.50 g, 10.47 mmol) was dried by azeotropic distillation with toluene (3*40 mL, 100 mL flask). A solution of dried WV-CA-070 (1.50 g, 10.47 mmol) and 4-methylmorpholine (2.12 g, 20.95 mmol) in toluene (20 mL) was added dropwise over 0.5 hr to an ice-cold solution of PCl$_3$ (1.44 g, 10.47 mmol) in toluene (20 mL, 100 mL three neck flask) at −10~0° C. in MeOH-ice bath. Then the reaction was warmed to 20° C. and stirred for 2 hr. The mixture was filtered carefully under Ar, the filter cake was washed with dry toluene (5 mL*2) under Ar and reduced to an oil by rotary evaporation (flushing with Ar) then under high vacuum below 30° C. The crude compound 5B was used in the next step reaction as yellow oil (1.50 g, crude).

3. Preparation of Compound WV-CA-070-dCiBu.

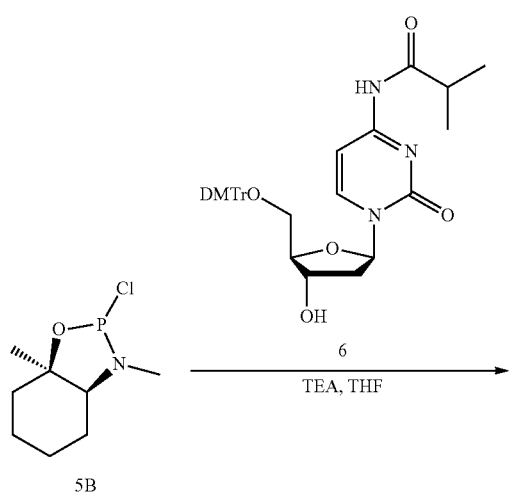

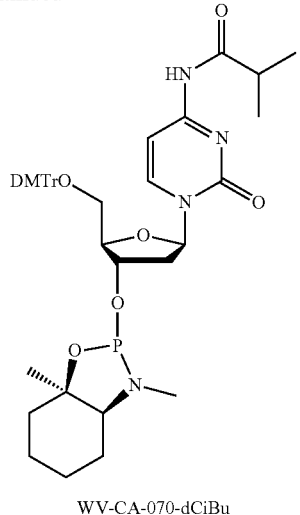

WV-CA-070-dCiBu

Compound 6 (3.00 g, 5.00 mmol) was dried by azeotropic distillation on a rotary evaporator (Ar flushing) with 1*40 mL anhydrous pyridine and 5*40 mL anhydrous toluene. The rotary temperature of the water bath can be up to 45° C. Dried compound 6 (3.00 g, 5.00 mmol) was dissolved in THF (20 mL), then TEA (3.54 g, 35.02 mmol) was added and the solution was cooled to −78° C. on an IPA/dry ice bath. A solution of the crude compound 5B (1.50 g, 7.22 mmol) in THF (20 mL) was added dropwise over 0.5 hr, and then the mixture was gradually warmed to 20° C. and stirred for 2 hr. TLC indicated a good conversion of compound 6 to product. The ice-cold mixture was washed into a separation funnel with CH$_2$Cl$_2$ (50 mL) then was washed with NaHCO$_3$ (sat., aqueous, 3*40 mL). The separated aqueous layer was extracted with CH$_2$Cl$_2$ (25 mL*2). The combined extract was dried over MgSO$_4$, filtered, and concentrated by rotary evaporation at 30° C. to afford the crude product. The crude solid foam was purified by column (washed with Petroleum ether contained 5% TEA, Ethyl acetate:Petroleum ether=3:1 to 5:1, contained 5% TEA) to afford product as white solid (3.3 g). The residue was concentrated in vacuo on oil pump at 25° C. for 0.5 hr to afford WV-CA-070-dCiBu as white solid (3 g). $^1$H NMR (400 MHz, CDCl$_3$): δ=8.31 (d, J=7.5 Hz, 1H), 8.21 (br. s., 1H), 7.38 (d, J=7.3 Hz, 2H), 7.32-7.17 (m, 7H), 7.06 (d, J=7.4 Hz, 1H), 6.81 (d, J=7.7 Hz, 4H), 6.18 (dd, J=4.1, 6.5 Hz, 1H), 4.87-4.76 (m, 1H), 4.06-3.98 (m, 1H), 3.76 (s, 6H), 3.48-3.34 (m, 2H), 2.70-2.40 (m, 6H), 2.29 (ddd, J=4.0, 6.7, 13.9 Hz, 1H), 2.18-2.07 (m, 1H), 1.86-1.71 (m, 1H), 1.62-1.11 (m, 14H). $^{31}$P NMR (400 MHz, CDCl$_3$): δ=157.773. TLC (Ethyl acetate:Petroleum ether=3:1, contained 5% TEA) R$_f$=0.23.

Example 71. Synthesis of WV-CA-070S & WV-CA-070-dCiBu

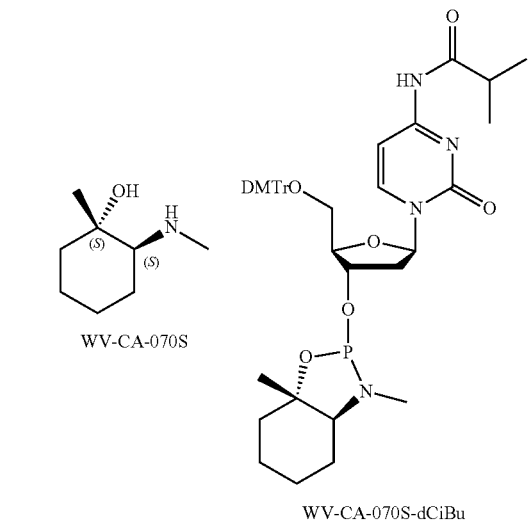

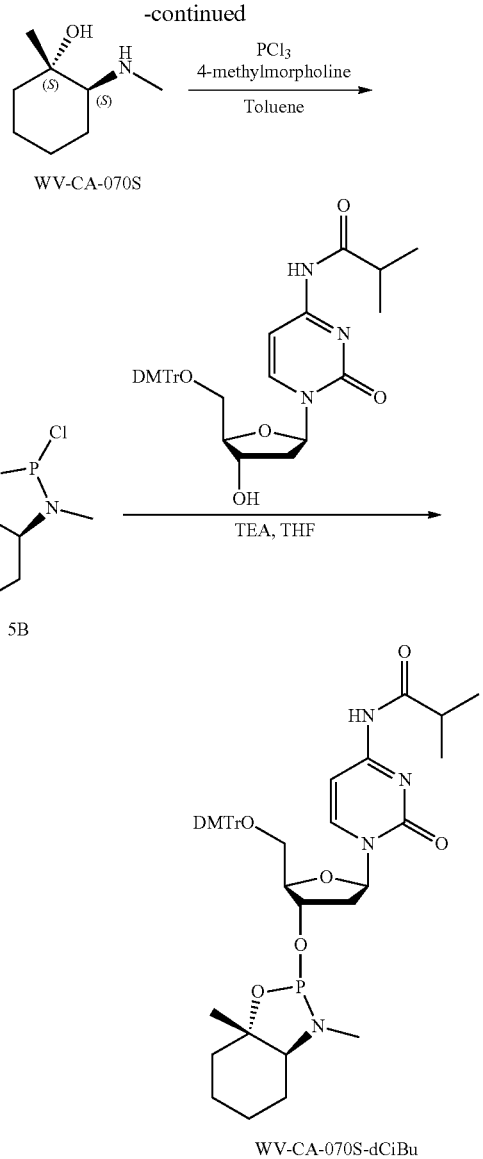

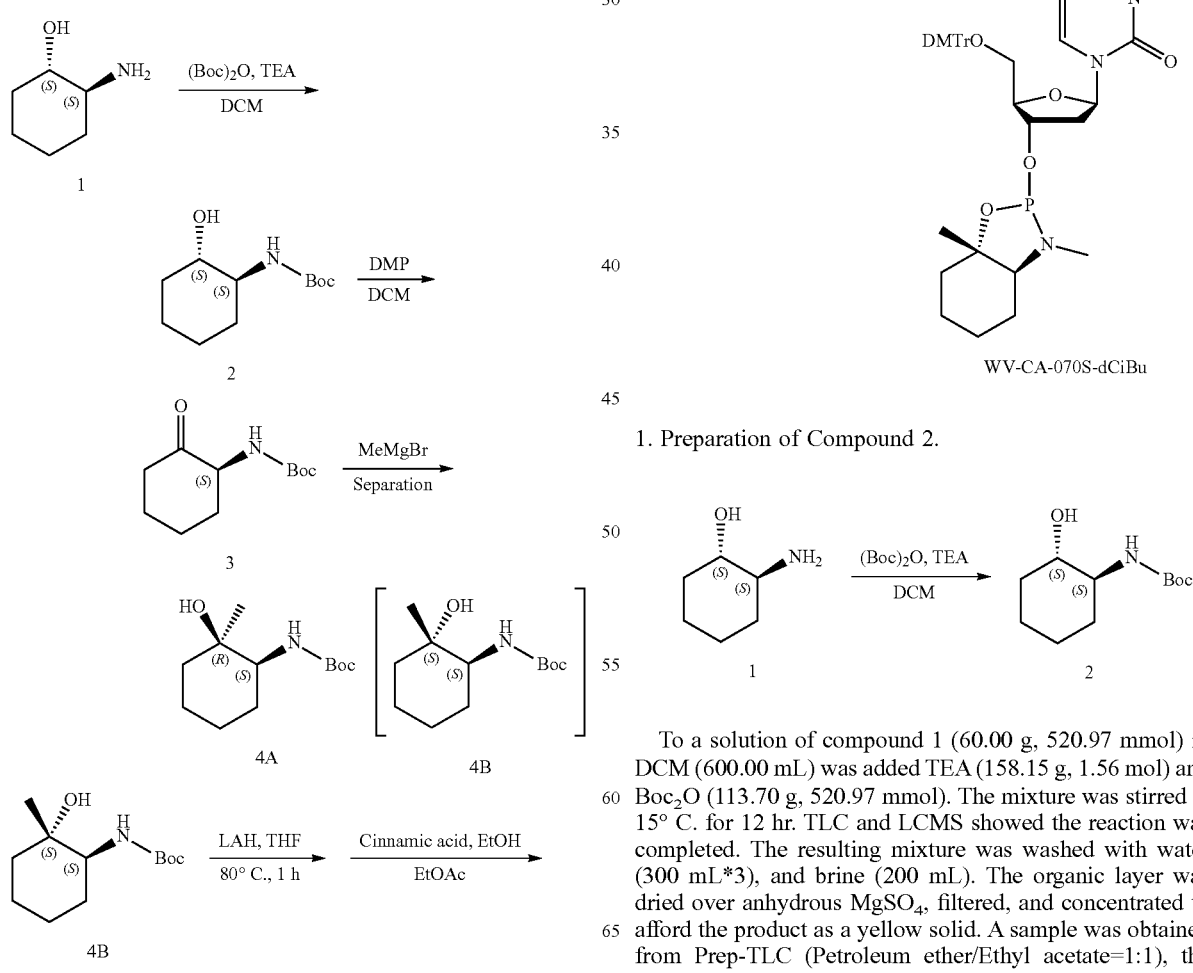

1. Preparation of Compound 2.

To a solution of compound 1 (60.00 g, 520.97 mmol) in DCM (600.00 mL) was added TEA (158.15 g, 1.56 mol) and Boc$_2$O (113.70 g, 520.97 mmol). The mixture was stirred at 15° C. for 12 hr. TLC and LCMS showed the reaction was completed. The resulting mixture was washed with water (300 mL*3), and brine (200 mL). The organic layer was dried over anhydrous MgSO$_4$, filtered, and concentrated to afford the product as a yellow solid. A sample was obtained from Prep-TLC (Petroleum ether/Ethyl acetate=1:1), the residue was purified on column (Petroleum ether/Ethyl acetate=10:1 to 1:1) to give compound 2 (97.00 g, 86.48%) as a white solid (97.00 g, 86.48%). $^1$H NMR (400 MHz, CDCl$_3$): δ=4.54 (br. s., 1H), 3.41-3.23 (m, 2H), 2.10-1.90 (m, 2H), 1.78-1.64 (m, 2H), 1.46 (s, 9H), 1.37-1.05 (m, 4H). TLC (Petroleum ether:Ethyl acetate=1:1) R$_f$=0.66.

2. Preparation of Compound 3.

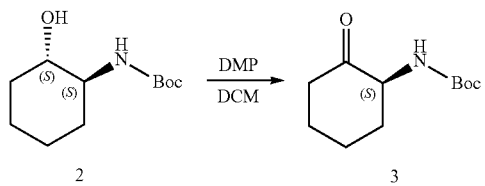

To a solution of compound 2 (40.00 g, 185.80 mmol) in DCM (400.00 mL) was added DMP (94.57 g) in portions at 0~5° C. for 0.5 hr. The white suspension was stirred at 15° C. for 1 hr. TLC showed compound 2 remained. DMP (15.76 g) was additionally added to the reaction at 20° C. and stirred for 1.5 hr. TLC showed compound 2 remained a little and one new spot was detected. The reaction was quenched with sat. Na$_2$SO$_3$ aq. and sat. NaHCO$_3$ aq. (V/V=3:2, 2 L), extracted with DCM (1 L*3). The combined organic layers were dried over anhydrous MgSO$_4$, filtered, and concentrated to afford a crude, which was purified by column (Petroleum ether:Ethyl acetate=10:1, 5:1) to obtain compound 3 as colorless oil (29.50 g, 74.45%). $^1$H NMR (400 MHz, CDCl$_3$): δ=5.48 (s, 1H), 4.24-4.18 (m, 1H), 2.57-2.35 (m, 3H), 2.10-2.09 (m, 4H), 1.85-1.35 (m, 13H). TLC (Petroleum ether:Ethyl acetate=3:11) R$_f$=0.43.

3. Preparation of Compound 4A & 4B.

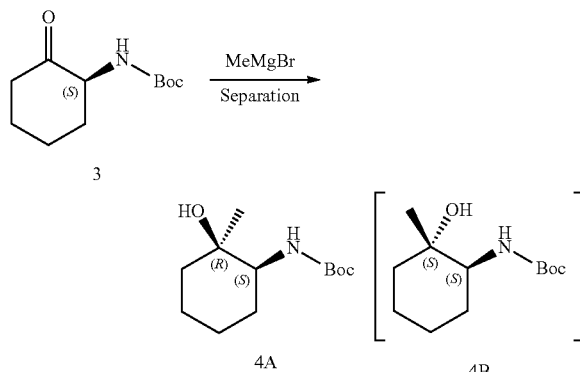

Into a 1 L three necked flask equipped with a low-temperature thermometer, MeMgBr (3 M, 115.27 mL) was added to the solution of compound 3 (29.50 g, 138.32 mmol) in THF (300.00 mL) at −60~−55° C. for 0.5 hr. Then the reaction was stirred at −60° C.~0° C. for 1 hr. TLC showed compound 3 remained a little. The reaction was continued stirred at 25° C. for 1.5 hr. TLC showed compound 3 remained a little, two new spot was detected. The desired product was detected on LCMS. The reaction was poured into sat. NH$_4$Cl aq. (500 mL) at 0° C. The residue was extracted with EtOAc (250 mL*3). The organic phase was separated, dried over Na$_2$SO$_4$, filtered and concentrated in vacuo to dryness. The residue (Combined with 50 g crude) was purified by MPLC*3 (SiO$_2$, Petroleum ether/Ethyl acetate=10:1 to 1:1) to obtain compound 4A (13.5 g), 4A as colorless oil (4 g contained a little compound 3), and compound 4B as white solid (30 g). Compound 4A: $^1$H NMR (400 MHz, CDCl$_3$): δ=4.80 (br. s., 1H), 3.37 (t, J=8.6 Hz, 1H), 1.62-1.80 (m, 3H), 1.17-1.58 ppm (m, 16H). Compound 4B: $^1$H NMR (400 MHz, CDCl$_3$): δ=4.53 (br. s., 1H), 3.68-3.35 (m, 2H), 1.80 (t, J=12.1 Hz, 2H), 1.72-1.58 (m, 2H), 1.54-1.08 (m, 15H). TLC (Petroleum ether:Ethyl acetate=5:1) R$_f$_4A=0.24 and R$_f$_4B=0.18.

4. Preparation of Compound WV-CA-070S.

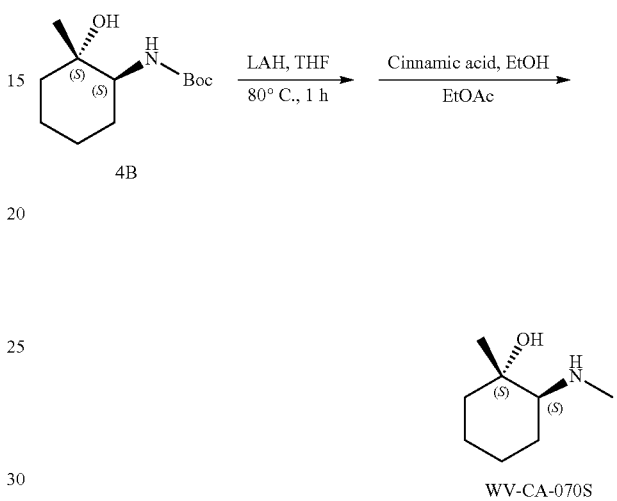

To a mixture solution of Compound 4B (10.00 g, 43.61 mmol) in THF (100.00 mL) was added LiAlH$_4$ (4.96 g, 130.83 mmol) in portions at 0° C. The mixture was stirred at 80° C. for 0.5 hr. TLC showed compound 4B was consumed; WV-CA-070S was detected. The reaction was slowly added sat. MgSO$_4$ (10 mL) at 0° C. The mixture was filtered through Celatom. The filter cake was washed with EtOAc (80 mL*3). The organic phase was dried over MgSO$_4$, filtered, and concentrated in vacuo to dryness to afford WV-CA-070S as white solid (5.30 g, crude). To a mixture of WV-CA-070S in EtOH (10.00 mL) was added cinnamic acid (5.48 g, 37.00 mmol). The mixture was heated at 90° C. for 30 minutes. The mixture was concentrated in vacuo to dryness. The white crude solid of cinnamic acid salt was dissolved in EtOAc (20 mL) at 80° C. for 0.5 hr until the mixture became clear. The solution was cooled to 20° C. slowly. A large amount of solid precipitated, which was filtered, and concentrated in vacuo to dryness to afford the cinnamic acid salt of WV-CA-070S as white solid (7.32 g, 67.90%). To a solution of cinnamic acid salt of WV-CA-070S (7.32 g, 25.12 mmol) in DCM (20.00 mL) was added dropwise 2 M aqueous of KOH (20.00 mL) at 20° C. until pH ~13. The reaction was stirred at 20° C. for 0.5 hr, and extracted with DCM (30 mL*2). The combined organic phase was dried over Na$_2$SO$_4$, and concentrated in vacuo to dryness to afford WV-CA-070S as white solid (3.2 g). $^1$H NMR (400 MHz, CDCl$_3$): δ=2.44 (s, 3H), 2.20 (dd, J=4.0, 11.9 Hz, 1H), 2.09-1.99 (m, 1H), 1.83-1.69 (m, 2H), 1.65 (dd, J=2.6, 9.7 Hz, 1H), 1.46-1.19 (m, 3H), 1.10 (s, 3H), 1.01-0.86 (m, 1H). $^{13}$C NMR (125.7 MHz, CDCl$_3$): δ=72.36, 67.77, 39.71, 34.64, 27.90, 25.26, 23.48, 20.22. LCMS: (M+H+): 144.1. TLC (Petroleum ether:Ethyl acetate=1:1) R$_f$=0.04.

5. Preparation of Compound 5B.

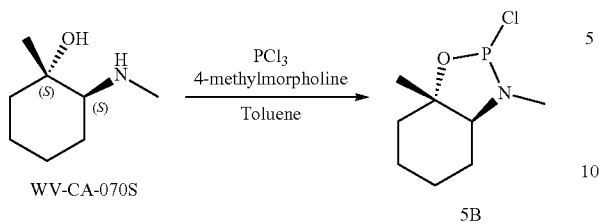

Compound WV-CA-070S (1.50 g, 10.47 mmol) was dried by azeotropic distillation with toluene (3*40 mL, 100 mL flask). A solution of dried WV-CA-070S (1.50 g, 10.47 mmol) and 4-methylmorpholine (2.12 g, 20.95 mmol) in toluene (20 mL) was added dropwise over 0.5 hr to an ice-cold solution of PCl$_3$ (1.44 g, 10.47 mmol) in toluene (20 mL, 100 mL two necked flask) at −10~−5° C. in MeOH-ice bath. Then the reaction was warmed to room temperature (20° C.) and stirred for 1.5 hr. The mixture was filtered carefully under Ar. The filer cake was washed with dry toluene (5 mL*2) under Ar and reduced to a yellow oil by rotary evaporation (flushing with Ar) then under high vacuum. Crude compound 5B was used in the next step reaction without further purification (2.00 g, crude).

6. Preparation of Compound WV-CA-070S-dCiBu.

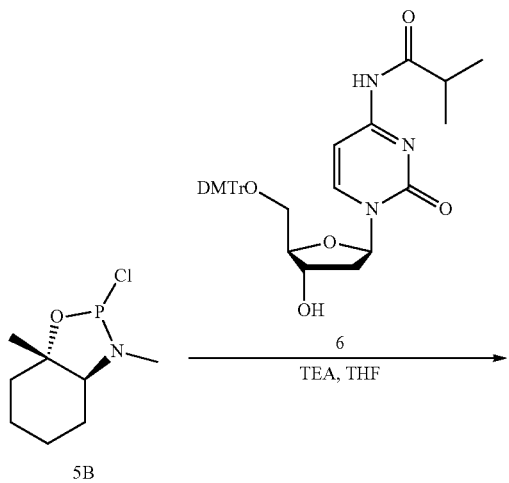

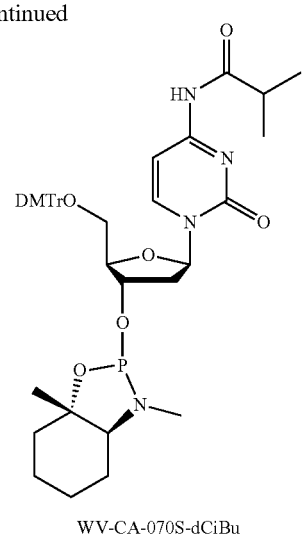

Compound 6 (4.00 g, 6.67 mmol) was dried by azeotropic distillation on a rotary evaporator (Ar flushing) with anhydrous pyridine (40 mL*1) and anhydrous toluene (40 mL*5). The rotary evaporation temperature of the water bath can be up to 45° C. Dried compound 6 (4.00 g, 6.67 mmol) was dissolved in THF (20 mL), then TEA (4.72 g, 46.69 mmol) was added and the solution was cooled to −78° C. on a IPA/dry ice bath A THF solution (20 mL) of the crude compound 5B (1.99 g, 9.60 mmol) was added dropwise over 0.5 hr, then the mixture was gradually warmed to 20° C. and stirred at 20° C. for 2 hr. TLC indicated a good conversion of compound 6 to the product. The ice-cold mixture was washed into a separation funnel with CH$_2$Cl$_2$ (50 mL), then extracted with NaHCO$_3$ (sat., aqueous, 3*40 mL). The NaHCO$_3$ layer was extracted with CH$_2$Cl$_2$ (25 mL*2). The combined extracts were dried over MgSO$_4$, and filtered; the solvent was removed by rotary evaporation at 30° C. to afford crude WV-CA-070S-dCiBu. The crude solid foam was purified by MPLC (Ethyl acetate:Petroleum ether=3:1 to 5:1, contained 5% TEA) to afford WV-CA-070S-dCiBu as white solid (0.8 g). $^1$H NMR (400 MHz, CDCl$_3$): δ=8.39 (d, J=7.5 Hz, 1H), 8.32 (br. s, 1H), 7.44 (d, J=7.4 Hz, 2H), 7.37-7.20 (m, 7H), 7.14 (d, J=7.4 Hz, 1H), 6.87 (d, J=7.5 Hz, 4H), 6.22 (dd, J=3.8, 6.3 Hz, 1H), 5.00-4.90 (m, 1H), 4.14 (d, J=7.2 Hz, 1H), 3.83 (s, 6H), 3.57-3.40 (m, 2H), 2.73 (td, J=6.8, 13.8 Hz, 1H), 2.66-2.48 (m, 4H), 2.45-2.33 (m, 2H), 2.02-1.68 (m, 5H), 1.67-1.16 (m, 17H). $^{31}$P NMR (400 MHz, CDCl$_3$): δ=164.25. TLC (Ethyl acetate:Petroleum ether=3:1, contained 5% TEA) R$_f$=0.16.

Example 72. Synthesis of WV-CA-071S

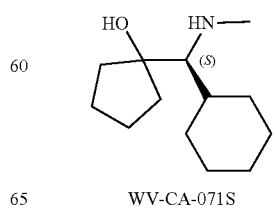

WV-CA-071S

General Scheme.

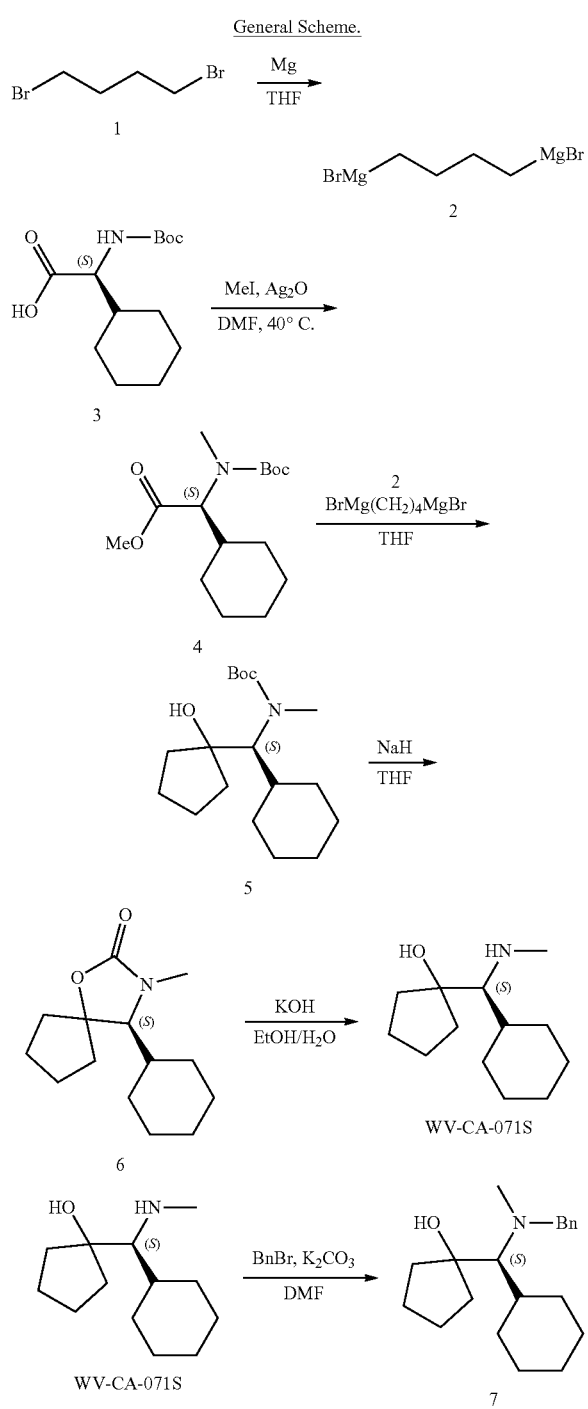

1. Preparation of Compound 2.

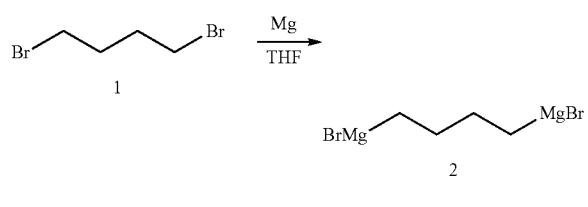

To a suspension of Mg (7.67 g, 315.36 mmol) in THF (150 mL) was added 1,4-dibromobutane (34.04 g, 157.68 mmol) (activated with one crystal of $I_2$) in THF (50 mL) for 1 hr at 20~60° C. during the addition. After stirred at 20° C. for 1 hr, the solution turned to white suspension. Mg was consumed. The reaction was completed. The Grignard reagent in THF was used directly in next step.

2. Preparation of Compound 4.

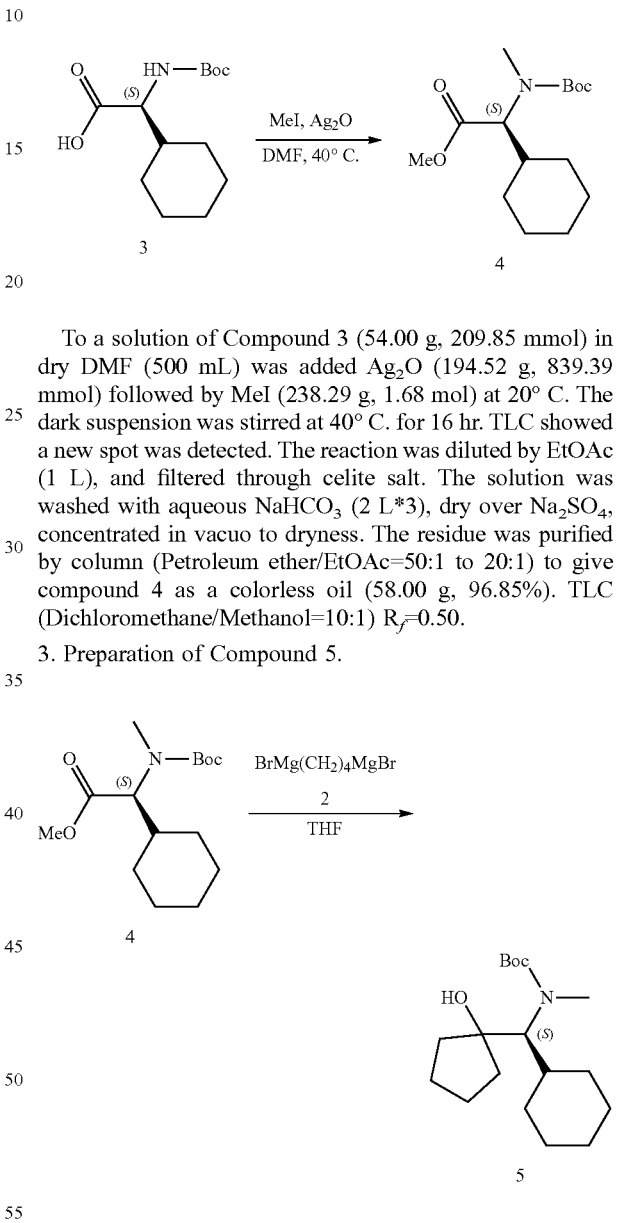

To a solution of Compound 3 (54.00 g, 209.85 mmol) in dry DMF (500 mL) was added $Ag_2O$ (194.52 g, 839.39 mmol) followed by MeI (238.29 g, 1.68 mol) at 20° C. The dark suspension was stirred at 40° C. for 16 hr. TLC showed a new spot was detected. The reaction was diluted by EtOAc (1 L), and filtered through celite salt. The solution was washed with aqueous $NaHCO_3$ (2 L*3), dry over $Na_2SO_4$, concentrated in vacuo to dryness. The residue was purified by column (Petroleum ether/EtOAc=50:1 to 20:1) to give compound 4 as a colorless oil (58.00 g, 96.85%). TLC (Dichloromethane/Methanol=10:1) $R_f$=0.50.

3. Preparation of Compound 5.

To a mixture of Grignard reagent (0.7 M, 225.26 mL) in THF was added dropwise the solution of Compound 4 (15.00 g, 52.56 mmol) in THF (15 mL) at −15° C. The mixture was stirred at −15~0° C. for 1 hr. TLC showed most of Compound 4 was consumed, and one new spot was detected. The resulting mixture was quenched with sat. $NH_4Cl$ aq. (100 mL) at 0° C., extracted with EtOAc (200 mL*3). The combined organic layers were dried over anhydrous $MgSO_4$, filtered, and concentrated in vacuo to dryness to give the crude of Compound 5 (16.00 g, crude) as colorless oil. TLC (Petroleum ether/EtOAc=10:1) $R_f$=0.71.

4. Preparation of Compound 6.

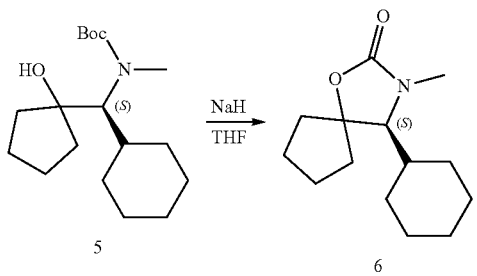

NaH (6.16 g, 154.11 mmol) was added to the solution of Compound 5 (16.00 g, 51.37 mmol) in THF (160 mL) at 0° C. The reaction was stirred at 0~15° C. for 1 hr. TLC and LCMS showed Compound 5 was consumed, one new spot was detected. The reaction mixture was poured into sat. NH$_4$Cl aq. (100 mL) at 0° C. The mixture was extracted with EtOAc (150 mL*3). The organic phase was separated, dried over Na$_2$SO$_4$, and concentrated in vacuo to dryness. The residue was purified on column (Petroleum ether/EtOAc=50:1 to 5:1). Compound 6 was obtained as a colorless oil (11.00 g, 90.23%). TLC (Petroleum ether/EtOAc=5:1) R$_f$=0.16.

5. Preparation of Compound 4.

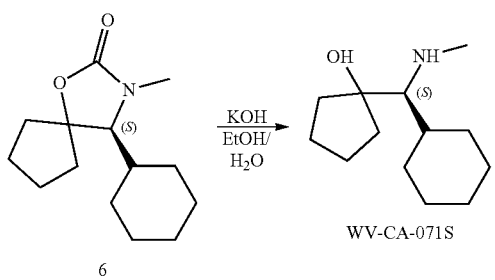

Compound 6 (11.00 g, 46.35 mmol) was dissolved in a KOH (40 g) (wt. ~40%) solution in EtOH-H$_2$O (1:1, v/v) (100 mL). The mixture was heated at refluxed (90° C.) for 24 hr LCMS showed Compound 6 remained. To the reaction was additionally added KOH (10 g). Stirring was continued at 90° C. for 24 hr. TLC and LCMS showed Compound 6 remained a little and desired product was detected. The resulting mixture was separated. The aqueous phase was extracted with DCM (100 mL*3), dried over anhydrous MgSO$_4$, filtered and concentrated to afford the product as crude, which was purified by column chromatography on silica gel (Petroleum ether/EtOAc=50:1, 20:1, 1:1) to afford WV-CA-071S (4.00 g, 40.84%) as a light-yellow oil, and 900 mg crude of WV-CA-071S. $^1$H NMR (400 MHz, CDCl$_3$): δ=2.53 (s, 3H), 2.14 (s, 1H), 1.89-1.57 (m, 14H), 1.33-0.96 (m, 5H). $^{13}$C NMR (125.7 MHz, CDCl$_3$): δ=83.23, 71.90, 40.59, 40.42, 38.31, 35.31, 33.39, 27.78, 27.05, 26.47, 23.52. LCMS: (M+H$^+$): 212.2. TLC (Petroleum ether/EtOAc=1:1) R$_f$=0.03.

6. Preparation of Compound 5.

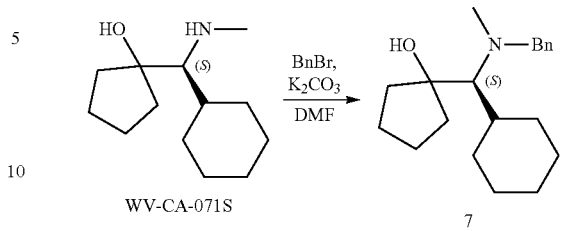

BnBr (89.02 mg, 520.49 μmol, 61.82 μL) was added to the solution of WV-CA-071S (100.00 mg, 473.17 μmol) and K$_2$CO$_3$ (78.48 mg, 567.80 μmol) in DMF (5 mL) at 15° C. The reaction was stirred at 15° C. for 16 hr. TLC and showed WV-CA-071S was remained, and one new spot was detected. The residue was purified by Prep-TLC (Petroleum ether/EtOAc=3:1). A sample of Compound 7 was obtained as colorless oil. $^1$H NMR (400 MHz, CDCl$_3$): δ=7.27-7.19 (m, 5H), 5.17 (br, 1H), 3.91-3.76 (m, 2H), 2.61 (d, J=8.8 Hz, 2H), 2.61 (s, 1H), 1.79-1.00 (m, 19H). TLC (Petroleum ether/EtOAc=3:1) R$_f$=0.57. HPLC purity=98.4%. SFC purity=100.0%.

Example 73. Synthesis of WV-CA-071S-dCiBu

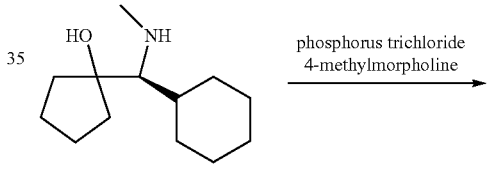

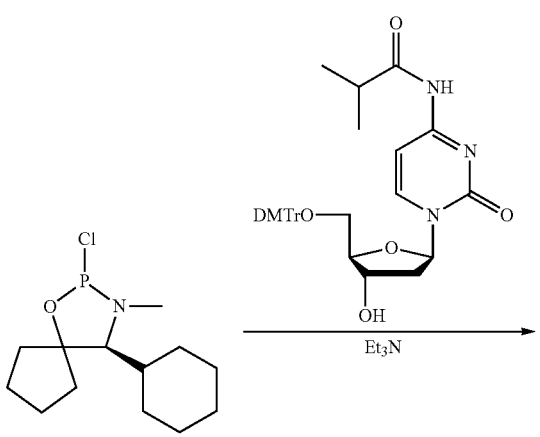

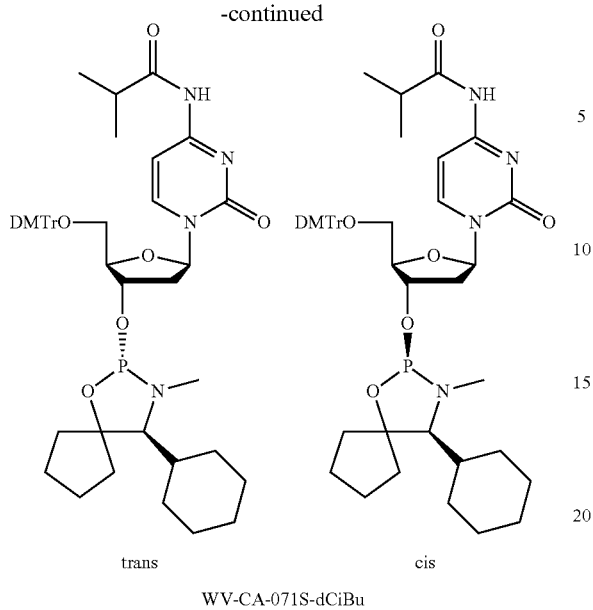
WV-CA-071S-dCiBu
Using WV-CA-071S as starting material, the title compound (3.68 g, 72%) as a white solid was prepared analogously to WV-CA-008S-dCiBu. $^{31}$P NMR (202 MHz, CDCl$_3$) δ 155.65 (94%, trans), 145.08 (6%, cis).
Example 74. Synthesis of WV-CA-074M & WV-CA-074M-dCiBu
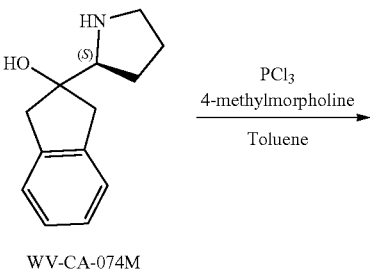
WV-CA-074M                WV-CA-074M-dCiBu
General Scheme.
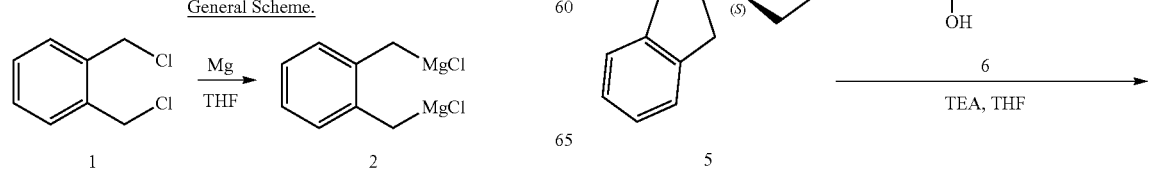
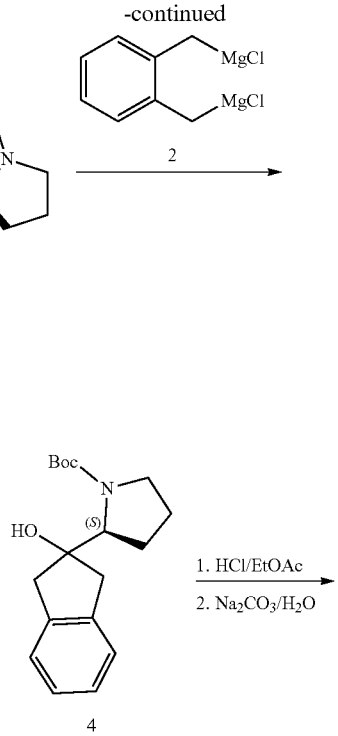
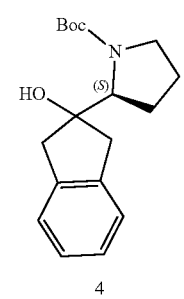
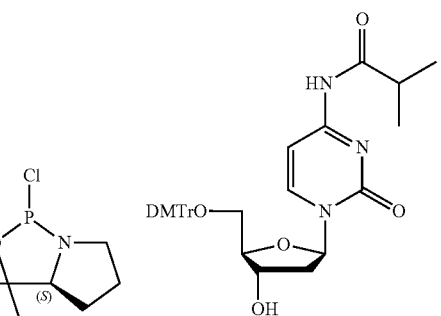
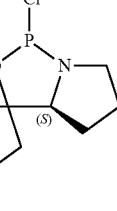

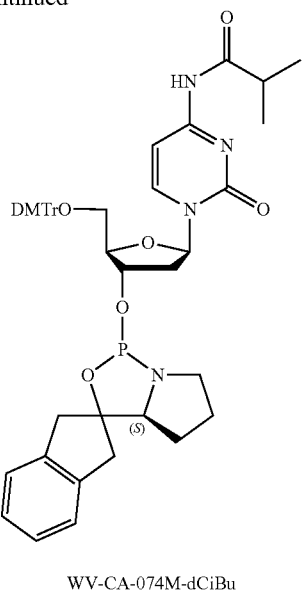

WV-CA-074M-dCiBu

1. Preparation of Compound 2.

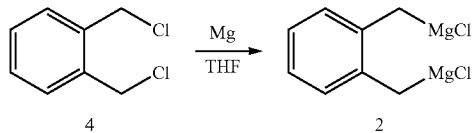

Mg (1.47 g, 60.60 mmol) was activated using a single crystal of iodine in THF (1.30 L). Compound 1 (100.00 g, 571.27 mmol) in THF (500 mL) was added dropwise to the magnesium mixture over a period of 8 hr and the mixture was stirred at 25° C. for 16 hr. Most of Mg was consumed. The reaction was almost completed and LCMS showed there was no compound 1 left. The Grignard reagent in THF was used directly in next step.

2. Preparation of Compound 4.

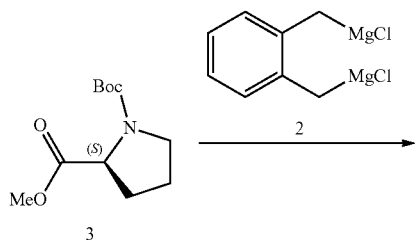

To a mixture of compound 2 (97.55 g, 436.15 mmol) in THF was added drop-wise a solution of compound 3 (20.00 g, 87.23 mmol) in THF (400 mL) at 0° C. The reaction mixture was stirred at 25° C. for 16 hr. TLC (Petroleum ether:Ethyl acetate=3:1) showed compound 3 was consumed. NH$_4$Cl (sat. 300 mL) was added and extracted with EtOAc (300 mL*3). The organic phase was dried over Na$_2$SO$_4$, filtered and concentrated. The residue was purified by column chromatography on silica gel (Petroleum ether: Ethyl acetate=100:1, 10:1). Compound 4 was got as yellow oil (27.60 g, crude). $^1$H NMR (400 MHz, CHLOROFORM-d) δ=7.147-7.178 (m, 4H), 4.202 (s, 1H), 3.691 (s, 1H), 3.199-3.311 (m, 2H), 2.895-3.103 (m, 4H), 2.033 (d, J=7.2 Hz, 1H), 1.824 (s, 1H), 1.698 (s, 1H), 1.625 (s, 1H), 1.505 (s, 9H). LCMS: (M+Na+): 325.9. TLC (Petroleum ether: Ethyl acetate=3:1) R$_f$=0.54.

3. Preparation of Compound WV-CA-074M.

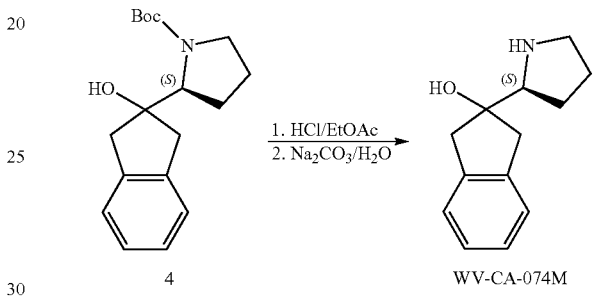

To a solution of compound 4 (20.00 g, 65.92 mmol) in EtOAc (100 mL) was added HCl/EtOAc (150 mL) at 0° C., and the reaction mixture was stirred at 20° C. for 3 hr. TLC (Petroleum ether:Ethyl acetate=3:1) showed the reaction was complete. The reaction mixture was filtered and the filter cake was dried under reduced pressure. The product of WV-CA-074M was got as yellow solid (10.90 g, 68.98%, HCl salt). To the solution of WV-CA-074M (11.40 g, 47.55 mmol, HCl salt) in H$_2$O (50 mL) was added Na$_2$CO$_3$ (100.00 mL) at 0° C. and the mixture was stirred at 0° C. for 1 hr. TLC (Dichloromethane:Methanol=5:1) showed there was no the desired product in the water phase. The mixture was extracted with DCM (150 mL*3). The organic phase was dried over Na$_2$SO$_4$ and concentrated. WV-CA-074M was got as yellow solid (6.50 g, 67.25% yield). $^1$H NMR (400 MHz, CHLOROFORM-d) δ=7.152-7.236 (m, 4H), 3.711-3.730 (m, 1H), 3.066-3.322 (m, 1H), 2.974-3.062 (m, 6H), 1.760-1.867 (m, 4H). $^{13}$C NMR (101 MHz, CHLOROFORM-d) δ=141.50, 126.70, 124.71, 81.30, 65.64, 46.78, 46, 67, 27.71, 27.64. LCMS: (M+H+): 204.1. TLC (Dichloromethane:Methanol=5:1) R$_f$=0.00. HPLC purity=100.0%. SFC purity=100.0%.

4. Preparation of Compound 5.

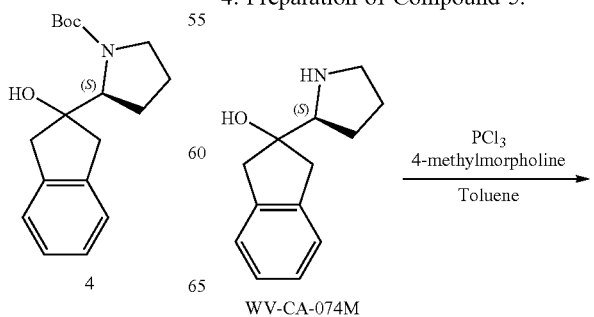

WV-CA-074M

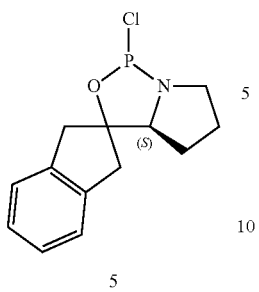

WV-CA-074M (2.00 g, 9.84 mmol) was dried by azeotropic rotary evaporation (Arflushing) with toluene (50 mL*3, water bath temperature=45° C.), then under high vacuum at 45° C. A mixture of dried WV-CA-074M (2.00 g, 9.84 mmol) and NMM (1.99 g, 19.68 mmol, 2.16 mL) was dissolved in toluene (15.00 mL) by sonication at 25° C. under argon (balloon) for 0.5 hr. The above solution which also contained a small amount of solid material, was added drop-wise via cannula over 30 minutes to the solution of PCl$_3$ (1.35 g, 9.84 mmol) in toluene (8.40 mL) at 0° C. After warming to 25° C. for 1 hr, the mixture was filtered carefully under vacuum/argon using the fitted filtration tube. The resulting filtrate was reduced by rotary evaporation (flushing with Ar) with water bath temperature (30° C.) then under high vacuum. Crude compound 5 was got as a pale yellow thick oil, which was used in next step (2.63 g, crude).

5. Preparation of Compound WV-CA-074M-dCiBu.

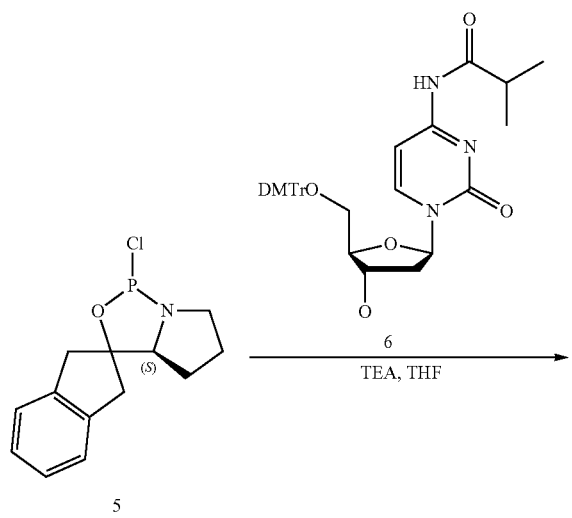

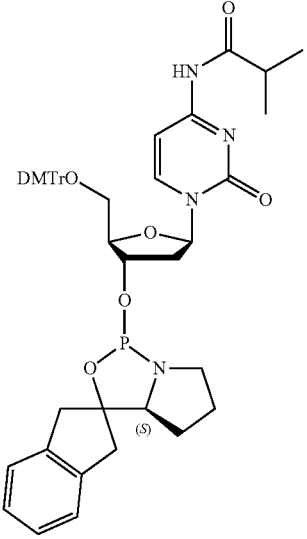

WV-CA-074M-dCiBu

Compound 6 (3.13 g, 5.23 mmol) was dried by azeotropic distillation on a rotary evaporator (Ar flushing) with 150 mL anhydrous pyridine (water bath temperature=40° C.) then 2*250 mL anhydrous toluene (water bath temperature=45-50° C.) ensuring that the compound is completely dissolved prior to removal of solvent at each stage of the drying process. The material should be allowed to become solid foam after solvent removal at each stage. Compound 6 (3.13 g, 5.23 mmol) was dissolved in THF (15 mL), then TEA (2.64 g, 26.13 mmol, 3.62 mL) was added and the solution was cooled at −60° C. Under magnetic stirring, a solution of crude compound 5 (2.10 g, 7.84 mmol) in THF (10 mL) was added through a cannula over 30 minutes—internal T monitored to T$_{max}$=−60° C. Then the reaction mixture was gradually warmed to 20° C. over 2.5 hr. TLC (Petroleum ether:Ethyl acetate=1:3) showed that the reaction was complete. The mixture was cooled to 10° C. then CHCl$_3$ (800 mL) was added keeping T below 10° C., followed by sat. NaHCO$_3$ (500 mL) all the while under magnetic stirring. The mixture was transferred to a separating funnel, then after thorough shaking for ~1 minute, the organic layer was separated, and washed with sat NaHCO$_3$ (2*250 mL). The aqueous layer was extracted at each washing stage with additional CHCl$_3$ (100 mL). The chloroform extracts were dried (MgSO$_4$), filtered and the solvent removed by rotary evaporation at 30° C. The crude solid foam was purified by column chromatography on silica gel (Petroleum ether:Ethyl acetate (5% TEA)=20:1, 1:1). WV-CA-074M-dCiBu was got as white solid foam (2.40 g, 55.26%). $^1$H NMR (400 MHz, CHLOROFORM-d) δ=8.146 (d, J=7.2 Hz, 1H), 7.23 (d, J=33.6 Hz, 2H), 7.161-7.183 (m, 6H), 7.037-7.043 (m, 6H), 6.710-6.737 (m, 4H), 6.186-6.215 (m, 1H), 4.667-4.729 (m, 1H), 4.126 (d, J=3.6 Hz, 1H), 3.679 (s, 6H), 3.578-3.590 (m, 2H), 3.257-3.345 (m, 2H), 2.971-3.084 (m, 4H), 2.637-2.671 (m, 2H), 2.210 (m, 1H), 1.658-1.783 (m, 3H), 1.324-1.343 (m, 1H), 1.107-1.122 (m, 6H). $^{31}$P NMR (162 MHz, CHLOROFORM-d) δ=158.75 (s, 1P). TLC (Petroleum ether:Ethyl acetate=3:1) R$_f$=0.41.

Example 75. Synthesis of WV-CA-074R, 074S, 074R-dCiBu and 074S-dCiBu

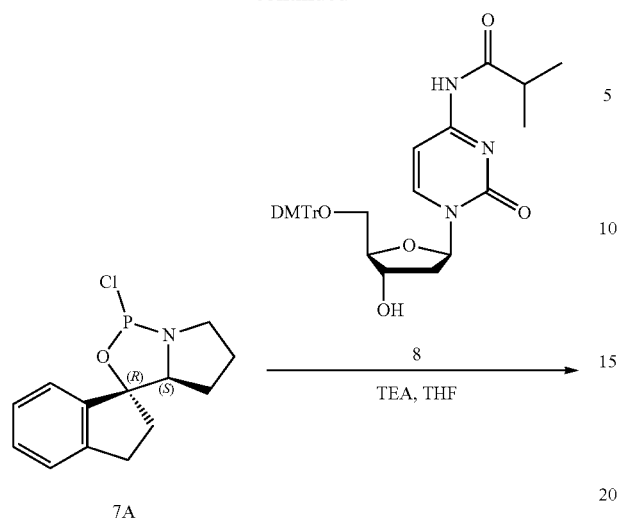

WV-CA-074R-dCiBu

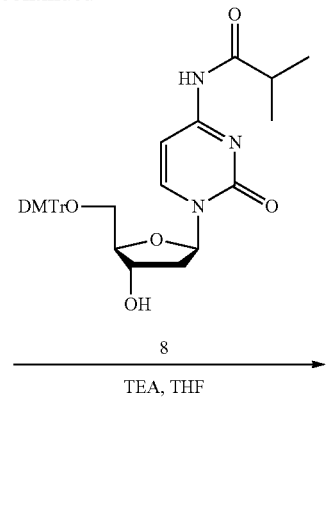

WV-CA-074S-dCiBu

1. Preparation of Compound 2.

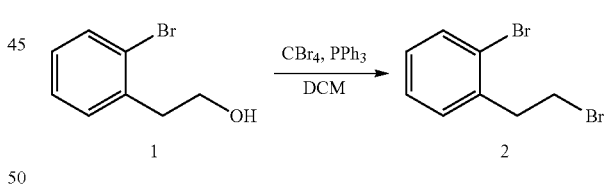

To a solution of compound 1 (72.00 g, 358.10 mmol) and PPh₃ (112.71 g, 429.72 mmol) in anhydrous DCM (800 mL) at 15° C. was added CBr₄ (142.51 g, 429.72 mmol). The resulting mixture was stirred at 15° C. for 16 hr. TLC showed the reaction was completed. The resulting mixture was concentrated to afford the product as a light-yellow crude oil. The residue crude was purified by column chromatography on silica gel (Petroleum ether) to afford compound 2 as a light-yellow oil (59.5 g, 62.9%). ¹H NMR (400 MHz, CHLOROFORM-d) δ=7.56 (br d, J=7.7 Hz, 1H), 7.30-7.24 (m, 2H), 7.17-7.10 (m, 1H), 3.63-3.56 (m, 2H), 3.30 (br t, J=7.5 Hz, 2H). TLC (Petroleum ether/Ethyl acetate=10:1) R$_f$=0.78.

2. Preparation of Compound 3.

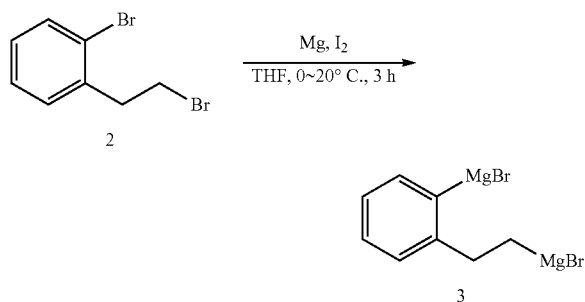

To a suspension of Mg (24.11 g, 991.83 mmol) and I₂ (60.00 mg, 236.40 µmol, 47.62 µL) in THF (1 L) was added a solution of compound 2 (119.00 g, 450.83 mmol) in THF (200 mL) (first 10% volume, when the reaction was initiated, and then added drop-wise the left over 1 h at 25-40° C.). The mixture was stirred at 15°-40° C. for another 2 hr. Most of Mg was consumed. The reaction was almost completed. The Grignard reagent 3 in THF was used directly in next step.

3. Preparation of Compound 5.

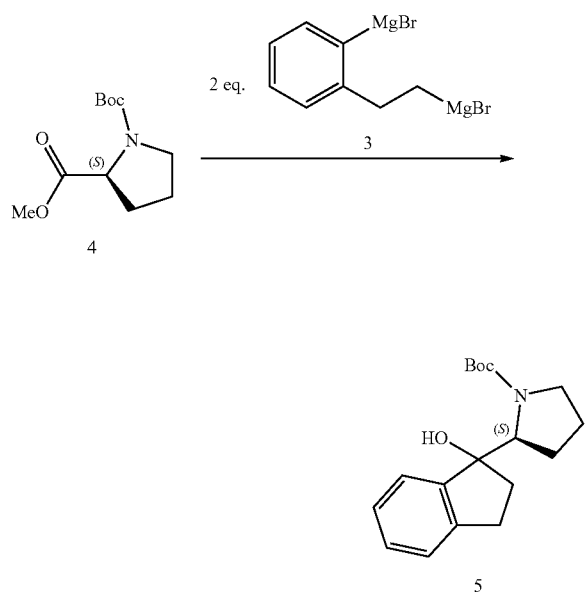

To a mixture of compound 3 (140.42 g, 449.26 mmol) in THF (previous step) was added drop-wise a solution of compound 4 (51.50 g, 224.63 mmol) in THF (200 mL) at 0° C. The mixture was stirred at 15° C. for 16 hr. TLC and LCMS showed compound 4 was consumed. The resulting mixture was quenched with sat. NH₄Cl aq. (1 L), extracted with EtOAc (800 mL*3). The combined organic layers were dried over anhydrous Na₂SO₄, filtered, and concentrated to afford the crude product, the crude was purified by silica gel with Petroleum ether/Ethyl acetate (1:0, 20:1, 10:1) to afford the product as crude light yellow oil (53.5 g, crude). LCMS: (M+Na⁺): 325.9. TLC (Petroleum ether/Ethyl acetate=3:1) $R_f$=0.49.

4. Preparation of Compound 6A and Compound 6B.

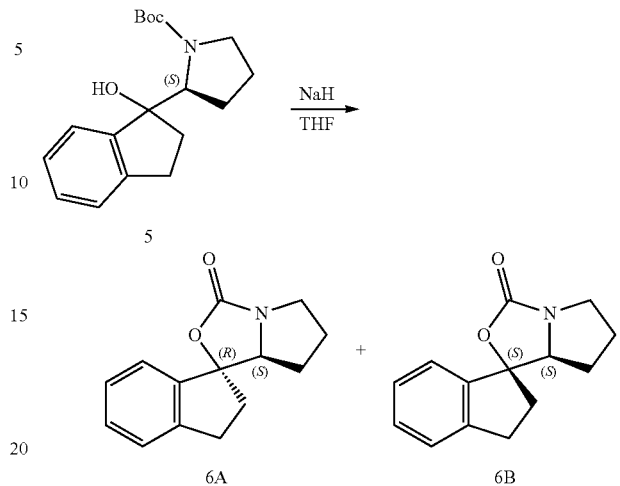

To a solution of compound 5 (45.00 g, 148.32 mmol) in THF (1.00 L) was added NaH (17.80 g, 444.96 mmol, 60% purity) at 15° C. The mixture was stirred at 15~40° C. for 3 hr. TLC showed the reaction was almost completed. The resulting mixture of two batches was poured into sat. NH₄Cl aq. (1500 mL), extracted with EtOAc (800 mL*3). The combined organic layers were dried over Na₂SO₄, filtered and concentrated. The precipitated solid was filtered and rinsed with Petroleum ether/EtOAc (1:1, 100 mL), dried to give compound 6B as a light yellow solid (13 g). The combined filtrate was concentrated to give a crude oil. The crude oil was purified by column chromatography on silica gel (Petroleum ether/Ethyl acetate, 20:1 to 3:1) to afford compound 6A as white solid (4.6 g, 13.53%); which was combined with compound 6B obtained above (13 g) and dissolved in DCM (100 mL) and EtOAc (150 mL). The resulting solution was concentrated until a large amount of solid crystallized, filtered and dried to give pure compound 6B as white solid (7.5 g, 22.06%). TLC (Petroleum ether/Ethyl acetate=3:1) $R_{f1}$=0.18, $R_{f2}$=0.21. Compound 6A: ¹H NMR (400 MHz, CHLOROFORM-d) δ=7.34-7.21 (m, 4H), 3.85-3.71 (m, 2H), 3.24 (br t, J=10.3 Hz, 1H), 3.02-2.85 (m, 2H), 2.52 (br t, J=6.3 Hz, 2H), 2.05 (br d, J=8.4 Hz, 1H), 1.89-1.76 (m, 1H), 1.52-1.37 (m, 2H). Chiral SFC purity: 100.0%. LCMS: (M+H⁺): 230.0, 98.2% purity. Compound 6B: ¹H NMR (400 MHz, CHLOROFORM-d) δ=7.50 (br d, J=6.4 Hz, 1H), 7.36-7.30 (m, 1H), 4.06-3.97 (m, 1H), 3.82-3.73 (m, 1H), 3.31 (br t, J=10.3 Hz, 1H), 3.15 (td, J=7.7, 15.7 Hz, 1H), 2.89 (br dd, J=8.6, 15.9 Hz, 1H), 2.50-2.41 (m, 1H), 2.38-2.29 (m, 1H), 2.20~2.09 (m, 1H), 2.00-1.86 (m, 2H), 1.73-1.59 (m, 1H). Chiral SFC purity: 97.1%. LCMS: (M+H⁺): 230.0, 97.2% purity.

5. Preparation of WV-CA-074R.

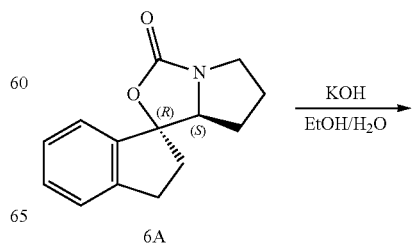

7. Preparation of WV-CA-074R-dCiBu.

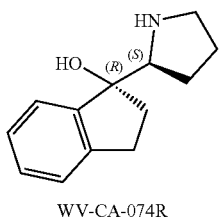

WV-CA-074R

Compound 6A (7.00 g, 30.53 mmol) was dissolved in a solution of KOH (80.00 g, 1.43 mol) in EtOH (60.00 mL) and H$_2$O (60.00 mL). The mixture was heated at 90° C. for 36 hr. TLC showed the reaction was completed, and LCMS showed a main peak with desired MS. The resulting mixture was extracted with DCM (120 mL*3). The combined organic layers were dried over anhydrous MgSO$_4$, filtered, and concentrated to afford the product as a crude, which was purified by column chromatography on silica gel (Dichloromethane/Methanol=5:1) to afford the product as a brown gum (5.3 g, 85.40%). $^1$H NMR (400 MHz, CHLOROFORM-d) δ=7.40 (br d, J=6.4 Hz, 1H), 7.27-7.15 (m, 3H), 3.37 (br t, J=5.7 Hz, 1H), 3.16-2.76 (m, 6H), 2.37-2.22 (m, 1H), 2.11 (q, J=10.2 Hz, 1H), 1.84-1.59 (m, 4H). $^{13}$C NMR (101 MHz, CHLOROFORM-d) δ 145.53, 143.46, 127.97, 126.36, 124.66, 124.22, 83.49, 64.46, 46.92, 39.44, 29.26, 26.47, 26.32. LCMS: (M+H$^+$): 204.1, 95.73% purity. Chiral SFC purity: 99.62%.

TLC (Dichloromethane/Methanol=10:1) R$_f$=0.

6. Preparation of Compound 7A.

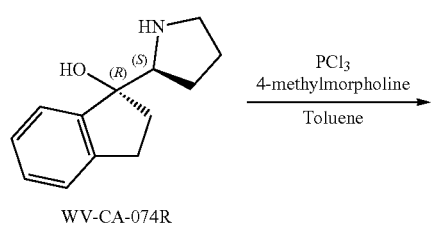

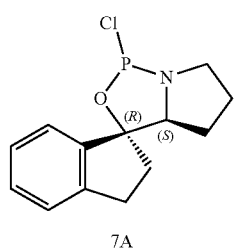

7A

WV-CA-074R (1.50 g, 7.38 mmol) was dried by azeotropic distillation on a rotary evaporator with toluene (20 mL*3). To a solution of PCl$_3$ (1.01 g, 7.38 mmol) in toluene (20 mL) was added a solution of WV-CA-074R (1.50 g, 7.38 mmol) and 4-methylmorpholine (1.49 g, 14.76 mmol) in toluene (20 mL) at 0° C. The mixture was stirred at 15~20° C. for 2 hr. The resulting mixture was filtered (flushed with Ar) and concentrated to afford a residue as a colorless oil. The crude product compound 7A was obtained as a yellow oil (1.40 g, crude), which was used into the next step without further purification.

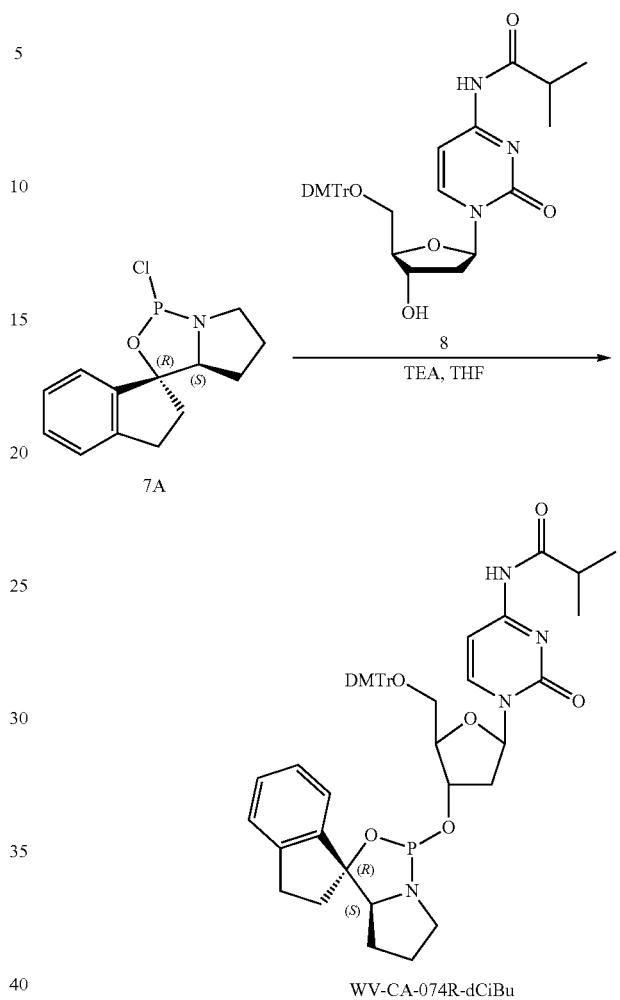

Compound 8 (2.24 g, 3.74 mmol) was dried by azeotropic distillation on a rotary evaporator with pyridine (20 mL) and toluene (20 mL*5). The dried compound 8 (2.24 g, 3.74 mmol) was dissolved in THF (25 mL), and then Et$_3$N (1.89 g, 18.68 mmol, 2.59 mL) was added. The mixture was cooled to −70° C. A solution of compound 7A (1.40 g, 5.23 mmol) in THF (25 mL) was added dropwise at −70° C., then warm to 23° C. over 0.5 hr. and stirred for another 2.5 hr. TLC showed one new major spot, and the starting material was partly remained. The resulting mixture was diluted with DCM (100 mL) at −10° C., washed with ice-cold sat. NaHCO$_3$ aq. (50 mL*3). The aqueous layer was extracted at each washing stage with additional DCM (50 mL). The organic layer was dried over anhydrous MgSO$_4$, filtered, and concentrated to afford a white foam (2.9 g). The MPLC column (flash Silica (CS), 40-60 μm, 60 A, 20 g) was basified by the elution at 80 mL/min with Petroleum ether (40 mL, 5% TEA) and Ethyl acetate (40 mL, 5% TEA). A solution of the crude in Petroleum ether (5 mL, 5% TEA) and Ethyl acetate (10 mL, 5% TEA) was loaded and purified with Petroleum ether (5% TEA):Ethyl acetate (5% TEA)=1:1 to 1:3. All solvent was dried over anhydrous Na$_2$SO$_4$. WV-CA-074R-dCiBu was obtained as a white solid (450.00 mg, 14.50%). $^1$H NMR (400 MHz, CHLOROFORM-d) δ=8.29 (d, J=7.4 Hz, 2H), 7.41 (br d, J=7.3 Hz, 2H), 7.34-7.18 (m, 13H), 7.13-7.05 (m, 1H), 6.82 (br d, J=8.2 Hz, 5H), 6.40-6.18 (m, 1H), 4.96-4.84 (m, 1H), 4.23 (br d, J=4.5 Hz, 1H), 4.09 (t, J=6.7 Hz, 1H), 3.85-3.70 (m, 7H), 3.64-3.45 (m, 3H), 3.17-3.05 (m, 1H), 2.91-2.75 (m, 3H), 2.61 (td, J=6.9, 13.8 Hz, 1H), 2.47-2.28 (m, 3H), 1.76-1.57 (m, 3H), 1.48-1.34 (m, 2H), 1.30-1.17 (m, 8H), 1.14-1.05 (m, 1H), 1.02-0.84 (m, 2H). $^{31}$P NMR (162 MHz, CHLOROFORM-d) δ=154.74 (s, 1P). TLC (Petroleum ether/Ethyl acetate=1:3, 5% TEA) $R_f$=0.28.

8. Preparation of WV-CA-074S.

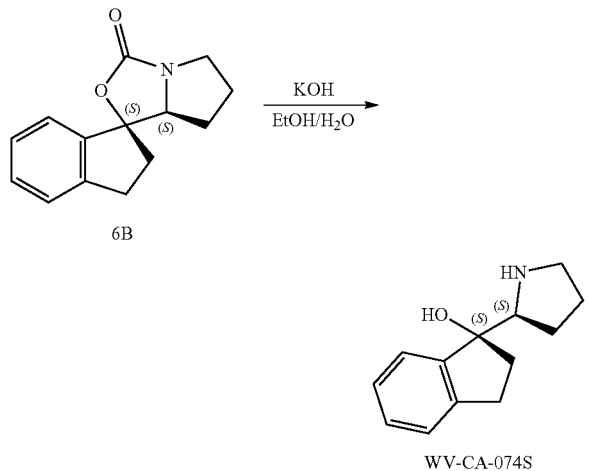

Compound 6B (7.00 g, 30.53 mmol) was dissolved in a solution of KOH (80.00 g, 1.43 mol) in EtOH (60.00 mL) and H$_2$O (60.00 mL). The mixture was heated at 90° C. for 36 hr. TLC showed the reaction was completed, and LCMS showed a main peak with desired MS. The resulting mixture was extracted with DCM (120 mL*3). The combined organic layers were dried over anhydrous MgSO$_4$, filtered, and concentrated to afford the product as a crude, which was purified by column chromatography on silica gel. (Dichloromethane/Methanol=5:1) to afford the product as a brown gum (7 g, crude). $^1$H NMR (400 MHz, CHLOROFORM-d) δ=7.55 (br s, 2H), 7.48-7.40 (m, 1H), 7.45 (br d, J=5.5 Hz, 1H), 7.28-7.08 (m, 3H), 3.88-3.69 (m, 1H), 3.34-2.99 (m, 3H), 2.87-2.67 (m, 1H), 2.40-2.12 (m, 2H), 2.00-1.64 (m, 6H). $^{13}$C NMR (101 MHz, CHLOROFORM-d) δ=145.97, 143.00, 129.03, 128.46, 126.89, 124.97, 82.80, 66.10, 46.08, 35.70, 29.94, 26.62, 25.17. LCMS: (M+H$^+$): 204.1, 86.70% purity. Chiral SFC purity: 99.72%. LCMS: (M+H$^+$): 204.1. TLC (Dichloromethane:Methanol=10:1) $R_f$=0.

9. Preparation of Compound 7B.

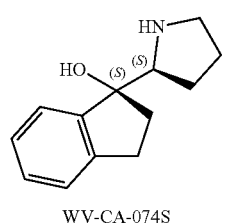

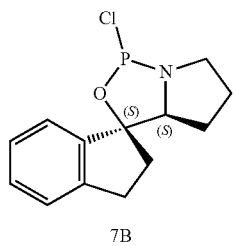

WV-CA-074S (1.50 g, 7.38 mmol) was dried by azeotropic distillation on a rotary evaporator with toluene (20 mL*3). To a solution of PCl$_3$ (1.01 g, 7.38 mmol) in toluene (20 mL) was added a solution of WV-CA-074S (1.50 g, 7.38 mmol) and 4-methylmorpholine (1.49 g, 14.76 mmol, 1.62 mL) in toluene (20 mL) at 0° C. The mixture was stirred at 15~20° C. for 2 hr. The resulting mixture was filtered (flushed with Ar) and concentrated to afford a residue as a colorless oil. The crude product compound 7B was obtained as a yellow oil (1.35 g, crude), which was used into the next step without further purification.

10. Preparation of WV-CA-074S-dCiBu.

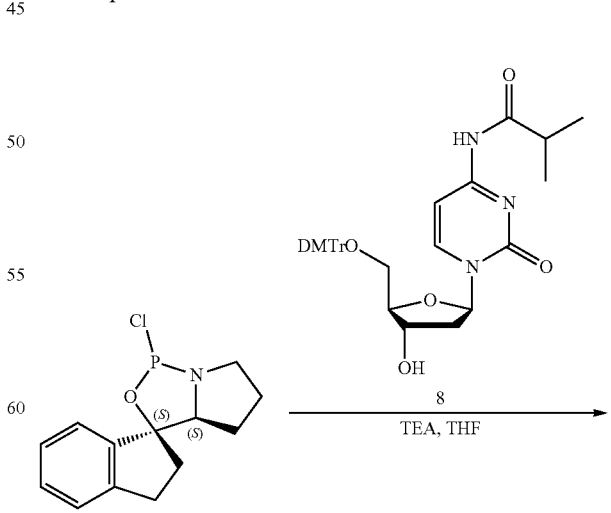

713
-continued

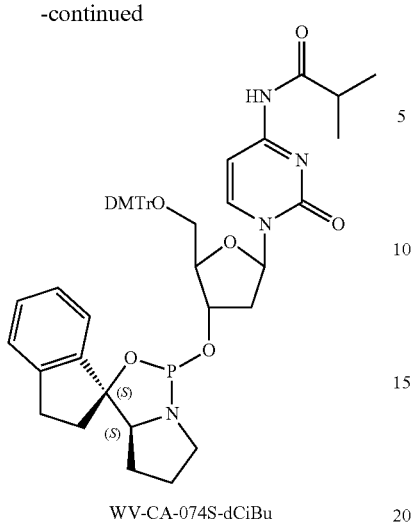

WV-CA-074S-dCiBu

Compound 8 (2.16 g, 3.60 mmol) was dried by azeotropic distillation on a rotary evaporator with pyridine (20 mL) and toluene (20 mL*5). The dried compound 8 (2.16 g, 3.60 mmol) was dissolved in THF (25 mL), and then Et₃N (1.82 g, 18.00 mmol, 2.50 mL) was added. The mixture was cooled to −70° C. A solution of compound 7B (1.35 g, 5.04 mmol) in THF (25 mL) was added dropwise at −70° C., then warm to 23° C. over 0.5 hr. and stirred for another 2.5 hr. TLC showed one new major spot and the starting material was partly remained. The resulting mixture was diluted with DCM (100 mL) at −10° C., washed with ice-cold sat. NaHCO₃ aq. (50 mL*3). The aqueous layer was extracted at each washing stage with additional DCM (50 mL). The organic layer was dried over anhydrous MgSO₄, filtered, and concentrated to afford a white foam (2.8 g). The MPLC column (flash Silica (CS), 40-60 μm, 60 A, 20 g) was basified by the elution at 80 mL/min with Petroleum ether (40 mL, 5% TEA) and Ethyl acetate (40 mL, 5% TEA). A solution of the crude in Petroleum ether (5 mL, 5% TEA) and Ethyl acetate (10 mL, 5% TEA) was loaded and purified with Petroleum ether (5% TEA):Ethyl acetate (5% TEA)=1:1 to 1:3. All solvent was dried over anhydrous Na₂SO₄. WV-CA-074S-dCiBu was obtained as a white solid (1.00 g, 33.43%). ¹H NMR (400 MHz, CDCl₃): δ=9.03-8.76 (m, 1H), 8.23 (d, J=7.4 Hz, 1H), 7.50 (d, J=7.5 Hz, 1H), 7.41-7.35 (m, 2H), 7.33-7.14 (m, 12H), 7.09 (br d, J=7.4 Hz, 1H), 6.83 (d, J=8.8 Hz, 4H), 6.27 (t, J=5.8 Hz, 1H), 4.92-4.79 (m, 1H), 4.09 (t, J=6.7 Hz, 1H), 4.12-4.00 (m, 1H), 3.83-3.77 (m, 6H), 3.86 (br d, J=3.5 Hz, 1H), 3.66-3.52 (m, 1H), 3.20~3.00 (m, 2H), 3.43-3.00 (m, 3H), 2.86-2.61 (m, 4H), 2.30-2.11 (m, 4H), 1.96-1.77 (m, 4H), 1.69-1.53 (m, 2H), 1.46-1.37 (m, 1H), 1.22 (dd, J=3.6, 6.8 Hz, 6H), 0.96 (t, J=7.4 Hz, 1H). ³¹P NMR (162 MHz, CHLOROFORM-d) δ=154.33 (s, 1P). TLC (Petroleum ether/Ethyl acetate=1:3, 5% TEA) R_f=0.28.

714

Example 76. Synthesis of WV-CA-075R and WV-CA-075 R-dCiBu

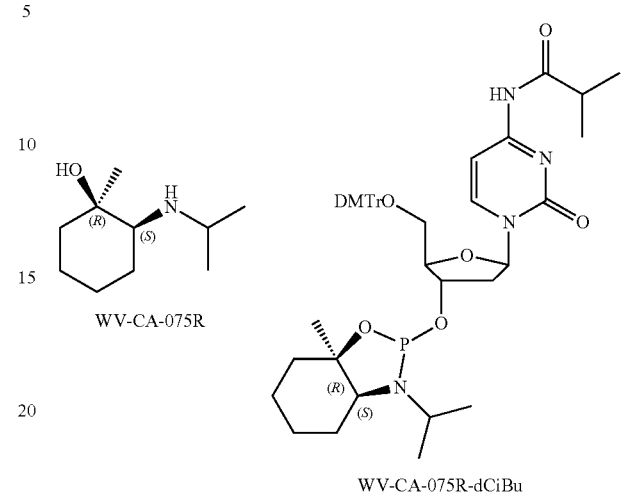

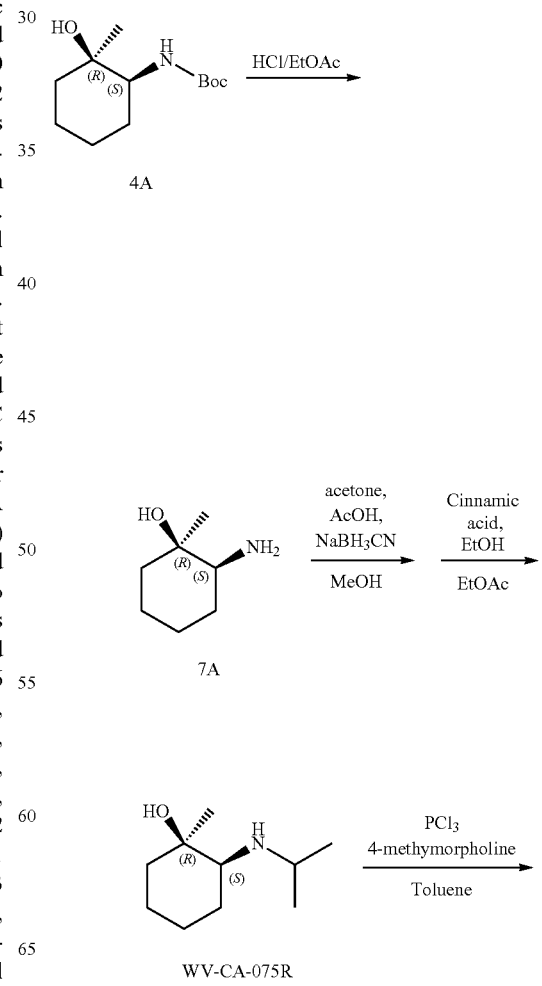

715
-continued

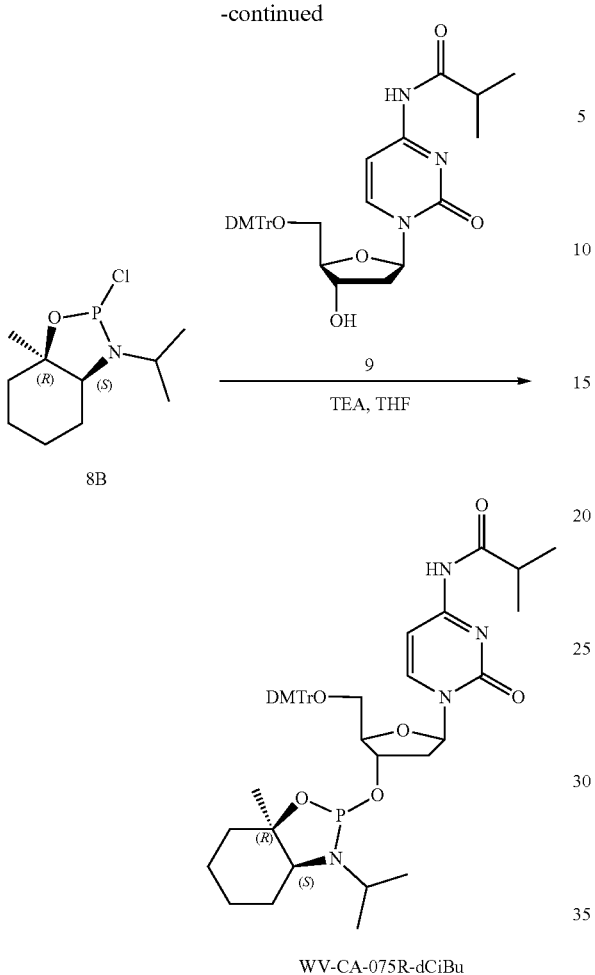

2. Preparation of Compound WV-CA-075R.

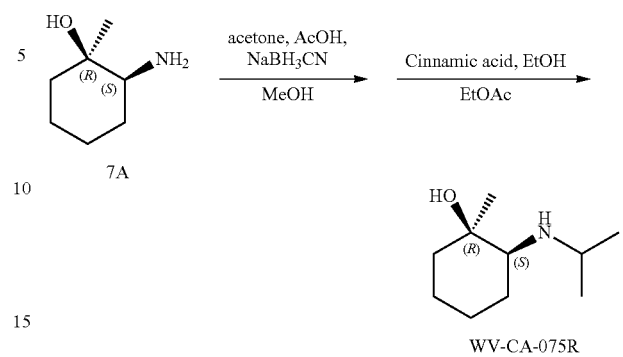

1. Preparation of Compound 7A.

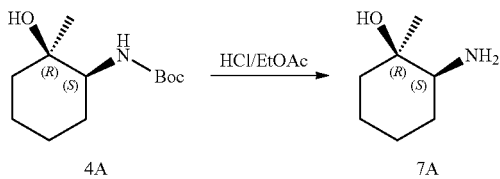

To a solution of compound 4A (10.00 g, 43.61 mmol) in EtOAc (20 mL) was added 4 M HCl/EtOAc (150 mL) at 15° C. The reaction was stirred at 20° C. for 5 hr. TLC and LCMS showed compound 4A was consumed completely. The reaction was concentrated in vacuum to dryness. The residue was washed with EtOAc (30 mL*3), filtered and concentrated in vacuum. The white solid was dissolved in sat. Na$_2$CO$_3$ (~150 mL), dried over freeze-dryer, and washed with DCM:MeOH=10:1 (150 mL*2). The organic phase was dried over MgSO$_4$, filtered, and concentrated in vacuum to dryness. Compound 7A was obtained as white solid (4.50 g, 79.87%). $^1$H NMR (400 MHz, CDCl$_3$): δ=2.62 (dd, J=4.3, 10.3 Hz, 1H), 2.11-1.94 (m, 2H), 1.76-1.67 (m, 1H), 1.65-1.58 (m, 1H), 1.57-1.48 (m, 2H), 1.46-1.34 (m, 2H), 1.30-1.20 (m, 2H), 1.13 (s, 3H). TLC (Petroleum ether/Ethyl acetate=3:1) R$_f$=0.00.

Acetone (12.14 g, 209.00 mmol, 15.37 mL) was added to the solution of compound 7A (5.40 g, 41.80 mmol) in MeOH (15.00 mL) followed by AcOH (525.00 mg, 8.74 mmol). The reaction was stirred for 0.5 hr at 20° C. Then NaBH$_3$CN (3.15 g, 50.16 mmol) was added to the reaction. The reaction was stirred at 20° C. for 3 hr. TLC and LCMS showed compound 7A was consumed and WV-CA-075R was detected. The reaction was partitioned between EtOAc (100 mL) and H$_2$O (100 mL). The separated aqueous phase was extracted with EtOAc (100 mL*5). The combined organic phase was dried over Na$_2$SO$_4$, filtered, and concentrated in vacuo to dryness to obtain crude of WV-CA-075R as yellow oil (7.00 g, crude). To a solution of crude WV-CA-075R (7.00 g, 40.87 mmol) in EtOH (20 mL) was added (E)-3-phenylprop-2-enoic acid (6.06 g, 40.87 mmol). The mixture was heated at 90° C. for 30 minutes. The mixture suspension was concentrated in vacuo to dryness. The white crude solid of WV-CA-075R was dissolved in EtOAc (20 mL) at 90° C. for 0.5 hr. The solution was cooled to 20° C. slowly. A large amount of solid precipitated, and was filtered. The filter cake was concentrated in vacuo to dryness to obtain the cinnamic acid salt of WV-CA-075R. The filtrate was concentrated in vacuo to dryness to give crude cinnamic salt of WV-CA-075R as white solid (10 g). To a solution of cinnamic acid salt of WV-CA-075R (3.50 g, 10.96 mmol) in DCM (50 mL) was added dropwise 2M aqueous of KOH (50 mL) at 20° C. until pH ~13. The reaction was stirred at 20° C. for 0.5 hr, and then extracted with DCM (30 mL*2). The combined organic phase was dried over Na$_2$SO$_4$, and concentrated in vacuo to dryness at 30° C. to afford WV-CA-075R as light yellow oil (1.50 g, 79.93%). The crude of cinnamic salt of WV-CA-075R (crude 10 g) was freed following this procedure to give WV-CA-075R (3.8 g). $^1$H NMR (400 MHz, CDCl$_3$): δ=2.86-2.76 (m, 1H), 2.37 (dd, J=4.2, 7.1 Hz, 1H), 1.66-1.28 (m, 9H), 1.19 (s, 3H), 1.08 (d, J=6.2 Hz, 3H), 1.03 (d, J=6.2 Hz, 3H). $^{13}$C NMR (125.7 MHz, CDCl$_3$): δ=77.32, 77.00, 76.68, 59.64, 47.32, 36.97, 27.83, 26.61, 24.18, 23.35, 22.61, 22.10. LCMS: (M+H+): 172.1.

3. Preparation of Compound 8B.

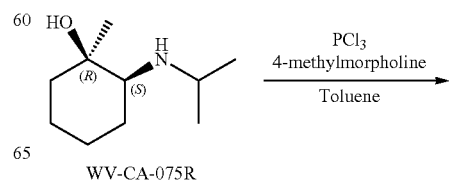

-continued

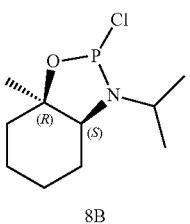

8B

WV-CA-075R (900.00 mg, 5.25 mmol) was dried by azeotropic distillation on a rotary evaporator with toluene (20 mL*3). To a solution of PCl₃ (721.61 mg, 5.25 mmol) in toluene (20 mL) was added a mixture of WV-CA-075R (900.00 mg, 5.25 mmol) and 4-methylmorpholine (1.06 g, 10.51 mmol) in toluene (20 mL) at 0° C. The mixture was stirred at 15~20° C. for 1 hr. The phosphoryl chloride was not suitable for detection and no monitoring. The resulting mixture was filtered (flushed with Ar) and concentrated to afford the compound 8B as a colorless oil (1.00 g, crude), which was used into the next step without further purification.

3. Preparation of WV-CA-075R-dCiBu.

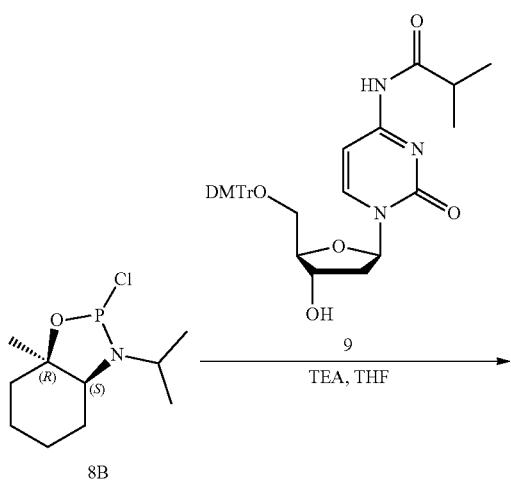

Compound 9 (1.70 g, 2.83 mmol) was dried by azeotropic distillation on a rotary evaporator with Pyridine (50 mL) and toluene (50 mL*5). The dried compound 9 (1.70 g, 2.83 mmol) was dissolved in THF (30.00 mL), and then TEA (1.43 g, 14.17 mmol) was added. The mixture was cooled to −70° C. A solution of compound 8B (1.00 g, 4.25 mmol) in THF (10 mL) was added dropwise at −70° C. After the addition, the mixture was warmed to 23° C. for 1.5 hr. TLC showed compound 9 was consumed and the reaction was completed. The resulting mixture was diluted with DCM (10 mL) at −10° C., washed with ice-cold sat. NaHCO₃ aq. (20 mL*3). The aqueous layer was extracted at each washing stage with additional DCM (50 mL). The organic layer was dried over anhydrous MgSO₄, filtered, and concentrated to afford a crude white foam (1.3 g). The silica gel (SiO₂, 100-200 mesh, 100 g) used for the column chromatography was basified by the elution with MeOH (2 column volumes, 300 mL), Ethyl acetate/5% Et₃N (1 column volume, 150 mL), gradient to 80% Ethyl acetate/Petroleum ether/5% Et₃N (80 mL) to 20% EA/hexane/5% Et₃N (80 mL). A solution of the crude product in DCM (60 mL, 5% TEA) and Petroleum ether (30 mL, 5% TEA) was loaded and purified with Petroleum ether (5% TEA):Ethyl acetate (5% TEA)=5: 1, 1:1 to afford WV-CA-075R-dCiBu as a white solid (1.10 g, 48.65%). All solvent was dried over anhydrous Na₂SO₄.
¹H NMR (400 MHz, CHLOROFORM-d) Shift=8.39-8.30 (m, 1H), 8.29 (br s, 1H), 7.47-7.41 (m, 2H), 7.37-7.30 (m, 7H), 7.28-7.22 (m, 1H), 7.07 (dd, J=7.6, 10.1 Hz, 1H), 6.87 (dd, J=1.5, 8.8 Hz, 4H), 6.28-6.18 (m, 1H), 4.86-4.73 (m, 1H), 4.13-4.08 (m, 1H), 3.83 (d, J=1.5 Hz, 6H), 3.56-3.17 (m, 4H), 2.94-2.85 (m, 1H), 2.95-2.85 (m, 1H), 2.73-2.53 (m, 1H), 2.74-2.51 (m, 1H), 2.39-2.29 (m, 1H), 2.20 (br t, J=9.2 Hz, 1H), 1.90-1.75 (m, 1H), 1.69-1.48 (m, 5H), 1.43 (dd, J=1.5, 6.7 Hz, 2H), 1.33 (s, 3H), 1.26-1.09 (m, 12H).
³¹P NMR (125.7 MHz, CDCl₃): δ=152.81, 143.23. TLC (Ethyl acetate/Petroleum ether=3:1, 5% TEA) R_f=0.53.

Example 77. Synthesis of WV-CA-075S & WV-CA-075S-dCiBu

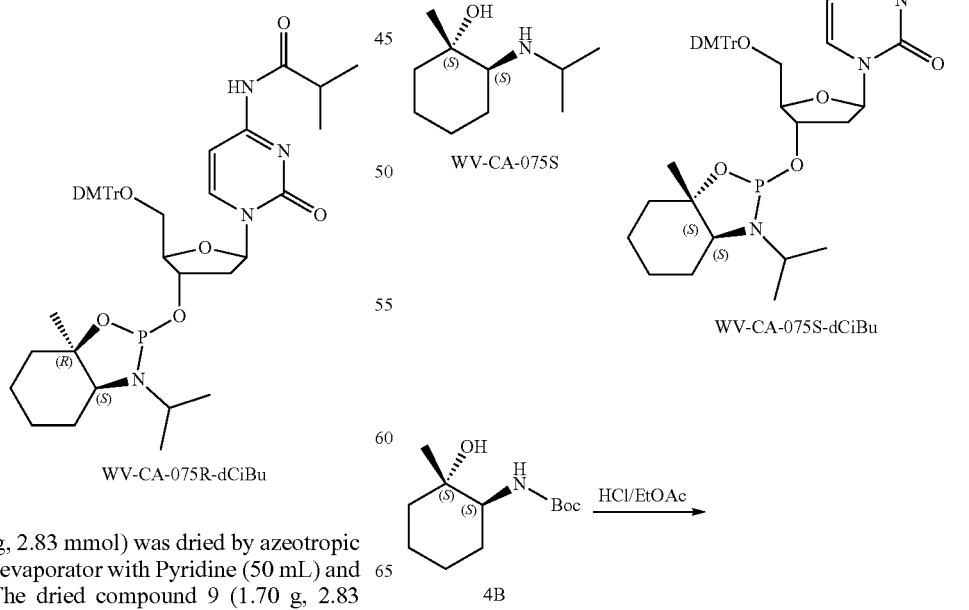

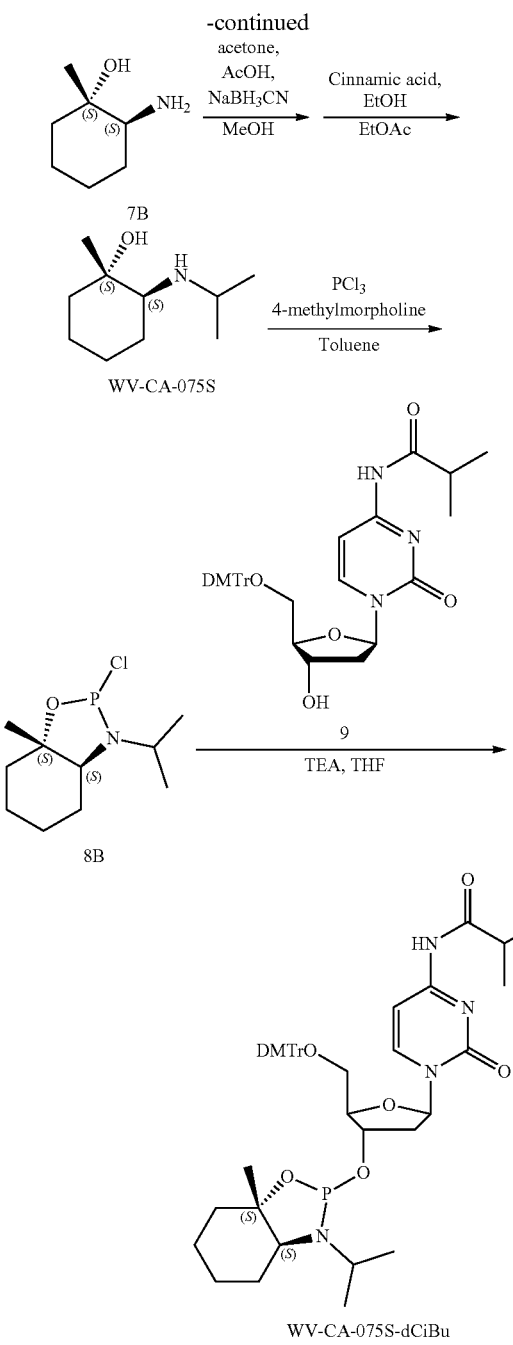

WV-CA-075S-dCiBu

1. Preparation of Compound 7B.

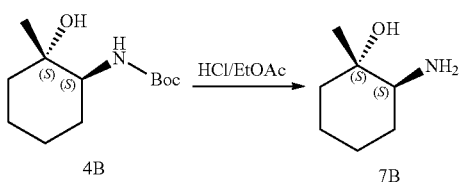

To a solution of compound 4B (10.00 g, 43.61 mmol) in EtOAc (20 mL) was added 4 M HCl/EtOAc (150 mL) at 15° C. The reaction was stirred at 20° C. for 5 hr. TLC and LCMS showed compound 4B was consumed completely. The reaction was concentrated in vacuo. The suspension was filtered and the filter cake was washed with EtOAc (15 mL*2). The HCl salt of compound 7B as white solid was concentrated in vacuo to dryness (6.8 g). The HCl salt of compound 4B was dissolved in DCM (50 mL) and sat. Na$_2$CO$_3$ (50 mL). The organic phase was separated and washed with sat. Na$_2$CO$_3$ (50 mL*2). The aqueous phase was extracted with DCM (100 mL*6). The combined organic phase was dried over Na$_2$SO$_4$, filtered, and concentrated in vacuo to dryness, to give compound 7B as yellow solid (1 g). The sat. Na$_2$CO$_3$ layer (~150 mL) was dried over freeze-dryer, washed with DCM:MeOH=10:1 (100 mL). The organic phase was filtered and concentrated in vacuum to dryness to give compound 7B as white solid (3.9 g). $^1$H NMR (400 MHz, CDCl$_3$): δ=2.57 (dd, J=4.2, 11.2 Hz, 1H), 2.12 (s, 3H), 1.78-1.56 (m, 4H), 1.40-1.12 (m, 4H), 1.11-1.07 (m, 3H). TLC (Petroleum ether:Ethyl acetate=3:1) R$_f$=0.00.

2. Preparation of Compound WV-CA-075S

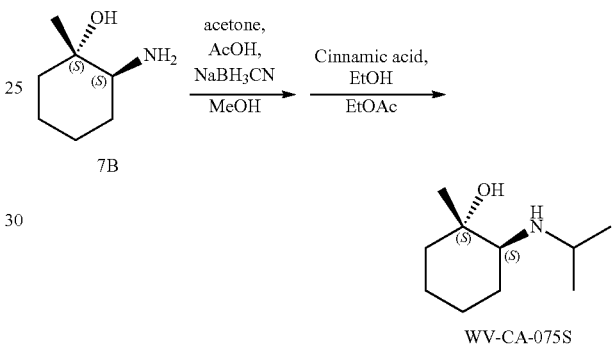

Acetone (9.66 g, 166.40 mmol, 12.23 mL) was added to the solution of compound 7B (4.30 g, 33.28 mmol) in MeOH (10.00 mL) followed by AcOH (315.00 mg, 5.25 mmol). The reaction was stirred for 0.5 hr at 20° C. Then NaBH$_3$CN (2.51 g, 39.94 mmol) was added to the reaction. The reaction was stirred at 20° C. for 3 hr. LCMS showed compound 7B was consumed and WV-CA-075S was detected. The reaction was partitioned between EtOAc (100 mL) and H$_2$O (100 mL). The aqueous phase was extracted with EtOAc (100 mL*5). The combined organic phase was dried over Na$_2$SO$_4$, filtered, and concentrated in vacuo to dryness to obtain crude of WV-CA-075S as yellow oil (5.40 g, crude). To a solution of crude WV-CA-075S (5.40 g, 31.53 mmol) in EtOH (20 mL) was added (E)-3-phenylprop-2-enoic acid (4.67 g, 31.53 mmol). The mixture was heated at 90° C. for 30 minutes. The mixture suspension was concentrated in vacuo to dryness. The white crude solid of P1 was dissolved in EtOAc (30 mL) at 90° C. for 0.5 hr. The solution was allowed to cool to 20° C. slowly. A large amount of solid precipitated and was filtered. The filter cake was concentrated in vacuo to dryness to obtain the cinnamic salt of WV-CA-075S. The filtrate was concentrated in vacuo to dryness to obtain crude cinnamic salt of WV-CA-075S as white solid (10 g). To a solution of cinnamic salt of WV-CA-075S (7.00 g, 21.91 mmol) in DCM (50 mL) was added dropwise 2M aqueous of KOH (50.00 mL) at 20° C. until pH ~13. The reaction was stirred at 20° C. for 0.5 hr. The reaction was extracted with DCM (30 mL*2). The combined organic phase was dried over Na$_2$SO$_4$, concentrated in vacuo to dryness at 30° C. to give WV-CA-075S (2.40 g, 63.94%) as light yellow oil (2.40 g, 63.94%). $^1$H NMR (400 MHz, CDCl₃): δ=2.92 (td, J=5.8, 12.1 Hz, 1H), 2.42-2.30 (m, 1H), 1.94 (br d, J=13.0 Hz, 1H), 1.83-1.70 (m, 2H), 1.64 (br d, J=9.7 Hz, 1H), 1.46-1.21 (m, 3H), 1.08 (br s, 6H), 1.04-0.98 (m, 3H). ¹³C NMR (125.7 MHz, CDCl₃): δ=71.44, 62.65, 45.71, 38.92, 29.56, 25.75, 24.69, 23.33, 22.95, 20.30. LCMS: (M+H+): 204.1.

3. Preparation of Compound 8B.

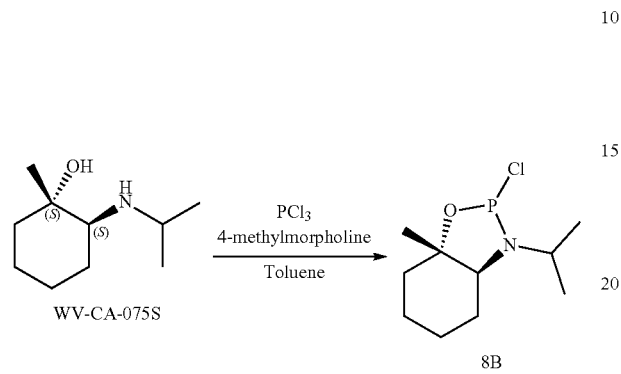

WV-CA-075S (500.00 mg, 2.92 mmol) was dried by azeotropic distillation with toluene (3*40 mL, 100 mL flask). A solution of dried WV-CA-075S (500.00 mg, 2.92 mmol) and 4-methylmorpholine (590.55 mg, 5.84 mmol) in toluene (15 mL) was added dropwise over 0.5 hr to an ice-cold solution of PCl₃ (400.89 mg, 2.92 mmol) in toluene (15 mL, 100 mL two neck flask) at −10~−5° C. in MeOH-ice bath Then the reaction was warmed to 20° C. and stirred for 1.5 hr. The mixture was filtered carefully under Ar. The filter cake was washed with dry toluene (5 mL*2) under Ar and reduced to an oil by rotary evaporation (flushing with Ar) then under high vacuum. The crude yellow oil compound 8B was used in the next step reaction without further purification (646.00 mg, 93.87%).

4. Preparation of Compound WV-CA-075S-dCiBu.

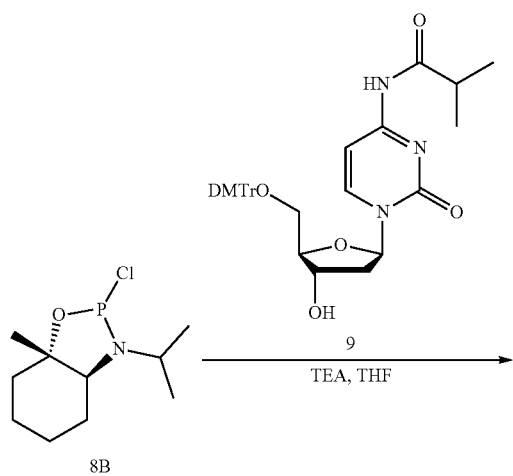

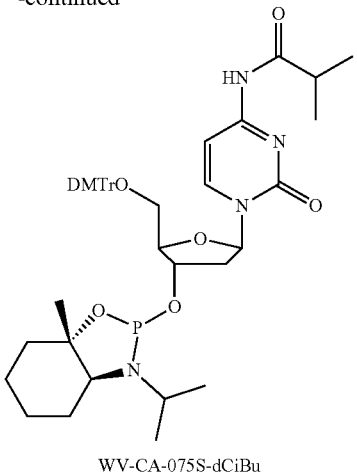

Compound 9 (1.20 g, 2.00 mmol) was dried by azeotropic distillation on a rotary evaporator (Ar flushing) with 1*40 mL anhydrous pyridine and 5*40 mL anhydrous toluene. The rotary temperature of the water bath can be up to 45° C. Dried compound 9 (1.20 g, 2.00 mmol) was dissolved in THF (15 mL), then TEA (1.42 g, 14.01 mmol) was added and the solution was cooled to −70° C. (inner temperature) on a IPA/dry ice bath A solution of the crude compound 8B (646.00 mg, 2.74 mmol) in THF (15 mL) was added dropwise over 0.5 hr, and then the mixture was gradually warmed to 20° C. and stirred at 20° C. for 2 hr. TLC indicated a good conversion. The ice-cold mixture was washed into a separation funnel with CH₂Cl₂ (50 mL) then was washed with NaHCO₃ (sat., aqueous, 3*40 mL). The sat. NaHCO₃ layer was extracted with CH₂Cl₂ (25 mL*2). The combined extract was dried over MgSO₄, filtered and the solvent removed by rotary evaporation at 30° C. to afford the crude product. Then crude solid foam was purified by MPLC (Ethyl acetate:Petroleum ether=3:1 to 5:1, contained 5% TEA) to afford the pure WV-CA-075S-dCiBu as white solid foam. ¹H NMR (400 MHz, CDCl₃): δ=8.51 (br s, 1H), 8.29 (d, J=7.5 Hz, 1H), 7.44 (d, J=7.7 Hz, 2H), 7.36-7.19 (m, 7H), 7.13-7.02 (m, 1H), 6.86 (dd, J=1.6, 8.9 Hz, 4H), 6.29-6.18 (m, 1H), 4.82-4.70 (m, 1H), 4.17-4.06 (m, 1H), 3.90-3.75 (m, 6H), 3.57-3.36 (m, 3H), 3.05 (ddd, J=3.2, 5.0, 12.1 Hz, 1H), 2.75-2.52 (m, 2H), 2.40-2.24 (m, 1H), 2.03-1.04 (m, 23H). ³¹P NMR (400 MHz, CDCl₃): δ=156.35, 142.59. TLC (Ethyl acetate:Petroleum ether=3:1, contained 5% TEA) R_f=0.45.

Example 78. Synthesis of WV-CA-076 and WV-CA-076-dCiBu
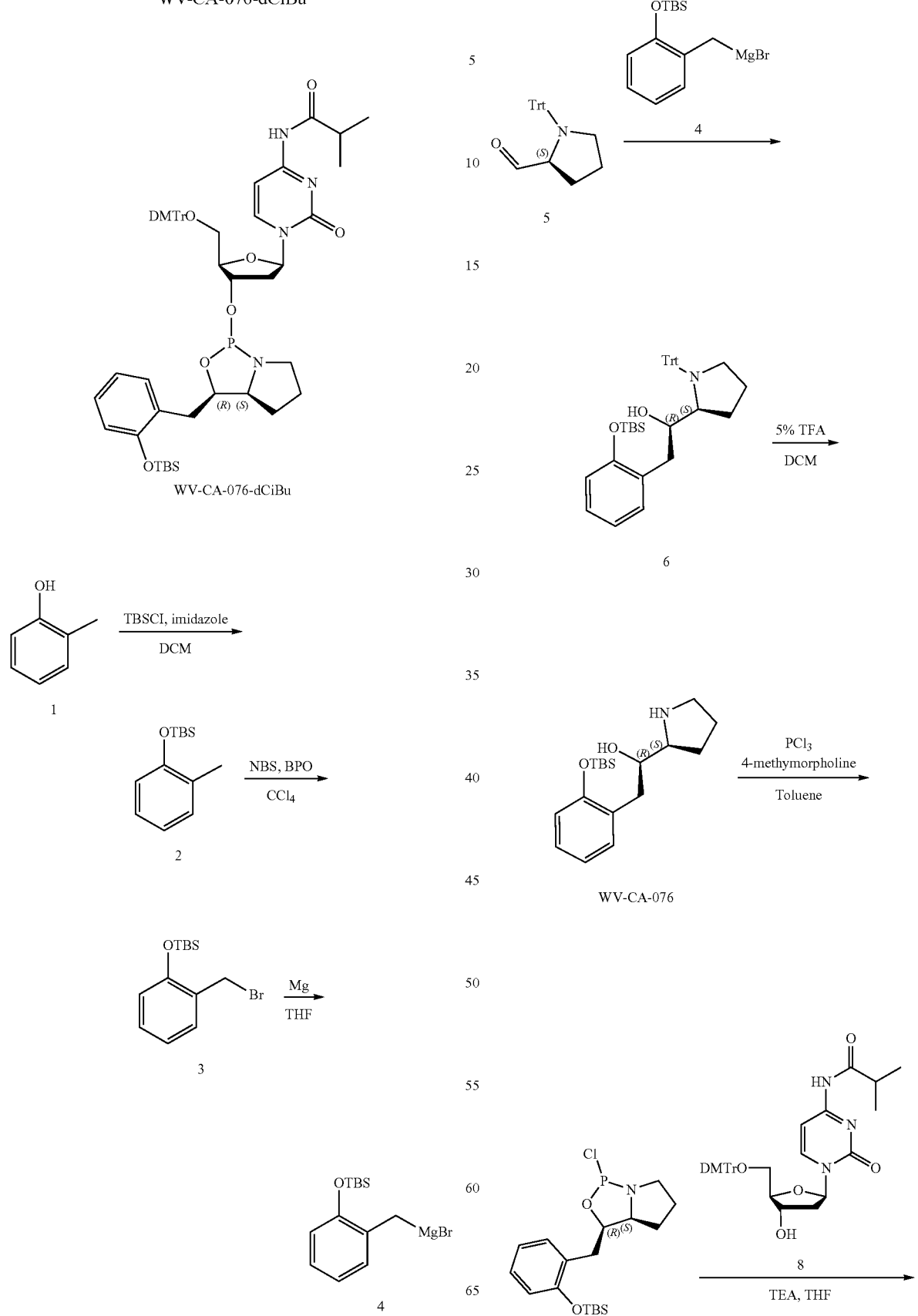

-continued

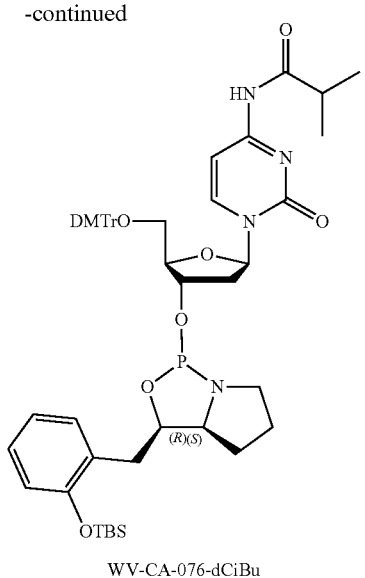

WV-CA-076-dCiBu

1. Preparation of Compound 2.

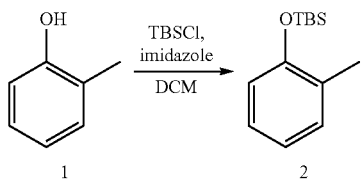

A mixture of compound 1 (80.00 g, 739.78 mmol), TBSCl (133.80 g, 887.74 mmol), imidazole (125.91 g, 1.85 mol) in DMF (320.00 mL) was degassed and purged with $N_2$ for 3 times, and then the mixture was stirred at 25° C. for 3 hr under $N_2$ atmosphere. TLC and LCMS indicated compound 1 was consumed completely and one new spot formed. The reaction was quenched with $NaHCO_3$ (150 mL) and then extracted with Petroleum ether (200 mL*2). The combined organic phase was washed with brine (200 mL*1), dried over anhydrous $Na_2SO_4$, filtered and concentrated in vacuo. Compound 2 was obtained as a colorless liquid (164.00 g, crude). LCMS: (M+H+): 223.3. TLC (Petroleum ether:Ethyl acetate=5:1) $R_f$=0.43.

2. Preparation of Compound 3.

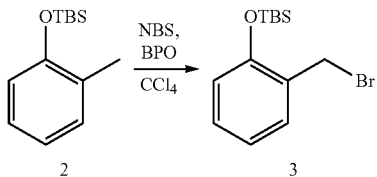

A mixture of compound 2 (164.00 g, 737.41 mmol), NBS (137.81 g, 774.28 mmol), and BPO (17.86 g, 73.74 mmol) in $CCl_4$ (1.00 L), and then the mixture was stirred at 80° C. for 12 hr. TLC showed compound 2 was consumed completely and one new spot formed. The reaction was quenched with $NaHCO_3$ (200 mL) and then extracted with petroleum ether (200 mL*3). The combined organic phase was washed with brine (200 mL*1), dried over anhydrous $Na_2SO_4$, filtered and concentrated in vacuo. The residue was purified by column chromatography ($SiO_2$, Petroleum ether/ Ethyl acetate=1/0 to 1:0). Compound 3 was obtained as a yellow liquid (202.00 g, crude). $^1$H NMR (400 MHz, $CDCl_3$): δ=7.04 (dd, J=7.72, 1.76 Hz, 1H), 6.91-6.86 (m, 1H), 6.62 (td, J=7.50, 1.10 Hz, 1H), 6.52 (dd, J=8.16, 0.88 Hz, 1H), 4.24 (s, 2H), 0.77 (s, 9H), 0.00 (s, 6H). TLC (Petroleum ether:Ethyl acetate=1:0) $R_f$=0.43.

3. Preparation of Compound 4.

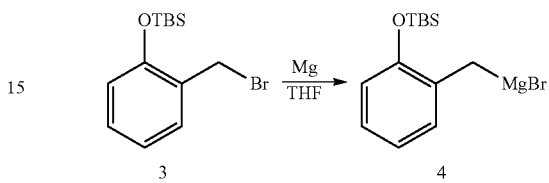

A mixture of Mg (3.87 g, 159.31 mmol) and $I_2$ (25.00 mg, 98.51 μmol) in THF (70 mL) was degassed and purged with $N_2$ for 3 times. To the mixture was added compound 3 (40.00 g, 132.76 mmol) in THF (60 mL) for 4 hr, and then the mixture was stirred at 25° C. for 1 hr under $N_2$ atmosphere. The color of the mixture was changed. The crude product compound 4 in THF was used into the next step without further purification (43.23 g, crude).

4. Preparation of Compound 6.

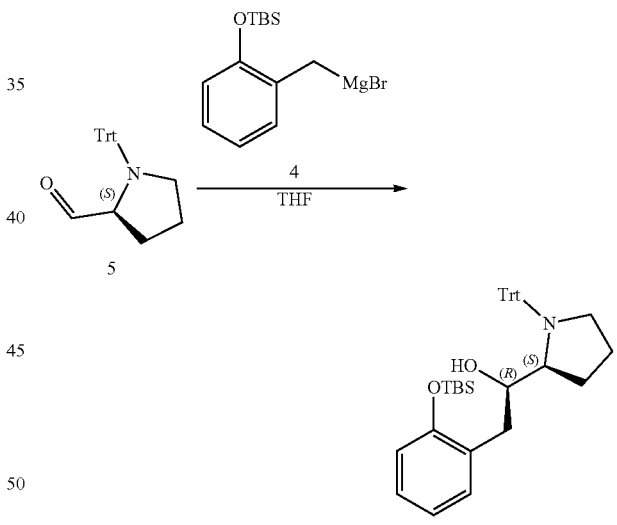

To a solution of compound 4 was added compound 5 (15.11 g, 44.26 mmol) in THF (45.00 mL) at 0° C. The mixture was stirred at 25° C. for 5 hr. TLC indicated compound 5 was consumed completely and one new spot formed. The reaction was clean according to the TLC. The reaction was quenched with sat. $NH_4Cl$ (50 mL) and then extracted with EtOAc (50 mL*2). The combined organic phase was washed with brine (100 mL*1), dried over anhydrous $Na_2SO_4$, filtered and concentrated in vacuo. The residue was purified by column chromatography ($SiO_2$, Petroleum ether/Ethyl acetate=70/1 to 10:1). Compound 6 (18.00 g, crude) was obtained as a yellow oil. TLC (Petroleum ether:Ethyl acetate=10:1) $R_f$=0.35.

5. Preparation of Compound WV-CA-076.

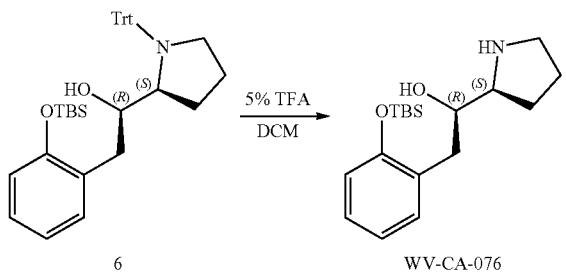

A mixture of compound 6 (12.00 g, 21.28 mmol, 1.00 eq.) in DCM (40.00 mL) was cooled to 0° C., and then to the mixture was added TFA (2.00 mL). The mixture was stirred at 25° C. for 2 hr. TLC indicated compound 6 was consumed completely and one new spot formed. The reaction was quenched with sat. NaHCO$_3$ (40 mL) at 0° C., and then extracted with EtOAc (40 mL*3). The combined organic phase was washed with brine (40 mL*1), dried over anhydrous Na$_2$SO$_4$, filtered and concentrated in vacuo. The residue was purified by column chromatography (SiO$_2$, Dichloromethane:Methanol=50/1 to 10/1, 5% TEA), Compound WV-CA-076 was obtained as a yellow oil (5.00 g, crude). $^1$H NMR (400 MHz, CDCl$_3$): δ=7.10-6.98 (m, 2H), 6.84-6.66 (m, 2H), 0.14 (d, J=4.63 Hz, 5H), 3.30 (br t, J=6.50 Hz, 1H), 3.04-2.96 (m, 2H), 2.80-2.59 (m, 3H), 2.01-1.68 (m, 4H), 0.91 (s, 8H). TLC (Dichloromethane/Methanol=10:1) R$_f$=0.06.

6. Preparation of Compound 7.

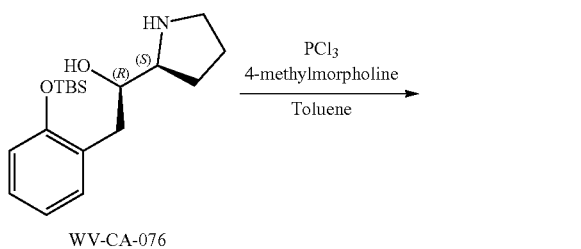

A mixture of PCl$_3$ (811.52 mg, 5.91 mmol) in toluene (10.00 mL) was degassed and purged with N$_2$ for 3 times, and then the mixture was cooled to -10° C., to which was added a solution of WV-CA-076 (1.90 g, 5.91 mmol) and NMM (1.20 g, 11.82 mmol) in toluene (10.00 mL), and then the mixture was stirred at 20° C. for 1 hr under N$_2$ atmosphere. The mixture was stirred at 15~20° C. for 1.5 hr. The phosphoryl chloride was not suitable for detection and no monitoring. The resulting mixture was filtered (flushed with Ar) and concentrated to afford the crude product compound 7 as a colorless oil, which was used into the next step without further purification (2.40 g, crude).

7. Preparation of WV-CA-076-dCiBu.

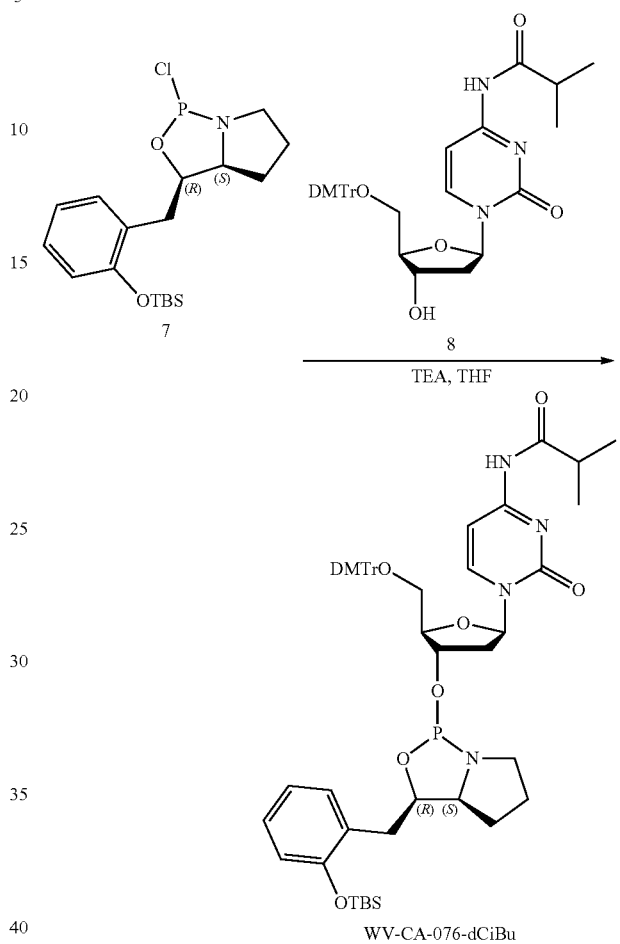

Compound 8 (2.28 g, 4.73 mmol) was dried by azeotropic distillation on a rotary evaporator with pyridine (50 mL) and toluene (50 mL*5). The dried compound 8 (2.02 g, 3.38 mmol) was dissolved in THF (30.00 mL), and then TEA (2.78 g, 27.50 mmol, 3.81 mL) was added. The mixture was cooled to -70° C. A solution of compound 7 (2.28 g, 4.73 mmol) in THF (20 mL) was added dropwise at -70° C., after the addition, the mixture was warmed to 23° C. for 1 hr. TLC (Ethyl acetate/Petroleum ether=3:1, 5% TEA) showed most of compound 8 disappeared. The resulting mixture was diluted with DCM (30 mL) at -10° C., washed with ice-cold sat. NaHCO$_3$ aq. (30 mL*3). The aqueous layer was extracted with additional DCM (50 mL) at each washing stage. The organic layer was dried over anhydrous MgSO$_4$, filtered, and concentrated to afford a white foam (crude, 5.7 g). The above crude material was purified on a CombiFlash instrument from Teledyne using a pre-treated silica gel column. A 40 g silica gel cartridge column was first pre-treated by eluting with 5 column volumes of methanol, before equilibration with 5 column volumes of 20% EtOAc/hexanes containing 5% Et$_3$N. 5.7 g of crude product was dissolved in a 2:1 volume:volume mixture of DCM:Petroleum ether containing 5% Et$_3$N, then loaded onto a 40 g silica column which had been equilibrated with 5 g column volumes of 20% Hexanes/EtOAc containing 5% Et$_3$N. After loading the sample on the column, the purification process was run using the following gradient: 20 to 80% EtOAc/hexanes containing 5% Et$_3$N, then the residual solvent was removed to afford WV-CA-076-dCiBu (400.00 mg, 12.47%) as a white solid. All solvent was dried over anhydrous Na$_2$SO$_4$ (400.00 mg, 12.47%). $^1$H NMR (400 MHz, CHLOROFORM-d) δ=8.17 (br s, 1H), 8.02 (d, J=7.5 Hz, 1H), 7.20~7.15 (m, 2H), 7.09-7.03 (m, 7H), 6.94-6.90 (m, 1H), 6.86-6.78 (m, 2H), 6.65-6.61 (m, 4H), 6.56-6.48 (m, 2H), 6.02 (t, J=5.8 Hz, 1H), 4.75 (td, J=5.6, 8.2 Hz, 1H), 4.61-4.48 (m, 1H), 3.79-3.72 (m, 1H), 3.59 (s, 6H), 3.58-3.54 (m, 1H), 3.42-3.21 (m, 2H), 3.03-2.88 (m, 1H), 2.83-2.74 (m, 1H), 2.65 (br dd, J=8.3, 14.1 Hz, 1H), 2.57-2.46 (m, 1H), 2.44-2.27 (m, 2H), 2.08-1.96 (m, 1H), 1.79-1.36 (m, 3H), 1.24-1.09 (m, 1H), 1.00 (dd, J=3.6, 6.8 Hz, 6H), 0.80-0.76 (m, 9H), 0.00 (d, J=0.9 Hz, 6H). $^{31}$P NMR (162 MHz, CHLOROFORM-d) δ=157.229 (s, 1P).

Example 79. Synthesis of WV-CA-078 and WV-CA-078-dCiBu

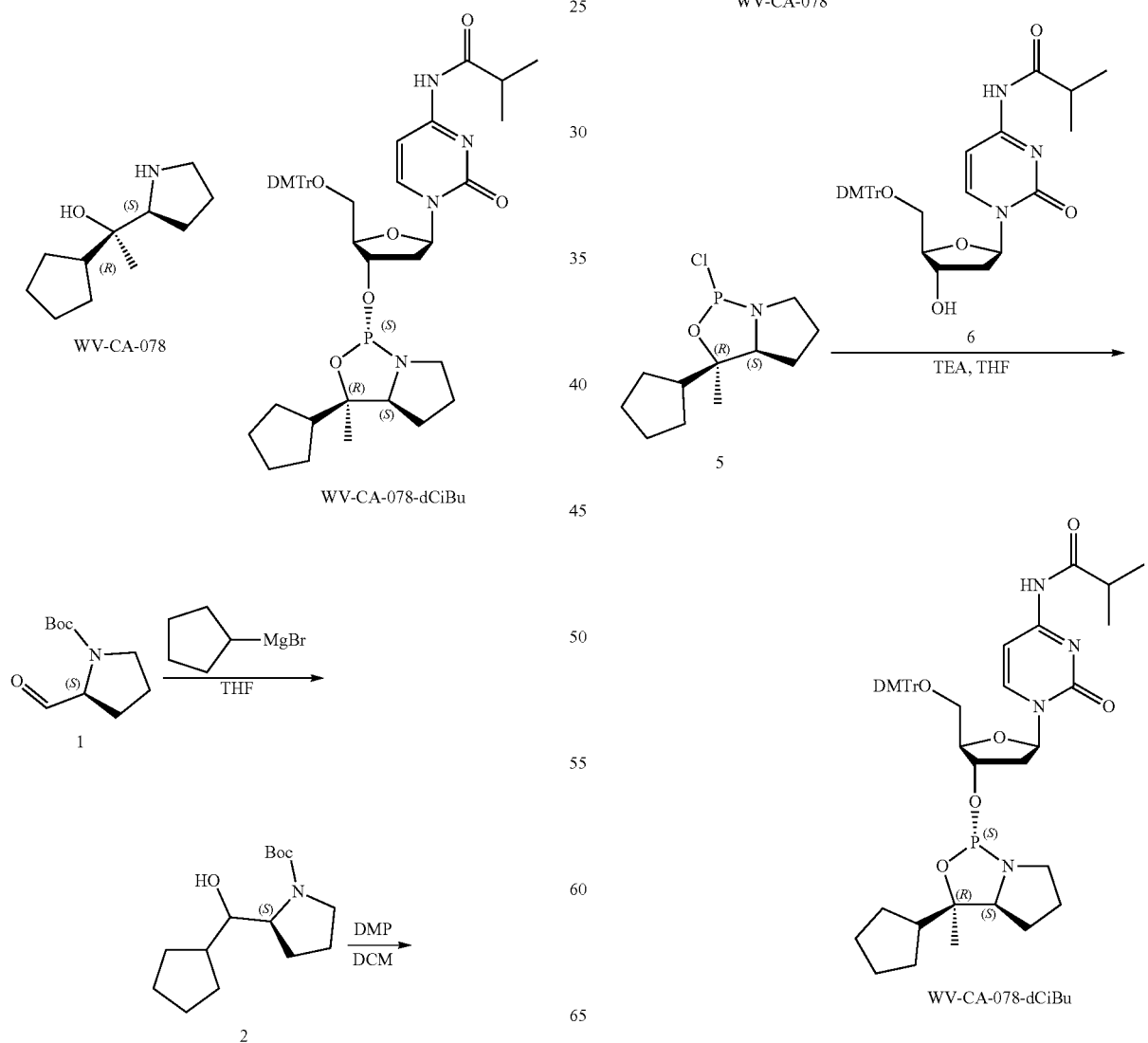

1. Preparation of Compound 2.

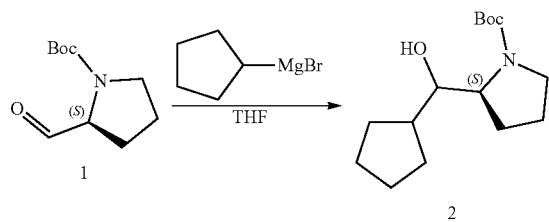

To a solution of compound 1 (30.00 g, 150.56 mmol) in THF (60.00 mL) was added bromo(cyclopentyl)magnesium (1 M, 301.12 mL) at −15-0° C. over 2 hr. The mixture was stirred at 0-15° C. for 2 hr. TLC showed compound 1 was consumed. The reaction mixture was slowly added into ice-cold NH$_4$Cl aq. (200 mL) at 0° C., and then extracted with ethyl acetate (300 mL*3), dried over Na$_2$SO$_4$, filtered and concentrated under reduced pressure to give a residue. The residue was purified by column chromatography (SiO$_2$, Petroleum ether/Ethyl acetate=50:1 to 1:1). Compound 2 was obtained as a colorless oil (22.00 g, 54.24%). $^1$H NMR (400 MHz, CHLOROFORM-d) δ=4.70 (br s, 1H), 3.83 (dt, J=3.7, 8.5 Hz, 1H), 3.44 (br s, 2H), 3.32-3.23 (m, 1H), 1.94-1.64 (m, 6H), 1.64-1.48 (m, 7H), 1.47-1.34 (m, 11H). TLC (Petroleum ether:Ethyl acetate=5:1) R$_f$=0.46.

2. Preparation of Compound 3.

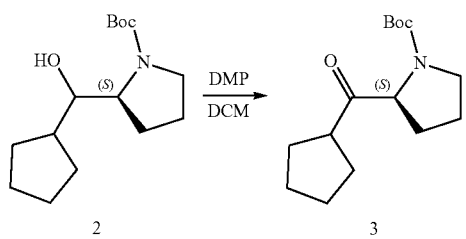

To a solution of compound 2 (22.00 g, 81.67 mmol) in DCM (220.00 mL) was added DMP (41.57 g, 98.00 mmol, 30.34 mL) at 0° C. The mixture was stirred at 10-20° C. for 2 hr. LCMS and TLC showed compound 2 was consumed and MS with the desired compound was detected. The mixture was diluted with DCM (200 mL) and quenched by the addition of Na$_2$SO$_3$ (200 mL) at 0° C. and stirring for 20 minutes. The organic layer was washed with NaHCO$_3$ (aq., 100 mL*2) and extracted with DCM (100 mL*3). The combined organic layers were dried over Na$_2$SO$_4$, filtered, and concentrated under reduced pressure to give a residue. The residue was purified by column chromatography (SiO$_2$, Petroleum ether/Ethyl acetate=50/1 to 5:1) to give 19 g compound 3 as a white solid (19 g, 87.02%). $^1$H NMR (400 MHz, CHLOROFORM-d) δ=4.47-4.27 (m, 1H), 3.55-3.35 (m, 2H), 3.04-2.91 (m, 1H), 2.23-1.96 (m, 1H), 1.87-1.63 (m, 9H), 1.60-1.52 (m, 2H), 1.43-1.36 (m, 10H). LCMS: (M+Na+): 289.9. Chiral SFC purity: 100.0%. TLC (Petroleum ether:Ethyl acetate=5:1) R$_f$=0.43.

3. Preparation of Compound 4.

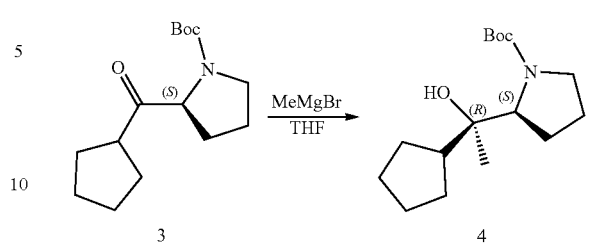

To a solution of compound 3 (18.70 g, 69.94 mmol) in THF (80.00 mL) was added MeMgBr (3 M, 69.94 mL) at −5-0° C. The mixture was stirred at 15° C. for 2 hr. LCMS and TLC showed compound 3 was consumed and MS with the desired compound was detected. The reaction mixture was added into ice-cold NH$_4$Cl (200 mL) at 0° C., and then extracted with ethyl acetate (200 mL*3), dried over Na$_2$SO$_4$, filtered and concentrated under reduced pressure to give a residue. The residue was purified by MPLC (SiO$_2$, Petroleum ether:Ethyl acetate=20:1 to 5:1) to give compound 4 was obtained as a yellow solid (15.50 g, 78.20%). $^1$H NMR (400 MHz, CHLOROFORM-d) δ=5.39 (br s, 1H), 3.89 (br t, J=6.6 Hz, 1H), 3.61 (br s, 1H), 3.18-3.07 (m, 1H), 1.97 (br s, 1H), 1.79 (br s, 2H), 1.72 (br s, 1H), 1.67-1.47 (m, 7H), 1.44 (s, 9H), 1.38 (br s, 2H), 1.07 (s, 3H). Chiral SFC purity: 100.0%. LCMS: (M+H+): 284.2. TLC (Petroleum ether:Ethyl acetate=5:1, three times) R$_f$=0.38.

4. Preparation of Compound WV-CA-078.

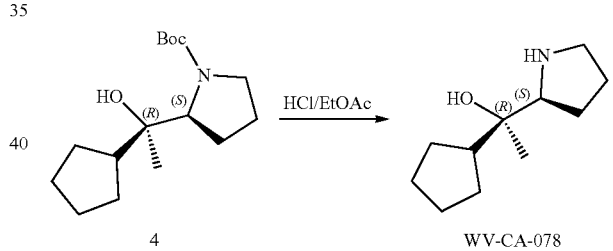

To a solution of compound 4 (12.00 g, 42.34 mmol) in EtOAc (20.00 mL) was added HCl/EtOAc (200.00 mL, 4 N) at 0° C. The mixture was stirred at 20° C. for 2 hr. TLC showed compound 4 was consumed. The mixture was concentrated under reduced pressure until 50 mL solvent remained, filtered to give a residue. The residue was dissolve in H$_2$O (20 mL), washed with EtOAc (20 mL*3), and added Na$_2$CO$_3$ (aq.) until over pH 11, and then the mixture was extracted with EtOAc (50 mL*6) and concentrated under reduced pressure to give compound WV-CA-078 as a yellow oil (6.9 g, 88.9%). $^1$H NMR (400 MHz, CHLOROFORM-d) δ=3.01 (br t, J=7.6 Hz, 1H), 2.96-2.85 (m, 2H), 2.50 (br s, 1H), 2.03-1.90 (m, 1H), 1.80-1.42 (m, 11H), 1.26-1.09 (m, 1H), 1.04 (s, 3H). $^{13}$C NMR (101 MHz, CHLOROFORM-d) δ=73.72, 65.80, 46.62, 46.49, 27.52, 26.92, 26.09, 25.72, 25.62, 25.16, 21.09. LCMS: (M+H+): 184.1, 100.0% purity. TLC (Petroleum ether:Ethyl acetate=3:1) R$_f$=0.

5. Preparation of Compound 5.

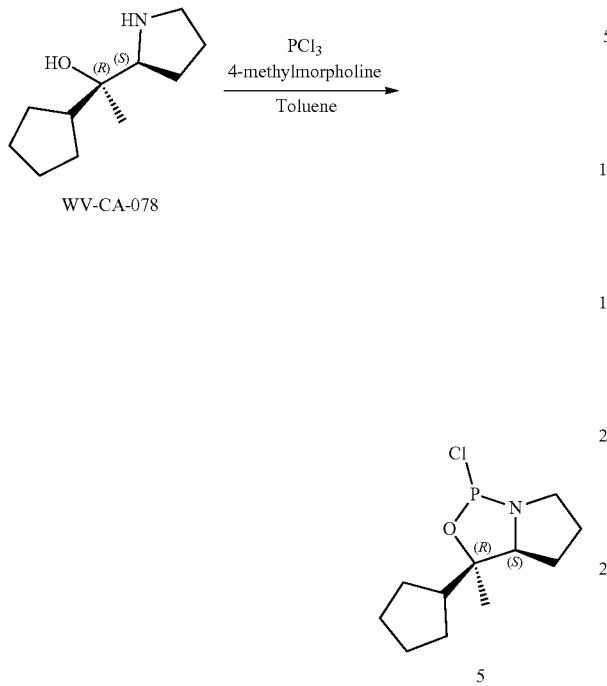

Compound WV-CA-078 (2.00 g, 10.91 mmol) was dried by azeotropic distillation on a rotary evaporator with toluene (40 mL*5). To a solution of PCl₃ (1.50 g, 10.91 mmol) in toluene (30 mL) was added a solution of compound WV-CA-078 (2.00 g, 10.91 mmol) and 4-methylmorpholine (2.21 g, 21.82 mmol, 2.40 mL) in toluene (30 mL) at −5-0° C. over 0.5 hr. The mixture was stirred at 15~20° C. for 1.5 hr. The resulting mixture was filtered (flushed with Ar) and concentrated to afford a residue as a colorless oil. The crude product compound 5 was obtained as a yellow oil (2.60 g, crude), which was used into the next step without further purification.

6. Preparation of Compound WV-CA-078-dCiBu.

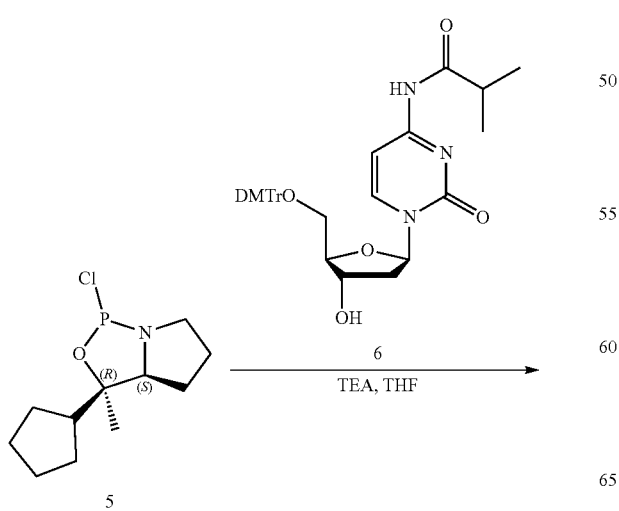

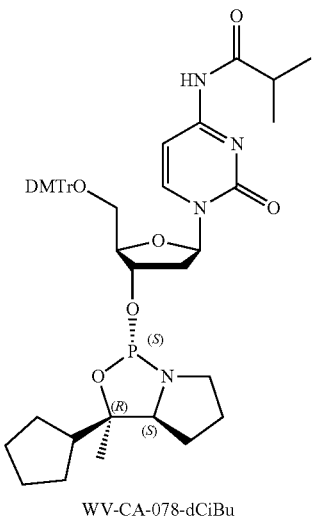

Compound 6 (4.20 g, 7.00 mmol) was dried by azeotropic distillation on a rotary evaporator with pyridine (40 mL) and toluene (40 mL*5). The dried compound 6 (4.20 g, 7.00 mmol) was dissolved in THF (30 mL), and then Et₃N (3.54 g, 35.00 mmol, 4.85 mL) was added. The mixture was cooled to −70° C. A solution of compound 5 (2.60 g, 10.50 mmol) in THF (30 mL) was added dropwise at −60-70° C., then warmed to 23° C. over 0.5 hr and stirred for another 1.5 hr. TLC showed one new major spot and compound 6 was partly remained. The resulting mixture was diluted with DCM (60 mL), washed with sat. NaHCO₃ aq. (30 mL*3). The organic layer was dried over anhydrous MgSO₄, filtered, and concentrated to afford a white foam. The residue was purified by MPLC (SiO₂, Petroleum ether:Ethyl acetate=5:1 to 1:2, 5% TEA). Compound WV-CA-078-dCiBu was obtained as a white solid (2.00 g, 35.23%). ¹H NMR (400 MHz, CHLOROFORM-d) δ=8.42 (br s, 1H), 8.16 (d, J=7.4 Hz, 1H), 7.33 (d, J=7.3 Hz, 2H), 7.27-7.13 (m, 8H), 6.98 (d, J=7.4 Hz, 1H), 6.77 (dd, J=1.4, 8.8 Hz, 4H), 6.18 (t, J=5.7 Hz, 1H), 4.69 (br dd, J=5.5, 8.9 Hz, 1H), 4.12 (br d, J=4.3 Hz, 1H), 3.73 (s, 6H), 3.47-3.27 (m, 4H), 3.10-2.95 (m, 1H), 2.66 (td, J=5.9, 13.6 Hz, 1H), 2.58-2.48 (m, 1H), 2.21 (td, J=5.9, 13.5 Hz, 1H), 2.03 (quin, J=8.3 Hz, 1H), 1.93-1.80 (m, 1H), 1.79-1.29 (m, 12H), 1.27 (s, 3H), 1.13 (dd, J=4.0, 6.8 Hz, 6H). ³¹P NMR (162 MHz, CHLOROFORM-d) δ=158.38 (s, 1P). TLC (Petroleum ether:Ethyl acetate=1:3, 5% TEA) R_f=0.28.

Example 80. Synthesis of WV-CA-078D

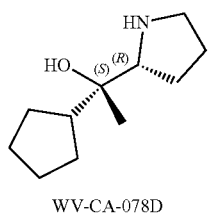

General Scheme

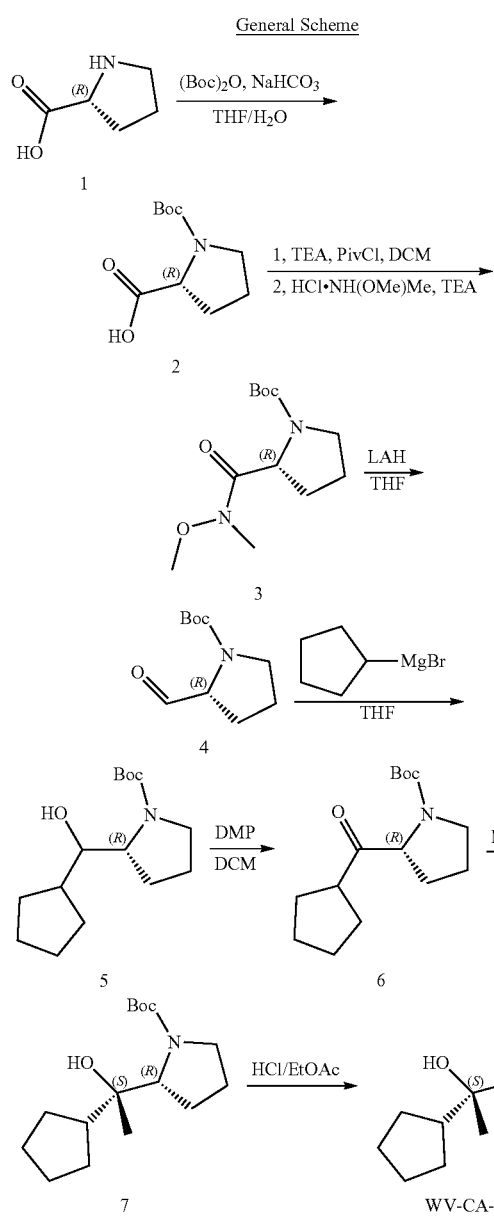

WV-CA-078D

1. Preparation of Compound 2.

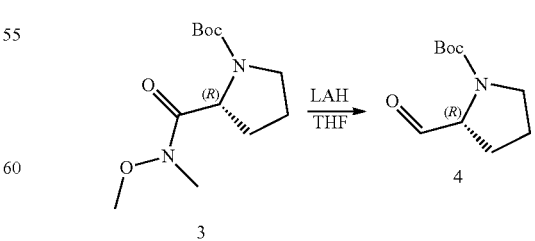

A solution of compound 1 (125.00 g, 1.09 mol) in NaHCO₃ aq. (1.50 L) was cooled in an ice bath at 0° C., treated dropwise with a solution of Boc₂O (261.68 g, 1.20 mol, 275.45 mL) in THF (700.00 mL) and stirred for 19 hr at 20° C. TLC showed the starting material was consumed completely, and one new spot was detected. In the following THF was removed under reduced pressure, the residue cooled to 0° C., then acidified by the addition of 400 mL of 3 N HCl solution and 1600 mL of 3 M HCl solution from pH=8 to 2 and extracted three times with 400 mL of EtOAc. After dried of the combined organic phases over Na₂SO₄, concentrate under reduced pressure and dried in oil pump vacuum to get compound 2 (204.00 g, 86.95% yield) as a white solid. ¹H NMR (400 MHz, CHLOROFORM-d) δ=4.46-4.17 (m, 1H), 3.62-3.29 (m, 2H), 2.46-2.22 (m, 1H), 2.13-1.83 (m, 3H), 1.55-1.34 (m, 9H). TLC (Petroleum ether:EtOAc=3:1) Rf=0.19.

2. Preparation of Compound 3.

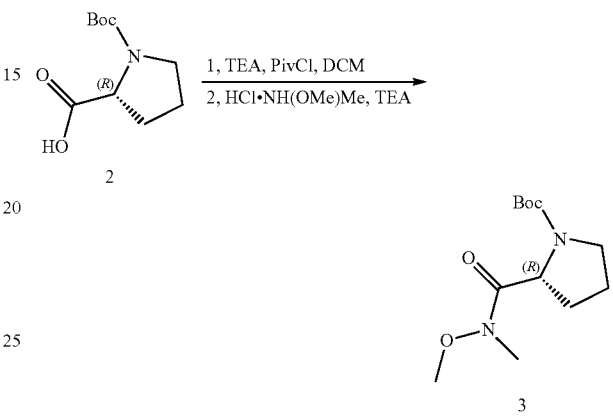

To a stirred solution of compound 2 (200.00 g, 929.15 mmol) in DCM (2.00 L) at −5° C. to 0° C., Et₃N (103.42 g, 1.02 mol, 141.68 mL) was added. After stirred for 15 minutes, trimethylacetyl chloride (117.64 g, 975.61 mmol, 120.04 mL) was added. After stirred for another 1 hr at 0° C., N, O-dimethylhydroxylamine hydrochloride (95.16 g, 975.61 mmol) was added in one pot, followed by dropwise addition of Et₃N (197.44 g, 1.95 mol, 270.47 mL). The reaction mixture was stirred for another 1.5 hr at 0° C. TLC showed the starting material was almost consumed; one new spot was shown on TLC. The mixture subjected to dilute by HCl (10%, 500 mL), extracted with EtOAc (500 mL*3). The combined organic layers were dried over Na₂SO₄, filtered, and concentrated under reduced pressure to give a residue. The mixture was purified by column chromatography (SiO₂, Petroleum ether/Ethyl acetate=30/1 to 5:1) to afford compound 3 (220.00 g, 851.69 mmol, 91.66% yield) as a yellow oil. ¹H NMR (400 MHz, CHLOROFORM-d) δ=4.73-4.47 (m, 1H), 3.76-3.63 (m, 3H), 3.58-3.27 (m, 2H), 3.13 (s, 3H), 2.22-2.05 (m, 1H), 1.96-1.71 (m, 3H), 1.46-1.31 (m, 9H). LCMS: (M+Na+) 281.1.

TLC (Petroleum ether:Ethyl acetate=3:1) R_f=0.06.

3. Preparation of Compound 4.

To a solution of compound 3 (220.00 g, 851.69 mmol) in THF (1.00 L) was slowly added LiAlH₄ (35.55 g, 936.86 mmol) at −15° C.-0° C. over 1 hr. The mixture was stirred at −10° C. for 1 hr. TLC showed compound 3 was consumed completely and one new spot was detected. Two batches of the reaction were quenched with sat. MgSO₄ (aq., 142 mL) at −10-0° C. The suspension was diluted with EtOAc (600 mL). The residue was filtered, washed with EtOAc (1000 mL). The organic phase was dried over anhydrous MgSO₄ and concentrated in vacuo to dryness in water bath at 30° C. to get compound 4 (333.00 g, crude) as a yellow oil was used into the next step without further purification. TLC (Petroleum ether:Ethyl acetate=5:1) $R_f$=0.48.

4. Preparation of Compound 5.

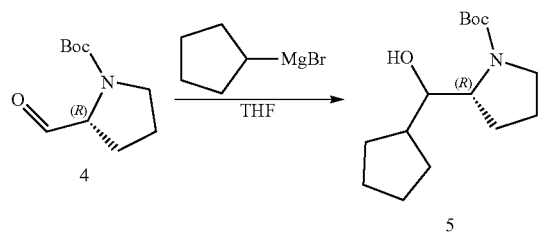

To a solution of compound 4 (166.50 g, 835.63 mmol) in THF (1.00 L) was added bromo(cyclopentyl)magnesium (2 M, 501.38 mL) at −15-0° C. over 2 hr. The mixture was stirred at 25° C. for 3 hr. TLC showed the starting material was partly remained. Then the mixture was added bromo(cyclopentyl)magnesium (2 M, 83.56 mL) at around 0° C. over 0.5 hr. The mixture was stirred at 25° C. for 16 hr. TLC showed the starting material was little remained. Two batches reaction mixture was slowly added in ice sat. NH₄Cl (aq., 2000 mL) at 0° C., and then extracted with ethyl acetate (2000 mL*3), dried over Na₂SO₄, filtered and concentrated under reduced pressure to give a residue. The residue was purified by column chromatography (SiO₂, Petroleum ether/Ethyl acetate=50:1 to 1:1) to give two batches of compound 5 as a yellow oil. Batch 1 (58 g), Batch 2 (80 g); 92 g crude recovered compound 4 as a yellow oil. ¹H NMR (400 MHz, CHLOROFORM-d) δ=4.68 (br s, 1H), 3.90-3.77 (m, 1H), 3.54-3.37 (m, 2H), 3.32-3.20 (m, 1H), 2.03-1.51 (m, 11H), 1.50-1.39 (m, 9H). TLC (Petroleum ether:Ethyl acetate=5:1) $R_f$=0.46.

5. Preparation of Compound 6.

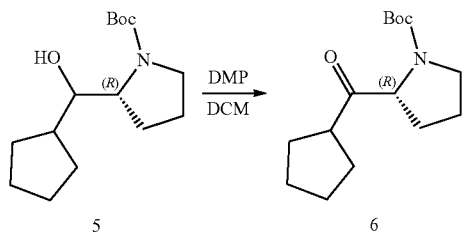

To a solution of compound 5 (138.00 g, 512.29 mmol) in DCM (1.00 L) was added DMP (260.74 g, 614.74 mmol, 190.32 mL) (Split three parts added in mixture) at 0° C. over 1 hr. The mixture was stirred at 10-20° C. for 3 hr. TLC showed compound 5 was consumed and one new spot was detected. The mixture was diluted and added CH₂Cl₂ (2000 mL) and quenched by addition sat. Na₂SO₃ (600 mL) and sat. NaHCO₃ (aq., 300 mL) at 0° C. and stirring for 20 minutes, extracted with CH₂Cl₂ (1500 mL*3). The combined organic layers were dried over Na₂SO₄, filtered, and concentrated under reduced pressure to give a residue. The residue was purified by column chromatography (SiO₂, Petroleum ether:Ethyl acetate=1:0, 100:1, 50:1, 20:1 to 5:1) to give 59 g compound 6 as a yellow oil and crude 25 g. The crude 25 g was purified by MPLC (SiO₂, Petroleum ether:Ethyl acetate=1:0, 5%, 10%, 15% to 25%) to give 4 g compound 6 as a yellow oil. ¹H NMR (400 MHz, CHLOROFORM-d) δ=4.52-4.27 (m, 1H), 3.60-3.33 (m, 2H), 3.07-2.88 (m, 1H), 2.25-2.00 (m, 1H), 1.94-1.52 (m, 10H), 1.49-1.35 (m, 9H). LCMS: (M+Na⁺): 290.0. TLC (Petroleum ether:Ethyl acetate=5:1) $R_f$=0.43.

6. Preparation of Compound 7.

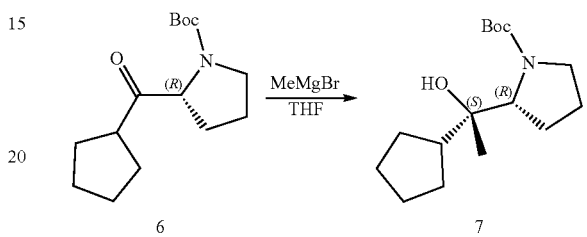

To a solution of compound 6 (76.00 g, 284.26 mmol) in THF (500.00 mL) was added MeMgBr (3 M, 284.26 mL) at −5-0° C. over 2 hr. The mixture was stirred at 25° C. for 2 hr. LCMS and TLC showed the starting material was consumed and MS with the desired compound was detected. The reaction mixture was added in ice sat. NH₄Cl (1000 mL) at 0° C., and then extracted with ethyl acetate (2000 mL*3), dried over Na₂SO₄, filtered and concentrated under reduced pressure to give a residue. The residue was purified by column chromatography (SiO₂, Petroleum ether:Ethyl acetate=1:0, 50:1, 20:1 to 5:1) to give crude 35 g, then crude 35 g was purified by MPLC (SiO₂, Petroleum ether:Ethyl acetate=50:1 to 5:1). Both of two parts purification got compound 7 as a yellow solid (63 g, 78.20%) and 2.3 g diastereoisomer a yellow oil. Compound 7 was detected by SFC. ¹H NMR (400 MHz, CHLOROFORM-d) δ=5.42 (br s, 1H), 3.99-3.82 (m, 1H), 3.63 (br s, 1H), 3.15 (td, J=7.2, 10.9 Hz, 1H), 2.10-1.32 (m, 22H), 1.10 (s, 3H). LCMS: (M+H⁺): 284.1. HPLC purity: 96.33%. Chiral SFC purity: 98.16%. TLC (Petroleum ether:EtOAc=5:1, three times) $R_f$=0.38.

7. Preparation of Compound WV-CA-078D.

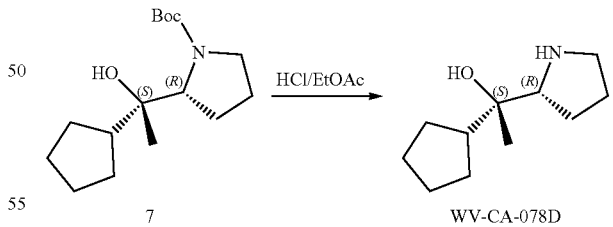

To a solution of compound 7 (62.50 g, 220.53 mmol) in EtOAc (70.00 mL) was added HCl/EtOAc (700.00 mL, 4 N) at 0° C. The mixture was stirred at 20° C. for 2 hr. TLC (Petroleum ether:Ethyl acetate=3:1, $R_f$=0) showed the starting material was consumed. The mixture was concentrated under reduced pressure until around 50 mL solvent was remained, filtered to give a residue. The residue was dissolved by H₂O (100 mL) and added sat. Na₂CO₃ (aq.) and KOH (2M, aq.) until over pH=11, then the mixture was extracted with DCM (600 mL*6), dried over Na₂SO₄, filtered and concentrated under reduced pressure at 35° C. water bath to give compound WV-CA-078D as a yellow oil (31 g, 76.69%). $^1$H NMR (400 MHz, CHLOROFORM-d) δ=3.02 (t, J=7.6 Hz, 1H), 2.97-2.86 (m, 2H), 2.79-2.53 (m, 2H), 2.05-1.92 (m, 1H), 1.80-1.41 (m, 11H), 1.23-1.08 (m, 1H), 1.08-0.99 (m, 3H). $^{13}$C NMR (101 MHz, CHLOROFORM-d): δ=73.70, 65.86, 46.63, 46.46, 27.53, 26.92, 26.04, 25.72, 25.61, 25.16, 21.06. LCMS: (M+H+): 184.0, 99.55% purity. TLC (Petroleum ether:EtOAc=3:1) R$_f$=0.

Example 81. Synthesis of WV-CA-078D-dCiBu

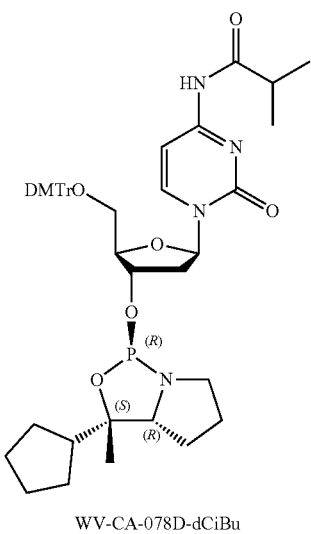

WV-CA-078D-dCiBu

General Scheme

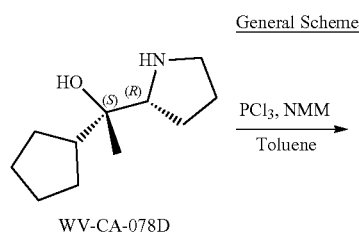

WV-CA-078D

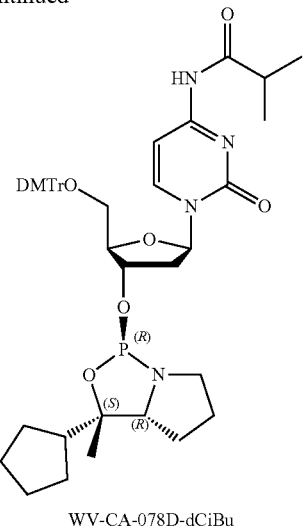

WV-CA-078D-dCiBu

1. Preparation of Compound 2.

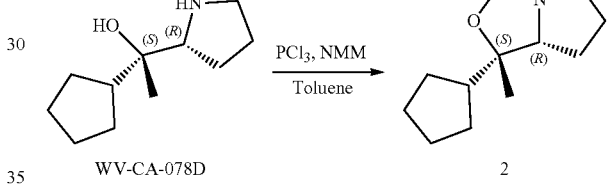

The compound WV-CA-078D (1.00 g, 5.46 mmol) was dried by azeotropic distillation on a rotary evaporator with toluene (20 mL*3). To a solution of PCl$_3$ (749.25 mg, 5.46 mmol) in toluene (10 mL) was added a solution of WV-CA-078D (1.00 g, 5.46 mmol) and NMM (1.10 g, 10.92 mmol, 1.20 mL) in toluene (15 mL) at 0° C. The mixture was stirred at 25° C. for 1 hr. Phosphoryl chloride was not suitable for detection. The resulting mixture was filtered (flushed with Ar) and concentrated to afford a residue as a light-yellow oil. The crude product compound 2 (1.20 g, crude) was used into the next step without further purification.

2. Preparation of Compound WV-CA-078D-dCiBu.

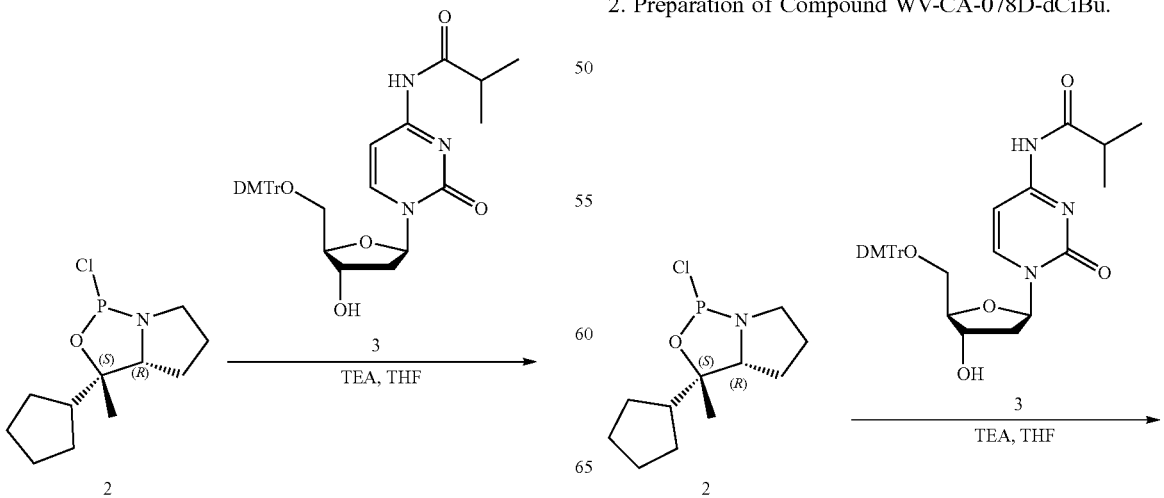

741
-continued

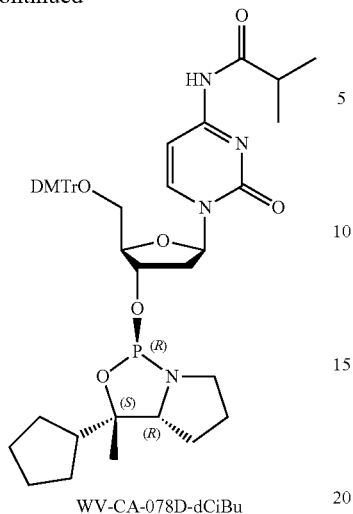

WV-CA-078D-dCiBu

Compound 3 (1.94 g, 3.23 mmol) was dried by azeotropic distillation on a rotary evaporator with pyridine (20 mL) and toluene (20 mL*5). The dried compound 3 (1.94 g, 3.23 mmol) was dissolved in THF (10 mL), and then TEA (2.29 g, 22.61 mmol, 3.13 mL) was added. The mixture was cooled to −70° C. A solution of compound 2 (1.20 g, 4.84 mmol) in THF (10 mL) was added dropwise at −70° C., then warmed to 25° C. over 0.5 hr and stirred for another 1 hr. TLC (Ethyl acetate:Petroleum ether=3:1, 5% TEA) showed compound 3 remained, and desired product was observed. The resulting mixture was diluted with DCM (50 mL), washed with sat. NaHCO₃ aq. (40 mL*3). The organic layer was dried over anhydrous MgSO₄, filtered, and concentrated to afford a white foam (2.9 g). The MPLC column (flash Silica (CS), 40-60 μm, 60 A, 20 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (25 mL, 5% TEA) was loaded and purified with Ethyl acetate (5% TEA):Petroleum ether (5% TEA)=20%~50%. All solvent was dried over anhydrous Na₂SO₄. Compound WV-CA-078D-dCiBu (1.20 g, 45.86% yield) was obtained as a white solid. $^1$H NMR (400 MHz, CHLOROFORM-d) δ=9.16 (br s, 1H), 8.40 (d, J=7.4 Hz, 1H), 7.42 (br d, J=7.8 Hz, 2H), 7.35-7.21 (m, 7H), 7.16 (d, J=7.4 Hz, 1H), 6.86 (br d, J=8.4 Hz, 4H), 6.21 (dd, J=4.3, 6.0 Hz, 1H), 4.87 (quin, J=6.9 Hz, 1H), 4.18-4.07 (m, 1H), 3.80 (s, 6H), 3.54-3.36 (m, 4H), 3.17-3.04 (m, 1H), 2.78-2.61 (m, 2H), 2.40-2.25 (m, 1H), 2.20~2.08 (m, 1H), 2.01-1.46 (m, 12H), 1.46-1.41 (m, 3H), 1.23-1.16 (m, 6H). $^{13}$C NMR (101 MHz, CHLOROFORM-d) δ=177.18, 162.61, 158.65, 158.63, 155.12, 144.60, 144.04, 135.56, 135.31, 130.17, 130.10, 130.03, 128.25, 128.15, 127.99, 127.06, 113.29, 96.33, 92.60, 92.49, 86.91, 86.59, 85.27, 85.21, 73.39, 69.95, 69.78, 61.26, 55.19, 45.88, 45.85, 45.54, 45.20, 40.92, 36.37, 28.49, 28.10, 27.91, 26.78, 26.74, 26.16, 26.06, 23.58, 19.19, 19.01. $^{31}$P NMR (162 MHz, CHLOROFORM-d) δ=159.29 (s, 1P). TLC (Ethyl acetate:Petroleum ether=3:1, 5% TEA), R$_f$=0.64.

742

Example 82. Synthesis of WV-CA-078D-2'-OMe-C$^{Ac}$

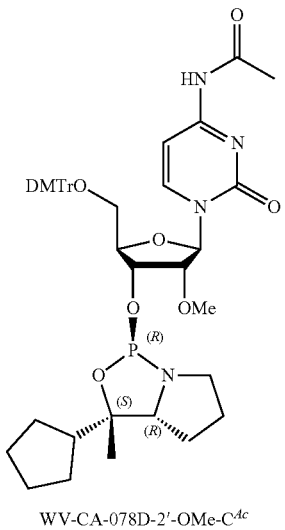

WV-CA-078D-2'-OMe-C$^{Ac}$

General Scheme

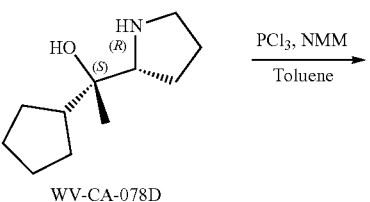

WV-CA-078D

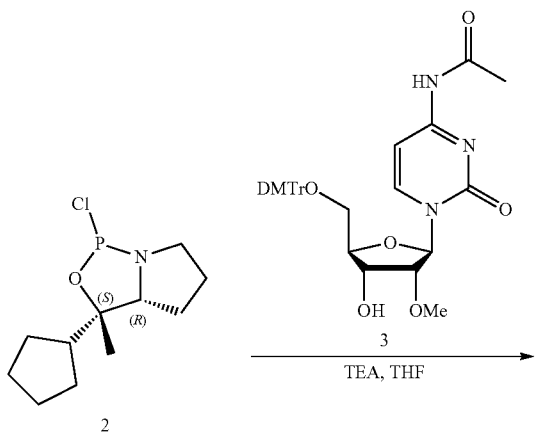

2. Preparation of Compound WV-CA-078D-2'-OMe-C$^{Ac}$

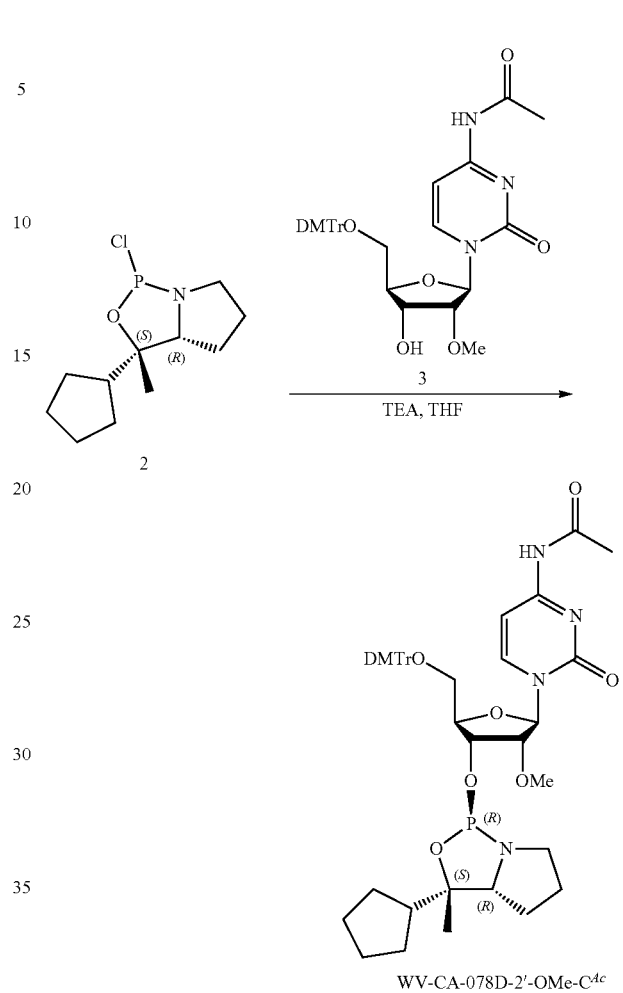

1. Preparation of Compound 2.

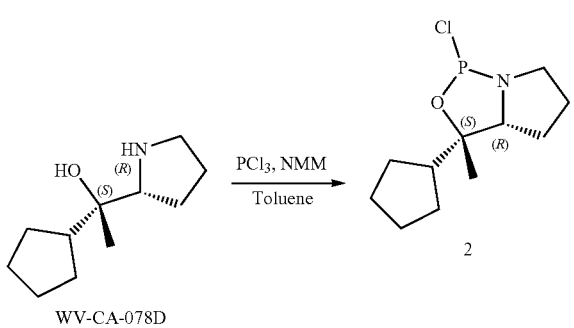

The compound WV-CA-078D (1.00 g, 5.46 mmol) was dried by azeotropic distillation on a rotary evaporator with toluene (20 mL*3). To a solution of PCl$_3$ (749.25 mg, 5.46 mmol) in toluene (10 mL) was added a solution of WV-CA-078D (1.00 g, 5.46 mmol) and NMM (1.10 g, 10.92 mmol, 1.20 mL) in toluene (15 mL) at 0° C. The mixture was stirred at 25° C. for 1 hr. Phosphoryl chloride was not suitable for detection. The resulting mixture was filtered (flushed with Ar) and concentrated to afford a residue as a light-yellow oil. The crude product compound 2 (1.20 g, crude) was used into the next step without further purification.

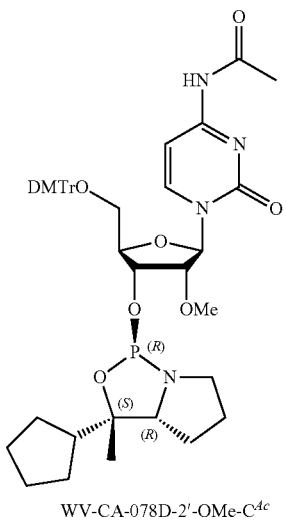

Compound 3 (1.94 g, 3.23 mmol) was dried by azeotropic distillation on a rotary evaporator with pyridine (20 mL) and toluene (20 mL*5). The dried compound 3 (1.94 g, 3.23 mmol) was dissolved in THF (10 mL), and then TEA (2.29 g, 22.61 mmol, 3.13 mL) was added. The mixture was cooled to −70° C. A solution of compound 2 (1.20 g, 4.84 mmol) in THF (10 mL) was added dropwise at −70° C., then warmed to 25° C. over 0.5 hr and stirred for another 1 hr. TLC (Ethyl acetate:Petroleum ether=3:1, 5% TEA) showed compound 3 remained, and desired product was observed. The resulting mixture was diluted with DCM (50 mL), washed with sat. NaHCO$_3$ aq. (40 mL*3). The aqueous layer was extracted at each washing stage with additional DCM (40 mL). The combined organic layer was dried over anhydrous MgSO$_4$, filtered, and concentrated to afford a white foam (2.94 g). The MPLC column (flash Silica (CS), 40-60 μm, 60 A, 20 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (25 mL, 5% TEA) was loaded and purified with Ethyl acetate (5% TEA):Petroleum ether (5% TEA)=20%~50%. All solvent was dried over anhydrous Na$_2$SO$_4$. Compound WV-CA-078D-2'-OMe-C$^{Ac}$ (1.20 g, 45.75% yield) was obtained as a white solid.

$^1$H NMR (400 MHz, CHLOROFORM-d) δ=10.42 (br s, 1H), 8.71 (d, J=7.5 Hz, 1H), 7.45 (br d, J=7.8 Hz, 2H), 7.39-7.24 (m, 7H), 7.08 (d, J=7.5 Hz, 1H), 6.87 (d, J=8.5 Hz, 4H), 5.98 (s, 1H), 4.75 (dt, J=4.8, 8.9 Hz, 1H), 4.28 (br d,

J=9.5 Hz, 1H), 3.82 (s, 6H), 3.78 (d, J=4.6 Hz, 1H), 3.66 (s, 3H), 3.61 (br d, J=11.5 Hz, 1H), 3.50 (br d, J=10.9 Hz, 1H), 3.43-3.34 (m, 2H), 3.04 (dq, J=4.4, 8.6 Hz, 1H), 2.28 (s, 3H), 2.13 (quin, J=8.0 Hz, 1H), 2.02-1.46 (m, 12H), 1.41 (s, 3H). $^{13}$C NMR (101 MHz, CHLOROFORM-d) δ=170.93, 163.25, 158.69, 158.67, 154.97, 145.04, 144.17, 135.37, 135.14, 130.31, 130.28, 128.35, 128.00, 127.11, 113.28, 96.80, 92.65, 92.54, 88.95, 87.07, 83.84, 81.32, 81.27, 73.25, 67.59, 67.46, 59.64, 58.46, 55.21, 45.81, 45.78, 45.15, 44.82, 34.43, 28.58, 28.21, 27.67, 27.11, 27.07, 26.13, 26.09, 24.80, 23.45. $^{31}$P NMR (162 MHz, CHLOROFORM-d) δ=155.55 (s, 1P). TLC (Ethyl acetate:Petroleum ether=3:1, 5% TEA), $R_f$=0.51.
Example 83. Synthesis of WV-CA-079 and WV-CA-079-dCiBu
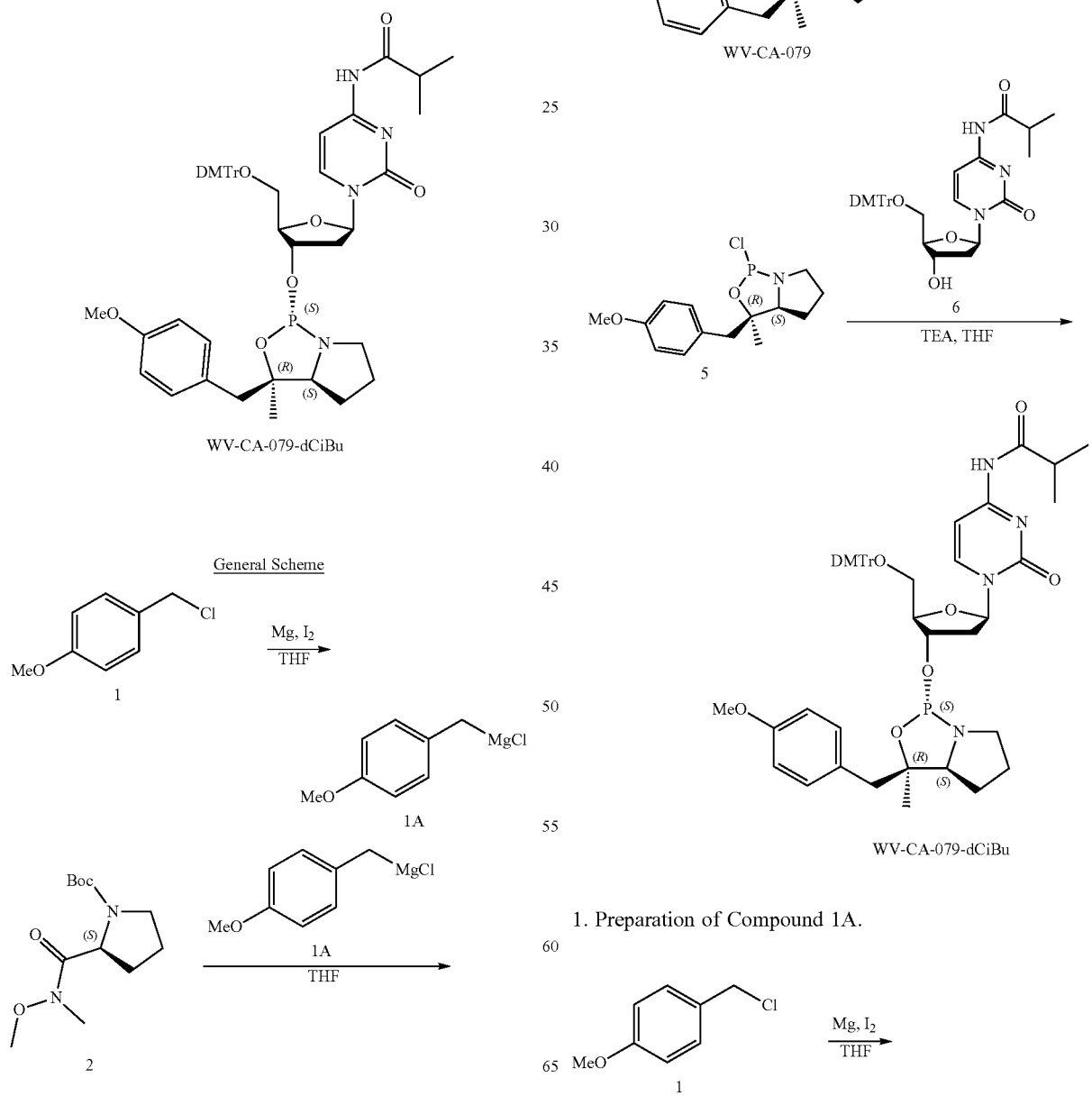
1. Preparation of Compound 1A.

-continued

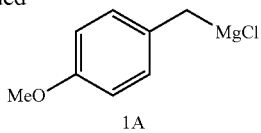

To a suspension of Mg (18.07 g, 743.24 mmol) and I₂ (100.00 mg, 394.00 µmol) in THF (120 mL) was added compound 1 (97.00 g, 619.37 mmol) in THF (620.00 mL) at 15~70° C. for 0.5 hr. The mixture was stirred at 60° C. for 1 hr. Mg was remained a little and the reaction was completed. The Grignard reagent in THF was used directly in next step.

2. Preparation of Compound 3.

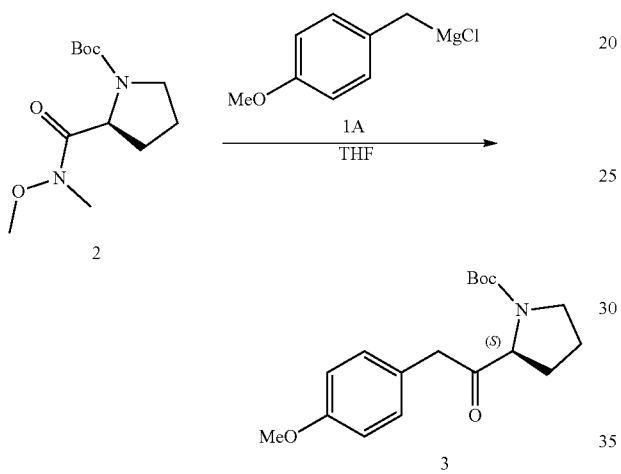

A solution of compound 2 (60.00 g, 232.28 mmol) in THF (400.00 mL) was added to the solution of compound 1A (112.20 g, 620.19 mmol) at 0~10° C. for 0.5 hr under N₂. Then the reaction was gradually warmed to 25° C. for 0.5 hr. The reaction was stirred at 15~25° C. for 12 hr. TLC showed the starting material was consumed. The mixture was poured into NH₄Cl (aq., 500 mL), the organic layer was separated and the aqueous layer was extracted with EtOAc (200 mL*2). The combined organics were washed with brine (300 mL), dried over Na₂SO₄, filtered and concentrated to get the crude, which was purified by silica gel chromatography (Petroleum ether/Ethyl acetate=30/1, 1/1) to afford the compound 3 as a yellow oil (47.00 g, 63.35%). ¹H NMR (400 MHz, CDCl₃): δ=7.16-7.03 (m, 2H), 6.90-6.79 (m, 2H), 4.48-4.26 (m, 1H), 3.80-3.74 (m, 4H), 3.57-3.30 (m, 2H), 1.81-1.71 (m, 3H), 1.48-1.35 (m, 10H). TLC (Petroleum ether:Ethyl acetate=3:1) $R_f$=0.30.

3. Preparation of Compound 4.

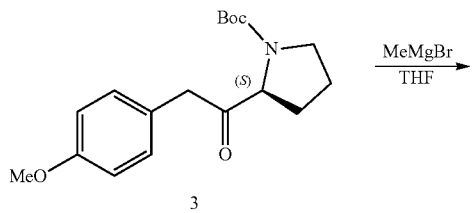

-continued

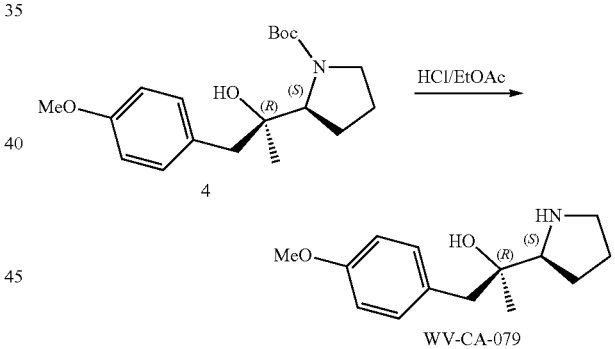

Into a 1000 mL three necked flask equipped with a low-temperature thermometer, bromo(methyl)magnesium (3 M, 242.65 mL) was added to the solution of compound 3 (46.50 g, 145.59 mmol) in THF (100.00 mL) at −60~−55° C. for 1 hr. The reaction was slowly warmed to 25° C. and stirred for 2.5 hr. TLC showed a little compound 3 remained, and one new spot was detected. The reaction was added into sat. NH₄Cl (2000 mL) at 0° C. The mixture was extracted with EtOAc (500 mL*3). The organic phase was separated and combined, dried over Na₂SO₄, filtered and concentrated in vacuum to dryness. The residue was purified by silica gel chromatography (Petroleum ether/Ethyl acetate=30/1, 10/1) to obtain compound 4 as colorless oil, and then the mixture was purified by re-crystallization from Petroleum ether (150 mL) to give the pure compound 4 as a white solid (26.50 g, 54.26%). ¹H NMR (400 MHz, CDCl₃): δ=7.17 (d, J=8.4 Hz, 2H), 6.82 (d, J=8.6 Hz, 2H), 5.82 (br s, 1H), 3.97 (t, J=7.4 Hz, 1H), 3.79 (s, 3H), 3.73 (br d, J=1.1 Hz, 1H), 3.29-3.06 (m, 1H), 2.70 (br d, J=13.5 Hz, 1H), 2.47 (br d, J=13.5 Hz, 1H), 2.17-1.96 (m, 1H), 1.93-1.65 (m, 3H), 1.53-1.41 (m, 9H), 1.03-0.88 (m, 3H). TLC (Petroleum ether:Ethyl acetate=3:1) $R_f$=0.38.

4. Preparation of WV-CA-079.

To a solution of compound 4 (25.00 g, 74.53 mmol) in EtOAc (30.00 mL) was added HCl/EtOAc (300.00 mL, 4 N) at 0° C. slowly, the mixture was stirred at 20° C. for 1 hr. TLC showed the starting material was consumed. The mixture was concentrated to remove most of solvent, and then the mixture was filtered. The filter cake was washed with Ethyl acetate (10 mL), and dried to get the crude HCl salt, which was dissolved in water (10 mL), and to the mixture was added Na₂CO₃(aq) until pH>11. The mixture was stirred for 30 minutes, then the mixture was extracted with DCM (35 mL*3). The combined organics were washed with brine (50 mL), dried over Na₂SO₄, filtered and concentrated to get the crude, to which was added Petroleum ether:Ethyl acetate=10:1 (200 mL), and the mixture was filtered to afford the filter cake 8 g and the filtrate 6 g. The filtrate was purified by silica gel chromatography (DCM: MeOH=50:1 to 10:1) to get the product (4 g). The filter cake was dissolved in water (10 mL) and KOH (2 M) was added until pH>12, and the mixture was stirred for 0.5 hr, and then extracted with DCM (50 mL*3). The combined organics were washed with brine (50 mL), dried over Na$_2$SO$_4$, filtered and concentrated to give the product (5 g). $^1$H NMR (400 MHz, CDCl$_3$): δ=7.20-7.09 (m, 2H), 6.88-6.81 (m, 2H), 3.90-3.73 (m, 3H), 3.10-2.89 (m, 3H), 2.82 (d, J=13.7 Hz, 1H), 2.57 (d, J=13.5 Hz, 1H), 2.40 (br s, 2H), 1.90-1.67 (m, 4H), 1.05 (s, 3H). $^{13}$C NMR (101 MHz, CDCl$_3$): δ=158.09, 131.41, 129.78, 113.44, 72.84, 66.03, 55.21, 46.88, 43.63, 26.26, 25.78, 25.27. LCMS: (M+H+): 236.1. TLC (Petroleum ether:Ethyl acetate=3:1) R$_f$=0. HPLC purity=98.6%. SFC purity=100.0%.

5. Preparation of Compound 5.

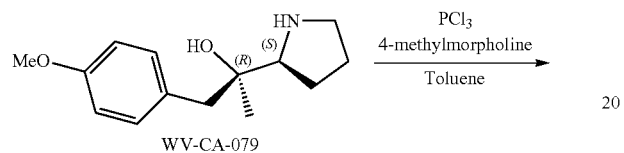

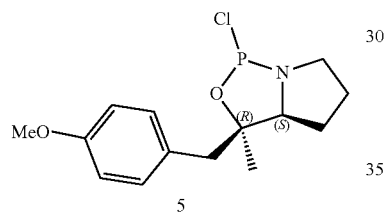

WV-CA-079 (2.00 g, 8.50 mmol) was dried by azeotropic distillation on a rotary evaporator with toluene (20 mL*3). To a solution of PCl$_3$ (1.17 g, 8.50 mmol) in toluene (25 mL) was added a solution of WV-CA-079 (2.00 g, 8.50 mmol) and 4-methylmorpholine (1.72 g, 17.00 mmol) in toluene (25 mL) at 0° C. The mixture was stirred at 15~20° C. for 1 hr. The phosphoryl chloride was not suitable for detection and no monitoring. The resulting mixture was filtered (flushed with Ar) and concentrated to afford the crude product compound 5 (2.20 g, crude) as a yellow oil, which was used into the next step without further purification.

6. Preparation of WV-CA-079-dCiBu.

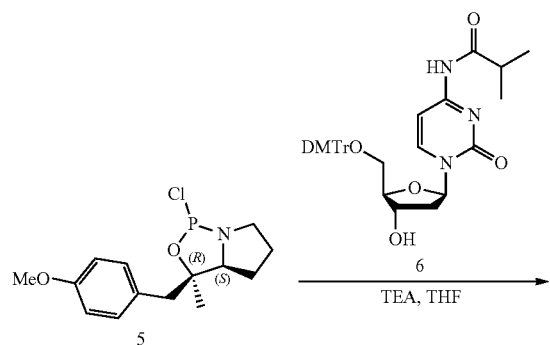

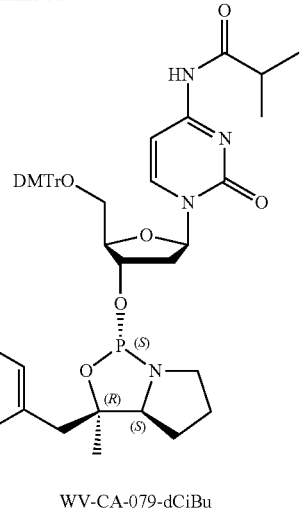

Compound 6 (2.93 g, 4.89 mmol) was dried by azeotropic distillation on a rotary evaporator with pyridine (50 mL) and toluene (50 mL*5). The dried compound 6 (2.93 g, 4.89 mmol) was dissolved in THF (50.00 mL), and then TEA (2.48 g, 24.47 mmol) was added. The mixture was cooled to −70° C. A solution of compound 5 (2.20 g, 7.34 mmol) in THF (10 mL) was added dropwise at −70° C., after the addition, the mixture was warmed to 23° C. for 1.5 hr. TLC showed compound 6 was consumed and the reaction was completed. The resulting mixture was diluted with DCM (30 mL) at −10° C., washed with ice-cold sat. NaHCO$_3$ aq. (30 mL*3). The aqueous layer was extracted at each washing stage with additional DCM (50 mL). The organic layer was dried over anhydrous MgSO$_4$, filtered, and concentrated to afford a white foam (crude, 5.7 g). The silica gel (SiO$_2$, 100-200 mesh, 40 g) used for the column chromatography was basified by the elution with MeOH (2 column volumes, 300 mL), Ethyl acetate/5% Et$_3$N (1 column volume, 150 mL), gradient to 80% Ethyl acetate/Petroleum ether/5% Et$_3$N (80 mL) to 20% EA/hexane/5% Et$_3$N (80 mL). A solution of the crude product in DCM (60 mL, 5% TEA) and Petroleum ether (30 mL, 5% TEA) was loaded and purified with Petroleum ether (5% TEA):Ethyl acetate (5% TEA)=5:1 to 1:1 to get WV-CA-079-dCiBu as a white solid (2.80 g, 66.21%). All solvent was dried over anhydrous Na$_2$SO$_4$. $^1$H NMR (400 MHz, CDCl$_3$): δ=8.39 (br. s, 1H), 8.22 (d, J=7.5 Hz, 1H), 7.42-7.19 (m, 9H), 7.16-7.06 (m, 3H), 6.91-6.77 (m, 6H), 6.24 (t, J=5.8 Hz, 1H), 4.86-4.78 (m, 1H), 4.14 (m, 1H), 3.87-3.76 (m, 9H), 3.64-3.46 (m, 2H), 3.43 (d, J=3.0 Hz, 2H), 3.06 (qd, J=7.1, 10.1 Hz, 1H), 2.81-2.68 (m, 2H), 2.66-2.47 (m, 2H), 2.25 (td, J=6.0, 13.7 Hz, 1H), 1.99-1.75 (m, 4H), 1.71-1.53 (m, 1H), 1.25-1.20 (m, 9H). $^{31}$P NMR (162 MHz, CDCl$_3$): δ=153.183 (s, 1P). TLC (Ethyl acetate/Petroleum ether=3:1, 5% TEA) R$_f$=0.54.

Example 84. Synthesis of WV-CA-080 and WV-CA-080-dCiBu
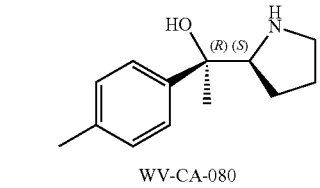
WV-CA-080
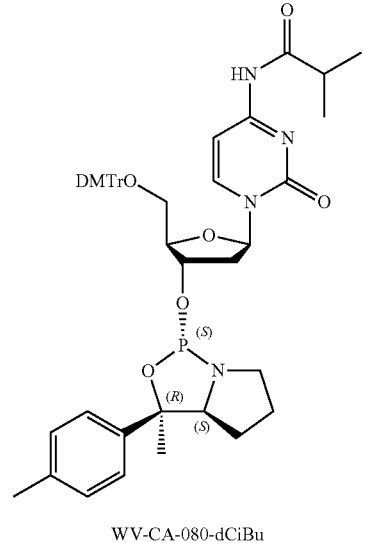
WV-CA-080-dCiBu
General Scheme
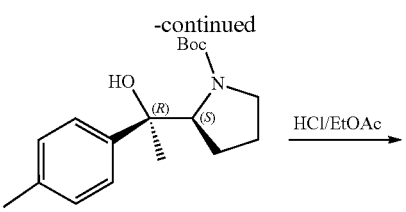
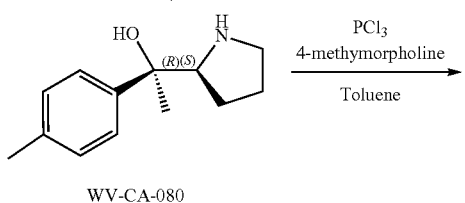
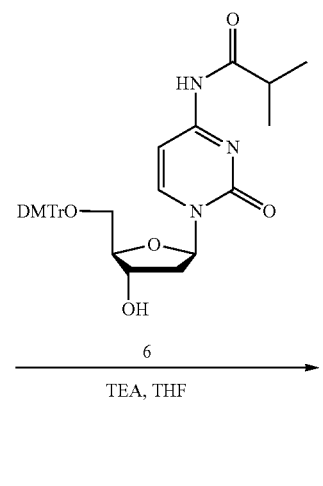
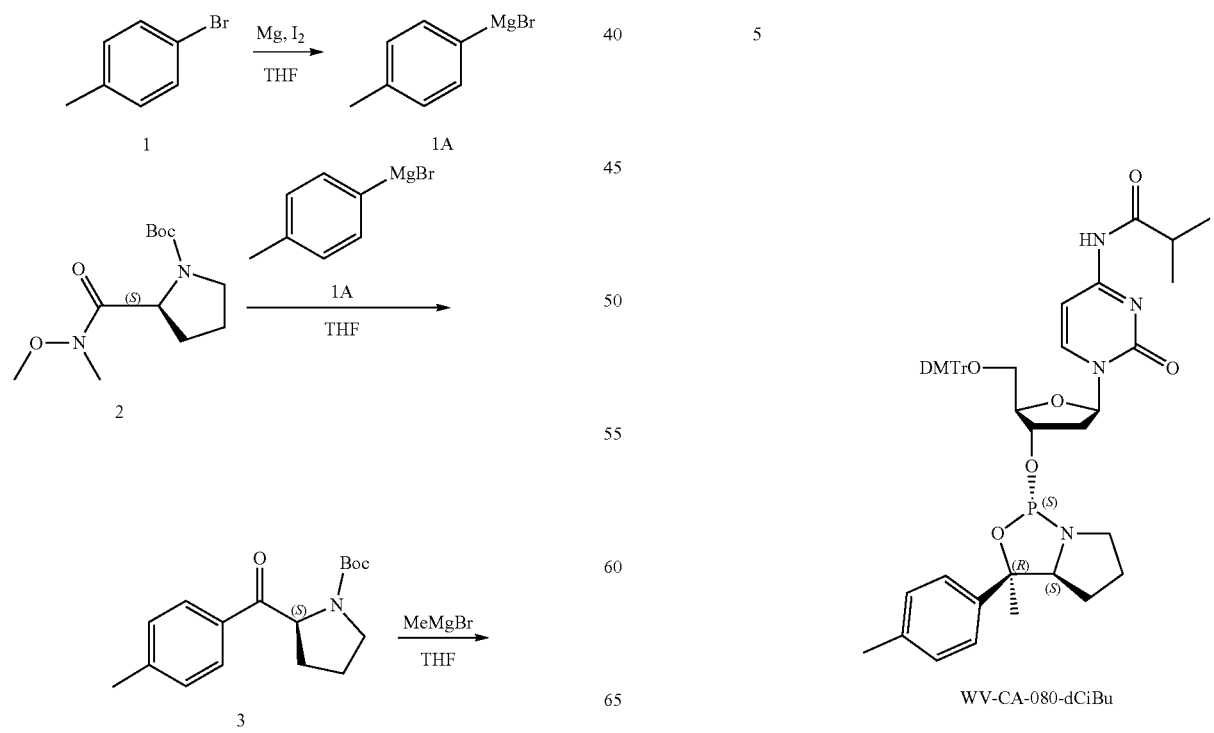

1. Preparation of Compound 1A.

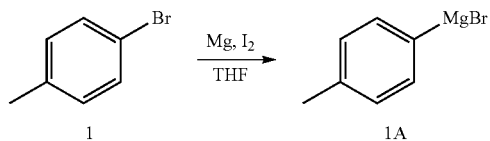

To a suspension of Mg (13.55 g, 557.46 mmol) and I₂ (100.00 mg, 394.00 mol, 79.37 μL) in THF (400.00 mL) was added compound 1 (79.45 g, 464.55 mmol, 57.16 mL) in THF (360.00 mL) at 20~70° C. for 0.5 hr. The mixture was stirred at 20° C. for 2 hr. A little Mg was remained. The reaction was completed. The crude compound 1A was used into the next step without further purification.

2. Preparation of Compound 3.

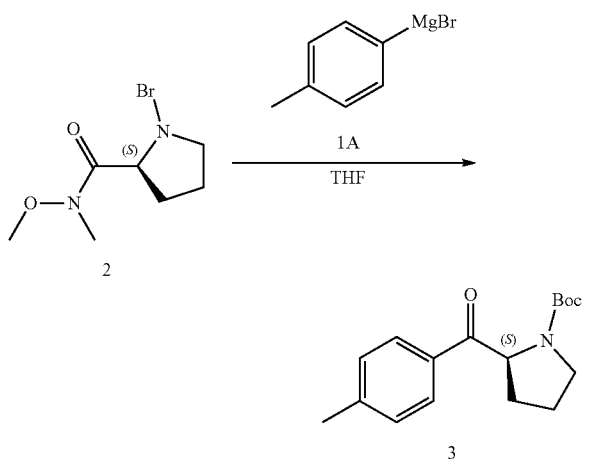

A solution of compound 2 (40.00 g, 154.85 mmol, 37.74 mL) in THF (100.00 mL) was added to the mixture of compound 1A (900.75 g, 464.55 mmol, 90.75 mL) at 0~10° C. for 0.5 hr under N₂. Then the reaction was gradually warmed to 25° C. for 0.5 hr. The reaction was stirred at 25° C. for 12 hr. The mixture was poured into NH₄Cl (aq, 500 mL). The organic was separated and the aqueous layer was extracted with EtOAc (200 mL*2). The combined organics were washed with brine (300 mL), dried over Na₂SO₄, filtered and concentrated to give the crude product, which was purified by silica gel chromatography (Petroleum ether/Ethyl acetate=30/1, 10/1) to afford the compound 3 as a white solid (30.00 g, 66.95%). ¹H NMR (400 MHz, CHLOROFORM-d) δ=7.98-7.71 (m, 2H), 7.34-7.09 (m, 2H), 3.78-3.30 (m, 2H), 2.43-2.35 (m, 3H), 2.34-2.19 (m, 1H), 1.89 (br d, J=6.4 Hz, 3H), 1.44 (s, 4H), 1.24 (s, 6H). TLC (Petroleum ether:Ethyl acetate=3:1) R$_f$=0.51.

3. Preparation of Compound 4.

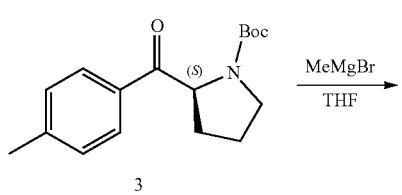

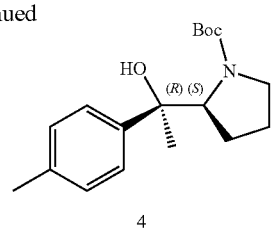

Into a 100 mL three necked flask equipped with a low-temperature thermometer, compound 2 (21.00 g, 72.57 mmol) in THF (200.00 mL) was added bromo(methyl)magnesium (3 M, 72.57 mL) at −30° C. Then the mixture was slowly warmed to 20° C. and stirred for 2 hr. The reaction was added into sat. NH₄Cl (400 mL) at 0° C. The mixture was extracted with EtOAc (400 mL*3). The separated and combined organic phase was dried over Na₂SO₄, filtered, and concentrated in vacuum to dryness. The residue was purified by silica gel chromatography (Petroleum ether/Ethyl acetate=30/1, 5/1) to give compound 3 as a white solid (21.00 g, 94.75%). ¹H NMR (400 MHz, CHLOROFORM-d) δ=7.30 (d, J=8.3 Hz, 2H), 7.10 (br d, J=7.9 Hz, 2H), 4.17 (dd, J=4.8, 8.3 Hz, 1H), 3.32 (br s, 1H), 2.51 (br s, 1H), 2.33 (s, 3H), 1.95 (br s, 1H), 1.78-1.62 (m, 2H), 1.58 (s, 3H), 1.51 (s, 9H), 1.06 (br s, 1H). TLC (Petroleum ether:Ethyl acetate=3:1) R$_f$=0.43. HPLC purity=1000.0%. SFC purity=100.0%.

4. Preparation of WV-CA-080.

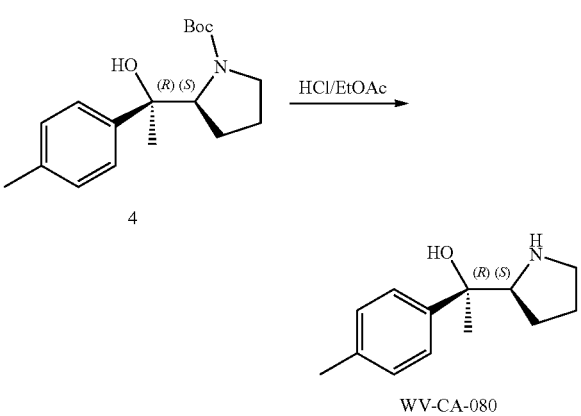

To a solution of compound 4 (12.00 g, 39.29 mmol) in EtOAc (50.00 mL) was added HCl/EtOAc (400.00 mL). The mixture was stirred at 20° C. for 2 hr. The mixture was concentrated and filtered to get the crude, which was washed with petroleum ether (200 mL), then dissolved in water (50 mL), after that, Na₂CO₃ (aq.) was added until pH>11, extracted with DCM (150 mL*3). The combined organics were dried over Na₂SO₄, filtered, and concentrated to get the product WV-CA-080 as a yellow oil (5.60 g, 69.43%). ¹H NMR (400 MHz, CHLOROFORM-d) δ=7.32 (d, J=7.9 Hz, 2H), 7.13 (d, J=7.9 Hz, 2H), 3.45 (t, J=7.9 Hz, 1H), 3.11-2.85 (m, 2H), 2.33 (s, 3H), 1.76-1.50 (m, 2H), 1.46 (s, 3H), 1.43-1.22 (m, 2H). ¹³C NMR (101 MHz, CHLOROFORM-d) δ=143.46, 135.62, 128.61, 124.70, 73.49, 66.70, 47.28, 30.13, 26.80, 26.06, 21.00. TLC (Petroleum ether:Ethyl acetate=3:1) R$_f$=0.00. LCMS: (M+H+): 206.1. HPLC purity=99.4%. SFC purity=100.0%.

5. Preparation of Compound 5.

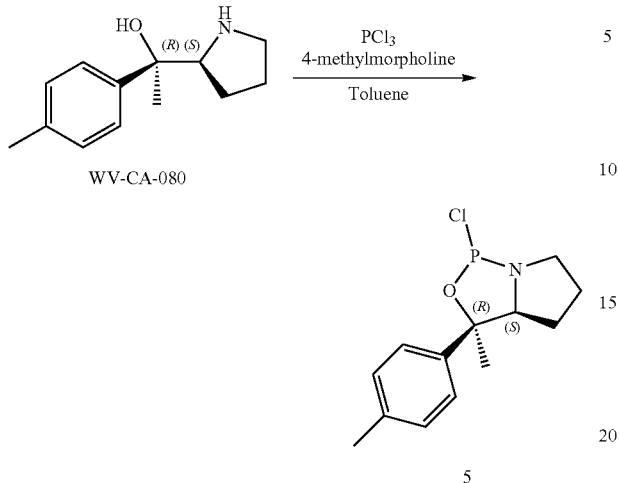

WV-CA-080 (1.70 g, 8.28 mmol) was dried by azeotropic distillation on a rotary evaporator with toluene (20 mL*3). To a solution of PCl₃ (1.14 g, 8.28 mmol) in toluene (20.00 mL) was added a solution of WV-CA-080 (1.70 g, 8.28 mmol) and 4-methylmorpholine (1.68 g, 16.56 mmol, 1.82 mL) in toluene (20.00 mL) at 0° C. The mixture was stirred at 15~20° C. for 1.5 hr. The phosphoryl chloride was not suitable for detection and no monitoring. The resulting mixture was filtered (flushed with Ar) and concentrated to afford the crude product compound 5 as a colorless oil, which was used into the next step without further purification (1.70 g). $^1$H NMR (400 MHz, CHLOROFORM-d) δ=7.55-6.99 (m, 4H), 3.77-3.73 (m, 1H), 4.00-3.69 (m, 1H), 3.35 (br s, 1H), 3.16-2.95 (m, 1H), 2.32-2.22 (m, 3H), 2.05-1.68 (m, 4H). $^{31}$P NMR (162 MHz, CHLOROFORM-d) δ=175.55 (s, 1P), 165.65 (s, 1P), 23.50 (s, 1P), −3.41 (s, 1P).

6. Preparation of WV-CA-080-dCiBu.

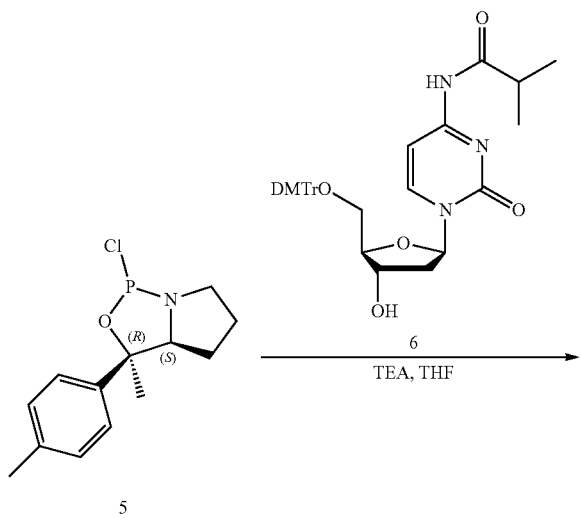

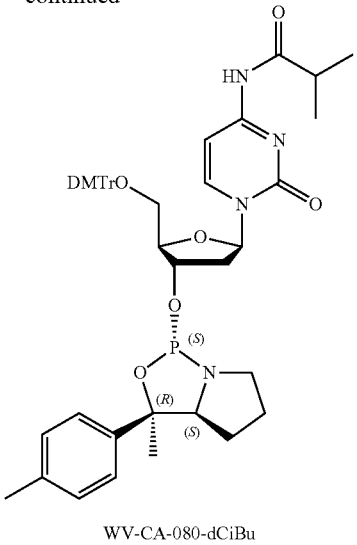

Compound 6 (2.50 g, 4.17 mmol) was dried by azeotropic distillation on a rotary evaporator with pyridine (50 mL) and toluene (50 mL*5). The dried compound 6 (2.50 g, 4.17 mmol) was dissolved in THF (25.00 mL), and then TEA (2.11 g, 20.84 mmol, 2.89 mL) was added. The mixture was cooled to −70° C. A solution of compound 5 (1.69 g, 6.25 mmol) in THF (20 mL) was added dropwise at −70° C., after the addition, the mixture was warmed to 23° C. for 1.5 hr. TLC showed compound 6 was consumed. The resulting mixture was diluted with DCM (50 mL) at −10° C., washed with ice-cold sat. NaHCO₃ aq. (50 mL*3). The aqueous layer was extracted with additional DCM (50 mL) at each washing stage. The organic layer was dried over anhydrous MgSO₄, filtered, and concentrated to afford a white foam (crude, 4.7 g). The above crude material was purified on a CombiFlash instrument from Teledyne using a pre-treated silica gel column. A 40 g silica gel cartridge column was first pre-treated by eluting with 5 column volumes of methanol, before equilibration with 5 column volumes of 20% EtOAc/hexanes containing 5% Et₃N. 4.7 g of crude product was dissolved in a 2:1 volume:volume mixture of DCM:Petroleum ether containing 5% Et₃N then loaded onto a 40 g silica column which had been equilibrated with 5 column volumes of 20% Hexanes/EtOAc containing 5% Et₃N. After loading the sample on the column, the purification process was run using the following gradient: 20 to 80% EtOAc/hexanes containing 5% Et₃N, then residual solvent was removed to afford WV-CA-080-dCiBu as a white solid (1.30 g, 37.43%). All solvent was dried over anhydrous Na₂SO₄. $^1$H NMR (400 MHz, CHLOROFORM-d) δ=8.30 (d, J=7.5 Hz, 1H), 8.22-8.08 (m, 1H), 7.45-7.38 (m, 2H), 7.34-7.19 (m, 8H), 7.18-7.09 (m, 4H), 7.06 (d, J=7.5 Hz, 1H), 6.85-6.77 (m, 4H), 6.26 (dd, J=5.0, 6.3 Hz, 1H), 4.94-4.85 (m, 1H), 4.25-4.18 (m, 1H), 3.83-3.77 (m, 1H), 3.75 (d, J=2.2 Hz, 6H), 3.60-3.36 (m, 3H), 3.10-2.97 (m, 1H), 2.84-2.74 (m, 1H), 2.61-2.49 (m, 1H), 2.42-2.31 (m, 4H), 1.74 (s, 3H), 1.63-1.34 (m, 4H), 1.21 (dd, J=3.3, 6.8 Hz, 6H). $^{13}$C NMR (101 MHz, CHLOROFORM-d) δ=162.40, 158.66, 144.60, 144.20, 136.54, 135.46, 135.41, 130.11, 128.69, 128.64, 128.27, 127.99, 127.11, 125.41, 125.31, 125.30, 113.30, 96.18, 91.65, 91.53, 86.96, 86.81, 85.42, 85.39, 73.10, 73.08, 71.25, 71.09, 64.33, 61.78, 55.16, 46.70, 46.35, 41.29, 41.24, 36.55, 30.66, 30.43, 29.73, 25.73, 25.70, 21.03, 21.00, 19.17, 19.12, 19.02. $^{31}$P NMR (162 MHz, CHLOROFORM-d) δ=157.98 (s, 1P). TLC (Ethyl acetate/Petroleum ether=3:1, 5% TEA) R$_f$=0.43.

Example 85. Synthesis of WV-CA-081 and WV-CA-081-dCiBu

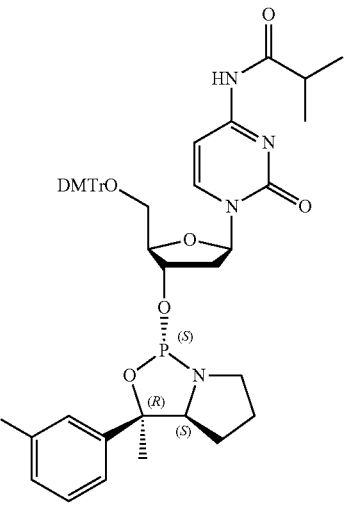

WV-CA-081

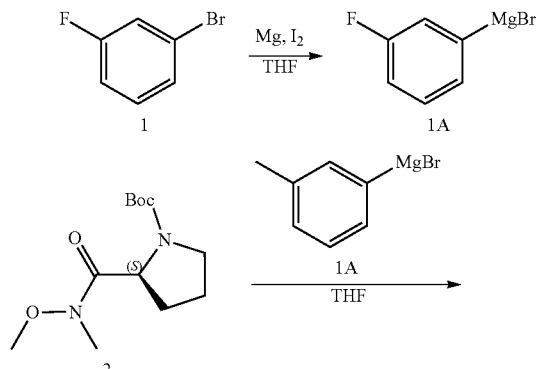

WV-CA-081-dCiBu

General Scheme

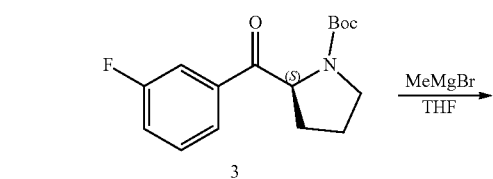

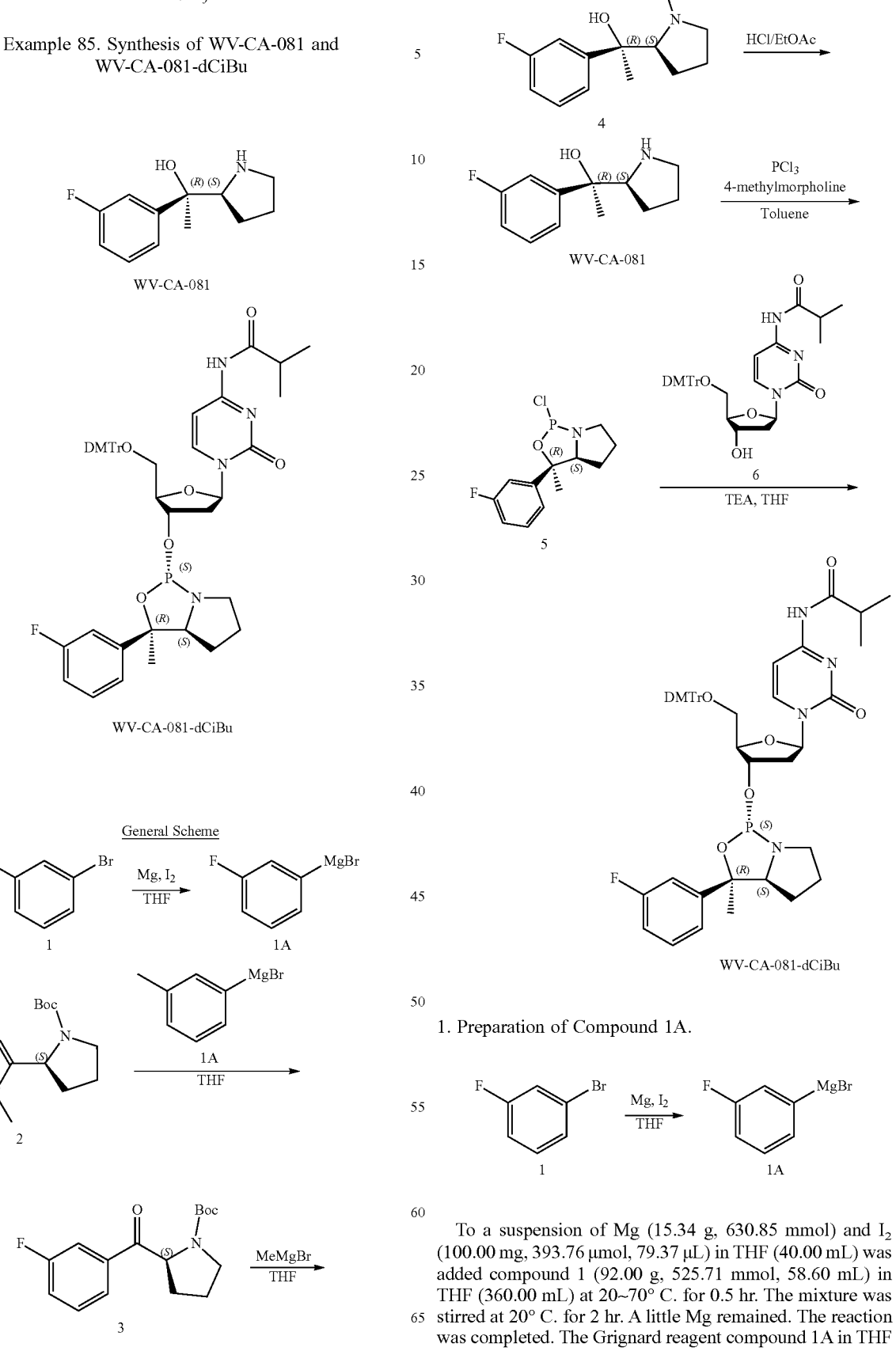

1. Preparation of Compound 1A.

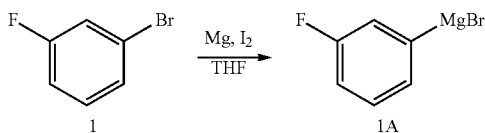

To a suspension of Mg (15.34 g, 630.85 mmol) and I$_2$ (100.00 mg, 393.76 μmol, 79.37 μL) in THF (40.00 mL) was added compound 1 (92.00 g, 525.71 mmol, 58.60 mL) in THF (360.00 mL) at 20~70° C. for 0.5 hr. The mixture was stirred at 20° C. for 2 hr. A little Mg remained. The reaction was completed. The Grignard reagent compound 1A in THF was used directly in the next step.

2. Preparation of Compound 3.

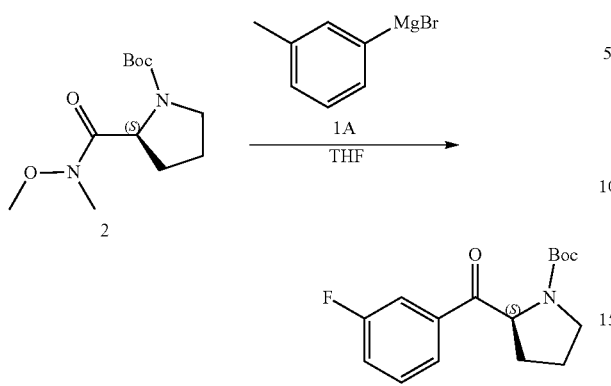

A solution of compound 2 (50.00 g, 193.57 mmol, 47.17 mL) in THF (100.00 mL) was added to the solution of compound 1A (104.83 g, 526.51 mmol, 102.77 mL) at 0° C. 10° C. for 0.5 hr under $N_2$. Then the reaction was gradually warmed to 25° C. for 0.5 hr. The reaction was stirred at 25° C. for 2 hr. The mixture was poured into $NH_4Cl$ (aq, 500 mL), the organic layer was separated and the aqueous layer was extracted with EtOAc (200 mL*2). The combined organics were washed with brine (300 mL), dried over $Na_2SO_4$, filtered and concentrated to get the crude compound 3 as a yellow liquid. (30.00 g, 52.84%). $^1$H NMR (400 MHz, CHLOROFORM-d) δ=7.72 (dd, J=7.7, 14.1 Hz, 1H), 7.67-7.57 (m, 1H), 7.49-7.37 (m, 1H), 7.31-7.17 (m, 1H), 5.41-4.95 (m, 1H), 3.81-3.23 (m, 2H), 2.47-2.15 (m, 1H), 2.03-1.76 (m, 3H), 1.54-1.12 (m, 9H). TLC (Petroleum ether/Ethyl acetate=3:1) $R_f$=0.41.

3. Preparation of Compound 4.

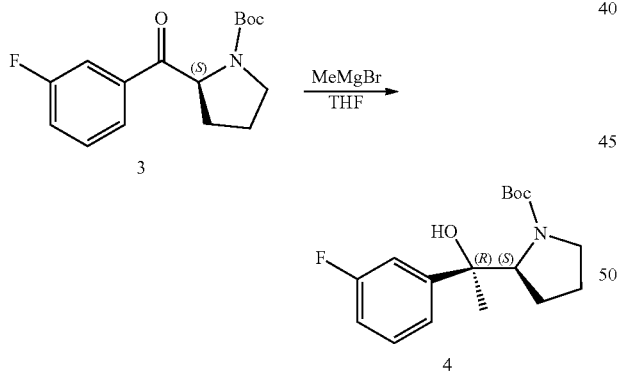

To a solution of bromo(methyl)magnesium (3 M, 102.27 mL) in THF (300.00 mL) was added compound 3 (30.00 g, 102.27 mmol) in THF (10 mL) at −30° C. The mixture was stirred at 20° C. for 2 hr. The mixture was poured into $NH_4Cl$ (aq, 500 mL) and extracted with EtOAc (200 mL*3). The combined organics were washed with brine (100 mL), dried over $Na_2SO_4$, filtered and concentrated to get the crude. The mixture was washed with petroleum ether (150 mL), filtered and the filter cake was dried to get compound 4 (30.00 g, 94.82%) as a white solid. $^1$H NMR (400 MHz, CHLOROFORM-d) δ=7.29-7.23 (m, 1H), 7.17 (br d, J=7.9 Hz, 2H), 6.98-6.90 (m, 1H), 4.18 (dd, J=5.0, 8.6 Hz, 1H), 3.33 (br s, 1H), 2.52 (br s, 1H), 2.00 (br s, 1H), 1.76-1.64 (m, 1H), 1.59 (s, 3H), 1.51 (s, 8H), 1.10 (br s, 1H). TLC (Petroleum ether/Ethyl acetate=3:1) $R_f$=0.43. HPLC purity=100.0%. SFC purity=100.0%.

4. Preparation of WV-CA-081.

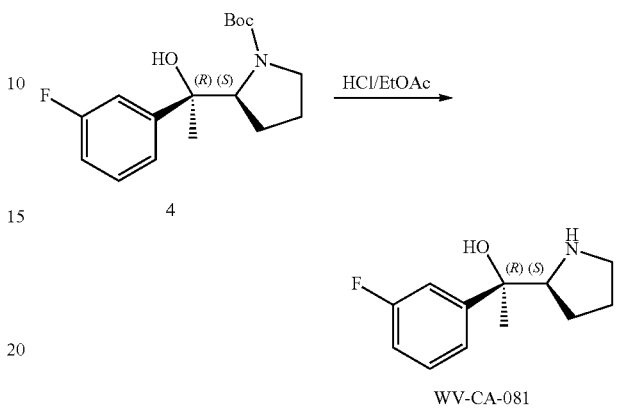

To a solution of compound 4 (29.00 g, 93.74 mmol) in EtOAc (200 mL) was added HCl/EtOAc (500.00 mL). The mixture was stirred at 20° C. for 2 hr. The mixture was concentrated to get the crude. The mixture was dissolved in water (50 mL), and then $Na_2CO_3$ (aq) was added until pH>11, extracted with DCM (150 mL*3). The combined organics were dried over $Na_2SO_4$, filtered, and concentrated to get the crude, which was dissolved in water (50 mL), and then KOH (aq.) was added until pH>11, stirred for 1 hr, then extracted with DCM (150 mL*3). The combined organic layers were dried over $Na_2SO_4$, filtered, and concentrated to get the product WV-CA-081 as a yellow oil (14.00 g, 71.37%). $^1$H NMR: (400 MHz, CHLOROFORM-d) δ=7.31-7.22 (m, 1H), 7.21-7.14 (m, 2H), 6.93-6.84 (m, 1H), 3.42 (t, J=7.7 Hz, 1H), 3.06-2.91 (m, 2H), 1.71-1.51 (m, 2H), 1.45 (s, 3H), 1.39-1.21 (m, 2H). $^{13}$C NMR (101 MHz, CHLOROFORM-d) δ=164.01, 161.58, 149.28, 129.38, 120.44, 112.54, 73.38, 66.48, 47.22, 29.96, 26.74, 26.05. TLC (Petroleum ether/Ethyl acetate=3:1) $R_f$=0.00. LCMS: (M+H+): 210.0. HPLC purity=98.4%. SFC purity=100.0%.

5. Preparation of Compound 5.

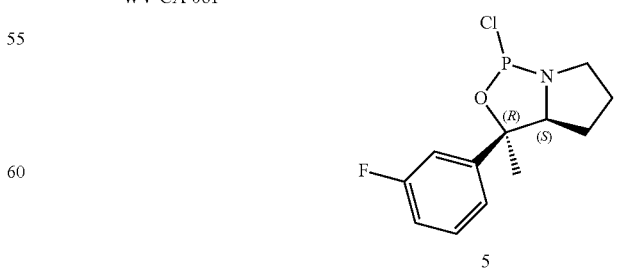

WV-CA-081 (3.00 g, 14.34 mmol) was dried by azeotropic distillation on a rotary evaporator with toluene (20 mL*3). To a solution of PCl₃ (3.00 g, 14.34 mmol) in toluene (30.00 mL) was added a solution of WV-CA-081 (3.00 g, 14.34 mmol) and 4-methylmorpholine (1.83 g, 18.08 mmol, 1.99 mL) in toluene (30.00 mL) at 0° C. The mixture was stirred at 15~20° C. for 1 hr. The phosphoryl chloride was not suitable for detection and no monitoring. The resulting mixture was filtered (flushed with Ar) and concentrated to afford the crude product compound 5 as a colorless oil, which was used into the next step without further purification (3.70 g, 94.28%).

6. Preparation of WV-CA-081-dCiBu.

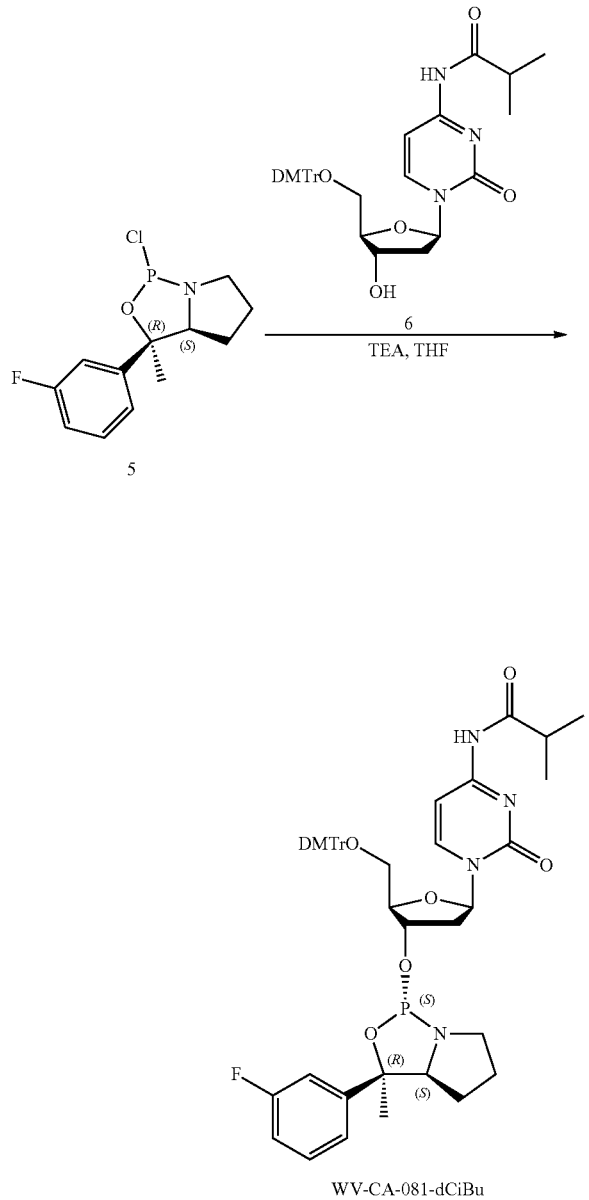

WV-CA-081-dCiBu

Compound 6 (5.30 g, 8.84 mmol) was dried by azeotropic distillation on a rotary evaporator with Pyridine (50 mL) and toluene (50 mL*5). The dried compound 6 (5.30 g, 8.84 mmol) was dissolved in THF (40.00 mL), and then TEA (4.47 g, 44.20 mmol, 6.12 mL) was added. The mixture was cooled to −70° C. A solution of compound 5 (3.63 g, 13.26 mmol) in THF (30 mL) was added dropwise at −70° C., after the addition, the mixture was warmed to 23° C. for 0.5 hr. TLC (Ethyl acetate/Petroleum ether=3:1, 5% TEA, $R_f$=0.46) showed compound 6 was consumed. The resulting mixture was diluted with DCM (30 mL) at −10° C., washed with ice-cold sat. NaHCO₃ aq. (30 mL*3). The aqueous layer was extracted with additional DCM (50 mL) at each washing stage. The organic layer was dried over anhydrous MgSO₄, filtered, and concentrated to afford a white foam (crude, 7.7 g). The above crude material was purified on a CombiFlash instrument from Teledyne using a pre-treated silica gel column. A 40 g silica gel cartridge column was first pre-treated by eluting with 5 column volumes of methanol, before equilibration with 5 column volumes of 20% EtOAc/hexanes containing 5% Et₃N. 7.7 g of crude product was dissolved in a 2:1 volume:volume mixture of DCM:Petroleum ether containing 5% Et₃N, then loaded onto a 40 g silica column which had been equilibrated with 5 column volumes of 20% Hexanes/EtOAc containing 5% Et₃N. After loading the sample on the column, the purification process was run using the following gradient: 20 to 80% EtOAc/hexanes containing 5% Et₃N, then residual solvent was removed to afford WV-CA-081-dCiBu as a white solid (4.80 g, 64.88%). All solvent was dried over anhydrous Na₂SO₄. ¹H NMR (400 MHz, CHLOROFORM-d) δ=8.91 (br s, 1H), 8.27 (br d, J=7.5 Hz, 1H), 7.40 (br d, J=8.2 Hz, 2H), 7.33-7.16 (m, 8H), 7.10 (br d, J=7.5 Hz, 1H), 7.02 (br d, J=7.7 Hz, 2H), 6.96-6.88 (m, 1H), 6.81 (br d, J=9.0 Hz, 4H), 6.26 (br t, J=5.2 Hz, 1H), 4.88 (br dd, J=5.5, 8.4 Hz, 1H), 4.25-4.16 (m, 1H), 3.80-3.69 (m, 7H), 3.51 (br s, 2H), 3.46-3.34 (m, 1H), 3.12-2.98 (m, 1H), 2.82-2.62 (m, 2H), 2.34 (td, J=5.8, 13.3 Hz, 1H), 1.74 (s, 3H), 1.63-1.47 (m, 2H), 1.44-1.29 (m, 2H), 1.20~1.12 (m, 6H). ¹³C NMR (101 MHz, CHLOROFORM-d) δ=176.88, 163.89, 162.41, 161.45, 158.67, 155.06, 146.66, 144.55, 144.12, 135.45, 135.36, 130.10, 130.08, 129.59, 129.51, 128.27, 127.99, 127.14, 121.00, 113.92, 113.70, 113.30, 112.70, 112.46, 96.20, 90.96, 90.86, 86.97, 86.81, 85.36, 85.33, 73.12, 73.10, 71.48, 71.31, 61.75, 60.38, 55.16, 46.68, 46.33, 41.22, 41.18, 36.55, 30.55, 29.90, 25.81, 25.77, 19.17, 19.01. ³¹P NMR (162 MHz, CHLOROFORM-d) δ=159.37 (s, 1P). TLC (Ethyl acetate/Petroleum ether=3:1, 5% TEA) $R_f$=0.46.

Example 86. Synthesis of WV-CA-082 and WV-CA-082-dCiBu

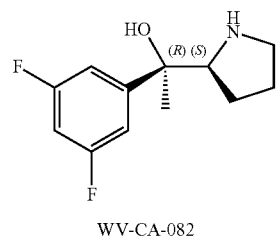

WV-CA-082

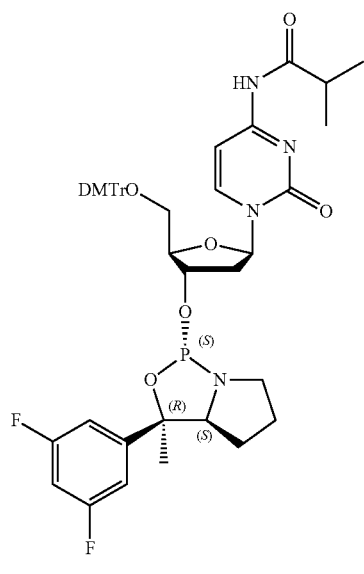
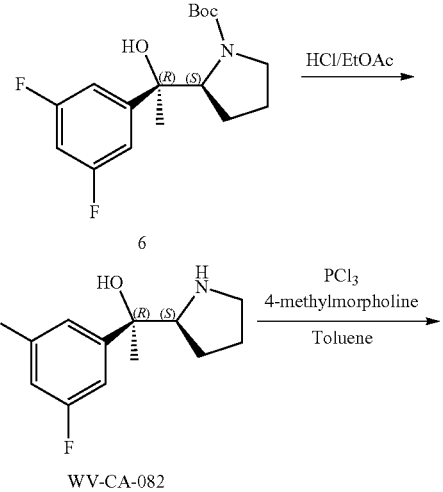
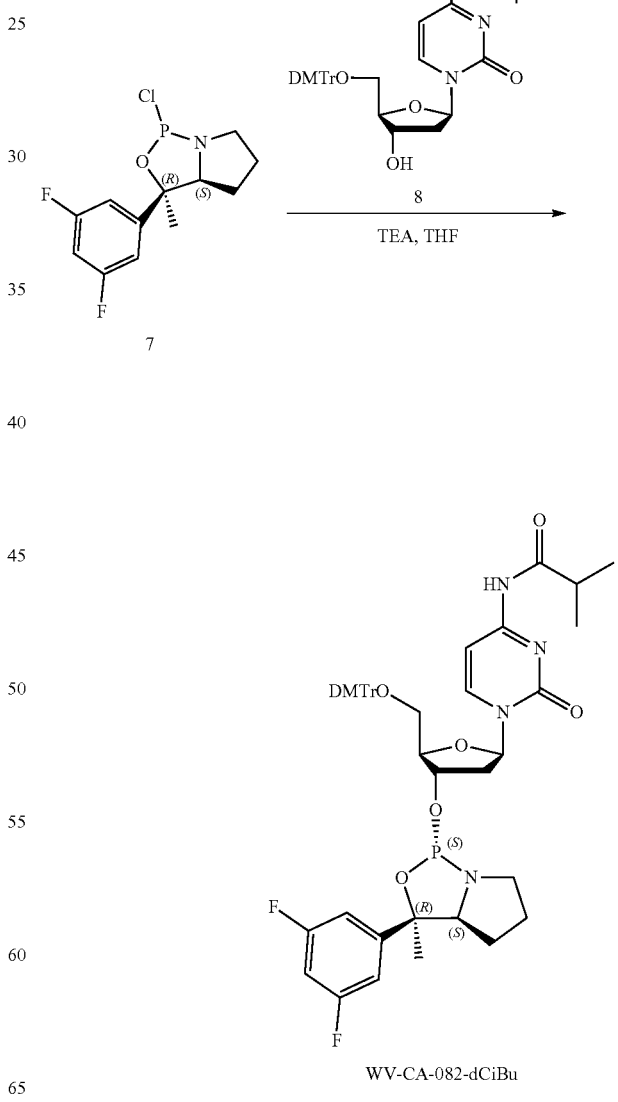

1. Preparation of Compound 2.

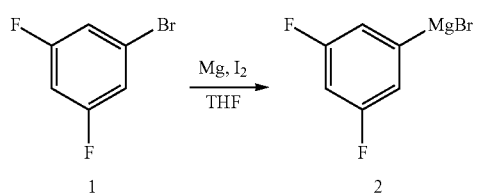
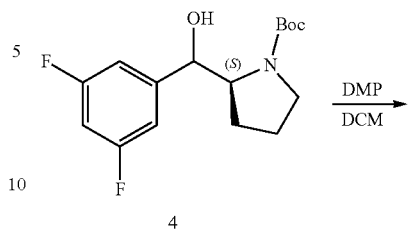

To a suspension of Mg (11.00 g, 452.40 mmol) and I₂ (40.00 mg, 157.60 μmol) in THF (230 mL) was added compound 1 (72.76 g, 377.00 mmol) in THF (54 mL) (first 10% volume, when the reaction was initiated, and then added dropwise the left over 2 hr at 50° C.). The mixture was stirred at 50° C. for another 1 hr. Most of Mg was consumed. The reaction was almost completed. The Grignard reagent in THF was used directly in next step.

2. Preparation of Compound 4.

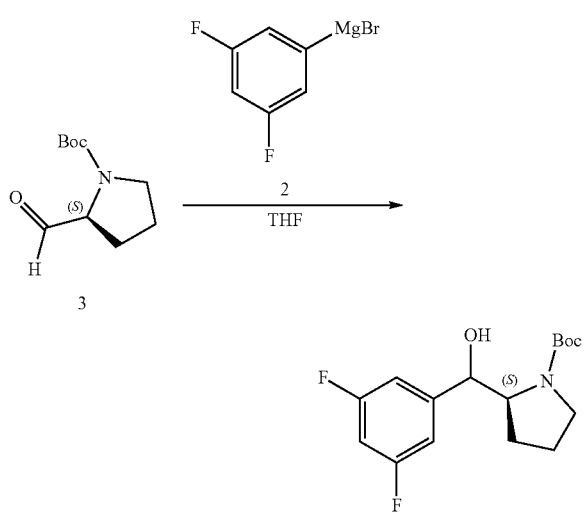

A solution of compound 3 (25.00 g, 125.47 mmol) in THF (100 mL) was added to the solution of compound 2 (81.79 g, 376.41 mmol) at −5~5° C. for 0.5 hr under N₂. Then the reaction was gradually warmed to 25° C. for 0.5 hr. The reaction was stirred at 15~25° C. for 15 hr. TLC showed compound 3 was almost consumed and one new spot was detected. The reaction mixture was quenched and added into ice-cold NH₄Cl (300 mL) at 0° C., and then diluted with EtOAc (300 mL) and extracted with EtOAc (300 mL*3). The combined organic layers were dried over Na₂SO₄, filtered, and concentrated under reduced pressure to give a residue. The residue was purified by MPLC (SiO₂, Petroleum ether/Ethyl acetate=50/1 to 1:1) to get compound 4 as a yellow oil (28.00 g, 71.22%). ¹H NMR (400 MHz, CHLOROFORM-d): δ=6.85 (br dd, J=6.6, 15.0 Hz, 2H), 6.73-6.58 (m, 1H), 6.04 (br s, 1H), 5.54 (br d, J=3.3 Hz, 1H), 4.50 (br d, J=6.8 Hz, 1H), 4.32-3.78 (m, 1H), 3.61-3.16 (m, 2H), 1.80-1.15 (m, 13H). TLC (Petroleum ether/Ethyl acetate=3:1) R$_f$=0.43.

3. Preparation of Compound 5.

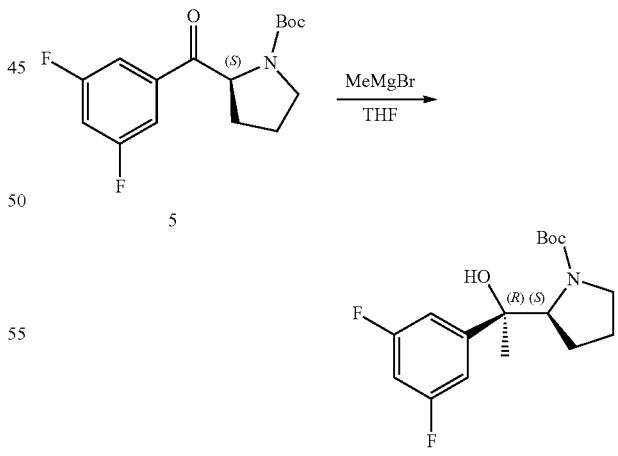

To a solution of compound 4 (28.00 g, 89.36 mmol) in DCM (280.00 mL) was added DMP (45.48 g, 107.23 mmol) at 0° C. The mixture was stirred at 10-20° C. for 2 hr. TLC and LCMS showed compound 4 was consumed and MS with the desired compound was detected. The mixture was diluted with CH₂Cl₂ (200 mL) and quenched by the addition of Na₂SO₃ (200 mL) at 0° C. and stirring for 20 minutes. The organic layer was washed with NaHCO₃ (aq., 100 mL*2) and extracted with CH₂Cl₂ (100 mL*3). The combined organic layers were dried over Na₂SO₄, filtered, and concentrated under reduced pressure to give a residue. The residue was purified by MPLC (SiO₂, Petroleum ether/Ethyl acetate=50/1 to 5:1) to give 24 g of the desired compound as a yellow oil. ¹H NMR (400 MHz, CHLOROFORM-d) δ=7.47 (br dd, J=5.9, 12.1 Hz, 2H), 7.13-6.95 (m, 1H), 5.24-5.03 (m, 1H), 3.73-3.40 (m, 2H), 2.40-2.22 (m, 1H), 2.02-1.81 (m, 3H), 1.50-1.23 (m, 9H). LCMS: (M+Na+): 334.1. TLC (Petroleum ether/Ethyl acetate=5:1) R$_f$=0.43.

4. Preparation of Compound 6.

To a solution of compound 5 (24.00 g, 77.09 mmol) in THF (100.00 mL) was added MeMgBr (3 M, 77.09 mL) at −5-0° C. under N₂ over 1 hr. The mixture was stirred at 15° C. for 3 hr. LCMS showed compound 5 was consumed and MS with the desired compound was detected. The reaction mixture was slowly added into ice-cold NH₄Cl (200 mL) at 0° C., and then diluted with EtOAc (300 mL) and extracted with EtOAc (300 mL*3). The combined organic layers were dried over Na₂SO₄, filtered, and concentrated under reduced pressure to give a residue. The residue was washed by petroleum ether (50 mL*2) and filtered to give 20 g of desired compound. Compound 6 was obtained as a white solid (20.00 g, 79.25%). ¹H NMR (400 MHz, CHLOROFORM-d) δ=7.05-6.89 (m, 2H), 6.70 (tt, J=2.3, 8.8 Hz, 1H), 6.57 (br s, 1H), 4.16 (dd, J=5.3, 8.6 Hz, 1H), 3.38 (br s, 1H), 2.57 (br s, 1H), 2.04 (br s, 1H), 1.76-1.63 (m, 1H), 1.62-1.41 (m, 14H). LCMS: (M+Na+): 352.2. HPLC purity=100.0%. SFC purity=100.0%.

5. Preparation of Compound WV-CA-082.

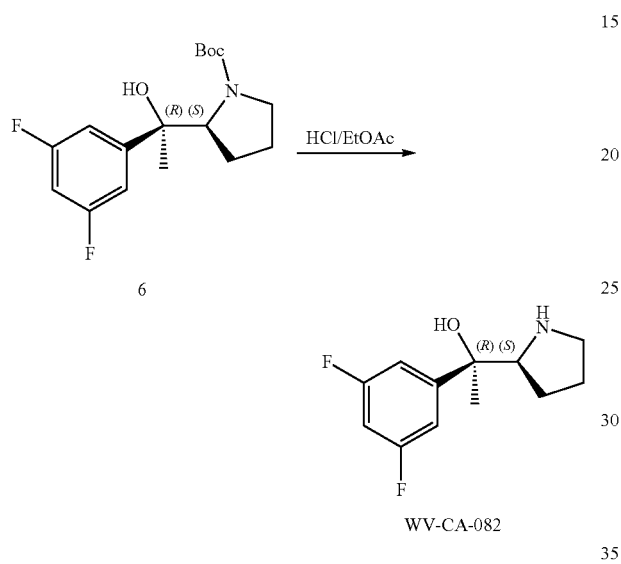

To a solution of compound 6 (20.00 g, 61.09 mmol) in EtOAc (10.00 mL) was added HCl/EtOAc (300.00 mL, 4 N). The mixture was stirred at 15° C. for 1 hr. TLC showed compound 6 was consumed. The mixture was concentrated under reduced pressure to give a residue. The residue was dissolved in H₂O (15 mL) and added Na₂CO₃ (aq.) until over pH 11, then the mixture was extracted with CH₂Cl₂ (100 mL*3), and concentrated under reduced pressure to give the product. Compound WV-CA-082 was obtained as a yellow oil (13.00 g, 93.64%). ¹H NMR: (400 MHz, CDCl₃) δ=7.01-6.91 (m, 2H), 6.64 (tt, J=2.3, 8.9 Hz, 1H), 3.39 (t, J=7.8 Hz, 1H), 3.08-2.91 (m, 2H), 1.75-1.52 (m, 2H), 1.43 (s, 3H), 1.38-1.20 (m, 2H). ¹³C NMR (101 MHz, CHLOROFORM-d) δ=164.14, 164.02, 161.69, 161.56, 150.77, 150.68, 108.08, 108.01, 107.89, 107.82, 101.51 (t, J=25.4 Hz, 1C), 73.38, 73.36, 66.25, 47.17, 29.82, 26.68, 26.01. LCMS: (M+H+): 228.1. TLC (Petroleum ether/Ethyl acetate=3:1, R_f=0). HPLC purity=100.0%. SFC purity=100.0%.

6. Preparation of Compound 7.

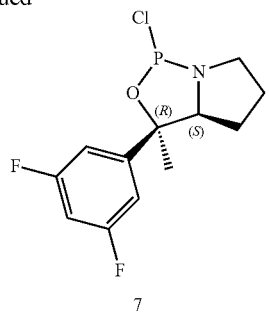

WV-CA-082 (2.00 g, 8.80 mmol) was dried by azeotropic distillation on a rotary evaporator with toluene (20 mL*3). To a solution of PCl₃ (1.21 g, 8.80 mmol) in toluene (25.00 mL) was added a solution of WV-CA-082 (2.00 g, 8.80 mmol) and 4-methylmorpholine (1.78 g, 17.60 mmol, 1.87 mL) in toluene (25.00 mL) at 0° C. The mixture was stirred at 15~20° C. for 1 hr. The phosphoryl chloride was not suitable for detection and no monitoring. The resulting mixture was filtered (flushed with Ar) and concentrated to afford the crude product compound 7 as a yellow oil (2.4 g, crude), the crude was used into the next step without further purification.

7. Preparation of Compound WV-CA-082-dCiBu.

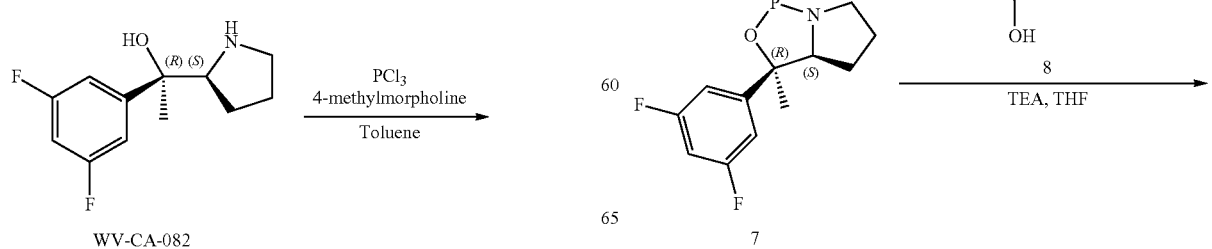

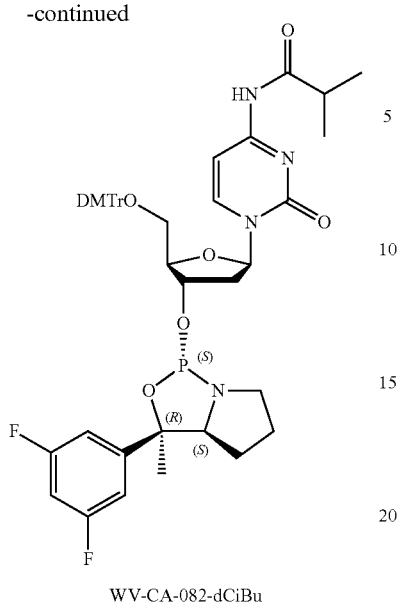

WV-CA-082-dCiBu

Compound 8 (3.30 g, 5.50 mmol) was dried by azeotropic distillation on a rotary evaporator with pyridine (50 mL) and toluene (50 mL*5). The dried compound 8 (3.30 g, 5.50 mmol) was dissolved in THF (50.00 mL), and then TEA (2.78 g, 27.50 mmol) was added. The mixture was cooled to −70° C. A solution of compound 7 (2.41 g, 8.25 mmol) in THF (20 mL) was added dropwise at −70° C., after the addition, the mixture was warmed to 23° C. for 0.5 hr TLC showed compound 8 was consumed and the reaction was completed. The resulting mixture was diluted with DCM (50 mL) at −10° C., washed with ice-cold sat. NaHCO₃ aq. (50 mL*3). The aqueous layer was extracted with additional DCM (50 mL) at each washing stage. The organic layer was dried over anhydrous MgSO₄, filtered, and concentrated to afford a white foam (crude, 7.7 g). The above crude material was purified on a CombiFlash instrument from Teledyne using either a pre-treated silica gel column. A 40 g silica gel cartridge column was first pre-treated by eluting with 5 column volumes of methanol, before equilibration with 5 column volumes of 20% EtOAc/hexanes containing 5% Et₃N. 7.7 g of crude product was dissolved in a 2:1 volume:volume mixture of DCM:Petroleum ether containing 5% Et₃N, then loaded onto a 40 g silica column which had been equilibrated with 5 column volumes of 20% Hexanes/EtOAc containing 5% Et₃N. After loading the sample on the column, the purification process was run using the following gradient: 20 to 80% EtOAc/hexanes containing 5% Et₃N, then the residual solvent was removed to afford WV-CA-082-dCiBu as a white solid (3.00 g, 63.81%). All solvent was dried over anhydrous Na₂SO₄. $^1$H NMR (400 MHz, CHLOROFORM-d) δ=8.37-8.21 (m, 2H), 7.40 (br d, J=7.5 Hz, 2H), 7.34-7.17 (m, 7H), 7.09 (br d, J=7.3 Hz, 1H), 6.82 (br d, J=8.8 Hz, 6H), 6.75-6.61 (m, 1H), 6.25 (t, J=5.6 Hz, 1H), 4.93-4.76 (m, 1H), 4.24-3.99 (m, 1H), 3.80-3.67 (m, 7H), 3.53-3.38 (m, 3H), 3.18-2.97 (m, 1H), 2.83-2.68 (m, 1H), 2.62-2.49 (m, 1H), 2.39-2.27 (m, 1H), 1.72 (s, 3H), 1.66-1.34 (m, 4H), 1.29-1.12 (m, 6H), 0.94-0.81 (m, 1H). $^{13}$CNMR (101 MHz, CHLOROFORM-d) δ=176.88, 164.11, 163.98, 162.43, 162.39, 161.64, 161.51, 158.70, 155.05, 144.50, 144.06, 135.48, 135.33, 130.10, 130.05, 128.29, 127.99, 127.16, 113.30, 108.62, 108.36, 102.35 (t, J=25.3 Hz, 1C), 96.22, 90.61, 90.49, 87.00, 86.83, 85.35, 85.32, 73.07, 73.04, 71.71, 71.54, 64.32, 61.81, 55.16, 46.61, 46.27, 41.18, 41.14, 36.58, 36.54, 30.65, 30.53, 29.94, 25.90, 25.86, 19.14, 19.11, 19.00, 13.68. $^{31}$P NMR (162 MHz, CHLOROFORM-d) δ=175.01 (s, 1P), 164.35 (s, 1P), 26.42 (s, 1P), 24.09 (s, 1P), 23.56 (s, 1P). TLC (Ethyl acetate/Petroleum ether=3:1, 5% TEA) R$_f$=0.43.

Example 87. Synthesis of WV-CA-083 and WV-CA-083-dCiBu

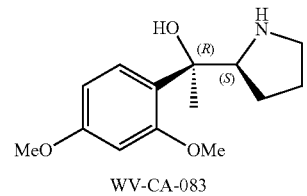

WV-CA-083

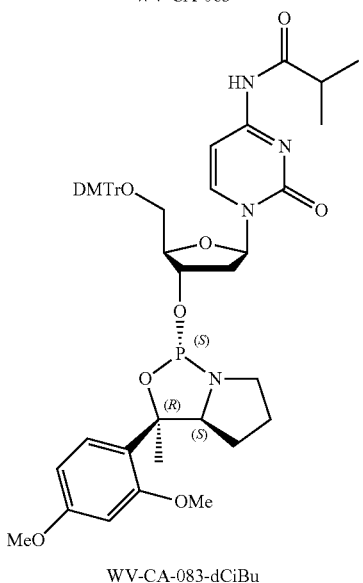

WV-CA-083-dCiBu

General Scheme.

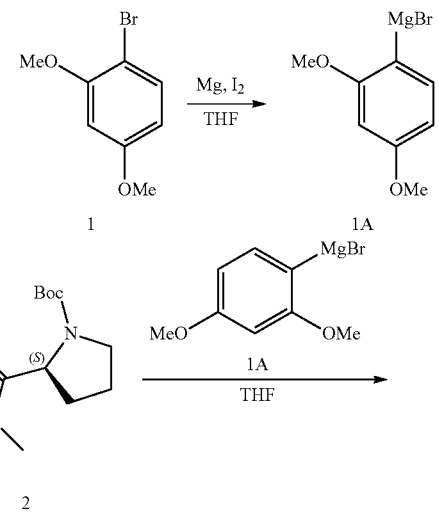

-continued

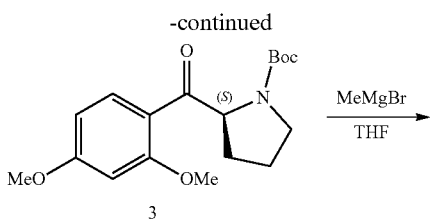

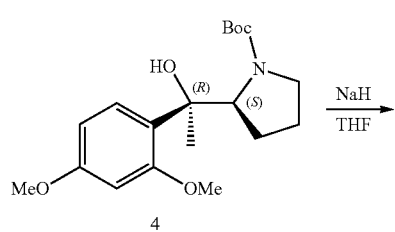

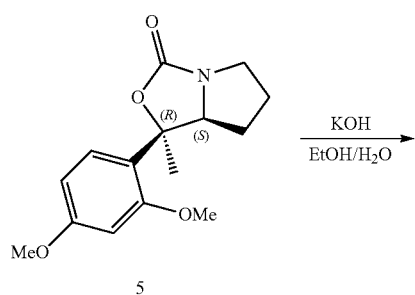

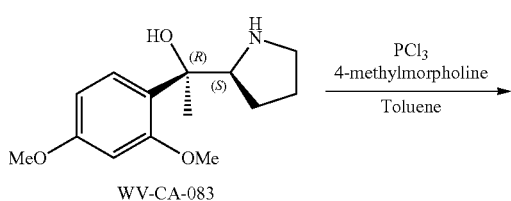

-continued

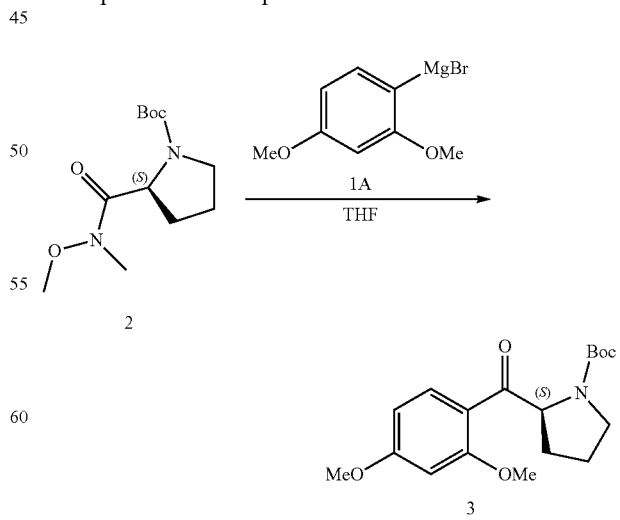

WV-CA-083-dCiBu

1. Preparation of Compound 1A.

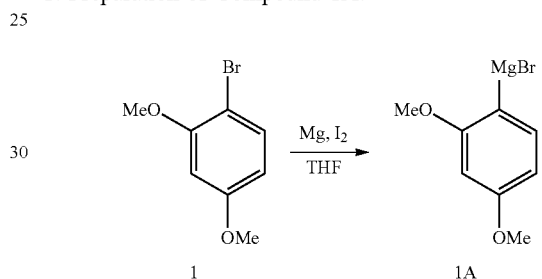

To a suspension of magnesium (16.95 g, 697.20 mmol) and I₂ (49.99 mg, 196.96 mol, 39.67 μL) in THF (200 mL) was added compound 1 (126.11 g, 581.00 mmol) in THF (235 mL) at 20~60° C. during addition for 1.5 hr. The mixture was stirred at 20~60° C. for 1.5 hr. Mg remained a little and the reaction was completed. Compound 1A in THF was used directly in the next step.

2. Preparation of Compound 3.

A solution of compound 2 in THF (100 mL) was added to the solution of compound 1A (140.17 g, 580.71 mmol) in THF at −5~5° C. for 1.5 hr under N₂. Then the reaction was gradually warmed to 25° C. for 0.5 hr. The reaction was stirred at 15~25° C. for 2 hr. TLC showed the starting material was consumed. The reaction mixture was quenched and added in ice-cold NH₄Cl (300 mL) at 0° C., and then diluted with EtOAc (300 mL) and extracted with EtOAc (300 mL*3). The combined organic layers were dried over Na₂SO₄, filtered, and concentrated under reduced pressure to give a residue. The residue was filtered and washed with petroleum ether (50 mL*3) to give 30 g of the compound 3 as a white solid. The filtrate was concentrated under reduced pressure to give a residue. The residue was purified by column chromatography (SiO₂, Petroleum ether/Ethyl acetate=50/1 to 1:1) to give 14 g product. Compound 3 was obtained as a white solid (44.00 g, 67.77%). ¹H NMR (400 MHz, CHLOROFORM-d) δ=7.97-7.75 (m, 1H), 6.58-6.35 (m, 2H), 5.37-5.09 (m, 1H), 3.89-3.78 (m, 6H), 3.68-3.52 (m, 1H), 3.48-3.33 (m, 1H), 2.27-2.13 (m, 1H), 1.95-1.74 (m, 3H), 1.47-1.22 (m, 9H). TLC (Petroleum ether/Ethyl acetate=3:1) R_f=0.27.

3. Preparation of Compound 4.

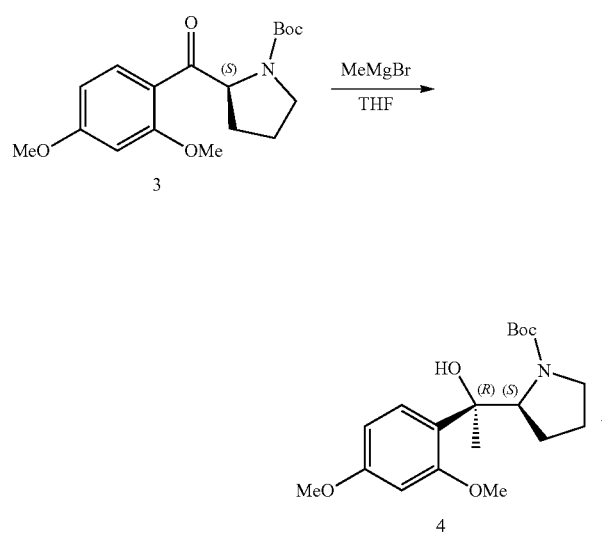

To a solution of compound 3 (44.00 g, 131.19 mmol) in THF (440.00 mL) was added MeMgBr (3 M, 131.19 mL) at −5-0° C. The mixture was stirred at −5-18° C. for 16 hr. TLC indicated compound 3 was consumed and one new spot formed. The reaction mixture was quenched by the addition of NH₄Cl at −5-0° C., and then diluted with EtOAc (400 mL), and extracted with EtOAc (400 mL*3). The combined organic layers were dried over Na₂SO₄, filtered, and concentrated under reduced pressure to give a residue. The residue was dissolved with DCM (10 mL), and then added EtOAc (10 mL), and petroleum ether (100 mL), concentrated under reduced pressure, filtered and recrystallization to give the first part of the product (21.5 g). Mother liquor was concentrated to dry and repeated the above operation to get the second part of the product (14.5 g). ¹H NMR (400 MHz, CHLOROFORM-d) δ=7.40 (d, J=8.2 Hz, 1H), 6.49-6.41 (m, 2H), 4.57 (br s, 1H), 3.80 (d, J=7.1 Hz, 6H), 3.13 (br s, 1H), 1.89-1.51 (m, 8H), 1.49-1.40 (m, 9H). LCMS: (M+Na): 374. TLC (Petroleum ether/Ethyl acetate=3:1) R_f=0.48. HPLC purity=98.233%. SFC purity=100%.

4. Preparation of Compound 5.

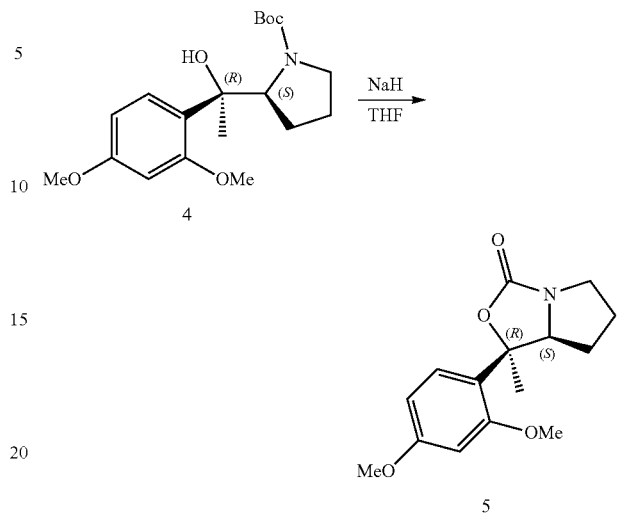

To a solution of compound 4 (34.00 g, 96.74 mmol) in THF (400.00 mL) was added NaH (5.80 g, 145.11 mmol, 60% purity) at 0° C. The mixture was stirred at 0-25° C. for 2 hr. TLC indicated compound 4 was consumed and one new spot formed. The mixture was added in ice NH₄Cl (300 mL) at 0° C. and then diluted with EtOAc (300 mL) and extracted with EtOAc (300 mL*3). The combined organic layers dried over Na₂SO₄, filtered, and concentrated under reduced pressure to give a residue. The residue was washed by petroleum ether (30 mL*3) to give 25 g of the product. Compound 5 was obtained as a white solid (25.00 g, 93.19%). ¹H NMR (400 MHz, CHLOROFORM-d) δ=7.45 (d, J=8.4 Hz, 1H), 6.50-6.42 (m, 2H), 3.99-3.90 (m, 1H), 3.80 (s, 6H), 3.72-3.61 (m, 1H), 3.17 (ddd, J=4.0, 9.6, 11.5 Hz, 1H), 1.96-1.71 (m, 5H), 1.62-1.51 (m, 1H), 1.02-0.86 (m, 1H). LCMS: (M+H+): 278. TLC (Petroleum ether:Ethyl acetate=3:1) R_f=0.30. HPLC purity=98.856%. SFC purity=100%.

5. Preparation of WV-CA-083.

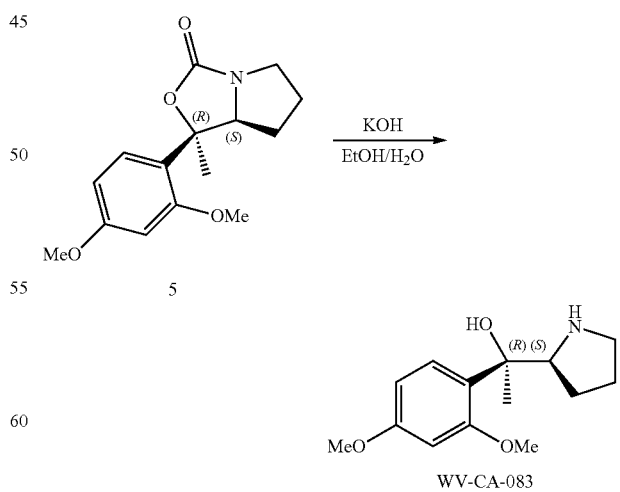

To a solution of compound 5 (25.00 g, 90.15 mmol) in EtOH (30.00 mL) and H₂O (30.00 mL) was added KOH (40.00 g, 713.09 mmol). The mixture was stirred at 90° C.

for 16 hr. TLC indicated compound 5 was consumed and one new spot formed. The reaction mixture was partitioned by CH$_2$Cl$_2$ (50 mL). The organic phase was separated, and the aqueous layer was extracted with CH$_2$Cl$_2$ (50 mL*3), dried over Na$_2$SO$_4$, filtered and concentrated under reduced pressure to give a residue. Compound WV-CA-083 was obtained as a yellow solid (21.00 g, 92.69%). $^1$H NMR (400 MHz, CHLOROFORM-d) δ=7.58 (d, J=8.5 Hz, 1H), 6.55-6.37 (m, 2H), 3.92 (t, J=8.1 Hz, 1H), 3.86-3.72 (m, 1H), 3.12-2.90 (m, 2H), 1.77-1.53 (m, 2H), 1.50 (s, 3H), 1.44-1.20 (m, 2H). $^{13}$C NMR (101 MHz, CHLOROFORM-d) δ ppm 26.47 (s, 1C) 27.06 (s, 1C) 27.89 (s, 1C) 47.33 (s, 1C) 55.13 (s, 1C) 55.24 (s, 1C) 63.96 (s, 1C) 73.49 (s, 1C) 98.83 (s, 1C) 103.52 (s, 1C) 127.14 (s, 1C) 127.55 (s, 1C) 156.80 (s, 1C) 159.41 (s, 1C). LCMS: (M+H+): 252.1. TLC (Dichloromethane/Methanol=10:1) R$_f$=0.03.

6. Preparation of Compound 6.

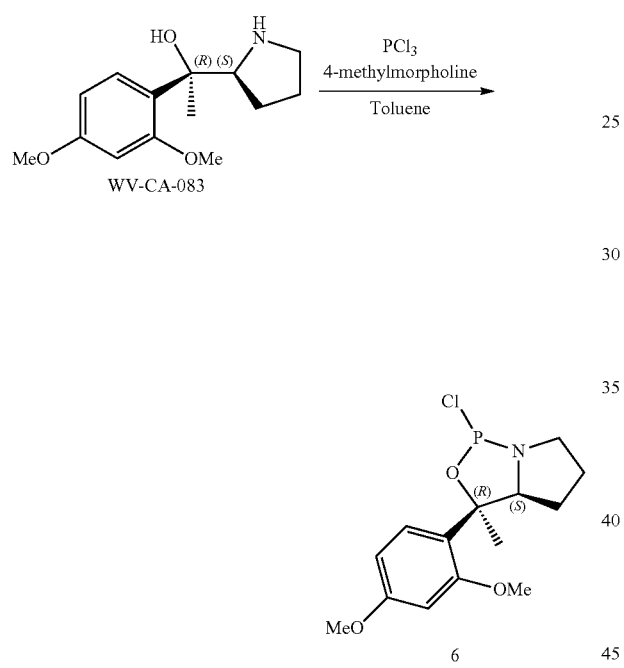

WV-CA-083 (3.10 g, 12.33 mmol) was dried by azeotropic distillation on a rotary evaporator with toluene (20 mL*3). To a solution of PCl$_3$ (1.69 g, 12.33 mmol) in toluene (30.00 mL) was added a solution of WV-CA-083 (3.10 g, 12.33 mmol) and 4-methylmorpholine (2.49 g, 24.66 mmol, 2.71 mL) in toluene (30.00 mL) at 0° C. The mixture was stirred at 15~20° C. for 1.5 hr. The phosphoryl chloride was not suitable for detection and no monitoring. The resulting mixture was filtered (flushed with Ar) and concentrated to afford compound 6, which was used into the next step without further purification (3.40 g, 87.34%).

7. Preparation of WV-CA-083-dCiBu.

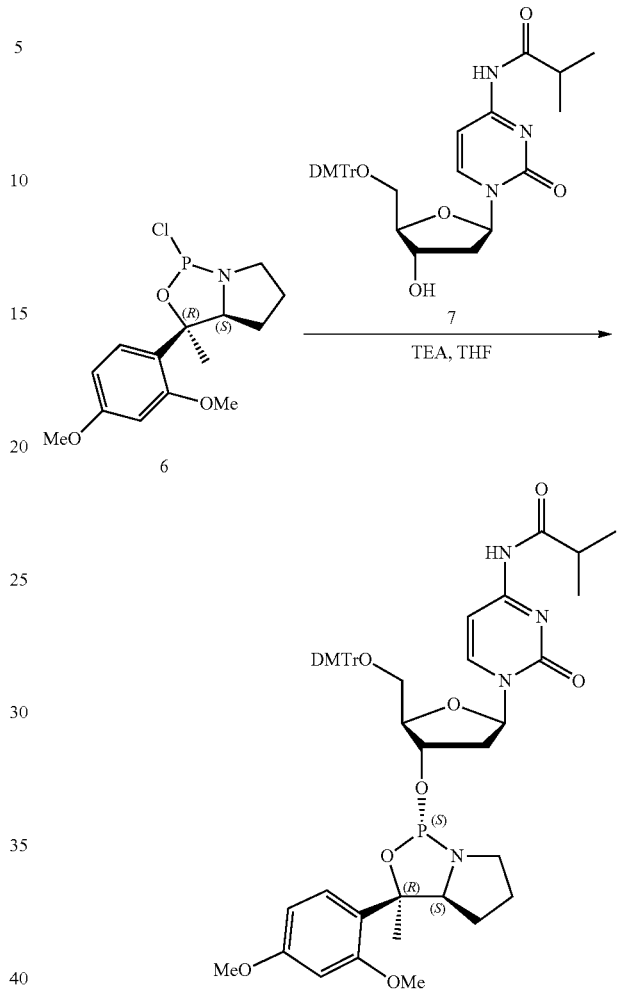

The compound 7 (4.30 g, 7.17 mmol) was dried by azeotropic distillation on a rotary evaporator with pyridine (50 mL) and toluene (50 mL*5). The dried compound 7 (4.30 g, 7.17 mmol) was dissolved in THF (30.00 mL), and then TEA (3.63 g, 35.85 mmol, 4.97 mL) was added. The mixture was cooled to −70° C. A solution of compound 6 (3.40 g, 10.76 mmol) in THF (30 mL) was added dropwise at −70° C., after the addition, the mixture was warmed to 23° C. for 0.5 hr. TLC showed the compound 7 was consumed and the reaction was completed. The resulting mixture was diluted with DCM (50 mL) at −10° C., washed with ice-cold sat. NaHCO$_3$ aq. (50 mL*3). The aqueous layer was extracted with additional DCM (50 mL) at each washing stage. The organic layer was dried over anhydrous MgSO$_4$, filtered, and concentrated to afford a white foam (crude, 7.3 g). The above crude material was purified on a CombiFlash instrument from Teledyne using a pre-treated silica gel column. A 40 g silica gel cartridge column was first pre-treated by eluting with 5 column volumes of methanol, before equilibration with 5 column volumes of 20% EtOAc/hexanes containing 5% Et$_3$N. 7.3 g of crude product was dissolved in a 2:1 volume:volume mixture of methylene chloride:Petroleum ether containing 5% Et$_3$N then loaded onto a 40 g silica column which had been equilibrated with 5 column volumes of 20% Hexanes/EtOAc containing 5% Et₃N. After loading the sample on the column, the purification process was run using the following gradient: 20 to 80% EtOAc/hexanes containing 5% Et₃N, then residual solvent was removed to afford WV-CA-083-dCiBu as a white solid. All solvent was dried over anhydrous Na₂SO₄ (4.50 g, 71.41%). ¹H NMR (400 MHz, CHLOROFORM-d) δ=8.53 (br d, J=7.9 Hz, 1H), 8.31 (d, J=7.5 Hz, 1H), 7.43 (dd, J=5.5, 7.9 Hz, 3H), 7.35-7.19 (m, 7H), 7.05 (br d, J=7.5 Hz, 1H), 6.83 (dd, J=1.9, 8.9 Hz, 4H), 6.48-6.40 (m, 2H), 6.24 (dd, J=4.4, 6.4 Hz, 1H), 4.97-4.84 (m, 1H), 4.26-4.18 (m, 1H), 3.96 (td, J=6.3, 9.5 Hz, 1H), 3.86-3.70 (m, 12H), 3.61-3.46 (m, 3H), 3.25-3.09 (m, 1H), 2.86-2.72 (m, 1H), 2.60 (qd, J=6.8, 13.8 Hz, 1H), 2.41-2.30 (m, 1H), 1.71 (s, 3H), 1.69-1.56 (m, 2H), 1.43-1.33 (m, 1H), 1.20 (ddd, J=2.3, 4.9, 6.9 Hz, 6H), 0.74 (qd, J=9.5, 12.1 Hz, 1H). ¹³C NMR (101 MHz, CHLOROFORM-d) δ=177.00 (br s, 1C), 162.45, 159.97, 158.65, 155.40, 155.07, 144.60, 144.22, 135.52, 135.44, 130.15, 130.11, 128.28, 128.00, 127.08, 126.70, 125.85, 125.81, 113.32, 103.50, 98.71, 96.20, 91.37, 91.25, 86.95, 86.76, 85.28, 85.25, 72.97, 72.95, 71.23, 71.04, 61.65, 60.36, 55.31, 55.16, 55.04, 46.89, 46.51, 41.22, 41.17, 36.46, 29.86, 29.69, 25.86, 25.82, 19.18, 19.11, 19.02. ³¹P NMR (162 MHz, CHLOROFORM-d) δ=161.01 (s, 1P). TLC (Ethyl acetate/Petroleum ether=3:1, 5% TEA) R$_f$=0.43.

Example 88. Synthesis of WV-CA-090

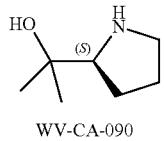

WV-CA-090

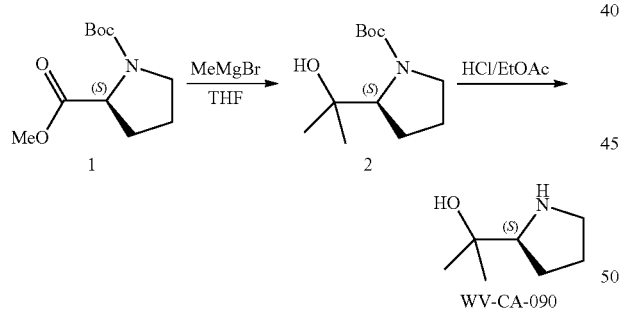

1. Preparation of Compound 2.

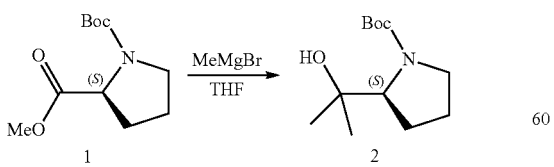

To a solution of compound 1 (50.00 g, 218.08 mmol) in THF (500.00 mL) was added MeMgBr (3 M, 218.08 mL) at −5° C. The mixture was stirred at −5-25° C. for 4 hr. TLC indicated compound 1 was consumed and one new spot formed. The reaction mixture was quenched by addition sat. NH₄Cl aq. 400 mL at −5-0° C., and then diluted with EtOAc 400 mL and extracted with EtOAc 400 mL (400 mL*3), dried over Na₂SO₄, filtered and concentrated under reduced pressure to give a residue. The residue was purified by column chromatography (SiO₂, Petroleum ether/Ethyl acetate=100/1 to 1/1) to get the product. Compound 2 was obtained as a white solid (36.00 g, 71.99%). ¹H NMR (400 MHz, CHLOROFORM-d) δ=5.89 (br s, 1H), 3.84 (t, J=7.4 Hz, 1H), 3.64 (br s, 1H), 3.27-3.06 (m, 1H), 2.22-1.92 (m, 1H), 1.88-1.49 (m, 3H), 1.48-1.36 (m, 9H), 1.18-0.98 (m, 1H), 1.18-0.95 (m, 5H). TLC (Plate 1: Petroleum ether:Ethyl acetate=5:1) R$_f$=0.41.

2. Preparation of WV-CA-090.

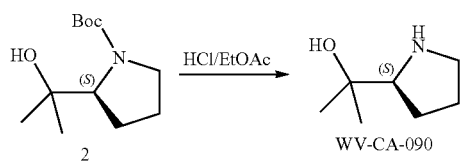

To a solution of compound 2 (36.00 g, 156.99 mmol) in EtOAc (30 mL) was added HCl/EtOAc (360.00 mL) at 0° C. The mixture was stirred at 0-25° C. for 2 hr. TLC indicated compound 2 was consumed and one new spot formed. The reaction mixture was concentrated under reduced pressure to remove solvent at 30-35° C., then to the residue was added H₂O (5 mL) and sat. Na₂CO₃ aq. until pH=11. The combined organic layers were washed with dichloromethane (300 mL*6), dried over Na₂SO₄, filtered and concentrated under reduced pressure to give a residue. WV-CA-090 was obtained as a yellow solid (14.00 g, 69.02%). ¹H NMR (400 MHz, CHLOROFORM-d) δ=3.05-2.84 (m, 3H), 1.81-1.52 (m, 4H), 1.13 (s, 3H), 1.09 (s, 3H). ¹³C NMR (101 MHz, CHLOROFORM-d) δ=70.31, 66.91, 46.95, 28.67, 26.36, 26.08, 25.10. LCMS: (M+H+): 130.1. TLC (Plate 1: Petroleum ether:Ethyl acetate=3:1) R$_f$=0.

Example 89. Synthesis of WV-CA-090-dCiBu

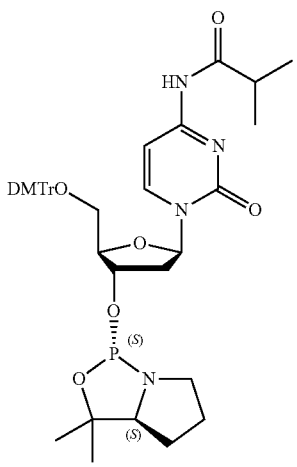

WV-CA-090-dCiBu

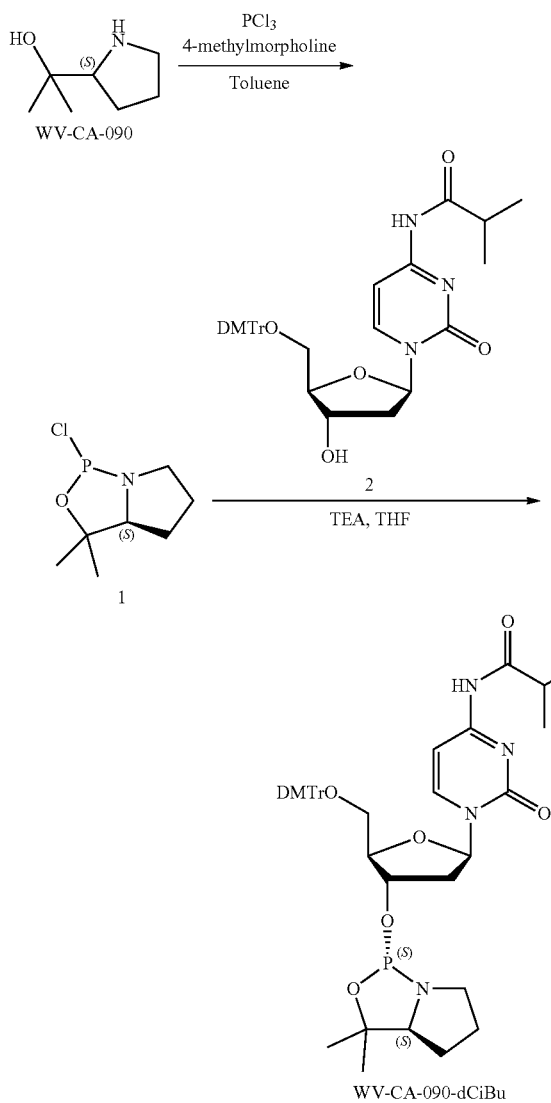

2. Preparation of WV-CA-090-dCiBu.

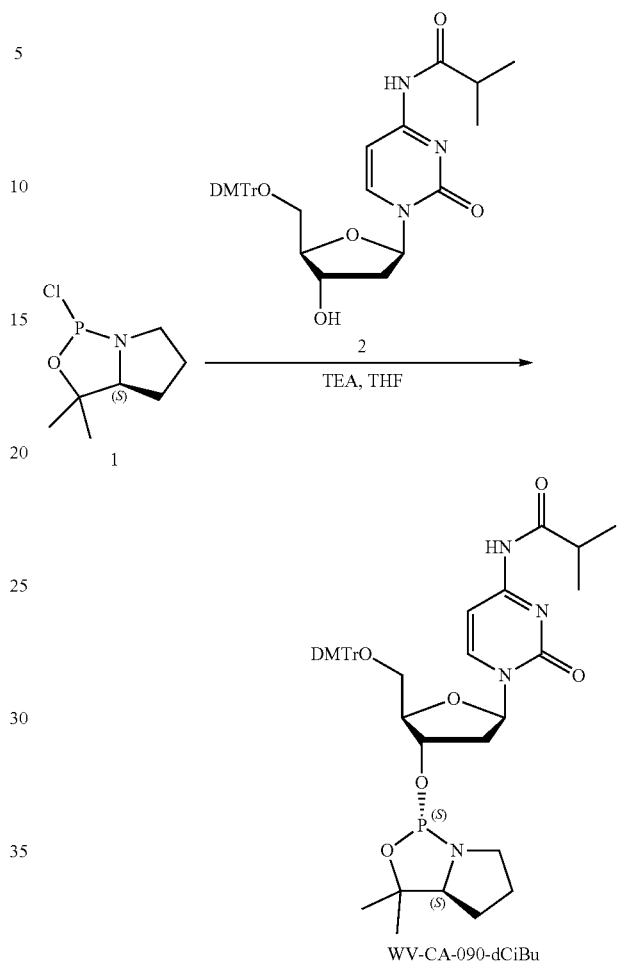

1. Preparation of Compound 1.

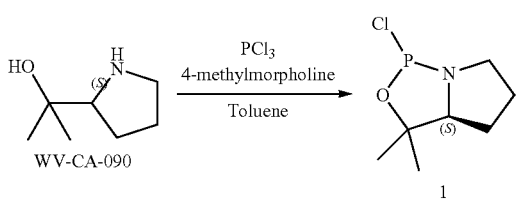

The WV-CA-090 (2.00 g, 15.48 mmol) was dried by azeotropic distillation on a rotary evaporator with toluene (20 mL*3). To a solution of PCl₃ (2.13 g, 15.48 mmol) in toluene (20.00 mL) was added a solution of WV-CA-090 (2.00 g, 15.48 mmol) and 4-methylmorpholine (3.13 g, 30.96 mmol) in toluene (20.00 mL) at 0° C. The mixture was stirred at 15~20° C. for 1.5 hr. The Phosphoryl chloride was not suitable for detection and no monitoring. The resulting mixture was filtered (flushed with Ar) and concentrated to afford the compound 1 (2.10 g, crude) was used into the next step without further purification.

The compound 2 (4.20 g, 7.00 mmol) was dried by azeotropic distillation on a rotary evaporator with pyridine (50 mL) and toluene (50 mL*5). The dried compound 2 (4.20 g, 7.00 mmol) was dissolved was dissolved in THF (30.00 mL), and then TEA (3.54 g, 35.02 mmol) was added. The mixture was cooled to −70° C. A THF (30 mL) solution of compound 1 (2.03 g, 10.51 mmol) was added dropwise at −70° C., after the addition, the mixture was warmed to 23° C. for 0.5 hr. TLC showed the compound 2 was consumed and the reaction was completed. The resulting mixture was diluted with DCM (50 mL) at −10° C., washed with ice-cold sat. NaHCO₃ aq. (50 mL*3). The aqueous layer was extracted at each and washing stage with additional DCM (50 mL). The organic layer was dried over anhydrous MgSO₄, filtered, and concentrated to afford a white foam (crude (7.5 g). The above crude material was purified on a CombiFlash instrument from Teledyne using either a pre-treated silica gel column. A 40 g silica gel cartridge column was first pre-treated by eluting with 5 column volumes of methanol, before equilibration with 5 column volumes of 20% EtOAc/Petroleum ether containing 5% Et₃N. 7.5 g of crude product was dissolved in a 2:1 volume:volume mixture of methylene chloride:Petroleum ether containing 5% Et₃N then loaded onto a 40 g silica column which had been equilibrated with 5 column volumes of 20% Petroleum ether/EtOAc containing 5% Et₃N. After loading the sample on the column, the purification process was run using the following gradient: 20 to 80% EtOAc/Petroleum ether containing 5% Et₃N, then the residual solvent was removed to afford WV-CA-090-dCiBu as a white solid (3.80 g, 71.73%). All solvent was dried over anhydrous Na₂SO₄. ¹H NMR (400 MHz, CDCl₃): δ=8.37-8.19 (m, 2H), 7.42-7.36 (m, 2H), 7.34-7.20 (m, 7H), 7.05 (d, J=7.3 Hz, 1H), 6.84 (dd, J=1.4, 8.9 Hz, 4H), 6.24 (t, J=5.6 Hz, 1H), 4.81-4.71 (m, 1H), 4.17-4.15 (m, 1H), 3.82-3.77 (m, 6H), 3.53-3.35 (m, 4H), 3.00 (qd, J=7.3, 10.1 Hz, 1H), 2.76-2.66 (m, 1H), 2.62-2.52 (m, 1H), 2.29 (td, J=5.8, 13.7 Hz, 1H), 1.83-1.65 (m, 3H), 1.46-1.34 (m, 4H), 1.28-1.15 (m, 9H). ¹³C NMR (101 MHz, CDCl₃): δ=177.09, 162.49, 158.68, 158.66, 155.05, 144.53, 144.12, 135.53, 135.32, 130.17, 130.07, 128.26, 127.97, 127.10, 113.27, 96.23, 87.42, 87.31, 86.86, 85.50, 85.48, 71.25, 71.24, 70.70, 70.60, 61.93, 55.21, 46.15, 45.81, 41.32, 41.29, 36.42, 29.59, 27.96, 26.88, 26.84, 24.74, 24.71, 19.19, 18.99. ³¹P NMR (162 MHz, CHLOROFORM-d): δ=153.55 (s, 1P). TLC (Ethyl acetate/Petroleum ether=3:1, 5% TEA) Rf=0.43.

Example 90. Synthesis of WV-CA-091

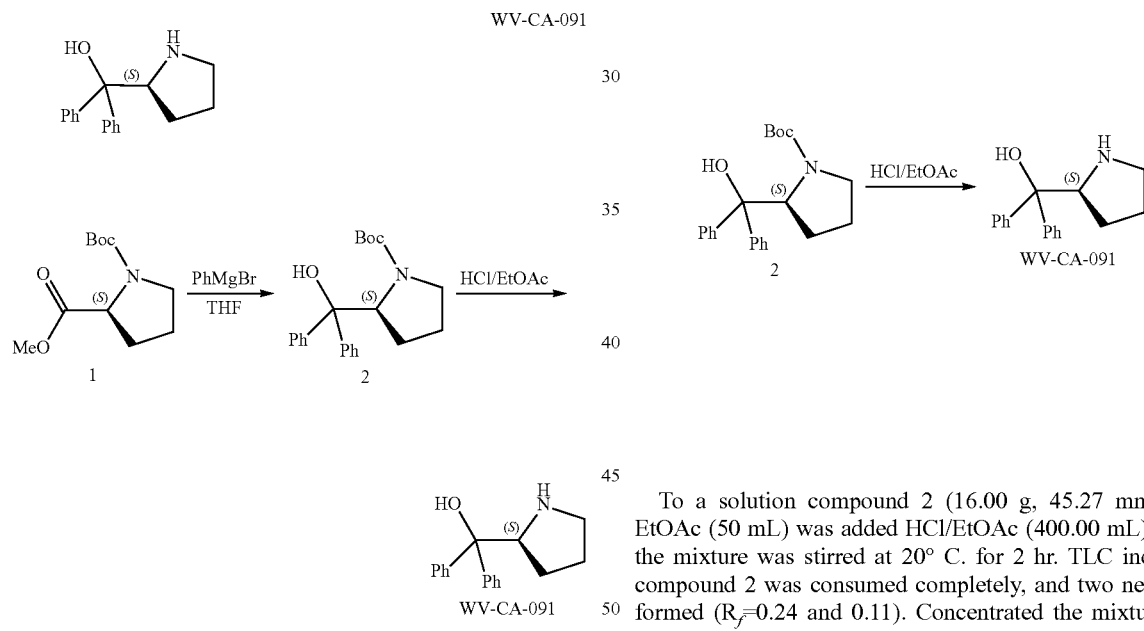

1. Preparation of Compound 2.

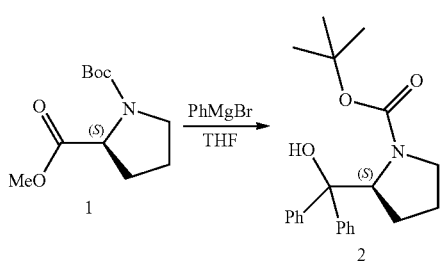

Bromo (phenyl) magnesium (3 M, 101.77 mL) in THF (200 mL) was added a solution of compound 1 (20.00 g, 87.23 mmol) in THF (300 mL) slowly via addition funnel at −20° C. After addition the mixture was stirred at 20° C. for 14 hr. TLC (Petroleum ether:Ethyl acetate=3:1) showed the starting material was consumed. The mixture was poured into NH₄Cl (aq., 500 mL), the organic layer was separated and the aqueous layer was extracted with EtOAc (300 mL*3). The combined organics were washed with brine (300 mL), dried over Na₂SO₄, filtered and concentrated to get the crude. The mixture was purified by washing with Petroleum ether to afford the product. Compound 2 was gotten as white solid (20.00 g, 64.87% yield). ¹H NMR (400 MHz, CHLOROFORM-d) δ=7.43-7.22 (m, 8H), 7.48-7.17 (m, 1H), 7.50-7.03 (m, 1H), 4.89 (dd, J=3.6, 8.9 Hz, 1H), 3.35 (br d, J=7.9 Hz, 1H), 2.86 (br s, 1H), 2.09 (qd, J=8.8, 13.4 Hz, 1H), 1.92 (tdd, J=4.1, 8.5, 12.9 Hz, 1H), 1.58 (s, 1H), 1.54-1.34 (m, 10H), 0.91-0.59 (m, 1H). TLC (Petroleum ether/Ethyl acetate=3:1) R_f=0.05.

2. Preparation of WV-CA-091.

To a solution compound 2 (16.00 g, 45.27 mmol) in EtOAc (50 mL) was added HCl/EtOAc (400.00 mL). Then the mixture was stirred at 20° C. for 2 hr. TLC indicated compound 2 was consumed completely, and two new spot formed (R_f=0.24 and 0.11). Concentrated the mixture and filtered to get the crude. The crude was washed with Petroleum ether (200 mL), then dissolved in water (50 mL), after that Na₂CO₃ (aq.) was added until pH>11, extracted with DCM (150 mL*3). The combined organics were dried over Na₂SO₄, filtered, and concentrated to get the crude-product. Compound WV-CA-091 was obtained as a yellow solid (6.90 g, 60.16%). ¹H NMR (400 MHz, CHLOROFORM-d) δ=7.58-7.52 (m, 2H), 7.51-7.44 (m, 2H), 7.27 (q, J=7.1 Hz, 4H), 7.18-7.10 (m, 2H), 4.24 (t, J=7.6 Hz, 1H), 4.32-4.16 (m, 1H), 3.06-2.98 (m, 1H), 2.97-2.88 (m, 1H), 1.76-1.67 (m, 2H), 1.76-1.67 (m, 1H), 1.66-1.52 (m, 2H). ¹³C NMR (101 MHz, CHLOROFORM-d) δ=148.14, 145.38, 128.19, 127.93, 126.42, 126.31, 125.83, 125.51, 64.46, 46.75, 26.27, 25.49. LCMS: (M+H+): 254.1. TLC (Petroleum ether/Ethyl acetate=3:1) R_f=0.11. HPLC purity=96.4%. SFC purity=100.0%.

Example 91. Synthesis of WV-CA-091-dCiBu

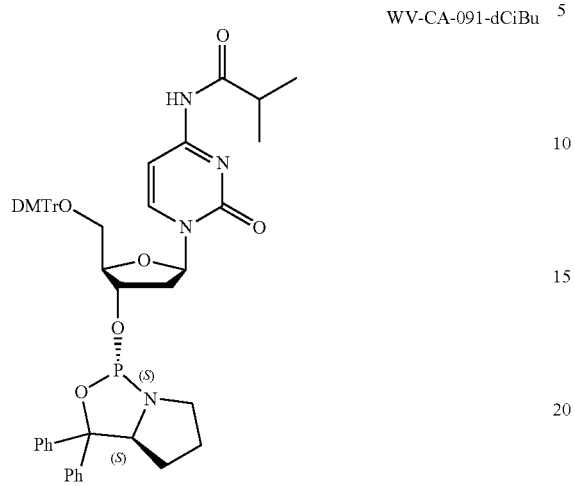

WV-CA-091-dCiBu

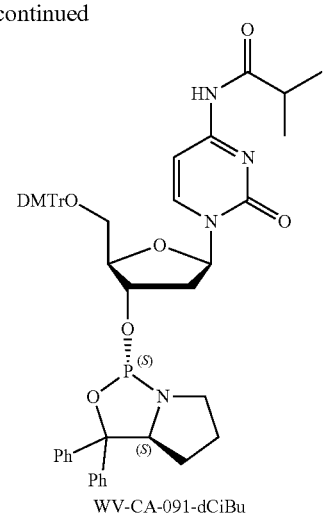

WV-CA-091-dCiBu

1. Preparation of Compound 2.

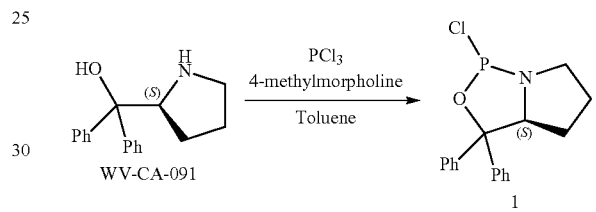

The WV-CA-091 (2.00 g, 15.48 mmol) as dried by azeotropic distillation on rotary evaporator with toluene (20 mL*3). To a solution of $PCl_3$ (1.08 g, 7.89 mmol in toluene (20.00 mL) was added a solution of WV-CA-091 (2.00 g, 7.89 mmol) and 4-methylmorpholine (1.60 g, 15.79 mmol) in toluene (20.00 mL) at 0° C. The mixture was stirred at 15~20° C. for 1.5 hr. The phosphoryl chloride was not suitable for detection and no monitoring. The resulting mixture was filtered (flushed with Ar) and concentrated to afford the compound 1 (2.20 g, crude) was used into the next step without further purification.

2. Preparation of WV-CA-091-dCiBu.

General Scheme.

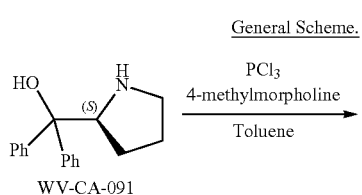

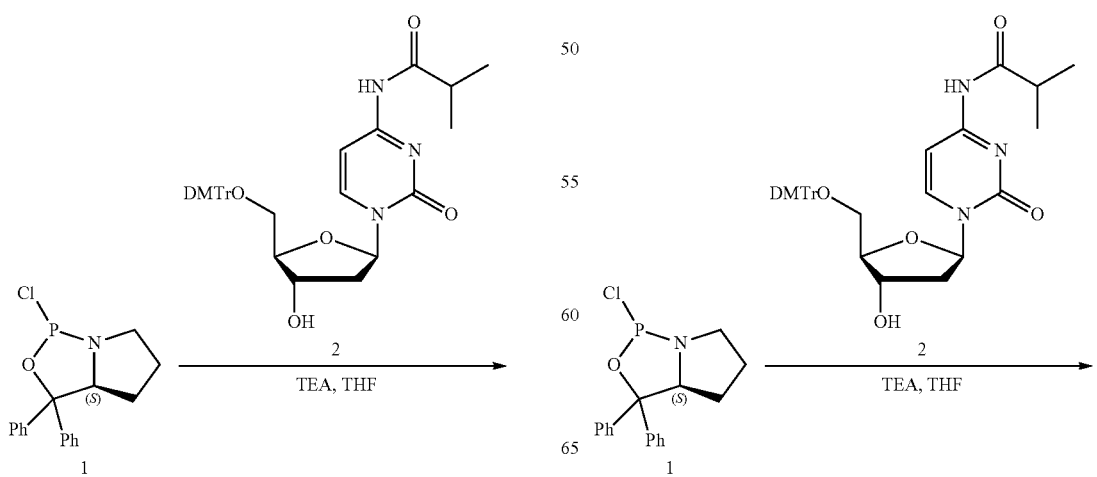

-continued

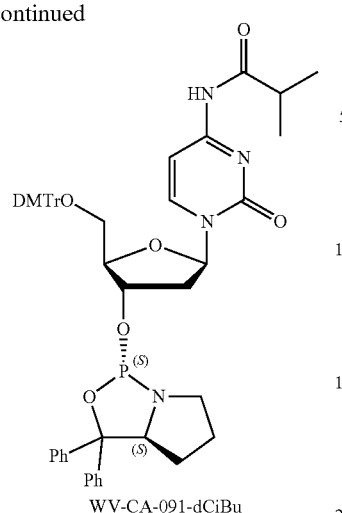

WV-CA-091-dCiBu

The compound 2 (3.50 g, 5.84 mmol) was dried by azeotropic distillation on a rotary evaporator with pyridine (50 mL) and toluene (50 mL*5). The dried compound 2 (3.50 g, 5.84 mmol) was dissolved in THF (60.00 mL), and then TEA (2.95 g, 29.18 mmol) was added. The mixture was cooled to −70° C. A THF (30 mL) solution of compound 1 (2.24 g, 8.75 mmol) was added dropwise at −70° C., and after the addition, the mixture was warm to 23° C. for 1.5 hr. TLC showed compound 2 was consumed and the reaction was completed. The resulting mixture was diluted with DCM (50 mL) at −10° C., washed with ice-cold sat. NaHCO$_3$ aq. (50 mL*3). The aqueous layer was extracted at each and washing stage with additional DCM (50 mL). The organic layer was dried over anhydrous MgSO$_4$, filtered, and concentrated to afford a white foam crude (6.3 g). The above crude material was purified on a CombiFlash instrument from Teledyne using either a pre-treated silica gel column. A 40 g silica gel cartridge column was first pre-treated by eluting with 5 column volumes of methanol, before equilibration with 5 column volumes of 20% EtOAc/Petroleum ether containing 5% Et$_3$N. 6.3 g of crude product was dissolved in a 2:1 volume:volume mixture of methylene chloride:Petroleum ether containing 5% Et$_3$N then loaded onto a 40 g silica column which had been equilibrated with 5 column volumes of 20% Petroleum ether/EtOAc containing 5% Et$_3$N. After loading the sample on the column, the purification process was run using the following gradient: 20 to 80% EtOAc/Petroleum ether containing 5% Et$_3$N, then the residual solvent was removed to afford WV-CA-091-dCiBu as a white solid (3.00 g, 58.45%). All solvent was dried over anhydrous Na$_2$SO$_4$. $^1$H NMR (400 MHz, CHLOROFORM-d) δ=8.08 (d, J=7.3 Hz, 1H), 7.93 (br s, 1H), 7.41-7.08 (m, 19H), 6.93 (br d, J=7.1 Hz, 1H), 6.85 (dd, J=2.0, 9.0 Hz, 4H), 6.07 (dd, J=4.4, 6.6 Hz, 1H), 4.56-4.43 (m, 2H), 3.80 (s, 6H), 3.73-3.68 (m, 1H), 3.45-3.35 (m, 2H), 3.28 (dd, J=3.0, 10.7 Hz, 1H), 2.88-2.76 (m, 1H), 2.60-2.44 (m, 3H), 1.96-1.87 (m, 1H), 1.68-1.40 (m, 4H), 1.27-1.24 (m, 6H). $^{13}$C NMR (101 MHz, CDCl$_3$): δ=176.99, 162.26, 158.71, 158.70, 154.80, 144.75, 144.18, 142.58, 142.55, 135.51, 135.37, 130.18, 130.09, 128.04 (dd, J=20.2, 36.3 Hz, 1C), 127.58, 127.16, 127.10, 126.72, 126.69, 113.25, 96.23, 94.90, 94.78, 86.89, 86.28, 84.79, 70.66, 70.55, 70.53, 61.56, 55.23, 46.34, 46.26, 46.00, 40.75, 36.51, 29.64, 25.65, 25.62, 19.23, 19.05. $^{31}$P NMR (162 MHz, CDCl$_3$): δ=145.63 (s, 1P), 145.53 (s, 1P). TLC (Ethyl acetate/Petroleum ether=3:1, 5% TEA, R$_f$=0.44.

Example 92. Synthesis of WV-CA-092

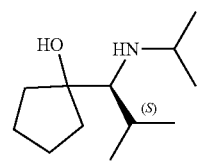

WV-CA-092

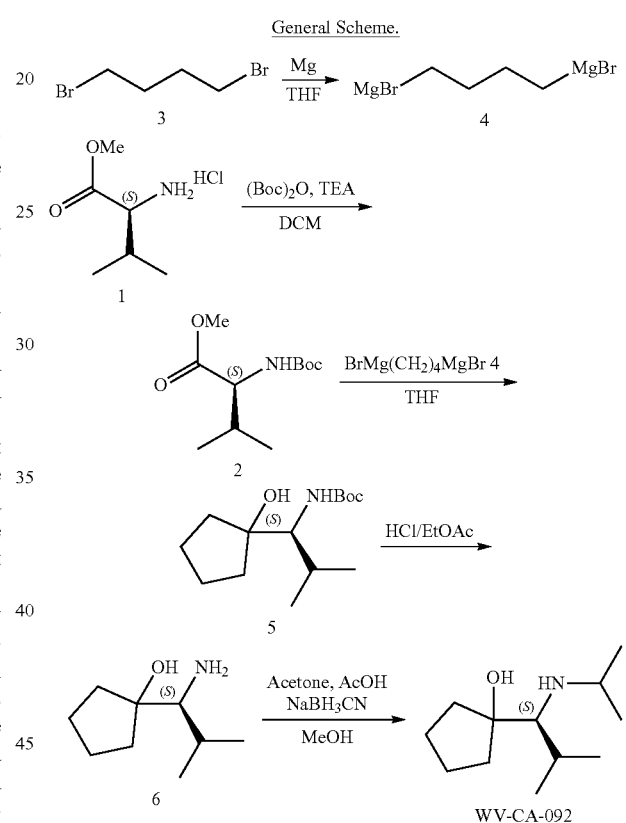

1. Preparation of Compound 2.

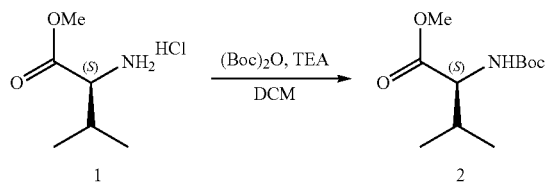

To a solution of compound 1 (70.00 g, 417.59 mmol HCl) in DCM (300 mL) was added Et$_3$N (126.77 g, 1.25 mol), then the mixture was cooled to 0° C. and slowly added (Boc)$_2$O (136.71 g, 626.39 mmol) (a solution in DCM (200 mL)) over 0.5 hr. The mixture was stirred at 20° C. for 5 hr. TLC showed the starting material was consumed and one major spot was detected. The resulting mixture was filtered, solid removed, and then the organic solvent was concentrated under reduced pressure to give a residue. The residue was purified by column chromatography (SiO$_2$, Petroleum ether:Ethyl acetate=100:1 to 5:1). Compound 2 was obtained as a colorless oil (69.00 g, 71.44%). $^1$H NMR (400 MHz, CHLOROFORM-d) δ=5.01 (br d, J=7.9 Hz, 1H), 4.20 (br dd, J=4.7, 8.9 Hz, 1H), 3.75-3.63 (m, 3H), 2.20~2.00 (m, 1H), 1.49-1.33 (m, 9H), 0.93 (d, J=6.8 Hz, 3H), 0.87 (d, J=6.8 Hz, 3H). TLC (Petroleum ether/Ethyl acetate=5:1) R$_f$=0.60.

2. Preparation of Compound 4.

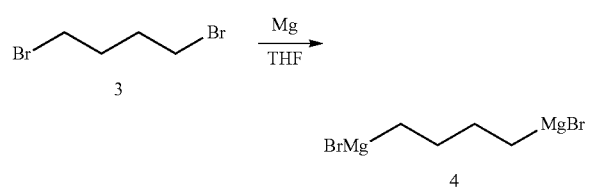

To a suspension of Mg (26.84 g, 1.10 mol) in THF (450 mL) was added compound 3 (198.64 g, 920.00 mmol) (activated with one crystal of I$_2$) in THF (470 mL) for 1 hr at 20~60° C. during addition. The yellow solution was stirred at 20° C. for 1 hr and the solution was turned to off-white suspension. Mg was almost consumed. The reaction was completed. The Grignard reagent in THF was used directly in next step.

3. Preparation of Compound 5.

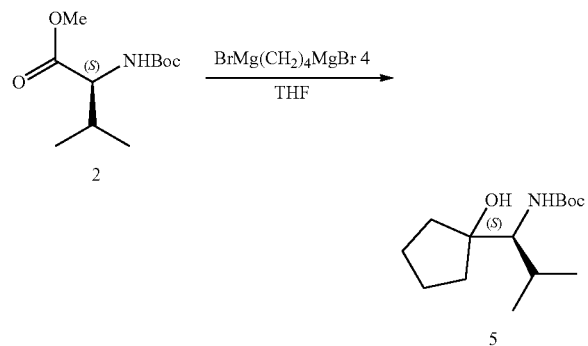

To a solution of methyl compound 2 (69.00 g, 298.33 mmol) in THF (200.00 mL) was added in compound 4 (1 M, 918.86 mL) at 0° C. over 1.5 hr. The mixture was stirred at 20° C. for 15.5 hr. TLC showed compound 2 was consumed. The reaction mixture was slowly added in ice NH$_4$Cl (300 mL) at 0° C., and then diluted with EtOAc (500 mL) and extracted with EtOAc (500 mL*3). The combined organic layers dried over Na$_2$SO$_4$, filtered, and concentrated under reduced pressure to give a residue. The residue was washed by Petroleum ether (30 mL*3) and filtered to give 45 g of desired compound as a white solid and 30 g crude. Compound 5 was obtained as a white solid (45.00 g, 58.61%). $^1$H NMR (400 MHz, CHLOROFORM-d): δ=4.94 (br d, J=9.7 Hz, 1H), 3.48-3.28 (m, 1H), 2.12-1.94 (m, 1H), 1.86-1.56 (m, 8H), 1.44 (s, 9H), 1.01-0.84 (m, 6H). TLC (Petroleum ether/Ethyl acetate=5:1) R$_f$=0.23.

4. Preparation of Compound 6.

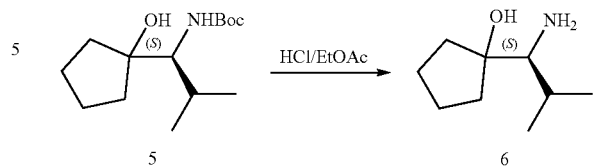

To a solution of compound 5 (45.00 g, 174.85 mmol) in EtOAc (30.00 mL) was added HCl/EtOAc (500.00 mL) at 0° C. The mixture was stirred at 20° C. for 2 hr. TLC showed compound 5 was consumed. The mixture was concentrated under reduced pressure to give a crude. The crude product compound 6 (33.00 g, crude, HCl) was used into the next step without further purification. TLC (Petroleum ether: Ethyl acetate=5:1) R$_f$=0.

5. Preparation of Compound WV-CA-092.

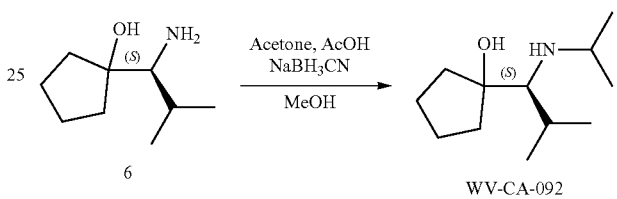

To a solution of compound 6 (33.00 g, 170.36 mmol, HCl) in MeOH (400.00 mL) was added Et$_3$N (17.24 g, 170.36 mmol). The mixture was stirred at 20° C. for 10 minutes. Then AcOH (3.07 g, 51.11 mmol) and acetone (19.79 g, 340.72 mmol) was added, and the mixture stirred at 20° C. for 20 minutes. NaBH$_3$CN (32.12 g, 511.08 mmol) was added and the mixture was stirred at 20° C. for 16 hr. LCMS showed intermediate was remained. NaBH$_3$CN (10.71 g, 170.36 mmol) was added and the reaction was stirred at 20° C. for 16 hr. LCMS and TLC showed the intermediate disappeared and the desired compound was detected by MS. The mixture was concentrated under reduced pressure to give a residue. The residue was washed by DCM (100 mL*3), filtered and removed the white solid (NaBH$_3$CN). The organic layer was concentrated under reduced pressure to give 30 g crude. The crude was dissolved in DCM (150 mL) and then washed by Na$_2$CO$_3$ (aq., 100 mL*3), the organic layers were dried over Na$_2$SO$_4$, filtered, and concentrated under reduced pressure to give a 21 g of desired compound as a white solid. Compound WV-CA-092 was obtained as a white solid (21.00 g, 61.84%). $^1$H NMR (400 MHz, CDCl$_3$): δ=2.94-2.80 (m, 1H), 2.43 (d, J=2.2 Hz, 1H), 2.02-1.88 (m, 1H), 1.86-1.71 (m, 2H), 1.69-1.49 (m, 4H), 1.47-1.34 (m, 2H), 1.03 (dd, J=1.9, 6.3 Hz, 6H), 0.97 (d, J=7.1 Hz, 3H), 0.88 (d, J=7.1 Hz, 3H). $^{13}$C NMR (101 MHz, CHLOROFORM-d) δ=82.91, 65.52, 48.12, 40.64, 35.17, 29.38, 23.89, 23.41, 23.36, 23.28, 16.96. LCMS: (M+H+): 200.2. TLC (Petroleum ether/Ethyl acetate=1:1) R$_f$=0.40.

Example 93. Synthesis of WV-CA-092-dCiBu

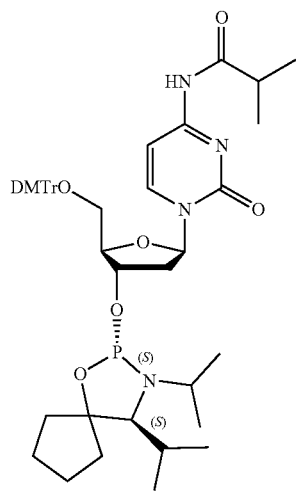

WV-CA-092-dCiBu

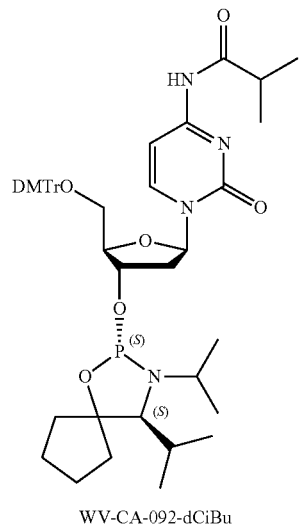

WV-CA-092-dCiBu

1. Preparation of Compound 1.

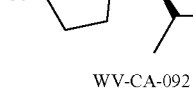

WV-CA-092

General Scheme.

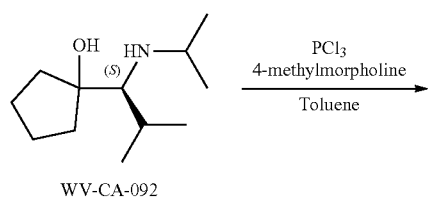

WV-CA-092

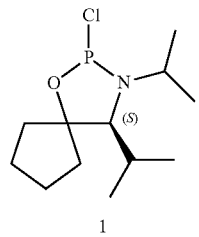

1

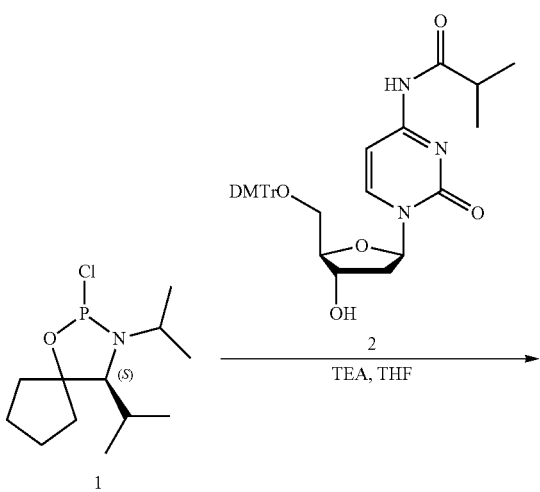

WV-CA-092 (2.00 g, 10.03 mmol) was dried by azeotropic distillation on a rotary evaporator with toluene (20 mL*3). To a solution of PCl$_3$ (1.38 g, 10.03 mmol) in toluene (20.00 mL) was added a solution of WV-CA-092 (2.00 g, 10.03 mmol) and 4-methylmorpholine (2.03 g, 20.06 mmol) in toluene (20.00 mL) at 0° C. The mixture was stirred at 15~20° C. for 1.5 hr. The phosphoryl chloride was not suitable for detection and no monitoring. The resulting mixture was filtered (flushed with Ar) and concentrated to afford the compound 1 (2.40 g, crude) was used into the next step without further purification.

2. Preparation of Compound WV-CA-092-dCiBu.

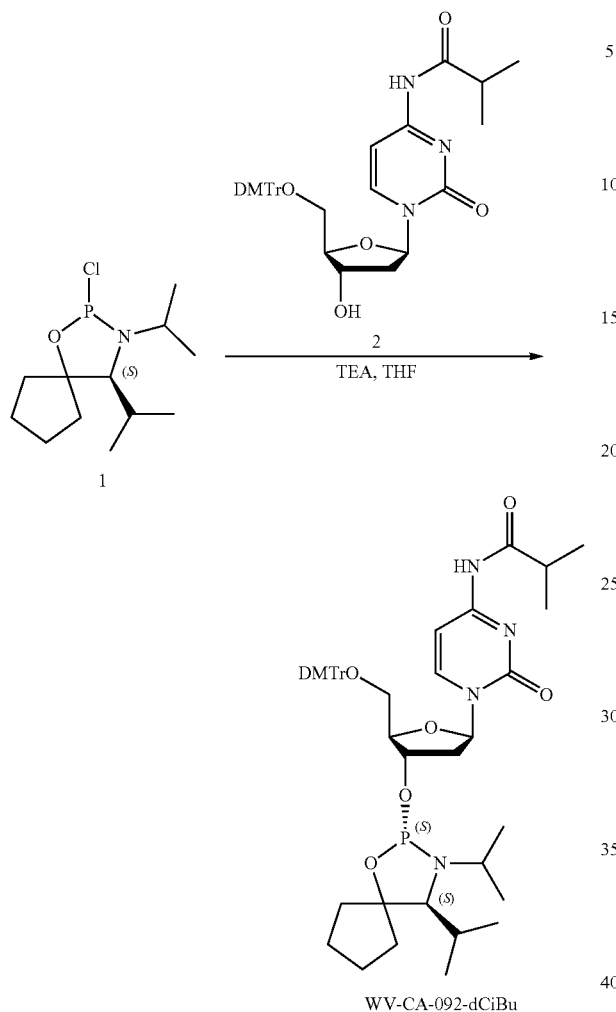

WV-CA-092-dCiBu

Compound 2 (3.50 g, 5.84 mmol) was dried by azeotropic distillation on a rotary evaporator with pyridine (50 mL) and toluene (50 mL*5). The dried compound 2 (3.50 g, 5.84 mmol) was dissolved was dissolved in THF (40.00 mL), and then TEA (2.95 g, 29.20 mmol) was added. The mixture was cooled to −70° C. A THF (20 mL) solution of compound 1 (2.31 g, 8.76 mmol) was added dropwise at −70° C., after the addition, the mixture was warmed to 28° C. for 0.5 hr. TLC showed the compound 2 was consumed and the reaction was completed. The resulting mixture was diluted with DCM (45 mL) at −10° C., washed with ice-cold sat. NaHCO₃ aq. (45 mL*3). The aqueous layer was extracted at each and washing stage with additional DCM (50 mL). The organic layer was dried over anhydrous MgSO₄, filtered, and concentrated to afford a white foam (crude (5.6 g). The above crude material was purified on a CombiFlash instrument from Teledyne using either a pre-treated silica gel column. A 40 g silica gel cartridge column was first pre-treated by eluting with 5 column volumes of methanol, before equilibration with 5 column volumes of 20% EtOAc/Petroleum ether containing 5% Et₃N. 5.6 g of crude product was dissolved in a 2:1 volume:volume mixture of (15 mL)/petroleum ether (7.5 mL) containing 5% Et₃N then loaded onto a 40 g silica column which had been equilibrated with 5 column volumes of 20% Petroleum ether/EtOAc containing 5% Et₃N. After loading the sample on the column, the purification process was run using the following gradient: 20 to 80% EtOAc/Petroleum ether containing 5% Et₃N, then residual solvent was removed to afford WV-CA-092-dCiBu as a white solid (2.50 g, 51.77%). All solvent was dried over anhydrous Na₂SO₄. ¹H NMR (400 MHz, CDCl₃): δ=6=8.37-8.32 (m, 1H), 7.47-7.41 (m, 2H), 7.36-7.26 (m, 7H), 7.06 (dd, J=7.5, 11.1 Hz, 1H), 6.87 (dd, J=1.4, 8.8 Hz, 4H), 6.23 (ddd, J=4.3, 6.7, 11.3 Hz, 1H), 4.90-4.72 (m, 1H), 4.11-4.06 (m, 1H), 3.82 (d, J=2.1 Hz, 6H), 3.57-3.38 (m, 2H), 3.31-3.12 (m, 1H), 2.94-2.88 (m, 1H), 2.74-2.55 (m, 2H), 2.41-2.15 (m, 1H), 1.94-1.66 (m, 6H), 1.64-1.50 (m, 3H), 1.42 (d, J=6.8 Hz, 1H), 1.25-1.17 (m, 11H), 1.00 (t, J=7.0 Hz, 4H), 0.90 (d, J=6.8 Hz, 1H). ¹³C NMR (101 MHz, CDCl₃): δ=162.18, 158.65, 158.62, 144.79, 144.67, 144.17, 144.09, 135.44 (dd, J=2.9, 16.9 Hz, 1C), 130.18, 130.11, 128.28, 127.97, 127.08, 127.01, 113.28, 98.94, 98.84, 96.37, 96.28, 96.04, 86.96, 86.87, 86.81, 86.78, 85.67, 85.62, 85.56, 70.10, 69.89, 68.28, 68.05, 68.00, 61.77, 61.42, 60.37, 55.20, 55.17, 48.90, 48.67, 41.57, 36.68, 36.65, 34.38, 30.69, 30.65, 30.11, 24.68, 24.49, 23.76, 22.76, 22.72, 22.20, 21.77, 21.03, 19.10, 19.02, 18.99, 17.81, 14.20. ³¹P NMR (162 MHz, CDCl₃) δ=149.32 (s, 1P), 145.10 (s, 1P). TLC (Ethyl acetate/Petroleum ether=3:1, 5% TEA) R_f=0.45.

Example 94. Synthesis of WV-CA-097

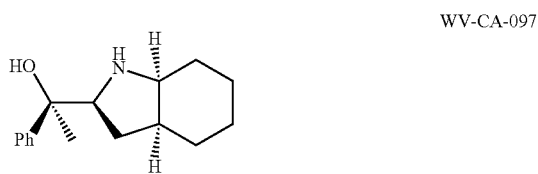 [SMILES: C[C@@](O)(c1ccccc1)[C@@H]1C[C@@H]2CCCC[C@@H]2N1]

WV-CA-097

General Scheme.

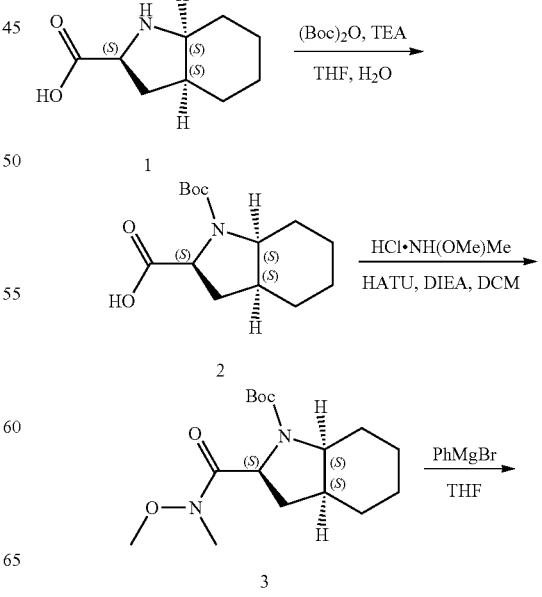

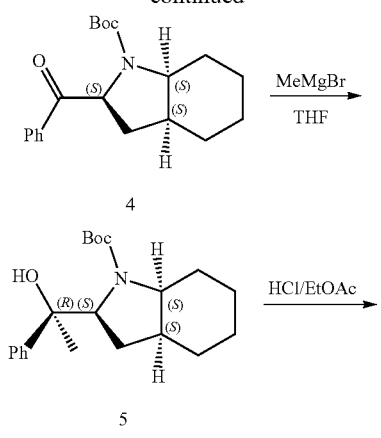

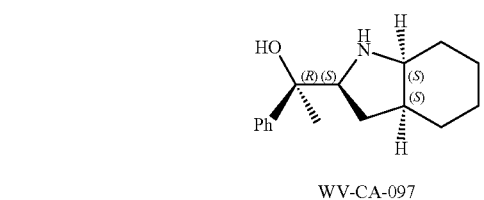

WV-CA-097

1. Preparation of Compound 2.

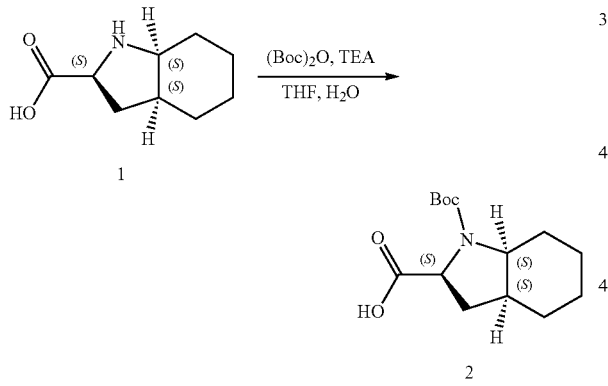

To a solution of compound 1 (50.00 g, 295.47 mmol) in THF (350 mL) and H$_2$O (150.00 mL) was added TEA (89.70 g, 886.41 mmol, 122.88 mL), and then dropwise added (Boc)$_2$O (77.38 g, 354.56 mmol, 81.45 mL) (a solution in 100 mL THF). The mixture was stirred at 20° C. for 16 hr. TLC showed compound 1 was consumed and one new spot was detected. The resulting mixture was diluted with EtOAc (300 mL) and H$_2$O (300 mL), and extracted with EtOAc (500 mL*3). The combined organic layers were dried over Na$_2$SO$_4$, filtered, and concentrated under reduced pressure to give compound 2 (41.00 g, 51.52% yield) as a yellow oil. $^1$H NMR (400 MHz, CHLOROFORM-d) δ=4.26-4.04 (m, 1H), 3.68 (br s, 1H), 3.03 (q, J=7.3 Hz, 2H), 2.31-2.17 (m, 1H), 2.17-1.89 (m, 3H), 1.68-1.53 (m, 2H), 1.51-1.32 (m, 11H), 1.27-1.15 (m, 4H). TLC (Dichloromethane:Methanol=10:1) R$_f$=0.1.

2. Preparation of Compound 3.

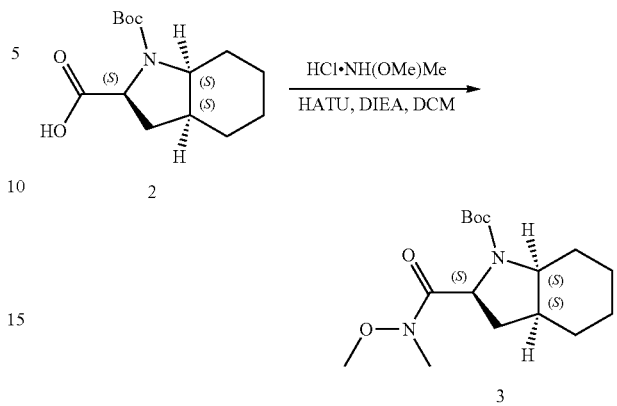

To a solution of compound 2 (20.00 g, 74.26 mmol), N-methoxymethanamine (8.69 g, 89.11 mmol, HCl salt) and HATU (31.06 g, 81.69 mmol) in DCM (200.00 mL) was slowly added DIEA (19.19 g, 148.52 mmol, 25.93 mL). The mixture was stirred at 20° C. for 16 hr. TLC showed the compound 2 was consumed and one new spot was detected. The resulting mixture was added H$_2$O (150 mL) and extracted with DCM (200 mL*3). The combined organic layers were dried over Na$_2$SO$_4$, filtered, and concentrated under reduced pressure to give a residue. The residue was purified by MPLC (SiO$_2$, Petroleum ether/Ethyl acetate=1:0 to 3:1). Compound 3 (17.00 g, 73.28% yield) was obtained as a white solid. $^1$H NMR (400 MHz, CHLOROFORM-d) δ=4.70-4.53 (m, 1H), 3.85-3.64 (m, 4H), 3.19 (d, J=2.4 Hz, 3H), 2.34-2.23 (m, 1H), 2.15-2.02 (m, 2H), 2.00-1.85 (m, 2H), 1.69-1.40 (m, 11H), 1.37 (s, 5H), 1.34-1.05 (m, 3H). TLC (Petroleum ether:Ethyl acetate=3:1) R$_f$=0.43.

3. Preparation of Compound 4.

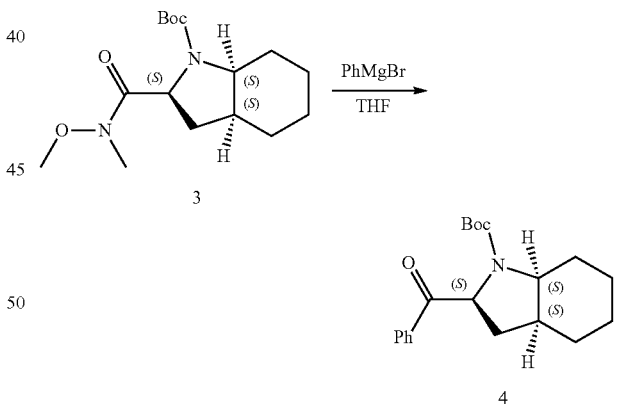

A solution of compound 3 (23.00 g, 73.62 mmol) in THF (150.00 mL) was degassed and purged with N$_2$ for 3 times, and then the mixture was cooled to ~5° C. and added PhMgBr (3 M, 73.62 mL) under N$_2$ atmosphere over 1 hr. Then the mixture was stirred at 20° C. for 3 hr under N$_2$ atmosphere. TLC and LCMS showed compound 3 was consumed and one new spot was detected. The reaction mixture was slowly added in ice NH$_4$Cl (200 mL) at 0° C., and then extracted with ethyl acetate (300 mL*3), dried over Na$_2$SO$_4$, filtered and concentrated under reduced pressure to give a residue. The residue was purified by MPLC (SiO$_2$, Petroleum ether/Ethyl acetate=1:0 to 5:1). Compound 4

(15.00 g, 61.85% yield) was obtained as a white solid. ¹H NMR (400 MHz, CHLOROFORM-d) δ=8.01-7.92 (m, 2H), 7.58-7.37 (m, 3H), 5.33-5.21 (m, 1H), 3.94-3.75 (m, 1H), 2.49-2.36 (m, 1H), 2.24-2.01 (m, 2H), 1.97-1.76 (m, 1H), 1.70-1.63 (m, 3H), 1.52-1.37 (m, 7H), 1.33-1.05 (m, 8H). LCMS: (M+Na+): 352.2. HPLC purity=85.06%. Chiral SFC purity=98.46%. TLC (Petroleum ether:Ethyl acetate=5:1) $R_f$=0.56.

4. Preparation of Compound 6.

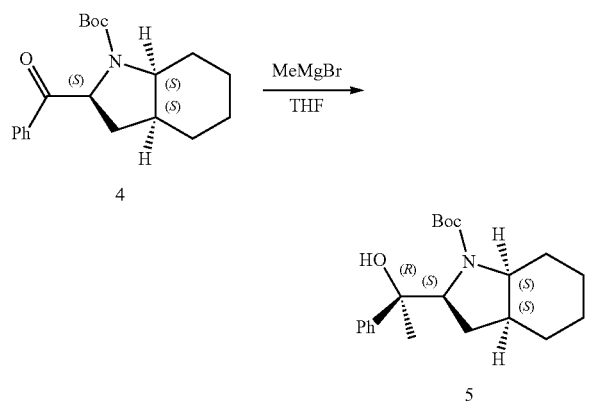

To a solution of compound 4 (15.00 g, 45.53 mmol) in THF (100.00 mL) was added MeMgBr (3 M, 45.53 mL) at −5° C. over 0.5 hr. The mixture was stirred at 20° C. for 2.5 hr. LCMS and TLC showed compound 4 was consumed and MS with the desired compound was detected. The reaction mixture was slowly added NH₄Cl (200 mL) at 0° C., and then extracted with ethyl acetate (300 mL*3), dried over Na₂SO₄, filtered and concentrated under reduced pressure to give a residue. The residue was purified by MPLC (SiO₂, Petroleum ether:Ethyl acetate=1:0 to 5:1). Compound 5 (11.00 g, 69.93% yield) was obtained as a white solid. ¹H NMR (400 MHz, CHLOROFORM-d) δ=7.96 (br s, 1H), 7.45-7.17 (m, 5H), 4.08 (dd, J=7.2, 10.7 Hz, 1H), 3.58-3.48 (m, 1H), 2.03 (qd, J=6.4, 13.1 Hz, 1H), 1.94-1.82 (m, 1H), 1.80-1.65 (m, 2H), 1.62-1.38 (m, 15H), 1.33-1.12 (m, 2H), 1.02-0.75 (m, 3H). LCMS: (M+Na+): 368.2. HPLC purity=73.33%. Chiral SFC purity=100.0%. TLC (Petroleum ether:Ethyl acetate=5:1) $R_f$=0.49.

5. Preparation of Compound WV-CA-097.

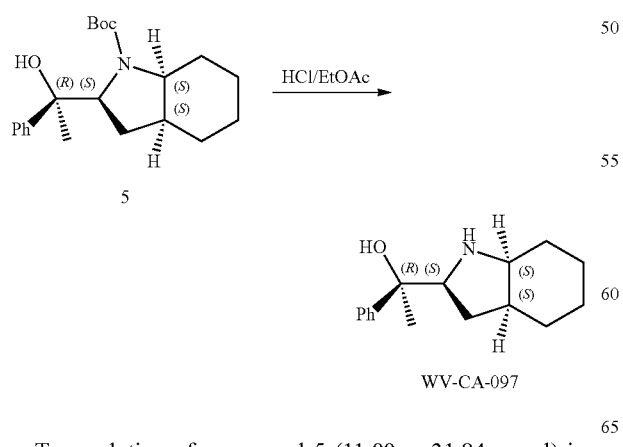

To a solution of compound 5 (11.00 g, 31.84 mmol) in EtOAc (10.00 mL) was added HCl/EtOAc (200.00 mL). The mixture was stirred at 20° C. for 2 hr. TLC showed compound 5 was consumed. The mixture was concentrated under reduced pressure to give a residue. The residue was dissolve by H₂O (10 mL) and added Na₂CO₃ (aq.) until over pH=11, then the mixture was extracted with DCM (100 mL*3) and concentrated under reduced pressure to give a 5.5 g of product (ee=97%). Batch 1: A solution of 5.5 g product in Petroleum ether (30 mL) and Ethyl acetate (2 mL) were refluxed at 100° C. for 0.5 hr and solid all disappeared. Then the mixture was cooled to 20° C. and after the solid appeared, filtered to give 2 g product. Batch 2: White solid formed in mother liquid, and then filtered to give 1.4 g product. Batch 3: White solid was appeared in mother liquid, and then filtered to give 1.6 g product. Three batches of product were combined to give compound WV-CA-097 (5.00 g, 64.00% yield) as a white solid. ¹H NMR (400 MHz, CHLOROFORM-d) δ=7.46-7.41 (m, 2H), 7.33-7.27 (m, 2H), 7.23-7.15 (m, 1H), 3.52 (t, J=8.3 Hz, 1H), 3.23-3.17 (m, 1H), 1.91 (sxt, J=6.7 Hz, 1H), 1.69-1.49 (m, 3H), 1.48-1.34 (m, 6H), 1.31-1.13 (m, 4H). ¹³C NMR (101 MHz, CHLOROFORM-d) δ=72.63, 66.31, 56.74, 37.49, 31.76, 30.69, 30.42, 28.11, 23.33, 22.45. LCMS: (M+H⁺): 246.2, 100.0% purity. Chiral SFC purity=100.0%. TLC (Petroleum ether:Ethyl acetate=3:1) $R_f$=0.

Example 95. Synthesis of WV-CA-097-dCiBu

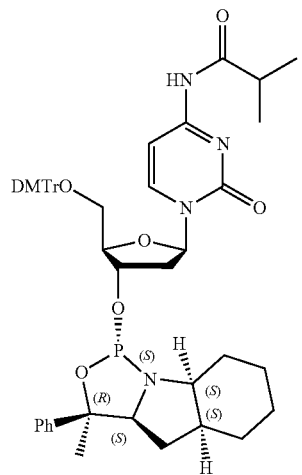

General Scheme.

-continued

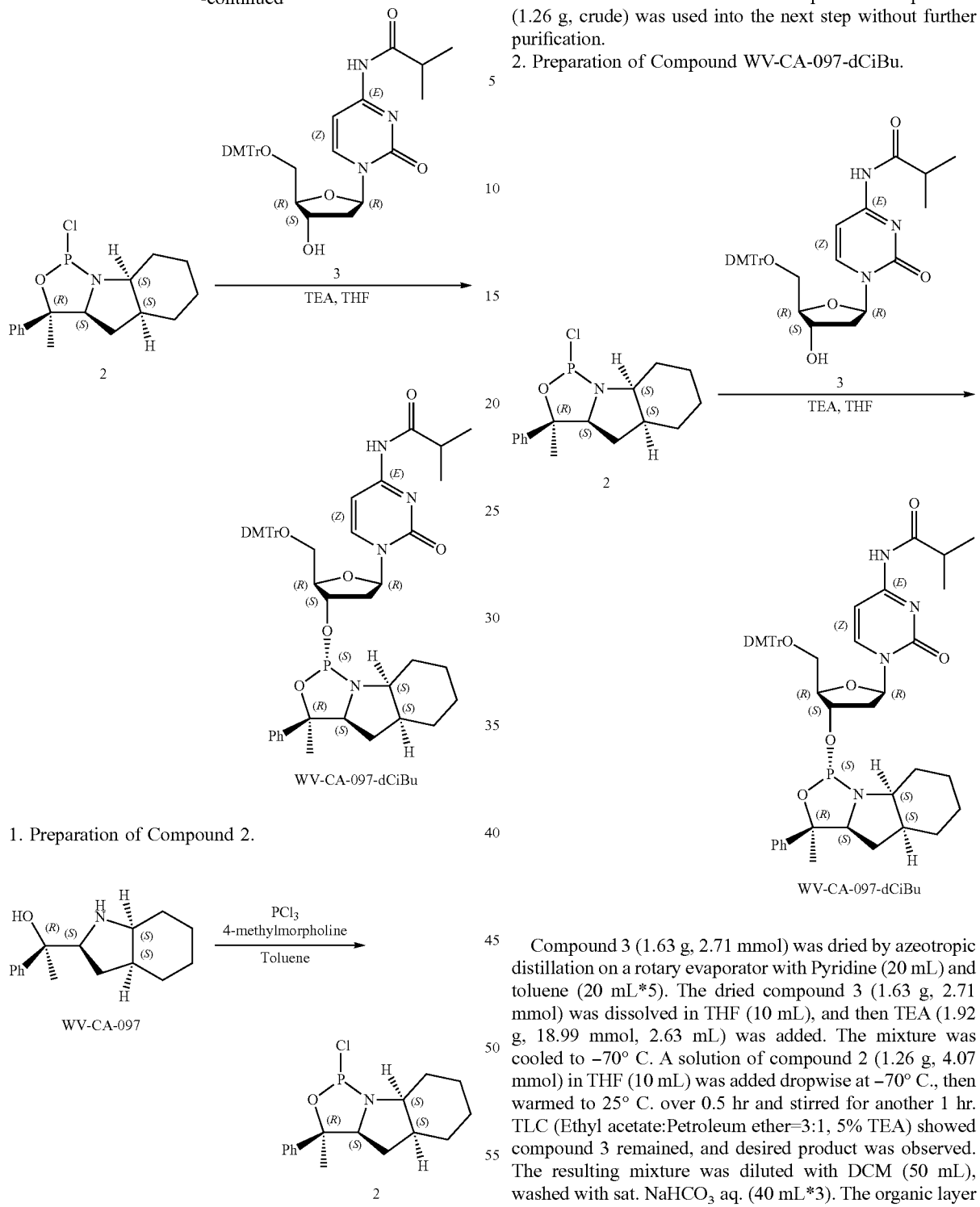

WV-CA-097-dCiBu

1. Preparation of Compound 2.

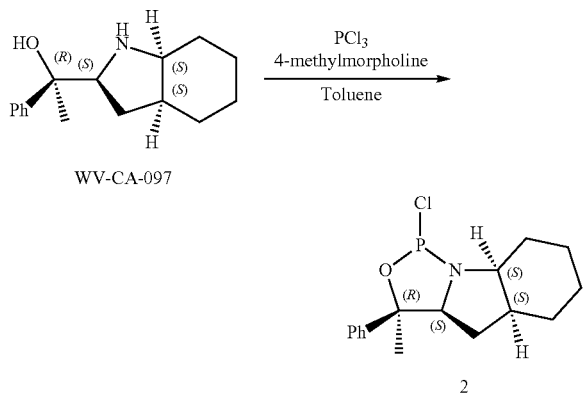

The compound WV-CA-097 (1.00 g, 4.08 mmol) was dried by azeotropic distillation on a rotary evaporator with toluene (20 mL*3). To a solution of trichlorophosphane (560.31 mg, 4.08 mmol) in toluene (10 mL) was added a solution of WV-CA-097 (1.00 g, 4.08 mmol) and NMM (825.38 mg, 8.16 mmol, 897.15 µL) in toluene (10 mL) at 0° C. The mixture was stirred at 25° C. for 1 hr. Phosphoryl chloride not suitable for detection. The resulting mixture was filtered (flushed with Ar) and concentrated to afford a residue as a colorless oil. The crude product compound 2 (1.26 g, crude) was used into the next step without further purification.

2. Preparation of Compound WV-CA-097-dCiBu.

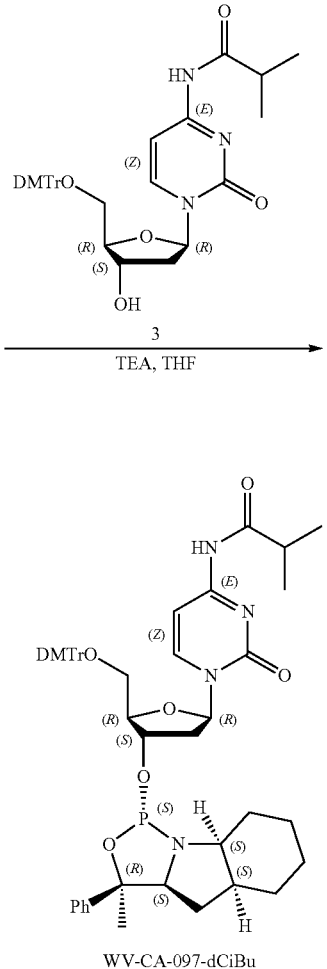

WV-CA-097-dCiBu

Compound 3 (1.63 g, 2.71 mmol) was dried by azeotropic distillation on a rotary evaporator with Pyridine (20 mL) and toluene (20 mL*5). The dried compound 3 (1.63 g, 2.71 mmol) was dissolved in THF (10 mL), and then TEA (1.92 g, 18.99 mmol, 2.63 mL) was added. The mixture was cooled to −70° C. A solution of compound 2 (1.26 g, 4.07 mmol) in THF (10 mL) was added dropwise at −70° C., then warmed to 25° C. over 0.5 hr and stirred for another 1 hr. TLC (Ethyl acetate:Petroleum ether=3:1, 5% TEA) showed compound 3 remained, and desired product was observed. The resulting mixture was diluted with DCM (50 mL), washed with sat. NaHCO$_3$ aq. (40 mL*3). The organic layer was dried over anhydrous MgSO$_4$, filtered, and concentrated to afford a white foam (2.8 g). The MPLC column (flash Silica (CS), 40-60 µm, 60 A, 20 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (25 mL, 5% TEA) was loaded and purified with Ethyl acetate (5% TEA):Petroleum ether (5% TEA)=20%~60%. All solvent was dried over anhydrous Na$_2$SO$_4$. Compound WV-CA-097-dCiBu (1.20 g, 50.49% yield) was obtained as a white solid. ¹H NMR (400 MHz, CHLOROFORM-d) δ=8.22 (d, J=7.4 Hz, 1H), 7.36-7.31 (m, 2H), 7.30-7.12 (m, 13H), 7.03 (d, J=7.4 Hz, 1H), 6.79-6.71 (m, 4H), 6.21 (t, J=5.7 Hz, 1H), 4.81-4.71 (m, 1H), 4.17-4.11 (m, 1H), 3.85-3.79 (m, 1H), 3.68 (d, J=1.9 Hz, 6H), 3.51-3.31 (m, 3H), 3.26-3.15 (m, 1H), 2.69 (td, J=5.9, 13.7 Hz, 1H), 2.61-2.52 (m, 1H), 2.34-2.13 (m, 3H), 1.85-1.80 (m, 1H), 1.66 (s, 3H), 1.51-1.22 (m, 10H), 1.14 (dd, J=3.5, 6.9 Hz, 6H). ¹³C NMR (101 MHz, CHLOROFORM-d) δ=158.65, 155.21, 144.60, 144.19, 143.42, 143.39, 135.41, 135.38, 130.14, 130.12, 128.26, 127.99, 127.85, 127.68, 127.12, 126.99, 126.76, 126.09, 125.87, 124.82, 113.28, 96.30, 89.95, 89.84, 86.92, 86.87, 85.71, 73.09, 73.06, 72.38, 71.12, 70.99, 62.02, 55.60, 55.45, 55.22, 55.17, 46.25, 41.67, 41.44, 36.57, 31.44, 31.31, 31.15, 30.30, 29.78, 26.79, 26.57, 23.09, 22.88, 22.41, 21.69, 21.40, 19.16, 19.05. ³¹P NMR (162 MHz, CHLOROFORM-d) δ=138.63 (s, 1P), 138.55 (s, 1P), 125.03 (s, 1P). TLC (Ethyl acetate: Petroleum ether=3:1, 5% TEA), R$_f$=0.67.

Example 96. Synthesis of WV-CA-098

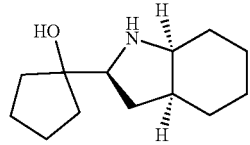

WV-CA-098

General Scheme.

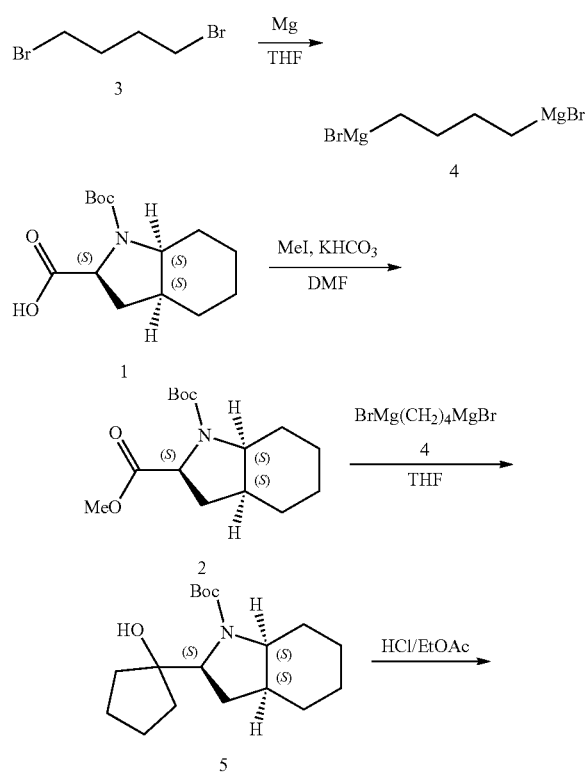

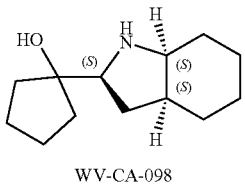

WV-CA-098

1. Preparation of Compound 2.

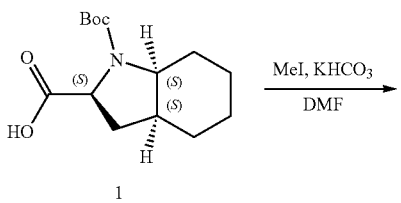

To a solution of compound 1 (20.00 g, 74.26 mmol) in DMF (200.00 mL) was added KHCO₃ (14.87 g, 148.52 mmol) and MeI (52.70 g, 371.30 mmol, 23.11 mL). The mixture was stirred at 20° C. for 16 hr. TLC (Petroleum ether:Ethyl acetate=3:1, R$_f$=0.50) showed compound 1 was consumed and one new spot was detected. The resulting mixture was concentrated under reduced pressure to give a residue. The residue was added Petroleum ether (100 mL*3) and filtered and removed the white solid, then organic phase was concentrated under reduced pressure to give a 16 g of product. Compound 2 (16.00 g, 76.04% yield) was obtained as a yellow oil. ¹H NMR (400 MHz, CHLOROFORM-d) δ=4.26-4.10 (m, 1H), 3.85-3.73 (m, 1H), 3.73-3.65 (m, 3H), 2.26 (td, J=5.8, 12.0 Hz, 1H), 2.14-1.87 (m, 3H), 1.71-1.55 (m, 4H), 1.51-1.05 (m, 14H). TLC (Petroleum ether:Ethyl acetate=3:1) R$_f$=0.50.

2. Preparation of Compound 4.

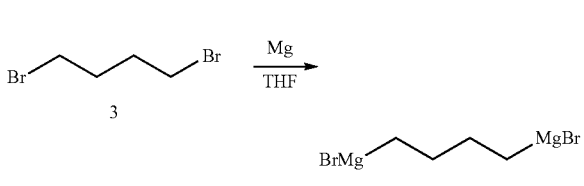

To a suspension of Mg (6.83 g, 280.80 mmol) in THF (100 mL) was added compound 3 (50.52 g, 234.00 mmol, 28.23 mL) (activated with one crystal of I₂) in THF (134 mL) for 1 hr at 20~60° C. during addition. The yellow solution was stirred at 20° C. for 1 hr and the solution was turned to off-white suspension. Mg was disappeared. The reaction was completed. The Grignard reagent in THF was used directly in next step.

3. Preparation of Compound 5.

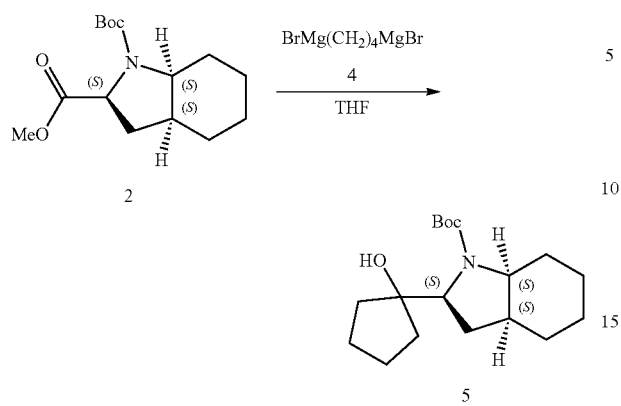

To a solution of compound 2 (22.00 g, 77.64 mmol) in THF (70.00 mL) was added in compound 4 (61.82 g, 233.70 mmol) at −5° C. The mixture was stirred at 20° C. for 3 hr. LCMS and TLC showed compound 2 was consumed and MS with desired compound was detected. The reaction mixture was slowly added in NH$_4$Cl (200 mL) at 0° C., and then extracted with ethyl acetate (300 mL*3), dried over Na$_2$SO$_4$, filtered and concentrated under reduced pressure to give a residue. The residue was purified by MPLC (SiO$_2$, Petroleum ether/Ethyl acetate=1:0 to 5:1). Compound 5 (12.00 g, 49.95% yield) was obtained as a white solid. $^1$H NMR (400 MHz, CHLOROFORM-d) δ=6.30 (br s, 1H), 4.00 (dd, J=6.8, 11.0 Hz, 1H), 3.82-3.68 (m, 1H), 2.19-1.97 (m, 1H), 1.93-1.75 (m, 4H), 1.73-1.68 (m, 2H), 1.65-1.42 (m, 19H), 1.32-1.05 (m, 3H). LCMS: (M+H$^+$): 332.2. HPLC purity: 90.56%. Chiral SFC purity=100.0%. TLC (Petroleum ether:Ethyl acetate=5:1) R$_f$=0.50.

4. Preparation of Compound WV-CA-098.

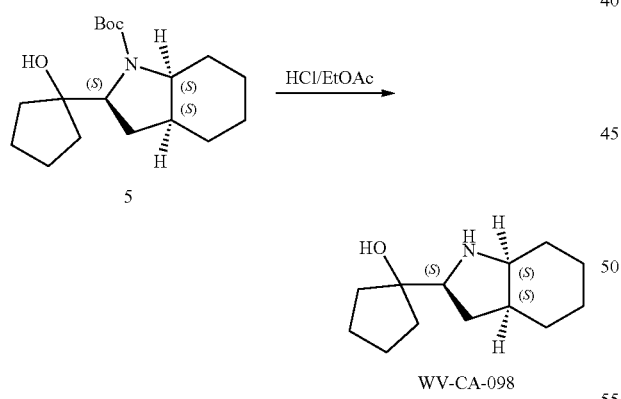

To a solution of compound 5 (12.00 g, 38.78 mmol) in EtOAc (10.00 mL) was added HCl/EtOAc (300.00 mL). The mixture was stirred at 20° C. for 3 hr. TLC showed the starting material was consumed. The mixture was concentrated under reduced pressure to give a residue. The residue was dissolved with H$_2$O (10 mL) and added Na$_2$CO$_3$ (aq.) and KOH (aq., 2M) until over pH=11, then the mixture was extracted with DCM (200 mL*3) and concentrated under reduced pressure to give a product. Compound WV-CA-098 (6.30 g, 77.61% yield) was obtained as a white solid. $^1$H NMR (400 MHz, CHLOROFORM-d) δ=3.50-3.20 (m, 1H), 3.19-3.08 (m, 2H), 1.99 (qd, J=6.8, 13.4 Hz, 1H), 1.91-1.73 (m, 3H), 1.70-1.36 (m, 13H), 1.35-1.17 (m, 2H). $^{13}$C NMR (101 MHz, CHLOROFORM-d) δ=80.94, 65.61, 56.71, 40.44, 37.44, 35.90, 31.87, 30.24, 28.49, 24.09, 23.96, 23.81, 22.17. LCMS: (M+H$^+$): 210.2, 99.39% purity. TLC (Petroleum ether:Ethyl acetate=3:1) R$_f$=0.

Example 97. Synthesis of WV-CA-098-dCiBu

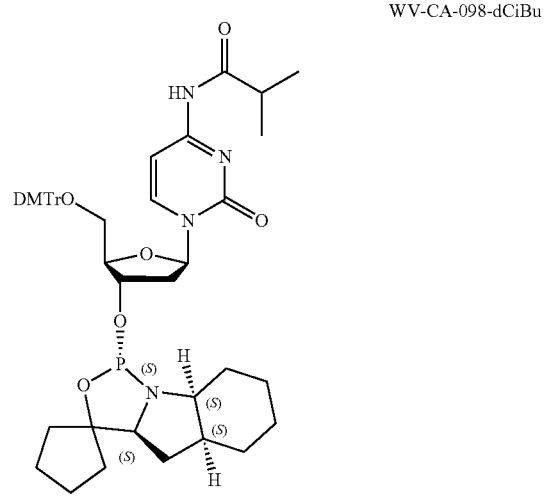

WV-CA-098-dCiBu

General Scheme.

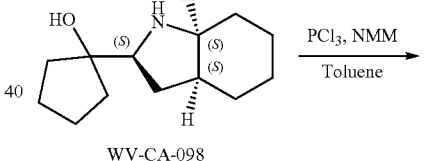

WV-CA-098

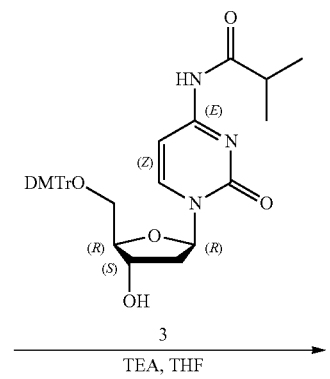

803
-continued

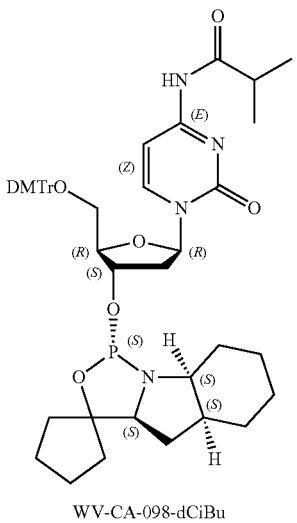

WV-CA-098-dCiBu

1. Preparation of Compound 2.

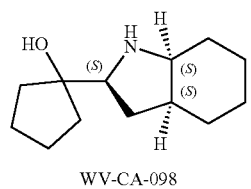

WV-CA-098

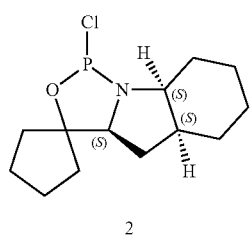

2

The compound WV-CA-098 (1.00 g, 4.78 mmol) was dried by azeotropic distillation on a rotary evaporator with toluene (20 mL*3). To a solution of PCl₃ (656.05 mg, 4.78 mmol) in toluene (10 mL) was added a solution of WV-CA-098 (1.00 g, 4.78 mmol) and NMM (966.99 mg, 9.56 mmol, 1.05 mL) in toluene (10 mL) at 0° C. The mixture was stirred at 25° C. for 1.5 hr. Phosphoryl chloride was not suitable for detection. The resulting mixture was filtered (flushed with Ar) and concentrated to afford a residue as a colorless oil. The crude product compound 2 (1.31 g, crude) was used into the next step without further purification.

804

2. Preparation of Compound WV-CA-098-dCiBu.

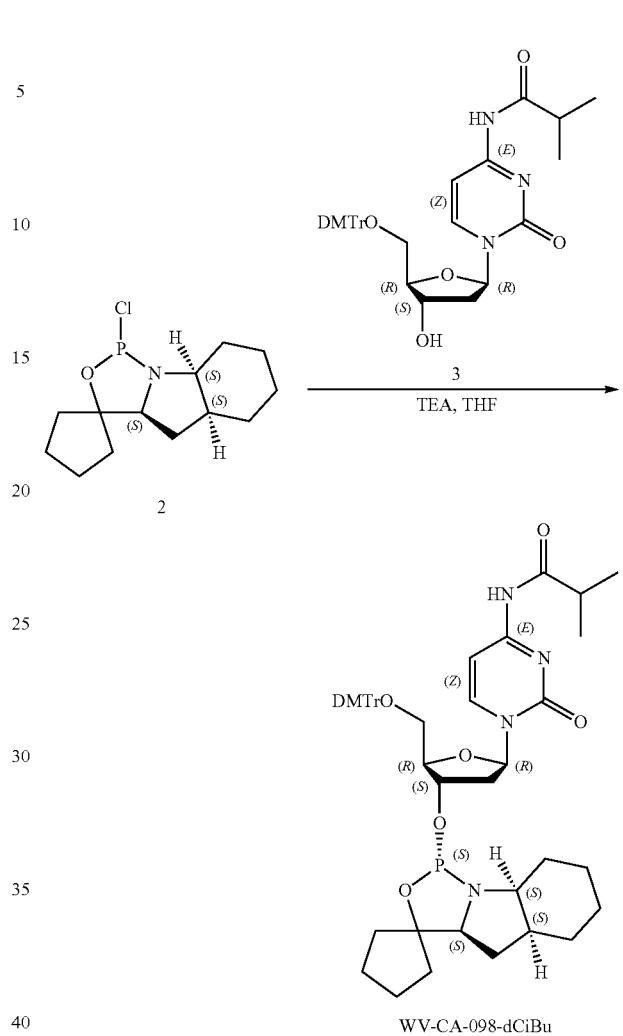

Compound 3 (1.91 g, 3.19 mmol) was dried by azeotropic distillation on a rotary evaporator with pyridine (20 mL) and toluene (20 mL*5). The dried compound 3 (1.91 g, 3.19 mmol) was dissolved in THF (15 mL), and then TEA (2.26 g, 22.35 mmol, 3.10 mL) was added. The mixture was cooled to −70° C. A solution of compound 2 (1.31 g, 4.79 mmol) in THF (15 mL) was added dropwise at −70° C., then warmed to 25° C. over 0.5 hr and stirred for another 1 hr. TLC (Ethyl acetate:Petroleum ether=3:1, 5% TEA) showed compound 3 remained, and desired product was observed. The resulting mixture was diluted with DCM (60 mL), washed with sat. NaHCO₃ aq. (30 mL*3). The organic layer was dried over anhydrous MgSO₄, filtered, and concentrated to afford a white foam (3.1 g). The MPLC column (flash Silica (CS), 40-60 μm, 60 A, 40 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (20 mL, 5% TEA) was loaded and purified with Ethyl acetate (5% TEA):Petroleum ether (5% TEA)=20%~60%. All solvent was dried over anhydrous Na₂SO₄. Compound WV-CA-098-dCiBu (2.10 g, 78.60% yield) was obtained as a white solid. ¹H NMR (400 MHz, CHLOROFORM-d) δ=8.26 (d, J=7.4 Hz, 1H), 8.15 (br. s, J=7.8 Hz, 1H), 7.44-7.38 (m, 2H), 7.36-7.24 (m, 8H), 7.09 (d, J=7.4 Hz, 1H), 6.86 (d, J=8.4 Hz, 4H), 6.28 (t, J=5.8 Hz, 1H), 4.77-4.66 (m, 1H), 4.19 (q, J=3.3 Hz, 1H), 3.83 (s, 6H), 3.76 (dd, J=6.8, 9.0 Hz, 1H), 3.57-3.32 (m, 3H), 2.74 (td, J=5.8, 13.4 Hz, 1H), 2.57 (spt, J=6.9 Hz, 1H), 2.38-2.23 (m, 2H), 2.05 (br d, J=5.6 Hz, 1H), 1.98-1.31 (m, 19H), 1.24 (dd, J=2.4, 6.9 Hz, 6H). $^{13}$C NMR (101 MHz, CHLOROFORM-d) δ=176.93, 162.34, 158.65, 155.10, 144.57, 144.14, 135.46, 135.35, 130.16, 130.09, 128.25, 127.95, 127.09, 113.24, 96.61, 96.50, 96.18, 86.99, 86.84, 85.83, 85.80, 70.93, 70.83, 68.10, 68.08, 62.29, 56.08, 55.92, 55.21, 41.27, 39.81, 36.56, 35.74, 35.72, 31.06, 30.94, 30.60, 30.57, 26.92, 23.23, 23.19, 23.10, 22.81, 21.80, 19.14, 19.00. $^{31}$P NMR (162 MHz, CHLOROFORM-d) δ=137.33 (s, 1P). TLC (Ethyl acetate:Petroleum ether=3:1, 5% TEA), R$_f$=0.69.

Example 98. Synthesis of WV-CA-111

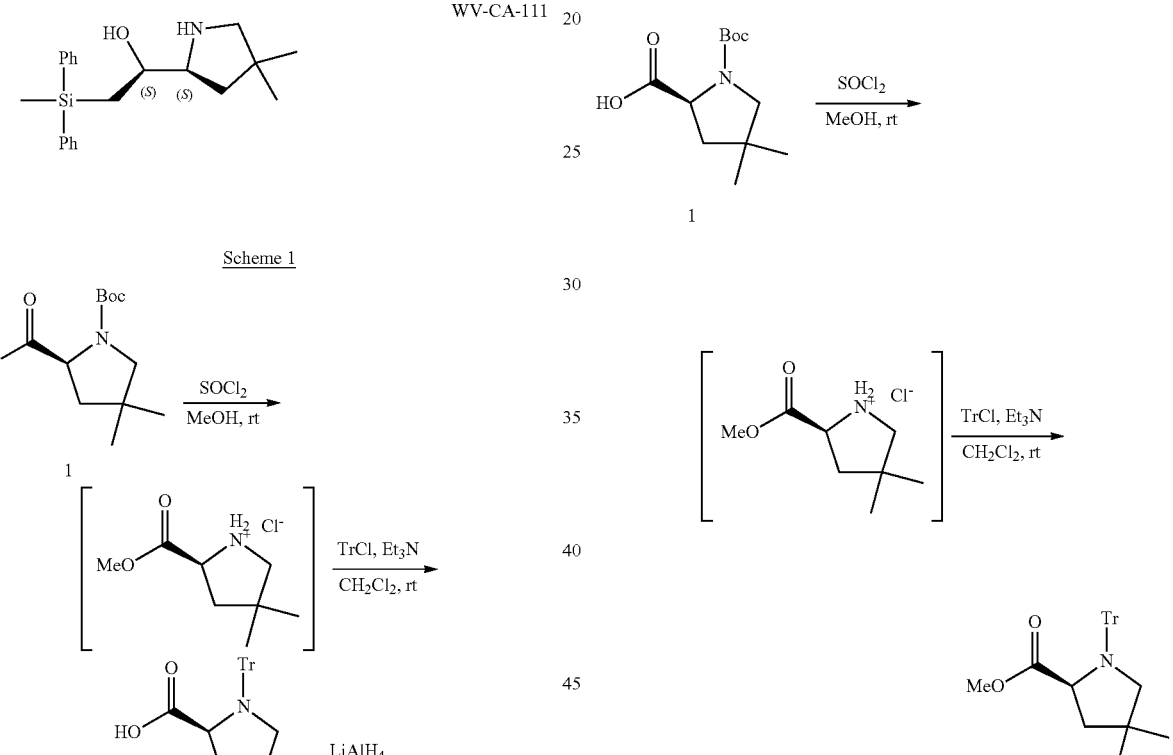

Scheme 1

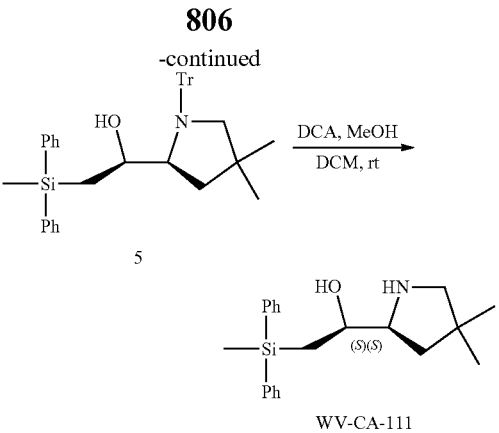

1. Preparation of Compound 2.

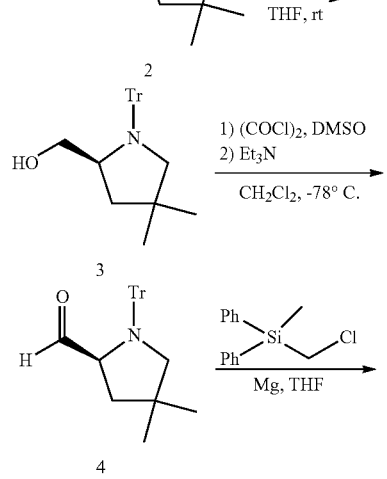

To a solution of 1 (23.7 g, 97.4 mmol, 1.00 eq.) in MeOH (100 mL) was slowly added thionyl chloride (14.2 mL, 195 mmol, 2.00 eq.) at 0° C. over 25 min. The mixture was stirred at room temperature for 3 h, then concentrated under reduced pressure. The residue was dissolved in DCM (170 mL) and added Et$_3$N (41 mL, 292 mmol, 3.00 eq.) at 0° C. To the mixture, trityl chloride (27.2 g, 97.4 mmol, 1.00 eq.) was added at 0° C., and the mixture warmed to room temperature and continued stirring for 17 h. The mixture was filtered and washed with DCM (100 mL). Filtrate was washed with saturated NaHCO$_3$ (170 mL*2), and back-extracted with DCM (50 mL*1). The combined organic layers were dried over Na$_2$SO$_4$, filtered, and concentrated to obtain compound 2 (43.51 g, crude, pale brown oil), which was used directly without further purification.

2. Preparation of Compound 3.

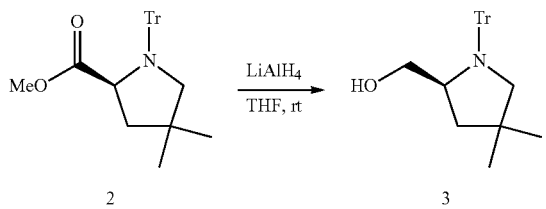

To a suspension of LiAlH₄ (3.92 g, 102.4 mmol, 1.00 eq.) in THF (160 mL), compound 2 (40.9 g, 102.4 mmol, 1.00 eq.) in THF (80 mL) was added portion wise at 0° C. over 30 min, and the mixture stirred for 4 h. To the mixture, Et₂O (140 mL) and saturated Na₂SO₄ (70 mL) was added at 0° C. and stirred for 16 h at room temperature. The mixture was filtered with celite, and washed with Et₂O (50 mL*4). Filtrate was washed with saturated NaCl (170 mL), and back-extracted with DCM (100 mL*2). The combined organic layers were dried over Na₂SO₄, filtered, and concentrated to obtain compound 3 (39.77 g, crude, pale brown foam), which was used directly without further purification.

3. Preparation of Compound 4.

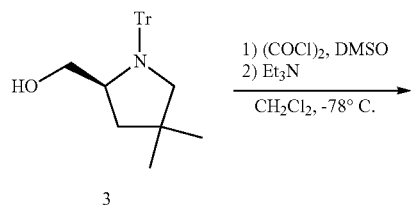

To a solution of oxalyl chloride (12.7 mL, 148 mmol, 1.50 eq.) in DCM (70 mL) was slowly added DMSO (14 mL, 197 mmol, 2.00 eq.) in DCM (33 mL) at −78° C. over 1 h and continued stirring at same temperature for 30 min. To the mixture, compound 3 (36.5 g, 98.4 mmol, 1.00 eq.) in DCM (65 mL) was added dropwise over 2 hr. at −78° C. and continued stirring at same temperature for 1.5 h. Then Et₃N (55 mL, 394 mmol, 4.00 eq.) was added to the mixture at −78° C., and continued stirring for 1.5 h. To the mixture, a mixture of saturated NH₄Cl (114 mL) and 28% NH₃ solution (57 mL) was slowly added at −78° C., and warmed to room temperature. Organic layer was separated and water layer was extracted with DCM (30 mL*2). The combined organic layers were dried over Na₂SO₄, filtered, and concentrated to obtain compound 4 (42.35 g, crude, pale brown oil), which was used directly without further purification.

4. Preparation of Compound 5.

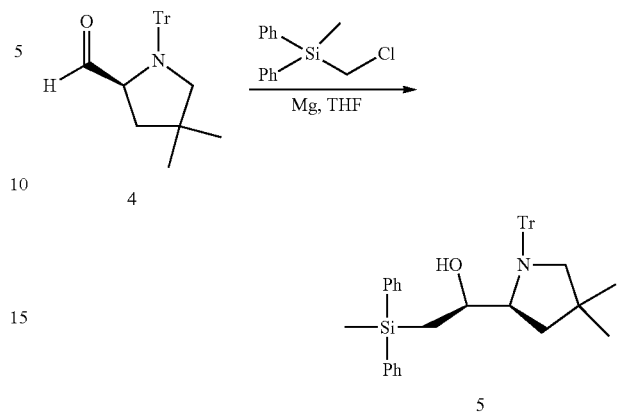

To a solution of methyldiphenylsilylmethyl magnesium chloride in THF prepared from chloromethyldiphenylmethylsilane (6.8 mL, 30.0 mmol, 2.34 eq.) and magnesium (730 mg, 30.0 mmol, 2.34 eq.) in THF (17 mL) was added 4 (4.73 g, 12.8 mmol, 1.00 eq.) in THF (30 mL) at −78° C. After stirred for 2.5 h, saturated aqueous NH₄Cl (80 mL) and EtOAc (80 mL) was added at 0° C., washed with saturated NH₄Cl (80 mL*2) and back-extracted with EtOAc (80 mL). The combined extract was dried over Na₂SO₄, filtered and concentrated under reduced pressure. The residue was chromatographed on silica gel (n-Hexane:Ethyl acetate=5:1) afforded 5 as a white foam (4.58 g, 71%). ¹H NMR (600 MHz, CDCl₃) δ 7.42-7.24 (m, 15H), 7.18-7.07 (m, 10H), 3.63-3.58 (m, 1H), 3.12 (d, J=10.2 Hz, 1H), 2.57 (dt, J=9.0, 1.8 Hz, 1H), 2.25 (brs, 1H), 2.08 (d, J=10.2 Hz, 1H), 1.82 (dd, J=12.6, 8.4 Hz, 1H), 1.21-1.14 (m, 5H), 0.84 (dd, J=14.7, 3.6 Hz, 1H), 0.36 (brs, 6H).

5. Preparation of Compound WV-CA-111.

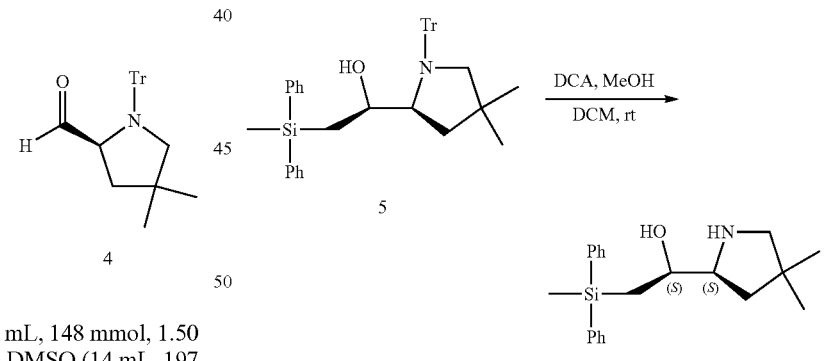

To a solution of compound 5 (7.37 g, 12.7 mmol, 1.00 eq.) in 10% MeOH/DCM (65 mL), 6% DCA/DCM (65 mL) was added and stirred for 10 min at room temperature. To the mixture, saturated NaHCO₃ (300 mL) was added, washed with saturated NaHCO₃ (300 mL), and back-extracted with DCM (130 mL). The combined extract was dried over Na₂SO₄, filtered and concentrated under reduced pressure. The residue was chromatographed on silica gel (3% MeOH in DCM) afforded WV-CA-112 as pale yellow solid (3.45 g, 80%). ¹H NMR (600 MHz, CDCl₃) δ 7.56-7.53 (m, 4H), 7.38-7.32 (m, 6H), 3.78-3.74 (m, 1H), 3.18-3.14 (m, 1H), 2.61 (d, J=11.4 Hz, 1H), 2.58 (d, J=10.2 Hz, 1H), 1.49 (dd, J=12.3, 10.2 Hz, 1H), 1.36-1.29 (m, 2H), 1.19 (dd, J=15.0, 5.4 Hz, 1H), 1.03 (s, 3H), 0.90 (s, 3H), 0.65 (s, 3H).

Example 99. Synthesis of WV-CA-111-dA$^{bz}$

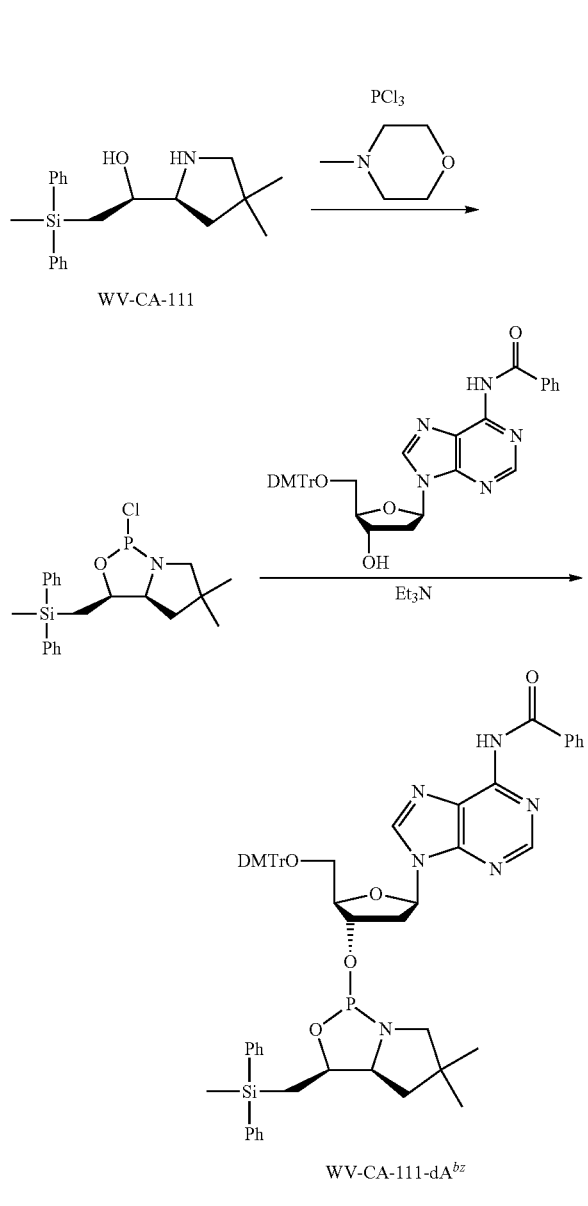

Using WV-CA-111 as starting material, the title compound (0.55 g, 45%) as a white solid was prepared analogously to WV-CA-008S-dC$^{iBu}$. $^1$H NMR (600 MHz, CDCl$_3$) δ 8.95 (brs, 1H), 8.70 (s, 1H), 8.12 (s, 1H), 8.02 (d, J=7.2 Hz, 2H), 7.59 (t, J=7.2 Hz, 1H), 7.54-7.44 (m, 6H), 7.38 (d, J=7.2 Hz, 2H), 7.30-7.16 (m, 13H), 6.78 (d, J=3.0 Hz, 2H), 6.76 (d, J=3.0 Hz, 2H), 6.38 (dd, J=7.8, 6.0 Hz, 1H), 4.88-4.83 (m, 1H), 4.80-4.75 (m, 1H), 4.08-4.05 (m, 1H), 3.73 (s, 6H), 3.56-3.50 (m, 1H), 3.34 (dd, J=10.5, 4.2 Hz, 1H), 3.28-3.21 (m, 2H), 2.86 (t, J=10.2 Hz, 1H), 2.69-2.63 (m, 1H), 2.45-2.39 (m, 1H), 1.55 (dd, J=14.4, 7.8 Hz, 1H), 1.38 (dd, J=15.0, 6.0 Hz, 1H), 1.20-1.15 (m, 1H), 1.11 (dd, J=11.7, 6.0 Hz, 1H), 1.07 (s, 3H), 0.96 (s, 3H), 0.62 (s, 3H). $^{31}$P NMR (243 MHz, CDCl$_3$) δ 152.78.

Example 100. Synthesis of WV-CA-112

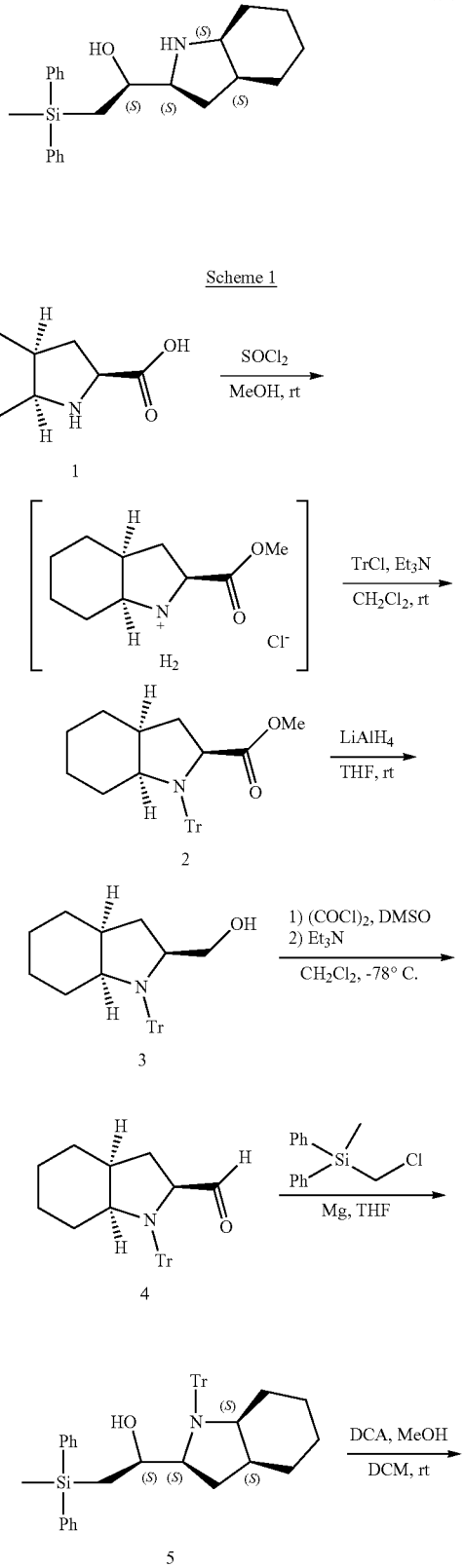

Scheme 1

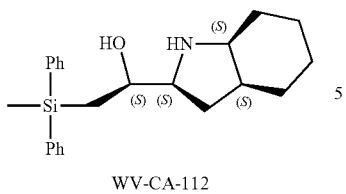

WV-CA-112

1. Preparation of Compound 2.

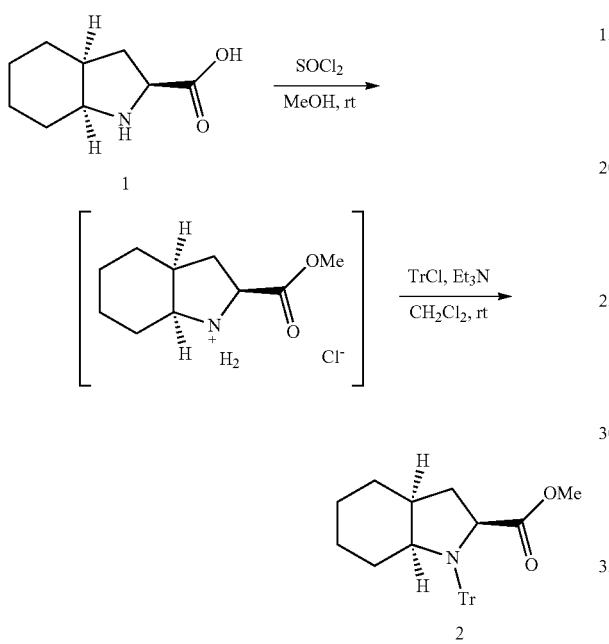

To a solution of 1 (5.10 g, 30.1 mmol, 1.00 eq.) in MeOH (30 mL) was slowly added thionyl chloride (4.4 mL, 60.2 mmol, 2.00 eq.) at 0° C. over 30 min. The mixture was stirred at room temperature for 3 h, then concentrated under reduced pressure. The residue was dissolved in DCM (50 mL) and added Et₃N (12.5 mL, 90.3 mmol, 3.00 eq.) at 0° C. To the mixture, trityl chloride (8.40 g, 30.1 mmol, 1.00 eq.) was added at 0° C., and the mixture warmed to room temperature and continued stirring for 16 h. The mixture was filtered and washed with DCM (50 mL). Filtrate was washed with saturated NaHCO₃ (50 mL*2), and back-extracted with DCM (30 mL*1). The combined organic layers were dried over Na₂SO₄, filtered, and concentrated to obtain compound 2 (13.73 g, crude, pale brown foam), which was used directly without further purification.

2. Preparation of Compound 3.

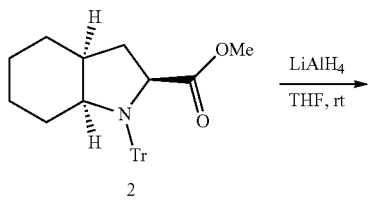

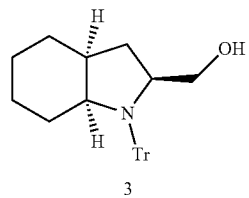

To a suspension of LiAlH₄ (1.44 g, 37.9 mmol, 1.26 eq.) in THF (60 mL), compound 2 (12.8 g, 30.1 mmol, 1.00 eq.) was added portion wise at 0° C. over 20 min, and the mixture stirred for 4 h. To the mixture, Et₂O (40 mL) and saturated Na₂SO₄ (20 mL) was added at 0° C. and stirred for 16 h at room temperature. The mixture was filtered with celite, and washed with Et₂O (10 mL*4). Filtrate was washed with saturated NaCl (50 mL), and back-extracted with DCM (30 mL*2). The combined organic layers were dried over Na₂SO₄, filtered, and concentrated to obtain compound 3 (13.55 g, crude, pale brown foam), which was used directly without further purification.

3. Preparation of Compound 4.

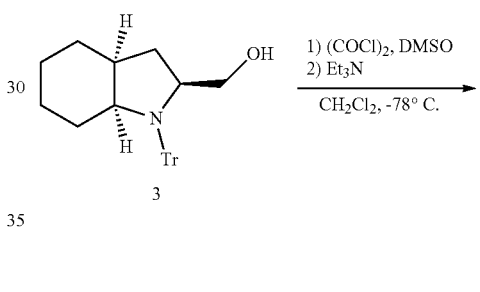

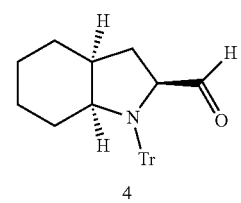

To a solution of oxalyl chloride (3.4 mL, 39.2 mmol, 1.50 eq.) in DCM (20 mL) was slowly added DMSO (3.7 mL, 52.2 mmol, 2.00 eq.) in DCM (10 mL) at −78° C. over 50 min and continued stirring at same temperature for 30 min. To the mixture, compound 3 (10.38 g, 26.1 mmol, 1.00 eq.) in DCM (20 mL) was added dropwise over 1.5 h at −78° C. and continued stirring at same temperature for 1.5 h. Then Et₃N (14.5 mL, 104.4 mmol, 4.00 eq.) was added to the mixture at −78° C. over 20 min, and continued stirring for 1.5 h. To the mixture, a mixture of saturated NH₄Cl (34 mL) and 28% NH₃ solution (17 mL) was slowly added at −78° C., and warmed to room temperature. Organic layer was separated and water layer was extracted with DCM (10 mL*2). The combined organic layers were dried over Na₂SO₄, filtered, and concentrated to obtain compound 4 (11.65 g, crude, pale brown solid), which was used directly without further purification.

4. Preparation of Compound 5.

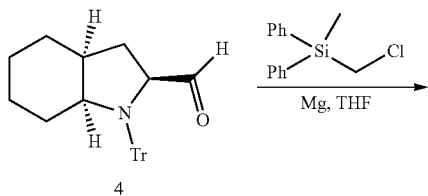

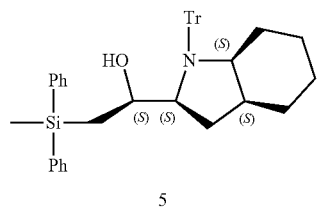

To a solution of methyldiphenylsilylmethyl magnesium chloride in THF prepared from chloromethyldiphenylmethylsilane (5.9 mL, 25.8 mmol, 3.00 eq.) and magnesium (629 mg, 25.8 mmol, 3.00 eq.) in THF (15 mL) was added 4 (2.79 g, 8.14 mmol, 1.00 eq.) in THF (26 mL) at −78° C. After stirred for 45 min, saturated aqueous NH$_4$Cl (70 mL) and EtOAc (70 mL) was added at 0° C., washed with saturated NH$_4$Cl (70 mL*2) and back-extracted with EtOAc (70 mL). The combined extract was dried over Na$_2$SO$_4$, filtered and concentrated under reduced pressure. The residue was chromatographed on silica gel (n-Hexane:Ethyl acetate=5:1) afforded 5 as a white foam (3.25 g, 62%). $^1$H NMR (600 MHz, CDCl$_3$) δ 7.49-7.25 (m, 15H), 7.19-7.08 (m, 10H), 4.07 (dt, J=9.0, 3.0 Hz, 1H), 3.33 (s, 1H), 3.22 (dt, J=8.9, 3.6 Hz, 1H), 2.91 (dt, J=11.6, 5.4 Hz, 1H), 2.12-2.07 (m, 1H), 2.04 (s, 1H), 1.84-1.70 (m, 2H), 1.63-1.57 (m, 1H), 1.33 (dd, J=14.4, 6.6 Hz, 1H), 1.25-1.15 (m, 2H), 1.06 (dd, J=14.4, 6.6 Hz, 2H), 0.98-0.86 (m, 2H), 0.36 (s, 3H), −0.10 (dd, J=12.9, 6.6 Hz, 1H).

5. Preparation of Compound 6.

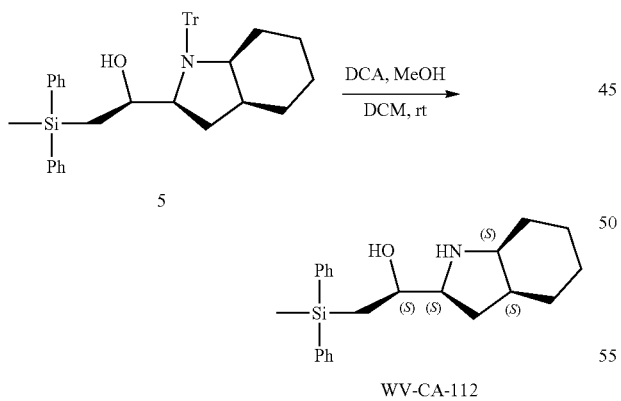

To a solution of compound 5 (3.23 g, 7.06 mmol, 1.00 eq.) in 5% MeOH/DCM (27 mL), 6% DCA/DCM (27 mL) was added and stirred for 10 min at room temperature. To the mixture, saturated NaHCO$_3$ (150 mL) was added, washed with saturated NaHCO$_3$ (150 mL), and back-extracted with DCM (54 mL). The combined extract was dried over Na$_2$SO$_4$, filtered and concentrated under reduced pressure. The residue was chromatographed on silica gel (3% MeOH in DCM) afforded WV-CA-112 as pale yellow oil (1.81 g, 93%). $^1$H NMR (600 MHz, CDCl$_3$) δ 7.56-7.52 (m, 4H), 7.37-7.31 (m, 6H), 3.77-3.73 (m, 1H), 3.09-3.04 (m, 2H), 1.94-1.87 (m, 1H), 1.63-1.16 (m, 12H), 0.65 (s, 3H).

Example 101. Synthesis of WV-CA-112-dA[bz]

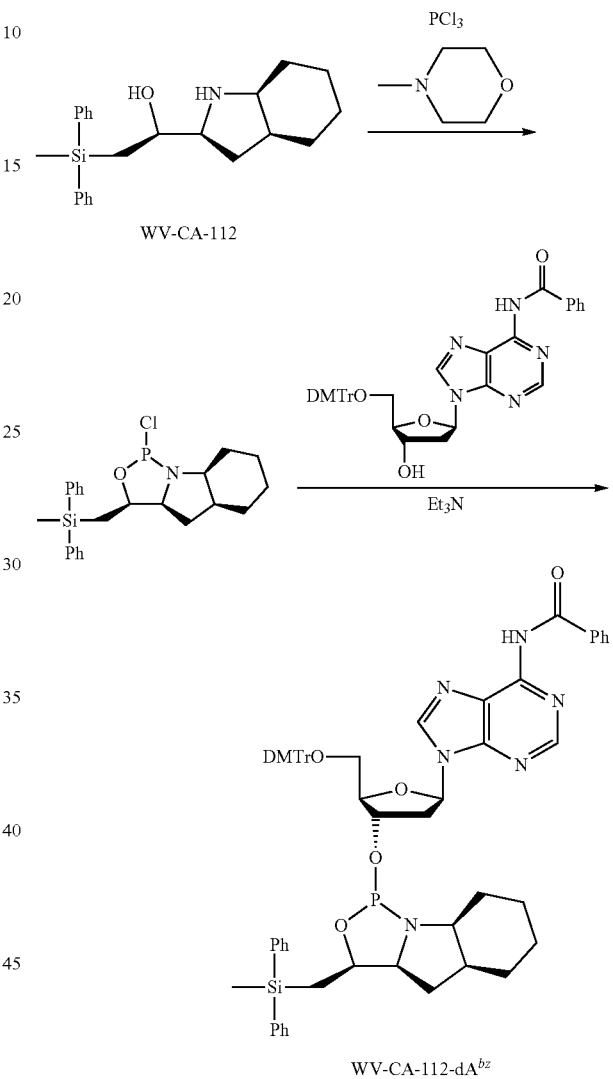

Using WV-CA-112 as starting material, the title compound (0.51 g, 49%) as a white solid was prepared analogously to WV-CA-008S-dC[iBu]. $^1$H NMR (600 MHz, CDCl$_3$) δ 8.96 (brs, 1H), 8.70 (s, 1H), 8.13 (s, 1H), 8.03 (d, J=7.8 Hz, 2H), 7.60 (t, J=7.6 Hz, 1H), 7.54-7.48 (m, 6H), 7.38 (d, J=7.2 Hz, 2H), 7.30-7.20 (m, 13H), 6.79-6.75 (m, 4H), 6.39 (t, J=6.6 Hz, 1H), 4.82-4.78 (m, 1H), 4.69-4.65 (m, 1H), 4.06-4.03 (m, 1H), 3.75 (s, 6H), 3.71-3.65 (m, 1H), 3.42-3.36 (m, 1H), 3.33 (dd, J=10.2, 4.2 Hz, 1H), 3.24 (dd, J=10.2, 4.2 Hz, 1H), 2.72-2.66 (m, 1H), 2.48-2.42 (m, 1H), 2.21-2.15 (m, 1H), 2.09-2.02 (m, 1H), 1.68-1.62 (m, 1H), 1.59-1.52 (m, 1H), 1.51-1.18 (m, 9H), 0.65 (s, 3H). $^{31}$P NMR (243 MHz, CDCl$_3$) δ 135.34.

Example 102. Synthesis of WV-CA-116-dCiBu

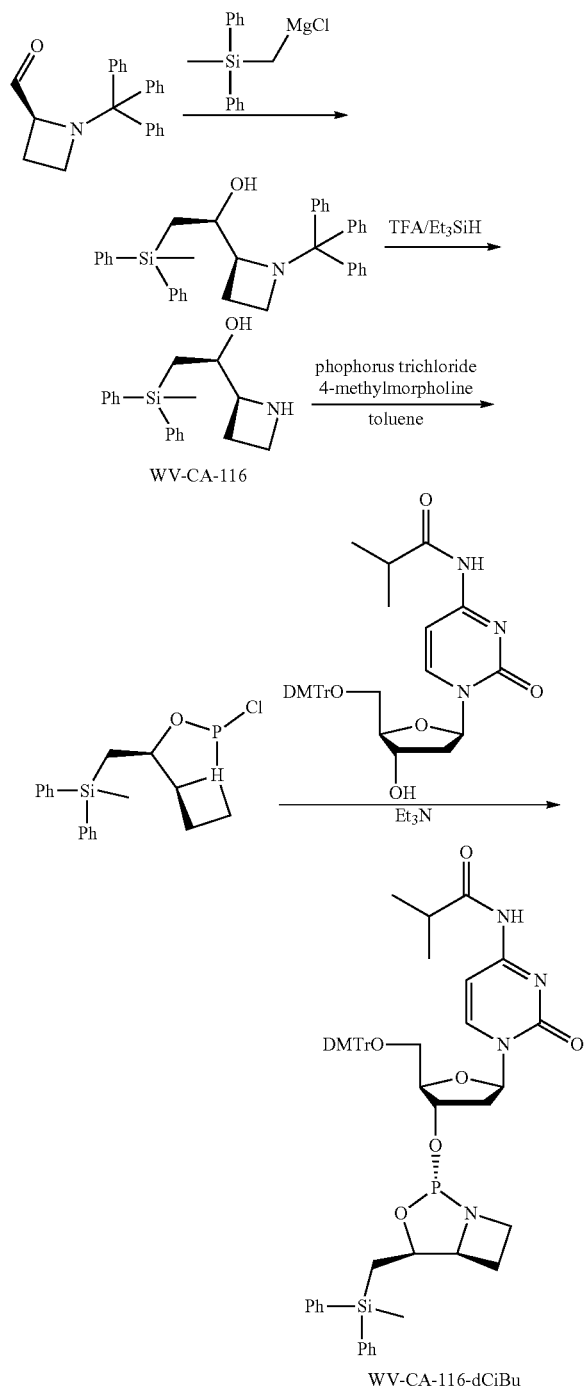

WV-CA-116

WV-CA-116-dCiBu

Step 1: (S)-2-(methyldiphenylsilyl)-1-((S)-1-tritylazetidin-2-yl)ethan-1-ol

A solution of (chloromethyl)(methyl)diphenylsilane (7.54 g, 30.5 mmol) in THF (10 mL) was added slowly to the magnesium (0.742 g, 30.5 mmol) in THF (50 mL) (activated with 1,2-dibromoethane) at 50-60° C. The reaction mixture was stirred at 65° C. for 3 hr until Mg was disappeared and at room temperature for overnight. In a separate flask, (S)-1-tritylazetidine-2-carbaldehyde (5.0 g, 15.27 mmol) was dissolved in THF (50 mL) at 0° C. To this solution, the Grignard was added at 0° C., and stirred at 0° C. for 1 hr, and then stirred at room temperature for overnight. The reaction mixture was quenched by sat. ammonium chloride, extracted with EtOAc (3×), dried over $Na_2SO_4$, and concentrated to give a yellow oil, which was purified by ISCO (120 gold column) eluting with hexane to 20% EtOAc in hexane to give (S)-2-(methyldiphenylsilyl)-1-((S)-1-tritylazetidin-2-yl)ethan-1-ol (6.52 g, 79%) as a white solid. $^1$H NMR (400 MHz, Chloroform-d) δ 7.46-7.12 (m, 25H), 3.71 (td, J=7.4, 2.3 Hz, 1H), 3.44-3.24 (m, 2H), 2.69 (dt, J=9.9, 7.8 Hz, 1H), 2.14-2.00 (m, 1H), 1.31-1.10 (m, 2H), 0.93-0.78 (m, 1H), 0.45 (s, 3H). MS (ESI), 540.5 (M+H)+.

Step 2: (S)-1-((S)-azetidin-2-yl)-2-(methyldiphenylsilyl)ethan-1-ol (WV-CA-116)

Using (S)-2-(methyldiphenylsilyl)-1-((S)-1-tritylazetidin-2-yl)ethan-1-ol as starting material, the title compound (0.68 g, 20%) as a white solid was prepared analogously to WV-CA-117 (step 2). $^1$H NMR (400 MHz, Chloroform-d) δ 7.54 (dt, J=7.7, 2.7 Hz, 4H), 7.35 (qd, J=5.5, 3.2 Hz, 6H), 3.80 (td, J=7.9, 3.3 Hz, 1H), 3.68-3.46 (m, 2H), 3.14 (ddd, J=8.9, 7.2, 3.5 Hz, 1H), 2.35 (dq, J=11.0, 8.7 Hz, 1H), 1.84 (dtd, J=11.4, 8.4, 3.6 Hz, 1H), 1.28 (dd, J=14.7, 8.4 Hz, 1H), 1.02 (dd, J=14.7, 6.0 Hz, 1H), 0.65 (s, 3H). MS (ESI), 298.3 (M+H)+.

Step 3 & 4: N-(1-((2R,4S,5R)-5-((bis(4-methoxyphenyl)(phenyl)methoxy) methyl)-4-(((2S,4S,5S)-4-((methyldiphenylsilyl)methyl)-3-oxa-1-aza-2-phosphabicyclo[3.2.0]heptan-2-yl)oxy)tetrahydrofuran-2-yl)-2-oxo-1,2-dihydropyrimidin-4-yl)isobutyramide (WV-CA-116-dCiBu)

Using WV-CA-116 as starting material, the title compound (0.46 g, 32.6%) as a white solid was prepared analogously to WV-CA-117-dCiBu (step 3& 4); 31P NMR (202 MHz, $CDCl_3$) δ 156.26.

Example 103. Synthesis of WV-CA-117-dCiBu

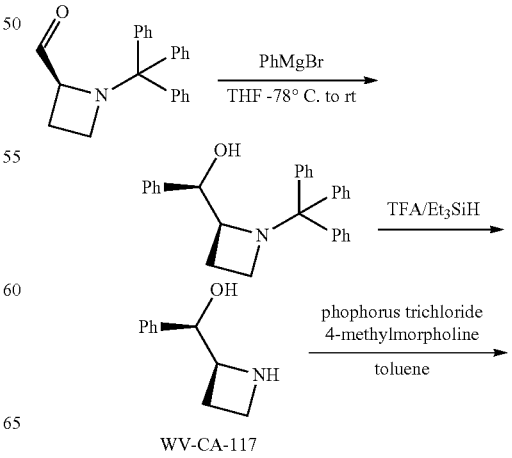

WV-CA-117

Step 1: (R)-phenyl((S)-1-tritylazetidin-2-yl)methanol

To a solution of (S)-1-tritylazetidine-2-carbaldehyde in anhydrous ether (20 mL) under Ar at −78° C. was added PhMgBr 1.0 M in THF (20.9 mL, 20.89 mmol) dropwise. After stirring at −78° C. for 4 hr, the reaction mixture was slowly warm to room temperature for overnight. The reaction mixture was quenched by sat. NH$_4$Cl solution (80 mL). Water (50 mL) was added into the reaction mixture. The organic layer was separated and the water layer was extracted with EtOAc (3×). The combined organic layer was dried over anhydrous Na$_2$SO$_4$ and concentrated under reduced pressure. LC-MS showed that the starting material was disappeared and the ratio of diastereomers product is 2:1. The crude product was purified by ISCO (220 g gold column) eluting with 0% EtOAc in hexane to 20% EtOAc in hexane (product come out at 6-8% EtOAc in hexane) to give the desired product (R)-phenyl((S)-1-tritylazetidin-2-yl)methanol (2.85 g, 61%) and (S)-phenyl((S)-1-tritylazetidin-2-yl) methanol (1.09 g, 23%). (R)-phenyl((S)-1-tritylazetidin-2-yl)methanol: $^1$H NMR (399 MHz, Chloroform-d) δ 7.56 (dtd, J=8.3, 2.7, 1.3 Hz, 6H), 7.37-7.27 (m, 5H), 7.27-7.12 (m, 9H), 4.55 (d, J=2.5 Hz, 1H), 3.86 (s, 1H), 3.46 (dddd, J=11.6, 9.1, 7.5, 2.6 Hz, 2H), 2.76 (q, J=8.4 Hz, 1H), 2.20-2.08 (m, 1H), 1.23-1.20 (m, 1H). MS (ESI), 406.3 (M+H)+.

Step 2: (R)-((S)-azetidin-2-yl)(phenyl)methanol (WV-CA-117)

(R)-phenyl((S)-1-tritylazetidin-2-yl)methanol (2.36 g, 5.82 mmol) at 0° C. was added DCM (10 mL) and TFA (10 mL) (color became red) and triethylsilane (6.51 mL, 40.7 mmol) (color disappeared). The mixture was stirred at room temperature for 30 minutes. TLC showed the reaction was complete. Solvent was evaporated under reduced pressure, and dilute with water, extracted with ether (1×), add 3 mL 1 N NaOH to water layer, back extracted with 5% IPA in DCM (4×), concentrated to give a white solid, which was purified by ISCO (24 g gold column) eluting with DCM to 30% MeOH in DCM (product at 20-30% MeOH in DCM) to give a white solid (0.703 g, 74%). $^1$H NMR (400 MHz, Chloroform-d) δ 7.37-7.20 (m, 5H), 4.62 (d, J=3.8 Hz, 1H), 4.21 (td, J=8.0, 3.5 Hz, 1H), 3.62 (td, J=8.7, 7.0 Hz, 1H), 3.24 (ddd, J=8.9, 7.1, 3.4 Hz, 1H), 2.93 (brs, 2H), 2.42 (dq, J=11.1, 8.7 Hz, 1H), 1.76 (dt, J=11.3, 8.0, 3.3 Hz, 1H). MS(ESI), 164.1 (M+H)+.

Step 3 & 4: N-(1-((2R,4S,5R)-5-((bis(4-methoxyphenyl)(phenyl)methoxy)methyl)-4-(((2R,4R,5S)-4-phenyl-3-oxa-1-aza-2-phosphabicyclo[3.2.0]heptan-2-yl)oxy)tetrahydrofuran-2-yl)-2-oxo-1,2-dihydropyrimidin-4-yl)isobutyramide (WV-CA-117-dCiBu)

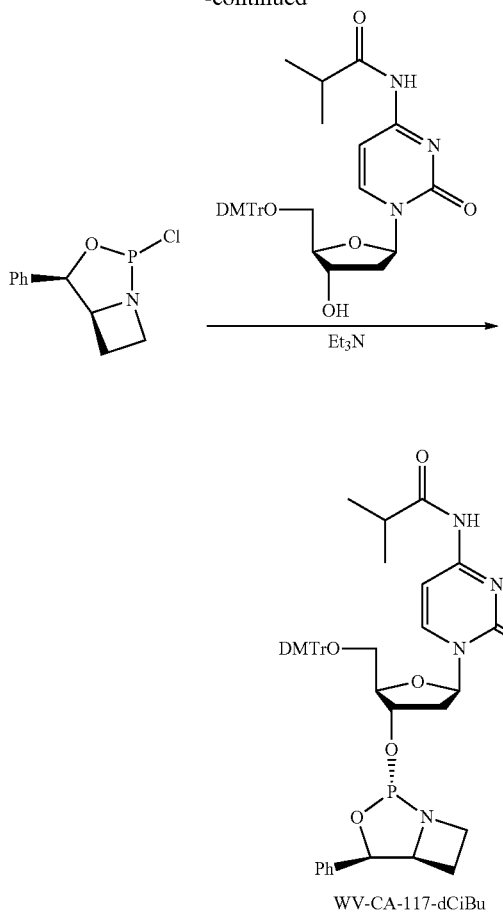

WV-CA-117-dCiBu (R)-((S)-azetidin-2-yl)(phenyl)methanol (0.652 g, 3.99 mmol) was dried by azeotropic distillation with toluene (3×10 mL). A solution of this dried (R)-((S)-azetidin-2-yl)(phenyl)methanol (0.652 g, 3.99 mmol) and 4-methylmorpholine (0.878 mL, 7.99 mmol) in ether (5 mL) was added to an ice-cold solution of trichlorophosphine (0.349 mL, 3.99 mmol) in ether (5 mL). Reaction mixture was warmed to room temperature and stirred for 40 minutes and then filtered under argon. Solvent removal under argon afforded (4R,5S)-2-chloro-4-phenyl-3-oxa-1-aza-2-phosphabicyclo[3.2.0]heptane as an oil which was used for the next step directly. The nucleoside N-(1-((2R,4S,5R)-5-((bis(4-methoxyphenyl)(phenyl)methoxy)methyl)-4-hydroxytetrahydrofuran-2-yl)-2-oxo-1,2-dihydropyrimidin-4-yl)isobutyramide (1.709 g, 2.85 mmol) was dried by azeotropic distillation first by pyridine (20 mL×1) and then by toluene (15 mL×3) and dried under vacuum for 24 hr. This dried compound was dissolved in dry THF (20 mL) followed by the addition of triethylamine (2.78 mL, 19.95 mmol) then cooled to −78° C. A THF solution (20 mL) of the above crude product (4R,5S)-2-chloro-4-phenyl-3-oxa-1-aza-2-phosphabicyclo[3.2.0]heptane was added dropwise over 10 minutes, then removed cooler bath and gradually warmed to room temperature and stirred at room temperature for 3 hr. The mixture at 0° C. was added sat. NaHCO$_3$ (50 mL), 1 N Na$_2$CO$_3$ (10 mL), and CHCl$_3$ (200 mL). The organic layer was separated, washed with sat. NaHCO$_3$ (2×). The combined water layer was re-extracted with CHCl$_3$ (100 mL), washed with sat. NaHCO$_3$. The CHCl$_3$ extract was dried over anhydrous Na$_2$SO$_4$, filtered and dried under rotary evaporation under 25° C. to afford the yellowish solid (2.24 g). TLC showed the product was not stable. The 300 mg crude product was re-dissolved in 10% TEA in 75% EtOAc in hexane (5 mL) loaded onto a short plug of silica gel eluting with 10% TEA in 75% EtOAc in hexane to give a white solid (120 mg). $^{31}$P NMR (202 MHz, CDCl$_3$) δ 159.30.

Example 104. Synthesis of WV-CA-118-dCiBu

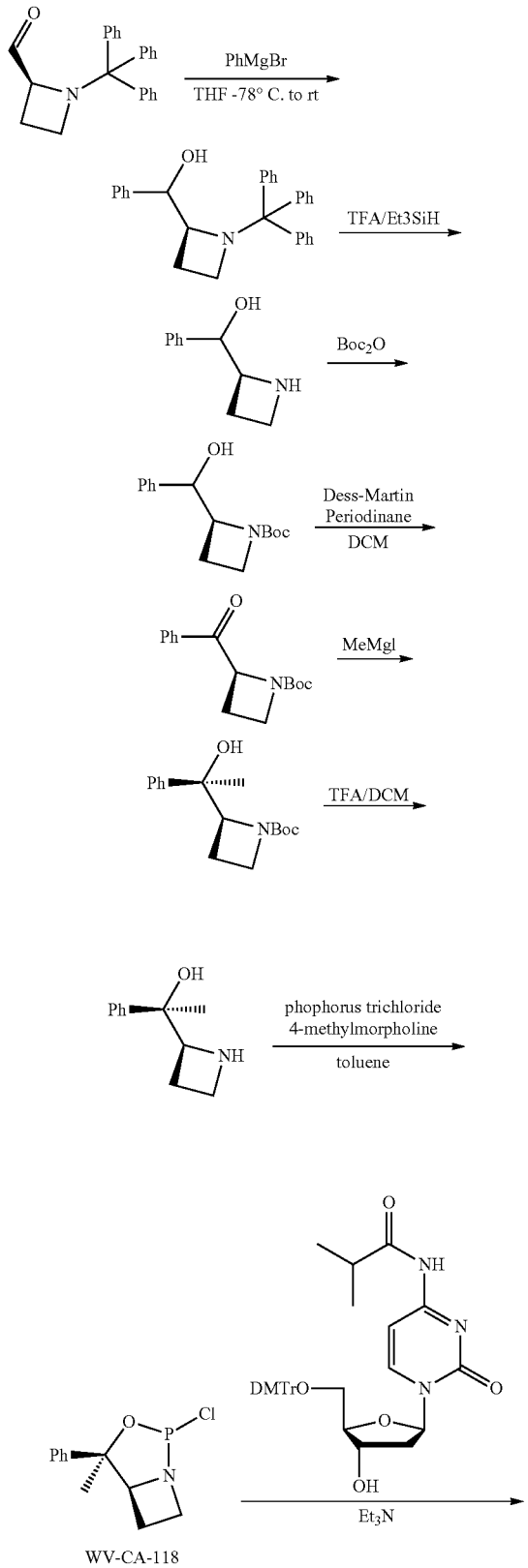

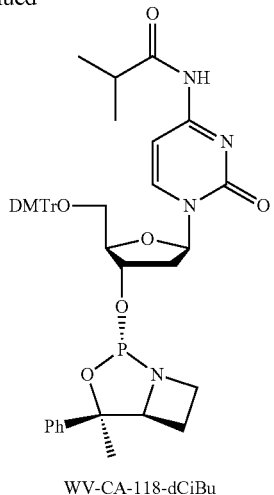

WV-CA-118-dCiBu

Step 1: (S)-azetidin-2-yl(phenyl)methanol

To a solution of (S)-1-tritylazetidine-2-carbaldehyde (6.67 g, 20.37 mmol) in anhydrous THF (45 mL) under Ar at −78° C. was added PhMgBr 1.0 M in THF (61.1 mL, 61.1 mmol) dropwise. After stirring at −78° C. for 10 minute, the reaction mixture was slowly warm to room temperature and stirred at room temperature for 20 hr. The reaction mixture was quenched by sat. NH$_4$Cl solution (80 mL). Water (100 mL) was added into the reaction mixture. The organic layer was separated and the water layer was extracted with EtOAc (3×). The combined organic layer was dried over anhydrous Na$_2$SO$_4$ and concentrated under reduced pressure to give (S)-azetidin-2-yl(phenyl)methanol (9.26 g, 112%). Without further purification, directly use for step 2. MS (ESI), 406.3 (M+H)+.

Step 2: (S)-azetidin-2-yl(phenyl)methanol

Phenyl((S)-1-tritylazetidin-2-yl)methanol (9.26 g) (all from GL04-22) at 0° C. was added DCM (40 mL) and TFA (30 mL) (color became red) and triethylsilane (16.27 mL, 102 mmol) (color disappeared). The mixture was stirred at room temperature for 30 minutes. TLC showed the reaction was complete. Solvent was evaporated under reduced pressure, and dilute with water, extracted with ether (1×), add 20 mL 1 N NaOH to water layer, back extracted with DCM (10×), concentrated to give (S)-azetidin-2-yl(phenyl)methanol (2.3 g, 14.09 mmol, 69.2% yield over 2 steps) as a colorless oil. MS (ESI), 164.1 (M+H)+.

Step 3: (S)-tert-butyl 2-benzoylazetidine-1-carboxylate

To a solution of (S)-azetidin-2-yl(phenyl)methanol (2.3 g, 14.09 mmol) in DCM (20 mL) and methanol (20 mL) at 0° C. was added di-tert-butyl dicarbonate (3.23 g, 14.80 mmol) and TEA (4.91 mL, 35.2 mmol). The reaction mixture was stirred at room temperature for 2 hr. LC-MS and TLC showed the reaction was complete and very clean. Solvents were evaporated, diluted with DCM, washed with sat. NaHCO$_3$, dried over Na$_2$SO$_4$, concentrated to give (2S)-tert-butyl 2-(hydroxy(phenyl)methyl)azetidine-1-carboxylate (3.74 g, 14.20 mmol, 101% yield) as an yellow oil. MS (ESI), 286.2 (M+Na)+.

Step 4: (S)-tert-butyl 2-benzoylazetidine-1-carboxylate

To a solution of (2S)-tert-butyl 2-(hydroxy(phenyl)methyl)azetidine-1-carboxylate (3.91 g, 14.85 mmol) in DCM (50 mL) was added a drop of water and Dess-Martin Periodinane (8.19 g, 19.30 mmol). The reaction mixture was stirred at room temperature for 1 hr. TLC showed the reaction was complete, diluted with DCM, washed with sat. NaHCO$_3$ and sodium thiosulfate (4:1), back extracted with DCM (2×), dried over Na$_2$SO$_4$, concentrated to give a residue, which was purified by ISCO (40 g) eluting with 10% EtOAc in hexane to 30% EtOAc in hexane (product come out at 20% EtOAc in hexane) to give a (S)-tert-butyl 2-benzoylazetidine-1-carboxylate as a white solid (3.23 g, 12.36 mmol, 83% yield). $^1$H NMR (400 MHz, Chloroform-d) δ 7.93-7.86 (m, 2H), 7.63-7.53 (m, 1H), 7.47 (t, J=7.6 Hz, 2H), 5.54 (dd, J=9.6, 5.5 Hz, 1H), 4.17-3.90 (m, 2H), 2.64 (dtd, J=11.2, 9.2, 6.3 Hz, 1H), 2.22-2.01 (m, 1H), 1.40 (s, 9H); MS (ESI) (M+Na)+284.2 (OK).

Step 5: tert-butyl (S)-2-((R)-1-hydroxy-1-phenylethyl)azetidine-1-carboxylate To a solution of MeMgI in ether (3.0 M, 48 mL, 144 mmol) in ether (50 mL) at −78° C. was added (S)-tert-butyl 2-benzoylazetidine-1-carboxylate (3.23 g, 12.36 mmol) in ether (20 mL). The reaction mixture was stirred at −78° C. for 10 minutes, at 0° C. for 4 hr and at room temperature for overnight. The reaction mixture was quenched by sat. ammonium chloride, extracted with EtOAc (3×), dried over sodium sulfate, concentrated to give a colorless oil. The crude product was purified by ISCO (80 g gold column) eluting with 10% EtOAc in hexane to 30% EtOAc in hexane to give tert-butyl (S)-2-((R)-1-hydroxy-1-phenylethyl)azetidine-1-carboxylate (0.80 g, 23.4%) as a colorless oil. $^1$H NMR (400 MHz, Chloroform-d) δ 7.47-7.39 (m, 2H), 7.38-7.29 (m, 2H), 7.31-7.21 (m, 1H), 5.07 (s, 1H), 4.48 (dd, J=8.9, 6.0 Hz, 1H), 3.64 (td, J=9.0, 6.4 Hz, 1H), 3.23 (s, 1H), 2.11-1.97 (m, 1H), 1.88 (ddt, J=11.8, 9.2, 6.2 Hz, 1H), 1.53 (s, 3H), 1.47 (s, 9H). MS (ESI), 278.4 (M+H)$^+$.

Step 6: (R)-1-((S)-azetidin-2-yl)-1-phenylethan-1-ol (WV-CA-118)

To a solution of (S)-tert-butyl 2-((R)-1-hydroxy-1-phenylethyl)azetidine-1-carboxylate (0.80 g, 2.88 mmol) in DCM (10 mL) was added TFA (3.0 mL). The reaction mixture was stirred at room temperature for 2 hr. Solvent was evaporated under reduced pressure to give a yellow oil, which was dissolved in DCM, added Na$_2$CO$_3$, stirred at room temperature for 10 minutes, added 1 N NaOH (3 mL), dried over Na$_2$SO$_4$, concentrated to give a white solid (R)-1-((S)-azetidin-2-yl)-1-phenylethanol (510 mg, 2.88 mmol, 100% yield). $^1$H NMR (400 MHz, Chloroform-d) δ 7.46-7.38 (m, 2H), 7.31 (dd, J=8.6, 6.9 Hz, 2H), 7.21 (t, J=7.4 Hz, 1H), 4.17 (t, J=8.0 Hz, 1H), 3.58 (td, J=8.8, 7.0 Hz, 1H), 3.14 (ddd, J=9.9, 7.3, 3.3 Hz, 1H), 2.14 (dq, J=11.3, 8.7 Hz, 1H), 1.65 (ddt, J=11.9, 8.1, 4.1 Hz, 1H), 1.35 (s, 3H).

Step 7 & 8: N-(1-((2R,4S,5R)-5-((bis(4-methoxyphenyl)(phenyl)methoxy)methyl)-4-(((2S,4R,5S)-4-methyl-4-phenyl-3-oxa-1-aza-2-phosphabicyclo[3.2.0]heptan-2-yl)oxy)tetrahydrofuran-2-yl)-2-oxo-1,2-dihydropyrimidin-4-yl)isobutyramide (WV-CA-118-dCiBu)

(R)-1-((S)-azetidin-2-yl)-1-phenylethanol (0.51 g, 2.88 mmol) was dried by azeotropic distillation with toluene (3×10 mL). A solution of this dried (R)-1-((S)-azetidin-2-yl)-1-phenylethanol (0.51 g, 2.88 mmol) and 4-methylmorpholine (0.652 mL, 5.93 mmol) in toluene (5 mL) was added to an ice-cold solution of trichlorophosphine (0.259 mL, 2.96 mmol) in toluene (5 mL). Reaction mixture was warmed to room temperature stirred for 40 minutes, and then filtered under argon. Solvent removal under argon afforded (4R,5S)-2-chloro-4-methyl-4-phenyl-3-oxa-1-aza-2-phosphabicyclo[3.2.0]heptane as an oil which was used for the next step directly. The nucleoside N-(1-((2R,4S,5R)-5-((bis(4-methoxyphenyl)(phenyl)methoxy)methyl)-4-hydroxytetrahydrofuran-2-yl)-2-oxo-1,2-dihydropyrimidin-4-yl)isobutyramide (1.234 g, 2.057 mmol) was dried by azeotropic distillation first by pyridine (10 mL×1) and then by toluene (15 mL×3) and dried under vacuum for 24 hr. This dried compound was dissolved in dry THF (10 mL) followed by the addition of TEA (2.0 mL, 14.40 mmol) then cooled to −78° C. A THF solution (10 mL) of the above crude product (4R,5S)-2-chloro-4-methyl-4-phenyl-3-oxa-1-aza-2-phosphabicyclo[3.2.0]heptane was added dropwise over 10 minutes, then removed cooling bath and gradually warmed to room temperature and stirred at 1.5 hr, TLC indicated a good conversion of SM to product. The mixture at 0° C. was added EtOAc (150 mL) and sat. NaHCO$_3$ (100 mL). The organic layer was separated, washed with sat. NaHCO$_3$ (1×). The combined water layer was re-extracted with EtOAc (100 mL), washed with sat. NaHCO$_3$. The EtOAc extract was dried over anhydrous Na$_2$SO$_4$, filtered and dried under rotary evaporation under 25° C. The crude product was purified by ISCO (24 g column) eluting with 5% TEA, 20% EtOAc in hexane to 5% TEA, 70% EtOAc in hexane to give N-(1-((2R,4S,5R)-5-((bis(4-methoxyphenyl)(phenyl)methoxy)methyl)-4-(((2S,4R,5S)-4-methyl-4-phenyl-3-oxa-1-aza-2-phosphabicyclo[3.2.0]heptan-2-yl)oxy)tetrahydrofuran-2-yl)-2-oxo-1,2-dihydropyrimidin-4-yl)isobutyramide (0.66 g, 0.820 mmol, 39.9% yield) as a white solid. 1H NMR (500 MHz, Chloroform-d) δ 8.42 (s, 1H), 8.29 (d, J=7.4 Hz, 1H), 7.45-7.39 (m, 2H), 7.36-7.22 (m, 11H), 7.09 (d, J=7.4 Hz, 1H), 6.87-6.78 (m, 5H), 6.24 (dd, J=6.5, 4.6 Hz, 1H), 4.82 (dq, J=11.6, 6.0 Hz, 1H), 4.61 (q, J=6.9 Hz, 1H), 4.20 (dt, J=5.7, 3.2 Hz, 1H), 3.81-3.69 (m, 8H), 3.54-3.42 (m, 3H), 2.78 (dt, J=13.4, 6.3 Hz, 1H), 2.59 (h, J=7.0 Hz, 1H), 2.37 (dt, J=14.0, 5.8 Hz, 1H), 2.04-1.18 (m, 10H); 31P NMR (202 MHz, CDCl3) δ 166.99.

Example 105. Synthesis of WV-CA-118S-dCiBu

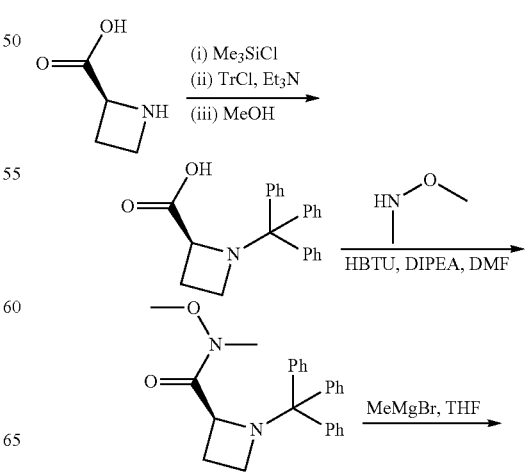

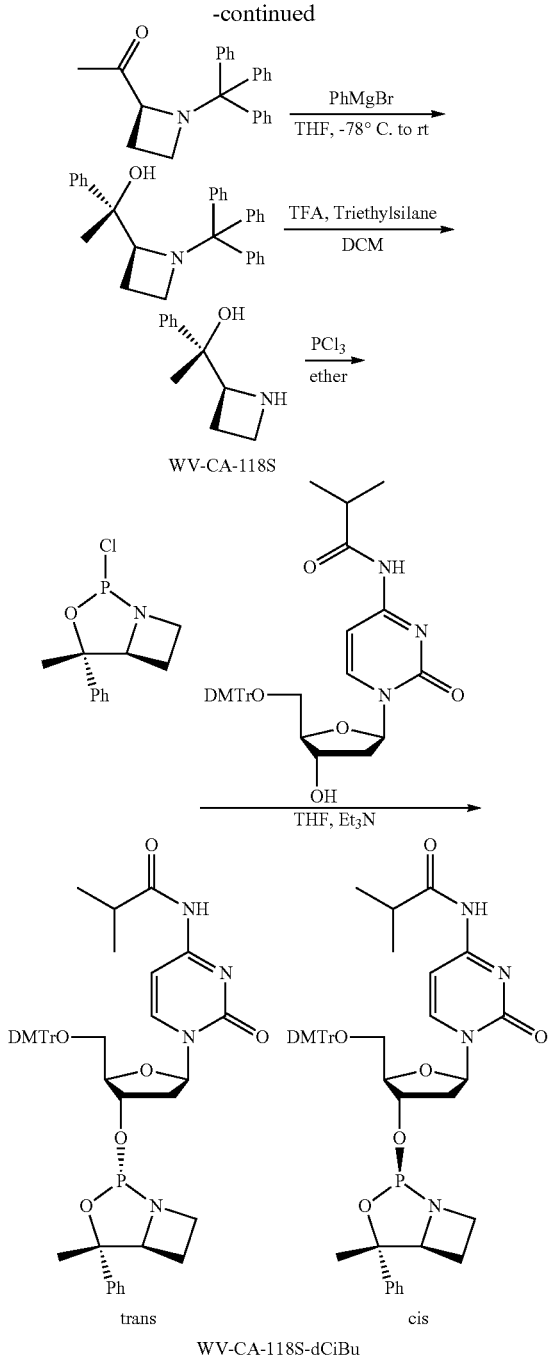

trans  cis

WV-CA-118S-dCiBu

Step 1: (S)-1-tritylazetidine-2-Carboxylic Acid

To a solution of (S)-azetidine-2-carboxylic acid (2.022 g, 20 mmol) in 36 mL CHCl$_3$-MeCN (5:1) was added TMSCl (2.54 mL, 20.01 mmol) at room temperature. The reaction mixture was heated at 63° C. using condenser for 2 hr and then allowed to attain room temperature. TEA (5.58 mL) was added slowly and (chloromethanetriyl)tribenzene (5.58 g, 20.00 mmol) was added slowly. The reaction mixture was stirred at room temperature for 1.5 hr, and 5 mL MeOH was added. Evaporation under reduced pressure left a residue, which was partitioned between DCM and 5% citric acid solution. The organic layer was dried over anhydrous sodium sulfate and purified by ISCO (80 g gold column) eluting with DCM to 20% MeOH in DCM (product at 6-10% MeOH in DCM) to give (S)-1-tritylazetidine-2-carboxylic acid as a white solid (6.46 g, 94% yield). MS (ESI), 366.3 (M+Na)$^+$.

Step 2: (S)—N-methoxy-N-methyl-1-tritylazetidine-2-carboxamide

A solution of (S)-1-Tritylazetidine-2-carboxylic acid in dry THF (25 mL) was added dropwise under Ar to a solution of LiAlH$_4$ (2.0 M in THF) (8.2 mL, 16.52 mmol) at room temperature. The reaction mixture was stirred at room temperature for 2 hr, and TLC showed that all starting material was consumed. The reaction mixture was quenched by Glaubler's Salt (Na$_2$SO$_4$·10 H$_2$O), filtered through celite, washed with EtOAc. Solvent was evaporated under reduced pressure to give (S)—N-methoxy-N-methyl-1-tritylazetidine-2-carboxamide as a foam solid (5.93 g, 97%). MS (ESI), 330.2 (M+H)+.

Step 3: (S)-1-(1-tritylazetidin-2-yl)ethanone

To a solution of (S)-(1-tritylazetidin-2-yl)methanol (5.65 g, 17.15 mmol) (GL01-04) in DCM (60 mL) was added Dess Martin Periodinate (8.00 g, 18.87 mmol). The reaction mixture was stirred at room temperature for 1.5 hr. TLC showed that starting material was disappeared and a new spot was generated above the start material (3:1 hexane/EtOAc). DCM (100 mL) was added and washed with sat. NaHCO$_3$ and Na$_2$SO$_3$ (1:1). The water layer was extracted with DCM (100 mL). The combined organic layer was dried over anhydrous sodium sulfate and purified by ISCO (80 g gold cartridge) eluting with 10% EtOAc in hexane to 30% EtOAc in hexane to give a yellowish solid (4.40 g. 78%). MS (ESI) (M+H$_3$O)+346.3.

Step 4: (S)-1-phenyl-1-((S)-1-tritylazetidin-2-yl)ethan-1-ol

To a solution of (S)-1-(1-tritylazetidin-2-yl)ethanone (4.70 g, 13.77 mmol) in anhydrous THF (150 mL) under Ar at −78° C. was added PhMgBr (1.0 M in THF, 34.4 mL, 34.4 mmol) dropwise. After stirring at −78° C. for 4 hr, the reaction mixture was slowly warm to room temperature for overnight. The reaction mixture was quenched by sat. NH$_4$Cl solution (150 mL) at 0° C. The reaction mixture was extracted with EtOAc (3×). The combined organic layer was dried over anhydrous Na$_2$SO$_4$ and concentrated under reduced pressure to give a residue, which was purified by ISCO (120 g gold column) eluting with hexane to 15% EtOAc in hexane (product comes out at 5-10% EtOAc in hexane to give the desired product as a white foam solid (4.01 g, 69%). MS (ESI) 420.2 (M+H)$^+$.

Step 5: (S)-1-((S)-azetidin-2-yl)-1-phenylethan-1-ol (WV-CA-118S)

(S)-1-phenyl-1-((S)-1-tritylazetidin-2-yl)ethanol (3.89 g, 9.27 mmol) at 0° C. was added DCM (15 mL) and TFA (12 mL) and triethylsilane (10.37 mL, 64.9 mmol). The mixture was stirred at room temperature for 1 hr. Solvent was evaporated under reduced pressure, and dilute with water, extracted with ether (2×), add 3 mL 1 N NaOH to water layer, back extracted with 5% IPA in DCM (4×), concentrated to give a white solid, which was purified by ISCO (24 g gold column) eluting with DCM to 30% MeOH in DCM (product at 20-30% MeOH in DCM) to give a white solid (1.295 g, 79%). ¹H NMR (400 MHz, Chloroform-d) δ 7.45-7.36 (m, 2H), 7.30 (dd, J=8.5, 6.9 Hz, 2H), 7.26-7.15 (m, 1H), 4.22 (t, J=7.9 Hz, 1H), 3.60-3.49 (m, 1H), 3.12 (ddd, J=9.3, 6.7, 2.9 Hz, 1H), 2.50 (dq, J=10.8, 8.8 Hz, 1H), 2.08 (dtd, J=10.8, 7.9, 2.9 Hz, 1H), 1.34 (s, 3H). MS (ESI) 178.3 (M+H)+.

Step 6 and 7: N-(1-((2R,4S,5R)-5-((bis(4-methoxy-phenyl)(phenyl)methoxy)methyl)-4-((((2S,4S,5S)-4-methyl-4-phenyl-3-oxa-1-aza-2-phosphabicyclo[3.2.0]heptan-2-yl)oxy)tetrahydrofuran-2-yl)-2-oxo-1,2-dihydropyrimidin-4-yl)isobutyramide (WV-CA-118S-dCiBu)

(S)-1-((S)-azetidin-2-yl)-1-phenylethanol (WV-CA-118S) (1.10 g, 6.21 mmol) was dried by azeotropic distillation with toluene (3×10 mL). A solution of this dried WV-CA-118S and 4-methylmorpholine (1.365 mL, 12.41 mmol) in ether (5 mL) was added to an ice-cold solution of trichlorophosphine (0.541 mL, 6.21 mmol) in ether (5 mL). Reaction mixture was warmed to room temperature and stirred for 40 minutes and then filtered under argon. Solvent was removed under argon to afford (4S,5S)-2-chloro-4-methyl-4-phenyl-3-oxa-1-aza-2-phosphabicyclo[3.2.0]heptane as an oil which was used for the next step directly. N-(1-((2R,4S,5R)-5-((bis(4-methoxyphenyl)(phenyl)methoxy)methyl)-4-hydroxytetrahydrofuran-2-yl)-2-oxo-1,2-dihydropyrimidin-4-yl)isobutyramide (2.66 g, 4.44 mmol) was dried by azeotropic distillation first by pyridine (20 mL×1) and then by toluene (15 mL×3) and dried under vacuum for 24 hr. This dried compound was dissolved in dry THF (20 mL) followed by the addition of triethylamine (4.33 mL, 31.1 mmol) then cooled to −78° C. A THF solution (20 mL) of the above crude product (4S,5S)-2-chloro-4-methyl-4-phenyl-3-oxa-1-aza-2-phosphabicyclo[3.2.0]heptane was added dropwise over 10 minutes, then removed cooler bath and gradually warmed to room temperature and stirred at 3 hr. The mixture at 0° C. was added sat. NaHCO₃ (50 mL), 1 N Na₂CO₃ (10 mL), and CHCl₃ (200 mL). The organic layer was separated, washed with sat. NaHCO₃ (2×). The combined water layer was re-extracted with CHCl₃ (100 mL), washed with sat. NaHCO₃. The chloroform extract was dried over anhydrous Na₂SO₄, filtered and dried under rotary evaporation under 25° C. The crude product was re-dissolved in 2.5% TEA in 80% EtOAc in hexane (10 mL) loaded onto 30 g silica gel eluting with 20% EtOAc in hexane with 2.5% TEA in hexane to 80% EtOAc in hexane with 2.5% TEA to give a white solid (1.785 g, 50%). ³¹P NMR (202 MHz, CDCl₃) δ 155.15 (98.5%, trans), 144.5 (1.5%, cis).

Example 106. Synthesis of WV-CA-119

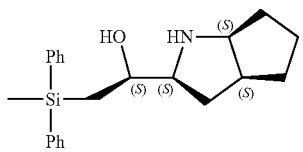
WV-CA-119

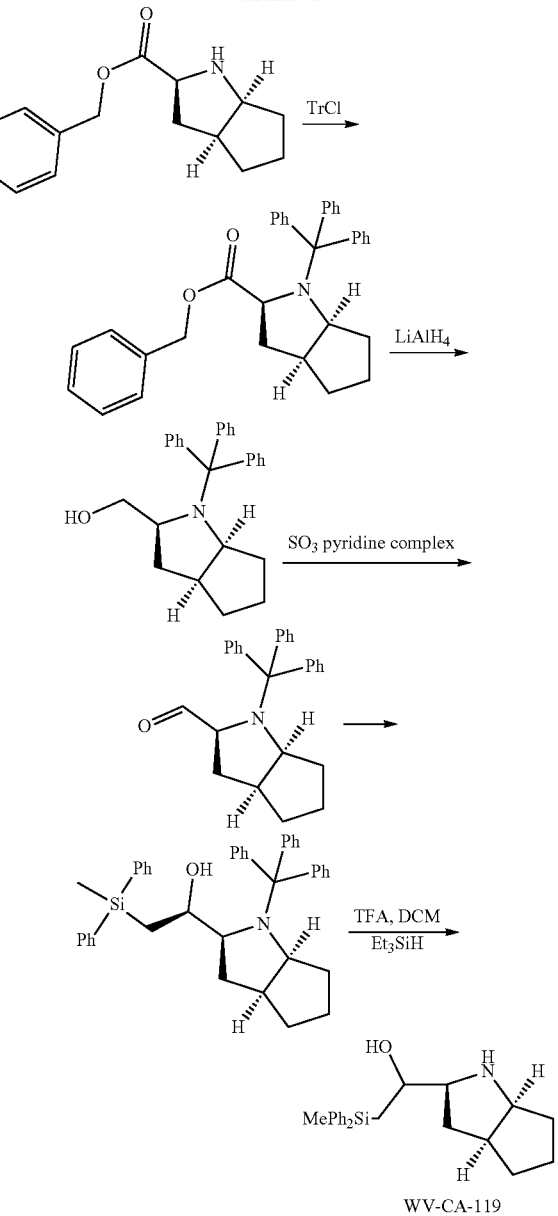

Step 1: benzyl (2S,3aS,6aS)-1-trityloctahydrocyclopenta[b]pyrrole-2-carboxylate

To a solution of (2S,3aS,6aS)-benzyl octahydrocyclopenta[b]pyrrole-2-carboxylate HCl salt (6.43 g, 22.82 mmol) and trimethylamine (12.72 ml, 91 mmol) in CHCl₃ (110 mL) at 0° C. was added (chloromethanetriyl)tribenzene (6.36 g, 22.82 mmol). The reaction mixture was stirred at room temperature for 3 hours. LC-MS and TLC showed starting material was disappeared. The reaction was quenched by saturated sodium bicarbonate, organic layer and water layer was separated, extracted with EtOAC, combined the organic layers, dried over sodium sulfate, concentrated to give benzyl (2S,3aS,6aS)-1-trityloctahydrocyclopenta[b]pyrrole-2-carboxylate as a white solid (11.50 g, 100%).

Step 2: ((2S,3aS,6aS)-1-trityloctahydrocyclopenta[b]pyrrol-2-yl)methanol

To a solution of (2S,3aS,6aS)-benzyl 1-trityloctahydrocyclopenta[b]pyrrole-2-carboxylate (8.0 g, 16.41 mmol) in THF (30 mL) at 0° C. was added LiAlH₄ (2.0 M in THF, 8.2 ml, 16.41 mmol). The reaction mixture was stirred at room temperature for overnight. The reaction was quenched by Na₂SO₄·H2O salt, filtered, and washed with EtOAc. Solvent was evaporated to give a residue which was purified by ISCO (120 g gold column) eluting with hexane to 20% EtOAc in hexane to give ((2S,3aS,6aS)-1-trityloctahydrocyclopenta[b]pyrrol-2-yl)methanol (4.20 g, 67%) as a colorless oil. MS (ESI), 384.4 (M+H)+.

Step 3: (2S,3aS,6aS)-1-trityloctahydrocyclopenta[b]pyrrole-2-carbaldehyde

To a solution of ((2S,3aS,6aS)-1-trityloctahydrocyclopenta[b]pyrrol-2-yl)methanol (18.87 g, 49.2 mmol) in DCM (210 mL) and DMSO (70 mL) was added triethylamine (34.3 ml, 246 mmol) and sulfur trioxide pyridine (23.49 g, 148 mmol). The reaction mixture was stirred at room temperature for 5 hours and quenched the reaction with water (400 mL). The organic layer was separated, concentrated, dissolved in EtOAc, washed with water layer, back-extracted with EtOAc (4×), dried over Na₂SO₄, concentrated to give a residue which was purified by ISCO (220 g gold) eluting with hexane to 10% EtOAc in hexane to give (2S,3aS,6aS)-1-trityloctahydrocyclopenta[b]pyrrole-2-carbaldehyde (10.15 g, 54%) as a white solid.

Step 4: (S)-2-(methyldiphenylsilyl)-1-((2S,3aS,6aS)-1-trityloctahydrocyclopenta[b]pyrrol-2-yl)ethan-1-ol Magnesium (0.783 g, 32.2 mmol) was taken up in THF (60 mL), then a solution of (chloromethyl)(methyl)diphenylsilane (7.95 g, 32.2 mmol) in THF (10 mL) was added to the Mg suspension (activated with 1,2-dibromoethane), was added to the Mg suspension at 50-60° C. The reaction mixture was stirred at 65° C. for 3 hrs until Mg was disappeared. In a separate flask, (S)-1-tritylpyrrolidine-2-carbaldehyde (5.0 g, 14.64 mmol) was dissolved in THF (50 mL) at −78° C. To this solution, the Grignard was added at −78° C., stirred at −78° C. for 10 minutes, stirred at 0° C. for 1 hour, and then stirred at room temperature for overnight. LC-MS showed the desired product. The reaction mixture was quenched by saturated ammonium chloride, extracted with EtOAc (3×), dried over Na₂SO₄, and concentrated to give a yellow oil, which was purified by ISCO (120 gold column) eluting with hexane to 20% EtOAc in hexane to give (S)-2-(methyldiphenylsilyl)-1-((2S,3aS,6aS)-1-trityloctahydrocyclopenta[b]pyrrol-2-yl)ethan-1-ol as a white solid (6.97 g, 86%). MS (ESI), 554.3 (M+H)+.

Step 5: (S)-2-(methyldiphenylsilyl)-1-((2S,3aS,6aS)-octahydrocyclopenta[b]pyrrol-2-yl)ethan-1-ol (S)-2-(Methyldiphenylsilyl)-1-((2S,3aS,6aS)-1-trityloctahydrocyclopenta[b]pyrrol-2-yl)ethanol (2.80 g, 4.71 mmol) in DCM (15 mL) at 0° C. was added TFA (10 mL) and triethylsilane (6.02 ml, 37.7 mmol). The reaction mixture was stirred at 0° C. for 10 minutes and at room temperature for 30 minutes. Solvent was evaporated under reduced pressure, diluted with DCM, adjusted pH>12 using 1 N NaOH, extracted with DCM (5×), dried over Na₂SO₄. Solvent was concentrated under reduced pressure, which was purified by ISCO (12 g) eluting with mobile phase A (DCM) to 40% mobile phase B (2.5% TEA in MeOH) to give (S)-2-(methyldiphenylsilyl)-1-((2S,3aS,6aS)-octahydrocyclopenta[b]pyrrol-2-yl)ethan-1-ol as a colorless oil (0.859 g, 52%). MS (ESI), 352.4 (M+H)⁺.

Example 107. Synthesis of WV-CA-119-dA$^{bz}$

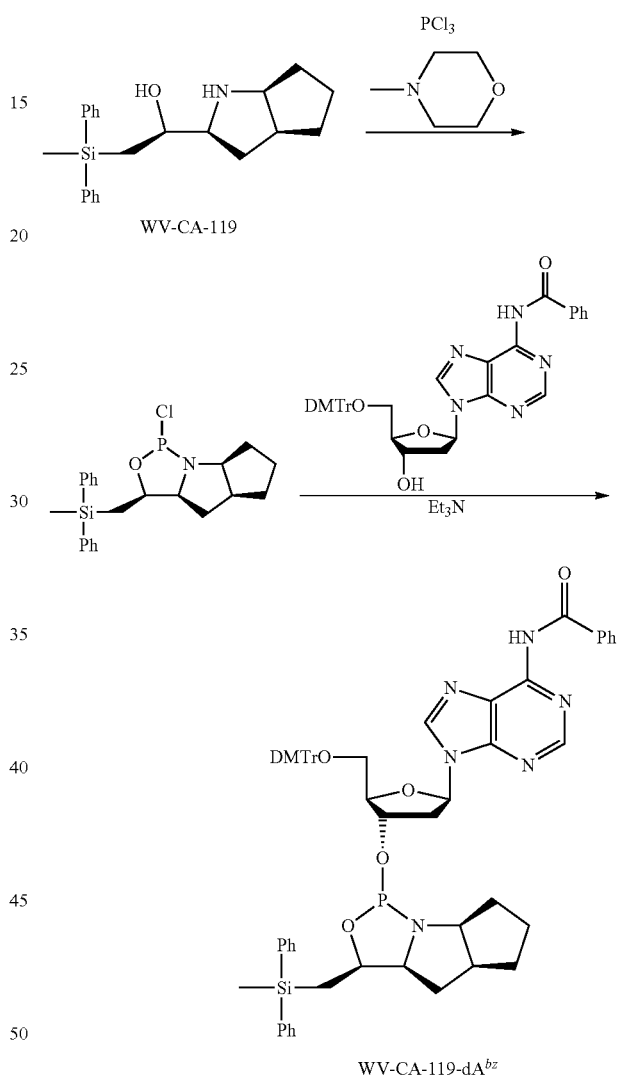

WV-CA-119-dA$^{bz}$

Using WV-CA-119 as starting material, the title compound (0.85 g, 58%) as a white solid was prepared analogously to WV-CA-008S-dC$^{iBu}$. ¹H NMR (600 MHz, CDCl₃) δ 8.97 (brs, 1H), 8.71 (s, 1H), 8.11 (s, 1H), 8.02 (d, J=7.2 Hz, 2H), 7.60 (t, J=7.5 Hz, 1H), 7.52 (t, J=7.8 Hz, 2H), 7.48-7.43 (m, 4H), 7.38 (d, J=7.2 Hz, 2H), 7.28-7.14 (m, 13H), 6.78-6.74 (m, 4H), 6.36 (t, J=6.6 Hz, 1H), 4.89-4.85 (m, 1H), 4.71 (dt, J=9.2, 5.4 Hz, 1H), 4.05-4.02 (m, 1H), 3.83-3.79 (m, 1H), 3.75 (s, 3H), 3.74 (s, 3H), 3.33-3.28 (m, 2H), 3.24 (dd, J=10.2, 4.2 Hz, 1H), 2.61-2.52 (m, 2H), 2.37-2.32 (m, 1H), 2.28-2.22 (m, 1H), 1.62-1.45 (m, 7H), 1.37 (dd, J=15.0, 5.4 Hz, 1H), 0.93-0.86 (m, 1H), 0.62 (s, 3H). ³¹P NMR (243 MHz, CDCl₃) δ 134.52.

Example 108. Synthesis of WV-CA-122-dCAc

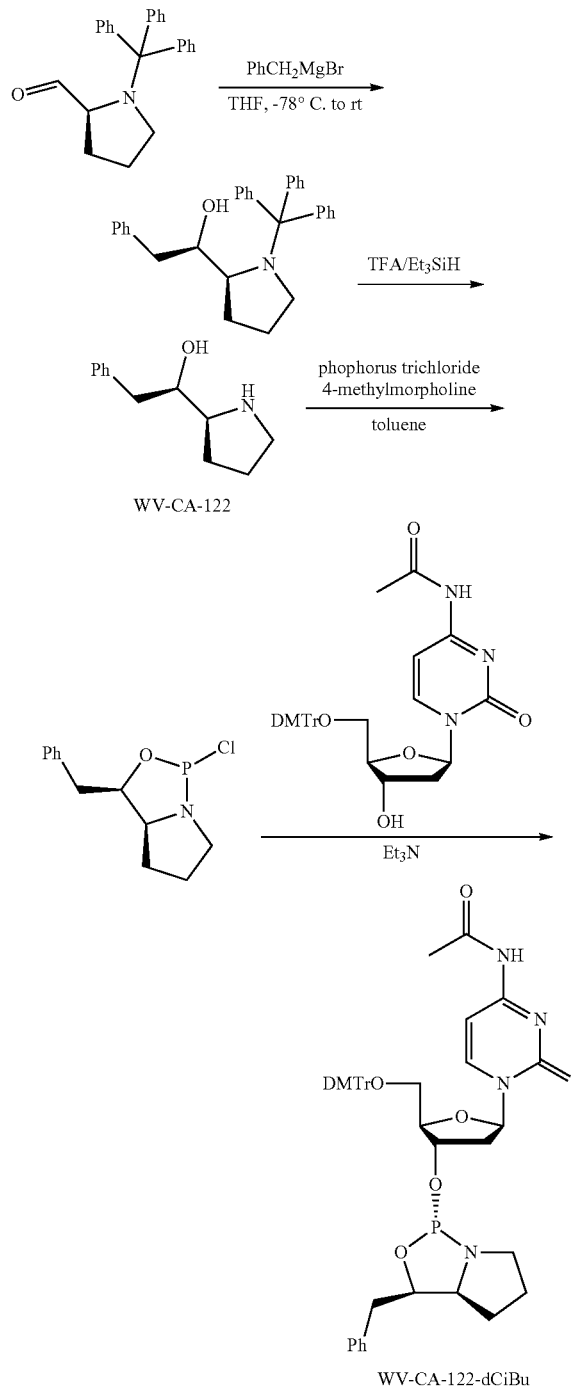

Step 1: (R)-2-phenyl-1-((S)-1-tritylpyrrolidin-2-yl)ethan-1-ol

To a solution of benzyl magnesium chloride (2.0 in THF) (58.5 mL, 117 mmol) in THF (50 mL) at −78° C. was added a solution of (S)-1-tritylpyrrolidine-2-carbaldehyde (10 g, 29.3 mmol) in THF (40 mL). The reaction mixture was stirred at −78° C. for 4 hr and slowly warmed to room temperature for overnight. The reaction was quenched by sat. ammonium chloride, extracted with EtOAc (3×), dried over anhydrous $Na_2SO_4$. Solvent was evaporated to give (R)-2-phenyl-1-((S)-1-tritylpyrrolidin-2-yl)ethan-1-ol (15.84 g) as a colorless oil. Without further purification, directly use for next step. MS (ESI), 434.7 (M+H)+.

Step 2: (R)-2-phenyl-1-((S)-pyrrolidin-2-yl)ethan-1-ol (WV-CA-122)

To a solution of (R)-2-phenyl-1-((S)-1-tritylpyrrolidin-2-yl)ethanol (12.70 g, 29.3 mmol) in DCM (50 mL) at 0° C. was added TFA (20 mL) followed by triethylsilane (23.40 mL, 147 mmol). The reaction mixture was stirred at room temperature for 30 minutes. LC-MS showed the reaction was complete. Solvent was evaporated under reduced pressure, adjusted pH>12 by 1 N NaOH (100 mL), back-extracted with DCM (5×) and CHCl3 (1×), concentrated to give a residue which was purified by ISCO (40 g gold column) eluting with mobile phase A to 50% mobile phase B (mobile phase A: DCM; mobile phase B: 2% TEA in methanol to give WV-CA-122 as a yellowish solid (4.84 g, 86%). $^1$H NMR (400 MHz, Chloroform-d) δ 7.34-7.17 (m, 5H), 3.86 (ddd, J=8.0, 5.8, 3.7 Hz, 1H), 3.09 (h, J=3.7 Hz, 1H), 3.03-2.93 (m, 1H), 2.93-2.67 (m, 3H), 2.36 (brs, 2H), 1.85-1.66 (m, 4H). MS (ESI), 192.2 (M+H)+.

Step 3 & 4: N-(1-((2R,4S,5R)-4-(((1R,3R,3aS)-3-benzyltetrahydro-1H,3H-pyrrolo[1,2-c][1,3,2]oxazaphosphol-1-yl)oxy)-5-((bis(4-methoxyphenyl)(phenyl)methoxy)methyl)tetrahydrofuran-2-yl)-2-oxo-1,2-dihydropyrimidin-4-yl)acetamide (WV-CA-122-dCAc)

(R)-2-phenyl-1-((S)-pyrrolidin-2-yl)ethanol (1.5 g, 7.84 mmol) was dried by azeotropic distillation with toluene (3×10 mL). A solution of this dried (R)-2-phenyl-1-((S)-pyrrolidin-2-yl)ethanol (1.5 g, 7.84 mmol) and 4-methylmorpholine (1.724 mL, 15.68 mmol) in ether (5 mL) was added to an ice-cold solution of trichlorophosphine (0.684 mL, 7.84 mmol) in ether (5 mL). Reaction mixture was warmed to room temperature, stirred for 40 minutes, and then filtered under argon. Solvent removal under argon afforded (3R,3aS)-3-benzyl-1-chlorohexahydropyrrolo[1,2-c][1,3,2]oxazaphosphole as an oil which was used for the next step directly. The nucleoside N-(1-((2R,4S,5R)-5-((bis(4-methoxyphenyl)(phenyl)methoxy)methyl)-4-hydroxytetrahydrofuran-2-yl)-2-oxo-1,2-dihydropyrimidin-4-yl)acetamide (2.99 g, 5.23 mmol) was dried by azeotropic distillation first by pyridine (20 mL×1), then by toluene (15 mL×3) and dried under vacuum for 24 hr. This dried compound was dissolved in dry THF (20 mL) followed by the addition of triethylamine (5.10 mL, 36.6 mmol) then cooled to −78° C. A THF solution (20 mL) of the above crude product (3R,3aS)-3-benzyl-1-chlorohexahydropyrrolo[1,2-c][1,3,2]oxazaphosphole was added dropwise over 10 minutes, then removed cooler bath and gradually warmed to room temperature and stirred at room temperature for 1.5 hr, TLC indicated a good conversion of SM to product. The mixture at −30° C. was added sat. $NaHCO_3$ (50 mL), 1 N $Na_2CO_3$ (10 mL), and EtOAc (150 mL). The organic layer was separated, washed with sat. $NaHCO_3$ (2×). The combined water layer was re-extracted with EtOAc (100 mL), washed with sat. $NaHCO_3$. The EtOAc extract was dried over anhydrous $Na_2SO_4$, filtered and dried under rotary evaporation under 25° C. The crude product was re-dissolved in 2.5% TEA in DCM (10 mL) loaded onto 30 g silica gel eluting with 70% EtOAc with 2.5% TEA in hexane to 80% EtOAc in hexane with 2.5% TEA to give the title product as a white solid (1.0 g, 24%). $^1$H NMR (400 MHz, Chloroform-d) δ 9.89 (s, 1H), 8.20 (d, J=7.5 Hz, 1H), 7.43-7.31 (m, 2H), 7.34-7.19 (m, 7H), 7.16 (dq, J=7.1, 3.9 Hz, 5H), 7.05 (d, J=7.5 Hz, 1H), 6.88-6.79 (m, 4H), 6.21 (t, J=5.8 Hz, 1H), 4.88-4.68 (m, 2H), 3.96 (d, J=4.1 Hz, 1H), 3.79 (s, 6H), 3.62-3.42 (m, 2H), 3.31 (d, J=3.0 Hz, 2H), 3.16 (tdd, J=10.6, 8.7, 4.0 Hz, 1H), 3.00 (ddd, J=31.8, 13.6, 7.4 Hz, 2H), 2.84 (dd, J=14.1, 5.8 Hz, 1H), 2.70 (dt, J=13.9, 5.8 Hz, 1H), 2.48 (q, J=7.1 Hz, 1H), 2.24 (s, 3H), 2.11-1.87 (m, 1H), 1.71-1.57 (m, 1H), 1.42-1.19 (m, 1H), 1.02 (d, J=6.6 Hz, 6H). $^{31}$P NMR (202 MHz, CD$_3$CN) δ 157.19.

Example 109. Synthesis of WV-CA-123

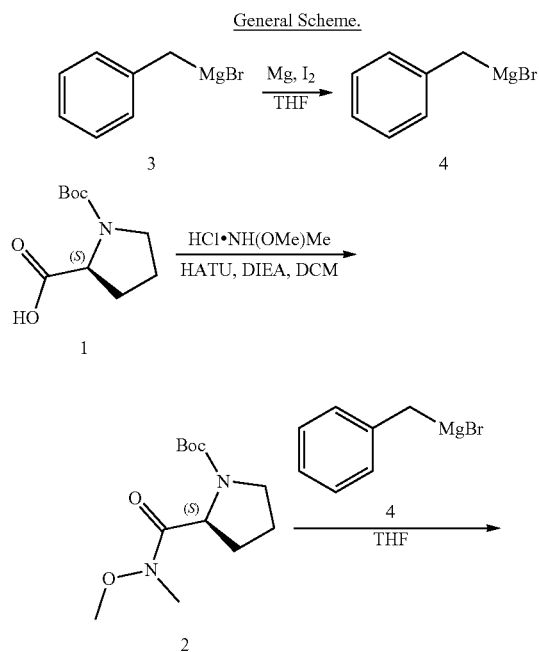

General Scheme.

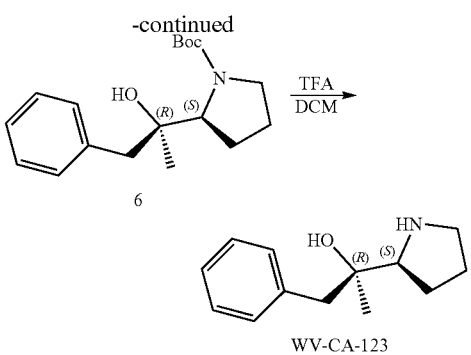

1. Preparation of Compound 2.

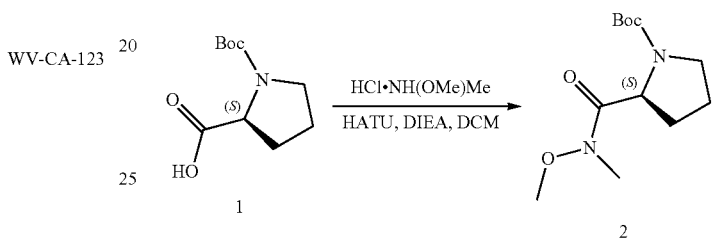

To a solution of compound 1 (150.00 g, 696.86 mmol), N-methoxymethanamine hydrochloride (498.92 mg, 5.12 mmol) and HATU (291.47 g, 766.55 mmol) in DCM (1.50 L) was slowly added DIEA (180.13 g, 1.39 mol, 243.42 mL) and stirred at 20° C. for 12 hr. TLC showed the starting material was consumed. H$_2$O (100 mL) was added and extracted with DCM (1 L*3). The combined organic was washed with brine (1 L), dried over Na$_2$SO$_4$, filtered and concentrated to get the crude. The residue was purified by silica gel chromatography (Petroleum ether:Ethyl acetate=30:1 to 10:1) to give compound 2 (170.00 g, 47.22% yield) as a colorless oil and 300 g crude. The crude was purified by column chromatography (SiO$_2$, Petroleum ether/Ethyl acetate=50/1 to 1:2) to give compound 2 (186.00 g) as a yellow oil. $^1$H NMR (400 MHz, CHLOROFORM-d) δ=4.69-4.41 (m, 1H), 3.77-3.61 (m, 3H), 3.56-3.26 (m, 3H), 3.11 (s, 3H), 2.20~2.01 (m, 1H), 1.97-1.70 (m, 3H), 1.35 (d, J=17.9 Hz, 8H), 1.44-1.28 (m, 1H). TLC (Petroleum ether: Ethyl acetate=1:1) R$_f$=0.43.

2. Preparation of Compound 4.

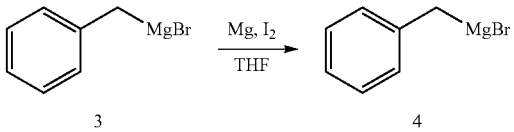

To a suspension of Mg (39.40 g, 1.62 mol) and a grain of I$_2$ in THF (225 mL) was added compound 3 (231.00 g, 1.35 mol, 160.42 mL) in THF (1125 mL) at 15~60° C. during addition for 5 hr. The mixture was stirred at 25° C. for 1 hr. Mg was remained a little. The reaction was completed. The Grignard reagent in THF was used directly in next step.

3. Preparation of Compound 5.

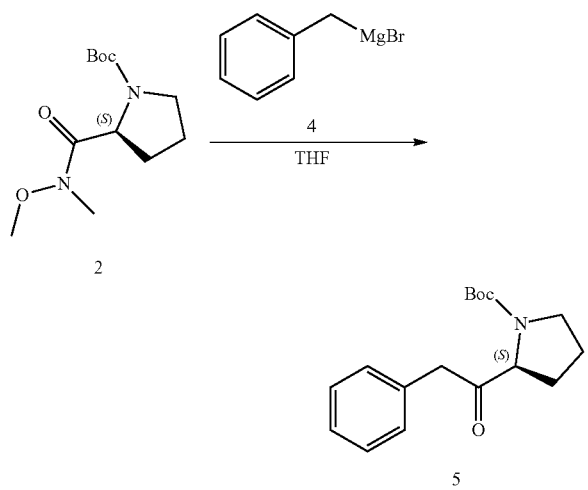

The solution of compound 2 (70.00 g, 270.99 mmol, 66.04 mL) in THF (200 mL) was added to the solution of compound 4 (1 M, 1.35 L) at −5~5° C. for 1.5 hr under $N_2$. Then the reaction was gradually warmed to 25° C. for 0.5 hr. The reaction was stirred at 15~25° C. for 16.5 hr. TLC showed the starting material was consumed. The reaction mixture was quenched by addition $NH_4Cl$ (1000 mL) at 0° C., and then diluted with EtOAc (1000 mL) and extracted with EtOAc (1000 mL*3). The combined organic layers dried over $Na_2SO_4$, filtered, and concentrated under reduced pressure to give a residue. The residue was purified by column chromatography ($SiO_2$, Petroleum ether/Ethyl acetate=100/1 to 5:1) to give compound 5 (44.00 g, 56.11% yield) as a light yellow solid. $^1$H NMR (400 MHz, CHLOROFORM-d) δ=7.41-7.15 (m, 5H), 4.46-4.27 (m, 1H), 3.89-3.71 (m, 2H), 3.61-3.32 (m, 2H), 2.15-1.88 (m, 1H), 1.81-1.74 (m, 3H), 1.52-1.35 (m, 9H). TLC (Petroleum ether:Ethyl acetate=3:1) $R_f$=0.43.

4. Preparation of Compound 6.

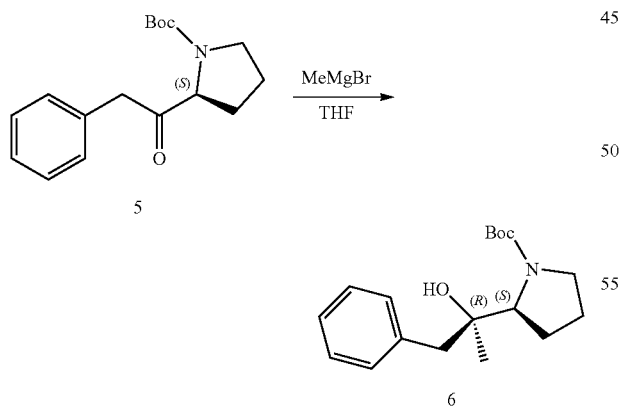

To a solution of Compound 5 (44.00 g, 152.05 mmol) in THF (150.00 mL) was added MeMgBr (3 M, 253.42 mL) at −5-0° C. over 1.5 hr. The mixture was stirred at 25° C. for 70.5 hr. TLC and LCMS showed the starting material was partly remained and MS with desired compound was detected. The reaction mixture was slowly added in ice $NH_4Cl$ (500 mL) at 0° C., and then diluted with EtOAc (500 mL) and extracted with EtOAc (500 mL*3). The combined organic layers dried over $Na_2SO_4$, filtered, and concentrated under reduced pressure to give a residue. The residue was purified by column chromatography (Petroleum ether:Ethyl acetate=50:1 to 1:1) to give recovered compound 5 (24.00 g, crude) was obtained as a yellow oil. To a solution of compound 5 (24.00 g, 82.94 mmol) in THF (170.00 mL) was added MeMgBr (3 M, 138.23 mL) at −5-0° C. over 1 hr. The mixture was stirred at 25° C. for 71 hr. TLC showed compound 5 was little remained and new spot was detected. The reaction mixture was slowly added in ice $NH_4Cl$ (300 mL) at 0° C., and then diluted with EtOAc (500 mL) and extracted with EtOAc (500 mL*3). The combined organic layers were dried over $Na_2SO_4$, filtered, and concentrated under reduced pressure to give a residue. The residue was purified by column chromatography (Petroleum ether:Ethyl acetate=50:1 to 1:1) to give 15 g crude. Then 15 g crude was combined with 10 g another part of crude. A solution of 25 g crude in Petroleum ether (90 mL) and Ethyl acetate (3 mL) were refluxed at 100° C. for 0.5 h and solid was all disappeared, then the mixture was cooled to 20° C. and waiting solid was appeared, filtered to give 6 g product. The mother liquid was concentrated to give crude (19 g). A solution of 19 g crude in Petroleum ether (90 mL) and Ethyl acetate (3 mL) were refluxed at 100° C. for 0.5 hr and solid was all disappeared, then the mixture was cooled to 20° C. and waiting solid was appeared, filtered to give 5 g product. The mother liquid was concentrated to give crude (13 g). The crude was purified by column chromatography (Petroleum ether:Ethyl acetate=50:1 to 1:1) to give 11 g crude. A solution of 11 g crude in Petroleum ether (50 mL) and Ethyl acetate (1 mL) were refluxed at 100° C. for 0.5 hr and solid all disappeared, then the mixture was cooled to 20° C. and waiting solid was appeared, filtered to give 4 g product. Compound 6 (9.20 g, 36.32% yield) (yield from conversion rate) was obtained as a white solid. 15 g product totally was obtained as a white solid. $^1$H NMR (400 MHz, CHLOROFORM-d) δ=7.29-7.18 (m, 5H), 5.86 (br s, 1H), 3.98 (t, J=7.4 Hz, 1H), 3.72 (br s, 1H), 3.24-3.16 (m, 1H), 2.76 (br d, J=13.2 Hz, 1H), 2.51 (br d, J=13.0 Hz, 1H), 2.10 (br s, 1H), 1.88 (br s, 1H), 1.73 (br s, 2H), 1.64-1.46 (m, 10H), 1.19-0.94 (m, 4H). TLC (Petroleum ether:Ethyl acetate=3:1, two times) $R_f$=0.43.

5. Preparation of Compound WV-CA-123.

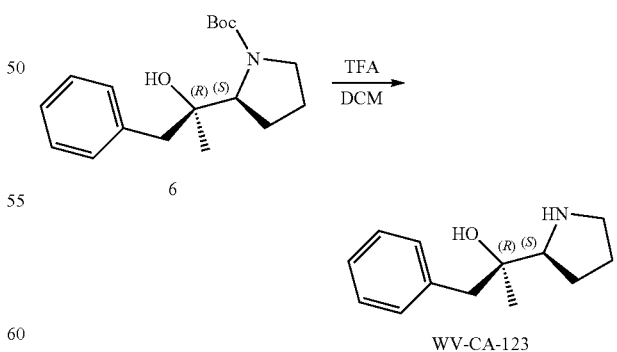

To a solution of compound 6 (15.00 g, 49.11 mmol) in DCM (100 mL), and then added the mixture DCM/TFA (100 mL/60 mL). The mixture was stirred at 20° C. for 2 hr. TLC showed the starting material was consumed. The mixture was concentrated under reduced pressure to give a residue.

The residue was dissolve by CH₂Cl₂ (20 mL) and added Na₂CO₃ (aq.) and KOH (2 M) until over pH ~11. Then the mixture was extracted with CH₂Cl₂ (100 mL*3) and concentrated under reduced pressure to give a product. Compound WV-CA-123 (8.60 g, 85.30% yield) was obtained as yellow oil. $^1$H NMR (400 MHz, CHLOROFORM-d) δ=7.27-7.11 (m, 5H), 3.03-2.92 (m, 1H), 2.90-2.84 (m, 2H), 2.82-2.77 (m, 1H), 2.54 (d, J=13.5 Hz, 1H), 1.85-1.59 (m, 4H), 0.96 (s, 3H). $^{13}$C NMR (101 MHz, CHLOROFORM-d) δ=137.64, 130.29, 127.72, 125.90, 72.59, 65.77, 46.69, 44.33, 26.09, 25.58, 25.06. LCMS: (M+H$^+$): 206.1, 97.10% purity. HPLC purity=98.97%. Chiral SFC purity=100.0%. TLC (Petroleum ether:Ethyl acetate=3:1) $R_f$=0.

Example 110. Synthesis of WV-CA-123-dCiBu

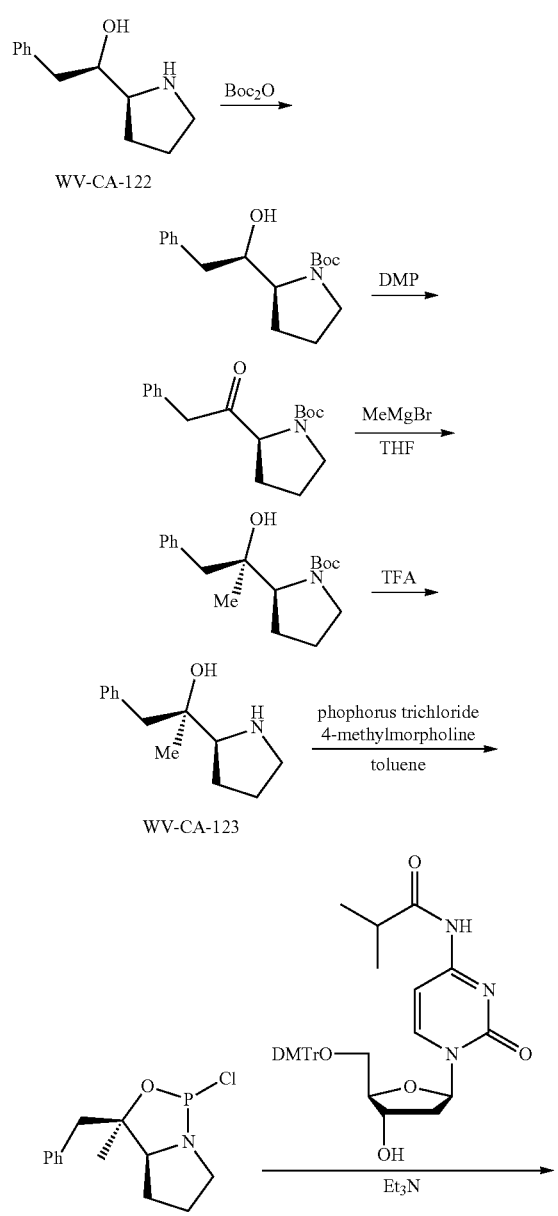

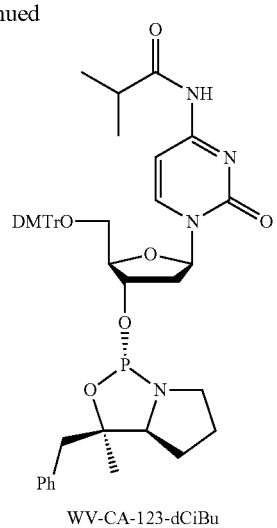

Step 1: tert-butyl (S)-2-((R)-1-hydroxy-2-phenylethyl)pyrrolidine-1-carboxylate

To a solution of 2-phenyl-1-((S)-pyrrolidin-2-yl)ethanol (2.22 g, 11.61 mmol) in DCM (30 mL) and methanol (30 mL) at 0° C. was added di-tert-butyl dicarbonate (2.66 g, 12.19 mmol) and TEA (4.04 mL, 29.0 mmol). The reaction mixture was stirred at room temperature for 2 hr. LC-MS showed the reaction was complete and very clean. Solvents were evaporated, diluted with DCM, washed with sat. NaHCO₃, dried over Na₂SO₄, and concentrated to give tert-butyl (S)-2-((R)-1-hydroxy-2-phenylethyl)pyrrolidine-1-carboxylate as a yellowish solid (3.50 g, 100%). Without purification, directly use for next step. MS (ESI), 314.3 (M+Na)$^+$.

Step 2: tert-butyl (S)-2-(2-phenylacetyl)pyrrolidine-1-carboxylate

To a solution of (2S)-tert-butyl 2-(1-hydroxy-2-phenylethyl)pyrrolidine-1-carboxylate (3.50 g, 12.01 mmol) in DCM (50 mL) was added a drop of water and Dess-Martin Periodinane (7.64 g, 18.02 mmol). The reaction mixture was stirred at room temperature for 2 hr. TLC showed the reaction was complete, diluted with DCM, washed with sat. NaHCO₃ and sodium thiosulfate (4:1), back extracted with DCM (2×), dried over Na₂SO₄, and concentrated to give a residue, which was purified by ISCO (40 g silica gel cartridge) eluting with hexane to 30% EtOAc in hexane (product come out at 20% EtOAc in hexane) to give tert-butyl (S)-2-(2-phenylacetyl)pyrrolidine-1-carboxylate as a colorless oil (3.03 g, 87%). MS (ESI), 312.3 (M+Na)$^+$.

Step 3: tert-butyl (S)-2-(2-phenylacetyl)pyrrolidine-1-carboxylate

To a solution of MeMgI in ether (3.0 M) (26.33 mL, 157 mmol) in ether (40 mL) at −0° C. was added a (S)-tert-butyl 2-(2-phenylacetyl)pyrrolidine-1-carboxylate (3.03 g, 10.47 mmol) in ether (15 mL). The reaction mixture was stirred at 0° C. for 10 minutes. Not all materials were dissolved, and 40 mL ether was added. The suspension was stirred at 0° C. for 4 hr, then at room temperature for overnight. The reaction mixture was quenched by sat. ammonium chloride, extracted with EtOAc (3×), dried over sodium sulfate, and concentrated to give a colorless oil. LC-MS showed the desired product (7.88 min, another isomer 8.10 min), and starting material (20%, 7.08 minutes). The crude product was purified by ISCO (80 g gold column) eluting with hexane to 20% EtOAc in hexane to give tert-butyl (S)-2-(2-phenylacetyl)pyrrolidine-1-carboxylate as a white solid (1.673 g, 52.3%). $^1$H NMR (400 MHz, Chloroform-d) δ 7.25 (s, 3H), 7.29-7.16 (m, 2H), 5.93 (s, 1H), 3.98 (t, J=7.4 Hz, 1H), 3.72 (brs, 1H), 3.26-3.14 (m, 1H), 2.75 (d, J=13.3 Hz, 1H), 2.51 (d, J=13.3 Hz, 1H), 2.11 (brs, 2H), 1.88 (brs, 2H), 1.59 (s, 3H), 1.49 (s, 9H); MS (ESI), 328.3 (M+Na)$^+$.

Step 4: (R)-1-phenyl-2-((S)-pyrrolidin-2-yl)propan-2-ol (WV-CA-123)

To a solution of (S)-tert-butyl 2-((R)-2-hydroxy-1-phenylpropan-2-yl)pyrrolidine-1-carboxylate (1.667 g, 5.46 mmol) in DCM (20 mL) was added TFA (7 mL). The reaction mixture was stirred at room temperature for 2 hr. TLC showed starting material was disappeared. Solvent was evaporated under reduced pressure to give a yellow oil, which was dissolved in DCM, adjusted pH>12 by 1 N NaOH, extracted with DCM (5×), dried over Na$_2$SO$_4$, and concentrated to give WV-CA-123 as a yellow oil (1.142 g, 100%). $^1$H NMR (400 MHz, Chloroform-d) δ 7.34-7.17 (m, 5H), 3.11-3.00 (m, 1H), 2.95 (td, J=5.4, 4.6, 2.0 Hz, 2H), 2.87 (d, J=13.3 Hz, 1H), 2.62 (d, J=13.3 Hz, 1H), 1.90-1.70 (m, 4H), 1.04 (s, 3H); MS (ESI), 206.3 (M+H)$^+$.

Step 5 & 6: N-(1-((2R,4S,5R)-4-(((1S,3R,3aS)-3-benzyl-3-methyltetrahydro-1H,3H-pyrrolo[1,2-c][1,3,2]oxazaphosphol-1-yl)oxy)-5-((bis(4-methoxyphenyl)(phenyl)methoxy)methyl)tetrahydrofuran-2-yl)-2-oxo-1,2-dihydropyrimidin-4-yl)isobutyramide (WV-CA-123-dCiBu)

Using WV-CA-123 as starting material, the title compound (1.38 g, 45.7%) as a white solid was prepared analogously to WV-CA-118-dCiBu (step 7 & 8). $^1$H NMR (500 MHz, Chloroform-d) δ 8.38 (s, 1H), 8.20 (d, J=7.5 Hz, 1H), 7.37 (d, J=7.1 Hz, 2H), 7.32-7.17 (m, 12H), 7.06 (d, J=7.5 Hz, 1H), 6.86-6.80 (m, 4H), 6.22 (t, J=5.8 Hz, 1H), 4.83-4.74 (m, 1H), 3.80 (s, 6H), 3.54 (dtd, J=10.4, 6.0, 5.2, 2.8 Hz, 2H), 3.45-3.35 (m, 2H), 3.04 (dq, J=10.2, 7.1 Hz, 1H), 2.82 (d, J=13.5 Hz, 1H), 2.69 (dt, J=13.8, 5.8 Hz, 1H), 2.63-2.50 (m, 2H), 2.23 (dt, J=13.8, 6.0 Hz, 1H), 1.84 (ddt, J=37.3, 18.9, 6.4 Hz, 2H), 1.65-1.16 (m, 12H). $^{31}$P NMR (202 MHz, CDCl$_3$) δ 153.76.

Example 111. Synthesis of WV-CA-124 and WV-CA-124-dCiBu

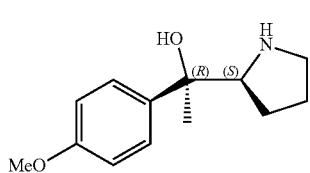

WV-CA-124

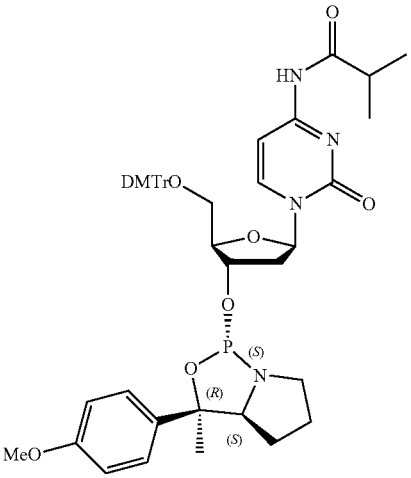

WV-CA-124-dCiBu

General Scheme.

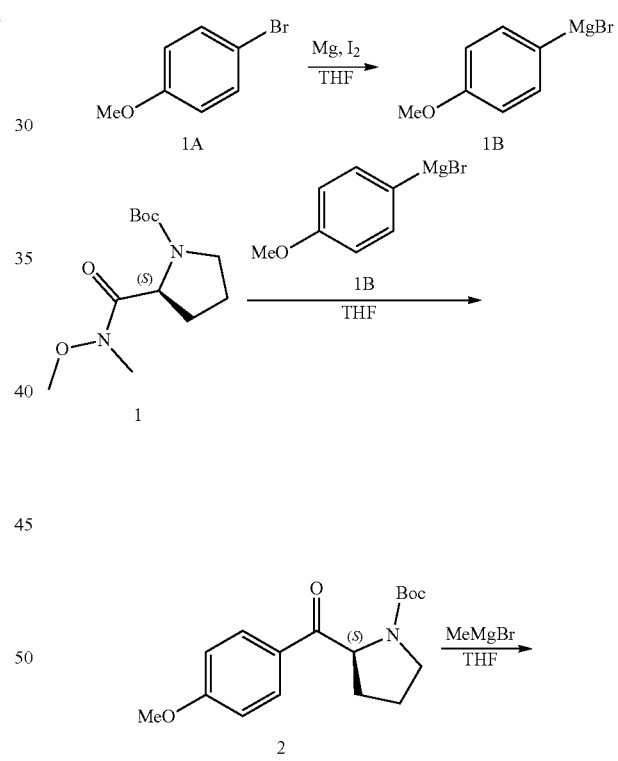

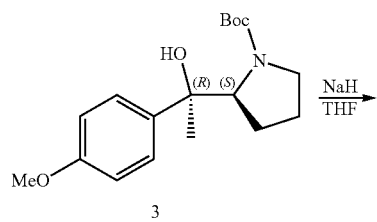

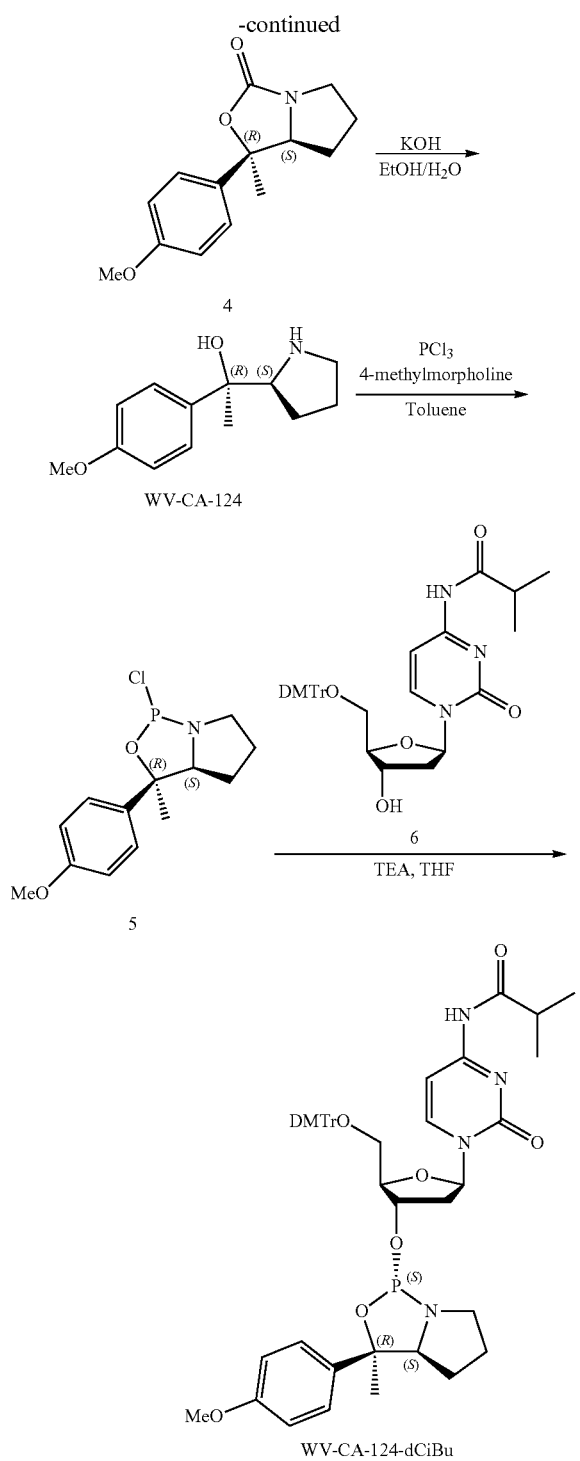

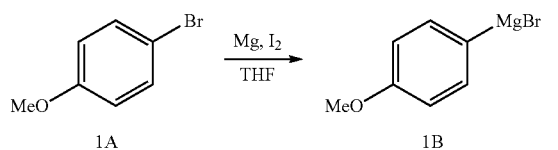

1. Preparation of Compound 1B.

A mixture of Mg (13.49 g, 554.99 mmol) and $I_2$ (50.00 mg, 197.00 μmol) in THF (260 mL) was degassed and purged with $N_2$ for 3 times, and then to the mixture was added compound 1A (86.50 g, 462.49 mmol) in THF (200 mL). The mixture was stirred at 25° C. for 1 hr under $N_2$ atmosphere. The color of the mixture changed. The crude product compound 1B was used into the next step without further purification (97.74 g, crude).

2. Preparation of Compound 2.

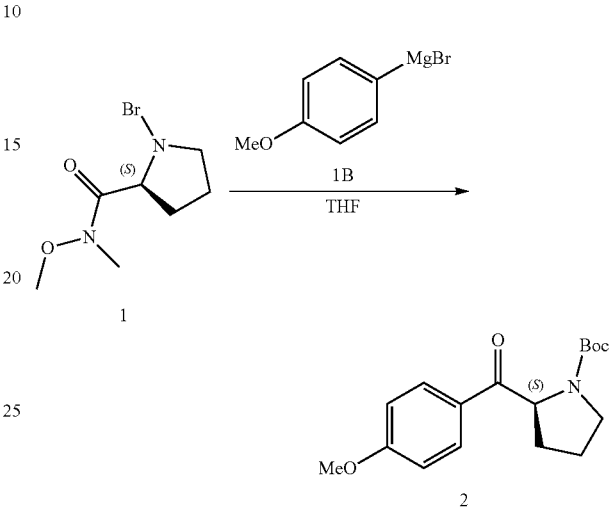

A solution of compound 1B (98.18 g, 464.55 mmol) in THF was cooled to 0° C., and then to the mixture was added compound 1 (40.00 g, 154.85 mmol) in THF (150.00 mL). The mixture was stirred at 25° C. for 2 hr under $N_2$ atmosphere. TLC indicated compound 1 was consumed completely and one new spot formed. The reaction was quenched with sat. $NH_4Cl$ (200 mL), and extracted with EtOAc (100 mL*3). The combined organic phase was washed with brine (200 mL*1), dried over anhydrous $Na_2SO_4$, filtered and concentrated in vacuo. The residue was purified by column chromatography ($SiO_2$, Petroleum ether/Ethyl acetate=100:1 to 20:1). Compound 2 (28.00 g, crude) was obtained as a white solid. $^1$H NMR (400 MHz, $CDCl_3$): δ=8.00-7.88 (m, 2H), 6.99-6.89 (m, 2H), 5.35-5.09 (m, 1H), 3.90-3.84 (m, 3H), 3.72-3.38 (m, 2H), 2.36-1.80 (m, 4H), 1.52-1.13 (m, 9H). TLC (Petroleum ether:Ethyl acetate=1:1) $R_f$=0.43.

3. Preparation of Compound 3.

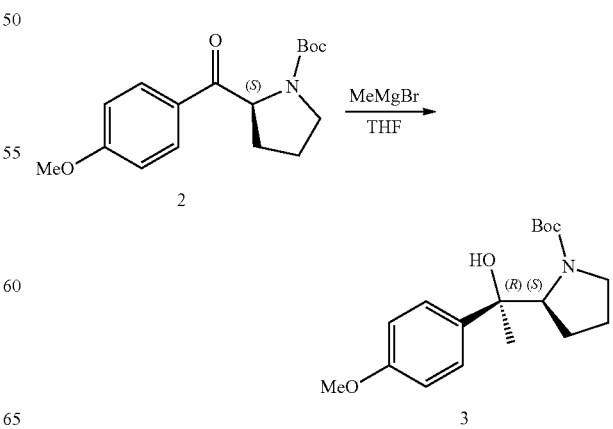

A mixture of compound 2 (21.00 g, 68.77 mmol) in THF (120.00 mL) was degassed and purged with N₂ for 3 times, and then the mixture was cooled to 0° C., and then to the mixture was added MeMgBr (1 M, 137.54 mL). The mixture was stirred at 25° C. for 2 hr under N₂ atmosphere. TLC indicated compound 2 was consumed completely, and one new spot formed. The reaction was quenched with sat. NH₄Cl (500 mL), and then extracted with EtOAc (150 mL*3). The combined organic phase was washed with brine (200 mL*1), dried over anhydrous Na₂SO₄, filtered and concentrated in vacuo. The residue was purified by column chromatography (SiO₂, Petroleum ether/Ethyl acetate=20/1 to 1:0). Compound 3 was obtained as a white solid (18.00 g, 81.44%). ¹H NMR (400 MHz, CDCl₃): δ=7.36-7.31 (m, 2H), 6.83 (d, J=8.82 Hz, 2H), 6.22 (br s, 1H), 4.16 (dd, J=8.49, 4.74 Hz, 1H), 3.87-3.75 (m, 3H), 3.31 (br s, 1H), 2.52 (br s, 1H), 1.95 (br s, 1H), 1.73-1.62 (m, 2H), 1.57 (s, 3H), 1.51 (s, 9H), 1.03 (br s, 1H). TLC (Petroleum ether: Ethyl acetate=1:1) R$_f$=0.43.

4. Preparation of Compound 4.

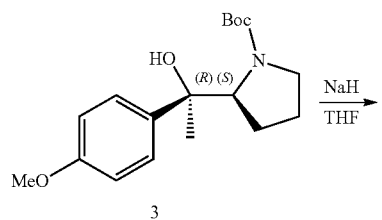

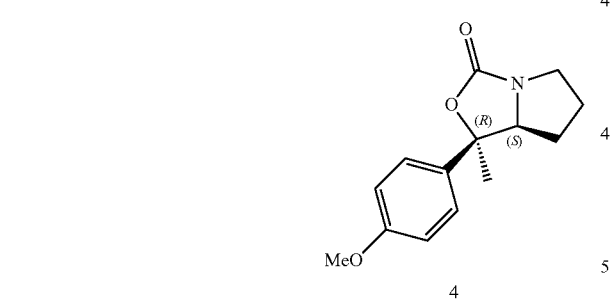

A mixture of compound 3 (17.00 g, 52.89 mmol) in THF (50.00 mL) was degassed and purged with N₂ for 3 times, and then the mixture was cooled to 0° C., and added NaH (10.58 g, 264.45 mmol). The mixture was stirred at 25° C. for 2 hr under N₂ atmosphere. TLC indicated compound 3 was consumed completely and one new spot formed. The reaction was quenched with sat. NH₄Cl (100 mL), and then extracted with EtOAc (50 mL*3). The combined organic phase was washed with brine (100 mL*1), dried over anhydrous Na₂SO₄, filtered and concentrated in vacuo. The residue was purified by re-crystallization from petroleum ether (50 mL). The crude product compound 4 was used into the next step without further purification (10.00 g, crude). TLC (Petroleum ether:Ethyl acetate=3:1) R$_f$=0.25.

5. Preparation of Compound WV-CA-124.

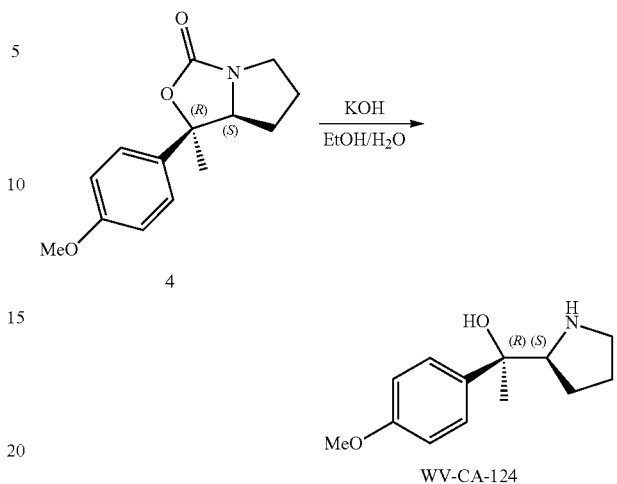

A mixture of compound 4 (10.00 g, 40.44 mmol) and KOH (16.00 g, 285.15 mmol) in EtOH (20.00 mL) and H₂O (20.00 mL) was stirred at 90° C. for 12 hr under N₂ atmosphere. TLC indicated compound 4 was consumed completely and one new spot formed. The solution was extracted with EtOAc (40 mL*3). The combined organic phase was washed with brine (50 mL*2), dried over anhydrous Na₂SO₄, filtered and concentrated in vacuum. Compound WV-CA-124 was obtained as a colorless oil (8.00 g, 89.40%). ¹H NMR (400 MHz, CDCl₃): δ=7.38-7.30 (m, 2H), 6.85 (d, J=8.16 Hz, 2H), 3.85-3.76 (m, 3H), 3.41 (t, J=7.94 Hz, 1H), 3.04-2.90 (m, 2H), 1.71-1.50 (m, 2H), 1.45 (d, J=0.88 Hz, 3H), 1.41-1.18 (m, 3H). ¹³C NMR (125.7 MHz, CDCl₃): δ=157.94, 138.64, 125.89, 113.22, 73.29, 66.89, 55.15, 47.25, 30.00, 26.75, 26.02. LCMS: (M+H+): 222.1. TLC (Dichloromethane/Methanol=10:1) R$_f$=0.04. HPLC purity=95.1%. SFC purity=100.0%.

6. Preparation of Compound 5.

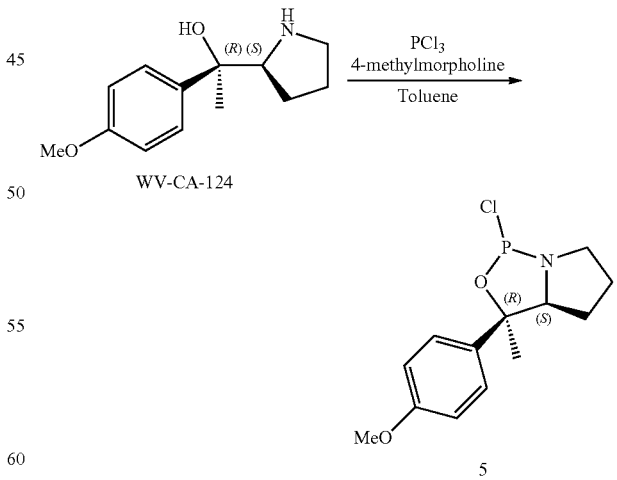

To a solution of PCl₃ (1.24 g, 9.04 mmol) in THF (50.00 mL) was added a solution of WV-CA-124 (2.00 g, 9.04 mmol) and 4-methylmorpholine (1.83 g, 18.08 mmol) in THF (50.00 mL) at 0° C. The mixture was stirred at 15~20° C. for 1.5 hr. The phosphoryl chloride was not suitable for detection and no monitoring. The resulting mixture was filtered (flushed with Ar) and concentrated to afford the crude product compound 5 as a colorless oil, which was used into the next step without further purification (2.40 g, crude).

7. Preparation of WV-CA-124-dCiBu.

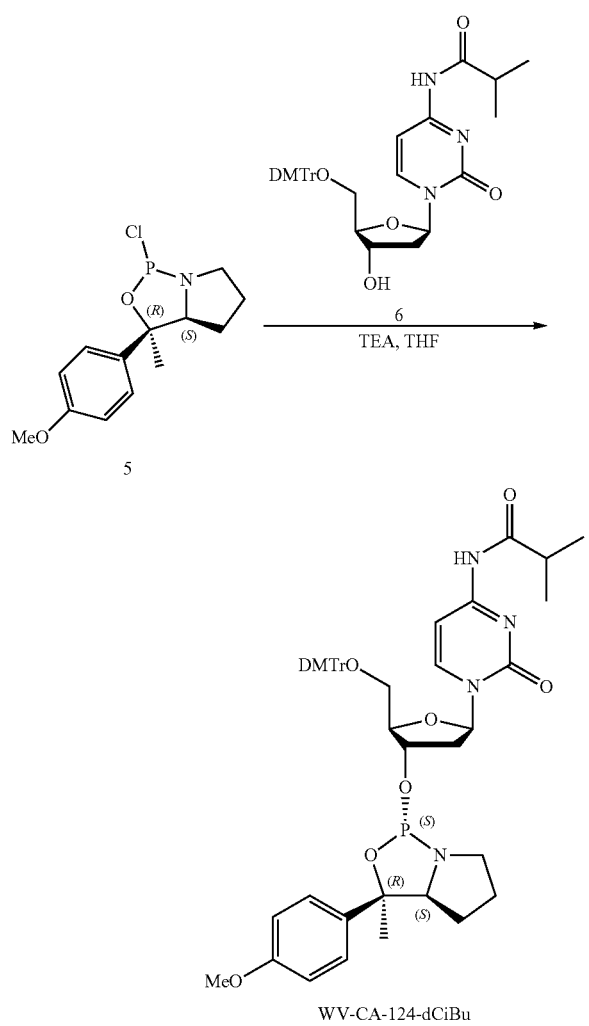

Compound 6 (3.30 g, 5.50 mmol) was dried by azeotropic distillation on a rotary evaporator with pyridine (50 mL) and toluene (50 mL*5). The dried compound 6 (3.30 g, 5.50 mmol) was dissolved in THF (30.00 mL), and then TEA (2.78 g, 27.50 mmol) was added. The mixture was cooled to −70° C. A solution of compound 5 (2.40 g, 8.41 mmol) in THF (20 mL) was added dropwise at −70° C., after the addition, the mixture was warmed to 23° C. for 1 hr. TLC (Ethyl acetate/Petroleum ether=3:1, 5% TEA, $R_f$=0.48) showed most of compound 6 disappeared. The resulting mixture was diluted with DCM (30 mL) at −10° C., washed with ice-cold sat. NaHCO$_3$ aq. (30 mL*). The aqueous layer was extracted with additional DCM (50 mL) at each washing stage. The organic layer was dried over anhydrous MgSO$_4$, filtered, and concentrated to afford a white foam (crude (5.7 g). The above crude material was purified on a CombiFlash instrument from Teledyne using a pre-treated silica gel column. A 40 g silica gel cartridge column was first pre-treated by eluting with 5 column volumes of methanol, before equilibration with 5 column volumes of 20% EtOAc/hexanes containing 5% Et$_3$N. 5.7 g of crude product was dissolved in a 2:1 volume:volume mixture of DCM:Petroleum ether containing 5% Et$_3$N, then loaded onto a 40 g silica column which had been equilibrated with 5 column volumes of 20% Hexanes/EtOAc containing 5% Et$_3$N. After loading the sample on the column, the purification process was run using the following gradient: 20 to 80% EtOAc/hexanes containing 5% Et$_3$N, then the residual solvent was removed to afford WV-CA-124-dCiBu as a white solid (2.10 g, 44.91%). All solvent was dried over anhydrous Na$_2$SO$_4$. $^1$H NMR (400 MHz, CHLOROFORM-d) δ=8.36 (br s, 1H), 8.29 (d, J=7.5 Hz, 1H), 7.41 (d, J=7.3 Hz, 2H), 7.34-7.15 (m, 9H), 7.07 (d, J=7.5 Hz, 1H), 6.88-6.79 (m, 6H), 6.26 (t, J=5.5 Hz, 1H), 4.94-4.85 (m, 1H), 4.25-4.18 (m, 1H), 3.82-3.78 (m, 3H), 3.75 (d, J=1.5 Hz, 6H), 3.74-3.69 (m, 1H), 3.51 (d, J=2.9 Hz, 2H), 3.46-3.36 (m, 1H), 3.07-2.96 (m, 1H), 2.82-2.73 (m, 1H), 2.64-2.53 (m, 1H), 2.40-2.30 (m, 1H), 1.73 (s, 3H), 1.65-1.33 (m, 3H), 1.21 (dd, J=4.2, 6.8 Hz, 6H), 1.01-0.94 (m, 1H). $^{13}$C NMR (125.7 MHz, CDCl$_3$): δ=176.83, 171.12, 162.34, 158.65, 158.55, 155.06, 144.62, 144.19, 135.83, 135.80, 135.45, 135.40, 130.11, 128.26, 127.99, 127.11, 126.58, 126.56, 113.30, 113.25, 96.15, 91.49, 91.38, 86.94, 86.81, 85.41, 85.38, 73.08, 73.07, 71.20, 71.06, 64.34, 61.75, 60.38, 55.24, 55.17, 46.70, 46.35, 41.27, 41.23, 36.58, 30.65, 30.34, 29.61, 25.71, 25.67, 21.05, 21.00, 19.16, 19.12, 19.01, 14.21, 13.70. $^{31}$P NMR (162 MHz, CHLOROFORM-d) δ=157.46.

Example 112. Synthesis of WV-CA-201

WV-CA-201

General Scheme.

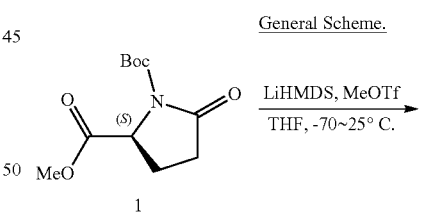

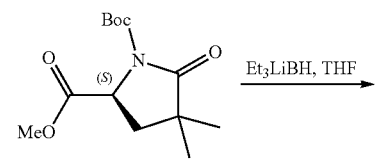

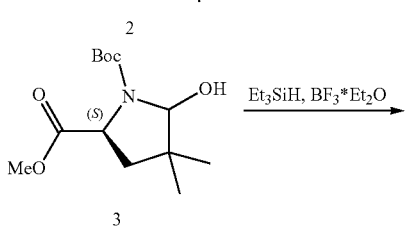

845

-continued

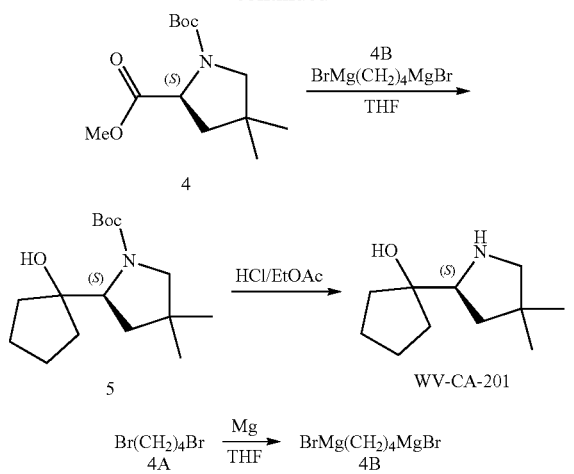

1. Preparation of Compound 2.

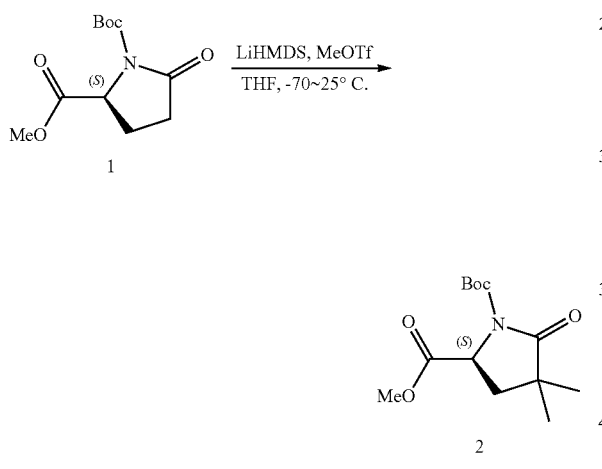

Compound 1 (25.00 g, 102.77 mmol) was dissolved in dry toluene (300.00 mL) and the solution was cooled to −70° C., prior to addition of LHMDS (1M, 123.32 mL) solution. After stirring under nitrogen atmosphere for 1 hr, methyl triflate (18.55 g, 113.05 mmol, 12.37 mL) was added dropwise via a syringe and the reaction mixture was stirred for 2 h before addition of LHMDS (1 M, 123.32 mL) followed by methyl triflate (18.55 g, 113.05 mmol, 12.37 mL). The mixture was stirred at −70° C. for 4 hr TLC indicated compound 1 was remained little and three new spot formed. The reaction was quenched with a sat. ammonium chloride solution (200 mL) and allowed to reach 20° C. The phases were separated and the aqueous layer was extracted three times with EtOAc (200 mL*3). Combined organic phases were dried over $Na_2SO_4$, filtered, and evaporated to give the crude product. The mixture was purified by silica gel chromatography (Petroleum ether/Ethyl acetate=30/1, 5/1) to afford compound 2 (14.24 g, 51.07% yield) as a white solid. $^1H$ NMR (400 MHz, CHLOROFORM-d) δ=4.51 (dd, J=5.2, 9.4 Hz, 1H), 3.83-3.66 (m, 3H), 2.19 (dd, J=9.3, 13.2 Hz, 1H), 1.96-1.81 (m, 1H), 1.48 (s, 9H), 11.19 (s, 6H). LCMS: (M+Na+): 293.9. TLC (Petroleum ether:Ethyl acetate=3:1) $R_f$=0.34.

846

2. Preparation of Compound 3.

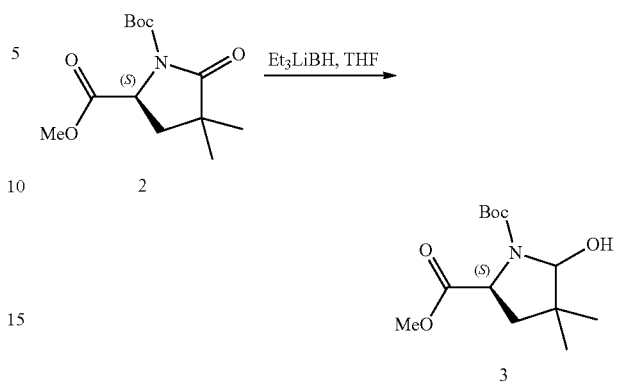

To a solution of compound 2 (25.00 g, 92.15 mmol) in THF (250.00 mL) at −70° C. was added dropwise a solution of Lithium triethylborohydride (1 M, 110.58 mL). The reaction mixture was stirred at −70° C. for 2 hr. TLC (Petroleum ether:Ethyl acetate=3:1, 3 times) showed the starting material was consumed, one new spot was detected. The mixture was quenched with sat. $NaHCO_3$ (150 mL). The resulting mixture was then allowed to warm to 0° C. A solution of $H_2O_2$ (31.34 g, 276.45 mmol, 26.56 mL, 30% purity) was added dropwise. The solution was stirred at 20° C. for 1 hr. The mixture was concentrated in vacuo to remove THF. The residue was extracted with EtOAc (100 mL*3), and the combined organic layers were dried over $Na_2SO_4$ and concentrated in vacuo to get the crude. The crude compound 3 was used without further purification. LCMS: (M+Na+): 296.1. TLC (Petroleum ether:Ethyl acetate=3:1) $R_f$=0.62.

3. Preparation of Compound 4.

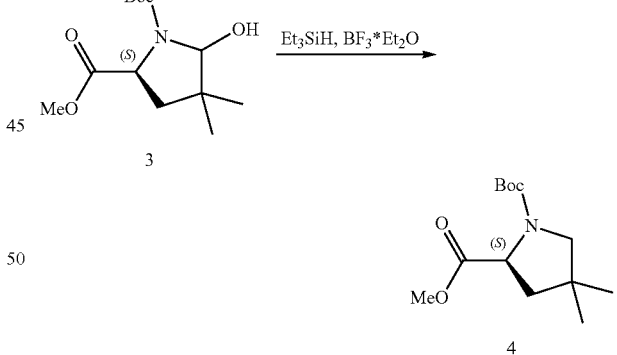

A solution of compound 3 (18.00 g, 65.86 mmol) and triethylsilane (9.19 g, 79.03 mmol, 12.59 mL) in DCM (100.00 mL) was cooled to −70° C. and $BF_3·Et_2O$ (11.22 g, 79.03 mmol, 9.75 mL) was then added dropwise under a nitrogen atmosphere. After 30 min, $BF_3·Et_2O$ (11.22 g, 79.03 mmol, 9.75 mL) and triethylsilane (9.19 g, 79.03 mmol, 12.59 mL) were added. The resulting mixture was stirred for 2 h at −70° C. TLC showed the starting material was almost consumed; one new spot was shown on TLC. The mixture was quenched with $NaHCO_3$ aq. (50 mL). The mixture was extracted with EtOAc (100 mL*3). The combined organic extracts were dried over $Na_2SO_4$ and concentrated in vacuo to get the crude. The crude was purified by column chromatography (SiO₂, Petroleum ether/Ethyl acetate=20/1 to 5:1) together to afford the product compound 4 (16.00 g, 94.41% yield) as a colorless oil. ¹H NMR (400 MHz, CHLOROFORM-d) δ=4.38-4.14 (m, 1H), 3.78-3.65 (m, 3H), 3.41-3.03 (m, 2H), 2.00 (dd, J=8.2, 12.3 Hz, 1H), 1.78-1.68 (m, 1H), 1.46-1.35 (m, 9H), 1.12-1.00 (m, 6H). LCMS: (M+Na+): 279.9. TLC (Petroleum ether:Ethyl acetate=3:1) R_f=0.55.

4. Preparation of Compound 4B.

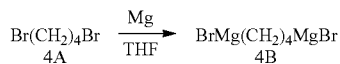

To a suspension of magnesium (10.88 g, 447.67 mmol) and I₂ (133.03 mg, 524.15 mol, 105.58 μL) in THF (100.00 mL) was added 1,4-dibromobutane (40.27 g, 186.53 mmol, 22.50 mL) in THF (300.00 mL) at 0° C. for 0.5 hr. The mixture was stirred at 20° C. for 2 hrs. Mg was remained a little. The Grignard reagent compound 4B in THF was used directly in next step.

5. Preparation of Compound 5.

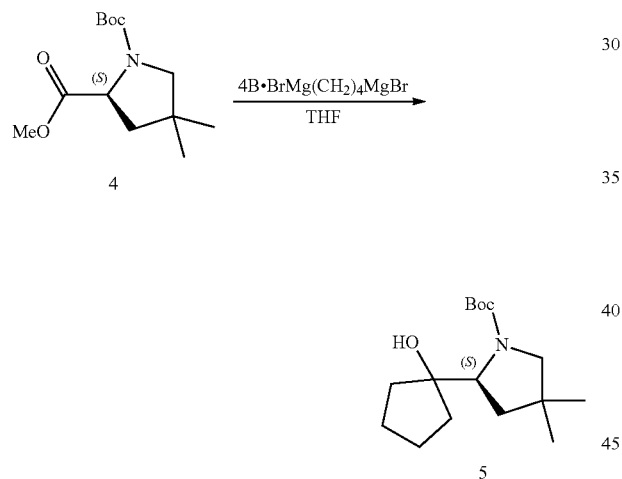

A mixture of compound 4B (49.34 g, 186.54 mmol) in THF (400.00 mL) was degassed and under N₂ atmosphere, and then compound 4 (16.00 g, 62.18 mmol) in THF (200.00 mL) was added, and the mixture was stirred at 25° C. for 2 hr. under N₂ atmosphere. TLC showed the starting material was consumed. The mixture was poured into NH₄Cl (aq, 500 mL). The organic was separated and the aqueous layer was extracted with EtOAc (300 mL*2). The combined organic was washed with brine (300 mL), dried over Na₂SO₄, filtered and concentrated to get the crude. The mixture was purified by silica gel chromatography (Petroleum ether/Ethyl acetate=30/1, 10/1) to afford compound 5 (9.80 g, 55.61% yield) as a colorless oil. ¹H NMR (400 MHz, CHLOROFORM-d) δ=5.44 (br s, 1H), 4.15 (br s, 1H), 3.43 (br s, 1H), 2.89 (br d, J=11.4 Hz, 1H), 1.93-1.71 (m, 4H), 1.66-1.50 (m, 6H), 1.46 (s, 9H), 1.07 (s, 3H), 0.95 (s, 3H). LCMS: (M+H+): 284.1. TLC (Petroleum ether:Ethyl acetate=3:1) R_f=0.71.

6. Preparation of Compound WV-CA-201.

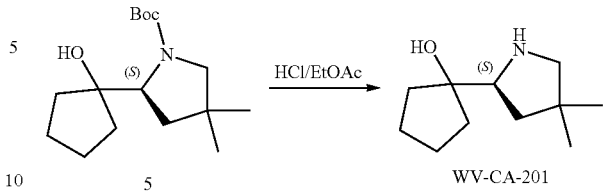

To a solution compound 5 (7.00 g, 24.70 mmol) in EtOAc (50.00 mL) was added HCl/EtOAc (100.00 mL). The mixture was stirred at 20° C. for 2 hrs. TLC showed the starting material was consumed. Concentrated the mixture and filtered to get the crude. The mixture was washed by Petroleum ether (20 mL), then dissolved in water (5 mL), after that Na₂CO₃ (aq., 10 mL) was added until pH>11, extracted with DCM (15 mL*3). The combined organic was dried over Na₂SO₄, filtered, and concentrated to get WV-CA-201 (3.00 g, 66.27% yield) as a yellow solid. ¹H NMR (400 MHz, CHLOROFORM-d) δ=3.26 (dd, J=7.5, 9.7 Hz, 1H), 2.67 (q, J=10.4 Hz, 2H), 1.84-1.74 (m, 2H), 1.60-1.34 (m, 6H), 1.04 (d, J=17.4 Hz, 6H). ¹³C NMR (101 MHz, CHLOROFORM-d) δ=81.71, 66.32, 60.27, 41.15, 39.94, 39.34, 35.85, 27.34, 27.27, 24.02.

LCMS: (M+H+): 184.2. LCMS purity=99.14%. TLC (Petroleum ether:Ethyl acetate=3:1) Rf=0.02. In another batch, to a solution of compound 5 (9.80 g, 34.58 mmol) in EtOAc (50.00 mL) was added HCl/EtOAc (100.00 mL). The mixture was stirred at 20° C. for 2 hr. TLC showed the starting material was consumed. Concentrated the mixture and filtered to get the crude. The mixture was washed by petroleum ether (50 mL), then dissolved in water (20 mL), after that sat. Na₂CO₃ (aq., 20 mL) was added until pH>11, extracted with DCM (50 mL*3). The combined organic was dried over Na₂SO₄, filtered, and concentrated to get WV-CA-201 (4.00 g, 21.82 mmol, 63.11% yield) as a yellow solid. ¹H NMR (400 MHz, CHLOROFORM-d) δ=3.26 (dd, J=7.5, 9.7 Hz, 1H), 2.67 (q, J=10.4 Hz, 2H), 1.84-1.74 (m, 2H), 1.60-1.34 (m, 8H), 1.04 (d, J=17.4 Hz, 6H). ¹³C NMR (100 MHz, CHLOROFORM-d) δ=81.86, 66.15, 60.57, 41.24, 40.03, 39.39, 35.67, 27.45, 27.34, 24.06, 24.00. LCMS: (M+H+): 184.2; LCMS purity=99.27%. TLC (Petroleum ether:Ethyl acetate=3:1) R_f=0.02.

Example 113. Synthesis of WV-CA-201-dCiBu

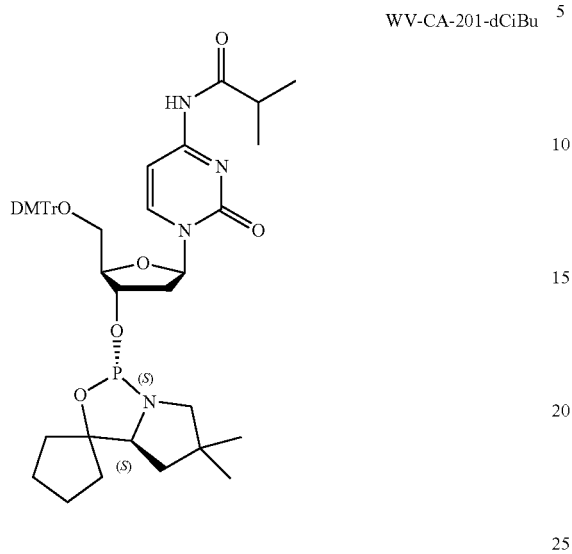

WV-CA-201-dCiBu

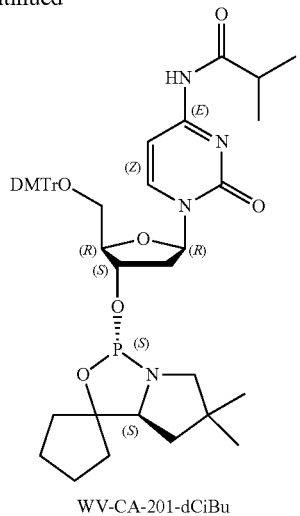

WV-CA-201-dCiBu

1. Preparation of Compound 2.

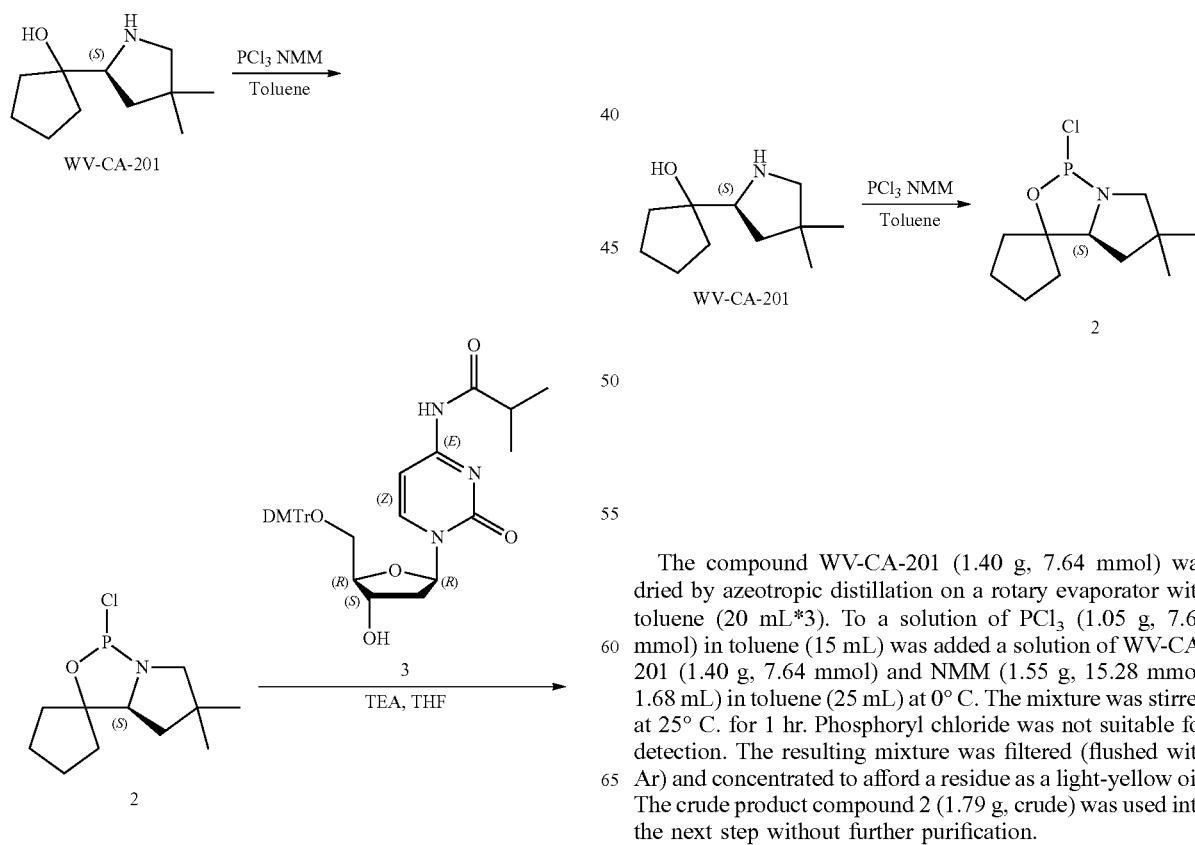

The compound WV-CA-201 (1.40 g, 7.64 mmol) was dried by azeotropic distillation on a rotary evaporator with toluene (20 mL*3). To a solution of $PCl_3$ (1.05 g, 7.64 mmol) in toluene (15 mL) was added a solution of WV-CA-201 (1.40 g, 7.64 mmol) and NMM (1.55 g, 15.28 mmol, 1.68 mL) in toluene (25 mL) at 0° C. The mixture was stirred at 25° C. for 1 hr. Phosphoryl chloride was not suitable for detection. The resulting mixture was filtered (flushed with Ar) and concentrated to afford a residue as a light-yellow oil. The crude product compound 2 (1.79 g, crude) was used into the next step without further purification.

2. Preparation of Compound WV-CA-201-dCiBu.

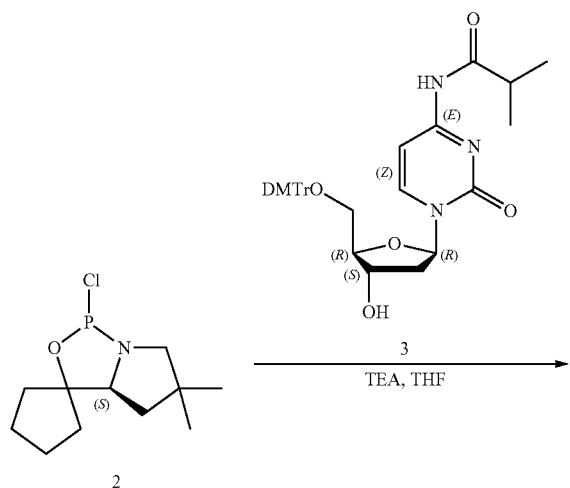

Compound 3 (2.89 g, 4.82 mmol) was dried by azeotropic distillation on a rotary evaporator with pyridine (20 mL) and toluene (20 mL*5). The dried compound 3 (2.89 g, 4.82 mmol) was dissolved in THF (15 mL), and then TEA (3.41 g, 33.74 mmol, 4.68 mL) was added. The mixture was cooled to −70'° C. A solution of compound 2 (1.79 g, 7.23 mmol) in THF (15 mL) was added dropwise at −70° C., then warmed to 25° C. over 0.5 hr and stirred for another 1 hr. TLC (Ethyl acetate:Petroleum ether=3:1, 5% TEA) showed compound 3 remained, and desired product was observed. The resulting mixture was diluted with DCM (50 mL), washed with sat. NaHCO₃ aq. (40 mL*3). The organic layer was dried over anhydrous MgSO₄, filtered and concentrated to afford a white foam (4.4 g). The MPLC column (flash Silica (CS), 40-60 μm, 60 A, 20 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (25 mL, 5% TEA) was loaded and purified with Ethyl acetate (5% TEA):Petroleum ether (5% TEA)=20%~60%. All solvent was dried over anhydrous Na₂SO₄. Compound WV-CA-201-dCiBu (1.40 g, 35.89% yield) was obtained as a white solid. ¹H NMR (400 MHz, CHLOROFORM-d) δ=8.19 (d, J=7.4 Hz, 1H), 8.17-8.11 (br. s, 1H), 7.36-7.31 (m, 2H), 7.27-7.15 (m, 8H), 6.98 (d, J=7.4 Hz, 1H), 6.78 (dd, J=1.6, 8.9 Hz, 4H), 6.17 (t, J=5.6 Hz, 1H), 4.74-4.64 (m, 1H), 4.13-4.07 (m, 1H), 3.75-3.71 (m, 6H), 3.64 (td, J=5.9, 10.2 Hz, 1H), 3.46-3.36 (m, 2H), 3.23-3.15 (m, 1H), 2.88 (t, J=9.8 Hz, 1H), 2.69 (td, J=6.1, 13.8 Hz, 1H), 2.48 (qd, J=6.9, 13.5 Hz, 2H), 2.27-2.18 (m, 1H), 2.08-1.99 (m, 1H), 1.80-1.45 (m, 10H), 1.41 (dd, J=5.9, 11.9 Hz, 1H), 1.14 (dd, J=3.0, 6.9 Hz, 6H), 1.02 (s, 6H). ¹³C NMR (101 MHz, CHLOROFORM-d) δ=176.91, 162.37, 158.65, 158.64, 155.07, 144.57, 144.13, 135.48, 135.33, 130.16, 130.08, 128.24, 127.97, 127.06, 113.27, 98.10, 97.99, 96.15, 86.94, 86.90, 85.44, 85.40, 71.57, 71.39, 70.27, 70.25, 61.98, 60.54, 55.20, 46.25, 44.77, 41.21, 41.14, 40.38, 40.34, 36.53, 35.85, 35.81, 28.21, 27.82, 27.81, 23.74, 22.93, 19.14, 19.02. ³¹P NMR (162 MHz, CHLOROFORM-d) δ=160.89 (s, 1P). TLC (Ethyl acetate:Petroleum ether=3:1, 5% TEA), R_f=0.35.

Example 114. Synthesis of WV-CA-202

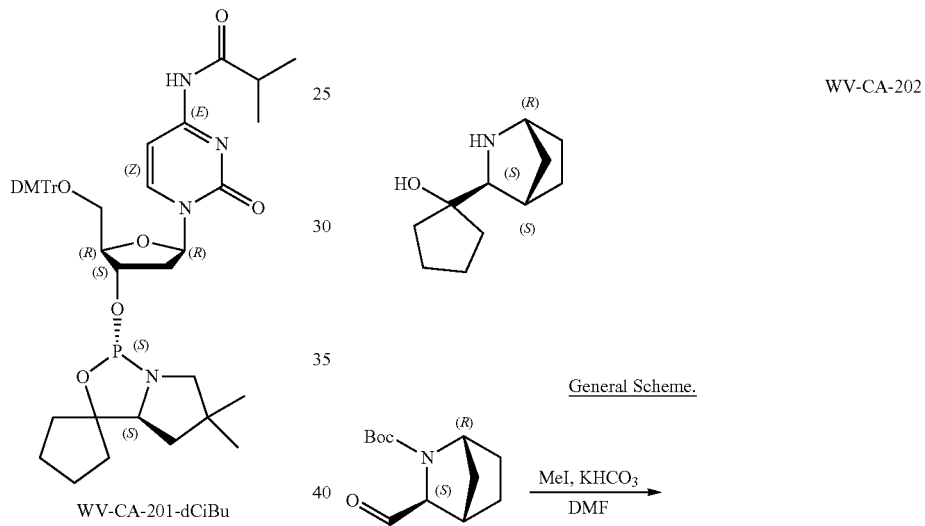

General Scheme.

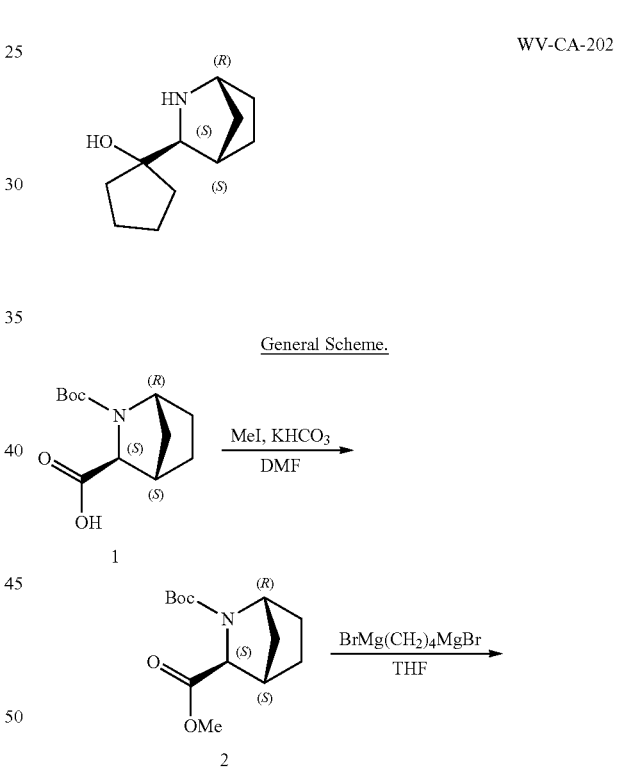

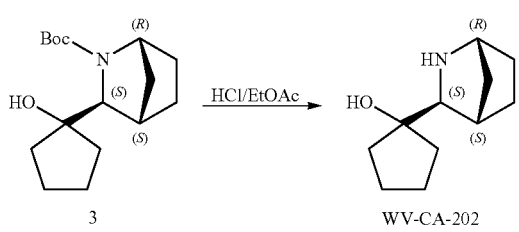

1. Preparation of Compound 2.

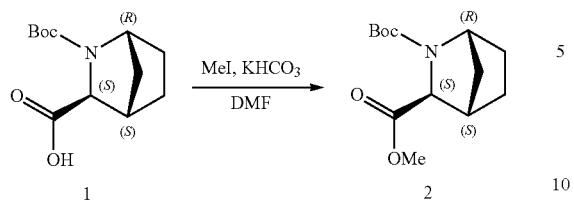

To a solution of compound 1 (30.00 g, 124.34 mmol) in DMF (260.00 mL) was added MeI (88.24 g, 621.70 mmol, 38.70 mL) and KHCO$_3$ (24.90 g, 248.68 mmol). The mixture was stirred at 25° C. for 16 hr. TLC indicated compound 1 was consumed and one new spot formed. The reaction mixture was partitioned between methyl tert-butyl ether 260 mL and H2O 520 mL. The organic phase was separated, washed with NaCl 100 mL dried over Na$_2$SO$_4$, filtered, and concentrated under reduced pressure to give a residue, which was no purification to give compound 2. Compound 2 was obtained as a yellow oil (31.00 g, 97.65%). $^1$H NMR (400 MHz, CHLOROFORM-d) δ=4.36-4.11 (m, 1H), 3.82-3.55 (m, 4H), 2.61 (br s, 1H), 1.87 (br dd, J=1.8, 7.9 Hz, 1H), 1.75-1.52 (m, 3H), 1.43-1.30 (m, 10H), 1.26-1.12 (m, 1H). LCMS: (M+H+): 256.0. TLC (Petroleum ether:Ethyl acetate=5:1) R$_f$=0.41.

2. Preparation of Compound 3.

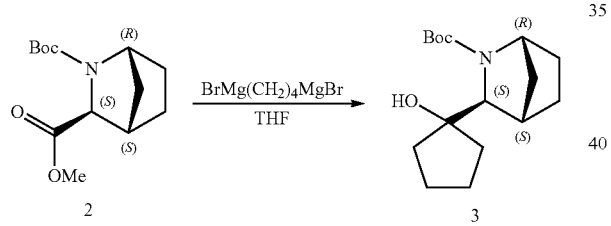

To a solution of compound 2 (31.00 g, 121.42 mmol) in THF (60.00 mL) was added BrMg(CH$_2$)$_4$MgBr (93.38 g, 356.59 mmol) at −5-0° C. in N$_2$. The mixture was stirred at −5-25° C. for 2.5 hr. TLC indicated compound 2 was consumed and one new spot formed. The reaction mixture was quenched by addition sat. NH$_4$Cl aq. 80 mL at 0° C., and then diluted with EA 100 mL and extracted with EA (100 mL*3). Dried over Na$_2$SO$_4$, filtered, and concentrated under reduced pressure to give a residue. The residue was purified by column chromatography (SiO$_2$, Petroleum ether/Ethyl acetate=1:0 to 1:1). Compound 3 was obtained as a colorless oil (20.00 g, 58.54%). $^1$H NMR (400 MHz, CHLOROFORM-d) δ=4.36-3.96 (m, 1H), 3.41 (br s, 1H), 2.57-2.34 (m, 1H), 2.09-1.21 (m, 21H), 1.20~1.08 (m, 1H), 0.99-0.73 (m, 1H). LCMS: (M+H$^+$): 282.2. TLC (Plate 1: Petroleum ether:Ethyl acetate=5:1) R$_f$=0.45. HPLC purity=97.854%. SFC purity=100.0%.

3. Preparation of WV-CA-202.

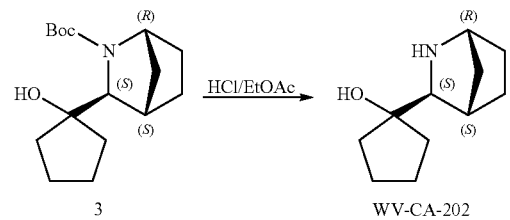

To a solution of compound 3 (19.00 g, 67.52 mmol) in EtOAc (10.00 mL) was added HCl/EtOAc (200.00 mL). The mixture was stirred at 25° C. for 2 hr. TLC indicated compound 3 was consumed and one new spot formed. The reaction mixture was concentrated under reduced pressure to remove solvent. The residue was diluted with Na$_2$CO$_3$ until pH=11 and extracted with DCM (200 mL*3). Dried over Na$_2$SO$_4$, filtered, and concentrated under reduced pressure to give a residue. WV-CA-202 was obtained as a white solid (11.00 g, 89.87%). $^1$H NMR (400 MHz, CHLOROFORM-d) δ=2.57 (s, 1H), 2.31 (br d, J=1.3 Hz, 1H), 1.87-1.17 (m, 14H), 1.05 (d, J=9.5 Hz, 1H). $^{13}$C NMR (101 MHz, CHLOROFORM-d) δ=82.64, 67.79, 55.41, 39.74, 38.90, 35.80, 35.26, 32.91, 30.26, 23.86, 23.46. LCMS: (M+H+): 182.1. TLC (Plate 1: Petroleum ether:Ethyl acetate=5:1) R$_f$=0.36.

Example 115. Synthesis of WV-CA-202-dCiBu

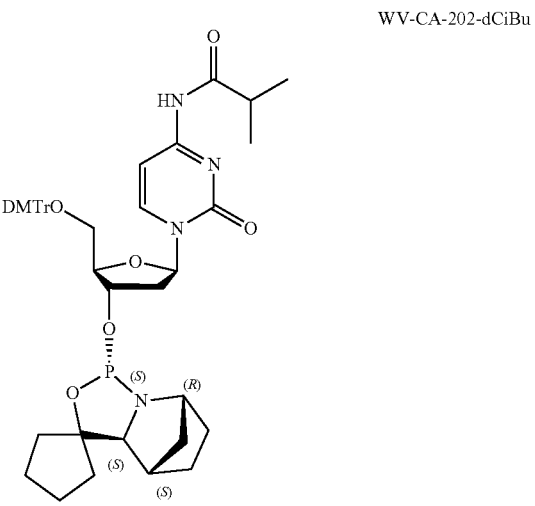

WV-CA-202-dCiBu

General Scheme.

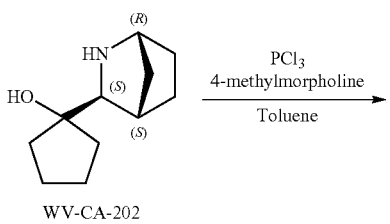

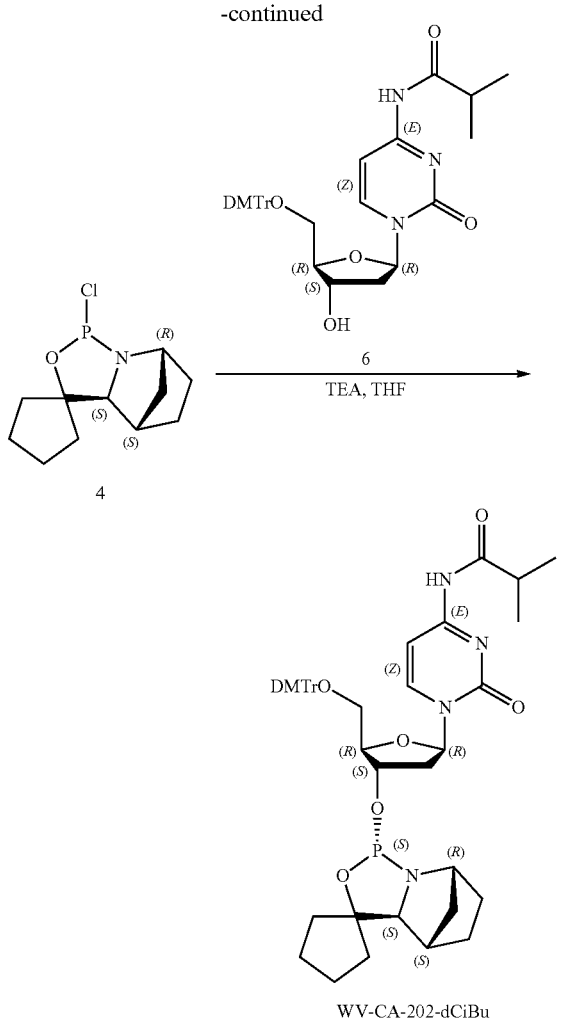

1. Preparation of Compound 4.

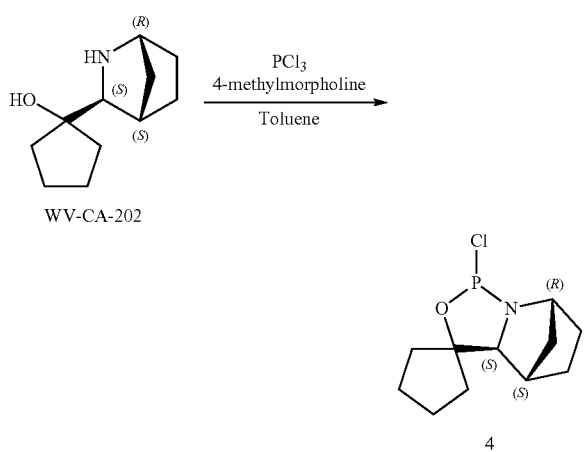

Compound WV-CA-202 (2.00 g, 11.03 mmol) was dried by azeotropic distillation on a rotary evaporator with toluene (20 mL*3). To a solution of PCl₃ (1.61 g, 11.70 mmol) in toluene (15 mL) was added a solution of compound WV-CA-202 (2.12 g, 11.70 mmol) and NMM (2.37 g, 23.39 mmol, 2.57 mL) in toluene (15 mL) at 0° C. The mixture was stirred at 25° C. for 1 hr Phosphoryl chloride, not suitable for detection. The resulting mixture was filtered (flushed with Ar) and concentrated to afford a residue as a light-yellow oil. The crude product compound 4 (2.49 g, crude) was used into the next step without further purification.

2. Preparation of Compound WV-CA-202-dCiBu.

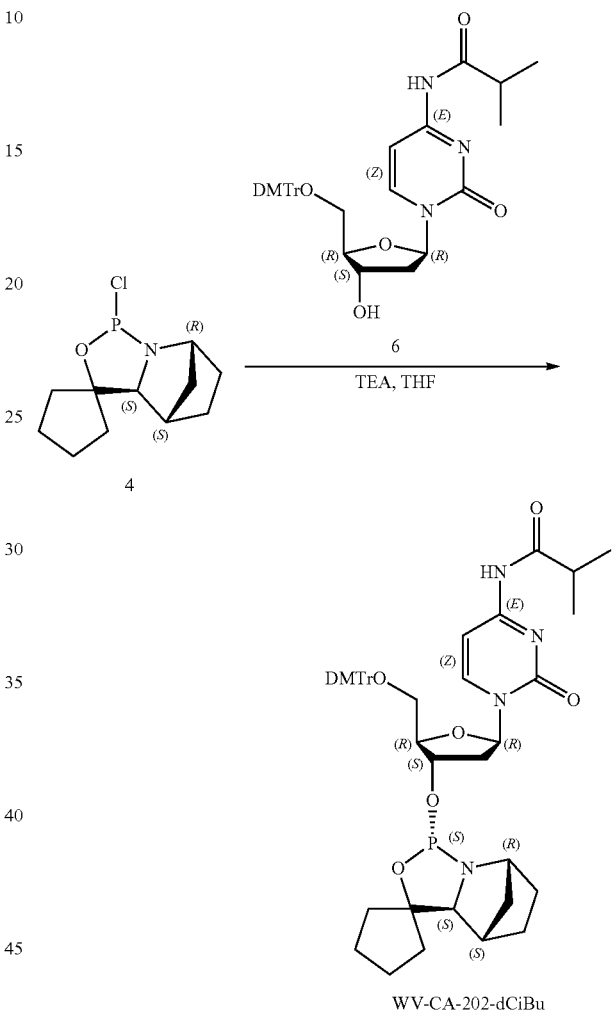

Compound 6 (4.05 g, 6.76 mmol) was dried by azeotropic distillation on a rotary evaporator with pyridine (20 mL) and toluene (30 mL*3). The dried compound 6 (4.05 g, 6.76 mmol) was dissolved in THF (15 mL), and then TEA (4.79 g, 47.32 mmol, 6.56 mL) was added. The mixture was cooled to −70° C. A solution of compound 4 (2.49 g, 10.14 mmol) in THF (15 mL) was added dropwise at −70° C., then warmed to 25° C. over 0.5 h and stirred for another 0.5 hr. TLC showed compound 6 was consumed, and a main new spot was observed. The resulting mixture was diluted with DCM (40 mL), washed with sat. NaHCO₃ aq. (20 mL*3). The organic layer was dried over anhydrous MgSO₄, filtered, and concentrated to afford a white foam (6.5 g crude). The MPLC column (flash Silica (CS), 40-60 μm, 60 A, 40 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (60 mL, 5% TEA) was loaded and purified with Ethyl acetate (5% TEA):Petroleum ether (5% TEA)=20% 70%. All solvent was dried over anhydrous Na₂SO₄. Compound WV-CA-202-dCiBu (4.00 g, 4.94 mmol, 73.08% yield) was obtained as a white solid. $^1$H NMR (400 MHz, CHLOROFORM-d) δ=8.70 (br s, 1H), 8.23 (d, J=7.5 Hz, 1H), 7.41 (d, J=7.5 Hz, 2H), 7.34-7.23 (m, 7H), 7.12 (d, J=7.5 Hz, 1H), 6.86 (d, J=7.7 Hz, 4H), 6.28 (t, J=5.8 Hz, 1H), 4.71 (qd, J=4.9, 9.6 Hz, 1H), 4.22 (br d, J=3.4 Hz, 1H), 3.87 (br d, J=8.9 Hz, 1H), 3.82 (s, 6H), 3.52-3.40 (m, 2H), 3.17 (d, J=2.5 Hz, 1H), 2.80 (td, J=5.6, 13.6 Hz, 1H), 2.66 (spt, J=6.9 Hz, 1H), 2.39-2.23 (m, 3H), 2.01-1.92 (m, 1H), 1.83-1.53 (m, 12H), 1.33 (br t, J=5.5 Hz, 1H), 1.22 (dd, J=4.2, 6.8 Hz, 6H), 1.14-1.08 (m, 1H). $^{13}$C NMR (101 MHz, CHLOROFORM-d) δ=162.28, 158.66, 158.65, 155.09, 144.59, 144.13, 135.48, 135.32, 130.15, 130.07, 128.21, 127.98, 127.08, 113.28, 98.74, 98.63, 96.12, 87.03, 86.90, 85.58, 85.55, 72.68, 72.65, 71.85, 71.71, 62.29, 60.39, 57.98, 57.66, 55.22, 42.37, 41.13, 41.09, 39.44, 36.97, 36.62, 34.76, 34.73, 31.52, 31.42, 28.29, 22.83, 22.69, 21.05, 19.13, 19.03, 14.21. $^{31}$P NMR (162 MHz, CHLOROFORM-d) δ=155.87 (s, 1P). TLC (Ethyl acetate: Petroleum ether=3:1, 5% TEA), R$_f$=0.4.

Example 116. Synthesis of WV-CA-206

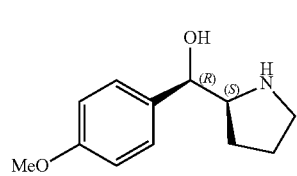

WV-CA-206

General Scheme.

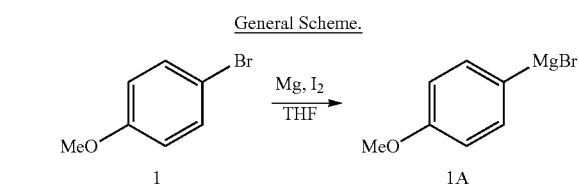

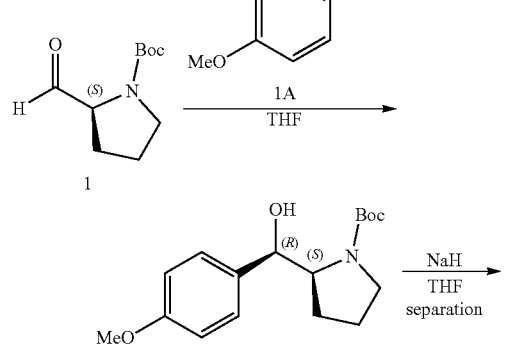

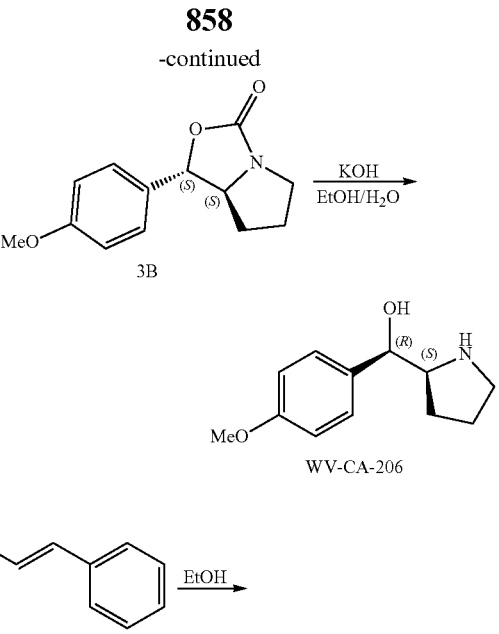

1. Preparation of Compound 1A.

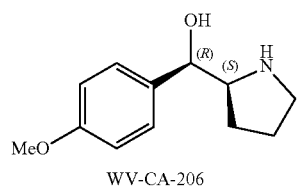

A mixture of Mg (8.73 g, 359.30 mmol), I₂ (20.00 mg, 78.80 μmol, 15.87 μL) in THF (300.00 mL) was added compound 1 (1.50 g, 8.02 mmol, 1.01 mL) in THF (300.00 mL) and then the mixture was stirred at 25° C. for 2 hr under N₂ atmosphere. Mg was consumed and the reaction was complete. The mixture was used directly without any purification.

2. Preparation of Compound 2.

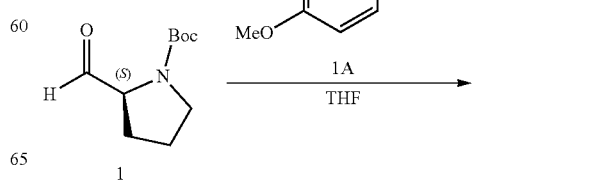

-continued

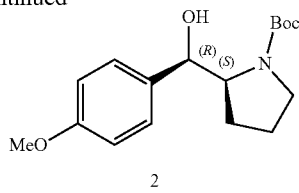

A mixture of compound 1A (1 M, 301.12 mL) was added to compound 1 (30.00 g, 150.56 mmol) dissolved in THF (200.00 mL) at −70° C., and the mixture was stirred at −70° C. for 1.5 hrs. TLC (Petroleum ether/Ethyl acetate=5:1, Rf=0.43) showed the starting material was consumed. The mixture was poured into $NH_4Cl$ (aq)/$NH_3 \cdot H_2O$=10:1 (1000 mL) and extracted with EtOAc (150 mL*3). The combined organic was washed with brine (200 mL), dried over $Na_2SO_4$, filtered and concentrated to get the crude. The mixture was purified by silica (Petroleum ether/Ethyl acetate=20:1, 10:1) to get compound 2 as a yellow oil (25.00 g, 54.02% yield). HPLC: HPLC purity=93.5%. SFC: SFC purity=40.7%.

3. Preparation of Compound 3A and compound 3B.

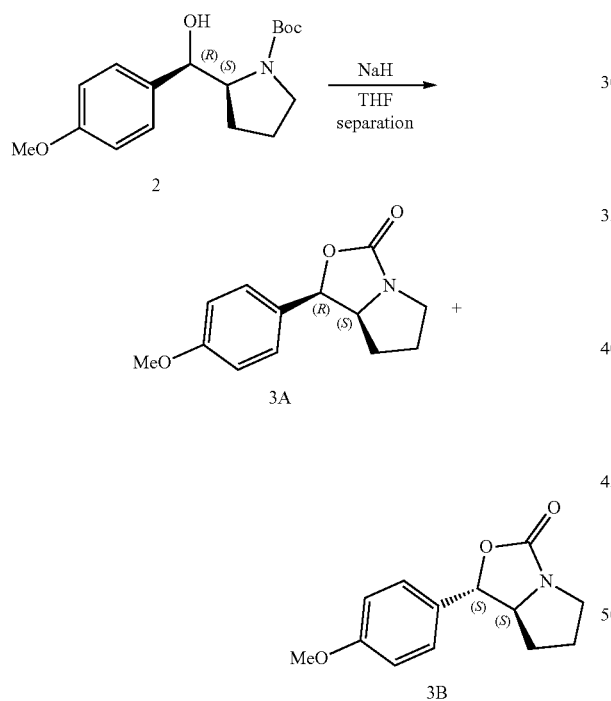

To a solution of compound 2 (25.00 g, 81.33 mmol) in THF (10.00 mL) was added NaH (4.88 g, 122.00 mmol, 60% purity). The mixture was stirred at 25° C. for 1 hr TLC (Petroleum ether/Ethyl acetate=3:1, Rf=0.24, 0.18) showed the starting material was consumed. Water (20 mL) was added and the mixture was extracted with EtOAc (120 mL*3). The combined organic was washed with brine (100 mL), dried over $Na_2SO_4$, filtered and concentrated to get the crude. The residue was purified by silica (Petroleum ether/Ethyl acetate=20:1, 10:1) to give compound 3A (6.50 g, 27.87 mmol, 34.26% yield) and compound 3B as yellow solids (5.00 g, 26.36% yield). SFC: SFC purity=100.0%.

4. Preparation of WV-CA-206.

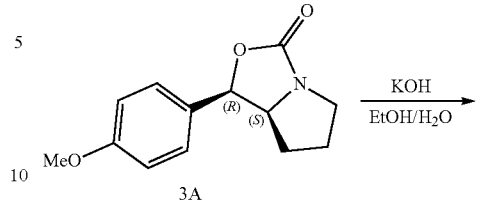

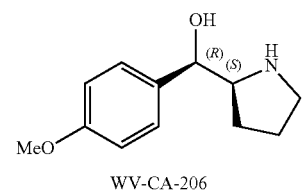

A solution of compound 3A (6.50 g, 27.87 mmol) and KOH (9.30 g, 66.33 mmol, 40%) in the mixture of EtOH (30.00 mL) and $H_2O$ (30.00 mL), the mixture was stirred at 65° C. for 2 hr. TLC (Petroleum ether/Ethyl acetate=3:1, Rf=0.01) showed the starting material was consumed. The mixture was concentrated to get the crude, and the residue was added water (20 mL) and then $Na_2CO_3$ (aq.) was added until pH>10, and the mixture was extracted with DCM (50 mL*3). The combined organic was dried over $Na_2SO_4$, filtered, and concentrated to get WV-CA-206 as a yellow oil (5.00 g, 86.54% yield). $^1$H NMR: (400 MHz, CHLOROFORM-d): δ=7.25-7.17 (m, 2H), 6.80 (d, J=8.8 Hz, 2H), 4.58 (d, J=4.6 Hz, 1H), 3.73 (s, 3H), 3.33-3.24 (m, 1H), 2.96-2.80 (m, 2H), 2.52 (br s, 2H), 1.71-1.52 (m, 3H), 1.49-1.39 (m, 1H). LCMS: (M+H+): 208.1, LCMS purity=99.0%. SFC: SFC purity=97.3% ee.

5. Purification of WV-CA-206.

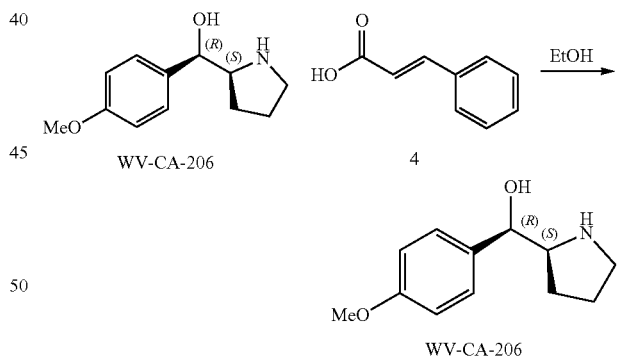

To a solution, WV-CA-206 (5.00 g, 24.12 mmol) in EtOH (30.00 mL). was added compound 4 (3.57 g, 24.12 mmol, 2.86 mL) and reflux at 90° C. for 0.5 hr, and then the mixture was dried in rotary evaporation to give the yellow solid. The yellow solid was added ethyl acetate (35 mL), and slowly dropped MeOH until the yellow solid become liquid at 90° C. for 2 hr. The mixture was filtered and the cake was washed with ethyl acetate (10 mL), and the cake was dissolved in water (10 mL) and the mixture was added sat. $Na_2CO_3$(aq) until pH>11. The mixture was extracted with DCM (15 mL*3). The combined organic was washed with brine (20 mL) then $Na_2CO_3$ (15 mL), dried over $Na_2SO_4$, filtered and concentrated to get the crude. The mixture was purified by silica (Dichloromethane/Methanol=20:1, 10:1) to get WV-CA-206 as a yellow solid (2.00 g, 40.01% yield). $^1$H NMR (400 MHz, CDCl$_3$): δ=7.31-7.21 (m, 2H), 6.90-6.77 (m, 2H), 4.68 (d, J=4.6 Hz, 1H), 3.87-3.75 (m, 3H), 3.36 (dt, J=4.7, 7.4 Hz, 1H), 3.06-2.75 (m, 4H), 1.83-1.41 (m, 4H). $^{13}$C NMR: δ=158.76, 134.29, 134.26, 127.03, 113.62, 73.81, 64.06, 55.22, 46.67, 25.39, 25.08. LCMS: (M+H$^+$): 208.1; LCMS purity=95.9%. SFC: SFC purity=100.0% ee.

Example 117. Synthesis of WV-CA-206-dCiBu

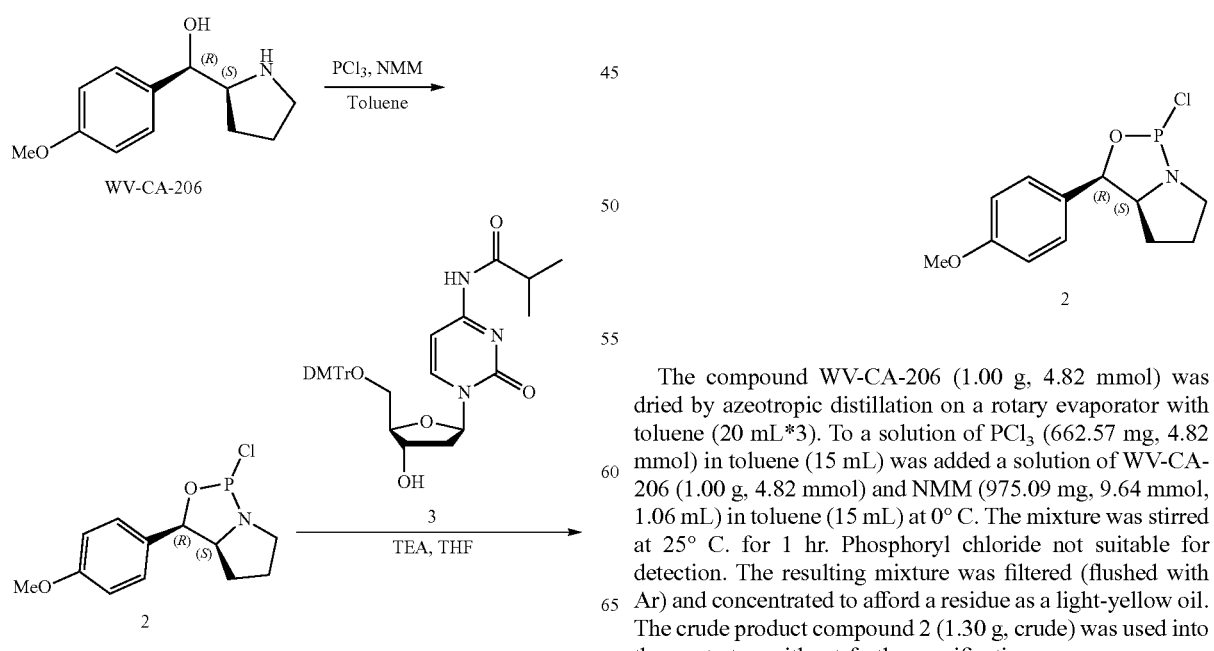

1. Preparation of Compound 2.

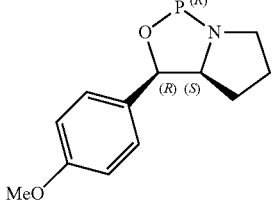

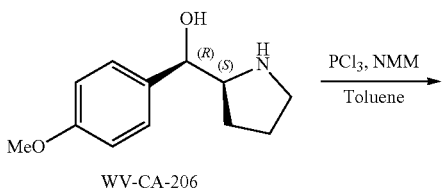

The compound WV-CA-206 (1.00 g, 4.82 mmol) was dried by azeotropic distillation on a rotary evaporator with toluene (20 mL*3). To a solution of PCl$_3$ (662.57 mg, 4.82 mmol) in toluene (15 mL) was added a solution of WV-CA-206 (1.00 g, 4.82 mmol) and NMM (975.09 mg, 9.64 mmol, 1.06 mL) in toluene (15 mL) at 0° C. The mixture was stirred at 25° C. for 1 hr. Phosphoryl chloride not suitable for detection. The resulting mixture was filtered (flushed with Ar) and concentrated to afford a residue as a light-yellow oil. The crude product compound 2 (1.30 g, crude) was used into the next step without further purification.

2. Preparation of Compound WV-CA-206-dCiBu.

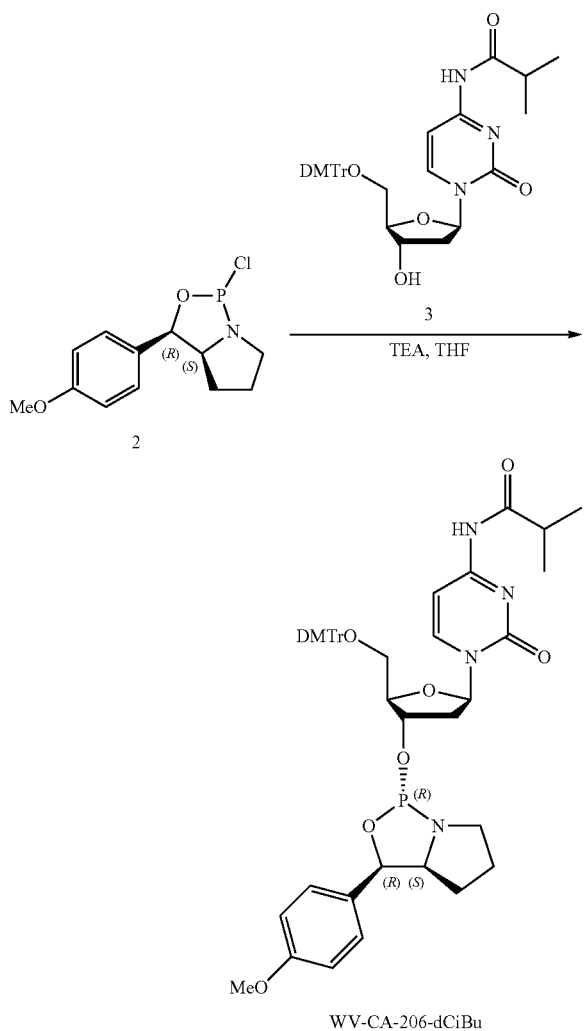

WV-CA-206-dCiBu

Compound 3 (1.91 g, 3.19 mmol) was dried by azeotropic distillation on a rotary evaporator with pyridine (20 mL) and toluene (20 mL*5). The dried compound 3 (1.91 g, 3.19 mmol) was dissolved in THF (15 mL), and then TEA (2.26 g, 22.33 mmol, 3.10 mL) was added. The mixture was cooled to −70° C. A solution of compound 2 (1.30 g, 4.79 mmol) in THF (15 mL) was added dropwise at −70° C., then warmed to 25° C. over 0.5 hr and stirred for another 1 hr. TLC (Ethyl acetate:Petroleum ether=3:1, 5% TEA) showed compound 3 remained, and desired product was observed. The resulting mixture was diluted with DCM (50 mL), washed with sat. NaHCO₃ aq. (40 mL*3). The organic layer was dried over anhydrous MgSO₄, filtered, and concentrated to afford a white foam (3 g). The MPLC column (flash Silica (CS), 40-60 μm, 60A, 40 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (20 mL, 5% TEA) was loaded and purified with Ethyl acetate (5% TEA):Petroleum ether (5% TEA)=20%~60%. All solvent was dried over anhydrous Na₂SO₄. Compound WV-CA-206-dCiBu (1.10 g, 41.34% yield) was obtained as a white solid. ¹H NMR (400 MHz, CHLOROFORM-d) δ=8.32-8.27 (br s, 1H), 8.26 (d, J=7.4 Hz, 1H), 7.42-7.38 (m, 2H), 7.34-7.17 (m, 9H), 7.10 (d, J=7.4 Hz, 1H), 6.92-6.87 (m, 2H), 6.84-6.79 (m, 4H), 6.28 (t, J=5.6 Hz, 1H), 5.70 (d, J=6.3 Hz, 1H), 4.90-4.81 (m, 1H), 4.23-4.17 (m, 1H), 3.88-3.84 (m, 1H), 3.83 (s, 3H), 3.79 (d, J=1.8 Hz, 6H), 3.65-3.53 (m, 1H), 3.48 (d, J=3.0 Hz, 2H), 3.35-3.26 (m, 1H), 3.19 (tt, J=6.6, 10.8 Hz, 1H), 2.82 (td, J=6.1, 13.8 Hz, 1H), 2.59 (quin, J=6.9 Hz, 1H), 2.40-2.31 (m, 1H), 1.70-1.60 (m, 2H), 1.23 (dd, J=3.1, 6.8 Hz, 6H), 1.05-0.92 (m, 2H). ¹³C NMR (101 MHz, CHLOROFORM-d) δ=176.93 (br s, 1C), 162.39, 159.00, 158.63, 155.13, 144.52, 144.15, 135.46, 135.38, 130.27, 130.23, 130.07, 130.03, 128.20, 127.97, 127.08, 126.73, 113.65, 113.28, 96.22, 86.92, 86.83, 85.57, 85.54, 82.13, 82.03, 71.47, 71.33, 67.46, 67.43, 61.91, 55.26, 55.20, 47.39, 47.04, 41.10, 41.06, 36.58, 34.46, 28.05, 26.01, 25.98, 23.32, 19.14, 19.02. ³¹P NMR (162 MHz, CHLOROFORM-d) δ=155.81 (s, 1P). TLC (Ethyl acetate:Petroleum ether=3:1, 5% TEA), R_f=0.35.

Example 118. Synthesis of WV-CA-207

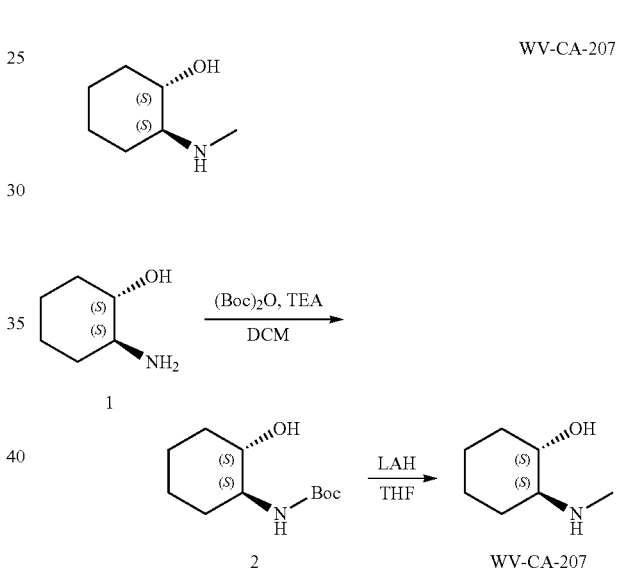

Preparation of Compound 2.

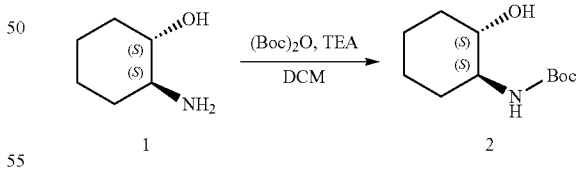

To a solution of compound 1 (10.00 g, 86.83 mmol) and di-tert-butyl dicarbonate (20.85 g, 95.51 mmol, 21.95 mL) in DCM (100.00 mL) was added TEA (26.36 g, 260.49 mmol, 36.11 mL) at 0° C. The mixture was stirred at 25° C. for 16 hr. TLC showed the reaction was completed. The resulting mixture was diluted with DCM (100 mL) and washed with water (60 mL*3). The organic layer was dried over anhydrous Na₂SO₄, filtered, and concentrated to afford the crude. The crude was purified by column (Petroleum ether:Ethyl acetate=25:1, 10:1, 5:1). Compound 2 (18.00 g, 96.29% yield) was obtained as a white solid. ¹H NMR (400

MHz, CHLOROFORM-d): δ=4.69-4.18 (m, 1H), 3.22 (br d, J=5.7 Hz, 2H), 2.05-1.82 (m, 2H), 1.71-1.58 (m, 2H), 1.38 (s, 9H), 1.30-0.97 (m, 4H). TLC (Petroleum ether:Ethyl acetate=3:1) R$_f$=0.23.

2. Preparation of WV-CA-207.

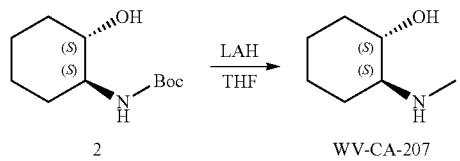

To a solution of compound 2 (15.00 g, 69.67 mmol) in THF (200.00 mL) was added LAH (13.22 g, 341.39 mmol, 98% purity) in portions at 0° C. The mixture was stirred at 80° C. for 2 hrs. TLC showed the starting material was consumed, one new spot was detected. The reaction was slowly added sat. MgSO$_4$ (30 mL) at 0° C. The mixture was filtered through Celatom. The filter cake was washed with EtOAc (100 mL*3). The organic phase was dried over MgSO$_4$, filtered, and concentrated in vacuo to dryness to afford the product. WV-CA-207 (7.20 g, 79.99% yield) as a colorless oil. $^1$H NMR (400 MHz, CHLOROFORM-d): δ=3.16 (dt, J=4.6, 9.6 Hz, 1H), 2.47-2.36 (m, 3H), 2.16-2.01 (m, 2H), 1.98 (br s, 1H), 1.84-1.59 (m, 2H), 1.33-1.12 (m, 3H), 1.04-0.76 (m, 1H). $^{13}$C NMR (101 MHz, CHLOROFORM-d): δ=73.18, 64.65, 33.23, 32.78, 29.18, 24.57, 24.04. LCMS: (M+H$^+$): 130.1. TLC (Dichloromethane:Methanol=10:1) R$_f$=0.04.

Example 119. Synthesis of WV-CA-207-dCiBu

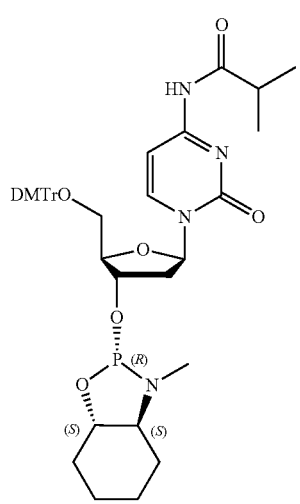

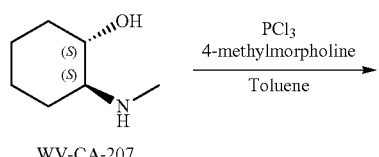

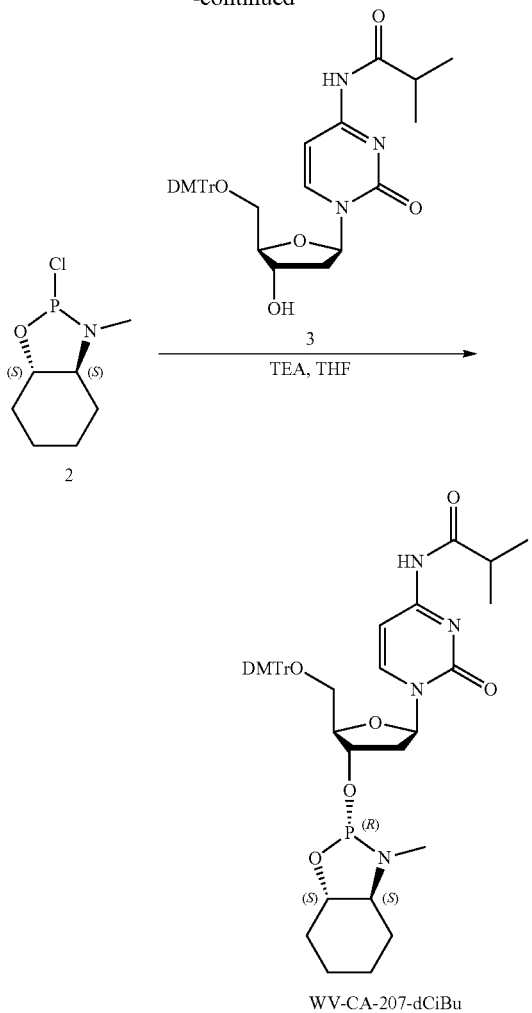

1. Preparation of Compound 2.

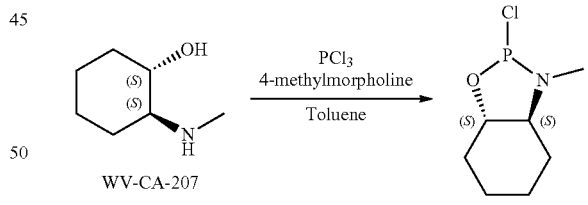

The compound WV-CA-207 (1.00 g, 7.74 mmol) was dried by azeotropic distillation on a rotary evaporator with toluene (20 mL*3). To a solution of PCl$_3$ (1.06 g, 7.74 mmol) in toluene (10 mL) was added a solution of WV-CA-207 (1.00 g, 7.74 mmol) and NMM (1.57 g, 15.48 mmol, 1.70 mL) in toluene (10 mL) at 0° C. The mixture was stirred at 25° C. for 1 hr. Phosphoryl chloride not suitable for detection. The resulting mixture was filtered (flushed with Ar) and concentrated to afford a residue as a colorless oil. The crude product compound 2 (1.25 g, 6.46 mmol, 83.46% yield) was used into the next step without further purification.

2. Preparation of Compound WV-CA-207-dCiBu.

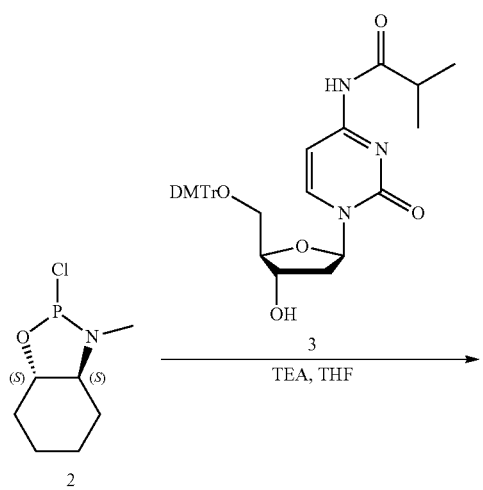

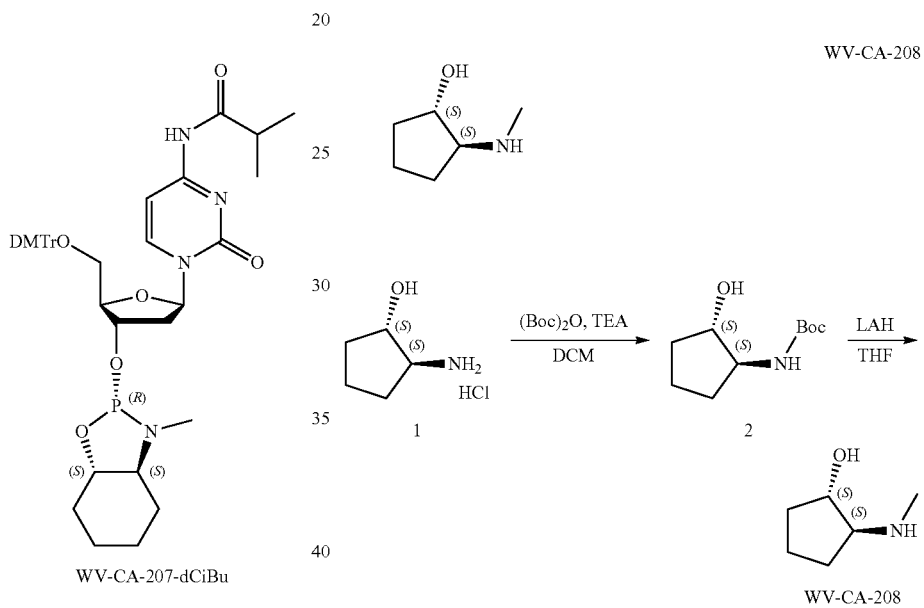

WV-CA-207-dCiBu

Compound 3 (2.58 g, 4.31 mmol) was dried by azeotropic distillation on a rotary evaporator with pyridine (20 mL) and toluene (30 mL*3). The dried compound 3 (2.58 g, 4.31 mmol) was dissolved in THF (10 mL), and then TEA (3.05 g, 30.15 mmol, 4.18 mL) was added. The mixture was cooled to −70° C. A solution of compound 2 (1.25 g, 6.46 mmol) in THF (10 mL) was added dropwise at −70° C., then warmed to 25° C. over 0.5 hr and stirred for another 1 hr. TLC (Ethyl acetate:Petroleum ether=3:1, 5% TEA) showed most of compound 3 was remained, and a new spot was observed. The resulting mixture was diluted with DCM (50 mL), washed with sat. NaHCO₃ aq. (30 mL*3). The organic layer was dried over anhydrous MgSO₄, filtered, and concentrated to afford a white foam. The MPLC column (flash Silica (CS), 40-60 μm, 60 A, 40 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (60 mL, 5% TEA) was loaded and purified with Ethyl acetate (5% TEA):Petroleum ether (5% TEA)=20%-70%. All solvent was dried over anhydrous Na₂SO₄. Compound WV-CA-207-dCiBu (1.00 g, 30.65% yield) was obtained as a white solid. $^1$H NMR (400 MHz, CHLOROFORM-d) δ=8.27 (d, J=7.4 Hz, 1H), 8.25-8.19 (m, 1H), 7.36-7.31 (m, 2H), 7.27-7.15 (m, 7H), 7.05 (d, J=7.4 Hz, 1H), 6.78 (dd, J=1.8, 8.8 Hz, 4H), 6.14 (dd, J=4.3, 6.5 Hz, 1H), 4.84 (qd, J=6.2, 9.1 Hz, 1H), 4.11-4.07 (m, 1H), 3.82-3.75 (m, 1H), 3.73 (s, 6H), 3.45-3.33 (m, 2H), 2.63-2.47 (m, 5H), 2.27 (ddd, J=4.4, 6.7, 13.9 Hz, 1H), 2.18 (dt, J=3.5, 10.3 Hz, 1H), 2.09-1.98 (m, 2H), 1.79-1.67 (m, 3H), 1.47-1.35 (m, 3H), 1.14 (dd, J=4.3, 6.9 Hz, 6H). $^{13}$C NMR (101 MHz, CHLOROFORM-d) δ=176.83, 162.35, 158.69, 158.66, 155.15, 144.58, 144.04, 135.50, 135.28, 130.15, 130.03, 128.22, 128.01, 127.11, 113.31, 96.22, 86.95, 86.59, 85.19, 85.13, 83.19, 83.11, 70.50, 70.34, 67.05, 61.39, 55.21, 41.32, 36.59, 34.45, 31.74, 31.38, 30.70, 30.68, 28.81, 23.93, 19.12, 19.02. $^{31}$P NMR (162 MHz, CHLOROFORM-d) δ=154.57 (s, 1P). TLC (Ethyl acetate:Petroleum ether=3:1, 5% TEA), $R_f$=0.29.

Example 120. Synthesis of WV-CA-208

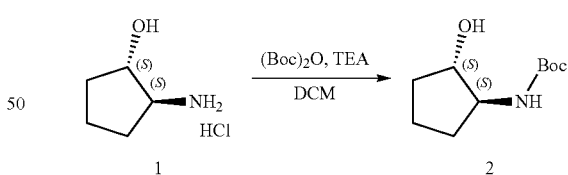

WV-CA-208

1. Preparation of Compound 2.

To a solution of compound 1 (12.00 g, 87.20 mmol, HCl salt) in DCM (100.00 mL) was added TEA (26.47 g, 261.61 mmol, 36.26 mL), then (Boc)₂O (22.84 g, 104.64 mmol, 24.04 mL) was dropped to the mixture. The mixture was stirred at 25° C. for 16 hrs. TLC showed the reaction was completed. The mixture was diluted with DCM (100 mL) and washed with water (60 mL*3). The organic layer was dried over anhydrous Na₂SO₄, filtered, and concentrated to afford a crude. The crude was purified by the mixture was purified by silica gel chromatography (Petroleum ether/Ethyl acetate=30/1, 5/1) to afford the product. The product was washed with Petroleum ethyl (300 mL) to get the compound 2 (14.00 g, 79.77% yield) as a white solid.

$^1$H NMR (400 MHz, CHLOROFORM-d): δ=4.65 (br s, 1H), 4.00-3.93 (m, 2H), 3.64-3.57 (m, 1H), 2.12-1.96 (m, 2H), 1.79-1.60 (m, 3H), 1.43 (s, 9H), 1.38-1.27 (m, 1H). LCMS: (M+Na$^+$): 224.1. TLC (Petroleum ether:Ethyl acetate=3:1) R$_f$=0.67.

2. Preparation of WV-CA-208.

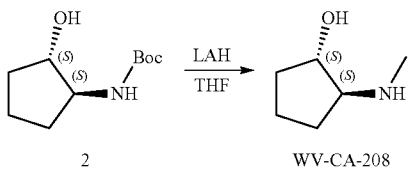

To a solution of compound 2 (14.00 g, 69.56 mmol) in THF (150.00 mL) was added LAH (13.20 g, 340.87 mmol, 98% purity) in portions at 0° C. The mixture was stirred at 80° C. for 2 hrs. TLC (Dichloromethane:Methanol=10:1) showed the starting material was consumed, one new spot was detected. The reaction was slowly added sat. MgSO$_4$ (26 mL) at 0° C. The mixture was filtered through Celatom. The filter cake was washed with EtOAc (200 mL*3). The organic phase was dried over MgSO$_4$, filtered, and concentrated in vacuo to dryness to afford the product. The residue was purified by column chromatography (SiO$_2$, Petroleum ether/Ethyl acetate=5:1 to 1:1) to get WV-CA-208 (3.93 g, 49.06% yield) as a yellow solid. $^1$H NMR (400 MHz, CHLOROFORM-d): δ=3.87 (q, J=6.2 Hz, 1H), 2.84-2.69 (m, 1H), 2.51-2.37 (m, 3H), 2.11-1.92 (m, 4H), 1.77-1.62 (m, 2H), 1.60-1.49 (m, 1H), 1.37-1.16 (m, 1H). $^{13}$C NMR (100 MHz, CHLOROFORM-d): δ=77.98, 68.69, 34.97, 32.88, 29.87, 20.49. LCMS: (M+H$^+$): 116.1; LCMS purity=99.38%. TLC (Dichloromethane:Methanol=10:1) R$_f$=0.13.

Example 121. Synthesis of WV-CA-209

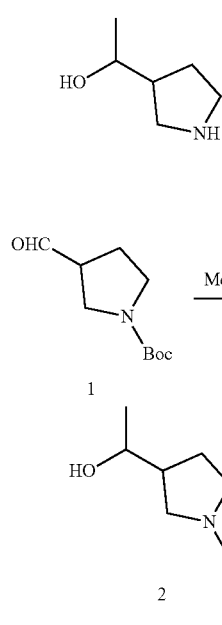

1. Preparation of Compound 2.

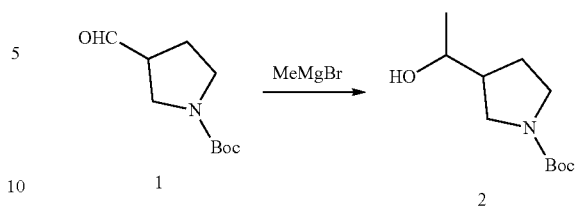

A mixture of compound 1 (15.00 g, 75.28 mmol) in THF (100.00 mL) was degassed and purged with N$_2$ for 3 times, and then the mixture was cooled to 0° C. and then the mixture was added MeMgBr (3M, 30.11 mL), then the solution was stirred at 25° C. for 2 hr under N$_2$ atmosphere. LC-MS showed compound 1 was consumed completely and one main peak with desired MS was detected. The reaction was quenched by sat. NaHCO$_3$ (100 mL, aq.) and then extracted with EtOAc (50 mL*3). The combined organic phase was washed with brine (100 mL*1), dried over anhydrous Na$_2$SO$_4$, filtered and concentrated in vacuo. The residue was purified by column chromatography (SiO$_2$, Petroleum ether/Ethyl acetate=10/1 to 4:1). Compound 2 (7.00 g, crude) was obtained as a yellow oil. $^1$H NMR (400 MHz, CDCl$_3$): δ=3.78-3.37 (m, 3H), 3.31-2.89 (m, 2H), 2.22-1.96 (m, 1H), 1.91-1.51 (m, 3H), 1.44 (s, 9H), 1.20 (br d, J=6.2 Hz, 3H). LCMS: (M-56+H$^+$): 160.2. TLC (Petroleum ether/Ethyl acetate=1:1) R$_f$=0.46.

2. Preparation of WV-CA-209.

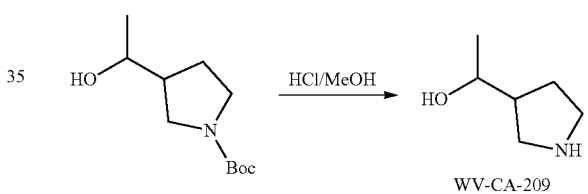

A solution of compound 2 (5.00 g, 23.22 mmol) in HCl/MeOH (50.00 mL, 6 N). The mixture was stirred at 25° C. for 2 hr. LC-MS showed compound 2 was consumed completely and one main peak with desired MS was detected. The mixture was concentrated in vacuo. The residue was purified by column chromatography (SiO$_2$, Dichloromethane:Methanol=501/1 to 0:1) with 5% TEA. WV-CA-209 was obtained as a yellow oil (1.50 g, crude). $^1$H NMR (400 MHz, CDCl$_3$): δ=3.74-3.54 (m, 1H), 3.02-2.58 (m, 4H), 2.08-1.75 (m, 2H), 1.70-1.35 (m, 1H), 1.22-1.03 (m, 3H). $^{13}$C NMR (125.7 MHz, CDCl$_3$): δ=70.76, 70.46, 50.48, 50.21, 49.28, 46.81, 46.79, 46.18, 29.38, 26.99, 22.61, 22.08. LCMS: (M+H$^+$): 161.0. TLC (Dichloromethane/Methanol=5:1) R$_f$=0.00.

Example 122. Synthesis of WV-CA-210A

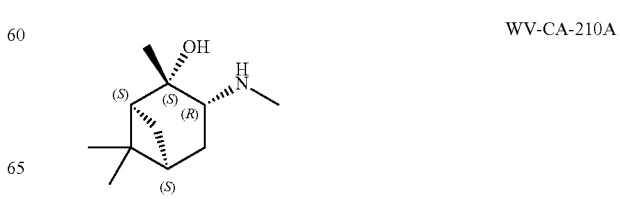

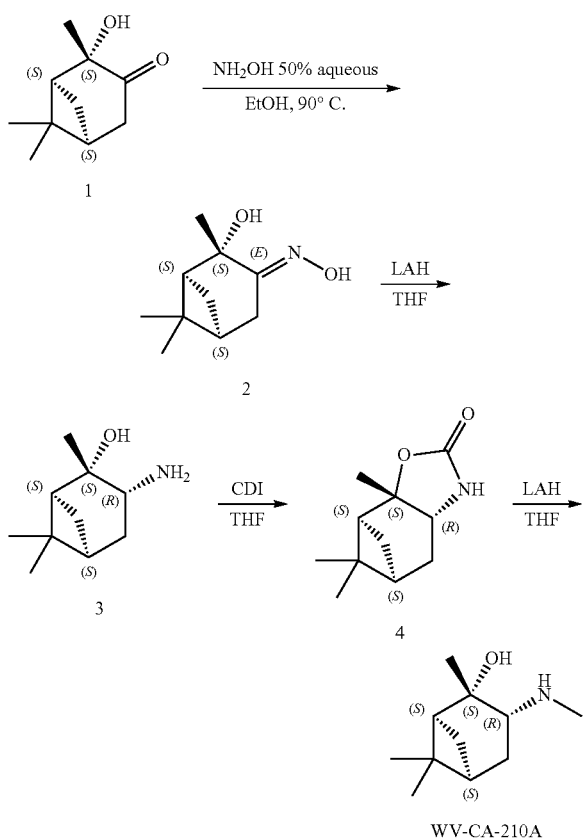

1. Preparation of Compound 2.

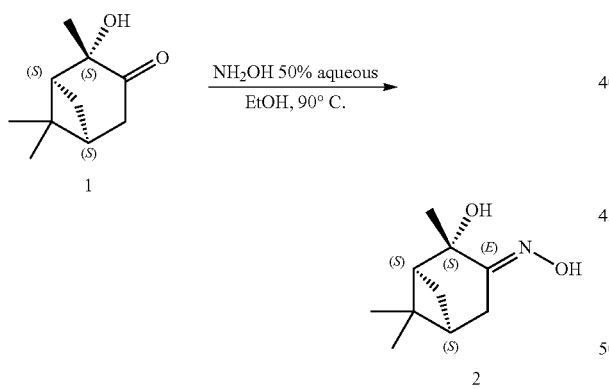

A mixture of compound 1 (10.00 g, 59.44 mmol) and hydroxylamine (11.78 g, 178.32 mmol), the mixture was stirred at 90° C. for 12 hr under $N_2$ atmosphere. LCMS and TLC (Petroleum ether/Ethyl acetate=3:1, Rf=0.14) showed the starting material was consumed. The resulting residue was re-dissolved in 2N NaOH (50 mL), and washed with hexane (50 mL). The aqueous layer was acidified with 12 N HCl, and extracted with ethyl acetate (50 mL*3). The extracts were washed with water (20 mL) and brine (20 mL), dried over $MgSO_4$, and the solvent was evaporated in vacuum. The mixture was purified by silica (Petroleum ether/Ethyl acetate=10:1) to get the compound 2 as a white solid (7.00 g, 64.27% yield). $^1$H NMR (400 MHz, $CDCl_3$): δ=2.71 (br d, J=7.3 Hz, 2H), 2.30 (br dd, J=2.3, 5.8 Hz, 1H), 1.97 (br d, J=5.7 Hz, 2H), 1.56-1.47 (m, 4H), 1.32-1.23 (m, 3H), 0.83 (s, 3H). LCMS: (M+Na$^+$): 205.9. TLC (Petroleum ether/Ethyl acetate=3:1) R$_f$=0.14.

2. Preparation of Compound 3.

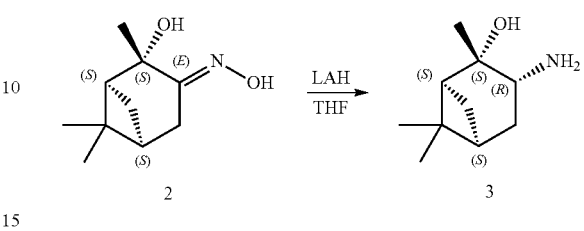

To an ice cooled suspension of $LiAlH_4$ (4.35 g, 114.60 mmol) in THF (150.00 mL) was added compound 2 (7.00 g, 38.20 mmol). The reaction mixture was stirred at 50° C. for 4 hr. TLC showed the starting material was consumed. The mixture was cooled to about 5° C., Ethyl acetate (4.3 mL), 10% aqueous NaOH (4.3 mL) and water (13 mL) were added dropwise, and the resulting mixture was stirred at room temperature for 0.5 hr. The insoluble material was removed by filtration through celite, and the filtrate was evaporated in vacuum. The residue was acidified with 10% HCl-methanol (5 mL), and ethyl ether (20 mL) was added. The resulting white solid was filtered and dried to give 5 g crude. The solid was dissolved in 1 N NaOH (10 mL), and the solution was extracted with DCM (20 mL*3), and dried over $MgSO_4$, evaporation of the solvent to give the compound 3 as a white solid (3.70 g, 57.22% yield). $^1$H NMR (400 MHz, CHLOROFORM-d): δ=3.19 (br dd, J=6.6, 9.5 Hz, 1H), 2.55-2.31 (m, 2H), 2.21-2.04 (m, 1H), 2.00-1.91 (m, 1H), 1.88-1.79 (m, 1H), 1.27 (br d, J=10.3 Hz, 2H), 1.20 (s, 3H), 1.13 (s, 3H), 0.95-0.82 (m, 3H). TLC (Petroleum ether/Ethyl acetate=3:1) R$_f$=0.02.

3. Preparation of Compound 4.

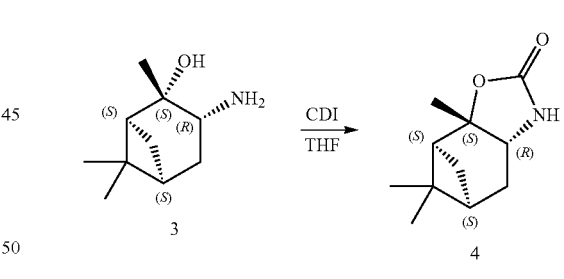

The compound 3 (3.70 g, 21.86 mmol) and CDI (3.90 g, 24.05 mmol) were dissolved in THF (40.00 mL). The reaction mixture was stirred at 25° C. for 1 hr. TLC showed the starting material was consumed. After water (30 mL) was added, the mixture was extracted with ethyl acetate (50 mL*3), and the extracts were washed with 1 N HCl (30 mL), and brine (20 mL), dried over $MgSO_4$ and concentrated to get compound 4 as a white solid (2.90 g, 67.94% yield). $^1$H NMR (400 MHz, $CDCl_3$): δ=5.79 (br s, 1H), 3.81-3.67 (m, 1H), 2.38-2.22 (m, 2H), 2.16 (t, J=5.4 Hz, 1H), 2.02-1.94 (m, 1H), 1.74 (td, J=2.8, 13.9 Hz, 1H), 1.50 (s, 3H), 1.32 (s, 3H), 0.88 (s, 3H). TLC (Petroleum ether/Ethyl acetate=1/1) R$_f$=0.43.

4. Preparation of WV-CA-210A.

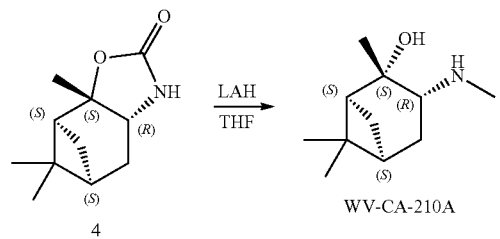

A mixture of LiAlH$_4$ (1.69 g, 44.55 mmol) in THF (60.00 mL) was degassed and purged with N$_2$ for 3 times, and then the mixture was added compound 4 (2.90 g, 14.85 mmol). The mixture was stirred at 60° C. for 12 hr under N$_2$ atmosphere. TLC (Petroleum ether/Ethyl acetate=3:1, Rf=0.02) and LCMS showed the starting material was consumed. The reaction mixture was cooled to about 0° C. Ethyl acetate (1.8 mL), 10% aqueous NaOH (1.8 mL) and water (5.4 mL) were added dropwise, and the resulting mixture was stirred at room temperature for 2 hr. The insoluble material was removed by filtration through celite, and the filtrate was evaporated in vacuum. The residue was acidified with 4 N HCl-Ethyl acetate (10 mL), and ethyl ether (30 mL) was added. The resulting white solid was filtered and dried to give the hydrochloride salt. The solid was dissolved in 1 N NaOH (100 mL), and the solution was extracted with DCM (100 mL*3), washed with brine (50 mL), dried over MgSO$_4$. Evaporation of the solvent gave WV-CA-210A as a white solid (2.05 g, 11.18 mmol, 75.32% yield). $^1$H NMR (400 MHz, CHLOROFORM-d): δ=2.69 (dd, J=5.8, 9.8 Hz, 1H), 2.53-2.36 (m, 4H), 2.05 (dtd, J=2.3, 6.1, 10.1 Hz, 1H), 1.90 (t, J=5.8 Hz, 1H), 1.79 (tt, J=3.0, 5.6 Hz, 1H), 1.27-1.14 (m, 8H), 0.90 (s, 3H). $^{13}$C NMR (101 MHz, CDCl$_3$): δ=71.45, 59.83, 54.31, 40.44, 38.32, 37.43, 37.21, 31.43, 28.06, 27.93, 24.05. LCMS: (M+H$^+$): 184.2; LCMS purity: 100.0%. TLC (Petroleum ether/Ethyl acetate=3:1) R$_f$=0.02.

Example 123. Synthesis of WV-CA-210B

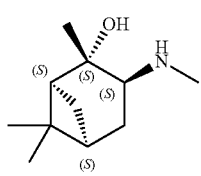

1. Preparation of WV-CA-210B.

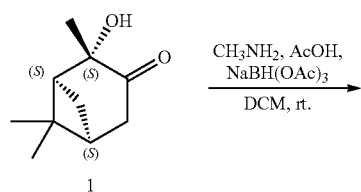

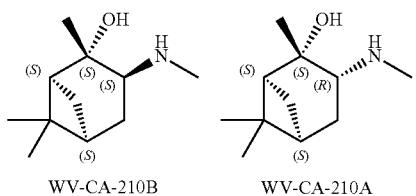

A mixture of compound 1 (10.00 g, 59.44 mmol), methylamine (1.5 M, 79.26 mL), and HOAc (356.95 mg, 5.94 mmol, 339.95 μL) was degassed and purged with N$_2$ for 3 times, and then NaBH(OAc)$_3$ (25.20 g, 118.88 mmol) was added. The mixture was stirred at 25° C. for 2 hr under N$_2$ atmosphere. LCMS and TLC showed the starting material was consumed. The mixture was concentrated to get the crude. The mixture was dissolved in EtOAc (20 mL) and stirred for 5 min then the mixture was filtered and the cake was washed with EtOAc (5 mL), the filtrate was concentrated to get the crude (6.2 g), and 5.2 g of the crude was purified by pre-HPLC (column: Luna C18 100*30 5u; mobile phase: [water (0.1% TFA)-ACN]; B %: 1%-32%, 14 min) to get the WV-CA-210B as a white solid (2.80 g, 15.28 mmol, 25.70% yield) and WV-CA-210A as a yellow oil (100.00 mg, 545.58 μmol, 0.92% yield). WV-CA-210B, $^1$H NMR (400 MHz, CDCl$_3$): δ=2.99 (t, J=8.9 Hz, 1H), 2.50 (s, 3H), 2.37-2.26 (m, 1H), 2.17-2.07 (m, 1H), 2.00-1.91 (m, 1H), 1.89-1.84 (m, 1H), 1.58 (d, J=10.1 Hz, 1H), 1.42 (br dd, J=8.4, 13.2 Hz, 1H), 1.34 (s, 3H), 1.24 (s, 3H), 0.89 (s, 3H). $^{13}$C NMR (101 MHz, CDCl$_3$): δ=62.87, 55.77, 40.25, 39.13, 35.73, 32.46, 27.67, 24.72, 24.51, 23.09. LCMS: (M+H$^+$) 184.2; LCMS purity=100.0%. TLC (Petroleum ether/Ethyl acetate=3:1) R$_f$=0.

Example 124. Synthesis of WV-CA-216

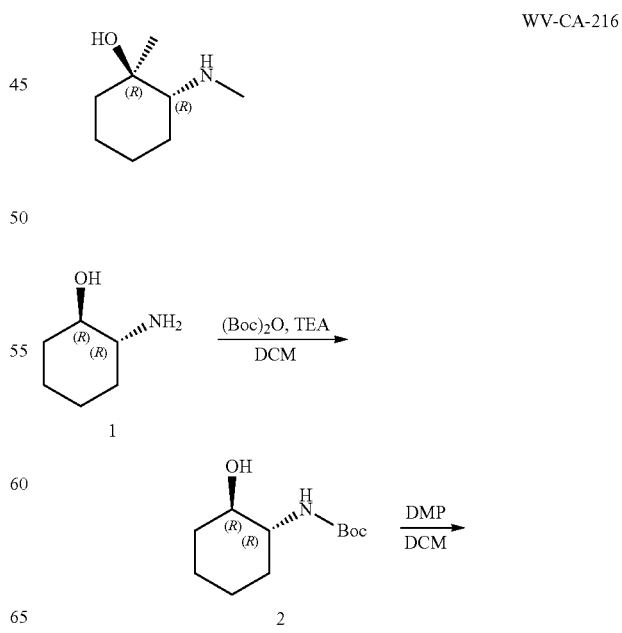

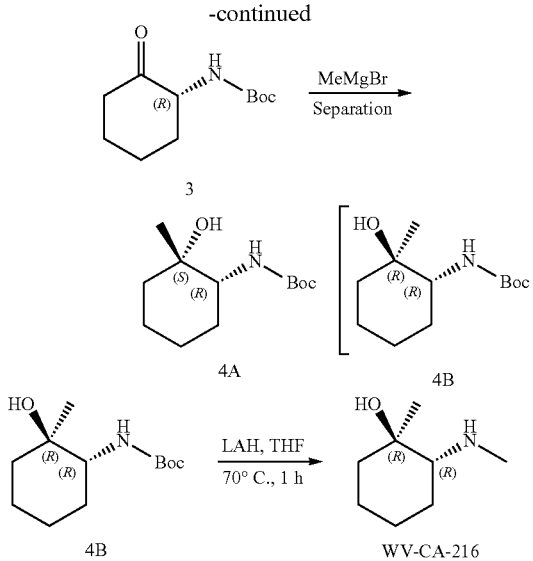

1. Preparation of Compound 2.

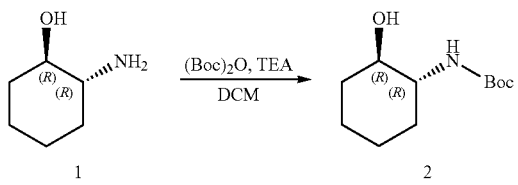

To a solution of compound 1 (150.00 g, 1.30 mol) in DCM (1 L) was added TEA (394.64 g, 3.90 mol, 540.60 mL) and then added (Boc)₂O (312.10 g, 1.43 mol, 328.53 mL) in DCM (500 mL). The mixture was stirred at 25° C. for 12 hr. TLC indicated compound 1 was consumed and one new spot formed. The reaction mixture was concentrated under reduced pressure to remove solvent, and then the residue was added H₂O (500 mL) and extracted with DCM (1000 mL*3). Dried over Na₂SO₄, filtered, and concentrated under reduced pressure to give a residue. Then the residue was washed with Petroleum Ether (300 mL*2), and filtered. Compound 2 (270.00 g, 1.25 mol, 96.47% yield) was obtained as a yellow solid. ¹H NMR (400 MHz, CHLOROFORM-d) δ=3.39-3.24 (m, 2H), 2.09-1.91 (m, 2H), 1.77-1.59 (m, 3H), 1.45 (s, 9H), 1.39-1.05 (m, 4H). TLC (Petroleum ether:Ethyl acetate=3:1) R$_f$=0.47.

2. Preparation of Compound 3.

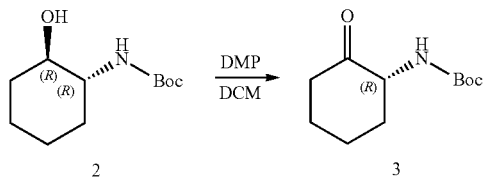

To a solution of compound 2 (160.00 g, 743.18 mmol) in DCM (1.60 L) was added DMP (378.26 g, 891.82 mmol, 276.10 mL) at 0-5° C. in 0.5 hr. The mixture was stirred at 0-25° C. for 2 hr. TLC indicated compound 2 was consumed completely and one new spot formed. The reaction was quenched with sat. Na₂SO₃ aq. and sat. NaHCO₃ aq. (V/V=3:2, 2 L), and extracted with DCM (1.5 L*3). The combined organic layers were dried over anhydrous MgSO₄, filtered, and concentrated to afford a crude. The residue was purified together with another batch crude (110 g scale of compound 2) by column chromatography (SiO₂, Petroleum ether/Ethyl acetate=1/0 to 1:1) to get 240 g crude product as a red oil, recrystallized to get 84 g product as white solid. Compound 3 (49.00 g, 229.76 mmol, 30.92% average yield) was obtained as a red oil. Recrystallization gave 84 g white solid. ¹H NMR (400 MHz, CHLOROFORM-d) δ=4.34-4.13 (m, 1H), 2.67-2.43 (m, 2H), 2.43-2.27 (m, 1H), 2.17-2.04 (m, 1H), 1.94-1.53 (m, 3H), 1.41 (s, 9H), 1.38-1.28 (m, 1H), 1.27-1.18 (m, 1H). LCMS: (M+Na+): 236.0. HPLC: HPLC purity=100%. SFC: SFC purity=99.4% ee. TLC (Petroleum ether:Ethyl acetate=5:1) R$_f$=0.44.

3. Preparation of Compound 4B.

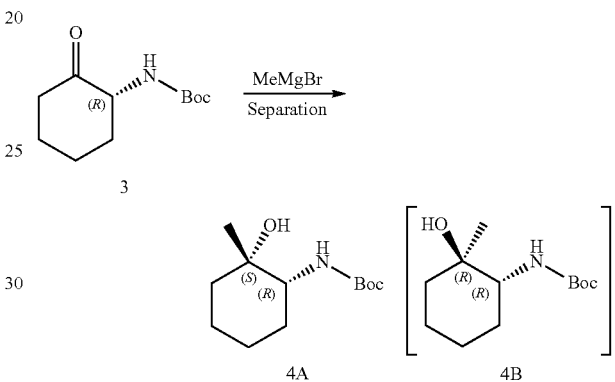

To a solution of compound 3 (112.00 g, 525.16 mmol) in THF (1.12 L) was added MeMgBr (3 M, 437.63 mL) at −60° C.-55° C. for 0.5 hr. The mixture was stirred at −60-0° C. for 1 hr. The mixture was stirred at 0-25° C. for 1.5 hr. TLC indicated compound 3 was consumed and two new spots formed. The reaction mixture was quenched by addition NH₄Cl (400 mL) at 0° C., and then diluted with EtOAc (400 mL) and extracted with EtOAc (400 mL*4). Dried over Na₂SO₄, filtered, and concentrated under reduced pressure to give a residue. The residue was purified by column chromatography (SiO₂, Petroleum ether/Ethyl acetate=1/0 to 0:1). 45 g product and 65 g crude product. Compound 4B (45.00 g, 196.23 mmol, 37.37% yield) was obtained as a white solid and 65 g of the mixture of compound 4A and compound 4B. ¹H NMR (400 MHz, CHLOROFORM-d) δ=3.66-3.38 (m, 2H), 1.79 (br t, J=13.2 Hz, 2H), 1.72-1.57 (m, 2H), 1.48 (br d, J=3.9 Hz, 1H), 1.44 (s, 9H), 1.39-1.14 (m, 3H), 1.10 (s, 3H).

4. Preparation of Compound WV-CA-216.

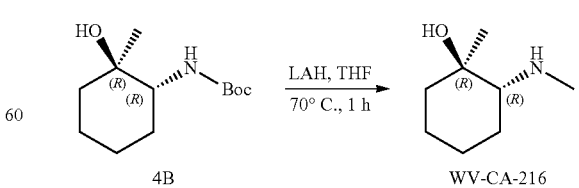

To a solution of compound 4B (22.00 g, 95.94 mmol) in THF (220.00 mL) was added LAH (10.92 g, 287.82 mmol) at 0° C. in 0.5 hr The mixture was stirred at 80° C. for 0.5 hr TLC (Petroleum ether:Ethyl acetate=5:1, R$_f$=0) indicated compound 4B was consumed and one new spot formed. The reaction was slowly added sat. MgSO$_4$ (22 mL) at 0° C. The mixture was filtered through Celatom. The filter cake was washed with EtOAc (30 mL*3). The organic phase was dried over MgSO$_4$, filtered, and concentrated in vacuo to dryness to afford crude product. The mixture was purification together with another batch (22 g scale of compound 4B). First used Petroleum Ether to wash the crude product and get 17 g product. Another residue was purified by column chromatography (SiO$_2$, Petroleum ether/Ethyl acetate=1/0 to Dichloromethane:Methanol=1:1) to get 3 g product. Altogether get 20 g product was put together with another part product (5.4 g) to get WV-CA-216 (25.4 g) as a yellow solid. $^1$H NMR (400 MHz, CHLOROFORM-d) δ=2.47-2.39 (s, 3H), 2.18 (dd, J=4.1, 11.6 Hz, 1H), 2.05-1.96 (m, 1H), 1.78-1.67 (m, 2H), 1.66-1.56 (m, 1H), 1.44-1.16 (m, 3H), 1.07 (s, 3H), 0.98-0.84 (m, 1H). $^{13}$C NMR (101 MHz, CHLOROFORM-d) δ=72.40, 67.83, 39.80, 34.64, 27.95, 25.24, 23.51, 20.24. LCMS: (M+H$^+$): 144.2; LCMS purity=100%.

Example 125. Synthesis of WV-CA-221, & WV-CA-222

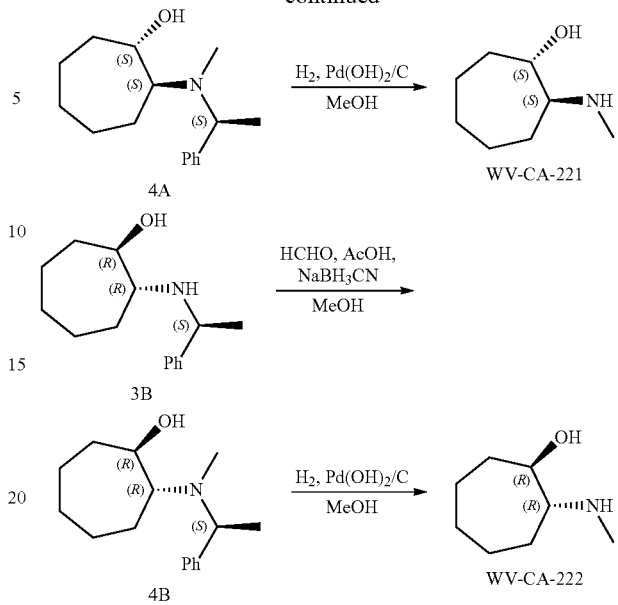

1. Preparation of Compound 2.

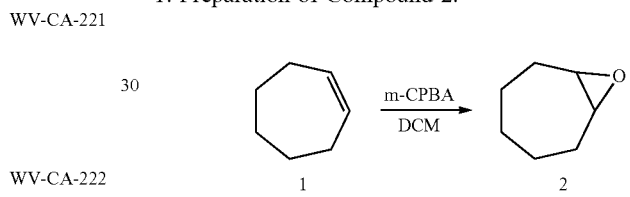

To a solution of m-CPBA (85.03 g, 418.84 mmol) in DCM (800.00 mL) was added cycloheptene (38.00 g, 395.13 mmol, 45.78 mL) dropwise at 15~40° C. The resulting solution was then stirred for 3 h at 25° C. TLC showed the reaction was completed. The reaction mixture was filtered and rinsed with DCM (500 mL). The combined filtrate was washed with sat. sodium bicarbonate solution (400 mL*3). The organic layer was dried (MgSO$_4$) filtered and evaporated under reduced pressure (30° C.) to yield a crude oil. The crude was purified by column (Petroleum ether:Ethyl acetate=1:0, 20:1) to afford the product as a colorless oil (34 g), and a crude oil (12 g). Compound 2 (46.00 g crude in total) was obtained as a colorless oil. $^1$H NMR (400 MHz, CHLOROFORM-d) δ=3.16-3.02 (m, 2H), 2.02-1.83 (m, 4H), 1.65-1.11 (m, 6H). TLC (Petroleum ether:Ethyl acetate=1:0), R$_f$=0.01.

2. Preparation of Compound 3A and 3B.

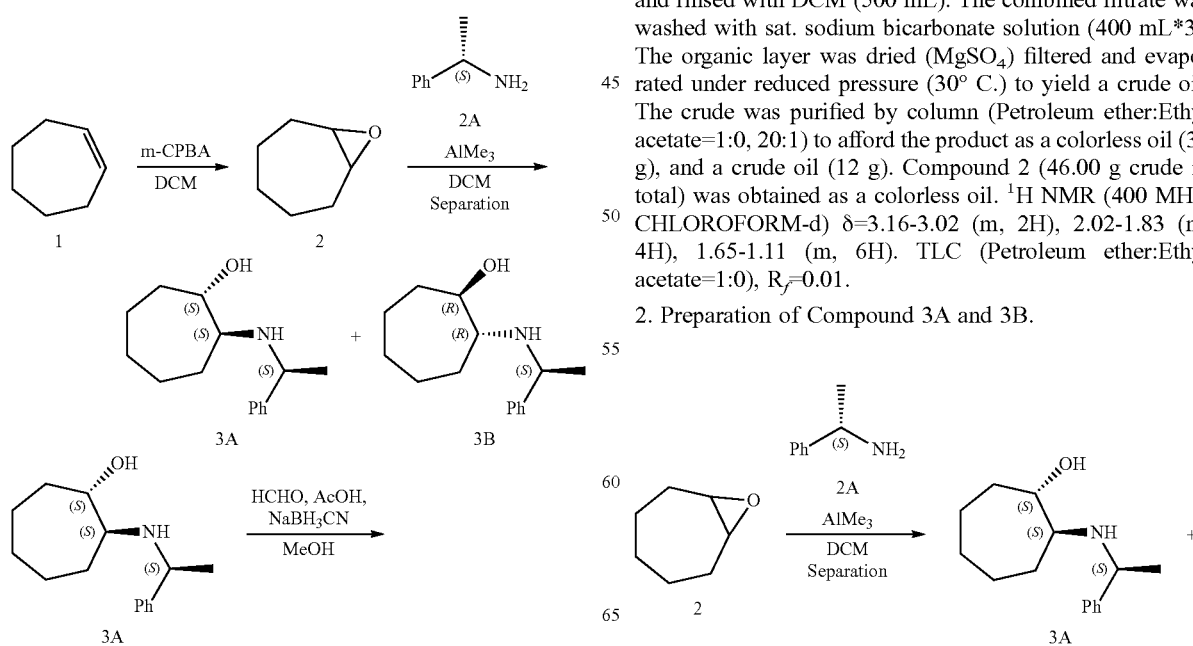

-continued

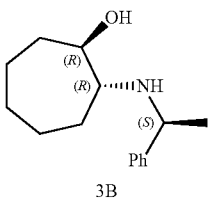

3B

A solution of AlMe$_3$ (2 M, 137.78 mL) was added dropwise at 0° C. to a rapidly stirred solution of compound 2A (33.39 g, 275.55 mmol, 35.15 mL) in 10 mL of DCM at 0° C. This solution was maintained for 1 hr at 0° C. and then a solution of compound 2 (34.00 g, 303.11 mmol) in 10 mL of DCM was added dropwise. The resulting solution was maintained for an additional 3 h at 0° C., and then left at 25° C. for 18 hr. TLC (Dichloromethane:Ethyl acetate=1:1) showed compound 2 was almost consumed, and compound 2A were partly remained. The resulting mixture was cooled to 0° C., added 53 g NaF, and cautiously added water (34 mL) under stirring. The mixture was filtered under reduced pressure through a pad of Na$_2$SO$_4$. The filtrate was concentrated to afford a light brown oil crude (61 g). The crude product was combined with another two batches of crude product (3.55 g crude, 20 g crude), and purified by column chromatography on silica gel two times (Petroleum ether: Ethyl acetate=1:0, 20:1, 20:1+2% TEA, 10:1+2% TEA) to afford compound 3A (11 g), compound 3B (13.2 g) as light yellow oil; and 45 g of the crude product. Compound 3A: $^1$H NMR (400 MHz, CHLOROFORM-d) δ=7.31 (d, J=4.2 Hz, 4H), 7.27-7.19 (m, 1H), 3.87 (q, J=6.4 Hz, 1H), 3.11 (dt, J=3.4, 8.9 Hz, 1H), 2.36 (dt, J=3.1, 9.6 Hz, 1H), 2.07-1.97 (m, 1H), 1.94-1.82 (m, 1H), 1.76-1.36 (m, 9H), 1.32 (d, J=6.4 Hz, 3H), 1.17-1.02 (m, 1H). LCMS: (M+H$^+$): 234.1; SFC purity=100%. TLC (Dichloromethane:Ethyl acetate=1: 1), Rf=0.30. Compound 3B: $^1$H NMR (400 MHz, CHLOROFORM-d) δ=7.34-7.26 (m, 4H), 7.24-7.18 (m, 1H), 3.95 (q, J=6.6 Hz, 1H), 3.15 (dt, J=3.6, 8.9 Hz, 1H), 2.06-1.95 (m, 2H), 1.87 (ddd, J=3.3, 6.7, 10.5 Hz, 1H), 1.70-1.08 (m, 13H). LCMS: (M+H$^+$): 234.0; SFC purity=98.5% de. TLC (Dichloromethane:Ethyl acetate=1:1), Rf=0.23.

3. Preparation of Compound 4A.

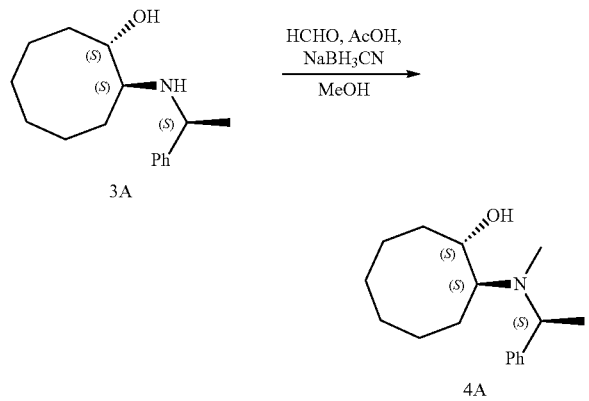

A mixture of compound 3A (11.00 g, 47.14 mmol), paraformaldehyde (12.74 g, 141.42 mmol), AcOH (537.84 mg, 8.96 mmol, 512.23 µL), NaBH$_3$CN (8.89 g, 141.42 mmol) in MeOH (100.00 mL) was degassed and purged with N$_2$ for 3 times, and then the mixture was stirred at 25° C. for 18 hr under N$_2$ atmosphere. TLC (Dichloromethane:Ethyl acetate=1:1) showed compound 3A was consumed, and one main new spot formed. The resulting mixture was concentrated to afford a residue, which was partitioned between water (100 mL) and DCM (150 mL). The separated aqueous layer was extracted with DCM (80 mL*3). The combined organic layers were washed with NaOH aq. (1M, 120 mL). The separated organic layer was dried over MgSO$_4$, filtered, and concentrated to afford the product as a light-yellow crude oil. The crude product was purified by column chromatography on silica gel (Petroleum ether:Ethyl acetate=20: 1, 20:1+1% TEA). Compound 4A (11.00 g, 94.34% yield) was obtained as a colorless oil. $^1$H NMR (400 MHz, CHLOROFORM-d) δ=7.35-7.18 (m, 5H), 4.48 (br s, 1H), 3.62 (q, J=6.6 Hz, 1H), 3.42 (dt, J=3.6, 8.9 Hz, 1H), 2.75 (dt, J=2.4, 9.6 Hz, 1H), 2.12-2.03 (m, 1H), 1.98 (s, 3H), 1.75-1.36 (m, 9H), 1.34 (d, J=6.6 Hz, 3H), 1.27-1.15 (m, 1H). LCMS: (M+H$^+$): 248.0. SFC purity=100%. TLC Dichloromethane:Ethyl acetate=1:1, Rf=0.76; Petroleum ether: Ethyl acetate=10:1, Rf=0.60.

4. Preparation of Compound 4B.

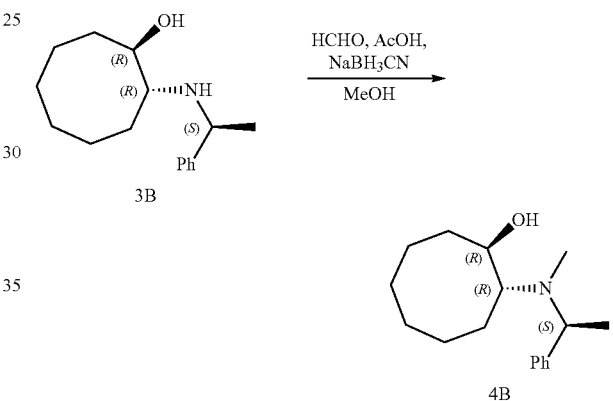

A mixture of compound 3B (13.20 g, 56.57 mmol), paraformaldehyde (15.29 g, 169.71 mmol), AcOH (525.00 mg, 8.74 mmol, 500.00 µL), NaBH$_3$CN (10.66 g, 169.71 mmol) in MeOH (130.00 mL) was degassed and purged with N$_2$ for 3 times, and then the mixture was stirred at 25° C. for 18 hr under N$_2$ atmosphere. TLC (Dichloromethane:Ethyl acetate=1:1) showed compound 3B was consumed, and one main new spot formed. The resulting mixture was concentrated to afford a residue, which was partitioned between water (120 mL) and DCM (150 mL). The separated aqueous layer was extracted with DCM (100 mL*3). The combined organic layers were washed with NaOH aq. (1M, 120 mL). The separated organic layer was dried over MgSO$_4$, filtered, and concentrated to afford the product as a light-yellow crude oil. The crude product was purified by column chromatography on silica gel (Petroleum ether:Ethyl acetate=20: 1, 20:1+1% TEA) to give compound 4B (10.00 g, 71.47% yield) as a colorless oil, and 3 g of the crude product. $^1$H NMR (400 MHz, CHLOROFORM-d) δ=7.33-7.27 (m, 2H), 7.26-7.19 (m, 3H), 4.45 (br s, 1H), 3.66 (q, J=6.5 Hz, 1H), 3.36 (dt, J=4.0, 9.2 Hz, 1H), 2.36-2.25 (m, 1H), 2.22 (s, 3H), 1.98-1.89 (m, 1H), 1.66-1.08 (m, 12H). LCMS: (M+H$^+$): 248.0. SFC purity=100%. TLC Dichloromethane:Ethyl acetate=1:1, Rf=0.76; Petroleum ether:Ethyl acetate=10:1, Rf=0.60.

5. Preparation of WV-CA-221.

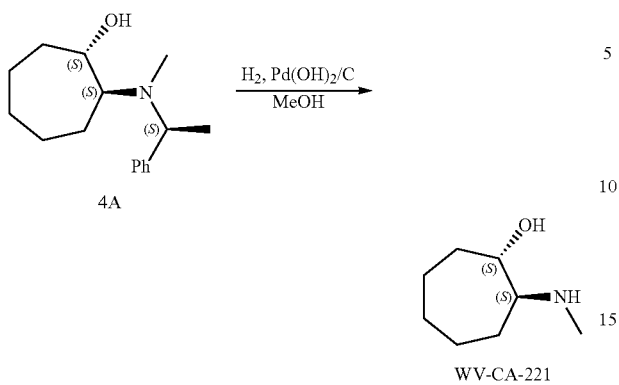

To a solution of compound 4A (11.00 g, 44.47 mmol) in MeOH (110.00 mL) was added Pd(OH)$_2$ (5.62 g, 4.00 mmol, 10% purity) under N$_2$ atmosphere. The suspension was degassed and purged with H$_2$ for 3 times. The mixture was stirred under H$_2$ (50 Psi) at 50° C. for 16 hr. TLC (Petroleum ether:Ethyl acetate=10:1) showed the reaction was completed. The resulting mixture was filtered through a pad of celite. The filtrate was concentrated to afford a light-yellow crude gum. The crude was purified by column chromatography on silica gel (Petroleum ether:Ethyl acetate=3:1, 1:1+ 5% TEA; Dichloromethane:Methanol=1:1+5% TEA). The concentrated residue was re-dissolved in DCM (50 mL), filtered and concentrated. The product WV-CA-221 (5.88 g, 92.32% yield, 100% purity) was obtained as a light-yellow oil. $^1$H NMR (400 MHz, CHLOROFORM-d) δ=3.28-3.19 (m, 1H), 3.05 (br s, 2H), 2.42 (s, 3H), 2.19 (dt, J=2.9, 9.5 Hz, 1H), 2.01-1.87 (m, 2H), 1.73-1.58 (m, 2H), 1.55-1.30 (m, 5H), 1.27-1.12 (m, 1H). $^{13}$C NMR (101 MHz, CHLOROFORM-d) δ=75.03, 67.18, 33.56, 33.15, 33.13, 28.44, 26.83, 24.04, 22.24. LCMS: (M+H$^+$): 144.2. TLC Petroleum ether:Ethyl acetate=10:1, R$_f$=0.

6. Preparation of WV-CA-222.

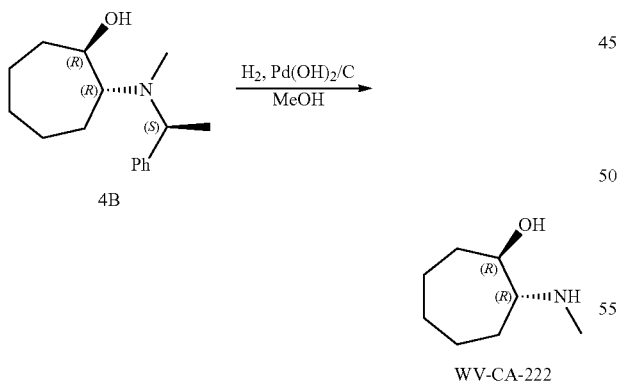

To a solution of compound 4B (10.00 g, 40.42 mmol) in MeOH (110.00 mL) was added Pd(OH)$_2$ (5.11 g, 3.64 mmol, 10% purity) under N$_2$ atmosphere. The suspension was degassed and purged with H$_2$ for 3 times. The mixture was stirred under H$_2$ (50 Psi) at 50° C. for 16 hr. TLC (Petroleum ether:Ethyl acetate=10:1) showed the reaction was completed. The resulting mixture was filtered through a pad of celite. The filtrate was concentrated to afford a light-yellow crude gum. The crude was purified by column chromatography on silica gel (Petroleum ether:Ethyl acetate=3:1, 1:1+ 5% TEA; Dichloromethane:Methanol=1:1+5% TEA). The concentrated residue was re-dissolved in DCM (50 mL), filtered and concentrated. The product WV-CA-222 (4.90 g, 84.64% yield) was obtained as a light-yellow oil. $^1$H NMR (400 MHz, CHLOROFORM-d) δ=3.28-3.17 (m, 1H), 2.87 (br s, 2H), 2.43 (s, 3H), 2.18 (dt, J=3.1, 9.5 Hz, 1H), 2.02-1.89 (m, 2H), 1.74-1.59 (m, 2H), 1.57-1.33 (m, 5H), 1.27-1.13 (m, 1H). $^{13}$C NMR (101 MHz, CHLOROFORM-d) δ=75.08, 67.18, 33.50, 33.19, 33.17, 28.52, 26.82, 24.04, 22.25. LCMS: (M+H$^+$): 144.2. TLC Petroleum ether:Ethyl acetate=10:1, R$_f$=0.

Example 126. Synthesis of WV-CA-222-dCiBu

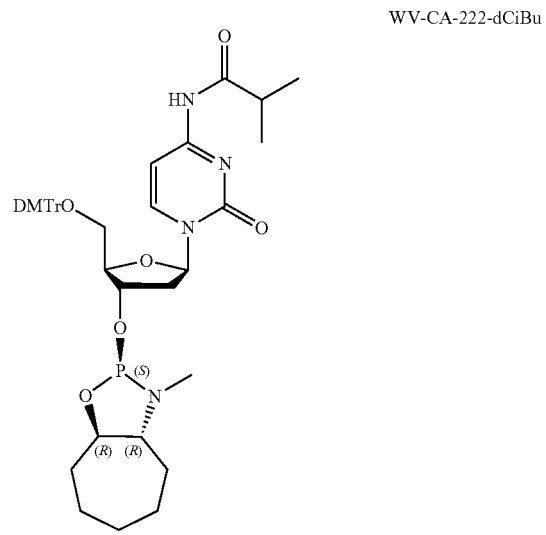

General Scheme.

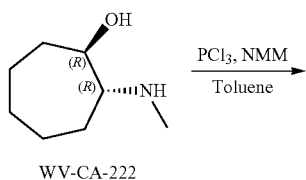

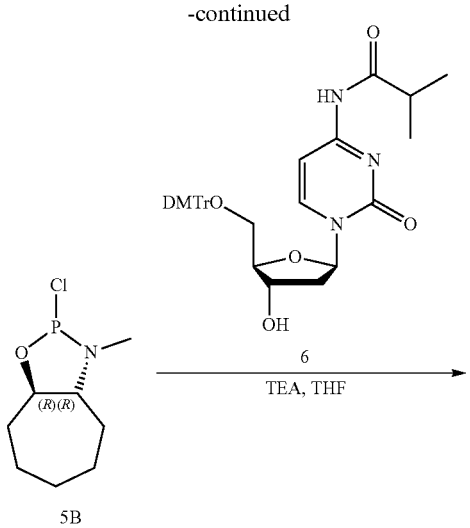

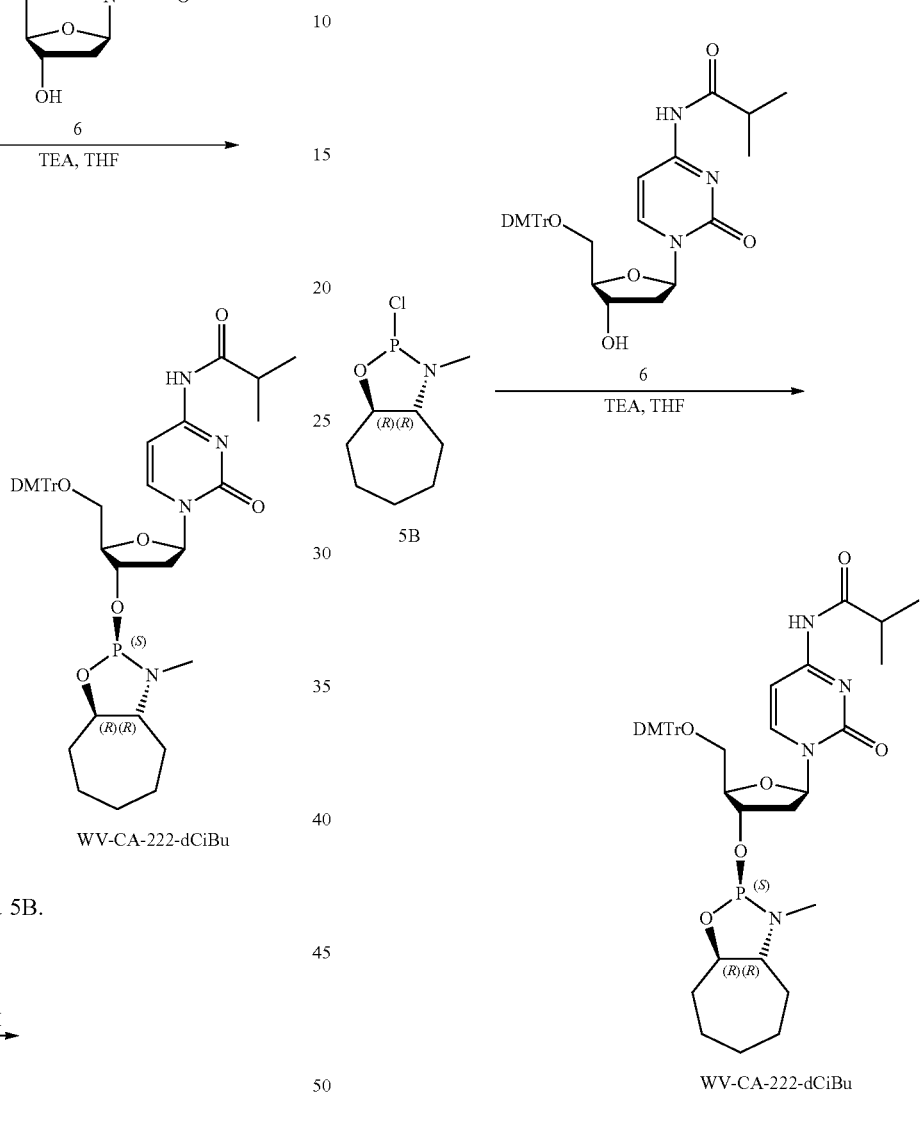

1. Preparation of Compound 5B.

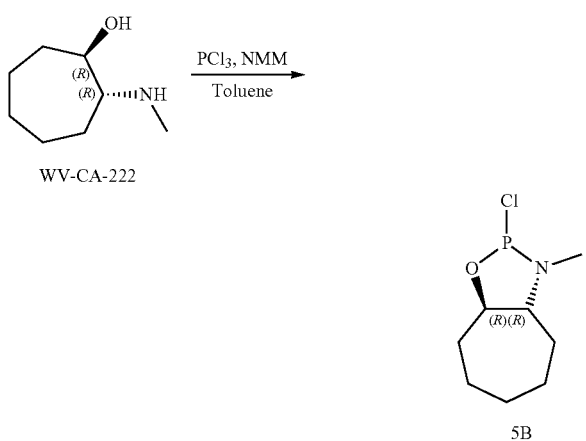

The compound WV-CA-221 (1.00 g, 6.98 mmol) was dried by azeotropic distillation on a rotary evaporator with toluene (20 mL*3). To a solution of PCl₃ (958.81 mg, 6.98 mmol) in toluene (10 mL) was added a solution of WV-CA-221 (1.00 g, 6.98 mmol) and NMM (1.41 g, 13.96 mmol, 1.54 mL) in toluene (10 mL) at 0° C. The mixture was stirred at 25° C. for 1 hr. Phosphoryl chloride was not suitable for detection. The resulting mixture was filtered (flushed with Ar) and concentrated to afford a residue as a light-yellow oil. The crude product compound 5B (1.10 g, crude) was used into the next step without further purification.

2. Preparation of Compound WV-CA-222-dCiBu.

Compound 6 (2.12 g, 3.53 mmol) was dried by azeotropic distillation on a rotary evaporator with pyridine (20 mL) and toluene (20 mL*5). The dried compound 6 (2.12 g, 3.53 mmol) was dissolved in THF (10 mL), and then TEA (2.50 g, 24.72 mmol, 3.43 mL) was added. The mixture was cooled to −70° C. A solution of compound 5B (1.10 g, 5.30 mmol) in THF (10 mL) was added dropwise at −70° C., then warmed to 25° C. over 0.5 hr and stirred for another 1 hr. TLC (Ethyl acetate:Petroleum ether=3:1, 5% TEA) showed compound 6 remained, and desired products was observed. The resulting mixture was diluted with DCM (50 mL), washed with sat. NaHCO₃ aq. (40 mL*3). The organic layer was dried over anhydrous MgSO₄, filtered, and concentrated to afford a white foam (3.1 g). The MPLC column (flash Silica (CS), 40-60 μm, 60 A, 20 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (25 mL, 5% TEA) was loaded and purified with Ethyl acetate (5% TEA):Petroleum ether (5% TEA)=20%~40%. All solvent was dried over anhydrous $Na_2SO_4$. Compound WV-CA-222-dCiBu (1.70 g, 62.55% yield) was obtained as a white solid.

$^1$H NMR (400 MHz, CHLOROFORM-d) δ=9.07 (br s, 1H), 8.26 (d, J=7.5 Hz, 1H), 7.41 (d, J=7.4 Hz, 2H), 7.35-7.21 (m, 7H), 7.13 (d, J=7.4 Hz, 1H), 6.85 (br d, J=7.5 Hz, 4H), 6.26 (t, J=5.6 Hz, 1H), 4.88-4.79 (m, 1H), 4.20 (dt, J=4.6, 9.6 Hz, 1H), 4.15-4.08 (m, 1H), 3.81 (s, 6H), 3.50-3.40 (m, 2H), 2.81-2.65 (m, 3H), 2.60 (d, J=11.9 Hz, 3H), 2.29-2.06 (m, 3H), 1.76-1.36 (m, 8H), 1.20 (t, J=6.5 Hz, 6H). $^{13}$C NMR (101 MHz, CHLOROFORM-d) δ=177.15, 162.56, 158.68, 158.66, 155.09, 144.50, 144.14, 135.52, 135.33, 130.14, 130.04, 128.24, 127.96, 127.10, 113.27, 96.31, 86.91, 86.86, 85.65 (dd, J=3.7, 5.9 Hz, 1C), 70.07, 69.96, 66.30, 66.26, 62.06, 55.20, 46.20, 41.37, 41.35, 36.40, 34.43, 32.22, 32.19, 31.12, 30.79, 29.80, 26.14, 25.05, 24.57, 19.19, 19.00. $^{31}$P NMR (162 MHz, CHLOROFORM-d) δ=148.82 (s, 1P). TLC (Ethyl acetate:Petroleum ether=3:1, 5% TEA), $R_f$=0.67.

Example 127. Synthesis of WV-CA-223, & WV-CA-224

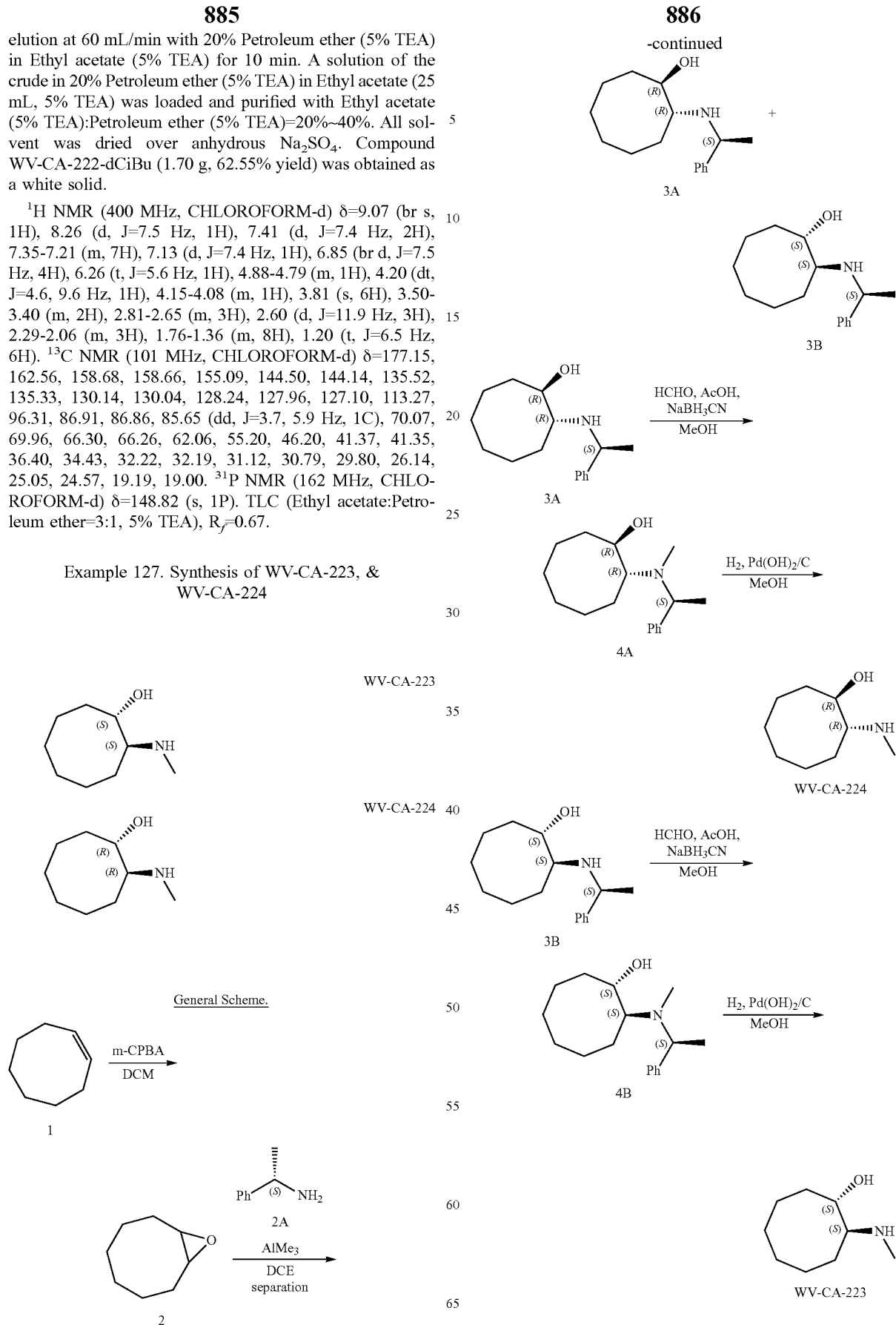

1. Preparation of Compound 2.

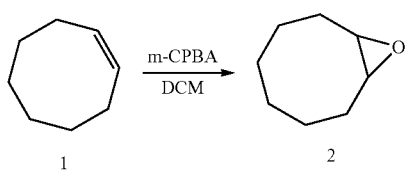 [SMILES: C1=C\CCCCCC/1 ; C1CCCC2OC2CC1]

To a solution of m-CPBA (195.29 g, 961.89 mmol) in DCM (2.00 L) was added cis-cyclooctene (100.00 g, 907.44 mmol, 117.65 mL) dropwise at 15~40° C. The resulting solution was then stirred for 3 h at 25° C. TLC showed the reaction was completed. The reaction mixture was filtered and rinsed with DCM (500 mL). The combined filtrate was washed with sat. sodium bicarbonate solution (500 mL*3). The organic layer was dried (MgSO$_4$) filtered and evaporated to yield a crude. The crude was purified by column (Petroleum ether:Ethyl acetate=40:1, 20:1) to afford the product as a colorless oil. Compound 2 (109.70 g, 95.79% yield) was obtained as a colorless oil. $^1$H NMR (400 MHz, CHLOROFORM-d) δ=2.92-2.86 (m, 2H), 2.18-2.09 (m, 2H), 1.67-1.39 (m, 8H), 1.35-1.20 (m, 2H). TLC (Petroleum ether:Ethyl acetate=1:0), R$_f$=0.01.

2. Preparation of Compound 3A and 3B.

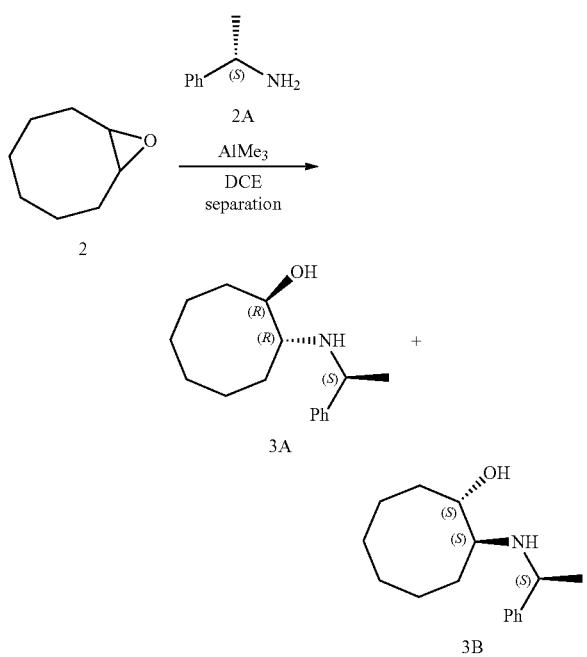

A solution of AlMe3 (2 M, 437.37 mL) was added dropwise at 0° C. to a rapidly stirred solution of compound 2A (106.00 g, 874.73 mmol, 111.58 mL) in 600 mL of 1,2-dichloroethane at 0° C. This solution was maintained for 1 h at 0° C. and then a solution of compound 2 (115.91 g, 918.47 mmol) in 600 mL of 1,2-dichloroethane was added dropwise. The resulting solution was heated at 25° C. for 35 hr. TLC (Dichloromethane:Ethyl acetate=1:1) showed compound 2A and compound 2 were partly remained. The mixture was heated at 85° C. for 72 hr. TLC (Dichloromethane:Ethyl acetate=1:1) showed compound 2A and compound 2 were partly remained. The resulting mixture was cooled to 0° C., added 154 g NaF, and cautiously added water (100 mL) under stirring. The mixture was filtered under reduced pressure through a pad of Na$_2$SO$_4$. The filtrate was concentrated to afford a light brown oil (220 g). The crude was purified by column (Petroleum ether:Ethyl acetate=1:0, 20:1, 10:1+3% TEA) to afford compound 3A (11.6 g), compound 3B (9.5 g), and a mixture of compound 3A and 3B (70 g) as light yellow oil. Compound 3A: $^1$H NMR (400 MHz, CHLOROFORM-d) δ=7.39-7.22 (m, 5H), 3.87 (q, J=6.4 Hz, 1H), 3.31-3.21 (m, 1H), 2.65-2.51 (m, 1H), 2.00-1.89 (m, 1H), 1.85-1.66 (m, 4H), 1.64-1.41 (m, 9H), 1.35 (d, J=6.4 Hz, 3H). LCMS: (M+H$^+$): 248.1. TLC (Dichloromethane:Ethyl acetate=1:1), R$_f$=0.30. Compound 3B: $^1$H NMR (400 MHz, CHLOROFORM-d) δ=7.36-7.28 (m, 4H), 7.26-7.21 (m, 1H), 3.94 (q, J=6.4 Hz, 1H), 3.28 (ddd, J=2.9, 6.9, 9.4 Hz, 1H), 2.27-2.16 (m, 1H), 1.92-1.76 (m, 3H), 1.69-1.38 (m, 11H), 1.36 (d, J=6.6 Hz, 3H). LCMS: (M+H$^+$): 248.1. TLC (Dichloromethane:Ethyl acetate=1:1), R$_f$=0.23.

3. Preparation of Compound 4A.

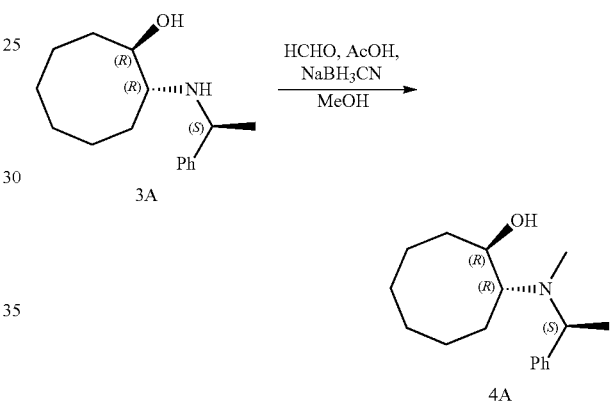

A mixture of compound 3A (11.60 g, 46.89 mmol), paraformaldehyde (12.67 g, 140.67 mmol), AcOH (534.99 mg, 8.91 mmol, 509.52 µL), NaBH$_3$CN (8.84 g, 140.67 mmol) in MeOH (120.00 mL) was degassed and purged with N$_2$ for 3 times, and then the mixture was stirred at 25° C. for 16 hr under N$_2$ atmosphere. LCMS showed the intermediated imine was observed. Additionally, added 4 g paraformaldehyde and 7 g NaBH$_3$CN, stirring was continued at 25° C. for 4 hr. TLC (Dichloromethane:Ethyl acetate=1:1) showed compound 3A was consumed, and one main new spot formed. The resulting mixture was concentrated to afford a residue, which was partitioned between water (100 mL) and DCM (150 mL). The separated aqueous layer was extracted with DCM (100 mL*3). The combined organic layers were dried over MgSO$_4$, filtered, and concentrated to afford the product as a light-yellow crude oil. The crude product was purified by column chromatography on silica gel (Petroleum ether:Ethyl acetate=20:1, 20:1+1% TEA). Compound 4A (8.20 g, 66.90% yield) was obtained as a colorless oil. $^1$H NMR (400 MHz, CHLOROFORM-d) δ=7.35-7.20 (m, 5H), 4.78 (br s, 1H), 3.62 (q, J=6.6 Hz, 1H), 3.49 (ddd, J=3.1, 7.2, 9.8 Hz, 1H), 3.04-2.92 (m, 1H), 2.04-1.93 (m, 4H), 1.80-1.47 (m, 10H), 1.37 (d, J=6.8 Hz, 3H), 1.33-1.20 (m, 1H). LCMS: (M+H$^+$): 262.1. SFC purity=100%. TLC Dichloromethane:Ethyl acetate=1:1, R$_f$=0.76; Petroleum ether:Ethyl acetate=10:1, R$_f$=0.60.

4. Preparation of Compound 4B.

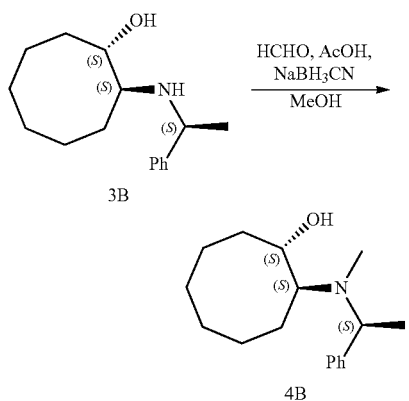

A mixture of compound 3B (9.50 g, 38.40 mmol), paraformaldehyde (10.38 g, 115.20 mmol), AcOH (530.36 mg, 8.83 mmol, 505.11 μL), NaBH$_3$CN (7.24 g, 115.20 mmol) in MeOH (120.00 mL) was degassed and purged with N$_2$ for 3 times, and then the mixture was stirred at 25° C. for 16 hr under N$_2$ atmosphere. Additionally, added 4 g paraformaldehyde and 7 g NaBH$_3$CN, stirring was continued at 25° C. for 4 hr. TLC (Dichloromethane:Ethyl acetate=1:1) showed compound 3B was consumed, and one main new spot formed. The resulting mixture was concentrated to afford a residue, which was partitioned between water (100 mL) and DCM (150 mL). The separated aqueous layer was extracted with DCM (100 mL*3). The combined organic layers were dried over MgSO$_4$, filtered, and concentrated to afford the product as a light-yellow crude oil. The crude product was purified by column chromatography on silica gel (Petroleum ether:Ethyl acetate=20:1, 20:1+1% TEA) to give 5.1 g product as a colorless oil, and a crude (3.7 g), which was further purified by column chromatography on silica gel (Petroleum ether:Ethyl acetate=20:1, 20:1+1% TEA) to give 1.7 g product as a colorless oil, and 1.2 g crude. Compound 4B (6.80 g, 67.73% yield) was obtained as a colorless oil. $^1$H NMR (400 MHz, CHLOROFORM-d) δ=7.35-7.20 (m, 5H), 4.78 (br s, 1H), 3.62 (q, J=6.6 Hz, 1H), 3.49 (ddd, J=3.1, 7.2, 9.8 Hz, 1H), 3.04-2.92 (m, 1H), 2.04-1.93 (m, 4H), 1.80-1.47 (m, 10H), 1.37 (d, J=6.8 Hz, 3H), 1.33-1.20 (m, 1H). LCMS: (M+H$^+$): 262.1. SFC purity >99%. TLC Dichloromethane:Ethyl acetate=1:1, R$_f$=0.73; Petroleum ether:Ethyl acetate=10:1, R$_f$=0.47.

5. Preparation of WV-CA-224.

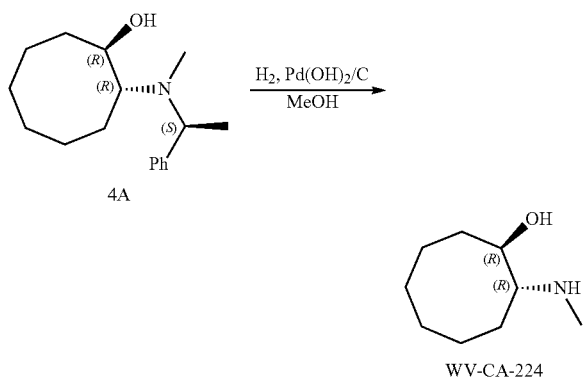

To a solution of compound 4A (8.40 g, 32.13 mmol) in MeOH (100.00 mL) was added Pd(OH)$_2$ (4.06 g, 2.89 mmol, 10% purity) under N$_2$ atmosphere. The suspension was degassed and purged with H$_2$ for 3 times. The mixture was stirred under H$_2$ (50 psi) at 50° C. for 16 hr. TLC (Petroleum ether:Ethyl acetate=10:1) showed the reaction was completed. The resulting mixture was filtered through a pad of celite. The filtrated was concentrated to afford a light-yellow crude gum. The crude was combined with another batch crude product (290 mg), and purified by column chromatography on silica gel (Petroleum ether:Ethyl acetate=3:1, 1:1+5% TEA; Dichloromethane:Methanol=1:1+5% TEA). The concentrated residue was re-dissolved in DCM (50 mL), filtered and concentrated to afford the product WV-CA-224 (4.69 g, 92.84% yield) as a light-yellow oil. $^1$H NMR (400 MHz, CHLOROFORM-d) δ=3.36-3.25 (m, 1H), 2.42 (s, 3H), 2.34-2.27 (m, 1H), 2.14 (br s, 2H), 1.97-1.79 (m, 2H), 1.75-1.38 (m, 10H). $^{13}$C NMR (101 MHz, CHLOROFORM-d) δ=74.16, 64.67, 33.39, 31.70, 28.40, 26.88, 25.64, 25.52, 23.14. LCMS: (M+H$^+$): 158.2. TLC Petroleum ether:Ethyl acetate=10:1, R$_f$=0.

6. Preparation of WV-CA-223.

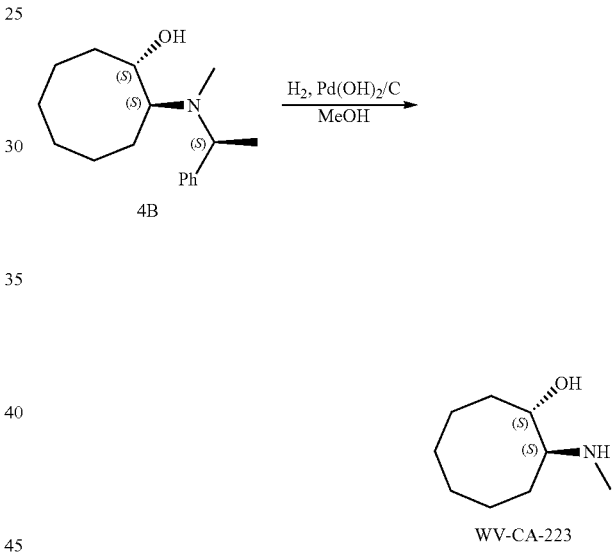

To a solution of compound 4B (7.20 g, 27.54 mmol) in MeOH (100.00 mL) was added Pd(OH)$_2$ (3.48 g, 2.48 mmol, 10% purity) under N$_2$ atmosphere. The suspension was degassed and purged with H$_2$ for 3 times. The mixture was stirred under H$_2$ (50 Psi) at 50° C. for 16 hr. TLC (Petroleum ether:Ethyl acetate=10:1) showed the reaction was completed. The resulting mixture was filtered through a pad of celite. The filtrated was concentrated to afford a light-yellow crude gum. The crude was purified by column chromatography on silica gel (Petroleum ether:Ethyl acetate=3:1, 1:1+5% TEA; Dichloromethane:Methanol=1:1+5% TEA). The concentrated residue was re-dissolved in DCM (50 mL), filtered and concentrated to afford the product WV-CA-223 (3.96 g, 91.43% yield) as a light-yellow oil. $^1$H NMR (400 MHz, CHLOROFORM-d) δ=3.36-3.24 (m, 1H), 2.45-2.40 (m, 3H), 2.39-2.11 (m, 3H), 1.98-1.78 (m, 2H), 1.76-1.39 (m, 10H). $^{13}$C NMR (101 MHz, CHLOROFORM-d) δ=74.18, 64.67, 33.40, 31.71, 28.38, 26.87, 25.64, 25.53, 23.14. LCMS: (M+H$^+$): 158.2. TLC Petroleum ether:Ethyl acetate=10:1, R$_f$=0.

Example 128. Synthesis of WV-CA-223-dCiBu

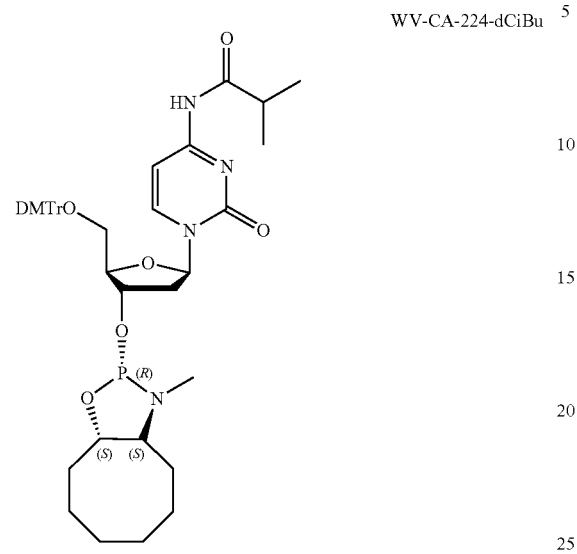

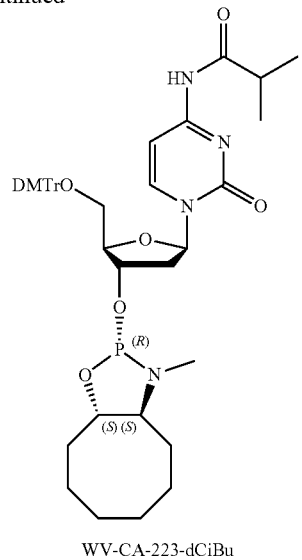

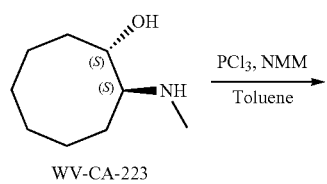

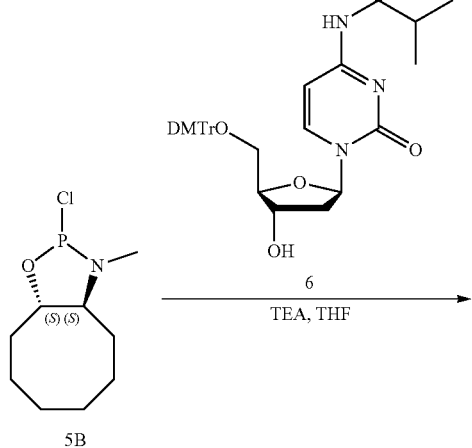

1. Preparation of Compound 5B.

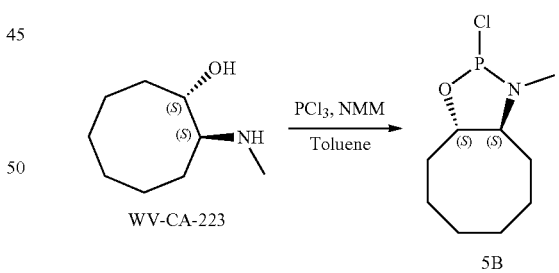

The compound WV-CA-223 (1.00 g, 6.36 mmol) was dried by azeotropic distillation on a rotary evaporator with toluene (20 mL*3). To a solution of PCl₃ (873.32 mg, 6.36 mmol) in toluene (10 mL) was added a solution of WV-CA-223 (1.00 g, 6.36 mmol) and NMM (1.29 g, 12.72 mmol, 1.40 mL) in toluene (10 mL) at 0° C. The mixture was stirred at 25° C. for 1 hr. Phosphoryl chloride was not suitable for detection. The resulting mixture was filtered (flushed with Ar) and concentrated to afford a residue as a colorless oil. The crude product compound 5B (1.20 g, crude) was used into the next step without further purification.

2. Preparation of Compound WV-CA-223-dCiBu.

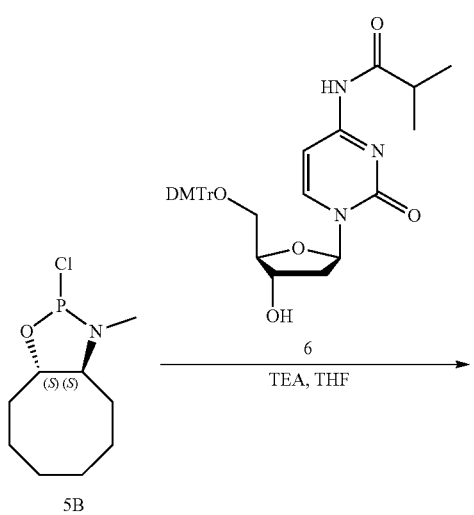

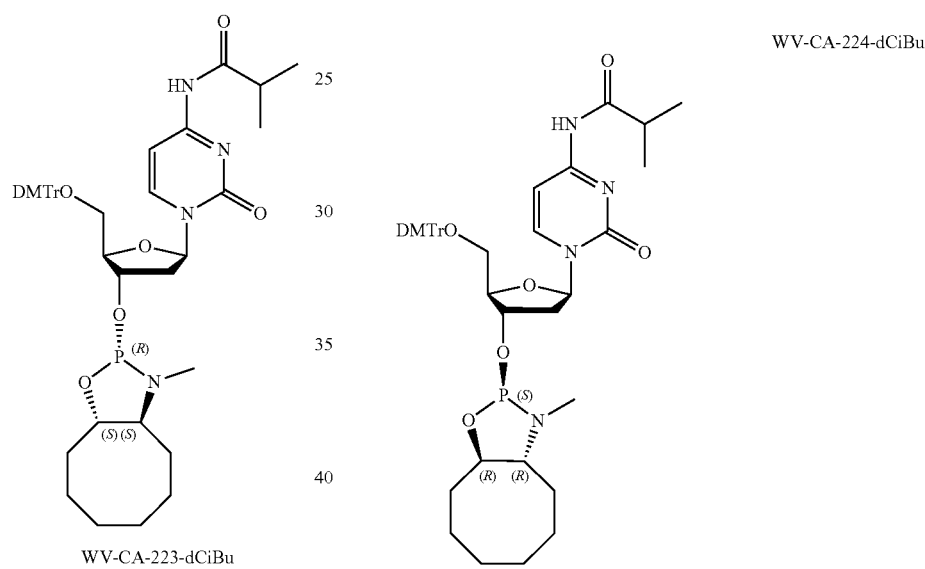

WV-CA-223-dCiBu

Compound 6 (2.16 g, 3.61 mmol) was dried by azeotropic distillation on a rotary evaporator with pyridine (20 mL) and toluene (20 mL*5). The dried compound 6 (2.16 g, 3.61 mmol) was dissolved in THF (15 mL), and then TEA (2.56 g, 25.26 mmol, 3.50 mL) was added. The mixture was cooled to −70° C. A solution of compound 5B (1.20 g, 5.41 mmol) in THF (15 mL) was added dropwise at −70° C., then warmed to 25° C. over 0.5 hr and stirred for another 1 hr. TLC (Ethyl acetate:Petroleum ether=3:1, 5% TEA) showed compound 6 was almost consumed, and desired product was observed. The resulting mixture was diluted with DCM (50 mL), washed with sat. NaHCO₃ aq. (40 mL*3). The organic layer was dried over anhydrous MgSO₄, filtered, and concentrated to afford a white foam (3.3 g). The MPLC column (flash Silica (CS), 40-60 μm, 60 A, 20 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (25 mL, 5% TEA) was loaded and purified with Ethyl acetate (5% TEA):Petroleum ether (5% TEA)=20%~40%. All solvent was dried over anhydrous Na₂SO₄. Compound WV-CA-223-dCiBu (2.00 g, 70.70% yield) was obtained as a white solid. $^1$H NMR (400 MHz, CHLOROFORM-d) δ=8.83 (br s, 1H), 8.29 (d, J=7.5 Hz, 1H), 7.42 (d, J=7.4 Hz, 2H), 7.36-7.23 (m, 7H), 7.14 (d, J=7.5 Hz, 1H), 6.86 (dd, J=1.4, 8.7 Hz, 4H), 6.25 (t, J=5.6 Hz, 1H), 4.80-4.72 (m, 1H), 4.45-4.37 (m, 1H), 4.10 (br s, 1H), 3.81 (s, 6H), 3.45 (dq, J=3.1, 10.8 Hz, 2H), 2.95-2.87 (m, 1H), 2.72-2.60 (m, 5H), 2.29-2.20 (m, 1H), 2.15-2.06 (m, 2H), 1.80-1.31 (m, 10H), 1.23-1.19 (m, 6H). $^{13}$C NMR (101 MHz, CHLOROFORM-d) δ=177.21, 162.63, 158.68, 158.66, 155.08, 144.50, 144.14, 135.53, 135.35, 130.12, 130.04, 128.23, 127.97, 127.09, 113.27, 96.36, 86.92, 86.81, 86.31, 86.21, 85.62, 85.60, 69.64, 69.53, 65.37, 65.33, 61.97, 55.19, 41.41, 41.38, 36.35, 35.92, 35.88, 33.92, 30.72, 30.40, 26.97, 26.84, 22.81, 22.32, 19.21, 19.00. $^{31}$P NMR (162 MHz, CHLOROFORM-d) δ=141.64 (s, 1P). TLC (Ethyl acetate:Petroleum ether=3:1, 5% TEA), R$_f$=0.60.

Example 129. Synthesis of WV-CA-224-dCiBu

WV-CA-224-dCiBu

General Scheme.

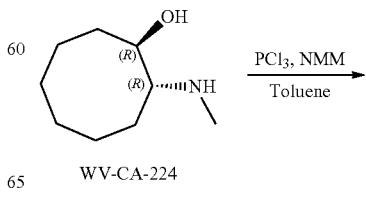

WV-CA-224

895

-continued

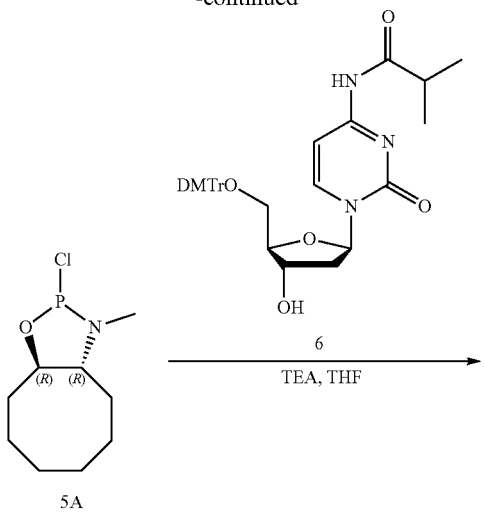

1. Preparation of Compound 5A.

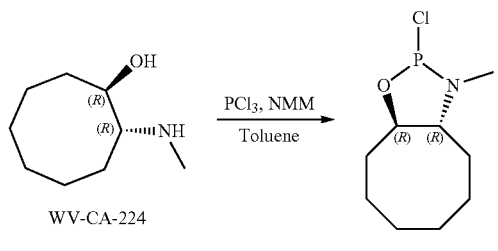

The compound WV-CA-224 (1.00 g, 6.36 mmol) was dried by azeotropic distillation on a rotary evaporator with toluene (20 mL*3). To a solution of PCl₃ (873.32 mg, 6.36 mmol) in toluene (10 mL) was added a solution of WV-CA-224 (1.00 g, 6.36 mmol) and NMM (1.29 g, 12.72 mmol, 1.40 mL) in toluene (10 mL) at 0° C. The mixture was stirred at 25° C. for 1 hr. Phosphoryl chloride was not suitable for detection. The resulting mixture was filtered (flushed with Ar) and concentrated to afford a residue as a colorless oil.

The crude product compound 5A (1.41 g, crude) was used into the next step without further purification.

2. Preparation of Compound WV-CA-224-dCiBu.

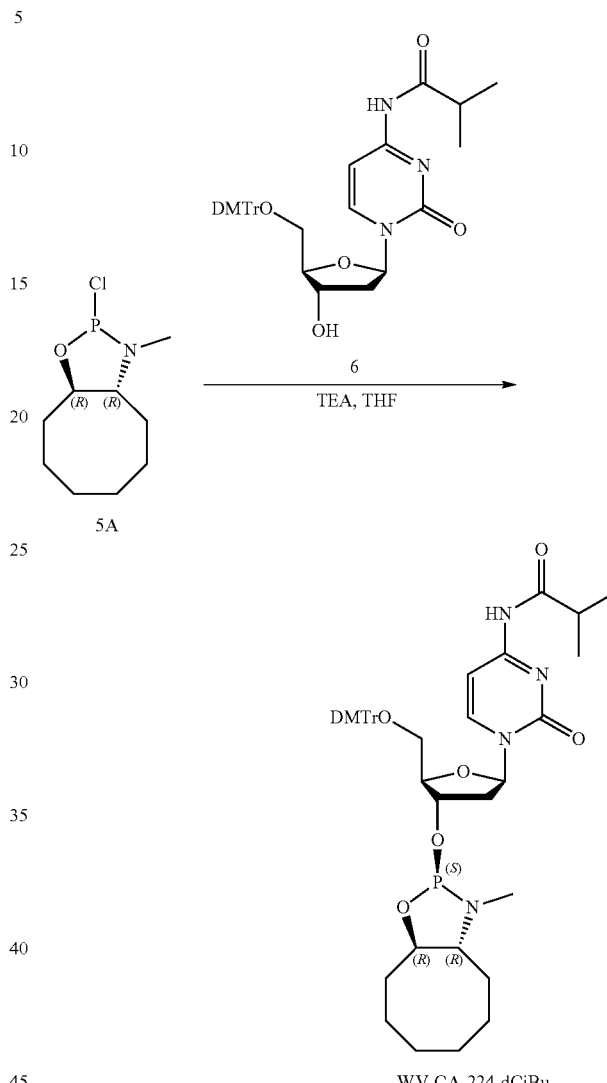

Compound 6 (2.54 g, 4.24 mmol) was dried by azeotropic distillation on a rotary evaporator with pyridine (20 mL) and toluene (20 mL*5). The dried compound 6 (2.54 g, 4.24 mmol) was dissolved in THF (15 mL), and then TEA (3.00 g, 29.68 mmol, 4.11 mL) was added. The mixture was cooled to −70° C. A solution of compound 5A (1.41 g, 6.36 mmol) in THF (15 mL) was added dropwise at −70° C., then warmed to 25° C. over 0.5 hr and stirred for another 1 hr. TLC (Ethyl acetate:Petroleum ether=3:1, 5% TEA) showed compound 6 remained, and the desired product was observed. The resulting mixture was diluted with DCM (50 mL), washed with sat. NaHCO₃ aq. (40 mL*3). The organic layer was dried over anhydrous MgSO₄, filtered, and concentrated to afford a white foam (3.78 g). The MPLC column (flash Silica (CS), 40-60 m, 60 A, 20 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (25 mL, 5% TEA) was loaded and purified with Ethyl acetate (5% TEA):Petroleum ether (5% TEA)=20%~70%. All solvent was dried over anhydrous Na$_2$SO$_4$. Compound WV-CA-224-dCiBu was obtained as a white solid (2.00 g, 2.55 mmol, 60.14% yield), which was purified by MPLC again. The MPLC column (flash Silica (CS), 40-60 μm, 60A, 20 g) was basified by the elution at 60 mL/min with 20% Petroleum ether (5% TEA) in Ethyl acetate (5% TEA) for 10 min. A solution of the crude in 20% Petroleum ether (5% TEA) in Ethyl acetate (25 mL, 5% TEA) was loaded and purified with Ethyl acetate (5% TEA):Petroleum ether (5% TEA)=20%~50%. All solvent was dried over anhydrous Na$_2$SO$_4$. Compound WV-CA-224-dCiBu (1.70 g) was obtained as a white solid. $^1$H NMR (400 MHz, CHLOROFORM-d) δ=8.90 (br s, 1H), 8.39 (d, J=7.4 Hz, 1H), 7.43 (d, J=7.4 Hz, 2H), 7.36-7.23 (m, 7H), 7.18 (d, J=7.4 Hz, 1H), 6.87 (dd, J=1.3, 8.7 Hz, 4H), 6.22 (dd, J=4.1, 6.3 Hz, 1H), 4.79-4.70 (m, 1H), 4.53-4.46 (m, 1H), 4.11-4.04 (m, 1H), 3.81 (s, 6H), 3.52-3.38 (m, 2H), 2.95-2.85 (m, 1H), 2.74-2.53 (m, 5H), 2.32 (ddd, J=4.1, 6.5, 13.7 Hz, 1H), 2.08 (br dd, J=4.1, 7.6 Hz, 2H), 1.80-1.28 (m, 10H), 1.21 (t, J=6.6 Hz, 6H). $^{13}$C NMR (101 MHz, CHLOROFORM-d) δ=177.13, 162.58, 158.68, 158.65, 155.08, 144.54, 144.09, 135.56, 135.37, 130.12, 130.01, 128.23, 128.01, 127.09, 113.31, 96.34, 86.96, 86.75, 86.65, 86.56, 85.25, 85.20, 69.15, 69.04, 65.56, 65.51, 61.40, 55.20, 46.12, 41.25, 36.39, 36.02, 35.98, 33.85, 30.82, 30.50, 26.95, 26.84, 22.86, 22.28, 19.20, 19.02. $^{31}$P NMR (162 MHz, CHLOROFORM-d) δ=141.23 (s, 1P). TLC (Ethyl acetate:Petroleum ether=3:1, 5% TEA), R$_f$=0.59.

Example 130. Synthesis of WV-CA-225

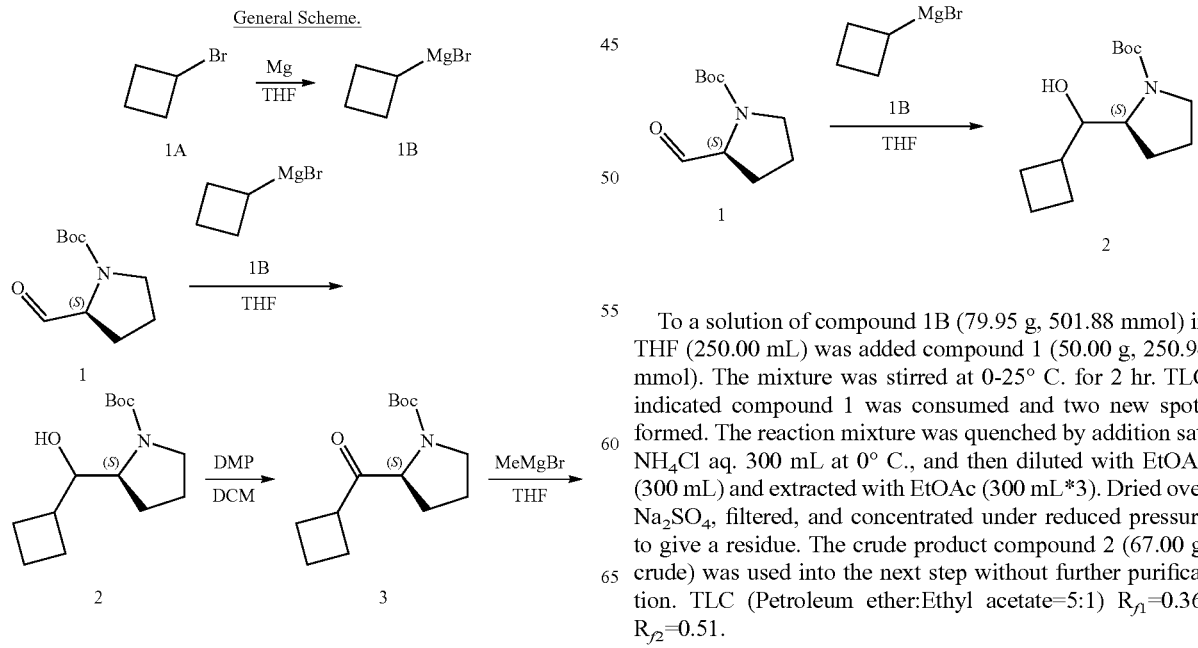

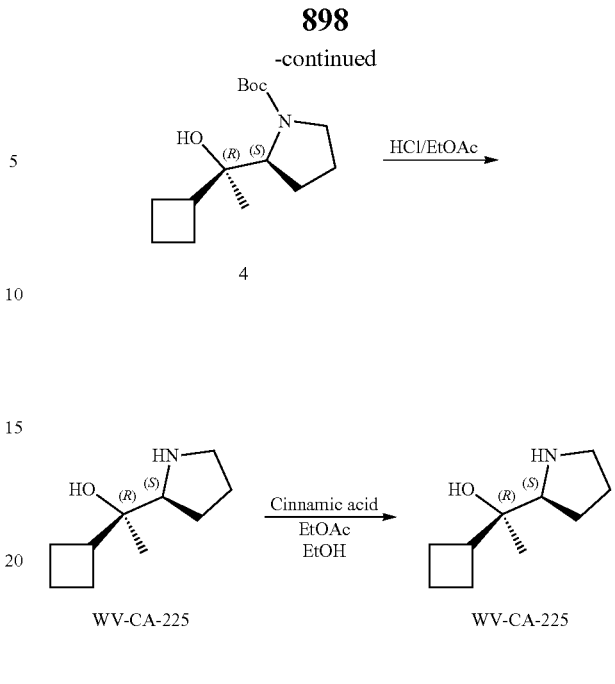

1. Preparation of Compound 1B.

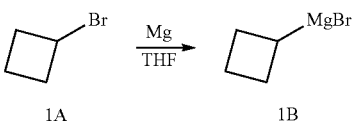

To a solution of magnesium (14.64 g, 602.26 mmol) in THF (502.00 mL) was added a grain of I$_2$, and then added bromocyclobutane (4.07 g, 30.15 mmol, 2.85 mL). The mixture was stirred at 25-60° C. for 2 hr. Mg was almost consumed. The crude product compound 1B was used into the next step without further purification.

2. Preparation of Compound 2.

To a solution of compound 1B (79.95 g, 501.88 mmol) in THF (250.00 mL) was added compound 1 (50.00 g, 250.94 mmol). The mixture was stirred at 0-25° C. for 2 hr. TLC indicated compound 1 was consumed and two new spots formed. The reaction mixture was quenched by addition sat. NH$_4$Cl aq. 300 mL at 0° C., and then diluted with EtOAc (300 mL) and extracted with EtOAc (300 mL*3). Dried over Na$_2$SO$_4$, filtered, and concentrated under reduced pressure to give a residue. The crude product compound 2 (67.00 g, crude) was used into the next step without further purification. TLC (Petroleum ether:Ethyl acetate=5:1) R$_{f1}$=0.36, R$_{f2}$=0.51.

3. Preparation of Compound 3.

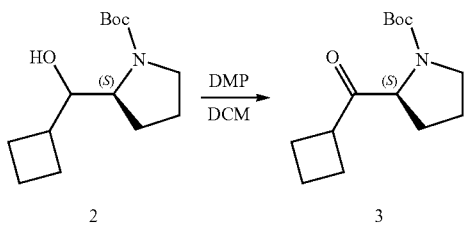

To a solution of compound 2 (67.00 g, 262.38 mmol) in DCM (670.00 mL) was added DMP (133.54 g, 314.86 mmol, 97.47 mL) at 0-5° C. in 0.5 hr. The mixture was stirred at 0-25° C. for 2 hr. TLC indicated compound 2 was consumed and one new spot formed. LC-MS showed compound 2 was consumed and one main peak with desired MS was detected. The reaction was quenched with sat. Na$_2$SO$_3$ aq. and sat. NaHCO$_3$ aq. (V/V=3:2, 5 L), filtered the solid, extracted with DCM (700 mL*3). The combined organic layers were dried over anhydrous MgSO$_4$, filtered, and concentrated to afford a crude. The residue was purified by column chromatography (SiO$_2$, Petroleum ether/Ethyl acetate=1/0 to 0:1). Get 52 g product. Compound 3 (52.00 g, 205.26 mmol, 78.23% yield) was obtained as a white solid. $^1$H NMR (400 MHz, CHLOROFORM-d) δ=4.38-4.16 (m, 1H), 3.59-3.33 (m, 3H), 2.38-2.18 (m, 2H), 2.17-1.90 (m, 4H), 1.88-1.70 (m, 4H), 1.51-1.33 (m, 9H). LCMS: (M+Na+): 276.1. TLC (Petroleum ether:Ethyl acetate=5:1) R$_f$=0.51.

4. Preparation of Compound 4.

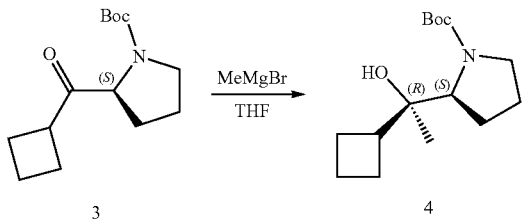

To a solution of compound 3 (51.00 g, 201.31 mmol) in THF (510.00 mL) was added MeMgBr (3 M, 67.10 mL) under N$_2$ at 0° C. The mixture was stirred at 0-25° C. for 2 hr. LC-MS showed compound 3 was remained. The reaction mixture was quenched by the addition of NH$_4$Cl (500 mL) at 0° C., and then diluted with EtOAc (400 mL) and extracted with EtOAc (400 mL*3). Dried over Na$_2$SO$_4$, filtered, and concentrated under reduced pressure to give a residue. The residue was purified by column chromatography (SiO$_2$, Petroleum ether/Ethyl acetate=1/0 to 1:1) get compound 4 (24 g). Compound 4 (24.00 g, 89.09 mmol, 44.26% yield) was obtained as a yellow oil. $^1$H NMR (400 MHz, CHLOROFORM-d) δ=3.84 (br t, J=7.5 Hz, 1H), 3.56 (br s, 1H), 3.09-2.95 (m, 1H), 2.44-2.29 (m, 1H), 2.16-2.02 (m, 2H), 1.99-1.91 (m, 1H), 1.87-1.55 (m, 7H), 1.41 (s, 9H), 1.02-0.86 (m, 3H). HPLC: HPLC purity=95.1%.

5. Preparation of Compound 4.

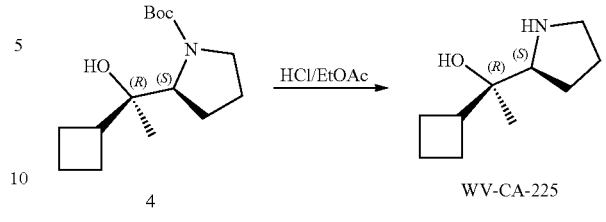

To a solution of compound 4 (23.90 g, 88.72 mmol) in EtOAc (10.00 mL) was added HCl/EtOAc (230.00 mL) at 0° C. The mixture was stirred at 0-25° C. for 2 hr. TLC indicated compound 4 was consumed and one new spot formed. The reaction mixture was concentrated under reduced pressure to remove solvent at 30-35° C. The residue was diluted with Na$_2$CO$_3$ until pH=11 and extracted with DCM (15 mL*3), dried over Na$_2$SO$_4$, filtered and concentrated under reduced pressure to give a residue. Compound WV-CA-225 (12.00 g, 70.90 mmol, 79.91% yield) was obtained as a white solid. H NMR: $^1$H NMR (400 MHz, CHLOROFORM-d) δ=3.19-3.00 (m, 2H), 2.95-2.79 (m, 3H), 2.47-2.32 (m, 1H), 2.17-2.02 (m, 1H), 1.99-1.86 (m, 1H), 1.84-1.50 (m, 9H), 1.05 (s, 3H). TLC (Petroleum ether:Ethyl acetate=5:1) R$_f$=0.

6. Purification of compound 4.

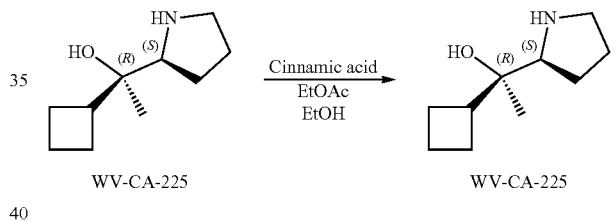

To a mixture of WV-CA-225 (10.00 g, 59.08 mmol) in EtOH (15.00 mL) was added cinnamic acid (8.75 g, 59.08 mmol, 7.00 mL). The mixture was heated at 90° C. for 30 min. The mixture was concentrated in vacuo to dryness. The white crude solid of cinnamic acid salt was dissolved in EtOAc (15 mL) at 80° C. for 0.5 h until the mixture became clear. The solution was cooled to 25° C. in 11 hr. A large amount of solid precipitated. Filtered and concentrated in vacuo to dryness to afford the cinnamic acid salt. The cinnamic acid salt of WV-CA-225 in H$_2$O (10.00 mL) was added dropwise sat. Na$_2$CO$_3$ aq. at 20° C. until pH>11. The reaction was stirred at 20° C. for 0.5 h, and extracted with DCM (60 mL*2). The combined organic phase was dried over Na$_2$SO$_4$, and concentrated in vacuo to dryness to afford product as a white solid. Compound WV-CA-225 (4.00 g, 23.63 mmol, 40.00% yield) was obtained as a white solid. $^1$H NMR (400 MHz, CHLOROFORM-d) δ=2.95-2.77 (m, 3H), 2.47-2.31 (m, 1H), 2.16-2.02 (m, 1H), 1.98-1.84 (m, 1H), 1.84-1.45 (m, 8H), 1.01 (s, 3H). $^{13}$C NMR (101 MHz, CHLOROFORM-d) δ=72.01, 65.99, 46.23, 42.81, 26.36, 25.71, 23.56, 23.44, 23.02, 17.79. LCMS: (M+H$^+$): 170.1, LCMS purity=100%.

Example 131. Synthesis of WV-CA-226

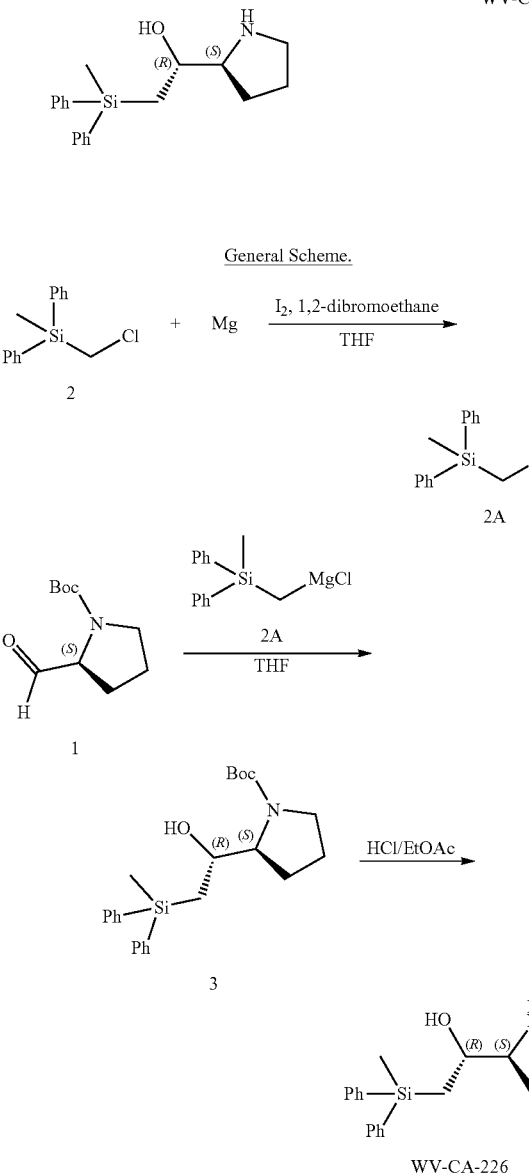

1. Preparation of Compound 2A.

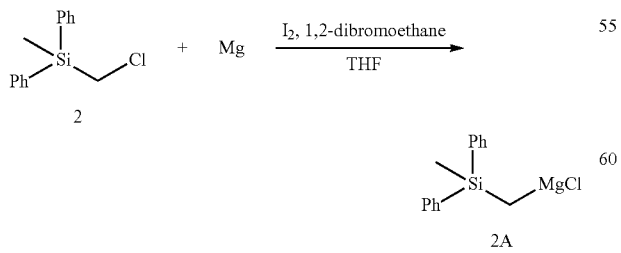

Mg (2.77 g, 114.00 mmol) was taken up in THF (26 mL), then a solution of compound 2 (18.76 g, 76.00 mmol) in THF (50 mL), was added to the Mg suspension (activated with I₂ (one crystal), and 1,2-dibromoethane (49.80 mg, 265.09 μmol, 20.00 μL)) with stirring at 60° C.) in a dropwise fashion over 0.5 hr keeping the temperature between 53-60° C. After complete addition, the mixture was then stirred for 1 hr at 53-54° C. Most of Mg was consumed. The reaction was almost completed. The Grignard reagent in THF was used directly in next step.

2. Preparation of Compound 3.

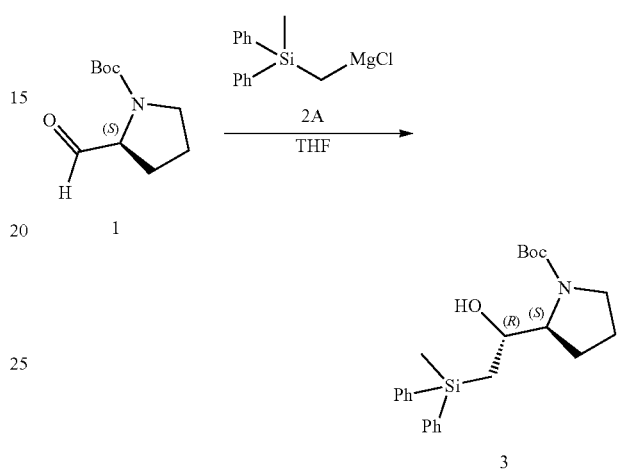

To a solution of compound 1 (5.00 g, 25.08 mmol) in THF (10.00 mL) was added in compound 2A (1 M, 75.25 mL) (previous step) at −5° C. The mixture was stirred at 20° C. for 16 hr. TLC showed compound 1 was consumed. The reaction mixture was slowly added into NH₄Cl (50 mL) at 0° C., and then extracted with ethyl acetate (100 mL*3), dried over Na₂SO₄, filtered and concentrated under reduced pressure to give a residue. The residue was purified by MPLC (SiO₂, Petroleum ether:Ethyl acetate=1:0 to 5:1). Compound 3 was obtained as a colorless oil (6.00 g, 58.11%). ¹H NMR (400 MHz, CDCl₃) δ=7.59-7.50 (m, 4H), 7.33 (br d, J=3.5 Hz, 6H), 4.66 (br s, 1H), 3.83-3.72 (m, 1H), 3.66 (br s, 1H), 3.43 (br s, 1H), 2.09-1.79 (m, 1H), 1.72 (br s, 2H), 1.59 (br s, 3H), 1.42 (s, 9H), 1.33-1.20 (m, 1H), 0.67 (s, 3H). TLC (Petroleum ether/Ethyl acetate=5:1) R_f=0.39.

3. Preparation of Compound WV-CA-226.

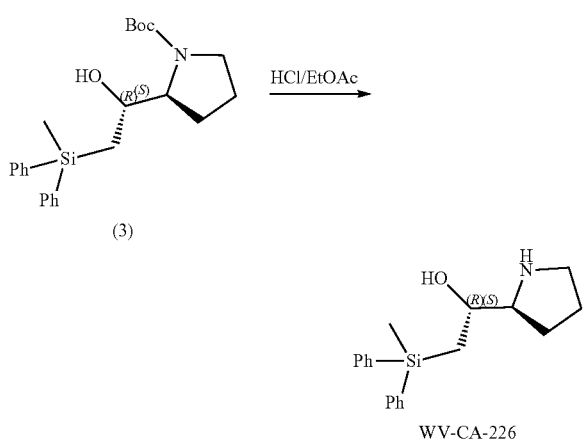

To a solution of compound 3 (5.80 g, 14.09 mmol) in EtOAc (5.00 mL) was added HCl/EtOAc (100.00 mL, 4 N). The mixture was stirred at 20° C. for 1 hr. TLC showed compound 3 was consumed. The reaction mixture was concentrated under reduced pressure to give a white solid. A solution of the white solid in H₂O (10 mL), the mixture was washed by EtOAc (10 mL). The aqueous phase was added Na₂CO₃ (aq.) to over pH=11, then extracted with DCM (100 mL*3). The combined organic layers were dried over Na₂SO₄, filtered, and concentrated under reduced pressure to give WV-CA-226 as a colorless oil (3.80 g, 86.58%). $^1$H NMR (400 MHz, CDCl₃) δ=7.60-7.52 (m, 4H), 7.40-7.29 (m, 6H), 3.73-3.45 (br. s, 2H), 3.39 (ddd, J=4.2, 7.2, 9.4 Hz, 1H), 2.96 (q, J=7.2 Hz, 1H), 2.88-2.70 (m, 2H), 1.85-1.55 (m, 3H), 1.40-1.17 (m, 3H), 0.73-0.63 (m, 3H). $^{13}$C NMR (101 MHz, CDCl₃) δ=138.04, 137.39, 134.56, 127.81, 127.76, 71.19, 66.35, 46.22, 28.39, 26.30, 20.97. LCMS: (M+H+): 312.1. LCMS purity: 96.9% purity. Chiral SFC purity: 95.8%. TLC (Petroleum ether:Ethyl acetate=3:1) $R_f$=0.

Example 132. Synthesis of WV-CA-227 and WV-CA-235

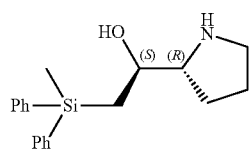

WV-CA-227

General Scheme.

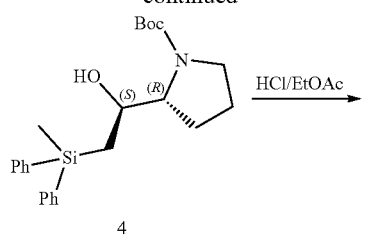

1. Preparation of Compound 2.

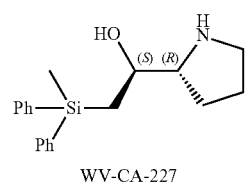

To a solution of compound 1 (10.00 g, 38.71 mmol) in THF (100.00 mL) was added LiAlH₄ (1.76 g, 46.45 mmol) at −10-0° C. The mixture was stirred at −10-0° C. for 1 hr. TLC showed compound 1 was consumed and new spot was detected. The mixture was quenched by addition MgSO₄ (aq., 3.5 mL) at −10-0° C., then diluted with ethyl acetate (100 mL), filtered and concentrated under reduced pressure to give a crude. Compound 2 (7.50 g, crude) was used into the next step without further purification. TLC (Petroleum ether:Ethyl acetate=3:1) $R_f$=0.51.

2. Preparation of Compound 3A.

Mg (4.23 g, 174.00 mmol) was taken up in THF (36 mL), then a solution of compound 3 (28.63 g, 116.00 mmol) in THF (80 mL) was added to the Mg suspension (activated with I₂ (one crystal), and 1,2-dibromoethane (49.80 mg, 265.09 μmol) with stirring at 60° C.) in a dropwise fashion over 0.5 hr keeping the temperature between 53-60° C. After complete addition, the mixture was then stirred for 1 hr at 53-54° C. Most of Mg was consumed. The reaction was almost completed. The Grignard reagent in THF was used directly in next step.

3. Preparation of Compound 4.

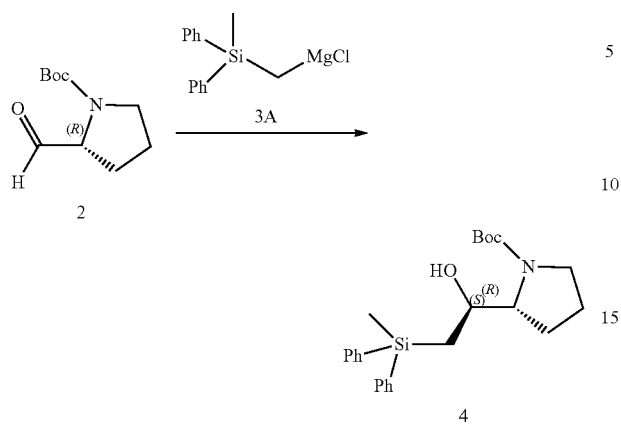

To a solution of compound 2 (7.50 g, 37.64 mmol) in THF (20.00 mL) was added in compound 3A (31.45 g, 115.93 mmol) (previous step) at 0° C. over 0.5 hr. The mixture was stirred at 0-20° C. for 16 hr. LCMS and TLC showed compound 2 were consumed and one major spot was detected. The reaction mixture was slowly added into NH$_4$Cl (50 mL) at 0° C., and then extracted with ethyl acetate (100 mL*3), dried over Na$_2$SO$_4$, filtered and concentrated under reduced pressure to give a residue. $^1$H NMR: The residue was purified by MPLC (SiO$_2$, Petroleum ether:Ethyl acetate=1:0 to 5:1). Compound 4 was obtained as a colorless oil (4.00 g, 25.82%). $^1$H NMR (400 MHz, CHLOROFORM-d) δ=7.62-7.52 (m, 4H), 7.43-7.31 (m, 6H), 4.68 (br s, 1H), 3.94-3.59 (m, 2H), 3.44 (br s, 1H), 3.29-3.18 (m, 1H), 2.16-1.78 (m, 1H), 1.78-1.66 (m, 4H), 1.44 (s, 9H), 1.38-1.18 (m, 2H), 0.72-0.56 (m, 3H). LCMS: (M+Na+): 434.1. TLC (Petroleum ether:Ethyl acetate=5:1) R$_f$=0.38.

4. Preparation of Compound WV-CA-227.

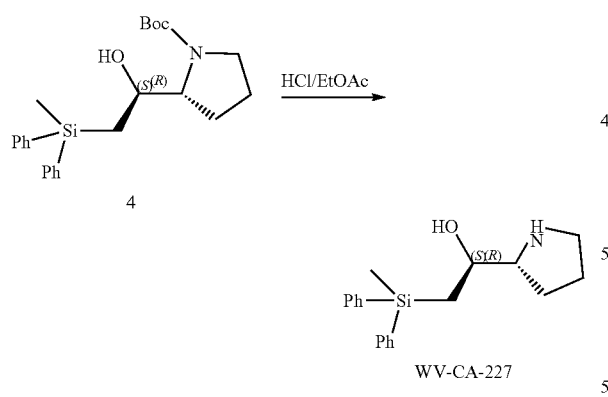

To a solution of compound 4 (3.80 g, 9.23 mmol) in EtOAc (5.00 mL) was added HCl/EtOAc (100.00 mL, 4 N). The mixture was stirred at 20° C. for 1 hr. TLC (Plate1) showed compound 4 was consumed. The reaction mixture was concentrated under reduced pressure to give a white solid. A solution of the white solid in H$_2$O (10 mL), the mixture was washed by EtOAc (10 mL). The aqueous phase was added Na$_2$CO$_3$ aq. to over pH=11, then extracted with DCM (100 mL*3). The combined organic layers were dried over Na$_2$SO$_4$, filtered, and concentrated under reduced pressure to give a crude (2.2 g). TLC (Plate 2). The crude was purified by MPLC (SiO$_2$, Petroleum ether:Ethyl acetate=5:1 to Dichloromethane:Methanol=30:1 to 10:1) to give Compound WV-CA-227 was obtained as a colorless oil (1.00 g, 34.78%). $^1$H NMR (400 MHz, CHLOROFORM-d) δ=7.59-7.49 (m, 4H), 7.39-7.28 (m, 5H), 3.49-3.39 (m, 1H), 3.34 (br s, 2H), 3.02 (q, J=7.1 Hz, 1H), 2.95-2.84 (m, 1H), 2.83-2.71 (m, 1H), 1.88-1.57 (m, 3H), 1.43-1.20 (m, 3H), 0.66 (s, 3H). $^{13}$C NMR (101 MHz, CHLOROFORM-d) δ=141.10, 140.50, 137.81, 137.72, 132.31, 132.25, 131.03, 130.97, 74.19, 69.53, 49.49, 31.63, 29.55, 24.23. LCMS: (M+H+): 312.3, LCMS purity: 95.3%. Chiral SFC purity: 99.8%. Plate 1: TLC (Petroleum ether:Ethyl acetate=3:1) R$_f$=0. Plate 2: TLC (Dichloromethane:Methanol=10:1) R$_f$=0.1.

WV-CA-235

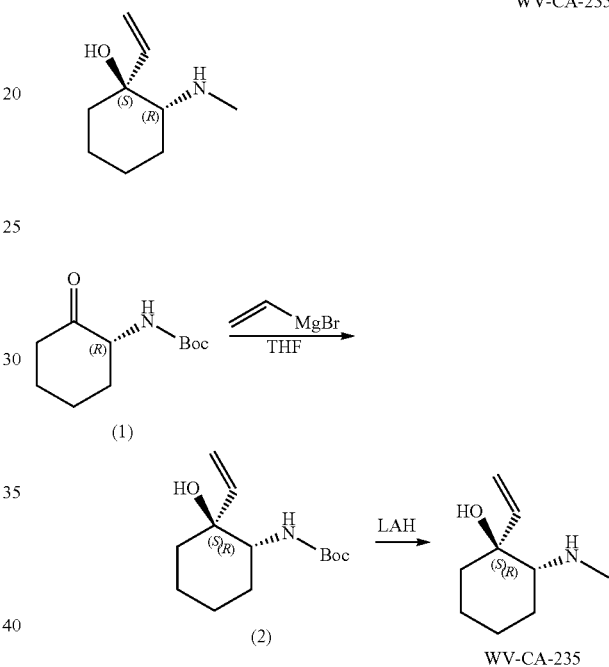

1. Preparation of Compound 2

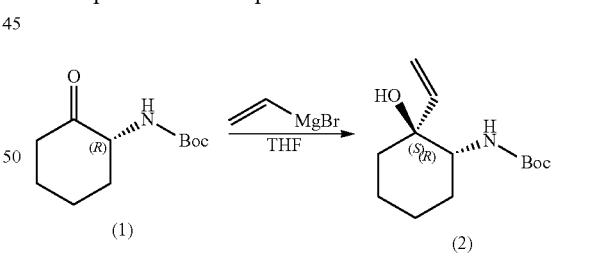

To a solution of compound 1 (20 g, 93.78 mmol) in THF (200 mL) was added bromo(vinyl)magnesium (1 M, 281.33 mL) at −60° C. The mixture was stirred at −60° C.-25° C. for 3 hr. TLC indicated compound 1 was remained a lot and two new spots formed. The reaction mixture was quenched by addition NH$_4$Cl 200 mL at 0° C., and then diluted with EtOAc 200 mL and extracted with EtOAc (100 mL*4). Dried over Na$_2$SO$_4$, filtered and concentrated under reduced pressure to give a residue. The residue was purified by column chromatography (SiO$_2$, Petroleum ether/Ethyl acetate=1/0 to 10:1). Compound tert-butyl N-[(1R,2S)-2-hydroxy-2-vinyl-cyclohexyl]carbamate (4 g, 16.58 mmol, 17.68% yield) was obtained as a yellow oil. $^1$H NMR (400 MHz, CHLOROFORM-d) δ=6.06 (dd, J=10.8, 17.1 Hz, 1H), 5.43 (dd, J=1.8, 17.1 Hz, 1H), 5.22 (dd, J=1.5, 10.8 Hz, 1H), 4.34 (br s, 1H), 3.50 (br s, 1H), 3.28 (br s, 1H), 1.81 (br d, J=12.5 Hz, 2H), 1.73-1.46 (m, 3H), 1.42-1.25 (m, 12H). TLC: (Petroleum ether:Ethyl acetate=3:1), $R_f$=0.41.

2. Preparation of Compound WV-CA-235

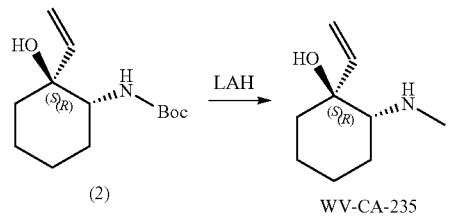

(2)    WV-CA-235

To a solution of compound 2 (3.5 g, 14.50 mmol) in THF (35 mL) was added LAH (1.65 g, 43.51 mmol) at 0° C. The mixture was stirred at 0-80° C. for 1 hr. TLC indicated compound 2 was consumed and one new spot formed. The reaction was slowly added sat. MgSO$_4$ (3 mL) at 0° C. The mixture was filtered through celatom. The filter cake was washed with EtOAc (30 mL*6). The organic phase was dried over MgSO$_4$, filtered and concentrated in vacuo to dryness to afford crude product. The residue was purified by column chromatography (SiO$_2$, Petroleum ether/Ethyl acetate=1/0 to 0:1). Compound WV-CA-235 (1.1 g, 7.09 mmol, 48.86% yield, 100% purity) was obtained as a yellow solid. $^1$H NMR (400 MHz, CHLOROFORM-d) δ=6.18 (dd, J=10.8, 17.2 Hz, 1H), 5.42 (dd, J=1.9, 17.1 Hz, 1H), 5.21 (dd, J=1.9, 10.9 Hz, 1H), 2.40 (s, 3H), 2.31 (dd, J=4.0, 11.9 Hz, 1H), 2.10-2.02 (m, 1H), 1.87-1.77 (m, 2H), 1.70-1.62 (m, 1H), 1.58-1.27 (m, 3H), 1.01 (dq, J=3.6, 12.5 Hz, 1H). $^{13}$C NMR (101 MHz, CHLOROFORM-d) δ=137.55, 114.23, 73.01, 66.13, 37.51, 32.69, 26.29, 24.16, 21.82. LCMS: (M+H$^+$): 156.1, 100% LCMS purity. TLC: (Dichloromethane:Methanol=10:1), $R_f$=0.04.

Example 133. Example Synthesis of Certain WV-CA-059 Derived Compounds

General Procedure I: In some embodiments, in an example procedure, a chiral auxiliary (174.54 mmol) was dried by azeotropic evaporation with anhydrous toluene (80 mL×3) at 35° C. in a rota-evaporator and dried under high vacuum for overnight. A solution of this dried chiral auxiliary (174.54 mmol) and 4-methylmorpholine (366.54 mmol) dissolved in anhydrous toluene (170 mL) was added to an ice-cooled (isopropyl alcohol-dry ice bath) solution of trichlorophosphine (37.07 g, 16.0 mL, 183.27 mmol) in anhydrous toluene (150 mL) placed in three neck round bottomed flask through cannula under Argon (start Temp: −10.0° C., Max: temp 0° C., 28 min addition) and the reaction mixture was warmed at 15° C. for 1 hr. After that the precipitated white solid was filtered by vacuum under argon using airfree filter tube (Chemglass: Filter Tube, 24/40 Inner Joints, 80 mm OD Medium Frit, Airfree, Schlenk). The solvent was removed with rota-evaporator under argon at low temperature (25° C.) and the crude semi-solid obtained was dried under vacuum overnight (~15 h) and was used for the next step directly.

General Procedure II: In some embodiments, in an example procedure, a nucleoside (9.11 mmol) was dried by co-evaporation with 60 mL of anhydrous pyridine at 35° C. followed by anhydrous toluene (60 mL×2) at 35° C. and dried under high vacuum for overnight. The dried nucleoside was dissolved in dry THF (78 mL), followed by the addition of triethylamine (63.80 mmol) and then cooled to −5° C. under Argon (for 2'F-dG case 1 eq of TMS-Cl used). The THF solution of the crude (made from general procedure I, 18.22 mmol), was added through cannula over 3 min then gradually warmed to room temperature. After 1 hr at room temperature, TLC indicated conversion of SM to product (total reaction time 1 h), the reaction mixture was then quenched with H$_2$O (9.11 mmol, 0.1 mL) at 0° C., and anhydrous MgSO$_4$ (9.11 mmol, ~1 g) was added and stirred for 10 min. Then the reaction mixture was filtered under argon using airfree filter tube, washed with THF, and dried under rotary evaporation at 26° C. to afford white crude solid product, which was dried under high vacuum overnight. The crude product was purified by ISCO-Combiflash system (80 g gold rediSep high performance silica column pre-equilibrated with EtOAc) using Ethyl acetate/Hexane with 5% TEA as a solvent (compound eluted at 60-65% EtOAc/Hexanes/5% Et$_3$N). After evaporation of column fractions pooled together, the residue was dried under high vacuum to afford the product as a white solid (60-95% yield).

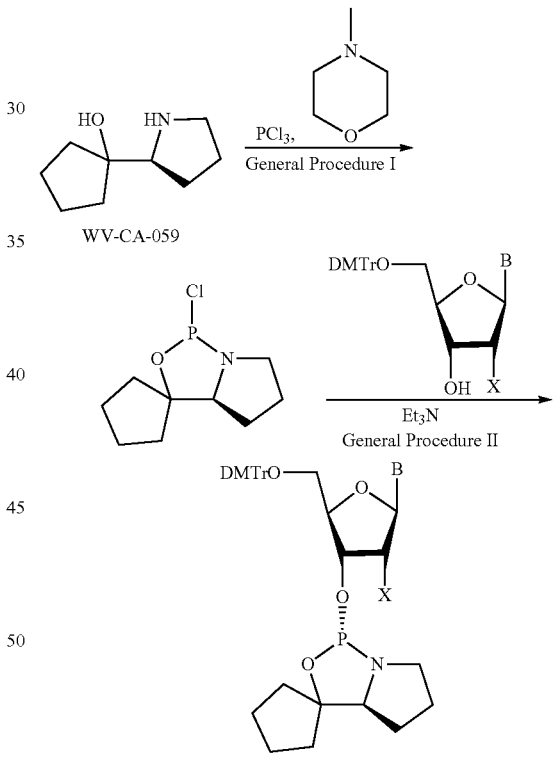

WV-CA-059: 1: X = OMe, B = A$^{Bz}$
2: X = F, B = dA$^{Bz}$
3: X = F, B = dC$^{Ac}$
4: X = F, B = dU
5: X = F, B = dG$^{iBu}$

Preparation of WV-CA-059-C1: (3a'S)-1'-chlorotetrahydro-1'H-spiro[cyclopentane-1,3'-pyrrolo[1,2-c][1,3,2]oxazaphosphole]. General Procedure I. $^{31}$P NMR (162 MHz, Chloroform-d) δ 170.01.

Preparation of WV-CA-059-2'OMe-A$^{Bz}$ (1): N-(9-((2R, 3R,4R,5R)-5-((bis(4-methoxyphenyl)(phenyl)methoxy)methyl)-3-methoxy-4-((((1'S,3a'S)-tetrahydro-1'H-spiro[cyclopentane-1,3'-pyrrolo[1,2-c][1,3,2]oxazaphosphol]-1'-yl)
oxy)tetrahydrofuran-2-yl)-4,5-dihydro-9H-purin-6-yl)
benzamide. General Procedure II. $[\alpha]_D^{23}$=+1.15 (c 1.92, CHCl$_3$). $^{31}$P NMR (162 MHz, Chloroform-d) δ 156.24. MS (EI$^+$) calculated for $C_{48}H_{51}N_6O_8P$ 870.3; found 871.3 (M+H).

Preparation of WV-CA-059-2'F-dA$^{Bz}$ (2): N-(9-((2R,3R,4R,5R)-5-((bis(4-methoxyphenyl)(phenyl)methoxy)methyl)-3-fluoro-4-(((1'S,3a'S)-tetrahydro-1'H-spiro[cyclopentane-1,3'-pyrrolo[1,2-c][1,3,2]oxazaphosphol]-1'-yl)oxy)tetrahydrofuran-2-yl)-4,5-dihydro-9H-purin-6-yl)benzamide. General Procedure II. $[\alpha]_D^{23}$=+12.49 (c 1.26, CHCl$_3$). $^{31}$P NMR (162 MHz, Chloroform-d) δ 155.38 (d, J=10.1 Hz). MS (EI$^+$) calculated for $C_{47}H_{48}FN_6O_7P$ 858.3; found 859.3 (M+H).

Preparation of WV-CA-059-2'F-dC$^{Ac}$ (3): N-(1-((2R,3R,4R,5R)-5-((bis(4-methoxyphenyl)(phenyl)methoxy)methyl)-3-fluoro-4-(((1'S,3a'S)-tetrahydro-1'H-spiro[cyclopentane-1,3'-pyrrolo[1,2-c][1,3,2]oxazaphosphol]-1'-yl)oxy)tetrahydrofuran-2-yl)-2-oxo-1,2-dihydropyrimidin-4-yl)acetamide. General Procedure II. $[\alpha]_D^{23}$=+55.69 (c 1.33, CHCl$_3$). $^{31}$P NMR (162 MHz, Chloroform-d) δ 157.82 (d, J=7.8 Hz). MS (EI$^+$) calculated for $C_{41}H_{46}FN_4O_8P$ 772.3; found 773.2 (M+H).

Preparation of WV-CA-059-2'F-dU (4): 1-((2R,3R,4R,5R)-5-((bis(4-methoxyphenyl)(phenyl)methoxy)methyl)-3-fluoro-4-(((1'S,3a'S)-tetrahydro-1'H-spiro[cyclopentane-1,3'-pyrrolo[1,2-c][1,3,2]oxazaphosphol]-1'-yl)oxy)tetrahydrofuran-2-yl)pyrimidine-2,4(1H,3H)-dione. General Procedure II. $[\alpha]_D^{23}$=+42.88 (c 1.67, CHCl$_3$). $^{31}$P NMR (162 MHz, Chloroform-d) δ 157.99 (d, J=9.1 Hz). MS (EI$^+$) calculated for $C_{39}H_{43}FN_3O_8P$ 731.2; found 754.2 (M+Na).

Preparation of WV-CA-059-2'F-dG$^{iBu}$ (5): N-(9-((2R,3R,4R,5R)-5-((bis(4-methoxyphenyl)(phenyl)methoxy)methyl)-3-fluoro-4-(((1'S,3a'S)-tetrahydro-1'H-spiro[cyclopentane-1,3'-pyrrolo[1,2-c][1,3,2]oxazaphosphol]-1'-yl)oxy)tetrahydrofuran-2-yl)-6-oxo-4,5,6,9-tetrahydro-1H-purin-2-yl)isobutyramide. General Procedure II. $[\alpha]_D^{23}$=+42.80 (c 1.39, CHCl$_3$). $^{31}$P NMR (162 MHz, Chloroform-d) δ 156.12 (d, J=11.2 Hz). MS (EI$^+$) calculated for $C_{44}H_{50}FN_6O_8P$ 840.3; found 841.3 (M+H).

Example 134. Example Synthesis of Certain WV-CA-059R Derived Compounds

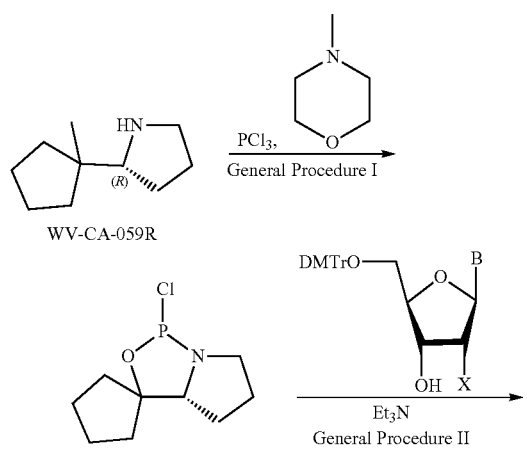

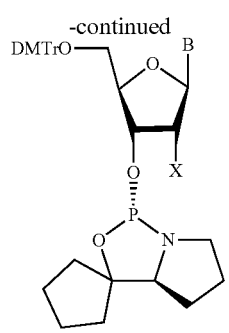

WV-CA-059R: 1: X = OMe, B = A$^{Bz}$
2: X = F, B = dA$^{Bz}$
3: X = F, B = dC$^{Ac}$
4: X = F, B = dU
5: X = F, B = dG$^{iBu}$

Preparation of WV-CA-059R-Cl: (3a'R)-1'-chlorotetrahydro-1'H-spiro[cyclopentane-1,3'-pyrrolo[1,2-c][1,3,2]oxazaphosphole]. General Procedure I. $^{31}$P NMR (162 MHz, Chloroform-d) δ 169.46.

Preparation of WV-CA-059R-2'F-dA$^{Bz}$ (1): N-(9-((2R,3R,4R,5R)-5-((bis(4-methoxyphenyl)(phenyl)methoxy)methyl)-3-fluoro-4-(((1'R,3a'R)-tetrahydro-1'H-spiro[cyclopentane-1,3'-pyrrolo[1,2-c][1,3,2]oxazaphosphol]-1'-yl)oxy)tetrahydrofuran-2-yl)-4,5-dihydro-9H-purin-6-yl)benzamide. General Procedure II. $[\alpha]_D^{23}$=−21.18 (c 1.35, CHCl3). $^{31}$P NMR (162 MHz, Chloroform-d) δ 155.69 (d, J=7.0 Hz). MS (EI$^+$) calculated for $C_{47}H_{48}FN_6O_7P$ 858.3; found 859.3 (M+H).

Preparation of WV-CA-059R-2'OMe-A$^{Bz}$ (2): N-(9-((2R,3R,4R,5R)-5-((bis(4-methoxyphenyl)(phenyl)methoxy)methyl)-3-methoxy-4-(((1'R,3a'R)-tetrahydro-1'H-spiro[cyclopentane-1,3'-pyrrolo[1,2-c][1,3,2]oxazaphosphol]-1'-yl)oxy)tetrahydrofuran-2-yl)-4,5-dihydro-9H-purin-6-yl)benzamide. General Procedure II. $[\alpha]_D^{23}$=−10.52 (c 1.35, CHCl3). $^{31}$P NMR (162 MHz, Chloroform-d) δ 156.39. MS (EI$^+$) calculated for $C_{48}H_{51}N_6O_8P$ 870.3; found 871.3 (M+H).

Preparation of WV-CA-059R-2'F-dC$^{Ac}$ (3): N-(1-((2R,3R,4R,5R)-5-((bis(4-methoxyphenyl)(phenyl)methoxy)methyl)-3-fluoro-4-(((1'R,3a'R)-tetrahydro-1'H-spiro[cyclopentane-1,3'-pyrrolo[1,2-c][1,3,2]oxazaphosphol]-1'-yl)oxy)tetrahydrofuran-2-yl)-2-oxo-1,2-dihydropyrimidin-4-yl)acetamide. General Procedure II. $[\alpha]_D^{23}$=+40.37 (c 1.82, CHCl3). $^{31}$P NMR (162 MHz, Chloroform-d) δ 158.59 (d, J=5.9 Hz). MS (EI$^+$) calculated for $C_{41}H_{46}FN_4O_8P$ 872.3; found 873.2 (M+H).

Preparation of WV-CA-059R-2'F-dU (4): 1-((2R,3R,4R,5R)-5-((bis(4-methoxyphenyl)(phenyl)methoxy)methyl)-3-fluoro-4-(((1'R,3a'R)-tetrahydro-1'H-spiro[cyclopentane-1,3'-pyrrolo[1,2-c][1,3,2]oxazaphosphol]-1'-yl)oxy)tetrahydrofuran-2-yl)pyrimidine-2,4(1H,3H)-dione. General Procedure II. $[\alpha]_D^{23}$=+20.17 (c 1.52, CHCl3). $^{31}$P NMR (162 MHz, Chloroform-d) δ 159.35 (d, J=6.3 Hz). MS (EI$^+$) calculated for $C_{39}H_{43}FN_3O_8P$ 731.2; found 754.2 (M+Na).

Preparation of WV-CA-059R-2'F-dG$^{iBu}$ (5): N-(9-((2R,3R,4R,5R)-5-((bis(4-methoxyphenyl)(phenyl)methoxy)methyl)-3-fluoro-4-(((1'R,3a'R)-tetrahydro-1'H-spiro [cyclopentane-1,3'-pyrrolo[1,2-c][1,3,2]oxazaphosphol]-1'-yl)oxy)tetrahydrofuran-2-yl)-6-oxo-4,5,6,9-tetrahydro-1H-purin-2-yl)isobutyramide. General Procedure II. $[\alpha]_D^{23}$=+5.95 (c 1.48, CHCl3). $^{31}$P NMR (162 MHz, Chloroform-d) δ 157.29 (d, J=7.0 Hz). MS (EI$^+$) calculated for $C_{44}H_{50}FN_6O_8P$ 840.3; found 841.3 (M+H).

Example 135. Example Synthesis of Certain WV-CA-070S Derived Compounds

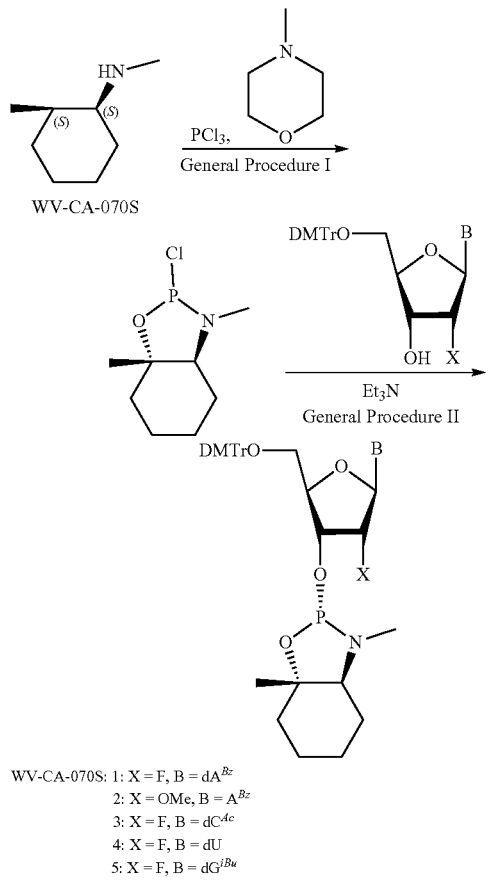

WV-CA-070S: 1: X = F, B = dA$^{Bz}$
2: X = OMe, B = A$^{Bz}$
3: X = F, B = dC$^{Ac}$
4: X = F, B = dU
5: X = F, B = dG$^{iBu}$

Preparation of WV-CA-070S-Cl: (3aS,7aS)-2-chloro-3,7a-dimethyloctahydrobenzo[d][1,3,2]oxazaphosphole. General Procedure I. $^{31}$P NMR (162 MHz, Chloroform-d) δ 178.44.

Preparation of WV-CA-070S-2'F-dA$^{Bz}$ (1): N-(9-((2R,3R,4R,5R)-5-((bis(4-methoxyphenyl)(phenyl)methoxy)methyl)-4-(((2S,3aS,7aS)-3,7a-dimethylhexahydrobenzo[d][1,3,2]oxazaphosphol-2(3H)-yl)oxy)-3-fluorotetrahydrofuran-2-yl)-9H-purin-6-yl)benzamide. General Procedure II. [α]$_D^{23}$=−31.59 (c 1.17, CHCl3). $^{31}$P NMR (162 MHz, Chloroform-d) δ 165.37 (d, J=8.3 Hz). MS (EI$^+$) calculated for C$_{46}$H$_{58}$FN$_6$O$_7$P 846.3; found 847.3 (M+H).

Preparation of WV-CA-070S-2'OMe-A$^{Bz}$ (2): N-(9-((2R,3R,4R,5R)-5-((bis(4-methoxyphenyl)(phenyl)methoxy)methyl)-4-(((2S,3aS,7aS)-3,7a-dimethylhexahydrobenzo[d][1,3,2]oxazaphosphol-2(3H)-yl)oxy)-3-methoxytetrahydrofuran-2-yl)-9H-purin-6-yl)benzamide. General Procedure II. [α]$_D^{23}$=−33.76 (c 1.11, CHCl3). $^{31}$P NMR (162 MHz, Chloroform-d) δ 165.32. MS (EI$^+$) calculated for C$_{47}$H$_{51}$FN$_6$O$_8$P 858.3; found 859.2 (M+H).

Preparation of WV-CA-070S-2'OMe-dC$^{Ac}$ (3): N-(1-((2R,3R,4R,5R)-5-((bis(4-methoxyphenyl)(phenyl)methoxy)methyl)-4-(((2S,3aS,7aS)-3,7a-dimethylhexahydrobenzo[d][1,3,2]oxazaphosphol-2(3H)-yl)oxy)-3-fluorotetrahydrofuran-2-yl)-2-oxo-1,2-dihydropyrimidin-4-yl)acetamide. General Procedure II. [α]$_D^{23}$=−19.49 (c 1.31, CHCl3). $^{31}$P NMR (162 MHz, Chloroform-d) δ 165.19 (d, J=6.7 Hz). MS (EI$^+$) calculated for C$_{40}$H$_{46}$FN$_4$O$_8$P 760.3; found 761.3 (M+H).

Preparation of WV-CA-070S-2'F-dU (4): 1-((2R,3R,4R,5R)-5-((bis(4-methoxyphenyl)(phenyl)methoxy)methyl)-4-(((2S,3aS,7aS)-3,7a-dimethylhexahydrobenzo[d][1,3,2]oxazaphosphol-2(3H)-yl)oxy)-3-fluorotetrahydrofuran-2-yl)pyrimidine-2,4(1H,3H)-dione. General Procedure II. [α]$_D^{23}$=−3.76 (c 1.42, CHCl3). $^{31}$P NMR (162 MHz, Chloroform-d) δ 165.40 (d, J=7.2 Hz). MS (EI$^+$) calculated for C$_{38}$H$_{43}$FN$_3$O$_8$P 719.2; found 758.5 (M+K).

Preparation of WV-CA-070S-2'F-dG$^{iBu}$ (5): N-(9-((2R,3R,4R,5R)-5-((bis(4-methoxyphenyl)(phenyl)methoxy)methyl)-4-(((2S,3aS,7aS)-3,7a-dimethylhexahydrobenzo[d][1,3,2]oxazaphosphol-2(3H)-yl)oxy)-3-fluorotetrahydrofuran-2-yl)-6-oxo-6,9-dihydro-1H-purin-2-yl)isobutyramide. General Procedure II. [α]$_D^{23}$=+46.33 (c 1.41, CHCl3). $^{31}$P NMR (162 MHz, Chloroform-d) δ 165.03 (d, J=8.4 Hz). MS (EI$^+$) calculated for C$_{43}$H$_{50}$FN$_6$O$_8$P 828.3; found 829.4 (M+H).

Example 136. Example Synthesis of Certain WV-CA-217 Derived Compounds

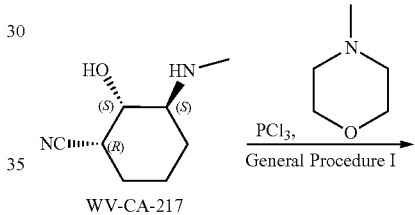

WV-CA-217

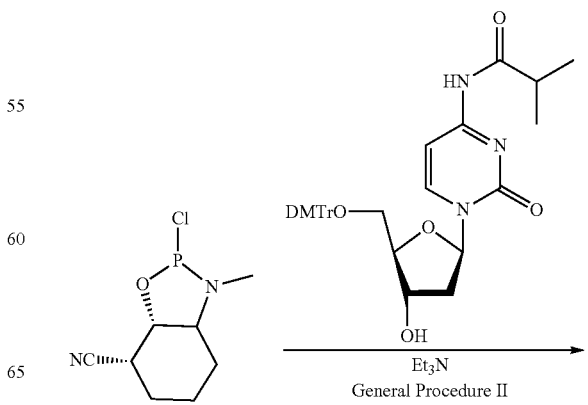

913

-continued

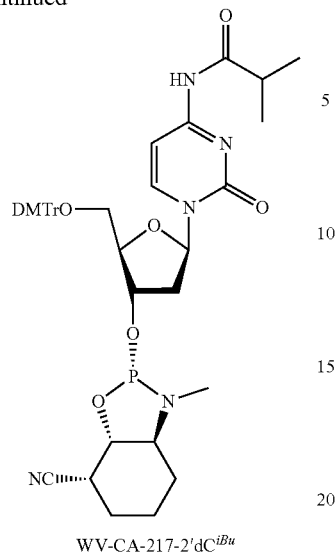

WV-CA-217-2'dC$^{iBu}$

Preparation of WV-CA-217-Cl: (3aS,7R,7aS)-2-chloro-3-methyloctahydrobenzo[d][1,3,2]oxazaphosphole-7-carbonitrile. General Procedure I. $^{31}$P NMR (162 MHz, Chloroform-d) δ 173.10.

Preparation of WV-CA-217-2'-dC$^{iBu}$: N-(1-((2R,4S,5R)-5-((bis(4-methoxyphenyl)(phenyl)methoxy)methyl)-4-(((2R,3aS,7R,7aS)-7-cyano-3-methylhexahydrobenzo[d][1,3,2]oxazaphosphol-2(3H)-yl)oxy)tetrahydrofuran-2-yl)-2-oxo-1,2-dihydropyrimidin-4-yl)isobutyramide. General Procedure II. [α]$_D^{23}$=+70.47 (c 1.38, CHCl3). $^{31}$P NMR (162 MHz, Chloroform-d) δ 155.12. MS (EI$^+$) calculated for C$_{42}$H$_{48}$N$_5$O$_8$P 781.3; found 782.3 (M+H).

Example 137. Example Synthesis of Certain WV-CA-216 Derived Compounds

914

-continued

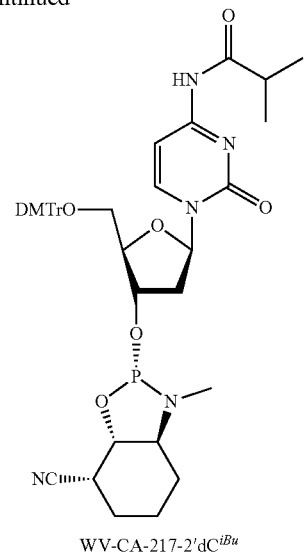

WV-CA-217-2'dC$^{iBu}$

Preparation of WV-CA-216-Cl: (3aR,7aR)-2-chloro-3,7a-dimethyloctahydrobenzo[d][1,3,2]oxazaphosphole. General Procedure I. $^{31}$P NMR (162 MHz, Chloroform-d) δ 178.56.

Preparation of WV-CA-216-2'-dC$^{iBu}$: N-(1-((2R,4S,5R)-5-((bis(4-methoxyphenyl)(phenyl)methoxy)methyl)-4-(((2R,3aR,7aR)-3,7a-dimethylhexahydrobenzo[d][1,3,2]oxazaphosphol-2(3H)-yl)oxy)tetrahydrofuran-2-yl)-2-oxo-1,2-dihydropyrimidin-4-yl)isobutyramide. General Procedure II. [α]$_D^{23}$=+75.32 (c 1.15, CHCl3). $^{31}$P NMR (162 MHz, Chloroform-d) δ 163.99. MS (EI$^+$) calculated for C$_{42}$H$_{51}$N$_4$O$_8$P 770.3; found 771.3 (M+H).

Example 138. Example Synthesis of Certain WV-CA-216 Derived Compounds

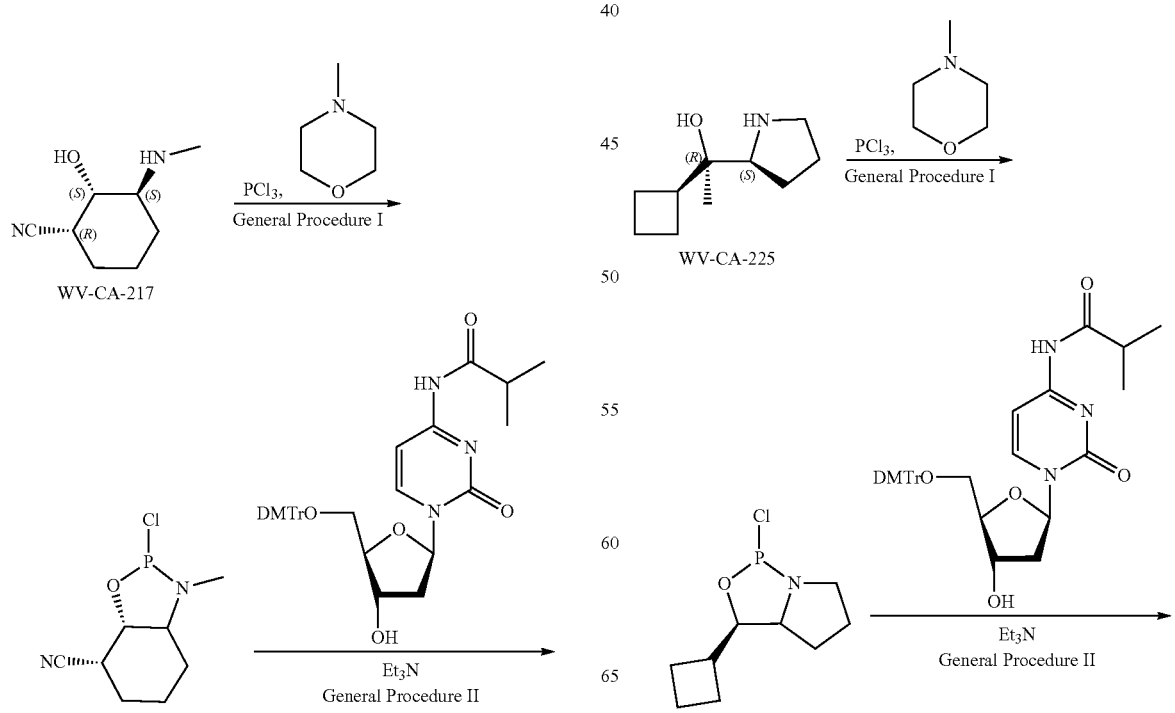

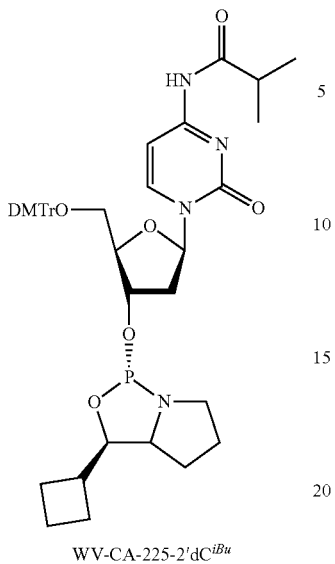

WV-CA-225-2'dC<sup>iBu</sup>

Preparation of WV-CA-225-Cl: (3R,3aS)-1-chloro-3-cyclobutyl-3-methyltetrahydro-1H,3H-pyrrolo[1,2-c][1,3,2]oxazaphosphole. General Procedure I. $^{31}$P NMR (162 MHz, Chloroform-d) δ 160.54.

Preparation of WV-CA-225-2'-dC$^{iBu}$: N-(1-((2R,4S,5R)-5-((bis(4-methoxyphenyl)(phenyl)methoxy)methyl)-4-(((1S,3R,3aS)-3-cyclobutyl-3-methyltetrahydro-1H,3H-pyrrolo[1,2-c][1,3,2]oxazaphosphol-1-yl)oxy)tetrahydrofuran-2-yl)-2-oxo-1,2-dihydropyrimidin-4-yl)isobutyramide. General Procedure II. $[\alpha]_D^{23}$=+23.39 (c 1.20, CHCl3). $^{31}$P NMR (162 MHz, Chloroform-d) δ 151.94. MS (EI$^+$) calculated for C$_{44}$H$_{53}$N$_4$O$_8$P 796.3; found 797.4 (M+H).

Example 139. Example Synthesis of Certain WV-CA-078 Derived Compounds

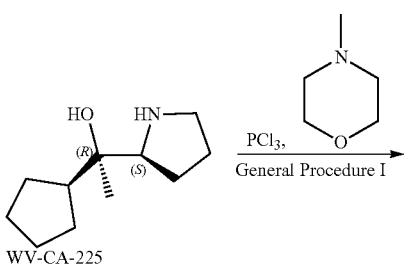

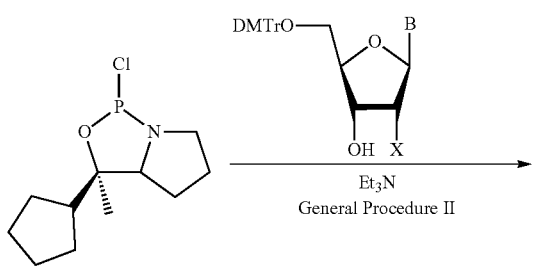

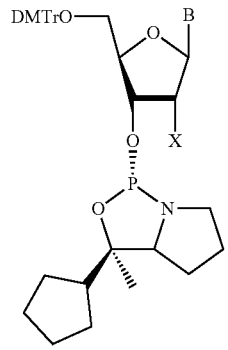

WV-CA-070S: 1: X = F, B = dA$^{Bz}$
2: X = OMe, B = A$^{Bz}$
3: X = F, B = dC$^{Ac}$
4: X = F, B = dU
5: X = F, B = dG$_{iBu}$

Preparation of WV-CA-078-Cl: (3R,3aS)-1-chloro-3-cyclopentyl-3-methyltetrahydro-1H,3H-pyrrolo[1,2-c][1,3,2]oxazaphosphole. General Procedure I. $^{31}$P NMR (162 MHz, Chloroform-d) δ 161.36, 172.77.

Preparation of WV-CA-078-2'F-dA$^{Bz}$ (1): N-(9-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-fluorotetrahydrofuran-2-yl)-9H-purin-6-yl)benzamide. General Procedure II. $[\alpha]_D^{23}$=+11.99 (c 1.21, CHCl3). $^{31}$P NMR (162 MHz, Chloroform-d) δ 156.41 (d, J=12.5 Hz). MS (EI$^+$) calculated for C$_{49}$H$_{52}$FN$_6$O$_7$P 886.3; found 887.8 (M+H).

Preparation of WV-CA-078-2'OMe-A$^{Bz}$ (2): N-(9-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-methoxytetrahydrofuran-2-yl)-9H-purin-6-yl)benzamide. General Procedure II. $[\alpha]_D^{23}$=+2.95 (c 1.43, CHCl3). $^{31}$P NMR (162 MHz, Chloroform-d) δ 156.69. MS (EI$^+$) calculated for C$_{40}$H$_{55}$N$_6$O$_8$P 898.3; found 899.8 (M+H).

Preparation of WV-CA-078-2'F-dC$^{Ac}$ (3): N-(1-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-fluorotetrahydrofuran-2-yl)-2-oxo-1,2-dihydropyrimidin-4-yl)acetamide. General Procedure II. $[\alpha]_D^{23}$=+57.44 (c 1.77, CHCl3). $^{31}$P NMR (162 MHz, Chloroform-d) δ 157.84 (d, J=8.4 Hz). MS (EI$^+$) calculated for C$_{43}$H$_{50}$FN$_4$O$_8$P 801.3; found 801.4 (M+H).

Preparation of WV-CA-078-2'F-dU (4): 1-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-fluorotetrahydrofuran-2-yl)pyrimidine-2,4(1H,3H)-dione. General Procedure II. $[\alpha]_D^{23}$=+46.16 (c 1.30, CHCl3). $^{31}$P NMR (162 MHz, Chloroform-d) δ 159.43 (d, J=6.4 Hz). MS (EI$^+$) calculated for C$_{41}$H$_{47}$FN$_3$O$_8$P 782.6; found 801.4 (M+Na).

Preparation of WV-CA-078-2'F-dG$^{iBu}$ (5): N-(9-((2R,3R,4R,5R)-5-((bis(4-methoxyphenyl)(phenyl)methoxy)methyl)-4-(((1S,3R,3aS)-3-cyclopentyl-3-methyltetrahydro-1H,3H-pyrrolo[1,2-c][1,3,2]oxazaphosphol-1-yl)oxy)-3-fluorotetrahydrofuran-2-yl)-6-oxo-6,9-dihydro-1H-purin-2-yl)isobutyramide. General Procedure II. $^{31}$P NMR (162 MHz, Chloroform-d) δ 155.64 (d, J=12.6 Hz). MS (EI+) calculated for $C_{46}H_{54}FN_6O_8P$ 782.6; found 869.8 (M+Na).

Example 140. Synthesis of Thymidine-5′-dimethyl-vinylphosphonate-2′-deoxy-3′-CNE Phosphoramidite

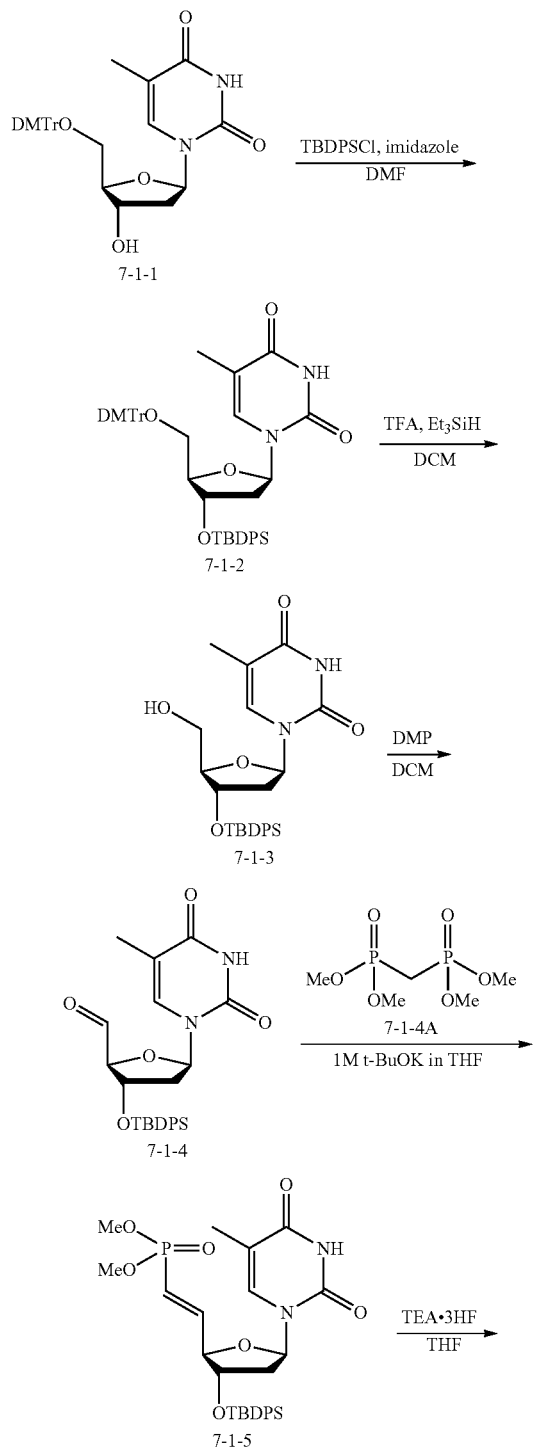

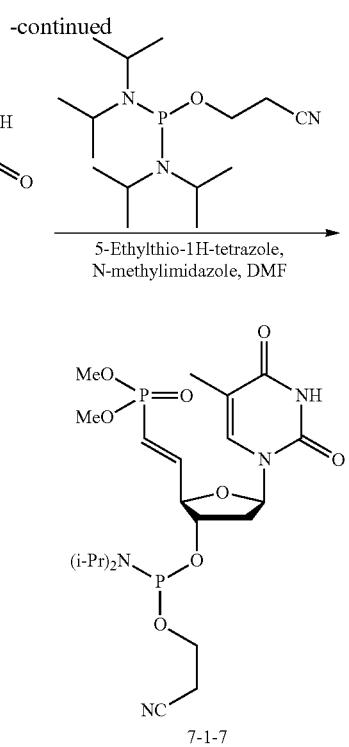

Preparation of Compound 7-1-2.

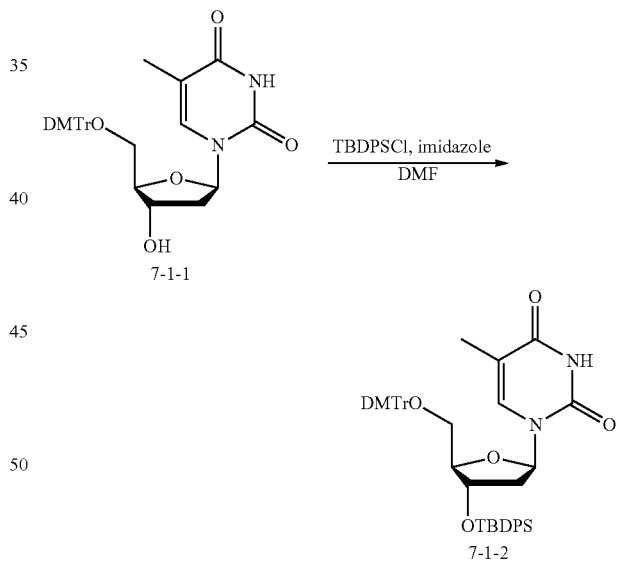

To a solution of compound 7-1-1 (20.00 g, 36.72 mmol, 1.00 eq.) in DMF (100.00 mL) was added imidazole (25.00 g, 367.20 mmol, 10.00 eq.) followed by TBDPSCl (50.47 g, 183.60 mmol, 47.17 mL, 5.00 eq.). The reaction mixture was stirred at 25° C. for 16 h. TLC (Dichloromethane:Methanol=1:1) showed compound 7-1-1 was consumed completely. EtOAc (300 mL) was added and the mixture was washed with water (60 mL*3). The organic phase was dried over $Na_2SO_4$, filtered and concentrated. The residue was purified by column chromatography on silica gel (Petroleum ether:Ethyl acetate=20:1, 1:1, 1:4). Compound 7-1-2 (30.00 g) was obtained as white foamy solid. $^1H$ NMR: ($CDCl_3$, 400 MHz) δ=8.165 (s, 1H), 7.575-7.080 (m, 21H), 6.718-6.741 (m, 4H), 6.473 (d, J=2.8 Hz, 1H), 4.520~4.534 (m, 1H), 4.037-4.043 (d, J=2.4 Hz, 1H), 3.758 (s, 6H), 3.184-3.217 (m, 1H), 2.841-2.874 (m, 1H), 2.319-2.338 (m, 1H), 2.025-2.078 (m, 1H), 1.321 (s, 3H), 1.021 (s, 9H).

Preparation of Compound 7-1-3.

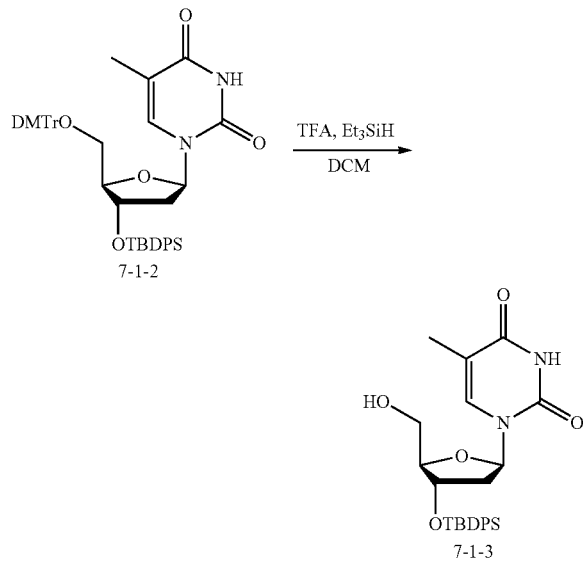

To a solution of compound 7-1-2 (25.00 g, 31.93 mmol, 1.00 eq.) in DCM (250 mL) was added TFA (8.37 g, 73.44 mmol, 5.44 mL, 2.30 eq.). The color of the solution turned to red. Et₃SiH (8.17 g, 70.24 mmol, 11.19 mL, 2.20 eq.) was added at 25° C. The reaction mixture was stirred at 25° C. for 2 h and the red solution became colorless. TLC (Petroleum ether:Ethyl acetate=1:1) showed compound 7-1-2 was consumed completely. The solvent was removed under reduced pressure, and the residue was dissolved in EtOAc (100 mL). The organic phase was washed with NaHCO₃ (40 mL), brine, dried over Na₂SO₄, filtered and concentrated. The residue was purified by column chromatography on silica gel (Petroleum ether:Ethyl acetate=20:1, 1:1). Compound 7-1-3 (9.80 g, 56.20% yield, 88% purity) was obtained as white solid. ¹H NMR: (CDCl₃, 400 MHz) δ=8.108 (s, 1H), 7.643 (s, 1H), 7.403-7.412 (m, 6H), 7.269 (d, J=4.8 Hz, 2H), 6.217 (d, J=5.6 Hz, 1H), 4.451 (s, 1H), 3.975 (s, 1H), 3.631 (d, J=12 Hz, 1H), 3.255 (s, 1H), 2.264-2.296 (m, 1H), 2.136-2.184 (m, 1H), 1.957 (s, 1H), 1.859 (s, 3H), 1.090 (s, 9H).

Preparation of Compound 7-1-4.

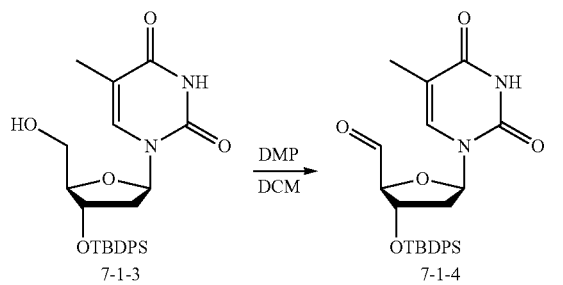

To a solution of compound 7-1-3 (18.00 g, 37.45 mmol, 1.00 eq.) in DCM (500 mL) was added DMP (17.47 g, 41.20 mmol, 12.75 mL, 1.10 eq.) at 0° C. The reaction mixture was stirred at 25° C. for 3 h. TLC (Petroleum ether:Ethyl acetate=1:1) showed the reaction was complete. Na₂SO₃ (sat., 100 mL) and NaHCO₃ (sat. 100 mL) was added successively. The mixture was extracted with DCM (100 mL*3). The organic phase was dried over Na₂SO₄ and concentrated. Compound 7-1-4 (17.92 g, crude) was obtained as yellow oil.

Preparation of Compound 7-1-5.

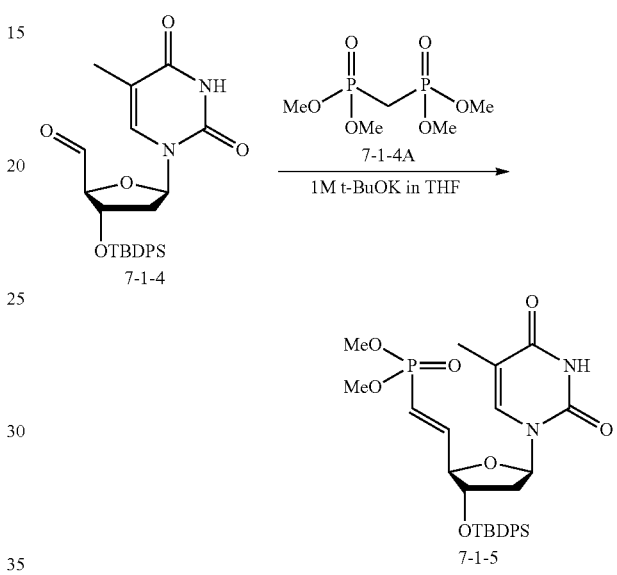

To a solution of compound 7-1-4A (16.08 g, 69.26 mmol, 1.85 eq.) in THF (29 mL) was added t-BuOK (1 M, 69.26 mL, 1.85 eq.) at 0° C. The mixture was stirred at 0° C. for 10 min, then warmed up to 25° C. for 30 min. The above mixture was added to a solution of compound 7-1-4 (17.92 g, 37.44 mmol, 1.00 eq.) in THF (36 mL) at 0° C. The reaction mixture was stirred at 0° C. for 1 h and then allowed to warm up to 25° C. in 80 min. TLC (Dichloromethane:Methanol=20:1) showed the reaction was complete. To the reaction mixture water (200 mL) was added and extracted with EtOAc (300 mL*4). The organic phase was dried (Na₂SO₄), filtered and concentrated. The residue was purified by column chromatography on silica gel (PE (10% DCM):EA=10:1, 1:8). Compound 7-1-5 (15.00 g) was obtained as yellow solid.

Preparation of Compound 7-1-6.

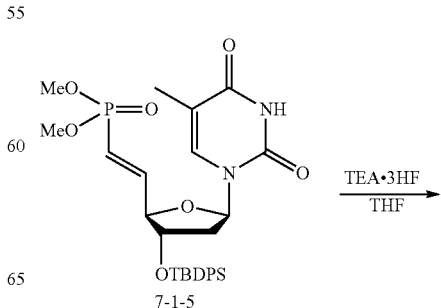

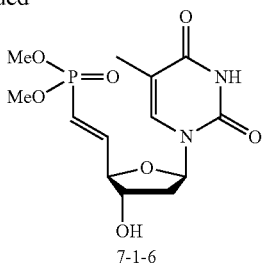

7-1-6

To a solution of compound 7-1-5 (21.00 g, 35.92 mmol, 1.00 eq.) in THF (60 mL) was added N, N-diethylethanamine; trihydrofluoride (28.95 g, 179.59 mmol, 29.24 mL, 5.00 eq.) at 25° C. The reaction mixture was stirred at 25° C. for 20 h. TLC (Dichloromethane:Methanol=10:1) showed the reaction was complete. The reaction mixture was concentrated under reduced pressure and the mixture was neutralized with $Na_2CO_3$ (aq., sat) until pH=7. The water phase was freeze-dried. The freeze-drying solid was washed with DCM:MeOH=10:1 (300 mL*2). The organic phase was concentrated. The residue obtained was purified by column chromatography on silica gel (Dichloromethane:Methanol=100:1, 100:8). Compound 7-1-6 (5.20 g, 15.02 mmol, 41.81% yield) was obtained as white solid. $^1$H NMR: ($CDCl_3$, 400 MHz) δ=9.521 (s, 1H), 7.120 (s, 1H), 6.974-7.074 (m, 1H), 6.372-6.405 (m, 1H), 5.961-6.050 (m, 1H), 4.684 (s, 1H), 4.504-4.518 (m, 1H), 4.393-4.409 (m, 1H), 3.726-3.775 (m, 6H), 3.151-3.180 (m, 2H), 2.411-2.427 (m, 1H), 1.930-2.218 (m, 1H), 1.927 (s, 3H).

Preparation of Compound 7-1-7.

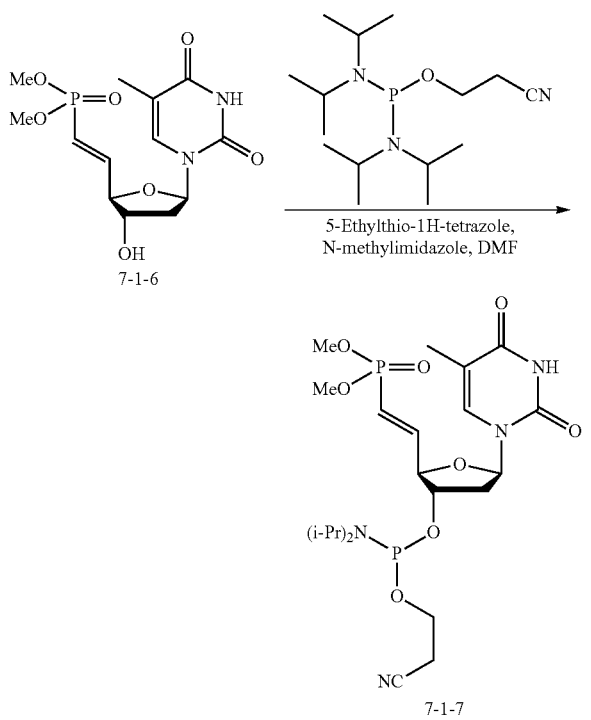

To a solution of compound 7-1-6 (3.80 g, 10.97 mmol, 1.00 eq.) in DMF (23 mL) was added 5-ethylsulfanyl-2H-tetrazole (1.43 g, 10.97 mmol, 1.00 eq.), 1-methylimidazole (1.80 g, 21.94 mmol, 1.75 mL, 2.00 eq.) and 3-bis(diisopropylamino)phosphanyloxypropanenitrile (4.96 g, 16.46 mmol, 5.22 mL, 1.50 eq.). The reaction mixture was stirred at 25° C. under $N_2$ for 3 h. TLC (Dichloromethane:Methanol=10:1) showed the reaction was complete. The reaction mixture was diluted with EtOAc (200 mL). The reaction mixture was washed with aq. saturated. $NaHCO_3$ solution (20 mL*4), dried over $Na_2SO_4$, filtered and concentrated under reduced pressure. The column was eluted with MeOH (20 min), EA (20 min), Petroleum ether (20 min), and Petroleum ether/Ethyl acetate (20 min). The residue thus obtained was purified by silica gel column chromatography (elution with Petroleum ether:EtOAc=10:1, 1:1 and then EtOAc/Acetonitrile=1000:1, 100:2, 100:4). Compound 7-1-7 (4.80 g, 8.78 mmol, 80.04% yield) was obtained as yellow solid. MS: LCMS, Calculated C22H36N4O8P2, 546.2008; Observed in +Ve mode 568.95; 569.43[M+Na]. $^1$H NMR: ($CDCl_3$, 400 MHz) δ=9.489 (s, 1H), 7.233 (s, 1H), 6.835-7.035 (m, 1H), 6.303-6.337 (m, 1H), 5.931-5.983 (m, 1H), 4.388-4.504 (m, 1H), 3.703-3.846 (m, 1H), 3.666-3.694 (m, 6H), 3.533-3.559 (m, 2H), 2.594-2.702 (m, 2H), 2.162-2.578 (m, 2H), 1.863 (s, 3H), 1.111-1.189 (m, 12H). $^{13}$C NMR (101 MHz, $CDCl_3$) δ 163.66, 162.54, 150.47, 150.40, 148.68, 148.61, 148.41, 148.35, 135.10, 135.01, 118.73, 118.25, 117.76, 117.61, 116.91, 116.85, 116.38, 111.74, 84.83, 84.79, 84.75, 84.72, 84.62, 84.56, 84.53, 84.50, 84.40, 84.33, 77.40, 77.29, 77.09, 76.77, 76.03, 75.87, 75.49, 75.48, 75.34, 75.32, 58.21, 58.19, 58.16, 58.12, 58.00, 57.92, 52.59, 52.55, 52.54, 52.52, 52.49, 52.46, 45.33, 45.27, 43.43, 43.40, 43.30, 43.27, 38.45, 38.40, 38.37, 36.45, 24.62, 24.57, 24.54, 24.49, 24.46, 22.96, 22.94, 22.88, 22.85, 20.47, 20.39, 20.37, 20.30, 20.11, 20.04, 12.50, 12.48. $^{31}$P NMR (162 MHz, $CDCl_3$) δ 149.40, 149.38, 19.99, 19.64, 14.10.

Example 141. Synthesis of Stereopure L-DPSE-5'-DMT-5'VP-dT Amidite, 7-2-8

Preparation of L-DPSE-NOPCl.

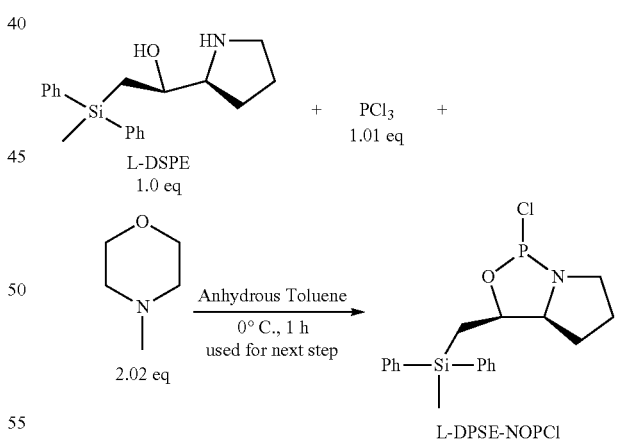

L-DPSE (8.82 g, 28.5 mmol) was dried by azeotropic evaporation with anhydrous toluene (60 ml) at 35° C. in a rotary evaporator and further dried in high vacuum for overnight. A solution of this dried L-DPSE and 4-methylmorpholine (5.82 g, 6.33 mL, 57.5 mmol) which was dissolved in anhydrous toluene (50 ml) was added to a solution of $PCl_3$ (4.0 g, 2.5 mL, 29.0 mmol) in anhydrous toluene (25 ml) placed in 250 mL three neck round bottomed flask which was cooled at −5° C. under argon (start Temp: −2° C., Max: 5° C. temp, 10 min addition) and the reaction mixture was stirred at 0° C. for another 40 min. After that the precipitated white solid was filtered by vacuum under argon using special filter tube (Chemglass: Medium Frit, Airfree, Schlenk). The solvent was removed by rotary evaporator under argon at bath temperature (25° C.) and the crude oily mixture was obtained and dried under vacuum overnight (~15 h) and used for next step.

Preparation of L-DPSE-5'-DMT-5'VP-dT Amidite.

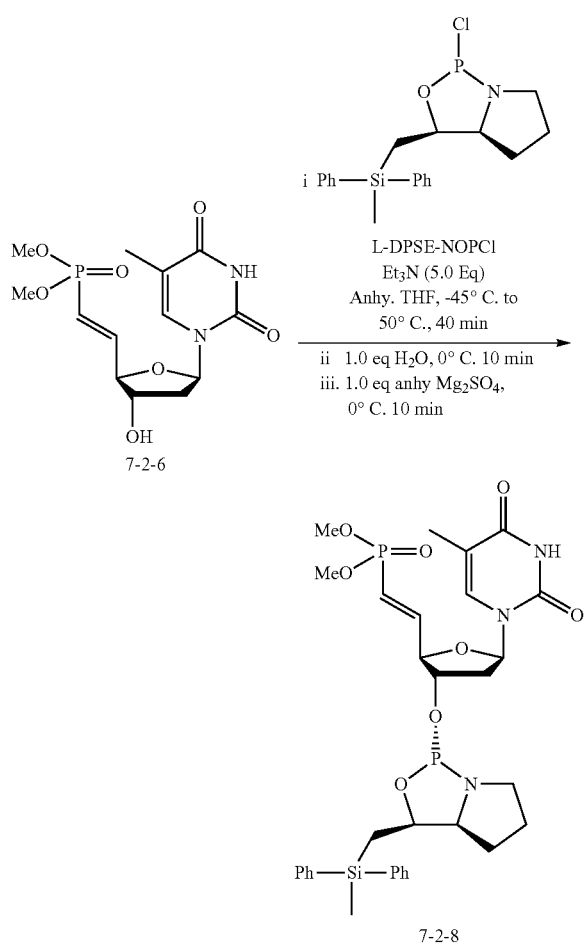

Compound 7-2-6 (7.0 g, 20.2 mmol) was dried two times by co-evaporation with 75 mL of anhydrous toluene at 45° C. and kept at high vacuum for overnight. Then the dried Compound 7-2-6, was dissolved in dry THF (70 mL) in a 250 mL three neck flasks under argon, followed by the addition of triethylamine (14 mL, 101 mmol) and the mixture was cooled to −45° C. To this cooled reaction mixture was added a solution of the crude L-DPSE-NOPCl (28.5 mmol, 1.4 eq, in THF 50 mL) from the previous step via syringe dropwise (~10 min, maintaining the internal temperature −40 to −35° C.). The reaction mixture was then gradually warmed to 5° C. After 30 min at 5° C., TLC and LC-MS analysis indicated the complete conversion of SM to product (total reaction time 2 h). The reaction mixture was cooled in an ice bath, and was quenched by addition of water (0.36 mL, 20.2 mmol) and stirred for 10 min followed by added anhydrous $Mg_2SO_4$ (3.0 g, 20.2 mmol). The reaction was filtered through Airfree, Schlenk filter tube, washed with dry THF (50 mL) and evaporated under rotary evaporation at 28° C. to afford the pale-yellow solid of the crude product, which was dried under high vacuum for overnight. The dried crude product was purified by 120 silica column (which was pre-deactivated with 3 column volume of ethyl acetate with 5% TEA) using ethyl acetate/hexane mixture with 5% TEA as a solvent. After column purification, fractions were analyzed by TLC and LC-MS and pooled together. Solvent was evaporated in a rotary evaporator at 28° C. and the residue was dried under high vacuum to afford the product as a white solid. Yield: 11.8 g (87%). $^1$H NMR (400 MHz, Chloroform-d) δ 7.46 (ddt, J=16.5, 7.6, 2.7 Hz, 4H), 7.33-7.17 (m, 6H), 6.93-6.88 (m, 1H), 6.75 (ddd, J=22.6, 17.2, 4.4 Hz, 1H), 6.16 (dd, J=7.5, 6.3 Hz, 1H), 5.85 (ddd, J=19.2, 17.1, 1.8 Hz, 1H), 4.71 (dt, J=8.7, 5.7 Hz, 1H), 4.38 (dp, J=10.7, 3.6 Hz, 1H), 4.15 (tt, J=5.6, 2.7 Hz, 1H), 3.68 (dd, J=11.1, 3.7 Hz, 6H), 3.55-3.29 (m, 2H), 3.09 (tdd, J=10.8, 8.8, 4.3 Hz, 1H), 2.11 (ddd, J=13.9, 6.3, 3.3 Hz, 1H), 1.96 (s, 1H), 1.87 (d, J=1.2 Hz, 3H), 1.85-1.73 (m, 2H), 1.70-1.49 (m, 2H), 1.38 (ddd, J=15.9, 10.4, 6.3 Hz, 2H), 1.26-1.11 (m, 2H), 0.60 (s, 3H). $^{31}$P NMR (162 MHz, $CDCl_3$) δ 152.41, 19.95. $^{13}$C NMR (101 MHz, $CDCl_3$) δ 171.07, 163.62, 163.59, 150.21, 150.19, 148.49, 148.43, 136.61, 135.84, 135.15, 134.57, 134.33, 129.48, 129.42, 127.97, 127.93, 127.81, 118.38, 116.50, 111.52, 85.02, 84.72, 84.70, 84.51, 84.48, 79.25, 79.16, 77.40, 77.28, 77.08, 76.76, 74.93, 74.91, 74.83, 74.81, 68.01, 67.98, 60.35, 52.60, 52.55, 52.47, 52.42, 47.03, 46.67, 38.12, 38.08, 27.18, 25.85, 25.82, 21.01, 17.58, 17.54, 14.19, 12.58, −3.00, −3.27. MS: LCMS, Calculated $C_{32}H_{41}N_3O_8P_2Si$, 685.7255: Observed in +Ve mode: 686.21 [M+H], 708.14 [M+Na].

Example 142. Synthesis of 5'-DMT-2'OMe-5-Lipid-3'-CNE Phosphoramidite—Incorporation of Desired Moieties Through Nucleobases

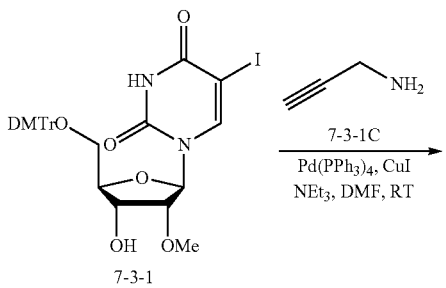

-continued

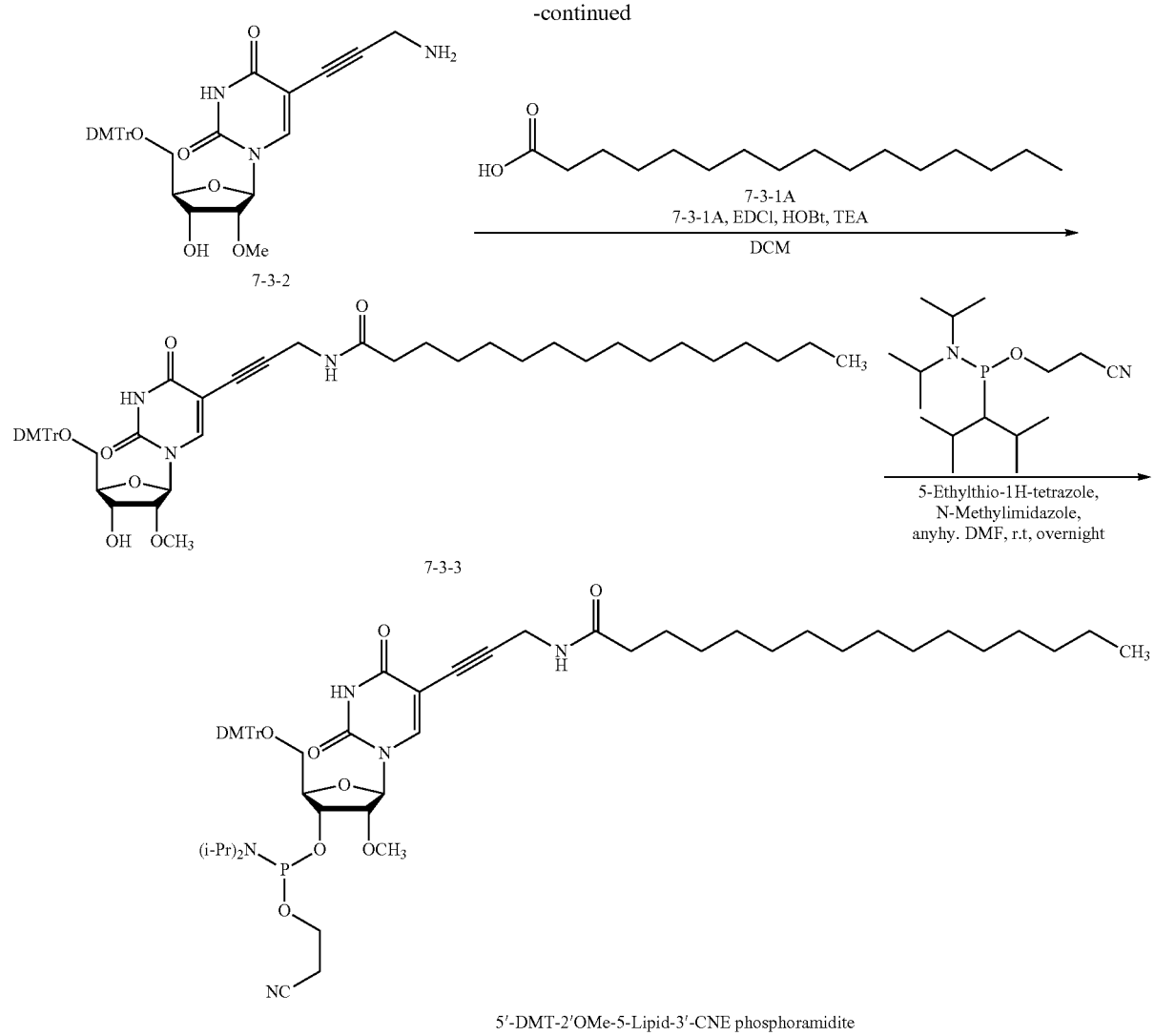

5′-DMT-2′OMe-5-Lipid-3′-CNE phosphoramidite

Preparation of Compound 7-3-2.

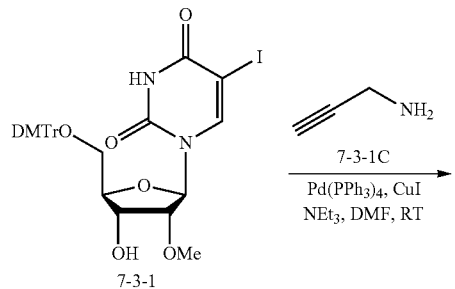

-continued

A mixture of compound 7-3-1 (13.00 g, 18.94 mmol), prop-2-yn-1-amine (2.09 g, 37.87 mmol, 2.43 mL), CuI (901.63 mg, 4.73 mmol), Pd(PPh$_3$)$_4$ (2.19 g, 1.89 mmol) and TEA (3.83 g, 37.87 mmol, 5.25 mL) in DMF (130 mL) was degassed and purged with N$_2$ for 3 times, and then the mixture was stirred at 25° C. for 12 hour under N$_2$ atmosphere and dark. LC-MS showed Compound 7-3-1 was consumed completely and one main peak with desired MS was detected. The mixture was concentrated in vacuo. The residue was purified by column chromatography (SiO$_2$, Dichloromethane/Methanol=100/1 to 0:1). Compound 7-3-2 (11.00 g, crude) was obtained as a yellow solid. $^1$H NMR (400 MHz, CDCl$_3$): δ=8.23 (s, 1H), 7.48-7.14 (m, 13H), 6.83 (br d, J=7.3 Hz, 5H), 5.94 (br s, 1H), 4.48 (br t, J=5.8 Hz, 2H), 4.05 (br d, J=6.4 Hz, 2H), 3.93 (br d, J=2.9 Hz, 1H), 3.81-3.70 (m, 8H), 3.62 (s, 4H), 3.52 (br d, J=11.0 Hz, 2H), 3.35 (br d, J=9.0 Hz, 1H). LCMS: (M+H$^+$): δ14.2. TLC (Dichloromethane/Methanol=10:1) Rf=0.19.

Preparation of Compound 7-3-3.

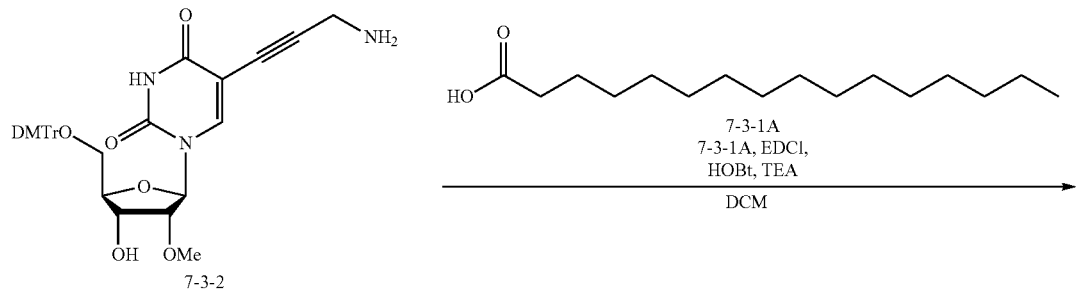

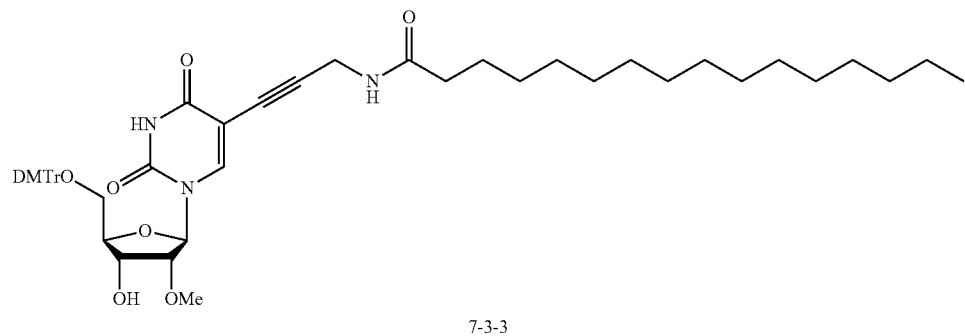

To a solution of palmitic acid (5.06 g, 19.72 mmol) in DCM (130 mL) was added TEA (3.63 g, 35.85 mmol, 4.97 mL), EDCI (5.15 g, 26.89 mmol), HOBt (3.63 g, 26.89 mmol), and Compound 7-3-3 (11.00 g, 17.93 mmol). The mixture was stirred at 25° C. for 1 hour. LC-MS showed Compound 7-3-3 was consumed completely and one main peak with desired MS was detected. The mixture was concentrated in vacuo. The residue was purified by column chromatography (SiO$_2$, Dichloromethane:Ethyl acetate=10/1 to 0:1 Dichloromethane:Ethyl acetate=100/1 to 0:1). Compound 7-3-3 (6.20 g, 40.58% yield) was obtained as a yellow solid. $^1$H NMR (400 MHz, CDCl$_3$): δ=8.25 (s, 1H), 7.50-7.14 (m, 10H), 6.90-6.77 (m, 4H), 5.93 (d, J=2.0 Hz, 1H), 5.01 (br s, 1H), 4.53-4.44 (m, 1H), 4.06 (br d, J=6.8 Hz, 1H), 3.94 (dd, J=2.0, 5.1 Hz, 1H), 3.83-3.73 (m, 9H), 3.63 (s, 3H), 3.55-3.48 (m, 1H), 3.39 (dd, J=2.5, 11.1 Hz, 1H), 2.79 (q, J=7.1 Hz, 1H), 1.85-1.76 (m, 2H), 1.50-1.41 (m, 2H), 1.24 (br s, 22H), 0.87 (t, J=6.7 Hz, 3H). $^{13}$CNMR (100 MHz, CDCl$_3$): δ=172.37, 162.32, 158.66, 158.58, 158.55, 149.58, 144.63, 142.49, 135.55, 135.44, 130.14, 130.00, 129.94, 128.08, 127.86, 126.91, 113.51, 113.35, 99.62, 89.56, 87.56, 86.85, 83.77, 83.68, 74.14, 68.49, 61.77, 58.82, 55.24, 45.30, 36.10, 31.89, 29.84, 29.67, 29.63, 29.49, 29.37, 29.33, 25.42, 22.66, 14.79, 14.11, 9.74. LCMS: (M+H$^+$): 850.4.

Preparation of 5'-DMT-2'OMe-5-Lipid-3'-CNE phosphoramidite.

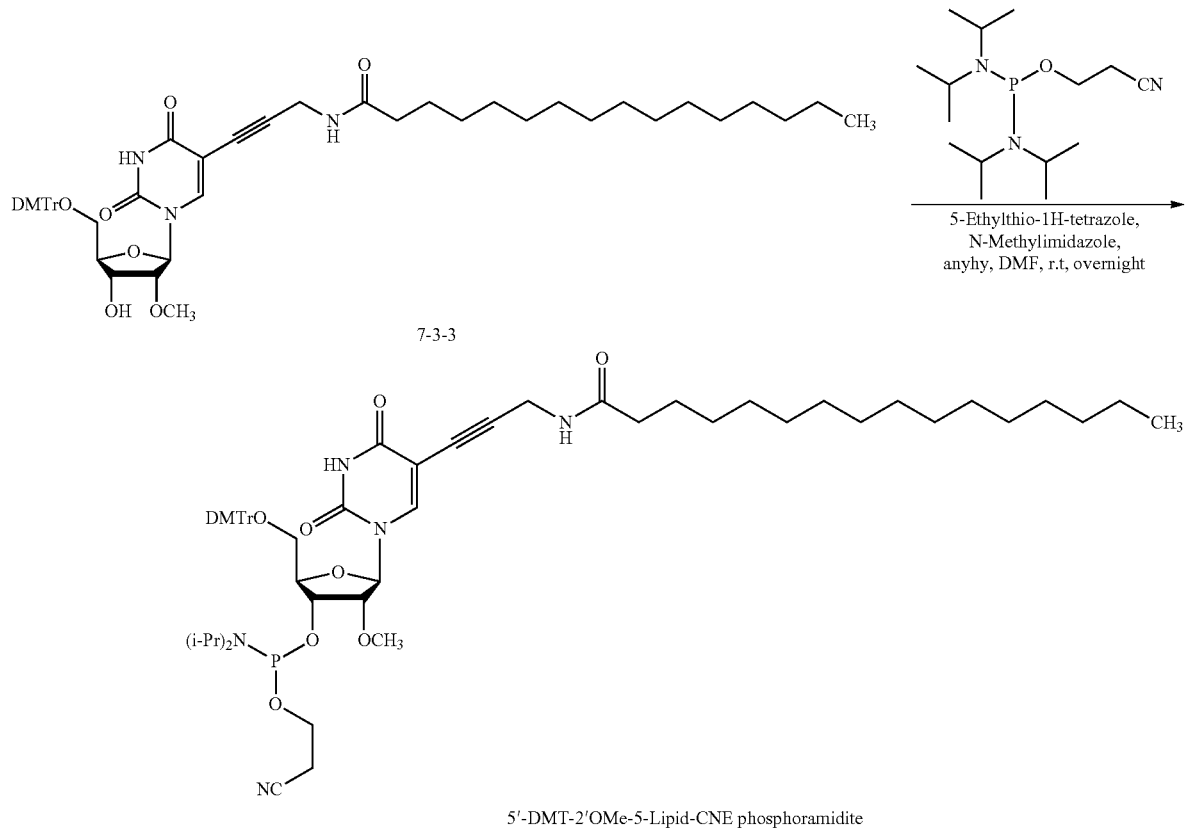

7-3-3

5-Ethylthio-1H-tetrazole,
N-Methylimidazole,
anyhy, DMF, r.t, overnight

5'-DMT-2'OMe-5-Lipid-CNE phosphoramidite

Compound 7-3-3 (2.8 g, 3.29 mmol) was co-evaporated with anhydrous toluene two times (25 mL×2) and dried under high vacuum overnight. The dried foamy solid was dissolved in anhydrous DMF (5 ml) and was added 5-ethylthio-1H-tetrazole (0.43 g, 3.29 mmol), N-methylimidazole (0.052 mL, 0.66 mmol) followed by 2-cynoethyl-N,N,N',N'-tetraisopropylphosphordiamidite (1.49 g, 4.93 mmol). The reaction mixture was stirred at room temperature under argon atmosphere for overnight. After TLC indicated completion, the reaction was diluted with EtOAc (70 mL) and washed with aq. saturated. NaHCO₃ solution (10 mL), and dried over Mg₂SO₄. The solvent was evaporated under reduced pressure and dried in high vacuum for night. The dried crude product was purified by Combi-Flash Rf (Teledyne ISCO) using 80 g silica column (which was pre-deactivated with 3 column volume of ethyl acetate with 5% TEA) with Hexane/Ethyl acetate/Acetonitrile which contains 5% TEA as an eluent to afford 5'-DMT-2'OMe-5-Lipid-3'CNE phosphoramidite as a foamy solid. Yield 3.1 g (90%). $^{31}$P NMR (162 MHz, CDCl₃) δ 150.58(s) 150.26(s). $^{13}$C NMR (101 MHz, CDCl₃) δ 172.20, 172.18, 161.78, 161.66, 158.70, 158.68, 149.45, 149.35, 144.71, 144.57, 142.69, 142.62, 137.91, 135.63, 135.53, 135.49, 135.40, 130.16, 130.11, 128.08, 128.06, 128.01, 127.00, 126.97, 117.71, 117.51, 113.39, 113.36, 113.32, 99.75, 99.46, 89.30, 89.26, 88.49, 88.00, 87.05, 86.84, 83.86, 83.04, 82.98, 82.93, 82.66, 77.39, 77.27, 77.07, 76.75, 74.45, 74.30, 69.88, 69.77, 69.64, 62.10, 61.24, 58.94, 58.92, 58.65, 58.47, 58.44, 57.97, 57.76, 55.30, 55.27, 43.35, 43.32, 43.23, 43.19, 36.11, 36.09, 33.26, 31.90, 29.88, 29.67, 29.65, 29.63, 29.58, 29.50, 29.37, 29.33, 25.41, 24.70, 24.64, 24.61, 24.57, 24.54, 24.50, 22.66, 20.47, 20.40, 20.34, 20.27, 14.82, 14.09. $^1$H NMR (400 MHz, Chloroform-d) δ 7.40 (dd, J=10.5, 7.6 Hz, 2H), 7.35-7.12 (m, 7H), 6.78 (ddd, J=9.0, 4.2, 2.7 Hz, 4H), 4.82 (dt, J=22.1, 4.9 Hz, 1H), 4.57-4.38 (m, 1H), 4.24-4.10 (m, 1H), 4.06-3.96 (m, 1H), 3.86-3.67 (m, 7H), 3.67-3.58 (m, 2H), 3.57-3.39 (m, 6H), 3.25 (ddd, J=13.5, 11.3, 2.8 Hz, 1H), 2.55 (t, J=6.1 Hz, 1H), 2.30 (t, J=6.2 Hz, 1H), 1.71 (qd, J=7.4, 7.0, 1.4 Hz, 2H), 1.38 (dtt, J=10.5, 7.7, 2.8 Hz, 2H), 1.09 (dd, J=6.7, 5.1 Hz, 17H), 0.97 (d, J=6.8 Hz, 3H), 0.80 (t, J=6.6 Hz, 3H). MS: LCMS: Calculated, C59H82N5O10P; 1051.5730; Observed +Ve mode: m/z: 1153.69 [M+Et₃N].

Example 143. Synthesis of 5'-(R)—C-Me-5'-DMT-dT-CNE Amidite

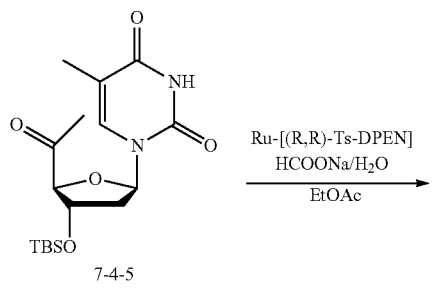

7-4-5

Ru-[(R,R)-Ts-DPEN]
HCOONa/H₂O
EtOAc

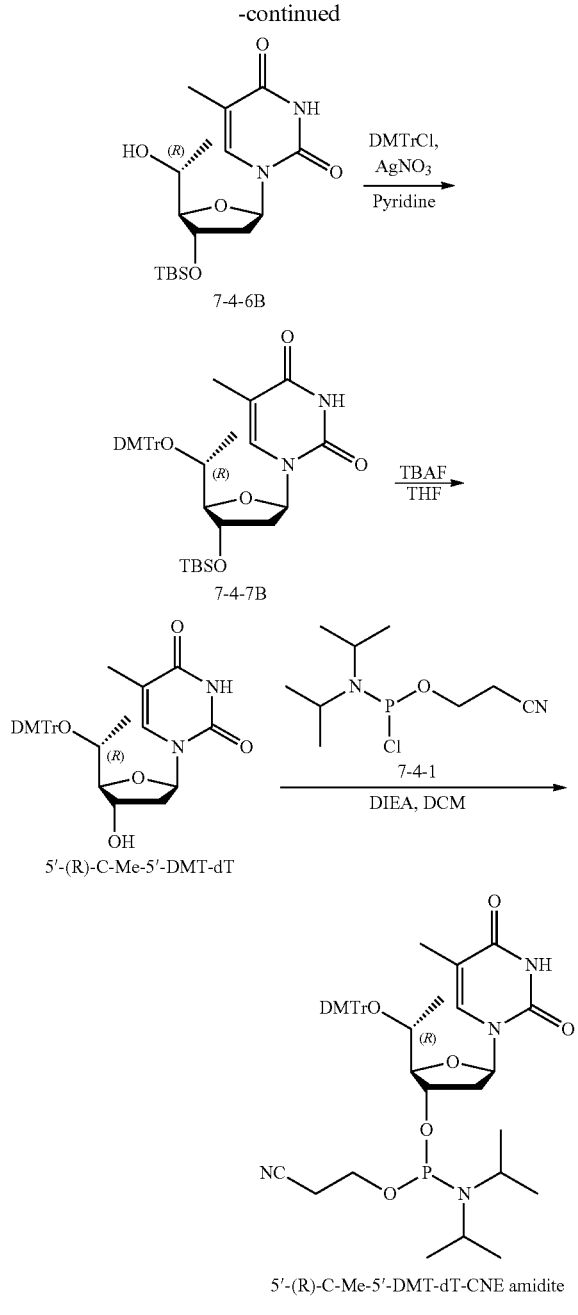

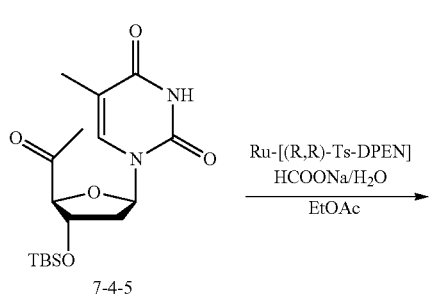

Preparation of Compound 7-4-6B.

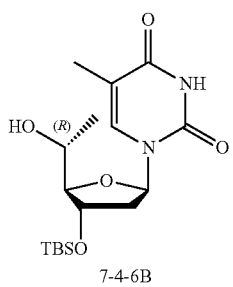

To a solution of compound 7-4-5 (46.00 g, 124.83 mmol) in a mixture of EtOAc (460.00 mL) and sodium formate (353.17 g, 5.19 mol) dissolved in Water (1.84 L), and then [[(1R,2R)-2-amino-1,2-diphenyl-ethyl]-(p-tolylsulfonyl)amino]-chloro-ruthenium; 1-isopropyl-4-methyl-benzene (1.59 g, 2.50 mmol) was added. The resulting two-phase mixture was stirred for 12 h at 25° C. under $N_2$. TLC showed the starting material was consumed. The mixture was extracted with EtOAc (50 mL*3). The combined organic was washed with brine (30 mL), dried over $Na_2SO_4$, filtered and concentrated to get the crude. The residue was purified by re-crystallization from Petroleum ether/Ethyl acetate=5:1 to give the compound 7-4-6B as a white solid (36.00 g, 77.83% yield) as a white solid. $^1$H NMR (400 MHz, DMSO-d6): δ=11.31 (s, 1H), 7.67 (s, 1H), 6.16 (dd, J=5.5, 8.8 Hz, 1H), 5.05 (d, J=5.1 Hz, 1H), 4.49 (br d, J=5.1 Hz, 1H), 3.78-3.70 (m, 1H), 3.55 (d, J=3.7 Hz, 1H), 2.20-2.09 (m, 1H), 1.96 (br dd, J=5.7, 13.0 Hz, 1H), 1.77 (s, 3H), 1.11 (d, J=6.4 Hz, 3H), 0.87 (s, 9H), 0.09 (s, 6H). HPLC: HPLC purity: 97.7%. SFC: SFC purity: 99.1%. TLC (Petroleum ether/Ethyl acetate=1:1) Rf=0.37.

Preparation of Compound 7-4-7B.

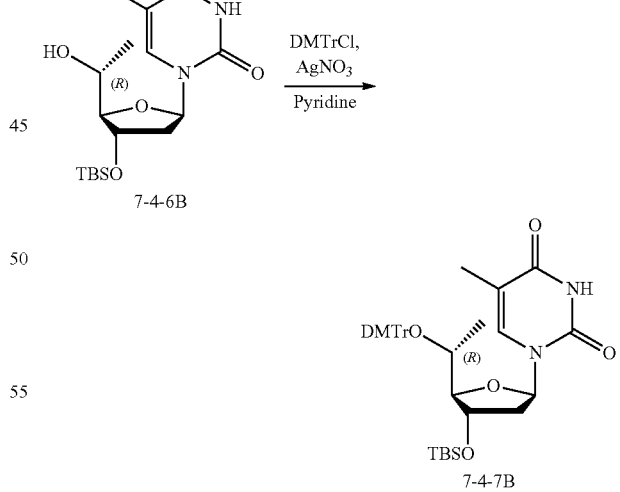

Compound 7-4-6B (18.00 g, 48.58 mmol) was dried by azeotropic distillation on a rotary evaporator with pyridine (100 mL) and toluene (100 mL*2). A solution of compound 7-4-6B (18.00 g, 48.58 mmol) and DMTCl (1.89 g, 5.59 mmol) in the mixture of pyridine (180.00 mL) and THF (720.00 mL) was degassed and purged with $N_2$ for 3 times and then $AgNO_3$ (14.19 g, 83.56 mmol) was added. The mixture was stirred at 25° C. for 15 hr. TLC showed the starting material was consumed. MeOH (5 mL) was added and stirred for 15 min and then the mixture was filtered and the cake was washed with toluene (300 mL*3). The filtrate was concentrated to obtain the compound 7-4-7B as a yellow oil (65.38 g, crude). The mixture was used directly to next step without any purification. TLC (Petroleum ether/Ethyl acetate) Rf=0.63.

Preparation of 5'-(R)—C-Me-5'-DMTr-dT.

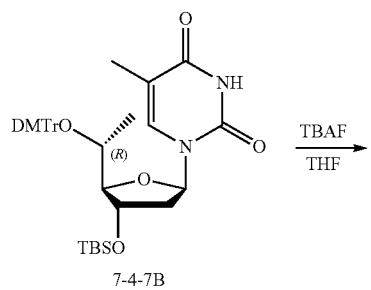

7-4-7B

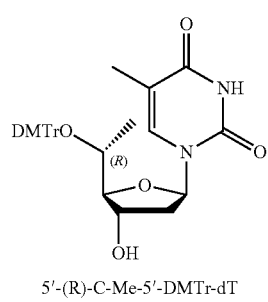

5'-(R)-C-Me-5'-DMTr-dT

To a solution of compound 7-4-7B (65.38 g, 97.16 mmol) in THF (650.00 mL) was added TBAF (1 M, 184.60 mL). The mixture was stirred at 25° C. for 12 hours. TLC showed the starting material was consumed. The mixture was concentrated to provide the crude and then sat. NaCl (5% aq., 200 mL*2) was added and the mixture was extracted with EtOAc (200 mL*3). The combined organic phase was dried over Na$_2$SO$_4$, filtered and concentrated to provide the crude product, which was purified by MPLC (Petroleum ether: Ethyl acetate 5:1, 1:1, 1:4, 5% TEA) to provide 5'-(R)—C-Me-5'-DMTr-dT as a white solid (47.50 g, 85.03 mmol, 87.52% yield). $^1$H NMR (400 MHz, DMSO-d6): δ=11.32 (s, 1H), 7.46 (br d, J=7.8 Hz, 2H), 7.37-7.25 (m, 6H), 7.23-7.16 (m, 1H), 7.07 (s, 1H), 6.89 (dd, J=4.6, 8.5 Hz, 4H), 6.12 (t, J=7.2 Hz, 1H), 5.27 (d, J=4.6 Hz, 1H), 4.54-4.46 (m, 1H), 3.73 (d, J=1.8 Hz, 6H), 3.62 (t, J=2.9 Hz, 1H), 3.40-3.34 (m, 1H), 2.09-2.02 (m, 2H), 1.40 (s, 3H), 0.77 (d, J=6.2 Hz, 3H). $^{13}$C NMR (101 MHz, DMSO-d6): δ=163.98, 158.58, 150.81, 146.95, 137.11, 136.79, 135.76, 130.49, 130.41, 128.20, 128.15, 127.04, 113.54, 113.52, 110.16, 89.87, 86.24, 83.35, 70.28, 70.05, 60.20, 55.47, 55.35, 21.20, 17.82, 14.52, 12.08. HPLC: HPLC purity: 98.7%. LC-MS: (M−H$^+$)=557.2; LCMS purity: 98.9%. SFC: SFC purity: 100.0%. TLC (Petroleum ether/Ethyl acetate=1:1, 5% TEA) Rf=0.02.

Preparation of 5'-(R)—C-Me-5'-DMT-dT-CNE-Amidite.

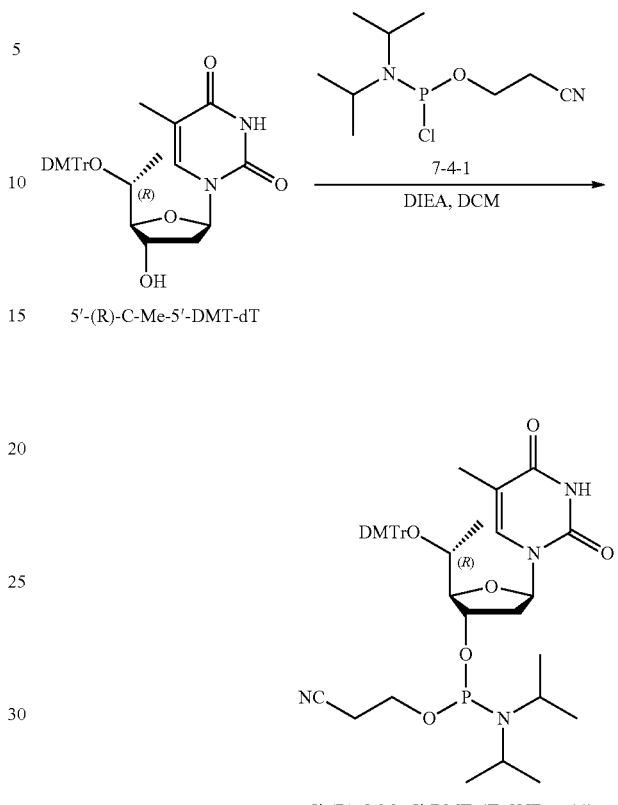

5'-(R)—C-Me-5'-OMT-dT (5 g, 8.95 mmol) was dried with toluene (50 mL). To a solution of DIEA (1.39 g, 10.74 mmol, 1.87 mL) and 5'-(R)—C-Me-5'-DMT-dT (5 g, 8.95 mmol) in anhydrous DCM (50 mL) was added compound 7-4-1 (2.76 g, 9.40 mmol) under N$_2$ at 0° C. The mixture was stirred at 15° C. for 2 h. TLC showed the starting material was consumed and two new spots were found. The mixture was quenched by addition of saturated aq. NaHCO$_3$ (20 mL) and extracted with DCM (30 mL*3). The combined organic phase was dried over Na$_2$SO$_4$, filtered and concentrated to provide the crude product, which was purified on a Combiflash instrument from Teledyne. A 40 g silica gel cartridge column was first pre-treated by eluting with 10% EtOAc/Petroleum ether containing 5% Et$_3$N (300 mL). The crude product was dissolved in a 2:1 volume:volume mixture of methylene chloride:petroleum ether containing 5% Et$_3$N and loaded onto the column. After loading, the purification process was run using the following gradient: 10 to 50% EtOAc/Petroleum ether containing 5% Et$_3$N. Fractions were collected. After evaporation of the solvent, 5'-(R)—C-Me-5'-DMT-dT-CNE-amidite was obtained as a white solid (3.6 g, 53% yield). $^1$H NMR (400 MHz, CHLOROFORM-d) δ=8.11 (br s, 1H), 7.53 (br d, J=7.7 Hz, 3H), 7.42 (br t, J=8.2 Hz, 4H), 7.32-7.17 (m, 4H), 7.07-6.99 (m, 1H), 6.84 (br d, J=8.2 Hz, 4H), 6.31 (br dd, J=5.5, 8.7 Hz, 1H), 4.94 (br s, 1H), 3.96-3.73 (m, 10H), 3.72-3.41 (m, 4H), 2.65 (td, J=6.1, 18.0 Hz, 2H), 2.53-2.37 (m, 1H), 2.10 (br d, J=8.2 Hz, 1H), 1.47 (br s, 4H), 1.33-1.16 (m, 15H), 1.00-0.90 (m, 3H). $^{31}$P NMR (162 MHz, CHLOROFORM-d) δ=148.81 (s, 1P), 148.35 (s, 1P).

Example 144. Synthesis of
5'-(S)—C-Me-5'-DMT-dT-CNE Amidite
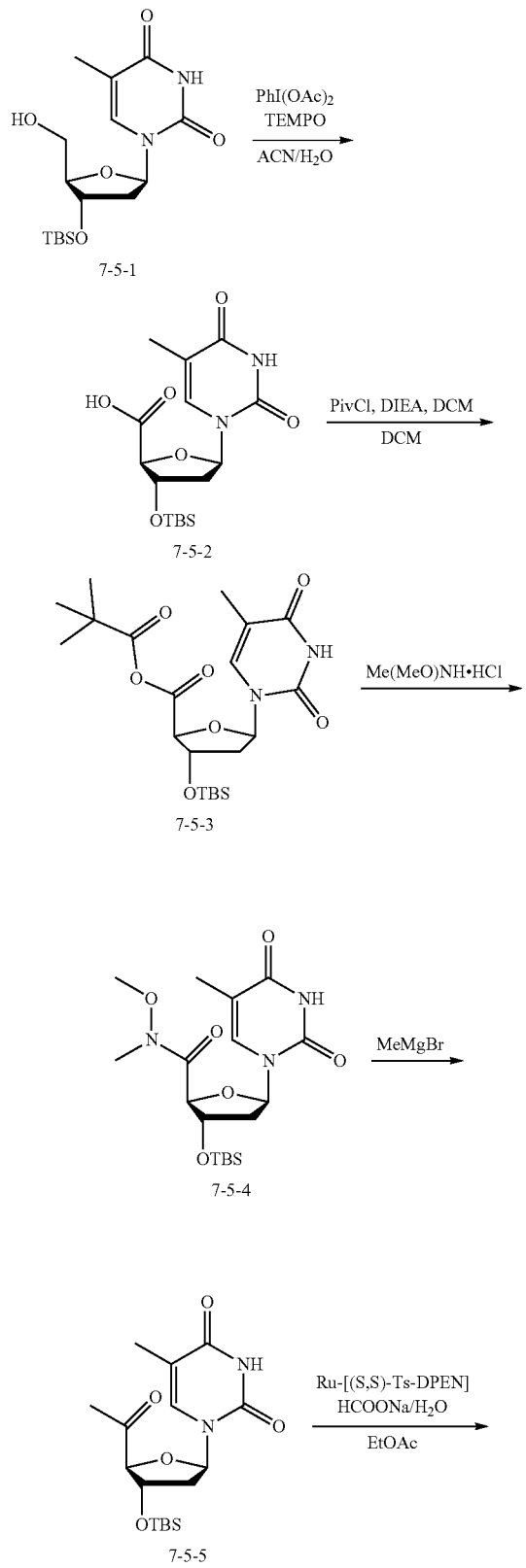
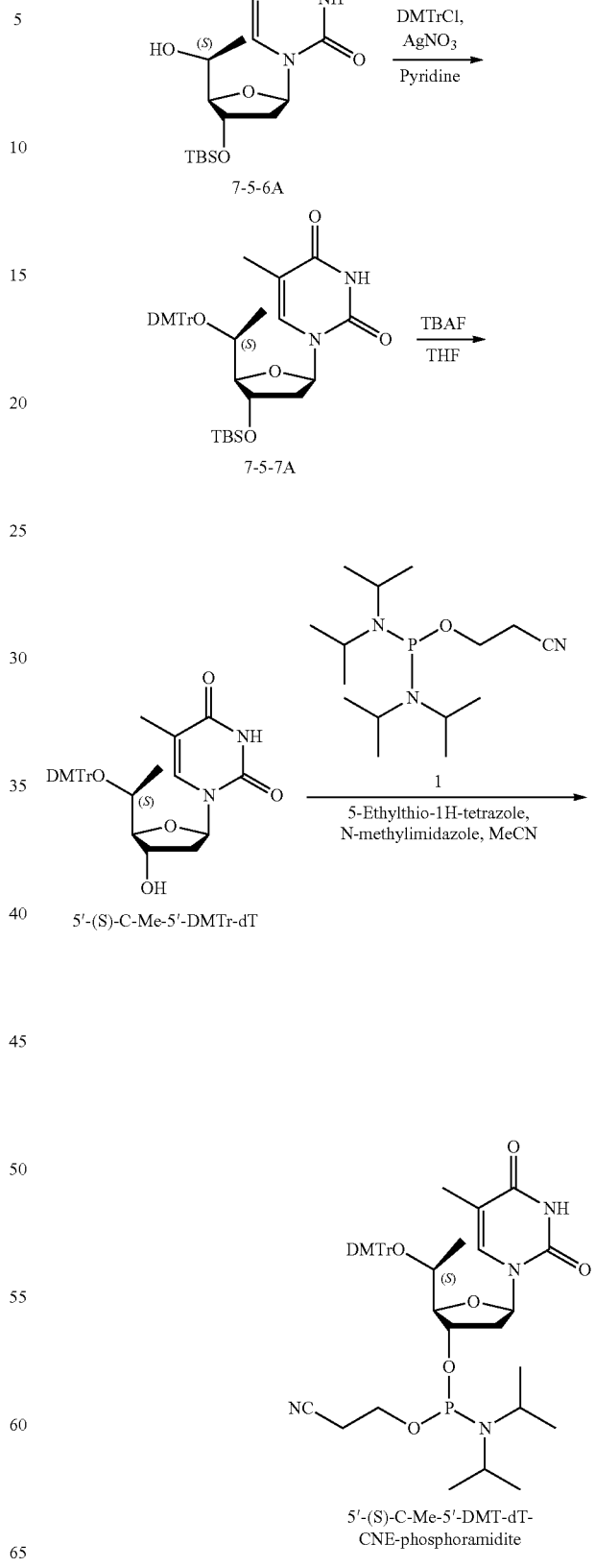

Preparation of Compound 7-5-2.

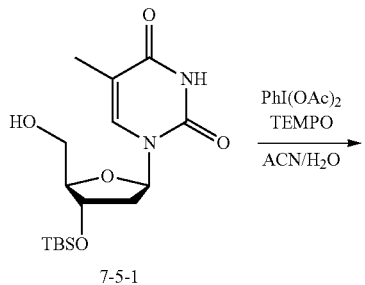

7-5-1

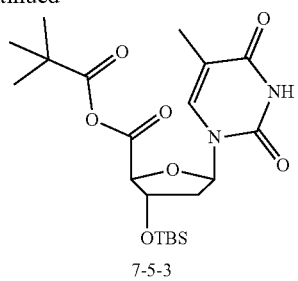

7-5-3

To a solution of compound 7-5-2 (50.00 g, 134.96 mmol) in DCM (500.00 mL) was added DIEA (34.89 g, 269.92 mmol, 47.15 mL) and 2,2-dimethylpropanoyl chloride (21.16 g, 175.45 mmol). The mixture was stirred at −10-0° C. for 1.5 hours. TLC showed the starting material was consumed. The mixture in DCM was used directly for next step. TLC (Petroleum ether/Ethyl acetate=1:1) Rf=0.15.

Preparation of Compound 7-5-4.

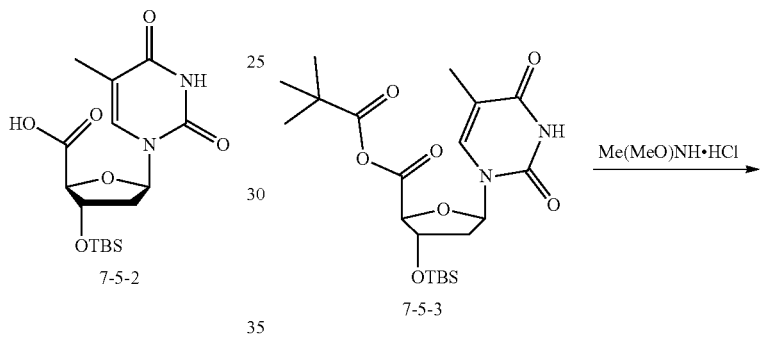

7-5-2 → 7-5-3

To a solution of compound 7-5-1 (63.00 g, 176.72 mmol) in the mixture of H$_2$O (250.00 mL) and MeCN (250.00 mL) was added PhI(OAc)$_2$ (125.23 g, 388.79 mmol) and TEMPO (5.56 g, 35.34 mmol) at 10° C. The mixture was stirred at 25° C. for 2 hours. TLC (Petroleum ether/Ethyl acetate=1:1, Rf=0) showed the starting material was consumed. The mixture was concentrated, and MTBE (1 L) was added. The mixture was stirred for 0.5 h and then filtered. The cake was washed with MTBE (1 L*2), and dried to provide compound 7-5-2 as a white solid (126 g, 96.23% yield). $^1$H NMR (400 MHz, DMSO): δ=11.21 (s, 1H), 7.89 (d, J=1.0 Hz, 1H), 6.18 (dd, J=5.9, 8.6 Hz, 1H), 4.61-4.41 (m, 1H), 4.17 (d, J=0.9 Hz, 1H), 2.51-2.26 (m, 3H), 2.09-1.85 (m, 2H), 1.74-1.58 (m, 3H), 0.90-0.58 (m, 10H), 0.00 (d, J=2.0 Hz, 6H). LC-MS: (M+H$^+$): 371.1. TLC (Petroleum ether/Ethyl acetate=1:1) Rf=0.

Preparation of Compound 7-5-3.

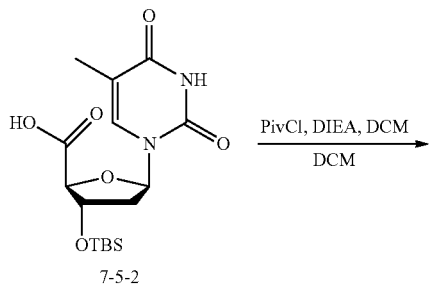

7-5-2

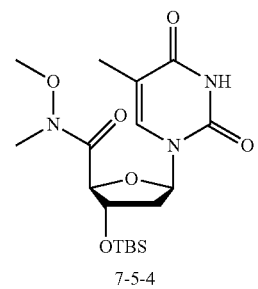

7-5-4

To compound 7-5-3 in DCM was added TEA (40.94 g, 404.55 mmol, 56.08 mL) and N-methoxymethanamine hydrochloride (19.73 g, 202.27 mmol). The mixture was stirred at 0° C. for 1 h. TLC showed the starting material was consumed. The mixture was washed with HCl (1N, 100 mL) and then aqueous NaHCO$_3$ (100 mL). The organic layer was dried over Na$_2$SO$_4$, filtered and concentrated to provide the crude product, which was purified by silica gel chromatography (Petroleum ether/Ethyl acetate=30/1, 0/1) to afford compound 7-5-4 as a white solid (95.5 g, 85.63% yield). $^1$H NMR (400 MHz, CDCl$_3$): δ=8.29 (s, 1H), 8.19 (br s, 1H), 6.46 (dd, J=5.1, 9.3 Hz, 1H), 4.71 (s, 1H), 4.38 (d, J=4.2 Hz, 1H), 3.65 (s, 3H), 3.15 (s, 3H), 2.18-2.08 (m, 1H), 2.00-1.90 (m, 1H), 1.87 (d, J=1.1 Hz, 3H), 0.88-0.74 (m, 10H), 0.00 (d, J=3.7 Hz, 6H). TLC (Petroleum ether/Ethyl acetate=1:1) Rf=0.43.

Preparation of Compound 7-5-5.

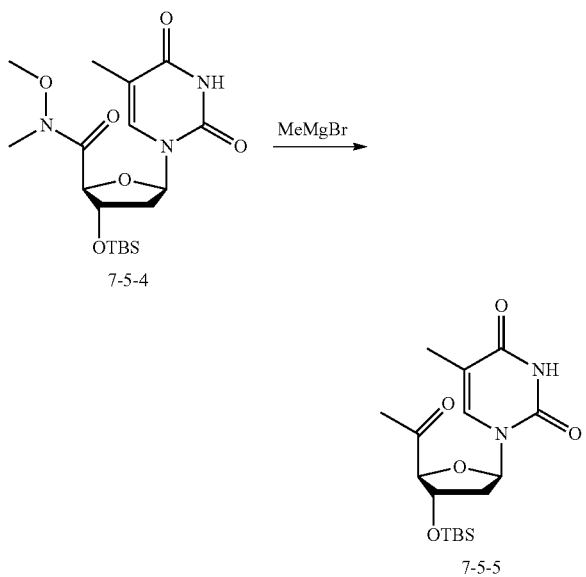

7-5-4

7-5-5

To a solution of compound 7-5-4 (115.00 g, 278.09 mmol) in THF (1.20 L) was added MeMgBr (3 M, 185.39 mL) at 0° C. The mixture was stirred at 0° C. for 2 h. TLC showed the starting material was consumed. To the mixture was added water (1 L) at 0° C. and the mixture was extracted with EtOAc (300 mL*2). The combined organic phase was dried over $Na_2SO_4$, filtered and concentrated to provide the compound 7-5-5 as a white solid (100.00 g, 97.58% yield). The mixture was used directly without further purification. $^1$H NMR (400 MHz, $CDCl_3$): δ=8.81 (br s, 1H), 7.95 (s, 1H), 6.41 (dd, J=5.6, 8.1 Hz, 1H), 4.60-4.40 (m, 2H), 2.40-2.16 (m, 4H), 1.98 (s, 3H), 1.02-0.83 (m, 10H), 0.14 (d, J=3.3 Hz, 6H), 0.20~0.00 (m, 1H). TLC (Petroleum ether/Ethyl acetate=1:1) Rf=0.68.

Preparation of Compound 7-5-6A.

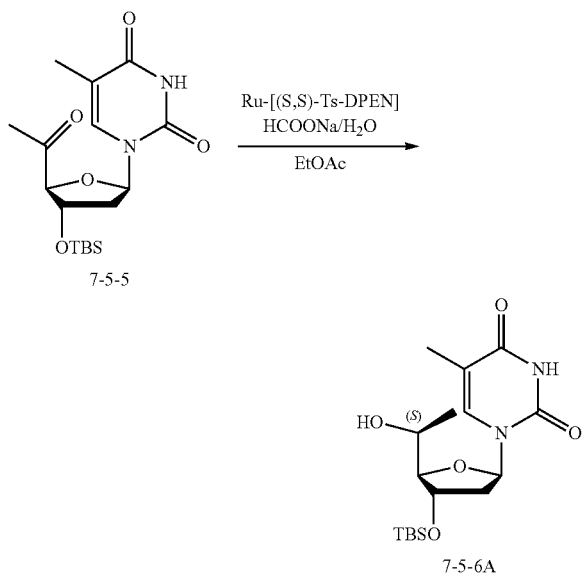

7-5-5

7-5-6A

To a solution of compound 7-5-5 (46.00 g, 124.83 mmol) in the mixture of EtOAc (460.00 mL) and sodium formate (353.17 g, 5.19 mol) dissolved in water (1.84 L), and N-[(1S,2S)-2-amino-1,2-diphenyl-ethyl]-4-methyl-benzenesulfonamide chlororuthenium; 1-isopropyl-4-methyl-benzene (1.59 g, 2.50 mmol) was added. The resulting two-phase mixture was stirred for 12 h at 25° C. under $N_2$. TLC showed the starting material was consumed. The mixture was extracted with EtOAc (500 mL*3). The combined organic was washed with brine (300 mL), dried over $Na_2SO_4$, filtered and concentrated to provide the crude product. The mixture was purified by MPLC (Petroleum ether/MTBE=10:1 to 1:1) seven times to provide compound 7-5-6A as a yellow oil (25.6 g, 57.53% yield). $^1$H NMR (400 MHz, DMSO-d6): δ=11.28 (s, 1H), 7.85 (s, 1H), 6.16 (t, J=6.8 Hz, 1H), 5.04 (d, J=4.6 Hz, 1H), 4.46-4.29 (m, 1H), 3.79 (br t, J=6.8 Hz, 1H), 3.59 (br s, 1H), 3.32 (s, 1H), 2.21-2.09 (m, 1H), 2.06-1.97 (m, 1H), 1.76 (s, 3H), 1.17-1.08 (m, 4H), 0.91-0.81 (m, 10H), 0.08 (s, 6H). SFC: SFC purity: 98.6%. TLC (Petroleum ether/Ethyl acetate=1:1) Rf=0.38.

Preparation of Compound 7-5-7A.

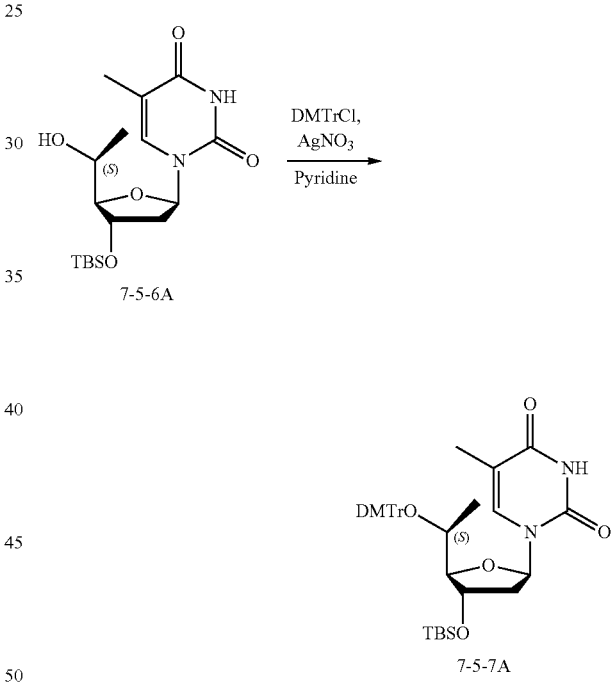

7-5-6A 7-5-7A

Compound 7-5-6A (12.80 g, 34.55 mmol) was dried by azeotropic distillation on a rotary evaporator with pyridine (100 mL) and toluene (100 mL*2). To a solution of compound 7-5-6A (12.80 g, 34.55 mmol) and DMTCl (1.89 g, 5.59 mmol) in the mixture of pyridine (120.00 mL) and THF (400.00 mL) was degassed and purged with $N_2$ for 3 times and then $AgNO_3$ (10.09 g, 59.43 mmol) was added. The mixture was stirred at 25° C. for 15 hr. TLC showed the starting material was consumed. MeOH (5 mL) was added and stirred for 15 min and then the mixture was filtered and the cake was washed with toluene (300 mL*3). The filtrate was concentrated to get the compound 7-7-7A as a yellow oil (46.50 g, crude). The mixture was used directly to next step without any purification. TLC (Petroleum ether/Ethyl acetate) Rf=0.63.

Preparation of 5'-(S)—C-Me-5'-DMT-dT.

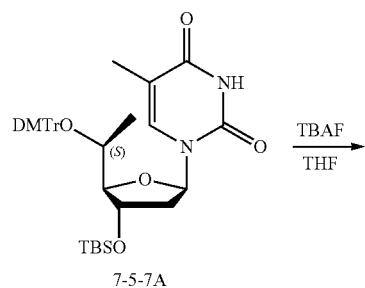

7-5-7A

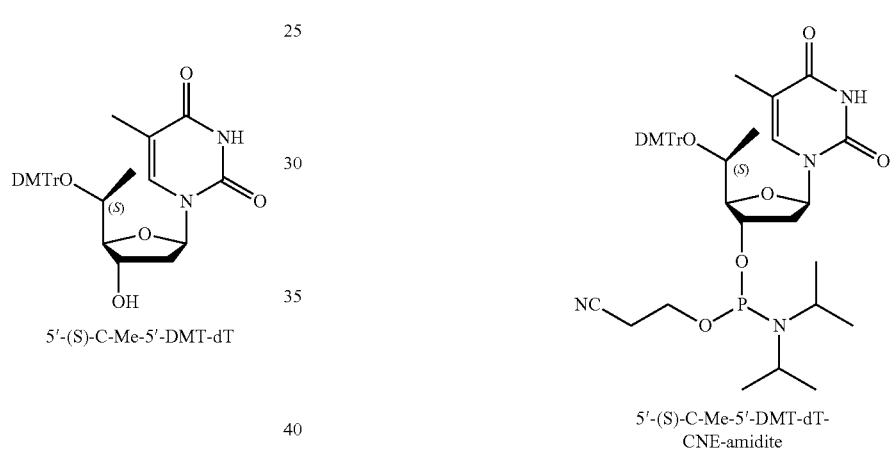

5'-(S)-C-Me-5'-DMT-dT

To a solution of compound 7-5-7A (46.50 g, 69.11 mmol) in THF (460.00 mL) was added TBAF (1 M, 131.31 mL). The mixture was stirred at 25° C. for 5 hrs. TLC showed the starting material was consumed. The mixture was concentrated and then sat. NaCl (5% aq., 200 mL) was added and the aqueous phase was extracted with EtOAc (200 mL*3). The combined organic layer was dried over Na₂SO₄, filtered and concentrated to provide the crude product, which was purified by MPLC (Petroleum ether/Ethyl acetate 5:1, 1:1, 1:4, 5% TEA) to provide 5'-(S)—C-Me-5'-DMT-dT as a white solid (29.0 g, 75.12% yield). ¹H NMR (400 MHz, DMSO-d6): δ=11.35 (s, 1H), 7.56 (s, 1H), 7.58-7.53 (m, 1H), 7.44 (d, J=7.8 Hz, 2H), 7.37-7.24 (m, 6H), 7.23-7.17 (m, 1H), 6.87 (t, J=8.3 Hz, 4H), 6.13 (t, J=6.9 Hz, 1H), 5.21 (d, J=4.9 Hz, 1H), 4.23 (br s, 1H), 3.73 (d, J=2.9 Hz, 6H), 3.67 (t, J=3.7 Hz, 1H), 3.57-3.46 (m, 1H), 2.23-2.04 (m, 2H), 1.67 (s, 3H), 1.70-1.65 (m, 1H), 0.71 (d, J=6.2 Hz, 3H). ¹³CNMR (101 MHz, DMSO-d6): δ=170.78, 164.16, 158.64, 158.59, 150.86, 146.71, 137.00, 136.75, 135.97, 130.65, 130.52, 128.38, 128.07, 127.11, 113.48, 110.11, 89.78, 86.41, 83.87, 70.58, 70.22, 60.21, 55.48, 21.20, 18.08, 14.53, 12.54. HPLC: HPLC purity: 98.4%. LCMS: (M−H⁺)=557.2; LCMS purity: 99.0%. SFC: SFC purity: 99.4%. TLC (Petroleum ether/Ethyl acetate=1:1, 5% TEA) Rf=0.01.

Preparation of 5'-(S)—C-Me-5'-DMT-dT-CNE-Amidite

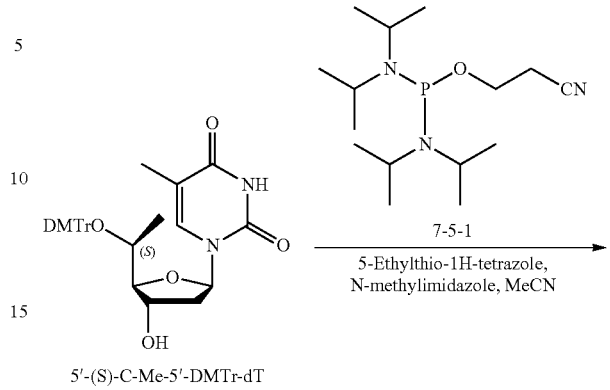

5'-(S)-C-Me-5'-DMTr-dT

5'-(S)-C-Me-5'-DMT-dT-CNE-amidite

To a solution of 5'-(S)—C-Me-5'-DMT-dT (5.00 g, 8.95 mmol) in MeCN (50.00 mL) was added 5-ethylsulfanyl-2H-tetrazole (1.17 g, 8.95 mmol), 1-methylimidazole (1.47 g, 17.90 mmol, 1.43 mL) and compound 7-5-1 (4.05 g, 13.43 mmol, 4.26 mL). The reaction mixture was stirred at 20° C. under N₂ for 2 hrs. TLC and LC-MS showed some starting material was consumed and the desired substance was formed. The reaction mixture was concentrated under reduced pressure, and the residue was diluted with EtOAc (20 mL). The reaction mixture was washed with aq. saturated NaHCO₃ solution (20 mL), dried over Na₂SO₄, filtered and concentrated to provide the crude product, which was purified by MPLC (Petroleum ether 5% TEA:Ethyl acetate from 10:1 to 1:1) to provide 5'-(S)—C-Me-5'-DMT-dT-CNE-amidite as a white solid (4.3 g, 63.31% yield). ¹H NMR (400 MHz, CHLOROFORM-d) δ=8.19 (br s, 1H), 7.69-7.60 (m, 1H), 7.54 (s, 1H), 7.43-7.33 (m, 2H), 7.32-7.07 (m, 8H), 6.73 (ddd, J=3.7, 5.8, 9.0 Hz, 4H), 6.27-6.15 (m, 1H), 4.49-4.37 (m, 1H), 3.82-3.65 (m, 8H), 3.63-3.55 (m, 2H), 3.53-3.39 (m, 3H), 2.50 (t, J=6.3 Hz, 1H), 2.46-2.31 (m, 1H), 2.29-2.19 (m, 1H), 2.16-2.04 (m, 1H), 1.68 (s, 3H), 1.20-1.00 (m, 13H), 0.95 (d, J=6.8 Hz, 3H), 0.92-0.74 (m, 4H). ³¹P NMR (162 MHz, CHLOROFORM-d) δ=149.11 (s, 1P), 148.99 (s, 1P).

Example 145. Synthesis of L-DPSE-5'-(R)—C-Me-5'-DMT-dT Amidite

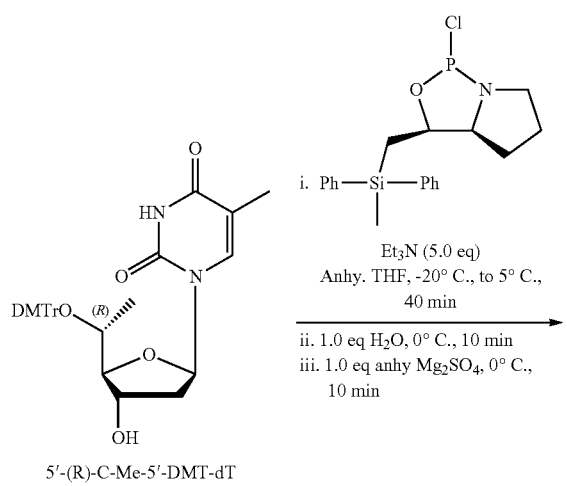

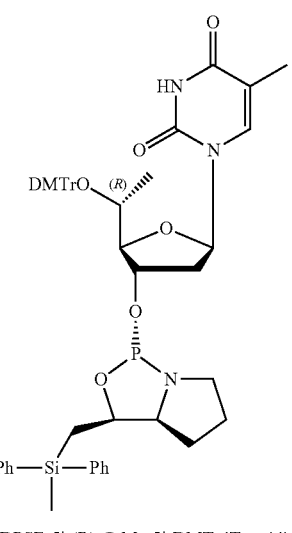

L-DPSE-5'-(R)-C-Me-5'-DMT-dT amidite

The 5'-(R)—C-Me-5'-OMT-dT (11.17 g, 20 mmol) was dried two times by co-evaporation with 80 mL of anhydrous toluene at 45° C. and kept at high vacuum for overnight. Then the dried 5'-(R)—C-Me-5'-OMT-dT was dissolved in dry THF (80 mL) in 500 mL three neck flasks under argon, followed by the addition of triethylamine (13.93 mL, 100 mmol) and the mixture was cooled to −40° C. To this cooled reaction mixture was added the solution of the crude L-DPSE-NOPCl (30 mmol, 1.4 eq, in THF 40 mL), from a stock through syringe dropwise (~15 min, maintaining the internal temperature −40- to −35° C.). The mixture was then gradually warmed to 5° C. After 30 min at 5° C., TLC and LC-MS analysis indicated the complete conversion of SM to product (total reaction time 2 h). The reaction mixture was cooled in an ice bath and the reaction quenched by addition of water (0.36 mL, 20 mmol). The mixture was stirred for 10 min followed by addition of anhydrous $Mg_2SO_4$ (3.0 g, 20 mmol). The reaction was filtered through Airfree, Schlenk filter tube, washed with dry THF (60 mL) and the solvent was evaporated under rotary evaporation at 28° C. to afford the crude product as a off-white solid which was dried under high vacuum for overnight. The dried crude product was purified by Combi-Flash Rf (Teledyne ISCO) using a 220 silica column (which was pre-deactivated with 3 column volume of ethyl acetate with 5% TEA) with ethyl acetate/hexane mixture contains 5% TEA as a solvent. Fractions were analyzed by TLC and LC-MS and pooled together. Solvent was evaporated in a rotary evaporator at 28° C. and the residue was dried under high vacuum to afford the product as a white solid. Yield: 16.3 g (91%). $^1$H NMR (400 MHz, Chloroform-d) δ 7.50-7.36 (m, 6H), 7.35-7.06 (m, 13H), 6.85 (d, J=1.4 Hz, 1H), 6.73 (dq, J=8.7, 3.2 Hz, 4H), 6.13 (dd, J=9.3, 5.3 Hz, 1H), 5.10 (td, J=7.8, 7.1, 3.4 Hz, 1H), 4.80 (dt, J=8.6, 5.8 Hz, 1H), 4.04 (q, J=7.1 Hz, 1H), 3.69 (d, J=2.3 Hz, 6H), 3.57-3.36 (m, 3H), 3.29-3.05 (m, 2H), 2.05 (dd, J=13.6, 5.5 Hz, 1H), 1.96 (s, 2H), 1.73-1.50 (m, 3H), 1.47-1.32 (m, 2H), 1.30 (d, J=1.2 Hz, 3H), 1.17 (t, J=7.2 Hz, 2H), 0.75 (d, J=6.5 Hz, 3H), 0.60 (s, 3H). $^{31}$P NMR (162 MHz, $CDCl_3$) δ 151.34 (s). MS: LCMS: Calculated, C51H56N3O8PSi, 897.3574; Observed +Ve mode: m/z: 898.52 [M+H]; 999.95 [M+Et3N]. $^{13}$C NMR (101 MHz, $CDCl_3$) δ 171.12, 163.83, 158.65, 158.61, 150.21, 146.50, 136.96, 136.71, 136.59, 135.94, 135.54, 134.60, 134.34, 130.24, 130.15, 129.45, 129.39, 128.02, 127.96, 127.94, 127.88, 127.79, 126.86, 113.17, 113.11, 110.93, 89.27, 89.25, 86.48, 83.68, 79.09, 78.99, 77.42, 77.30, 77.10, 76.78, 71.78, 71.70, 70.26, 68.39, 68.36, 60.39, 55.24, 47.19, 46.83, 46.09, 39.48, 39.44, 27.35, 25.97, 25.93, 21.05, 18.33, 17.85, 17.81, 14.23, 11.73, 11.45.

Example 146. Synthesis of L-DPSE-5'-(S)—C-Me-5'-DMT-dT Amidite

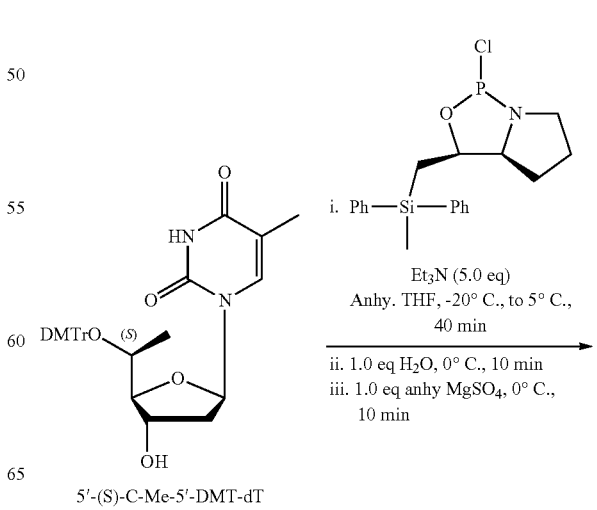

-continued

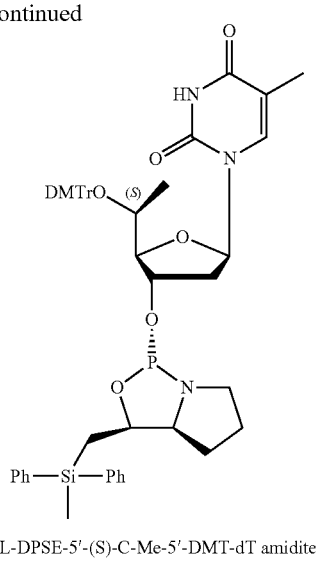

L-DPSE-5'-(S)-C-Me-5'-DMT-dT amidite

5'-(S)—C-Me-5'-OMT-dT (1.20 g, 2 mmol) was dried two times by co-evaporation with 20 mL of anhydrous toluene at 45° C. and kept at high vacuum for overnight. Then the dried 5'-(S)—C-Me-5'-OMT-dT was dissolved in dry THF (20 mL) in a 100 mL three neck flasks under argon, followed by the addition of triethylamine (1.4 mL, 10 mmol) and the mixture was cooled to −40° C. To this cooled reaction mixture was added the solution of the crude L-DPSE-NOPCl (3 mmol, 1.5 eq, in THF 3.0 mL) from a stock was through syringe dropwise ~5 min (maintaining the internal temperature −40° C., then gradually warmed to 5° C.). After 30 min at 5° C., TLC and LC-MS analysis indicated complete conversion of SM to product (total reaction time 1.5 h). The reaction mixture was cooled in an ice bath and the reaction was quenched by addition of water (0.036 mL, 2 mmol). The mixture was stirred for 10 min, followed by addition of anhydrous $MgSO_4$ (0.3 g, 2 mmol). The reaction was filtered through Airfree, Schlenk filter tube and washed with dry THF (20 mL). The solvent was evaporated under rotary evaporation at 28° C. to provide the off-white solid which was dried under high vacuum for overnight. The dried crude product was purified by Combi-Flash Rf (Teledyne ISCO) using 40 g silica column (which was pre-deactivated with 3 column volume of ethyl acetate with 5% TEA) with ethyl acetate/hexane mixture containing 5% TEA as a solvent. After column purification, fractions were analyzed by TLC and LC-MS and were pooled together and evaporated in a rotary evaporator at 28° C. The residue was dried under high vacuum to afford L-DPSE-5'-(S)—C-Me-5'-DMT-dT amidite as a white solid. Yield: 1.27 g (70%). $^{31}P$ NMR (162 MHz, $CDCl_3$) δ 149.73 (s). MS: LC-MS; Calculated: $C_{51}H_{56}N_3O_8PSi$, 897.3574; Observed +Ve mode: m/z: 898.56[M+H].

Example 147. Synthesis of L-DPSE-5'-DMT-5-C6-aminolinker amidite—Incorporation of Desired Moieties Through Nucleobases

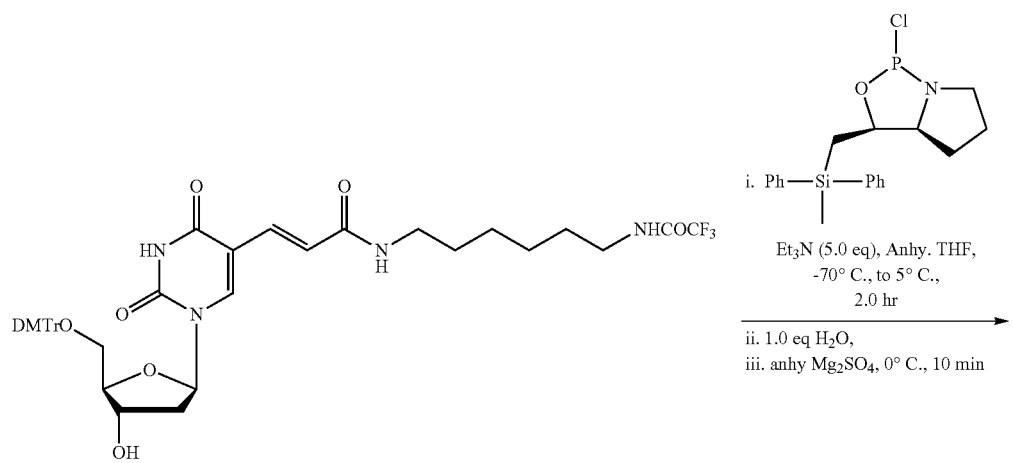

-continued

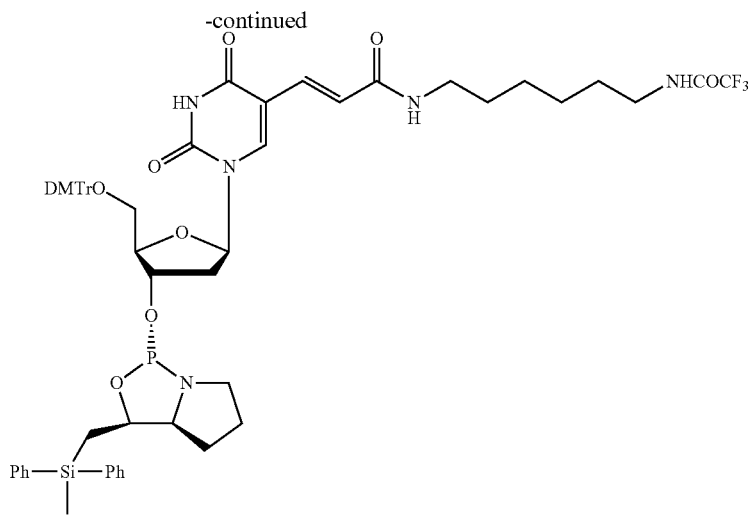

The 5'-DMT-5-C6 aminoTFA-dT (25 g, 31.5 mmol, from Berry& Associates Inc) was dried two times by co-evaporation with 100 mL of anhydrous toluene at 45° C. and kept at high vacuum for overnight. Then the dried material was dissolved in dry THF (100 mL) in 500 mL three neck flasks under argon, followed by the addition of triethylamine (21.92 mL, 157 mmol) and then was cooled to −70° C. To this cooled reaction mixture was added a solution of the crude L-DPSE-NOPCl (44 mmol, 1.4 eq, in THF 44 mL), from a stock via syringe dropwise (~15 min, maintaining the internal temperature −60- to 50° C.). The mixture was gradually warmed to 5° C. After 30 min at 5° C., TLC and LC-MS analysis indicated complete conversion of SM to product (total reaction time 2 h). The reaction mixture was cooled in an ice bath and quenched by addition of water (0.56 mL, 31.5 mmol) and stirred for 10 min followed by added anhydrous $Mg_2SO_4$ (3.8 g, 31.5 mmol). The reaction was filtered through Airfree, Schlenk filter tube, washed with dry THF (80 mL), and evaporated under rotary evaporation at 28° C. to afford the crude product as off-white solid, which was dried under high vacuum for overnight. The dried crude product was purified by Combi-Flash Rf (Teledyne ISCO) using 220 silica column (which was pre-deactivated with 3 column volume of ethyl acetate with 5% TEA) with ethyl acetate/hexane mixture contains 5% TEA as a solvent. After column purification fractions were analyzed by TLC and LC-MS, and pooled together. Solvent was evaporated in a rotary evaporator at 28° C. and the residue was dried under high vacuum to afford the product as a white solid. Yield: 30 g (88%). MS: LC-MS; Calculated: $C_{60}H_{67}F_3N_5O_{10}PSi$, 1133.4347; Observed in +Ve mode: 1235.55 (M+Et3N). $^1$H NMR (400 MHz, Chloroform-d) δ 7.78 (s, 1H), 7.40 (ddd, J=9.8, 6.5, 2.2 Hz, 5H), 7.32 (d, J=7.3 Hz, 2H), 7.30-7.09 (m, 15H), 6.99 (d, J=15.5 Hz, 1H), 6.76 (dd, J=8.9, 2.7 Hz, 4H), 6.54 (d, J=15.5 Hz, 1H), 5.12 (t, J=6.1 Hz, 1H), 4.66-4.49 (m, 2H), 4.04 (q, J=7.1 Hz, 1H), 3.81 (q, J=3.0 Hz, 1H), 3.67 (s, 6H), 3.41 (ddt, J=14.8, 10.2, 7.7 Hz, 1H), 3.30-3.13 (m, 4H), 3.12-2.91 (m, 4H), 1.96 (s, 2H), 1.92-1.69 (m, 2H), 1.58 (ddt, J=15.1, 11.6, 8.0 Hz, 1H), 1.50-1.29 (m, 5H), 1.18 (tq, J=15.8, 8.8, 8.0 Hz, 9H), 0.52 (s, 3H). $^{31}$P NMR (162 MHz, $CDCl_3$) δ 150.88 (s). $^{13}$C NMR (101 MHz, $CDCl_3$) δ 171.18, 165.77, 161.89, 158.76, 158.74, 157.85, 157.49, 157.12, 156.76, 149.17, 144.52, 139.69, 136.68, 135.86, 135.53, 135.44, 134.54, 134.30, 131.15, 129.97, 129.89, 129.44, 129.38, 128.09, 127.93, 127.91, 127.18, 122.36, 120.31, 117.44, 114.58, 113.42, 113.39, 111.72, 110.53, 86.65, 86.04, 86.02, 85.67, 79.28, 79.19, 77.42, 77.31, 77.11, 76.79, 73.20, 73.12, 68.05, 68.02, 63.09, 60.41, 55.27, 46.96, 46.60, 45.81, 40.48, 39.56, 38.88, 29.33, 28.52, 27.23, 25.83, 21.04, 17.55, 17.52, 14.20.

Example 148. Synthesis of 5-Alkynyl Thioacetate-5'-DMT-3'CNE-2'OMe-U amidite

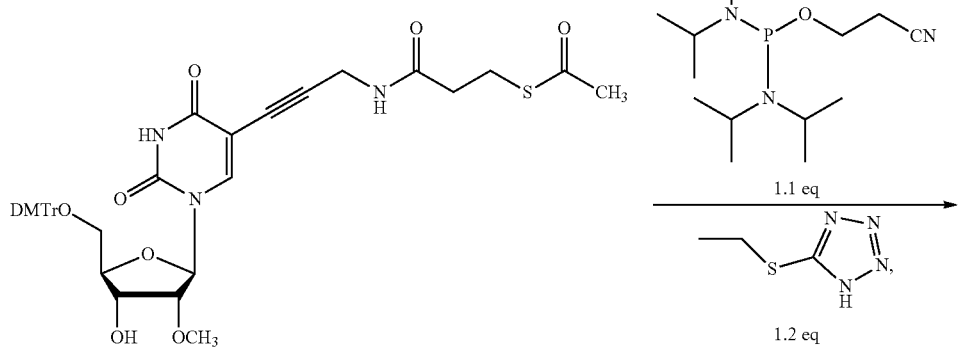

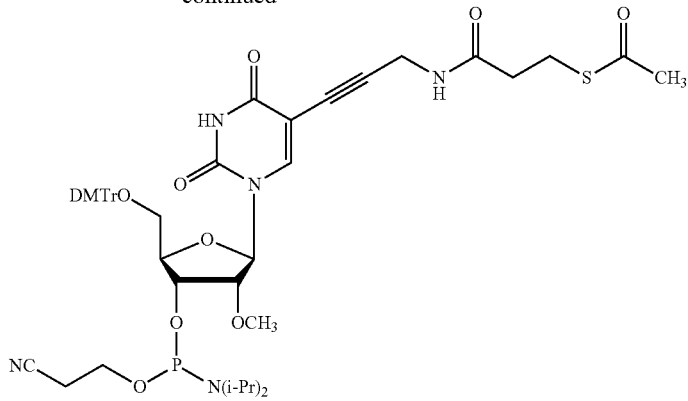

7-9-2

Compound 7-9-1 (5.0 g, 6.72 mmol) was co-evaporated with anhydrous toluene two times (40 mL×2) and dried under high vacuum for overnight. The dried yellow solid was dissolved in anhydrous THF (14 ml, ~0.5 mmol/mL) under argon and to the solution was added 5-ethylthio-1H-tetrazole (1.05 g, 8.07 mmol), N-methylimidazole (0.045 g, 0.044 mL, 0.67 mmol) followed by 2-cynoethyl-N,N,N',N'-tetraisopropylphosphordiamidite (2.23 g, 2.34 mL, 7.39 mmol). The reaction mixture was stirred at room temperature under argon for 5 h. TLC (solvent system: 40% $CH_3CN$/EtOAC/5% TEA) which was pre-equilibrated with the above solvent system indicated the completion of reaction at 5 h, which was also confirmed with LC-MS. The reaction mixture was diluted with EtOAc (100 mL) and the solution was transferred to separating funnel, washed with aq. saturated. $NaHCO_3$ solution (40 mL) and dried over anhydrous $Mg_2SO_4$. The dried solution was evaporated under rotary evaporation at bath temperature 28° C. to afford the crude product as off-yellow solid which was further dried under high vacuum for overnight. The dried crude product was purified in Combi-Flash Rf (Teledyne ISCO) using 80 g flash silica column, which was pre-deactivated with 2 column volume (CV 125 mL, 60 mL/min), of ethyl acetate with 5% TEA, followed by equilibration with 20% EtOAc/Hexane for 2 column volume. The compound was purified using Hexane/EtOAc/CH3CN mixture containing 5% TEA as a solvent system. After purification column fractions were analyzed by TLC and LC-MS. Desired fractions were pooled together and evaporated in a rotary evaporator at 28° C. and was dried under high vacuum afforded 7-9-2-CNE amidite as white solid. Yield: 4.8 g (76%). MS: LC-MS; Calculated: C48H58N5O11PS, 943.35; Observed in +Ve mode: m/z 1045.92 (M+Et3N). $^1$H NMR (400 MHz, Chloroform-d) δ 8.36-8.07 (m, 1H), 7.47-7.09 (m, 10H), 6.78 (dt, J=9.1, 3.8 Hz, 4H), 5.87 (dd, J=26.6, 3.1 Hz, 1H), 4.73 (d, J=14.9 Hz, 1H), 4.57-4.30 (m, 1H), 4.21-4.00 (m, 2H), 3.86-3.32 (m, 17H), 3.23 (ddd, J=13.0, 11.2, 2.5 Hz, 1H), 2.91 (td, J=7.0, 2.4 Hz, 2H), 2.54 (q, J=6.1 Hz, 1H), 2.27 (d, J=24.2 Hz, 4H), 1.96 (d, J=7.1 Hz, 3H), 1.21-0.82 (m, 14H). $^{31}$P NMR (162 MHz, $CDCl_3$) δ 150.60 (s), 150.24 (s). $^{13}$C NMR (101 MHz, $CDCl_3$) δ 195.80, 169.61, 161.45, 158.70, 158.68, 149.06, 144.75, 144.61, 142.82, 135.67, 135.58, 135.48, 135.38, 130.18, 130.16, 130.12, 128.14, 128.11, 128.09, 128.02, 127.01, 117.69, 117.53, 113.42, 113.38, 113.34, 99.60, 99.33, 88.98, 88.95, 88.50, 88.06, 87.06, 86.85, 83.89, 82.99, 82.62, 77.34, 77.22, 77.02, 76.70, 74.55, 74.40, 69.74, 69.62, 62.04, 61.26, 60.38, 58.97, 58.59, 58.47, 58.45, 57.89, 57.68, 55.34, 55.31, 43.33, 43.21, 35.44, 35.41, 30.54, 29.95, 24.71, 24.65, 24.63, 24.58, 24.56, 24.49, 21.04, 20.50, 20.43, 20.38, 20.31, 14.20.

Example 149. Example Procedure for Oligonucleotide Synthesis

In some embodiments, oligonucleotides were synthesized using automated synthesis on MerMade 12 DNA/RNA synthesizer according to synthetic cycles in Table 5 below, using 1 µmol synthesis column and 1 µmol (20 mg @ 50 µmol/g loading) of succinyl linked $dC^{Ac}$ on CPG (Link Technologies). The synthesis cycle was performed with removal of the terminal 5'-O-DMTr group (DMT Off). After completion of the automated oligonucleotide synthesis, the HCP support was washed with dry ACN and dried under vacuum. After completion of the synthesis, 4 mg dry solid support was weighed into vial. Then 150 µL of 0.5 M DBN, 0.25M BSTFA in acetonitrile was added to this 4 mg dry solid support, and incubated at room temperature for 3 minutes. 300 µL AMA was then added and the mixture was heated at 50° C. for 45 min (or 300 µL ammonium hydroxide and heated at 55° C. for overnight). The reaction mixture was cooled down to room temperature, then subjected to speed vacuum to less than 50 µL, diluted with water to 0.5 mL, and filtered through 0.2 micron syringe filter. The samples were analyzed by RP HPLC.

TABLE 5

Example Oligonucleotide Synthesis on DNA/RNA Synthesizer MerMade-12 (Chirally Controlled Phosphorothioate).

| step | reaction | reagent | delivery vol (mL) | wait time (sec) |
|---|---|---|---|---|
| 1 | detritylation | 3% TCA in DCM | 4 × 1 | N.A. |
| 2 | coupling | 0.15 M chiral phosphoramidite in IBN + 2M CMPT in ACN | 2 × 0.5 | 2 x 300 (DNA) |
| 3 | capping 1 | 10:10:80 $Ac_2O$:lutidine:THF | 1 | 60 |
| 4 | capping 2 | 10:10:80 $Ac_2O$:lutidine:THF + 16% NMI in THF | 1 | 60 |

TABLE 5-continued

Example Oligonucleotide Synthesis on DNA/RNA
Synthesizer MerMade-12 (Chirally Controlled Phosphorothioate).

| step | reaction | reagent | delivery vol (mL) | wait time (sec) |
|---|---|---|---|---|
| 5 | sulfurization | 0.3 M S-(2-cyanoethyl) methylthiosulfonate and sodium methanethiosulfonate (1% w/w over S-(2-cyanoethyl) methylthiosulfonate) in ACN/BSTFA | 1 | 600 |

Example RP-HPLC Method for Oligonucleotides PGP 2087, FR

Buffer A: 50 mM TEAA, pH 9.6 (adjusted with TEA)

Buffer B: ACN

Column: XBridge $C_8$, 3.5 µm, 4.6×150 mm, Part #186003034

Buffer heater set temperature=35° C.

Signal monitored at 260 and 280 nm

Gradient Used:

| Time | Flow (mL/min) | % A | % B | Curve |
|---|---|---|---|---|
| Initial |  | 99 | 1 |  |
| 2 | 1 | 99 | 1 | 1 |
| 22 | 1 | 70 | 30 | 6 |
| 25 | 1 | 5 | 95 | 6 |
| 25.5 | 1 | 5 | 95 | 6 |
| 30 | 1 | 99 | 1 | 1 |

Example 150. Example Procedure for Measuring pKa Value 5.6 mg (0.040 mmol) of an example amino alcohol [(R)-2-((S)-pyrrolidin-2-yl)but-3-yn-2-ol], WV-CA-002, was dissolved in 2 mL MDA (Methanol-Dioxane-Acetonitrile, 1:1:1 ratio) mixture followed by addition of 2 mL 0.15 M KCl solution. To this clear solution was added 6 µL of con. HCl and stirred well. This solution was titrated against 1 M NaOH solution. NaOH solution was added in 2 (or 4) ml increments. During the addition of each increment of NaOH solution, pH of the solution was recorded using a pH meter until a pH of 12 was measured. The measured titration values were analyzed (graph pad software was used) to determine the first derivative of the volume of NaOH used in the titration. This first derivative value is the pKa of the amino alcohol. For example data, see FIG. 1. Additional example results were provided in Table 6. pKa can also be calculated through various methods, including those in commercial software and online tools. In some embodiments, calculated values were different from measured values using methods described in the present disclosure.

TABLE 6

Example data.

| No. | Structure | pKa |
|---|---|---|
| WV-CA-002 | 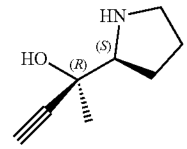 | 9.24 |
| WV-CA-002-S | 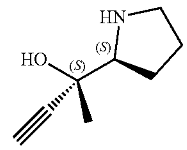 | 9.44 |
| WV-CA-003 | 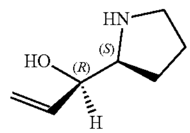 | 9.84 |
| WV-CA-004 | 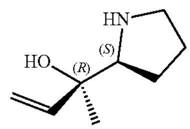 | 10.43 |
| WV-CA-005-L | 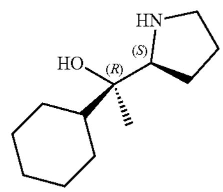 | 10.65 |
| WV-CA-005-D | 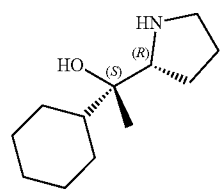 | 10.7 |
| WV-CA-008 | 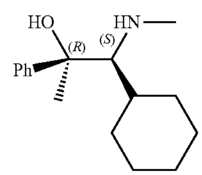 | 9.39 |
| WV-CA-008-S | 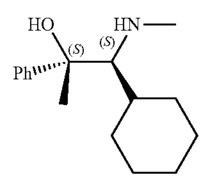 | 9.94 |
| WV-CA-011 | 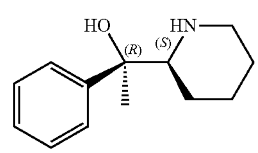 | 9.82 |

TABLE 6-continued

Example data.

| No. | Structure | pKa |
|---|---|---|
| WV-CA-011-S | 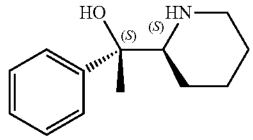 | 9.91 |
| WV-CA-012 | 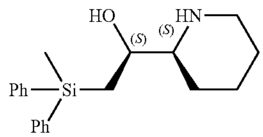 | 10.11 |
| WV-CA-012-R | 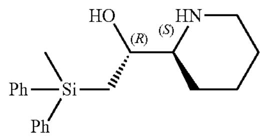 | 10.1 |
| WV-CA-014 | 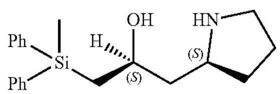 | 10.68 |
| WV-CA-014-R | 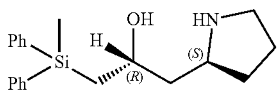 | 10.67 |
| WV-CA-024 | 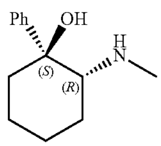 | 8.86 |
| WV-CA-026 | 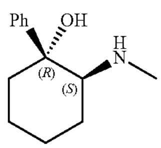 | 8.84 |
| WV-CA-027 | 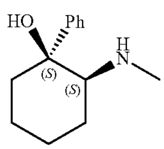 | 9.88 |
| WV-CA-031 | 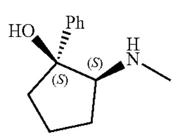 | 9.85 |
| WV-CA-041-L | 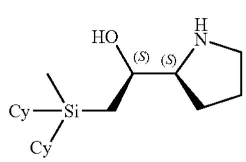 | Sample Insoluble in MDA |
| WV-CA-041-D | 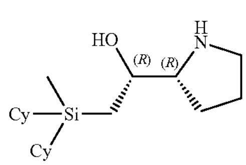 | Sample Insoluble in MDA |
| WV-CA-042 (mixture) | | 10.73 |
| WV-CA-043 (mixture) | | 10.70 |
| WV-CA-044 (mixture) | | 10.64 |
| WV-CA-045 | | Insoluble in MDA mixture |
| WV-CA-046 | | Insoluble in MDA mixture |
| WV-CA-047 | | 9.20 |
| WV-CA-050 | | 10.29 |
| WV-CA-051 | | 10.48 |
| WV-CA-052 | | Low quality data in example |
| WV-CA-053 | | 10.79 |

TABLE 6-continued

Example data.

| No. | Structure | pKa |
|---|---|---|
| WV-CA-054 | 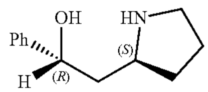 | 10.54 |
| WV-CA-056 | 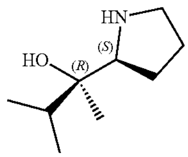 | 10.48 |
| WV-CA-056-S | 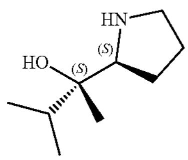 | 10.52 |
| WV-CA-057 | 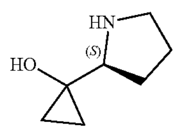 | 10.57 |
| WV-CA-059 | 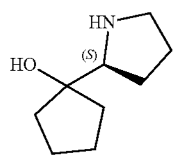 | 10.53 |
| WV-CA-059R | 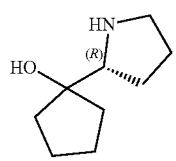 | 10.41 |
| WV-CA-060 | 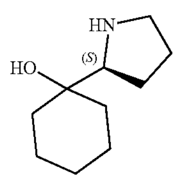 | 10.63 |
| WV-CA-062 | 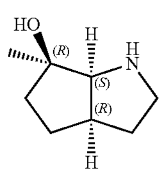 | 10.43 |
| WV-CA-062S | 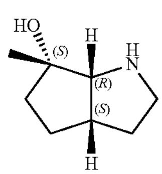 | 10.37 |
| WV-CA-063S | 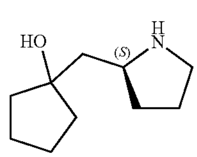 | 11.04 |
| WV-CA-064S | | 10.49 |
| WV-CA-065S | | 10.18 |
| WV-CA-066R | | 10.08 |
| WV-CA-067 | | 10.32 |
| WV-CA-068S | | 10.60 |
| WV-CA-069S | | 10.76 |
| WV-CA-070 | | 10.4 |
| WV-CA-070S | | 9.99 |
| WV-CA-071S | | 9.93 |
| WV-CA-074S | | 9.92 |

TABLE 6-continued

Example data.

| No. | Structure | pKa |
|---|---|---|
| WV-CA-074R | | 9.95 |
| WV-CA-074M | | 9.98 |
| WV-CA-075S | | 10.28 |
| WV-CA-075R | | 10.19 |
| WV-CA-078 | | 10.62 |
| WV-CA-079 | | 10.28 |
| WV-CA-080 | | 10.08 |
| WV-CA-081 | | 9.77 |
| WV-CA-082 | 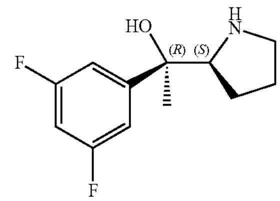 | 9.86 |
| WV-CA-083 | 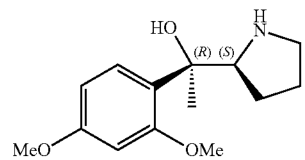 | 10.83 |
| WV-CA-123 | 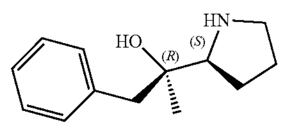 | 10.18 |
| WV-CA-124 | 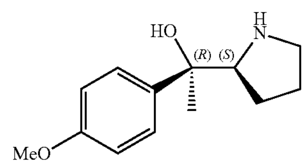 | 10.14 |
| WV-CA-090 | 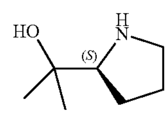 | 10.33 |
| WV-CA-091 | 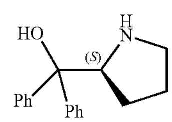 | 9.61 |
| WV-CA-092 | 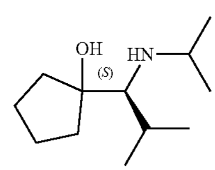 | 9.53 |
| WV-CA-096 | 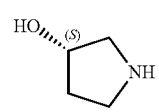 | 10.24 |
| WV-CA-097 | 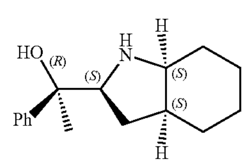 | 10.26 |
| WV-CA-098 | 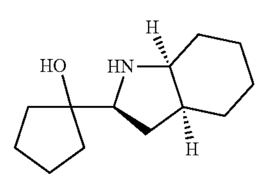 [SMILES: OC1([C@@H]2C[C@@H]3CCCC[C@@H]3N2)CCCC1] | 10.54 |

TABLE 6-continued

Example data.

| No. | Structure | pKa |
|---|---|---|
| WV-CA-201 | 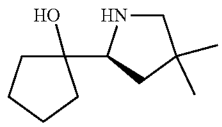 | 10.26 |
| WV-CA-202 | 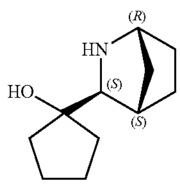 | 10.71 |
| WV-CA-206 | 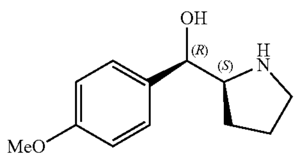 | 9.88 |
| WV-CA-207 | 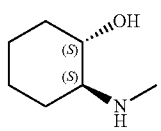 | 10.07 |
| WV-CA-208 | 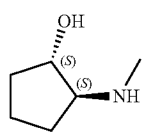 | 9.66 |
| WV-CA-209 | 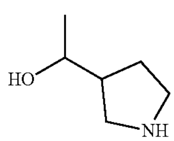 | 10.79 |
| WV-CA-210A | 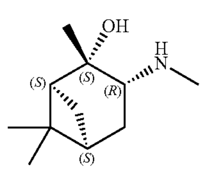 | 10.67 |
| WV-CA-210B | 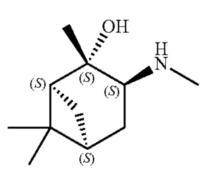 | 9.40 |
| WV-CA-078D | 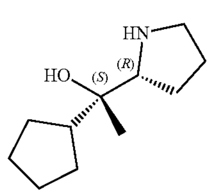 | 10.70 |
| WV-CA-216 | | 10.80 |
| WV-CA-221 | | 10.20 |
| WV-CA-222 | | 10.06 |
| WV-CA-223 | | 10.33 |
| WV-CA-224 | | 10.22 |
| WV-CA-225 | | 9.6 |
| WV-CA-089B | | 9.85 |

Example 151. Example Use of Provided Compounds for Oligonucleotide Synthesis Among other things, provided technologies (e.g., compounds, methods, etc.) can be particularly useful for preparing oligonucleotides and compositions thereof, e.g., those provided in US/2011/0294124, US/2015/0211006, US/2017/0037399, WO/2017/015555, and WO/2017/062862, oligonucleotides and compositions of each which are incorporated herein by reference. In some embodiments, certain provided compounds are useful as chiral auxiliaries. In some embodiments, certain provided compounds are useful as phosphoramidite monomers, which can be used either directly without isolation or after isolation. In some embodiments, certain provided compounds are oligonucleotides. Among other things, provided compounds provide a variety of properties, e.g., yields, selectivity (e.g., stereoselectivity when used as chiral auxiliaries, chiral phosphorus phosphoramidite monomers, etc.), stability (e.g., under deprotection and/or cleavage conditions, under cycle conditions, under conditions of certain step(s) (e.g., coupling, modifying, and/or deblocking, etc.), etc.), product purity, etc. In some embodiments, compounds can provide high yields, selectivity, purity, etc., for formation of typical chiral internucleotidic linkages (e.g., those non-first internucleotidic linkages from solid supports and not between C and C, etc.). In some embodiments, certain chiral internucleotidic linkages are particularly challenging for formation in terms of yields, selectivity, and/or purity, etc., e.g., certain internucleotidic linkages described in the present disclosure (e.g., example internucleotidic linkages between certain dCdC dimers when one of the dC is the first nucleoside attached to, e.g., solid supports using linkers described in the examples). In some embodiments, compounds provide high yields, selectivity, purity, etc., for formation of typical chiral internucleotidic linkages may not provide high yields, selectivity, purity, etc., for formation of challenging chiral internucleotidic linkages, e.g., those described in the examples. Among other things, the present disclosure provides challenging conditions (e.g., formation of example phosphoramidites, formation of example challenging internucleotidic linkages, etc.) that may be utilized to differentiate technologies that typically provide high yields, selectivity, purity, etc., so that certain technologies can be selected for challenging conditions. In some embodiments, a condition is coupling of C to C linked to solid support (e.g., Ac-dC SynBase™ CPG 500/100 S; Item Number: 2357; Link Technologies Ltd.). Applicant notes that provided technologies are generally useful, among other things, for forming typical, and/or, challenging chiral internucleotidic linkages. Example results of dC oligomer preparation, which can be particularly challenging, are provided in Table 7 below. In some embodiments, an SOCICS cycle is as described in Cycle A and Example 149. In some embodiments, a DPSE cycle is as described in Cycle C. Other example oligonucleotides and compositions thereof, e.g., those described in US/2011/0294124, US/2015/0211006, US/2017/0037399, WO/2017/015555, and WO/2017/062862, oligonucleotides and compositions of each which are incorporated herein by reference, etc. can also be prepared using provided compounds and methods in accordance with the present disclosure.

In some embodiments, certain results were obtained according to protocols below, using, e.g., DPSE cycles. Applicant notes that in some embodiments, coupling with dA-DPSE phosphoramidite monomers can be a challenging reaction and can be used to differentiate phosphoramidite monomers and/or chiral auxiliaries that work well for typical, non-challenging oligonucleotide synthesis.

WV-CA-104 (Run 8), -012, -045, and -046: $(S_P)$-AC and all $(S_P)$-$A_4C$ were synthesized using automated synthesis on nS-8II DNA/RNA synthesizer according to the synthetic cycle summarized below, using 1 μmol synthesis column and 1.5 μmol (50 mg @ 30 μmol/g loading) of succinyl-piperidine linked $dC^{ibu}$ on HCP. The synthesis cycle was performed with removal of the terminal 5'-O-DMTr group (DMT Off). After completion of the automated oligonucleotide synthesis, 1 mL of 40% $MeNH_2$ was added and the mixture was heated at 65° C. for 15 min. The reaction mixture was cooled down to room temperature, added 1.6 mL of DMSO and 1 mL of TEA-3HF, and the mixture was heated at 50° C. for 1 h. The reaction mixture was cooled down to room temperature, added 0.8 mL of 50 mM NaOAc, filtered through 0.2 micron syringe filter. The samples were analyzed by RP-UPLC.

| step | reaction | reagent | delivery vol (mL) | wait time (sec) |
|---|---|---|---|---|
| 1 | detritylation | 3% DCA in Toluene | 2 × 5 | N.A. |
| 2 | coupling | 0.15M chiral monomer in IBN + 0.5M CMIMT in ACN | 0.48 | 300 |
| 3 | capping | 20% $Ac_2O$, 30% lutidine in ACN + 16% NMI in ACN | 1.2 | 90 |
| 4 | sulfurization | 0.1M POS in ACN | 0.8 | 300 |

Example RP HPLC Method:

Buffer A: 100 mM TEAA

Buffer B: ACN

Column: Waters, ACQUITY UPLC BEH $C_{18}$, 1.7 μm, 2.1×150 mm

Column heater set temperature=55° C.

Signal monitored at 260 nm

Gradient Used:

| Time | Flow (ml/min) | % A | % B | Curve |
|---|---|---|---|---|
| Initial | | 99 | 1 | |
| 30 | 0.3 | 70 | 30 | 6 |

WV-CA-104 (Run 9), -050 (Run 1): $(S_P)$-AC and all $(S_P)$-$A_4C$ were synthesized using automated synthesis on nS-8II DNA/RNA synthesizer according to the synthetic cycle summarized below, using 1 μmol synthesis column and 1.5 μmol (50 mg @ 30 μmol/g loading) of succinyl-piperidine linked $dC^{ibu}$ on HCP. The synthesis cycle was performed with removal of the terminal 5'-O-DMTr group (DMT Off). After completion of the automated oligonucleotide synthesis, 1 mL of 40% $MeNH_2$ was added and the mixture was heated at 65° C. for 15 min. The reaction mixture was cooled down to room temperature, added 1.6 mL of DMSO and 1 mL of TEA-3HF, and the mixture was heated at 50° C. for 1 h. The reaction mixture was cooled down to room temperature, added 0.8 mL of 50 mM NaOAc, filtered through 0.2 micron syringe filter. The samples were analyzed by RP-UPLC.

| step | reaction | reagent | delivery vol (mL) | wait time (sec) |
|---|---|---|---|---|
| 1 | detritylation | 3% DCA in Toluene | 2 × 5 | N.A. |
| 2 | coupling | 0.15M chiral monomer in IBN + 0.5M CMIMT in ACN | 0.48 | 300 |
| 3 | capping | 20% $Ac_2O$, 30% lutidine in ACN + 16% NMI in ACN | 1.2 | 90 |
| 4 | sulfurization | 0.1M POS in ACN | 0.8 | 300 |

Example RP HPLC Method:

Buffer A: 100 mM TEAA

Buffer B: ACN

Column: Waters, ACQUITY UPLC BEH C18, 1.7 μm, 2.1×150 mm

Column heater set temperature=55° C.

Signal monitored at 260 nm

Gradient Used:

| Time | Flow (ml/min) | % A | % B | Curve |
|---|---|---|---|---|
| Initial | | 99 | 1 | |
| 30 | 0.3 | 70 | 30 | 6 |

WV-CA-104 (Run 10), -050 (Run 2): ($S_P$)-AC and all ($S_P$)-$A_4$C were synthesized using automated synthesis on nS-8II DNA/RNA synthesizer according to the synthetic cycle summarized below, using 1 µmol synthesis column and 1.5 µmol (18 mg @ 81.5 µmol/g loading) of succinyl-piperidine linked $dC^{ibu}$ on PS5G. The synthesis cycle was performed with removal of the terminal 5'-O-DMTr group (DMT Off). After completion of the automated oligonucleotide synthesis, the PS5G support was washed with dry ACN and dried under vacuum, and solid support was transferred into vial. The support was treated with 1 mL of 0.1M TBAF in ACN for 30 min at room temperature, filtered and washed with ACN. Then the solid support transferred into vial, 1 mL of AMA was added and the mixture was heated at 45° C. for 45 min. The reaction mixture was cooled down to room temperature, then subjected to speed vacuum to less than 0.5 mL, diluted with water to 1 mL, and filtered through 0.2 micron syringe filter. The samples were analyzed by RP-UPLC.

| step | reaction | reagent | delivery vol (mL) | wait time (sec) |
|---|---|---|---|---|
| 1 | detritylation | 3% DCA in Toluene | 2 × 5 | N.A. |
| 2 | coupling | 0.15M chiral monomer in IBN + 0.5M CMIMT in ACN | 0.48 | 300 |
| 3 | capping | 20% $Ac_2O$, 30% lutidine in ACN + 16% NMI in ACN | 1.2 | 90 |
| 4 | sulfurization | 0.1M POS in ACN | 0.8 | 300 |

Example RP HPLC Method:
 Buffer A: 100 mM TEAA
 Buffer B: ACN
 Column: Waters, ACQUITY UPLC BEH $C_{18}$, 1.7 µm, 2.1×150 mm
 Column heater set temperature=55° C.
 Signal monitored at 260 nm
Gradient Used:

| Time | Flow (ml/min) | % A | % B | Curve |
|---|---|---|---|---|
| Initial | | 99 | 1 | |
| 30 | 0.3 | 70 | 30 | 6 |

WV-CA-104 (Run 11), -051, -052: ($S_P$)-dA-$C_{OMe}$ and all ($S_P$)-$(dA)_4$-$C_{OMe}$ were synthesized using automated synthesis on nS-8II DNA/RNA synthesizer according to the synthetic cycle summarized below, using 1 µmol synthesis column and 1.5 µmol (18 mg @ 83 µmol/g loading) of succinyl-piperidine linked 2'OMe-$C^{Ac}$ on PS5G. The synthesis cycle was performed with removal of the terminal 5'-O-DMTr group (DMT Off). After completion of the automated oligonucleotide synthesis, the PS5G support was washed with dry ACN and dried under vacuum, and solid support was transferred into vial. The support was treated with 1 mL of 1M TEA-HF in DMF-$H_2O$ (3:1, v/v) at 65° C. for 1 h. Then the mixture was cooled to room temperature, filtered and washed with ACN. Then the solid support transferred into vial, 1 mL of AMA was added and the mixture was heated at 45° C. for 45 min. The reaction mixture was cooled down to room temperature, then subjected to speed vacuum to less than 0.5 mL, diluted with water to 1 mL, and filtered through 0.2 micron syringe filter. The samples were analyzed by RP-UPLC.

| step | reaction | reagent | delivery vol (mL) | wait time (sec) |
|---|---|---|---|---|
| 1 | detritylation | 3% DCA in Toluene | 2 × 5 | N.A. |
| 2 | coupling | 0.15M chiral monomer in IBN + 0.5M CMIMT in ACN | 0.48 | 300 |
| 3 | capping | 20% $Ac_2O$, 30% lutidine in ACN + 16% NMI in ACN | 1.2 | 90 |
| 4 | sulfurization | 0.1M POS in ACN | 0.8 | 300 |

Example RP HPLC Method:
 Buffer A: 100 mM TEAA
 Buffer B: ACN
 Column: Waters, ACQUITY UPLC BEH $C_{18}$, 1.7 µm, 2.1×150 mm
 Column heater set temperature=55° C.
 Signal monitored at 260 nm
Gradient Used:

| Time | Flow (ml/min) | % A | % B | Curve |
|---|---|---|---|---|
| Initial | | 99 | 1 | |
| 30 | 0.3 | 70 | 30 | 6 |

WV-CA-104 (Run 7), -112 (Run 5), and -119: ($S_P$)-AC and all ($S_P$)-$A_4$C were synthesized using automated synthesis on nS-8II DNA/RNA synthesizer according to the synthetic cycle summarized below, using 1 µmol synthesis column and 1.5 µmol (50 mg @ 30 µmol/g loading) of succinyl-piperidine linked $dC^{ibu}$ on HCP. The synthesis cycle was performed with removal of the terminal 5'-O-DMTr group (DMT Off). After completion of the automated oligonucleotide synthesis, 1 mL of 40% $MeNH_2$ was added and the mixture was heated at 65° C. for 15 min. The reaction mixture was cooled down to room temperature, added 1.6 mL of DMSO and 1 mL of TEA-3HF, and the mixture was heated at 50° C. for 1 h. The reaction mixture was cooled down to room temperature, added 0.8 mL of 50 mM NaOAc, filtered through 0.2 micron syringe filter. The samples were analyzed by RP-UPLC.

| step | reaction | reagent | delivery vol (mL) | wait time (sec) |
|---|---|---|---|---|
| 1 | detritylation | 3% DCA in Toluene | 2 × 5 | N.A. |
| 2 | coupling | 0.15M chiral monomer in IBN + 0.5M CMIMT in ACN | 0.48 | 300 |
| 3 | capping | 20% $Ac_2O$, 30% lutidine in ACN + 16% NMI in ACN | 1.2 | 90 |
| 4 | sulfurization | 0.1M POS in ACN | 0.8 | 300 |

Example RP HPLC Method:
 Buffer A: 100 mM TEAA
 Buffer B: ACN
 Column: Waters, ACQUITY UPLC BEH $C_{18}$, 1.7 µm, 2.1×150 mm
 Column heater set temperature=55° C.
 Signal monitored at 260 nm Gradient Used:

| Time | Flow (ml/min) | % A | % B | Curve |
|---|---|---|---|---|
| Initial | | 99 | 1 | |
| 30 | 0.3 | 70 | 30 | 6 |

WV-CA-104 (Runs 5 and 6), -110 (Runs 1 and 2): ($S_P$)-AT were synthesized using automated synthesis on nS-8II DNA/RNA synthesizer according to the synthetic cycle summarized below, using 1 μmol synthesis column and 1.7 μmol (50 mg @ 34 μmol/g loading) of succinyl-piperidine linked dT$^{Bz}$ on HCP. The synthesis cycle was performed with removal of the terminal 5'-O-DMTr group (DMT Off). After completion of the automated oligonucleotide synthesis, the HCP support was washed with dry ACN and dried under vacuum, and dry solid support was transferred into vial. 1 mL of AMA was added and the mixture was heated at 45° C. for 30 min. The reaction mixture was cooled down to room temperature, then subjected to speed vacuum to less than 0.5 mL, diluted with water to 1 mL, and filtered through 0.2 micron syringe filter. The samples were analyzed by RP-UPLC.

| step | Reaction | reagent | delivery vol (mL) | wait time (sec) |
|---|---|---|---|---|
| 1 | detritylation | 3% DCA in Toluene | 2 × 5 | N.A. |
| 2 | Coupling | 0.15M chiral monomer in IBN + 0.5M CMIMT in ACN | 0.48 | 300 |
| 3 | Capping | 20% Ac$_2$O, 30% lutidine in ACN + 16% NMI in ACN | 1.2 | 90 |
| 4 | sulfurization | 0.1M POS in ACN | 0.8 | 300 |

Example RP HPLC Method:
  Buffer A: 100 mM TEAA
  Buffer B: ACN
  Column: Waters, ACQUITY UPLC BEH C$_{18}$, 1.7 μm, 2.1×150 mm
  Column heater set temperature=55° C.
  Signal monitored at 260 nm
Gradient Used:

| Time | Flow (ml/min) | % A | % B | Curve |
|---|---|---|---|---|
| Initial | | 99 | 1 | |
| 30 | 0.3 | 70 | 30 | 6 |

WV-CA-104 (Runs 1-4), -111 (Runs 1-4), and -112 (Runs 1-4): ($S_P$)-AT were synthesized using automated synthesis on nS-8II DNA/RNA synthesizer according to the synthetic cycle summarized below, using 1 μmol synthesis column and 1.75 μmol (50 mg @ 35 μmol/g loading) of succinyl-piperidine linked dT$^{Bz}$ on HCP. The synthesis cycle was performed with removal of the terminal 5'-O-DMTr group (DMT Off). After completion of the automated oligonucleotide synthesis, the HCP support was washed with dry ACN and dried under vacuum, and dry solid support was transferred into vial. 1 mL of AMA was added and the mixture was heated at 45° C. for 30 min. The reaction mixture was cooled down to room temperature, then subjected to speed vacuum to less than 0.5 mL, diluted with water to 1 mL, and filtered through 0.2 micron syringe filter. The samples were analyzed by RP-UPLC.

| step | reaction | reagent | delivery vol (mL) | wait time (sec) |
|---|---|---|---|---|
| 1 | detritylation | 3% DCA in Toluene | 2 × 5 | N.A. |
| 2 | coupling | 0.15M chiral monomer in IBN + (0.45M ETT in ACN (Run 1, 2)) or (0.5M CMIMT in ACN (Run 3, 4)) | 0.48 | 300 |
| 3 | capping | 20% Ac$_2$O, 30% lutidine in ACN + 16% NMI in ACN | 1.2 | 90 |
| 4 | sulfurization | 0.1M POS in ACN | 0.8 | 300 |

RP HPLC Method:
  Buffer A: 100 mM TEAA
  Buffer B: ACN
  Column: Waters, ACQUITY UPLC BEH C$_{18}$, 1.7 μm, 2.1×150 mm
  Column heater set temperature=55° C.
  Signal monitored at 260 nm
Gradient Used:

| Time | Flow (ml/min) | % A | % B | Curve |
|---|---|---|---|---|
| Initial | | 99 | 1 | |
| 30 | 0.3 | 70 | 30 | 6 |

WV-CA-104 (Run 3), -111 (Run 3), and -112 (Run 3): All-($S_P$)-A$_4$T were synthesized using automated synthesis on nS-8II DNA/RNA synthesizer according to the synthetic cycle summarized below, using 1 μmol synthesis column and 1.75 μmol (50 mg @ 35 μmol/g loading) of succinyl-piperidine linked dT$^{Bz}$ on HCP. The synthesis cycle was performed with removal of the terminal 5'-O-DMTr group (DMT Off). After completion of the automated oligonucleotide synthesis, the HCP support was washed with dry ACN and dried under vacuum, and solid support was transferred into vial. The support was treated with 1 mL of 0.1M TBAF in ACN for 2 h at room temperature, filtered and washed with ACN. Then the solid support transferred into vial, 1 mL of AMA was added and the mixture was heated at 45° C. for 30 min. The reaction mixture was cooled down to room temperature, then subjected to speed vacuum to less than 0.5 mL, diluted with water to 1 mL, and filtered through 0.2 micron syringe filter. The samples were analyzed by RP-UPLC.

| step | reaction | Reagent | delivery vol (mL) | wait time (sec) |
|---|---|---|---|---|
| 1 | detritylation | 3% DCA in Toluene | 2 × 5 | N.A. |
| 2 | coupling | 0.15M chiral monomer in IBN + 0.5M CMIMT in CAN | 0.48 | 300 |
| 3 | capping | 20% Ac$_2$O, 30% lutidine in ACN + 16% NMI in CAN | 1.2 | 90 |
| 4 | sulfurization | 0.1M POS in CAN | 0.8 | 300 |

Example RP HPLC Method:
  Buffer A: 100 mM TEAA
  Buffer B: ACN
  Column: Waters, ACQUITY UPLC BEH C$_{18}$, 1.7 μm, 2.1×150 mm
  Column heater set temperature=55° C.
  Signal monitored at 260 nm Gradient Used:

| Time | Flow (ml/min) | % A | % B | Curve |
|---|---|---|---|---|
| Initial | | 99 | 1 | |
| 30 | 0.3 | 70 | 30 | 6 |

In some embodiments, for compounds of formula I-e, when both $R^1$ and $R^3$ are hydrogen, $R^5$ is —$CH_3$, $R^6$ is hydrogen, —OH and —$N(R^5)(R^6)$ are trans, 6, 7, 8-membered cycloalkyl Ring A can provide phosphoramidites with higher stability and yields than 5-membered cycloalkyl Ring A (which, in some conditions, can be of low stability and difficult to isolate). In some embodiments, phosphoramidites from

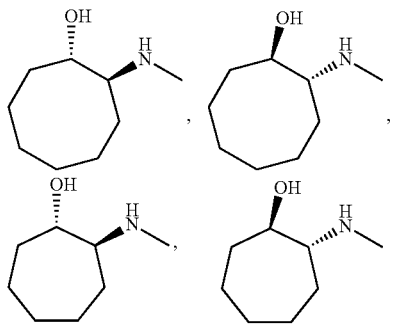

can provide better diastereoselectivity than those from

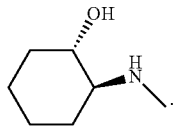

In some embodiments, for compounds wherein $R^1$ is aryl and $R^2$ is alkyl (e.g., methyl), both electron donating aryl substitution groups and electron withdrawing substation groups provide high yields and/or stereoselectivity. In some embodiments, $R^1$ and $R^2$ being non-bulky alkyl and/or benzyl provide high yields and high stereoselectivity, e.g., compared to $R^1$ and $R^2$ being both aryl and both isopropyl.

In some embodiments, $R^1$ and $R^2$ are taken together to form an optionally substituted ring, for example cycloalkyl ring. In some embodiments, without the intention to be limited by any theory, Applicant notes that properties of rings formed by $R^1$ and $R^2$ taken together may be utilized to modulate properties (e.g., ring strain, electronics, and reactivity, etc.) of oxazaphospholidine ring in provided compounds of formula IV, IV-a, IV-b, IV-c-1, IV-c-2, IV-d, IV-e, V, V-a, V-b, V-c-1, V-c-2, V-d, V-e, VI, VI-a, VI-b, VI-c, VI-c-1, VI-c-2, VI-d, or VI-e, or salts thereof. In some embodiments, compounds comprising optionally substituted cyclohexyl or cyclopentyl rings formed by $R^1$ and $R^2$ taken together provide high yields and diastereoselectivity.

In some embodiments, $R^5$ and one of $R^3$ and $R^4$ are taken together to form an optionally substituted ring. In some embodiments, provided compounds comprise Ring A'. In some embodiments, compounds comprising 4-membered such ring moieties provide high yields and/or stereoselectivity, e.g., compared to certain compounds comprising 6-membered piperidine ring moieties under certain tested challenging conditions. In some embodiments, such rings are 5-membered and are substituted. In some embodiments, compounds comprising rings with various substitution patterns can deliver high yields and/or diastereoselectivity. In some embodiments, compounds comprising rings of various substitution patterns deliver higher yields and/or diastereoselectivity than certain compounds comprising the 5,6-bicyclic pattern in

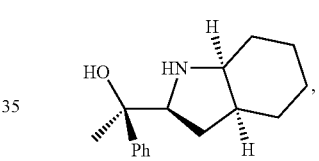

under certain tested challenging conditions. In some embodiments, rings formed by $R^5$ and one of $R^3$ and $R^4$ taken together, or Ring A', are 6-membered. In some embodiments, compounds comprising 5'-membered ring moieties provide higher yields and diastereoselectivity than certain compounds comprising 6-membered ring moieties, or certain compounds with the 5'-membered ring moieties removed, under certain tested challenging conditions.

TABLE 7

Example data.

| No. | Monomer $^{31}$P Resonance (ppm) | Monomer Yield % | Monomer trans/cis | Dimer Cycle | Dimer Activator | Dimer HPLC Area % dC | Dimer HPLC Area % dCC (PO) | Dimer HPLC Area % dCC (Rp) |
|---|---|---|---|---|---|---|---|---|
| WV-CA-002 | 149.9 | 50% | >99/1 | SOSICS[1] | CMPT | 25.44 | 3.21 | 0.40 |
| WV-CA-003 | 155.6 | 37 | >99/1 | SOSICS | CMPT | 6.53 | 3.33 | 1.81 |
| WV-CA-005-L | 165.2 | 70% | >99/1 | SOSICS | CMPT | 10.9756 | 0.5404 | 0.6921 |
| WV-CA-005-D | 165.6 | 71% | >99/1 | SOSICS | CMPT | 10.7919 | 0.5767 | 85.9478 |
| WV-CA-008-S | 150.5 | 76% | >99/1 | SOSICS | CMPT | 83.31 | 0.55 | 5.97 |
| WV-CA-011-S | 148 | 67% | 93/5[2] | SOSICS | CMPT | 76.98 | 2.47 | 2.41 |
| WV-CA-012 | 131.5/139.6/ 136.8 | 70% | 59/35/6 | DPSE | 0.5M CMIMT | 13.80 | 0.25 | 57.75 |
| WV-CA-024 | 163.9 | 44% | 85/15[3] | SOSICS | CMPT | 3.95 | 1.02 | 4.69 |
| WV-CA-025 | 152.2 | 69% | 95/5 | SOSICS | CMPT | 50.3482 | 0.5542 | 5.1613 |
| WV-CA-026 | 164.9 | 39% | 90/10[4] | SOSICS | CMPT | 3.7919 | 0.8648 | 90.8545 |
| WV-CA-027 | 152.2 | 77% | 95.5/4.5 | SOSICS | CMPT | 42.968 | 0.636 | 47.0728 |
| WV-CA-031 | 4 peaks | 28% | | SOSICS | CMPT | 100.00 | 0.00 | 0.00 |
| WV-CA-045 | 141.2/137.2/ 135.3 | 71% | 72/18/10 | DPSE | 0.5M CMIMT | 10.34 | 0.86 | 61.66 |

TABLE 7-continued

Example data.

| | | | | | | | | |
|---|---|---|---|---|---|---|---|---|
| WV-CA-046 | 136.8/145.5/ 142.0 | 73% | 80/11/9 | DPSE | 0.5M CMIMT | 6.81 | 0.90 | 29.03 |
| WV-CA-047 | 143.9 | 18% | >1/99 | SOSICS | CMPT | 23.43 | 0.83 | 7.32 |
| WV-CA-050 (Run 1) | 155.4 | 62% | >99/1 | DPSE | 0.5M CMIMT | 0.74 | 6.30 | 1.56 |
| WV-CA-050 (Run 2) | | | | DPSE | 0.5M CMIMT | 1.50 | 3.27 | 1.55 |
| WV-CA-051 | 155.0 | 53% | >99/1 | DPSE | 0.5M CMIMT | 14.04 | 1.19 | 2.27 |
| WV-CA-052 | 154.9 | 39% | >99/1 | DPSE | 0.5M CMIMT | 15.03 | 1.59 | 2.33 |
| WV-CA-053 | 133.8/137.6 | 43% | 72/28 | SOSICS | CMPT | 40.4914 | 0.6205 | 45.8627 |
| WV-CA-056 | 166.2 | 79% | >98/2 | SOSICS | CMPT | 8.05 | 0.66 | 3.49 |
| WV-CA-056-S | 147.3 | 60% | >99/1 | SOSICS | CMPT | 20.2741 | 0.2216 | 9.2876 |
| WV-CA-057 | 155.1 | 45% | >99/1 | SOSICS | CMPT | 9.9999 | 0.00 | 0.00 |
| WV-CA-059-R | 159 | 62% | >99/1 | SOCICS | CMPT | 7.15 | 1.73 | 90.17 |
| WV-CA-059 | 158.4 | 64% | 100/0 | SOSICS | CMPT | 5.5686 | 0.4474 | 1.017 |
| WV-CA-060 | 156.3 | 63% | 100/0 | SOSICS | CMPT | 7.8884 | 0.3918 | 2.1565 |
| WV-CA-061 | 150.7 | 48% | 81/19 | SOSICS | CMPT | 45.8889 | 0.5981 | 46.7151 |
| WV-CA-063-S | 135.2/134.0 | 39% | 72/28 | SOSICS | CMPT | 92.50 | 0.00 | 5.02 |
| WV-CA-064-S | 147.9 | 84% | 93/7 | SOSICS | CMPT | 55.52 | 0.93 | 12.36 |
| WV-CA-065-S | 162.3 | 50% | 100/0 | SOSICS | CMPT | 5.52 | 2.99 | 2.78 |
| WV-CA-066-R | 139.7/132.3 | 20% | 62/38 | SOSICS | CMPT | 100.00 | 0.00 | 0.00 |
| WV-CA-067 | 154.8 | 52% | 98/2 | | | | | |
| WV-CA-068-S | 152.7 | 45% | >99/1 | SOSICS | CMPT | 10.08 | 0.57 | 3.01 |
| WV-CA-069-S | 141.7/143.2 | 46% | 92/8 | SOSICS | CMPT | 65.28 | 1.78 | 7.01 |
| WV-CA-070 | 155.7/144.6 | 77% | 94/6 | | | | | |
| WV-CA-070-S | 164.2/146.0 | 16% | 92/8 | SOCICS | CMPT | 2.61 | 1.76 | 90.48 |
| WV-CA-071-S | 156.2 | 72% | 94/6 | SOSICS | CMPT | 74.21 | 1.93 | 5.18 |
| WV-CA-074-R | 154.7 | 15% | >99/1 | | | | | |
| WV-CA-074-M | 158.8 | 58% | 100/0 | SOSICS | CMPT | 13.90 | 2.63 | 1.90 |
| WV-CA-074-S | 154.2/142.4 | 33% | >98:2 | | | | | |
| WV-CA-075-S | | 31% | 20/80 | | | | | |
| WV-CA-076 | 157.2 | 28% | 98/2 | | | | | |
| WV-CA-078 | 158 | 35% | 99/1 | SOSICS | CMPT | 8.79 | 1.51 | 1.13 |
| WV-CA-079 | 153.2 | 66% | 100/0 | SOSICS | CMPT | 14.42 | 1.49 | 0.84 |
| WV-CA-080 | 158.0/149.4 | 37% | >99/1 | SOSICS | CMPT | 15.65 | 1.46 | 0.31 |
| WV-CA-081 | 159.4 | 65% | >99:1 | SOSICS | CMPT | 19.55 | 1.51 | 0.31 |
| WV-CA-082 | 160 | 64% | 100/0 | SOSICS | CMPT | 23.24 | 1.44 | 0.72 |
| WV-CA-083 | 161.0/146.1 | 71% | 96:04:00 | SOSICS | CMPT | 32.23 | 1.63 | 0.00 |
| WV-CA-090 | 153.6 | 72% | 98.6/1.4 | SOSICS | CMPT | 7.45 | 1.68 | 3.06 |
| WV-CA-091 | 145.6 | 58% | 100/0 | SOSICS | CMPT | 56.40 | 1.39 | 1.21 |
| WV-CA-092 | 149.3, 145.1 | 52 | 59/41 | SOSICS | CMPT | 87.07 | 0.00 | 8.70 |
| WV-CA-097 | 138.6, 125.0 | 50% | 72/28 | SOSICS | CMPT | 66.15 | 1.01 | 9.33 |
| WV-CA-098 | 137.3 | 79% | 100/0 | SOSICS | CMPT | 42.54 | 1.86 | 4.48 |
| WV-CA-100-L (Run 1) | | | >99:1 | SOSICS | CMPT | 13.48 | 0.49 | 2.04 |
| WV-CA-100-L (Run 2) | | | | SOSICS | CMPT | 13.56 | 0.54 | 2.28 |
| WV-CA-100-L (Run 3) | | | | SOSICS | CMPT | 14.50 | 0.49 | 0.39 |
| WV-CA-100-L (Run 7) | | | | SOSICS | CMPT | 11.58 | 0.42 | 0.75 |
| WV-CA-100-L (Run 8) | | | | SOSICS | CMPT | 10.79 | 0.44 | 0.85 |
| WV-CA-100-L (Run 9) | | | | SOSICS | CMPT | 11.21 | 0.65 | 1.42 |
| WV-CA-100-L (Run 10) | | | | SOSICS | CMPT | 11.00 | 0.54 | 1.05 |
| WV-CA-100-L (Run 11) | | | | SOSICS | CMPT | 14.20 | 1.68 | 0.48 |
| WV-CA-100-L (Run 12) | | | | SOSICS | CMPT | 14.03 | 1.88 | 0.45 |
| WV-CA-100-L (Run 13) | | | | SOSICS | CMPT | 15.2376 | 1.2385 | 0.1218 |
| WV-CA-100-L (Run 14) | | | | SOSICS | CMPT | 14.02 | 1.60 | 0.12 |
| WV-CA-100-L (Run 15) | | | | SOSICS | CMPT | 14.1041 | 1.5804 | 0.6135 |
| WV-CA-100-L (Run 16) | | | | SOSICS | CMPT | 13.68 | 1.75 | 0.56 |

TABLE 7-continued

Example data.

| | | | | | | | | |
|---|---|---|---|---|---|---|---|---|
| WV-CA-100-L (Run 17) | | | | SOSICS | CMPT | 14.24 | 2.32 | 0.55 |
| WV-CA-100-D (Run 1) | | | >99:1 | | | | | |
| WV-CA-100-D (Run 2) | | | | | | | | |
| WV-CA-100-D (Run 3) | | | | | | | | |
| WV-CA-100-D (Run 9) | | | | | | | | |
| WV-CA-100-D (Run 11) | | | | | | | | |
| WV-CA-100-D (Run 13) | | | | | | | | |
| WV-CA-100-D (Run 14) | | | | | | | | |
| WV-CA-100-D (Run 15) | | | | | | | | |
| WV-CA-102 | | | >99:1 | | | | | |
| WV-CA-103 | | | >99:1 | | | | | |
| WV-CA-104 (Run 1) | | | 99:1 | DPSE | 0.45M ETT | 14.28 | | 0.66 |
| WV-CA-104 (Run 2) | | | | DPSE | 0.45M ETT | 12.90 | | 0.67 |
| WV-CA-104 (Run 3) | | | | DPSE | 0.5M CMIMT | 9.22 | | 0.13 |
| WV-CA-104 (Run 4) | | | | DPSE | 0.5M CMIMT | 14.19 | | 0.13 |
| WV-CA-104 (Run 5) | | | | DPSE | 0.5M CMIMT | 3.18 | | 1.01 |
| WV-CA-104 (Run 6) | | | | DPSE | 0.5M CMIMT | 2.75 | | 1.07 |
| WV-CA-104 (Run 7) | | | | DPSE | 0.5M CMIMT | 0.73 | 0.69 | 1.37 |
| WV-CA-104 (Run 8) | | | | DPSE | 0.5M CMIMT | 1.43 | 0.86 | 1.03 |
| WV-CA-104 (Run 9) | | | | DPSE | 0.5M CMIMT | 1.04 | 0.81 | 1.65 |
| WV-CA-104 (Run 10) | | | | DPSE | 0.5M CMIMT | 1.20 | 0.79 | 1.65 |
| WV-CA-104 (Run 11) | | | | DPSE | 0.5M CMIMT | 4.80 | 0.63 | 2.06 |
| WV-CA-105 | | | 99:1 | | | | | |
| WV-CA-110[5] (Run 1) | | | | DPSE | 0.5M CMIMT | 0.84 | | 1.89 |
| WV-CA-110 (Run 2) | | | | DPSE | 0.5M CMIMT | 2.69 | | 2.19 |
| WV-CA-111 (Run 1) | 152.8 | 45% | >99/1 | DPSE | 0.45M ETT | 11.40 | | 1.16 |
| WV-CA-111 (Run 2) | | | | DPSE | 0.45M ETT | 8.51 | | 1.31 |
| WV-CA-111 (Run 3) | | | | DPSE | 0.5M CMIMT | 10.80 | | 0.37 |
| WV-CA-111 (Run 4) | | | | DPSE | 0.5M CMIMT | 4.73 | | 0.40 |
| WV-CA-112[6] (Run 1) | 135.30% | 49% | 98/2 | DPSE | 0.45M ETT | 12.13 | | 1.04 |
| WV-CA-112 (Run 2) | | | | DPSE | 0.45M ETT | 6.34 | | 1.22 |
| WV-CA-112 (Run 3) | | | | DPSE | 0.5M CMIMT | 7.24 | | 0.37 |
| WV-CA-112 (Run 4) | | | | DPSE | 0.5M CMIMT | 13.51 | | 0.24 |
| WV-CA-112 (Run 5) | | | | DPSE | 0.5M CMIMT | 1.34 | 0.64 | 1.31 |
| WV-CA-118 | 167 | 40% | >99/1 | SOSICS | CMPT | 6.40 | 3.13 | 0.77 |
| WV-CA-118S | 155.2 | 50% | 98.5/1.5 | SOSICS | CMPT | 9.61 | 1.27 | 7.04 |
| WV-CA-119 | 134.5 | 58% | >99/1 | DPSE | 0.5M CMIMT | 1.40 | 0.50 | 0.72 |
| WV-CA-122 | 157.2 | 24% | 98/0[7] | SOSICS | CMPT | 6.04 | 0.00 | 0.77 |
| WV-CA-123 | 153.8 | 45.70% | 100/0 | SOSICS | CMPT | 12.17 | 0.63 | 1.06 |
| WV-CA-124 | 157.5 | 45% | >99/1 | SOSICS | CMPT | 23.81 | 2.14 | 1.36 |
| WV-CA-160 | | | | SOSICS | CMPT | 40.4914 | 0.6205 | 45.8627 |
| WV-CA-164 | | | | SOSICS | CMPT | 20.2741 | 0.2216 | 9.2876 |
| WV-CA-165 | | | | SOSICS | CMPT | 9.6479 | | |
| WV-CA-168 | | | | SOSICS | CMPT | 5.5686 | 0.4474 | 1.017 |
| WV-CA-169 | | | | SOSICS | CMPT | 7.8884 | 0.3918 | 2.1565 |
| WV-CA-170 | | | | SOSICS | CMPT | 45.8889 | 0.5981 | 46.7151 |

TABLE 7-continued

Example data.

| No. | | | | | | | | |
|---|---|---|---|---|---|---|---|---|
| WV-CA-201 | 160.9 | 36% | 99/1 | SOSICS | CMPT | 12.43 | 2.53 | 2.03 |
| WV-CA-202 | 155.9 | 73% | 99/1 | SOSICS | CMPT | 13.69 | 2.10 | 0.83 |
| WV-CA-206 | | 41% | 99/1 | SOSICS | CMPT | 77.99 | 1.25 | 0.80 |
| WV-CA-207 | 155.6 | 31% | 99/1 | SOSICS | CMPT | 33.39 | 1.20 | 24.80 |
| WV-CA-221 | 149.3 | 62% | 94/6 | SOSICS | CMPT | 30.46 | 2.33 | 46.40 |
| WV-CA-222 | 148.8 | 63% | 95/5 | SOSICS | CMPT | 25.83 | 2.17 | 2.96 |
| WV-CA-223 | 141.6 | 71% | 93/7 | SOSICS | CMPT | 41.23 | 2.37 | 2.30 |
| WV-CA-224 | 141.2 | 60% | 93/7 | SOSICS | CMPT | 44.27 | 2.04 | 36.82 |
| WV-CA-225 | 151.9 | 73% | 99/1 | SOSICS | CMPT | 12.71 | 1.78 | 1.48 |
| WV-CA-216 | 163.9 | 60% | 98/2 | SOSICS | CMPT | 2.24 | 1.78 | 4.56 |

| No. | Dimer HPLC Area % dCC (Sp) | Dimer dCC(-S) | Dimer d.r. | Dimer Rp/Sp | Dimer Conv. % | Pentamer Cycle | Pentamer Activator | Pentamer Average Yield |
|---|---|---|---|---|---|---|---|---|
| WV-CA-002 | 10.75 | 22.35 | 96.41 | Sp | 22.2 | | | |
| WV-CA-003 | 87.49 | 3.59 | 97.97 | Sp | 87.8 | SOSICS | CMPT | 92.45 |
| WV-CA-005-L | 84.352 | 0.63 | 99.19 | Sp | 79.8 | SOSICS | CMPT | 90.20 |
| WV-CA-005-D | 0.441 | 0.66 | 99.49 | Rp | 80.3 | SOSICS | CMPT | 88.62 |
| WV-CA-008-S | 0.28 | 8.04 | 95.45 | Rp | 4.0 | SOSICS | CMPT | 97.34 |
| WV-CA-011-S | 0.00 | 50.61 | 100.00 | Rp | 3.1 | | | |
| WV-CA-012 | 28.20 | 0.29 | 67.19 | Rp | 68.6 | | | |
| WV-CA-024 | 88.00 | 1.09 | 94.94 | Sp | 92.3 | SOSICS | CMPT | 92.07 |
| WV-CA-025 | 42.775 | 1.14 | 89.23 | Sp | 32.8 | | | |
| WV-CA-026 | 2.7404 | 0.92 | 97.07 | Rp | 92.7 | | | |
| WV-CA-027 | 3.3719 | 1.25 | 93.32 | Rp | 37.6 | | | |
| WV-CA-031 | 0.00 | | | Sp | 0.0 | | | |
| WV-CA-045 | 27.14 | 0.96 | 69.44 | Rp | 75.2 | | | |
| WV-CA-046 | 63.25 | 0.97 | 68.54 | Sp | 82.7 | | | |
| WV-CA-047 | 64.80 | 1.13 | 89.86 | Sp | 61.2 | | | |
| WV-CA-050 (Run 1) | 91.40 | 6.35 | 98.32 | Sp | 97.9 | DPSE | 0.5M CMIMT | 92.74 |
| WV-CA-050 (Run 2) | 93.57 | 3.32 | 98.37 | Sp | 95.8 | DPSE | 0.5M CMIMT | 91.65 |
| WV-CA-051 | 82.50 | 1.38 | 97.32 | Sp | 68.1 | | | |
| WV-CA-052 | 81.05 | 1.87 | 97.21 | Sp | 66.4 | | | |
| WV-CA-053 | 11.777 | 1.07 | 79.57 | Rp | 42.2 | | | |
| WV-CA-056 | 84.70 | 0.74 | 96.04 | Sp | 84.8 | SOSICS | CMPT | 89.50 |
| WV-CA-056-S | 69.456 | 0.28 | 88.21 | Sp | 66.4 | SOSICS | CMPT | 70.91 |
| WV-CA-057 | 1.80 | 0.00 | 100.00 | Sp | 8.3 | | | |
| WV-CA-059-R | 0.95 | 1.86 | 98.96 | Rp | 86.8 | SOCICS | CMPT | 93.34 |
| WV-CA-059 | 92.058 | 0.48 | 98.91 | Sp | 89.5 | SOSICS | CMPT | 93.53 |
| WV-CA-060 | 88.619 | 0.43 | 97.62 | Sp | 85.4 | SOSICS | CMPT | 90.83 |
| WV-CA-061 | 2.2635 | 1.21 | 95.38 | Rp | 35.4 | | | |
| WV-CA-063-S | 2.48 | 0.00 | 66.93 | Rp | 3.9 | | | |
| WV-CA-064-S | 0.87 | 6.54 | 93.44 | Rp | 11.4 | | | |
| WV-CA-065-S | 88.72 | 3.16 | 96.96 | Sp | 89.7 | SOSICS | CMPT | 92.56 |
| WV-CA-066-R | 0.00 | | | Sp | 0.0 | | | |
| WV-CA-067 | | | | Sp | | | | |
| WV-CA-068-S | 84.89 | 0.65 | 96.58 | Sp | 81.6 | SOSICS | CMPT | 88.58 |
| WV-CA-069-S | 22.77 | 5.64 | 76.46 | Sp | 19.7 | | | |
| WV-CA-070 | | | | Sp | | | | |
| WV-CA-070-S | 5.16 | 1.81 | 94.60 | Rp | 95.0 | SOCICS | CMPT | 97.84 |
| WV-CA-071-S | 0.60 | 24.97 | 89.58 | Rp | 5.0 | | | |
| WV-CA-074-R | | | | Sp | | | | |
| WV-CA-074-M | 76.00 | 3.26 | 97.56 | Sp | 74.6 | SOSICS | CMPT | 84.86 |
| WV-CA-074-S | | | | Sp | | | | |
| WV-CA-075-S | | | | Sp | | | | |
| WV-CA-076 | | | | Sp | | | | |
| WV-CA-078 | 87.08 | 1.68 | 98.72 | Sp | 83.8 | SOSICS | CMPT | 91.05 |
| WV-CA-079 | 82.71 | 1.75 | 98.99 | Sp | 74.9 | SOSICS | CMPT | 87.20 |
| WV-CA-080 | 79.53 | 1.80 | 99.61 | Sp | 72.5 | SOSICS | CMPT | 84.40 |
| WV-CA-081 | 74.97 | 1.97 | 99.59 | Sp | 66.6 | SOSICS | CMPT | 80.65 |
| WV-CA-082 | 68.93 | 2.02 | 98.96 | Sp | 60.8 | SOSICS | CMPT | 73.53 |
| WV-CA-083 | 48.58 | 3.25 | 100.00 | Sp | 44.1 | SOSICS | CMPT | 61.00 |
| WV-CA-090 | 86.04 | 1.85 | 96.57 | Sp | 86.1 | SOSICS | CMPT | 90.83 |
| WV-CA-091 | 39.44 | 3.30 | 97.02 | Sp | 27.4 | | | |
| WV-CA-092 | 0.00 | 0.00 | 100.00 | Rp | 4.8 | | | |
| WV-CA-097 | 18.53 | 3.50 | 66.51 | Sp | 18.1 | | | |
| WV-CA-098 | 49.12 | 3.35 | 91.64 | Sp | 39.8 | | | |
| WV-CA-100-L (Run 1) | 82.20 | 0.58 | 97.58 | Sp | 76.1 | SOSICS | CMPT | 86.60 |
| WV-CA-100-L (Run 2) | 82.61 | 0.63 | 97.32 | Sp | 76.2 | SOSICS | CMPT | 86.29 |
| WV-CA-100-L (Run 3) | 82.95 | 0.58 | 99.53 | Sp | 74.6 | SOSICS | CMPT | 86.02 |

TABLE 7-continued

Example data.

| | | | | | | | | |
|---|---|---|---|---|---|---|---|---|
| WV-CA-100-L (Run 7) | 86.50 | 0.48 | 99.14 | Sp | 79.3 | | | |
| WV-CA-100-L (Run 8) | 86.65 | 0.50 | 99.02 | Sp | 80.5 | | | |
| WV-CA-100-L (Run 9) | 85.20 | 0.75 | 98.36 | Sp | 79.8 | SOSICS | CMPT | 88.96 |
| WV-CA-100-L (Run 10) | 85.57 | 0.62 | 98.79 | Sp | 80.1 | | | |
| WV-CA-100-L (Run 11) | 84.11 | 1.95 | 99.43 | Sp | 75.5 | SOSICS | CMPT | 86.72 |
| WV-CA-100-L (Run 12) | 84.09 | 2.18 | 99.47 | Sp | 75.7 | | | |
| WV-CA-100-L (Run 13) | 82.791 | 1.47 | 99.85 | Sp | 73.7 | SOSICS | CMPT | 85.10 |
| WV-CA-100-L (Run 14) | 81.55 | 1.92 | 99.85 | Sp | 75.1 | SOSICS | CMPT | 86.56 |
| WV-CA-100-L (Run 15) | 82.691 | 1.86 | 99.26 | Sp | 75.3 | SOSICS | CMPT | 85.05 |
| WV-CA-100-L (Run 16) | 82.25 | 2.07 | 99.32 | Sp | 75.8 | SOSICS | CMPT | |
| WV-CA-100-L (Run 17) | 81.56 | 2.75 | 99.33 | Sp | 75.0 | | | |
| WV-CA-100-D (Run 1) | | | | Sp | | SOSICS | CMPT | 86.60 |
| WV-CA-100-D (Run 2) | | | | Sp | | SOSICS | CMPT | 86.29 |
| WV-CA-100-D (Run 3) | | | | Sp | | SOSICS | CMPT | 86.02 |
| WV-CA-100-D (Run 9) | | | | Sp | | SOSICS | CMPT | 88.96 |
| WV-CA-100-D (Run 11) | | | | Sp | | SOSICS | CMPT | 86.72 |
| WV-CA-100-D (Run 13) | | | | Sp | | SOSICS | CMPT | 85.10 |
| WV-CA-100-D (Run 14) | | | | Sp | | SOSICS | CMPT | 86.56 |
| WV-CA-100-D (Run 15) | | | | Sp | | SOSICS | CMPT | 85.05 |
| WV-CA-104 (Run 1) | 85.06 | 0.00 | 99.23 | Sp | 69.6 | | | |
| WV-CA-104 (Run 2) | 86.43 | 0.00 | 99.23 | Sp | 72.0 | | | |
| WV-CA-104 (Run 3) | 90.65 | 0.00 | 99.86 | Sp | 79.0 | DPSE | 0.5M CMIMT | 94.39 |
| WV-CA-104 (Run 4) | 85.68 | 0.00 | 99.85 | Sp | 69.8 | | | |
| WV-CA-104 (Run 5) | 95.81 | 0.00 | 98.96 | Sp | 92.1 | | | |
| WV-CA-104 (Run 6) | 96.18 | 0.00 | 98.90 | Sp | 93.1 | | | |
| WV-CA-104 (Run 7) | 97.21 | 0.70 | 98.61 | Sp | 97.9 | DPSE | 0.5M CMIMT | 94.49 |
| WV-CA-104 (Run 8) | 96.67 | 0.87 | 98.95 | Sp | 96.0 | | | |
| WV-CA-104 (Run 9) | 96.51 | 0.82 | 98.32 | Sp | 97.1 | DPSE | 0.5M CMIMT | 92.99 |
| WV-CA-104 (Run 10) | 96.36 | 0.80 | 98.32 | Sp | 96.6 | DPSE | 0.5M CMIMT | 95.27 |
| WV-CA-104 (Run 11) | 92.51 | 0.66 | 97.82 | Sp | 87.4 | | | |
| WV-CA-110 (Run 1) | 97.27 | 0.00 | 98.09 | Sp | 97.8 | | | |
| WV-CA-110 (Run 2) | 95.13 | 0.00 | 97.75 | Sp | 93.2 | | | |
| WV-CA-111 (Run 1) | 87.45 | 0.00 | 98.69 | Sp | 74.8 | | | |
| WV-CA-111 (Run 2) | 90.18 | 0.00 | 98.57 | Sp | 80.4 | | | |
| WV-CA-111 (Run 3) | 88.83 | 0.00 | 99.59 | Sp | 75.9 | DPSE | 0.5M CMIMT | 95.44 |
| WV-CA-111 (Run 4) | 94.87 | 0.00 | 99.58 | Sp | 88.5 | | | |
| WV-CA-112 (Run 1) | 86.83 | 0.00 | 98.82 | Sp | 73.4 | | | |
| WV-CA-112 (Run 2) | 92.44 | 0.00 | 98.70 | Sp | 84.9 | | | |
| WV-CA-112 (Run 3) | 92.39 | 0.00 | 99.60 | Sp | 83.0 | DPSE | 0.5M CMIMT | 83.58 |

TABLE 7-continued

Example data.

| | | | | | | | | |
|---|---|---|---|---|---|---|---|---|
| WV-CA-112 (Run 4) | 86.26 | 0.00 | 99.72 | Sp | 71.0 | | | |
| WV-CA-112 (Run 5) | 96.72 | 0.65 | 98.66 | Sp | 96.3 | DPSE | 0.5M CMIMT | 85.69 |
| WV-CA-118 | 87.49 | 3.42 | 99.13 | Sp | 87.9 | SOSICS | CMPT | 92.08 |
| WV-CA-118S | 81.05 | 1.42 | 92.01 | Sp | 82.5 | SOSICS | CMPT | 92.08 |
| WV-CA-119 | 97.38 | 0.51 | 99.27 | Sp | 97.3 | DPSE | 0.5M CMIMT | 84.70 |
| WV-CA-122 | 57.72 | 0.00 | 98.68 | Sp | 83.1 | | | |
| WV-CA-123 | 84.45 | 0.73 | 98.76 | Sp | 78.2 | SOSICS | CMPT | 87.57 |
| WV-CA-124 | 67.25 | 3.02 | 98.02 | Sp | 60.1 | SOSICS | CMPT | 66.99 |
| WV-CA-160 | 11.7766 | 1.07 | 79.57 | Rp | 42.2 | | | |
| WV-CA-164 | 69.4561 | 0.28 | 88.21 | Sp | 66.4 | | | |
| WV-CA-165 | | | | Sp | 0.0 | | | |
| WV-CA-168 | 92.0584 | 0.48 | 98.91 | Sp | 89.5 | | | |
| WV-CA-169 | 88.6194 | 0.43 | 97.62 | Sp | 85.4 | | | |
| WV-CA-170 | 2.2635 | 1.21 | 95.38 | Rp | 35.4 | | | |
| WV-CA-201 | 81.30 | 2.95 | 97.56 | Sp | 77.8 | SOSICS | CMPT | 87.59 |
| WV-CA-202 | 82.10 | 2.47 | 98.99 | Sp | 75.9 | SOSICS | CMPT | 85.60 |
| WV-CA-206 | 14.83 | 7.42 | 94.86 | Sp | 9.9 | | | |
| WV-CA-207 | 11.33 | 3.22 | 68.64 | Rp | 36.2 | | | |
| WV-CA-221 | 8.38 | 4.07 | 84.71 | Rp | 48.7 | | | |
| WV-CA-222 | 50.72 | 3.89 | 94.49 | Sp | 52.3 | | | |
| WV-CA-223 | 34.47 | 6.06 | 93.75 | Sp | 32.5 | | | |
| WV-CA-224 | 2.39 | 4.94 | 93.90 | Rp | 32.1 | | | |
| WV-CA-225 | 81.99 | 2.09 | 98.22 | Sp | 77.3 | SOSICS | CMPT | 71.26 |
| WV-CA-216 | 89.54 | 1.85 | 95.15 | Sp | 95.6 | SOSICS | CMPT | 77.41 |

[1] In some embodiments, chiral auxiliary not completely released.
[2] trans:cis:diastereomer = 93:5:2.
[3] trans/othes = 85/15.
[4] trans/othes = 90/10.
[5,6] In some embodiments, for some runs a version of amino free HCP without nucleosides (when purchased; loading of first nucleoside performed for oligonucleotide synthesis) was used and provided relatively lower yields.
[7] trans:cis:diastereomer = 98:0:2.

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described in the present disclosure. It is, therefore, to be understood that the foregoing embodiments are presented by way of example only and that, within the scope of the appended claims and equivalents thereto, claimed technologies may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:
1. A compound having the structure of formula V-b:

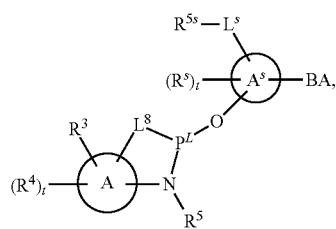

or a salt thereof, wherein:
$P^L$ is P;

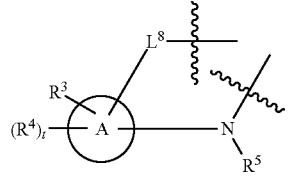

is of such a structure that

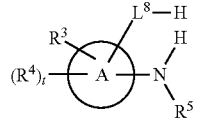

is a compound of formula I-e or a salt thereof:

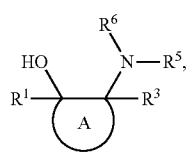

wherein:
-$L^8$-H is the —OH shown in formula I-e;
t is 1;
Ring A is an optionally substituted 6-membered ring having 0-4 heteroatoms;
each of $R^1$, $R^3$, $R^4$, and $R^5$ is independently —H, -$L^s$-R, halogen, —CN, —NO$_2$, -$L^s$-Si(R)$_3$, —OR, —SR, or —N(R)$_2$;
$R^6$ is —H;
—NHR$^5$ is —NR$^5$R$^6$ shown in formula I-e;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, and —OP(OR')[B(R')$_3$]O—, and one or more carbon atoms are optionally and independently replaced with Cy$^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;
BA is an optionally substituted group selected from a natural nucleobase moiety and a modified nucleobase moiety;
each R$^s$ is independently —H, halogen, —CN, —N$_3$, —NO, —NO$_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;
Ring A$^s$ is

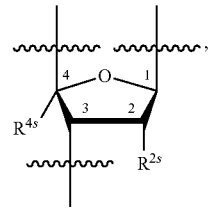

wherein each of R$^{2s}$ and R$^{4s}$ is independently R$^s$;
R$^{5s}$ is R$^s$;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

2. The compound of claim 1, wherein $R^3$ is —H.
3. The compound of claim 2, wherein $R^1$ is optionally substituted $C_{1-6}$ aliphatic.
4. The compound of claim 3, wherein $R^1$ is methyl.
5. The compound of claim 2, wherein $R^1$ is optionally substituted phenyl.
6. The compound of claim 2, wherein $R^5$ is optionally substituted $C_{1-6}$ aliphatic.
7. The compound of claim 3, wherein $R^5$ is optionally substituted $C_{1-6}$ aliphatic.
8. The compound of claim 5, wherein $R^5$ is optionally substituted $C_{1-6}$ aliphatic.
9. The compound of claim 6, wherein $R^5$ is methyl.
10. The compound of claim 7, wherein $R^5$ is methyl.
11. The compound of claim 8, wherein $R^5$ is methyl.
12. The compound of claim 1, wherein BA is an optionally substituted group which group is selected from

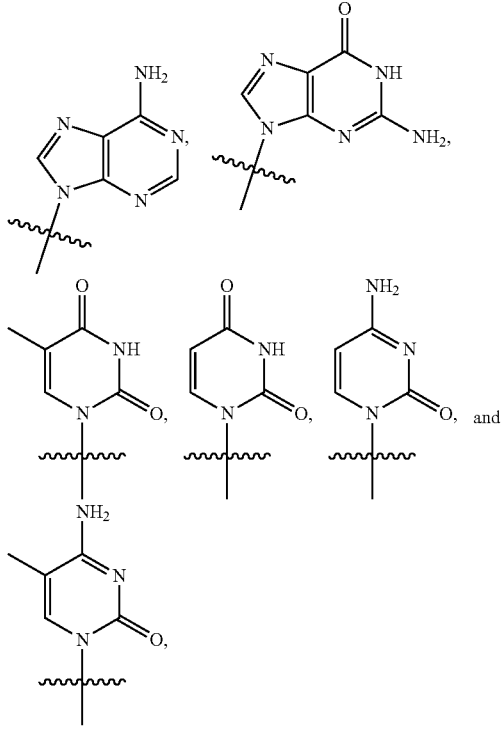

and tautomeric forms thereof.

13. The compound of claim 12, wherein $R^{2s}$ is —H.
14. The compound of claim 12, wherein $R^{2s}$ is —F.
15. The compound of claim 12, wherein $R^{2s}$ is —OR, wherein R is optionally substituted $C_{1-6}$ aliphatic.
16. The compound of claim 12, wherein $R^{2s}$ is —OMe.
17. The compound of claim 12, wherein $R^{2s}$ is —MOE.
18. The compound of claim 12, wherein Ring $A^s$ is optionally substituted

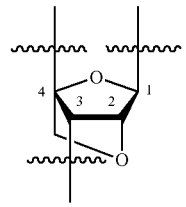

19. The compound of claim 1, wherein the compound of formula I-e

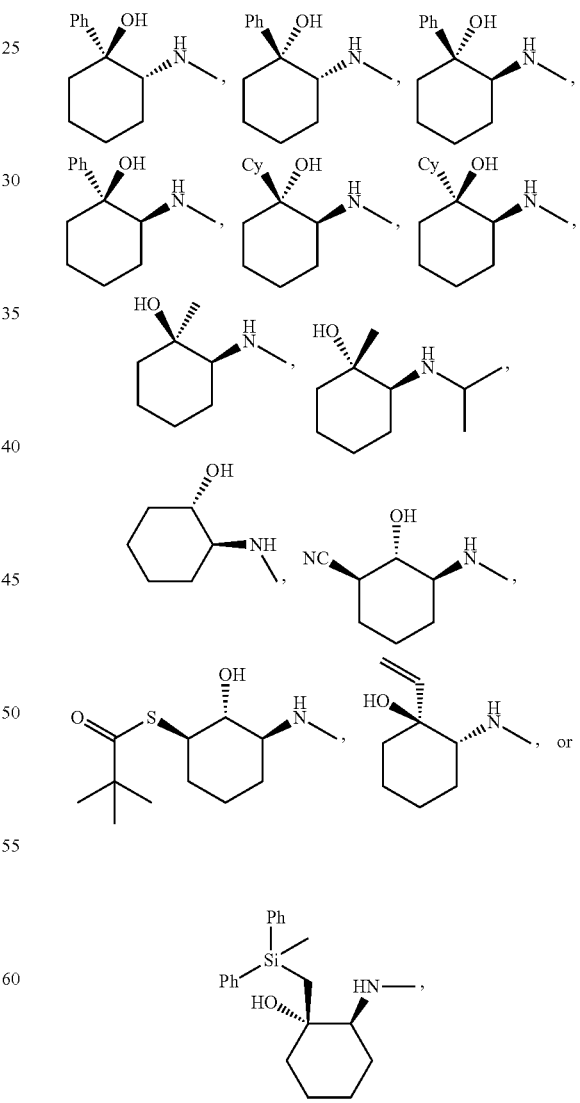

or a salt thereof.

20. The compound of claim 1, wherein the compound of formula I-e
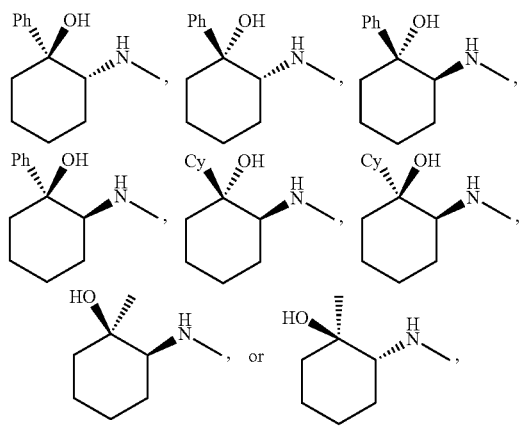
or a salt thereof.
21. The compound of claim 1, wherein the compound of formula I-e
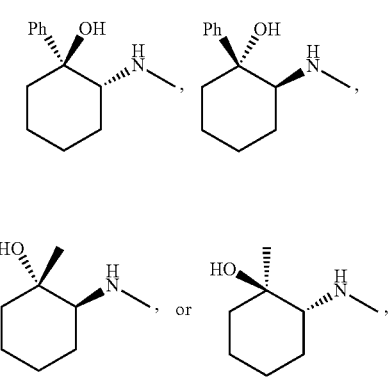
or a salt thereof.
* * * * *

SEQUENCE LISTING

```
Sequence total quantity: 1
SEQ ID NO: 1            moltype = DNA  length = 20
FEATURE                 Location/Qualifiers
misc_feature            1..20
                        note = Description of Combined DNA/RNA Molecule: Synthetic
                        oligonucleotide
modified_base           4..5
                        mod_base = OTHER
                        note = uracil
modified_base           16..18
                        mod_base = OTHER
                        note = uracil
modified_base           20
                        mod_base = OTHER
                        note = uracil
```

```
source          1..20
                mol_type = other DNA
                organism = synthetic construct
SEQUENCE: 1
agcttcttgt ccagctttat                                              20
```